(12) United States Patent
Cooper et al.

(10) Patent No.: US 8,546,404 B2
(45) Date of Patent: Oct. 1, 2013

(54) COMPOUNDS THAT ARE ERK INHIBITORS

(75) Inventors: Alan B. Cooper, West Caldwell, NJ (US); Yongqi Deng, Newton, MA (US); Gerald W. Shipps, Jr., Stoneham, MA (US); Neng-Yang Shih, Lexington, MA (US); Hugh Y. Zhu, Scotch Plains, NJ (US); Robert Sun, Natick, MA (US); Joseph M. Kelly, Parlin, NJ (US); Ronald J. Doll, Convent Station, NJ (US); Yang Nan, Malden, MA (US); Tong Wang, Cambridge, MA (US); Jagdish A. Desai, Monroe Township, NJ (US); James J-S Wang, Westfield, NJ (US); Youhao Dong, Cambridge, MA (US); Vincent S. Madison, Mountain Lakes, NJ (US); Li Xiao, Cranbury, NJ (US); Alan W. Hruza, Hackettstown, NJ (US); M. Arshad Siddiqui, Newton, MA (US); Ahmed A. Samatar, West Windsor, NJ (US); Sunil Paliwal, Monroe Township, NJ (US); Hon-Chung Tsui, East Brunswick, NJ (US); Azim Alan Celebi, Clark, NJ (US); Yiji Wu, Scotch Plains, NJ (US); Sobhana Babu Boga, Scotch Plains, NJ (US); Abdul-Basit Alhassan, Scotch Plains, NJ (US); Xiaolei Gao, Scotch Plains, NJ (US); Liang Zhu, Somerville, MA (US); Mehul Patel, Waltham, MA (US)

(73) Assignee: Merck Sharp & Dohme, Rahway, NJ (US)

( * ) Notice: Subject to any disclaimer, the term of this patent is extended or adjusted under 35 U.S.C. 154(b) by 1627 days.

(21) Appl. No.: 11/810,282

(22) Filed: Jun. 5, 2007

(65) Prior Publication Data

US 2009/0118284 A1 May 7, 2009

Related U.S. Application Data

(63) Continuation-in-part of application No. 11/636,954, filed on Dec. 11, 2006, now abandoned.

(60) Provisional application No. 60/749,856, filed on Dec. 13, 2005.

(51) Int. Cl.
*A01N 43/54* (2006.01)
*C07D 239/42* (2006.01)
*C07D 401/04* (2006.01)

(52) U.S. Cl.
USPC ........... 514/256; 514/247; 514/277; 514/396; 544/315; 546/1; 546/184; 546/361.1; 548/356.1; 548/360.1

(58) Field of Classification Search
USPC ............ 546/1, 184, 361.1; 548/356.1, 360.1, 548/361.1; 514/247, 256, 277, 396; 544/315
See application file for complete search history.

(56) References Cited

U.S. PATENT DOCUMENTS

| | | |
|---|---|---|
| 6,696,443 B2 | 2/2004 | Mavunkel et al. |
| 6,831,175 B2 | 12/2004 | Li et al. |
| 6,897,231 B2 | 5/2005 | Bhagwat et al. |
| 7,208,513 B2 | 4/2007 | Bhagwat et al. |
| 7,211,594 B2 | 5/2007 | Bhagwat et al. |
| 7,214,679 B2 | 5/2007 | Mavunkel et al. |
| 7,220,771 B2 | 5/2007 | Bhagwat et al. |
| 7,429,609 B2 | 9/2008 | Ohi et al. |
| 2002/0103229 A1 | 8/2002 | Bhagwat et al. |
| 2002/0198214 A1 | 12/2002 | Mavunkel et al. |
| 2003/0055068 A1 | 3/2003 | Bebbington et al. |
| 2003/0187026 A1 | 10/2003 | Li et al. |
| 2004/0077877 A1 | 4/2004 | Bhagwat et al. |
| 2004/0127536 A1 | 7/2004 | Bhagwat et al. |

(Continued)

FOREIGN PATENT DOCUMENTS

| | | |
|---|---|---|
| GB | 2 306 108 A | 4/1987 |
| GB | 2 323 845 A | 7/1998 |

(Continued)

OTHER PUBLICATIONS

Wolff, M.E., "Burger's Medicinal Chemistry", 5th Ed., Part 1, pp. 975-977 (1995).*
Banker et al., "Modern Pharmaceuticals", 3rd Ed., p. 596 (1996).*
Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.TheOncologist.com].*

(Continued)

*Primary Examiner* — Paul V. Ward
(74) *Attorney, Agent, or Firm* — Henry C. Jeanette; David A. Muthard

(57) ABSTRACT

Disclosed are the ERK inhibitors of formula 1.0:

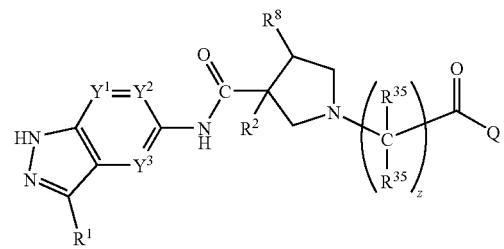

(1.0)

and the pharmaceutically acceptable salts, esters and solvates thereof. Q is a piperidine or piperazine ring that can have a bridge or a fused ring. The piperidine ring can have a double bond in the ring. All other substitutents are as defined herein. Also disclosed are methods of treating cancer using the compounds of formula 1.0.

76 Claims, No Drawings

(56) References Cited

U.S. PATENT DOCUMENTS

| | | |
|---|---|---|
| 2004/0127538 A1 | 7/2004 | Oinuma et al. |
| 2005/0009876 A1 | 1/2005 | Bhagwat et al. |
| 2005/0107386 A1 | 5/2005 | Narla et al. |
| 2005/0107457 A1 | 5/2005 | Bhagwat et al. |
| 2007/0060616 A1 | 3/2007 | Bennett et al. |
| 2007/0149484 A1 | 6/2007 | Claus et al. |
| 2007/0185112 A1 | 8/2007 | Mavunkel et al. |
| 2007/0191604 A1 | 8/2007 | Cooper et al. |
| 2007/0232610 A1 | 10/2007 | Deng et al. |
| 2007/0265333 A1 | 11/2007 | Fu et al. |
| 2008/0004287 A1 | 1/2008 | Ma et al. |
| 2008/0007509 A1 | 1/2008 | Lankhorst et al. |
| 2009/0011284 A1 | 1/2009 | Wang et al. |
| 2009/0062355 A1 | 3/2009 | Lizawa et al. |
| 2009/0118284 A1 | 5/2009 | Cooper et al. |

FOREIGN PATENT DOCUMENTS

| | | |
|---|---|---|
| GB | 2400101 A | 10/2004 |
| WO | WO 97/45412 A1 | 12/1997 |
| WO | WO 99/03498 A1 | 1/1999 |
| WO | WO 99/10325 | 3/1999 |
| WO | WO 01/56557 A2 | 8/2001 |
| WO | WO 01/57022 A2 | 8/2001 |
| WO | WO 01/68619 A1 | 9/2001 |
| WO | WO 01/72721 A2 | 10/2001 |
| WO | WO 02/10137 | 2/2002 |
| WO | WO 02/22604 | 3/2002 |
| WO | WO 02/22610 | 3/2002 |
| WO | WO02/46158 | 6/2002 |
| WO | WO 02/50065 | 6/2002 |
| WO | WO 02/064586 | 8/2002 |
| WO | WO 02/088090 | 11/2002 |
| WO | WO 02/088097 A1 | 11/2002 |
| WO | WO 03/011854 A1 | 2/2003 |
| WO | WO 03/011855 A2 | 2/2003 |
| WO | WO 03/035626 A2 | 5/2003 |
| WO | WO 03/091246 | 11/2003 |
| WO | WO 03/099212 A2 | 12/2003 |
| WO | WO 2004/026867 A2 | 4/2004 |
| WO | WO 2004/083203 A1 | 9/2004 |
| WO | WO 2005/002673 A1 | 1/2005 |
| WO | WO 2005/063258 A1 | 7/2005 |
| WO | WO 2005/100338 A1 | 10/2005 |
| WO | WO 2005/100342 | 10/2005 |
| WO | WO 2005/113541 | 12/2005 |
| WO | WO 2005/113546 A1 | 12/2005 |
| WO | WO 20061040569 A1 | 4/2006 |
| WO | WO 2006/071644 A1 | 7/2006 |
| WO | WO 2006/136008 A1 | 12/2006 |
| WO | WO 2007/044401 A2 | 4/2007 |
| WO | WO 2007/044420 A1 | 4/2007 |
| WO | WO 2007/070398 | 6/2007 |
| WO | WO 2007/097937 | 8/2007 |
| WO | WO 2008/121742 A2 | 10/2008 |
| WO | WO 2008/153858 | 12/2008 |
| WO | WO 2008/154241 A1 | 12/2008 |
| WO | WO 2008/156739 | 12/2008 |
| WO | WO 2009/105500 | 8/2009 |
| WO | 2011041152 A1 | 4/2011 |

OTHER PUBLICATIONS

PCT International Search Report for PCT Application No. PCT/US2008/007509 of the above identified application. Mailed date: Sep. 30, 2008.

PCT International Search Report for PCT Application No. PCT/US2006/046959 of the above identified application. Mailed date: May 18, 2007.

PCT International Search Report for PCT Application No. PCT/US2008/006979 of the above identified application. Mailed date: Oct. 8, 2008.

PCT International Search Report for PCT Application No. PCT/US2009/034447 of the above identified application. Mailed date: Jun. 10, 2009.

PCT International Search Report for PCT Application No. PCT/US2007/003665 of the above identified application. Mailed date: Jul. 9, 2007.

PCT International Search Report for PCT Application No. PCT/US2008/007509 (WO 2008/156739). Mailed date: Sep. 30, 2008.

PCT International Search Report for PCT Application No. PCT/US2006/046959 (WO 2007/070398) . Mailed date: May 18, 2007.

PCT International Search Report for PCT Application No. PCT/US2008/006979 (WO 2008/153858). Mailed date: Oct. 8, 2008.

PCT International Search Report for PCT Application No. PCT/US2009/034447 (WO 2009/105500). Mailed date: Jun. 10, 2009.

PCT International Search Report for PCT Application No. PCT/US2007/003665 (WO 2007/097937). Mailed date: Jul. 9, 2007.

* cited by examiner

COMPOUNDS THAT ARE ERK INHIBITORS

REFERENCE TO RELATED APPLICATIONS

This application is a Continuation-In-Part of U.S. application Ser. No. 11/636,954 filed Dec. 11, 2006, which in turn claims the benefit of Provisional Application Ser. No. 60/749,856 filed Dec. 13, 2005.

BACKGROUND

The processes involved in tumor growth, progression, and metastasis are mediated by signaling pathways that are activated in cancer cells. The ERK pathway plays a central role in regulating mammalian cell growth by relaying extracellular signals from ligand-bound cell surface tyrosine kinase receptors such as erbB family, PDGF, FGF, and VEGF receptor tyrosine kinase. Activation of the ERK pathway is via a cascade of phosphorylation events that begins with activation of Ras. Activation of Ras leads to the recruitment and activation of Raf, a serine-threonine kinase. Activated Raf then phosphorylates and activates MEK1/2, which then phosphorylates and activates ERK1/2. When activated, ERK1/2 phosphorylates several downstream targets involved in a multitude of cellular events including cytoskeletal changes and transcriptional activation. The ERK/MAPK pathway is one of the most important for cell proliferation, and it is believed that the ERK/MAPK pathway is frequently activated in many tumors. Ras genes, which are upstream of ERK1/2, are mutated in several cancers including colorectal, melanoma, breast and pancreatic tumors. The high Ras activity is accompanied by elevated ERK activity in many human tumors. In addition, mutations of BRAF, a serine-threonine kinase of the Raf family, are associated with increased kinase activity. Mutations in BRAF have been identified in melanomas (60%), thyroid cancers (greater than 40%) and colorectal cancers. These observations indicate that the ERK1/2 signalling pathway is an attractive pathway for anticancer therapies in a broad spectrum of human tumours.

Therefore, a welcome contribution to the art would be small-molecules (i.e., compounds) that inhibit ERK activity (i.e., ERK1 and ERK2 activity), which small-molecules would be useful for treating a broad spectrum of cancers, such as, for example, melanoma, pancreatic cancer, thyroid cancer, colorectal cancer, lung cancer, breast cancer, and ovarian cancer. Such a contribution is provided by this invention.

SUMMARY OF THE INVENTION

This invention provides compounds that inhibit the activity of ERK1 and/or the activity of ERK2.

The compounds of this invention also inhibit the phosphorylation of ERK1 and ERK2.

Thus, this invention provides compounds that are ERK inhibitors (i.e., ERK1 inhibitors and/or ERK2 inhibitors), said compounds being of the formula 1.0:

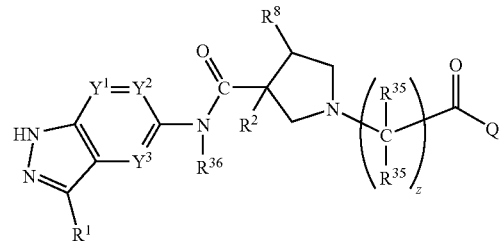

(1.0)

or the pharmaceutically acceptable salts, esters and solvates thereof, wherein:

$Y^1$, $Y^2$, and $Y^3$ are each independently selected from the group consisting of: C, N and substituted carbon;

Q is selected from the group consisting of: piperidinyl, piperazinyl, tetrahydropyridinyl (e.g., 1,2,3,6-tetrahydropyridinyl), bridged piperazinyl, bridged piperidinyl, bridged tetrahydropyridinyl, substituted piperidinyl, substituted piperazinyl, substituted tetrahydropyridinyl (e.g., a substituted 1,2,3,6-tetrahydro-pyridinyl), bridged substituted piperazinyl, bridged substituted piperidinyl, and bridged substituted tetrahydropyridinyl;

z is 1 to 3 (and preferably 1); and $R^1$, $R^2$, $R^8$, $R^{35}$ and $R^{36}$ are as defined below.

This invention provides compounds of formula 1.0 (for example, as described in any one of Embodiment Nos. 1 to 165) in pure or isolated form.

This invention provides compounds of formula 1.0 (for example, as described in any one of Embodiment Nos. 1 to 165) in pure form.

This invention provides compounds of formula 1.0 (for example, as described in any one of Embodiment Nos. 1 to 165) in isolated form.

This invention provides compounds of formula 1.0.

This invention provides pharmaceutically acceptable salts of the compounds of formula 1.0.

This invention provides pharmaceutically acceptable esters of the compounds of formula 1.0.

This invention provides solvates of the compounds of formula 1.0.

This invention provides the final compounds of Examples 1 to 827.

This invention also provides a pharmaceutical composition comprising an effective amount of at least one (e.g., 1, 2 or 3, 1 or 2, and usually 1) compound of formula 1.0 (for example, as described in any one of Embodiment Nos. 1 to 166) and a pharmaceutically acceptable carrier.

This invention also provides a pharmaceutical composition comprising an effective amount of at least one (e.g., 1, 2 or 3, 1 or 2, and usually 1) compound of formula 1.0 (for example, as described in any one of Embodiment Nos. 1 to 166) and an effective amount of at least one other (e.g., 1, 2 or 3, 1 or 2, and usually 1) pharmaceutically active ingredient (such as, for example, a chemotherapeutic agent), and a pharmaceutically acceptable carrier.

This invention also provides a method of inhibiting ERK (i.e., inhibiting the activity of ERK) in a patient in need of such treatment comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method of inhibiting ERK1 (i.e., inhibiting the activity of ERK1) in a patient in need of such treatment comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method of inhibiting ERK2 (i.e., inhibiting the activity of ERK2) in a patient in need of such treatment comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method of inhibiting ERK1 and ERK2 (i.e., inhibiting the activity of ERK1 and ERK2) in a patient in need of such treatment comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method of treating cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166) in combination with at least one (e.g., 1, 2 or 3, 1 or 2, and usually 1) signal transduction inhibitor.

This invention also provides a method of treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166) in combination with at least one (e.g., 1, 2 or 3, 1 or 2, and usually 1) signal transduction inhibitor.

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma, in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating lung cancer, pancreatic cancer, colon cancer (e.g., colorectal cancer), myeloid leukemias (e.g., AML, CML, and CMML), thyroid cancer, myelodysplastic syndrome (MDS), bladder carcinoma, epidermal carcinoma, melanoma, breast cancer, prostate cancer, head and neck cancers (e.g., squamous cell cancer of the head and neck), ovarian cancer, brain cancers (e.g., gliomas, such as glioma blastoma multiforme), cancers of mesenchymal origin (e.g., fibrosarcomas and rhabdomyosarcomas), sarcomas, tetracarcinomas, nuroblastomas, kidney carcinomas, hepatomas, non-Hodgkin's lymphoma, multiple myeloma, or anaplastic thyroid carcinoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), wherein said cancer is selected from the group consisting of: melanoma, pancreatic cancer, thyroid cancer, colorectal cancer, lung cancer, breast cancer, and ovarian cancer.

This invention also provides a method for treating cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent wherein said cancer is selected from the group consisting of: melanoma, pancreatic cancer, thyroid cancer, colorectal cancer, lung cancer, breast cancer, and ovarian cancer.

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), wherein said cancer is selected from the group consisting of: melanoma, pancreatic cancer, thyroid cancer, colorectal cancer, lung cancer, breast cancer, and ovarian cancer.

This invention also provides a method for treating cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent wherein said cancer is selected from the group consisting of: melanoma, pancreatic cancer, thyroid cancer, colorectal cancer, lung cancer, breast cancer, and ovarian cancer.

This invention also provides a method for treating melanoma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating melanoma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating melanoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating melanoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating pancreatic cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating pancreatic cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating pancreatic cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating pancreatic cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating thyroid cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating thyroid cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 1661), in combination with an effective amount of at least one (e.g., 1, 2 or 3, 1 or 2, or 1) chemotherapeutic agent.

This invention also provides a method for treating thyroid cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating thyroid cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating colorectal cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating colorectal cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating colorectal cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating colorectal cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating lung cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating lung cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating lung cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating lung cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating breast cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating breast cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating breast cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating breast cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating ovarian cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating ovarian cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating ovarian cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating ovarian cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides methods of treating breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 (for example, as described in any one of Embodiment Nos. 1 to 166) in combination with hormonal therapies (i.e., antihormonal agents).

This invention also provides methods of treating breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166) in combination with hormonal therapies (i.e., antihormonal agents).

This invention also provides methods of treating breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 (for example, as described in any one of Embodiment Nos. 1 to 166) in combination with hormonal therapies (i.e., antihormonal agents), and in combination with an effective amount of at least one (e.g., 1, 2 or 3, 1 or 2, or 1) chemotherapeutic agent.

This invention also provides methods of treating breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166) in combination with hormonal therapies (i.e., antihormonal agents), and in combination with an effective amount of at least one (e.g., 1, 2 or 3, 1 or 2, or 1) chemotherapeutic agent.

The methods of treating breast cancer described herein include the treatment of hormone-dependent metastatic and advanced breast cancer, adjuvant therapy for hormone-dependent primary and early breast cancer, the treatment of ductal carcinoma in situ, and the treatment of inflammatory breast cancer in situ.

The methods of treating hormone-dependent breast cancer can also be used to prevent breast cancer in patients having a high risk of developing breast cancer.

Thus, this invention also provides methods of preventing breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 (for example, as described in any one of Embodiment Nos. 1 to 166) in combination with hormonal therapies (i.e., antihormonal agents).

This invention also provides methods of preventing breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166) in combination with hormonal therapies (i.e., antihormonal agents).

This invention also provides methods of preventing breast cancer (i.e., post-menopausal and premenopausal breast cancer, e.g., hormone-dependent breast cancer) in a patient in need of such treatment, said treatment comprising the administration of an effective amount of at least one (e.g., 1, 2 or 3, 1 or 2, and usually 1) compound of formula 1.0 (for example, as described in any one of Embodiment Nos. 1 to 166) in combination with hormonal therapies (i.e., antihormonal agents), and in combination with an effective amount of at least one (e.g., 1, 2 or 3, 1 or 2, or 1) chemotherapeutic agent.

This invention also provides methods of preventing breast cancer (i.e., post-menopausal and premenopausal breast cancer, e.g., hormone-dependent breast cancer) in a patient in need of such treatment, said treatment comprising the administration of an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166) in combination with hormonal therapies (i.e., antihormonal agents), and in combination with an effective amount of at least one (e.g., 1, 2 or 3, 1 or 2, or 1) chemotherapeutic agent.

This invention also provides a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating brain cancer (e.g., glioma, such as glioma blastoma multiforme) a in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating brain cancer (e.g., glioma, such as glioma blastoma multiforme) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating brain cancer (e.g., glioma, such as glioma blastoma multiforme) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of a chemotherapeutic agent wherein said chemotherapeutic agent is temozolomide.

This invention also provides a method for treating brain cancer (e.g., glioma, such as glioma blastoma multiforme) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of a chemotherapeutic agent, wherein said chemotherapeutic agent is temozolomide.

This invention also provides a method for treating prostate cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating prostate cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating prostate cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating prostate cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating myelodysplastic syndrome in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating myelodysplastic syndrome in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating myelodysplastic syndrome in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating myelodysplastic syndrome in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating myeloid leukemias in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating acute myelogenous leukemia (AML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating acute myelogenous leukemia (AML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating acute myelogenous leukemia (AML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating acute myelogenous leukemia (AML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating chronic myelomonocytic leukemia (CMML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating chronic myelomonocytic leukemia (CMML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating chronic myelomonocytic leukemia (CMML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating chronic myelomonocytic leukemia (CMML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating chronic myelogenous leukemia (chronic myeloid leukemia, CML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating chronic myelogenous leukemia (chronic myeloid leukemia, CML) in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating chronic myelogenous leukemia (chronic myeloid leukemia, CML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating chronic myelogenous leukemia (chronic myeloid leukemia, CML) in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating myeloid leukemias in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating myeloid leukemias in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating bladder cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating bladder cancer in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating bladder cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating bladder cancer in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating non-Hodgkin's lymphoma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating non-Hodgkin's lymphoma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating non-Hodgkin's lymphoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating non-Hodgkin's lymphoma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating multiple myeloma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166).

This invention also provides a method for treating multiple myeloma in a patient in need of such treatment, said method comprising administering to said patient an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

This invention also provides a method for treating multiple myeloma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166).

This invention also provides a method for treating multiple myeloma in a patient in need of such treatment, said method comprising administering to said patient an effective amount of a pharmaceutical composition comprising an effective amount of at least one (e.g., 1, 2 or 3, 1 or 2, and usually 1) compound of formula 1.0 (for example, as described in any one of Embodiment Nos. 1 to 166), in combination with an effective amount of at least one (e.g., 1, 2 or 3, 1 or 2, or 1) chemotherapeutic agent.

In the methods of this invention the compounds of this invention can be administered concurrently or sequentially (i.e., consecutively) with the chemotherapeutic agents or the signal transduction inhibitor.

The methods of treating cancers described herein can optionally include the administration of an effective amount of radiation (i.e., the methods of treating cancers described herein optionally include the administration of radiation therapy).

DETAILED DESCRIPTION OF THE INVENTION

As described herein, unless otherwise indicated, the use of a drug or compound in a specified period is per treatment cycle. For example, once a day means once per day of each day of the treatment cycle. Twice a day means twice per day each day of the treatment cycle. Once a week means one time per week during the treatment cycle. Once every three weeks means once per three weeks during the treatment cycle.

The following abbreviations have the following meanings unless defined otherwise:

ACN Acetonitrile
AcOH Acetic acid
DAST (diethylamino)sulfur trifluoride
DCC Dicyclohexylcarbodiimide
DCU Dicyclohexylurea
DCM Dichloromethane
DI Deionized water
DIAD Diisopropylazodicarboxylate
DIEA Diisopropylethylamine
DMAP 4-Dimethylaminopyridine
DME Dimethoxyethane
DMF Dimethylformamide
DMFDMA N,N-Dimethylformamide dimethylacetal
DMSO Dimethyl sulfoxide
DTT Dithiothreitol
EDCl 1-(3-dimethylamino-propyl)-3-ethylcarbodiimide hydrochloride
EtOAc Ethyl acetate
EtOH Ethanol
HATU N,N,N',N'-Tetramethyl-O-(7-Azabenzotriazol-1-yl)Uronium hexafluorophosphate
Hex hexanes
HOBt 1-Hydroxylbenzotriazole
HPLC High pressure liquid chromatography
LCMS Liquid chromatography mass spectrometry
LDA Lithium diisopropylamide
mCPBA meta-Chloroperoxybenzoic acid
MeOH Methanol
MTT (3-[4,5-dimethyl-thiazol-2-yl]-2,5-diphenyltetrazolium bromide, Thiazolyl blue)
NMR Nuclear magnetic resonance
PFP Pentafluorophenol
PMB p-methoxybenzyl
Pyr Pyridine
Rb Round bottom flask
Rbt Round bottom flask
RT Room temperature
SEMCl 2-(Trimethylsily)ethoxy methyl chloride
TEA Triethylamine
Tr Triphenyl methane
Trt Triphenyl methane
TrCl Triphenyl methane chloride
TFA Trifluoroacetic acid
THF Tetrahydrofuran
TLC Thin layer chromatography
TMS Trimethylsilyl As used herein, unless otherwise specified, the following terms have the following meanings:

"anti-cancer agent" means a drug (medicament or pharmaceutically active ingredient) for treating cancer;

"antineoplastic agent" means a drug (medicament or pharmaceutically active ingredient) for treating cancer (i.e., a chemotherapeutic agent);

"at least one", as used in reference to the number of compounds of this invention means for example 1-6, generally 1-4, more generally 1, 2 or 3, and usually one or two, and more usually one;

"at least one", as used in reference to the number of chemotherapeutic agents used, means for example 1-6, generally 1-4, more generally 1, 2 or 3, and usually one or two, or one;

"chemotherapeutic agent" means a drug (medicament or pharmaceutically active ingredient) for treating cancer (i.e., and antineeoplastic agent);

"compound" with reference to the antineoplastic agents, includes the agents that are antibodies;

"concurrently" means (1) simultaneously in time (e.g., at the same time); or (2) at different times during the course of a common treatment schedule;

"consecutively" means one following the other;

"different" as used in the phrase "different antineoplastic agents" means that the agents are not the same compound or structure; preferably, "different" as used in the phrase "different antineoplastic agents" means not from the same class of antineoplastic agents; for example, one antineoplastic agent is a taxane, and another antineoplastic agent is a platinum coordinator compound;

"effective amount" or "therapeutically effective amount" is meant to describe an amount of compound or a composition of the present invention, or an amount of radiation, effective in treating or inhibiting the diseases or conditions described herein, and thus producing the desired therapeutic, ameliorative, inhibitory or preventative effect; thus, for example, in the methods of treating cancer described herein "effective amount" (or "therapeutically effective amount") means, for example, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor; for example, in the treatment of lung cancer (e.g., non small cell lung cancer) a therapeutically effective amount is that amount that alleviates or eliminates cough, shortness of breath and/or pain; also, for example, an effective amount, or a therapeutically effective amount of the ERK inhibitor (i.e., a compound of this invention) is that amount which results in the reduction in ERK (ERK1 and/or ERK2) activity and phosphorylation; the reduction in ERK activity may be determined by the analysis of pharmacodynamic markers such as phosphorylated RSK1,2 and phosphorylated ERK1,2, using techniques well known in the art;

"Ex" in the tables represents "Example";

"one or more" has the same meaning as "at least one";

"patient" means an animal, such as a mammal (e.g., a human being, and preferably a human being);

"prodrug" means compounds that are rapidly transformed, for example, by hydrolysis in blood, in vivo to the parent compound, i.e., to the compounds of formula 1.0 or to a salt and/or to a solvate thereof; a thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference; the scope of this invention includes Prodrugs of the novel compounds of this invention;

sequentially-represents (1) administration of one component of the method ((a) compound of the invention, or (b) chemotherapeutic agent, signal transduction inhibitor and/or radiation therapy) followed by administration of the other component or components; after administration of one component, the next component can be administered substantially immediately after the first component, or the next component can be administered after an effective time period after the first component; the effective time period is the amount of time given for realization of maximum benefit from the administration of the first component; and "solvate" means a physical association of a compound of this invention with one or more solvent molecules; this physical association involves varying degrees of ionic and covalent bonding, including hydrogen bonding; in certain instances the solvate will be capable of isolation, for example when one or more solvent molecules are incorporated in the crystal lattice of the crystalline solid; "solvate" encompasses both solution-phase and isolatable solvates; non-limiting examples of suitable solvates include ethanolates, methanolates, and the like; "hydrate" is a solvate wherein the solvent molecule is $H_2O$.

As used herein, unless otherwise specified, the following terms have the following meanings, and unless otherwise specified, the definitions of each term (i.e., moiety or substituent) apply when that term is used individually or as a component of another term (e.g., the definition of aryl is the same for aryl and for the aryl portion of arylalkyl, alkylaryl, arylalkynyl, and the like):

"acyl" means an H—C(O)—, alkyl-C(O)—, alkenyl-C(O)—, Alkynyl-C(O)—, cycloalkyl-C(O)—, cycloalkenyl-C(O)—, or cycloalkynyl-C(O)— group in which the various groups are as defined below (and as defined below, the alkyl, alkenyl, alkynyl, cycloalkyl, cycloalkenyl and cycloalkynyl moieties can be substituted); the bond to the parent moiety is through the carbonyl; preferred acyls contain a lower alkyl; Non-limiting examples of suitable acyl groups include formyl, acetyl, propanoyl, 2-methylpropanoyl, butanoyl and cyclohexanoyl;

"alkenyl" means an aliphatic hydrocarbon group (chain) comprising at least one carbon to carbon double bond, wherein the chain can be straight or branched, and wherein said group comprises about 2 to about 15 carbon atoms; Preferred alkenyl groups comprise about 2 to about 12 carbon atoms in the chain; and more preferably about 2 to about 6 carbon atoms in the chain; branched means that one or more lower alkyl groups, such as methyl, ethyl or propyl, or alkenyl groups are attached to a linear alkenyl chain; "lower alkenyl" means an alkenyl group comprising about 2 to about 6 carbon atoms in the chain, and the chain can be straight or branched; the term "substituted alkenyl" means that the alkenyl group is substituted by one or more independently selected substituents, and each substituent is independently selected from the group consisting of: halo, alkyl, aryl, cycloalkyl, cyano, alkoxy and —S(alkyl); non-limiting examples of suitable alkenyl groups include ethenyl, propenyl, n-butenyl, 3-methylbut-2-enyl, n-pentenyl, octenyl and decenyl;

"alkoxy" means an alkyl-O— group (i.e., the bond to the parent moiety is through the ether oxygen) in which the alkyl group is unsubstituted or substituted as described below; non-limiting examples of suitable alkoxy groups include methoxy, ethoxy, n-propoxy, isopropoxy, n-butoxy and heptoxy;

"alkoxycarbonyl" means an alkyl-O—CO— group (i.e., the bond to the parent moiety is through the carbonyl) wherein the alkyl group is unsubstituted or substituted as previously defined; non-limiting examples of suitable alkoxycarbonyl groups include methoxycarbonyl and ethoxycarbonyl;

"alkyl" (including the alkyl portions of other moieties, such as trifluoroalkyl and alkyloxy) means an aliphatic hydrocarbon group (chain) that can be straight or branched wherein said group comprises about 1 to about 20 carbon atoms in the chain; preferred alkyl groups comprise about 1 to about 12 carbon atoms in the chain; more preferred alkyl groups comprise about 1 to about 6 carbon atoms in the chain; branched means that one or more lower alkyl groups, such as methyl, ethyl or propyl, are attached to a linear alkyl chain; "lower alkyl" means a group comprising about 1 to about 6 carbon atoms in the chain, and said chain can be straight or branched; the term "substituted alkyl" means that the alkyl group is substituted by one or more independently selected substituents, and wherein each substituent is independently selected from the group consisting of: halo, aryl, cycloalkyl, cyano, hydroxy, alkoxy, alkylthio, amino, —NH(alkyl), —NH(cycloalkyl), —N(alkyl)$_2$, carboxy, —C(O)O-alkyl and —S(alkyl); non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl;

"alkylaryl" (or alkaryl) means an alkyl-aryl-group (i.e., the bond to the parent moiety is through the aryl group) wherein the alkyl group is unsubstituted or substituted as defined above, and the aryl group is unsubstituted or substituted as defined below; preferred alkylaryls comprise a lower alkyl group; non-limiting examples of suitable alkylaryl groups include o-tolyl, p-tolyl and xylyl;

"alkylheteroaryl" means an alkyl-heteroaryl-group (i.e., the bond to the parent moiety is through the heteroaryl group) wherein the alkyl is unsubstituted or substituted as defined above and the heteroaryl group is unsubstituted or substituted as defined below;

"alkylsulfinyl" means an alkyl-S(O)— group (i.e., the bond to the parent moiety is through the sulfinyl) wherein the alkyl group is unsubstituted or substituted as previously defined; preferred groups are those in which the alkyl group is lower alkyl;

"alkylsulfonyl" means an alkyl-S($O_2$)— group (i.e., the bond to the parent moiety is through the sulfonyl) wherein the alkyl group is unsubstituted or substituted as previously defined; preferred groups are those in which the alkyl group is lower alkyl;

"alkylthio" means an alkyl-S— group (i.e., the bond to the parent moiety is through the sulfur) wherein the alkyl group is unsubstituted or substituted as previously described; non-limiting examples of suitable alkylthio groups include methylthio, ethylthio, i-propylthio and heptylthio;

"alkynyl" means an aliphatic hydrocarbon group (chain) comprising at least one carbon to carbon triple bond, wherein the chain can be straight or branched, and wherein the group comprises about 2 to about 15 carbon atoms in the; preferred alkynyl groups comprise about 2 to about 12 carbon atoms in the chain; and more preferably about 2 to about 4 carbon atoms in the chain; Branched means that one or more lower alkyl groups, such as methyl, ethyl or propyl, are attached to a linear alkynyl chain; "lower alkynyl" means an alkynyl group comprising about 2 to about 6 carbon atoms in the chain, and the chain can be straight or branched; non-limiting examples of suitable alkynyl groups include ethynyl, propynyl, 2-butynyl, 3-methylbutynyl, n-pentynyl, and decynyl; the term "substituted alkynyl" means that the alkynyl group is substituted by one or more independently selected, and each substituent is independently selected from the group consisting of alkyl; aryl and cycloalkyl;

"amino means a —$NH_2$ group;

"aralkenyl" (or arylalkenyl) means an aryl-alkenyl-group (i.e., the bond to the parent moiety is through the alkenyl group) wherein the aryl group is unsubstituted or substituted as defined below, and the alkenyl group is unsubstituted or substituted as defined above; preferred aralkenyls contain a lower alkenyl group; non-limiting examples of suitable aralkenyl groups include 2-phenethenyl and 2-naphthylethenyl;

"aralkyl" (or arylalkyl) means an aryl-alkyl-group (i.e., the bond to the parent moiety is through the alkyl group) wherein the aryl is unsubstituted or substituted as defined below and the alkyl is unsubstituted or substituted as defined above; preferred aralkyls comprise a lower alkyl group; non-limiting examples of suitable aralkyl groups include benzyl, 2-phenethyl and naphthalenylmethyl;

"aralkyloxy" (or arylalkyloxy) means an aralkyl-O— group (i.e., the bond to the parent moiety is through the ether oxygen) wherein the aralkyl group is unsubstituted or substituted as previously described; non-limiting examples of suitable aralkyloxy groups include benzyloxy and 1- or 2-naphthalenemethoxy;

"aralkoxycarbonyl" means an aralkyl-O—C(O)— group (i.e., the bond to the parent moiety is through the carbonyl) wherein the aralkyl group is unsubstituted or substituted as previously defined; a non-limiting example of a suitable aralkoxycarbonyl group is benzyloxycarbonyl;

"aralkylthio" means an aralkyl-S— group (i.e., the bond to the parent moiety is through the sulfur) wherein the aralkyl group is unsubstituted or substituted as previously described; a non-limiting example of a suitable aralkylthio group is benzylthio;

"aroyl" means an aryl-C(O)— group (i.e., the bond to the parent moiety is through the carbonyl) wherein the aryl group is unsubstituted or substituted as defined below; non-limiting examples of suitable groups include benzoyl and 1- and 2-naphthoyl;

"aryl" (sometimes abbreviated "ar") means an aromatic monocyclic or multicyclic ring system comprising about 6 to about 14 carbon atoms, preferably about 6 to about 10 carbon atoms; the aryl group can be optionally substituted with one or more independently selected "ring system substituents" (defined below). Non-limiting examples of suitable aryl groups include phenyl and naphthyl;

"arylalkynyl" means an aryl-alkynyl-group (i.e., the bond to the parent moiety is through the alkynyl group) wherein the aryl group is unsubstituted or substituted as defined above, and the alkynyl group is unsubstituted or substituted as defined above;

"arylaminoheteroaryl" means an aryl-amino-heteroaryl group (i.e., the bond to the parent moiety is through the heteroaryl group) wherein the aryl group is unsubstituted or substituted as defined above, the amino group is as defined above (i.e., a —NH— here), and the heteroaryl group is unsubstituted or substituted as defined below;

"arylheteroaryl" means an aryl-heteroaryl group- (i.e., the bond to the parent moiety is through the heteroaryl group) wherein the aryl group is unsubstituted or substituted as defined above, and the heteroaryl group is unsubstituted or substituted as defined below;

"aryloxy" means an aryl-O— group (i.e., the bond to the parent moiety is through the ether oxygen) wherein the aryl group is unsubstituted or substituted as defined above; non-limiting examples of suitable aryloxy groups include phenoxy and naphthoxy;

"aryloxycarbonyl" means an aryl-O—C(O)— group (i.e., the bond to the parent moiety is through the carbonyl) wherein the aryl group is unsubstituted or substituted as previously defined; non-limiting examples of suitable aryloxycarbonyl groups include phenoxycarbonyl and naphthoxycarbonyl;

"arylsulfinyl" means an aryl-S(O)— group (i.e., the bond to the parent moiety is through the sulfinyl) wherein aryl is unsubstituted or substituted as previously defined;

"arylsulfonyl" means an aryl-S($O_2$)— group (i.e., the bond to the parent moiety is through the sulfonyl) wherein aryl is unsubstituted or substituted as previously defined;

"arylthio" means an aryl-S— group (i.e., the bond to the parent moiety is through the sulfur) wherein the aryl group is unsubstituted or substituted as previously described; non-limiting examples of suitable arylthio groups include phenylthio and naphthylthio;

"cycloalkenyl" means a non-aromatic mono or multicyclic ring system comprising about 3 to about 10 carbon atoms, preferably about 5 to about 10 carbon atoms that contains at least one carbon-carbon double bond; preferred cycloalkenyl rings contain about 5 to about 7 ring atoms; the cycloalkenyl can be optionally substituted with one or more independently selected "ring system substituents" (defined below); Non-limiting examples of suitable monocyclic cycloalkenyls include cyclopentenyl, cyclohexenyl, cycloheptenyl, and the like; a non-limiting example of a suitable multicyclic cycloalkenyl is norbornylenyl;

"cycloalkyl" means a non-aromatic mono- or multicyclic ring system comprising about 3 to about 7 carbon atoms, preferably about 3 to about 6 carbon atoms; the cycloalkyl can be optionally substituted with one or more independently selected "ring system substituents" (defined below); non-limiting examples of suitable monocyclic cycloalkyls include cyclopropyl, cyclopentyl, cyclohexyl, cycloheptyl and the like; non-limiting examples of suitable multicyclic cycloalkyls include 1-decalin, norbornyl, adamantyl and the like;

"cycloalkylalkyl" means a cycloalkyl-alkyl-group (i.e., the bond to the parent moiety is through the alkyl group) wherein the cycloalkyl moiety is unsubstituted or substituted as defined above, and the alkyl moiety is unsubstituted or substituted as defined above;

"halo" means fluoro, chloro, bromo, or iodo groups; preferred halos are fluoro, chloro or bromo, and more preferred are fluoro and chloro;

"halogen" means fluorine, chlorine, bromine, or iodine; preferred halogens are fluorine, chlorine and bromine;

"haloalkyl" means an alkyl, as defined above, wherein one or more hydrogen atoms on the alkyl is replaced by a halo group, as defined above;

"heteroaralkenyl" means a heteroaryl-alkenyl-group (i.e., the bond to the parent moiety is through the alkenyl group) wherein the heteroaryl group is unsubstituted or substituted as defined below, and the alkenyl group is unsubstituted or substituted as defined above;

"heteroaralkyl" (or heteroarylalkyl) means a heteroaryl-alkyl-group (i.e., the bond to the parent moiety is through the alkyl group) in which the heteroaryl is unsubstituted or substituted as defined below, and the alkyl group is unsubstituted or substituted as defined above; preferred heteroaralkyls comprise an alkyl group that is a lower alkyl group; non-limiting examples of suitable aralkyl groups include pyridylmethyl, 2-(furan-3-yl)ethyl and quinolin-3-ylmethyl;

"heteroaralkylthio" means a heteroaralkyl-S— group wherein the heteroaralkyl group is unsubstituted or substituted as defined above;

"heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination; preferred heteroaryls comprise about 5 to about 6 ring atoms; the "heteroaryl" can be optionally substituted by one or more independently selected "ring system substituents" (defined below); the prefix aza, oxa or thia before the heteroaryl root name means that at least a nitrogen, oxygen or sulfur atom, respectively, is present as a ring atom; a nitrogen atom of a heteroaryl can be optionally oxidized to the corresponding N-oxide; non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl, fluoropyridine

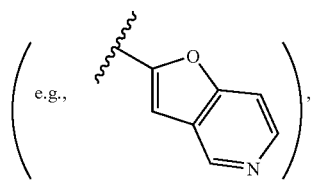

and the like;

"heteroarylalkynyl" (or heteroaralkynyl) means a heteroaryl-alkynyl-group (i.e., the bond to the parent moiety is through the alkynyl group) wherein the heteroaryl group is unsubstituted or substituted as defined above, and the alkynyl group is unsubstituted or substituted as defined above;

"heteroarylaryl" (or heteroararyl) means a heteroaryl-aryl-group (i.e., the bond to the parent moiety is through the aryl group) wherein the heteroaryl group is unsubstituted or substituted as defined above, and the aryl group is unsubstituted or substituted as defined above;

"heteroarylheteroarylaryl" means a heteroaryl-heteroaryl-group (i.e., the bond to the parent moiety is through the last heteroaryl group) wherein each heteroaryl group is independently unsubstituted or substituted as defined above;

"heteroarylsulfinyl" means a heteroaryl-SO— group wherein the heteroaryl group is unsubstituted or substituted as defined above;

"heteroarylsulfonyl" means a heteroaryl-SO$_2$— group wherein the heteroaryl group is unsubstituted or substituted as defined above;

"heteroarylthio" means a heteroaryl-S— group wherein the heteroaryl group is unsubstituted or substituted as defined above;

"heterocyclenyl" (or heterocycloalkenyl) means a non-aromatic monocyclic or multicyclic ring system comprising about 3 to about 10 ring atoms, preferably about 5 to about 10 ring atoms, in which one or more of the atoms in the ring system is an element other than carbon (for example one or more heteroatoms independently selected from the group consisting of nitrogen, oxygen and sulfur atom), and which contains at least one carbon-carbon double bond or carbon-nitrogen double bond; there are no adjacent oxygen and/or sulfur atoms present in the ring system; Preferred heterocyclenyl rings contain about 5 to about 6 ring atoms; the prefix aza, oxa or thia before the heterocyclenyl root name means that at least a nitrogen, oxygen or sulfur atom, respectively, is present as a ring atom; the heterocyclenyl can be optionally substituted by one or more independently selected "Ring system substituents" (defined below); the nitrogen or sulfur atom of the heterocyclenyl can be optionally oxidized to the corresponding N-oxide, S-oxide or S,S-dioxide; non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, and the like; Non-limiting examples of suitable oxaheterocyclenyl groups include 3,4-dihydro-2H-pyran, dihydrofuranyl, fluorodihydrofuranyl, and the like; A non-limiting example of a suitable multicyclic oxaheterocyclenyl group is 7-oxabicyclo[2.2.1]heptenyl; non-limiting examples of suitable monocyclic thiaheterocyclenyl rings include dihydrothiophenyl, dihydrothiopyranyl, and the like;

"heterocycloalkylalkyl" (or heterocyclylalkyl) means a heterocycloalkyl-alkyl-group (i.e., the bond to the parent moiety is through the alkyl group) wherein the heterocycloalkyl group (i.e., the heterocyclyl group) is unsubstituted or substituted as defined below, and the alkyl group is unsubstituted or substituted as defined above;

"heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination; there are no adjacent oxygen and/or sulfur atoms present in the ring system; preferred heterocyclyls contain about 5 to about 6 ring atoms; the prefix aza, oxa or thia before the heterocyclyl root name means that at least a nitrogen, oxygen or sulfur atom respectively is present as a ring atom; the heterocyclyl can be optionally substituted by one or more independently selected "ring system substituents" (defined below); the nitrogen or sulfur atom of the heterocyclyl can be optionally oxidized to the corresponding N-oxide, S-oxide or S,S-dioxide; non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like;

"hydroxyalkyl" means a HO-alkyl-group wherein the alkyl group is substituted or unsubstituted as defined above; preferred hydroxyalkyls comprise a lower alkyl; Non-limiting examples of suitable hydroxyalkyl groups include hydroxymethyl and 2-hydroxyethyl; and "ring system substituent" means a substituent attached to an aromatic or non-aromatic ring system that, for example, replaces an available hydrogen on the ring system; ring system substituents are each independently selected from the group consisting of: alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $R^{60}R^{65}N-$, $R^{60}R^{65}N$-alkyl-, $R^{60}R^{65}NC(O)-$ and $R^{60}R^{65}NSO_2-$, wherein $R^{60}$ and $R^{65}$ are each independently selected from the group consisting of: hydrogen, alkyl, aryl, and aralkyl; "Ring system substituent" also means a cyclic ring of 3 to 7 ring atoms, wherein 1-2 ring atoms can be heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring; Non-limiting examples include:

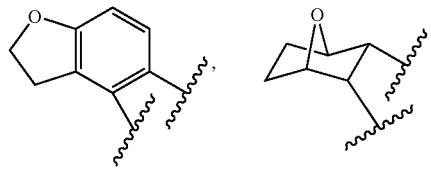 [SMILES: *c1ccc2c(c1*)CCO2 ; *C1C2CCC(O2)C1*]

and the like.

Lines drawn into a ring mean that the indicated bond may be attached to any of the substitutable ring carbon atoms.

Any carbon or heteroatom with unsatisfied valences in the text, schemes, examples, structural formulae, and any Tables herein is assumed to have the hydrogen atom or atoms to satisfy the valences.

One or more compounds of the invention may also exist as, or optionally converted to, a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, capsules, pills and the like. Similarly, the herein-described methods of treating a patient by administering a pharmaceutical composition of the present invention is also intended to encompass the administration of the afore-said bulk composition and individual dosage units.

Prodrugs of the compounds of the invention are also contemplated herein. The term "prodrug", as employed herein, denotes a compound that is a drug precursor which, upon administration to a subject, undergoes chemical conversion by metabolic or chemical processes to yield a compound of formula 1.0 or a salt and/or solvate thereof. A discussion of prodrugs is provided in T. Higuchi and V. Stella, *Prodrugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of formula 1.0, or a pharmaceutically acceptable salt, hydrate or solvate of the compound, contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxy-methyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxy-carbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino $(C_2-C_3)$alkyl, and the like.

Similarly, if a compound of formula 1.0 contains an alcohol functional group, a prodrug can be formed by the replacement of the hydrogen atom of the alcohol group with a group such as, for example, $(C_1-C_6)$alkanoyloxymethyl, 1-(($C_1-C_6$)alkanoyl-oxy)ethyl, 1-methyl-1-(($C_1-C_6$)alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate), and the like.

If a compound of formula 1.0 incorporates an amine functional group, a prodrug can be formed by the replacement of a hydrogen atom in the amine group with a group such as, for example, $R^{70}$-carbonyl, $R^{70}$O-carbonyl, $NR^{70}R^{75}$-carbonyl where $R^{70}$ and $R^{75}$ are each independently $(C_1-C_{10})$alkyl, $(C_3-C_7)$cycloalkyl, benzyl, or $R^{70}$-carbonyl is a natural α-aminoacyl or natural α-aminoacyl, —$C(OH)C(O)OY^{80}$ wherein $Y^{80}$ is H, $(C_1-C_6)$alkyl or benzyl, —$C(OY^{82})Y^{84}$ wherein $Y^{82}$ is $(C_1-C_4)$alkyl and $Y^{84}$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —$C(Y^{86})Y^{88}$ wherein $Y^{86}$ is H or methyl and $Y^{88}$ is mono-N- or di-N,N-$(C_1-C_6)$alkylamino morpholino, piperidin-1-yl or pyrrolidin-1-yl, and the like.

This invention also includes the compounds of this invention in isolated and purified form.

Polymorphic forms of the compounds of formula 1.0, and of the salts, solvates and prodrugs of the compounds of formula 1.0, are intended to be included in the present invention.

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

The compounds of formula 1.0 form salts that are also within the scope of this invention. Reference to a compound of formula 1.0 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula 1.0 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable salts) are preferred. Salts of the compounds of the formula 1.0 may be formed, for example, by reacting a compound of formula 1.0 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylenediamine), N-methyl-D-glucamines, N-methyl-D-glucamides, t-butyl amines, piperazine, phenylcyclohexyl-amine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid and base salts are intended to be pharmaceutically acceptable salts within the scope of the invention and all acid and base salts are considered equivalent to the free forms of the corresponding compounds for purposes of the invention.

Compounds of formula 1.0, and salts, solvates and prodrugs thereof, may exist in their tautomeric form (for example, as an amide or imino ether). All such tautomeric forms are contemplated herein as part of the present invention.

In hetero-atom containing ring systems of this invention, there are no hydroxyl groups on carbon atoms adjacent to a N, O or S, and there are no N or S groups on carbon adjacent to another heteroatom. Thus, for example, in the ring:

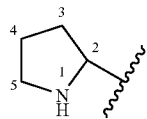

there is no —OH attached directly to carbons marked 2 and 5.

The compounds of formula 1.0 may exist in different tautomeric forms, and all such forms are embraced within the scope of the invention. Also, for example, all keto-enol and imine-enamine forms of the compounds are included in the invention.

Tautomeric forms such as, for example, the moieties:

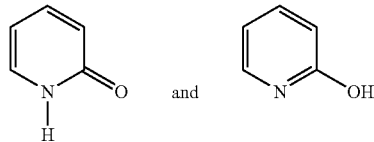 [SMILES: O=c1cccc[nH]1 ; "and" ; Oc1ccccn1]

are considered equivalent in certain embodiments of this invention.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^3$, etc.) occurs more than one time in any moiety or in any compound of formula 1.0, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of formula 1.0 (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of formula 1.0 can generally be prepared by following procedures analogous to those disclosed in the Schemes and/or in the Examples hereinbelow, by substituting an appropriate isotopically labelled reagent for a non-isotopically labelled reagent.

This invention provides compounds of formula 1.0:
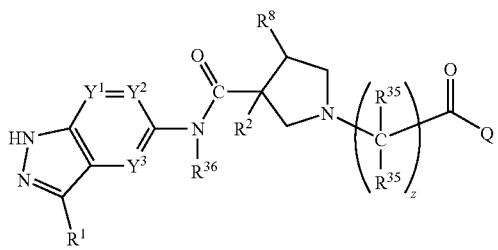
(1.0)
or the pharmaceutically acceptable salts, esters or solvates thereof, wherein:
$Y^1$, $Y^2$, and $Y^3$ are each independently selected from the group consisting of: —CH=, —N= and —CR$^9$= (preferably $Y^1$, $Y^2$, and $Y^3$ are each —CH=);
z is 1 to 3 (i.e., 1, 2 or 3, and preferably 1);
Q is a substituent selected from the group consisting of:

(2.1)
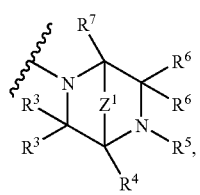
(2.2)

(2.3)
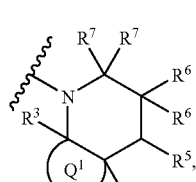
(2.4)
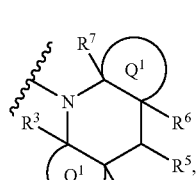
(2.5)
(2.6)
(2.7)
(2.8)
(2.9)
(2.10)
(2.11)
(2.12)
(2.13)
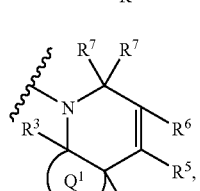
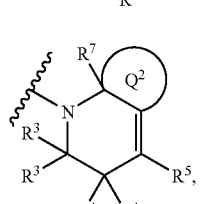
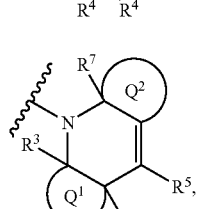

-continued (2.14) 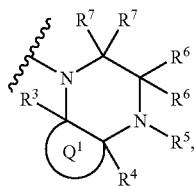

(2.15) 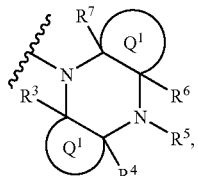

(2.16) 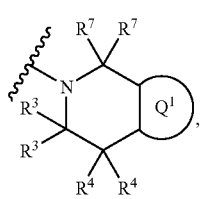

(2.17) 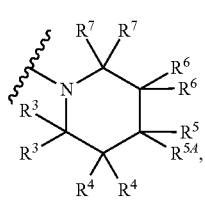

(2.18) 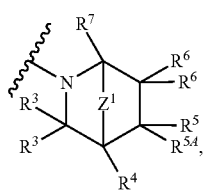

(2.19) 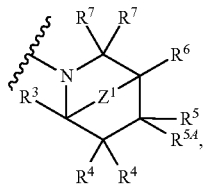

(2.20) 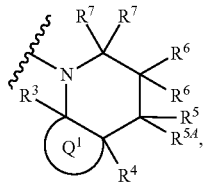

(2.21) 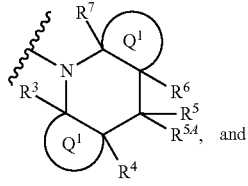 and

-continued (2.22) 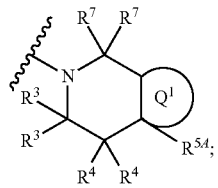

Each $Q^1$ represents a ring independently selected from the group consisting of: cycloalkyl, substituted cycloalkyl, heterocycloalkyl, substituted heterocycloalkyl, aryl, substituted aryl, heteroaryl, and substituted heteroaryl, wherein said substituted rings are substituted with 1 to 3 substituents independently selected from the group consisting of: halo (e.g., Cl, F, Br) and the $R^{10}$ moieties; provided that when $Q^1$ is aryl, heteroaryl, substituted aryl or substituted heteroaryl then the carbon atoms at the ring junction (i.e., the two carbon atoms common to the fused rings) are not substituted;

$Q^2$ represents a ring selected from the group consisting of: cycloalkyl, substituted cycloalkyl, heterocycloalkyl, and substituted heterocycloalkyl, wherein said substituted rings are substituted with 1 to 3 substituents independently selected from the group consisting of: the $R^{10}$ moieties;

$Z^1$ represents —$(C(R^{24})_2)_w$— wherein each $R^{24}$ is independently selected from the group consisting of: H, alkyl (e.g., $C_1$ to $C_6$ alkyl, for example methyl) and F, and wherein w is 1, 2 or 3, and generally w is 1 or 2, and usually w is 1, and wherein in one example each $R^{24}$ is H, and in another example w is 1, and in another example each $R^{24}$ is H and w is 1, preferably w is 1 and each $R^{24}$ is H (i.e., preferably $Z^1$ is —$CH_2$—);

$Z^2$ is selected from the group consisting of: —$N(R^{44})$—, —O— and —$C(R^{46})_2$— (e.g., $Z^2$ is —NH—, —O— or —$CH_2$—);

m is 1 to 6;
n is 1 to 6;
p is 0 to 6;
t is 0, 1, or 2;
$R^1$ is selected from the group consisting of:
(1) —CN,
(2) —$NO_2$,
(3) —$OR^{10}$,
(4) —$SR^{10}$,
(5) —$N(R^{10})_2$,
(6) $R^{10}$,
(7) —$C(O)R^{10}$ (in one example $R^{10}$ is a 4 to 6 membered heterocycloalkyl ring, in another example $R^{10}$ is a 4 to 6 membered heterocycloalkyl ring comprising one nitrogen atom, and in another example $R^{10}$ is a 4 to 6 membered heterocycloalkyl ring comprising one nitrogen atom wherein said ring is bound to the carbonyl moiety (—C(O)—) through the ring nitrogen),
(8) —$(C(R^{30})_2)_n$—$NR^{32}$—C(O)—$R^{10}$ (e.g., —$(CH_2)_n$—NH—C(O)—$R^{10}$, for example wherein n is 1), wherein in one example n is 1, each $R^{30}$ is H, $R^{32}$ is H, and $R^{10}$ is selected from the group consisting of: cycloalkyl (e.g., cyclopropyl) and alkyl (e.g., methyl and i-propyl), and wherein in another example n is 1, each $R^{30}$ is H, $R^{32}$ is H, and $R^{10}$ is selected from the group consisting of: methyl, i-propyl and cyclopropyl,
(9) —$(C(R^{30})_2)_n$—$NR^{32}$—S(O)$_t$—$R^{10}$ (e.g., —$(CH_2)_n$—NH—S(O)$_t$—$R^{10}$, for example wherein n is 1 and t is 2) wherein in one example n is 1, each $R^{30}$ is H, $R^{32}$ is H, t is 2, and $R^{10}$ is selected from the group consisting of:

cycloalkyl (e.g., cyclopropyl) and alkyl (e.g., methyl and i-propyl), and wherein in another example n is 1, each $R^{30}$ is H, $R^{32}$ is H, t is 2, $R^{10}$ is selected from the group consisting of: methyl, i-propyl and cyclopropyl, and wherein in another example n is 1, each $R^{30}$ is H, $R^{32}$ is H, t is 2, and $R^{10}$ is methyl,

(10) —$(C(R^{30})_2)$—$NR^{32}$—C(O)—$N(R^{32})$—$R^{10}$ (e.g., —$(CH_2)_n$—NH—C(O)—NH—$R^{10}$, for example wherein n is 1) wherein in one example n is 1, each $R^{30}$ is H, each $R^{32}$ is H, and $R^{10}$ is alkyl (e.g., methyl and i-propyl), and wherein in another example n is 1, each $R^{30}$ is H, each $R^{32}$ is H, and $R^{10}$ is selected from the group consisting of: methyl and i-propyl, (11)

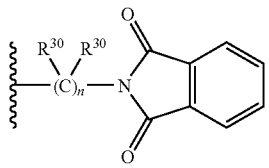

wherein in one example n is 1 and each $R^{30}$ is H, i.e., a moiety of the formula:

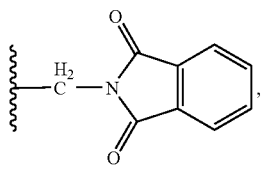 [SMILES: *CN1C(=O)c2ccccc2C1=O ; ","]

(12) —$CF_3$,

(13) —$C(O)OR^{10}$ wherein in one example $R^{10}$ is selected from the group consisting of: H, alkyl (e.g., methyl and isopropyl) and cyclopropyl (e.g., cyclopropyl), and wherein in another example $R^{10}$ is selected from the group consisting of: H and alkyl, and wherein in another example $R^{10}$ is selected from the group consisting of: H and methyl,

(14) —$(C(R^{30})_2)_n R^{13}$ (e.g., —$(CH_2)_n R^{13}$) wherein in one example n is 1, each $R^{30}$ is H, and $R^{13}$ is selected from the group consisting of: —OH and —$N(R^{10})_2$, wherein each $R^{10}$ is independently selected, and wherein in another example n is 1, each $R^{30}$ is H, and $R^{13}$ is selected from the group consisting of: —OH and —$N(R^{10})_2$, and each $R^{10}$ is H (i.e., $R^{13}$ is —OH or —$NH_2$),

(15) alkenyl (e.g., —CH=$CHCH_3$),

(16) —$NR^{32}$—C(O)—$R^{14}$ (e.g., —NH—C(O)—$R^{14}$) wherein in one example $R^{32}$ is H and $R^{14}$ is selected from the group consisting of: cycloalkyl (e.g., cyclopropyl), alkyl (e.g., methyl and propyl), aryl (e.g., phenyl), amino (i.e., —$NH_2$), and heteroaryl (e.g., pyridyl, such as, for example 2-pyridyl, 3-pyridyl, 4-pyridyl, pyrazolyl and imidazolyl), and wherein in another example $R^{32}$ is H and $R^{14}$ is selected from the group consisting of: cyclopropyl, methyl, propyl, phenyl, and amino, (17)

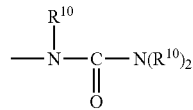

wherein each $R^{10}$ is independently selected, for example:
(a) in one example moiety (20) is:

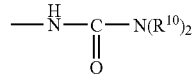

wherein each $R^{10}$ is independently selected,
(b) in another example moiety (20) is:

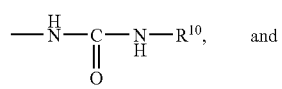 and (c) in another example moiety (20) is:

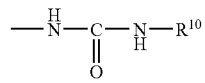

wherein $R^{10}$ is selected from the group consisting of: aryl (e.g., phenyl) and alkyl (e.g., ethyl, and preferably $R^{10}$ is phenyl or ethyl, (18)

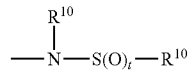

wherein each $R^{10}$ is independently selected, and wherein in one example each $R^{10}$ is independently selected and t is 2, and wherein in another example moiety (18) is —NH—$S(O)_t$—$R^{10}$, and wherein in another example moiety (18) is —NH—$S(O)_t$—$R^{10}$ wherein t is 2, and wherein in another example moiety (18) is —NH—$S(O)_t$—$R^{10}$. t is 2, and $R^{10}$ is alkyl (e.g., methyl), (19)

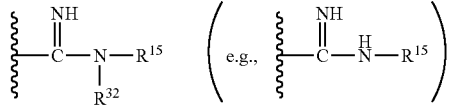

(also written as —$C(NH)N(R^{15})R^{32}$ and —$C(NH)NH(R^{15})$, respectively), wherein in one example $R^{15}$ is —OH, and in another example $R^{32}$ is H and $R^{15}$ is —OH,

(20) —C(O)—$NR^{32}$—$(C(R^{30})_2)_p$—$OR^{10}$ (e.g., —C(O)—NH—$(CH_2)_p$—$OR^{10}$, and, for example, —C(O)—NH—$(CH_2)_p$—$OR^{10}$ wherein p is 2) wherein:
(a) in one example p is 2,
(b) in another example $R^{32}$ is H, (c) in another example $R^{10}$ is selected from the group consisting of: H and alkyl (e.g., methyl),
(d) in another example $R^{10}$ is selected from the group consisting of: H and alkyl (e.g., methyl), and $R^{32}$ is H,
(e) in another example $R^{10}$ is selected from the group consisting of: H and alkyl (e.g., methyl), $R^{32}$ is H, an p is 2,
(f) in another example $R^{32}$ is H, each $R^{30}$ is H, and $R^{10}$ is alkyl,
(g) in another example $R^{32}$ is H, each $R^{30}$ is H, and $R^{10}$ is methyl,
(h) in another example $R^{32}$ is H, each $R^{30}$ is H, p is 2 and $R^{10}$ is alkyl, and
(i) in another example $R^{32}$ is H, each $R^{30}$ is H, p is 2 and $R^{10}$ is methyl,

(21) —C(O)N($R^{10}$)$_2$ wherein each $R^{10}$ is independently selected, and preferably each $R^{10}$ is independently selected from the group consisting of: (a) H, (b) alkyl (e.g., methyl, butyl, and i-propyl), (c) heteroaryl (e.g., pyridyl), (d) aryl (e.g., phenyl), and (e) cycloalkyl (e.g., cyclopropyl), wherein for example, each $R^{10}$ is selected from the group consisting of: H, methyl, butyl, i-propyl, pyridyl, phenyl and cyclopropyl, wherein, for example, said —C(O)N($R^{10}$)$_2$ moiety is selected from the group consisting of: —C(O)NH$_2$, —C(O)NH(CH$_3$), —C(O)NH(CH)(CH$_3$)$_2$ (i.e., —C(O)NH(i-propyl)), —C(O)NH(C$_4$H$_9$), —C(O)NH(C$_6$H$_5$) (i.e., —C(O)NH(phenyl)), —C(O)NH(C$_3$H$_5$) (i.e., —C(O)NH(cyclopropyl), and —C(O)NH(C$_5$H$_4$N) (i.e., —C(O)NH(pyridyl), such as

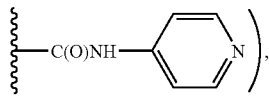

(22) —C(O)—N$R^{32}$—C($R^{18}$)$_3$ (e.g., —C(O)—NH—C($R^{18}$)$_3$) wherein each $R^{18}$ is independently selected from the group consisting of: $R^{10}$ and —C(O)O$R^{19}$, and $R^{19}$ is selected from the group consisting of: alkyl (e.g., methyl) and substituted arylalkyl (e.g., —CH$_2$C$_6$H$_4$OH (i.e., hydroxybenzyl) such as, for example, -p-CH$_2$C$_6$H$_4$OH (i.e., p-OHbenzyl), and wherein:
(a) in one example $R^{18}$ and $R^{19}$ are as defined above with the proviso that at least one $R^{18}$ substituent is other than H (e.g., in one example one $R^{18}$ is H and the remaining two $R^{18}$ groups are other than H, and in another example two $R^{18}$ substituents are H and the remaining $R^{18}$ substituent is other than H),
(b) in another example $R^{18}$ is selected from the group consisting of: H, aryl (e.g., phenyl), substituted aryl (e.g., substituted phenyl, such as, for example halophenyl-, such as, for example, fluorophenyl (e.g., o-F-phenyl)), and —C(O)O$R^{19}$,
(c) in another example $R^{18}$ is selected from the group consisting of: H, phenyl, fluorophenyl (e.g., o-F-phenyl), —C(O)OCH$_3$, —C(O)OCH$_2$C$_6$H$_4$OH (i.e., —C(O)O(OHbenzyl), such as, —C(O)O(p-OHbenzyl)),
(d) in another example $R^{18}$ is selected from the group consisting of: H, aryl (e.g., phenyl), substituted aryl (e.g., substituted phenyl, such as, for example halophenyl-, such as, for example, fluorophenyl (e.g., o-F-phenyl)), and —C(O)O$R^{19}$, provided that at least one $R^{18}$ substituent is other than H (e.g., in one example one $R^{18}$ is H and the remaining two $R^{18}$ groups are other than H, and in another example two $R^{18}$ substituents are H and the remaining $R^{18}$ substituent is other than H),
(e) in another example $R^{18}$ is selected from the group consisting of: H, phenyl, fluorophenyl (e.g., o-F-phenyl), —C(O)OCH$_3$, —C(O)OCH$_2$C$_6$H$_4$OH (i.e., —C(O)O(OHbenzyl), such as, —C(O)O(p-OHbenzyl)), provided that at least one $R^{18}$ substitutent is other than H (e.g., in one example one $R^{18}$ is H and the remaining two $R^{18}$ groups are other than H, and in another example two $R^{18}$ substituents are H and the remaining $R^{18}$ substituent is other than H),
(f) in another example $R^{32}$ is H, and each $R^{18}$ is independently selected from the group consisting of: $R^{10}$ and —C(O)O$R^{19}$, and $R^{19}$ is selected from the group consisting of: alkyl (e.g., methyl) and substituted arylalkyl (e.g., —CH$_2$C$_6$H$_4$OH (i.e., hydroxybenzyl) such as, for example, -p-CH$_2$C$_6$H$_4$OH (i.e., p-OHbenzyl),
(g) in another example $R^{32}$ is H and $R^{18}$ and $R^{19}$ are as defined in paragraph (a),
(h) in another example $R^{32}$ is H and $R^{18}$ and $R^{19}$ are as defined in paragraph (b),
(i) in another example $R^{32}$ is H and $R^{18}$ and $R^{19}$ are as defined in paragraph (c),
(j) in another example $R^{32}$ is H and $R^{18}$ and $R^{19}$ are as defined in paragraph (d),
(k) in another example $R^{32}$ is H and $R^{18}$ and $R^{19}$ are as defined in paragraph (e), and
(l) in another example $R^{32}$ is H and $R^{18}$ and $R^{19}$ are as defined in paragraph (f),

(23) —C(O)—N$R^{32}$—(C($R^{30}$)$_2$)$_n$—C(O)—N($R^{10}$)$_2$ (e.g., —C(O)—NH—(CH$_2$)$_n$—C(O)—NH$_2$), and wherein:
in one example $R^{32}$ is H,
in another example each $R^{30}$ is H,
in another example n is 1,
in another example n is 1 and $R^{32}$ is H,
in another example each $R^{10}$ is H,
in another example $R^{32}$ is H and each $R^{30}$ is H,
in another example $R^{32}$ is H, each $R^{30}$ is H and n is 1,
in another example $R^{32}$ is H, each $R^{30}$ is H, n is 1, and each $R^{10}$ is H,
in another example $R^{32}$ is H, n is 1, each $R^{30}$ is independently selected from the group consisting of: H and alkyl, and each $R^{10}$ is independently selected from the group consisting of: H and alkyl, and
in another example $R^{32}$ is H, n is 1, and each $R^{30}$ is independently selected from the group consisting of: H, methyl, ethyl and i-propyl (or each $R^{30}$ is independently selected from the group consisting of H and i-propyl, or one $R^{30}$ is i-propyl and the other $R^{30}$ is H), and each $R^{10}$ is independently selected from the group consisting of: H methyl, ethyl and i-propyl (or each $R^{10}$ is H),

(24) heterocycloalkenyl, such as, for example:

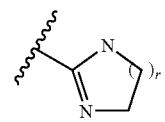

wherein r is 1 to 3, and wherein in one example r is 1, i.e., in one example the heterocycloalkenyl is dihydroimidazolyl, such as, for example:

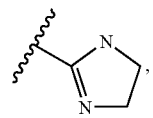

(25)

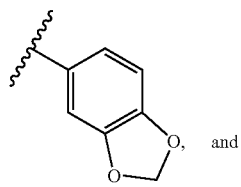, and

(26) arylalkenyl-(aralkenyl-), for example, aryl($C_2$ to $C_6$)alkenyl-, such as for example, —CH=CH-phenyl;

$R^2$ is selected from the group consisting of:
(1) H,
(2) —CN,
(3) halo (e.g., F),
(4) alkyl (e.g., $C_1$ to $C_6$ alkyl, such as, for example, methyl, ethyl and propyl),
(5) substituted alkyl (e.g., substituted $C_1$ to $C_6$ alkyl, such as, for example, substituted methyl and substituted ethyl) wherein said substituted alkyl is substituted with 1 to 3 substitutents (e.g., 1 substituent) selected from the group consisting of: (a) —OH, (b) —O-alkyl (e.g., —O—($C_1$-$C_3$alkyl), such as, for example, —OCH$_3$), (c) —O-alkyl (e.g., —O—($C_1$-$C_3$alkyl)) substituted with 1 to 3 F atoms (examples of said —O-substituted alkyl portion include, but are not limited to, —OCHF$_2$ and —OCF$_3$), and (d) —N($R^{40}$)$_2$ wherein each $R^{40}$ is independently selected from the group consisting of: (i) H, (ii) $C_1$-$C_3$ alkyl (e.g., methyl), (iii) —CF$_3$, and (e) halo (for example F, Cl, and Br, and also for example F, examples of a halo substituted alkyl group include, but are not limited to, —CHF$_2$), (examples of said substituted alkyl groups described in (5) include but are not limited to —CH(OH)CH$_3$, —CH$_2$OH, and —CH$_2$OCH$_3$),
(6) alkynyl (e.g., ethynyl),
(7) alkenyl (e.g., —CH$_2$—CH=CH$_2$),
(8) —(CH$_2$)$_m$$R^{11}$,
(9) —N($R^{26}$)$_2$,
(10) —OR$^{23}$ (e.g., —OH, —OCH$_3$ and —O-phenyl),
(11) —N($R^{26}$)C(O)$R^{42}$ wherein in one example $R^{26}$ is H or $C_1$ to $C_6$ alkyl (e.g., methyl) and $R^{42}$ is alkyl (e.g., methyl), and in another example —N($R^{26}$)C(O)$R^{42}$ is —NHC(O)CH$_3$,
(12) cycloalkyl (e.g., $C_3$ to $C_6$ cycloalkyl, such as, for example, cyclopropyl and cyclohexyl),
(13) cycloalkylalkyl (e.g., $C_3$ to $C_6$ cycloalkyl-($C_1$ to $C_3$)alkyl-, such as, for example, cyclopropyl-CH$_2$— and cyclohexyl-CH$_2$—),
(14)

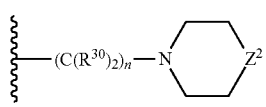

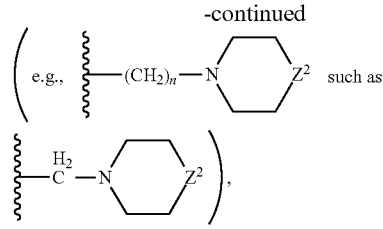

(15) —O-(substituted alkyl) wherein said substituted alkyl is substituted with 1 to 3 F atoms (examples of said —O-(substituted alkyl) moiety include, but are not limited to, —OCHF$_2$ and —OCF$_3$),
(16) —S(O)$_t$-alkyl, such as, for example, (a) —S-alkyl (i.e., t is 0) such as, for example, —S—CH$_3$, and (b) —S(O)$_2$-alkyl (i.e., t is 2) such as, for example, —S(O)$_2$CH$_3$,
(17) —C(O)-alkyl (e.g., —C(O)CH$_3$),
(18)

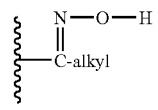

wherein methyl is an example of said alkyl moiety,
(19)

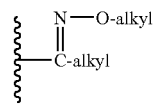

wherein each alkyl is independently selected, examples of this moiety include, but are not limited to:

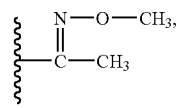

(20)

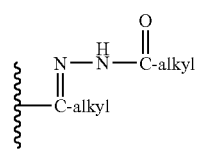

which each alkyl is independently selected, examples of this moiety include, but are not limited to,

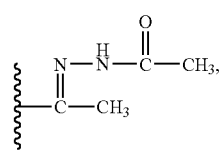

(21)

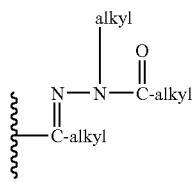

wherein each alkyl is independently selected,

(22) —N(R$^{48}$)—C(O)—R$^{48}$ wherein each R$^{48}$ is independently selected from the group consisting of: H and alkyl (e.g., C$_1$ to C$_6$ alkyl, such as, for example, methyl), and wherein examples of this moiety include, but are not limited to, —NH—C(O)—H, and —N(CH$_3$)—C(O)H, and

(23) —C(O)-alkyl, such as, for example, —C(O)—(C$_1$-C$_6$ alkyl), such as, for example, —C(O)CH$_3$; and
wherein:

(a) in one example said (14) moiety is

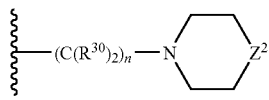

and n is 1, (b) in another example said (14) moiety is

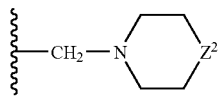

(i.e., n is 1, and each R$^{30}$ is H),
(c) in another example Z$^2$ is —NH— in (a),
(d) in another example Z$^2$ is —NH— in (b),
(e) in another example Z$^2$ is —NH— in (a),
(f) in another example Z$^2$ is —O— in (b),
(g) in another example Z$^2$ is —CH$_2$— in (a),
(h) in another example Z$^2$ is —CH$_2$— in (b),
(i) in another example R$^2$ is —(CH$_2$)$_m$R$^{11}$ and m is 1,
(j) in another example R$^2$ is —N(R$^{26}$)$_2$,
(k) in another example R$^2$ is —N(R$^{26}$)$_2$, and each R$^{26}$ is H (i.e., R$^2$ is —NH$_2$),
(l) in another example R$^2$ is —OR$^{23}$, and
(m) in another example R$^2$ is —OH (i.e., R$^{23}$ is H);
each R$^3$, R$^4$, R$^5$, R$^6$ and R$^7$ is independently selected from the group consisting of:
(1) H,
(2) alkenyl (e.g., —CH$_2$CH=CH$_2$),
(3) substituted alkenyl,
(4) alkyl,
(5) substituted alkyl,
(6) cycloalkyl,
(7) substituted cycloalkyl,
(8) cycloalkylalkyl-,
(9) substituted cycloalkylalkyl-,
(10) heterocycloalkyl,
(11) substituted heterocycloalkyl,
(12) heterocycloalkylalkyl-,
(13) substituted heterocycloalkylalkyl-,
(14) —C(O)R$^{10}$ wherein in one example R$^{10}$ is selected from the group consisting of: alkyl (e.g., C$_1$ to C$_6$, e.g., methyl),
(15) arylheteroaryl- (e.g., phenylthiadiazolyl-),
(16) substituted arylheteroaryl- (e.g., substituted phenylthiadiazolyl-),
(17) heteroarylaryl-, such as, for example, pyrimidinylphenyl-, pyrazinylphenyl-, pyridinylphenyl- (i.e., pyridylphenyl-), furanylphenyl-, thienylphenyl-, thiazolylphenyl-, oxadiazolylphenyl-, and pyridazinylphenyl-,
(18) substituted heteroarylaryl-, such as, for example, substituted pyrimidinylphenyl-, substituted pyrazinylphenyl-, substituted pyridinylphenyl- (i.e., substituted pyridylphenyl-), substituted furanylphenyl-, substituted thienylphenyl-, substituted thiazolylphenyl-, substituted pyrimidinylphenyl, substituted oxadiazolylphenyl-, and substituted pyridazinylphenyl-,
(19) aryl (e.g., phenyl),
(20) substituted aryl (e.g., substituted phenyl),
(21) heteroaryl (e.g., thiazolyl, thienyl, pyridyl, and pyrimidinyl),
(22) substituted heteroaryl (e.g., substituted thiazolyl, substituted pyridyl and substituted pyrimidinyl), examples of substituted heteroaryl groups include, for example bromothiazolyl-, bromopyrimidinyl-, fluoropyrimidinyl-, and ethenylpyrimidinyl-,
(23) heteroarylheteroaryl- (e.g., pyrimidinylpyridyl-, pyrimidinylthiazolyl-, and pyrimidinylpyrazinyl-),
(24) substituted heteroarylheteroaryl- (e.g., substituted pyrimidinylpyridyl-, and substituted pyrimidinylpyrazinyl-),
(25) arylaminoheteroaryl- (e.g., phenyl-NH-oxadiazolyl-),
(26) substituted arylaminoheteroaryl- (e.g., substituted phenyl-NH-oxadiazolyl-),
(27) arylalkynyl- (e.g., aryl(C$_2$ to C$_4$)alkynyl such as, for example phenylethynyl-),
(28) substituted arylalkynyl- (e.g., substituted aryl(C$_2$ to C$_4$)alkynyl-, such as, for example, substituted phenylethynyl-),
(29) heteroarylalkynyl- (e.g., heteroaryl(C$_2$ to C$_4$)alkynyl-, such as, for example, pyrimidinylethynyl-),
(30) substituted heteroarylalkynyl- (e.g., substituted heteroaryl(C$_2$ to C$_4$)alkynyl-, such as, for example substituted pyrimidinylethynyl-),
(31) benzoheteroaryl (i.e., a fused phenyl and heteroaryl rings), such as, for example, benzothiazole and quinoxaline;
wherein said R$^3$, R$^4$, R$^5$, R$^6$ and R$^7$ substituted groups (7), (9), (11), (13), (16), (18), (20), (22), (24), (26), (28) and (30) are substituted with 1 to 3 substituents independently selected from the group consisting of: —NH$_2$, —NHR$^{20}$ (e.g., —NHCH$_2$CH$_3$ and —NHCH$_3$), —N(R$^{20}$)$_2$ wherein each R$^{20}$ is independently selected, alkyl (e.g., C$_1$ to C$_6$ alkyl, e.g., methyl, ethyl, and i-propyl), alkenyl (e.g., C$_2$ to C$_6$ alkenyl, such as, for example —CH=CH$_2$), halo (e.g., F, Cl and Br, and in another example F), —C(O)—NH—R$^{28}$ (e.g., —C(O)—NH—CH$_3$), —C(O)OR$^{28}$ (e.g., —C(O)OC$_2$H$_5$), —C(O)R$^{28}$ (e.g., —C(O)CH$_3$), and —OR$^{20}$ (e.g., —OCH$_3$),
wherein said R$^3$, R$^4$, R$^5$, R$^6$ and R$^7$ substituted groups (3) and (5) are substituted with 1 to 3 substituents independently selected from the group consisting of: —NH$_2$, halo (e.g., F, Cl and Br, and in another example F), —C(O)—NH—R$^{28}$ (e.g., —C(O)—NH—CH$_3$), —C(O)OR$^{28}$ (e.g., —C(O)OC$_2$H$_5$), and —C(O)R$^{28}$ (e.g., —C(O)CH$_3$), and wherein:
in one example said substituted heteroarylaryl (moiety (18) above) is substituted with 1 to 3 substituents independently selected from the group consisting of: —NH$_2$, alkyl (e.g., C$_1$ to C$_6$ alkyl, e.g., methyl), halo (e.g., F, Cl and Br, such as, for example F), in another example said substituted aryl (moiety (20) above) is substituted with 1 to 3 substituents independently selected from the group consisting of halo (e.g., F, Cl and Br), —C(O)—NH—R$^{28}$ (e.g., —C(O)—NH—CH$_3$), —C(O)OR$^{28}$ (e.g., —C(O)O—C$_2$H$_5$), and —C(O)R$^{28}$ (e.g., —C(O)CH$_3$), and in another example said substituted heteroaryl (moiety (22) above) is substituted with 1 to 3 substitutents selected from the group consisting of: halo (e.g., Br, F, and Cl), alkenyl (e.g., C$_2$ to C$_6$ alkenyl, such as, for example, —CH=CH$_2$);

R$^{5,4}$ is selected from the group consisting of: halo (for example, F, Cl, and Br, and in another example F), —OH, alkyl (e.g., C$_1$ to C$_6$ alkyl, such as, for example, —CH$_3$), —O-alkyl (such as, for example, —O—(C$_1$ to C$_6$ alkyl), also, for example, —O—(C$_1$ to C$_3$ alkyl), also for example, —O—(C$_1$ to C$_2$ alkyl), and in one example —O—CH$_3$);

R$^8$ is selected from the group consisting of: H, —OH, —N(R$^{10}$)$_2$ (e.g., —NH$_2$), —NR$^{10}$C(O)R$^{12}$ (e.g., —NHC(O)CH$_3$), and alkyl (e.g., methyl);

each R$^9$ is independently selected from the group consisting of: halogen, —CN, —NO$_2$, —OR$^{10}$, —SR$^{10}$, —N(R$^{10}$)$_2$, and R$^{10}$;

each R$^{10}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl-, substituted alkylaryl-, heterocycloalkenyl

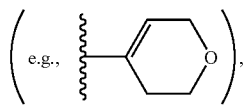

and substituted heterocycloalkenyl, and wherein:
said R$^{10}$ substituted alkyl is substituted with 1 to 3 substituents independently selected from the group consisting of: —NH$_2$, —NHR$^{20}$, —NO$_2$, —CN, —OR$^{26}$, halo (e.g., F, Cl and Br, and in another example F), —C(O)—NH—R$^{26}$ (e.g., —C(O)—NH—CH$_3$, i.e., R$^{26}$ is alkyl, such as methyl), —C(O)OR$^{26}$ (e.g., —C(O)OC$_2$H$_5$, i.e., R$^{26}$ is alkyl, such as ethyl), and —C(O)R$^{26}$ (e.g., —C(O)CH$_3$, i.e., R$^{26}$ is alkyl, such as methyl), and said R$^{10}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —NH$_2$, (2) —NO$_2$, (3) —CN, (4) —OH, (5) —OR$^{20}$, (6) —OCF$_3$, (7) alkyl (e.g., C$_1$ to C$_6$ alkyl) substituted with 1 to 3 independently selected halo atoms (e.g., F, Cl and Br), examples of the substituted alkyl include, but are not limited to, —CF$_3$, —CHF$_2$ and —CH$_2$F, (8) —C(O)R$^{38}$ (e.g., R$^{38}$ is H or alkyl (e.g., C$_1$ to C$_6$ alkyl, such as, for example, methyl or ethyl), for example, R$^{38}$ is alkyl (e.g., methyl), thus, an example of —C(O)R$^{38}$ is —C(O)CH$_3$), (9) alkyl (e.g., C$_1$ to C$_6$ alkyl, e.g., methyl, ethyl, and i-propyl), (10) alkenyl (e.g., C$_2$ to C$_6$ alkenyl, such as, for example —CH=CH$_2$), (11) halo (e.g., F, Cl and Br, and in another example F), (12) —C(O)—NH—R$^{26}$ (e.g., —C(O)—NH—CH$_3$), (13) —C(O)OR$^{38}$ (e.g., R$^{38}$ is H or alkyl (e.g., C$_1$ to C$_6$ alkyl, such as, for example, methyl or ethyl), for example, R$^{38}$ is alkyl (e.g., methyl or ethyl), thus, for example, —C(O)OR$^{38}$ is —C(O)OC$_2$H$_5$), (14) —C(O)—NR$^{32}$—(C(R$^{30}$)$_2$)$_n$—N(R$^{38}$)$_2$ (e.g., —C(O)—NH—(CH$_2$)$_n$—N(R$^{38}$)$_2$) (wherein (a) in one example R$^{32}$ is H, (b) in another example each R$^{30}$ is H, (c) in another example n is 2, (d) in another example each R$^{38}$ is independently selected, (e) in another example each R$^{38}$ is independently selected from the group consisting of: H and alkyl (e.g., methyl), (f) in another example R$^{32}$ is H, each R$^{30}$ is H, and each R$^{38}$ is independently selected, (g) in another example R$^{32}$ is H, each R$^{30}$ is H, and each R$^{38}$ is independently selected from the group consisting of: H and alkyl (e.g., methyl), (15) —S(O)$_t$R$^{38}$ (wherein in one example t is 2, and in another example R$^{38}$ is alkyl (e.g., methyl or isopropyl), and in another example t is 2 and R$^{38}$ is alkyl (e.g., methyl or isopropyl)), (16) —C(O)—NR$^{32}$—R$^{38}$ (e.g., —C(O)—NR$^{32}$—R$^{38}$) (wherein one example R$^{32}$ is H, in another example R$^{38}$ is alkyl (e.g., propyl), and in another example R$^{32}$ is H and R$^{38}$ is alkyl (e.g., propyl)), (17) —NR$^{32}$—C(O)—R$^{38}$ (e.g., —NH—C(O)—R$^{38}$) (wherein in one example R$^{32}$ is H, in another example R$^{38}$ is alkyl (e.g., methyl), and in another example R$^{32}$ is H and R$^{38}$ is alkyl (e.g., methyl)), (18)

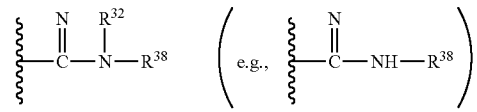

(wherein in one example R$^{32}$ is H, in another example R$^{38}$ is H, and in another example R$^{32}$ is H and R$^{38}$ is H), (19) —NHR$^{20}$ (e.g., —NHCH$_3$, —NHC$_2$H$_5$), (20) cycloalkyl (e.g., C$_3$ to C$_6$ cycloalkyl, such as, for example, cyclopropyl), (21) —O-alkyl-O—R$^{20}$ (e.g., —O—(C$_1$ to C$_6$)alkyl-OR$^{20}$, such as, for example, —O—CH$_2$CH$_2$—OCH$_3$), (22) hydroxyalkyl (e.g., hydroxy(C$_1$ to C$_6$)alkyl, such as, for example, —CH$_2$OH and —C(CH$_3$)$_2$OH), (23) —N(R$^{20}$)$_2$ wherein each R$^{20}$ is independently selected (e.g., —N(CH$_3$)$_2$), (24) -alkyl-OR$^{20}$ (e.g., —(C$_1$ to C$_6$)alkyl-OR$^{20}$, such as, for example, —CH$_2$OCH$_3$), (25) —O-alkyl-OH (e.g., —O—(C$_1$ to C$_6$)alkyl-OH, such as, for example, —O—CH$_2$—CH$_2$—OH), (26) —NH(hydroxyalkyl) (e.g., —NH(hydroxy(C$_1$ to C$_6$)alkyl, such as, for example, —NH(CH$_2$CH$_2$OH)), and (27) oxazolidinone, such as, for example,

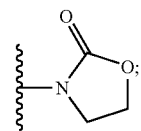

R$^{11}$ is selected from the group consisting of: F, —OH, —CN, —OR$^{10}$, —NHNR$^1$R$^{10}$, —SR$^{10}$ and heteroaryl (e.g., triazolyl, such as, for example,

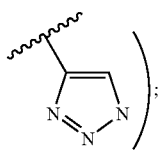 [SMILES: *c1c[nH]nn1]

$R^{12}$ is selected from the group consisting of: alkyl, aryl, heteroaryl, cycloalkyl, cycloalkylalkyl, heterocycloalkyl and heterocycloalkylalkyl;

$R^{14}$ is selected from the group consisting of: alkyl, aryl, heteroaryl, cycloalkyl, cycloalkylalkyl-, heterocycloalkyl, alkylheterocycloalkyl, heterocycloalkylalkyl-, alkylheteroaryl- and alkylaryl-;

$R^{15}$ is selected from the group consisting of: H, —OH, alkyl, aryl, heteroaryl, cycloalkyl, cycloalkylalkyl-, heterocycloalkyl and heterocycloalkylalkyl-, alkylheteroaryl- and alkylaryl-;

$R^{20}$ represents alkyl (e.g., $C_1$ to $C_6$ alkyl, such as, for example, methyl, ethyl or isopropyl);

$R^{23}$ is selected from the group consisting of: H, alkyl (e.g., $C_1$ to $C_6$ alkyl, such as, for example, methyl and i-propyl), aryl (e.g., phenyl), cycloalkyl (e.g., $C_3$ to $C_6$ cycloalkyl, such as, for example, cyclopropyl and cyclohexyl), and cycloalkylalkyl- (e.g., $C_3$ to $C_6$ cycloalkylalkyl-, such as —(CH$_2$)$_n$-cycloalkyl, such as —(CH$_2$)$_n$—(C$_3$ to C$_6$)cycloalkyl, wherein each H of each —(CH$_2$)$_n$— moiety can independently be substituted with an alkyl group (e.g., $C_1$ to $C_6$ alkyl, such as, for example, methyl), and wherein in one example n is 1 and the —CH$_2$— moiety is not substituted, that is, —CH$_2$-cycloalkyl, such as, —CH$_2$-cyclopropyl, is an example of said cycloalkylalkyl- moiety);

each $R^{26}$ is independently selected from the group consisting of: H and alkyl (e.g., $C_1$ to $C_6$ alkyl, such as, for example, methyl and ethyl);

$R^{28}$ is alkyl (e.g., $C_1$ to $C_6$ alkyl, such as, for example, methyl or ethyl);

each $R^{30}$ is independently selected from the group consisting of: H, alkyl (e.g., $C_1$ to $C_6$ alkyl, such as for example methyl, ethyl and i-propyl), and F, and wherein in one example each $R^{30}$ is H;

each $R^{32}$ is independently selected from the group consisting of: H and alkyl (e.g., $C_1$ to $C_6$ alkyl, such as, for example methyl, ethyl and propyl), and wherein each $R^{32}$ is generally H;

each $R^{35}$ is independently selected from the group consisting of: H and $C_1$ to $C_6$ alkyl (e.g., methyl, ethyl, i-propyl, and propyl), and wherein in one example both $R^{35}$ substitutents are the same or different alkyl groups (e.g., both $R^{35}$ groups are the same alkyl group, such as methyl), and in another example one $R^{35}$ group is H and the other $R^{35}$ group is alkyl, such as methyl), and in another example each $R^{35}$ is preferably H;

$R^{36}$ is selected from the group consisting of: H, alkyl (e.g., $C_1$ to $C_6$ alkyl, such as, for example, methyl, ethyl and propyl), and —O-alkyl (e.g., —O—(C$_1$ to C$_6$) alkyl, such as, for example, —O—(C$_1$ to C$_2$) alkyl, such as, for example, —OCH$_3$), and preferably $R^{36}$ is selected from the group consisting of H and methyl, and more preferably $R^{36}$ is H;

each $R^{38}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl-, and wherein:

said $R^{38}$ substituted alkyl is substituted with 1 to 3 substituents independently selected from the group consisting of: —NH$_2$, —NO$_2$, —CN, —OR$^{26}$, halo (e.g., F, Cl and Br, and in another example F), —C(O)—NH—R$^{28}$ (e.g., —C(O)—NH—CH$_3$), —C(O)OR$^{28}$ (e.g., —C(O)OC$_2$H$_5$), and —C(O)R$^{28}$ (e.g., —C(O)CH$_3$), and said $R^{38}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —NH$_2$, (2) —NO$_2$, (3) —CN, (4) —OH, (5) —OR$^{20}$, (6) —OCF$_3$, (7) —CF$_3$, (8) —C(O)R$^{26}$ (e.g., R$^{26}$ is H or C$_1$ to C$_6$ alkyl, such as, for example, methyl or ethyl, for example, R$^{26}$ is alkyl (e.g., methyl), thus, an example of —C(O)R$^{26}$ is —C(O)CH$_3$), (9) alkyl (e.g., C$_1$ to C$_6$ alkyl, e.g., methyl, ethyl, and i-propyl), (10) alkenyl (e.g., C$_2$ to C$_6$ alkenyl, such as, for example —CH═CH$_2$), (11) halo (e.g., F, Cl and Br, and in another example F), (12) —C(O)—NH—R$^{26}$ (e.g., —C(O)—NH—CH$_3$), (13) —C(O)OR$^{26}$ (e.g., R$^{26}$ is H or e.g., C$_1$ to C$_6$ alkyl, such as, for example, methyl or ethyl, for example, R$^{26}$ is alkyl (e.g., methyl or ethyl), thus, for example, —C(O)OR$^{26}$ is —C(O)OC$_2$H$_5$), (14) —C(O)—NR$^{32}$—(C(R$^{30}$)$_2$)$_n$—N(R$^{26}$)$_2$ (e.g., —C(O)—NH—(CH$_2$)$_n$—N(R$^{26}$)$_2$) (wherein (a) in one example R$^{32}$ is H, (b) in another example each R$^{30}$ is H, (c) in another example n is 2, (d) in another example each R$^{26}$ is independently selected, (e) in another example each R$^{26}$ is independently selected from the group consisting of: H and methyl), (f) in another example R$^{32}$ is H, each R$^{30}$ is H, and each R$^{26}$ is independently selected, (g) in another example R$^{32}$ is H, each R$^{30}$ is H, and each R$^{26}$ is independently selected from the group consisting of: H and methyl), (15) —S(O)$_t$R$^{26}$ (wherein in one example t is 2, and in another example R$^{26}$ is methyl, and in another example t is 2 and R$^{26}$ is methyl), (16) —C(O)N(R$^{32}$)(R$^{26}$) (wherein in one example R$^{32}$ is H, in another example R$^{26}$ is alkyl (e.g., propyl), and in another example R$^{32}$ is H and R$^{26}$ is alkyl (e.g., propyl)), (17) —NR$^{32}$C(O)R$^{26}$ (e.g., —NHC(O)R$^{26}$) (wherein in one example R$^{32}$ is H, in another example R$^{26}$ is alkyl (e.g., methyl), and in another example R$^{32}$ is H and R$^{26}$ is alkyl (e.g., methyl)), (18)

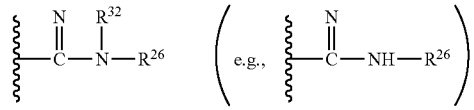

(wherein in one example R$^{32}$ is H, in another example R$^{26}$ is H, and in another example R$^{32}$ is H and R$^{26}$ is H); and (19) —NHR$^{20}$;

$R^{42}$ is selected from the group consisting of: alkyl (e.g., $C_1$ to $C_6$ alkyl, such as, for example —CH$_3$), aryl (e.g., phenyl), heteroaryl (e.g., thiazolyl and pyridyl), and cycloalkyl (e.g., $C_3$ to $C_6$ cycloalkyl, such as, for example, cyclopropyl);

$R^{44}$ is selected from the group consisting of: H, alkyl (e.g., $C_1$ to $C_6$ alkyl, such as, for example, $C_1$ to $C_3$ alkyl, such as, for example, methyl, ethyl and i-propyl), cycloalkyl (e.g., $C_3$ to $C_6$ cycloalkyl, such as, for example, cyclopropyl and cyclohexyl), and cycloalkylalkyl (e.g., (C$_3$ to C$_6$)cycloalkyl(C$_1$ to C$_6$)alkyl, such as, for example, (C$_3$ to C$_6$)cycloalkyl(C$_1$ to $C_3$)alkyl, such as, for example, ($C_3$ to $C_6$)cycloalkyl-methyl-, such as, for example, cyclopropyl-methyl- and cyclohexyl-methyl-), and in one example, $R^{44}$ is H; and Each $R^{46}$ is independently selected from the group consisting of: H, alkyl (e.g., $C_1$ to $C_6$ alkyl, such as, for example, $C_1$ to $C_3$ alkyl, such as, for example, methyl, ethyl and i-propyl), cycloalkyl (e.g., $C_3$ to $C_6$ cycloalkyl, such as, for example, cyclopropyl and cyclohexyl), and cycloalkylalkyl (e.g., ($C_3$ to $C_6$)cycloalkyl($C_1$ to $C_6$)alkyl, such as, for example, ($C_3$ to $C_6$)cycloalkyl($C_1$ to $C_3$)alkyl, such as, for example, ($C_3$ to $C_6$)cycloalkyl-methyl-, such as, for example, cyclopropyl-methyl- and cyclohexyl-methyl-), and in one example, each $R^{46}$ is H.

When $R^1$ is a cycloalkyl group (i.e., $R^1$ is $R^{10}$ wherein $R^{10}$ is cycloalkyl), examples of said cycloalkyl group include, but are limited to, cyclopropyl and cyclobutyl.

When $R^1$ is a heterocycloalkyl group (i.e., $R^1$ is $R^{10}$ wherein $R^{10}$ is heterocycloalkyl), examples of said heterocycloalkyl group include, but are limited to, morpholinyl, pyrrolidinyl, piperidinyl and piperazinyl.

When $R^1$ is a heteroaryl group (i.e., $R^1$ is $R^{10}$ and $R^{10}$ is heteroaryl), examples of said heteroaryl group include, but are not limited to, (a) unsubstituted heteroaryl,
(b) heteroaryl substituted with 1 to 3 substituents independently selected from the group consisting of: —C(O)$R^{38}$ (e.g., $R^{38}$ is alkyl such as methyl), —NH$R^{20}$ (e.g., —NHCH$_3$), —O$R^{20}$ (e.g., —OCH$_3$), cycloalkyl (e.g., cyclopropyl) and halo (e.g., Cl),
(c) heteroaryl selected from the group consisting of: pyrrolyl, pyrazolyl, imidazolyl, furanyl, thienyl, thiazolyl, pyridyl, pyridyl N—O, and pyrimidinyl,
(d) heteroaryl selected from the group consisting of: pyrrolyl, pyrazolyl, imidazolyl, furanyl, thienyl, thiazolyl, pyridyl, pyridyl N—O, and pyrimidinyl, wherein said heteroaryl is substituted with 1 to 3 substituents independently selected from the group consisting of: —C(O)$R^{38}$ (e.g., $R^{38}$ is alkyl such as methyl), —NH$R^{20}$ (e.g., —NHCH$_3$), —O$R^{20}$ (e.g., —OCH$_3$), cycloalkyl (e.g., cyclopropyl) and halo (e.g., Cl), and
(e) heteroaryl selected from the group consisting of: thienyl substituted with —C(O)$R^{38}$ (such as, for example, thienyl substituted with —C(O)CH$_3$), thiazolyl substituted with —NH$R^{20}$ such as, for example (thazolyl substituted with —NHCH$_3$), pyridyl substituted with halo (such as, for example, pyridyl substituted with —Cl), pyridyl substituted with —O$R^{20}$ (such as, for example, pyridyl substituted with methyl), and pyrimidinyl substituted with —O$R^{20}$ (such as, for example, pyrimidinyl substituted with —OCH$_3$).

When $R^1$ is a heteroarylalkyl group (i.e., $R^1$ is $R^{10}$ and $R^{10}$ is heteroarylalkyl), examples of said heteroarylalkyl group include, but are not limited to, (a) unsubstituted heteroarylalkyl-
(b) heteroarylalkyl-substituted with 1 to 3 substituents independently selected from the group consisting of: —C(O)$R^{38}$ (e.g., $R^{38}$ is alkyl such as methyl), —NH$R^{20}$ (e.g., —NHCH$_3$), —O$R^{20}$ (e.g., —OCH$_3$), and halo (e.g., Cl),
(c) heteroarylalkyl-selected from the group consisting of: pyrrolylalkyl- (e.g., pyrrolylCH$_2$—), pyrazolylalkyl- (e.g., pyrazolylCH$_2$—), imidazolylalkyl- (e.g., imdazolyl-CH$_2$—), furanylalkyl- (e.g., furanylCH$_2$—), thienylalkyl- (e.g., thienylCH$_2$—), thiazolylalkyl- (e.g., thiazolylCH$_2$—), pyridylalkyl- (e.g., pyridylCH$_2$—), pyridyl N—O alkyl- (e.g., pyridyl(N—O)CH$_2$—), and pyrimidinylalkyl- (e.g., pyrimidinylCH$_2$—),
(d) heteroarylalkyl-selected from the group consisting of: pyrrolylalkyl- (e.g., pyrrolylCH$_2$—), pyrazolylalkyl- (e.g., pyrazolylCH$_2$—), imidazolylalkyl- (e.g., imdazolylCH$_2$—), furanylalkyl- (e.g., furanylCH$_2$—), thienylalkyl- (e.g., thienylCH$_2$—), thiazolylalkyl- (e.g., thiazolylCH$_2$—), pyridylalkyl- (e.g., pyridylCH$_2$—), pyridyl N—O alkyl- (e.g., pyridyl(N—O)CH$_2$—), and pyrimidinylalkyl- (e.g., pyrimidinylCH$_2$—), wherein said heteroaryl is substituted with 1 to 3 substituents independently selected from the group consisting of: —C(O)$R^{38}$ (e.g., $R^{38}$ is alkyl such as methyl), —NH$R^{20}$ (e.g., —NHCH$_3$), —O$R^{20}$ (e.g., —OCH$_3$), and halo (e.g., Cl), and
(e) heteroarylalkyl-selected from the group consisting of: thienylalkyl-substituted with a —C(O)$R^{20}$ group (such as, for example, thienylCH$_2$— substituted with —C(O)CH$_3$), thiazolylalkyl-substituted with —NH$R^{20}$ such as, for example (thazolylCH$_2$-substituted with —NHCH$_3$), pyridylalkyl-substituted with halo (such as, for example, pyridylCH$_2$-substituted with —Cl), pyridylalkyl-substituted with —O$R^{20}$ (such as, for example, pyridylCH$_2$— substituted with methyl), and pyrimidinylalky-substituted with —O$R^{20}$ (such as, for example, pyrimidinylCH$_2$— substituted with —OCH$_3$).

When $R^1$ is an aryl group (i.e., $R^1$ is $R^{10}$ and $R^{10}$ is aryl), examples of said aryl group include, but are not limited to, phenyl and naphthyl, and preferably phenyl.

When $R^1$ is an arylalkyl group (i.e., $R^1$ is $R^{10}$ and $R^{10}$ is arylalkyl), examples of said arylalkyl group include, but are not limited to, —(C($R^{30}$)$_2$)$_n$phenyl (e.g., —(CH$_2$)$_n$phenyl), wherein in one example said arylalkyl- is —(C($R^{30}$)$_2$)$_n$phenyl wherein n is 1, and in another example said arylalkyl- is —(CH$_2$)$_n$phenyl wherein n is 1 (i.e., said arylalkyl- is benzyl).

When $R^1$ is a substituted arylalkyl group (i.e., $R^1$ is $R^{10}$ and $R^{10}$ is a substituted arylalkyl), examples of said substituted arylalkyl group include, but are not limited to, —(C($R^{30}$)$_2$)$_n$ substituted phenyl (e.g., —(CH$_2$)$_n$substituted phenyl), wherein in one example said substituted arylalkyl- is —(C($R^{30}$)$_2$)$_n$ substituted phenyl wherein n is 1, and in another example said substituted arylalkyl- is —(CH$_2$)$_n$substituted phenyl wherein n is 1 (i.e., said substituted arylalkyl- is substituted benzyl), wherein the aryl moiety of said substituted arylalkyl is substituted with 1 to 3 substituents independently selected from the group consisting of: halo (e.g., F, Cl and Br), —CF$_3$, and —O$R^{20}$ (e.g., —OCH$_3$).

Those skilled in the art will appreciate that when $Q^1$ is aryl, substituted aryl, heteroaryl or substituted heteroaryl the two carbon atoms common to the two fused rings are not substituted. Thus, there is no $R^3$ and no $R^4$ groups in 2.9 when $Q^1$ is aryl, substituted aryl, heteroaryl or substituted heteroaryl. There is no $R^3$ and no $R^4$ groups in 2.10 when $Q^1$ fused to the $R^3$ and $R^4$ positions is aryl, substituted aryl, heteroaryl or substituted heteroaryl. There is no $R^6$ and no $R^7$ groups in 2.10 when $Q^1$ fused to the $R^6$ and $R^7$ positions is aryl, substituted aryl, heteroaryl or substituted heteroaryl. There is no $R^3$ and no $R^4$ groups in 2.11 when $Q^1$ fused to the $R^3$ and $R^4$ positions is aryl, substituted aryl, heteroaryl or substituted heteroaryl. There is no $R^3$ and no $R^4$ groups in 2.13 when $Q^1$ fused to the $R^3$ and $R^4$ positions is aryl, substituted aryl, heteroaryl or substituted heteroaryl. There is no $R^3$ and no $R^4$ groups in 2.14 when $Q^1$ fused to the $R^3$ and $R^4$ positions is aryl, substituted aryl, heteroaryl or substituted heteroaryl. There is no $R^3$ and no $R^4$ groups in 2.15 when $Q^1$ fused to the $R^3$ and $R^4$ positions is aryl, substituted aryl, heteroaryl or substituted heteroaryl. There is no $R^6$ and no $R^7$ groups in 2.15 when $Q^1$ fused to the $R^3$ and $R^4$ positions is aryl, substituted aryl, heteroaryl or substituted heteroaryl.

In one embodiment of the compounds of formula 1.0, z is 1. Thus, in this embodiment the compounds of formula 1.0 have the formula 1.0A1:

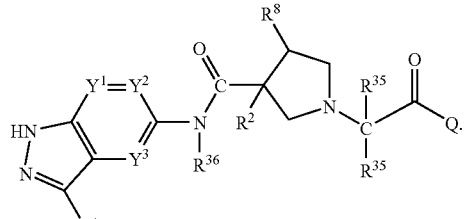

(1.0A1)

In another embodiment of the compounds of formula 1.0, z is 1 and $R^{36}$ is H. Thus, in this embodiment the compounds of formula 1.0 have the formula 1.0A:

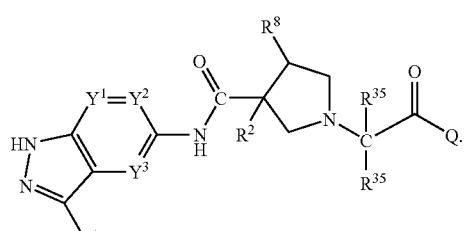

(1.0A)

In another embodiment of the compounds of formula 1.0, Z is 1 and $R^{36}$ is —OCH$_3$.

In another embodiment of the compounds of formula 1.0, z is 1, and each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H).

In another embodiment of the compounds of formula 1.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H, methyl, ethyl and propyl.

In another embodiment of the compounds of formula 1.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is selected from the group consisting of: H and methyl.

In another embodiment of the compounds of formula 1.0, z is 1, each $R^{35}$ is independently selected from the group consisting of: H, methyl, ethyl, i-propyl and propyl (e.g., one $R^{35}$ is H and the other is methyl, or both $R^{35}$ substituents are methyl, or preferably both $R^{35}$ substitutents are H), and $R^{36}$ is: H.

In another embodiment of the compounds of formula 1.0, each $R^{35}$ is H. Thus, in this embodiment the compounds of formula 1.0 have the formula 1.0B1:

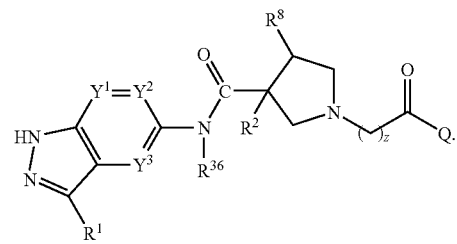

(1.0B1)

In another embodiment of the compounds of formula 1.0, each $R^{35}$ is H and $R^{36}$ is H. Thus, in this embodiment the compounds of formula 1.0 have the formula 1.0B:


(1.0B)

In another embodiment of the compounds of formula 1.0, z is preferably 1 and each $R^{35}$ is preferably H. Thus, in this embodiment the compounds of formula 1.0 have the formula 1.0C1:

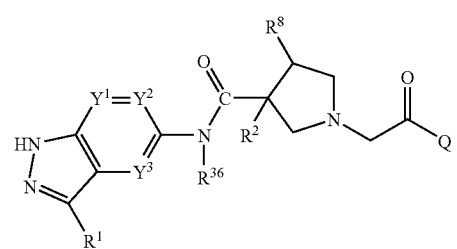

(1.0C1)

In another embodiment of the compounds of formula 1.0, z is preferably 1, each $R^{35}$ is preferably H, and $R^{36}$ is H. Thus, preferably the compounds of formula 1.0 have the formula 1.0C:

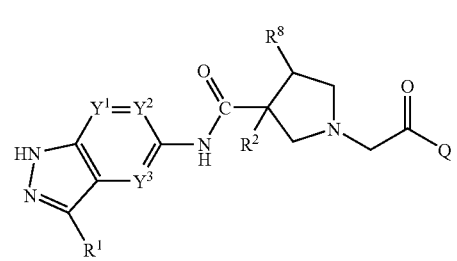

(1.0C)

Another embodiment of this invention is directed to compounds of formula 1.0 having the formula 1.1A:

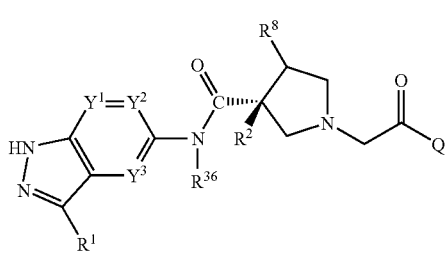

(1.1A)

Another embodiment of this invention is directed to compounds of formula 1.0 having the formula 1.1:

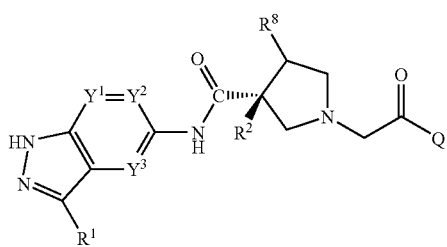

(1.1)

wherein all substituents are as defined for formula 1.0.

Another embodiment of this invention is directed to compounds of formulas 1.0 and 1.1A wherein $Y^1$, $Y^2$ and $Y^3$ are —CH=. Thus, one embodiment of this invention is directed to compounds of formula 1.2A:

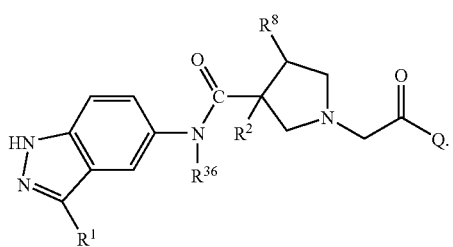

(1.2A)

Another embodiment of this invention is directed to compounds of formulas 1.0 and 1.1 wherein $Y^1$, $Y^2$, and $Y^3$ are —CH=. Thus, one embodiment of this invention is directed to compounds of formula 1.2:

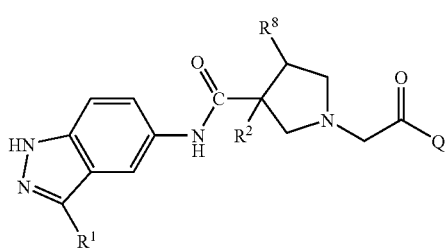

(1.2)

wherein all substitutents are as defined for formula 1.0.

Another embodiment of this invention is directed to compounds of formula 1.0 having the formula 1.3A:

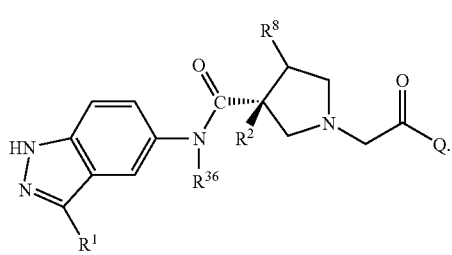

(1.3A)

Another embodiment of this invention is directed to compounds of formula 1.0 having the formula 1.3:

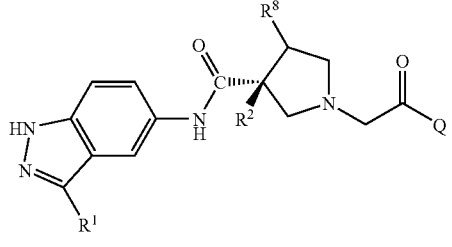

(1.3)

wherein all substituents are as defined for formula 1.0.

Examples of Q include, but are not limited to: moieties 2.1, 2.2, 2.3, 2.4, 2.5, 2.6, 2.7, 2.8, 2.9, 2.10, 2.11, 2.14, or 2.15 wherein each $R^3$, $R^4$, $R^6$, and $R^7$ is independently selected from the group consisting of: H and alkyl (e.g., $C_1$ to $C_6$ alkyl, such as, for example methyl).

Examples of Q also include, but are not limited to: moieties 2.1, 2.2, 2.3, 2.4, 2.5, 2.6, 2.7, 2.8, 2.9, 2.10, 2.11, 2.14, or 2.15 wherein each $R^3$, $R^4$, $R^6$, and $R^7$ is H.

Examples of Q also include, but are not limited to: moieties 2.17, 2.18, 2.19, 2.20 and 2.21 wherein each $R^3$, $R^4$, $R^6$, and $R^7$ is independently selected from the group consisting of: H and alkyl (e.g., $C_1$ to $C_6$ alkyl, such as, for example methyl).

Examples of Q also include, but are not limited to: moieties 2.17, 2.18, 2.19, 2.20 and 2.21 wherein each $R^3$, $R^4$, $R^6$, and $R^7$ is H.

Examples of Q include, but are not limited to: moieties 2.12, 2.13, or 2.16 wherein each $R^3$, $R^4$, and $R^7$ is independently selected from the group consisting of: H and alkyl (e.g., $C_1$ to $C_6$ alkyl, such as, for example methyl).

Examples of Q also include, but are not limited to: moieties 2.12, 2.13, or 2.16 wherein each $R^3$, $R^4$, and $R^7$ is H.

Examples of Q include, but are not limited to: moiety 2.22 wherein each $R^3$, $R^4$, and $R^7$ is independently selected from the group consisting of: H and alkyl (e.g., $C_1$ to $C_6$ alkyl, such as, for example methyl).

Examples of Q also include, but are not limited to: moiety 2.22 wherein each $R^3$, $R^4$, and $R^7$ is H.

Thus, in one example of Q, Q is moiety 2.1 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.1 wherein each $R^3$, $R^4$, $R^6$, and $R^7$ is independently selected from the group consisting of: H and methyl.

In another example of Q, Q is moiety 2.1 wherein each $R^3$, $R^4$, $R^6$, and $R^7$ is H.

In another example of Q, Q is moiety 2.2 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.2 wherein each $R^3$, $R^4$, $R^6$, and $R^7$ is independently selected from the group consisting of: H and methyl.

In another example of Q, Q is moiety 2.2 wherein each $R^3$, $R^4$, $R^6$, and $R^7$ is H.

In another example of Q, Q is moiety 2.3 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.3 wherein each $R^3$, $R^4$, $R^6$, and $R^7$ is independently selected from the group consisting of: H and methyl.

In another example of Q, Q is moiety 2.3 wherein each $R^3$, $R^4$, $R^6$, and $R^7$ is H.

In another example of Q, Q is moiety 2.4 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.4 wherein each $R^3$, $R^4$, $R^6$, and $R^7$ is independently selected from the group consisting of: H and methyl.

In another example of Q, Q is moiety 2.4 wherein each $R^3$, $R^4$, $R^6$, and $R^7$ is H.

In another example of Q, Q is moiety 2.5 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.5 wherein each $R^3$, $R^4$, $R^6$, and $R^7$ is independently selected from the group consisting of: H and methyl.

In another example of Q, Q is moiety 2.5 wherein each $R^3$, $R^4$, $R^6$, and $R^7$ is H.

In another example of Q, Q is moiety 2.6 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.6 wherein each $R^3$, $R^4$, $R^6$, and $R^7$ is independently selected from the group consisting of: H and methyl.

In another example of Q, Q is moiety 2.7 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.7 wherein each $R^3$, $R^4$, $R^6$, and $R^7$ is independently selected from the group consisting of: H and methyl.

In another example of Q, Q is moiety 2.7 wherein each $R^3$, $R^4$, $R^6$, and $R^7$ is H.

In another example of Q, Q is moiety 2.8 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.8 wherein each $R^3$, $R^4$, $R^6$, and $R^7$ is independently selected from the group consisting of: H and methyl.

In another example of Q, Q is moiety 2.8 wherein each $R^3$, $R^4$, $R^6$, and $R^7$ is H.

In another example of Q, Q is moiety 2.9 or 2.10 wherein each $R^3$, $R^4$, $R^6$, and
$R^7$ is independently selected from the group consisting of: H and alkyl (e.g., $C_1$ to $C_6$ alkyl, such as, for example methyl).

In another example of Q, Q is moiety 2.9 or 2.10 wherein each $R^3$, $R^4$, $R^6$, and
$R^7$ is independently selected from the group consisting of: H and methyl.

In another example of Q, Q is moiety 2.9 or 2.10 wherein each $R^3$, $R^4$, $R^6$, and
$R^7$ is H.

In another example of Q, Q is moiety 2.11 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.11 wherein each $R^3$, $R^4$, $R^6$, and $R^7$ is independently selected from the group consisting of: H and methyl.

In another example of Q, Q is moiety 2.11 wherein each $R^3$, $R^4$, $R^6$, and $R^7$ is H.

In another example of Q, Q is moiety 2.12 or 2.13 wherein each $R^3$, $R^4$, and $R^7$ is independently selected from the group consisting of: H and alkyl (e.g., $C_1$ to $C_6$ alkyl, such as, for example methyl).

In another example of Q, Q is moiety 2.12 or 2.13 wherein each $R^3$, $R^4$, and $R^7$ is independently selected from the group consisting of: H and methyl.

In another example of Q, Q is moiety 2.12 or 2.13 wherein each $R^3$, $R^4$, and $R^7$ is H.

In another example of Q, Q is moiety 2.14 or 2.15 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.14 or 2.15 wherein each $R^3$, $R^4$, $R^6$, and $R^7$ is independently selected from the group consisting of: H and methyl.

In another example of Q, Q is moiety 2.14 or 2.15 wherein each $R^3$, $R^4$, $R^6$, and $R^7$ is H.

In another example of Q, Q is moiety 2.16 wherein each $R^3$, $R^4$, and $R^7$ is H.

In another example of Q, Q is moiety 2.17 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.17 wherein each $R^3$, $R^4$, $R^6$, and $R^7$ is independently selected from the group consisting of: H and methyl.

In another example of Q, Q is moiety 2.17 wherein each $R^3$, $R^4$, $R^6$, and $R^7$ is H.

In another example of Q, Q is moiety 2.18 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.18 wherein each $R^3$, $R^4$, $R^6$, and $R^7$ is independently selected from the group consisting of: H and methyl.

In another example of Q, Q is moiety 2.18 wherein each $R^3$, $R^4$, $R^6$, and $R^7$ is H.

In another example of Q, Q is moiety 2.19 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.19 wherein each $R^3$, $R^4$, $R^6$, and $R^7$ is independently selected from the group consisting of: H and methyl.

In another example of Q, Q is moiety 2.19 wherein each $R^3$, $R^4$, $R^6$ and $R^7$ is H.

In another example of Q, Q is moiety 2.20 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.20 wherein each $R^3$, $R^4$, $R^6$, and $R^7$ is independently selected from the group consisting of: H and methyl.

In another example of Q, Q is moiety 2.20 wherein each $R^3$, $R^4$, $R^6$, and $R^7$ is H.

In another example of Q, Q is moiety 2.21 wherein each $R^3$, $R^4$, $R^6$, and $R^7$ is independently selected from the group consisting of: H and alkyl (e.g., $C_1$ to $C_6$ alkyl, such as, for example methyl).

In another example of Q, Q is moiety 2.21 wherein each $R^3$, $R^4$, $R^6$, and $R^7$ is independently selected from the group consisting of: H and methyl.

In another example of Q, Q is moiety 2.21 wherein each $R^3$, $R^4$, $R^6$, and $R^7$ is H.

In another example of Q, Q is moiety 2.22 wherein each $R^3$, $R^4$, and $R^7$ is independently selected from the group consisting of: H and alkyl (e.g., $C_1$ to $C_6$ alkyl, such as, for example methyl).

In another example of Q, Q is moiety 2.22 wherein each $R^3$, $R^4$, and $R^7$ is independently selected from the group consisting of: H and methyl.

In another example of Q, Q is moiety 2.22 wherein each $R^3$, $R^4$, and $R^7$ is H.

Another example of the Q substituent 2.3 is:

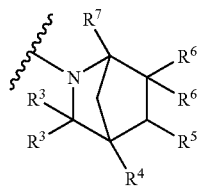

(2.3A)

(i.e., each $R^{24}$ is H and w is 1).

Another example of the Q sutituent 2.3 is:

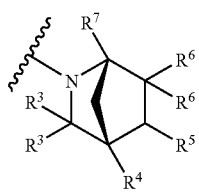

(2.3B)

(i.e., each $R^{24}$ is H and w is 1).

Another example of the Q substitutent 2.3 is:

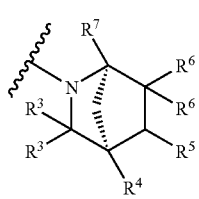

(2.3C)

(i.e., each $R^{24}$ is H and w is 1).

An example of the Q substituent 2.4 is:

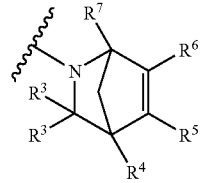

(2.4A)

(i.e., each $R^{24}$ is H and w is 1).

Another example of the Q substituent 2.4 is:

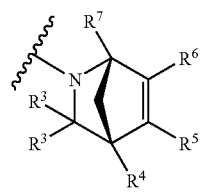

(2.4B)

(i.e., each $R^{24}$ is H and w is 1).

Another example of the Q substituent 2.4 is:

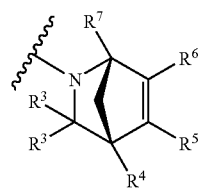

(2.4C)

(i.e., each $R^{24}$ is H and w is 1).

An example of the Q substituent 2.5 is:

(2.5A)

(i.e., each $R^{24}$ is H and w is 1).

Another example of the Q substituent 2.5 is:

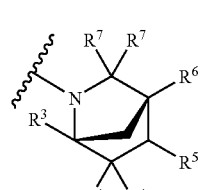

(2.5B)

(i.e., each $R^{24}$ is H and w is 1).

Another example of the Q substituent 2.5 is:

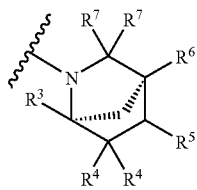
(2.5C)

(i.e., each $R^{24}$ is H and w is 1).

An example of the Q substituent 2.6 is:

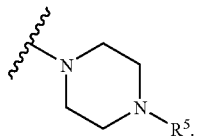
(2.6A)

An example of the Q substituent 2.7 is:

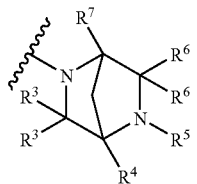
(2.7A)

(i.e., each $R^{24}$ is H and w is 1).

An example of the Q substituent 2.7 is:

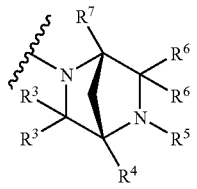
(2.7B)

(i.e., each $R^{24}$ is H and w is 1).

An example of the Q substituent 2.7 is:

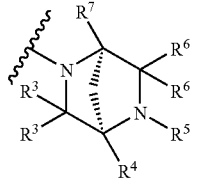
(2.7C)

(i.e., each $R^{24}$ is H and w is 1).

An example of the Q substituent 2.8 is:

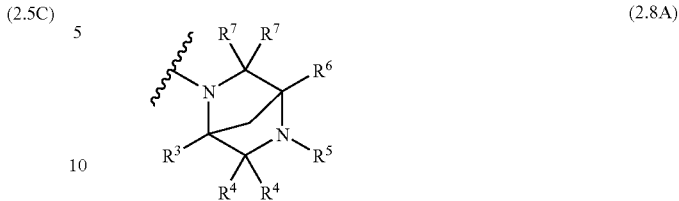
(2.8A)

(i.e., each $R^{24}$ is H and w is 1).

Another example of the Q substituent 2.8 is:

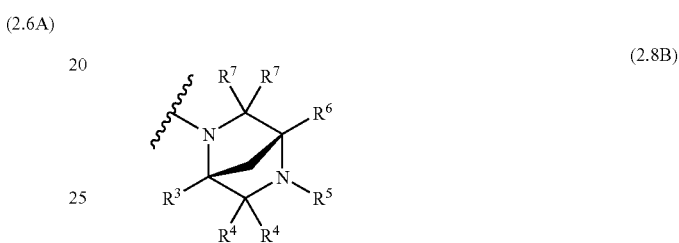
(2.8B)

(i.e., each $R^{24}$ is H and w is 1).

Another example of the Q substituent 2.8 is:

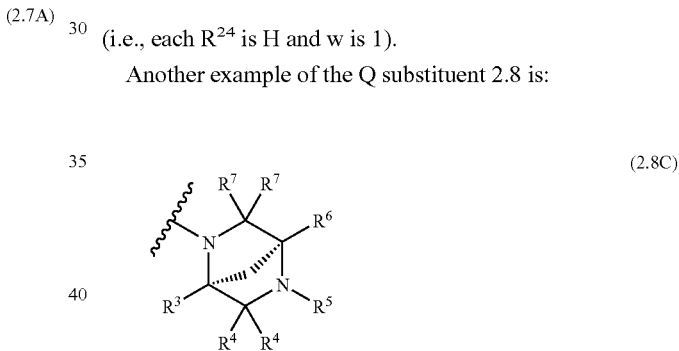
(2.8C)

(i.e., each $R^{24}$ is H and w is 1).

Another example of the Q substituent 2.3 is:

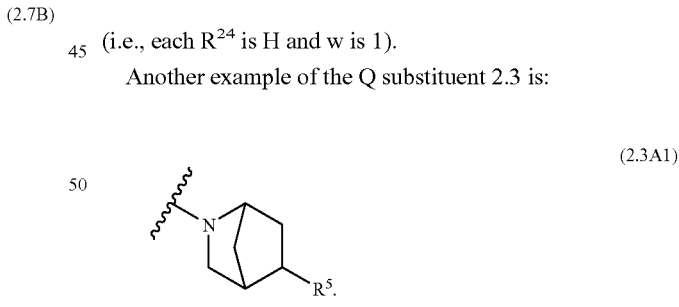
(2.3A1)

Another example of the Q substituent 2.3 is:

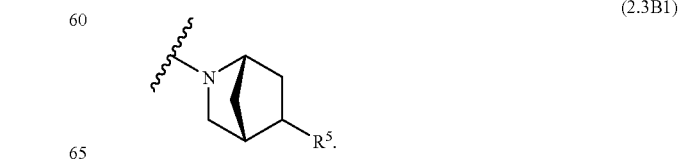
(2.3B1)

Another example of the Q substituent 2.3 is:

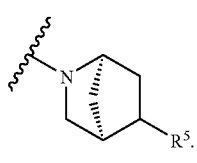
(2.3C1)

Another example of the Q substituent 2.4 is:

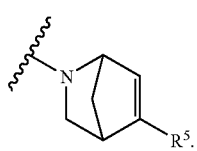
(2.4A1)

Another example of the Q substituent 2.4 is:

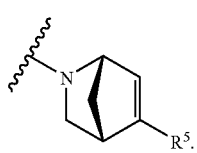
(2.4B1)

Another example of the Q substituent 2.4 is:

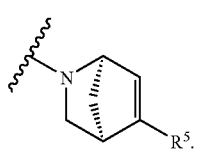
(2.4C1)

Another example of the Q substituent 2.5 is:

(2.5A1)

Another example of the Q substituent 2.5 is:

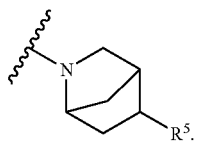
(2.5B1)

Another example of the Q substituent 2.5 is:

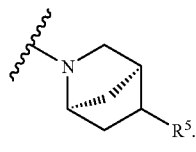
(2.5C1)

Another example of the Q substituent 2.7 is:

(2.7A1)

Another example of the Q substituent 2.7 is:

(2.7B1)

Another example of the Q substituent 2.7 is:

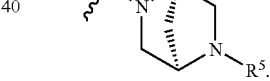
(2.7C1)

Another example of the Q substituent 2.8 is:

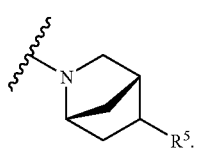
(2.8A1)

Another example of the Q substituent 2.8 is:

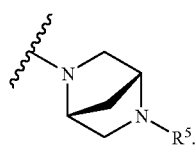
(2.8B1)

Another example of the Q substituent 2.8 is:

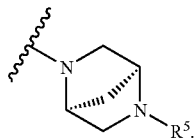
(2.8C1)

Another example of the Q substitutent is the piperazine ring:

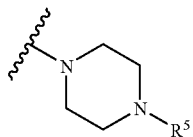

substituted with one or two substituents independently selected from the group consisting of $R^3$ groups, provided that said one or two substitutents are not H. In one embodiment said substituents are selected from the group consisting of alkyl groups (e.g., $C_1$ to $C_6$ alkyl, e.g., methyl). In another embodiment there is one substituent on said piperazine ring. In another embodiment there is one substituent on said piperazine ring and said substituent is methyl.

Another example of the Q substituent is the piperazine ring:

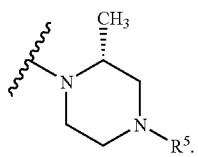

Another example of the Q substitutent is the piperidine ring:

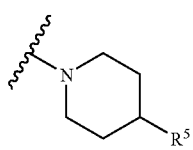

substituted with one or two substituents independently selected from the group consisting of $R^3$ groups, provided that said one or two substitutents are not H. In one embodiment said substituents are selected from the group consisting of alkyl groups (e.g., $C_1$ to $C_6$ alkyl, e.g., methyl). In another embodiment there is one substituent on said piperidine ring. In another embodiment there is one substituent on said piperidine ring and said substituent is methyl.

In one example of the Q substituent 2.16

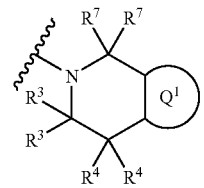
(2.16)

$Q^1$ is heteroaryl.

In another example of the Q substituent 2.16 $Q^1$ is aryl.

Thus, one example of the Q substituent 2.16 is 2.16A:

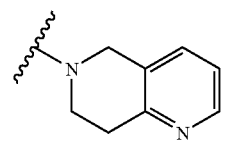
(2.16A)

(i.e., $Q^1$ is pyridyl, and each $R^3$, $R^4$ and $R^7$ is H).

In another example, the Q substituent 2.16 is 2.16A1:

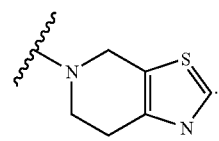
(2.16A1)

Another example of the Q substitutent 2.16 is 2.16B:

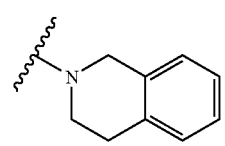
(2.16B)

(i.e., $Q^1$ is phenyl, and each $R^3$, $R^4$ and $R^7$ is H).

Another example of the Q substituent 2.16 is 2.16C

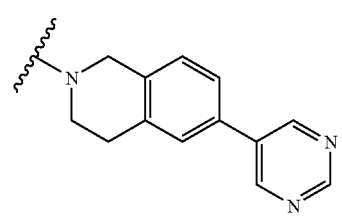
(2.16C)

(i.e., $Q^1$ is substituted phenyl, and each $R^3$, $R^4$ and $R^7$ is H).

Another example of the Q substituent 2.16 is 2.16D

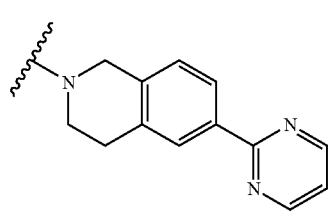
(2.16D)

(i.e., $Q^1$ is substituted phenyl, and each $R^3$, $R^4$ and $R^7$ is H).

Another example of the Q substituent 2.16 is 2.16E

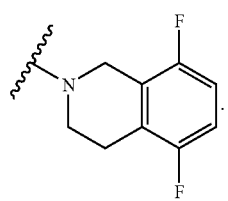
(2.16E)

When the Q substitutent comprises two $Q^1$ rings, each $Q^1$ ring is independently selected. Generally, the $Q^1$ cycloalkyl rings and the $Q^1$ substituted cycloalkyl rings comprise 5 to 7 ring carbons. In general, the heterocycloalkyl $Q^1$ rings and the substituted heterocycloalkyl $Q^1$ rings comprise 5 to 7 ring carbons and comprise 1 to 3 (generally 1 or 2, or generally 1) ring heteroatoms selected from the group consisting of: O, N and S. In general, the heteroaryl $Q^1$ rings and the substituted heteroaryl $Q^1$ rings comprise 5 to 7 ring carbons and comprise 1 to 3 (generally 1 or 2, or generally 1) ring heteroatoms selected from the group consisting of: O, N and S. Examples of the $Q^1$ rings include, but are not limited to: piperidinyl, piperazinyl, pyranyl, pyrrolidinyl, morpholinyl, thiomorpholinyl, pyridyl, pyrimidinyl, pyrrolyl, pyrazolyl, furanyl, thienyl, thiazolyl, imidazolyl, cyclopentyl, cyclohexyl and cycloheptyl. Examples of the $Q^1$ rings also include, but are not limited to: substituted piperidinyl, substituted piperazinyl, substituted pyranyl, substituted pyrrolidinyl, substituted morpholinyl, substituted thiomorpholinyl, substituted pyridyl, substituted pyrimidinyl, substituted pyrrolyl, substituted pyrazolyl, substituted furanyl, substituted thienyl, substituted thiazolyl, substituted imidazolyl, substituted cyclopentyl, substituted cyclohexyl and substituted cycloheptyl wherein said substituted $Q^1$ rings are substituted with 1 to 3 substitutents selected from the $R^{10}$ moieties.

Generally, the $Q^2$ cycloalkyl rings and the $Q^2$ substituted cycloalkyl rings comprise 5 to 7 ring carbons. In general, the heterocycloalkyl $Q^2$ rings and the substituted heterocycloalkyl $Q^1$ rings comprise 5 to 7 ring carbons and comprise 1 to 3 (generally 1 or 2, or generally 1) ring heteroatoms selected from the group consisting of: O, N and S.

Examples of the $Q^2$ rings include, but are not limited to: piperidinyl, piperazinyl, pyranyl, pyrrolidinyl, cyclopentyl, cyclohexyl and cycloheptyl. Examples of the $Q^2$ rings also include, but are not limited to: substituted piperidinyl, substituted piperazinyl, substituted pyranyl, substituted pyrrolidinyl, substituted morpholinyl, substituted thiomorpholinyl, substituted cyclopentyl, substituted cyclohexyl and substituted cycloheptyl wherein said substituted $Q^1$ rings are substituted with 1 to 3 substitutents selected from the $R^{10}$ moieties.

In one example the Q substituent 2.17 is:

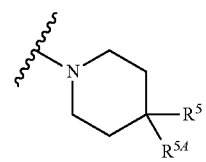
(2.17A)

wherein $R^{5A}$ is halo.

Another example of the Q substituent 2.17 is:

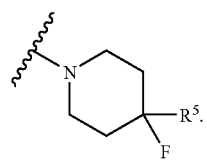
(2.17B)

Another example of the Q substituent 2.17 is:

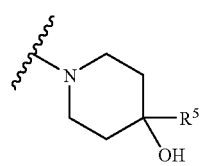
(2.17C)

Another example of the Q substituent 2.17 is:

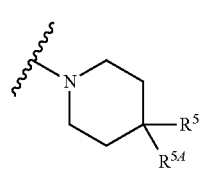
(2.17D)

wherein $R^{5A}$ is alkoxy, i.e., —O—($C_1$ to $C_6$)alkyl, such as, for example, —O—($C_1$ to $C_3$)alkyl, or —O—($C_1$ to $C_2$)alkyl.

Another example of the Q substituent 2.17 is:

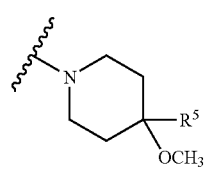
(2.17E)

Another example of the Q substituent 2.17 is:

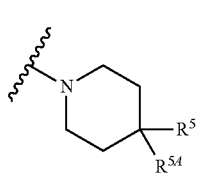

(2.17F)

wherein $R^{5A}$ is alkyl (e.g., —($C_1$ to $C_6$)alkyl, such as, for example, —($C_1$ to $C_3$)alkyl, or —($C_1$ to $C_2$)alkyl).

Thus, another example of the Q substituent 2.17 is:

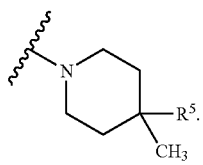

(2.17G)

Another example of the Q substituent 2.17 is:

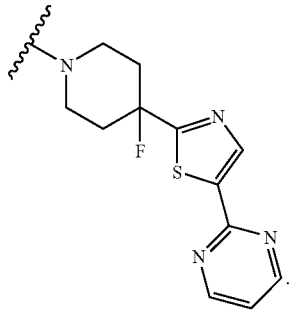 [SMILES: *N1CCC(F)(c2ncc(-c3ncccn3)s2)CC1]

Another example of the Q substituent 2.17 is:

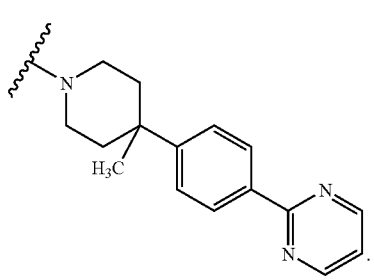 [SMILES: *N1CCC(C)(c2ccc(-c3ncccn3)cc2)CC1 ; "."]

Another example of the Q substituent 2.17 is:

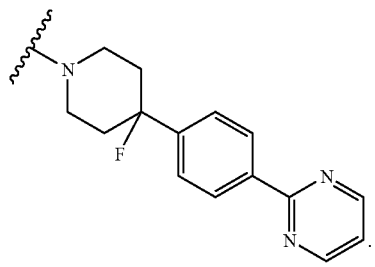 [SMILES: *N1CCC(F)(c2ccc(-c3ncccn3)cc2)CC1 ; "."]

An example of the Q substituent 2.2 is:

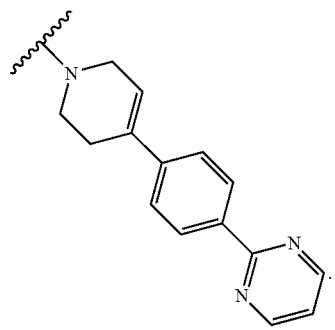 [SMILES: *N1CC=C(c2ccc(-c3ncccn3)cc2)CC1]

Another example of the Q substituent 2.2 is:

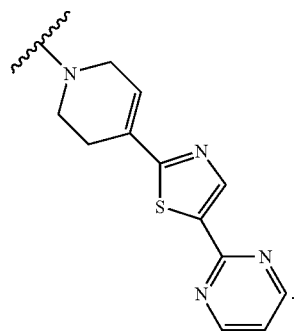 [SMILES: *N1CC=C(c2ncc(-c3ncccn3)s2)CC1]

Another example of the Q substituent 2.2 is:

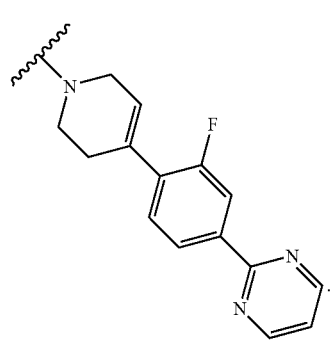 [SMILES: *N1CC=C(c2ccc(-c3ncccn3)cc2F)CC1]

Another example of the Q substituent 2.2 is:
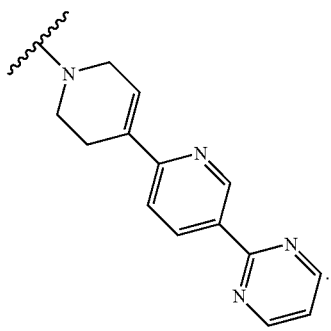 [SMILES: *N1CC=C(c2ccc(-c3ncccn3)cn2)CC1]
Another example of the Q substituent 2.2 is:
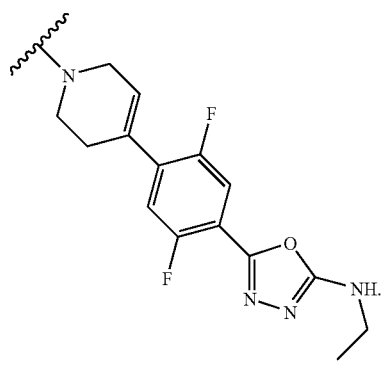 [SMILES: *N1CC=C(c2cc(F)c(-c3nnc(NCC)o3)cc2F)CC1]
Another example of the Q substituent 2.2 is:
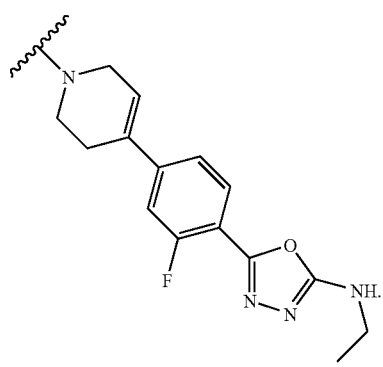 [SMILES: *N1CC=C(c2ccc(-c3nnc(NCC)o3)c(F)c2)CC1]
Another example of the Q substituent 2.2 is:
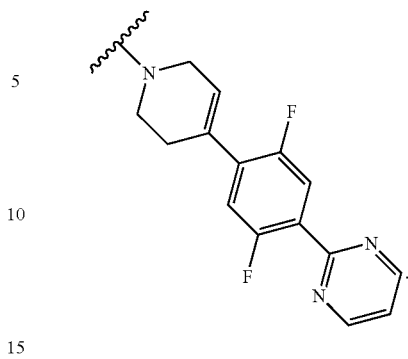
Another example of the Q substituent 2.2 is:
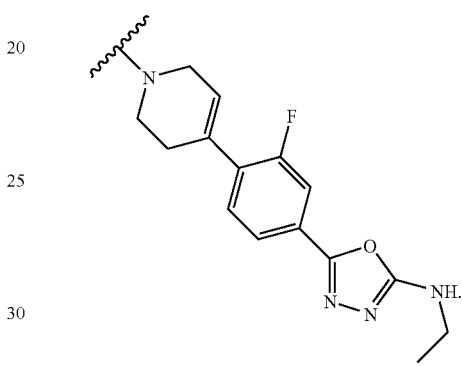
Another example of the Q substituent 2.6 is:
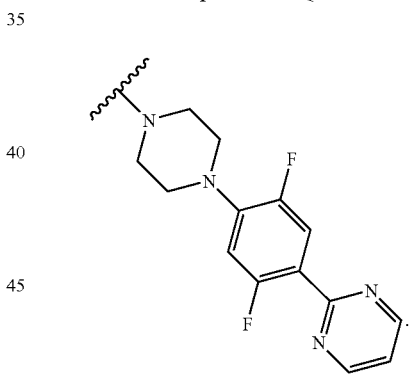
Examples of $R^1$ for the compounds of this invention (e.g., compounds of formulas 1.0, 1.0A1, 1.0B1, 1.0C1, 1.1, 1.1A, 1.2, 1.2A, 1.3 and 1.3A) include, but are not limited to:
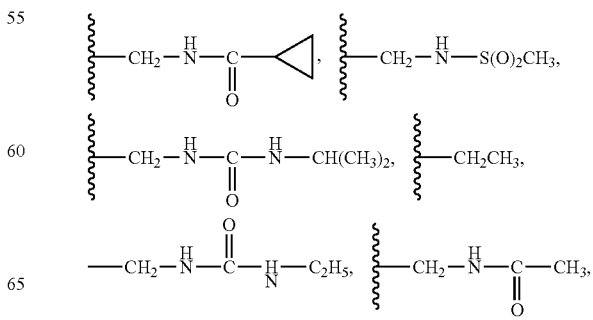

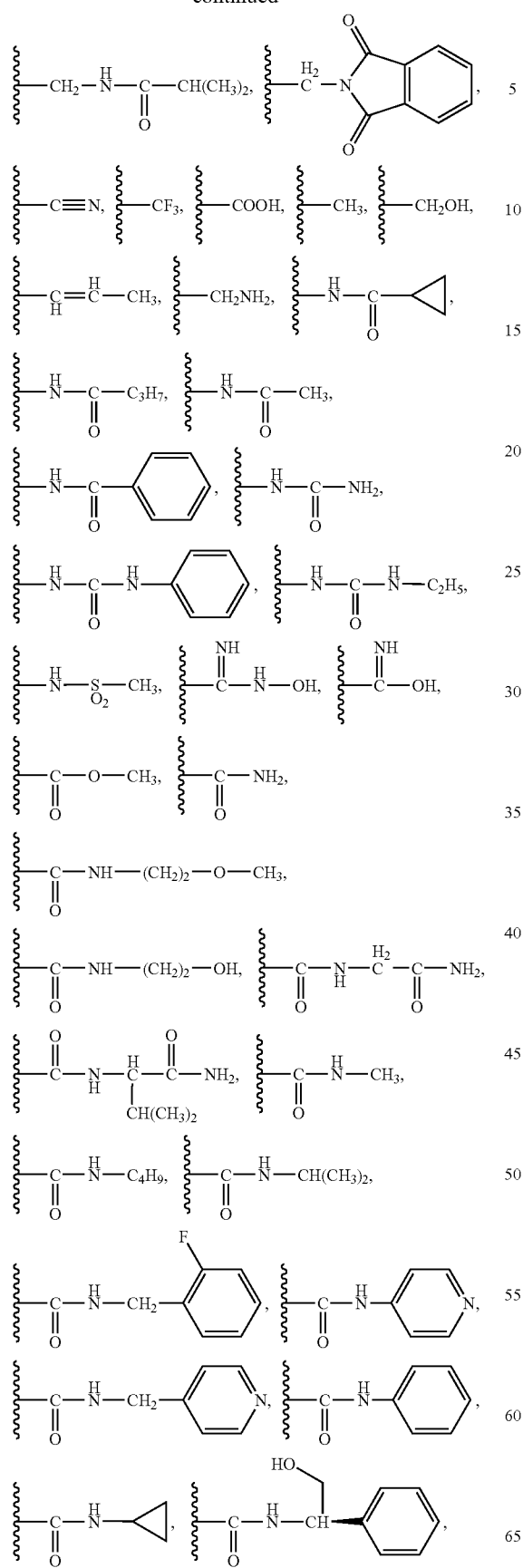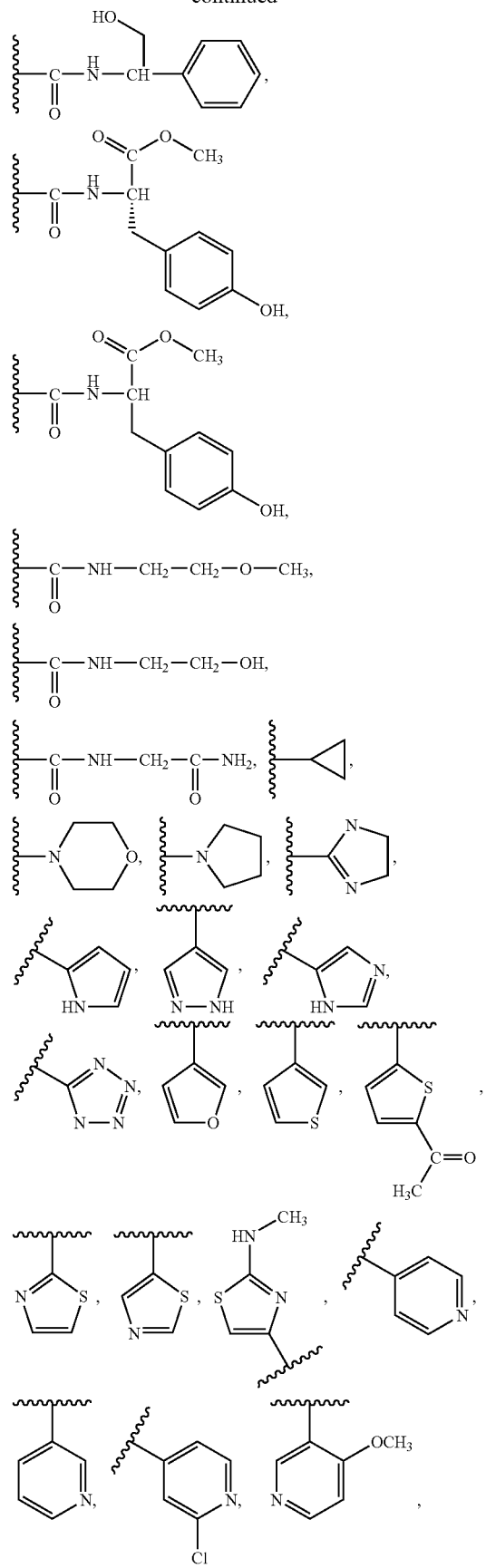

-continued
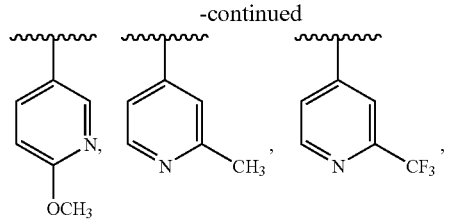
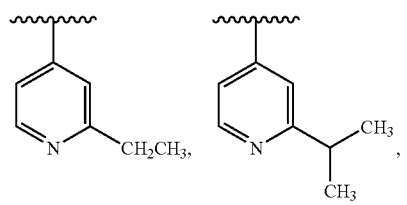
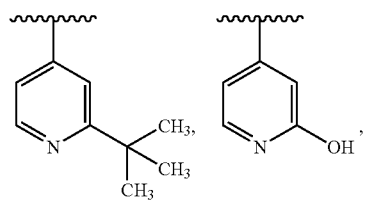
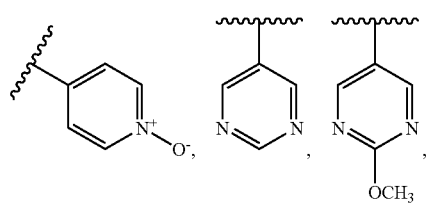
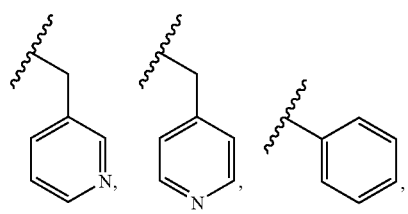
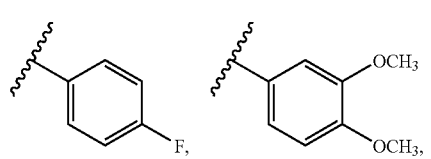
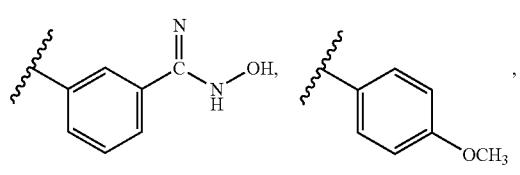
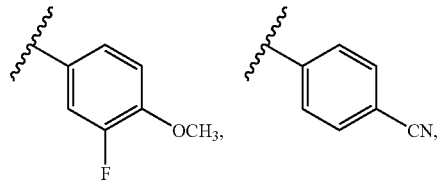
-continued
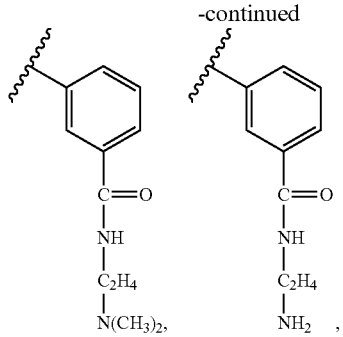
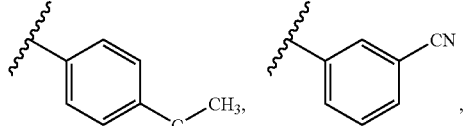
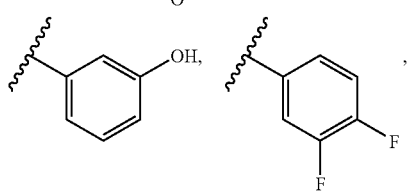
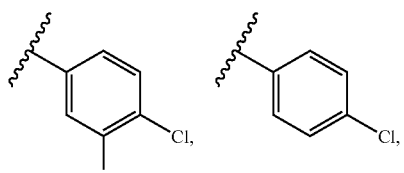
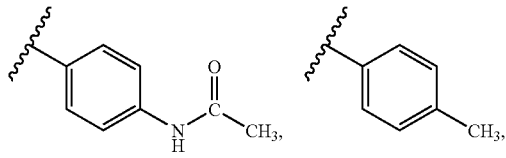
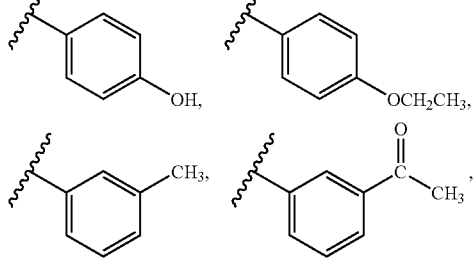
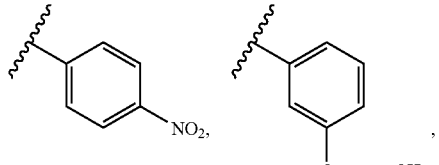
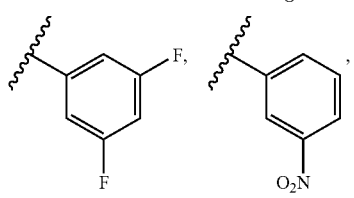

71
-continued
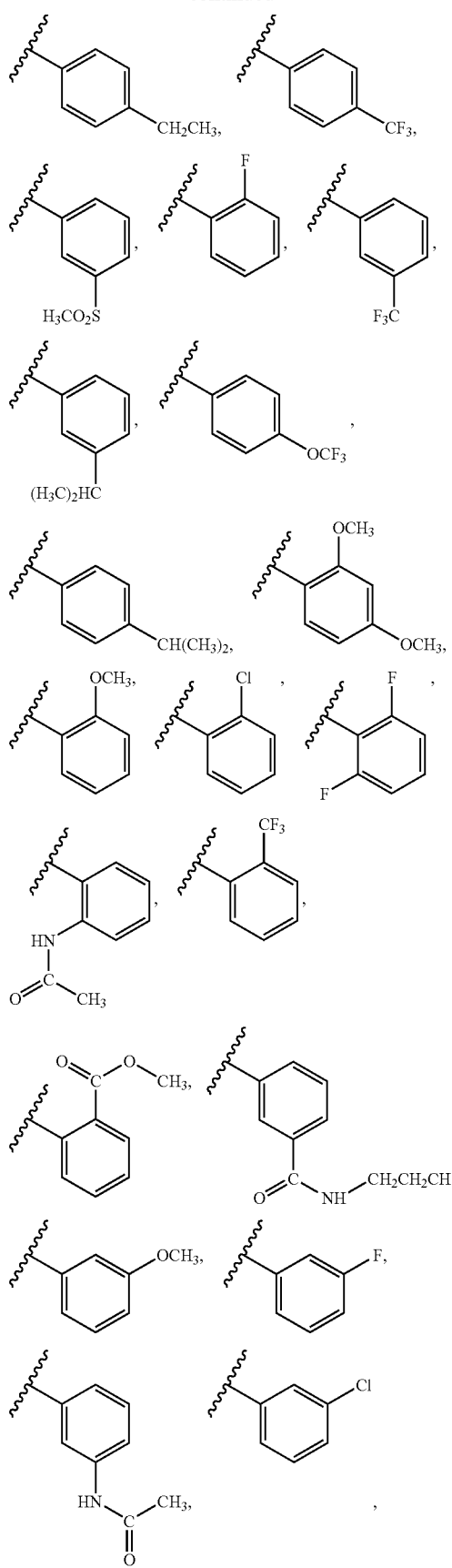
72
-continued
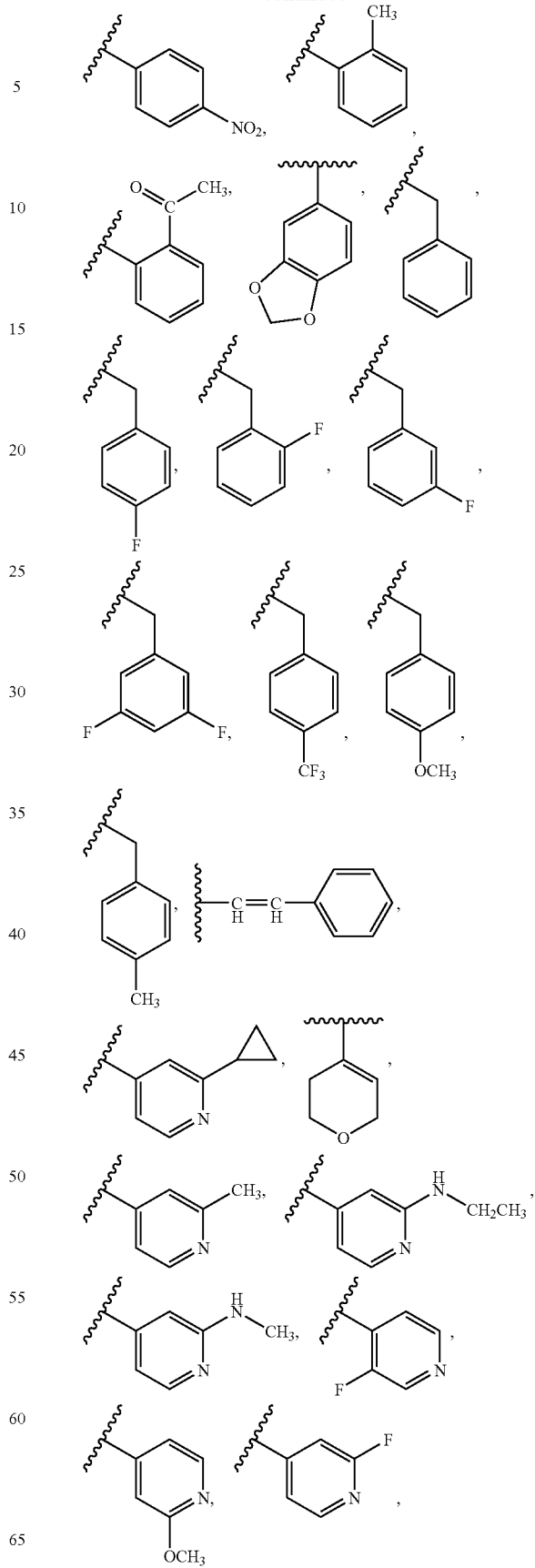

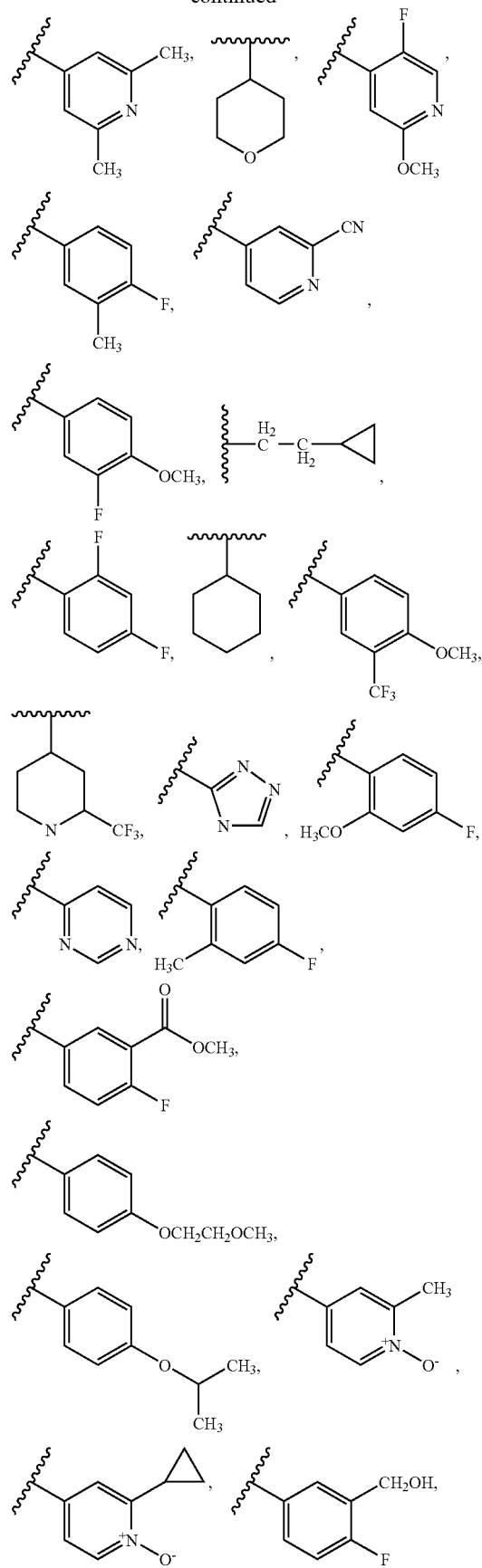
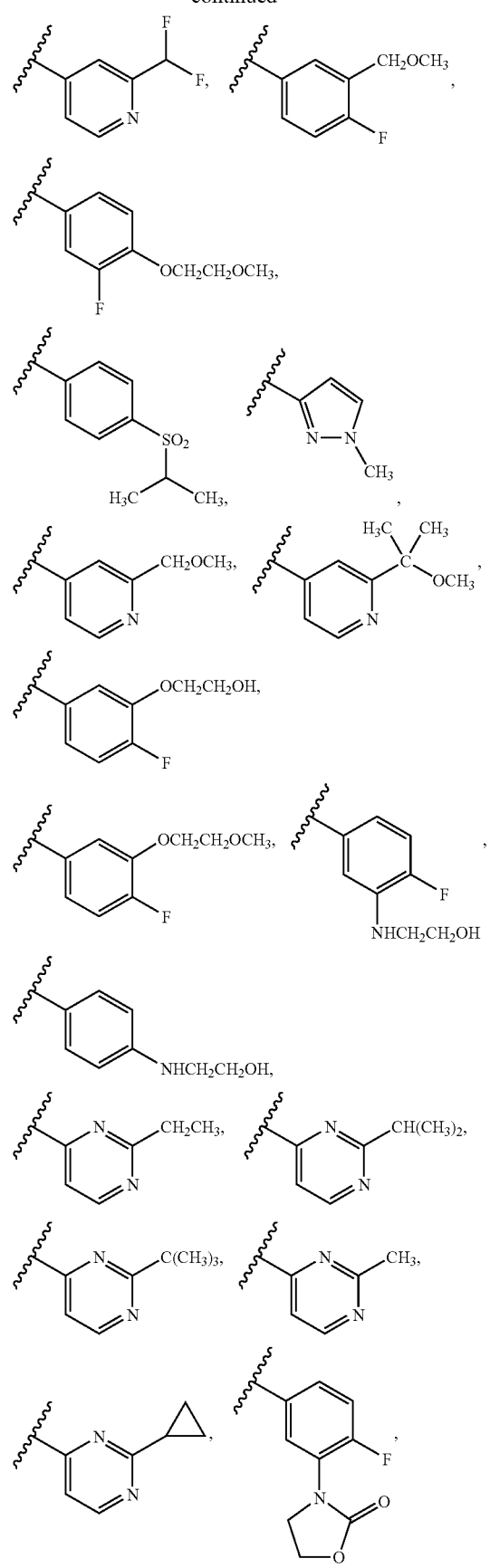

-continued

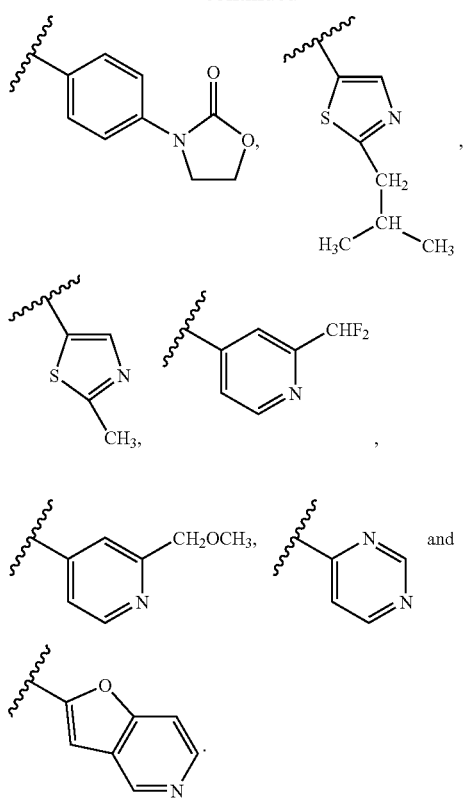

In one embodiment of this invention, R¹ is selected from the group consisting of:

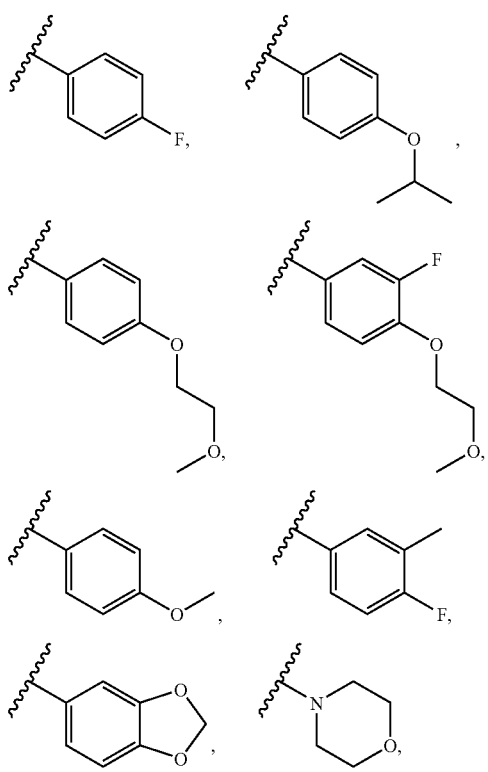

-continued

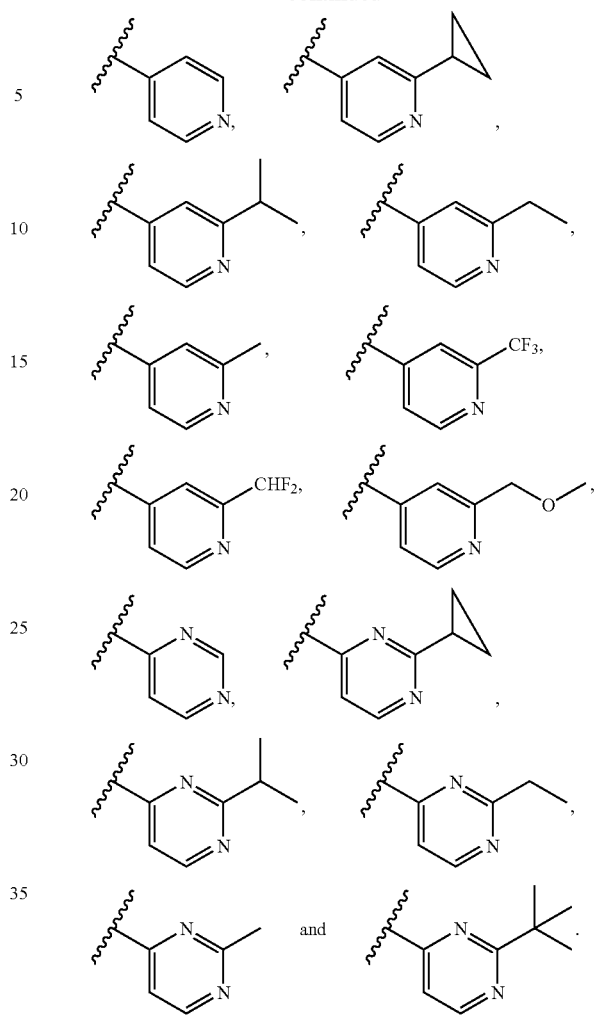

R¹, in one embodiment of this invention, is aryl (e.g., phenyl).

R¹, in one embodiment of this invention is substituted aryl, such as,

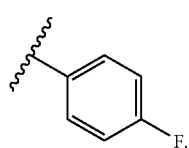 [SMILES: *c1ccc(F)cc1]

R¹, in another embodiment of this invention, is heteroaryl (e.g., in one embodiment R¹ is pyridyl N-oxide, and in another embodiment R¹ is pyridyl, such as

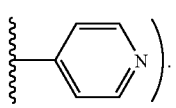

R¹, in one embodiment of this invention, is substituted heteroaryl (e.g., substituted pyridyl).

R¹, in one embodiment of this invention, is substituted heteroaryl (e.g., substituted pyridyl), such as, for example:

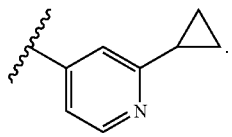

In another embodiment of this invention R¹ is:

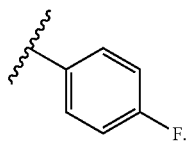 [SMILES: *c1ccc(F)cc1]

In another embodiment of this invention R¹ is:

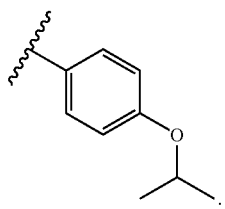 [SMILES: *c1ccc(OC(C)C)cc1]

In another embodiment of this invention R¹ is:

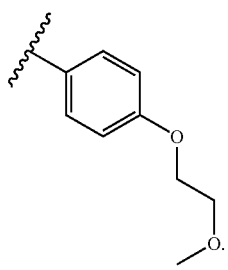 [SMILES: *c1ccc(OCCOC)cc1]

In another embodiment of this invention R¹ is:

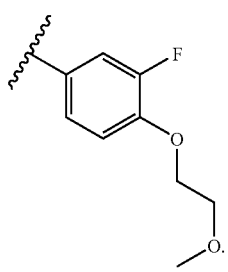 [SMILES: *c1ccc(OCCOC)c(F)c1]

In another embodiment of this invention R¹ is:

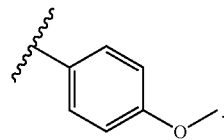 [SMILES: *c1ccc(OC)cc1]

In another embodiment of this invention R¹ is:

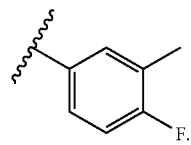 [SMILES: *c1ccc(F)c(C)c1]

In another embodiment of this invention R¹ is:

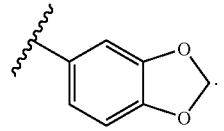 [SMILES: *c1ccc2c(c1)OCO2]

In another embodiment of this invention R¹ is:

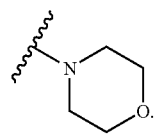

In another embodiment of this invention R¹ is:

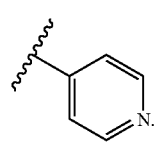

In another embodiment of this invention R¹ is:

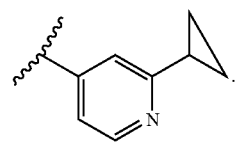 [SMILES: *c1ccnc(C2CC2)c1]

In another embodiment of this invention R¹ is:

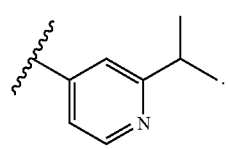 [SMILES: *c1ccnc(C(C)C)c1]

In another embodiment of this invention R¹ is:

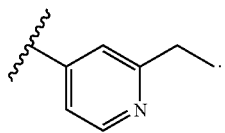 [SMILES: *c1ccnc(CC)c1]

In another embodiment of this invention R¹ is:

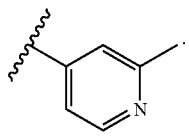 [SMILES: *c1ccnc(C)c1]

In another embodiment of this invention R¹ is:

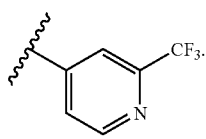 [SMILES: *c1ccnc(C(F)(F)F)c1]

In another embodiment of this invention R¹ is:

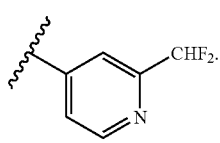 [SMILES: *c1ccnc(C(F)F)c1]

In another embodiment of this invention R¹ is:

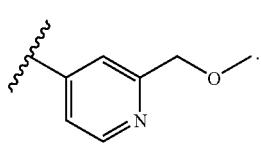 [SMILES: *c1ccnc(COC)c1]

In another embodiment of this invention R¹ is:

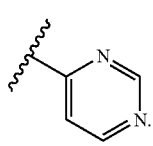

In another embodiment of this invention R¹ is:

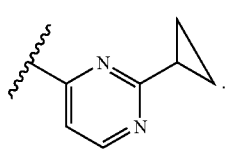 [SMILES: *c1ccnc(C2CC2)n1]

In another embodiment of this invention R¹ is:

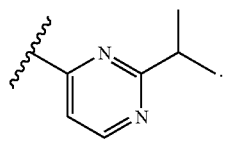 [SMILES: *c1ccnc(C(C)C)n1]

In another embodiment of this invention R¹ is:

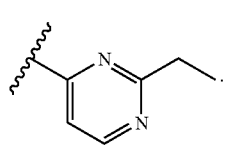 [SMILES: *c1ccnc(CC)n1]

In another embodiment of this invention R¹ is:

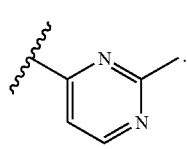 [SMILES: *c1ccnc(C)n1]

In another embodiment of this invention R¹ is:

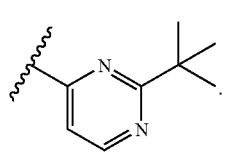 [SMILES: *c1ccnc(C(C)(C)C)n1]

In another embodiment of this invention R¹ is:

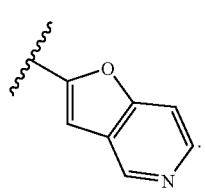 [SMILES: *c1cc2cnccc2o1]

Examples of R⁵ for the compounds of this invention (e.g., compounds of formulas 1.0, 1.0A1, 1.0B1, 1.0C1, 1.1, 1.1A, 1.2, 1.2A, 1.3 and 1.3A) include but are not limited to:

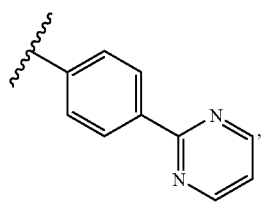

-continued
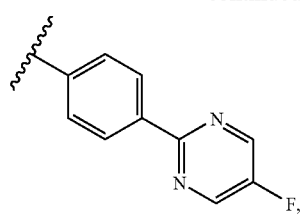
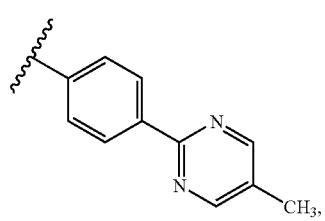
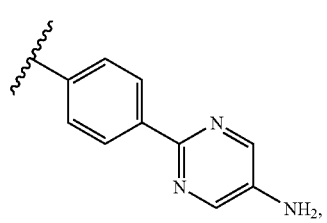
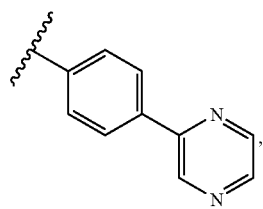
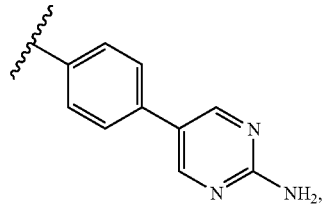
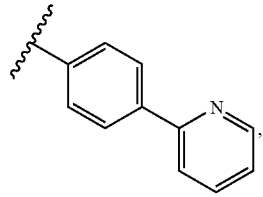
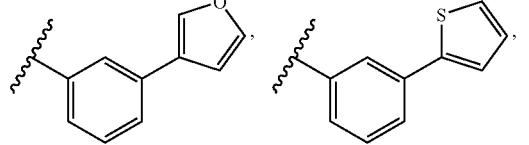
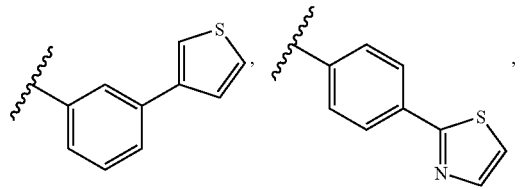
-continued
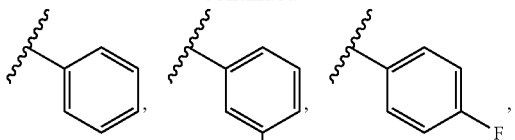
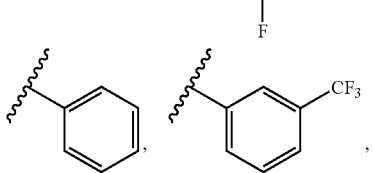
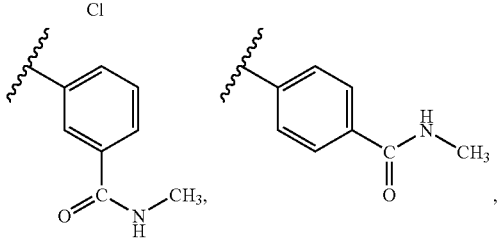
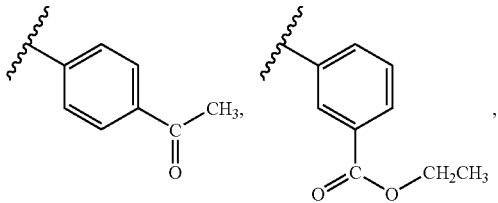
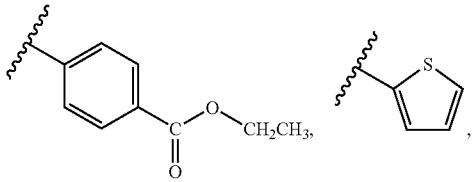
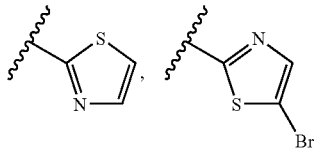
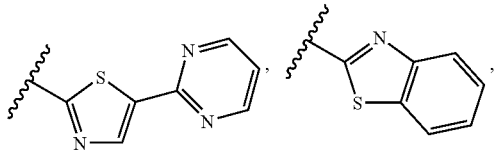
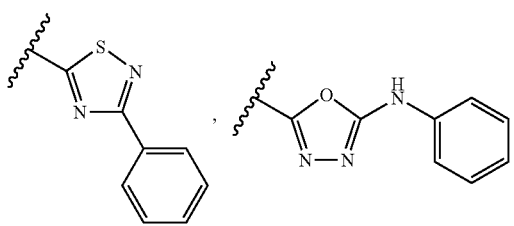
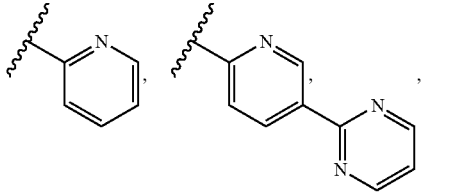

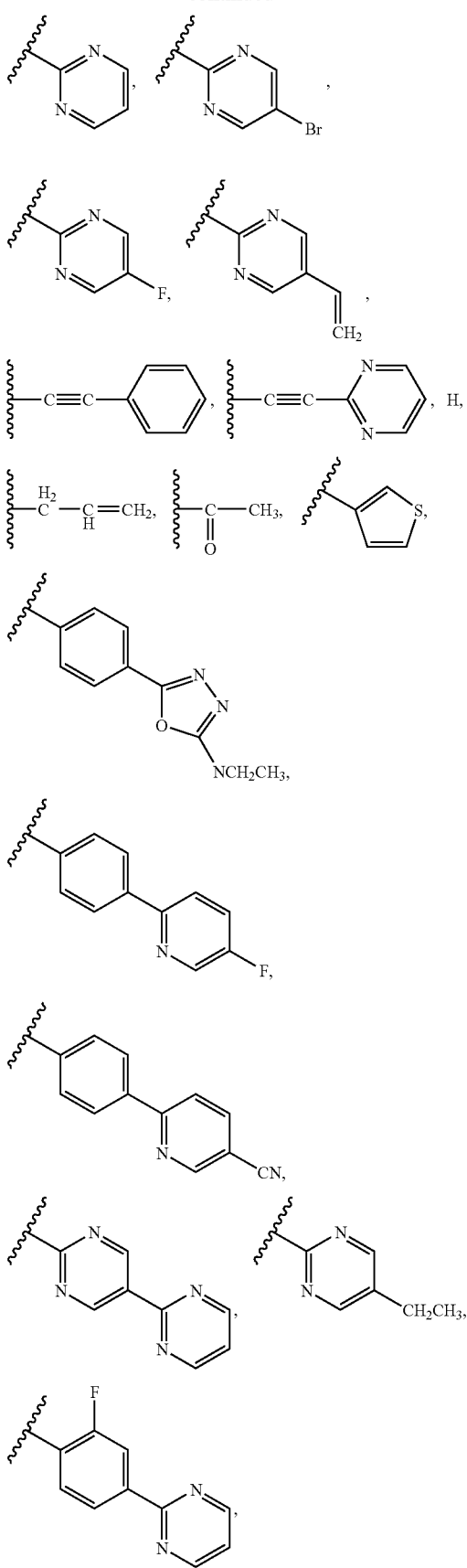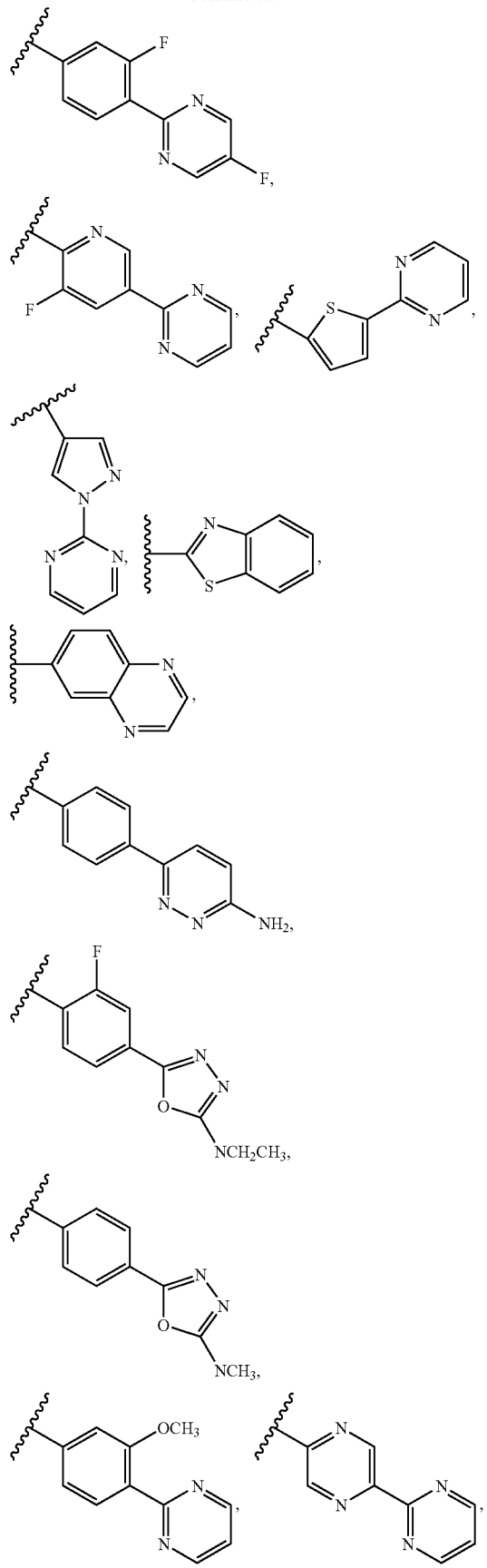

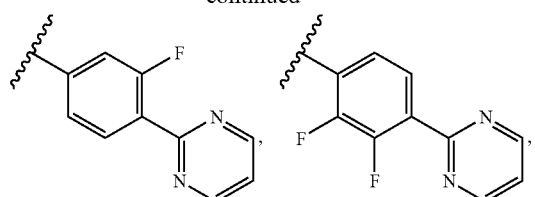
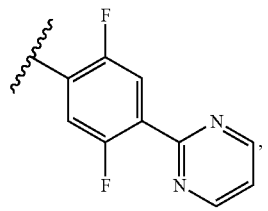
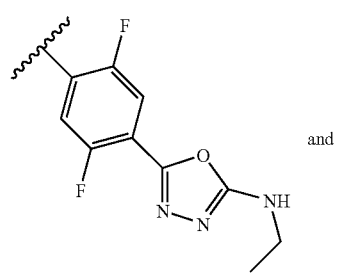
and
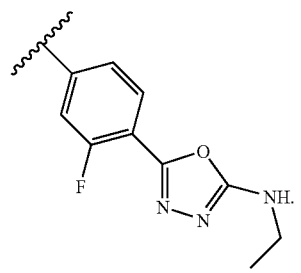
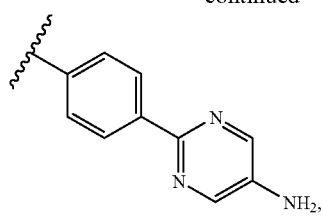
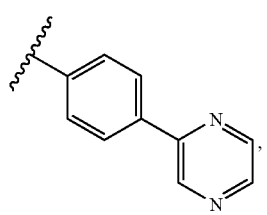
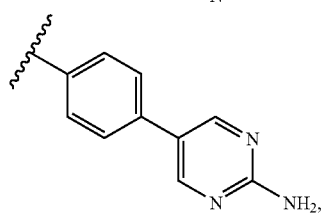
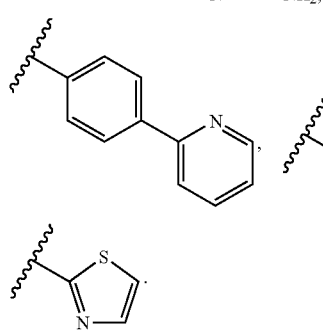 
and
In another embodiment of this invention, $R^5$ is selected from the group consisting of:
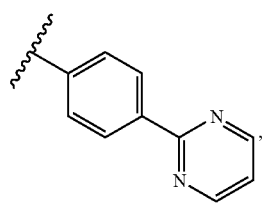
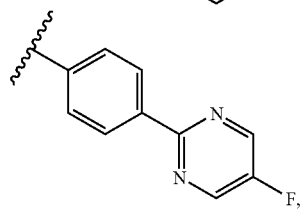
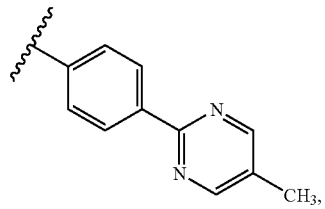
In another embodiment of this invention, $R^5$ is selected from the group consisting of:
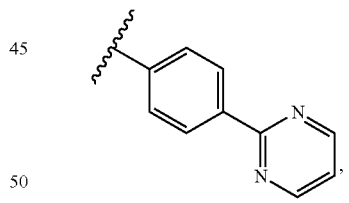
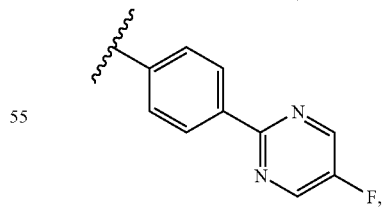
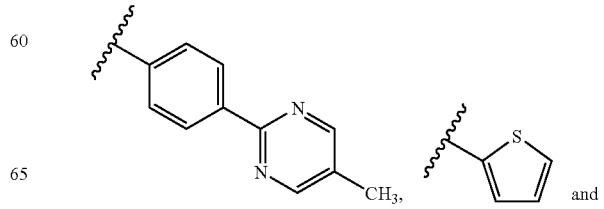
and

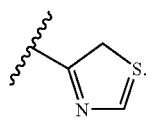
In another embodiment of this invention, $R^5$ is selected from the group consisting of:
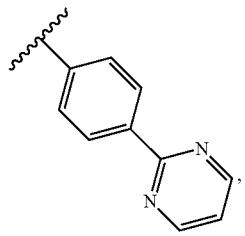 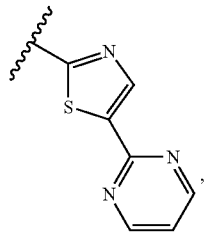
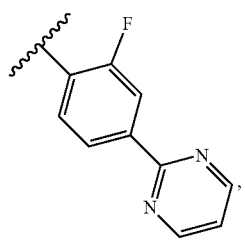 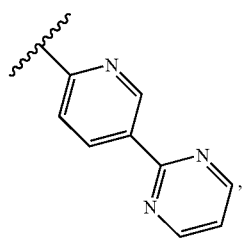
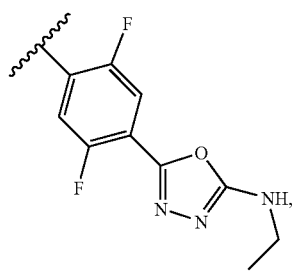
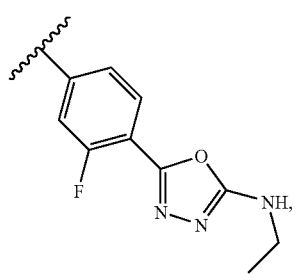
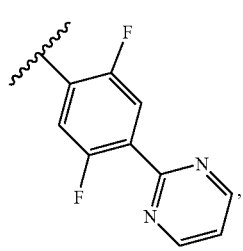
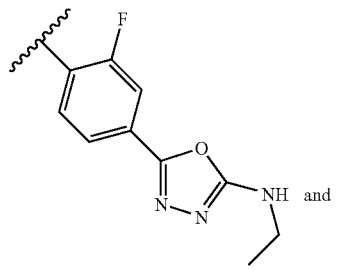
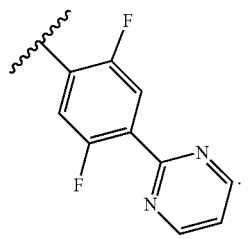
In another embodiment of this invention, $R^5$ is:
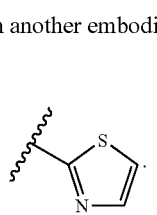
In another embodiment of this invention, $R^5$ is:
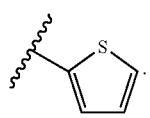
In another embodiment of this invention, $R^5$ is:
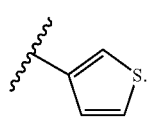
In another embodiment of this invention, $R^5$ is:
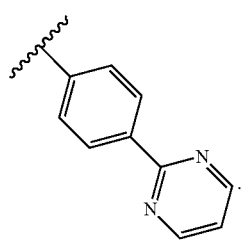 [SMILES: *c1ccc(-c2ncccn2)cc1]

In another embodiment of this invention, R⁵ is:

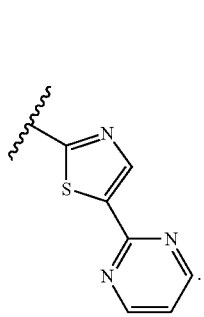 [SMILES: *c1ncc(-c2ncccn2)s1]

In another embodiment of this invention, R⁵ is:

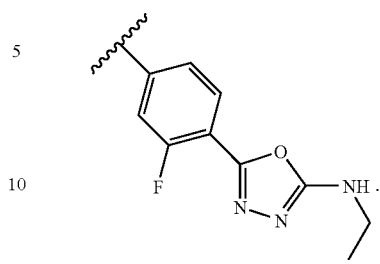

In another embodiment of this invention, R⁵ is:

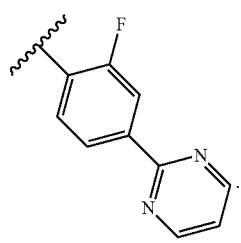 [SMILES: *c1ccc(-c2ncccn2)cc1F]

In another embodiment of this invention, R⁵ is:

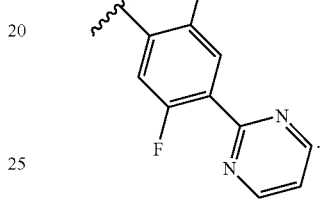

In another embodiment of this invention, R⁵ is:

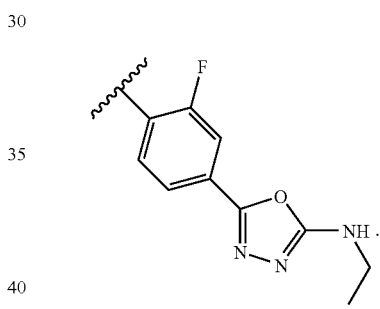

In another embodiment of this invention, R⁵ is:

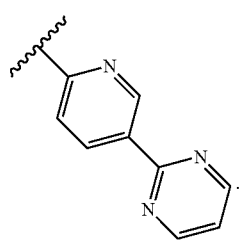 [SMILES: *c1ccc(-c2ncccn2)cn1]

In another embodiment of this invention, R⁵ is:

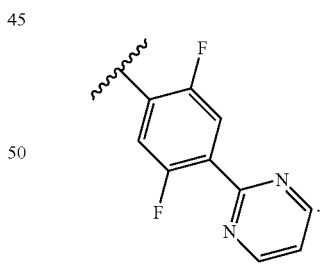

In another embodiment of this invention, R⁵ is:

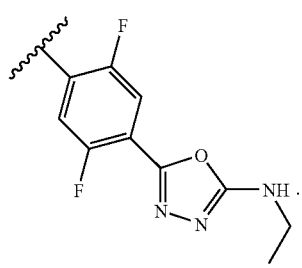 [SMILES: *c1cc(F)c(-c2nnc(NCC)o2)cc1F]

$R^2$, in one embodiment of this invention, is $—(CH_2)_m R^{11}$, wherein $R^{11}$ is $—OR^{10}$.

$R^2$, in another embodiment of this invention, is $—(CH_2)_m R^{11}$, wherein $R^{11}$ is $—OR^{10}$, and $R^{10}$ is H or alkyl.

$R^2$, in another embodiment of this invention, is $—(CH_2)_m R^{11}$, wherein $R^{11}$ is $—OR^{10}$, and $R^{10}$ alkyl (e.g., methyl).

$R^2$, in another embodiment of this invention, is $—(CH_2)_m R^{11}$, wherein m is 1 and $R^{11}$ is $—OR^{10}$.

$R^2$, in another embodiment of this invention, is $—(CH_2)_m R^{11}$, wherein m is 1, $R^{11}$ is $—OR^{10}$, and $R^{10}$ is H or alkyl.

$R^2$, in another embodiment of this invention, is —$(CH_2)_m$ $R^{11}$, wherein m is 1, $R^{11}$ is —$OR^{10}$, and $R^{10}$ alkyl.

$R^2$, in another embodiment of this invention, is —$(CH_2)_m$ $R^{11}$ wherein m is 1, $R^{11}$ is —$OR^{10}$, and $R^{10}$ methyl (i.e., $R^2$ is —$CH_2OCH_3$).

$R^2$, in another embodiment of this invention, is —$OR^{23}$ wherein $R^{23}$ is alkyl, and said alkyl is methyl (i.e., $R^2$ is —$OCH_3$).

$R^2$, in another embodiment of this invention, is alkynyl. An example of an alkynyl group is ethynyl:

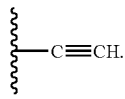

Another example of an alkynyl group is propynyl:

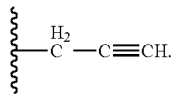

$R^2$, in another embodiment of this invention, is alkenyl. An example of an alkenyl group is —$CH_2$—$CH$=$CH_2$.

$R^2$, in another embodiment of this invention, is —$OCH_3$.

$R^2$, in another embodiment of this invention, is —$S(O)_t$-alkyl.

$R^2$, in another embodiment of this invention, is —S-alkyl (i.e., t is 0) such as, for example, —S—$CH_3$.

$R^2$, in another embodiment of this invention, is —$S(O)_2$-alkyl (i.e., t is 2) such as, for example, —$S(O)_2CH_3$.

$R^2$, in another embodiment of this invention, is —$SCH_3$.

$R^2$, in another embodiment of this invention, is —$S(O)_2CH_3$.

$R^2$, in another embodiment of this invention, is ethynyl

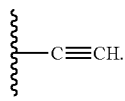

$R^2$, in another embodiment of this invention, is —$CH_2OCH_3$.

Preferably $R^2$ is selected from the group consisting of: ethynyl, —$OCH_3$, and —$CH_2OCH_3$.

Additional examples of the $R^2$—$(CH_2)_mR^{11}$ group include, but are not limited to —$CH_2OH$, —$CH_2CN$, —$CH_2OC_2H_5$, —$(CH_2)_3OCH_3$, —$CH_2F$ and —$CH_2$-triazolyl, such as,

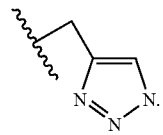

Additional examples of $R^2$ include, but are not limited to, H, —$CH_2$-morpholinyl, —$SCH_3$, —$OC_2H_5$, —$OCH(CH_3)_2$, —$CH_2N(CH_3)_2$, —CN, —$CH(OH)CH_3$, —$C(O)CH_3$, —$CH_2C$≡$CCH_3$, —$CH(CH_3)_2$, —$C(CH_3)$=$CH_2$, —$C(CH_3)$=$NOCH_3$, —$C(CH_3)$=$NOH$, —$C(CH_3)$=$NNHC(O)CH_3$, —$NH_2$, —$NHC(O)H$, —$NHCH_3$, —$CH_2$—O—$CH_2$-cyclopropyl, —$CH_2$—O—$CHF_2$, —$OCHF_2$, —$CHF_2$, —$CH_2C(CH_3)$=$CH_3$, —$CH_2CH_2CH_3$, —$N(CH_3)_2$, —$CH_2CH_3$, —$CF_3$, —CH=$CH_2$, and —$C(OH)(CH_3)_2$.

$R^3$, in one embodiment of this invention, is independently selected from the group consisting of: H and alkyl.

$R^3$, in another embodiment of this invention, is independently selected from the group consisting of: H and methyl.

$R^3$, in another embodiment of this invention, is H.

$R^4$, in one embodiment of this invention, $R^4H$.

$R^4$, in another embodiment of this invention, is selected from the group consisting of: H and alkyl.

$R^4$, in another embodiment of this invention, is selected from the group consisting of: H and methyl.

$R^6$, in one embodiment of this invention, is $R^6H$.

$R^7$, in one embodiment of this invention, is independently selected from the group consisting of: H and alkyl.

$R^7$, in another embodiment of this invention, is independently selected from the group consisting of: H and methyl.

$R^7$, in one embodiment of this invention, is H.

$R^8$, in one embodiment of this invention, is H.

$Y^1$, in one embodiment of this invention, is carbon.

$Y^2$, in one embodiment of this invention, is carbon.

$Y^3$ in one embodiment of this invention, is carbon.

$Y^1$, $Y^2$ and $Y^3$, in one embodiment of this invention, are carbon.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16, and each $R^3$, $R^4$, and $R^7$ is independently selected from the group consisting of: H and methyl.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16A, and each $R^3$, $R^4$, and $R^7$ is independently selected from the group consisting of: H and methyl.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16B, and each $R^3$, $R^4$, and $R^7$ is independently selected from the group consisting of: H and methyl.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16, and each $R^3$, $R^4$, and $R^7$ is H.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16A, and each $R^3$, $R^4$, and $R^7$ is H.

One embodiment of this invention is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16B, and each $R^3$, $R^4$, and $R^7$ is H.

The compounds of this invention inhibit the activity of ERK1 and ERK2 Thus, this invention further provides a method of inhibiting ERK in mammals, especially humans, by the administration of an effective amount (e.g., a therapeutically effective amount) of one or more (e.g., one) compounds of this invention. The administration of the compounds of this invention to patients, to inhibit ERK1 and/or ERK2, is useful in the treatment of cancer.

In any of the methods of treating cancer described herein, unless stated otherwise, the methods can optionally include the administration of an effective amount of one or more (e.g., 1, 2 or 3, or 1 or 2, or 1) chemotherapeutic agents. The chemotherapeutic agents can be administered currently or sequentially with the compounds of this invention.

The methods of treating cancer described herein include methods wherein a combination of drugs (i.e., compounds, or pharmaceutically active ingredients, or pharmaceutical compositions) are used (i.e., the methods of treating cancer of this invention include combination therapies). Those skilled in the art will appreciate that the drugs are generally administered individually as a pharmaceutical composition. The use of a pharmaceutical composition comprising more than one drug is within the scope of this invention.

In any of the methods of treating cancer described herein, unless stated otherwise, the methods can optionally include the administration of an effective amount of radiation therapy. For radiation therapy, γ-radiation is preferred.

Examples of cancers which may be treated by the methods of this invention include, but are not limited to: (A) lung cancer (e.g., lung adenocarcinoma and non small cell lung cancer), (B) pancreatic cancers (e.g., pancreatic carcinoma such as, for example, exocrine pancreatic carcinoma), (C) colon cancers (e.g., colorectal carcinomas, such as, for example, colon adenocarcinoma and colon adenoma), (D) myeloid leukemias (for example, acute myelogenous leukemia (AML), CML, and CMML), (E) thyroid cancer, (F) myelodysplastic syndrome (MDS), (G) bladder carcinoma, (H) epidermal carcinoma, (I) melanoma, (J) breast cancer, (K) prostate cancer, (L) head and neck cancers (e.g., squamous cell cancer of the head and neck), (M) ovarian cancer, (N) brain cancers (e.g., gliomas, such as glioma blastoma multiforme), (O) cancers of mesenchymal origin (e.g., fibrosarcomas and rhabdomyosarcomas), (P) sarcomas, (Q) tetracarcinomas, (R) nuroblastomas, (S) kidney carcinomas, (T) hepatomas, (U) non-Hodgkin's lymphoma, (V) multiple myeloma, and (W) anaplastic thyroid carcinoma.

Chemotherapeutic agents (antineoplastic agent) include but are not limited to: microtubule affecting agents, alkylating agents, antimetabolites, natural products and their derivatives, hormones and steroids (including synthetic analogs), and synthetics.

Examples of alkylating agents (including nitrogen mustards, ethylenimine derivatives, alkyl sulfonates, nitrosoureas and triazenes) include: Uracil mustard, Chlormethine, Cyclophosphamide (Cytoxan®), Ifosfamide, Melphalan, Chlorambucil, Pipobroman, Triethylene-melamine, Triethylenethiophosphoramine, Busulfan, Carmustine, Lomustine, Streptozocin, Dacarbazine, and Temozolomide.

Examples of antimetabolites (including folic acid antagonists, pyrimidine analogs, purine analogs and adenosine deaminase inhibitors) include: Methotrexate, 5-Fluorouracil, Floxuridine, Cytarabine, 6-Mercaptopurine, 6-Thioguanine, Fludarabine phosphate, Pentostatine, and Gemcitabine.

Examples of natural products and their derivatives (including vinca alkaloids, antitumor antibiotics, enzymes, lymphokines and epipodophyllotoxins) include: Vinblastine, Vincristine, Vindesine, Bleomycin, Dactinomycin, Daunorubicin, Doxorubicin, Epirubicin, Idarubicin, Paclitaxel (paclitaxel is a microtubule affecting agent and is commercially available as Taxol®), Paclitaxel derivatives (e.g. taxotere), Mithramycin, Deoxyco-formycin, Mitomycin-C, L-Asparaginase, Interferons (especially IFN-a), Etoposide, and Teniposide.

Examples of hormones and steroids (including synthetic analogs) include: 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, and Zoladex.

Examples of synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Examples of other chemotherapeutics include: Navelbene, CPT-11, Anastrazole, Letrazole, Capecitabinbe, Reloxafine, and Droloxafine.

A microtubule affecting agent (e.g., paclitaxel, a paclitaxel derivative or a paclitaxel-like compound), as used herein, is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents, useful in the methods of this invention, are well known to those skilled in the art and include, but are not limited to: Allocolchicine (NSC 406042), Halichondrin B (NSC 609395), Colchicine (NSC 757), Colchicine derivatives (e.g., NSC 33410), Dolastatin 10 (NSC 376128), Maytansine (NSC 153858), Rhizoxin (NSC 332598), Paclitaxel (Taxol®, NSC 125973), Paclitaxel derivatives (e.g., Taxotere, NSC 608832), Thiocolchicine (NSC 361792), Trityl Cysteine (NSC 83265), Vinblastine Sulfate (NSC 49842), Vincristine Sulfate (NSC 67574), Epothilone A, Epothilone, Discodermolide (see Service, (1996) Science, 274:2009), Estramustine, Nocodazole, MAP4, and the like. Examples of such agents are described in, for example, Bulinski (1997) J. Cell Sci. 110:3055-3064, Panda (1997) Proc. Natl. Acad. Sci. USA 94:10560-10564, Muhlradt (1997) Cancer Res. 57:3344-3346, Nicolaou (1997) Nature 387:268-272, Vasquez (1997) Mol. Biol. Cell. 8:973-985, and Panda (1996) J. Biol. Chem. 271:29807-29812.

Chemotherapeutic agents with paclitaxel-like activity include, but are not limited to, paclitaxel and paclitaxel derivatives (paclitaxel-like compounds) and analogues. Paclitaxel and its derivatives (e.g. Taxol and Taxotere) are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz (1992) Trends Pharmacol. Sci. 13: 134-146, Rowinsky (1990) J. Natl. Canc. Inst. 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:37-47).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. For example, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45(2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) J. Molec. Biol., 89: 737-758. U.S. Pat. No. 5,569,720 also provides in vitro and in vivo assays for compounds with paclitaxel-like activity.

Thus, in the methods of this invention wherein at least one chemotherapeutic agent is used, examples of said chemotherapeutic agents include those selected from the group consisting of: microtubule affecting agents, alkylating agents, antimetabolites, natural products and their derivatives, hormones and steroids (including synthetic analogs), and synthetics.

In the methods of this invention wherein at least one chemotherapeutic agent is used, examples of said chemotherapeutic agents also include: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

In the methods of this invention wherein at least one chemotherapeutic agent is used, examples of such chemotherapeutic agents include:

(1) taxanes such as paclitaxel (TAXOL®) and/or docetaxel (Taxotere®);

(2) platinum coordinator compounds, such as, for example, carboplatin, cisplatin and oxaliplatin (e.g. Eloxatin);

(3) EGF inhibitors that are antibodies, such as: HER2 antibodies (such as, for example trastuzumab (Herceptin®), Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sutton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), CI 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA);

(4) EGF inhibitors that are small molecules, such as, Tarceva™ (OSI-774, OSI Pharmaceuticals, Inc.), and Iressa (ZD 1839, Astra Zeneca);

(5) VEGF inhibitors that are antibodies such as: bevacizumab (Genentech, Inc.), and IMC-1C11 (ImClone Systems), DC 101 (a KDR VEGF Receptor 2 from ImClone Systems);

(6) VEGF kinase inhibitors that are small molecules such as SU 5416 (from Sugen, Inc), SU 6688 (from Sugen, Inc.), Bay 43-9006 (a dual VEGF and bRAF inhibitor from Bayer Pharmaceuticals and Onyx Pharmaceuticals);

(7) estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.);

(8) anti-tumor nucleoside derivatives such as 5-fluorouracil, gemcitabine, capecitabine, cytarabine (Ara-C), fludarabine (F-Ara-A), decitabine, and chlorodeoxyadenosine (Cda, 2-Cda);

(9) epothilones such as BMS-247550 (Bristol-Myers Squibb), and EPO906 (Novartis Pharmaceuticals);

(10) topoisomerase inhibitors such as topotecan (Glaxo SmithKline), and Camptosar (Pharmacia);

(11) vinca alkaloids, such as, navelbine (Anvar and Fabre, France), vincristine and vinblastine;

(12) antibodies that are inhibitors of αVβ3 integrins, such as, LM-609 (see, Clinical Cancer Research, Vol. 6, page 3056-3061, August 2000, the disclosure of which is incorporated herein by reference thereto);

(13) folate antagonists such as Methotrexate (MTX), and Premetrexed (Alimta);

(14) ribonucleotide reductase inhibitors, such as Hydroxyurea (HU);

(15) anthracyclines, such as Daunorubicin, Doxorubicin (Adriamycin), and Idarubicin;

(16) biologics, such as interferon (e.g., Intron-A and Roferon), pegylated interferon (e.g., Peg-Intron and Pegasys), and Rituximab (Rituxan, antibody used for the treatment of non-Hodgkin's lymphoma);

(17) thalidomide (or related imid);

(18) Bcr/abl kinase inhibitors, such as, for example Gleevec (STI-571), AMN-17, ONO12380, SU11248 (Sunitinib) and BMS-354825

(19) MEK1 and/or MEK2 inhibitors, such as PD0325901 and Arry-142886 (AZD6244);

(20) IGF-1 and IGF-2 inhibitors that are small molecules, such as, for example, NVP-AEW541;

(21) small molecule inhibitors of RAF and BRAF kinases, such as, for example, BAY 43-9006 (Sorafenib);

(22) small molecule inhibitors of cell cycle dependent kinases such as CDK1, CDK2, CDK4 and CDK6, such as, for example, CYC202, BMS387032, and Flavopiridol;

(23) alkylating agents, such as, for example, Temodar® brand of temozolomide;

(24) farnesyl protein transferase inhibitors, such as, for example:
- (a) Sarasar® brand of Ionifarnib (i.e., 4-[2-[4-(3,10-dibromo-8-chloro-6,11-dihydro-5H-benzo[5,6]cyclohepta[1,2-b]hyridin-11-yl)-1-piperidinyl)-2-oxoethyl]-1-piperidinecarboxamide, see for example, U.S. Pat. No. 5,874,442 issued Feb. 23, 1999, and U.S. Pat. No. 6,632,455 issued Oct. 14, 2003 the disclosures of each being incorporated herein by reference thereto),
- (b) Zarnestra® brand of tipifarnib (i.e., (R)-6-amino[(4-chlorophenyl)(1-methyl-1H-imidazol-5-yl)methyl]-4-(3-chlorophenyl)-1-methyl-2(1H)-quinolinone, see for example, WO 97/16443 published May 9, 1997 and U.S. Pat. No. 5,968,952 issued Oct. 19, 1999, the disclosures of each being incorporated herein by reference thereto), and
- (c) Bristol-Myers Squibb 214662:

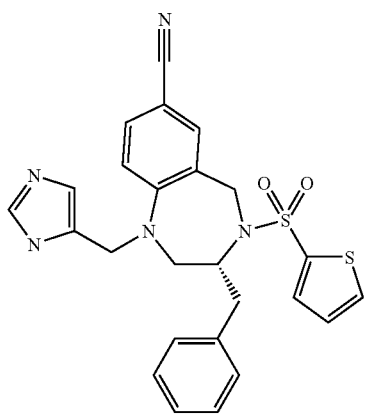 [SMILES: N#Cc1ccc2c(c1)CN(S(=O)(=O)c1cccs1)[C@H](Cc1ccccc1)CN2Cc1cnc[nH]1]

(see WO97/30992 published Aug. 28, 1997, U.S. Pat. No. 6,011,029 issued Jan. 4, 2000, and U.S. Pat. No. 6,455,523, the disclosures of each being incorporated herein by reference thereto).

The Bcr/abl kinase inhibitors, EGF receptor inhibitors, and HER-2 antibodies (EGF receptor inhibitors that are antibodies) described above are also known as signal transduction inhibitors. Therefore, chemotherapeutic agents, as used herein, include signal transduction inhibitors.

Typical signal transduction inhibitors, that are chemotherapeutic agents, include but are not limited to: (i) Bcr/abl kinase inhibitors such as, for example, STI 571 (Gleevec), (ii) Epidermal growth factor (EGF) receptor inhibitor such as, for example, Kinase inhibitors (Iressa, OSI-774) and antibodies (Imclone: C225 [Goldstein et al. (1995), Clin Cancer Res. 1:1311-1318], and Abgenix: ABX-EGF) and (iii) HER-2/neu receptor inhibitors such as, for example, Herceptin® (trastuzumab).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N.J. 07645-1742, USA), the Physician's Desk Reference, 56$^{th}$ Edition, 2002 (published by Medical Economics company, Inc. Montvale, N.J. 07645-1742), and the Physician's Desk Reference, 57$^{th}$ Edition, 2003 (published by Thompson PDR, Montvale, N.J. 07645-1742); the disclosures of which is incorporated herein by reference thereto.

For example, the compound of formula 1.0 (e.g., a pharmaceutical composition comprising the compound of formula 1.0); can be administered orally (e.g., as a capsule), and the chemotherapeutic agents can be administered intravenously, usually as an IV solution. The use of a pharmaceutical composition comprising more than one drug is within the scope of this invention.

The compound of formula 1.0 and the chemotherapeutic agents are administered in therapeutically effective dosages to obtain clinically acceptable results, e.g., reduction or elimination of symptoms or of the tumor. Thus, the compound of formula 1.0 and chemotherapeutic agents can be administered concurrently or consecutively in a treatment protocol. The administration of the chemotherapeutic agents can be made according to treatment protocols already known in the art.

In general when more than one chemotherapeutic agent is used in the methods of this invention, the chemotherapeutic agents are administered on the same day either concurrently or consecutively in their standard dosage form. For example, the chemotherapeutic agents are usually administered intravenously, preferably by an IV drip using IV solutions well known in the art (e.g., isotonic saline (0.9% NaCl) or dextrose solution (e.g., 5% dextrose)).

When two or more chemotherapeutic agents are used, the chemotherapeutic agents are generally administered on the same day; however, those skilled in the art will appreciate that the chemotherapeutic agents can be administered on different days and in different weeks. The skilled clinician can administer the chemotherapeutic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15

The compounds of this invention and chemotherapeutic agents can be administered in a treatment protocol that usually lasts one to seven weeks, and is repeated typically from 6 to 12 times. Generally the treatment protocol can last one to four weeks. Treatment protocols of one to three weeks can also be used. A treatment protocol of one to two weeks can also be used. During this treatment protocol or cycle the compounds of this invention can be administered daily while the chemotherapeutic agents can be administered one or more times a week. Generally, a compound of this invention can be administered daily (i.e., once per day), and in one embodiment twice per day, and the chemotherapeutic agent is administered once a week or once every three weeks. For example, the taxanes (e.g., Paclitaxel (e.g., Taxol®) or Docetaxel (e.g., Taxotere®)) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the compounds of this invention can be administered discontinuously rather than continuously during the treatment cycle. Thus, for example, during the treatment cycle the compounds of this invention can be administered daily for a week and then discontinued for a week, with this administration repeating during the treatment cycle. Or the compounds of this invention can be administered daily for two weeks and discontinued for a week, with this administration repeating during the treatment cycle. Thus, the compounds of this invention can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the compounds of this invention are not dosed do not have to equal the number of days (or weeks) wherein the compounds of this invention are dosed. Usually, if a discontinuous dosing protocol is used, the number of days or weeks that the compounds of this invention are dosed is at least equal or greater than the number of days or weeks that the compounds of this invention are not dosed.

The chemotherapeutic agent could be given by bolus or continuous infusion. The chemotherapeutic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days), with the pattern repeating during the treatment cycle.

The compounds of this invention can be administered orally, preferably as a solid dosage form, and in one embodiment as a capsule, and while the total therapeutically effective daily dose can be administered in one to four, or one to two divided doses per day, generally, the therapeutically effective dose is given once or twice a day, and in one embodiment twice a day. The compounds of this invention can be administered in an amount of about 50 to about 400 mg once per day, and can be administered in an amount of about 50 to about 300 mg once per day. The compounds of this invention are generally administered in an amount of about 50 to about 350 mg twice a day, usually 50 mg to about 200 mg twice a day, and in one embodiment about 75 mg to about 125 mg administered twice a day, and in another embodiment about 100 mg administered twice a day.

If the patient is responding, or is stable, after completion of the therapy cycle, the therapy cycle can be repeated according to the judgment of the skilled clinician. Upon completion of the therapy cycles, the patient can be continued on the compounds of this invention at the same dose that was administered in the treatment protocol, or, if the dose was less than 200 mg twice a day, the dose can be raised to 200 mg twice a day. This maintenance dose can be continued until the patient progresses or can no longer tolerate the dose (in which case the dose can be reduced and the patient can be continued on the reduced dose).

The chemotherapeutic agents, used with the compounds of this invention, are administered in their normally prescribed dosages during the treatment cycle (i.e., the chemotherapeutic agents are administered according to the standard of practice for the administration of these drugs). For example: (a) about 30 to about 300 mg/m$^2$ for the taxanes; (b) about 30 to about 100 mg/m$^2$ for Cisplatin; (c) AUC of about 2 to about 8 for Carboplatin; (d) about 2 to about 4 mg/m$^2$ for EGF inhibitors that are antibodies; (e) about 50 to about 500 mg/m$^2$ for EGF inhibitors that are small molecules; (f) about 1 to about 10 mg/m$^2$ for VEGF kinase inhibitors that are antibodies; (g) about 50 to about 2400 mg/m$^2$ for VEGF inhibitors that are small molecules; (h) about 1 to about 20 mg for SERMs; (i) about 500 to about 1250 mg/m$^2$ for the anti-tumor nucleosides 5-Fluorouracil, Gemcitabine and Capecitabine; (j) for the anti-tumor nucleoside Cytarabine (Ara-C) 100-200 mg/m$^2$/day for 7 to 10 days every 3 to 4 weeks, and high doses for refractory leukemia and lymphoma, i.e., 1 to 3 gm/m$^2$ for one hour every 12 hours for 4-8 doses every 3 to four weeks; (k) for the anti-tumor nucleoside Fludarabine (F-ara-A) 10-25 mg/m$^2$/day every 3 to 4 weeks; (l) for the anti-tumor nucleoside Decitabine 30 to 75 mg/m$^2$ for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m$^2$ for epothilones; (o) about 1 to about 350 mg/m$^2$ for topoisomerase inhibitors; (p) about 1 to about 50 mg/m$^2$ for vinca alkaloids; (q) for the folate antagonist Methotrexate (MTX) 20-60 mg/m$^2$ by oral, IV or IM every 3 to 4 weeks, the intermediate dose regimen is 80-250 mg/m$^2$ IV over 60 minutes every 3 to 4 weeks, and the high dose regimen is 250-1000 mg/m$^2$ IV given with leucovorin every 3 to 4 weeks; (r) for the folate antagonist Premetrexed (Alimta) 300-600 mg/m$^2$ (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m$^2$ every 3 to 4 weeks (preferably used for solid tumors such as non-small cell lung cancer, colorectal cancer and ovarian cancer); (u) for the anthracycline daunorubicin 10-50 mg/m$^2$/day IV for 3-5 days every 3 to 4 weeks; (v) for the anthracycline Doxorubicin (Adriamycin) 50-100 mg/m$^2$ IV continuous infusion over 1-4 days every 3 to 4 weeks, or 10-40 mg/m$^2$ IV weekly; (w) for the anthracycline Idarubicin 10-30 mg/m$^2$ daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); (z) for the biologic Rituximab (Rituxan) (antibody used for non-Hodgkin's lymphoma) 200-400 mg/m$^2$ IV weekly over 4-8 weeks for 6 months; (aa) for the alkylating agent temozolomide 75 mg/m$^2$ to 250 mg/m$^2$, for example, 150 mg/m$^2$, or for example, 200 mg/m$^2$, such as 200 mg/m$^2$ for 5 days; and (bb) for the MEK1 and/or MEK2 inhibitor PD0325901, 15 mg to 30 mg, for example, 15 mg daily for 21 days every 4 weeks.

Gleevec can be used orally in an amount of about 200 to about 800 mg/day.

Thalidomide (and related imids) can be used orally in amounts of about 200 to about 800 mg/day, and can be continuously dosed or used until releapse or toxicity. See for example Mitsiades et al., "Apoptotic signaling induced by immunomodulatory thalidomide analoqs in human multiple myeloma cells; therapeutic implications", Blood, 99(12):4525-30, Jun. 15, 2002, the disclosure of which is incorporated herein by reference thereto.

The FPT inhibitor Sarasar®) (brand of Ionifarnib) can be administered orally (e.g., capsule) in amounts of about 50 to about 200 mg given twice a day, or in amounts of about 75 to about 125 mg given twice a day, or in amounts of about 100 to about 200 mg given twice a day, or in an amount of about 100 mg given twice a day.

Paclitaxel (e.g., Taxol®), for example, can be administered once per week in an amount of about 50 to about 100 mg/m$^2$ and in another example about 60 to about 80 mg/m$^2$. In another example Paclitaxel (e.g., Taxol®) can be administered once every three weeks in an amount of about 150 to about 250 mg/m² and in another example about 175 to about 225 mg/m².

In another example, Docetaxel (e.g., Taxotere®) can be administered once per week in an amount of about 10 to about 45 mg/m². In another example Docetaxel (e.g., Taxotere®) can be administered once every three weeks in an amount of about 50 to about 100 mg/m².

In another example Cisplatin can be administered once per week in an amount of about 20 to about 40 mg/m². In another example Cisplatin can be administered once every three weeks in an amount of about 60 to about 100 mg/m².

In another example Carboplatin can be administered once per week in an amount to provide an AUC of about 2 to about 3. In another example Carboplatin can be administered once every three weeks in an amount to provide an AUC of about 5 to about 8.

Other embodiments of this invention are described below. The embodiments have been numbered for the purpose of making it easier to refer to the embodiments. The term "in any one of Embodiment Nos." or the term "of any of Embodiment Nos.", as used below, means that the particular embodiment using that term is intended to cover any one of the embodiments referred to as if any one of the referred to embodiments had been individually described. "Nos." is an abbreviation for Numbers.

Embodiment No. 1 is directed to a compound of formula 1.0, preferably a compound of formula 1.0C, wherein Q is selected from the group consisting of substituents 2.1, 2.2, 2.3, 2.3A, 2.3B, 2.3C, 2.4A, 2.4B, 2.4C, 2.5A, 2.5B, 2.5C, 2.6A, 2.7A, 2.7B, 2.7C, 2.8A, 2.8B, 2.8C, 2.9 to 2.14, 2.15, 2.16 (e.g., 2.16A or 2.16B), 2.17, 2.17A, 2.17B, 2.17C, 2.17D, 2.17E, 2.18, 2.19, 2.20, 2.21 and 2.22.

Embodiment No. 2 is directed to a compound of formula 1.1 wherein Q is selected from the group consisting of substituents 2.1, 2.2, 2.3, 2.3A, 2.3B, 2.3C, 2.4A, 2.4B, 2.4C, 2.5A, 2.5B, 2.5C, 2.6A, 2.7A, 2.7B, 2.7C, 2.8A, 2.8B, 2.8C, 2.9 to 2.14, 2.15, 2.16 (e.g., 2.16A or 2.16B), 2.17, 2.17A, 2.17B, 2.17C, 2.17D, 2.17E, 2.18, 2.19, 2.20, 2.21 and 2.22.

Embodiment No. 3 is directed to a compound of formula 1.2 wherein Q is selected from the group consisting of substituents 2.1, 2.2, 2.3, 2.3A, 2.3B, 2.3C, 2.4A, 2.4B, 2.4C, 2.5A, 2.5B, 2.5C, 2.6A, 2.7A, 2.7B, 2.7C, 2.8A, 2.8B, 2.8C, 2.9 to 2.14, 2.15, 2.16 (e.g., 2.16A or 2.16B), 2.17, 2.17A, 2.17B, 2.17C, 2.17D, 2.17E, 2.18, 2.19, 2.20, 2.21 and 2.22.

Embodiment No. 4 is directed to a compound of formula 1.3 wherein Q is selected from the group consisting of substituents 2.1, 2.2, 2.3, 2.3A, 2.3B, 2.3C, 2.4A, 2.4B, 2.4C, 2.5A, 2.5B, 2.5C, 2.6A, 2.7A, 2.7B, 2.7C, 2.8A, 2.8B, 2.8C, 2.9 to 2.14, 2.15, 2.16 (e.g., 2.16A or 2.16B), 2.17, 2.17A, 2.17B, 2.17C, 2.17D, 2.17E, 2.18, 2.19, 2.20, 2.21 and 2.22.

Embodiment No. 5 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.1.

Embodiment No. 6 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent 0 is 2.2.

Embodiment No. 7 is directed to a compound of formula 1.0 (e.g., 1.1, 1.1A, 1.2, 1.2A, 1.3 or 1.3A) wherein substituent Q is 2.3 (e.g., 2.3A, 2.3B or 2.3C).

Embodiment No. 8 is directed to a compound of formula 1.0, preferably a compound of formula 1.0C, (e.g., 1.1, 1.1A, 1.2, 1.2A, 1.3 or 1.3A) wherein substituent Q is 2.4 (e.g., 2.4A, 2.4B or 2.4C).

Embodiment No. 9 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.5 (e.g., 2.5A, 2.5B or 2.5C).

Embodiment No. 10 is directed to any of compounds of formulas to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent 0 is 2.6 (e.g., 2.6A).

Embodiment No. 11 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.7.

Embodiment No. 12 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.8.

Embodiment No. 13 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.9.

Embodiment No. 14 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.10.

Embodiment No. 15 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.11.

Embodiment No. 16 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.12.

Embodiment No. 17 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.13.

Embodiment No. 18 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.14.

Embodiment No. 19 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.15.

Embodiment No. 20 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.16.

Embodiment No. 21 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent 0 is 2.17 (e.g., 2.17A, 2.17B, 2.17C, 2.17D, or 2.17E).

Embodiment No. 22 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.18.

Embodiment No. 23 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.19.

Embodiment No. 24 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.20.

Embodiment No. 25 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.21.

Embodiment No. 26 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is 2.22.

Embodiment No. 27 is directed to a compound of formula 1.3 wherein substituent Q is 2.1.

Embodiment No. 28 is directed to a compound of formula 1.3 wherein substituent Q is 2.2.

Embodiment No. 29 is directed to a compound of formula 1.3 wherein substituent Q is 2.3.

Embodiment No. 30 is directed to a compound of formula 1.3 wherein substituent Q is 2.6.

Embodiment No. 31 is directed to a compound of formula 1.3 wherein substituent Q is 2.6A.

Embodiment No. 32 is directed to a compound of formula 1.3 wherein substituent Q is 2.7A.

Embodiment No. 33 is directed to a compound of formula 1.3 wherein substituent Q is 2.7B.

Embodiment No. 34 is directed to a compound of formula 1.3 wherein substituent Q is 2.7C.

Embodiment No. 35 is directed to a compound of formula 1.3 wherein substituent Q is 2.17.

Embodiment No. 36 is directed to a compound of formula 1.3 wherein substituent Q is 2.17A.

Embodiment No. 37 is directed to a compound of formula 1.3 wherein substituent Q is 2.17B.

Embodiment No. 38 is directed to a compound of formula 1.3 wherein substituent Q is 2.17C.

Embodiment No. 39 is directed to a compound of formula 1.3 wherein substituent Q is 2.17D.

Embodiment No. 40 is directed to a compound of formula 1.3 wherein substituent Q is 2.17E.

Embodiment No. 41 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein each $R^3$, $R^4$, $R^6$, and $R^7$ is independently selected from the group consisting of: H and alkyl.

Embodiment No. 42 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein each $R^3$, $R^4$, $R^6$, and $R^7$ is independently selected from the group consisting of: H and methyl.

Embodiment No. 43 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein each $R^3$, $R^4$, $R^6$, and $R^7$ is H.

Embodiment No. 44 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.1, 2.2, 2.3A, 2.3B, and 2.3C.

Embodiment No. 45 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.1, 2.2, 2.3A, 2.3B, and 2.3C, and each $R^3$, $R^4$, $R^6$, and $R^7$ is independently selected from the group consisting of: H and alkyl.

Embodiment No. 46 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.1, 2.2, 2.3A, 2.3B, and 2.3C, and each $R^3$, $R^4$, $R^6$, and $R^7$ is independently selected from the group consisting of: H and methyl.

Embodiment No. 47 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.1, 2.2, 2.3A, 2.3B, and 2.3C, and each $R^3$, $R^4$, $R^6$, and $R^7$ is H.

Embodiment No. 48 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moiety 2.17.

Embodiment No. 49 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moiety 2.17, and each $R^3$, $R^4$, $R^6$, and $R^7$ is independently selected from the group consisting of: H and alkyl.

Embodiment No. 50 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moiety 2.17, and each $R^3$, $R^4$, $R^6$, and $R^7$ is independently selected from the group consisting of: H and methyl.

Embodiment No. 51 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moiety 2.17, and each $R^3$, $R^4$, $R^6$, and $R^7$ is H.

Embodiment No. 52 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.1, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 53 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.2, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 54 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.3A, 2.3B, 2.3C, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 55 is directed to a compound of formula 1.2 or 1.3 wherein each $R^3$, $R^4$, $R^6$, and $R^7$ is independently selected from the group consisting of: H and alkyl.

Embodiment No. 56 is directed to a compound of formula 1.2 or 1.3 wherein each $R^3$, $R^4$, $R^6$, and $R^7$ is independently selected from the group consisting of: H and methyl.

Embodiment No. 57 is directed to a compound of formula 1.2 or 1.3 wherein each $R^3$, $R^4$, $R^6$, and $R^7$ is H.

Embodiment No. 58 is directed to a compound of formula 1.2 or 1.3 wherein Q is selected from the group consisting of: moieties 2.1, 2.2, 2.3A, 2.3B and 2.3C.

Embodiment No. 59 is directed to a compound of formula 1.2 or 1.3 wherein substituent Q is selected from the group consisting of: moieties 2.1, 2.2, 2.3A, 2.3B and 2.3C, and each $R^3$, $R^4$, $R^6$, and $R^7$ is independently selected from the group consisting of: H and alkyl.

Embodiment No. 60 is directed to a compound of formula 1.2 or 1.3 wherein substituent Q is selected from the group consisting of: moieties 2.1, 2.2, 2.3A, 2.3B and 2.3C, and each $R^3$, $R^4$, $R^6$, and $R^7$ is independently selected from the group consisting of: H and methyl.

Embodiment No. 61 is directed to a compound of formula 1.2 or 1.3 wherein Q is selected from the group consisting of: moieties 2.1, 2.2, 2.3A, 2.3B and 2.3C, and each $R^3$, $R^4$, $R^6$, and $R^7$ is H.

Embodiment No. 62 is directed to a compound of formula 1.2 or 1.3 wherein substituent Q is moiety 2.17.

Embodiment No. 63 is directed to a compound of formula 1.2 or 1.3 wherein substituent Q is moiety 2.17, and each $R^3$, $R^4$, $R^6$, and $R^7$ is independently selected from the group consisting of: H and alkyl.

Embodiment No. 64 is directed to a compound of formula 1.2 or 1.3 wherein substituent Q is moiety 2.17, and each $R^3$, $R^4$, $R^6$, and $R^7$ is independently selected from the group consisting of: H and methyl.

Embodiment No. 65 is directed to a compound of formula 1.2 or 1.3 wherein substituent Q is moiety 2.17, and each $R^3$, $R^4$, $R^6$, and $R^7$ is H.

Embodiment No. 66 is directed to a compound of formula 1.2 or 1.3 wherein substituent Q is selected from the group consisting of: moiety 2.1, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 67 is directed to a compound of formula 1.2 or 1.3 wherein Q is selected from the group consisting of: moiety 2.2, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 68 is directed to a compound of formula 1.2 or 1.3 wherein substituent Q is selected from the group consisting of: moieties 2.3A, 2.3B and 2.3C, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 69 is directed to a compound of formula 1.3 wherein each $R^3$, $R^4$, $R^6$, and $R^7$ is independently selected from the group consisting of: H and alkyl.

Embodiment No. 70 is directed to a compound of formula 1.3 wherein each $R^3$, $R^4$, $R^6$, and $R^7$ is independently selected from the group consisting of: H and methyl.

Embodiment No. 71 is directed to a compound of formula 1.3 wherein each $R^3$, $R^4$, $R^6$, and $R^7$ is H.

Embodiment No. 72 is directed to a compound of formula 1.3 wherein substituent Q is selected from the group consisting of: moieties 2.1, 2.2, 2.3A, 2.3B and 2.3C.

Embodiment No. 73 is directed to a compound of formula 1.3 wherein Q is selected from the group consisting of: moieties 2.1, 2.2, 2.3A, 2.3B and 2.3C, and each $R^3$, $R^4$, $R^6$, and $R^7$ is independently selected from the group consisting of: H and alkyl.

Embodiment No. 74 is directed to a compound of formula 1.3 wherein Q is selected from the group consisting of: moieties 2.1, 2.2, 2.3A, 2.3B and 2.3C, and each $R^3$, $R^4$, $R^6$, and $R^7$ is independently selected from the group consisting of: H and methyl.

Embodiment No. 75 is directed to a compound of formula 1.3 wherein substituent Q is selected from the group consisting of: moieties 2.1, 2.2, 2.3A, 2.3B and 2.3C, and each $R^3$, $R^4$, $R^6$, and $R^7$ is H.

Embodiment No. 76 is directed to a compound of formula 1.3 wherein Q is moiety 2.17.

Embodiment No. 77 is directed to a compound of formula 1.3 wherein substituent Q is moiety 2.17, and each $R^3$, $R^4$, $R^6$, and $R^7$ is independently selected from the group consisting of: H and alkyl.

Embodiment No. 78 is directed to a compound of formula 1.3 wherein substituent Q is moiety 2.17, and each $R^3$, $R^4$, $R^6$, and $R^7$ is independently selected from the group consisting of: H and methyl.

Embodiment No. 79 is directed to a compound of formula 1.3 wherein Q is moiety 2.17, and each $R^3$, $R^4$, $R^6$, and $R^7$ is H.

Embodiment No. 80 is directed to a compound of formula 1.3 wherein Q is selected from the group consisting of: moiety 2.1, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 81 is directed to a compound of formula 1.3 wherein substituent Q is selected from the group consisting of: moiety 2.2, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 82 is directed to a compound of formula 1.3 wherein substituent Q is selected from the group consisting of: moieties 2.3A1, 2.3B and 2.3C, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 83 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.6, 2.7A, 2.7B and 2.7C.

Embodiment No. 84 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.6, 2.7A, 2.7B and 2.7C, and each $R^3$, $R^4$, $R^6$, and $R^7$ is independently selected from the group consisting of: H and alkyl.

Embodiment No. 85 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.6, 2.7A, 2.7B and 2.7C, and each $R^3$, $R^4$, $R^6$, and $R^7$ is independently selected from the group consisting of: H and methyl.

Embodiment No. 86 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.6, 2.7A, 2.7B and 2.7C, and each $R^3$, $R^4$, $R^6$, and $R^7$ is H.

Embodiment No. 87 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moiety 2.6, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 88 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moiety 2.7A, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 89 is directed to a compound of formula 1.0, preferably a compound of formula 1.0C1 and more preferably a compound of formula 1.0C, (e.g., 1.1, 1.1A, 1.2, 1.2A, 1.3 or 1.3A) wherein substituent Q is selected from the group consisting of: moieties 2.7B and 2.7C, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 90 is directed to a compound of formula 1.2 or 1.3 wherein substituent Q is selected from the group consisting of: moieties 2.6, 2.7A, 2.7B and 2.7C.

Embodiment No. 91 is directed to a compound of formula 1.2 or 1.3 wherein substituent Q is selected from the group consisting of: moieties 2.6, 2.7A, 2.7B and 2.7C, and each $R^3$, $R^4$, $R^6$, and $R^7$ is independently selected from the group consisting of: H and alkyl.

Embodiment No. 92 is directed to a compound of formula 1.2 or 1.3 wherein substituent Q is selected from the group consisting of: moieties 2.6, 2.7A, 2.7B and 2.7C, and each $R^3$, $R^4$, $R^6$, and $R^7$ is independently selected from the group consisting of: H and methyl.

Embodiment No. 93 is directed to a compound of formula 1.2 or 1.3 wherein substituent Q is selected from the group consisting of: moieties 2.6, 2.7A, 2.7B and 2.7C, and each $R^3$, $R^4$, $R^6$, and $R^7$ is independently selected from the group consisting of: H.

Embodiment No. 94 is directed to a compound of formula 1.2 or 1.3 wherein Q is selected from the group consisting of: moiety 2.6, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 95 is directed to a compound of formula 1.2 or 1.3 wherein Q is selected from the group consisting of: moiety 2.7A, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 96 is directed to a compound of formula 1.2 or 1.3 wherein substituent Q is selected from the group consisting of: moieties 2.7A and 2.7B, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 97 is directed to a compound of formula 1.3 wherein substituent Q is selected from the group consisting of: moieties 2.6, 2.7A, 2.7B and 2.7C.

Embodiment No. 98 is directed to a compound of formula 1.3 wherein substituent Q is selected from the group consisting of: moieties 2.6, 2.7A, 2.7B and 2.7C, and each $R^3$, $R^4$, $R^6$, and $R^7$ is independently selected from the group consisting of: H and alkyl.

Embodiment No. 99 is directed to a compound of formula 1.3 wherein substituent Q is selected from the group consisting of: moieties 2.6, 2.7A, 2.7B and 2.7C, and each $R^3$, $R^4$, $R^6$, and $R^7$ is independently selected from the group consisting of: H and methyl.

Embodiment No. 100 is directed to a compound of formula 1.3 wherein Q is selected from the group consisting of: moieties 2.6, 2.7A, 2.7B and 2.7C, and each $R^3$, $R^4$, $R^6$, and $R^7$ is H.

Embodiment No. 101 is directed to a compound of formula 1.3 wherein substituent Q is selected from the group consisting of: moiety 2.6, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 102 is directed to a compound of formula 1.3 wherein substituent Q is selected from the group consisting of: moiety 2.7A, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 103 is directed to a compound of formula 1.3 wherein substituent Q is selected from the group consisting of: moieties 2.7B and 2.7C, and: (1) each $R^3$, $R^4$, $R^6$, and $R^7$ is independently selected from the group consisting of: H and alkyl, or (2) each $R^3$, $R^4$, $R^6$, and $R^7$ is independently selected from the group consisting of: H and methyl, or (3) each $R^3$, $R^4$, $R^6$, and $R^7$ is H.

Embodiment No. 104 is directed to a compound of any one of Embodiment Nos. 1 to 103, wherein $R^1$ is selected from the group consisting of:

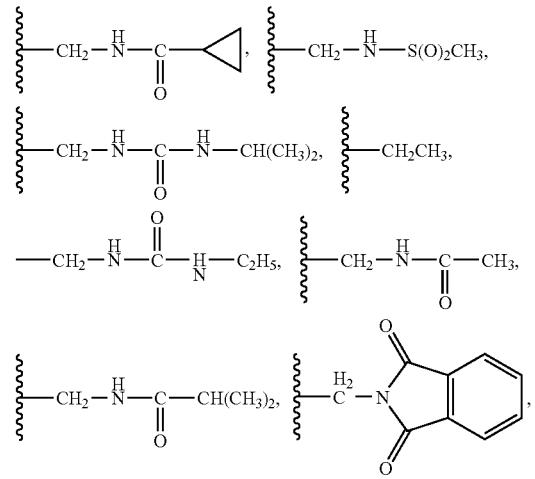

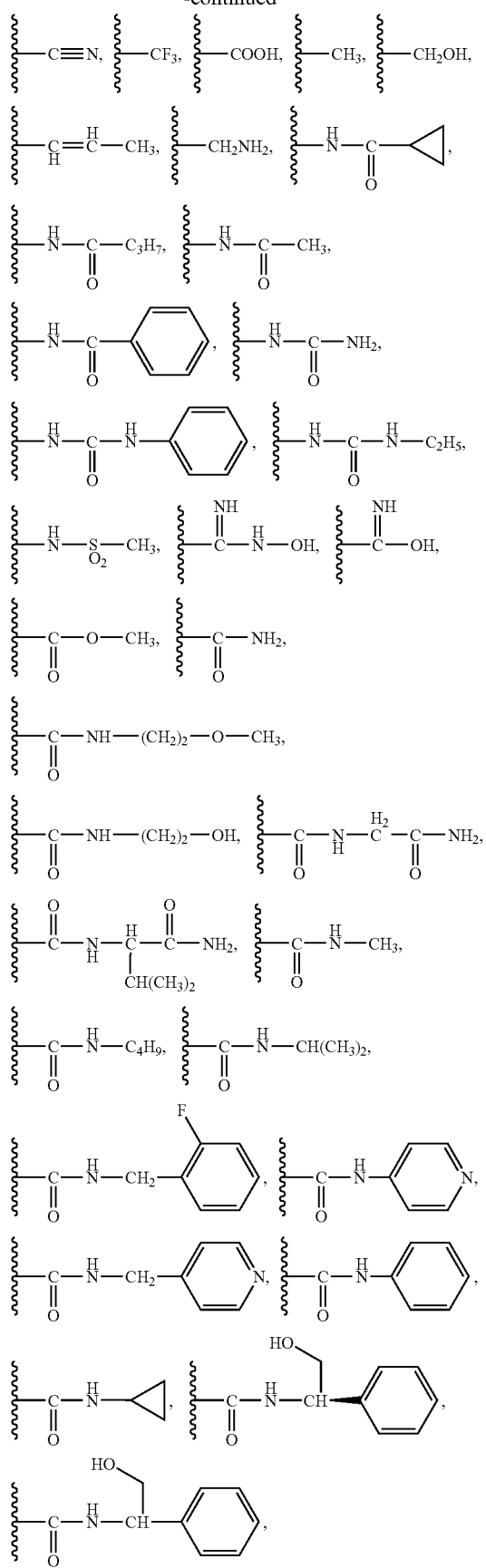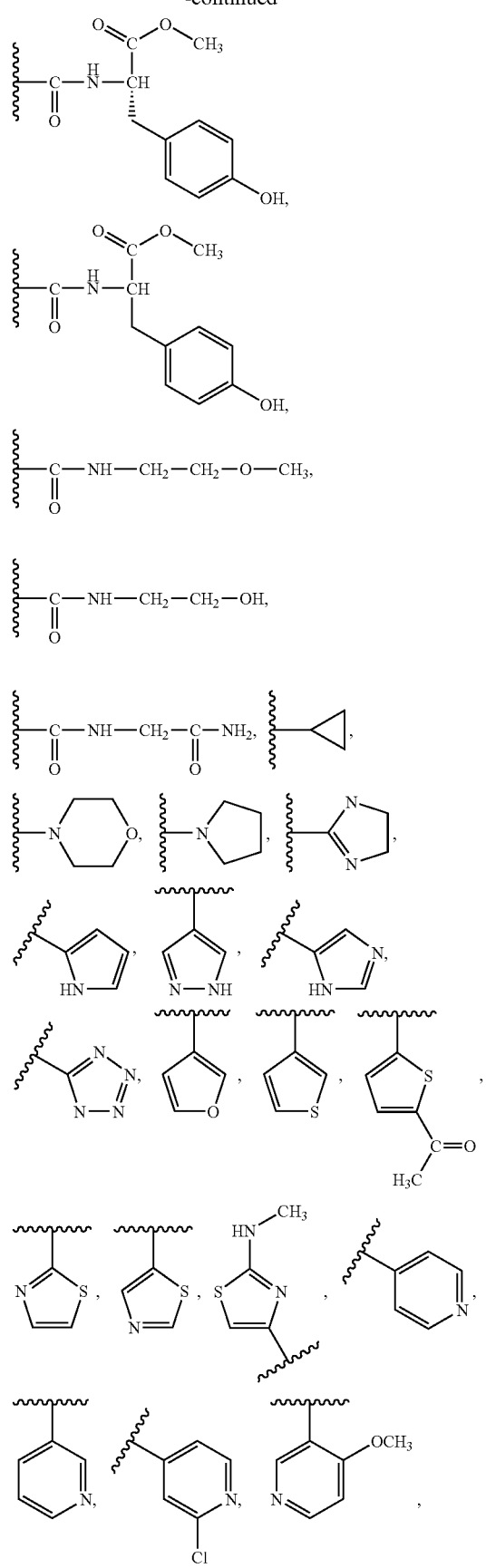

111
-continued
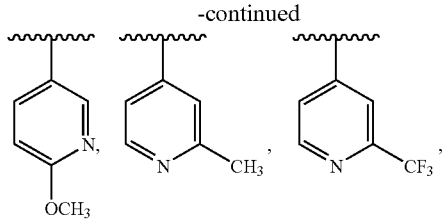
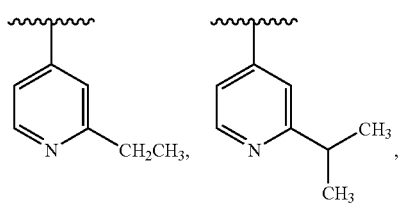
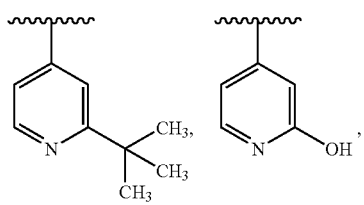
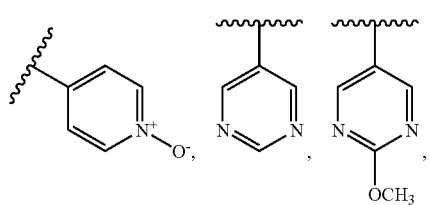
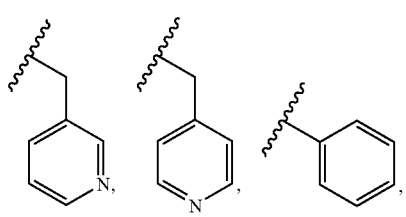
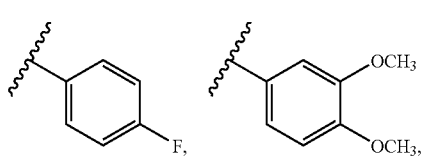
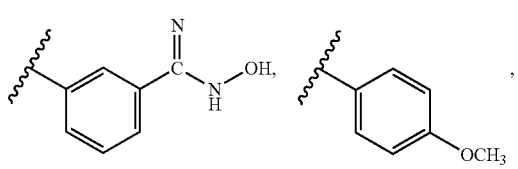
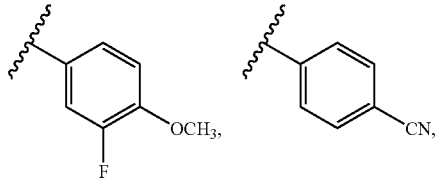
112
-continued
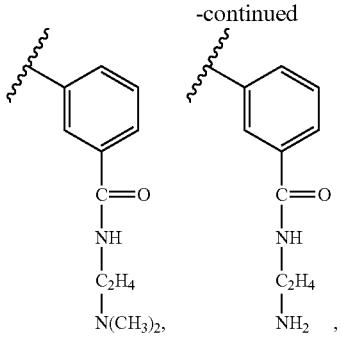
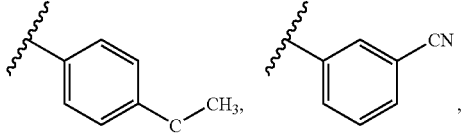
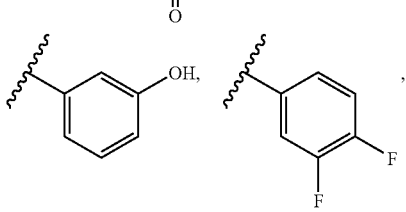
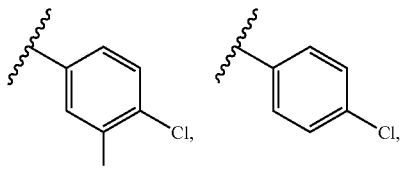
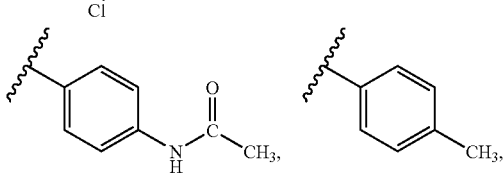
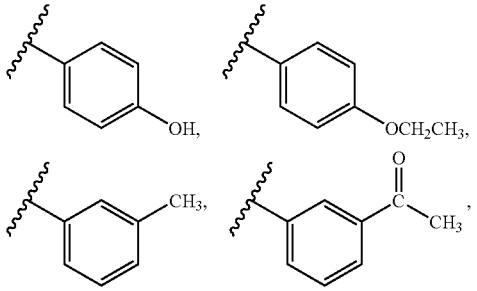
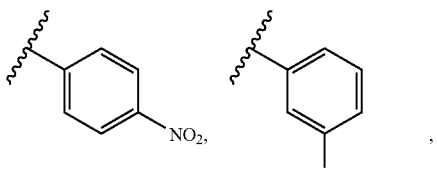
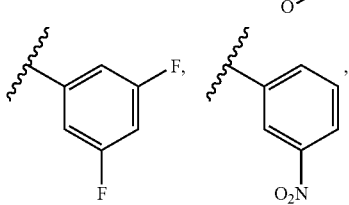

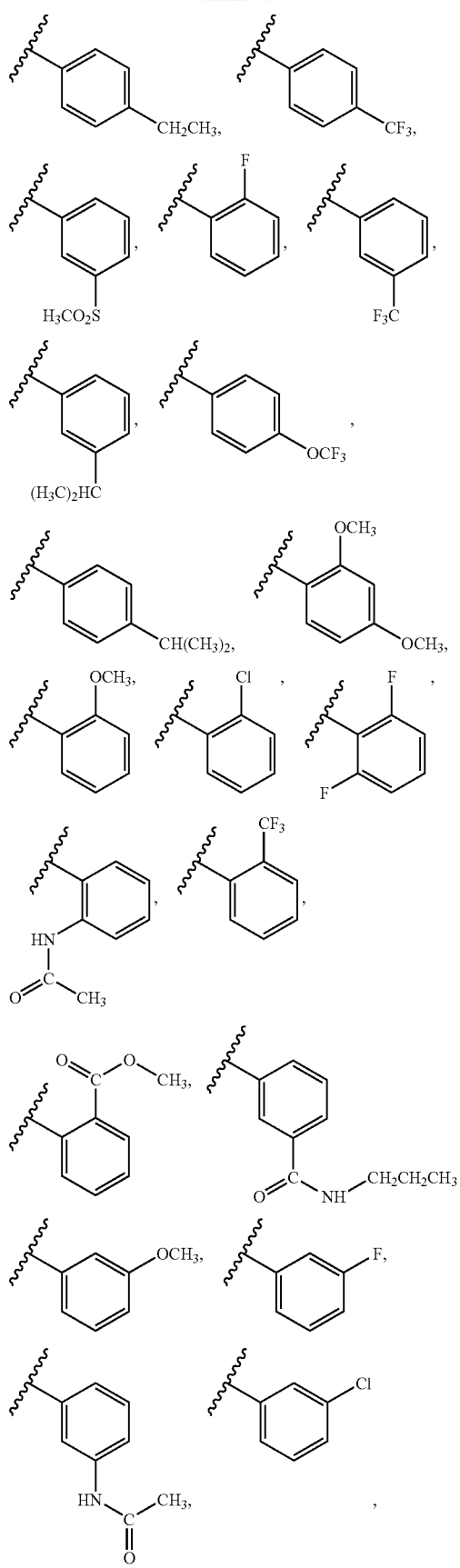
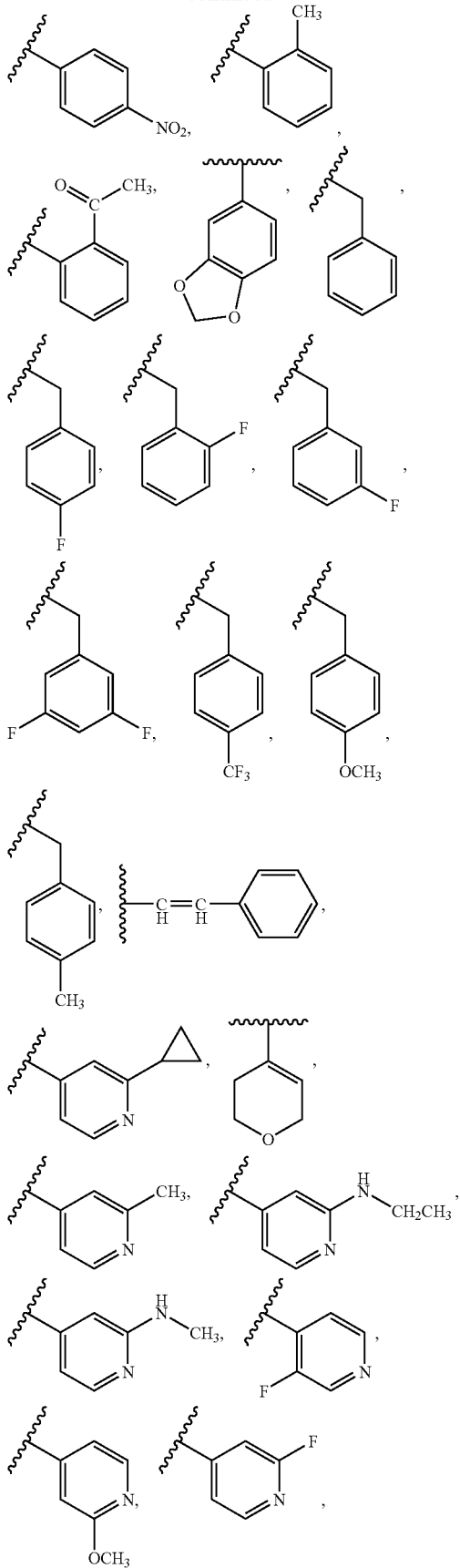

115
-continued
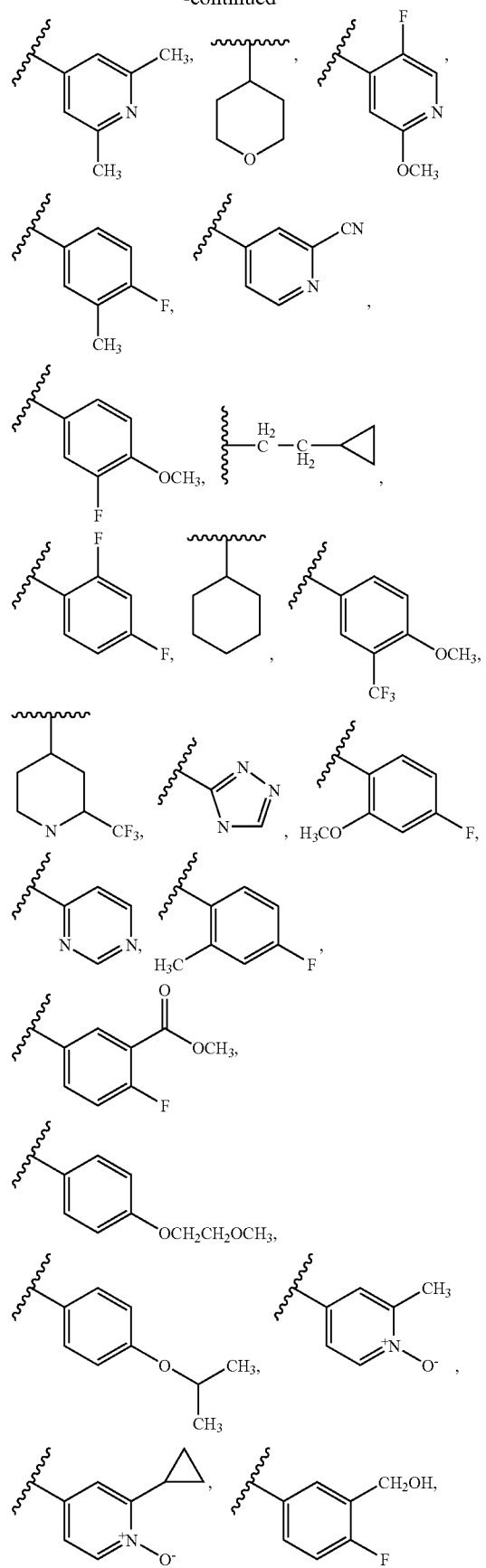
116
-continued
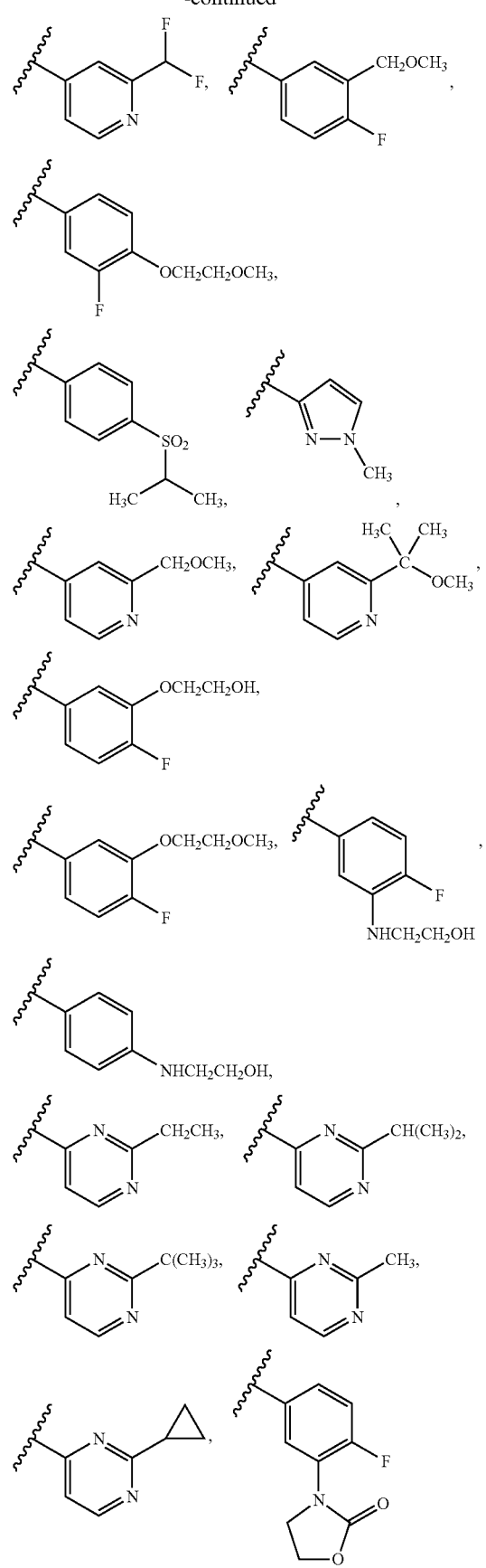

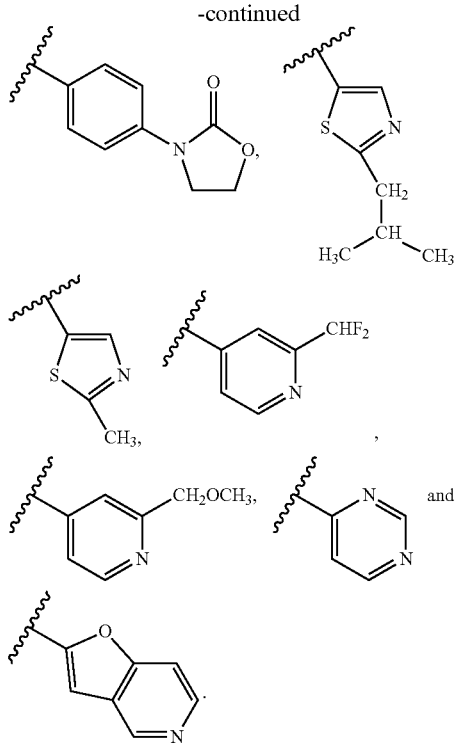

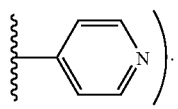

Embodiment No. 105 is directed to a compound of any one of Embodiment Nos. 1 to 103, wherein $R^1$ is aryl (e.g., phenyl).

Embodiment No. 106 is directed to a compound of any one of Embodiment Nos. 1 to 103, wherein $R^1$ is substituted aryl (e.g., substituted phenyl).

Embodiment No. 107 is directed to a compound of any one of Embodiment Nos. 1 to 103, wherein $R^1$ is heteroaryl (e.g., pyridyl, such as

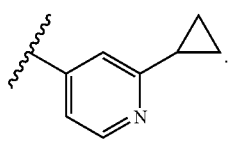 [SMILES: *c1ccnc(C2CC2)c1]

Embodiment No. 108 is directed to a compound of any one of Embodiment Nos. 1 to 103, wherein $R^1$ is substituted heteroaryl (e.g., substituted pyridyl).

Embodiment No. 109 is directed to a compound of any one of Embodiment Nos. 1 to 103, wherein $R^1$ is pyridyl substituted with cycloalkyl (e.g., cyclopropyl).

Embodiment No. 110 is directed to a compound of any one of Embodiment Nos. 1 to 103, wherein $R^1$ is pyridyl substituted with cyclopropyl.

Embodiment No. 111 is directed to a compound of any one of Embodiment Nos. 1 to 103, wherein $R^1$ is:

Embodiment No. 112 is directed to a compound of any one of Embodiment Nos. 1 to 103, wherein $R^1$ is phenyl substituted with halo.

Embodiment No. 113 is directed to a compound of any one of Embodiment Nos. 1 to 103, wherein $R^1$ is phenyl substituted with F.

Embodiment No. 114 is directed to a compound of any one of Embodiment Nos. 1 to 103, wherein $R^1$ is p-F-phenyl.

Embodiment No. 115 is directed to a compound of any one of Embodiment Nos. 1 to 103, wherein $R^1$ is pyridyl substituted with —$CF_3$.

Embodiment No. 116 is directed to a compound of any one of Embodiment Nos. 1 to 103, wherein $R^1$ is:

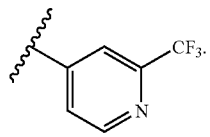 [SMILES: *c1ccnc(C(F)(F)F)c1]

Embodiment No. 117 is directed to a compound of any one of Embodiment Nos. 1 to 103, wherein $R^1$ is pyridyl substituted with alkyl.

Embodiment No. 118 is directed to a compound of any one of Embodiment Nos. 1 to 103, wherein $R^1$ is pyridyl substituted with methyl.

Embodiment No. 119 is directed to a compound of any one of Embodiment Nos. 1 to 103, wherein $R^1$ is:

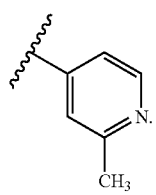

Embodiment No. 120 is directed to a compound of any one of Embodiment Nos. 1 to 103 wherein $R^5$ is selected from the group consisting of:

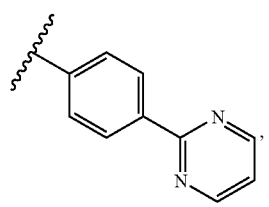

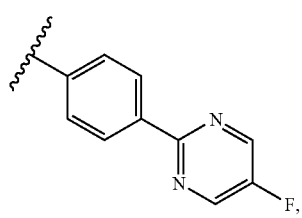

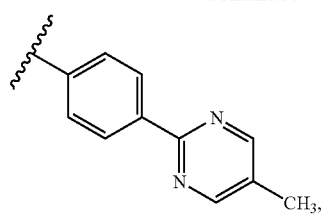
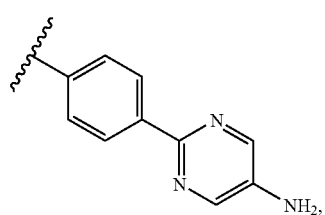
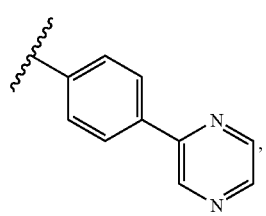
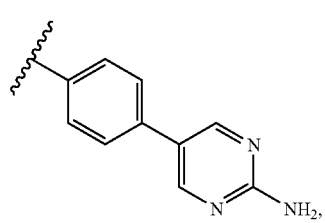
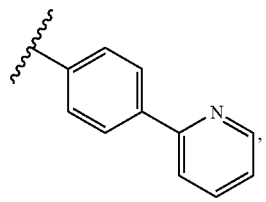
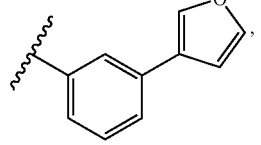
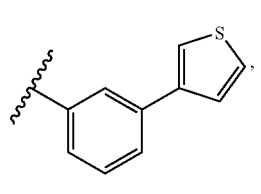
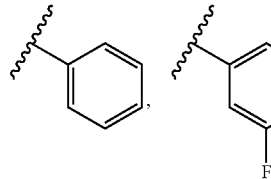
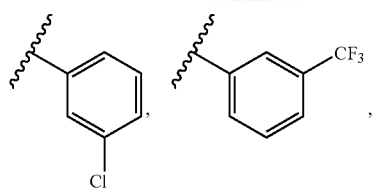
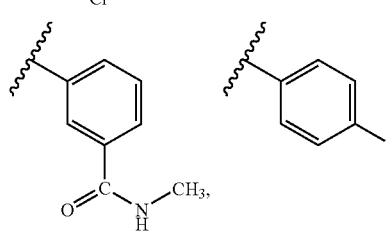
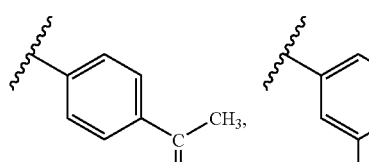
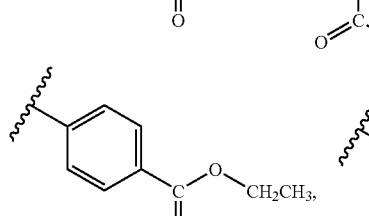
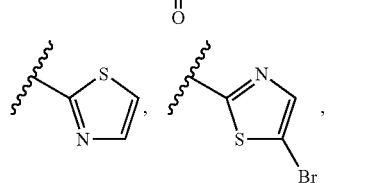
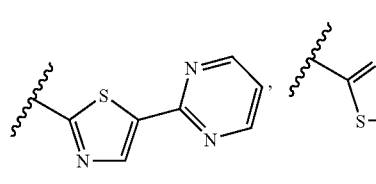
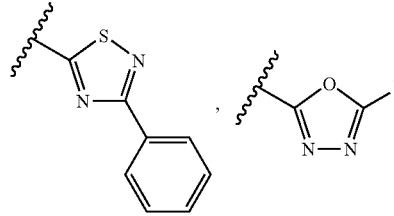
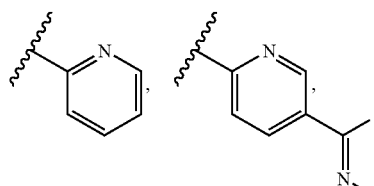
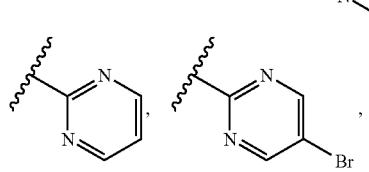

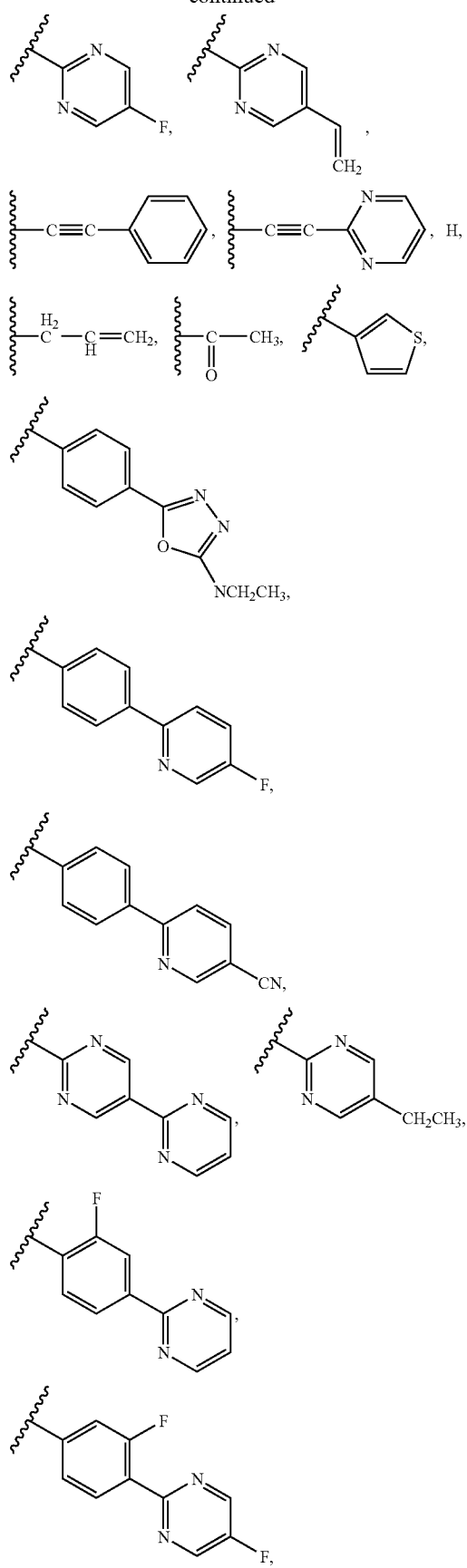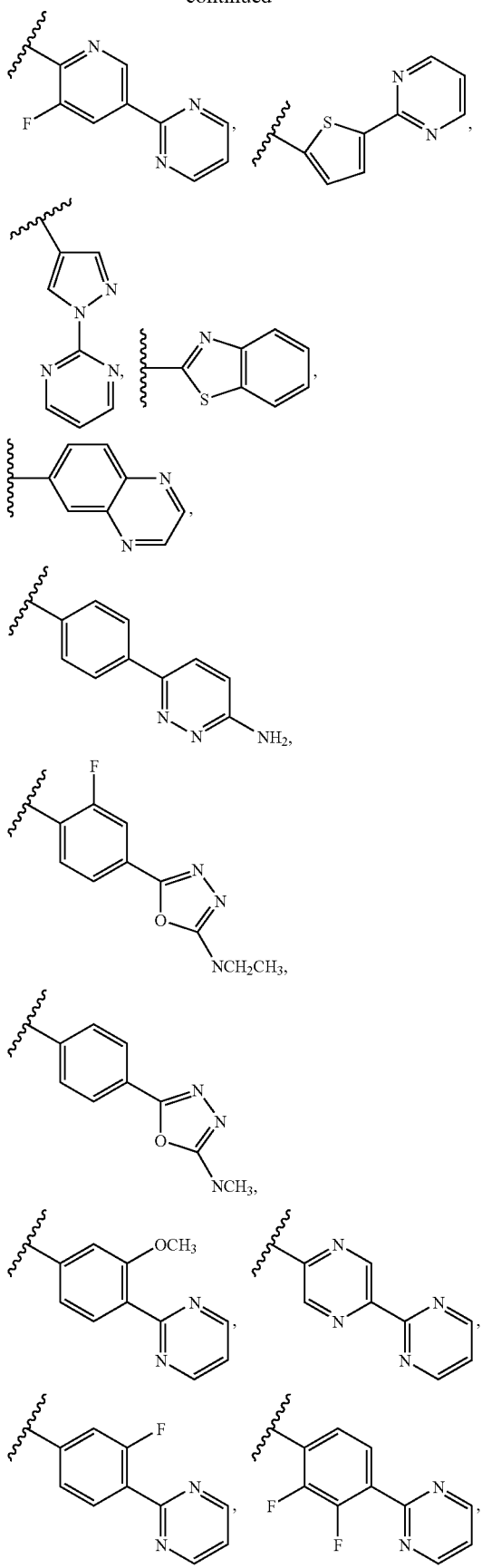

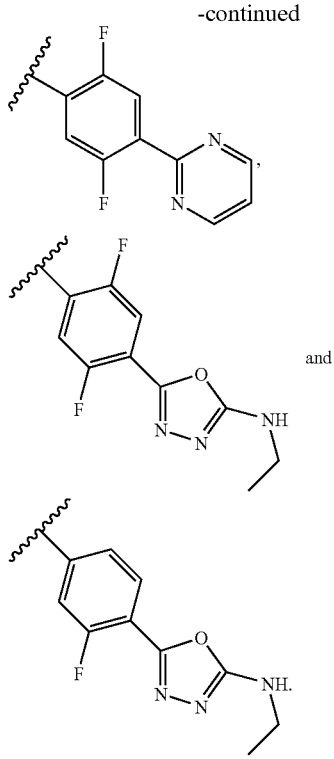

Embodiment No. 121 is directed to a compound of any one of Embodiment Nos. 1 to 103 wherein $R^5$ is selected from the group consisting of:

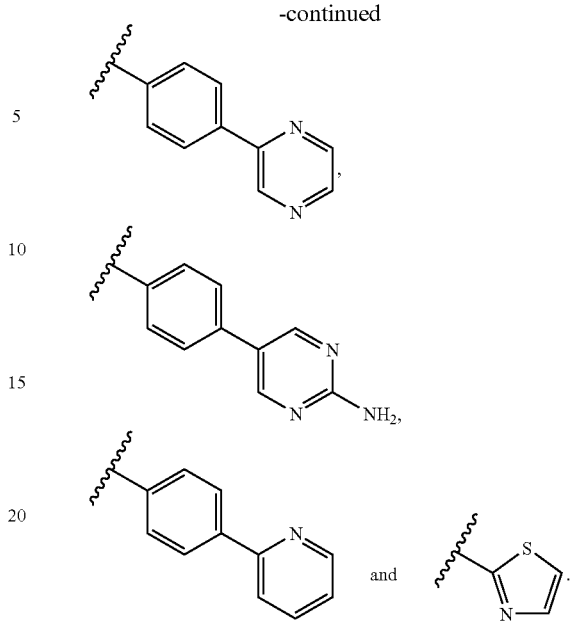

Embodiment No. 122 is directed to a compound of any one of Embodiment Nos. 1 to 103 wherein $R^5$ is selected from the group consisting of:

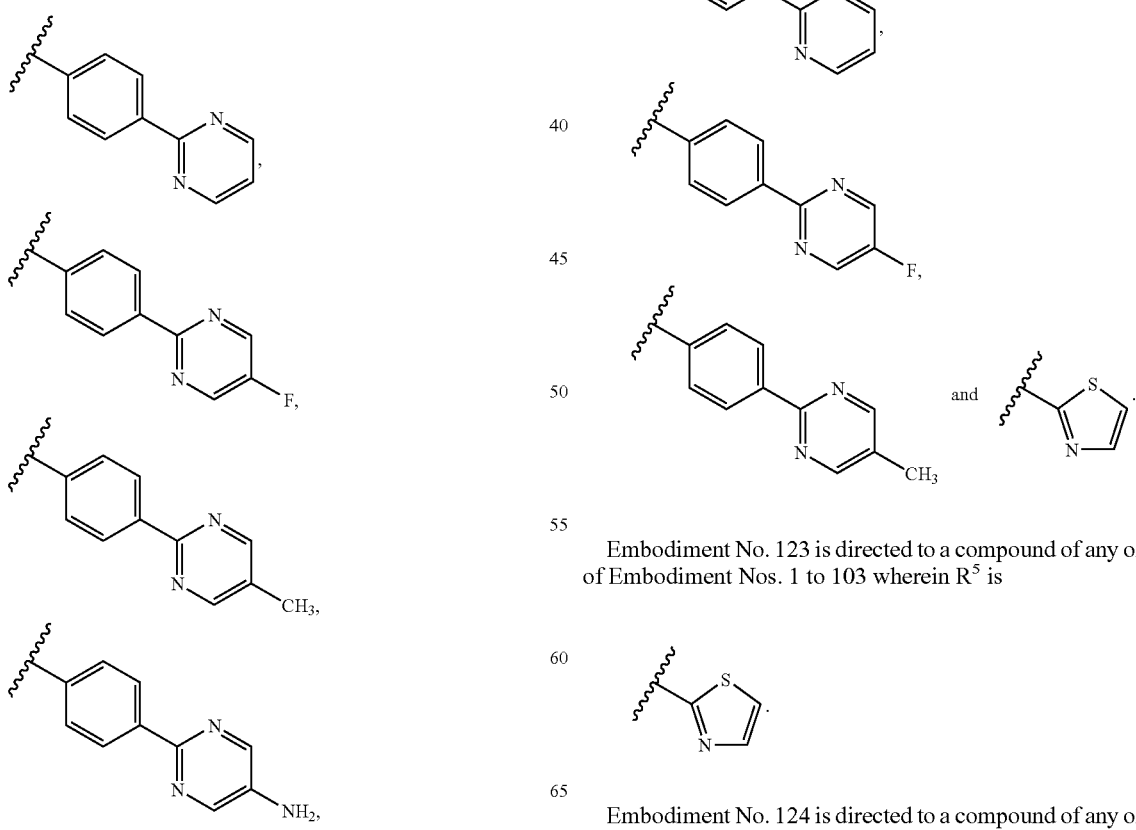

Embodiment No. 123 is directed to a compound of any one of Embodiment Nos. 1 to 103 wherein $R^5$ is Embodiment No. 124 is directed to a compound of any one of Embodiment Nos. 1 to 103 wherein $R^5$ is Embodiment No. 125 is directed to a compound of any one of Embodiment Nos. 1 to 103 wherein $R^5$ is

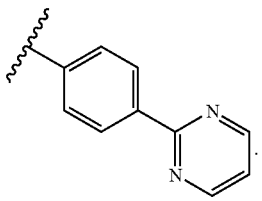 [SMILES: *c1ccc(-c2ncccn2)cc1]

Embodiment No. 126 is directed to a compound of any one of Embodiment Nos. 1 to 103 wherein $R^5$ is


Embodiment No. 127 is directed to a compound of any one of Embodiment Nos. 1 to 103 wherein $R^5$ is

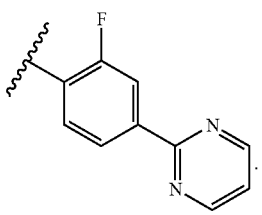 [SMILES: *c1ccc(-c2ncccn2)cc1F]

Embodiment No. 128 is directed to a compound of any one of Embodiment Nos. 1 to 103 wherein $R^1$ is selected from the group consisting of the $R^1$ groups of anyone of Embodiment Nos. 104, 105, 106, 107, 108, 109, 110, 111, 112, 113, 114, 115, 116, 117, 118, or 119 and wherein $R^5$ is selected from the group consisting of the $R^5$ groups in any one of Embodiment Nos. 120, 121, 122, 123, 124, 125, 126, or 127.

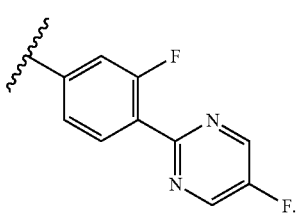 [SMILES: *c1ccc(-c2ncc(F)cn2)c(F)c1]

Embodiment No. 129 is directed to a compound of any one of Embodiment Nos. 1 to 128 wherein $R^2$ is selected from the group consisting of H, —CH$_2$OH and —CH$_2$F.

Embodiment No. 130 is directed to a compound of any one of Embodiment Nos. 1 to 128 wherein $R^2$ is H.

Embodiment No. 131 is directed to a compound of any one of Embodiment Nos. 1 to 128 wherein $R^2$ is —OR$^{23}$ wherein $R^{23}$ is alkyl.

Embodiment No. 132 is directed to a compound of any one of Embodiment Nos. 1 to 128 wherein $R^2$ is —OCH$_3$.

Embodiment No. 133 is directed to a compound of any one of Embodiment Nos. 1 to 128 wherein $R^2$ is —CN.

Embodiment No. 134 is directed to a compound of any one of Embodiment Nos. 1 to 128 wherein $R^2$ is —OCHF$_2$.

Embodiment No. 135 is directed to a compound of any one of Embodiment Nos. 1 to 30, 32 to 35, 41, 42, 44 to 46, 48 to 50, 52 to 56, 58 to 60, 62 to 64, 66 to 70, 72 to 74, 76 to 78, 80 to 85, 87 to 92, 94 to 99 and 101 to 134 wherein $R^3$ is —CH$_3$, provided that, as those skilled in the art will appreciate, Embodiment No. 135 does not apply to any previous embodiment wherein $R^3$ has already been limited to H.

Embodiment No. 136 is directed to a compound of any one of Embodiment Nos. 1 to 30, 32 to 35, 41, 42, 44 to 46, 48 to 50, 52 to 56, 58 to 60, 62 to 64, 66 to 70, 72 to 74, 76 to 78, 80 to 85, 87 to 92, 94 to 99 and 101 to 134 wherein $R^4$ is —CH$_3$, provided that, as those skilled in the art will appreciate, Embodiment No. 135 does not apply to any previous embodiment wherein $R^4$ has already been limited to H.

Embodiment No. 137 is directed to a compound of any one of Embodiment Nos. 1 to 15, 18 to 19, 21 to 30, 32 to 35, 41 to 42, 44 to 46, 48 to 50, 52 to 56, 58 to 60, 62, 64, 66 to 70, 72 to 74, 76 to 78, 80 to 85, 87 to 92, 94 to 99 and 101 to 134 wherein $R^6$ is —CH$_3$, provided that, as those skilled in the art will appreciate, Embodiment No. 135 does not apply to any previous embodiment wherein $R^6$ has already been limited to H, or wherein $R^6$ is absent from the formula (e.g., when Q is 2.12, 2.13 or 2.16).

Embodiment No. 138 is directed to a compound of any one of Embodiment Nos. 1 to 30, 32 to 35, 41, 42, 44 to 46, 48 to 50, 52 to 56, 58 to 60, 62 to 64, 66 to 70, 72 to 74, 76 to 78, 80 to 85, 87 to 92, 94 to 99 and 101 to 134 wherein $R^7$ is —CH$_3$, provided that, as those skilled in the art will appreciate, Embodiment No. 135 does not apply to any previous embodiment wherein $R^7$ has already been limited to H.

Embodiment No. 139 is directed to a compound selected from the group consisting of the final compounds of Examples 1 to 610, and 611.

Embodiment No. 140 is directed to a compound selected from the group consisting of the final compounds of Examples 6, 336, 412, 413, 462, 469, 480, 487, 489, and 571.

Embodiment No. 141 is directed to a compound selected from the group consisting of the final compounds of Examples 1, 2, 5, 6, 7, 9, 11, 12, 13, 18, 19, 22, 23, 24, 25, 26, 27, 28, 61, 88, 89, 183, 184, 186, 188, 189, 190, 191, 192, 193, 196, 197, 198, 199, 202, 203, 204, 205, 250, 251, 253, 254, 255, 256, 257, 258 and 259.

Embodiment No. 142 is directed to the final compound of Example 6.

Embodiment No. 143 is directed to the final compound of Example 183.

Embodiment No. 144 is directed to the final compound of Example 184.

Embodiment No. 145 is directed to the final compound of Example 186.

Embodiment No. 146 is directed to the final compound of Example 188.

Embodiment No. 147 is directed to the final compound of Example 189.

Embodiment No. 148 is directed to the final compound of Example 190.

Embodiment No. 149 is directed to the final compound of Example 191.

Embodiment No. 150 is directed to the final compound of Example 192.

Embodiment No. 151 is directed to the final compound of Example 193.

Embodiment No. 152 is directed to the final compound of Example 336.

Embodiment No. 153 is directed to the final compound of Example 412.

Embodiment No. 154 is directed to the final compound of Example 413.

Embodiment No. 155 is directed to the final compound of Example 462.

Embodiment No. 156 is directed to the final compound of Example 469.

Embodiment No. 157 is directed to the final compound of Example 480.

Embodiment No. 158 is directed to the final compound of Example 487.

Embodiment No. 159 is directed to the final compound of Example 489.

Embodiment No. 160 is directed to the final compound of Example 571.

Embodiment No. 161 is directed to the final compound of Example 459.

Embodiment No. 162 is directed to the final compound of Example 622.

Embodiment No. 163 is directed to the final compound of Example 613.

Embodiment No. 164 is directed to the final compound of Example 825.

Embodiment No. 165 is directed to the final compound of Example 479.

Embodiment No. 166 is directed to a compound of any one of Embodiment Nos. 1 to 165 in pure and isolated form.

Embodiment No. 167 is directed to a pharmaceutical composition comprising an effective amount of at least one compound (e.g., 1, 2 or 3, or 1 or 2, or 1, and usually 1) of formula 1.0, preferably a compound of formula 1.0C, and a pharmaceutically acceptable carrier.

Embodiment No. 168 is directed to a pharmaceutical composition comprising an effective amount of a compound of formula 1.0, preferably a compound of formula 1.0C, and a pharmaceutically acceptable carrier.

Embodiment No. 169 is directed to a pharmaceutical composition comprising an effective amount of at least one compound (e.g., 1, 2 or 3, or 1 or 2, or 1, and usually 1) of formula 1.1, and a pharmaceutically acceptable carrier.

Embodiment No. 170 is directed to a pharmaceutical composition comprising an effective amount of a compound of formula 1.1 and a pharmaceutically acceptable carrier.

Embodiment No. 171 is directed to a pharmaceutical composition comprising an effective amount of at least one compound (e.g., 1, 2 or 3, or 1 or 2, or 1, and usually 1) of formula 1.2, and a pharmaceutically acceptable carrier.

Embodiment No. 172 is directed to a pharmaceutical composition comprising an effective amount of a compound of formula 1.2 and a pharmaceutically acceptable carrier.

Embodiment No. 173 is directed to a pharmaceutical composition comprising an effective amount of at least one compound (e.g., 1, 2 or 3, or 1 or 2, or 1, and usually 1) of formula 1.3, and a pharmaceutically acceptable carrier.

Embodiment No. 174 is directed to a pharmaceutical composition comprising an effective amount of a compound of formula 1.3 and a pharmaceutically acceptable carrier.

Embodiment No. 175 is directed to a pharmaceutical composition comprising an effective amount of at least one compound (e.g., 1, 2 or 3, or 1 or 2, or 1, and usually 1) of any one of Embodiment Nos. 1 to 165 and a pharmaceutically acceptable carrier.

Embodiment No. 176 is directed to a pharmaceutical composition comprising an effective amount of a compound of any one of Embodiment Nos. 1 to 165 and a pharmaceutically acceptable carrier.

Embodiment No. 177 is directed to a pharmaceutical composition comprising an effective amount of at least one compound (e.g., 1, 2 or 3, or 1 or 2, or 1, and usually 1) of Embodiment No. 166 and a pharmaceutically acceptable carrier.

Embodiment No. 178 is directed to a pharmaceutical composition comprising an effective amount of one compound of Embodiment No. 166 and a pharmaceutically acceptable carrier.

Embodiment No. 179 is directed to a pharmaceutical composition of any one of Embodiment Nos. 167 to 178 further comprising an effective amount of at least one (e.g., 1, 2 or 3, or 1 or 2, or 1, and usually 1) other active pharmaceutically active ingredient.

Embodiment No. 180 is directed to a pharmaceutical composition of any one of Embodiment Nos. 167 to 178 further comprising an effective amount of another (i.e., one other) pharmaceutically active ingredient.

Embodiment No. 181 is directed to a pharmaceutical composition of any one of Embodiment Nos. 167 to 178 further comprising an effective amount of at least one (e.g., 1, 2 or 3, or 1 or 2, or 1, and usually 1) chemotherapeutic agent.

Embodiment No. 182 is directed to a pharmaceutical composition of any one of Embodiment Nos. 167 to 178 further comprising an effective amount of a chemotherapeutic agent.

Embodiment No. 183 is directed to a method of treating cancer in a patient in need of such treatment, said method comprising administering to said patient an effective amount of at least one (1, 2 or 3, or 1 or 2, or 1, and usually 1) compound of formula 1.0 (preferably formula 1.0C).

Embodiment No. 184 is directed to a method of treating cancer in a patient in need of such treatment, said method comprising administering to said patient an effective amount of one compound of formula 1.0 (preferably formula 1.0C).

Embodiment No. 185 is directed to a method of treating cancer in a patient in need of such treatment, said method comprising administering to said patient an effective amount of at least one (1, 2 or 3, or 1 or 2, or 1, and usually 1) compound of formula 1.1.

Embodiment No. 186 is directed to a method of treating cancer in a patient in need of such treatment, said method comprising administering to said patient an effective amount of one compound of formula 1.1.

Embodiment No. 187 is directed to a method of treating cancer in a patient in need of such treatment, said method comprising administering to said patient an effective amount of at least one (1, 2 or 3, or 1 or 2, or 1, and usually 1) compound of formula 1.2.

Embodiment No. 188 is directed to a method of treating cancer in a patient in need of such treatment, said method comprising administering to said patient an effective amount of one compound of formula 1.2.

Embodiment No. 189 is directed to a method of treating cancer in a patient in need of such treatment, said method comprising administering to said patient an effective amount of at least one (1, 2 or 3, or 1 or 2, or 1, and usually 1) compound of formula 1.3.

Embodiment No. 190 is directed to a method of treating cancer in a patient in need of such treatment, said method comprising administering to said patient an effective amount of one compound of formula 1.3.

Embodiment No. 191 is directed to a method of treating cancer in a patient in need of such treatment, said method comprising administering to said patient an effective amount of at least one (1, 2 or 3, or 1 or 2, or 1, and usually 1) compound of any one of Embodiment Nos. 1 to 166.

Embodiment No. 192 is directed to a method of treating cancer in a patient in need of such treatment, said method comprising administering to said patient an effective amount of a compound of any one of Embodiment Nos. 1 to 166.

Embodiment No. 193 is directed to a method of treating cancer in any one of Embodiment Nos. 183 to 192 further comprising the administration of an effective amount of at least one (1, 2 or 3, or 1 or 2, or 1, and usually 1) chemotherapeutic agent.

Embodiment No. 194 is directed to a method of treating cancer in any one of Embodiment Nos. 183 to 192 further comprising the administration of an effective amount of a chemotherapeutic agent.

Embodiment No. 195 is directed to a method of treating cancer in a patient in need of such treatment comprising administering to said patient an effective amount of a pharmaceutical composition of any one of Embodiment Nos. 167 to 182.

Embodiment No. 196 is directed to a method of treating cancer in a patient in need of such treatment comprising administering to said patient an effective amount of a pharmaceutical composition of any one of Embodiment Nos. 167 to 178.

Embodiment No. 197 is directed to a method of treating cancer in a patient in need of such treatment comprising administering to said patient an effective amount of a pharmaceutical composition of any one of Embodiment Nos. 167 to 178, in combination with an effective amount of at least one (1, 2 or 3, or 1 or 2, or 1, and usually 1) chemotherapeutic agent Embodiment No. 198 is directed to a method of treating cancer in a patient in need of such treatment comprising administering to said patient an effective amount of a pharmaceutical composition of any one of Embodiment Nos. 167 to 178, in combination with an effective amount of one chemotherapeutic agent.

Embodiment No. 199 is directed to a method of treating cancer of any one of Embodiment Nos. 193, 194, 197 and 198 wherein the chemotherapeutic agent is selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688.

Embodiment No. 200 is directed to a method of treating cancer of any one of Embodiment Nos. 193, 194, 197 and 198 wherein the chemotherapeutic agent is selected from the group consisting of: paclitaxel, docetaxel, carboplatin, cisplatin, navelbine, gemcitabine, and Herceptin.

Embodiment No. 201 is directed to a method of treating cancer of any one of Embodiment Nos. 193, 194, 197 and 198 wherein the chemotherapeutic agent is selected from the group consisting of: Cyclophasphamide, 5-Fluorouracil, Temozolomide, Vincristine, Cisplatin, Carboplatin, and Gemcitabine.

Embodiment No. 202 is directed to a method of treating cancer of any one of Embodiment Nos. 193, 194, 197 and 198 wherein the chemotherapeutic agent is selected from the group consisting of: Gemcitabine, Cisplatin and Carboplatin.

This invention also provides a method of treating cancer in a patient in need of such treatment, said treatment comprising administering to said patient a therapeutically effective amount at least one (e.g., 1, 2 or 3, or 1 or 2, or 1, and usually 1) compound of formula 1.0 (for example, as described in any one of Embodiment Nos. 1 to 166), and therapeutically effective amounts of at least one (e.g., 1, 2 or 3, or 1 or 2, or 2, or 1) chemotherapeutic agent selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

This invention also provides a method of treating cancer in a patient in need of such treatment, said treatment comprising administering to said patient a therapeutically effective amount at least one (e.g., 1, 2 or 3, or 1 or 2, or 1, and usually 1) compound of formula 1.0 (for example, as described in any one of Embodiment Nos. 1 to 166), and therapeutically effective amounts of at least two (e.g., 2 or 3, or 2, and usually 2) different antineoplastic agents selected from the group consisting of: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αVβ3 integrins, (13) folate antagonists, (14) ribonucleotide reductase inhibitors, (15) anthracyclines, (16) biologics; (17) inhibitors of angiogenesis and/or suppressors of tumor necrosis factor alpha (TNF-alpha) such as thalidomide (or related imid), (18) Bcr/abl kinase inhibitors, (19) MEK1 and/or MEK 2 inhibitors that are small molecules, (20) IGF-1 and IGF-2 inhibitors that are small molecules, (21) small molecule inhibitors of RAF and BRAF kinases, (22) small molecule inhibitors of cell cycle dependent kinases such as CDK1, CDK2, CDK4 and CDK6, (23) alkylating agents, and (24) farnesyl protein transferase inhibitors (also know as FPT inhibitors or FTI (i.e., farnesyl transfer inhibitors)).

This invention also provides a method of treating cancer in a patient in need of such treatment, said method comprising administering to said patient therapeutically effective amounts at least one (e.g., 1, 2 or 3, or 1 or 2, or 1, and usually 1) compound of formula 1.0 (for example, as described in any one of Embodiment Nos. 1 to 166), and an antineoplastic agent selected from the group consisting of: (1) EGF inhibitors that are antibodies, (2) EGF inhibitors that are small molecules, (3) VEGF inhibitors that are antibodies, and (4) VEGF inhibitors that are small molecules. Radiation therapy can also be used in conjunction with this above combination therapy, i.e., the above method using a combination of compounds of the invention and antineoplastic agent can also comprise the administration of a therapeutically effect amount of radiation.

This invention also provides a method of treating leukemias (e.g., acute myeloid leukemia (AML), and chronic myeloid leukemia (CML)) in a patient in need of such treatment, said method comprising administering to said patient therapeutically effective amounts at least one (e.g., 1, 2 or 3, or 1 or 2, or 1, and usually 1) compound of formula 1.0 (for example, as described in any one of Embodiment Nos. 1 to 166), and: (1) Gleevec and interferon to treat CML; (2) Gleevec and pegylated interferon to treat CML; (3) Gleevec to treat CML; (4) an anti-tumor nucleoside derivative (e.g., Ara-C) to treat AML; or (5) an anti-tumor nucleoside derivative (e.g., Ara-C) in combination with an anthracycline to treat AML.

This invention also provides a method of treating non-Hodgkin's lymphoma in a patient in need of such treatment, said method comprising administering therapeutically effective amounts at least one (e.g., 1, 2 or 3, or 1 or 2, or 1, and usually 1) compound of formula 1.0 (for example, as described in any one of Embodiment Nos. 1 to 166) and: (1) a biologic (e.g., Rituxan); (2) a biologic (e.g., Rituxan) and an anti-tumor nucleoside derivative (e.g., Fludarabine); or (3) Genasense (antisense to BCL-2).

This invention also provides a method of treating multiple myeloma in a patient in need of such treatment, said method comprising administering to said patient therapeutically effective amounts of at least one (e.g., 1, 2 or 3, or 1 or 2, or 1, and usually 1) compound of formula 1.0 (for example, as described in any one of Embodiment Nos. 1 to 166) and: (1) a proteosome inhibitor (e.g., PS-341 from Millenium); or (2) Thalidomide (or related imid).

This invention also provides a method of treating cancer in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) at least one (e.g., 1, 2 or 3, or 1 or 2, or 2, or 1) antineoplastic agent selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, and (12) antibodies that are inhibitors of αVβ3 integrins.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) at least one (e.g., 1, 2 or 3, or 1 or 2, or 2, or 1) antineoplastic agent selected from the group consisting of: (1) taxanes, (2) platinum coordinator compounds, (3) EGF inhibitors that are antibodies, (4) EGF inhibitors that are small molecules, (5) VEGF inhibitors that are antibodies, (6) VEGF kinase inhibitors that are small molecules, (7) estrogen receptor antagonists or selective estrogen receptor modulators, (8) anti-tumor nucleoside derivatives, (9) epothilones, (10) topoisomerase inhibitors, (11) vinca alkaloids, and (12) antibodies that are inhibitors of αVβ3 integrins.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) at least one (e.g., 1, 2 or 3, or 1 or 2, or 2, or 1) antineoplastic agent selected from the group consisting of: (1) taxanes, (2) platinum coordinator compounds, (3) anti-tumor nucleoside derivatives, (4) topoisomerase inhibitors, and (5) vinca alkaloids.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 166), (b) carboplatin, and (c) paclitaxel.

This invention also provides a method of treating non small cell lung cancer in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), (b) cisplatin, and (c) gemcitabine.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 166), (b) carboplatin, and (c) gemcitabine.

This invention also provides a method of treating non small cell lung cancer in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 166), (b) Carboplatin, and (c) Docetaxel.

This invention also provides a method of treating cancer in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) an antineoplastic agent selected from the group consisting of: (1) EGF inhibitors that are antibodies, (2) EGF inhibitors that are small molecules, (3) VEGF inhibitors that are antibodies, (4) VEGF kinase inhibitors that are small molecules.

This invention also provides a method of treating squamous cell cancer of the head and neck, in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) at least one (e.g., 1, 2 or 3, or 1 or 2, or 2, or 1) antineoplastic agent selected from the group consisting of: (1) taxanes, and (2) platinum coordinator compounds.

This invention also provides a method of treating squamous cell cancer of the head and neck, in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) at least one (e.g., 1, 2 or 3, or 1 or 2, or 2, or 1) antineoplastic agent selected from the group consisting of: (1) taxanes, (2) platinum coordinator compounds, and (3) anti-tumor nucleoside derivatives (e.g., 5-Fluorouracil).

This invention also provides a method of treating CML in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 166), (b) Gleevec, and (c) interferon (e.g., Intron-A).

This invention also provides a method of treating CML in a patient in need of such treatment comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 166), (b) Gleevec; and (c) pegylated interferon (e.g., Peg-Intron, and Pegasys).

This invention also provides a method of treating CML in a patient in need of such treatment comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 166) and (b) Gleevec.

This invention also provides a method of treating CMML in a patient in need of such treatment, said method comprising administering to said patient therapeutically effective amounts of at least one (e.g., 1, 2 or 3, or 1 or 2, or 1, and usually 1) compound of formula 1.0 (for example, as described in any one of Embodiment Nos. 1 to 166).

This invention also provides a method of treating AML in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) an anti-tumor nucleoside derivative (e.g., Cytarabine (i.e., Ara-C)).

This invention also provides a method of treating AML in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), (b) an anti-tumor nucleoside derivative (e.g., Cytarabine (i.e., Ara-C)), and (c) an anthracycline.

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) Rituximab (Rituxan).

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), (b) Rituximab (Rituxan), and (c) an anti-tumor nucleoside derivative (e.g., Fludarabine (i.e., F-ara-A).

This invention also provides a method of treating non-Hodgkin's lymphoma in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) Genasense (antisense to BCL-2).

This invention also provides a method of treating multiple myeloma in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) a proteosome inhibitor (e.g., PS-341 (Millenium)).

This invention also provides a method of treating multiple myeloma in a patient in need of such treatment, said method comprising administering to said patient therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) Thalidomide or related imid.

This invention also provides a method of treating multiple myeloma in a patient in need of such treatment, said method comprising administering therapeutically effective amounts of: (a) at least one (e.g., 1, 2 or 3, or 1 or 2, or 1, and usually 1) compound of formula 1.0 (for example, as described in any one of Embodiment Nos. 1 to 166), and (b) Thalidomide.

This invention is also directed to the methods of treating cancer described herein, particularly those described above, wherein in addition to the administration of the compound of formula 1.0 (for example, as described in any one of Embodiment Nos. 1 to 166) and antineoplastic agents, radiation therapy is also administered prior to, during, or after the treatment cycle.

This invention also provides a method for treating cancer (e.g., lung cancer, prostate cancer and myeloid leukemias) in a patient in need of such treatment, said method comprising administering to said patient (1) an effective amount of at least one (e.g., 1, 2 or 3, or 1 or 2, or 1, and usually 1) compound of formula 1.0 (for example, as described in any one of Embodiment Nos. 1 to 166), in combination with (2) at least one (e.g., 1, 2 or 3, or 1 or 2, or 2, or 1) antineoplastic agent, microtubule affecting agent and/or radiation therapy.

This invention also provides a method of treating cancer in a patient in need of such treatment, said method comprising administering to said patient an effective amount of at least one (e.g., 1, 2 or 3, or 1 or 2, or 1, and usually 1) compound of formula 1.0 (for example, as described in any one of Embodiment Nos. 1 to 166) in combination with an effective amount of at least one (e.g., 1, 2 or 3, or 1 or 2, or 1, and usually 1) signal transduction inhibitor.

Thus, in one example (e.g., treating non small cell lung cancer): (1) the compound of formula 1.0 (for example, as described in any one of Embodiment Nos. 1 to 166) is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once per week in an amount of about 50 to about 100 mg/m$^2$, and in another example about 60 to about 80 mg/m$^2$, and (3) Carboplatin is administered once per week in an amount to provide an AUC of about 2 to about 3.

In another example (e.g., treating non small cell lung cancer): (1) the compound of formula 1.0 (for example, as described in any one of Embodiment Nos. 1 to 166) is administered in an amount of about 50 mg to about 200 mg twice a day, and in another example about 75 mg to about 125 mg administered twice a day, and yet in another example about 100 mg administered twice a day, (2) Paclitaxel (e.g., Taxol® is administered once per week in an amount of about 50 to about 100 mg/m$^2$, and in another example about 60 to about 80 mg/m$^2$, and (3) Cisplatin is administered once per week in an amount of about 20 to about 40 mg/m$^2$.

In another example (e.g., treating non small cell lung cancer): (1) the compound of formula 1.0 (for example, as described in any one of Embodiment Nos. 1 to 166) is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m$^2$, and (3) Carboplatin is administered once per week in an amount to provide an AUC of about 2 to about 3.

In another example (e.g., treating non small cell lung cancer): (1) the compound of formula 1.0 (for example, as described in any one of Embodiment Nos. 1 to 166) is administered in an amount of about 50 mg to about 200 mg twice a day, and in another example about 75 mg to about 125 mg administered twice a day, and in yet another example about 100 mg administered twice a day, (2) Docetaxel (e.g., Taxotere®) is administered once per week in an amount of about 10 to about 45 mg/m$^2$, and (3) Cisplatin is administered once per week in an amount of about 20 to about 40 mg/m$^2$.

In another example (e.g., treating non small cell lung cancer): (1) the compound of formula 1.0 (for example, as described in any one of Embodiment Nos. 1 to 166) is administered in an amount of about 50 mg to about 200 mg twice a day, and in another example about 75 mg to about 125 mg administered twice a day, and in yet another example about 100 mg administered twice a day, (2) Paclitaxel (e.g., Taxol®) is administered once every three weeks in an amount of about 150 to about 250 mg/m$^2$, and in another example about 175 to about 225 mg/m$^2$, and in yet another example 175 mg/m$^2$, and (3) Carboplatin is administered once every three weeks in an amount to provide an AUC of about 5 to about 8, and in another example 6.

In another example of treating non small cell lung cancer: (1) the compound of formula 1.0 (for example, as described in any one of Embodiment Nos. 1 to 166) is administered in an amount of 100 mg administered twice a day, (2) Paclitaxel (e.g., Taxol® is administered once every three weeks in an amount of 175 mg/m$^2$, and (3) Carboplatin is administered once every three weeks in an amount to provide an AUC of 6.

In another example (e.g., treating non small cell lung cancer): (1) the compound of formula 1.0 (for example, as described in any one of Embodiment Nos. 1 to 166) is administered in an amount of about 50 mg to about 200 mg twice a day, and in another example about 75 mg to about 125 mg administered twice a day, and in yet another example about 100 mg administered twice a day, (2) Paclitaxel (e.g., Taxol® is administered once every three weeks in an amount of about 150 to about 250 mg/m$^2$, and in another example about 175 to about 225 mg/m$^2$, and (3) Cisplatin is administered once every three weeks in an amount of about 60 to about 100 mg/m$^2$.

In another example (e.g., treating non small cell lung cancer): (1) the compound of formula 1.0 (for example, as described in any one of Embodiment Nos. 1 to 166) is administered in an amount of about 50 mg to about 200 mg twice a day, and in another example about 75 mg to about 125 mg administered twice a day, and in yet another example about 100 mg administered twice a day, (2) Docetaxel (e.g., Taxotere® is administered once every three weeks in an amount of about 50 to about 100 mg/m$^2$, and (3) Carboplatin is administered once every three weeks in an amount to provide an AUC of about 5 to about 8.

In another example (e.g., treating non small cell lung cancer): (1) the compound of formula 1.0 (for example, as described in any one of Embodiment Nos. 1 to 166) is administered in an amount of about 50 mg to about 200 mg twice a day, In another example about 75 mg to about 125 mg administered twice a day, and in yet another example about 100 mg administered twice a day, (2) Docetaxel (e.g., Taxotere® is administered once every three weeks in an amount of about 50 to about 100 mg/m$^2$, and (3) Cisplatin is administered once every three weeks in an amount of about 60 to about 100 mg/m$^2$.

In another example for treating non small cell lung cancer using the compounds of formula 1.0, Docetaxel and Carboplatin: (1) the compound of formula 1.0 (for example, as described in any one of Embodiment Nos. 1 to 166) is administered in an amount of about 50 mg to about 200 mg twice a day, and in another example about 75 mg to about 125 mg administered twice a day, and in yet another example about 100 mg administered twice a day, (2) Docetaxel (e.g., Taxotere® is administered once every three weeks in an amount of about 75 mg/m$^2$, and (3) Carboplatin is administered once every three weeks in an amount to provide an AUC of about 6.

In another example of the treatments of non-small cell lung cancer described above the Docetaxel (e.g., Taxotere®) and Cisplatin, the Docetaxel (e.g., Taxotere®) and Carboplatin, the Paclitaxel (e.g., Taxol®) and Carboplatin, or the Paclitaxel (e.g., Taxol®) and Cisplatin are administered on the same day.

In another example (e.g., CML): (1) the compound of formula 1.0 (for example, as described in any one of Embodiment Nos. 1 to 166) is administered in an amount of about 100 mg to about 200 mg administered twice a day, (2) Gleevec is administered in an amount of about 400 to about 800 mg/day orally, and (3) interferon (Intron-A) is administered in an amount of about 5 to about 20 million IU three times per week.

In another example (e.g., CML): (1) the compound of formula 1.0 (for example, as described in any one of Embodiment Nos. 1 to 166) is administered in an amount of about 100 mg to about 200 mg administered twice a day, (2) Gleevec is administered in an amount of about 400 to about 800 mg/day orally, and (3) pegylated interferon (Peg-Intron or Pegasys) is administered in an amount of about 3 to about 6 micrograms/kg/day.

In another example (e.g., non-Hodgkin's lymphoma): (1) the compound of formula 1.0 (for example, as described in any one of Embodiment Nos. 1 to 166) is administered in an amount of about 50 mg to about 200 mg twice a day, and in another example about 75 mg to about 125 mg administered twice a day, and in yet another example about 100 mg administered twice a day, and (2) Genasense (antisense to BCL-2) is administered as a continuous IV infusion at a dose of about 2 to about 5 mg/kg/day (e.g., 3 mg/kg/day) for 5 to 7 days every 3 to 4 weeks.

In another example (e.g., multiple myeloma): (1) the compound of formula 1.0 (for example, as described in any one of Embodiment Nos. 1 to 166) is administered in an amount of about 50 mg to about 200 mg twice a day, and in another example about 75 mg to about 125 mg administered twice a day, and in yet another example about 100 mg administered twice a day, and (2) the proteosome inhibitor (e.g., PS-341-Millenium) is administered in an amount of about 1.5 mg/m$^2$ twice weekly for two consecutive weeks with a one week rest period.

In another example (e.g., multiple myeloma): (1) the compound of formula 1.0 (for example, as described in any one of Embodiment Nos. 1 to 166) is administered in an amount of about 50 mg to about 200 mg twice a day, and in another example about 75 mg to about 125 mg administered twice a day, and in yet another example about 100 mg administered twice a day, and (2) the Thalidomide (or related imid) is administered orally in an amount of about 200 to about 800 mg/day, with dosing being continuous until relapse or toxicity.

In one embodiment of the methods of treating cancer of this invention, the chemotherapeutic agents are selected from the group consisting of: paclitaxel, docetaxel, carboplatin, cisplatin, gemcitabine, tamoxifen, Herceptin, Cetuximab, Tarceva, Iressa, bevacizumab, navelbine, IMC-1C11, SU5416 and SU6688.

In another embodiment of the methods of treating cancer of this invention, the chemotherapeutic agents are selected from the group consisting of: paclitaxel, docetaxel, carboplatin, cisplatin, navelbine, gemcitabine, and Herceptin.

Thus, one embodiment of this invention is directed to a method of treating cancer comprising administering to a patient in need of such treatment therapeutically effective amounts of the compound of formula 1.0 (for example, as described in any one of Embodiment Nos. 1 to 166), a taxane, and a platinum coordination compound.

Another embodiment of this invention is directed to a method of treating cancer comprising administering to a patient in need of such treatment therapeutically effective amounts of the compound of formula 1.0 (for example, as described in any one of Embodiment Nos. 1 to 166), a taxane, and a platinum coordination compound, wherein said compound of formula 1.0 is administered every day, said taxane is administered once per week per cycle, and said platinum coordinator compound is administered once per week per cycle. In another embodiment the treatment is for one to four weeks per cycle.

Another embodiment of this invention is directed to a method of treating cancer comprising administering to a patient in need of such treatment therapeutically effective amounts of the compound of formula 1.0 (for example, as described in any one of Embodiment Nos. 1 to 166), a taxane, and a platinum coordination compound, wherein said compound of formula 1.0 is administered every day, said taxane is administered once every three weeks per cycle, and said platinum coordinator compound is administered once every three weeks per cycle. In another embodiment the treatment is for one to three weeks per cycle.

Another embodiment of this invention is directed to a method of treating cancer comprising administering to a patient in need of such treatment therapeutically effective amounts of the compound of formula 1.0 (for example, as described in any one of Embodiment Nos. 1 to 166), paclitaxel, and carboplatin. In another embodiment, said compound of formula 1.0 is administered every day, said paclitaxel is administered once per week per cycle, and said carboplatin is administered once per week per cycle. In another embodiment the treatment is for one to four weeks per cycle.

Another embodiment of this invention is directed to a method of treating cancer comprising administering to a patient in need of such treatment therapeutically effective amounts of the compound of formula 1.0 (for example, as described in any one of Embodiment Nos. 1 to 166), paclitaxel, and carboplatin. In another embodiment, said compound of formula 1.0 is administered every day, said paclitaxel is administered once every three weeks per cycle, and said carboplatin is administered once every three weeks per cycle. In another embodiment the treatment is for one to three weeks per cycle.

Another embodiment of this invention is directed to a method for treating non small cell lung cancer in a patient in need of such treatment comprising administering daily a therapeutically effective amount of the compound of formula 1.0 (for example, as described in any one of Embodiment Nos. 1 to 166), administering a therapeutically effective amount of carboplatin once a week per cycle, and administering a therapeutically effective amount of paclitaxel once a week per cycle, wherein the treatment is given for one to four weeks per cycle. In another embodiment said compound of formula 1.0 is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering daily a therapeutically effective amount of a compound of formula 1.0 (for example, as described in any one of Embodiment Nos. 1 to 166), administering a therapeutically effective amount of carboplatin once every three weeks per cycle, and administering a therapeutically effective amount of paclitaxel once every three weeks per cycle, wherein the treatment is given for one to three weeks. In another embodiment compound of formula 1.0 is administered twice per day. In another embodiment said carboplatin and said paclitaxel are administered on the same day, and in another embodiment said carboplatin and said paclitaxel are administered consecutively, and in another embodiment said carboplatin is administered after said paclitaxel.

Another embodiment of this invention is directed to a method for treating non small cell lung cancer in a patient in need of such treatment comprising administering about 50 to about 200 mg of a compound of formula 1.0 (for example, as described in any one of Embodiment Nos. 1 to 166) twice a day, administering carboplatin once per week per cycle in an amount to provide an AUC of about 2 to about 8 (and in another embodiment about 2 to about 3), and administering once per week per cycle about 60 to about 300 mg/m$^2$ (and in another embodiment about 50 to 100 mg/m$^2$, and in yet another embodiment about 60 to about 80 mg/m$^2$) of paclitaxel, wherein the treatment is given for one to four weeks per cycle. In another embodiment said compound of formula 1.0 is administered in amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

In another embodiment, this invention is directed to a method for treating non small cell lung cancer in a patient in need of such treatment comprising administering about 50 to about 200 mg of a compound of formula 1.0 (for example, as described in any one of Embodiment Nos. 1 to 166) twice a day, administering carboplatin once every three weeks per cycle in an amount to provide an AUC of about 2 to about 8 (in another embodiment about 5 to about 8, and in another embodiment 6), and administering once every three weeks per cycle about 150 to about 250 mg/m$^2$ (and in another embodiment about 175 to about 225 mg/m$^2$, and in another embodiment 175 mg/m$^2$) of paclitaxel, wherein the treatment is given for one to three weeks. In another embodiment said compound of formula 1.0 is administered in an amount of about 75 to about 125 mg twice a day, and in another embodiment about 100 mg twice a day. In another embodiment said carboplatin and said paclitaxel are administered on the same day, and in another embodiment said carboplatin and said paclitaxel are administered consecutively, and in another embodiment said carboplatin is administered after said paclitaxel.

Other embodiments of this invention are directed to methods of treating cancer as described in the above embodiments (i.e., the embodiments directed to treating cancer and to treating non small cell lung cancer with a taxane and platinum coordinator compound) except that in place of paclitaxel and carboplatin the taxanes and platinum coordinator compounds used together in the methods are: (1) docetaxel (Taxotere®) and cisplatin; (2) paclitaxel and cisplatin; and (3) docetaxel and carboplatin. In another embodiment of the methods of this invention cisplatin is used in amounts of about 30 to about 100 mg/m$^2$. In the another embodiment of the methods of this invention docetaxel is used in amounts of about 30 to about 100 mg/m$^2$.

In another embodiment this invention is directed to a method of treating cancer comprising administering to a patient in need of such treatment therapeutically effective amounts of a compound of formula 1.0 (for example, as described in any one of Embodiment Nos. 1 to 166), a taxane, and an EGF inhibitor that is an antibody.

In another embodiment the taxane used is paclitaxel, and the EGF inhibitor is a HER2 antibody (in one embodiment Herceptin) or Cetuximab, and in another embodiment Herceptin is used. The length of treatment, and the amounts and administration of said compound of formula 1.0 and the taxane are as described in the embodiments above. The EGF inhibitor that is an antibody is administered once a week per cycle, and in another embodiment is administered on the same day as the taxane, and in another embodiment is administered consecutively with the taxane. For example, Herceptin is administered in a loading dose of about 3 to about 5 mg/m$^2$ (in another embodiment about 4 mg/m$^2$), and then is administered in a maintenance dose of about 2 mg/m$^2$ once per week per cycle for the remainder of the treatment cycle (usually the cycle is 1 to 4 weeks). In one embodiment the cancer treated is breast cancer.

In another embodiment this invention is directed to a method of treating cancer comprising administering to a patient in need of such treatment therapeutically effective amounts of: (1) a compound of formula 1.0 (for example, as described in any one of Embodiment Nos. 1 to 166), (2) a taxane, and (3) an antineoplastic agent selected from the group consisting of: (a) an EGF inhibitor that is a small molecule, (b) a VEGF inhibitor that is an antibody, and (c) a VEGF kinase inhibitor that is a small molecule. In another embodiment, the taxane paclitaxel or docetaxel is used. In another embodiment the antineoplastic agent is selected from the group consisting of: tarceva, Iressa, bevacizumab, SU5416, SU6688 and BAY 43-9006. The length of treatment, and the amounts and administration of said compound of formula 1.0 and the taxane are as described in the embodiments above. The VEGF kinase inhibitor that is an antibody is usually given once per week per cycle. The EGF and VEGF inhibitors that are small molecules are usually given daily per cycle. In another embodiment, the VEGF inhibitor that is an antibody is given on the same day as the taxane, and in another embodiment is administered concurrently with the taxane. In another embodiment, when the EGF inhibitor that is a small molecule or the VEGF inhibitor that is a small molecule is administered on the same day as the taxane, the administration is concurrently with the taxane. The EGF or VEGF kinase inhibitor is generally administered in an amount of about 10 to about 500 mg/m$^2$.

In another embodiment this invention is directed to a method of treating cancer comprising administering to a patient in need of such treatment therapeutically effective amounts of a compound of formula 1.0 (for example, as described in any one of Embodiment Nos. 1 to 166), an anti-tumor nucleoside derivative, and a platinum coordination compound.

Another embodiment of this invention is directed to a method of treating cancer comprising administering to a patient in need of such treatment therapeutically effective amounts of a compound of formula 1.0 (for example, as described in any one of Embodiment Nos. 1 to 166), an anti-tumor nucleoside derivative, and a platinum coordination compound, wherein said compound of formula 1.0 is administered every day, said anti-tumor nucleoside derivative is administered once per week per cycle, and said platinum coordinator compound is administered once per week per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of a compound of formula 1.0 (for example, as described in any one of Embodiment Nos. 1 to 166), an anti-tumor nucleoside derivative, and a platinum coordination compound, wherein said compound of formula 1.0 is administered every day, said an anti-tumor nucleoside derivative is administered once per week per cycle, and said platinum coordinator compound is administered once every three weeks per cycle. Although the treatment can be for one to four weeks per cycle, in one embodiment the treatment is for one to seven weeks per cycle.

Another embodiment of this invention is directed to a method of treating cancer comprising administering to a patient in need of such treatment therapeutically effective amounts of a compound of formula 1.0 (for example, as described in any one of Embodiment Nos. 1 to 166), gemcitabine, and cisplatin. In another embodiment, said compound of formula 1.0 is administered every day, said gemcitabine is administered once per week per cycle, and said cisplatin is administered once per week per cycle. In one embodiment the treatment is for one to seven weeks per cycle.

Another embodiment of this invention is directed to a method of treating cancer comprising administering to a patient in need of such treatment therapeutically effective amounts of a compound of formula 1.0 (for example, as described in any one of Embodiment Nos. 1 to 166), gemcitabine, and cisplatin. In another embodiment, said compound of formula 1.0 is administered every day, said gemcitabine is administered once per week per cycle, and said cisplatin is administered once every three weeks per cycle. In another embodiment the treatment is for one to seven weeks.

Another embodiment of this invention is directed to a method of treating cancer comprising administering to a patient in need of such treatment therapeutically effective amounts of a compound of formula 1.0 (for example, as described in any one of Embodiment Nos. 1 to 166), gemcitabine, and carboplatin. In another embodiment said compound of formula 1.0 is administered every day, said gemcitabine is administered once per week per cycle, and said carboplatin is administered once per week per cycle. In another embodiment the treatment is for one to seven weeks per cycle.

Another embodiment of this invention is directed to a method of treating cancer comprising administering to a patient in need of such treatment therapeutically effective amounts of a compound of formula 1.0 (for example, as described in any one of Embodiment Nos. 1 to 166), gemcitabine, and carboplatin. In another embodiment said compound of formula 1.0 is administered every day, said gemcitabine is administered once per week per cycle, and said carboplatin is administered once every three weeks per cycle. In another embodiment the treatment is for one to seven weeks per cycle.

In the above embodiments using gemcitabine, the compound of formula 1.0 (for example, as described in any one of Embodiment Nos. 1 to 166) and the platinum coordinator compound are administered as described above for the embodiments using taxanes. Gemcitabine is administered in an amount of about 500 to about 1250 mg/m². In one embodiment the gemcitabine is administered on the same day as the platinum coordinator compound, and in another embodiment consecutively with the platinum coordinator compound, and in another embodiment the gemcitabine is administered after the platinum coordinator compound.

Another embodiment of this invention is directed to a method of treating cancer in a patient in need of such treatment comprising administering to said patient a compound of formula 1.0 (for example, as described in any one of Embodiment Nos. 1 to 166) and an antineoplastic agent selected from: (1) EGF inhibitors that are antibodies, (2) EGF inhibitors that are small molecules, (3) VEGF inhibitors that are antibodies, and (4) VEGF kinase inhibitors that are small molecules all as described above. The treatment is for one to seven weeks per cycle, and generally for one to four weeks per cycle. The compound of formula 1.0 is administered in the same manner as described above for the other embodiments of this invention. The small molecule antineoplastic agents are usually administered daily, and the antibody antineoplastic agents are usually administered once per week per cycle. In one embodiment the antineoplastic agents are selected from the group consisting of: Herceptin, Cetuximab, Tarceva, Iressa, bevacizumab, IMC-1C11, SU5416, SU6688 and BAY 43-9006.

In the embodiments of this invention wherein a platinum coordinator compound is used as well as at least one other antineoplastic agent, and these drugs are administered consecutively, the platinum coordinator compound is generally administered after the other antineoplastic agents have been administered.

Other embodiments of this invention include the administration of a therapeutically effective amount of radiation to the patient in addition to the administration of a compound of formula 1.0 (for example, as described in any one of Embodiment Nos. 1 to 166) and antineoplastic agents in the embodiments described above. Radiation is administered according to techniques and protocols well know to those skilled in the art.

Another embodiment of this invention is directed to a pharmaceutical composition comprising at least two different chemotherapeutic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising a compound of formula 1.0 (for example, as described in any one of Embodiment Nos. 1 to 166) and at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising a compound of formula 1.0 (for example, as described in any one of Embodiment Nos. 1 to 166) and at least one antineoplastic agent and a pharmaceutically acceptable carrier for intravenous administration. Preferably the pharmaceutically acceptable carrier is an isotonic saline solution (0.9% NaCl) or a dextrose solution (e.g., 5% dextrose).

Other embodiments of this invention are directed to the use of a combination of at least one (e.g., one) compound of formula 1.0 (for example, as described in any one of Embodiment Nos. 1 to 166) and drugs for the treatment of breast cancer, i.e., this invention is directed to a combination therapy for the treatment of breast cancer. Those skilled in the art will appreciate that the compounds of formula 1.0 and drugs are generally administered as individual pharmaceutical compositions. The use of a pharmaceutical composition comprising more than one drug is within the scope of this invention.

Thus, another embodiment of this invention is directed to a method of treating (or preventing) breast cancer (i.e., postmenopausal and premenopausal breast cancer, e.g., hormone-dependent breast cancer) in a patient in need of such treatment comprising administering to said patient a therapeutically effective amount of at least one (e.g., one) compound of formula 1.0 (for example, as described in any one of Embodiment Nos. 1 to 166) and a therapeutically effective amount of at least one antihormonal agent selected from the group consisting of: (a) aromatase inhibitors, (b) antiestrogens, and (c) LHRH analogues; and said treatment optionally including the administration of at least one chemotherapeutic agent.

The compound of formula 1.0 is preferably administered orally, and in one embodiment is administered in capsule form.

Examples of aromatase inhibitors include but are not limited to: Anastrozole (e.g., Arimidex), Letrozole (e.g., Femara), Exemestane (Aromasin), Fadrozole and Formestane (e.g., Lentaron).

Examples of antiestrogens include but are not limited to: Tamoxifen (e.g., Nolvadex), Fulvestrant (e.g., Faslodex), Raloxifene (e.g., Evista), and Acolbifene.

Examples of LHRH analogues include but are not limited to: Goserelin (e.g., Zoladex) and Leuprolide (e.g., Leuprolide Acetate, such as Lupron or Lupron Depot).

Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

Preferably, when more than one antihormonal agent is used, each agent is selected from a different category of agent. For example, one agent is an aromatase inhibitor (e.g., Anastrozole, Letrozole, or Exemestane) and one agent is an antiestrogen (e.g., Tamoxifen or Fulvestrant).

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and at least one antihormonal agent selected from the group consisting of: (a) aromatase inhibitors, (b) antiestrogens, and (c) LHRH analogues; and administering an effective amount of at least one chemotherapeutic agent.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and at least one antihormonal agent selected from the group consisting of: (a) aromatase inhibitors, (b) antiestrogens, and (c) LHRH analogues.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and at least one antihormonal agent selected from the group consisting of: (a) aromatase inhibitors, and (b) antiestrogens.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), at least one antihormonal agent selected from the group consisting of: (a) aromatase inhibitors and (b) antiestrogens; and at least one chemotherapeutic agent.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and at least one aromatase inhibitor.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), at least one aromatase inhibitor, and at least one chemotherapeutic agent.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 166); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide; and administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 166); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene, and (c) LHRH analogues that are selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 166); and (2) at least one antihormonal agent selected from the group consisting of: (a) aromatase inhibitors that are selected from the group consisting of Anastrozole, Letrozole, Exemestane, Fadrozole and Formestane, and (b) antiestrogens that are selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 166); and (2) at least one antihormonal agent selected from the group consisting of: (a) aromatase inhibitors that are selected from the group consisting of Anastrozole, Letrozole, Exemestane, Fadrozole and Formestane, (b) antiestrogens that are selected from the group consisting of: Tamoxifen, Fulvestrant, Raloxifene, and Acolbifene; and administering an effective amount of at least one chemotherapeutic agents are selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 166); and (2) at least one aromatase inhibitor selected from the group consisting of Anastrozole, Letrozole, Exemestane, Fadrozole and Formestane.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 166); (2) at least one aromatase inhibitor that is selected from the group consisting of Anastrozole, Letrozole, Exemestane, Fadrozole and Formestane; and (3) administering an effective amount of at least one chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 166); (2) at least one aromatase inhibitor; and (3) at least one LHRH analogue.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 166); (2) at least one antiestrogen; and (3) at least one LHRH analogue.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 166); (2) at least one aromatase inhibitor that is selected from the group consisting of Anastrozole, Letrozole, Exemestane, Fadrozole and Formestane; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of: (1) at least one (e.g., one) compound of formula 1.0 (for example, as described in any one of Embodiment Nos. 1 to 166); (2) at least one antiestrogen that is selected from the group consisting of: Tamoxifen, Fulvestrant, Raloxifene, and Acolbifene; and (3) at least one LHRH analogue that is selected from the group consisting of: Goserelin and Leuprolide.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and Letrazole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and Exemestane.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and Formestane.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and Goserelin.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166) and Leuprolide.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Anastrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Letrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Exemestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Fadrozole, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Formestane, and an antiestrogen selected from the group consisting of: Tamoxifen, Fulvestrant, Raloxifene, and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Anastrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Letrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Exemestane, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Fadrozole, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Formestane, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Anastrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Letrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Exemestane, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Fadrozole, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Formestane, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Anastrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Letrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Exemestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Fadrozole, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Formestane, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Raloxifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Goserelin, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Leuprolein, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Anastrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Letrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Exemestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Fadrozole, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Formestane, an antiestrogen selected from the group consisting of: Tamoxifen, Fulvestrant, Raloxifene, and Acolbifene, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Anastrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Letrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Exemestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Fadrozole, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Formestane, Tamoxifen, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Anastrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Letrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Exemestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Fadrozole, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Formestane, Fulvestrant, and a chemotherapeutic agent selected from the group consisting of: Trastuzumab, Gefitinib, Erlotinib, Bevacizumab, Cetuximab, and Bortezomib.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Goserelin and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Goserelin, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Goserelin, and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Goserelin and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Leuprolide, and Tamoxifen.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Leuprolide, and Fulvestrant.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Leuprolide, and Raloxifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Leuprolide and Acolbifene.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Goserelin and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Goserelin and Letrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Goserelin and Exemestane.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Goserelin and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Goserelin and Formestane.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Leuprolide and Anastrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Leuprolide and Letrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Leuprolide and Exemestane.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Leuprolide and Fadrozole.

Another embodiment of this invention is directed to a method of treating or preventing breast cancer in a patient in need of such treatment wherein said treatment comprises administering a therapeutically effective amount of at least one (e.g., one) compound of formula 1.0 (for example, as described in any one of Embodiment Nos. 1 to 166), Leuprolide and Formestane.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 166) and Anastrozole.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 166) and Letrozole.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 166) and Exemestane.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 166) and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 166) and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 166), Anastrozole, and Fulvestrant.

Another embodiment of this invention is directed to the treatment or prevention of breast cancer in a patient in need of such treatment, said treatment comprising the administration of a therapeutically effective amount of at least one compound of formula I (e.g., one), Letrozole, and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 166), Exemestane, and Fulvestrant.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 166), Anastrozole, and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 166), Letrozole, and Tamoxifen.

Another embodiment of this invention is directed to the treatment or prevention of breast cancer in a patient in need of such treatment, said treatment comprising the administration of a therapeutically effective amount of at least one (e.g., one) compound of formula 1.0 (for example, as described in any one of Embodiment Nos. 1 to 166), Exemestane, and Tamoxifen.

Other embodiments of this invention are directed to any of the above described embodiments for the treatment of Breast Cancer wherein the chemotherapeutic agent is Trastuzumab.

Other embodiments of this invention are directed to any of the above described embodiments for the treatment or prevention of Breast Cancer wherein the method is directed to the treatment of breast cancer.

The compound of formula 1.0 (for example, as described in any one of Embodiment Nos. 1 to 166), antihormonal agents and chemotherapeutic agents can be administered concurrently or sequentially.

The antihormonal agents and optional chemotherapeutic agents are administered according to their protocols, dosage amounts, and dosage forms that are well know to those skilled in the art (e.g., the Physician's Desk Reference or published literature). For example, for Tamoxifen, Fulvestrant, Raloxifene, Anastrozole, Letrozole, Exemestane, Leuprolide and Goserelin, see the Physician's Desk Reference, $57^{th}$ Edition, 2003, published by Thomas PDR at Montvale, N.J. 07645-1742, the disclosure of which is incorporated herein by reference thereto.

In general, in the embodiments directed to the methods of treating Breast Cancer: (1) the compound of formula 1.0 (for example, as described in any one of Embodiment Nos. 1 to 166) can be administered daily (e.g., once per day, and in one embodiment twice a day), (2) the aromatase inhibitors can be administered in accordance with the known protocol for the aromatase inhibitor used (e.g., once per day), (3) the antiestrogens can be administered in accordance with the known protocol for the antiestrogen used (e.g., from once a day to once a month), (4) the LHRH analogue can be administered in accordance with the known protocol for the LHRH analogue used (e.g., once a month to once every three months), and (5) the chemotherapeutic agent can be administered in accordance with the known protocol for the chemotherapeutic agent used (e.g., from once a day to once a week).

Radiation therapy, if administered in the above treatments for breast cancer, is generally administered according to known protocols before administration of the compound of formula 1.0 (for example, as described in any one of Embodiment Nos. 1 to 166), antihormonal agents and optional chemotherapeutic agents.

Treatment according to the methods of treating breast cancer is continuous (i.e., a continuous dosing schedule is followed). The treatment is continued until there is a complete response, or until the skilled clinician determines that the patient is not benefiting from the treatment (for example, when there is disease progression).

The continuous treatment protocol for breast cancer can be changed to a discontinuous treatment schedule if, in the judgment of the skilled clinician, the patient would benefit from a discontinuous treatment schedule with one or more of the administered drugs. For example, the compound of formula 1.0 (for example, as described in any one of Embodiment Nos. 1 to 166) can be given using a discontinous treatment schedule while the remaining drugs used in the treatment are given as described herein. An example of a discontinuous treatment protocol for the compound of formula 1.0 (for example, as described in any one of Embodiment Nos. 1 to 166) is a repeating cycle of three weeks with the compound of formula 1.0 followed by one week without the compound of formula 1.0.

After a complete response is achieved with the breast cancer treatment, maintenance therapy with the compound of formula 1.0 (for example, as described in any one of Embodiment Nos. 1 to 166) can be continued using the dosing described in the methods of this invention. Maintenance therapy can also include administration of the antihormonal agents using the dosing described in the methods of this invention. Maintenance therapy can just be with the antihormonal agents. For example, after a complete response is achieved, an aromatase inhibitor (e.g., Anastrozole, Letrozole or Exemestane) can be continued for up to five years. Or, for example, an antiestrogen, e.g., Tamoxifen, may be used for up to five years after a complete response is achieved. Or, for example, an antiestrogen (e.g., Tamoxifen) can be used for up to five years after a complete response is achieved followed by the use of an aromatase inhibitor (e.g., Anastrozole, Letrozole or Exemestane) for up to five years.

In the embodiments directed to the treatment of breast cancer described above, the compound of formula 1.0 (for example, as described in any one of Embodiment Nos. 1 to 166) is administered continuously in a total daily dose of about 100 mg to about 600 mg. Usually this amount is administered in divided doses, and in one embodiment this amount is administered twice a day. In one embodiment the compound of formula 1.0 (for example, as described in any one of Embodiment Nos. 1 to 166) is dosed twice a day in an amount of about 50 mg to about 300 mg per dose. In another embodiment the compound of formula 1.0 (for example, as described in any one of Embodiment Nos. 1 to 166) is dosed twice a day in an amount of about 100 mg to about 200 mg per dose. Examples include the compound of formula 1.0 (for example, as described in any one of Embodiment Nos. 1 to 166) being dosed twice a day at 100 mg per dose. Examples also include the compound of formula 1.0 (for example, as described in any one of Embodiment Nos. 1 to 166) being dosed twice a day at 200 mg per dose.

Anastrozole is administered p.o. and is dosed once a day in amounts of about 0.5 to about 10 mg per dose, and in one embodiment in an amount of about 1.0 mg per dose.

Letrozole is administered p.o. and is dosed once a day in amounts of about 1.0 to about 10 mg per dose, and in one embodiment in an amount of about 2.5 mg per dose.

Exemestane is administered p.o. and is dosed once a day in amounts of about 10 to about 50 mg per dose, and in one embodiment in an amount of about 25 mg per dose.

Fadrozole is administered p.o. and is dosed twice a day in amounts of about 0.5 to about 10 mg per dose, and in one embodiment in an amount of about 2.0 mg per dose.

Formestane is administered i.m. and is dosed once every two weeks in amounts of about 100 to about 500 mg per dose, and in one embodiment in an amount of about 250 mg per dose.

Tamoxifen is administered p.o. and is dosed once a day in amounts of about 10 to about 100 mg per dose, and in one embodiment in an amount of about 20 mg per dose.

Fulvestrant is administered i.m. and is dosed once a month in amounts of about 100 to about 1000 mg per dose, and in one embodiment in an amount of about 250 mg per dose.

Raloxifene is administered p.o. and is dosed once a day in amounts of about 10 to about 120 mg per dose, and in one embodiment in an amount of about 60 mg per dose.

Acolbifene is administered p.o. and is dosed once a day in amounts of about 5 to about 20 mg per dose, and in one embodiment in an amount of about 20 mg per dose.

Goserelin is administered s.c. and is dosed once a month, or once every three months, in amounts of about 2 to about 20 mg per dose, and in one embodiment in an amount of about 3.6 mg per dose when administered once a month, and in another embodiment in an amount of about 10.8 mg per dose when administered once every three months.

Leuprolide is administered s.c. and is dosed once a month, or once every three months, in amounts of about 2 to about 20 mg per dose, and in one embodiment in an amount of about 3.75 mg per dose when administered once a month, and in another embodiment in an amount of about 11.25 mg per dose when administered once every three months.

Trastuzumab is administered by i.v. and is dosed once a week in amounts of about 2 to about 20 mpk per dose, and in one embodiment in an amount of about 2 mpk per dose. Trastuzumab is generally initially administered in a loading dose that is generally twice the dose of the weekly dose. Thus, for example, a 4 mpk loading dose is administered and then dosing is 2 mpk per dose per week.

Gefitinib is administered p.o. and is dosed once a day in amounts of about 100 to about 1000 mg per dose, and in one embodiment in an amount of about 250 mg per dose.

Erlotinib is administered p.o. and is dosed once a day in amounts of about 100 to about 500 mg per dose, and in one embodiment in an amount of about 150 mg per dose.

Bevacizumab is administered i.v. and is dosed once every two weeks in amounts of about 2.5 to about 15 mg per kilogram of body weight per dose, and in one embodiment in an amount of about 10 mg per kilogram per dose.

Cetuximab is administered i.v. and is dosed once a week in amounts of about 200 to about 500 mg per meter squared dose, and in one embodiment in an amount of about 250 mg per meter squared per dose.

Bortezomib is administered i.v. and is dosed twice a week for 2 weeks followed by a 10 day rest period (21 day treatment cycle) for a maximum of 8 treatment cycles in amounts of about 1.0 to about 2.5 mg per meter squared per dose, and in one embodiment in an amount of about 1.3 mg per meter squared per dose.

Thus in one embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) orally in an amount of about 50 mg to about 300 mg per dose wherein each dose is administered twice a day, and (2) Anastrozole p.o. in an amount of about 0.5 to about 10 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) orally in an amount of about 100 to 200 mg per dose, wherein each dose is administered twice a day, and (2) Anastrozole in an amount of about 1.0 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) orally in an amount of about 50 mg to about 300 mg per dose wherein each dose is administered twice a day, and (2) Letrozole p.o. in an amount of about 1.0 to about 10 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) orally in an amount of about 100 to 200 mg per dose, wherein each dose is administered twice a day, and (2) Letrozole p.o. in an amount of about 2.5 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) orally in an amount of about 50 mg to about 300 mg per dose wherein each dose is administered twice a day, and (2) Exemestane p.o. in an amount of about 10 to about 50 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) orally in an amount of about 100 to 200 mg per dose, wherein each dose is administered twice a day, and (2) Exemestane in an amount of about 25 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) orally in an amount of about 50 mg to about 300 mg per dose wherein each dose is administered twice a day, and (2) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) orally in an amount of about 100 to 200 mg per dose, wherein each dose is administered twice a day, and (2) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 50 mg to about 300 mg per dose wherein each dose is administered twice a day, and (2) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 100 to 200 mg per dose, wherein each dose is administered twice a day, and (2) Tamoxifen p.o. in an amount of about 20 mg per dose wherein each dose is given once a day.

In other embodiments of the invention breast cancer is treated in a patient in need of such treatment wherein said treatment comprises the administration of the compound of formula 1.0 (for example, as described in any one of Embodiment Nos. 1 to 166), one of the aromatase inhibitors (e.g., Anastrozole, Letrozole, or Exemestane, and in one embodiment Anastrozole), and one of the antiestrogens (e.g., Fulvestrant or Tamoxifen), wherein the compound of formula 1.0, aromatase inhibitor and antiestrogen are administered in the dosages described above.

Thus, for example in another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o in an amount of about 100 to 200 mg per dose, wherein each dose is administered twice a day, (2) Anastrozole p.o. in an amount of about 1.0 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 50 mg to about 300 mg per dose wherein each dose is administered twice a day, (2) Letrozole p.o in an amount of about 1.0 to about 10 mg per dose wherein each dose is given once a day, and (3) Fulvestrant in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 100 to 200 mg per dose, wherein each dose is administered twice a day, (2) Letrozole p.o. in an amount of about 2.5 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 50 mg to about 300 mg per dose wherein each dose is administered twice a day, (2) Exemestane p.o. in an amount of about 10 to about 50 mg per dose wherein each dose is given once a day, and (3) Fulvestrant i.m. in an amount of about 100 to about 1000 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 100 to 200 mg per dose, wherein each dose is administered twice a day, (2) Exemestane p.o. in an amount of about 25 mg per dose wherein each dose is given once a day, and (3) Fulvestrant i.m. in an amount of about 250 mg per dose wherein each dose is given once a month.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 50 mg to about 300 mg per dose wherein each dose is administered twice a day, (2) Anastrozole p.o. in an amount of about 0.5 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 100 to 200 mg per dose, wherein each dose is administered twice a day, (2) Anastrozole p.o. in an amount of about 1.0 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 50 mg to about 300 mg per dose wherein each dose is administered twice a day, (2) Letrozole p.o. in an amount of about 1.0 to about 10 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 100 to 200 mg per dose, wherein each dose is administered twice a day, (2) Letrozole p.o. in an amount of about 2.5 mg per dose wherein each dose is given once a day, and (3) Tamoxifen p.o. in an amount of about 20 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 50 mg to about 300 mg per dose wherein each dose is administered twice a day, (2) Exemestane p.o. in an amount of about 10 to about 50 mg per dose wherein each dose is given once a day, and (3) Tamoxifen p.o. in an amount of about 10 to about 100 mg per dose wherein each dose is given once a day.

In another embodiment of this invention breast cancer is treated (or prevented) in a patient in need of such treatment wherein said treatment comprises administering to said patient: (1) the compound of formula 1.0 (for example, as described in any one of Embodiment Nos. 1 to 166) p.o. in an amount of about 100 to 200 mg per dose, wherein each dose is administered twice a day, (2) Exemestane p.o. in an amount of about 25 mg per dose wherein each dose is given once a day, and (3) Tamoxifen p.o. in an amount of about 20 mg per dose wherein each dose is given once a day.

Those skilled in the art will appreciate that when other combinations of antihormonal agents are used, the individual antihormonal agent is used in the amounts specified above for that individual antihormonal agent.

Other embodiments of the treatment of Breast Cancer are directed to the methods of treating Breast Cancer described above wherein the compound of formula 1.0 (for example, as described in any one of Embodiment Nos. 1 to 166) is dosed twice a day in an amount of about 100 mg per dose.

Other embodiments of the treatment of Breast Cancer are directed to the methods of treating Breast Cancer described above wherein the compound of formula 1.0 (for example, as described in any one of Embodiment Nos. 1 to 166) is dosed twice a day in an amount of about 200 mg per dose.

Other embodiments of the treatment of Breast Cancer are directed to the methods of treating Breast Cancer described above wherein a chemotherapeutic agent is administered in addition to the compound of formula 1.0 (for example, as described in any one of Embodiment Nos. 1 to 166) and antihormonal agent (or antihormonal agents). In these embodiments the dosage ranges of the compound of formula 1.0 and antihormonal agents are as those described above in the combination therapies, or those described above for the individual compound of formula I and antihormonal agents, and the dosages of the chemotherapeutic agents are those described above for the individual chemotherapeutic agent. The dosages for the chemotherapeutic agents are well known in the art.

Other embodiments of this invention are directed to pharmaceutical compositions comprising the compound of formula 1.0 (for example, as described in any one of Embodiment Nos. 1 to 166) and at least one antihormonal agent and a pharmaceutically acceptable carrier.

Other embodiments of this invention are directed to pharmaceutical compositions comprising the compound of formula 1.0 (for example, as described in any one of Embodiment Nos. 1 to 166), at least one antihormonal agent, at least one chemotherapeutic agent, and a pharmaceutically acceptable carrier.

Other embodiments of this invention are directed to pharmaceutical compositions comprising the compound of formula 1.0 (for example, as described in any one of Embodiment Nos. 1 to 166), at least one chemotherapeutic agent, and a pharmaceutically acceptable carrier.

Those skilled in the art will appreciate that the compounds (drugs) used in the methods of this invention are available to the skilled clinician in pharmaceutical compositions (dosage forms) from the manufacturer and are used in those compositions. So, the recitation of the compound or class of compounds in the above described methods can be replaced with a recitation of a pharmaceutical composition comprising the particular compound or class of compounds. For example, the embodiment directed to a method of treating cancer comprising administering to a patient in need of such treatment therapeutically effective amounts of the compound of formula 1.0, a taxane, and a platinum coordination compound, includes within its scope a method of treating cancer comprising administering to a patient in need of such treatment therapeutically effective amounts of a pharmaceutical composition comprising the compound of formula 1.0, a pharmaceutical composition comprising a taxane, and a pharmaceutical composition comprising a platinum coordination compound.

Those skilled in the art will recognize that the actual dosages and protocols for administration employed in the methods of this invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula 1.0 and the chemotherapeutic agents will be regulated according to the judgment of the attending clinician (physician) considering such factors as age, condition and size of the patient as well as severity of the cancer being treated.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgement of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of an chemotherapeutic agent according to the individual patient's needs, as the treatment proceeds. All such modifications are within the scope of the present invention.

The particular choice of antihormonal agents, optional chemotherapeutic agents and optional radiation will depend upon the diagnosis of the attending physicians and their judgment of the condition of the patient and the appropriate treatment protocol.

The determination of the order of administration, and the number of repetitions of administration of the antihormonal agents, optional chemotherapeutic agents and optional radiation during a treatment protocol, is well within the knowledge of the skilled physician after evaluation of the breast cancer being treated and the condition of the patient.

Thus, in accordance with experience and knowledge, the practicing physician can modify each protocol for the administration of antihormonal agents, optional chemotherapeutic agents and optional radiation according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds of the invention can be made according to the processes described below.

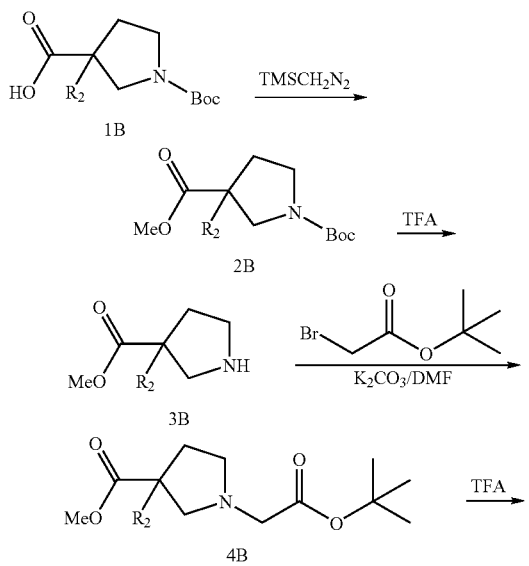

Scheme 1

-continued

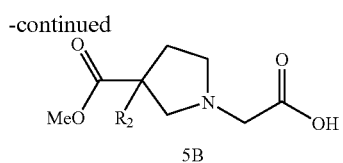

5B

The appropriately substituted pyrrolidine is prepared as follows. The methyl ester of pyrrolidine 1B is prepared by reaction with TMSdiazomethane. After removing the BOC protecting group, compound 3B is reacted with bromo-tert-.butylacetate to obtain 4B. The tert.butyl ester is then removed to obtain intermediate 5B.

Scheme 2

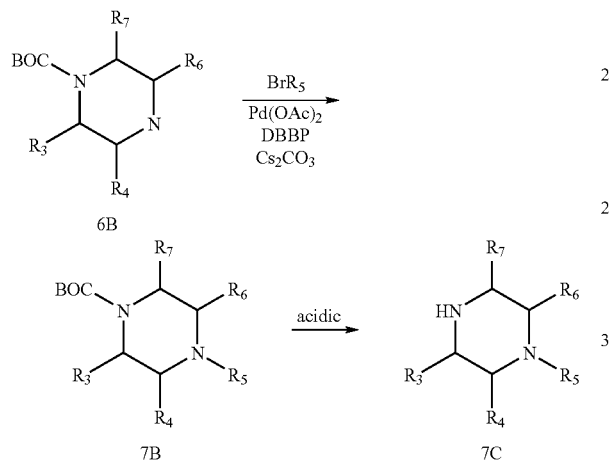

The $R^5$ substituted piperazine is prepared by Buchwald type coupling of the piperazine 6B with an aryl bromide in the presence of palladium to obtain the piperazine 7B. The BOC group is removed using acidic conditions (e.g., TFA) to give piperazine 7C.

Scheme 3

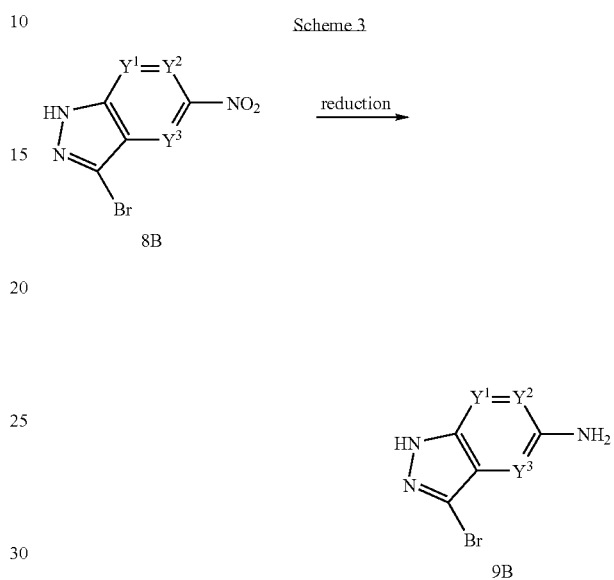

The indazole bromide 9B is prepared by reduction of the indazole nitro compound 8B using reducing conditions such as palladium on carbon in the presence of hydrogen atmosphere.

Scheme 4

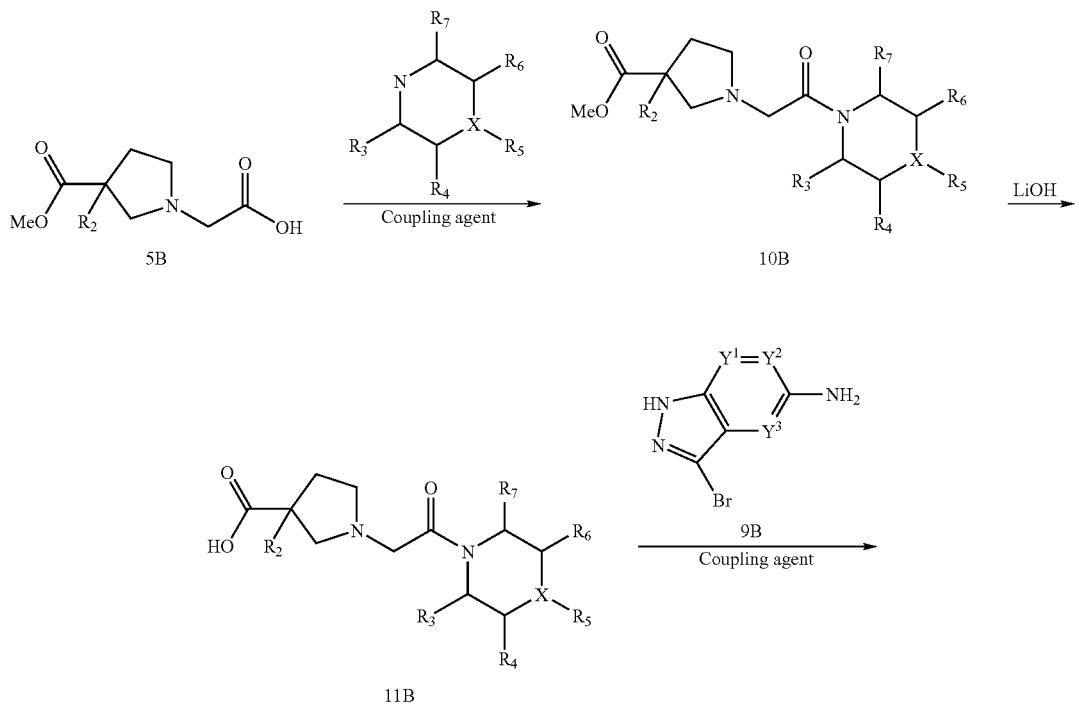

-continued

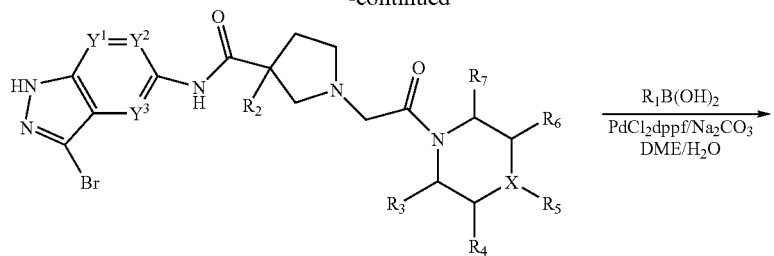

12B

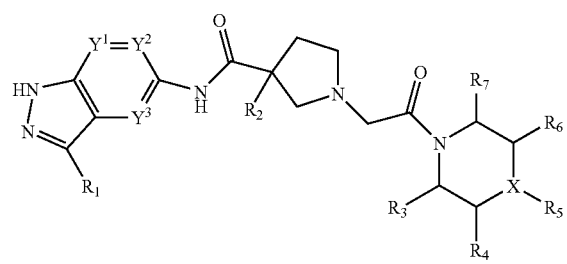

13B

The final molecule is assembled by coupling the pyrrolidine 5B with the piperazine (X is N, see compound 7C from Scheme 2), or with the piperidine (X is C, prepared in Schemes 11 or 12, or prepared according to the Examples described herein, or prepared according to methods well known to those skilled in the art), using standard coupling conditions such as HATU in DMF to obtain 10B. After hydrolysis of the methyl ester to obtain 11B, the indazole intermediate 9B is then coupled using standard coupling conditions such as HATU in DMF to obtain 12B. The indazole is then derivatized at the 3 position by suzuki coupling with an a boronic acid to obtain the final product 13B.

Scheme 5

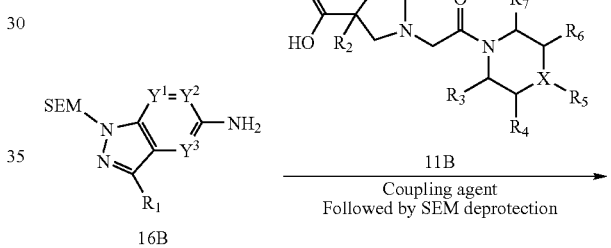

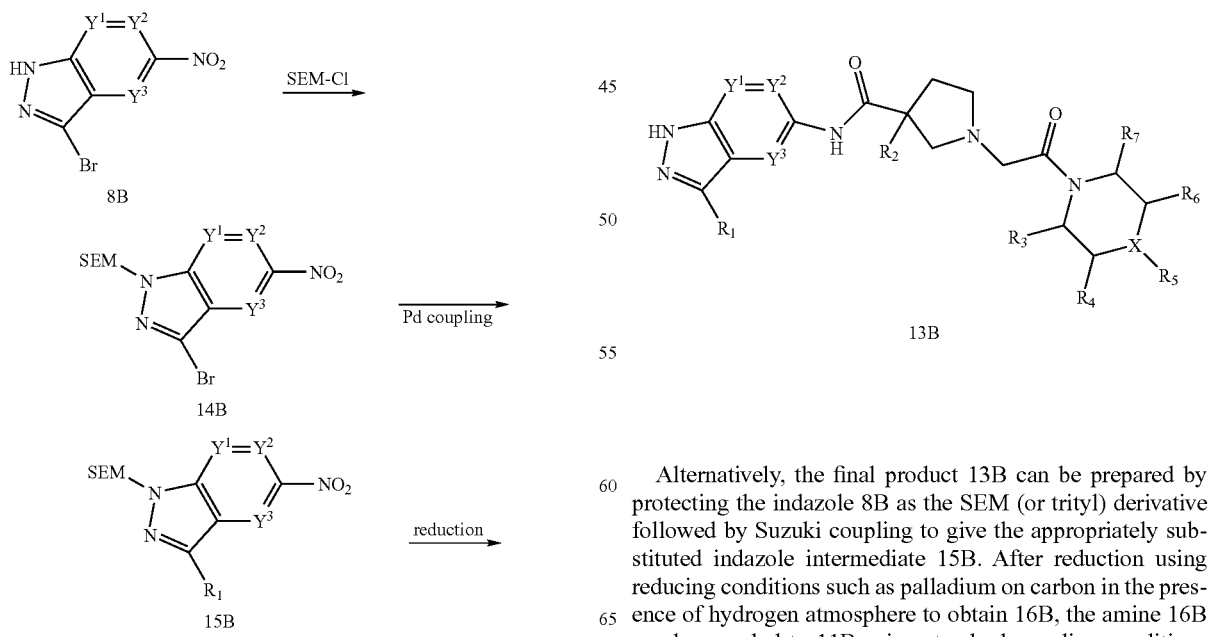

Alternatively, the final product 13B can be prepared by protecting the indazole 8B as the SEM (or trityl) derivative followed by Suzuki coupling to give the appropriately substituted indazole intermediate 15B. After reduction using reducing conditions such as palladium on carbon in the presence of hydrogen atmosphere to obtain 16B, the amine 16B can be coupled to 11B using standard coupling conditions such as HATU in DMF to obtain 13B.

Scheme 6

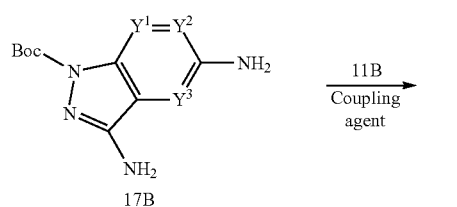

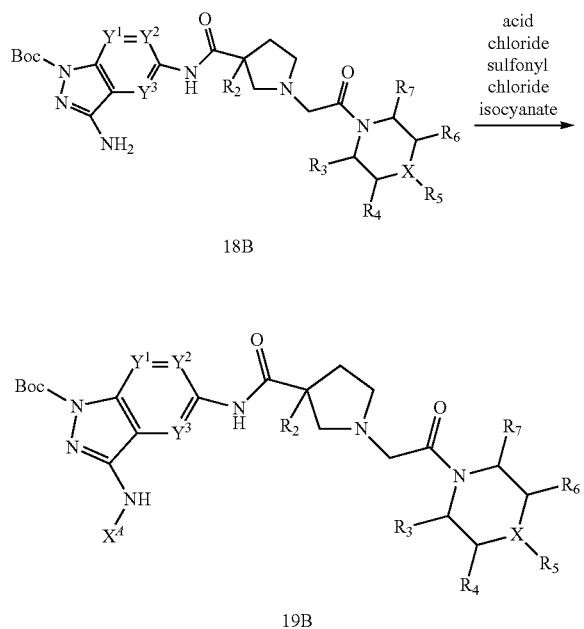

3-Amino substituted indazole derivatives can be prepared according to general Scheme 6 by coupling the Boc protected 3,5-diamino indazole 17B with 11B under standard coupling conditions such as HATU in DMF to obtain 18B. The 3-amino group can then be reacted with acid chlorides, sulfonyl chlorides and isocyanates to prepare the corresponding amides, sulfonamides and ureas 19B respectively.

Those skilled in the art will appreciate that the moiety —NHX$^A$ represents the amino substituted R$^1$ groups, such as, —N(R$^{10}$)$_2$, —NR$^{32}$—C(O)—R$^{14}$, —N(R$^{10}$)C(O)N(R$^{10}$)$_2$, and —N(R$^{10}$)S(O)$_t$R$^{10}$.

Scheme 7

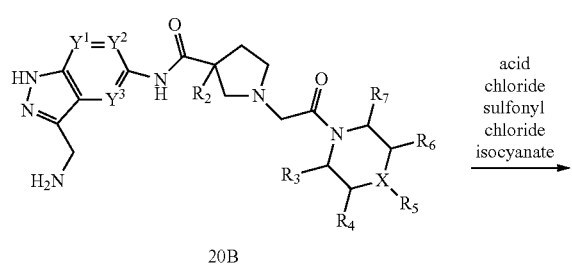

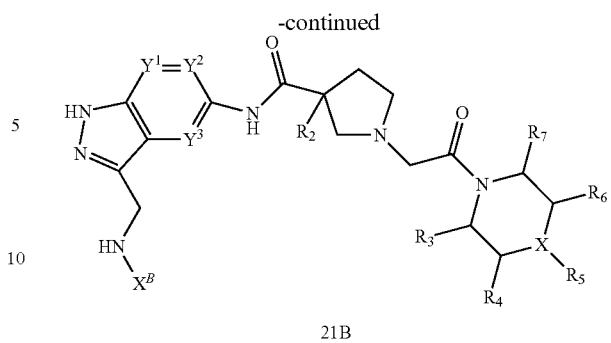

The amino methyl indazole derivative 20B can be prepared according to Example 76 step 1 through 4 by substituting the appropriately substituted rings. The 3-aminomethyl group can then be reacted with acid chlorides, sulfonyl chlorides and isocyanates to prepare the corresponding amides, sulfonamides and ureas 21B respectively.

Those skilled in the art will appreciate that the moiety —CH$_2$NHX$^B$ represents the amino substituted methyl R$^1$ groups, such as, —C(R$^{30}$)$_2$)$_n$—NR$^{32}$—C(O)—R$^{10}$ (wherein n is 1 and each R$^{30}$ is H), —(C(R$^{30}$)$_2$)$_n$—NR$^{32}$—S(O)—R$^{10}$ (wherein n is 1 and each R$^{30}$ is H), —(C(R$^{30}$)$_2$)$_n$—NR$^{32}$—C(O)—N(R$^{32}$)—R$^{10}$ (wherein n is 1 and each R$^{30}$ is H), —(C(R$^{30}$)$_2$)$_n$R$^{13}$ (wherein n is 1, each R$^{30}$ is H and R$^{13}$ is —N(R$^{10}$)$_2$),

Scheme 8

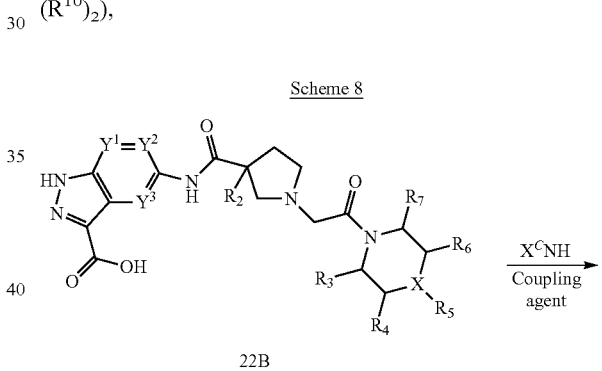

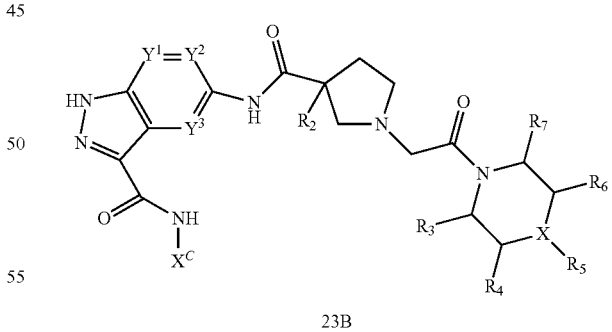

The amide compound 23B can be prepared by following Example 87 substituting the appropriate compound 11B (General Scheme 4). The resulting acid 22B is then coupled with the appropriate amine under standard coupling conditions such as in the presence of EDC/HOBt to obtain 23B.

Those skilled in the art will appreciate that the moiety —C(O)NHX$^C$ represents the amide R$^1$ groups, such as, —C(O)N(R$^{10}$)$_2$ and —C(O)—NR$^{32}$—C(R$^{18}$)$_3$

Scheme 9

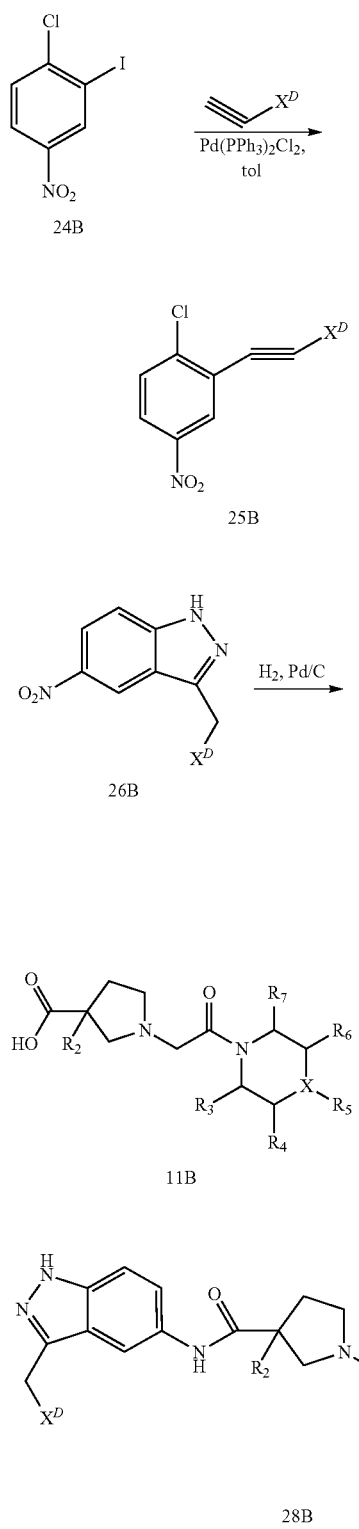

Indazoles of type 27B can be prepared by reacting 24B with the appropriately substituted acetylene in the presence of Pd(PPh₃)₂Cl₂ in toluene to obtain 25B. After heating with hydrazine to obtain 26B, 27B is obtained after hydrogenation. Coupling of 27B with 11B under standard coupling conditions such as HATU or EDC/HOBt gives 28B.

The moiety —CH$_2$X$^D$ represents R$^1$ groups that are an R$^{10}$ substituent, such as, alkyl, heteroarylalkyl, and arylalkyl.

Scheme 10

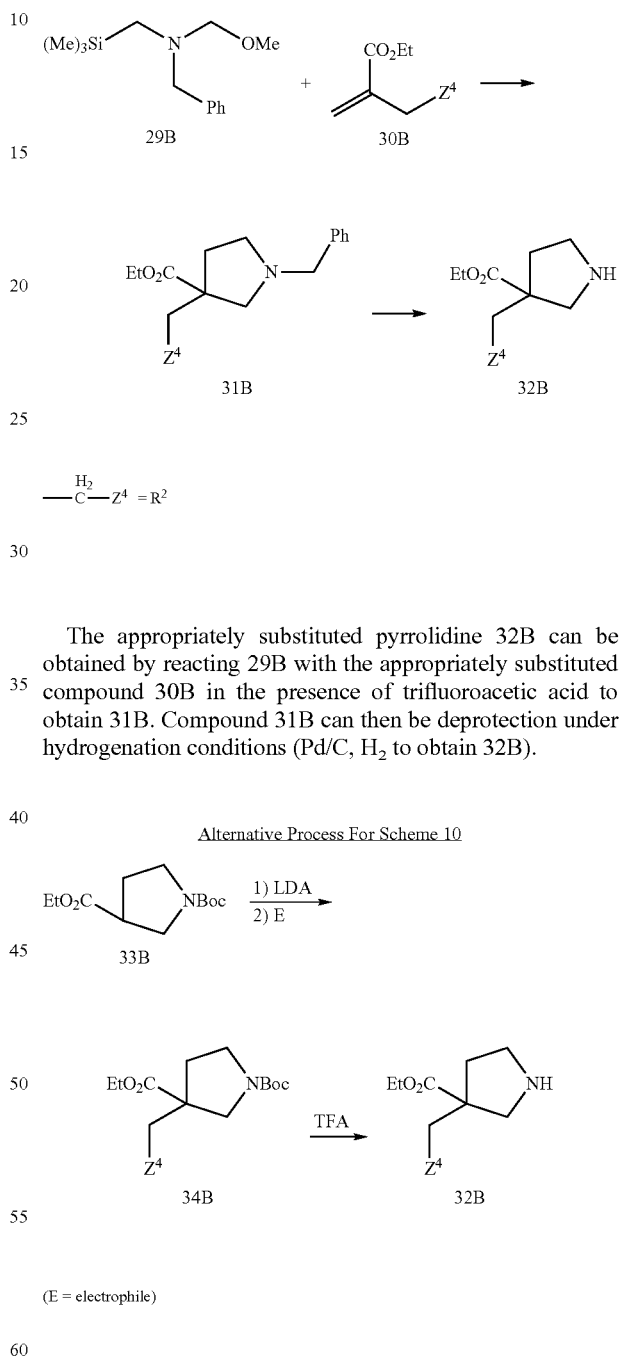

The appropriately substituted pyrrolidine 32B can be obtained by reacting 29B with the appropriately substituted compound 30B in the presence of trifluoroacetic acid to obtain 31B. Compound 31B can then be deprotection under hydrogenation conditions (Pd/C, H$_2$ to obtain 32B).

(E = electrophile)

Alternatively, 32B can be obtain by reaction 33B with LDA followed by the addition of a suitable electrophile such as allylbromide, as in example 127, to obtain 34B. Treatment of 34B with trifluoroacetic acid yields 32B.

Scheme 11

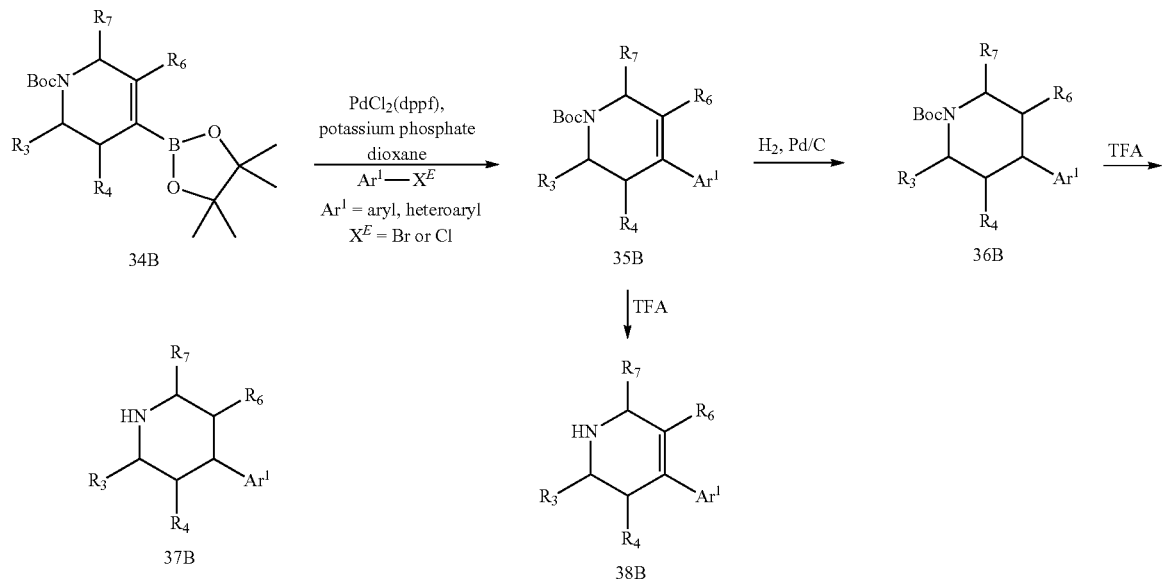

Aryl or heteroaryl substituted piperidines can be prepared by Suzuki coupling of an aryl or heteroaryl halide with the pinicolboronate 34B to obtain 35B. The ring double bond can then be hydrogenated to obtain 36B followed by removal of the Boc protecting group under trifluoroacetic acid conditions. Alternatively the double bond can be retained and the Boc group removed to give 38B.

followed by removal of the Boc protecting group under trifluoroacetic acid conditions. Alternatively the Boc protecting group from 40B can be removed under trifluoroacetic acid conditions to give 43B.

Compounds of this invention are exemplified in the following examples, which should not be construed as limiting the scope of the disclosure. Alternative mechanistic pathways Scheme 12

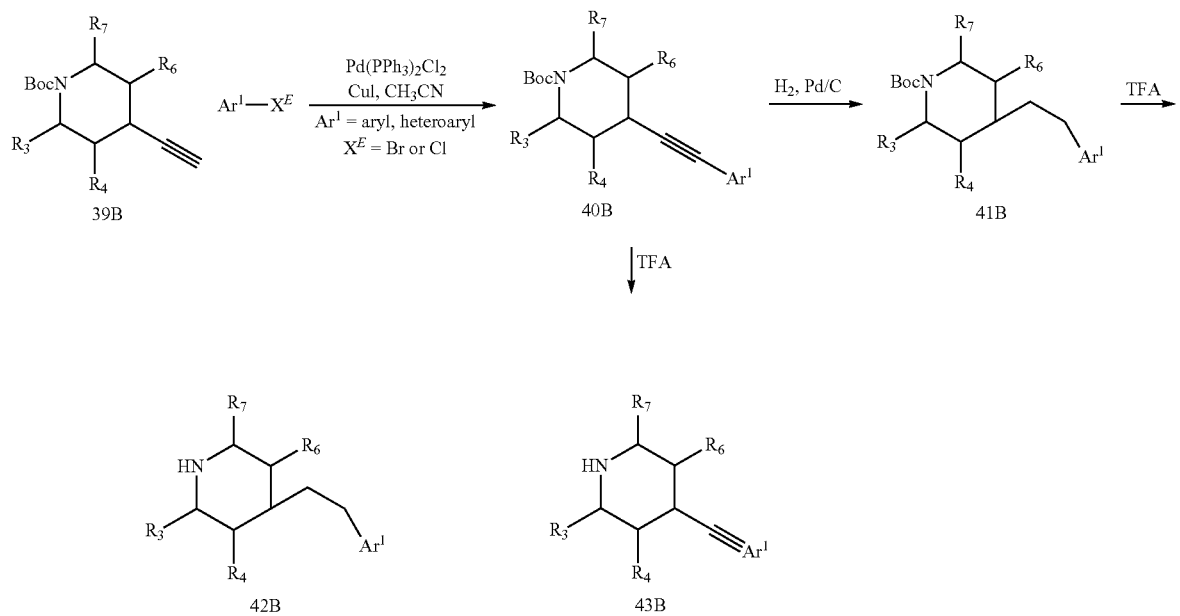

Similarly aryl or heteroaryl substituted piperizines with a 2 carbon spacer can be prepared as shown in Scheme 12 by coupling an aryl or heteroaryl halide with an acetylene derivative 39B that can be prepared according to procedures known in the art to obtain 40B. 40B can then be reduced to 41B and analogous structures within the scope of the invention may be apparent to those skilled in the art.

The LCMS conditions are: (1) column: C-18 reverse phase, 5 um, 4.6×50 mm, (2) MS:PE Sciex API-150EX, and (3) HPLC: Shimadzu LC-10 ADvp, 1 ml/min, linerar gradient 10% acetonitrile in water to 95% acetonitrile in water, both contain 0.05% TFA

Example 1

Step (1)

Preparation of Pyrrolidine-3-carboxylic acid methyl ester

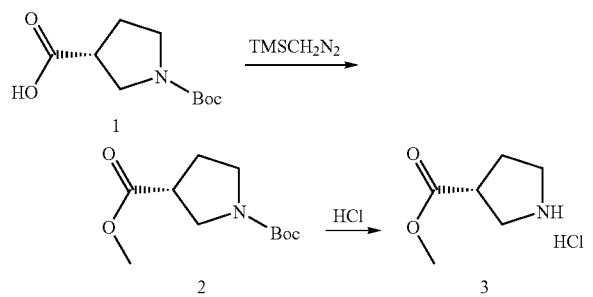

R-pyrrolidine-1,3-dicarboxylic acid 1-tert-butyl ester (2.15 gm, 10 mmol) was dissolved in 12 ml of toluene and 3.5 ml of methanol. Trimethylsilyidiazomethane 2N solution in hexanes (6.56 ml, 13.12 mmol) was added dropwise and the reaction mixture stirred for 2 hours. The mixture was evaporated to obtain 2.1 gm of an oil. The oil was dissolved in dichloromethane (15 ml) and 5 ml of 4N hydrochloric acid in dioxane added. The reaction mixture was stirred for 1 hr and evaporated to give an oil that crystallizes to give 1.68 gm of title product.

Step 2

Preparation of 1-tert-Butoxycarbonylmethyl-pyrrolidine-3-carboxylic acid methyl ester

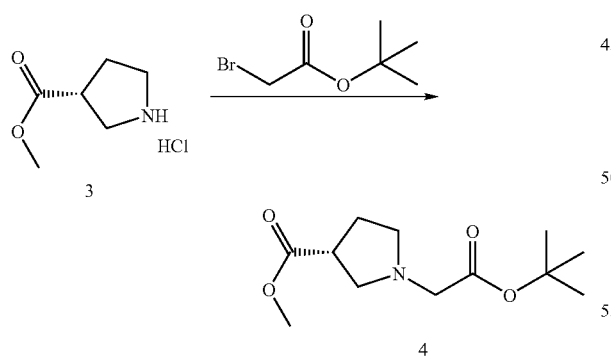

R-pyrrolidine-3-carboxylic acid methyl ester (1.5 gm, 9.1 mmol) was dissolved in N,N-dimethylformamide (45 ml). Diisopropylethylamine (5.7 ml, 31 ml) was added followed by cesium carbonate (4.35 gm, 13.3 mmol). Tert. butylbromoacetate (1.5 ml, 10 mmol) was added dropwise and the reaction mixture stirred for 1 hr. Brine was added to the reaction mixture which was then extracted with ethylacetate three times. The ethylacetate extracts were dried over magnesium sulfate, filtered and evaporated to obtain crude title product. The crude product was chromatographed to obtain 2.15 gm, 97% of title product.

Step 3

Preparation of 1-Carboxymethyl-pyrrolidine-3-carboxylic acid methyl ester

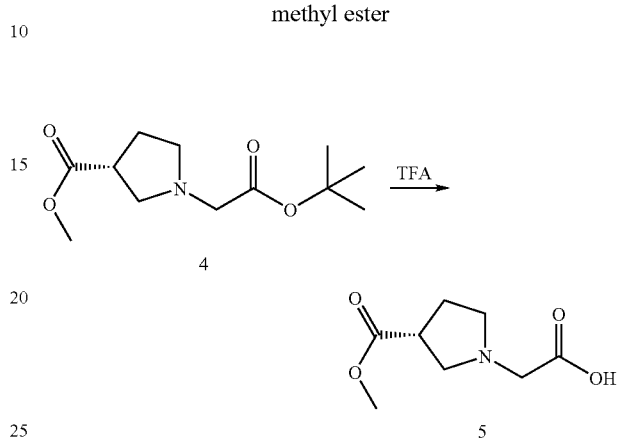

R-1-tert-Butoxycarbonylmethyl-pyrrolidine-3-carboxylic acid methyl ester (2.15 gm, 8.8 mmol) was dissolved in 20 ml of 50% trifluoroacetic acid/dichloromethane and stirred for 2 hrs. The reaction mixture was evaporated to an oil and exchanged with hydrochloric acid by dissolving in 20 ml of dichloromethane and adding 10 ml of 1N HCl in ether to obtain 3.35 gm of a gummy solid.

Step 4

Preparation of 4-(4-Bromo-phenyl)-piperazine-1-carboxylic acid tert-butyl ester

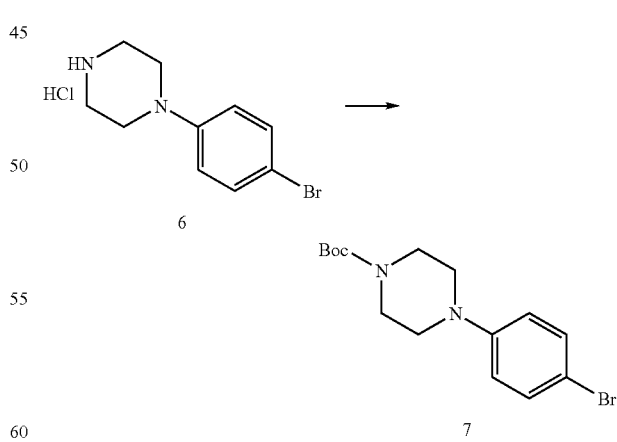

1-(4-Bromo-phenyl)-piperazine hydrochloride (9 gm, 38 mmol) was dissolved in 250 ml of dichloromethane and 9 ml of triethylamine added. Di-tert.butyldicarbonate (8.34 gm, 39 mmol) was added and the reaction mixture stirred for 1 hr. The reaction mixture was washed with a solution of saturated sodium bicarbonate (100 ml), the organic layer separated, dried over magnesium sulfate and evaporated to obtain 10.19 gm of crystalline product.

Step 5

Preparation of 4-(4-boronic acid-phenyl)-piperazine-1-carboxylic acid tert-butyl ester

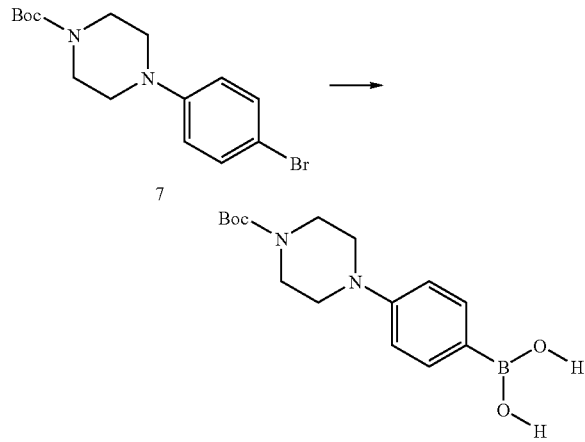

4-(4-Bromo-phenyl)-piperazine-1-carboxylic acid tert-butyl ester (10.19 gm, 30 mmol) was dissolved in 26 ml of tetrahydrofuran. The mixture was cooled to −78 C under a dry nitrogen atmosphere. A 2.5 N solution nButyl lithium in hexanes (26 ml, 65 mmol) was added dropwise and stirred for 30 min. Triisopropylborate (14.68 ml, 63.6 mmol) was added over 10 min. and the reaction mixture let warm to ambient temperature gradually. The reaction mixture was stirred for 18 hrs. A saturated solution of Ammonium chloride (75 ml) was added and the reaction mixture stirred for 5 min. 85% o-Phosphoric acid (7.27 gm) was added and the reaction mixture stirred for 1 hr. The reaction mixture was extracted with ethylacetate three times, dried over magnesium sulfate, filtered and evaporated. The crude product was chromatographed on a silica column to obtain 5.74 gm of title product.

Step 6

Preparation of 4-(4-Pyrimidin-2-yl-phenyl)-piperazine-1-carboxylic acid tert-butyl ester

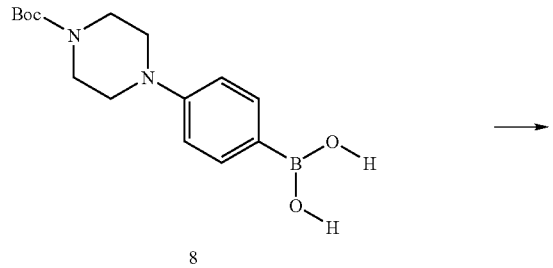

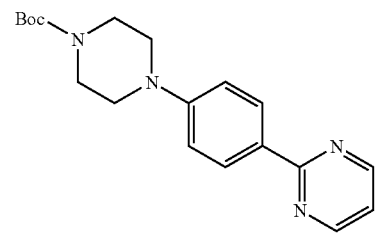

4-(4-boronic acid-phenyl)-piperazine-1-carboxylic acid tert-butyl ester (5.93 gm, 19.3 mmol) was dissolved in 50 ml of a 50% mixture of N,N-dimethylformamide/water. K2CO3 (16 gm) was added and the mixture de-gased and purged with nitrogen. Pd (dppf)2Cl2 (1.57 gm) and 2-chloropyrimidine (2.72 gm) was added and the reaction mixture stirred at 80 C. After 8 hours the product was extracted into ethylacetate, dried over magnesium sulfate, filtered and evaporated. The crude product was chromatographed on silica gel to obtain 5.03 gm (76.6%) of title product.

Step 7

Preparation of 2-(4-piperazin-1-yl-phenyl)-pyrimidine

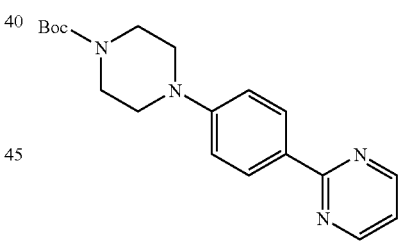

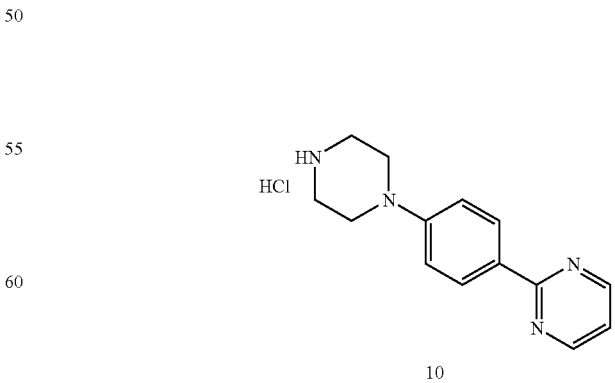

4-(4-Pyrimidin-2-yl-phenyl)-piperazine-1-carboxylic acid tert-butyl ester 5.03 gm was dissolved in 25 ml dichloromethane and 10 ml of 4N HCl dioxane added. After stirring for 2 hrs, the mixture was then evaporated to obtain the title product.

Step 8

Preparation of 1-{2-Oxo-2-[4-(4-pyrimidin-2-yl-phenyl)-piperazin-1-yl]-ethyl}-pyrrolidine-3-carboxylic acid methyl ester

5 + 10 ⟶

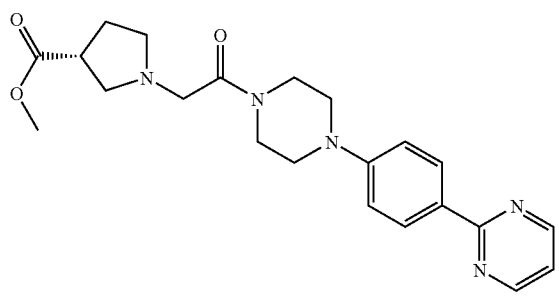

11

2-(4-piperazin-1-yl-phenyl)-pyrimidine (compound 10 from Step 7, 14.7 mmol) and 1-Carboxymethyl-pyrrolidine-3-carboxylic acid methyl ester (compound 5 from Step 3, 17.6 mmol) were dissolved in 72 ml of DMF. Triethylamine (8 ml, 57 mmol), 1-hydroxybenztriazole (2.29 gm) and 1-(3-dimethylaminopropyl)-3-ethylcarbodiimide hydrochloride (EDCl) (3.43 gm, 18 mmol) were added and the reaction mixture stirred for 24 hrs. After washing with brine, extracting with dichloromethane, and drying over magnesium sulfate, the mixture was evaporated and chromatographed on silica gel to obtain 5.0 gm of title product.

Step 9

Preparation of 1-{2-Oxo-2-[4-(4-pyrimidin-2-yl-phenyl)-piperazin-1-yl]-ethyl}-pyrrolidine-3-carboxylic acid

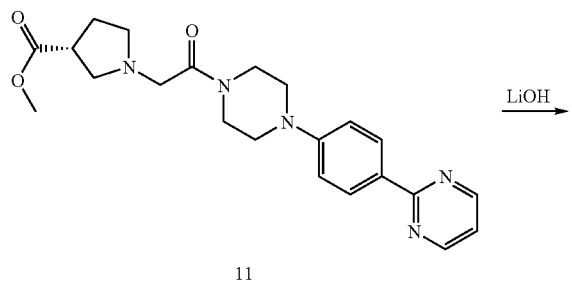

11

⟶ LiOH

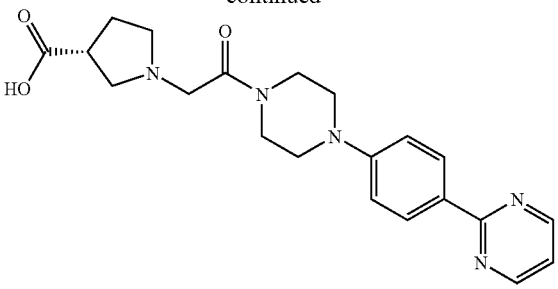

12

1-{2-Oxo-2-[4-(4-pyrimidin-2-yl-phenyl)-piperazin-1-yl]-ethyl}-pyrrolidine-3-carboxylic acid methyl ester (compound 11 from Step 8, 3.3 gm, 8.06 mmol) was dissolved in methanol and 10 ml of 1N lithium hydroxide added. The reaction mixture was stirred for 18 hrs. 10 ml of 1N HCl was added to the reaction mixture and evaporated to a white solid (3.94 gm)

Step 10

Preparation of 1-{2-Oxo-2-[4-(4-pyrimidin-2-yl-phenyl)-piperazin-1-yl]-ethyl}-pyrrolidine-3-carboxylic acid [3-(4-fluoro-phenyl)-1H-indazol-5-yl]-amide 12 + 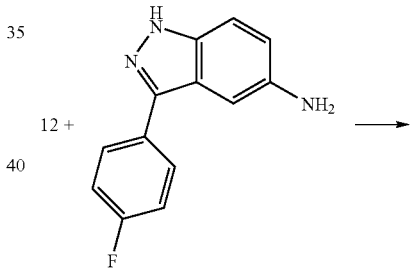 ⟶

13

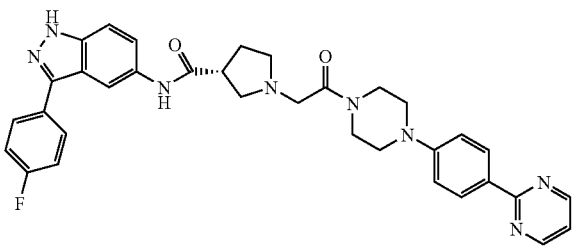

14

3-(4-Fluoro-phenyl)-1H-indazol-5-ylamine (0.11 gm, 0.5 mmol) and 1-{2-Oxo-2-[4-(4-pyrimidin-2-yl-phenyl)-piperazin-1-yl]-ethyl}-pyrrolidine-3-carboxylic acid (compound 12 from Step 9, 0.125 gm, 0.25 mmol) were dissolved in 4 ml of DMF. O-(7-azabenzotriazol-1-yl-)-N,N,N,N-tetramethyluronium hexafluorophosphate (HATU) (0.24 gm, 0.63 mmol) and triethylamine (0.1 ml, 0.76 mmol) were added to the reaction mixture and the mixture stirred for 18 hrs. The reaction mixture was added to bring and extracted with dichloromethane. After drying over magnesium sulfate and filtered, the mixture was evaporated and chromatographed to obtain 36.7 mg of title product.

Example 2

Step 1

Preparation of 3-Bromo-1H-indazol-5-ylamine

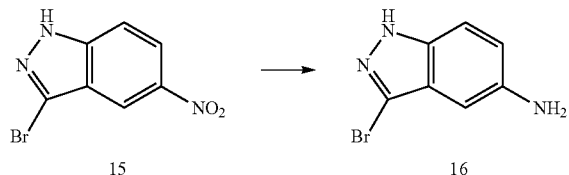 [SMILES: O=[N+]([O-])c1ccc2[nH]nc(Br)c2c1 ; Nc1ccc2[nH]nc(Br)c2c1]

Bromide 15 (4.2 g, 17.4 mmol, prepared according to procedure of Barbet, Eur. J. Med. Chem. Chim. Ther.; Fr; 21; 4; 1986, 359) and stannous chloride hydrate (17.0 g, 75.3 mmol) were dissolved in EtOH (35 mL). The crude was stirred at 70° C. for 2.5 hrs. The crude was cooled to rt and poured into ice water (50 ml). The PH was made basic via addition of 15% wt NaOH (100 mL). The aq layer was extracted with EtOAc. The EtOAc layer was dried over MgSO$_4$, filtered, and evaporated to give 1.82 g of the crude product.

Step 2

Preparation of 1-{2-Oxo-2-[4-(4-pyrimidin-2-yl-phenyl)-piperazin-1-yl]-ethyl}1-pyrrolidine-3-carboxylic acid (3-bromo-1H-indazol-5-yl)-amide

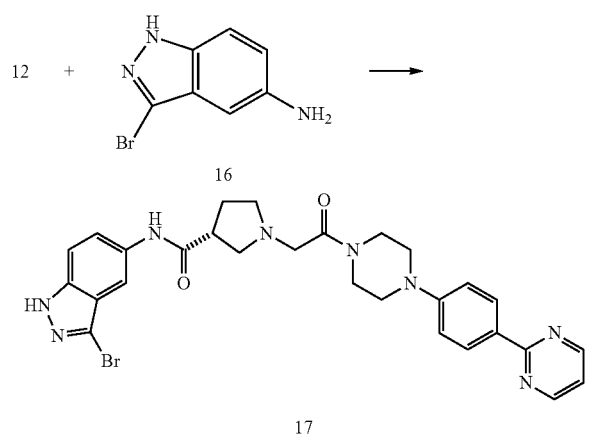

Crude 3-bromo-1H-indazol-5-ylamine 16 (403 mg, 1.9 mmol) and carboxylic acid 12 from Example 1 Step 9 (357 mg, 0.90 mmol) were dissolved in CH$_2$Cl$_2$ (3 mL) and DMF (3 ML). To the crude was added triethylamine (1.01 mL), and HATU (722 mg, 1.9 mmol). The crude was stirred at rt for 5 hrs under a stream of nitrogen. To the crude was added additional portions of 3-bromo-1H-indazol-5-ylamine 16 (300 mg, 1.42 mmol), HATU (500 mg, 1.32 mmol), and diisopropylethylamine (0.3 mL). To the crude was added CH$_2$Cl$_2$ (5 mL) and DMF (3 ML). The crude was stirred overnight under a stream of nitrogen. The crude was quenched with sat. NaHCO$_3$ at rt. The crude was diluted in EtOAc. The organic layer was washed with water, brine, dried over Na$_2$SO$_4$, filtered, and evaporated. The crude was chromatographed to give 367 mg of the product.

Step 3

Preparation of 1-{2-Oxo-2-[4-(4-pyrimidin-2-yl-phenyl)-piperazin-1-yl]-ethyl}-pyrrolidine-3-carboxylic acid[3-(3-cyano-phenyl)-1H-indazol-5-yl]-amide

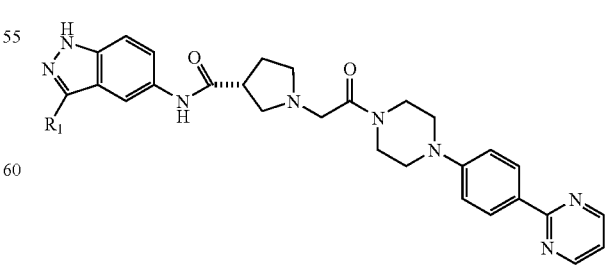

To a solution of bromide 17 from Step 2 (107 mg, 0.18 mmol) in DME (2 mL) and distilled water (0.5 mL) in a 5 mL conical microwave reaction vessel was added boronic acid (107 mg, 0.73 mmol), Na$_2$CO$_3$ (100 mg, 0.94 mmol), and PdCl$_2$dppf (59 mg, 0.072 mmol). The crude was sealed with reaction vessel cap. The crude was heated at 120° C. in an EMRY optimizer microwave for 600 secs. The crude was cooled and quenched with water at rt. The aq layer was extracted with CH$_2$Cl$_2$, The organic layer was dried over Na$_2$SO$_4$, filtered, and evaporated. The crude was purified via prep plate to give 55 mg of the product. LC Mass Spec M+1 @retention time: 612.1@3.17

Examples 3 to 60

Following a procedure similar to that of Example 2, compound 17 was reacted with R$^1$B(OH)$_2$ to prepare, via the microwave Suzuki reaction, the compound 19:

wherein R$^1$ is defined in Table 1. In Table 1 "Ex" represents "Example".

TABLE 1

| Ex | R¹ | LCMass Spec M + 1 @ ret. time |
|---|---|---|
| 3 | phenyl | 587 @ 3.61 mi |
| 4 | 4-fluorophenyl | — |
| 5 | 4-methoxyphenyl | 617.1 @ 2.86 min |
| 6 | pyridin-4-yl | — |
| 7 | 3,4-dimethoxyphenyl | 647.2 @ 2.83 |
| 8 | 2-chloropyridin-4-yl | — |
| 9 | 4-methoxypyridin-3-yl | — |
| 10 | benzo[d][1,3]dioxol-5-yl | — |
| 11 | 4-cyanophenyl | 612.1 @ 3.09 |

TABLE 1-continued

| Ex | R¹ | LCMass Spec M + 1 @ ret. time |
|---|---|---|
| 12 | pyrrol-2-yl | 576.3 @ 2.5 |
| 13 | 4-acetylphenyl | 629.3 @ 2.57 |
| 14 | 3-(N-propylcarbamoyl)phenyl | — |
| 15 | 3-fluoro-4-methoxyphenyl | — |
| 16 | 2-methoxypyrimidin-5-yl | — |
| 17 | pyridin-3-yl | — |
| 18 | 6-methoxypyridin-3-yl | — |
| 19 | 3-hydroxyphenyl | 603.1 @ 2.87 |
| 20 | pyrazol-4-yl | — |

TABLE 1-continued

| Ex | R¹ | LCMass Spec M + 1 @ ret. time |
|---|---|---|
| 21 | 4-acetyl-thiophen-2-yl | 635.2 @ 3.13 |
| 22 | 3,4-difluorophenyl | — |
| 23 | 3,4-dichlorophenyl | — |
| 24 | 3-methoxyphenyl | 617.1 @ 3.24 |
| 25 | 3-fluorophenyl | 605.1 @ 3.24 |
| 26 | 3-acetamidophenyl | 644.2 @ 2.87 |
| 27 | 4-methylphenyl | 601.1 @ 3.29 |
| 28 | pyrimidin-5-yl | — |
| 29 | 4-hydroxyphenyl | 601.1 @ 2.81 |
| 30 | 4-ethoxyphenyl | 631.2 @ 3.13 |
| 31 | 3-methylphenyl | 601.1 @ 3.27 |
| 32 | 3-acetylphenyl | 629.1 @ 3.02 |
| 33 | thiazol-2-yl | 594 @ 3.35 |
| 34 | 3-chlorophenyl | 621.1 @ 3.40 |
| 35 | 4-nitrophenyl | 632.1 @ 3.31 |
| 36 | 3-(methoxycarbonyl)phenyl | 645.2 @ 3.22 |
| 37 | 3,5-difluorophenyl | — |

TABLE 1-continued

| Ex | R¹ | LCMass Spec M + 1 @ ret. time |
|---|---|---|
| 38 | 3-NO₂-phenyl | 632.1 @ 3.29 |
| 39 | 4-ethyl-phenyl | 615.1 @ 3.24 |
| 40 | 4-CF₃-phenyl | 655.1 @ 3.48 |
| 41 | 4-Cl-phenyl | 621.1 @ 3.38 |
| 42 | 3-SO₂Me-phenyl | 652 @ 2.97 |
| 43 | 2-F-phenyl | 605.1 @ 2.94 |
| 44 | thiazol-5-yl | 594 @ 3.13 |
| 45 | 3-CF₃-phenyl | 655.1 @ 3.48 |
| 46 | 3-isopropyl-phenyl | 629.1 @ 3.51 |
| 47 | 4-OCF₃-phenyl | — |
| 48 | cyclopropyl | — |
| 49 | 4-(NCOCH₃)-phenyl | 644.1 @ 3.54 |
| 50 | 4-isopropyl-phenyl | 629.1 @ 3.56 |
| 51 | 2,4-di-OMe-phenyl | 647.2 @ 2.9 |
| 52 | 2-Cl-phenyl | 621.1 @ 2.73 |
| 53 | 2-Me-phenyl | 601.1 @ 3.13 |
| 54 | 2-acetyl-phenyl | 629.1 @ 2.98 |
| 55 | 2,6-di-F-phenyl | 623.1 @ 3.08 |

TABLE 1-continued

| Ex | R[1] | LCMass Spec M + 1 @ ret. time |
|---|---|---|
| 56 | ![NAc-phenyl] (Ac = CH₃C(O)—) | 644.2 @ 2.85 |
| 57 | ![CF₃-phenyl] | 655.1 @ 3.38 |
| 58 | ![CO₂Me-phenyl] | 645.2 @ 3.05 |
| 59 | ![OMe-phenyl] | 617.1 @ 2.83 |
| 60 | ![F-phenyl] | 605.1 @ 2.94 |

Example 61

Step 1

Preparation of 3-Bromo-5-nitro-1-trityl-1H-indazole

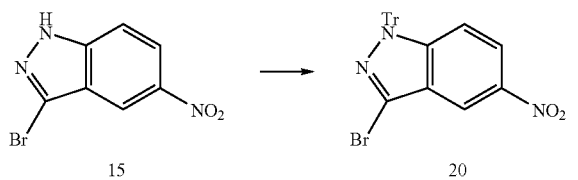

To a solution of 15 (3.8 g, 15.7 mmol) in CH₃CN (100 mL) was added potassium carbonate (10.42 g, 75.4 mmol) followed by the addition of TrCl (15.9 g, 56.4 mmol) at rt for 48 h. The solvent was evaporated and the crude was dissolved in CH₂Cl₂. The crude was quenched with water. The aq. layer was extracted with CH₂Cl₂. The combined organic layer was washed with H₂O, brine, dried over MgSO₄, filtered, and evaporated. The solid crude was placed onto a filter funnel and washed with 20% EtOAc/hexane (1 L) and 5% EtOAc/hexane (500 mL). The crude solid was collected from the filter and dried overnight to afford 7 g of the product.

Step 2

Preparation of 5-Nitro-1-trityl-3-(1-trityl-1H-imidazol-4-yl)-1H-indazole

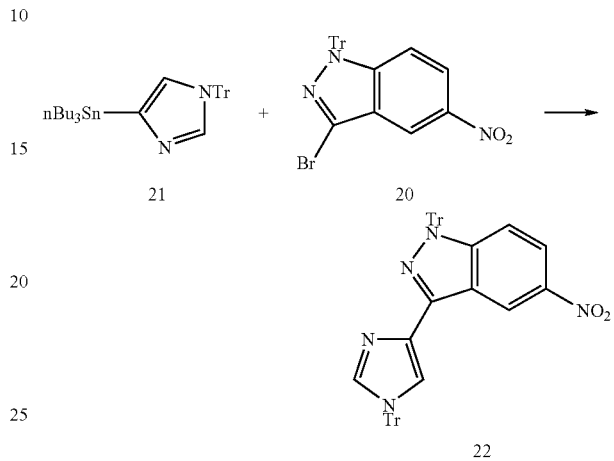

A solution of 21 (2.73 g, 6.19 mmol, prepared according to Jetter, M. C.; Reitz, A. B. *Synthesis*, 1998, 829-831), bromide 36 (0.73 g, 2.07 mmol) and Pd(PPh₃)₄ (474 mg, 0.41 mmol) in toluene (10 mL) was heated at 100° C. under an atmosphere of nitrogen for 18 hrs. The crude was cooled, evaporated, and chromatographed to provide 730 mg of the product.

Step 3

Preparation of 1-Trityl-3-(1-trityl-1H-imidazol-4-yl)-1H-indazol-5-ylamine

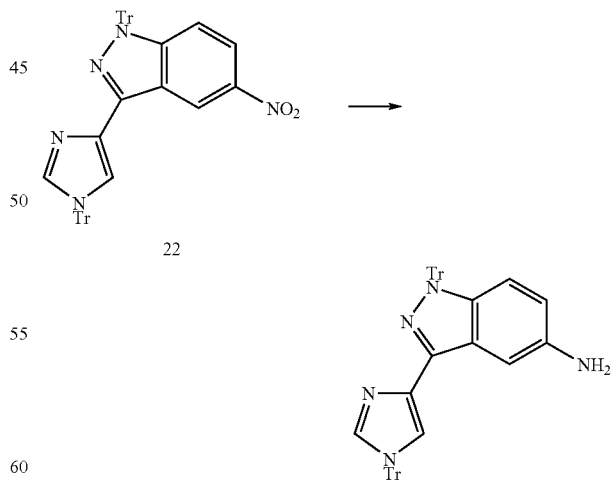

To a solution of 22 (730 mg, 1.02 mmol g, 17.4 mmol) in MeOH (150 mL) was added 10% wt Pd/C (700 mg). The crude was capped with a 3-way stopcock with connections to both vacuum and also a balloon of hydrogen gas. The crude was degassed using house vacuum and repressurrized with hydrogen gas. The process was repeated 5×. The crude was stirred under an atmosphere of hydrogen at rt for 3 hrs. The crude was filtered through a microfiber filter. The filtrate was evaporated and used in the following reaction without further purification.

Step 4

Preparation of 3-(1H-Imidazol-4-yl)-1H-indazol-5-ylamine

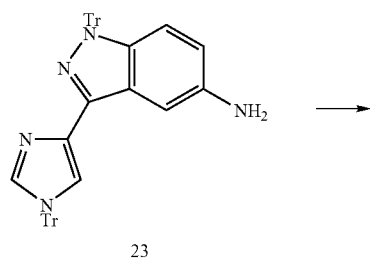

To a solution of ylamine 23 (crude 420 mg, 1.02 mmol) in CH$_2$Cl$_2$ (8 mL) and H$_2$O (1 mL) was added TFA (1 mL) at rt. The crude was stirred at rt for 60 hrs. The crude was quenched with sat. NaHCO$_3$ at rt. The crude was evaporated and filtered through a plug of Na$_2$SO$_4$. The crude was evaporated and purified via preparation plates to give 120 mg of the product.

Step 5

Preparation of 1-{2-Oxo-2-[4-(4-pyrimidin-2-yl-phenyl)-piperazin-1-yl]-ethyl}-pyrrolidine-3-carboxylic acid [3-(1H-imidazol-4-yl)-1H-indazol-5-yl]-amide

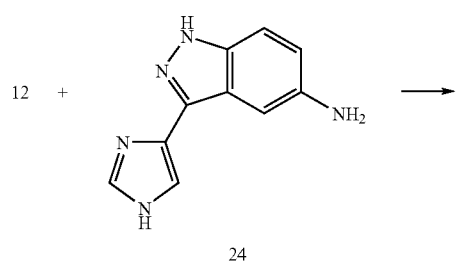

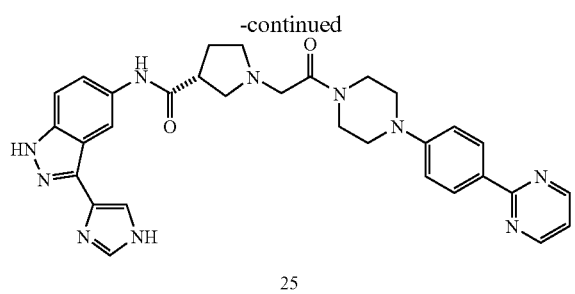

Amine 24 (82 mg, 0.41 mmol) and carboxylic acid 12 (81 mg, 0.21 mmol) were dissolved in CH$_2$Cl$_2$ (2 mL) and DMF (2 ML). To the crude was added TEA (1.16 mL), and HATU (156 mg, 0.41 mmol). The crude was stirred at rt for 22 hrs under a stream of nitrogen. The crude was quenched with sat. NaHCO$_3$ at rt and filtered over a plug of silica gel. The crude was evaporated and purified via preparation plates to give 17 mg of the product.

Example 62

Step 1

Preparation of 3-Bromo-5-nitro-1-(2-trimethylsilanyl-ethoxymethyl)-1H-indazole

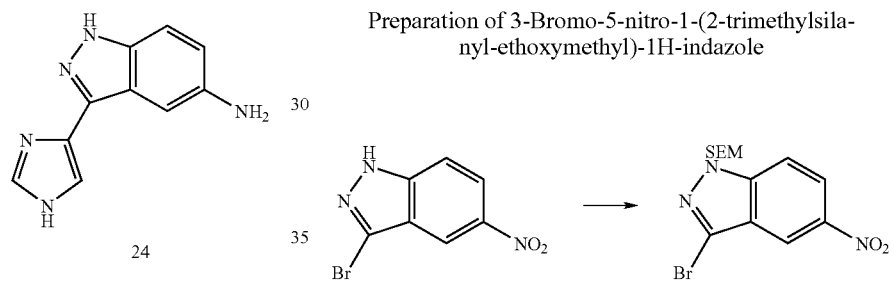

To a solution of 15 (7.9 g, 32.6 mmol) in DMF (163 mL) was added 60% wt NaH (2.0 g, 49 mmol) portionwise over 5 mins at rt. The crude was stirred at rt for 30 mins before the addition of SEMCl (7.5 mL, 42.4 mmol) at rt. The crude was stirred at rt for 58 hrs. The crude was quenched with H$_2$O and diluted in EtOAc. The aq. layer was extracted with EtOAc 3×. The combined organic layer was washed with H$_2$O, brine, dried over MgSO$_4$, filtered, and evaporated. The crude was chromatographed to give 7.4 g of the product.

Step 2

Preparation of 5-Amino-1-(2-trimethylsilanyl-ethoxymethyl)-1H-indazole-3-carbonitrile

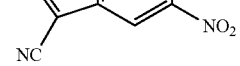

To a solution of bromide 26 (550 mg, 1.34 mmol) in DMF (5 mL) in a 10 mL microwave reaction vessel was added ZnCN$_2$ (160 mg, 1.34 mmol), and PdCl$_2$dppf (320 mg, 0.39 mmol). The crude was sealed with reaction vessel cap. The crude was heated at 180° C. in an EMRY optimizer microwave for 1800 secs. The crude was cooled and quenched with water at rt. The crude was diluted in EtOAc and washed with H₂O 3×. The organic layer was dried over Na₂SO₄, filtered, and evaporated. The crude was chromatographed to give 150 mg of the product.

Step 3

Preparation of 5-Amino-1-(2-trimethylsilanyl-ethoxymethyl)-1H-indazole-3-carbonitrile

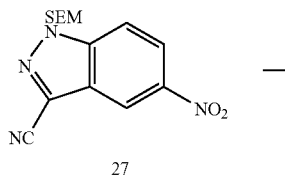 → 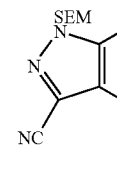

To a solution of nitrile 27 (150 mg, 0.47 mmol) in EtOAc (5 mL) was added 10% wt Pd/C (30 mg). The crude was capped with a 3-way stopcock with connections to both vacuum and also a balloon of hydrogen gas. The crude was degassed using house vacuum and repressurized with hydrogen gas. The process was repeated 5×. The crude was stirred at rt for 4 hrs. The crude was filtered through a microfiber filter. The filtrate was evaporated and purified via preparation plate to give 70 mg of the product.

Step 4

Preparation of 1-{2-Oxo-2-[4-(4-pyrimidin-2-yl-phenyl)-piperazin-1-yl]-ethyl}-pyrrolidine-3-carboxylic acid [3-cyano-1-(2-trimethylsilanyl-ethoxymethyl)-1H-indazol-5-yl]-amide 12 + 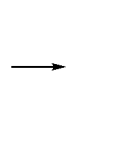 →

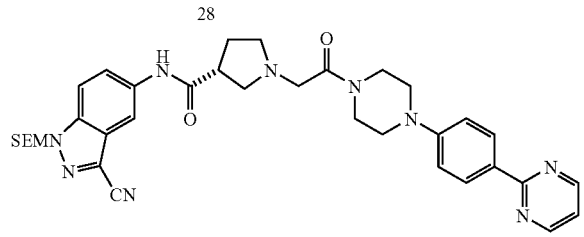

Amine 28 (242 mg, 0.84 mmol) and carboxylic acid 12 (162 mg, 0.42 mmol) were dissolved in CH₂Cl₂ (2 mL) and DMF (2 ML). To the crude was added DIPEA (0.3 mL, 1.68 mmol), and HATU (326 mg, 0.84 mmol). The crude was stirred at rt for 18 hrs under a stream of nitrogen. The crude was quenched with sat. NaHCO₃ at rt. The crude was diluted in EtOAc. The organic layer was washed with water, brine, dried over Na₂SO₄, filtered, and evaporated. The crude was chromatographed to give 212 mg of the product.

Step 5

Preparation of 1-{2-Oxo-2-[4-(4-pyrimidin-2-yl-phenyl)-piperazin-1-yl]-ethyl}-pyrrolidine-3-carboxylic acid (3-cyano-1H-indazol-5-yl)-amide 29 → 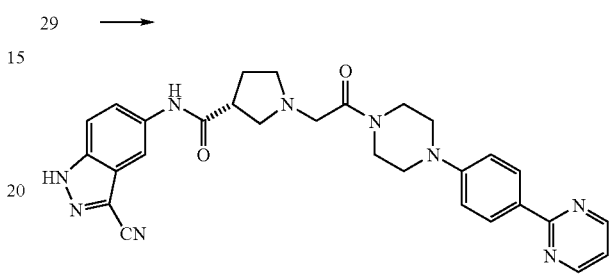

To a solution of 29 (20 mg, 0.03 mmol) in CH₂Cl₂ (2 mL) was added TFA (2 mL) at rt. The crude was stirred at rt for 18 hrs. The crude was evaporated and quenched with sat. NaHCO₃ at rt. The crude was evaporated and filtered through a plug of silica gel and evaporated. The crude was purified via preparation plate to give 13 mg of the product.

Example 63

Step 1

Preparation of 1-{2-Oxo-2-[4-(4-pyrimidin-2-yl-phenyl)-piperazin-1-yl]-ethyl}-pyrrolidine-3-carboxylic acid [3-(1H-tetrazol-5-yl)-1-(2-trimethylsilanyl-ethoxymethyl)-1H-indazol-5-yl]-amide 29 → 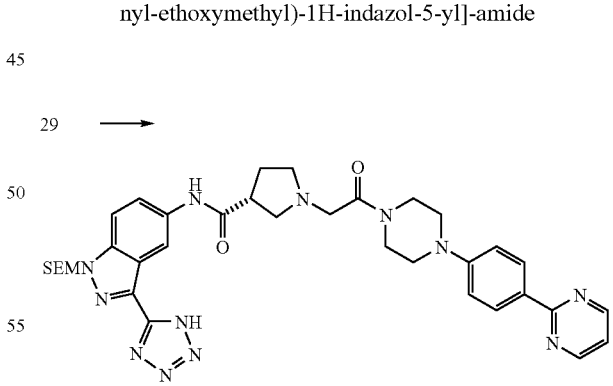

To a solution of 29 from Example 62 Step 4 (40 mg, 0.061 mmol) in DMF was added NaN₃ (12 mg, 0.18 mmol) and NH₄Cl (13 mg, 0.24 mmol). The crude was stirred at 100° C. for 18 hrs. The crude was cool, evaporated, and filtered through a plug of cotton. The crude was evaporated and purified via preparation plate to give 31 mg of a mixture of two isomers.

Step 2

Preparation of 1-{2-Oxo-2-[4-(4-pyrimidin-2-yl-phenyl)-piperazin-1-yl]-ethyl}-pyrrolidine-3-carboxylic acid [3-(1H-tetrazol-5-yl)-1H-indazol-5-yl]-amide

31 ⟶

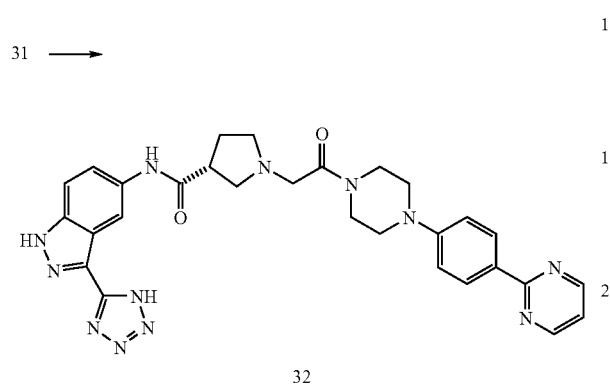

32

To a solution of 31 from Step 1 (31 mg, 0.054 mmol, 2 isomers) in CH₂Cl₂ (2 mL) was added TFA (2 mL) at rt. The crude was stirred at rt for 5 hrs. The crude was evaporated and quenched with sat. NaHCO₃ at rt. The crude was evaporated and filtered through a plug of silica gel and evaporated. The crude was purified via preparation plate to give 13 mg of the product.

Example 64

Step 1

Preparation of 5-[(1-{2-Oxo-2-[4-(4-pyrimidin-2-yl-phenyl)-piperazin-1-yl]-ethyl}-pyrrolidine-3-carbonyl)-amino]-1-(2-trimethylsilanyl-ethoxymethyl)-1H-indazole-3-carboximidic acid

29 ⟶

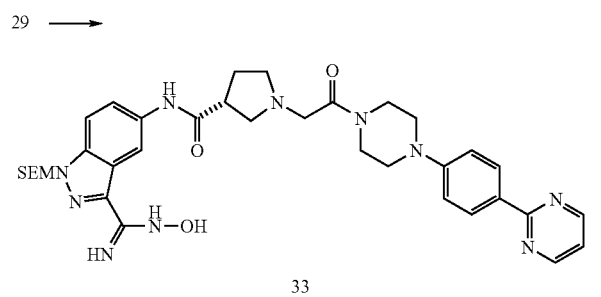

33

To a solution of nitrile 29 from Example 63 Step 4 (40 mg, 0.06 mmol) in EtOH (0.4 mL) was added DIPEA (0.1 mL, 0.6 mmol) and NH₂OH·HCl (21 mg, 0.3 mmol) at rt. The crude was stirred at 45° C. for 18 hrs. The crude was cooled, evaporated, and filtered through a plug of cotton. The crude was evaporated and purified via preparation plate to give 18 mg of the product.

Step 2

Preparation of 5-[(1-{2-Oxo-2-[4-(4-pyrimidin-2-yl-phenyl)-piperazin-1-yl]-ethyl}-pyrrolidine-3-carbonyl)-amino]-1H-indazole-3-carboximidic acid

33 ⟶

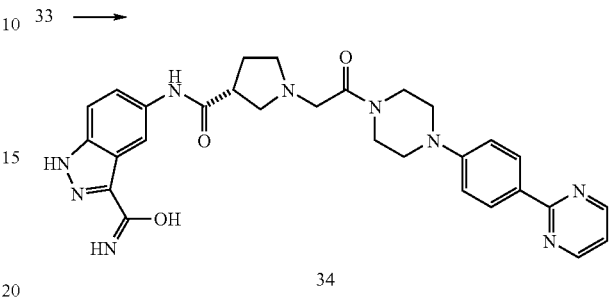

34

To a solution of 33 from Step 1 (18 mg, 0.03 mmol) in CH₂Cl₂ (2 mL) was added TFA (2 mL) at rt. The crude was stirred at rt for 5 hrs. The crude was evaporated and quenched with sat. NaHCO₃ at rt. The crude was evaporated and filtered through a plug of silica gel and evaporated. The crude was purified via preparation plate to give 18 mg of the product.

Example 65

Step 1

Preparation of 3-Amino-5-[(1-{2-oxo-2-[4-(4-pyrimidin-2-yl-phenyl)-piperazin-1-yl]-ethyl}-pyrrolidine-3-carbonyl)-amino]-indazole-1-carboxylic acid tert-butyl ester

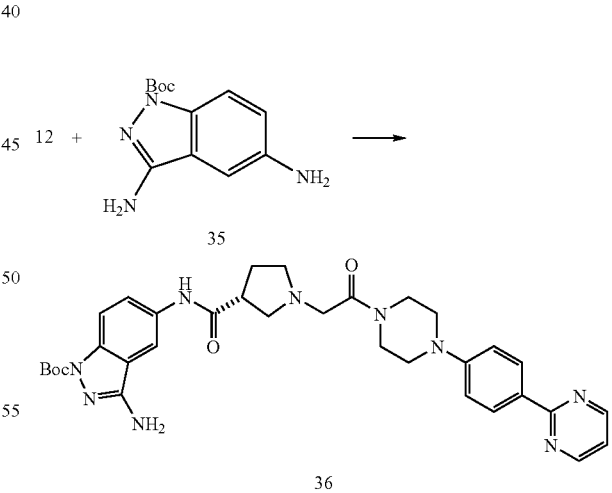

To a solution of amine 35 (283 mg, 1.14 mmol, prepared according to WO 03/064397) in CH₂Cl₂ (5 mL) and DMF (3 mL) was added carboxylic acid 12 from Example 1 Step 9 (375 mg, 0.95 mmol), diisopropylethylamine (0.4 mL, 2.28 mmol), and HATU (433 mg, 1.14 mmol). The crude was stirred overnight at rt under a stream of nitrogen. To the crude was added additional portions of amine 35 (283 mg, 1.14 mmol), HATU (433 mg, 1.14 mmol), and diisopropylethylamine (0.4 mL, 2.28 mmol). To the crude was added CH₂Cl₂ (5 mL) and DMF (3 ML). The crude was stirred at rt for a total of 85 hrs under a stream of nitrogen. The crude was quenched with sat. NaHCO₃ at rt. The crude was diluted in EtOAc. The organic layer was washed with water, brine, dried over Na₂SO₄, filtered, and evaporated. The crude was chromatographed to give 410 mg of the product.

Step 2

Preparation of 3-Acetylamino-5-[(1-{2-oxo-2-[4-(4-pyrimidin-2-yl-phenyl)-piperazin-1-yl]-ethyl}-pyrrolidine-3-carbonyl)-amino]-indazole-1-carboxylic acid tert-butyl ester

36 ⟶

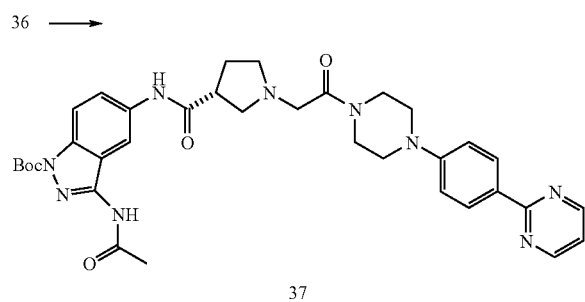

37

Step 3

Preparation of 1-{2-Oxo-2-[4-(4-pyrimidin-2-yl-phenyl)-piperazin-1-yl]-ethyl}-pyrrolidine-3-carboxylic acid (3-acetylamino-1H-indazol-5-yl)-amide

37 ⟶

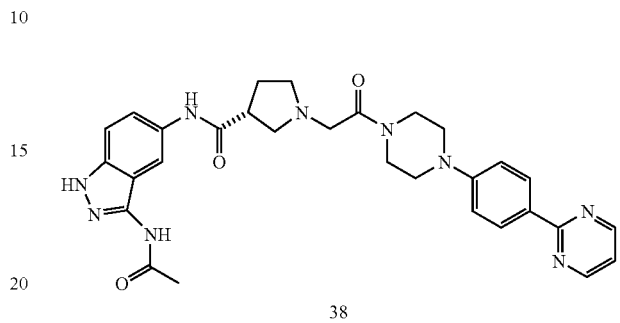

38

To a solution of 37 from Step 2 (20 mg, 0.03 mmol) 37 in CH₂Cl₂ (2 mL) was added TFA (2 mL) at rt. The crude was stirred at rt for 17 hrs. The crude was quenched with sat. NaHCO₃ at rt. The crude was partitioned between EtOAc and H₂O. The organic layer was washed with H₂O, brine, dried over MgSO₄, filtered, and evaporated. The crude was chromatographed to give 6.1 mg of the product.

Examples 66-73

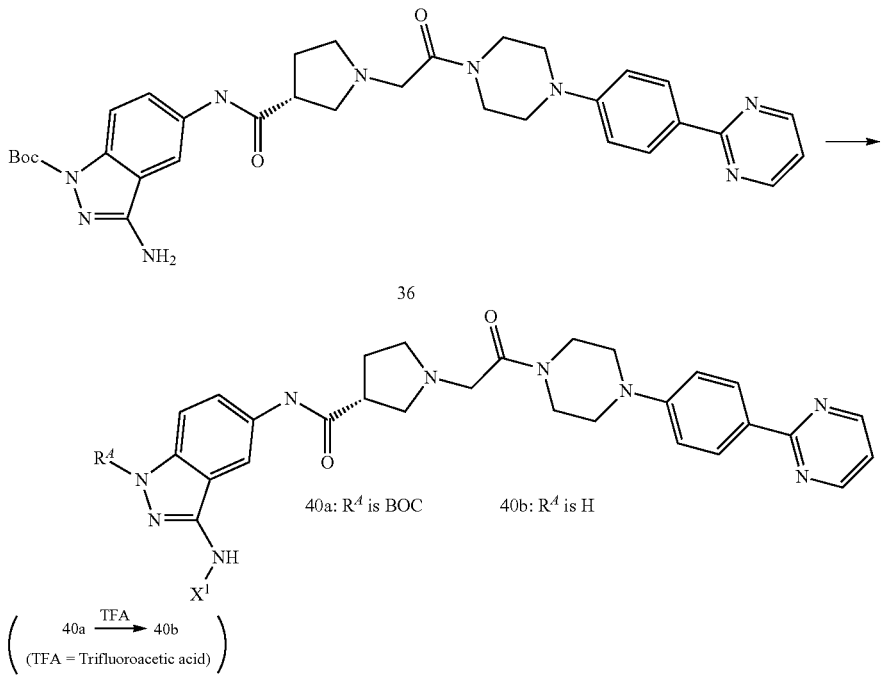

To a solution of 36 from Step 1 in CH₂Cl₂ (0.3 mL) and pyridine (0.3 mL) was added acetyl chloride (50 ul, 0.7 mmol) at rt. The crude was stirred at rt for 30 mins. The crude was quenched with sat. NaHCO₃ at rt. The crude was partitioned between EtOAc and H₂O. The organic layer was washed with H₂O, brine, dried over MgSO₄, filtered, and evaporated. The crude was chromatographed to give 20 mg of the product.

Compound 36 was used to prepare compounds of formula 40b wherein $X^1$ is defined in Table 2. To obtain the desired $X^1$ substitutent, Compound 36 is reacted with $X^1$'s corresponding commercially available acid chloride, isocyanate or sulfonyl chloride. The BOC group is then removed with trifluoroacetic acid. In Table 2 "Ex" represents "Example".

TABLE 2

| Ex | X¹ | LCMass Spec M + 1 @ ret. time |
|---|---|---|
| 66 | H | 526.1 @ 2.13 |
| 67 | benzoyl | 630.1 @ 2.71 |
| 68 | cyclopropylcarbonyl | 594.3 @ 2.12 |
| 69 | butanoyl | 596.3 @ 2.15 |
| 70 | phenylcarbamoyl | 645.4 @ 2.60 |
| 71 | methylsulfonyl | 604.3 @ 2.10 |
| 72 | ethylcarbamoyl | 597.3 @ 2.20 |
| 73 | carbamoyl | 669.3 @ 1.98 |

Example 74

Step 1

Preparation of 3-Morpholin-4-yl-5-nitro-1H-indazole

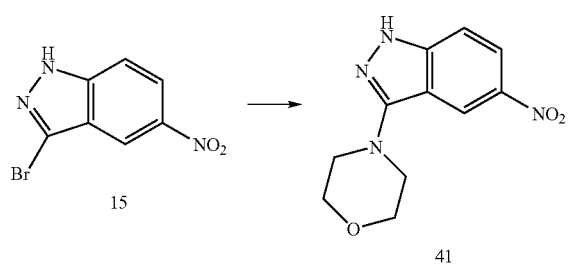 [SMILES: O=[N+]([O-])c1ccc2[nH]nc(Br)c2c1 ; O=[N+]([O-])c1ccc2[nH]nc(N3CCOCC3)c2c1]

3-Bromo-5-nitro-1H-indazole (0.5 gm, 2 mmol) was dissolved in 3.5 ml of morpholine and heated in a sealed tube for 40 hrs. The mixture was then cooled and added to ethylacetate, washed with brine and dried over magnesium sulfate. After chromatography on silica gel using 20-50% ethylacetate/hexanes as eluent the title compound was obtained (210 mg, 0.85 mmol).

Step 2

Preparation of 3-Morpholin-4-yl-1H-indazol-5-ylamine

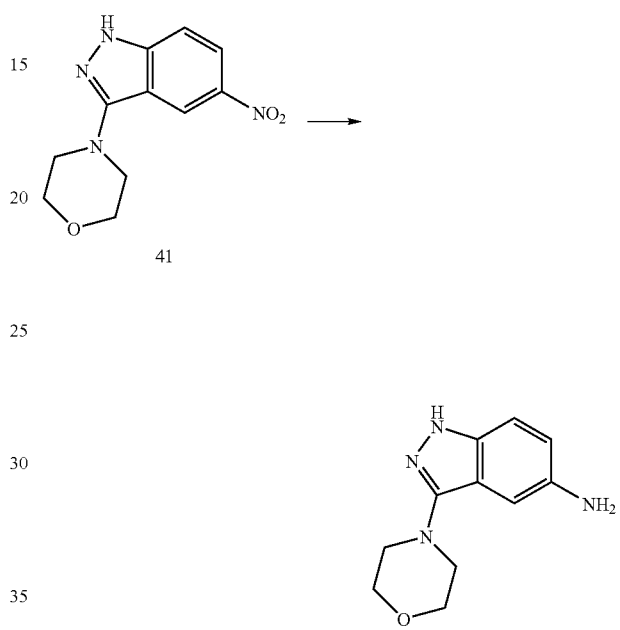

3-Morpholin-4-yl-5-nitro-1H-indazole (210 mg) was dissolved in 10 ml of methanol and the mixture hydrogenated at 1 atm of hydrogen using 10% Pd/C (50 mg) as catalyst. After 24 hrs, the mixture was filtered and evaporated for use in the next step.

Step 3

Preparation of 1-{2-Oxo-2-[4-(4-pyrimidin-2-yl-phenyl)-piperazin-1-yl]-ethyl}-pyrrolidine-3-carboxylic acid (3-morpholin-4-yl-1H-indazol-5-yl)-amide

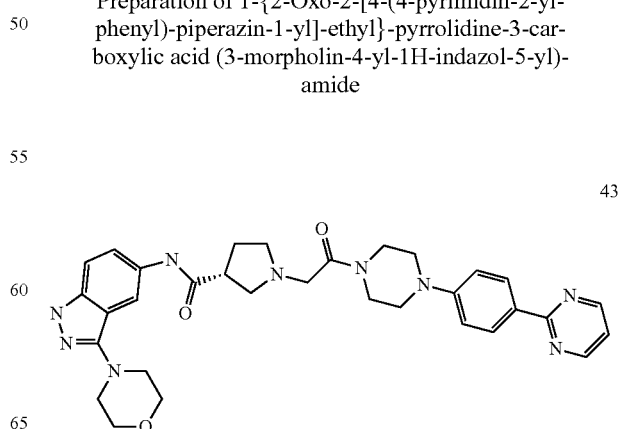

The title compound was prepared following the procedure in Example 1 Step 10 except amine 42 from Step 2 was used instead of amine 13.

Example 75

Preparation of 1-{2-Oxo-2-[4-(4-pyrimidin-2-yl-phenyl)-piperazin-1-yl]-ethyl}-pyrrolidine-3-carboxylic acid (3-pyrrolidin-1-yl-1H-indazol-5-yl)-amide

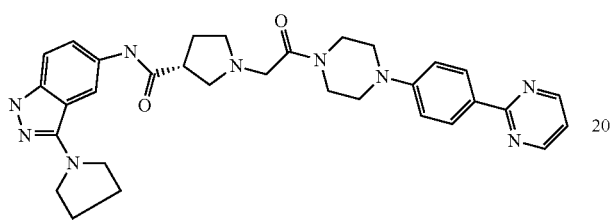

44

The title compound was prepared following the procedures in Example 74, Steps 1 and 2, and Example 1, Step 10, by using pyrrolidine instead of morpholine in Example 74, Step 1. The amine prepared following the procedure of Example 76, Steps 1 and 2, is used instead of amine 13 in the procedure of Example 1, Step 10.

Example 76

Step 1

Preparation of 3-Bromomethyl-5-nitro-indazole-1-carboxylic acid tert-butyl ester

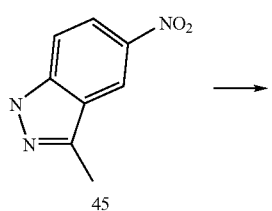

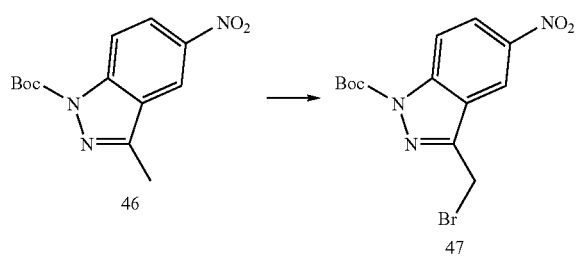

3-Methyl-5-nitro-1H-indazole (1.89 gm, 10.2 mmol) was dissolved in 20 ml of acetonitrile. A catalytic amount of DMAP followed by triethylamine (2.13 ml, 1.5 eq) and di-tert.butyldicarbonate (2.88 gm, 1.3 eq) was added and stirred for 3 hrs. The reaction mixture was evaporated to dryness and dissolved in ethyl acetate and washed with 0.1 N HCl. The ethyl acetate layer was washed twice with water, dried over magnesium sulfate and chromatographed on silica gel to give a 2.05 gm of Boc compound. The entire amount of Boc compound was dissolved in 20 ml of CCl4 and benzoylperoxide (179 mg, 0.74 mmol) and N-bromosuccinimide (1.45 gm, 8.14 mmol) were added. The reaction mixture was refluxed for 2 hrs. After 2 hrs 179 mg of benzoylperoxide was added and the reaction mixture refluxed for 18 hrs. The reaction mixture was cooled and washed with water and dried over magnesium sulfate. After chromatography on silica gel, 1.32 gm of title product was obtained.

Step 2

Preparation of 2-(5-Nitro-1H-indazol-3-ylmethyl)-isoindole-1,3-dione

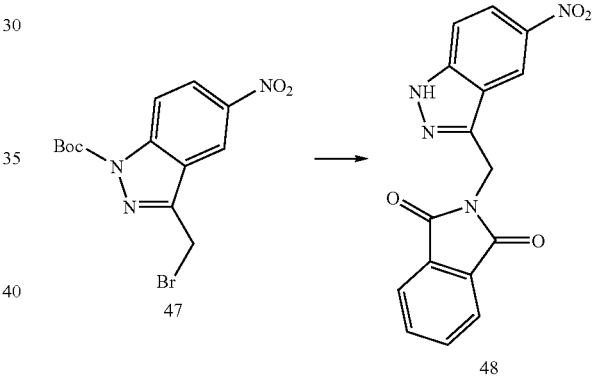

3-Bromomethyl-5-nitro-indazole-1-carboxylic acid tert-butyl ester (0.63 g, 1.77 mmol) and potassium phthalimide (0.396 g, 1.2 eq) were stirred in DMF (1 mL) at 80° C. for two hours. TLC (20% EtOAc/hexane) showed starting material consumed and new products formed. After DMF was evaporated, a residue, 1.33 g, was obtained. The resulting residue was stirred in DCM and filtered. The filtration cake then washed with DCM followed by hexane. The evaporation of the filtrate gave 0.79 g of crude. Flash chromatograph (20-30% EtOAc/hexane) gave a mixture, two spots shown on TLC. During the sample preparation, solid precipitated and the solid was collected, 95 mg. MS showed de-Boc product, $(M+H)^+$ at 323. An adequate amount of this mixture was treated with TFA in DCM for two hours. TLC showed one spot and MS gave $(M+H)^+$ at 323. The remaining mixture was stirred in a mixture of TFA (6 mL) and DCM (10 mL) for two hours. Evaporation of TFA and DCM gave the desired product, 0.71 g, (quant. yield).

Step 3

Preparation of 2-(5-Amino-1H-indazol-3-ylmethyl)-isoindole-1,3-dione

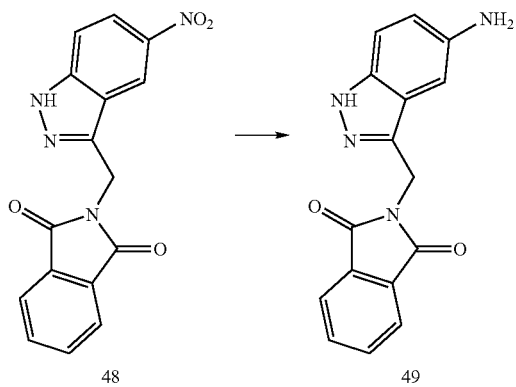 [SMILES: O=C1c2ccccc2C(=O)N1Cc1n[nH]c2ccc([N+](=O)[O-])cc12 ; Nc1ccc2[nH]nc(CN3C(=O)c4ccccc4C3=O)c2c1]

48 → 49

2-(5-Nitro-1H-indazol-3-ylmethyl)-isoindole-1,3-dione (0.71 gm) was dissolved in methanol and hydrogenated at 1 atm. using 10% Pd/C (catalytic) for 18 hrs. The catalyst was filtered and the mixture evaporated to obtain 614 mg of title product.

Step 4

Preparation of 1-{2-Oxo-2-[4-(4-pyrimidin-2-yl-phenyl)-piperazin-1-yl]-ethyl}-pyrrolidine-3-carboxylic acid [3-(1,3-dioxo-1,3-dihydro-isoindol-2-ylmethyl)-1H-indazol-5-yl]-amide

49 + 12 →

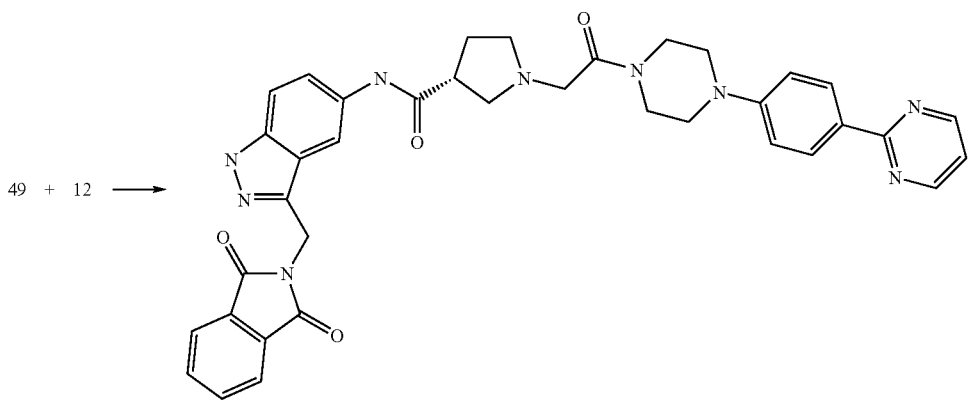

50

2-(5-Amino-1H-indazol-3-ylmethyl)-isoindole-1,3-dione (compound 49 from Step 3, 614 gm, 2 mmol) and compound 12 (from Example 1 Step 9) were dissolved in 10 ml of DMF. O-(7-azabenzotriazol-1-yl-)-N,N,N,N-tetramethyluronium hexafluorophosphate (HATU) (660 mg, 1.7 mmol) and diisopropylethylamine (0.9 ml, 5 eq.). After stirring 4 hours, the reaction mixture was added to brine and extracted with ethylacetate, dried over magnesium sulfate and evaporated. The crude was chromatographed on silica gel to obtain 440 mg of title product.

Example 77

Preparation of 1-{2-Oxo-2-[4-(4-pyrimidin-2-yl-phenyl)-piperazin-1-yl]-ethyl}-pyrrolidine-3-carboxylic acid (3-aminomethyl-1H-indazol-5-yl)-amide

50 →

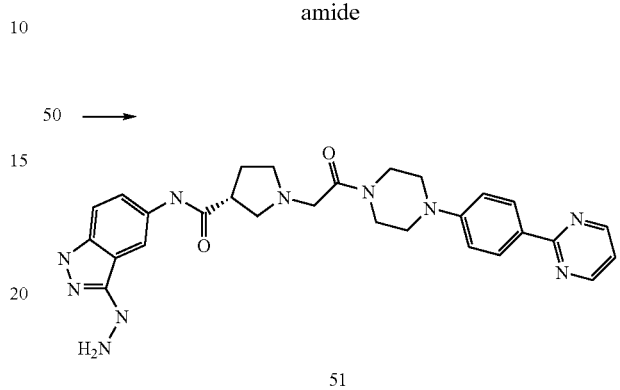

51

1-{2-Oxo-2-[4-(4-pyrimidin-2-yl-phenyl)-piperazin-1-yl]-ethyl}-pyrrolidine-3-carboxylic acid [3-(1,3-dioxo-1,3-dihydro-isoindol-2-ylmethyl)-1H-indazol-5-yl]-amide (compound 50 from Example 78, 424 mg, 0.633 mmol) was dissolved in ethanol and 0.31 ml of hydrazine hydrate. The mixture was heated at 80 C for 20 hrs and then evaporated to dryness. The mixture was chromatographed on silica gel to obtain 100 mg of title product.

Examples 78 to 84

Following a procedure similar to that of Examples 66 to 73 compound 51 (from Example 77) was used to prepare compounds of formula 52 wherein $X^2$ is defined in Table 3. To obtain the desired final compound in Examples 78, 80 and 81, Compound 51 is reacted with $X^2$'s corresponding commercially available acid chloride. To obtain the desired final compound in Example 79, 83 and 84 Compound 51 is reacted with $X^2$'s corresponding commercially available isocyanate. To obtain the desired final compound in Example 82, Compound 51 is reacted with $X^2$'s corresponding to commercially available sulfonyl chloride. In Table 3 "Ex" represents "Example".

TABLE 3

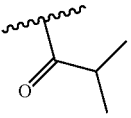

| Ex | X² |
|----|----|
| 78 | —C(O)CH₃ |
| 79 | —C(O)NH₂ |
| 80 | 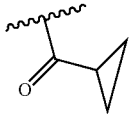 |
| 81 | 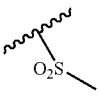 |
| 82 | 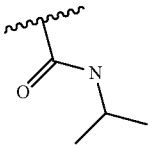 [SMILES: *C(=O)NC(C)C] |
| 83 | 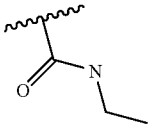 [SMILES: *C(=O)NCC] |
| 84 | 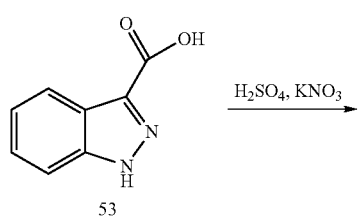 |

Example 85

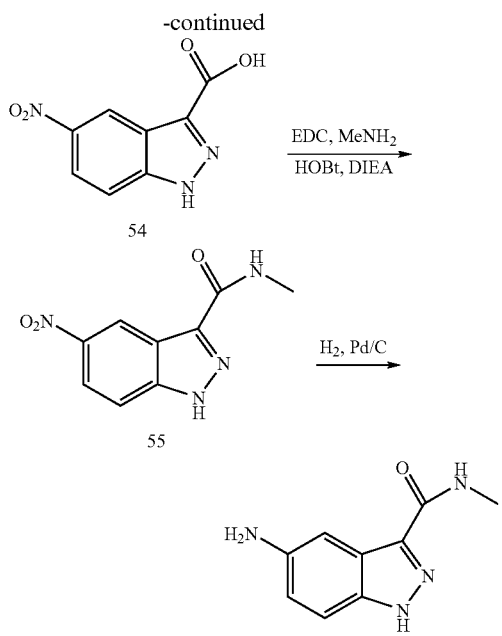

Step 1

Preparation of 5-Nitro-1H-indazole-3-carboxylic acid (54)

To a suspension of indazole-3-carboxylic acid (compound 53, 3.0 g, 18 mmol) in 18 mL of concentrated sulfuric acid at 0 C was added potassium nitrate (2.0 g, 18 mmol). The reaction was stirred overnight at room temperature, poured into 150 mL of ice and extracted three times with ethyl acetate. The combined organic layer was washed with brine, dried and concentrated to give compound 54 (2.9 g) as the major isomer.

Step 2

Preparation of 5-Nitro-1H-indazole-3-carboxylic acid methylamide (55)

To a solution of compound 54 (100 mg, 0.483 mmol), methylamine hydrochloride (52.2 mg, 0.773 mmol), HOBt (130 mg, 0.966 mmol) and DIEA (0.34 mL, 1.95 mmol) in N-methylpyrrolidinone was added 1-(3-dimethylaminopropyl)-3-ethylcarbodiimide hydrochloride (148 mg, 0.773 mmol). The reaction was stirred at room temperature for 2 hrs and diluted with 10 mL of ethyl acetate. The mixture was washed with water and a yellow solid precipitated. The precipitate was collected by filtration to give compound 55 (67 mg).

Step 3

Preparation of 5-Amino-1H-indazole-3-carboxylic acid methylamide (56)

To a suspension of compound 55 (65 mg) in 5 mL of methanol was added catalytic amount of 5% palladium on carbon. The mixture was stirred under a hydrogen atmosphere at room temperature for 4 hrs and filtered through celite. The filtrate was concentrated to afford compound 56 (59 mg).

Example 86

Step 1

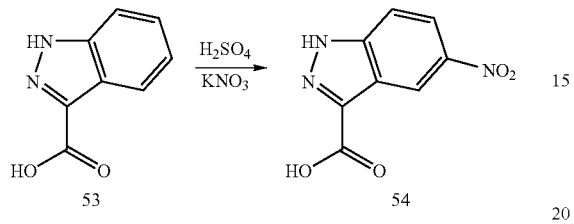

To a suspension of indazole-3-carboxylic acid (3.0 g, 18 mmol) in 18 mL of concentrated sulfuric acid at 0 C was added potassium nitrate (2.0 g, 18 mmol). The reaction was stirred overnight at room temperature, poured into 150 mL of ice and extracted three times with ethyl acetate (90 mL total). The combined organic layer was washed with brine, dried and concentrated to give (54) (2.9 g) as the major product.

Step 2

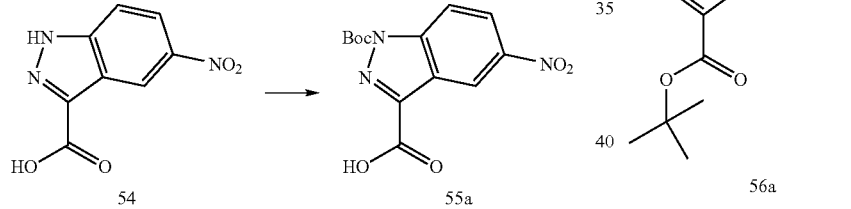

To a solution of compound 54 (230 mg, 1.11 mmol) in 5 mL of THF was added sodium hydroxide solution (1 M, 3.3 mL, 3.33 mmol), and then t-butyl dicarbonate (364 mg, 1.67 mmol). The reaction was stirred at room temperature overnight and treated with 3.4 mL of 1 N HCl. The mixture was extracted with ethyl acetate three times. The combined organic layer was dried over sodium sulfate and concentrated to provide compound 55a (307 mg).

Step 3

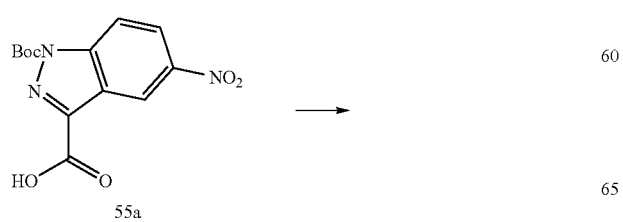

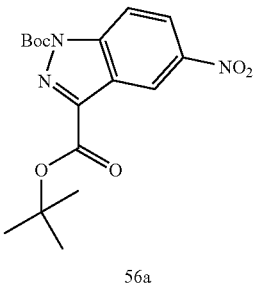

To a solution of compound 55a (307 mg, 1.00 mmol) was added N,N'-diisopropyl-t-butyl isourea (880 mg, 4.00 mmol). The reaction was heated to reflux overnight and filtered. The filtrate was concentrated and purified by column chromatography (3:1 hexane/ethyl acetate) to provide compound 56a (179 mg).

Step 4

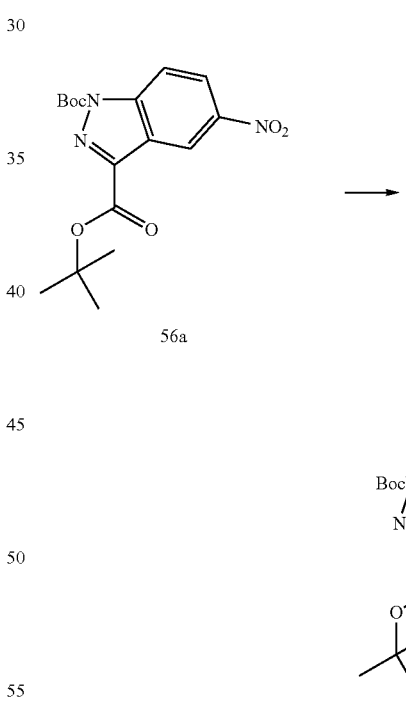

To a mixture of compound 56a (150 mg, 0.413 mmol) in 5 mL of methanol was added catalytic amount of 5% palladium on carbon. The mixture was stirred under a hydrogen atmosphere at room temperature overnight and filtered through celite. The filtrate was concentrated to provide compound 57 (98 mg). The material was used as such without further purification.

Step 5

57 + 12 ⟶

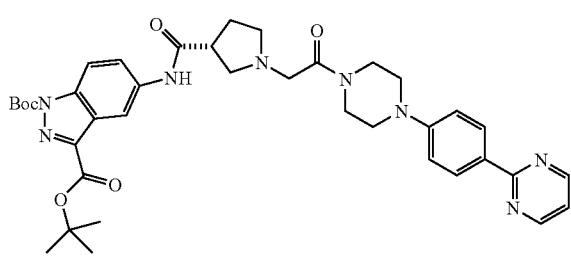

58

To a solution of compound 57, from Step 4, (98 mg, 0.29 mmol), 12 (TFA salt with LiCl, 211 mg, 0.29 mmol) 1-hydroxybenztriazole (40 mg, 0.29 mmol) and diisopropylamine (0.15 mL, 0.90 mmol) in DMF was added 1-(3-dimethylamino-propyl)-3-ethylcarbodiimide hydrochloride (EDCl) (73 mg, 0.38 mmol). The reaction was stirred overnight at room temperature for 2 hrs, concentrated and purified by reverse phase chromatography to give 58 as a TFA salt (180 mg).

Step 6

58 —TFA/DCM→

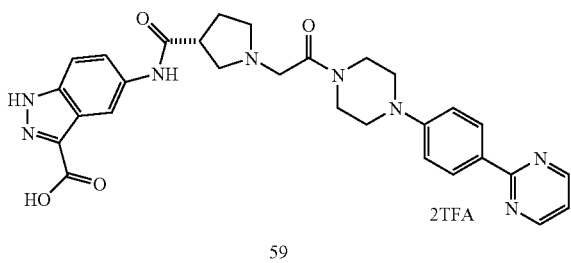

59

Compound 58, from Step 5, (180 mg, 0.192 mmol) was treated with TFA/DCM (3 mL/3 mL) at room temperature. The reaction was stirred for 1 h and concentrated to provide 59 (115 mg).

Step 7

59 —HATU, n-BuNH₂, DMF→

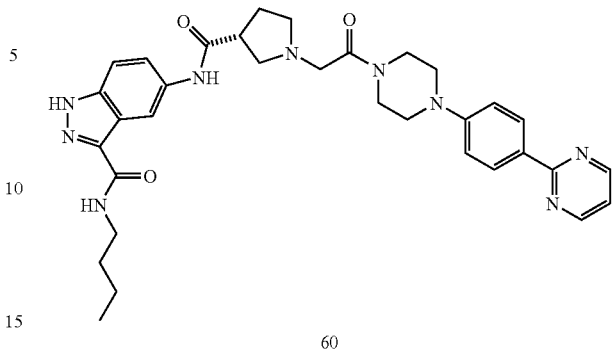

60

To a solution of compound 59 (10 mg, 0.013 mmol) and n-butylamine (1.9 mg, 0.026 mmol) in 1.5 mL of DMF was added HATU (14 mg). The reaction was stirred at room temperature for 2 hrs and concentrated. The residue was purified by reverse-phase chromatography to give 60 (5 mg).

Example 87

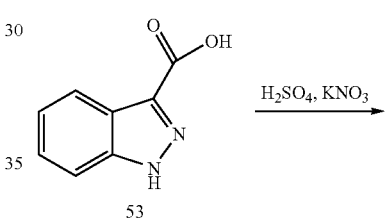

53

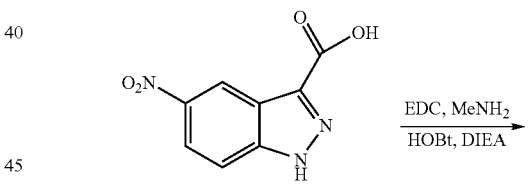

54

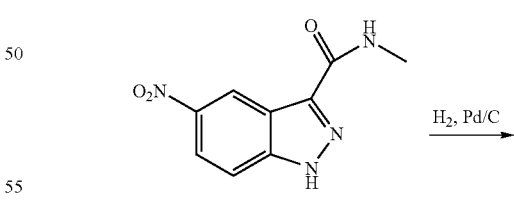

55

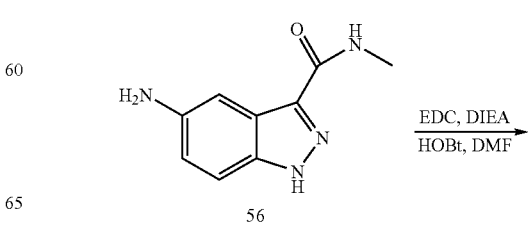

56

Examples 88 to 97

Compounds of formula 62:

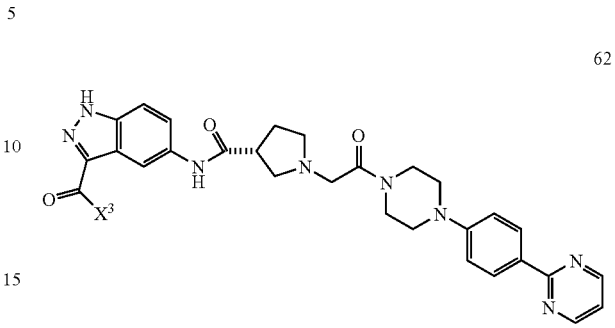

wherein $X^3$ is defined in Table 4 were prepared from compound 59 (from Example 86 Step 6) following a procedure similar to that described in Example 86 Step 7 and using the corresponding amine of $X^3$. In Table 4 "Ex" represents "Example".

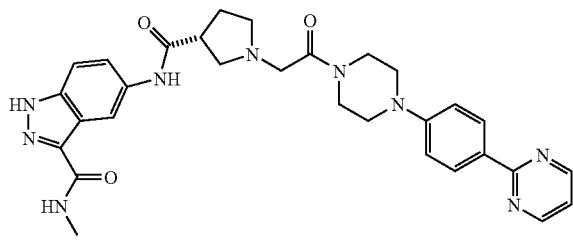

Step 1

To a suspension of indazole-3-carboxylic acid (compound 53, 3.0 g, 18 mmol) in 18 mL of concentrated sulfuric acid at 0 C was added potassium nitrate (2.0 g, 18 mmol). The reaction was stirred overnight at room temperature, poured into 150 mL of ice and extracted three times with ethyl acetate. The combined organic layer was washed with brine, dried and concentrated to give compound 54 (2.9 g) as the major isomer.

Step 2

To a solution of compound 54 (100 mg, 0.483 mmol), methylamine hydrochloride (52.2 mg, 0.773 mmol), HOBt (130 mg, 0.966 mmol) and DIEA (0.34 mL, 1.95 mmol) in N-methylpyrrolidinone was added 1-(3-dimethylaminopropyl)-3-ethylcarbodiimide hydrochloride (148 mg, 0.773 mmol). The reaction was stirred at room temperature for 2 hrs and diluted with 10 mL of ethyl acetate. The mixture was washed with water and a yellow solid precipitated. The precipitate was collected by filtration to give compound 55 (67 mg).

Step 3

To a suspension of compound 55 (65 mg) in 5 mL of methanol was added catalytic amount of 5% palladium on carbon. The mixture was stirred under a hydrogen atmosphere at room temperature for 4 hrs and filtered through celite. The filtrate was concentrated to afford compound 56 (59 mg).

Step 4

Compound 56 was reacted with compound 12 (Example 1 Step 9) following the procedure of Example 1, Step 10, to prepare compound 61 Mass Spec.: 610, LCMS Retention Time 3.58 minutes.

TABLE 4

| Ex | $X^3$ | Retention time (min) | Mass Spec |
|---|---|---|---|
| 88 | | 3.33 | 596 |
| 89 | | 2.84 | 568 |
| 90 | | 3.11 | 594 |
| 91 | | 2.42 | 612 |
| 92 | | 3.71 | 662 |

TABLE 4-continued

| Ex | X³ | Retention time (min) | Mass Spec |
|---|---|---|---|
| 93 | (pyridin-4-ylmethyl)amino | 2.44 | 645 |
| 94 | (2-hydroxyethyl)amino | 2.63 | 598 |
| 95 | (carbamoylmethyl)amino | 2.54 | 611 |
| 96 | (2-hydroxy-1-phenylethyl)amino | 3.28 | 674 |
| 97 | phenylamino | 3.72 | 630 |

Example 98

Step 1

Preparation of 1-tert-Butoxycarbonylmethyl-pyrrolidine-3-carboxylic acid, Lithium salt

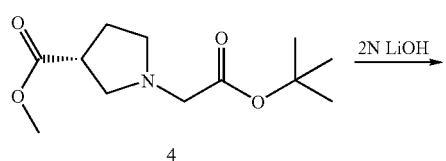

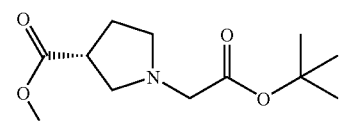

1-tert-Butoxycarbonylmethyl-pyrrolidine-3-carboxylic acid methyl ester 4 (see Example 1 Step 2) (0.753 g, 3.098 mmol) was dissolved in MeOH/THF (10 ml; 1/1) and 2N Lithium hydroxide (1.5 ml; 3 mmol) was added. The resultant solution was stirred for 2 hours, and solvent was evaporated yielding title compound 63 as a white solid (0.71 g, 100%). Mass Spec ES (230, MH).

Step 2

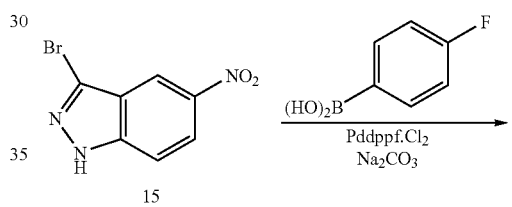

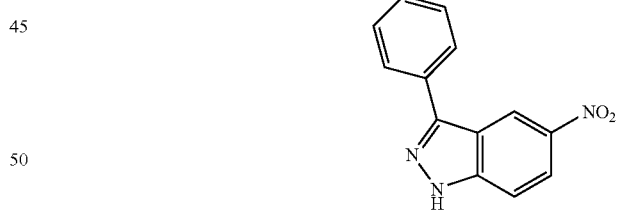

3-Bromo-5-nitro-1H-indazole (Compound 15 (see Example 2 Step 2), 0.5 g, 2.06 mmol), 4-Fluorophenylboronic acid (720 mg, 5.14 mmol), Pd(dppf)Cl₂ (252 mg, 0.31 mmol), and Na₂CO₃ (657 mg, 6.20 mmol) were added to a 25 ml microwave vessel. DME (16 ml) and H₂O (4 ml) were added subsequently. The mixture was heated under microwave at 150° C. for 20 min. The reaction mixture was then filtered through a pad of celite. The filtrate was concentrated, and purified by flash column (25% EtOAc/Hex) to yield Compound 64 (0.3 g, 1.17 mmol).

Step 3

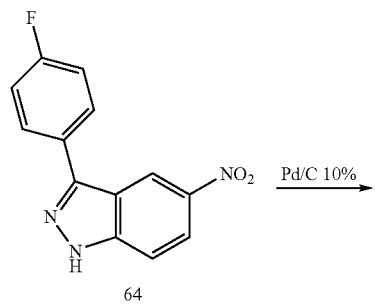

Compound 64 (0.57 g, 2.22 mmol) was dissolved in EtOAc (20 ml)/MeOH (20 ml). Pd/C (10 wt. %, cat.) was added. The mixture was subjected to 50 PSI H₂ on a par apparatus at room temperature over night. The reaction was then filtered. The filtrate was concentrated to yield Compound 65 (492 mg, 2.16 mmol).

Step 4

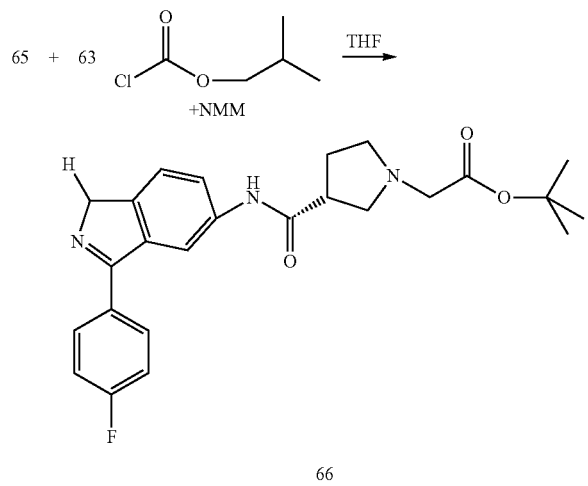

1-tert-Butoxycarbonylmethyl-pyrrolidine-3-carboxylic acid, Lithium salt 63 (from Step 1) (665 mg, 2.83 mmol) and N-Methyl morpholine (0.84 ml, 7.65 mmol) were dissolved in THF (50 ml) then cooled solution to 0 C. Isobutyl chloroformate (0.37 ml, 2.83 mmol) in THF (20 ml) was added dropwise, and stirred at 0° C. for 1 hour. 3-(4-Fluoro-phenyl)-1H-indazol-6-ylamine 65 (from Step 2) (576 mg, 2.54 mmol) in THF (20 ml) was added dropwise then stirred at room temperature for 1 hour. The reaction mixture was diluted with EtOAC (150 ml), Water (60 ml) and 5% NaOH (10 ml). Organic layer was separated, dried over MgSO₄, and solvent evaporated yielding a residue which was dissolved and stirred in Methanol (30 ml) and 1N NaOH (10 ml) for 10 minutes. Reaction was concentrated, residue extracted with EtOAc (200 ml) washed with H₂O (30 ml), dried over Na₂SO₄, filtered and concentrated yielding title compound 66 as a white solid (700 mg, 63%).

Step 5

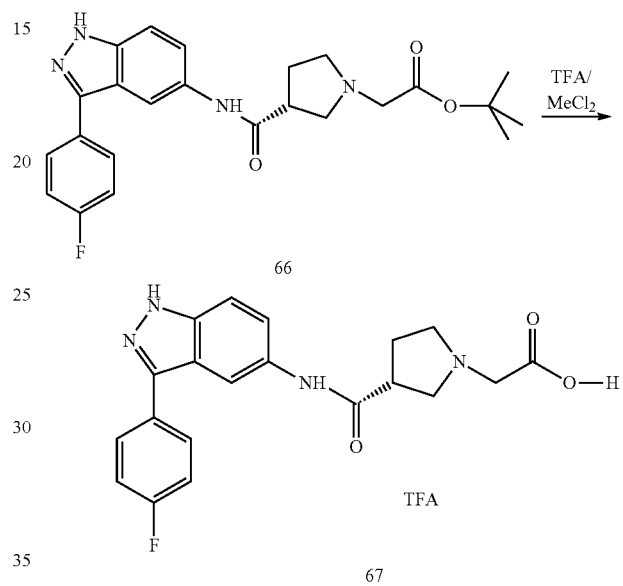

Compound 66 (700 mg, 1.60 mmol) was stirred in trifluoroacetic acid (20%, 10 ml) for 2 hours, then the solvent was evaporated yielding the title compound as trifluoroacetate salt 67 as a white solid. (790 mg, 100%) ESMS (MH, 383).

Step 6

Preparation of 2-(6-Bromo-pyridin-3-yl)-pyrimidine

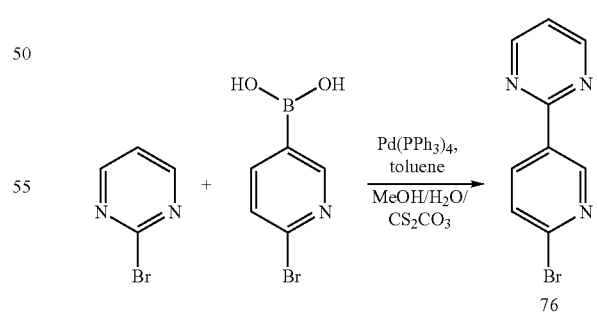

A mixture of 2-bromopyrimidine (0.43 g, 2.70 mmol), 2-bromopyridine-5-boronic acid (0.55 g, 2.72 mmol), tetrakis (triphenylphosphine)palladium(0) (300 mg, 0.259 mmol), cesium carbonate (1.15 g, 3.03 mmol) was stirred in MeOH/toluene/water (15 ml, 1/1/1) at reflux temperature overnight. The reaction was cooled to room temperature and diluted with EtOAc (200 ml) and water (50 ml). The organic layer was separated, dried over MgSO$_4$, filtered and solvent evaporated yielding a residue which was purified on silica gel eluting with 25% v/v EtOAc/hexanes yielding product 76 as white solid. (0.55 g, 85%) ESMS (MH, 236).

Step 7

Preparation of 2-(6-piperazin-1-yl-pyridin-3-yl)-pyrimidine

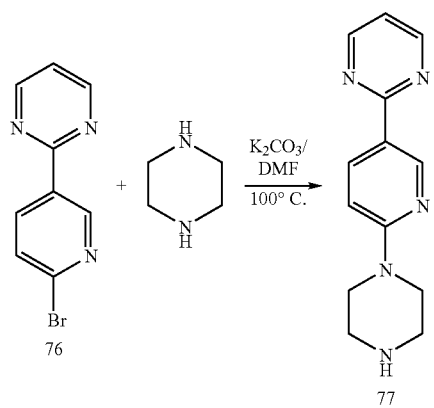

A mixture of 2-(6-Bromo-pyridin-3-yl)-pyrimidine 76 (100 mg, 0.425 mmol), potassium carbonate (100 mg, 0.724 mmol), and piperazine (100 mg, 1.16 mmol) in DMF (5 ml) were stirred at 100° C. for 1 hour. The reaction was cooled, solvent evaporated under reduced pressure, and the residue dissolved in MeCl$_2$ (150 ml), washed with H$_2$O (50 ml), dried over MgSO$_4$, filtered and evaporated solvent yielding title product 77 as a white solid (100 mg, 98%). ESMS (MH, 242).

Step 8

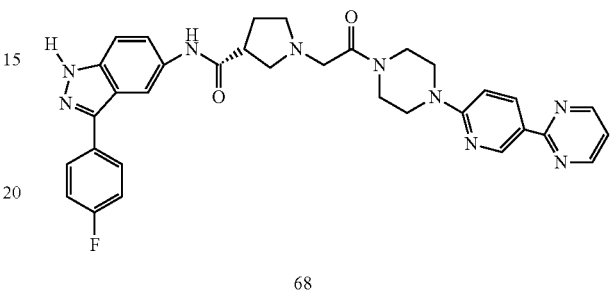

68

Added triethylamine (0.1 ml, 0.7 mmol) to solution of {3-[3-(4-Fluoro-phenyl)-1H-indazol-6-ylcarbamoyl]-pyrrolidin-1-yl}-acetic acid trifluoroacetate 67 (Step 5) (50 mg, 0.1008 mmol), 2-(6-piperazin-1-yl-pyridin-3-yl)-pyrimidine 77 (Step 7) (60 mg, 0.248 mmol), 1-(3-dimethylaminopropyl)-3-ethylcarbodiimide hydrochloride (EDCl) (50 mg, 0.261 mmol), 1-hydroxybenztriazole monohydrate (30 mg, 0.222 mmol) in DMF (2 ml), then stirred overnight at room temperature. The solvent was evaporated and residue purified on silica gel eluting with 7% v/v MeOH/MeCl$_2$/NH$_4$OH yielding product 68 as white solid (33 mg, 54%). LCMS (MH, 606) Retention time=2.46 minutes.

Examples 99 to 101

Following a procedure similar to that of Example 98, and using the appropriate reagents, the compounds in Table 5 were obtained. In Table 5 "Ex" represents "Example".

TABLE 5

| Ex | Compound | Mass Spec LCMS MH | Retention time Minutes |
|---|---|---|---|
| 99 | | 620 | 2.45 |

TABLE 5-continued

| Ex | Compound | Mass Spec LCMS MH | Retention time Minutes |
|---|---|---|---|
| 100 | | 620 | 2.43 |
| 101 | | 647 | 3.23 |

Example 102

Step 1

Preparation of 1-Chloro-2-iodo-4-nitro-benzene

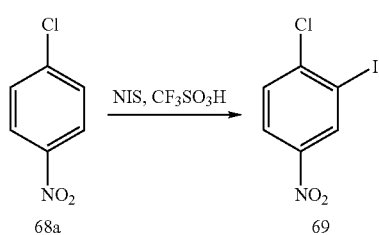 [SMILES: O=[N+]([O-])c1ccc(Cl)cc1 ; O=[N+]([O-])c1ccc(Cl)c(I)c1]

N-Iodosuccinimide (1.71 g, 7.60 mmol) was added to a solution of 1-chloro-4-nitrobenzene (1.17 g, 7.42 mmol) in trifluoromethanesulfonic acid (10 ml) at 0° C., then stirred 1 hour at room temperature. The reaction was quenched with ice-water and extracted with MeCl$_2$ (3×50 ml). Organics were combined washed with 10% sodium bisulfite (20 ml) then dried over Na$_2$SO$_4$, filtered and evaporated solvent yielding the title compound as a white solid (1.3 g, 62%).

Step 2

Preparation of 1-Chloro-2-(2-fluoro-phenylethynyl)-4-nitro-benzene

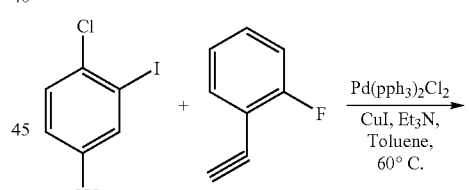

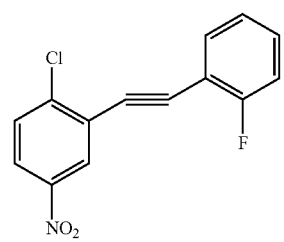

Triethylamine (0.2 ml, 1.43 mmol) was added to a suspension of 1-Chloro-2-iodo-4-nitro-benzene 69 (Step 1) (100 mg, 0.354 mmol), 1-ethynyl-2-fluorobenzene (100 mg, 0.832 mmol), copper iodide (100 mg, 0.525 mmol), Pd(PPh$_3$)$_2$Cl$_2$ (100 mg, 0.142 mmol) in dimethylformamide (2 ml) at room temperature, then stirred at 70° C. for 2 hours. Reaction was cooled to room temperature and extracted with ether (50 ml), washed with water (20 ml), dried (MgSO₄), filtered and solvent evaporated yielding a residue which chromatographed on silica gel eluting with 20% v/v MeCl₂/hexanes yielding title product 70 as pale yellow solid (80 mg, 82%).

Step 3

Preparation of
3-(2-Fluoro-benzyl)-5-nitro-1H-indazole

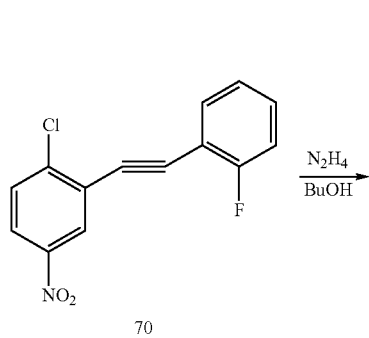

Hydrazine.monohydrate (0.2 ml, 4.1 mmol) was added to a solution of 1-chloro-2-(2-fluoro-phenylethynyl)-4-nitrobenzene 70 (Step 2) (80 mg, 0.29 mmol) in n-butanol (3 ml) then refluxed for 2 hours. The mixture was cooled and solvent evaporated under reduced pressure. The residue was purified on silica gel eluting with 5% v/v MeOH/MeCl₂ yielding product as yellow solid (60 mg, 76%) ESMS (MH, 272).

Step 4

Preparation of
3-(2-Fluoro-benzyl)-1H-indazol-5-ylamine

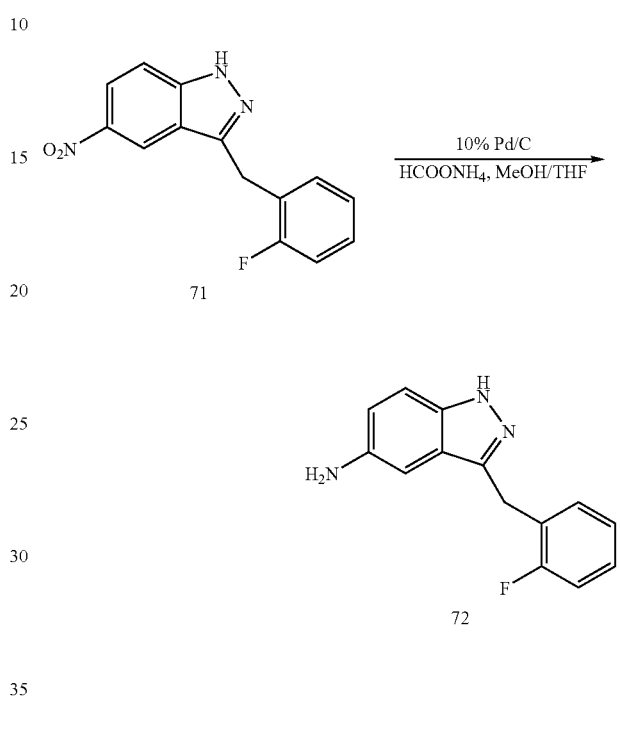

Ammonium formate (50 mg, 0.792 mmol) and 10% Pd/C (5 mg) were added to a solution of 3-(2-fluoro-benzyl)-5-nitro-1H-indazole (50 mg, 0.184 mmol) in MeOH/THF (3 ml, 1/1) then refluxed for 3 hours. The reaction was diluted with MeOH (20 ml) and filtered through a celite pad. The solvent was evaporated, residue dissolved in MeCl₂, dried over Na₂SO₄, filtered and solvent evaporated yielding title compound as white solid (40 mg, 88%) ESMS (MH, 242).

Step 5

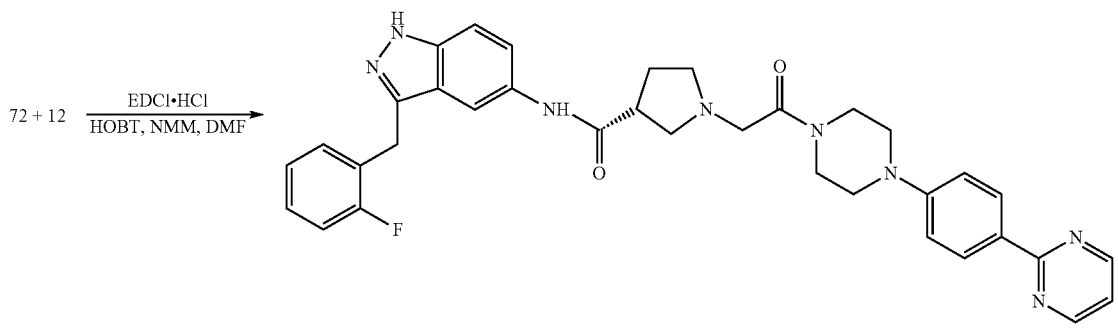

Added N-methylmorpholine (0.2 ml) to solution of 3-(2-Fluoro-benzyl)-1H-indazol-5-ylamine 72 (Step 4) (5 mg, 0.0207 mmol), 1-{2-Oxo-2-[4-(4-pyrimidin-2-yl-phenyl)-piperazin-1-yl]-ethyl}-pyrrolidine-3-carboxylic acid 12 (see Example 1 Step 9) (8 mg, 0.0202 mmol), 1-(3-dimethylaminopropyl)-3-ethylcarbodiimide hydrochloride (EDCl) (5 mg, 0.026 mmol), 1-hydroxybenztriazole monohydrate (3 mg, 0.022 mmol) in DMF (2 ml), then stirred overnight at room temperature. The solvent was evaporated and residue purified on silica gel eluting with 7% v/v MeOH/MeCl$_2$/NH$_4$OH yielding product as white solid (5 mg, 39%) ESMS (MH, 619).

Examples 103 to 112

Following a procedure similar to that of Example 102, and using the appropriate reagents, compounds of formula 74:

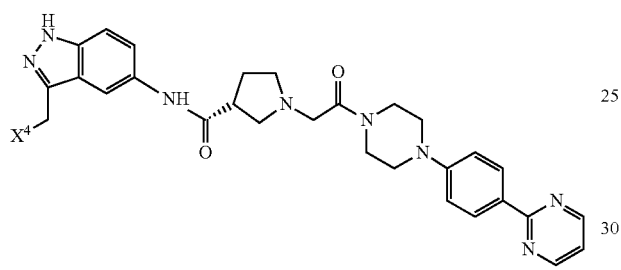

74 wherein X$^4$ is defined in Table 6 were prepared. The arrow indicates the point of attachment of the X$^4$ substituent to the rest of the molecule. No arrow is shown for Example 109 because attachment to any of the carbons of the X$^4$ phenyl group results in the same final compound of formula 74. In Table 6 "Ex" represents "Example".

TABLE 6

| Ex | X$^4$ | Mass Spec (ESMS, MH) | Retention time minutes |
|---|---|---|---|
| 103 | (3-fluorophenyl) | 619 | 3.10 |
| 104 | (4-fluorophenyl) | 619 | 2.79 |
| 105 | (1-methylimidazol-5-yl) | 606 | 2.31 |
| 106 | (3,5-difluorophenyl) | 637 | 3.43 |
| 107 | (4-methylphenyl) | 615 | 3.13 |
| 108 | (4-methoxyphenyl) | 631 | 3.17 |
| 109 | (phenyl) | 601 | 2.70 |
| 110 | (pyridin-3-yl) | 602 | 2.36 |
| 111 | (pyridin-4-yl) | 602 | 2.41 |
| 112 | (4-trifluoromethylphenyl) | 669 | 3.24 |

Examples 113 to 118

Following a procedure similar to that of Example 102 and using the appropriate reagents, and using 1-{2-[4-(3-Chlorophenyl)-piperazin-1-yl]-2-oxo-ethyl}-pyrrolidine-3-carboxylic acid 75:

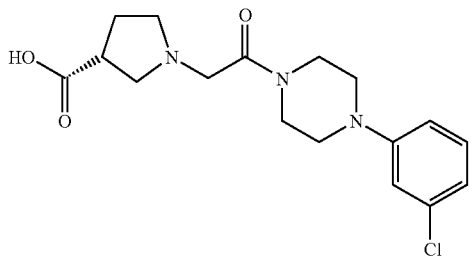

in place of 12, the compounds of formula 76:

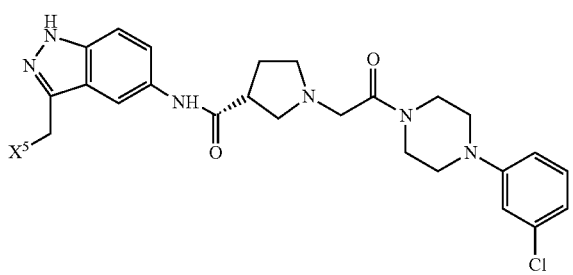

76 wherein $X^5$ is defined in Table 7 were prepared. The arrow indicates the point of attachment of the $X^5$ substitutent to the rest of the molecule. In Table 7 "Ex" represents "Example".

TABLE 7

| Ex | $X^5$ | Mass Spec ESMS (MH) | Retention time (minutes) |
|---|---|---|---|
| 113 | N-methylimidazolyl | 561 | 2.63 |
| 114 | pyridyl | 558 | 2.67 |
| 115 | 2-fluorophenyl | 575 | 3.40 |
| 116 | 3-trifluoromethylphenyl | 625 | 3.59 |

TABLE 7-continued

| Ex | $X^5$ | Mass Spec ESMS (MH) | Retention time (minutes) |
|---|---|---|---|
| 117 | 3-fluorophenyl | 575 | 3.30 |
| 118 | 4-fluorophenyl | 575 | 3.52 |

Example 119

Step 1

Preparation of 5-Methyl-2-[4-(3-(S)-methyl-piper-azin-1-yl)-phenyl]-pyrimidine

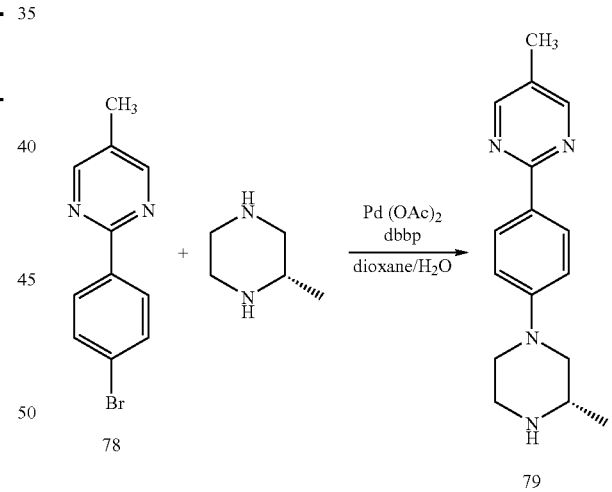

A mixture of 2-(4-bromophenyl)-5-methylpyrimidine 78 (250 mg, 1.008 mmol), palladium acetate (50 mg), cesium carbonate (400 mg, 1.23 mmol), (S)-2-methyl piperazine (200 mg, 2 mmol) and 2-Di-t-butylphosphino)-biphenyl (50 mg, 0.167 mmol) was stirred in dioxane:water (10 ml, v/v 5:1) at reflux temperature for 4 hours. The reaction was cooled, diluted with $MeCl_2$ (100 ml) and $H_2O$ (50 ml). The organic layer was separated, dried ($MgSO_4$), filtered and solvent evaporated. The residue was purified by chromatography eluting with 100% EtOAc then with 10% v/v MeOH/EtOAc/ $NH_4OH$ yielding product 79 as a white solid. (220 mg. 81%) ESMS (MH, 269).

Step 2

79 + 67 —EDCl, HOBT / DMF, (C₂H₅)₃N→

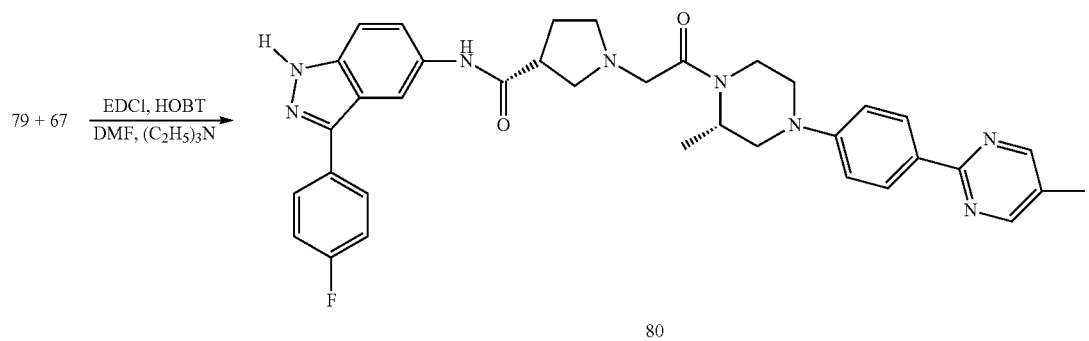

80

Following a procedure similar to that of Example 98, Step 8, but substituting 79 for 77, the title compound 80 was obtained as a white solid (ESMS, MH 633), Retention Time: 3.07 minutes.

Examples 120 to 123

Following a procedure similar to that of Example 119, and using the appropriate reagent in place of 79 compounds of Examples 120, 121, and 123 in Table 8 were prepared, and the compound of Example 122 could be prepared. In Table 8 "Ex" represents "Example".

TABLE 8

| Ex | Compound | Mass spec LCMS MH | Retention time (minutes) |
|---|---|---|---|
| 120 | | 633 | 3.45 |
| 121 | | 548 | 2.36 |

TABLE 8-continued

| Ex | Compound | Mass spec LCMS MH | Retention time (minutes) |
|---|---|---|---|
| 122 | | — | — |
| 123 | | 647 | 3.23 |

Example 124

Step 1

Preparation of
5-(4-Bromo-phenyl)-pyrimidin-2-ylamine

Step 2

Preparation of
5-(4-piperazin-1-yl-phenyl)-pyrimidin-2-ylamine

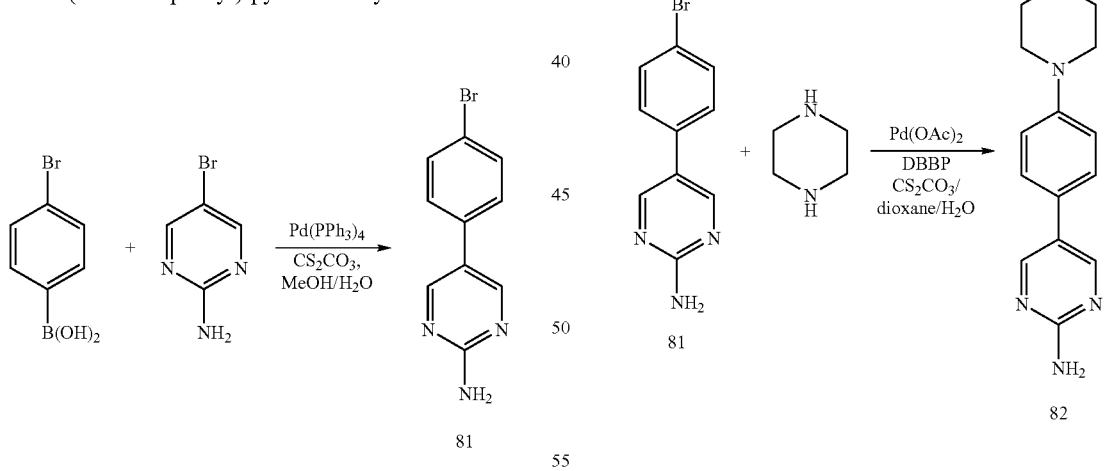

A mixture of 5-bromo-pyrimidin-2-ylamine (0.8 g, 4.59 mmol), 4-bromophenyl boronic acid (1 g, 4.97 mmol), tetrakis(triphenylphosphine)palladium(0) (300 mg, 0.259 mmol), cesium carbonate (1.15 g, 3.03 mmol) was stirred in MeOH/H$_2$O (20 ml, 1/1) at reflux temperature overnight. The reaction was cooled to room temperature and diluted with EtOAc (200 ml) and water (50 ml). The organic layer was separated, dried over MgSO$_4$, filtered and solvent evaporated yielding a residue which was purified on silica gel eluting with 85% v/v EtOAc/hexanes yielding product 81 as white solid. (0.7 g, 63%). ESMS (MH, 250).

A mixture of 5-(4-bromo-phenyl)-pyrimidin-2-ylamine (100 mg, 0.401 mmol), palladium acetate (20 mg, 0.089 mmol), cesium carbonate (200 mg, 0.62 mmol), piperazine (100 mg, 1.16 mmol) and 2-di-t-butylphosphino)-biphenyl (50 mg, 0.167 mmol) was stirred in dioxane:water (10 ml, v/v 5:1) at reflux temperature for 4 hours. The reaction was cooled, diluted with MeCl$_2$ (100 ml) and H$_2$O (50 ml). The organic layer was separated, dried (MgSO$_4$), filtered and solvent evaporated. The residue was purified by chromatography eluting with 100% EtOAc then with 10% v/v MeOH/EtOAc/NH$_4$OH yielding product 82 as a white solid. (70 mg. 68%) ESMS (MH, 256).

Step 3

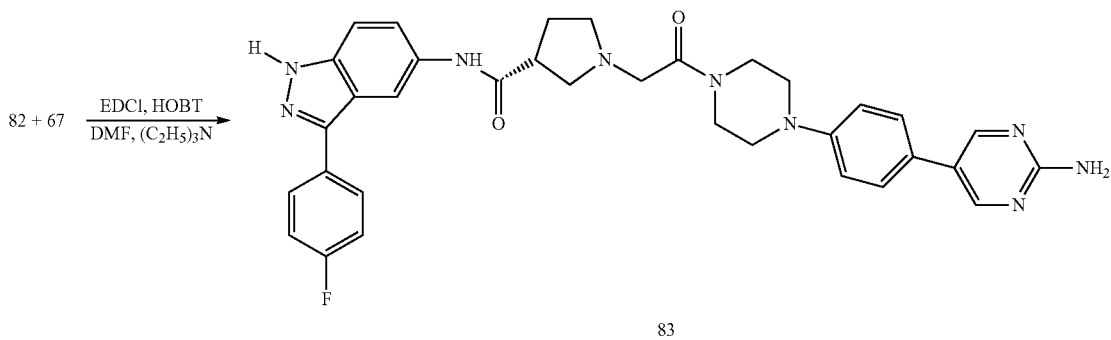

Following a procedure similar to that described in Example 98 Step 8, but substituting 82 for 77, the title product 83 was obtained as a white solid (ESMS, MH 620) $C_{34}H_{35}N_9FO_2$ LCMS (MH 620) Retention time=2.52 minutes.

Example 125

Step 1

Preparation of 2-(tert-butyl-dimethyl-silanyloxymethyl)-acrylic acid ethyl ester

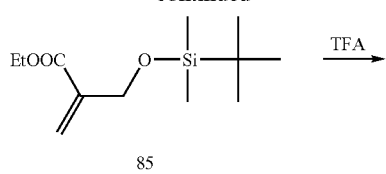

To a stirred solution of 2-hydroxymethyl-acrylic acid ethyl ester (260 mg, 2 mmol) and imidazole (163 mg, 2.4 mmol) in dry DMF (5 ml) was added tert-butyldimethylsilyl chloride (362 mg, 2.4 mmol). The reaction mixture was stirred overnight and diluted with ether, washed with water three times and dried over $MgSO_4$. Solvent was removed under reduced pressure to provide a crude product that was purified by column chromatography using a solution of ethyl acetate in hexanes (1:6) to obtain the title product (463 mg, 95%).

Step 2

Preparation of 1-benzyl-3-(tert-butyl-dimethyl-silanyloxymethyl)-pyrrolidine-3-carboxylic acid ethyl ester

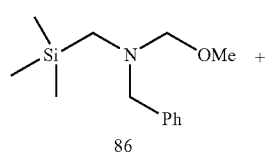

-continued

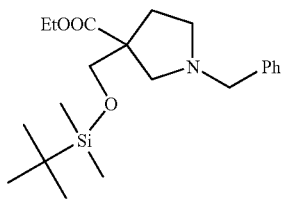

To a cold solution of 2-(tert-butyl-dimethyl-silanyloxymethyl)-acrylic acid ethyl ester (463 mg, 1.89 mmol) and N-(methoxymethyl)-N-(trimethylsilylmethyl)benzyl-amine (540 μl, 2.11 mmol) in dichloromethane (3 ml) was added at 0° C. trifluoroacetic acid (26 μl, 0.34 mmol). The resulting solution was warmed to room temperature in two hours. The crude product was purified by column chromatography on silica get eluting with a solution of ethyl acetate in hexanes (1:10, 1:5) to give the title compound (490 mg, 69%).

Step 3

Preparation of 3-(tert-butyl-dimethyl-silanyloxymethyl)-pyrrolidine-3-carboxylic acid ethyl ester

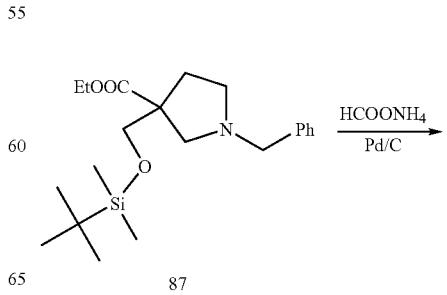

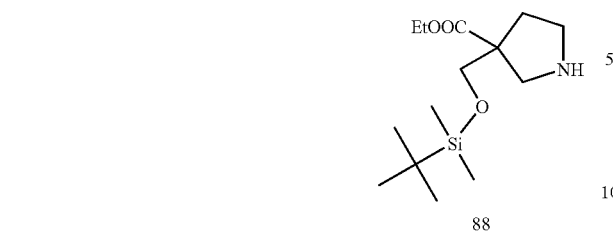

A mixture of 1-benzyl-3-(tert-butyl-dimethyl-silanyloxymethyl)-pyrrolidine-3-carboxylic acid ethyl ester (690 mg, 1.83 mmol), ammonium formate (461 mg, 7.31 mmol), 10% Pd/C (100 mg) in methanol (10 ml) and water (1 ml) was refluxed overnight. The mixture was filtered through celite, washed with ethyl acetate. The combined filtrate was concentrated and the residue was taken into ethyl acetate, washed with brine and dried over MgSO₄. Evaporation of solvent provided the title compound as oil (444 mg, 84%).

Step 4

Synthesis of 1-tert-butoxycarbonylmethyl-3-(tert-butyl-dimethyl-silanyloxymethyl)-pyrrolidine-3-carboxylic acid ethyl ester

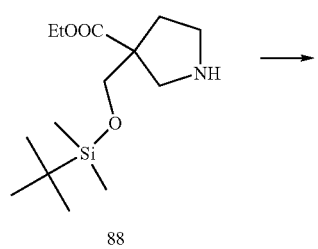

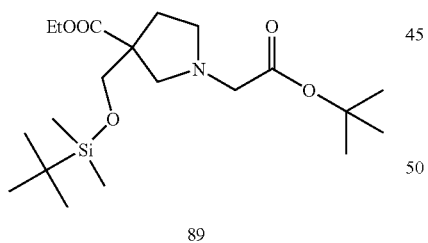

To a stirred mixture of 3-(tert-butyl-dimethyl-silanyloxymethyl)-pyrrolidine-3-carboxylic acid ethyl ester (444 mg, 1.54 mmol), triethylamine (214 µl, 1.54 mmol) and cesium carbonate (251 mg, 0.77 mmol) in acetonitrile (5 ml) was added tert-butyl bromoacetate (351 µl, 2.38 mmol) slowly. The mixture was stirred for 1 hour, filtered and concentrated. The residue was diluted with ethyl acetate, washed with water and dried over MgSO4. Solvent was removed under reduced pressure to give a crude product that was purified by column chromatography on silica gel. Elution with a solution of ethyl acetate in hexanes (1:4) provided 580 mg (94%) of the title compound.

Step 5

Preparation of 1-tert-butoxycarbonylmethyl-3-hydroxymethyl-pyrrolidine-3-carboxylic acid ethyl ester

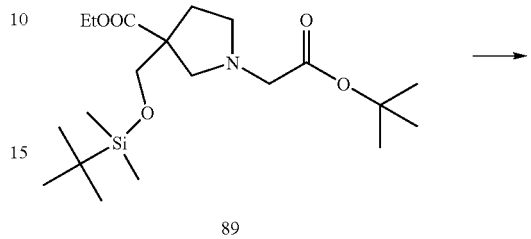

Tetrabutylammonium fluoride (1.8 ml, 1M in THF) was added to 1-tert-butoxycarbonylmethyl-3-(tert-butyl-dimethyl-silanyloxymethyl)-pyrrolidine-3-carboxylic acid ethyl ester (726 mg, 1.8 mmol). The reaction solution was stirred for half hour and purified by column chromatography using solution of ethyl acetate in hexanes (1:1), then ethyl acetate to provide the title product (350 mg, 68%).

Step 6

Preparation of methyl 2-(methoxymethyl)acrylate

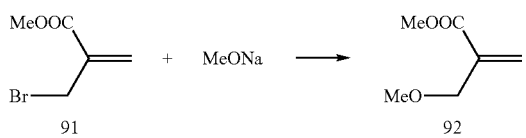

To a stirred mixture of methyl 2-(bromomethyl)acrylate (239 µl, 2 mmol) in petroleum ether (3 ml) was added potassium carbonate (276 mg, 2 mmol), followed by sodium methoxide (119 mg, 2.2 mmol) and methanol (450 µl). The resulting mixture was stirred overnight, filtered, concentrated to a residue that was purified by column chromatography eluting with 10% ether in hexanes to provide the title compound (150 mg, 58%). (Reference: J. Med. Chem.; 42; 15; 1999; 2760-2773.)

Step 7

Preparation of
1-benzyl-3-methoxymethyl-pyrrolidine-3-carboxylic acid methyl ester

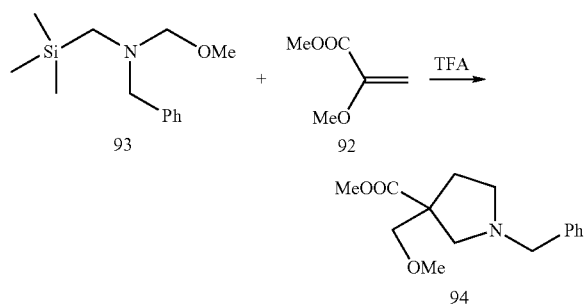

To a stirred solution of methyl 2-(methoxymethyl)acrylate (176 mg, 1.35 mmol) and N-(methoxymethyl)-N-(trimethylsilylmethyl)benzylamine (416 µl, 1.63 mmol) in dichloromethane (2 ml) was added at 0° C. trifluoroacetic acid (21 µl, 0.27 mmol). The resulting solution was warmed to room temperature and stirred overnight. The crude product was purified by column chromatography on silica, eluted with a solution of ethyl acetate in hexanes (1:3), then 5% methanol in ethyl acetate to give the title compound (293 mg, 82%).

Step 8

Preparation of
3-methoxymethyl-pyrrolidine-3-carboxylic acid methyl ester

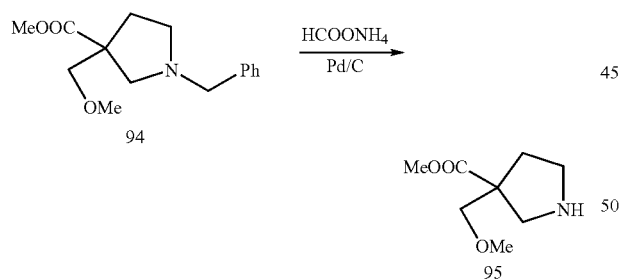

A mixture of 1-benzyl-3-methoxymethyl-pyrrolidine-3-carboxylic acid methyl ester (373 mg, 1.42 mmol), ammonium formate (358 mg, 5.68 mmol), 10% Pd/C (100 mg) and methanol (6 ml) was refluxed overnight. The mixture was filtered through Celite, washed with ethyl acetate. The combined filtrate was concentrated and the residue was taken into ethyl acetate, washed with small amount of water. Aqueous layer was isolated, extracted with dichloromethane three times. The dichloromethane extracts were combined with previous ethyl acetate extracts and dried over MgSO$_4$. Evaporation of solvents provided the title compound as oil (140 mg, 57%).

Step 9

Preparation of 1-tert-butoxycarbonylmethyl-3-methoxymethyl-pyrrolidine-3-carboxylic acid methyl ester

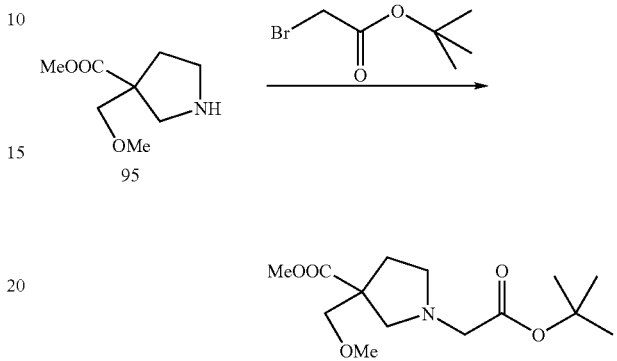

To a stirred mixture of 3-methoxymethyl-pyrrolidine-3-carboxylic acid methyl ester (140 mg, 0.81 mmol), triethylamine (112 µl, 0.82 mmol) and cesium carbonate (263 mg, 0.81 mmol) in acetonitrile (2 ml) was added tert-butyl bromoacetate (119 µl, 0.81 mmol) slowly. The mixture was stirred for 15 minutes, filtered and concentrated. The residue was purified by column chromatography on silica gel. Elution with a solution of ethyl acetate and hexanes (1:2) provided 118 mg (51%) of the title compound.

Step 10

Preparation of 1-carboxymethyl-3-methoxymethyl-pyrrolidine-3-carboxylic acid methyl ester

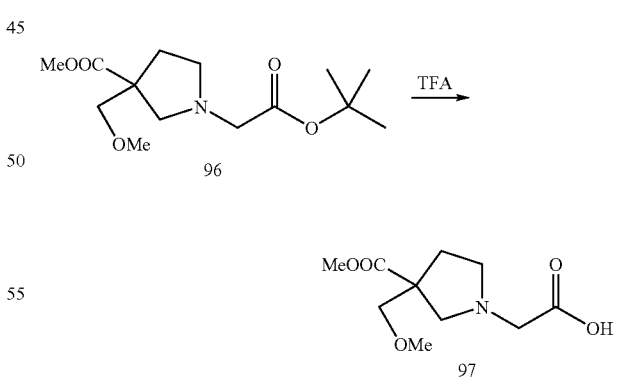

The 1-tert-butoxycarbonylmethyl-3-methoxymethyl-pyrrolidine-3-carboxylic acid methyl ester (118 mg) was treated with trifluoroacetic acid (2 ml), stirred for 20 minutes and evaporated to a residue that was exchanged with hydrochloric acid (1 ml, 4N) and lyophilized overnight to a gummy title product.

Step 11

Preparation of 3-methoxymethyl-1-{2-oxo-2-[4-(4-pyrimidin-2-yl-phenyl)-piperazin-1-yl]-ethyl}-pyrrolidine-3-carboxylic acid methyl ester

97 + 10 ⟶

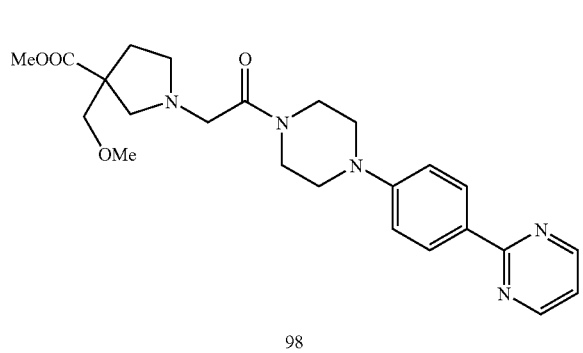

98

To a solution of 1-carboxymethyl-3-methoxymethyl-pyrrolidine-3-carboxylic acid methyl ester (compound 97) (0.21 mmol), 2-(4-piperazin-1-yl-phenyl)-pyrimidine (compound 10, see Example 1 Step 7) (0.21 mmol), O-(7-azabenzotriazol-1-yl-)-N,N,N', N'-tetramethyluronium hexafluorophosphate (HATU) (78 mg, 0.21 mmol) in dry DMF (2 ml) was added N,N-diisopropylethylamine (108 μl, 0.62 mmol). The reaction mixture was stirred for 4 hours, and evaporated to a residue that was partitioned in ethyl acetate and saturated sodium carbonate. Organic layer was isolated, washed with water, brine and dried over magnesium sulfate. Evaporation of solvent provided a crude product which was chromatographed with 5% methanol in dichloromethane to furnish the title compound (97 mg).

Step 12

Preparation of 3-methoxymethyl-1-{2-oxo-2-[4-(4-pyrimidin-2-yl-phenyl)-piperazin-1-yl]-ethyl}-pyrrolidine-3-carboxylic acid

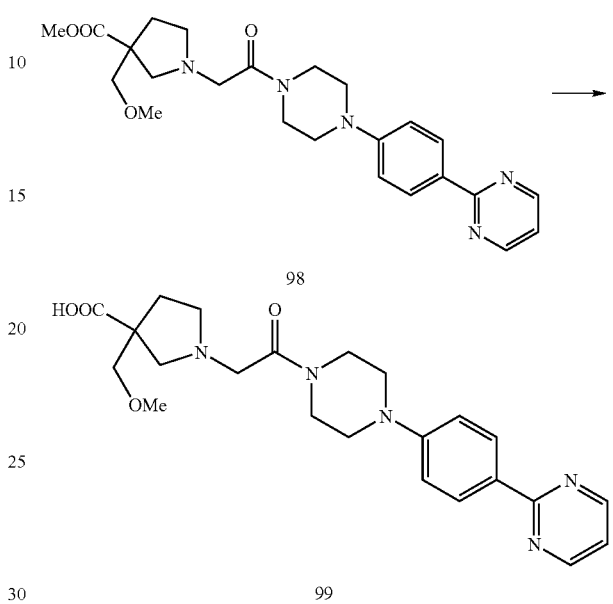

The 1-carboxymethyl-3-methoxymethyl-pyrrolidine-3-carboxylic acid methyl ester (97 mg, 0.21 mmol) was saponified with lithium hydroxide monohydrate (27 mg, 0.64 mmol) in tetrahydrofuran and water (2:1, 3 ml) for 2 hours. The reaction mixture was acidified with 4 N HCl and lyophilized overnight to provide the title compound which was directly used in the next step synthesis.

Step 13

Preparation of 3-methoxymethyl-1-{2-oxo-2-[4-(4-pyrimidin-2-yl-phenyl)-piperazin-1-yl]-ethyl}-pyrrolidine-3-carboxylic acid [3-(4-fluoro-phenyl)-1H-indazol-5-yl]-amide

99 + 65 ⟶

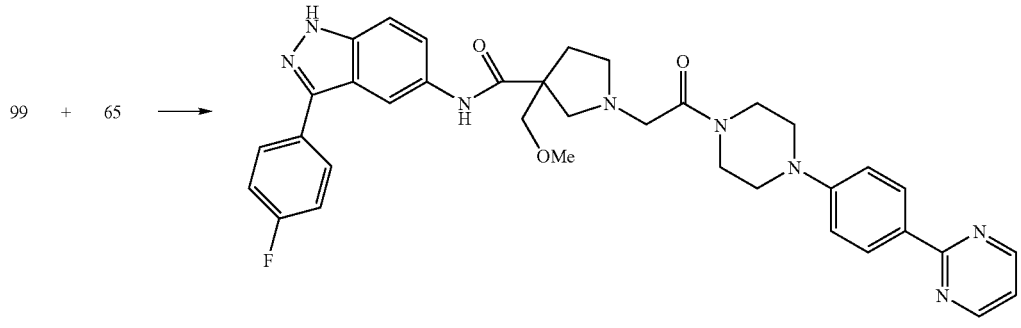

The 3-methoxymethyl-1-{2-oxo-2-[4-(4-pyrimidin-2-yl-phenyl)-piperazin-1-yl]-ethyl}-pyrrolidine-3-carboxylic acid (0.049 mmol), 1-hydroxybenztriazole (7 mg, 0.052 mmol) and 1-(3-dimethylaminopropyl)-3-ethylcarbodiimide hydrochloride (EDCl) (10 mg, 0.052 mmol) were dissolved in dry DMF (1 ml). 3-(4-Fluoro-phenyl)-1H-indazol-5-ylamine (12 mg, 0.053 mmol) was added and the reaction mixture was stirred overnight and directly subjected to purification by reversed phase HPLC to obtain 9.15 mg of the title product.

Mass Spec.: 649, Retention Time: 3.93 minutes.

Example 126

Step 1

Preparation of 2-fluoromethyl-acrylic acid ethyl ester

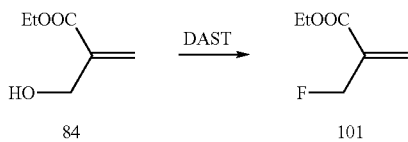

To a solution of (diethylamino)sulfur trifluoride (DAST) (363 µl, 2.76 mmol) in dichloromethane (1 ml) was slowly added at −78 C a solution of 2-hydroxylmethyl acrylic acid ethyl ester (300 mg, 2.31 mmol) in dichloromethane (3 ml). The reaction mixture was allowed to warm to room temperature, re-chilled to −78 C and additional DAST (100 µl, 0.76 mmol) was added to ensure complete reaction. The reaction mixture was let to warm to room temperature and quenched with saturated sodium carbonate. Organic layer was isolated, washed with water, brine and dried (MgSO$_4$). The dichloromethane solution was directly passed through a short silica gel pad, eluted with dichloromethane and the product fractions were collected. The combined fractions (ca. 12 ml) will be directly used in the next step synthesis without further concentration.

Step 2

Preparation of 1-benzyl-3-fluoromethyl-pyrrolidine-3-carboxylic acid ethyl ester

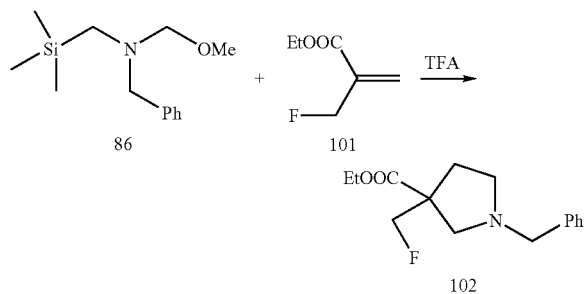

N-(methoxymethyl)-N-(trimethylsilylmethyl)benzylamine (548 µl, 2.14 mmol) was dissolved in the dichloromethane solution of the 2-fluoromethyl-acrylic acid ethyl ester from the previous reaction and chilled to 0 C. A solution of trifluoroacetic acid (67 µl, 0.87 mmol) in dichloromethane (0.5 ml) was added slowly. The reaction mixture was allowed to warm to room temperature in two hours and directly chromatographed on silica gel. Elution with solutions of ethyl acetate in hexanes (1:5, 1:4, 1:3) obtained the title product (143 mg) as oil.

Example 127

Preparation of 3-Allyl-pyrrolidine-1,3-dicarboxylic acid 1-tert-butyl ester 3-methyl ester

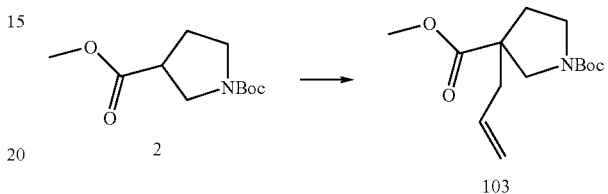

Pyrrolidine-1,3-dicarboxylic acid 1-tert-butyl ester 3-methyl ester 2 (see Example 1, Step 1) (4.58 g, 20 mmol) was dissolved in THF (100 mL) and cooled down to −78° C. in a dry ice-acetone bath. LDA (12 mL, 2.0 M, 24 mmol) was then added dropwise. The mixture was stirred at −78° C. for 1 hr. Allyl bromide (5.3 mL, 61 mmol) was added in neat. The reaction was allowed to warm to rt naturally and stirred for 24 hrs. It was then quenched with sat. NH4Cl solution, extracted with ethyl acetate 2×150 mL. The organic layer was washed with brine, dried (MgSO4) and concentrated. The crude was purified on silica gel column using 4:1 hexanes/ethyl acetate to get the title compound (3.6 g) as a yellow oil. MS (292, MNa).

Example 128

Step 1

Preparation of (S,S)-5-[4-(4,4,5,5-Tetramethyl-[1,3,2]dioxaborolan-2-yl)-phenyl]-2,5-diaza-bicyclo[2.2.1]heptane-2-carboxylic acid tert-butyl ester

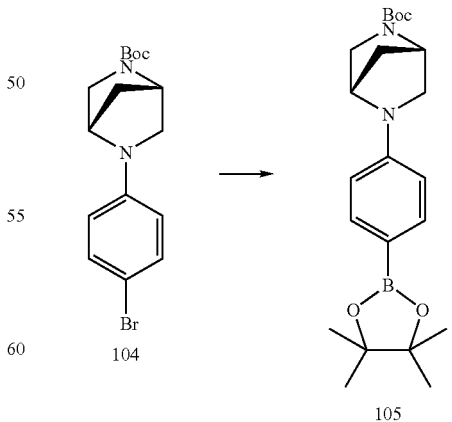

A mixture of (S,S)-5-(4-Bromo-phenyl)-2,5-diaza-bicyclo[2.2.1]heptane-2-carboxylic acid tert-butyl ester (4.0 g, 11.3 mmol), Bis(pinacolato)diboron (4.0 g, 15.7 mmol), KOAc (3.2 g) and Cl₂Pd(dppf)CH₂Cl₂ (800 mg) in 40 mL dioxane was evacuated and recharged with N₂ several times. The reaction mixture was then heated to 85° C. overnight. After cooling down to rt, 150 mL ethyl acetate and 30 mL water was added. The mixture was filtered through a pad of Celite and washed with additional ethyl acetate. The separated organic layer was dried (MgSO4) and concentrated. The crude was purified on silica gel column eluting with 30% to 50% ethyl acetate/hexanes to yield the title compound as a white solid (3.3 g). MS (401, MH)

Step 2

Preparation of (S,S)-5-[4-(5-Fluoro-pyrimidin-2-yl)-phenyl]-2,5-diaza-bicyclo[2.2.1]-heptane-2-carboxylic acid tert-butyl ester

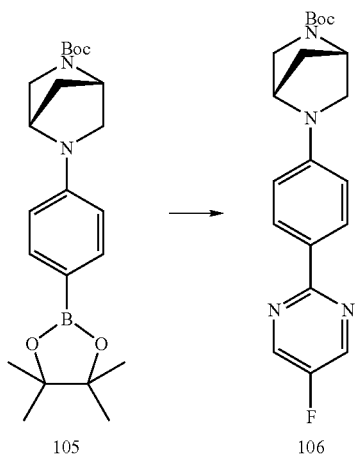

A mixed DMF/H2O (5 mL/5 mL) solution of (S,S)-5-[4-(4,4,5,5-Tetramethyl-[1,3,2]dioxaborolan-2-yl)-phenyl]-2,5-diaza-bicyclo[2.2.1]heptane-2-carboxylic acid tert-butyl ester (800 mg, 2 mmol), 2-chloro-5-fluoro-pyrimidine (340 mg, 2.6 mmol), K₂CO₃ (552 mg, 4 mmol) and Cl₂Pd(dppf)CH₂Cl₂ (160 mg) was evacuated and recharged with N₂ several times. The reaction was heated at 70° C. over 18 hrs. After cooling down to rt, 40 mL ethyl acetate and 10 mL water was added. The mixture was filtered through a pad of Celite and washed with additional ethyl acetate. The separated organic layer was dried (MgSO₄) and concentrated. The crude was purified on silica gel column eluting with 50% ethyl acetate/hexanes to yield the title compound (420 mg) as a light yellow solid.

In a similar manner, 106a:

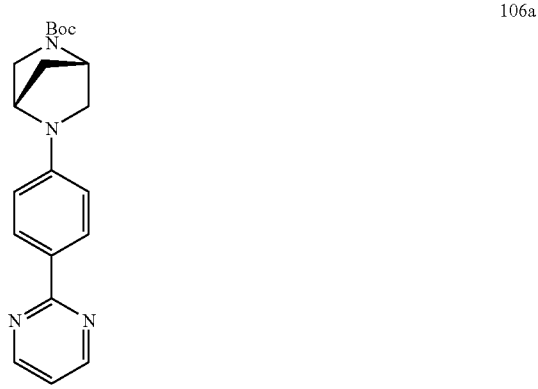 [SMILES: CC(C)(C)OC(=O)N1C[C@@H]2C[C@H]1CN2c1ccc(-c2ncccn2)cc1]

was prepared by substituting 2-chloropyrimidine for 2-chloro-5-fluoro-pyrimidine.

Example 129

Preparation of 4-[4-(5-Fluoro-pyrimidin-2-yl)-phenyl]-piperazine-1-carboxylic acid tert-butyl ester

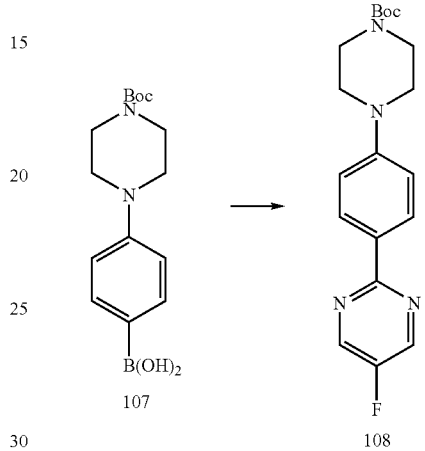

4-[4-(5-Fluoro-pyrimidin-2-yl)-phenyl]-piperazine-1-carboxylic acid tert-butyl ester was prepared similarly as the above substituting (S,S)-5-[4-(4,4,5,5-tetra-methyl[1,3,2]dioxaborolan-2-yl)-phenyl]-2,5-diaza-bicyclo[2.2.1]heptane2-carboxylic acid tert-butyl ester with 4-[4-(tert-Butoxycarbony)piperazin-1-yl]phenylboronic acid (C. Chen et. al. J. Org. Chem. 2003, 68, 2633).

Example 130

Preparation of (S,S)-5-(5-Vinyl-pyrimidin-2-yl)-2,5-diaza-bicyclo[2.2.1]heptane-2-carboxylic acid tert-butyl ester

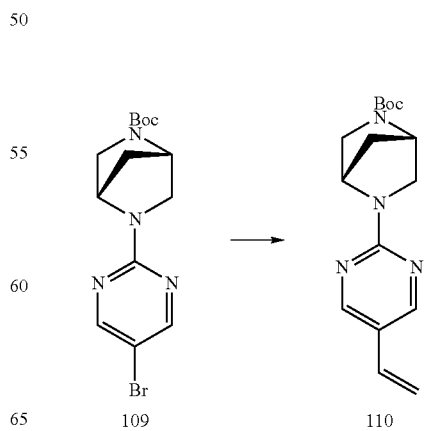

(S,S)-5-(5-Bromo-pyrimidin-2-yl)-2,5-diaza-bicyclo[2.2.1]heptane-2-carboxylic acid tert-butyl ester (177 mg, 0.5 mmol), tributyl vinyl tin (634 mg, 2 mmol) and Cl₂Pd(dppf)CH₂Cl₂ (60 mg) was mixed in DMF (3 mL). The mixture was heated at 90° C. over 3 days. The cooled down reaction was participate between ethyl acetate (50 mL) and H₂O (10 mL). The organic layer was washed with H₂O (10 mL), brine (10 mL), dried (MgSO₄) and filtered. The conc. filtrate was purified on silica gel column eluting with 33% to 50% ethyl acetate/hexanes to yield the title compound as a white solid (54 mg). MS (303, MH).

Example 131

Preparation of 1H-Pyrazolo[3,4-b]pyridin-5-ylamine

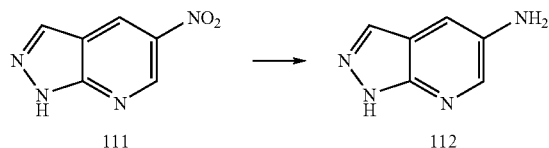 [SMILES: O=[N+]([O-])c1cnc2[nH]ncc2c1 ; Nc1cnc2[nH]ncc2c1]

5-Nitro-1H-pyrazolo[3,4-b]pyridine (prepared according to the procedure in Can. J. Chem. 1988, 66(3), 420) (133 mg, 0.81 mmol) was mixed with SnCl₂ (1.09) in EtOH/CH₃Ph (4 mL/2 mL) and heated at 70° C. for 3 hrs. The reaction was cooled to rt and concentrated to dryness. The residue was participated between 1.0 N NaOH (10 mL) and ethyl acetate (50 mL). The organic layer was washed with brine once, dried (MgSO₄) and filtered. The filtrate was concentrated and the resulting crude was purified by prep. TLC using 10:2 CH₂Cl₂/Methanol (2 N NH₃). The title compound (15.0 mg) was isolated as a yellow solid.

Example 132

Preparation of 4-Hydroxy-4-thiazol-2-yl-piperidine-1-carboxylic acid tert-butyl ester

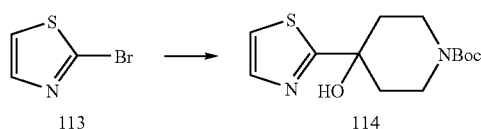 [SMILES: Brc1nccs1 ; CC(C)(C)OC(=O)N1CCC(O)(c2nccs2)CC1]

2-Bromo-thiazole (0.27 mL, 2.99 mmol) was dissolved in Et₂O (8 mL) and cooled down to −78° C. BuLi (1.3 mL, 2.5 M) was added dropwise. The resulting yellow solution was stirred at −78° C. for 45 min. 4-Oxo-piperidine-1-carboxylic acid tert-butyl ester (720 mg, 3.61 mmol) in Et₂O (5 mL) was then added dropwise. The reaction temperature rose to rt naturally overnight. H₂O (10 mL) was added to quench the reaction and extracted with ethyl acetate. The combined organic layer was dried (MgSO₄), filtered and concentrated. The residue was purified on silica gel column eluting with 33% to 50% ethyl acetate/hexanes to give 4-Hydroxy-4-thiazol-2-yl-piperidine-1-carboxylic acid tert-butyl ester (800 mg) as a colorless oil.

Example 133

Step 1

Preparation of 4-Thiazol-2-yl-piperazine-1-carboxylic acid tert-butyl ester

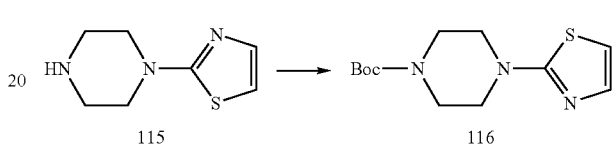

To a solution of 1-thiazol-2-yl-piperazine (2 g, 12 mmol), triethylamine (2.4 g, 24 mmol) and DMAP (150 mg, 1.2 mmol) in acetonitrile (15 ml) was added di-tert-butyl dicarbonate. The resulted reaction mixture was stirred at RT for 3 hours. Then water (20 mL) was added and the formed slurry was stirred for 30 min. The formed product was collected by filtration and washed with water. After dry in air, 2.8 g product was obtained (90% yield)

Step 2

Preparation of 4-(5-Bromo-thiazol-2-yl)-piperazine-1-carboxylic acid tert-butyl ester

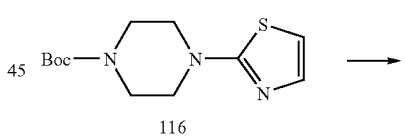

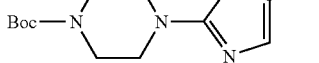

To a mixture containing 4-thiazol-2-yl-piperazine-1-carboxylic acid tert-butyl ester (0.5 g, 1.9 mmol) and cesium carbonate (0.62 mmol) in chloroform (5 mL) at 0° C., bromine (110 mL) was added through a syringe. After the addition, the reaction mixture was stirred at room temperature for 1 hour. Water was added and the organic layer was collected and dried over sodium sulfate. After removal of solvent, 0.6 g of product was obtained (95% yield).

Example 134

Preparation of 5-Thiazol-2-yl-2,5-diaza-bicyclo[2.2.1]heptane-2-carboxylic acid tert-butyl ester

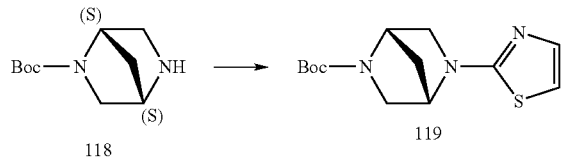

A mixture of 2-bromothiazole (200 mg, 1.22 mmol), palladium acetate (15 mg, 0.06 mmol), sodium tert-butoxide (217 mg, 2.26 mmol), (S,S) 2,5-diaza-bicyclo[2.2.1]heptane-2-carboxylic acid tert-butyl ester (280 mg, 1.4 mmol) and 2-Di-t-butylphosphino)-biphenyl (37 mg, 0.118 mmol) was stirred in dioxane (10 ml) at 80° C. for overnight. The reaction was cooled, diluted with ethyl acetate (40 ml) and $H_2O$ (50 ml). The organic layer was separated, dried ($Na_2SO_4$), filtered and solvent evaporated. The residue was purified by chromatography eluting with 5% MeOH/DCM yielding product as a white solid. (180 mg, 52% yield)

Example 135

Step 1

Preparation of 4-(5-Pyrimidin-2-yl-thiazol-2-yl)-piperazine-1-carboxylic acid tert-butyl ester

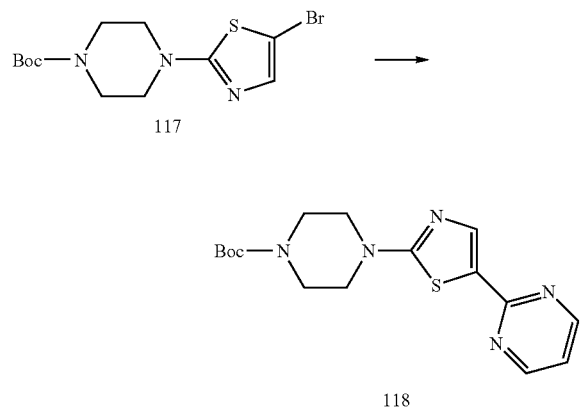

A round bottom flask containing 4-(5-bromo-thiazol-2-yl)-piperazine-1-carboxylic acid tert-butyl ester (100 mg, 0.29 mmol), 2-tributylstannanyl-pyrimidine (130 mg, 0.36 mmol), cesium fluoride (85 mg, 0.56 mmol) and palladium di-tert-butylphosphine was degassed three times with Ar. Dioxane was added and the formed reaction mixture was stirred at 90° C. overnight under Ar. Then the reaction mixture was filter through celite and the solvent was removed under vacuum and crude product was used directly in the next step.

Step 2

Preparation of 2-(2-piperazin-1-yl-thiazol-5-yl)-pyrimidine

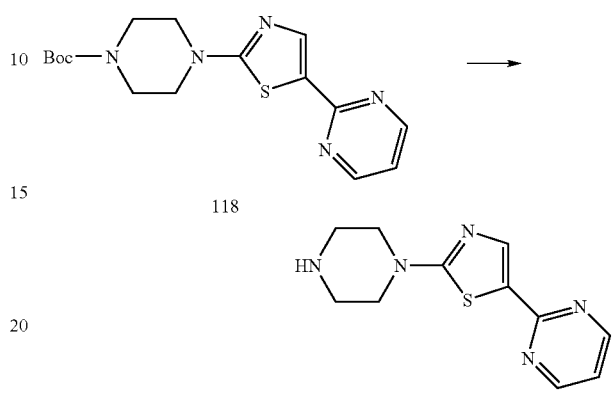

To the crude product obtained in the previous step, was added 90% TFA (1 mL) and the reaction mixture was stirred at ambient temperature for 1 hour. The excess TFA was removed under vacuum and the residue was purified using prep-HPLC to give desired product (45 mg, 44% yield for two steps) as TFA salt.

Step 3

Preparation of 5-[(1-{2-Oxo-2-[4-(5-pyrimidin-2-yl-thiazol-2-yl)-piperazin-1-yl]-ethyl}-pyrrolidine-3-carbonyl)-amino]-1H-indazole-3-carboxylic acid methylamide

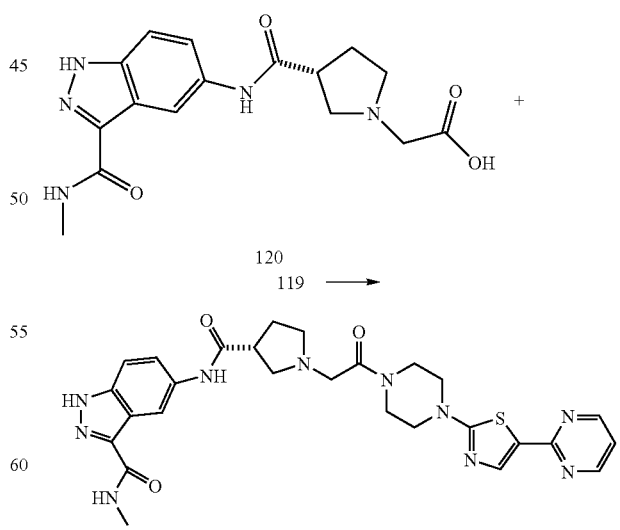

To a solution of [3-(3-methylcarbamoyl-1H-indazol-5-yl-carbamoyl)-pyrrolidin-1-yl]-acetic acid (15 mg, 0.043 mmol, prepared by a procedure similar to that of Example 98 using the indazole of Example 85 instead of indazole 65) and HOBt (7 mg, 0.052 mmol) in DMF (0.5 mL) at 0° C., EDCl (10 mg, 0.052 mmol) was added and the resulted reaction mixture was stirred at this temperature for 0.5 hour. To this solution was added 2-(2-piperazin-1-yl-thiazol-5-yl)-pyrimidine (18 mg, 0.052 mmol) made from previous step, followed by DIEA (7 µL). The reaction was stirred at 0° C. for 1 hour and was gradually warm up to room temperature and was continuously stirred for overnight. Ethyl acetate (5 mL) was then added, followed by water (10 mL). The organic layer was collected, dry over sodium sulfate, evaporate of solvent and residue was purified using prep-HPLC. To the solution obtained from HPCL, HCl (1N, 2 mL) was added and the solution was brought to dryness under vacuum. The formed residue was then dissolved in acetonitrile/water (3:1) and was lyophilized to give desired product (10 mg, 38% yield) as hydrochloride salt.

Example 136

Step 1

Preparation of 4-(4-Bromo-phenyl)-piperidine-1-carboxylic acid tert-butyl ester

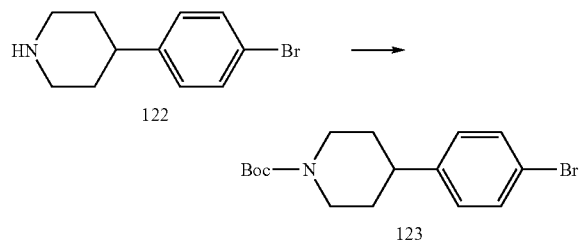

To a solution of 4-(4-bromo-phenyl)-piperidine (2.8 g, 12 mmol), triethylamine (2.4 g, 24 mmol) and DMAP (150 mg, 1.2 mmol) in acetonitrile (15 ml) was added di-tert-butyl dicarbonate. The resulted reaction mixture was stirred at RT for 3 hours. Then water (20 mL) was added and the formed slurry was stirred for 30 min. The formed product was collected by filtration and washed with water. After dry in air, 3.8 g product was obtained (95% yield).

Step 2

Preparation of 4-(4-Pyrimidin-2-yl-phenyl)-piperidine-1-carboxylic acid tert-butyl ester

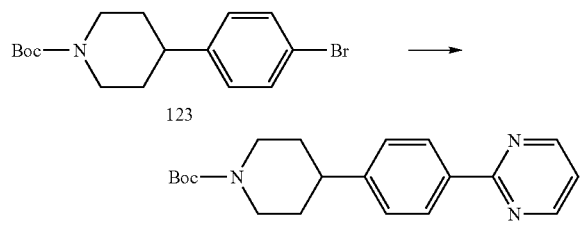

A mixture containing 4-(4-bromo-phenyl)-piperidine-1-carboxylic acid tert-butyl ester (100 mg, 0.29 mmol), 2-tributylstannanyl-pyrimidine (130 mg, 0.36 mmol), cesium fluoride (85 mg, 0.56 mmol) and palladium di-tert-butylphosphine was degassed three times with Ar. Dioxane was added and the formed reaction mixture was stirred at 90° C. overnight under Ar. Then the reaction mixture was filter through celite and the solvent was removed under vacuum and crude product was used directly in the next step.

Step 3

Preparation of 2-(4-Piperidin-4-yl-phenyl)-pyrimidine

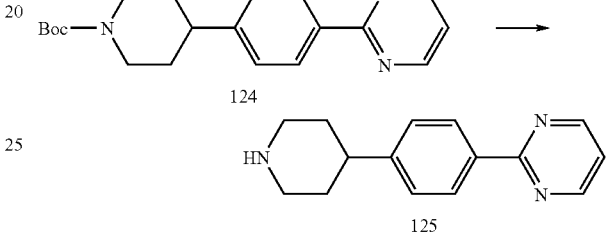

To the crude product obtained in the previous step, was added 90% TFA (1 mL) and the reaction mixture was stirred at ambient temperature for 1 hour. The excess TFA was removed under vacuum and the residue was purified using prep-HPLC to give desired product (38 mg, 37% yield for two steps) as TFA salt.

Example 137

Step 1

Preparation of 4-Thiazol-2-yl-3,6-dihydro-2H-pyridine-1-carboxylic acid tert-butyl ester

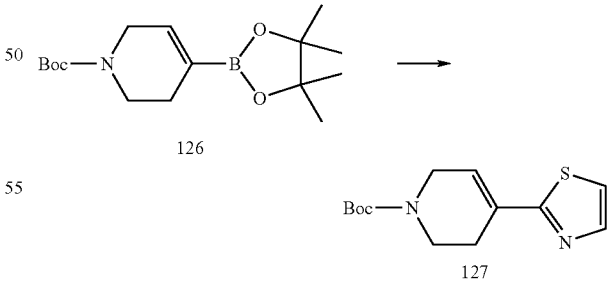

To a mixture of (N-tert-butoxycarbonyl)-1,2,3,6-tetrahydropyridine-2-boronic acid pinacol ester (100 mg, 0.32 mmol), 2-bromothiazole (64 mg, 0.39 mmol), PdCl$_2$(dppf) (24 mg, 0.03 mmol) and potassium phosphate (213 mg, 1 mmol) was degassed three times with Ar, was added dioxane. The formed reaction mixture was then heated at 80° C. overnight under Ar. After the reaction was complete, the mixture was filter through celite and was chromatographed on a silica column (10% ethyl acetate/DCM) to obtain desired product (30 mg, 35% yield).

Step 2

Preparation of 4-Thiazol-2-yl-1,2,3,6-tetrahydro-pyridine

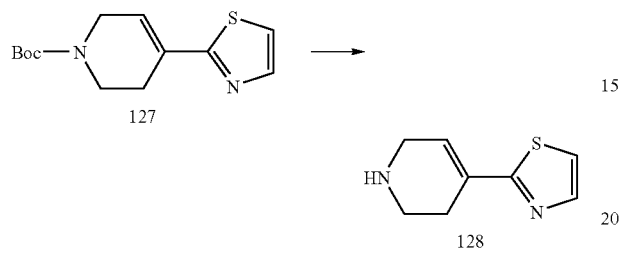

To the product obtained in the previous step, was added 90% TFA (1 mL) and the reaction mixture was stirred at ambient temperature for 1 hour. The excess TFA was removed under vacuum and the residue was purified using prep-HPLC to give desired product (15 mg, 50% yield) as TFA salt.

Example 138

Step 1

Preparation of 4-(methoxy-methyl-carbamoyl)-piperidine-1-carboxylic acid tert-butyl ester

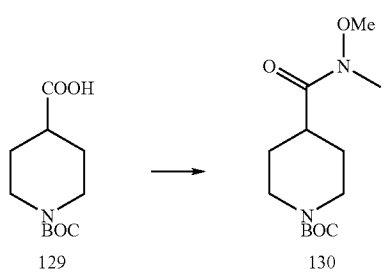

N,O-dimethylhydroxylamine hydrochloride (851 mg, 8.72 mmols) was suspended in dichloromethane (6 ml) and cooled to 0 C. N,N'-diisopropylethylamine (1.66 ml, 9.53 mmols) was added and the mixture was stirred at 0 C until a clear solution was obtained. The resulting solution was kept at 0 C for further use. Boc-isonipecotic acid (2 g, 8.72 mmol), 1-hydroxybenzotriazole (1.2 g, 8.88 mmols) and 1-(3-dimethylaminopropyl)-3-ethylcarbodiimide hydrochloride (EDCl) (1.83 g, 9.58 mmols) were dissolved in DMF (15 ml) and cooled to 0 C. The solution of N,O-dimethylhydroxylamine in dichloromethane was added with stirring, and the resulting reaction mixture was allowed to stir overnight at room temperature. DMF was removed under reduced pressure and residue was partitioned between ethyl acetate and 10% citric acid. Organic layer was isolated, washed with water, saturated NaHCO$_3$, water and brine and dried over MgSO$_4$. Solvent was removed under reduced pressure and the residue was purified on silica gel eluting with ethyl acetate in hexanes (2:1) to provide the title compound (1.88 g, 79%). LCMS m/e (295, M+Na).

Step 2

Preparation of 4-formyl-piperidine-1-carboxylic acid tert-butyl ester

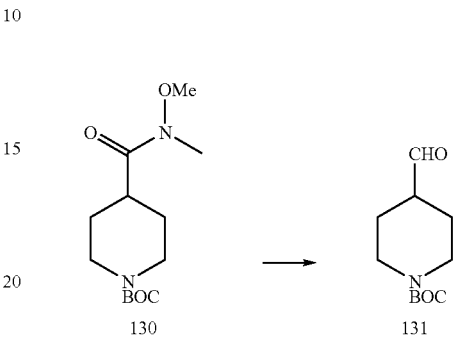

To a mixture of lithium aluminum hydride (1M THF solution, 4.4 ml) in ether (4 ml) was added dropwise at −60 C 4-(methoxy-methyl-carbamoyl)-piperidine-1-carboxylic acid tert-butyl ester (1 g, 3.67 mmols) in ether (6 ml). The reaction mixture was allowed to warm to 0-5 C and then re-cooled to −60 C. Celite was added and reaction was quenched with a solution of KHSO$_4$ (19) in water (3 ml), filtered through Celite. The filtrate was washed with cold 1N HCl, saturated NaHCO$_3$, brine and dried (MgSO$_4$) and concentrated. The residue was purified by column chromatography on silica gel eluting with ethyl acetate in hexanes (1:1) to provide title compound (656 mg, 84%). (*Org. Prep. Proced. Int.*, 2000, 32, 96.)

Example 139

Step 1

Preparation of 4-methyl-benzenesulfonyl azide

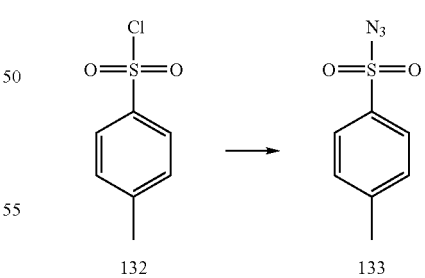

To a solution of tosyl chloride (4 g, 21 mmols) in acetone (60 ml) was added at 0-5 C a solution of sodium azide (1.37 g, 21 mmols) and the resulting solution was stirred at that temperature for 2 hours. Acetone was removed and the aqueous mixture was extracted with ether three times. The combined extracts were dried over MgSO$_4$. Evaporation of solvents provided tosyl azide (4 g, 97%). (*Eur. J. Org. Chem.* 2003, 821-832.)

Step 2

Preparation of (1-diazo-2-oxo-propyl)-phosphonic acid dimethyl ester

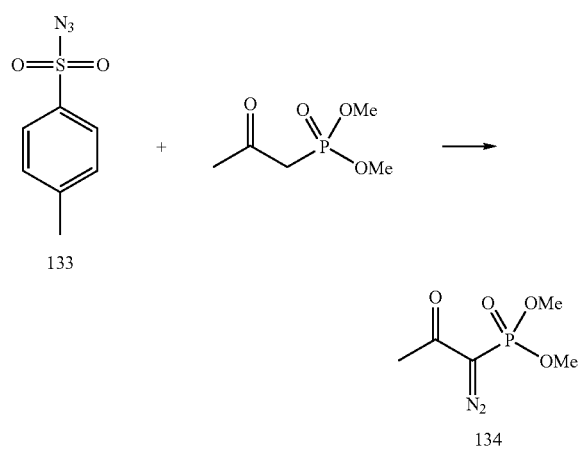

To a suspension of NaH (60% in mineral oil, 0.83 g, 20.8 mmols) in THF (50 ml) was added dropwise at 0 C (2-oxo-propyl)-phosphonic acid dimethyl ester (3.1 g, 18.7 mmols) in THF (50 ml), and the solution was stirred at 0 C for one hour. Tosyl azide (4 g, 20 mmols) was added in one portion, stirred at 0 C for 10 minutes, filtered through Celite and concentrated. The residue was purified by column chromatography on silica gel using ethyl acetate to yield the title compound (2.9 g, 81%) as oil. (*Eur. J. Org. Chem.* 2003, 821-832.)

Step 3

Preparation of 4-ethynyl-piperidine-1-carboxylic acid tert-butyl ester

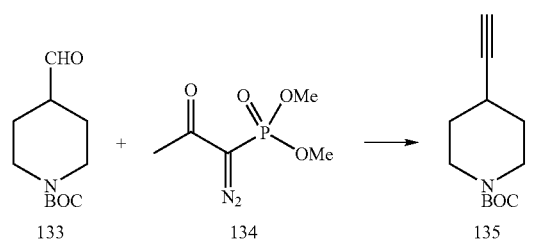

At 0 C, to a stirred mixture of 4-formyl-piperidine-1-carboxylic acid tert-butyl ester (358 mg, 1.68 mmols) and potassium carbonate (464 mg, 3.36 mmols) in methanol (16 ml) was added dropwise a solution of (1-diazo-2-oxo-propyl)-phosphonic acid dimethyl ester (323 mg, 1.68 mmols) in methanol (2 ml). The resulting mixture was stirred at room temperature overnight, filtered and concentrated. The residue was chromatographed on silica gel using a solution of ethyl acetate in hexanes (1:5) to provide the title compound (308 mg, 88%) as colorless crystals. LCMS m/e (154, M-t-Bu+2H). (*J. Am. Chem. Soc.* 2003, 125, 3714.)

Step 4

Preparation of 4-phenylethperidine-1-carboxylic acid tert-butyl ester

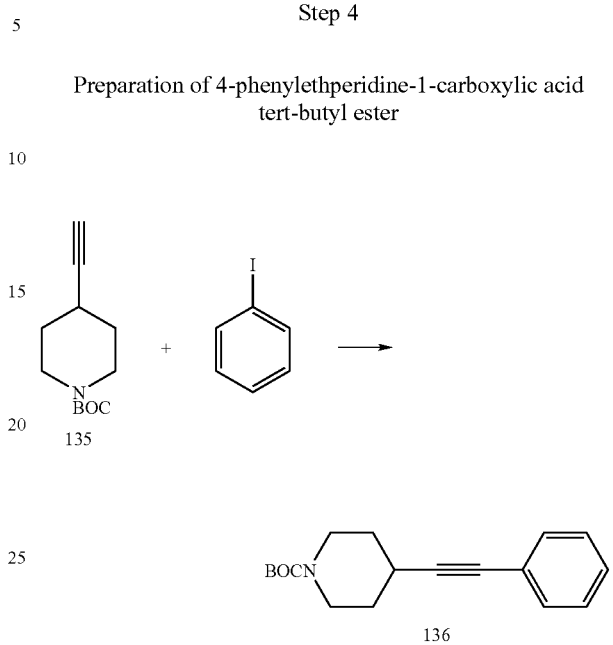

Iodobenzene (135 µl, 1.2 mmols), 4-ethynyl-piperidine-1-carboxylic acid tert-butyl ester (209 mg, 1 mmols) and triethylamine (167 µl, 1.2 mmols) were dissolved in acetonitrile (6 ml). Dichlorobis(triphenylphosphine)palladium(II) (35 mg, 0.05 mmols) and CuI (10 mg, 0.05 mmols) were added, and reaction mixture was stirred at room temperature overnight and continued to stir at 50 C for two more hours before partitioning between ethyl acetate and water. Organic layer was isolated, washed with 1 N HCl, brine and dried (MgSO$_4$). Solvents were removed and residue was purified by column chromatography on silica gel using solutions of ethyl acetate in hexanes (1:4; 1:2) to yield the title compound (74 mg). LCMS m/e (230, M-t-Bu+2H)

Step 5

Preparation of 4-phenylethynyl-piperidine

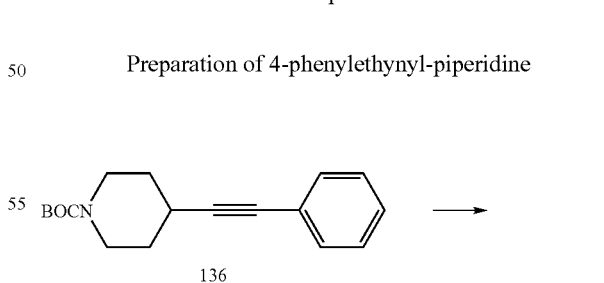

4-Phenylethynyl-piperidine-1-carboxylic acid tert-butyl ester was treated with TFA for 10 minutes and concentrated, lyophilized to provide the title product.

Example 140

Step 1

Preparation of 4-pyrimidin-2-ylethynyl-piperidine-1-carboxylic acid tert-butyl ester

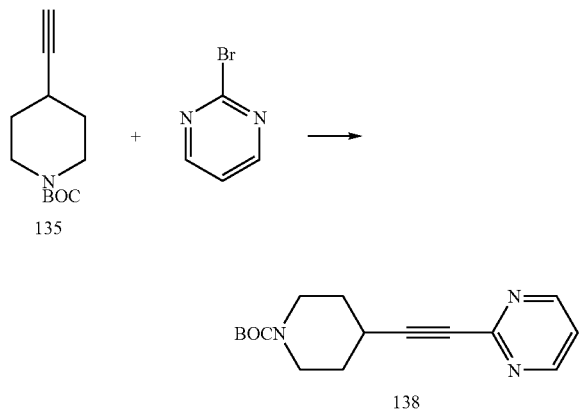

To a suspension of 2-bromopyrimidine (175 mg, 1.1 mmols), dichlorobis(triphenylphosphine)palladium(II) (35 mg, 0.05 mmols) and CuI (10 mg, 0.05 mmols) was added a solution of 4-ethynyl-piperidine-1-carboxylic acid tert-butyl ester (209 mg, 1 mmol). The mixture was stirred overnight, filtered through Celite, concentrated. The residue was partitioned between ethyl acetate and water, organic layer was isolated, dried (MgSO$_4$), and concentrated. The residue was chromatographed on silica gel eluting with ethyl acetate in hexanes (1:1) to give un-reacted 2-bromopyrimidine (130 mg), then the title compound (23 mg). LCMS m/e (288, M+H).

Step 2

Preparation of 2-piperidin-4-ylethynyl-pyrimidine

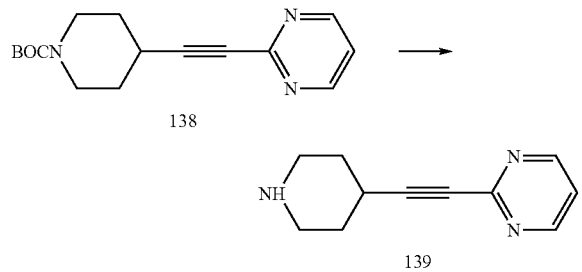

4-Pyrimidin-2-ylethynyl-piperidine-1-carboxylic acid tert-butyl ester was treated with TFA for 10 minutes and concentrated, lyophilized to provide the title product.

Example 141

Preparation of 5-({1-[2-oxo-2-(4-phenylethynyl-piperidin-1-yl)-ethyl]-pyrrolidine-3-carbonyl}-amino)-1H-indazole-3-carboxylic acid methylamide

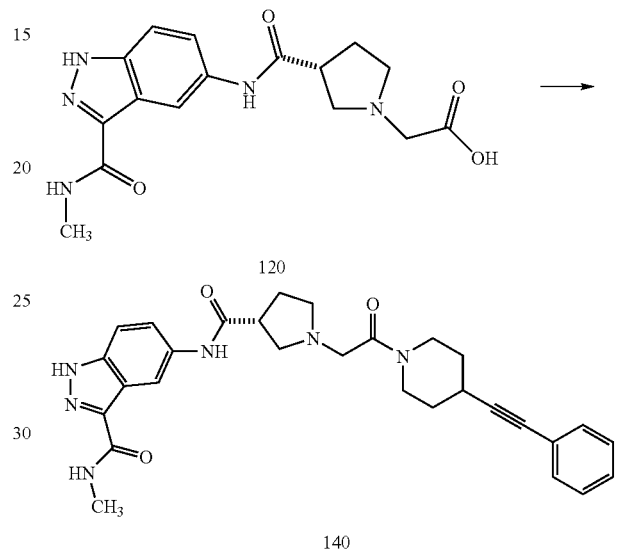

A solution of [3-(3-methylcarbamoyl-1H-indazol-5-ylcarbamoyl)-pyrrolidin-1-yl]-acetic acid (0.13 mmols), 4-phenylethynyl-piperidine (0.13 mmols), 1-hydroxybenztriazole (18 mg, 0.13 mmol) and 1-(3-dimethylaminopropyl)-3-ethylcarbodiimide hydrochloride (EDCl) (27 mg, 0.14 mmol) and DIEA (45 µl, 0.26 mmols) was stirred overnight and directly subjected to purification by reversed phase HPLC to obtain 16 mg of the title product.

Example 142

Preparation of 5-({1-[2-oxo-2-(4-pyrimidin-2-yl-ethynyl-piperidin-1-yl)-ethyl]-pyrrolidine-3-carbonyl}-amino)-1H-indazole-3-carboxylic acid methylamide

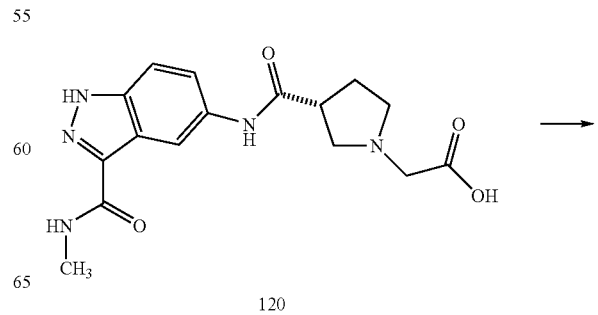

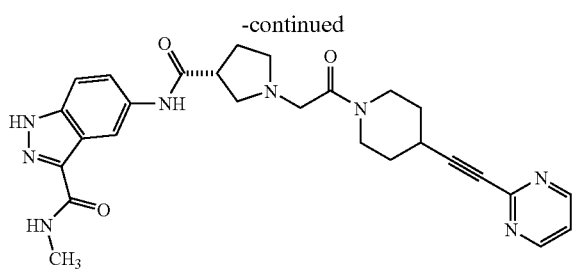

141

Following a procedure similar to that of Example 141, but using 2-piperidin-4-ylethynyl-pyrimidine instead of 4-phenylethynyl-piperidine the title compound was prepared.

Examples 143 to 151

Following a procedure similar to Example 135, Step 3, but using the appropriately substituted piperazine, and the suitably substituted indazole, and the appropriate amine for MeNH$_2$ in Example 87, the compounds in Table 9 can be prepared.

TABLE 9

| Example | COMPOUND |
|---------|----------|
| 143 | |
| 144 | |
| 145 | |
| 146 | |

TABLE 9-continued
| Example | COMPOUND |
|---|---|
| 147 | 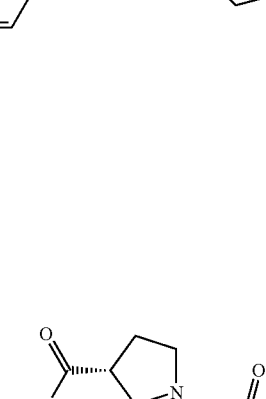 |
| 148 | 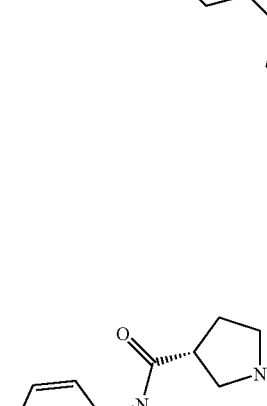 |
| 149 | 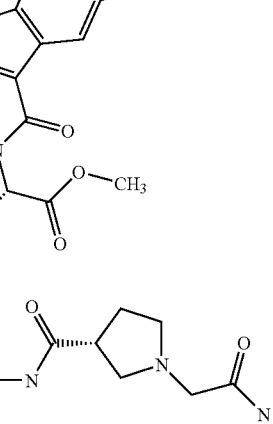 |
| 150 | 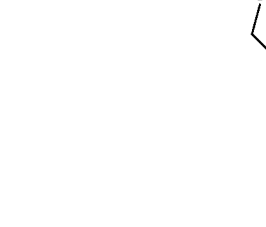 |

TABLE 9-continued

| Example | COMPOUND |
|---------|----------|
| 151 | (structure) |

Examples 152 to 155

Following a procedure similar to that of Example 85, but using the appropriately substituted piperazine derivative, as prepared according to the procedures in Examples 128-134, the compounds in Table 10 were prepared.

TABLE 10

| Example | COMPOUND |
|---------|----------|
| 152 | (structure) |
| 153 | (structure) |
| 154 | (structure) |

TABLE 10-continued

| Example | COMPOUND |
|---|---|
| 155 | *(structure)* |

Example 156

Following a procedure similar to that of Example 125, Using compound 90 from Example 125 Step 5 in place of compound 96 in Step 10, and using 4-piperazin-1-yl-thiazolyl in place of 2-(4-piperazin-1-yl-phenyl)-pyrimidine in Step 11, the compound in Table 11 was prepared.

TABLE 11

| Example | Compound | Mass Spec | Retention time (minutes) |
|---|---|---|---|
| 156 | *(structure)* | 564 | 2.68 |

Examples 157 and 158

Following a procedure similar to that of Example 125, but using the appropriate pyrrolidene and substituted piperazine, as in Example 128, the compounds in Table 12 can be prepared. In Table 12 "Ex" represents "Example".

TABLE 12

| Ex | Compound | Mass Spec | Retention time (minutes) |
|---|---|---|---|
| 157 | *(structure)* | 649 | 3.74 |

TABLE 12-continued
| Ex | Compound | Mass Spec | Retention time (minutes) |
|---|---|---|---|
| 158 |  | 647 | 3.56 |
Examples 159 to 164
Following procedures similar to those described herein, for example, Examples 98, 133 and 135, the compounds in Table 13 were prepared. In Table 13 "Ex" represents "Example".
TABLE 13
| EX | Structure | MS (ESMS, MH) | Retention time (min.) |
|---|---|---|---|
| 159 |  | 594 | 3.25 |
| | (substitute  in Ex. 98 and see Ex. 135) | | |
| 160 | (see Ex. 133) | 516 | 2.65 |

TABLE 13-continued

| EX | Structure | MS (ESMS, MH) | Retention time (min.) |
|---|---|---|---|
| 161 | [structure: 3-(4-fluorophenyl)-1H-indazol-5-yl pyrrolidine carboxamide with piperazinyl-thiazole] (see Ex. 98 and Ex. 133) | 534 | 2.8 |
| 162 | [structure: 3-(3,4-difluorophenyl)-1H-indazol-5-yl analog] (substitute 3,4-difluorophenyl-B(OH)$_2$ for F-phenyl-B(OH)$_2$ in Ex. 98 and see Ex. 133) | 552 | 2.95 |
| 163 | [structure: 3-(4-methoxyphenyl)-1H-indazol-5-yl analog] (substitute 4-methoxyphenyl-B(OH)$_2$ for F-phenyl-B(OH)$_2$ in Ex. 98 and see Ex. 133) | 546 | 3.02 |

TABLE 13-continued

| EX | Structure | MS (ESMS, MH) | Retention time (min.) |
|---|---|---|---|
| 164 | 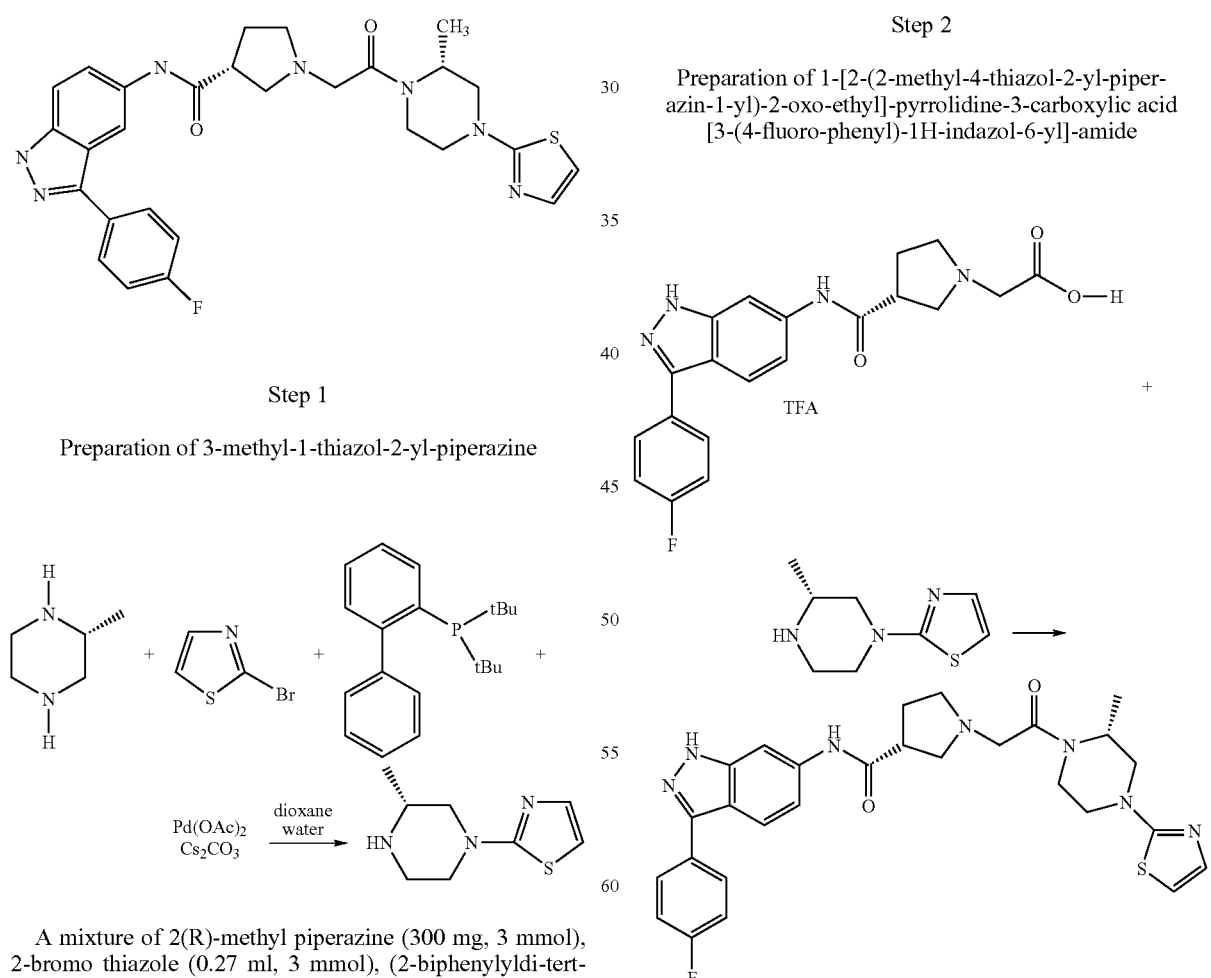 | 518 | 1.93 |

(substitute (HO)₂B-[pyrimidin-5-yl] for F-[phenyl]-B(OH)₂ in Ex. 98 and see Ex. 133)

Example 165

Step 1

Preparation of 3-methyl-1-thiazol-2-yl-piperazine

A mixture of 2(R)-methyl piperazine (300 mg, 3 mmol), 2-bromo thiazole (0.27 ml, 3 mmol), (2-biphenylyldi-tert-butylphosphine (134 mg, 0.449 mmol), palladium acetate (101 mg, 0.45 mmol), and cesium carbonate (1.46 g, 4.49 mmol) in dioxane 25 ml (v/v 5/1) was kept at reflux temperature for 2 hours, then cooled to room temperature, then filtered through celite, then concentrated and then purified by chromatography eluting with 12% MeOH/MeCl₂/NH₄OH to yield the product as a white solid (145 mg, 26%).

Step 2

Preparation of 1-[2-(2-methyl-4-thiazol-2-yl-piperazin-1-yl)-2-oxo-ethyl]-pyrrolidine-3-carboxylic acid [3-(4-fluoro-phenyl)-1H-indazol-6-yl]-amide A mixture of 3-methyl-1-thiazol-2-yl-piperazine (11 mg, 0.060 mmol), {3-[3-(4-fluorophenyl)-1H-indazol-6-ylcarbamoyl]-pyrrolidin-1-yl}-acidic acid, trifluoroacetate (30 mg, 0.06 mmol), EDCl.HCl (11 mg, 0.06 mmol), 1-hydroxybenzotriazole (9 mg, 0.066) mmol) and NMM (0.04 ml) was stirred in DMF (2 ml) overnight at room temperature. The reaction was diluted with EtOAc (50 ml), washed with brine (20 ml), dried over MgSO₄, filtered and the solvent was evaporated. The resulting material was purified on reverse phase HPLC (C₁₈ column), eluting with acetonitrile:water, yielding product which was dissolved in MeCl₂ basified with saturated NaHCO₃, dried over MgSO₄, filtered and solvent evaporated yielding title product (10 mg). LCMS MH 548. Retention time: 2.36 minutes.

Examples 166 to 179

Following procedures similar to those described herein, for example, Examples 85, 98, 137 and 136, the compounds in Table 14 were prepared. In Table 14 "Ex" represents "Example".

TABLE 14

TABLE 14-continued
| EX | Structure | MS (ESMS, MH) | Retention time (min.) |
|----|-----------|---------------|----------------------|
| 169 | 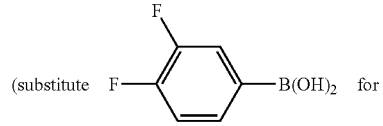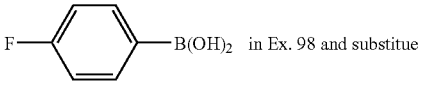 (substitute for in Ex. 98 and substitue for in Ex. 137) | 560 | 4.27 |
| 170 | 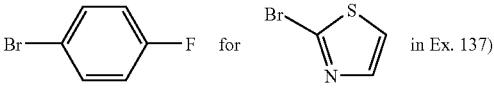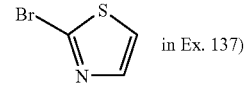 (substitute for in Ex. 98 and substitue for in Ex. 137) | 554 | 4.01 |

TABLE 14-continued
| EX | Structure | MS (ESMS, MH) | Retention time (min.) |
|---|---|---|---|
| 171 | 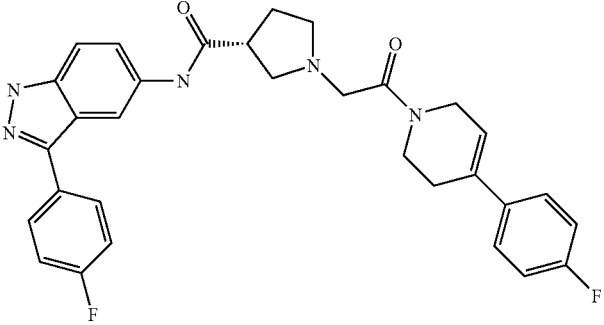 (see Ex. 98 and substitute 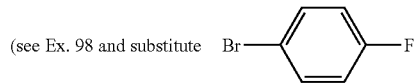 for 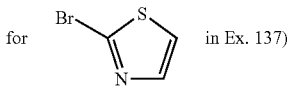 in Ex. 137) | 542 | 4.11 |
| 172 | 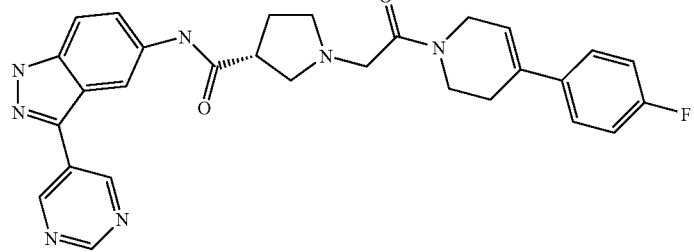 (substitute 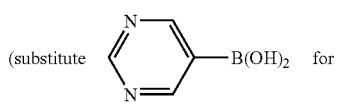—B(OH)₂ for 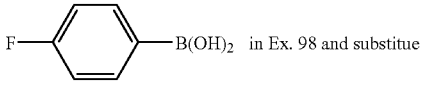—B(OH)₂ in Ex. 98 and substitue 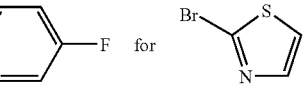 for  in Ex. 137) | 526 | 3.35 |

TABLE 14-continued

| EX | Structure | MS (ESMS, MH) | Retention time (min.) |
|---|---|---|---|
| 173 | (substitute phenyl-B(OH)₂ for F-phenyl-B(OH)₂ in Ex. 98) | 526 | 1.51 |
| 174 | (substitute phenyl-B(OH)₂ for F-phenyl-B(OH)₂ in Ex. 98) | 542 | 1.59 |
| 175 | (substitute phenyl-B(OH)₂ for F-phenyl-B(OH)₂ in Ex. 98) | 576 | 1.64 |

TABLE 14-continued

| EX | Structure | MS (ESMS, MH) | Retention time (min.) |
|---|---|---|---|
| 176 | 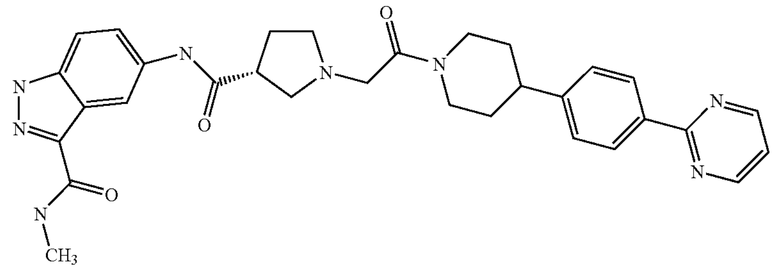 | 567 | 3.16 |

(see Ex. 85 and Ex. 136)

| 177 | | 586 | 3.85 |

(substitute phenyl-B(OH)₂ for F-phenyl-B(OH)₂ in Ex. 98 and see Ex. 136)

| 178 | | | |

(substitute pyridyl-B(OH)₂ for F-phenyl-B(OH)₂ in Ex. 98 and see Ex. 132)

TABLE 14-continued
| EX | Structure | MS (ESMS, MH) | Retention time (min.) |
|---|---|---|---|
| 179 | 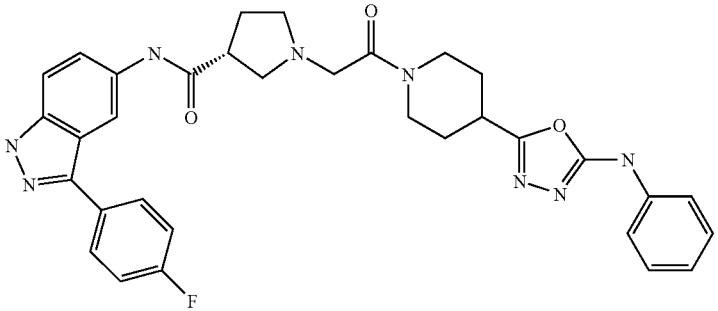<br>(see Ex. 98) | | |
Examples 181 and 183 to 259
Following procedures similar to those described herein, for example, Examples 1, 3 to 60, 85, 98, 128, 183, 184, the compounds in Table 15 were prepared. In Table 15 "Ex" represents "Example".
TABLE 15
| EX | COMPOUND |
|---|---|
| 181 | 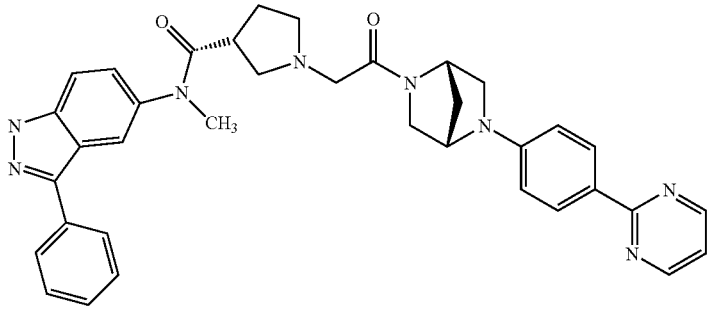 |
| 183 | 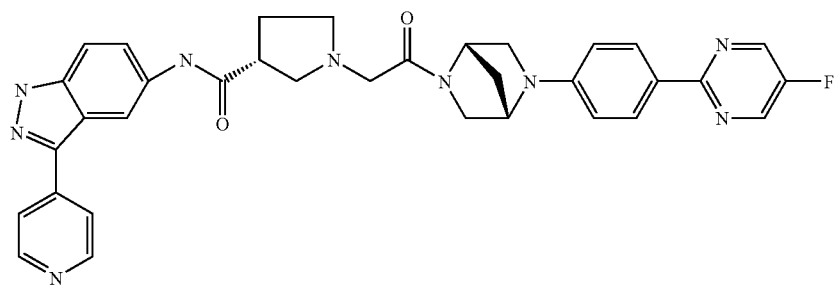<br>(substitute 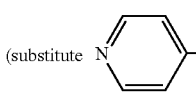 for 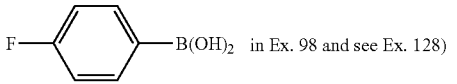 in Ex. 98 and see Ex. 128) |

TABLE 15-continued
| EX | COMPOUND |
|---|---|
| 184 | 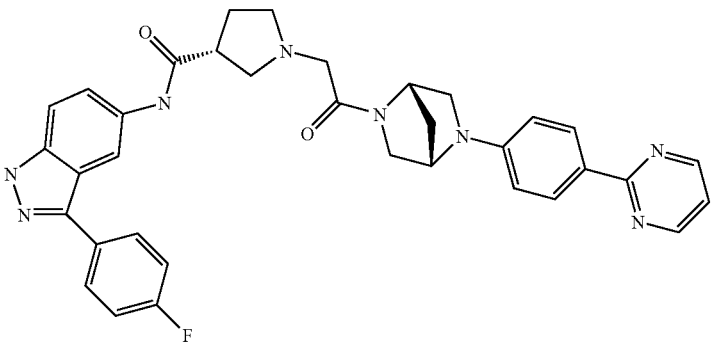 |
| | (substitute 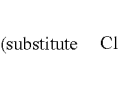 for 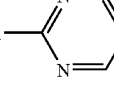 in Ex. 128 and see Ex. 98) |
| 185 | 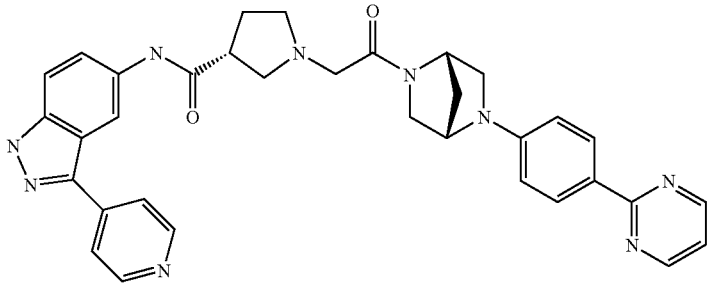 |
| | (see Ex. 183 and Ex. 184) |
| 186 | 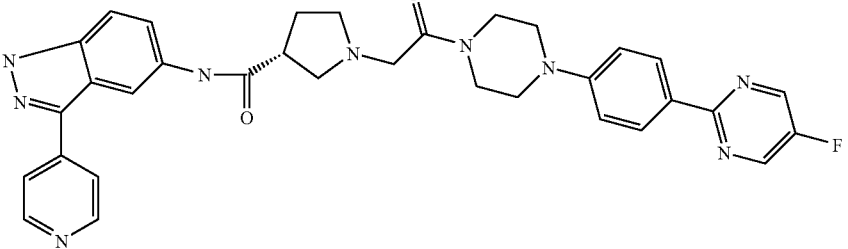 |

TABLE 15-continued
| EX | COMPOUND |
|---|---|
| 187 | 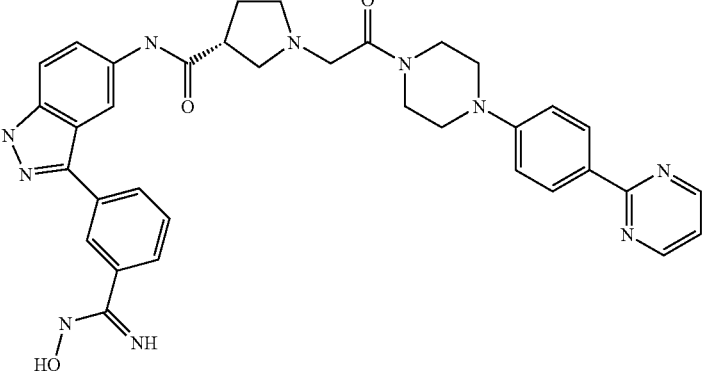 |
| 188 | 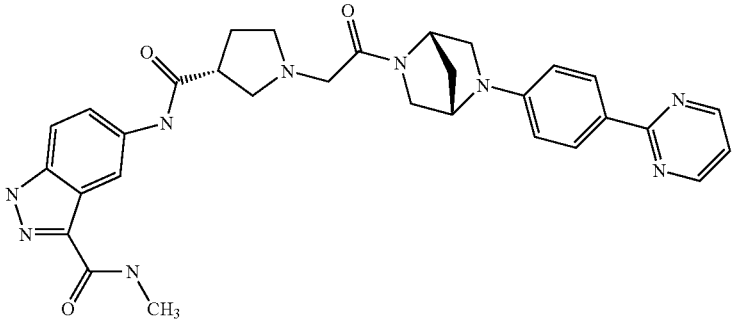<br><br>(substitute 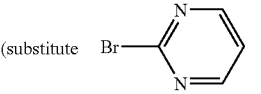 for 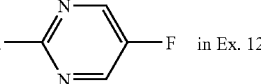 in Ex. 128 and see Ex. 85) |
| 189 | 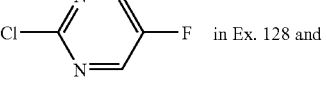<br><br>(substitute 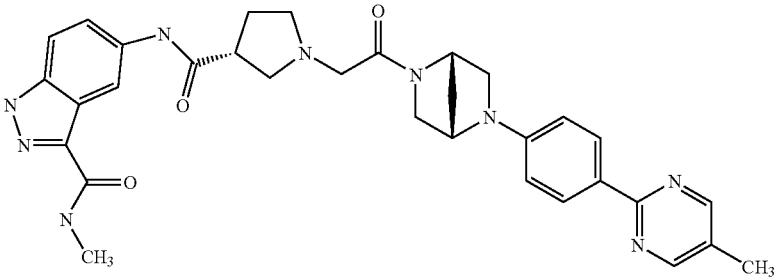 for 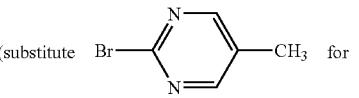 in Ex. 128 and see Ex. 85) |

TABLE 15-continued
| EX | COMPOUND |
|---|---|
| 190 | 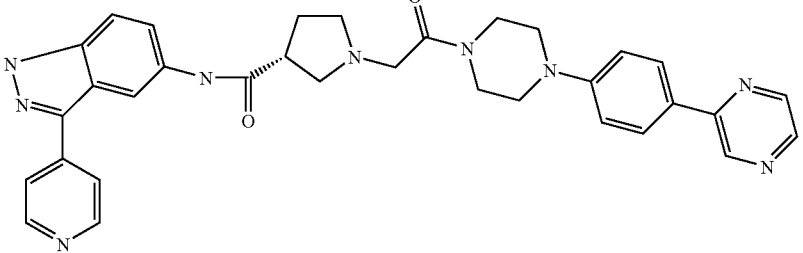 |
| | 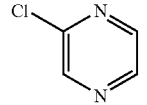 |
| | (substitute ... for ... in Ex. 1 Step 6 and see Examples 3 to 60) |
| 191 | 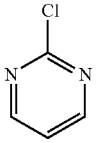 |
| | (see Examples 3 to 60 and Ex. 1) |
| 192 | 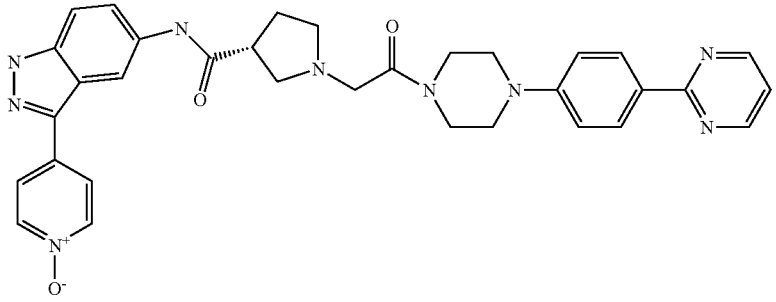 |

TABLE 15-continued

| EX | COMPOUND |
|---|---|
| 193 | |
| 194 | |
| 195 | (see Ex. 1) |
| 196 | |

TABLE 15-continued

| EX | COMPOUND |
|---|---|
| 197 | |
| 198 | |
| 199 | |
| 200 | |

TABLE 15-continued
| EX | COMPOUND |
|---|---|
| 201 | 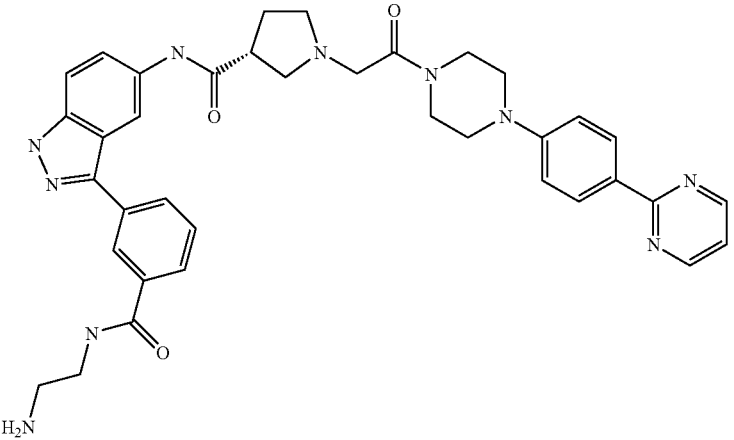 [SMILES: NCCNC(=O)c1cccc(-c2n[nH]c3ccc(NC(=O)[C@@H]4CCN(CC(=O)N5CCN(c6ccc(-c7ncccn7)cc6)CC5)C4)cc23)c1] |
| 202 | 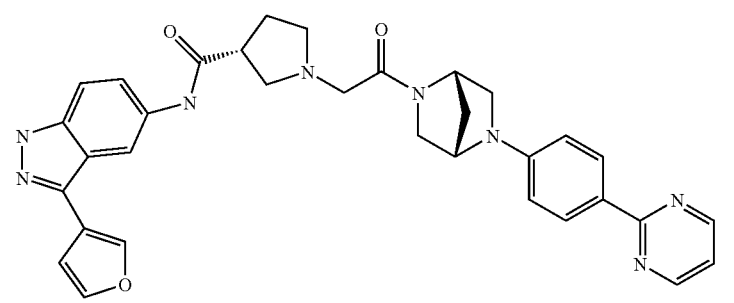 [SMILES: O=C(Nc1ccc2[nH]nc(-c3ccoc3)c2c1)[C@@H]1CCN(CC(=O)N2C[C@@H]3C[C@H]2CN3c2ccc(-c3ncccn3)cc2)C1] |
| 203 | 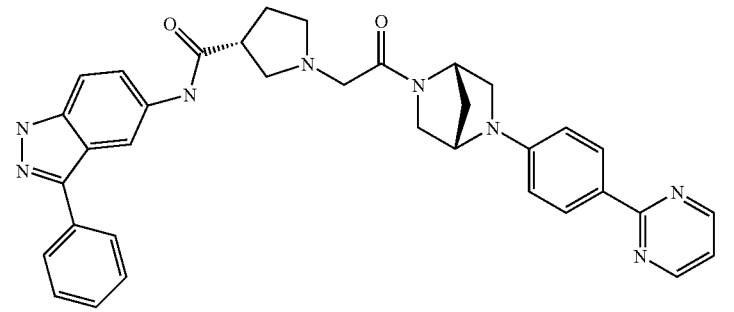 [SMILES: O=C(Nc1ccc2[nH]nc(-c3ccccc3)c2c1)[C@@H]1CCN(CC(=O)N2C[C@@H]3C[C@H]2CN3c2ccc(-c3ncccn3)cc2)C1] |
| 204 | 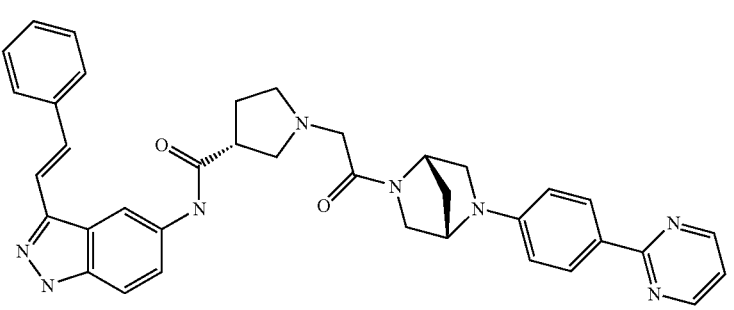 [SMILES: O=C(Nc1ccc2[nH]nc(/C=C/c3ccccc3)c2c1)[C@@H]1CCN(CC(=O)N2C[C@@H]3C[C@H]2CN3c2ccc(-c3ncccn3)cc2)C1] |

TABLE 15-continued
| EX | COMPOUND |
|----|----------|
| 205 | 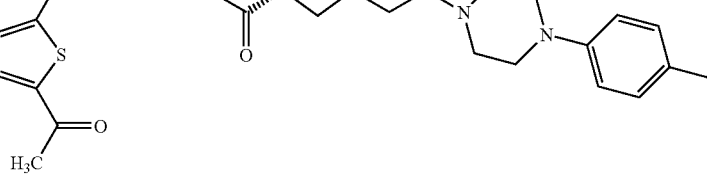 |
| 206 | 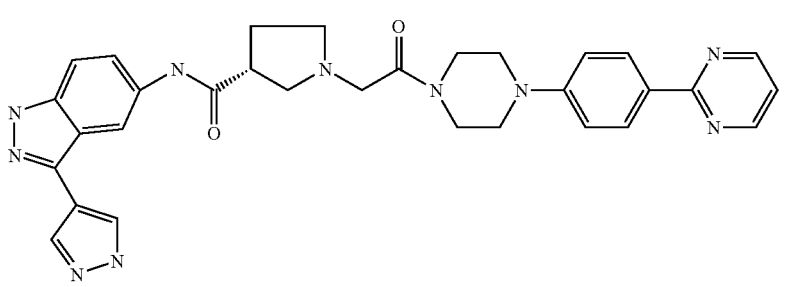 [SMILES: O=C(Nc1ccc2[nH]nc(-c3cn[nH]c3)c2c1)[C@@H]1CCN(CC(=O)N2CCN(c3ccc(-c4ncccn4)cc3)CC2)C1] |
| 207 |  |
| 208 |  |
| 209 | 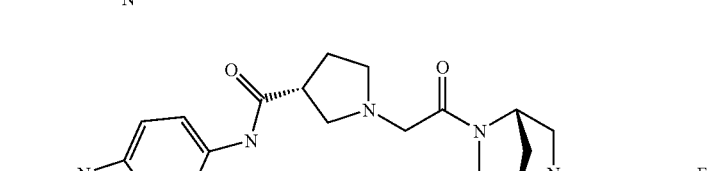 |

TABLE 15-continued
| EX | COMPOUND |
|---|---|
| 210 | 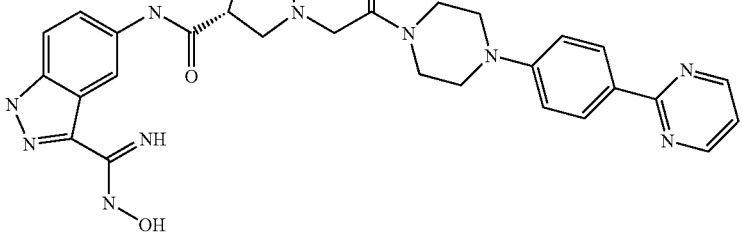 |
| 211 | 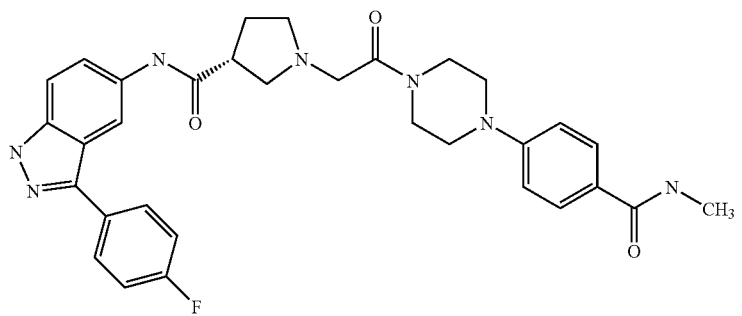 [SMILES: CNC(=O)c1ccc(N2CCN(C(=O)CN3CC[C@@H](C(=O)Nc4ccc5[nH]nc(-c6ccc(F)cc6)c5c4)C3)CC2)cc1] |
| 212 | 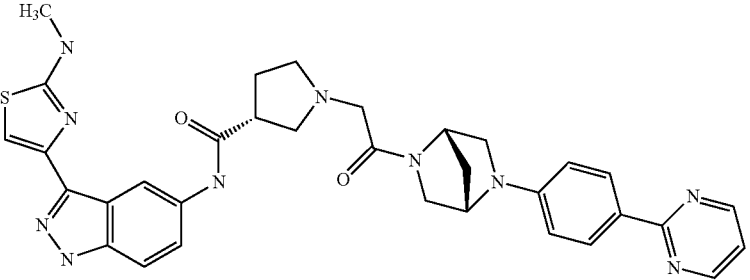 [SMILES: CNc1nc(-c2n[nH]c3ccc(NC(=O)[C@@H]4CCN(CC(=O)N5C[C@@H]6C[C@H]5CN6c5ccc(-c6ncccn6)cc5)C4)cc23)cs1] |
| 213 | 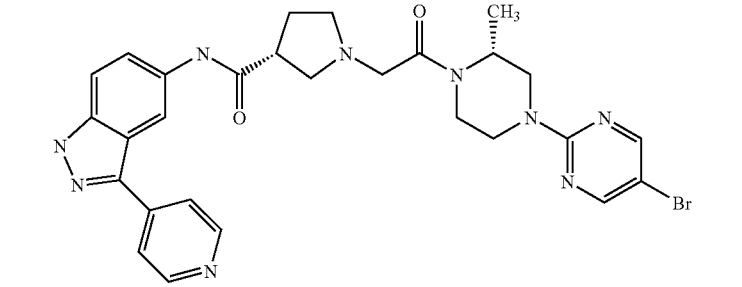 [SMILES: C[C@@H]1CN(c2ncc(Br)cn2)CCN1C(=O)CN1CC[C@@H](C(=O)Nc2ccc3[nH]nc(-c4ccncc4)c3c2)C1] |
| 214 | 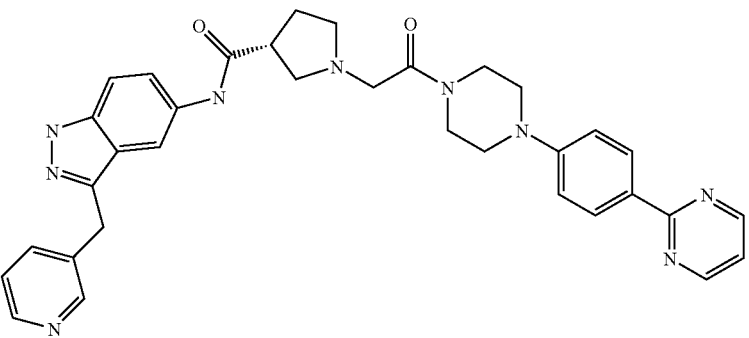 [SMILES: O=C(Nc1ccc2[nH]nc(Cc3cccnc3)c2c1)[C@@H]1CCN(CC(=O)N2CCN(c3ccc(-c4ncccn4)cc3)CC2)C1] |

TABLE 15-continued

| EX | COMPOUND |
|---|---|
| 215 | |
| 216 | |
| 217 | |
| 218 | |

TABLE 15-continued
| EX | COMPOUND |
|---|---|
| 219 | 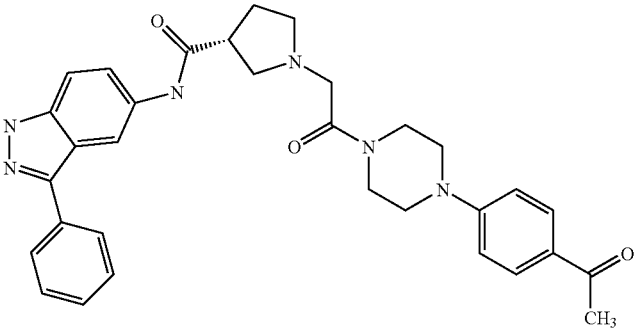 [SMILES: CC(=O)c1ccc(N2CCN(C(=O)CN3CC[C@@H](C(=O)Nc4ccc5[nH]nc(-c6ccccc6)c5c4)C3)CC2)cc1] |
| 220 | 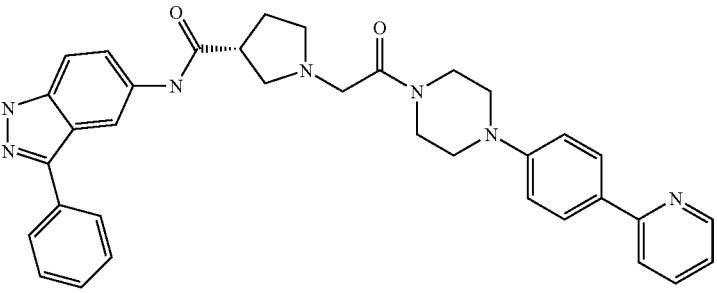 [SMILES: O=C(Nc1ccc2[nH]nc(-c3ccccc3)c2c1)[C@@H]1CCN(CC(=O)N2CCN(c3ccc(-c4ccccn4)cc3)CC2)C1] |
| 221 | 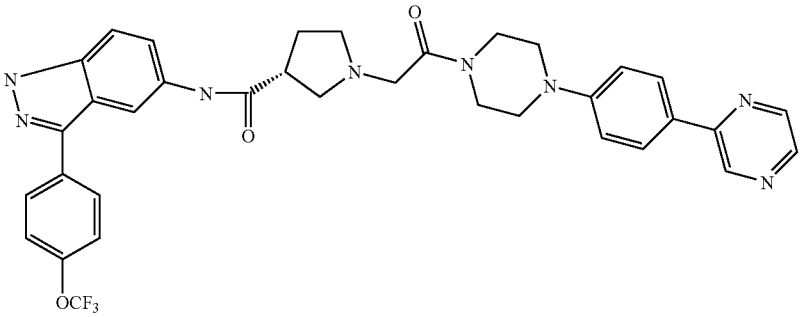 [SMILES: O=C(Nc1ccc2[nH]nc(-c3ccc(OC(F)(F)F)cc3)c2c1)[C@@H]1CCN(CC(=O)N2CCN(c3ccc(-c4cnccn4)cc3)CC2)C1] |
| 222 | 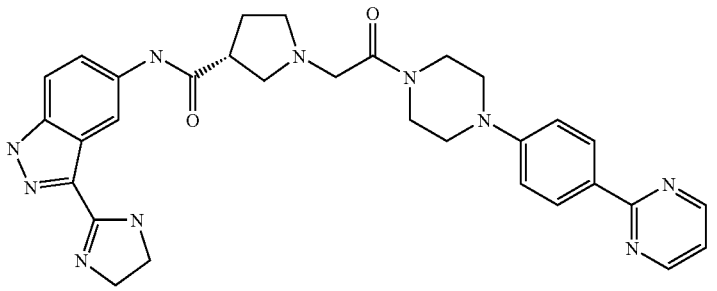 [SMILES: O=C(Nc1ccc2[nH]nc(C3=NCCN3)c2c1)[C@@H]1CCN(CC(=O)N2CCN(c3ccc(-c4ncccn4)cc3)CC2)C1] |
| 223 | 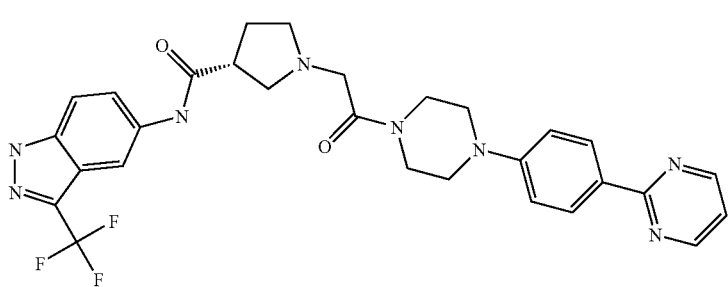 [SMILES: O=C(Nc1ccc2[nH]nc(C(F)(F)F)c2c1)[C@@H]1CCN(CC(=O)N2CCN(c3ccc(-c4ncccn4)cc3)CC2)C1] |

TABLE 15-continued
| EX | COMPOUND |
|---|---|
| 224 |  |
| 225 | 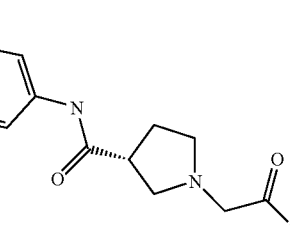 |
| 226 | 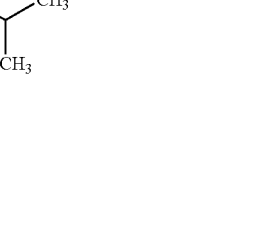 |
| 227 | 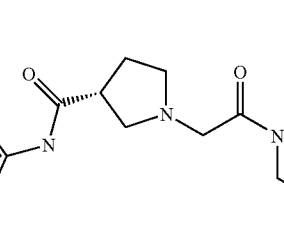 |

TABLE 15-continued

| EX | COMPOUND |
|---|---|
| 228 | |
| 229 | |
| 230 | |
| 231 | |
| 232 | |

TABLE 15-continued
| EX | COMPOUND |
|---|---|
| 233 | 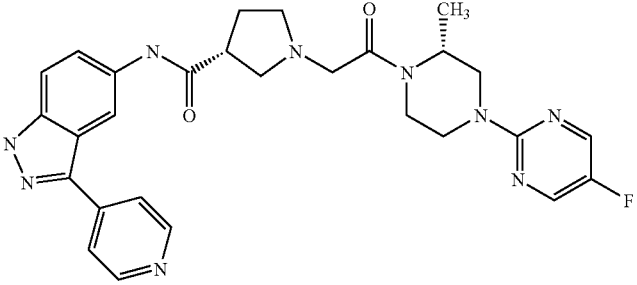 [SMILES: C[C@@H]1CN(c2ncc(F)cn2)CCN1C(=O)CN1CC[C@@H](C(=O)Nc2ccc3[nH]nc(-c4ccncc4)c3c2)C1] |
| 234 | 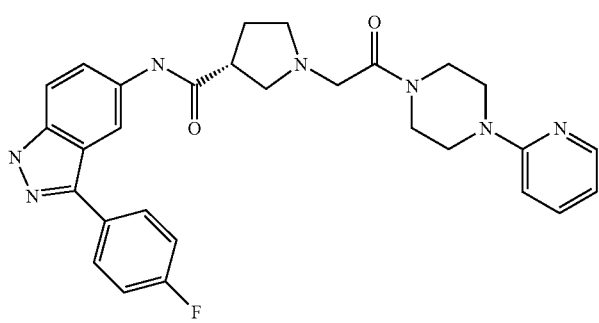 [SMILES: O=C(Nc1ccc2[nH]nc(-c3ccc(F)cc3)c2c1)[C@@H]1CCN(CC(=O)N2CCN(c3ccccn3)CC2)C1] |
| 235 | 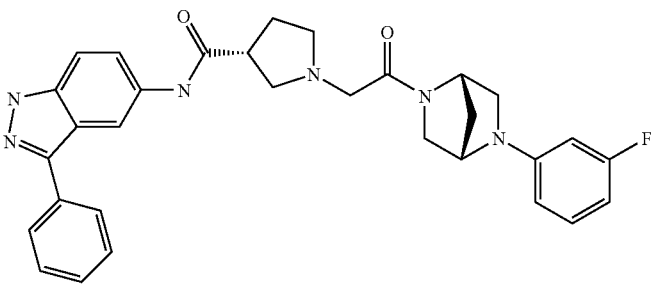 [SMILES: O=C(Nc1ccc2[nH]nc(-c3ccccc3)c2c1)[C@@H]1CCN(CC(=O)N2C[C@@H]3C[C@H]2CN3c2cccc(F)c2)C1] |
| 236 | 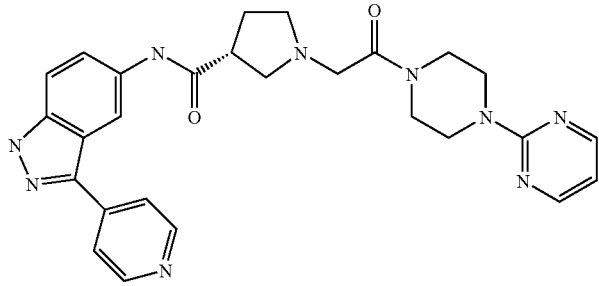 [SMILES: O=C(Nc1ccc2[nH]nc(-c3ccncc3)c2c1)[C@@H]1CCN(CC(=O)N2CCN(c3ncccn3)CC2)C1] |
| 237 | 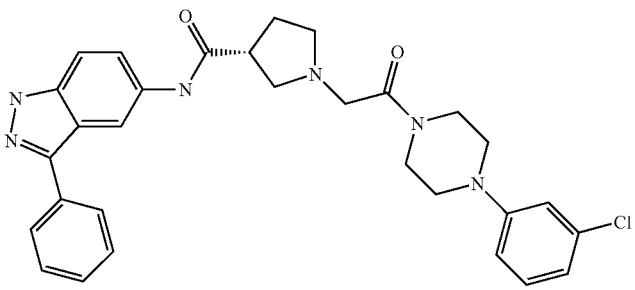 [SMILES: O=C(Nc1ccc2[nH]nc(-c3ccccc3)c2c1)[C@@H]1CCN(CC(=O)N2CCN(c3cccc(Cl)c3)CC2)C1] |

TABLE 15-continued
| EX | COMPOUND |
|---|---|
| 238 | 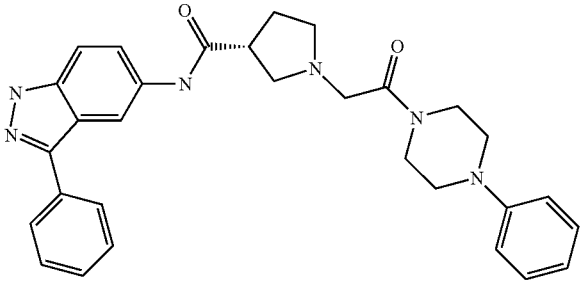 [SMILES: O=C(Nc1ccc2[nH]nc(-c3ccccc3)c2c1)[C@@H]1CCN(CC(=O)N2CCN(c3ccccc3)CC2)C1] |
| 239 | 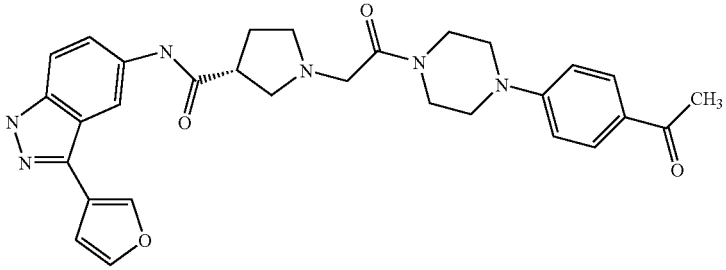 [SMILES: CC(=O)c1ccc(N2CCN(C(=O)CN3CC[C@@H](C(=O)Nc4ccc5[nH]nc(-c6ccoc6)c5c4)C3)CC2)cc1] |
| 240 | 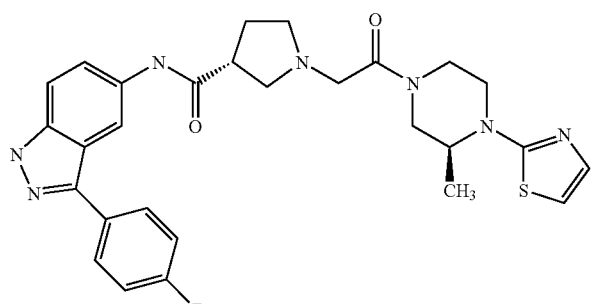 |
| 241 | 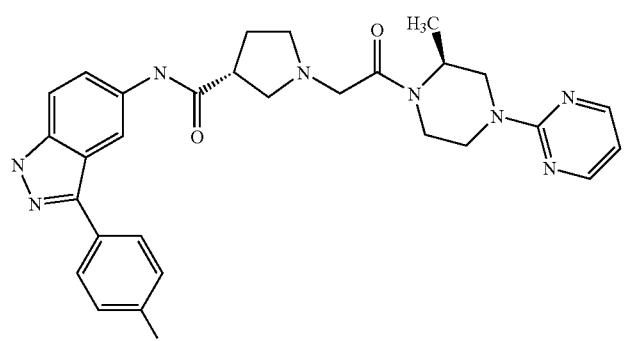 |

TABLE 15-continued

| EX | COMPOUND |
|---|---|
| 242 | |
| 243 | |
| 244 | |
| 245 | |

TABLE 15-continued

| EX | COMPOUND |
|---|---|
| 246 | |
| 247 | |
| 248 | |
| 249 | |
| 250 | |

TABLE 15-continued

| EX | COMPOUND |
|---|---|
| 251 | |
| 252 | |
| 253 | |
| 254 | |
| 255 | |

TABLE 15-continued
| EX | COMPOUND |
|---|---|
| 256 | 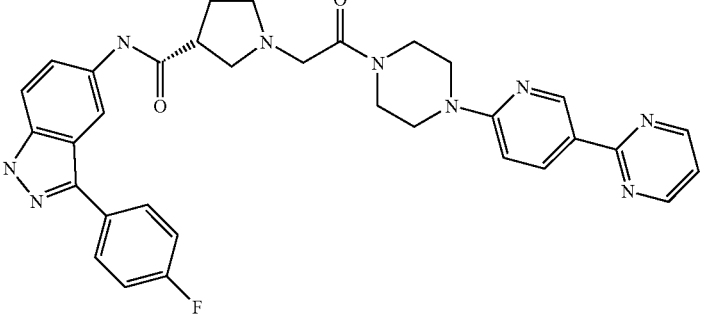 |
| 257 | 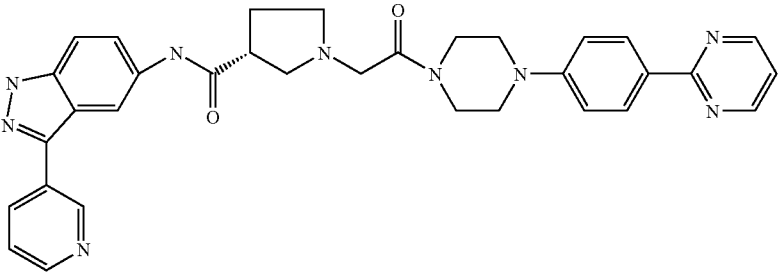 [SMILES: O=C(Nc1ccc2[nH]nc(-c3cccnc3)c2c1)[C@@H]1CCN(CC(=O)N2CCN(c3ccc(-c4ncccn4)cc3)CC2)C1] |
| 258 | 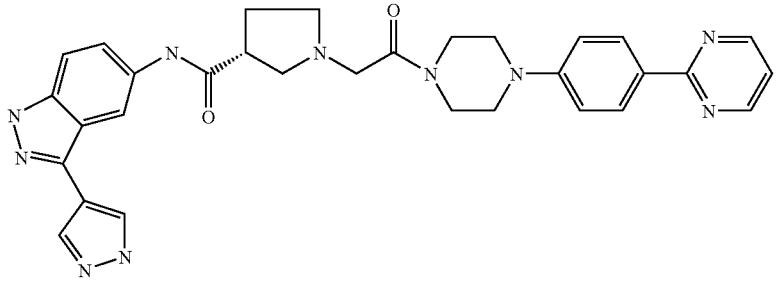 [SMILES: O=C(Nc1ccc2[nH]nc(-c3cn[nH]c3)c2c1)[C@@H]1CCN(CC(=O)N2CCN(c3ccc(-c4ncccn4)cc3)CC2)C1] |
| 259 | 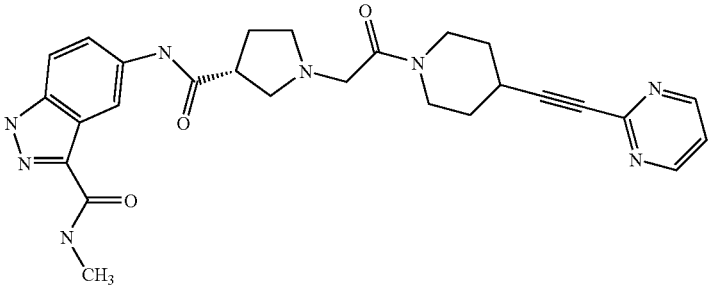 [SMILES: CNC(=O)c1n[nH]c2ccc(NC(=O)[C@@H]3CCN(CC(=O)N4CCC(C#Cc5ncccn5)CC4)C3)cc12] |

Examples 260 to 334

Using the intermediates made from Preparations 1 to 15 described below, and following the procedures described in the reaction Schemes described above, the compounds in Table 16 below were prepared. In Table 16 "Ex" represents "Example".

Preparation 1

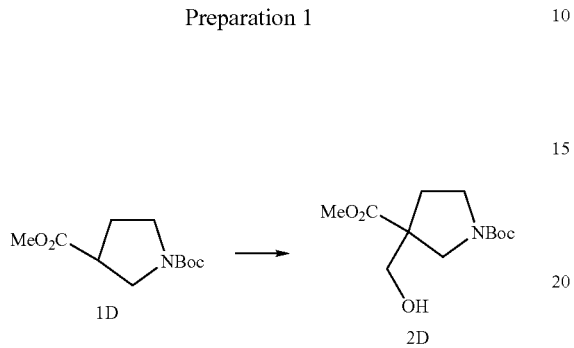

1D

2D

To a solution of LDA (33.5 mmol, 16.7 mL, 2 M in toluene) in 50 mL THF cooled at −78 deg C. was added a solution of 1D (5.9 g, 25.7 mmol) in 50 mL THF drop wise. The crude was stirred at −78 deg C. for 45 mins. To the crude was bubbled formaldehyde gas, freshly generated from cracking of para-formaldehyde (12 g, 400 mmol). The crude was stirred at −78 deg C. for an additional 30 mins. To the crude was added sat NH$_4$Cl (200 mL). The crude was warmed to rt. The crude was diluted in EtOAc. The organic layer was washed with brine and dried over MgSO$_4$, filtered, and conc. in vacuum. The crude was purified on Biotage using EtOAc/hexane (3:7)->EtOAc/hexane (1:1) to give 6.6 g (57%) of the product as a yellow oil.

Preparation 2

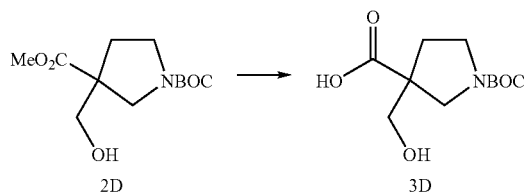

2D

3D

To a solution of ester 2D (2.5 g, 9.6 mmol) in MeOH (100 mL) was added 1 N NaOH (48 mL, 48.2 mmol) at rt. The crude was stirred at rt overnight. To the crude was added 1 N HCl (47.5 mL, 47.5 mmol). The crude was stirred at rt for 5 mins. PH of crude is made to 5 using PH paper. The crude was conc in vacuum and azeotroped 2x with toluene and dried under high vacuum for use in the HATU coupling with amine 4D in Preparation 3 below.

Preparation 3

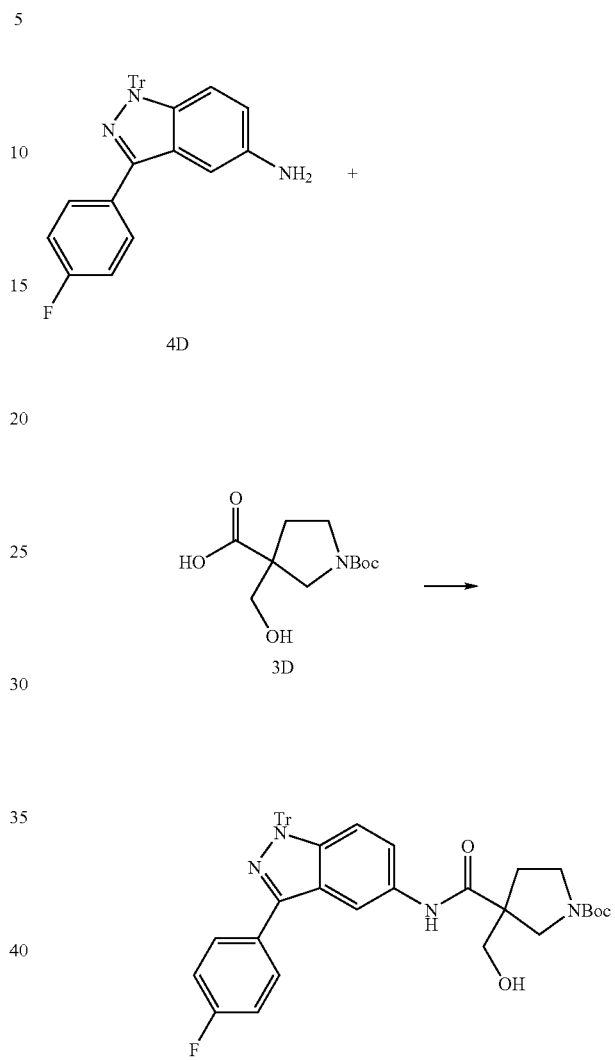

To a suspension of acid 3D and amine 4D (5.52 g, 12.5 mmol) in DMF (15 mL) and CH$_2$Cl$_2$ (75 mL) was added DIPEA (5 mL, 28.8 mmol) and HATU (5.8 g, 12.5 mmol) at rt. The crude was stirred at rt overnight under a stream of nitrogen. To the crude was added brine and CH$_2$Cl$_2$. The aq layer was extracted with EtOAc 2x. The combined organic layer was dried over MgSO$_4$, filtered, and conc in vacuum. To the crude was added MeOH (200 mL), THF (20 mL) and NaOH (1N, 25 mL, 25 mmol). The crude was stirred at rt for overnight. To the crude was added HCl (1N, 20 mL). The crude was stirred at rt for 5 mins. The crude was conc in vacuum and dissolved in H$_2$O and CH$_2$Cl$_2$. The aq layer was extracted with EtOAc 2x. The combined organic layer was dried over MgSO$_4$, filtered, and conc in vacuum. The crude was purified on Biotage using EtOAc/hexane (2:5)->EtOAc/hexane (3:2) to give 2.8 g (42%) of an off white solid 5D. MS (M+H+=697.25).

Preparation 4

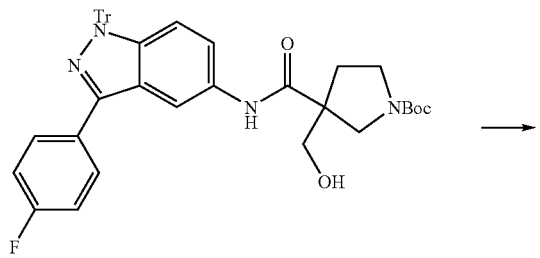

5D

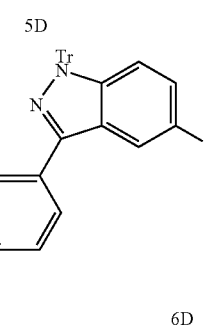

6D

To a solution of alcohol 5D (3.9 g, 5.6 mmol) in CH$_2$Cl$_2$ (65 mL) was added solid NaHCO$_3$ (1.4 g, 16.8 mmol) and DMP (3.6 g, 8.4 mmol) at rt. The crude was stirred at rt for 1.5 hr. To the crude was added sat. sodium thiosulfate and sat. NaHCO$_3$ (150 mL: 150 mL) at rt. The crude was vigorously stirred at rt for 30 mins. The aq layer was extracted with CH$_2$Cl$_2$ 2×. The combined organic layer was washed with brine, dried over MgSO$_4$, filtered, and conc in vacuum to give 3.9 g of 6D (quantitative). MS (M+H+, 695.24)

Preparation 5

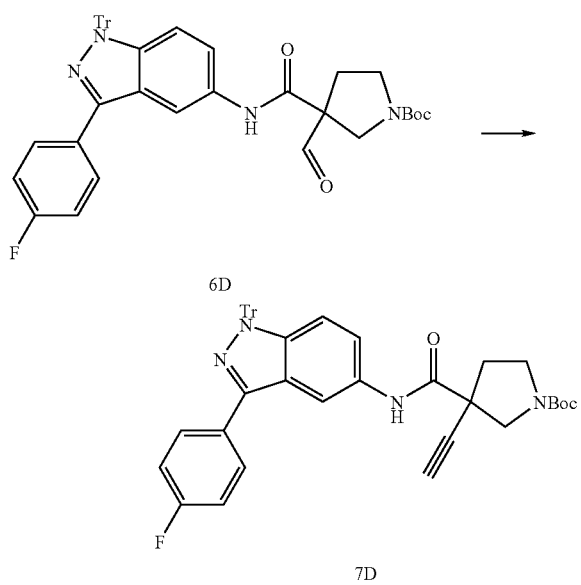

6D

7D

To a solution of crude aldehyde 6D (571 mg, 0.82 mmol) in MeOH (18 mL) was added K$_2$CO$_3$ (1.13 g, 8.2 mmol) and dimethyl-1-diazo-2-oxopropylphosphonate (prepared according to Miller, S.; Liepold, B.; Roth, G. J.; Bestmann, H. J. *Synlett*, 1996, 521-522) (474 mg, 2.5 mmol) at rt. The crude was stirred at rt for 1.5 hr. To the crude was added sat. NaHCO$_3$ and EtOAc. The aq layer was extracted with EtOAc. The combined organic layer was washed with brine, dried over MgSO$_4$, filtered, and conc in vacuum. The crude was purified via prep plate using EtOAc/hexane (3:7) to give 408 mg of 7D (72%) as a white solid. LCMS (M+H+, 691.4, rt=6.15)

Preparation 6

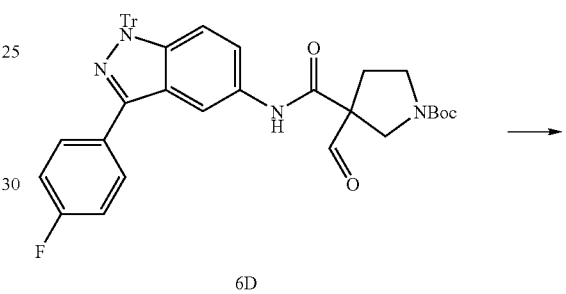

6D

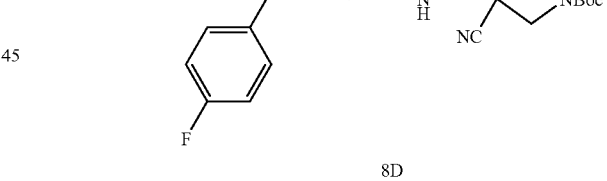

8D

To a solution of crude aldehyde 6D (315 mg, 0.45 mmol) in THF (2 mL) was added 28% wt NH$_4$OH (6 mL). The crude was stirred at rt for 2 mins before the addition of iodine (126 mg, 0.50 mmol). The crude was stirred at rt for 45 mins. The crude was quenched with sat. Na$_2$SO$_3$ and stirred vigorously for 15 mins. The crude was diluted in CH$_2$Cl$_2$. The aq layer was extracted with CH$_2$Cl$_2$. The combined organic layer was washed with aq NH$_4$Cl, brine, dried over MgSO$_4$, filtered, and conc in vacuum. The crude was purified via prep plate using EtOAc/hexane (2:5) to give 139 mg of 8D (45%) as a yellow solid. MS (M+H+, 692.27).

Preparation 7

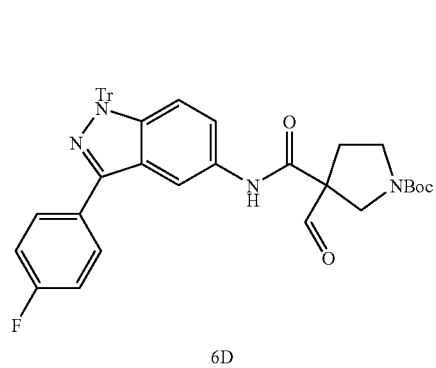

6D

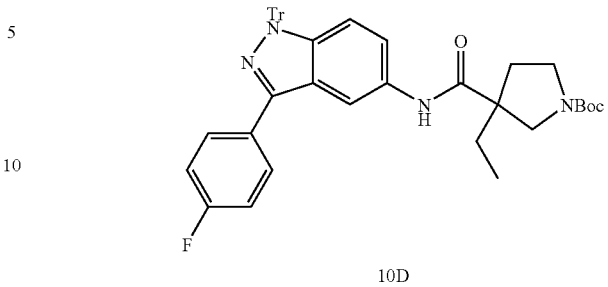

10D

To a solution of olefin 9D (60 mg, 0.086 mmol) in MeOH (10 mL) was added catalytic amount of 10% wt palladium on carbon. The mixture was stirred under a hydrogen atmosphere at room temperature overnight and filtered through celite. The filtrate was concentrated to provide 10D (47 mg). The material was used as such without further purification. MS (M+Na+, 717.28).

Preparation 9

Preparation of 3-Prop-2-ynyl-pyrrolidine-1,3-dicarboxylic acid 1-tert-butyl ester 3-methyl ester

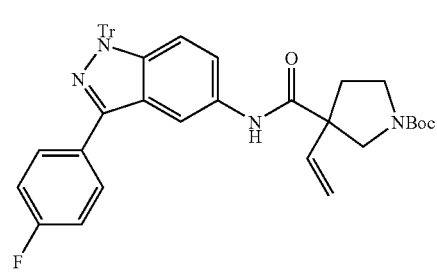

9D

To a solution of crude aldehyde 6D (600 mg, 0.86 mmol) in THF (5 mL) cooled to −40 deg C. was added a solution of Tebbe's reagent (0.5 mL, 0.25 mmol, 0.5 M solution in toluene). The crude was warmed to 0 deg C. in 1.5 hrs. The crude was diluted with ether and quenched with 1 N NaOH (1 mL, 1 mmol) at rt. The crude was stirred at rt for 10 mins. The crude was filtered through celite and concentrated in vacuum. The crude was purified via Biotage using EtOAc/hexane to give 165 mg of 9D (28%) as a yellow solid. MS (M+Na+, 715.24).

Preparation 8

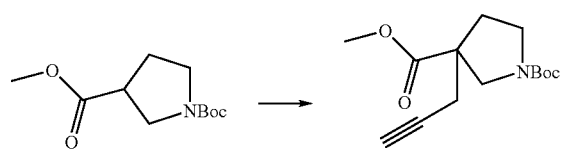

1D     2E

Pyrrolidine-1,3-dicarboxylic acid 1-tert-butyl ester 3-methyl ester 1 (6 mmol) was dissolved in THF (20 mL) and cooled down to −78° C. in a dry ice-acetone bath. LDA (5 mL, 2.0 M, 10 mmol) was then added dropwise. The mixture was stirred at −78° C. for 1 hr. Propargyl bromide (1.5 mL) was added in neat. The reaction was allowed to warm to rt naturally and stirred for 24 hrs. It was then quenched with sat. NH4Cl solution, extracted with ethyl acetate 2×50 mL. The organic layer was washed with brine, dried (MgSO4) and concentrated. The crude was purified on silica gel column using 4:1 hexanes/ethyl acetate to get the title compound (0.65 g) as an off-white gum. MS (267, M+H)

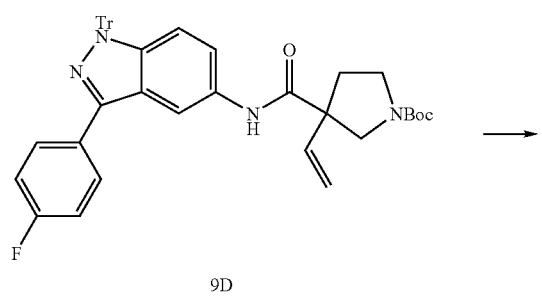

9D

Preparation 10

Preparation of 1-{2-Oxo-2-[4-(4-pyrimidin-2-yl-phenyl)-piperazin-1-yl]-ethyl}-3-(3H-[1,2,3]triazol-4-ylmethyl)-pyrrolidine-3-carboxylic acid [3-(4-fluoro-phenyl)-1H-indazol-5-yl]-amide

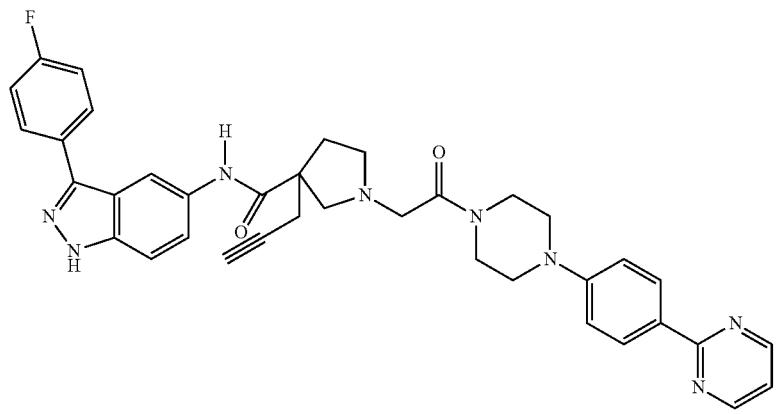

3E

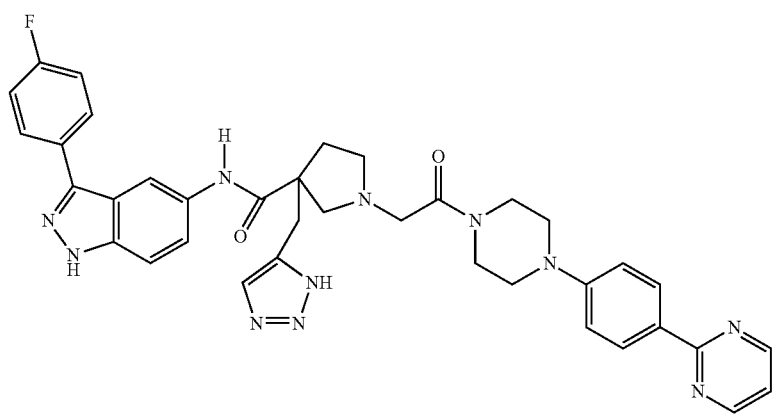

4E

1-{2-Oxo-2-[4-(4-pyrimidin-2-yl-phenyl)-piperazin-1-yl]-ethyl}-3-prop-2-ynyl-pyrrolidine-3-carboxylic acid [3-(4-fluoro-phenyl)-1H-indazol-5-yl]-amide 3E (0.085 g, 0.13 mmol) and CuI (1.3 mg) was suspended in 9:1 DMF/MeOH (1 mL) under Ar in a sealed vessel. TMSN3 (23 mg, 0.2 mmol) was then added. The mixture was heated at 100° C. overnight. After cooling to rt, the concentrated crude residue was purified by prep-TLC in 10% 2N—NH3/MeOH/CH$_2$Cl$_2$ to yield 4E as a solid (36 mg). MS (686, M+H)

Preparation 11

Preparation of 3-(3-Methoxy-propyl)-pyrrolidine-1,3-dicarboxylic acid 1-tert-butyl ester 3-methyl ester

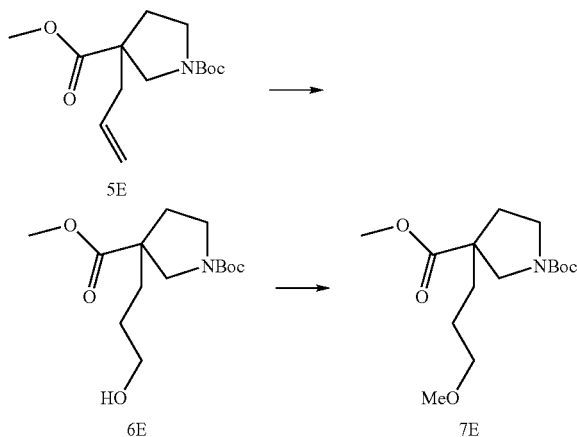

3-Allyl-pyrrolidine-1,3-dicarboxylic acid 1-tert-butyl ester 3-methyl ester 5E (538 mg, 2 mmol) was dissolved in THF (4 mL) and cooled to 0° C.. BH3 (3.8 mL, 1.0 M THF soln) was added in dropwise. After stirring at 0° C. for 15 mins, reaction was raised to rt for another 15 mins. 8 mL 1:1 EtOH/THF, 8 mL PH7 buffer and 8 mL 30% H2O2 were then added sequentially. The mixture was stirred at rt overnight and then partitioned between ethyl acetate (50 mL) and brine (30 mL). The organic layer was dried and concentrated. The residue was purified on silica eluting with 2:1 to 1:1 hexanes/ethyl acetate to obtain 6E (326 mg) as a colorless oil. MS (310, M+Na).

3-(3-Hydroxy-propyl)-pyrrolidine-1,3-dicarboxylic acid 1-tert-butyl ester 3-methyl ester 6E (90 mg) was dissolved in a mixture of THF/DMF (1.5 mL/0.5 mL) at rt. MeI (0.1 mL) was added followed by NaH (40 mg, 40% suspension). After 90 mins, the reaction was quenched with sat. NH4Cl soln and extracted with ethyl acetate. The organic layer was washed with brine, dried and conc. to yield 7E (96 mg) as a colorless oil. MS (324, M+Na).

Preparation 12

Preparation of 3-Fluoro-pyrrolidine-1,3-dicarboxylic acid 1-tert-butyl ester 3-methyl ester

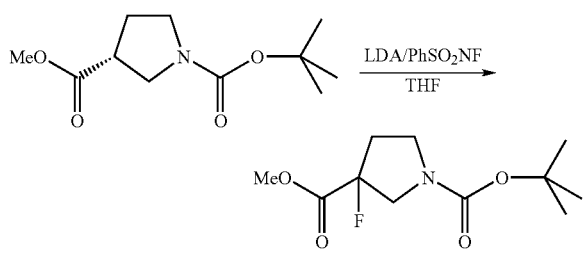

n-Butyl lithium (2.5M/Hexanes, 3.83 ml; 9.575 mmol) added dropwise to solution of diisopropylamine (1.36 ml; 9.62 mmol) at −78° C. Solution was allowed warm to room temperature and stirred for 30 minutes, then cooled to −78° C. A solution of Pyrrolidine-1,3-dicarboxylic acid 1-tert-butyl ester 3-methyl ester (2 g, 8.72 mmol) in THF (10 ml) was added dropwise, warmed to −40° C. for 1 hour, then cooled to −70° C. A solution of N-fluorobenzene-sulfonimide (3.02 g, 9.57 mmol) in THF (15 ml) was added dropwise, stirred at −78° C. for 1 hour, then stirred at room temperature overnight. Precipitated solid was filtered, washed with EtOAc (2×150 ml). Organic layer was washed with 1N HCl (30 ml), brine (100 ml), dried (MgSO$_4$), filtered and solvent evaporated. The residue was chromatographed on silica gel eluting with 10% v/v EtOc/hexanes yielding product as colorless oil (1.38 g: 64% yield). MS (ESMS, MH 249).

Preparation 13

Preparation of 3-(1-Acetoxy-ethyl)-1-benzyl-pyrrolidine-3-carboxylic acid methyl ester (3)

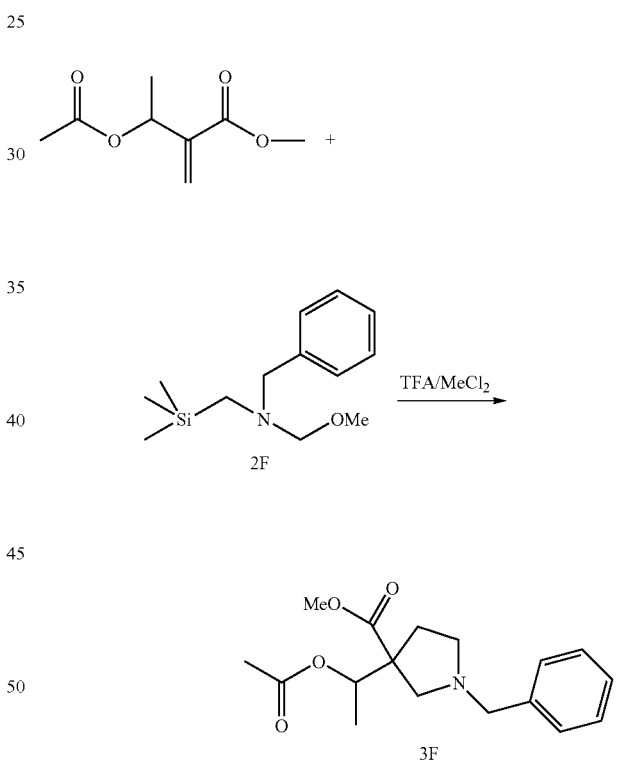

Trifluoroacetic acid (0.5 g, 4.38 mmol) was added to a solution of methyl-3-acetoxy-2-methylenebutyrate (5 g, 29.03 mmol) (1) and N-Methoxymethyl-N-trimethylsilylmethylbenzylamine (6.89 g, 29.03 mmol) (2) in MeCl$_2$ (100 ml) at 0° C., then stirred overnight at room temperature. The solvent was evaporated, and residue extracted with EtOAc (200 ml), NaHCO$_3$ (30 ml and H$_2$O (100 ml). The organic layer was separated, dried (MgSO$_4$), filtered and solvent evaporated yielding an oil which chromatographed on silica gel eluting with 30% v/v (EtOAc/hexanes) yielding product (3) as colorless oil (7.53 g, 85% yield). ESMS MH, 306 (C$_{17}$H$_{23}$NO$_4$)

Preparation 14

Preparation of 1-Benzyl-3-(1-hydroxy-ethyl)-pyrrolidine-3-carboxylic acid (4)

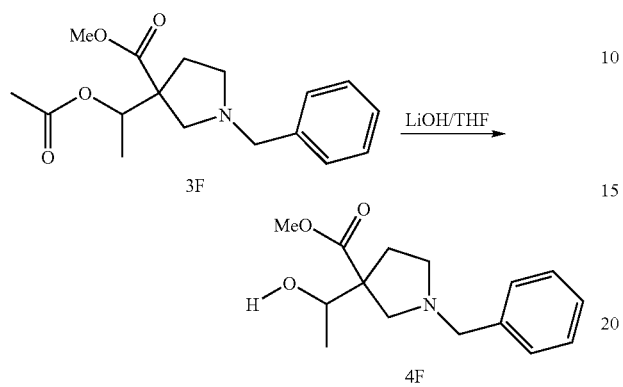

Lithium hydroxide (0.6 g, 14.29 mmol) in H$_2$O (5 ml) was added to a solution of 3-(1-Acetoxy-ethyl)-1-benzyl-pyrrolidine-3-carboxylic acid methyl ester (3F) (2 g, 6.55 mmol) in THF:MeOH (5:1 v/v) (30 ml) at room temperature, then refluxed for 1 hour. The solution was cooled and solvent evaporated yielding the product as the lithium salt of 4F. (2.0 g, 100%) ESMS (MH, 250)

Preparation 15

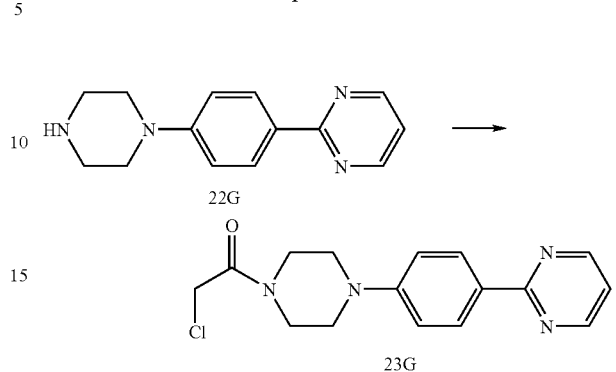

To a solution of 22G (1.54 g, 6.24 mmol) and TEA (1.16 mL, 8.11 mmol) in CH$_2$Cl$_2$ (60 mL) cooled in an ice bath was added chloroacetyl chloride (0.6 mL, 7.49 mmol) dropwise. The crude was stirred at 0 deg C. for 10 mins. To the crude was added water. The layers were separated, and the aq layer was extracted with CH$_2$Cl$_2$. The combined org. layer was washed with brine, dried over MgSO$_4$, filtered, and conc in vacuum to give 2.06 g of crude 23G. MS (M+H+, 317.4)

TABLE 16

| Ex | Compound |
|---|---|
| 260 | ![compound 260] |
| 261 | ![compound 261] Mass Spec (ESMS, MH): 628 <br> Retention Time minutes: 2.27 |

TABLE 16-continued
| Ex | Compound |
|---|---|
| 262 | 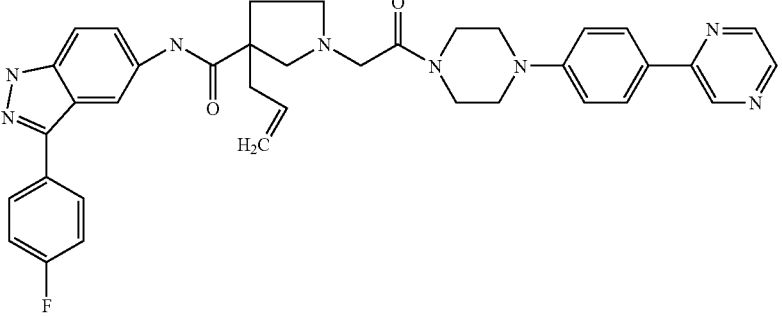<br>Mass Spec (ESMS, MH): 645<br>Retention Time minutes: 2.96 |
| 263 | 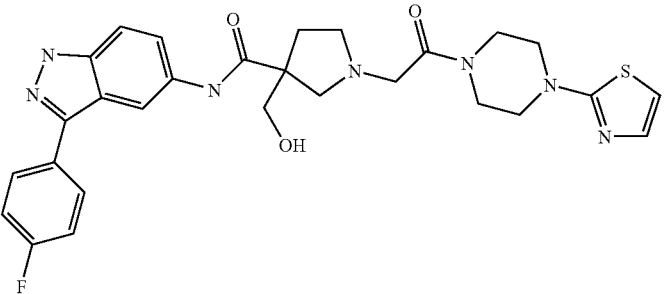 [SMILES: O=C(CN1CCC(CO)(C(=O)Nc2ccc3[nH]nc(-c4ccc(F)cc4)c3c2)C1)N1CCN(c2nccs2)CC1]<br>Mass Spec (ESMS, MH): 564<br>Retention Time minutes: 2.68 |
| 264 | 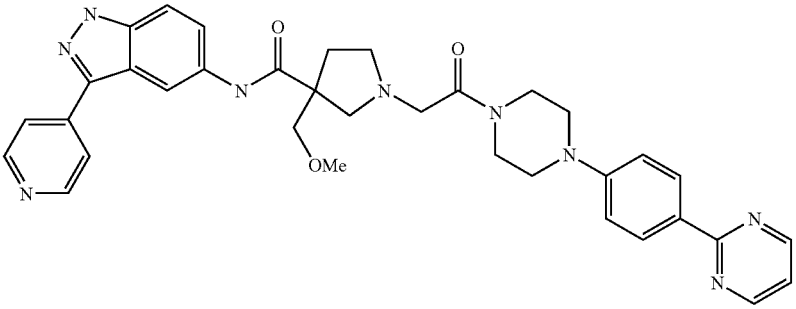 [SMILES: COCC1(C(=O)Nc2ccc3[nH]nc(-c4ccncc4)c3c2)CCN(CC(=O)N2CCN(c3ccc(-c4ncccn4)cc3)CC2)C1]<br>Mass Spec (ESMS, MH): 632<br>Retention Time minutes: 2.67 |
| 265 | 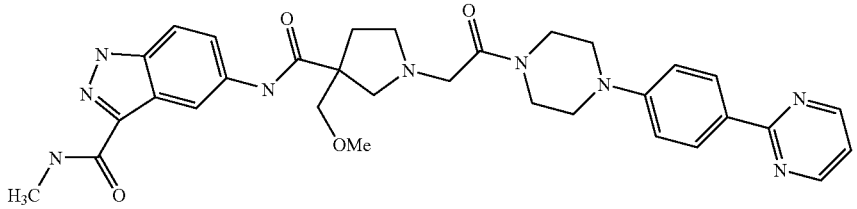 [SMILES: CNC(=O)c1n[nH]c2ccc(NC(=O)C3(COC)CCN(CC(=O)N4CCN(c5ccc(-c6ncccn6)cc5)CC4)C3)cc12]<br>Mass Spec (ESMS, MH): 612<br>Retention Time minutes: 3.01 |

TABLE 16-continued

| Ex | Compound |
|---|---|
| 266 | [Structure: 3-(4-fluorophenyl)-1H-indazol-5-yl amide of fluoropyrrolidine carboxamide linked via CH2C(O) to diazabicyclic amine N-substituted with 2-pyridyl]<br>Mass Spec (ESMS, MH): 572<br>Retention Time minutes: 2.5 |
| 267 | [Structure: 3-(4-fluorophenyl)-1H-indazol-5-yl amide of 3-fluoropyrrolidine-3-carboxamide linked via CH2C(O) to 2-methylpiperazine N-substituted with 5-(pyrimidin-2-yl)pyridin-2-yl]<br>Mass Spec (ESMS, MH): 638<br>Retention Time minutes: 2.68 |
| 268 | [Structure: 3-(4-fluorophenyl)-1H-indazol-5-yl amide of 3-fluoropyrrolidine-3-carboxamide linked via CH2C(O) to piperazine N-substituted with 5-(pyrimidin-2-yl)pyridin-2-yl]<br>Mass Spec (ESMS, MH): 624<br>Retention Time minutes: 2.61 |
| 269 | [Structure: 3-(pyridin-4-yl)-1H-indazol-5-yl amide of 3-(fluoromethyl)pyrrolidine-3-carboxamide linked via CH2C(O) to diazabicyclic amine N-substituted with 4-(pyrimidin-2-yl)phenyl]<br>Mass Spec (ESMS, MH): 632<br>Retention Time minutes: 2.51 |

TABLE 16-continued
| Ex | Compound |
|---|---|
| 270 | 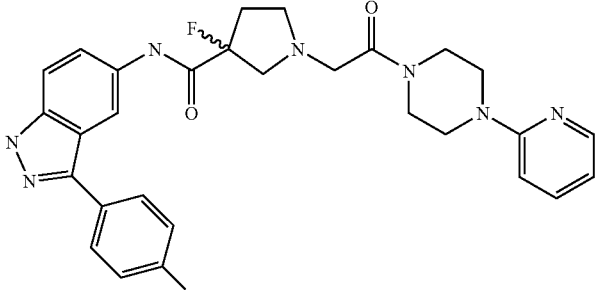
Mass Spec (ESMS, MH): 546
Retention Time minutes: 2.70 |
| 271 | 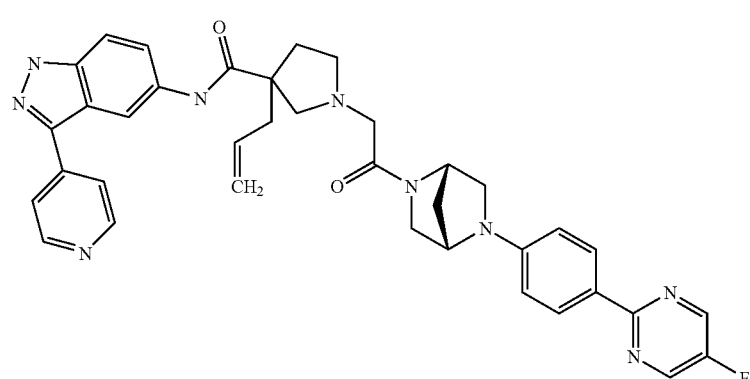
Mass Spec (ESMS, MH): 658
Retention Time minutes: 2.88 |
| 272 | 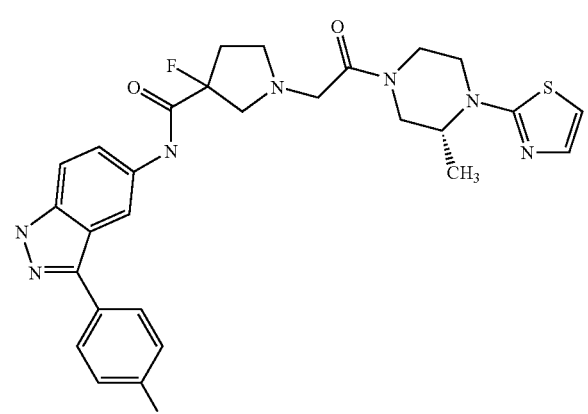
Mass Spec (ESMS, MH): 566
Retention Time minutes: 2.66 |
| 273 | 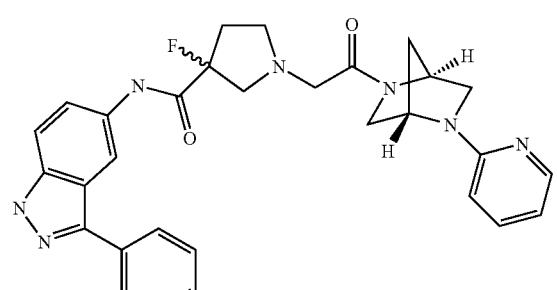
Mass Spec (ESMS, MH): 558
Retention Time minutes: 2.49 |

TABLE 16-continued
| Ex | Compound |
|---|---|
| 274 | 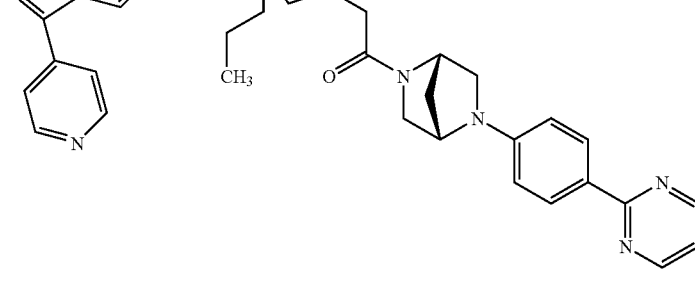
Mass Spec (ESMS, MH): 660
Retention Time minutes: 2.54 |
| 275 | 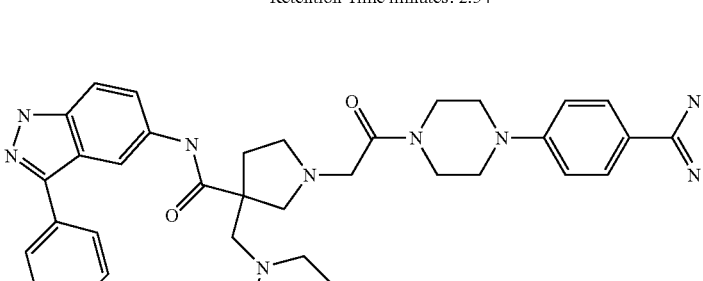
Mass Spec (ESMS, MH): 704
Retention Time minutes: 3.72 |
| 276 | 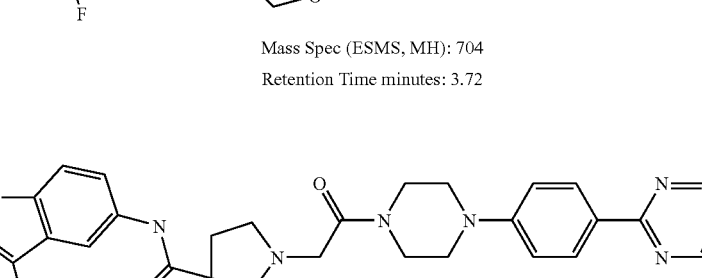
Mass Spec (ESMS, MH): 638
Retention Time minutes: 2.82 |
| 277 | 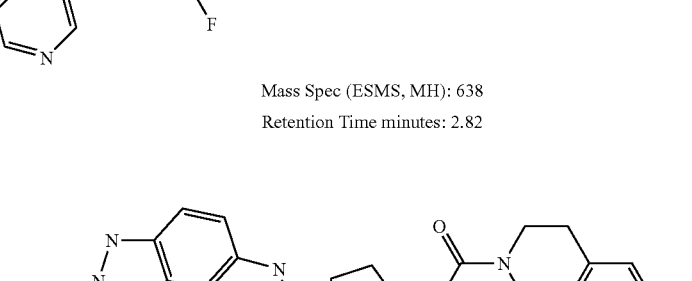
Mass Spec (ESMS, MH): 514
Retention Time minutes: 1.64 |

TABLE 16-continued

| Ex | Compound |
|---|---|
| 278 | Mass Spec (ESMS, MH): 620<br>Retention Time minutes: 3.25 |
| 279 | Mass Spec (ESMS, MH): 622<br>Retention Time minutes: 3.27 |
| 280 | Mass Spec (ESMS, MH): 515<br>Retention Time minutes: 1.75 |
| 281 | Mass Spec (ESMS, MH): 503<br>Retention Time minutes: 1.44 |
| 282 | Mass Spec (ESMS, MH): 549<br>Retention Time minutes: 1.73 |

TABLE 16-continued
| Ex | Compound |
|---|---|
| 283 | 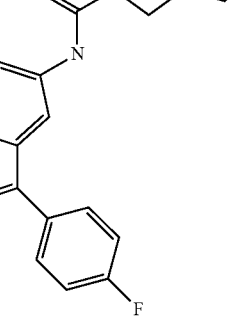
Mass Spec (ESMS, MH): 651
Retention Time minutes: 3.09 |
| 284 | 
Mass Spec (ESMS, MH): 561
Retention Time minutes: 2.62 |
| 285 | 
Mass Spec (ESMS, MH): 612
Retention Time minutes: 2.84 |
| 286 | 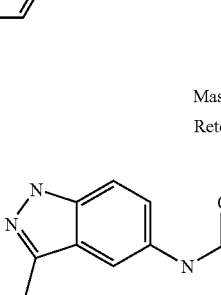
Mass Spec (ESMS, MH): 616
Retention Time minutes: 1.89 |

TABLE 16-continued

| Ex | Compound |
|---|---|
| 287 | Mass Spec (ESMS, MH): 704<br>Retention Time minutes: 2.59 |
| 288 | Mass Spec (ESMS, MH): 611<br>Retention Time minutes: 2.30 |
| 289 | Mass Spec (ESMS, MH): 628<br>Retention Time minutes: 2.25 |
| 290 | Mass Spec (ESMS, MH): 630<br>Retention Time minutes: 2.54 |

TABLE 16-continued

| Ex | Compound |
|---|---|
| 291 | Mass Spec (ESMS, MH): 663<br>Retention Time minutes: 3.22 |
| 292 | Mass Spec (ESMS, MH): 626<br>Retention Time minutes: 2.31 |
| 293 | Mass Spec (ESMS, MH): 643<br>Retention Time minutes: 3.22 |
| 294 | Mass Spec (ESMS, MH): 646<br>Retention Time minutes: 2.26 |

TABLE 16-continued
| Ex | Compound |
|---|---|
| 295 | 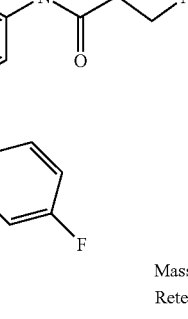
Mass Spec (ESMS, MH): 665
Retention Time minutes: 3.24 |
| 296 | 
Mass Spec (ESMS, MH): 649
Retention Time minutes: 3.15 |
| 297 | 
Mass Spec (ESMS, MH): 649
Retention Time minutes: 3.16 |
| 298 | 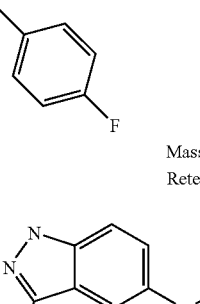
Mass Spec (ESMS, MH): 513
Retention Time minutes: 2.66 |

TABLE 16-continued
| Ex | Compound |
|---|---|
| 299 | 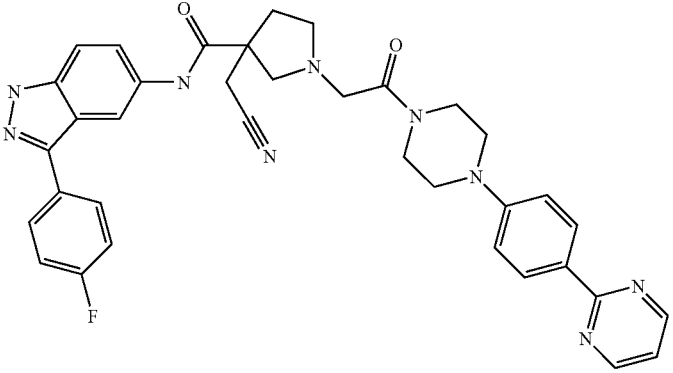 [SMILES: N#CCC1(C(=O)Nc2ccc3[nH]nc(-c4ccc(F)cc4)c3c2)CCN(CC(=O)N2CCN(c3ccc(-c4ncccn4)cc3)CC2)C1]<br>Mass Spec (ESMS, MH): 644<br>Retention Time minutes: 3.14 |
| 300 | 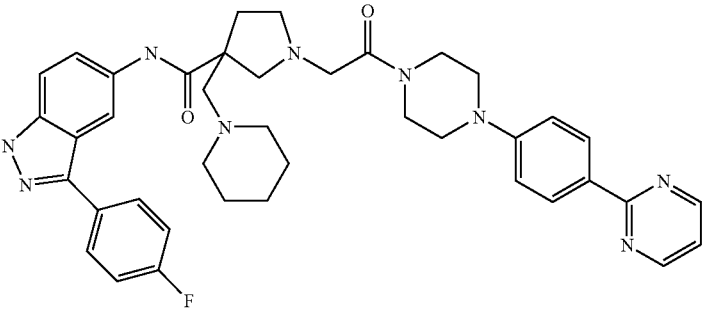 [SMILES: O=C(CN1CCC(CN2CCCCC2)(C(=O)Nc2ccc3[nH]nc(-c4ccc(F)cc4)c3c2)C1)N1CCN(c2ccc(-c3ncccn3)cc2)CC1] |
| 301 | 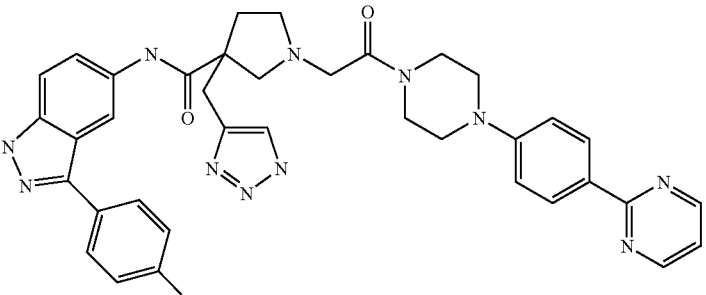<br>Mass Spec (ESMS, MH): 686<br>Retention Time minutes: 2.79 |
| 302 | <br>Mass Spec (ESMS, MH): 650<br>Retention Time minutes: 3.07 |

TABLE 16-continued
| Ex | Compound |
|---|---|
| 303 | <br>Mass Spec (ESMS, MH): 662<br>Retention Time minutes: 3.05 |
| 304 | <br>Mass Spec (ESMS, MH): 647<br>Retention Time minutes: 2.23 |
| 305 | 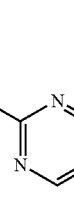<br>Mass Spec (ESMS, MH): 561<br>Retention Time minutes: 1.86 |
| 306 | <br>Mass Spec (ESMS, MH): 5.58<br>Retention Time minutes: 2.37 |

TABLE 16-continued
| Ex | Compound |
|---|---|
| 307 | 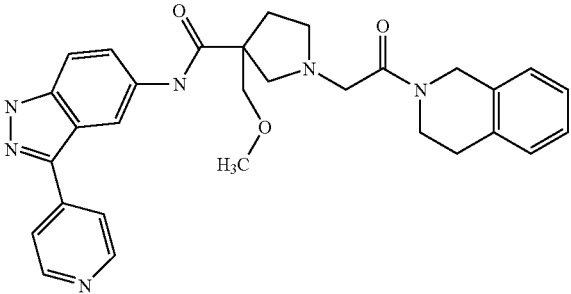 [SMILES: COCC1(C(=O)Nc2ccc3[nH]nc(-c4ccncc4)c3c2)CCN(CC(=O)N2CCc3ccccc3C2)C1]<br>Mass Spec (ESMS, MH): 525<br>Retention Time minutes: 2.68 |
| 308 | 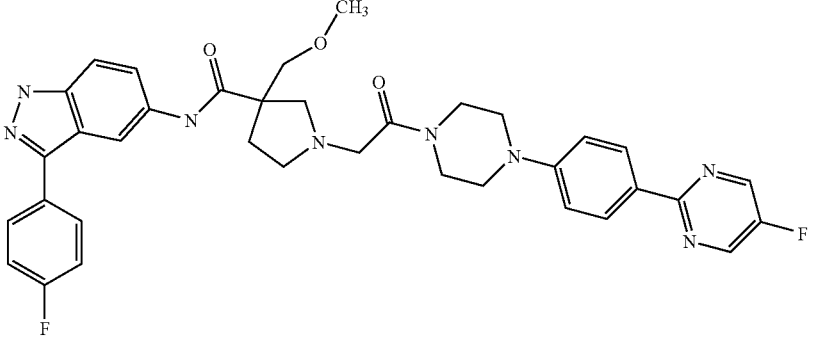 [SMILES: COCC1(C(=O)Nc2ccc3[nH]nc(-c4ccc(F)cc4)c3c2)CCN(CC(=O)N2CCN(c3ccc(-c4ncc(F)cn4)cc3)CC2)C1] |
| 309 | 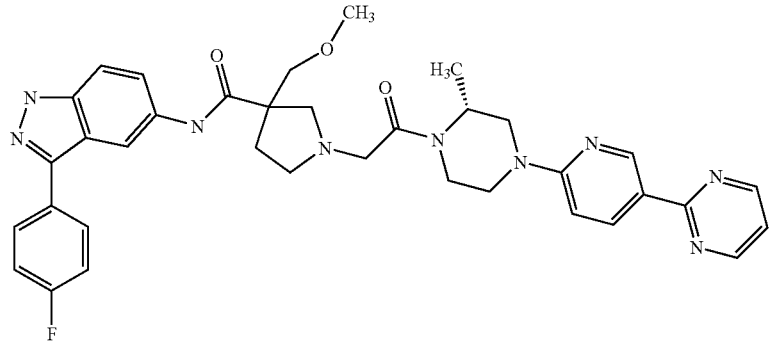 [SMILES: COCC1(C(=O)Nc2ccc3[nH]nc(-c4ccc(F)cc4)c3c2)CCN(CC(=O)N2CCN(c3ccc(-c4ncccn4)cn3)C[C@H]2C)C1] |
| 310 | 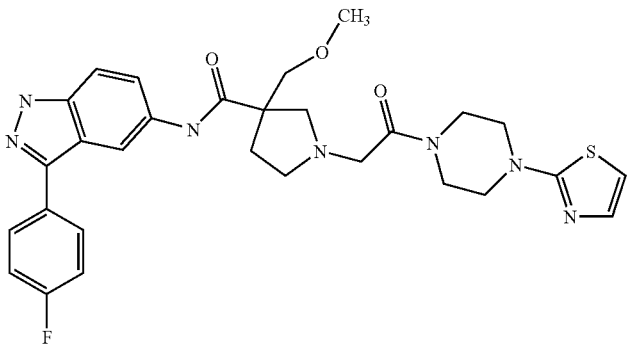 [SMILES: COCC1(C(=O)Nc2ccc3[nH]nc(-c4ccc(F)cc4)c3c2)CCN(CC(=O)N2CCN(c3nccs3)CC2)C1] |

TABLE 16-continued

| Ex | Compound |
|---|---|
| 311 | |
| 312 | |
| 313 | |
| 314 | |

Mass Spec (ESMS, MH): 666

Retention Time minutes: 3.70

TABLE 16-continued
| Ex | Compound |
|---|---|
| 315 | 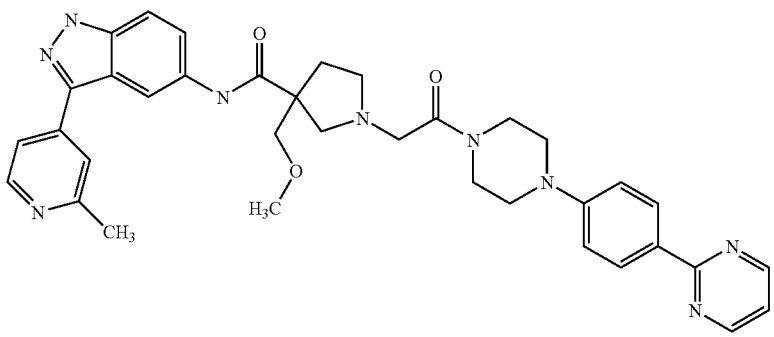 [SMILES: COCC1(C(=O)Nc2ccc3[nH]nc(-c4ccnc(Cl)c4)c3c2)CCN(CC(=O)N2CCN(c3ccc(-c4ncccn4)cc3)CC2)C1]<br>Mass Spec (ESMS, MH): 646<br>Retention Time minutes: 2.70 |
| 316 | 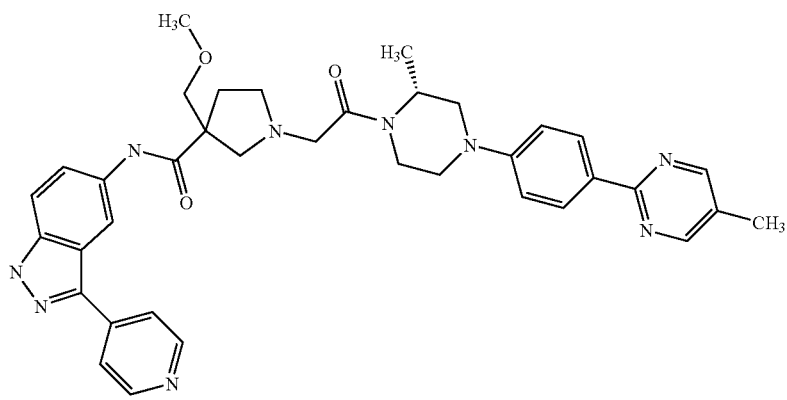 [SMILES: COCC1(C(=O)Nc2ccc3[nH]nc(-c4ccncc4)c3c2)CCN(CC(=O)N2CCN(c3ccc(-c4ncc(C)cn4)cc3)C[C@H]2C)C1]<br>Mass Spec (ESMS, MH): 660<br>Retention Time minutes: 2.48 |
| 317 | 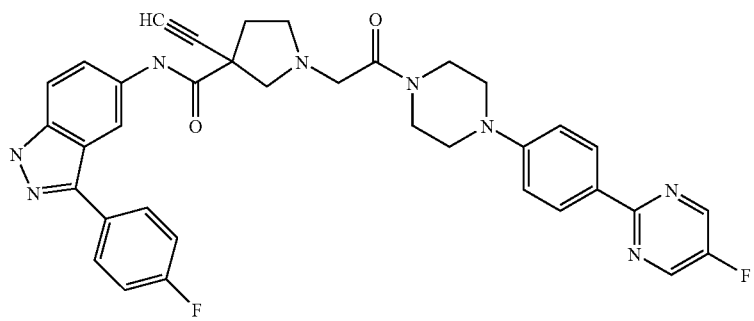 [SMILES: C#CC1(C(=O)Nc2ccc3[nH]nc(-c4ccc(F)cc4)c3c2)CCN(CC(=O)N2CCN(c3ccc(-c4ncc(F)cn4)cc3)CC2)C1]<br>Mass Spec (ESMS, MH): 647<br>Retention Time minutes: 2.98 |

TABLE 16-continued
| Ex | Compound |
|---|---|
| 318 | 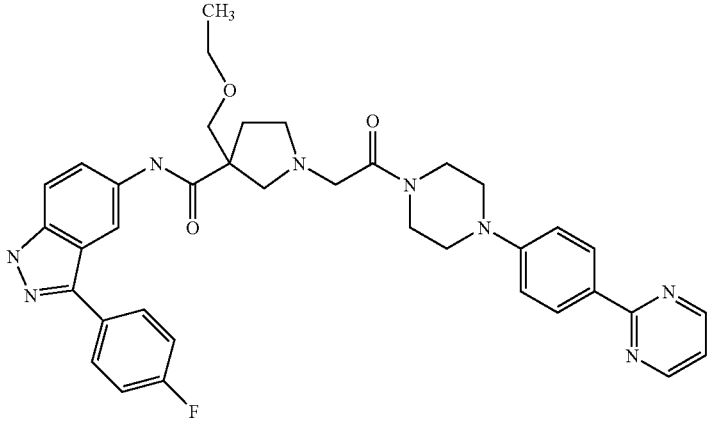 [SMILES: CCOCC1(C(=O)Nc2ccc3[nH]nc(-c4ccc(F)cc4)c3c2)CCN(CC(=O)N2CCN(c3ccc(-c4ncccn4)cc3)CC2)C1]<br>Mass Spec (ESMS, MH): 663<br>Retention Time minutes: 2.79 |
| 319 | 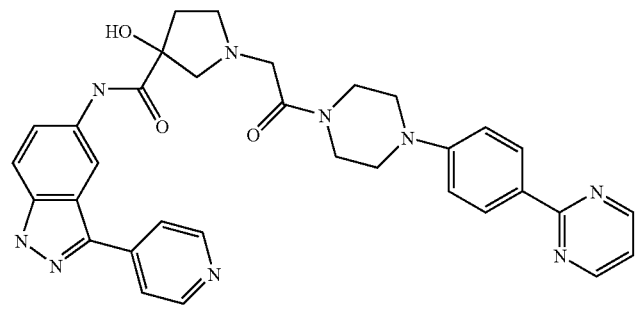 [SMILES: O=C(CN1CCC(O)(C(=O)Nc2ccc3[nH]nc(-c4ccncc4)c3c2)C1)N1CCN(c2ccc(-c3ncccn3)cc2)CC1] |
| 320 | 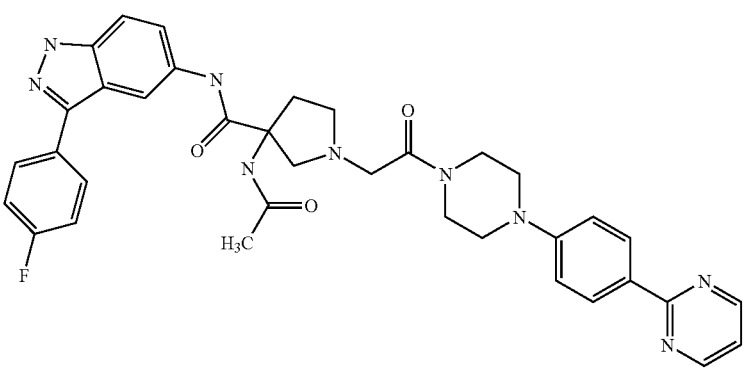 [SMILES: CC(=O)NC1(C(=O)Nc2ccc3[nH]nc(-c4ccc(F)cc4)c3c2)CCN(CC(=O)N2CCN(c3ccc(-c4ncccn4)cc3)CC2)C1]<br>Mass Spec (ESMS, MH): 662<br>Retention Time minutes: 2.73 |
| 321 | 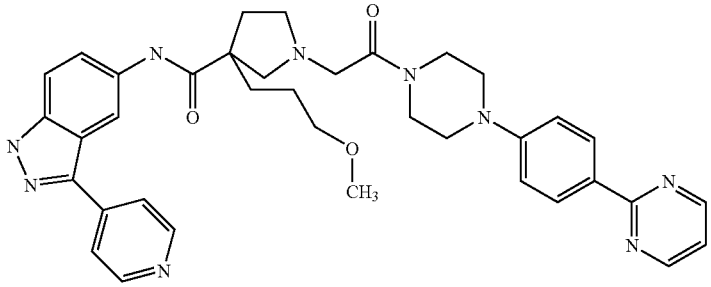 [SMILES: COCCCC1(C(=O)Nc2ccc3[nH]nc(-c4ccncc4)c3c2)CCN(CC(=O)N2CCN(c3ccc(-c4ncccn4)cc3)CC2)C1]<br>Mass Spec (ESMS, MH): 660<br>Retention Time minutes: 1.93 |

TABLE 16-continued
| Ex | Compound |
|----|----------|
| 322 | 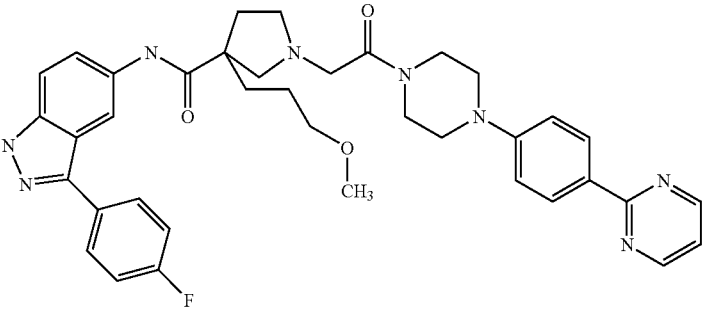 [SMILES: COCCCC1(C(=O)Nc2ccc3[nH]nc(-c4ccc(F)cc4)c3c2)CCN(CC(=O)N2CCN(c3ccc(-c4ncccn4)cc3)CC2)C1]
Mass Spec (ESMS, MH): 677
Retention Time minutes: 2.70 |
| 323 | 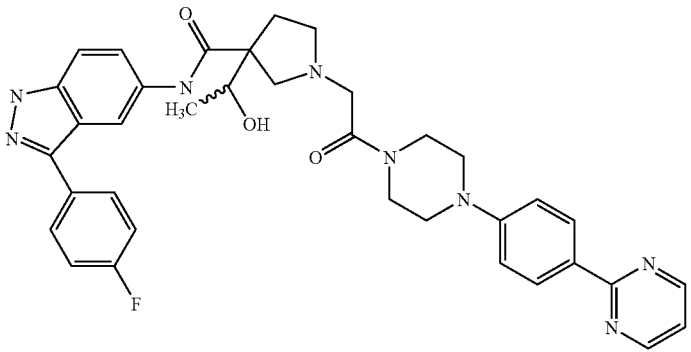 [SMILES: CC(O)C1(C(=O)Nc2ccc3[nH]nc(-c4ccc(F)cc4)c3c2)CCN(CC(=O)N2CCN(c3ccc(-c4ncccn4)cc3)CC2)C1]
Mass Spec (ESMS, MH): 649
Retention Time minutes: 2.72 |
| 324 | 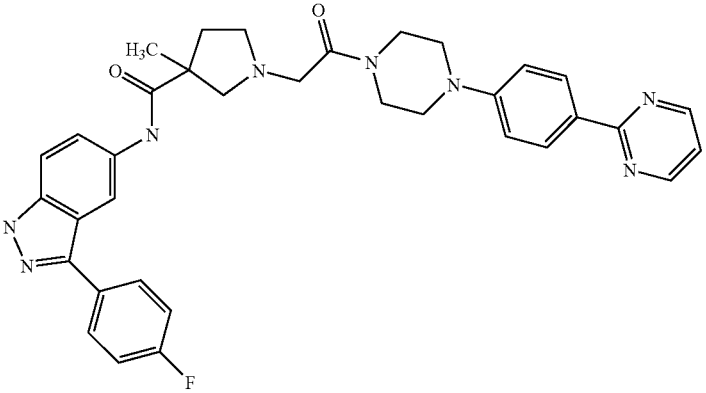 [SMILES: CC1(C(=O)Nc2ccc3[nH]nc(-c4ccc(F)cc4)c3c2)CCN(CC(=O)N2CCN(c3ccc(-c4ncccn4)cc3)CC2)C1]
Mass Spec (ESMS, MH): 619
Retention Time minutes: 3.61 |

TABLE 16-continued
| Ex | Compound |
|---|---|
| 325 | 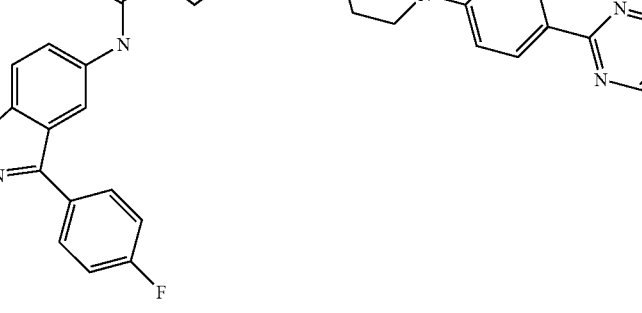<br>Mass Spec (ESMS, MH): 621<br>Retention Time minutes: 3.69 |
| 326 | 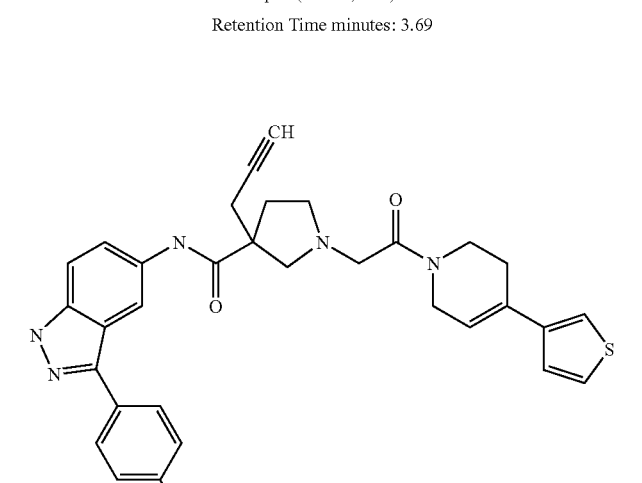<br>Mass Spec (ESMS, MH): 568<br>Retention Time minutes: 3.52 |
| 327 | 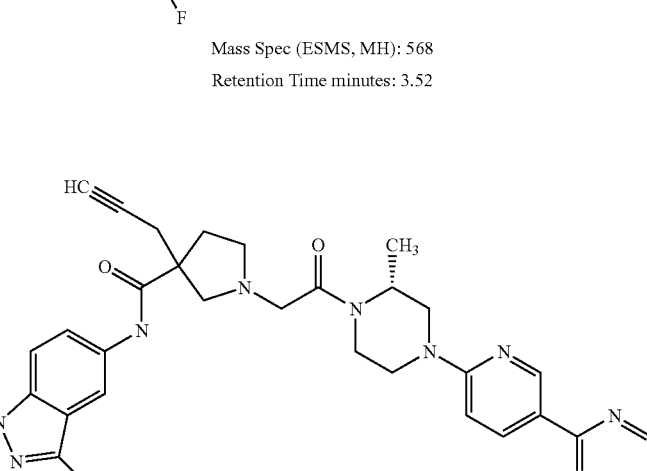<br>Mass Spec (ESMS, MH): 658<br>Retention Time minutes: 2.68 |

| Ex | Compound |
|---|---|
| 328 | 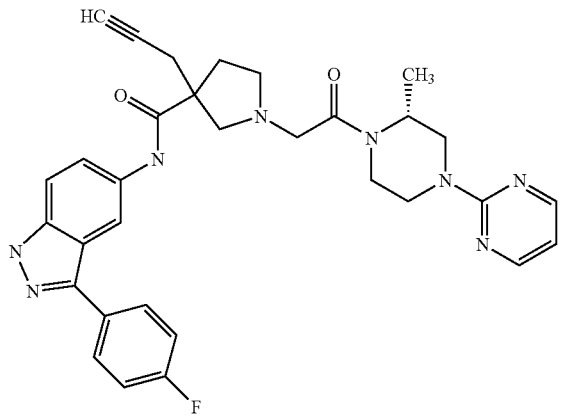 [SMILES: C#CCC1(C(=O)Nc2ccc3[nH]nc(-c4ccc(F)cc4)c3c2)CCN(CC(=O)N2CCN(c3ncccn3)C[C@H]2C)C1]
Mass Spec (ESMS, MH): 581
Retention Time minutes: 2.95 |
| 329 | 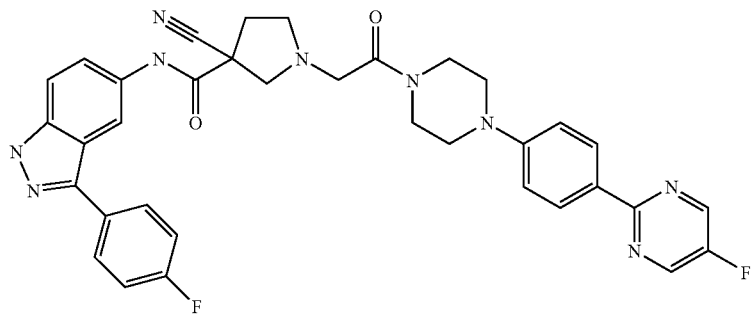 [SMILES: N#CC1(C(=O)Nc2ccc3[nH]nc(-c4ccc(F)cc4)c3c2)CCN(CC(=O)N2CCN(c3ccc(-c4ncc(F)cn4)cc3)CC2)C1]
Mass Spec (ESMS, MH): 648
Retention Time minutes: 3.18 |
| 330 | 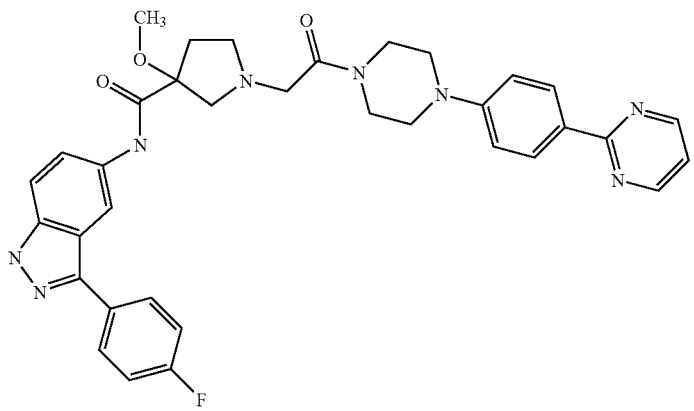 [SMILES: COC1(C(=O)Nc2ccc3[nH]nc(-c4ccc(F)cc4)c3c2)CCN(CC(=O)N2CCN(c3ccc(-c4ncccn4)cc3)CC2)C1]
Mass Spec (ESMS, MH): 635
Retention Time minutes: 3.82 |

TABLE 16-continued
| Ex | Compound |
|---|---|
| 331 | 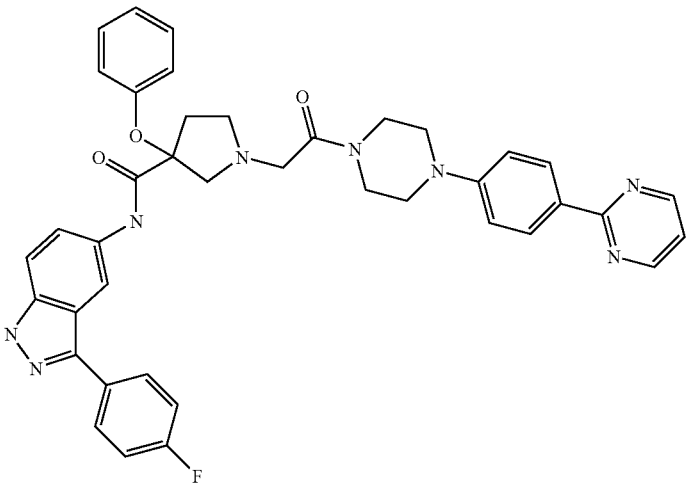 [SMILES: O=C(CN1CCC(Oc2ccccc2)(C(=O)Nc2ccc3[nH]nc(-c4ccc(F)cc4)c3c2)C1)N1CCN(c2ccc(-c3ncccn3)cc2)CC1] |
| 332 | 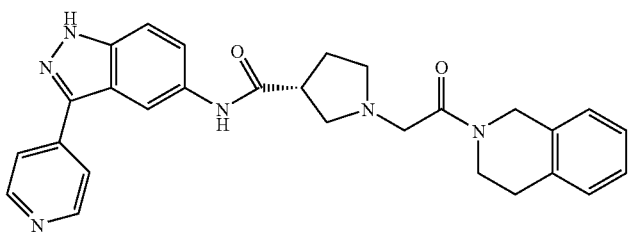 [SMILES: O=C(Nc1ccc2[nH]nc(-c3ccncc3)c2c1)[C@@H]1CCN(CC(=O)N2CCc3ccccc3C2)C1]
Mass Spec (ESMS, MH): 481
Retention Time minutes: 2.55 |
| 333 | 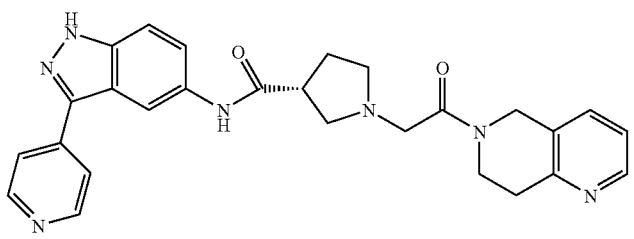 [SMILES: O=C(Nc1ccc2[nH]nc(-c3ccncc3)c2c1)[C@@H]1CCN(CC(=O)N2CCc3ncccc3C2)C1] |
| 334 | 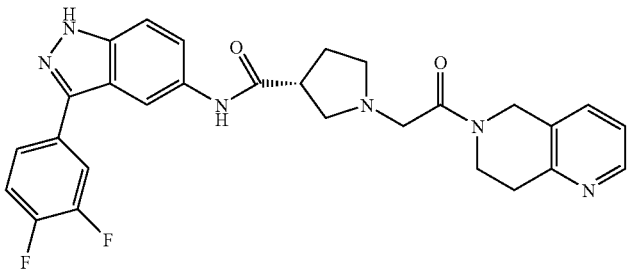 [SMILES: O=C(Nc1ccc2[nH]nc(-c3ccc(F)c(F)c3)c2c1)[C@@H]1CCN(CC(=O)N2CCc3ncccc3C2)C1] |

Example 335

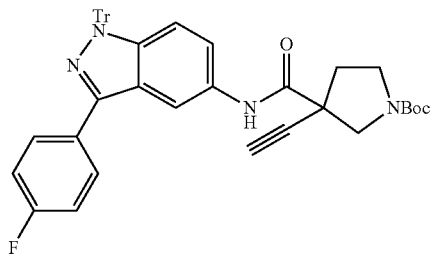

7D

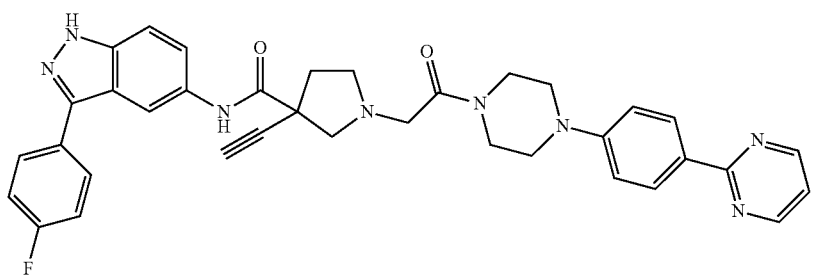

To a solution of 7D (Preparation 5 in Examples 260-334) (206 mg, 0.30 mmol) in CH$_2$Cl$_2$ (3 mL) was added TFA (3 mL). The crude was stirred at rt for 2 hrs. The crude was partially conc in vacuum. The crude was quenched with MeOH (5 mL). The crude was conc in vacuum and azeotroped with toluene 2× and dried under high vac prior to further use. To this crude amine and TEA (0.3 mL, excess) in dioxane (2 mL) was added crude 23G (Preparation 15 in Examples 260-334) (132 mgs, 0.42 mmol) at rt. The crude was stirred at 80 deg C. under nitrogen overnight. The crude was quenched with water and diluted in EtOAc. The layers were separated, and the aq layer was extracted with CH$_2$Cl$_2$ 2×. The combined org. layer was washed with brine, dried over Na$_2$SO$_4$, filtered, and conc in vacuum. The crude was purified via prep plate using 2M NH$_3$ in MeOH/CH$_2$Cl$_2$ (5/95) to give 116 mgs (62%) of an off white solid. LCMS (M+H+, 647.4, retention time=2.98 min)

Example 336

Preparation of 3-Methoxymethyl-1-{2-[4-(4-pyrimidin-2-yl-phenyl)-3,6-dihydro-2H-pyridin-1-yl]-acetyl}-pyrrolidine-3-carboxylic acid [3-(2-cyclopropyl-pyridin-4-yl)-1H-indazol-5-yl]-amide

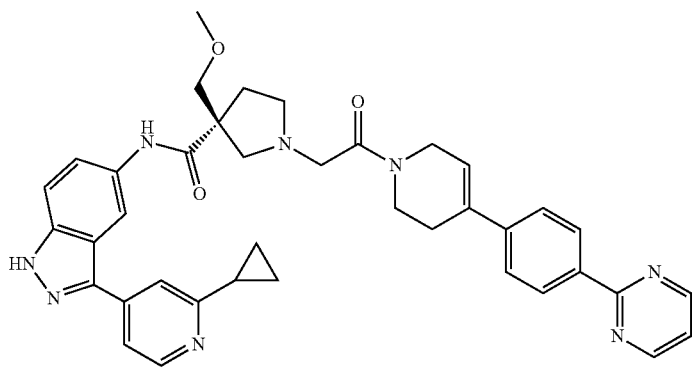

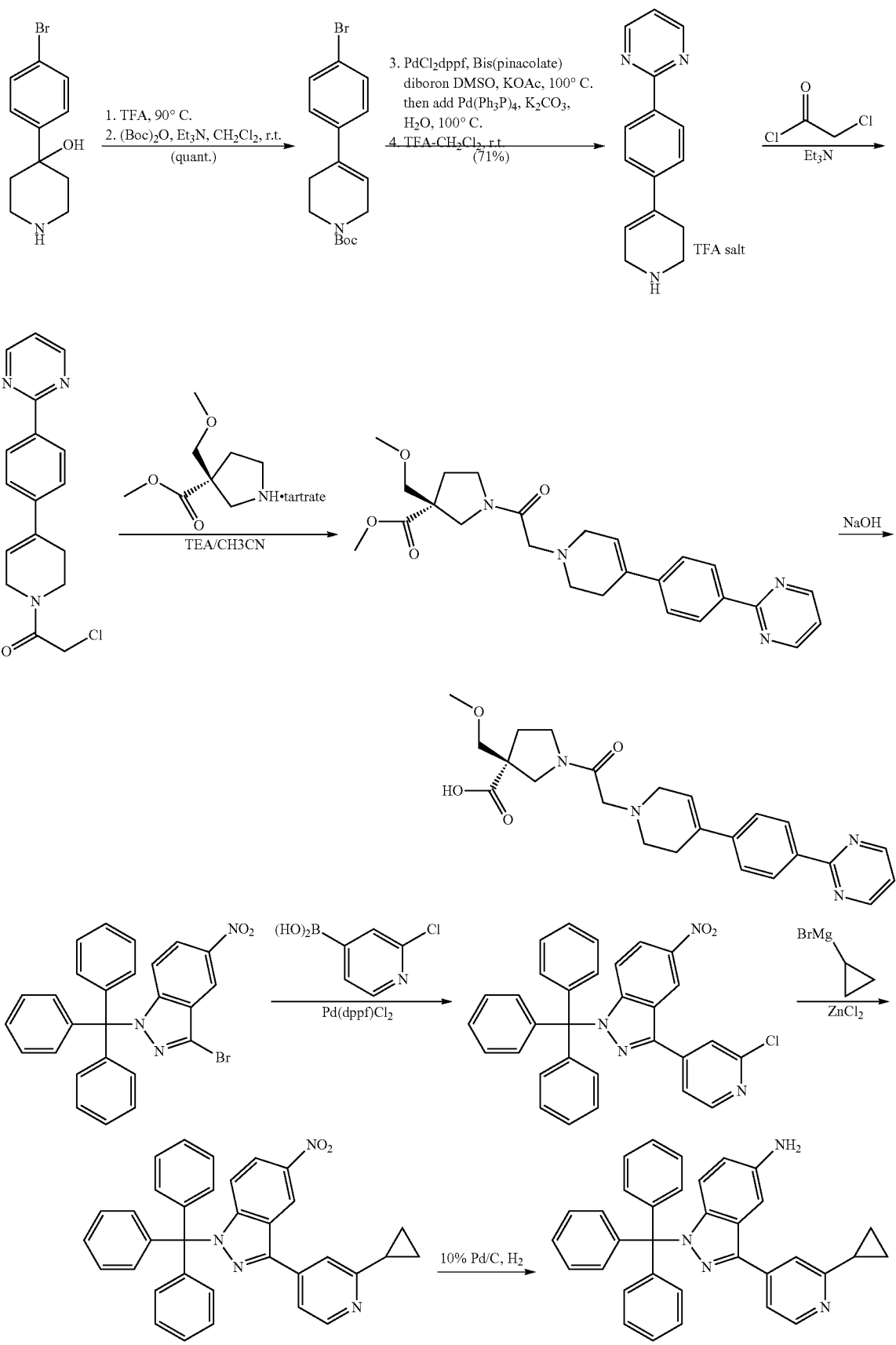

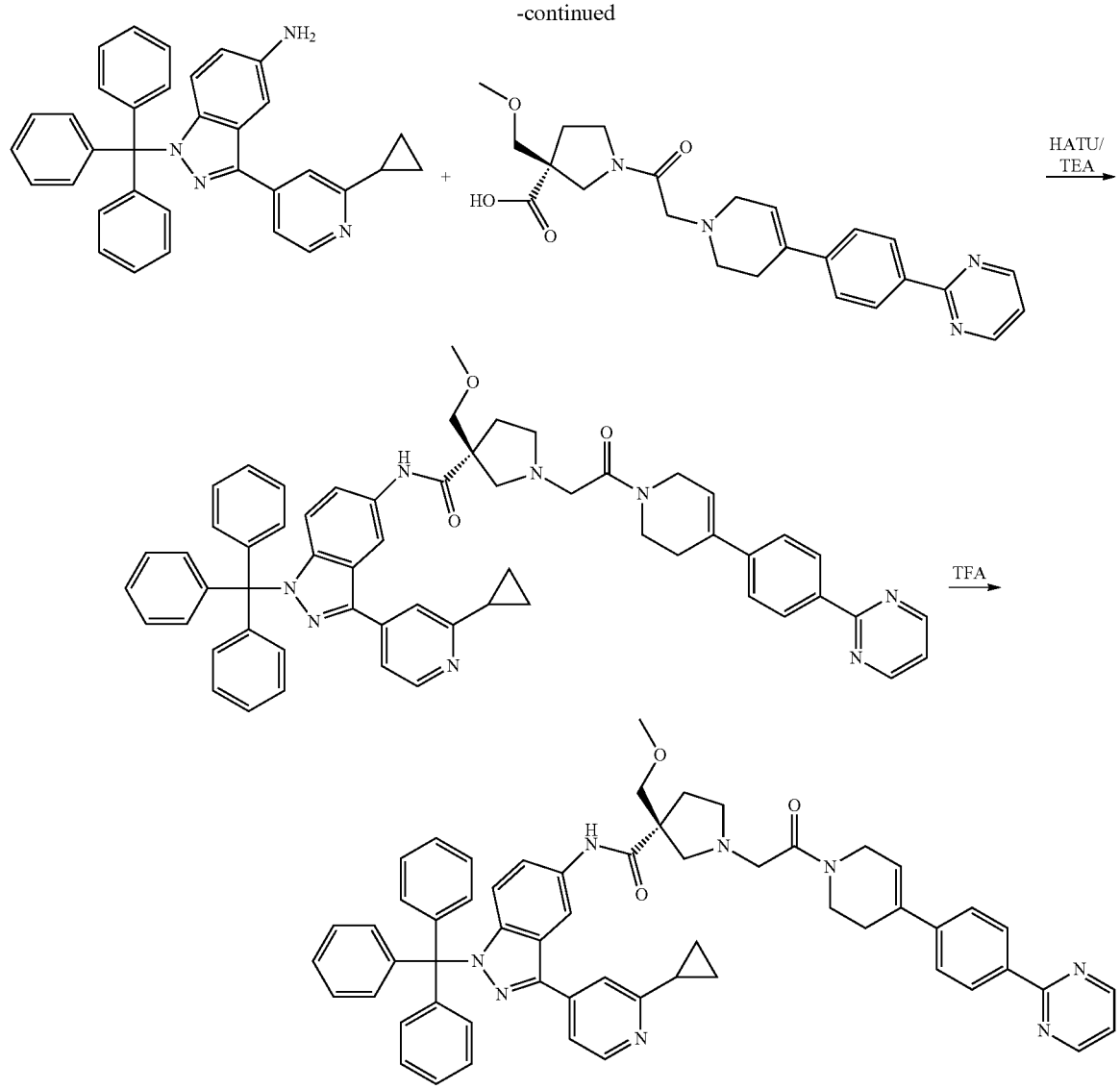

Procedure for the Preparation of 2-[4-(1,2,3,6-Tetrahydro-pyridin-4-yl)-phenyl]-pyrimidine trifluoroacetic acid salt

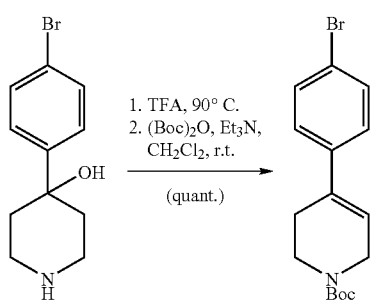 [SMILES: OC1(c2ccc(Br)cc2)CCNCC1 ; CC(C)(C)OC(=O)N1CC=C(c2ccc(Br)cc2)CC1]

Step 1

4-(4-Bromophenyl)-4-piperidinol (68 g, 0.27 mol) was added in small portions to a solution of trifluoroacetic acid (205 ml) at r.t. and the mixture was heated at 90° C. for 2 hr. Solvents were then removed in vacuum to give 4-(4-bromophenyl)-1,2,3,6-tetrahydropyridine as pale yellow oil. The yellow oil was used in the next step without further purification.

Step 2

4-(4-Bromophenyl)-1,2,3,6-tetrahydropyridine (crude from step 1) was stirred in dichloromethane (500 ml) at r.t. Triethylamine (148 ml, 1.06 mol) followed by (Boc)₂O (87 g, 0.40 mol) were added. The suspension slowly dissolved and the yellow solution was stirred at r.t. for 2 hr. The mixture was washed with water (×2), dried (MgSO₄) and chromatograph through a short pad of silica. The fractions with the product 4-(4-Bromophenyl)-3,6-dihydro-2H-pyridine-1-carboxylic acid tert-butyl ester were combined and solvents were removed in vacuum to give pale yellow oil which solidified on standing at r.t. to become white solid (91 g, quant.)

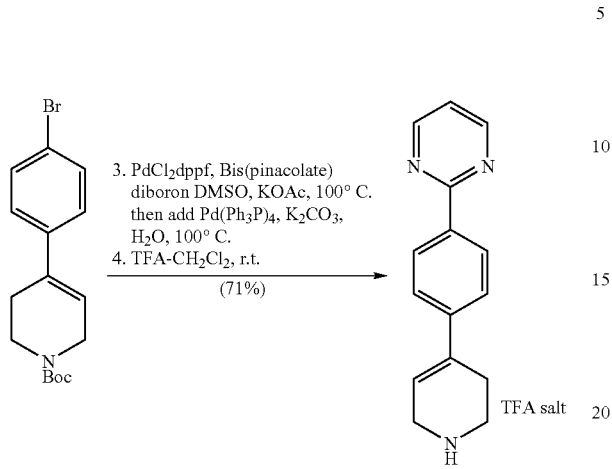

Step 3

4-(4-Bromophenyl)-3,6-dihydro-2H-pyridine-1-carboxylic acid tert-butyl ester (19.5 g, 0.058 mol), bis(pinacolate) diboron (22.0 g, 0.086 mol), $PdCl_2(dppf).CH_2Cl_2$ (4.74 g, 0.0058 mol), potassium acetate (17.0 g, 0.17 mol) were weighted into a 1 L 2-necked round bottomed flask equipped with a reflux condenser. Methyl sulfoxide (400 ml) was added and the mixture was purged with nitrogen for 20 min before it was heated at 100° C. for 2 hr under nitrogen. The mixture was cooled to r.t. Potassium carbonate (40 g, 0.29 mol), 2-bromopyrimidine (11.0 g, 0.070 mol) and water (200 ml) were added. The mixture was again purged with nitrogen for 20 min. Palladium tetrakistriphenylphosphine (2.4 g, 0.0029 mol) was added and the final mixture was stirred at 100° C. for a further 2 hr. After being cooled to r.t., ethyl acetate and water were added. The mixture was filtered through a pad of Celite. Layers were separated and the organic layer was washed with water (×2). The combined aqueous layers were extracted with ethyl acetate (×1). The combined organic layers were stirred with enough charcoal to give a yellow solution. The mixture was filtered through a pad of Celite and the solvents in the filtrate were removed in vacuum to give 4-(4-pyrimidin-2-yl-phenyl)-3,6-dihydro-2H-pyridine-1-carboxylic acid tert-butyl ester as dark brown oil.

Step 4

4-(4-pyrimidin-2-yl-phenyl)-3,6-dihydro-2H-pyridine-1-carboxylic acid tert-butyl ester (crude from step 3) was dissolved in dichloromethane (200 ml) and trifluoroacetic acid (22 ml, 0.29 mol) was added at r.t. The mixture was stirred at r.t. for 5 hr and solvents were removed in vacuum. Diethyl ether was added and off-white solid was formed. The solid was filtered and washed with diethyl ether to give a salt (14.4 g, 71%).

Preparation of 2-Chloro-1-[4-(4-pyrimidin-2-yl-phenyl)-3,6-dihydro-2H-pyridin-1-yl]-ethanone 2-[4-(1,2,3,6-Tetrahydro-pyridin-4-yl)-phenyl]-pyrimidine trifluoroacetate (2.3 g, 9.7 mmol) was dissolved in 75 ml of dichloromethane and 4.1 ml of triethylamine added at 0 C. Chloroacetylchloride (0.92 ml, 11.7 mmol) was added and the reaction mixture stirred for 30 min. The reaction mixture was washed with a solution of saturated sodium bicarbonate (80 ml), the organic layer separated, dried over magnesium sulfate and evaporated to obtain 2.41 g of crystalline product. Chiral salt resolution of 3-methoxy-pyrrolidine-3-carboxylic acid methyl ester

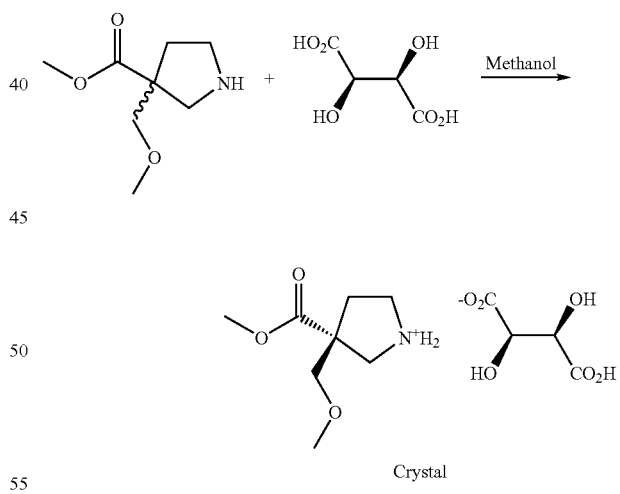

To a solution of 3-Methoxymethyl-pyrrolidine-3-carboxylic acid methyl ester (6.1 g, 35.8 mmol) in methanol (50 mL) was added L-tartaric acid (5.11 g, 34 mmol) and the formed mixture was sonicated to ensure the dissolve of tartaric acid. The solution was left standing at room temperature and crystals started forming after less than 10 minutes. After standing at RT for over night, the formed crystal was filtered, washed with cold methanol and was re-crystallized using 25 mL of methanol to give 2.2 gram material.

Preparation of 3-Methoxymethyl-1-{2-[4-(4-pyrimidin-2-yl-phenyl)-3,6-dihydro-2H-pyridin-1-yl]-acetyl}-pyrrolidine-3-carboxylic acid methyl ester

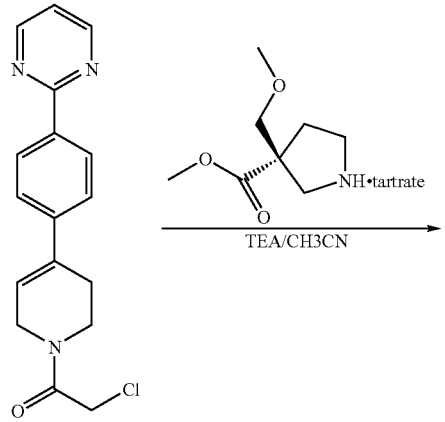

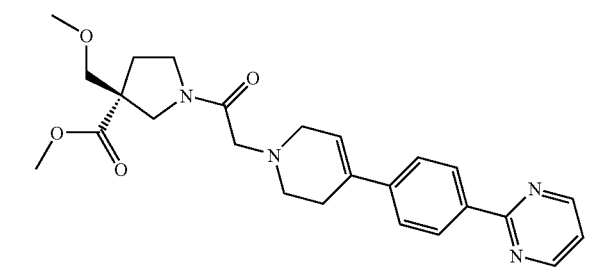

3-Methoxymethyl-pyrrolidine-3-carboxylic acid methyl ester tartaric acid salt 1.54 gm, 4.85 mmol) in 25 ml of acetonitrile was added 2-Chloro-1-[4-(4-pyrimidin-2-yl-phenyl)-3,6-dihydro-2H-pyridin-1-yl]-ethanone (2.2 gm, 5.82 mmol), triethylamine (3.4 ml, 24.3 mmol) and the reaction mixture stirred at 80 C for 18 hrs. The reaction mixture was evaporated, and extracted into dichloromethane from water. The dichloromethane extracts were dried over $Na_2SO_4$, filtered and evaporated. The mixture was chromatographed on silica gel using 2-3% MeOH/dichlormethane to obtain 1.5 gm of title compound.

Preparation of 3-(2-Chloro-pyridin-4-yl)-5-nitro-1-trityl-1H-indazole

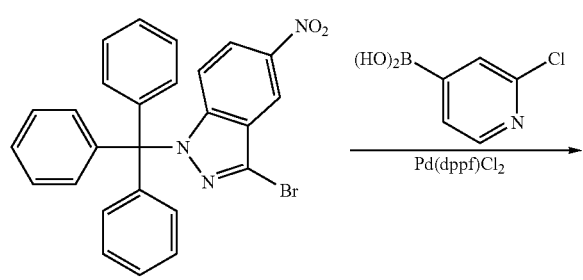

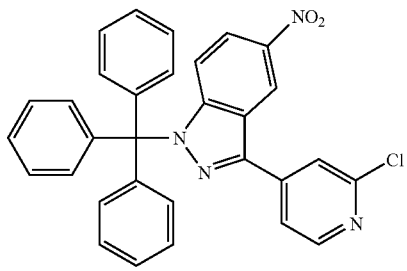

3-Bromo-5-nitro-1-trityl-1H-indazole (24.3 gm, 50 mmol) was stirred and degassed under nitrogen in dioxane/water (150/60 ml). Pyridine-2-chloro-4-boronic acid (8.7 gm, 55 mmol), Pd(dppf)Cl2 (4.1 gm, 5 mmol) and $K_3PO_4$ (26.5 g, 125 mmol) added. The reaction mixture was stirred at 80 C for 18 hrs. The reaction mixture was evaporated to dryness, dissolved in dichloromethane, filtered through a silica gel plug and washed with 20% ethylacetate/hexanes to obtain 22 gm of title product.

Preparation of 3-(2-Cyclopropyl-pyridin-4-yl)-5-nitro-1-trityl-1H-indazole

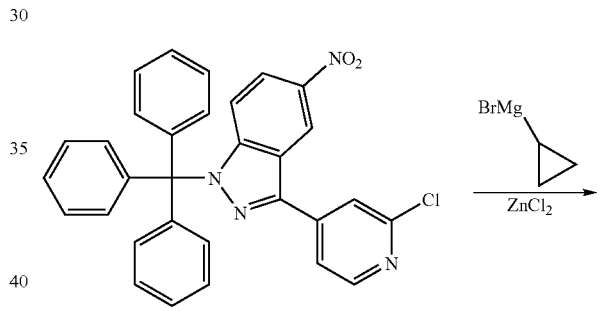

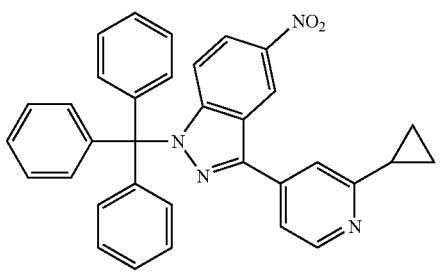

To a tube under nitrogen was added 36.2 ml ZnCl2 (0.5 M in THF, 18.02 mmol) followed by cyclopropylmagnesium bromide (34 ml of 0.5 M in THF soln., 16 mmol). The resultant mixture was stirred for 20 min at r.t. NMP (23 ml) was added, stirred for 5 min followed by 3-(2-Chloro-pyridin-4-yl)-5-nitro-1-trityl-1H-indazole (5.5 gm, 10.6 mmol) and $Pd[P(tBu)_3]_2$ (0.108 gm, 0.22 mmol). The tube was sealed under nitrogen and stirred at 100 C for 18 hrs. The reaction mixture was then cooled and evaporated to dryness. Silica gel chromatography using 5-20% ethylacetate/hexanes gave 2.1 g of title product.

Preparation of 3-(2-Cyclopropyl-pyridin-4-yl)-1-trityl-1H-indazol-5-ylamine

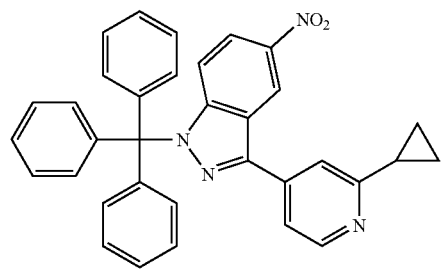

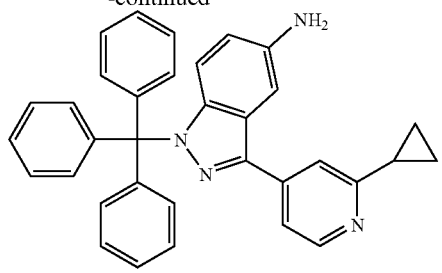

3-(2-Cyclopropyl-pyridin-4-yl)-5-nitro-1-trityl-1H-indazole (2 gm) was dissolved in 20 mol of 50% methanol/toluene and balloon hydrogenated for 18 hrs in the presence of 0.4 gm of 50% by weight 10% Pd/C. The reaction mixture was filtered and evaporated to give the title product.

Preparation of 3-Methoxymethyl-1-{2-[4-(4-pyrimidin-2-yl-phenyl)-3,6-dihydro-2H-pyridin-1-yl]-acetyl}-pyrrolidine-3-carboxylic acid [3-(2-cyclopropyl-pyridin-4-yl)-1-trityl-1H-indazol-5-yl]-amide

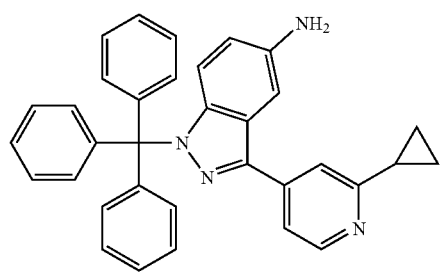

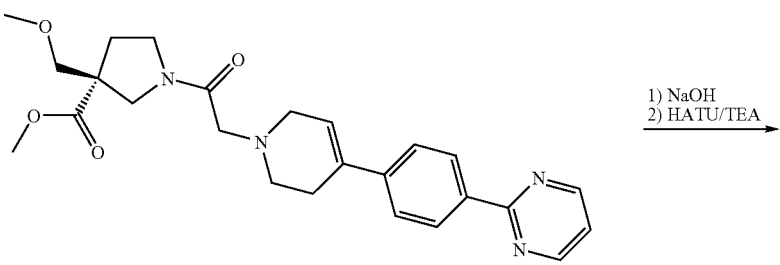

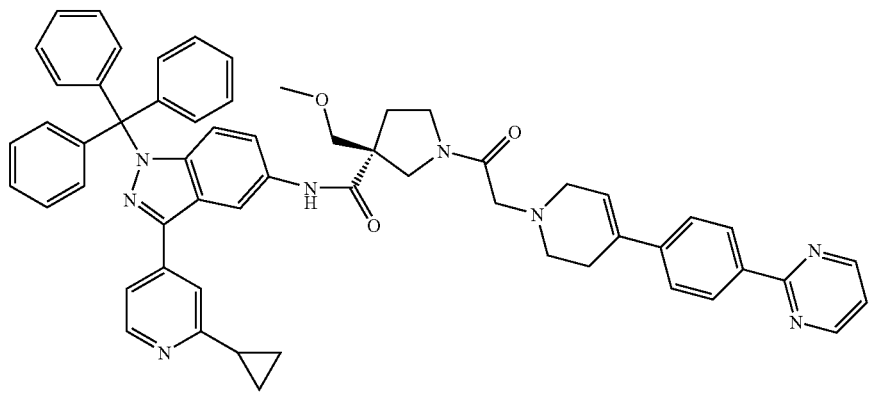

3-Methoxymethyl-1-{2-[4-(4-pyrimidin-2-yl-phenyl)-3,6-dihydro-2H-pyridin-1-yl]-acetyl}-pyrrolidine-3-carboxylic acid methyl ester (500 mg, 1.11 mmol) was added to a solution of 10 ml of 50% methanol/dichloromethane. 5 mL of 1N NaOH was added and the reaction mixture stirred for 18 hrs. 5.5 ml of 1N HCl was added and the reaction mixture evaporated to dryness. To the crude reaction mixture was added 3-(2-Cyclopropyl-pyridin-4-yl)-1-trityl-1H-indazol-5-ylamine (601 mg, 1.22 mmol), HATU (464 mg, 6.66 mmol), triethylamine (0.93 ml, 6.66 mmol) and 10 ml of 50% N,N-dimethylformamide/dichloromethane. The reaction mixture was stirred for 18 hrs. followed by washing with brine and extracted with ethylacetate 3×. After evaporation of the organic layers, the crude reaction mixture was chromatographed on silica gel using 1-3% 2N NH$_3$/methanol/dichlormethane as the eluent to obtain 570 mg of title product.

Preparation of 3-Methoxymethyl-1-{2-[4-(4-pyrimidin-2-yl-phenyl)-3,6-dihydro-2H-pyridin-1-yl]-acetyl}-pyrrolidine-3-carboxylic acid [3-(2-cyclopropyl-pyridin-4-yl)-1H-indazol-5-yl]-amide

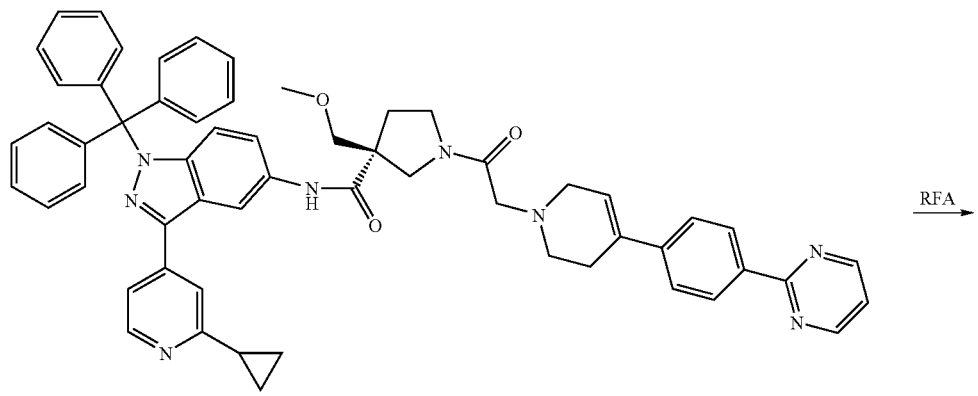

3-Methoxymethyl-1-{2-[4-(4-pyrimidin-2-yl-phenyl)-3,6-dihydro-2H-pyridin-1-yl]-acetyl}-pyrrolidine-3-carboxylic acid [3-(2-cyclopropyl-pyridin-4-yl)-1-trityl-1H-indazol-5-yl]-amide (570 mg, 0.63 mmol) was dissolved in 4 ml of trifluoroacetic acid (TFA), 10 ml dichloromethane and 2 ml of water and the reaction mixture was stirred for 18 hrs. The reaction mixture was evaporated and chromatographed on silica gel using 3-5% 2N NH$_3$/methanol/dichlormethane to obtain 444 mg of title product. MS (M+1)=669. Retention time (minutes) 2.67.

Scheme 13

Preparation of 3-(3,6-Dihydro-2H-pyran-4-yl)-1-trityl-1H-indazol-5-ylamine and 3-(Tetrahydro-pyran-4-yl)-1-trityl-1H-indazol-5-ylamine

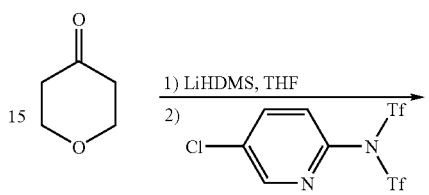

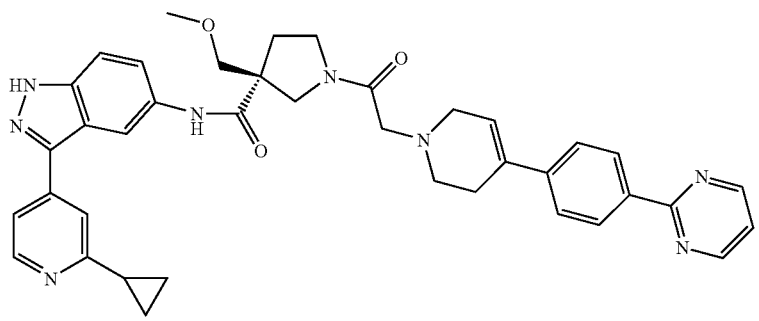

-continued

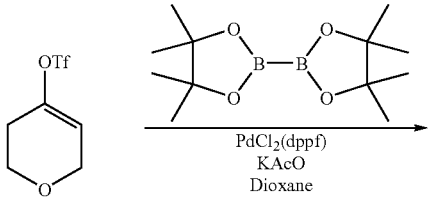

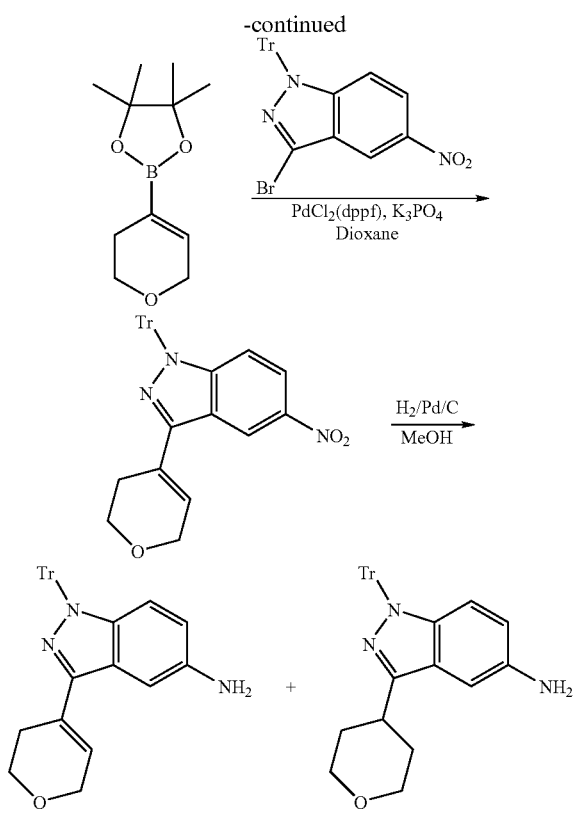

Step 1: Preparation of Trifluoro-methanesulfonic acid 3,6-dihydro-2H-pyran-4-yl ester To a solution of 4-tetrahydropyranone (2 g, 0.02 mol) in THF (10 mL) at −78° C., LiHMDS (1 M, 11 ml) was added dropwise through a syringe. The formed solution was then stirred at −78° C. for about 1 hour. The reaction was warmed up to room temperature briefly and was cooled back to −78° C. Then 2-[N,N-bis(trifluoromethylsulfonyl)amino]-5-chloropyrine (7.85 g, 0.02 mol) was added in four portions. The resulted reaction mixture was gradually warmed up to room temperature and was stirred for overnight. After removal of solvent, the residue was purified using chromatography (eluted with DCM/Hexane=80/20) to give product as a colorless oil (3 g).

Step 2: Preparation of 4-(4,4,5,5-Tetramethyl-[1,3,2]dioxaborolan-2-yl)-3,6-dihydro-2H-pyran A 250 mL round bottom flask containing trifluoro-methanesulfonic acid 3,6-dihydro-2H-pyran-4-yl ester (2.7 g, 11.6 mmol), PdCl₂(dppf) (440 mg, 0.6 mmol) and potassium acetate (3 g, 36 mmol) in dioxane (20 mL) was flushed with Ar three times. The reaction mixture was heated at 80° C. for overnight. After the reaction was cooled to room temperature, the reaction mixture was filter through a column packed with celite and the filtrate was concentrated. The residue was purified using column chromatography (10% hexane in dichloromethane) and product was obtained as white solid (2 g, 81% yield).

Step 3: Preparation of 3-(3,6-Dihydro-2H-pyran-4-yl)-5-nitro-1-trityl-1H-indazole A mixture containing 4-(4,4,5,5-Tetramethyl-[1,3,2]dioxaborolan-2-yl)-3,6-dihydro-2H-pyran (0.8 g, 3.8 mmol), 3-Bromo-5-nitro-1-trityl-1H-indazole (2 g, 4.0 mmol), PdCl₂(dppf) (150 mg, 0.2 mmol) and potassium phosphate (2.6 g, 12 mmol) in dioxane (10 mL) was flushed with Ar and was heated at 80° C. for overnight under Ar. LC-MS indicated the completion of reaction and the mixture was filter through celite. The filtrate was concentrated and was purified on a column (10 hexane in dichloromethane) to give 1.2 g of product (64% yield).

Step 4: Preparation of 3-(3,6-Dihydro-2H-pyran-4-yl)-1-trityl-1H-indazol-5-ylamine and 3-(Tetrahydro-pyran-4-yl)-1-trityl-1H-indazol-5-ylamine To a solution of 3-(3,6-Dihydro-2H-pyran-4-yl)-5-nitro-1-trityl-1H-indazole (100 mg, 0.2 mmol) in methanol was added and Pd/C (10%, 20 mg). The reaction mixture was evacuated under vacuum and hydrogen gas was filled. After repeated three times the reaction was kept under hydrogen atmosphere overnight at room temperature. LCMS showed the starting material was consumed completely and both 3-(3,6-dihydro-2H-pyran-4-yl)-1-trityl-1H-indazol-5-ylamine and 3-(tetrahydro-pyran-4-yl)-1-trityl-1H-indazol-5-ylamine were obtained. The two products were separated using prep-HPLC to give both product in 60% and 40% yield respectively.

Preparation 16

Step 1: Preparation of (2-Nitrophenyl)-(2-trimethylsilanylthiazol-5-yl)methanone

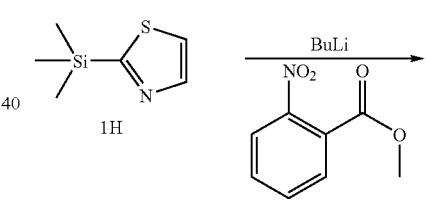

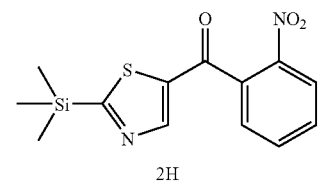

To a solution of 2-trimethylsilylthiazole (2.0 g, 12.7 mmol) in THF at −78 C was added BuLi (5.08 mL, 2.5 M, 12.7 mmol). The reaction was stirred at −78 C for 0.5 hr and methyl 2-nitrobenzoate (2.69 mL, 19.1 mmol) was added. The suspension was stirred at room temperature for 2 hr and quenched with ammonium chloride solution. The mixture was extracted with ethyl acetate and the combined organic layer was dried over sodium sulfate, concentrated and purified by column chromatography to give 2H (680 mg)

Step 2: Preparation of (2-Aminophenyl)-thiazol-5-yl-methanone

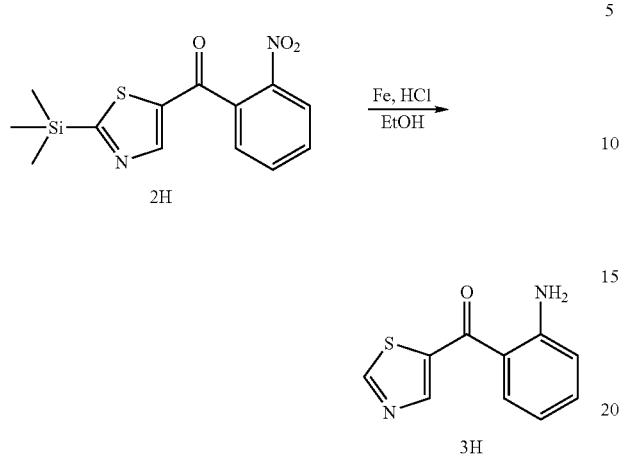

To a solution of 2H (631 mg, 2.72 mmol) in ethanol/H2O (12 mL/0.5 mL) was added iron (1.5 g, 27.2 mmol), then concentrated HCl (0.5 mL). The reaction was heated to reflux for 2.5 hr and filtered. The filtrated was neutralized with 1.0 N NaOH (5 mL) and extracted with ethyl acetate. The combined organic layer was dried over sodium sulfate, concentrated and purified by column chromatography to give 3H (280 mg)

Step 3: Preparation of 3-Thiazol-5-yl-1H-indazole

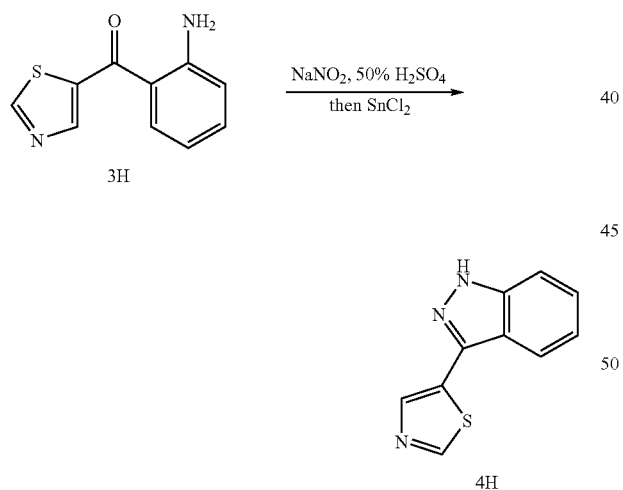

To a solution of 3H (241 mg, 0.103 mmol) in 3 mL of 50% sulfuric acid at 0 C was added sodium nitrite (97.4 mg, 0.125 mmol). The reaction was stirred at 0 C for 1 hr and room temperature for 5 minutes and chilled to 0 C. To this was added SnCl$_2$ (673 mg, 0.310 mmol) and stirred at 0 C for 1 hr. The suspension was diluted with water and extracted with ethyl acetate. The combined organic layer was washed with 1 N NaOH solution, dried over sodium sulfate, concentrated and purified by column chromatography to give 4H (149 mg)

Step 4: Preparation of 5-Nitro-3-thiazol-5-yl-1H-indazole

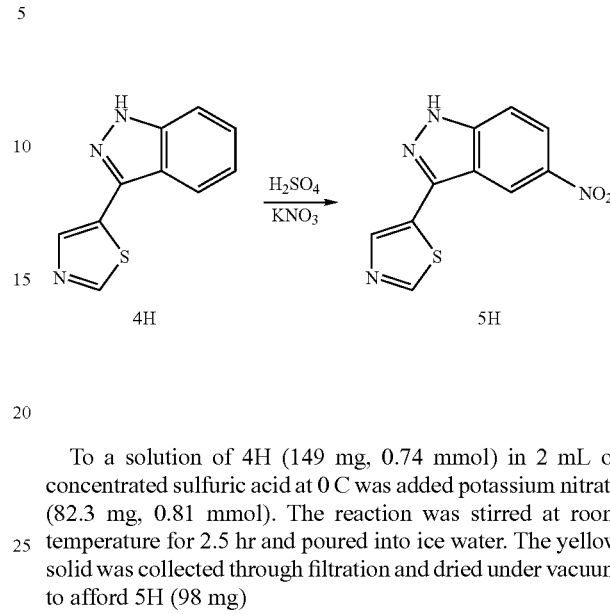

To a solution of 4H (149 mg, 0.74 mmol) in 2 mL of concentrated sulfuric acid at 0 C was added potassium nitrate (82.3 mg, 0.81 mmol). The reaction was stirred at room temperature for 2.5 hr and poured into ice water. The yellow solid was collected through filtration and dried under vacuum to afford 5H (98 mg)

Step 5: Preparation of 3-Thiazol-5-yl-1H-indazol-5-ylamine

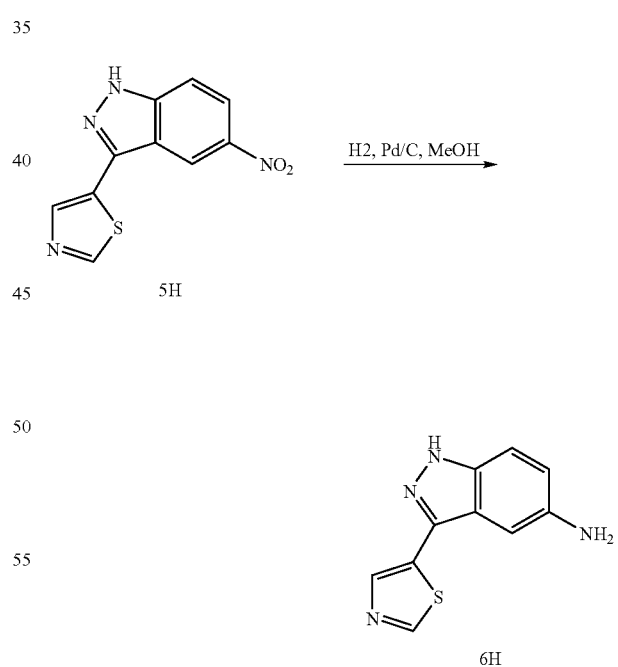

A suspension of 5H (98 mg, 0.39 mmol) and catalytic amount of Pd on carbon (5%) in methanol was stirred under a hydrogen atmosphere overnight and filtered through celite. The filtrate was concentrated to provide 6H (62 mg)

Preparation 17

Step 1: Preparation of 3-(3-Trifluoromethylphenyl)-5-nitro-1-trityl-1H-indazole

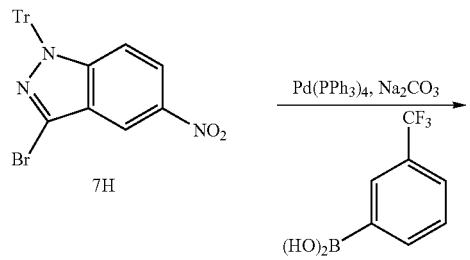

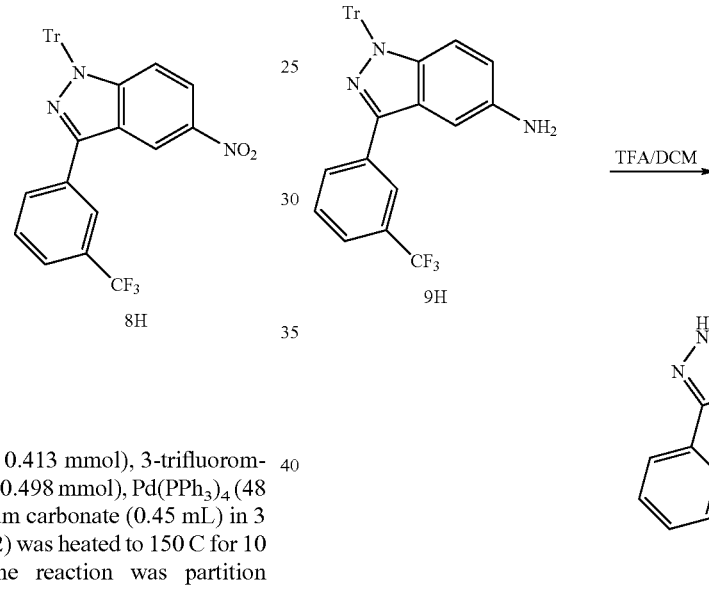

A suspension of 7H (200 mg, 0.413 mmol), 3-trifluoromethylphenylboronic acid (94 mg, 0.498 mmol), Pd(PPh₃)₄ (48 mg, 0.041 mmol) and 2 M sodium carbonate (0.45 mL) in 3 mL of dioxane/EtOH/H₂O (7/3/2) was heated to 150 C for 10 minutes using microwave. The reaction was partition between ethyl acetate and water. The organic layer was dried over sodium sulfate, concentrated and purified by column chromatography to afford 8H (189 mg)

Step 2: Preparation of 3-(3-Trifluoromethyl-phenyl)-1-trityl-1H-indazol-5-ylamine

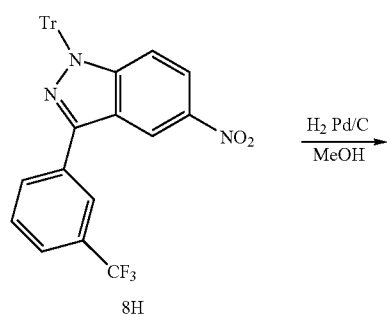

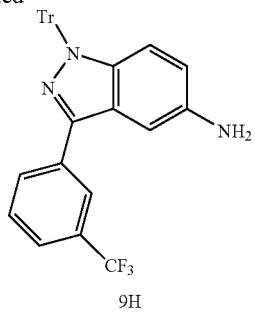

A suspension of 8H (189 mg, 0.350 mmol) and catalytic amount of Pd on carbon (5%) in methanol was stirred under a hydrogen atmosphere overnight and filtered through celite. The filtrate was concentrated to provide 9H (139 mg)

Step 3: Preparation of 3-(3-Trifluoromethyl-phenyl)-1H-indazol-5-ylamine

A solution of 9H (139 mg, 0.268 mmol) in 2 mL of TFA/DCM (1/1) was stirred at room temperature for 1 hr and concentrated. The residue was purified by column chromatography to afford 10H (61.7 mg)

Preparation 18

Preparation of 3-(4-Methoxy-3-trifluoromethyl-phenyl)-1H-indazol-5-ylamine

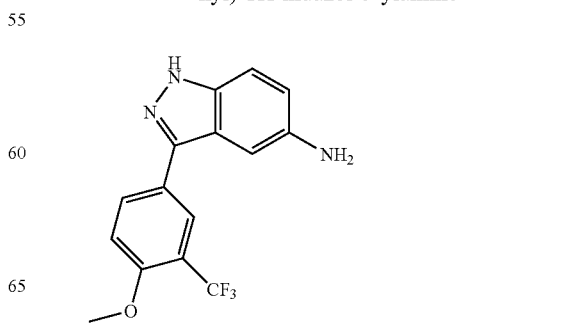

3-(4-Methoxy-3-trifluoromethyl-phenyl)-1H-indazol-5-ylamine was prepared using essentially the same scheme for preparing 10H. The boronic acid for the first step was 4-methoxy-3-trifluoromethylphenylboronic acid.

Preparation 19

Preparation of 3-Cyclohexyl-1H-indazol-5-ylamine

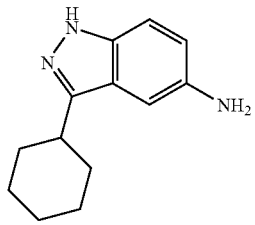 [SMILES: Nc1ccc2[nH]nc(C3CCCCC3)c2c1]

3-Cyclohexyl-1H-indazol-5-ylamine was prepared using essentially the same scheme for preparing 10H. The boronic acid for the first step was 1-cyclohexene-boronic acid.

Preparation 20

Preparation of 3-(2-Fluoro-pyridin-4-yl)-1H-indazol-5-ylamine

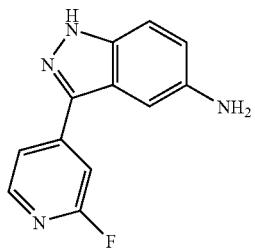 [SMILES: Nc1ccc2[nH]nc(-c3ccnc(F)c3)c2c1]

3-(2-Fluoro-pyridin-4-yl)-1H-indazol-5-ylamine was prepared using essentially the same scheme for preparing 10H. The boronic acid for the first step was 3-fluoro-4-pyridineboronic acid pinacol ester.

Preparation 21

Preparation of 4-fluoro-4-thiazol-2-yl-piperidine-1-carboxylic acid tert-butyl ester 7I

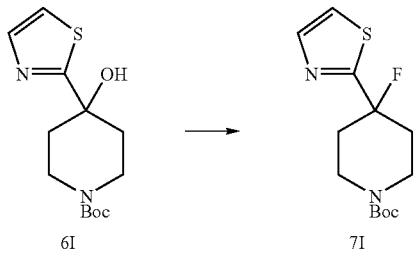 [SMILES: CC(C)(C)OC(=O)N1CCC(O)(c2nccs2)CC1 ; CC(C)(C)OC(=O)N1CCC(F)(c2nccs2)CC1 ; "6I" ; "7I"]

4-Hydroxy-4-thiazol-2-yl-piperidine-1-carboxylic acid tert-butyl ester 6I (500 mg, 1.76 mmol) was dissolved in $CH_2Cl_2$ (20 mL) and cooled to 0° C. DAST (0.46 mL, 3.52 mmol) was then added. The mixture was stirred at 0° C. for 1 hr and then quenched with sat. $NaHCO_3$. The separated organic layer was dried and concentrated in vacuo. The crude was purified with silica gel column (eluting with 12.5% ethyl acetate in hexanes) to yield an off-white solid (443 mg) as the title compound.

Preparation 21A

Step 1

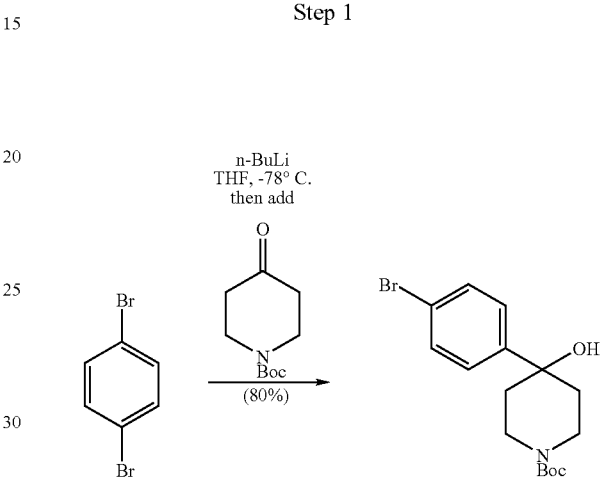

To a solution of 1,4-dibromobenzene (1.0 g, 4.24 mmol) in tetrahydrofuran (10 ml) at −78° C. under nitrogen, a solution of n-butyl lithium (1.7 ml, 4.24 mmol, 1.6M in hexane) was added slowly. The mixture was allowed to warm from −78° C. to −20° C. in 1 hr. A solution of piperidone (703 mg, 3.53 mmol) in tetrahydrofuran (5 ml) was added at −78° C. and the mixture was stirred at the same temperature for 1 hr. Saturated ammonium chloride solution was added and the mixture was allowed to warm to r.t. Water and ethyl acetate were added and layers were separated. The aqueous layer was extracted with ethyl acetate (×2). The combined organic layers were dried ($MgSO_4$) and filtered. Solvents were removed in vacuum and column chromatography [ethyl acetate-hexane, 5:1 (v/v)] gave 4-(4-bromophenyl)-4-hydroxypiperidine-1-carboxylic acid tert-butyl ester (1.0 g, 80%) as colorless oil.

Step 2

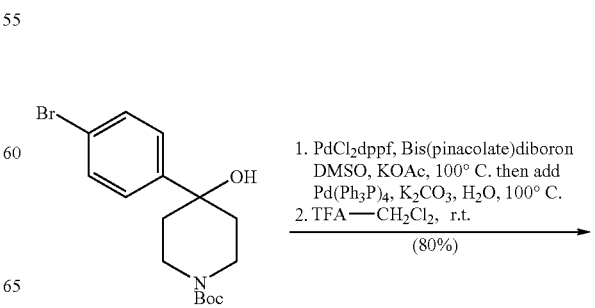

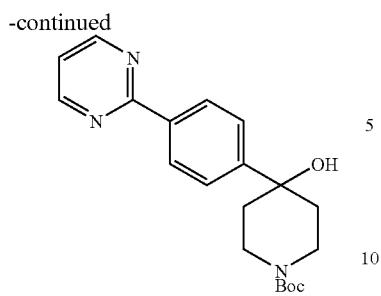

4-(4-bromophenyl)-4-hydroxypiperidine-1-carboxylic acid tert-butyl ester (800 mg, 2.25 mmol), bis(pinacolate) diboron (856 mg, 3.37 mmol), PdCl$_2$(dppf).CH$_2$Cl$_2$ (184 mg, 0.23 mmol), potassium acetate (660 mg, 6.74 mmol) were weighted into a sealed-tube. Methyl sulfoxide (20 ml) was added and the mixture was purged with nitrogen for 20 min before it was heated at 100° C. for 2 hr under nitrogen. The mixture was cooled to r.t. Potassium carbonate (1.55, 11.2 mmol), 2-bromopyrimidine (429 mg, 2.70 mmol) and water (10 ml) were added. The mixture was again purged with nitrogen for 20 min. Palladium tetrakistriphenylphosphine (260 mg, 0.23 mmol) was added and the final mixture was stirred at 100° C. for a further 2 hr. After being cooled to r.t., ethyl acetate and water were added. The mixture was filtered through a pad of Celite. Layers were separated and the organic layer was washed with water (×2). The combined aqueous layers were extracted with ethyl acetate (×1). The combined organic layers were dried (MgSO$_4$) and filtered. Solvents were removed in vacuum and column chromatography [ethyl acetate-hexane, 1:1 (v/v)] gave 4-hydroxy-4-(4-pyrimidin-2-ylphenyl)-piperidine-1-carboxylic acid tert-butyl ester (639 mg, 80%) as colorless oil.

Preparation 22

Preparation of 4-methoxy-4-(4-pyrimidin-2-yl-phenyl)-piperidine-1-carboxylic acid tert-butyl ester 9I

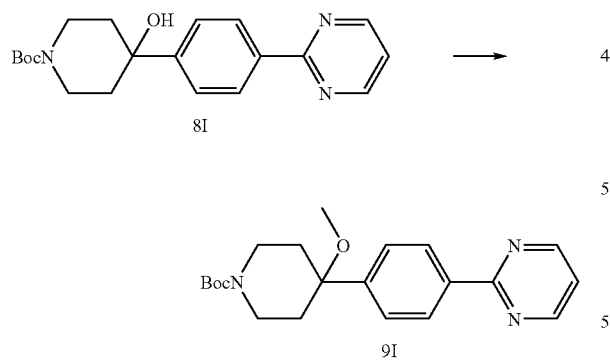

4-Hydroxy-4-(4-pyrimidin-2-yl-phenyl)-piperidine-1-carboxylic acid tert-butyl ester 8I (138 mg, 0.39 mmol) was dissolved in DMF (2 mL) and cooled to 0° C. MeI (0.1 mL) was added followed by the addition of NaH (26 mg, 60% suspension in mineral oil). After 30 min at 0° C., the reaction was quenched with sat. NH$_4$Cl and extracted with ethyl acetate. The combined organic layers was washed with brine, dried and concentrated in vacuo. The residue was purified with prep TLC plates (developing with 50% ethyl acetate/hexanes) to yield a colorless film (80 mg) as the title compound.

Preparation 23

Preparation of 4-bromo-2,6-dimethyl-pyridine 11I

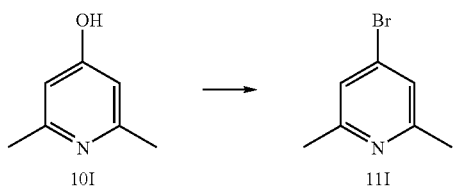

2,6-Dimethyl-pyridin-4-ol 10I (6.16 g, 50 mmol), PBr$_5$ (11.9 g, 27.65 mmol) and POBr$_3$ (2.5 mL, 24.6 mmol) was combined and CHCl$_3$ (2.5 mL) was added. The reaction was heated at 100° C. for 5 hrs and then cooled in an ice bath. Solid KOH was added till PH reached 7-8 followed by extraction with Et$_2$O (3×75 mL). The combined ether layer was dried and evaporated in vacuo to give a thick clear crude oil (10.1 g) as the title compound.

Preparation 24

Preparation of 2,6-dimethyl-4-pyridine boronic acid 12I

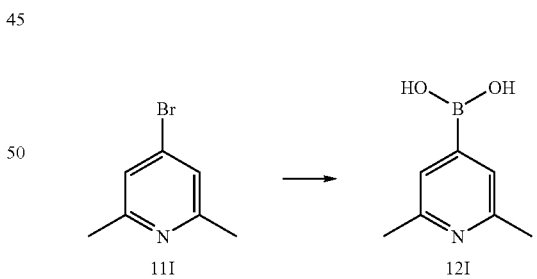

4-Bromo-2,6-dimethyl-pyridine (910 mg, 4.9 mmol) and triisopropyl borate (2.3 mL, 10 mmol) in THF (10 mL) were cooled in a −78° C. bath. BuLi (2.7 M, 7 mL) was added in drop wise. After 3 hrs, the bath was removed. The reaction was acidified with 1N HCl till pH=1. The separated aqueous layer was neutralized with NaOH and subsequently extracted with ethyl acetate. A crude white solid was obtained (800 mg) as the title compound.

Preparation 25

Preparation of 2-trifluoromethyl-4-pyridine boronic acid 14I

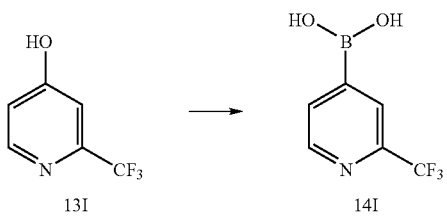

The title compound was prepared from 2-trifluoromethyl-pyridin-4-ol (13I) by a procedure essentially similar to that described in Chem. Het. Cpds, 1997, p. 995, the disclosure of which is incorporated herein by reference thereto.

Example 337

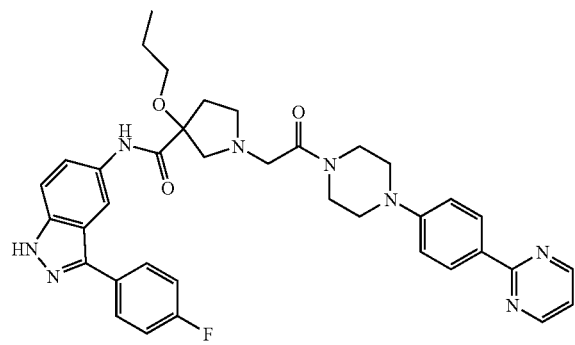 [SMILES: CCCOC1(C(=O)Nc2ccc3[nH]nc(-c4ccc(F)cc4)c3c2)CCN(CC(=O)N2CCN(c3ccc(-c4ncccn4)cc3)CC2)C1]

Step 1: Synthesis of 2-allyloxy-acrylic acid ethyl ester

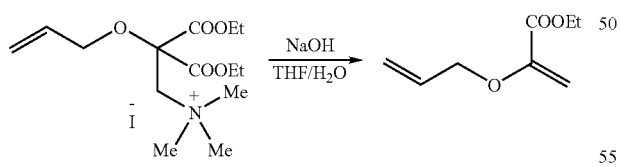

The (2-allyloxy-2,2-bis-ethoxycarbonyl-ethyl)-trimethylammonium iodide was prepared according to a procedure essentially similar to that described in J. Am. Chem. Soc. 1987, 109, 1170-1186, the disclosure of which is incorporated herein by reference thereto. At 0 C, a solution of NaOH (1N, 6 ml) was added into a stirred solution of (2-allyloxy-2,2-bis-ethoxycarbonyl-ethyl)-trimethyl-ammonium iodide (2.1 g) in DMSO and water (9:1, 35 ml) and resulting solution was allowed to stir at room temperature overnight. The reaction mixture was diluted with ether, washed with water three times, brine and dried (MgSO₄). After evaporation of solvent, the title compound (431 mg) was obtained.

Step 2: Synthesis of 3-allyloxy-1-benzyl-pyrrolidine-3-carboxylic acid ethyl ester

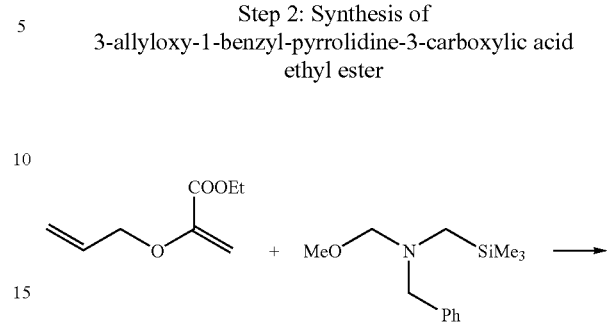

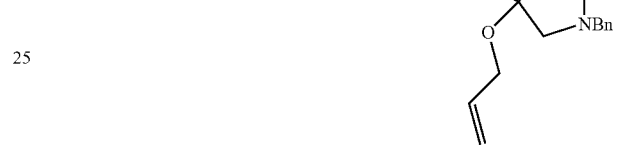

To a stirred solution of the 2-allyloxy-acrylic acid ethyl ester (431 mg) and N-(methoxymethyl)-N-(trimethylsilylmethyl)benzylamine (847 μl) in dichloromethane (10 ml) was added at 0° C. trifluoroacetic acid (21 μl). The resulting solution was warmed to room temperature and stirred overnight. The crude product was purified by column chromatography on silica gel, eluted with a solution of ethyl acetate in hexanes (25-100%) to give the title compound (341 mg).

Step 3: Synthesis of 3-propoxy-pyrrolidine-3-carboxylic acid ethyl ester

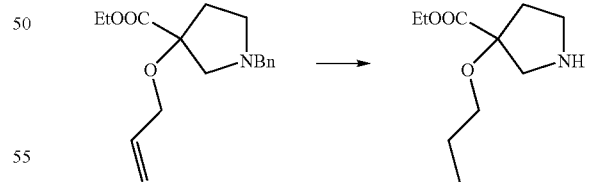

A mixture of 3-allyloxy-1-benzyl-pyrrolidine-3-carboxylic acid ethyl ester (145 mg), ammonium formate (126 mg), 10% Pd/C (20 mg) and methanol (4 ml) was refluxed for 40 minutes. The mixture was filtered through Celite, washed with ethyl acetate. The combined filtrate was concentrated and the residue was taken into ethyl acetate, washed with brine and dried over MgSO₄. Evaporation of solvent provided the title compound as oil (84 mg).

Step 4: Synthesis of 1-{2-Oxo-2-[4-(4-pyrimidin-2-yl-phenyl)-piperazin-1-yl]-ethyl}-3-propoxy-pyrrolidine-3-carboxylic acid [3-(4-fluoro-phenyl)-1H-indazol-5-yl]-amide

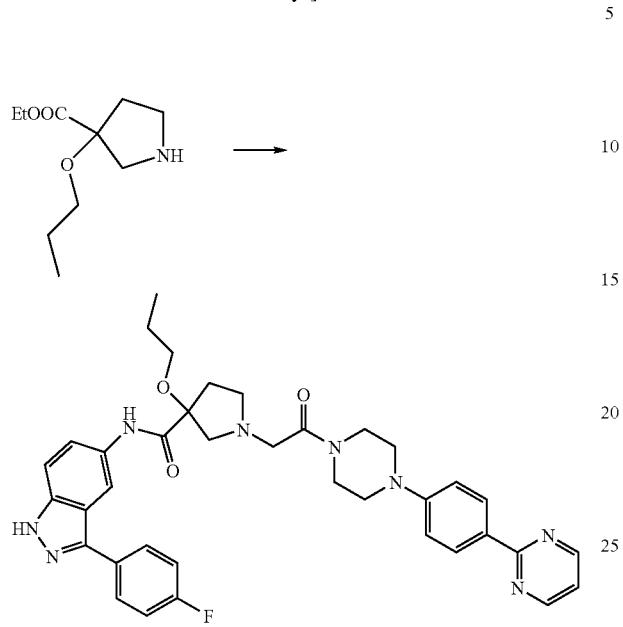

Synthesis of 1-{2-Oxo-2-[4-(4-pyrimidin-2-yl-phenyl)-piperazin-1-yl]-ethyl}-3-propoxy-pyrrolidine-3-carboxylic acid [3-(4-fluoro-phenyl)-1H-indazol-5-yl]-amide from 3-propoxy-pyrrolidine-3-carboxylic acid ethyl ester was essentially similar to the procedures described above for preparing compounds with a pyrrolidine moiety in the core structure, for example, 1, 3, 60, 85, 98, 128, 183 and 184.

Preparation 26

Intermediate To The Synthesis of 3-Morpholin-4-ylmethyl-1-[2-oxo-2-(4-thiophen-3-yl-3,6-dihydro-2H-pyridin-1-yl)-ethyl]-pyrrolidine-3-carboxylic acid [3-(2-methyl-pyridin-4-yl)-1H-indazol-5-yl]-amide

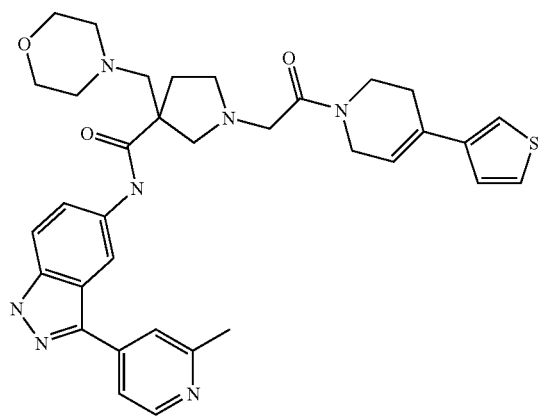 [SMILES: Cc1cc(-c2n[nH]c3ccc(NC(=O)C4(CN5CCOCC5)CCN(CC(=O)N5CC=C(c6ccsc6)CC5)C4)cc23)ccn1]

Step 1: Synthesis of 2-morpholin-4-ylmethyl-acrylic acid methyl ester

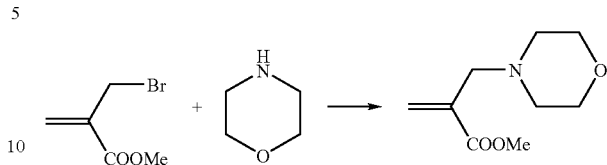

To a mixture of methyl 2-(bromomethyl)acrylate (119 µl, 1 mmol) and $K_2CO_3$ (138 mg, 1 eq) in acetonitrile (2 ml) was added morpholine (96 µl, 1.1 mmols). The mixture was stirred overnight, filtered and concentrated. The residue was partitioned between ether and water, and organic layer was isolated, washed with brine and dried ($MgSO_4$). Solvent was removed and residue was purified by column chromatography. Ethyl acetate eluted out the title compound as clear oil (110 mg, 59%).

Step 2: Synthesis of 1-benzyl-3-morpholin-4-ylmethyl-pyrrolidine-3-carboxylic acid methyl ester

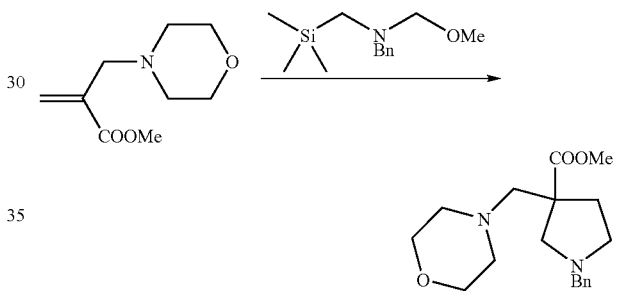

To a stirred cold solution (0° C.) of 2-morpholin-4-ylmethyl-acrylic acid methyl ester (110 mg, 0.594 mmols) and N-(methoxylmethyl)-N-(trimethylsilylmethyl)-benzylamine (182 µl, 0.71 mmols) in dichloromethane (2 ml) was added slowly trifluoroacetic acid (9 µl, 0.12 mmols). The resulting solution was allowed to stir at rt overnight and directly purified by column chromatography eluting with ethyl acetate to provide title compound as clear oil (86 mg, 45%).

Preparation 27

Intermediate To The Synthesis of 1-{2-Oxo-2-[4-(4-pyrimidin-2-yl-phenyl)-piperazin-1-yl]-ethyl}-3-trifluoromethyl-pyrrolidine-3-carboxylic acid [3-(4-fluoro-phenyl)-1H-indazol-5-yl]-amide

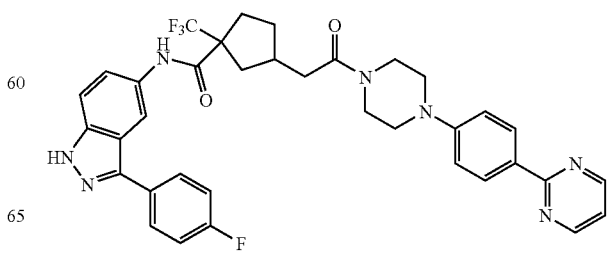

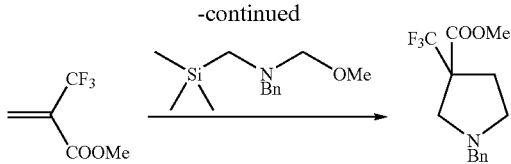

To a stirred cold solution (0° C.) of 2-trifluoromethyl-acrylic acid methyl ester (308 mg, 2 mmol) and N-(methoxylmethyl)-N-(trimethylsilylmethyl)benzylamine (529 µl, 4.8 mmol) in dichloromethane (3 ml) was added slowly trifluoroacetic acid (31 µl). The resulting solution was allowed to stir at rt overnight and directly purified by column chromatography eluting with ethyl acetate in hexane (1:4) to provide 1-benzyl-3-trifluoromethyl-pyrrolidine-3-carboxylic acid methyl ester as oil (438 mg, 76%).

Preparation 28

Preparation of
3-difluoromethyl-pyrrolidine-1,3-dicarboxylic acid
1-tert-butyl ester 3-ethyl ester (2J)

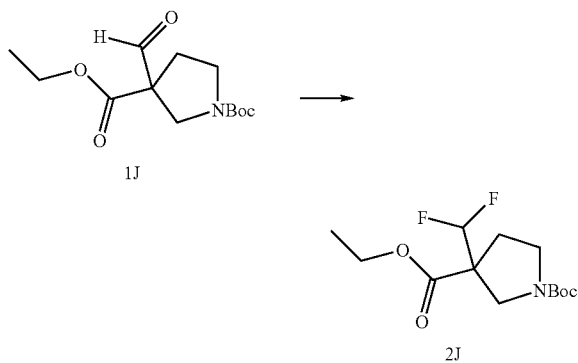

3-Formyl-pyrrolidine-1,3-dicarboxylic acid 1-tert-butyl ester 3-ethyl ester 1J (270 mg, 1 mmol) was dissolved in CH$_2$Cl$_2$ (5 mL) at r.t. followed by addition of DAST (1.0 mL). After 16 hrs, the mixture was cooled to 0 C and quenched with sat. NaHCO$_3$ solution followed by extraction of CH$_2$Cl$_2$ (2×5 mL). The combined organic layers was dried and concentrated in vacuo. The crude was purified using flash column (eluting with 20% to 33% ethyl acetate in hexanes) to yield 2J (280 mg) as a yellow oil.

Preparation 29

Preparation of
3-But-2-ynyl-pyrrolidine-1,3-dicarboxylic acid
1-tert-butyl ester 3-methyl ester

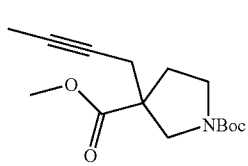

3-But-2-ynyl-pyrrolidine-1,3-dicarboxylic acid 1-tert-butyl ester 3-methyl ester 5J was prepared essentially similarly as 3-prop-2-ynyl-pyrrolidine-1,3-dicarboxylic acid 1-tert-butyl ester 3-methyl ester by substituting 3-bromo-propyne with 1-bromo-but-2-yne Preparation 30

Preparation of
3-Methylsulfanyl-pyrrolidine-1,3-dicarboxylic acid
1-tert-butyl ester 3-methyl ester

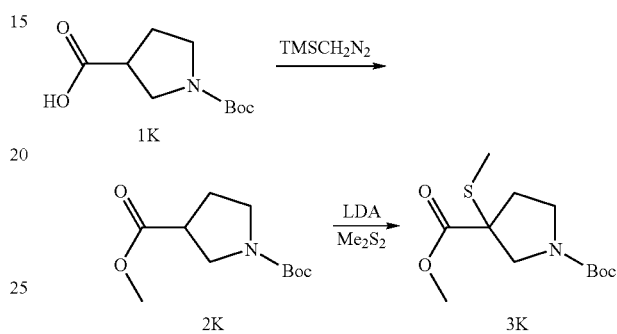

Pyrrolidine-1,3-dicarboxylic acid 1-tert-butyl ester (4.3 gm, 20 mmol) was dissolved in 28 mL of toluene and 3.5 ml of methanol. Trimethylsilyidiazomethane 2N solution in hexanes (13 ml, 26 mmol) was added dropwise at 0° C. and the reaction mixture stirred for 10 min at ambient temperature. The mixture was evaporated to obtain 4.3 gm of oil 2K.

To the oil 2K (0.5 gm, 2.1 mmol) dissolved in tetrahydrofuran (15 ml) 1.2 ml of lithium diisopropylamide 2N solution in hexanes was added dropwise and the reaction mixture stirred for 1 hr at −78° C. and let warm to ambient temperature gradually. The reaction mixture was stirred for 18 hrs. A saturated solution of Ammonium chloride (25 ml) was added and the reaction mixture stirred for 5 min. The reaction mixture was extracted with ethyl acetate three times (3×25 ml), dried over magnesium sulfate, filtered and evaporated to give 0.386 g of title product 3K.

Preparation 31

Preparation of
1-Benzyl-3-ethoxy-pyrrolidine-3-carboxylic acid
ethyl ester

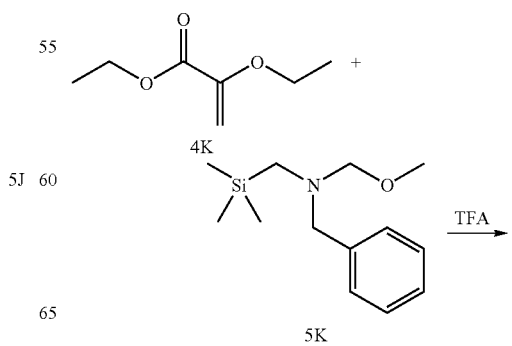

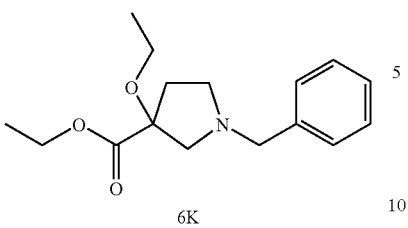

6K

To a stirred solution of 2-ethoxyacrylate (3 g, 20 mmol) (prepared according to a procedure in *Helv. Chem. Acta.* 1989, 72, 213-223, the disclosure of which is incorporated herein by reference thereto) and N-(methoxymethyl)-N-(trimethylsilylmethyl)benzylamine (6.36 ml, 24 mmol) in dichloromethane (30 ml) was added at 0° C. a solution of trifluoroacetic acid (0.072 ml, 0.3 mmol) in dichloromethane (2 ml). The resulting solution was warmed to room temperature and stirred overnight. The crude product was purified by column chromatography on silica gel eluting with a solution of ethyl acetate in hexane (1:2) to give the title compound 6K (2.1 g, 37%).

Preparation 32

Preparation of 1-Benzyl-3-isopropoxy-pyrrolidine-3-carboxylic acid methyl ester

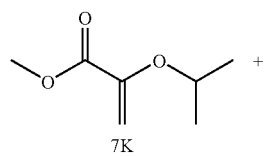

7K

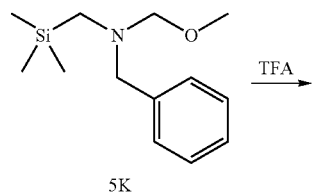

5K

8K

To a stirred solution of 2-iso-propoxymethylacrylate (2 g, 14 mmol) (prepared according to a procedure in *Syn. commun.* 1977, 7, 43-48, the disclosure of which is incorporated herein by reference thereto) and N-(methoxymethyl)-N-(trimethylsilylmethyl)benzylamine (4.26 ml, 17 mmol) in dichloromethane (25 ml) was added at 0° C. a solution of trifluoroacetic acid (0.2 ml, 3 mmol) in dichloromethane (2 ml). The resulting solution was warmed to room temperature and stirred overnight. The crude product was purified by column chromatography on silica gel eluting with a solution of ethyl acetate in hexane (1:2) to give the title compound 8K (1.06 g, 28%).

Examples 338-347

Following procedures similar to those described herein, for example, Examples 1, 3 to 60, 85, 98, 128, 183, 184, the compounds in Table 17 were prepared. "Ex." represents Example.

TABLE 17

| Ex. | Compound | Mass Spec LCMS MH | Retention time Minutes |
|---|---|---|---|
| 338 | | 651 | 2.89 |

TABLE 17-continued
| Ex. | Compound | Mass Spec LCMS MH | Retention time Minutes |
|---|---|---|---|
| 339 | 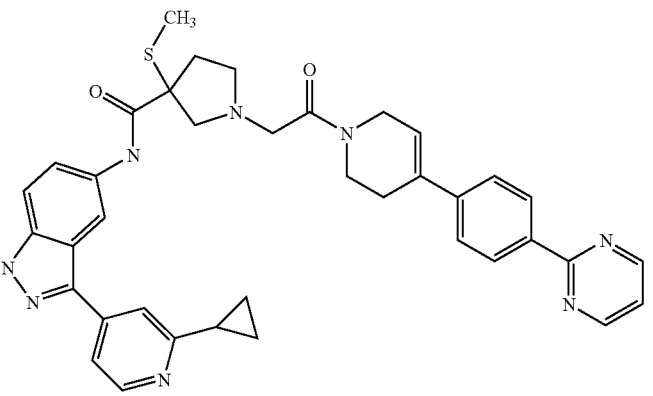 [SMILES: CSC1(C(=O)Nc2ccc3[nH]nc(-c4ccnc(C5CC5)c4)c3c2)CCN(CC(=O)N2CC=C(c3ccc(-c4ncccn4)cc3)CC2)C1] | 671 | 2.30 |
| 340 | 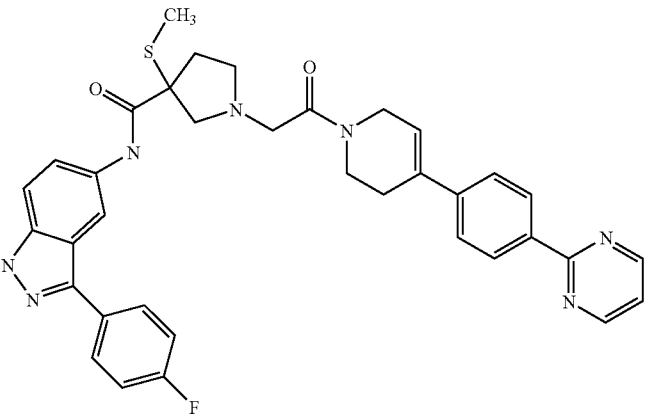 [SMILES: CSC1(C(=O)Nc2ccc3[nH]nc(-c4ccc(F)cc4)c3c2)CCN(CC(=O)N2CC=C(c3ccc(-c4ncccn4)cc3)CC2)C1] | 648 | 3.10 |
| 341 | 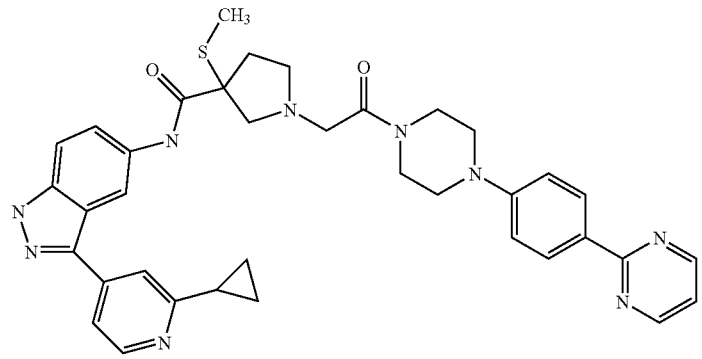 [SMILES: CSC1(C(=O)Nc2ccc3[nH]nc(-c4ccnc(C5CC5)c4)c3c2)CCN(CC(=O)N2CCN(c3ccc(-c4ncccn4)cc3)CC2)C1] | 674 | 2.17 |

TABLE 17-continued
| Ex. | Compound | Mass Spec LCMS MH | Retention time Minutes |
|---|---|---|---|
| 342 | 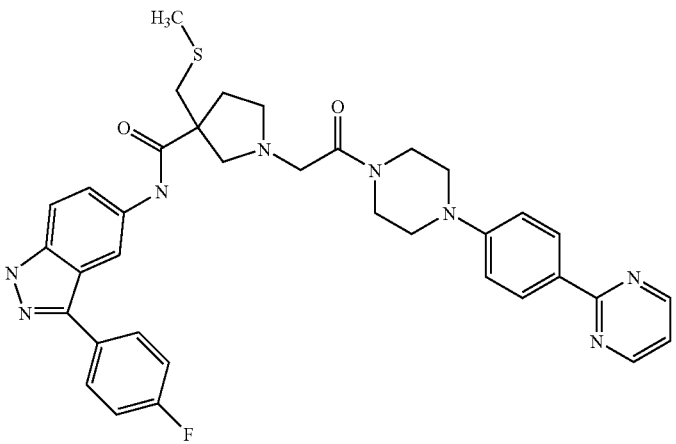 [SMILES: CSCC1(C(=O)Nc2ccc3[nH]nc(-c4ccc(F)cc4)c3c2)CCN(CC(=O)N2CCN(c3ccc(-c4ncccn4)cc3)CC2)C1] | 665 | 1.42 |
| 343 | 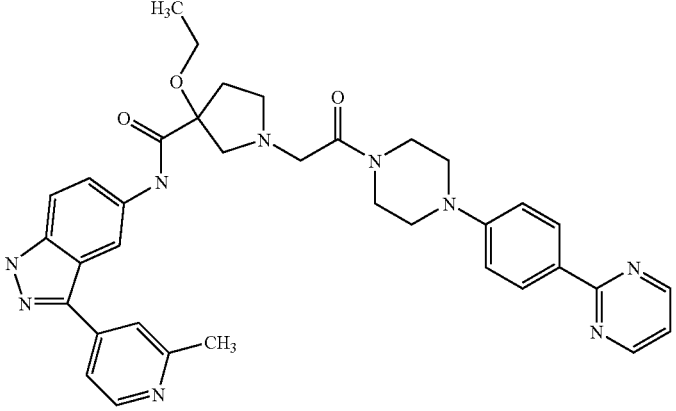 [SMILES: CCOC1(C(=O)Nc2ccc3[nH]nc(-c4ccnc(C)c4)c3c2)CCN(CC(=O)N2CCN(c3ccc(-c4ncccn4)cc3)CC2)C1] | 646 | 2.19 |
| 344 | 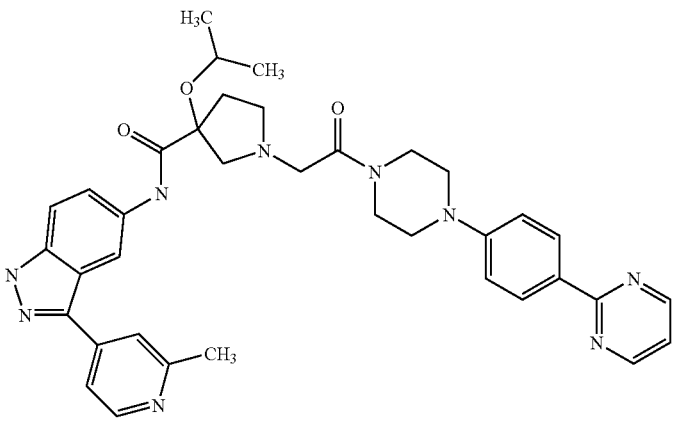 [SMILES: Cc1cc(-c2n[nH]c3ccc(NC(=O)C4(OC(C)C)CCN(CC(=O)N5CCN(c6ccc(-c7ncccn7)cc6)CC5)C4)cc23)ccn1] | 676 | 2.31 |

TABLE 17-continued
| Ex. | Compound | Mass Spec LCMS MH | Retention time Minutes |
|---|---|---|---|
| 345 | 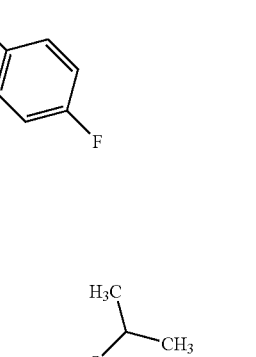 | 649 | 3.01 |
| 346 | 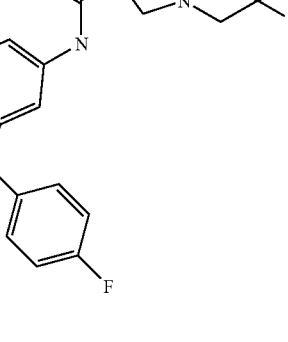 | 663 | 3.21 |
| 347 | 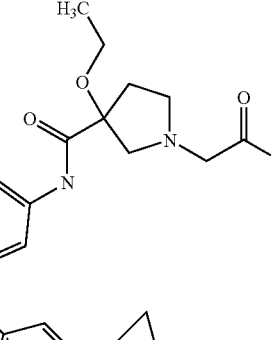 | 672 | 3.32 |

Examples 348-349

Step 1: Preparation of 2-dimethylaminomethyl-acrylic acid methyl ester

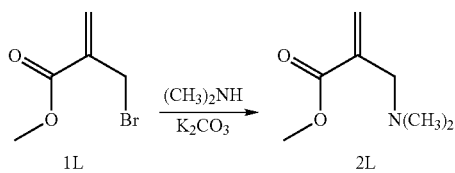

To a stirred solution of 2-bromomethyl-acrylic acid methyl ester (1 g, 5.59 mmol) in dry $CH_3CN$ (20 ml) was added 2M solution of dimethylamine in THF (3.07 ml, 6.14 mmol) followed by $K_2CO_3$ (0.93 g, 6.7 mmol). The reaction mixture was stirred overnight, filtered and washed with $CH_2Cl_2$. The filtrate was concentrated. The crude product was used in next reaction without further purification.

Step 2: Preparation of 1-benzyl-3-dimethylaminomethyl-pyrrolidine-3-carboxylic acid methyl ester

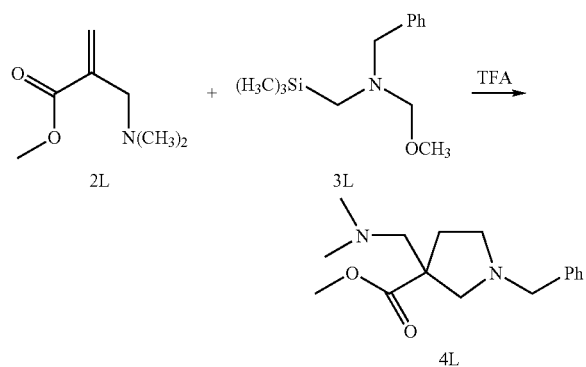

To a cold solution of 2-dimethylaminomethyl-acrylic acid methyl ester (0.266 g, 1.86 mmol) and N-(methoxymethyl)-N-(trimethylsilylmethyl)benzyl-amine (1.43 ml, 5.59 mmol) in dichloromethane (25 ml) was added at 0° C. trifluoroacetic acid (83 μl, 1.12 mmol). The resulting solution was warmed to room temperature and stirred for 72 hours. Saturated aq. $NaHCO_3$ (60 ml) was added to the reaction mixture and stirred for 10 minutes. Diluted with dichloromethane (50 ml) and the organic layer was separated. The organic layer was dried over $Na_2SO_4$, filtered and concentrated. The crude product was purified by column chromatography on silica get eluting with a solution of ethyl acetate in hexanes (1:2) followed by $CH_2Cl_2/MeOH/NH_4OH$ (9/1/0.01) to give the title compound (400 mg, 78%).

Step 3: Preparation of 3-dimethylaminomethyl-pyrrolidine-3-carboxylic acid methyl ester

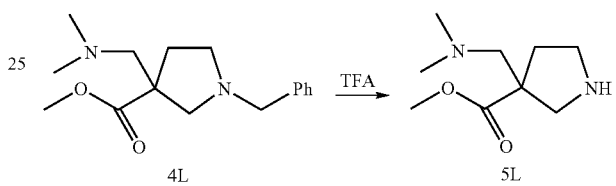

A mixture of 1-benzyl-3-dimethylaminomethyl-pyrrolidine-3-carboxylic acid methyl ester (400 mg), 10% Pd/C (40 mg) and methanol (30 ml) was shaken in a hydrogen parr shaker at 45 psi for overnight. The mixture was filtered through celite, washed with ethyl acetate. The combined filtrate was concentrated to give the title compound as oil (260 mg, 96%).

Using 5 L and following procedures essentially similar to those described herein, for example, Examples 1, 3 to 60, 85, 98, 128, 183, 184, the compounds in Table 18 were prepared. "Ex." represents Example.

TABLE 18

| Ex | Compound | Mass spec LCMS MH | Retention time (minutes) |
|---|---|---|---|
| 348 | | 659 | 2.55 |

TABLE 18-continued
| Ex | Compound | Mass spec LCMS MH | Retention time (minutes) |
|---|---|---|---|
| 349 | 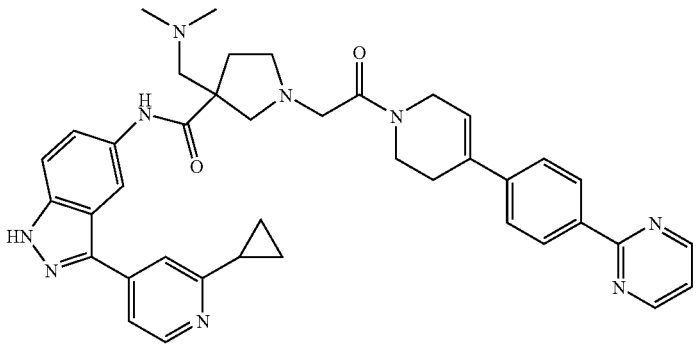 [SMILES: CN(C)CC1(C(=O)Nc2ccc3[nH]nc(-c4ccnc(C5CC5)c4)c3c2)CCN(CC(=O)N2CC=C(c3ccc(-c4ncccn4)cc3)CC2)C1] | 682 | 2.07 |
Examples 350-352
Following procedures similar to those described herein, for example, Examples 1, 3 to 60, 85, 98, 128, 183, 184, the compounds in Table 19 were prepared. "Ex." represents Example.
TABLE 19
| Ex | Compound | Mass spec LCMS MH | Retention time (minutes) |
|---|---|---|---|
| 350 | 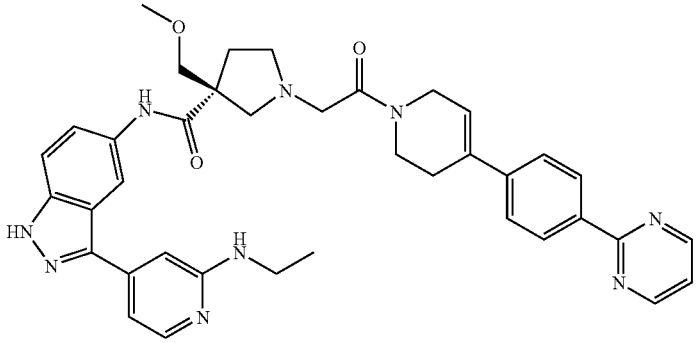 [SMILES: CCNc1cc(-c2n[nH]c3ccc(NC(=O)[C@]4(COC)CCN(CC(=O)N5CC=C(c6ccc(-c7ncccn7)cc6)CC5)C4)cc23)ccn1] | 672 | 2.38 |
| 351 | 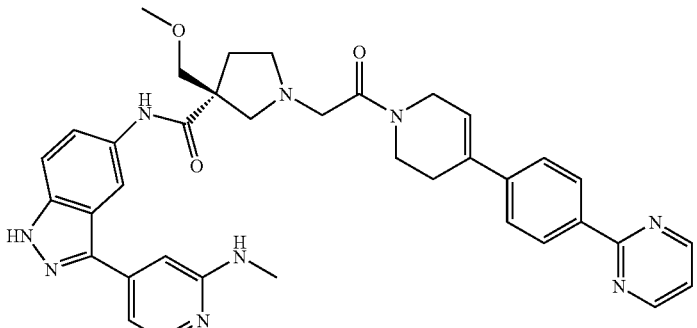 | 658 | 2.43 |

TABLE 19-continued

| Ex | Compound | Mass spec LCMS MH | Retention time (minutes) |
|---|---|---|---|
| 352 | | 658 | 2.28 |

Preparation 33

Preparation of 3-{[3-(2-Cyclopropyl-pyridin-4-yl)-1-trityl-1H-indazol-6-yl]-methyl-carbamoyl}-3-methoxy-pyrrolidine-1-carboxylic acid tertbutyl ester (4M)

3-[3-(2-Cyclopropyl-pyridin-4-yl)-1-trityl-1H-indazol-6-ylcarbamoyl]-3-methoxy-pyrrolidine-1-carboxylic acid tert-butyl ester 3M (216 mg, 0.3 mmol) was dissolved in THF (10 mL) at r.t. To this solution was added NaH (40 mg, 60% suspension in mineral oil, 1 mmol). After stirring for 10 min, CH₃I (0.6 mL, 9.6 mmol) was added. The reaction was worked up after 4 hrs by quenching with sat. NH₄Cl solution. After extraction with ethyl acetate, the combined organic layers was dried and concentrated in vacuo to obtain 4M. 4M is used as the resulting crude.

Preparation 34

Preparation of 2-[6-(3-R-Methyl-piperazin-1-yl)-pyridin-3-yl]-pyrimidine

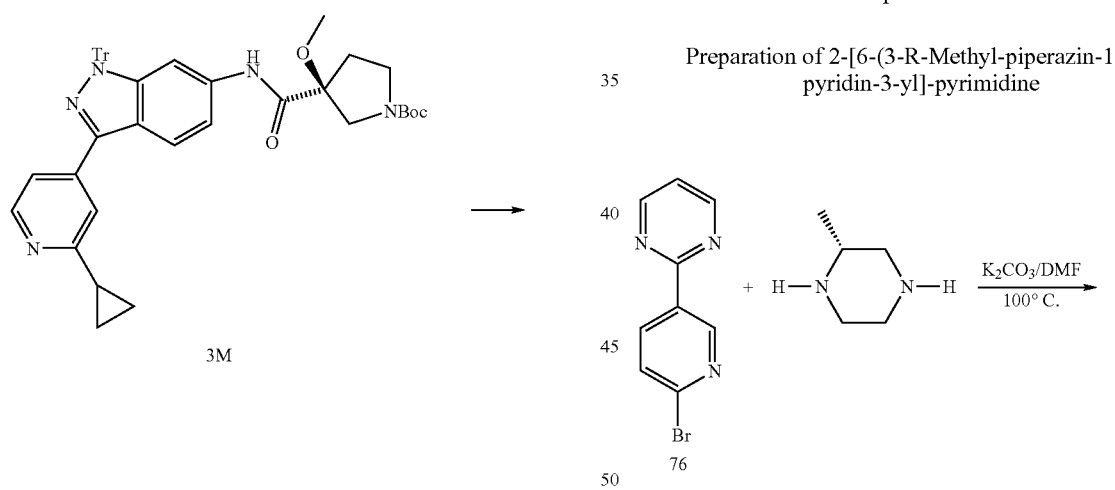

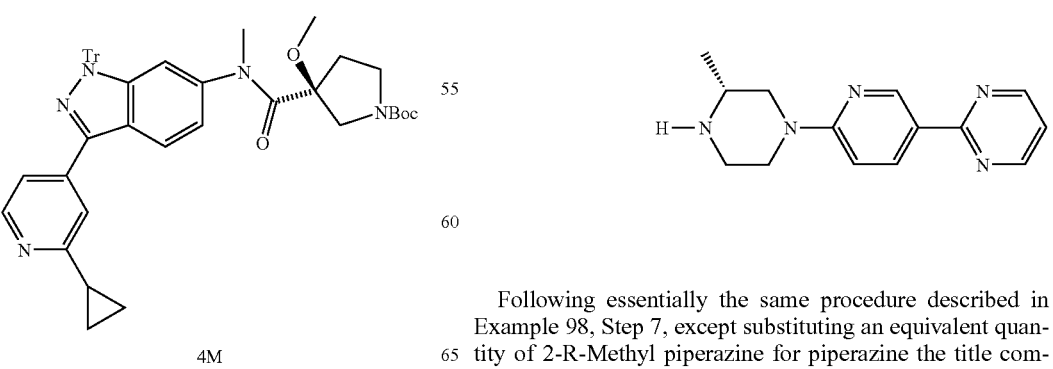

Following essentially the same procedure described in Example 98, Step 7, except substituting an equivalent quantity of 2-R-Methyl piperazine for piperazine the title compound is obtained as a white solid (ESMS MH, 256) 95% Yield.

Example 353

Preparation of 3-Ethynyl-1-{2-[2-methyl-4-(5-pyrimidin-2-yl-pyridin-2-yl)-piperazin-1-yl]-2-oxo-ethyl}-pyrrolidine-3-carboxylic acid [3-(4-fluoro-phenyl)-1H-indazol-5-yl]-amide

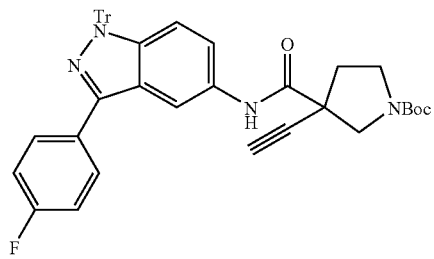

7D

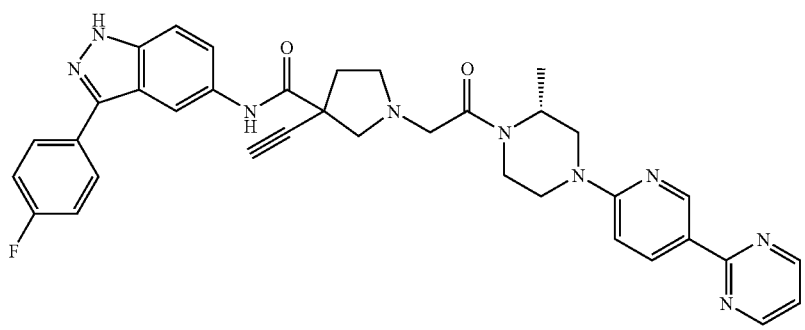

Following essentially the same procedure as Example 335, except substituting an equivalent quantity of 2-[6-(3-R-Methyl-piperazin-1-yl)-pyridin-3-yl]-pyrimidine for 23G, the title compound was obtained as a white solid (60%) LCMS (MH, 644.4) Retention time=2.52 minutes.

This racemate was resolved into two single isomers using Chiralpak AD column eluting with 70:30 Hexanes:Isopropanol containing 0.2% Diethylamine.

Isomer A (LCMS) MH 644
Isomer B (LCMS) MH 644

Example 354

Preparation of 3-(1-Hydroxy-ethyl)-1-{2-oxo-2-[4-(4-pyrimidin-2-yl-phenyl)-piperazin-1-yl]-ethyl}-pyrrolidine-3-carboxylic acid [3-(4-fluoro-phenyl)-1H-indazol-5-yl]-amide (1N) (Example 323 in Table 16)

1N

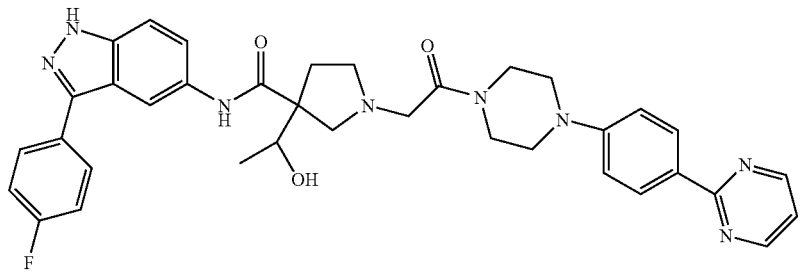

Step 1: Preparation of 3-(1-Acetoxy-ethyl)-1-benzyl-pyrrolidine-3-carboxylic acid methyl ester (2N)

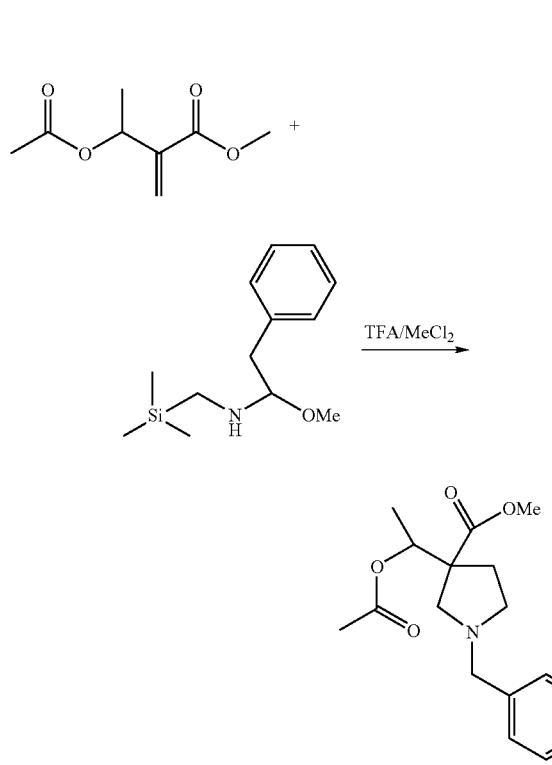

Trifluoroacetic acid (0.5 g, 4.38 mmol) was added to a solution of methyl-3-acetoxy-2-methylenebutyrate (5 g, 29.03 mmol) and N-methoxymethyl-N-trimethylsilyl benzylamine (6.89 g, 29.03 mmol) in MeCl$_2$ (50 ml) at 0° C. then stirred overnight at room temperature. The solvent was evaporated and the residue extracted with EtOAc (200 ml) and H$_2$O (50 ml) and saturated NaHCO$_3$ solution (50 ml). The organic layer was separated, dried over MgSO$_4$ filtered and evaporated solvent. The residue chromatographed on silica gel eluting with (v:v) EtOAc:hexanes 3:1 yielding compound 2N as a colorless oil (7 g, 81.7%) LCMS (MH, 306) Retention time=2.08 minutes.

Step 2: Preparation of 1-Benzyl-3-(1-hydroxy-ethyl)-pyrrolidine-3-carboxylic acid methyl ester (3N)

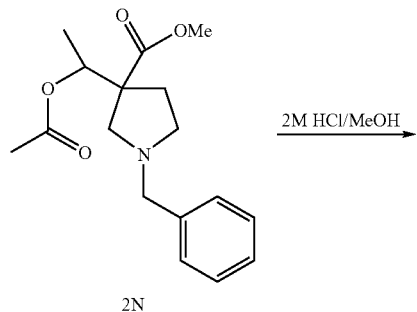

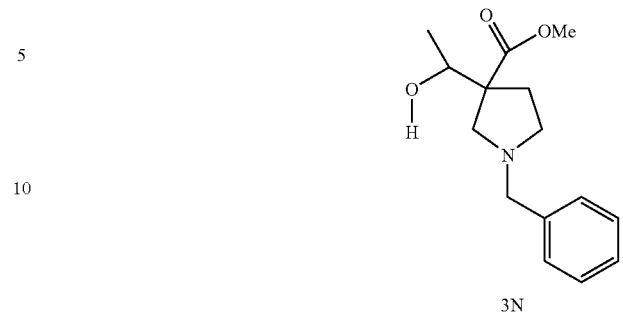

2M HCl (25 ml) was added to a solution of 3-(1-Acetoxy-ethyl)-1-benzyl-pyrrolidine-3-carboxylic acid methyl ester (2N) (5 g, 16.39 mmol) in MeOH (50 ml) at room temperature, then refluxed for 2 hours. The solvent was evaporated yielding the product (4.39, 100%) ESMS (MH, 264).

Step 3: Preparation of 1-Benzyl-3-(1-hydroxy-ethyl)-pyrrolidine-3-carboxylic acid, Lithium salt (4N)

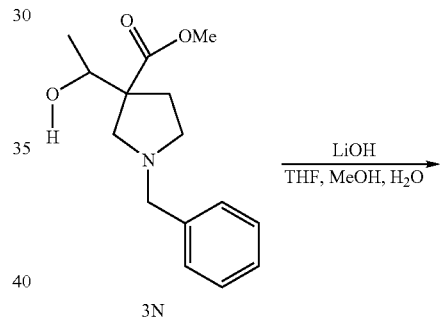

Lithium Hydroxide monohydrate (0.95 g, 16.37 mmol) was added to a solution of 1-Benzyl-3-(1-hydroxy-ethyl)-pyrrolidine-3-carboxylic acid methyl ester (3N) (4 g, 15.20 mmol) in MeOH/THF (1/1, 30 ml) at room temperature then refluxed for 2 hours. The reaction was cooled and solvent evaporated yielding product (4N) as a solid (4 g, 100%) ESMS (MH, 250).

Step 4: Preparation of 1-Benzyl-3-(1-hydroxy-ethyl)-pyrrolidine-3-carboxylic acid [3-(4-fluoro-phenyl)-1-trityl-indazol-5-yl]-amide (5N)

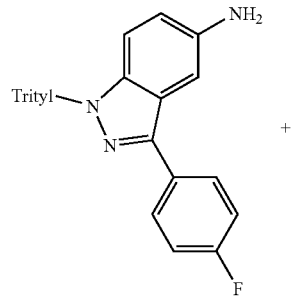

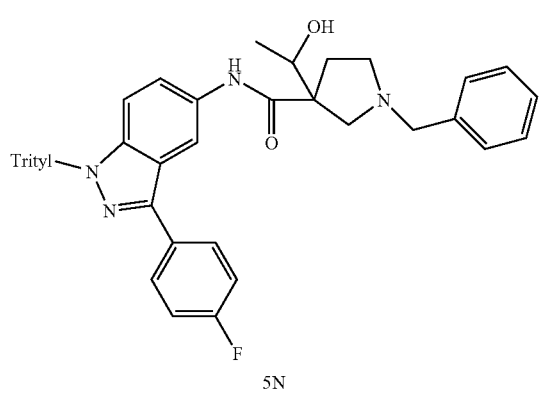

Triethylamine (0.5 ml, 6.81 mmol), EDCl (200 mg, 1.047 mmol) HOBT.H₂O (150 mg, 1.11 mmol) were added to a solution of the indazole (200 mg, 0.426 mmol) and 1-benzyl-3-(1-hydroxy-ethyl)-pyrrolidine-3-carboxylic acid, Lithium salt (4N) (200 mg, 0.803 mmol) in DMF (3 ml) at room temperature, then stirred overnight at ambient temperature. The solvent was evaporated and the residue chromatographed on silica gel eluting with 1:1 v:v EtOAc: Hexanes yielding product 5N (80 mg, 27%) ESMS (MH, 701).

Step 5: Preparation of 3-(1-Hydroxy-ethyl)-pyrrolidine-3-carboxylic acid [3-(4-fluoro-phenyl)-1Trityl-indazol-5-yl]-amide (6)

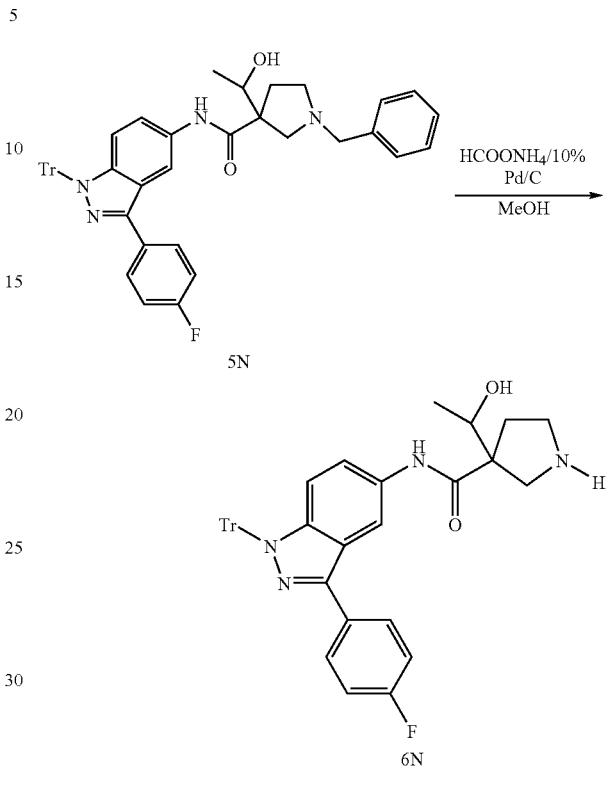

Added ammonium formate (100 mg, 1.58 mmol) to a suspension of 1-Benzyl-3-(1-hydroxy-ethyl)-pyrrolidine-3-carboxylic acid [3-(4-fluoro-phenyl)-1-trityl-indazol-5-yl]-amide (5N) (80 mg, 0.114 mmol) and 10% Pd/C (5 mg) in MeOH (5 ml) at room temperature then refluxed for 4 hours. The reaction was cooled, diluted with MeOH (20 ml) and filtered through a celite pad. The filtrate was concentrated and the residue dissolved in MeCl₂ (40 ml), dried over MgSO₄, filtered and solvent evaporated yielding 6N as a solid (60 mg, 87%) ESMS (MH, 611).

Step 6: Preparation of 3-(1-Hydroxy-ethyl)-1-{2-oxo-2-[4-(4-pyrimidin-2-yl-phenyl)-piperazin-1-yl]-ethyl}-pyrrolidine-3-carboxylic acid [3-(4-fluoro-phenyl)-1Trityl-indazol-5-yl]-amide (7N)

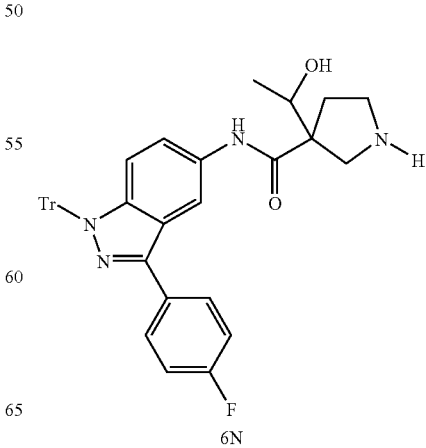

+

Diastereomer A (20 mg, 42%) LCMS (MH, 649) Retention time=2.70 minutes

Diastereomer B (18 mg, 38%) LCMS (MH, 649) Retention time=2.68 minutes.

Example 355

Step 1: Preparation of 3-(1-Hydroxy-ethyl)-1-{2-[2-methyl-4-(5-pyrimidin-2-yl-pyridin-2-yl)-piperazin-1-yl]-2-oxo-ethyl}-pyrrolidine-3-carboxylic acid [3-(4-fluoro-phenyl)-1Trityl-indazol-5-yl]-amide (9N)

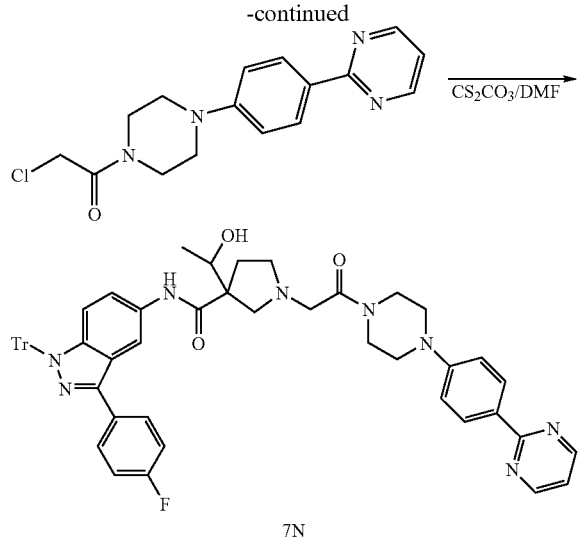

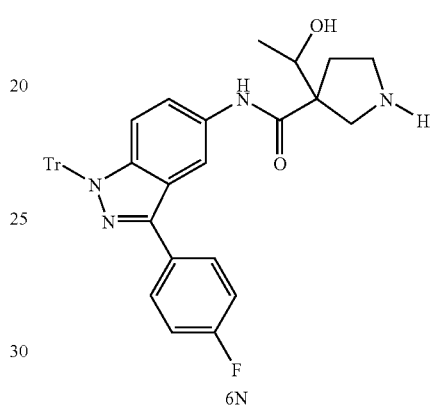

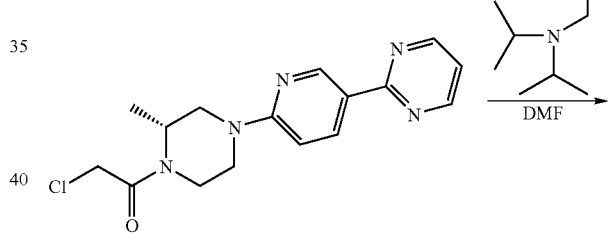

Added Cesium carbonate (60 mg, 0.184 mmol) to a solution of 3-(1-Hydroxy-ethyl)-pyrrolidine-3-carboxylic acid [3-(4-fluoro-phenyl)-1Trityl-indazol-5-yl]-amide (6N) (60 mg, 0.098 mmol) and 2-chloro-1-[4-(4-pyrimidin-2-yl-phenyl)-piperazin-1-yl]-ethanone (50 mg, 0.158 mmol) in DMF (2 ml) at room temperature, then stirred overnight.

The reaction mixture was diluted with Ether (30 ml), insoluble solids filtered, and the solvent was evaporated. The residue was chromatographed on silica gel eluting with 7% MeOH/MeCl$_2$ yielding 7N as a white solid (65 mg, 75%) LCMS (MH, 891). Retention time=4.42 minutes.

Step 7: Preparation of 3-(1-Hydroxy-ethyl)-1-{2-oxo-2-[4-(4-pyrimidin-2-yl-phenyl)-piperazin-1-yl]-ethyl}-pyrrolidine-3-carboxylic acid [3-(4-fluoro-phenyl)-1H-indazol-5-yl]-amide (1N)

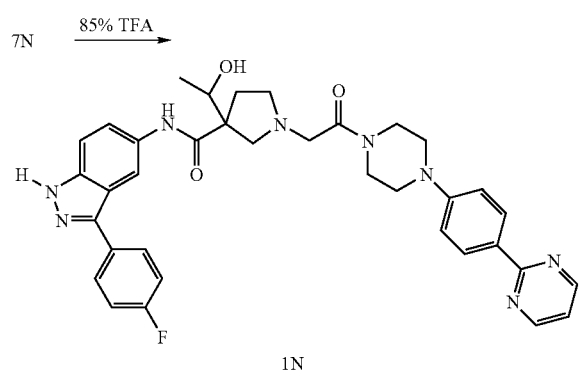

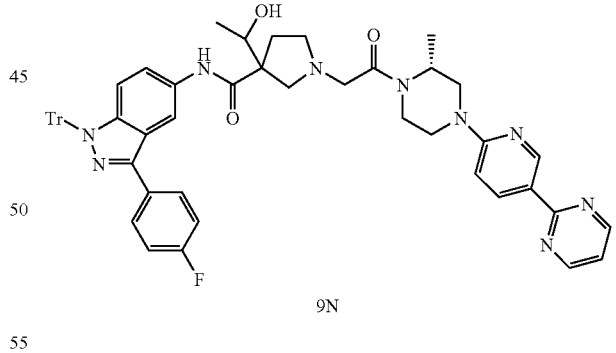

Stirred 3-(1-Hydroxy-ethyl)-1-{2-oxo-2-[4-(4-pyrimidin-2-yl-phenyl)-piperazin-1-yl]-ethyl}-pyrrolidine-3-carboxylic acid [3-(4-fluoro-phenyl)-1Trityl-indazol-5-yl]-amide (7N) (65 mg, 0.073 mmol) in 85% TFA (2 ml) at room temperature overnight. Evaporated solvent. Added EtOAc (50 ml) H$_2$O (20 ml) 2M NaOH (3 ml). Separated organic layer, dried over MgSO$_4$, filtered and solvent evaporated yielding a residue which purified on silica gel eluting with 5% v/v MeOH:EtOAc yielding two diastereomeric racemates.

Added N—N-Diisopropylethylamine (0.3 ml, 1.72 mmol) to a mixture of 3-(1-Hydroxy-ethyl)-pyrrolidine-3-carboxylic acid [3-(4-fluoro-phenyl)-1Trityl-indazol-5-yl]-amide (6N) (600 mg, 0.98 mmol) and 2-Chloro-1-[2-methyl-4-(5-pyrimidin-2-yl-pyridin-2-yl)-piperazin-1-yl]-ethanone (360 mg, 1.15 mmol) in DMF (10 ml) at room temperature. The solvent was evaporated and the residue extracted with MeCl$_2$ (100 ml) and H$_2$O (50 ml). The organic layer was separated, washed with saturated NaCl solution (20 ml), dried over MgSO$_4$, filtered and solvent evaporated yielding 9N as a solid (750 mg, 84%) ESMS (MH, 906).

Step 2: Preparation of 3-Acetyl-1-{2-[2-methyl-4-(5-pyrimidin-2-yl-pyridin-2-yl)-piperazin-1-yl]-2-oxo-ethyl}-pyrrolidine-3-carboxylic acid [3-(4-fluoro-phenyl)-1Trityl-indazol-5-yl]-amide (10N)

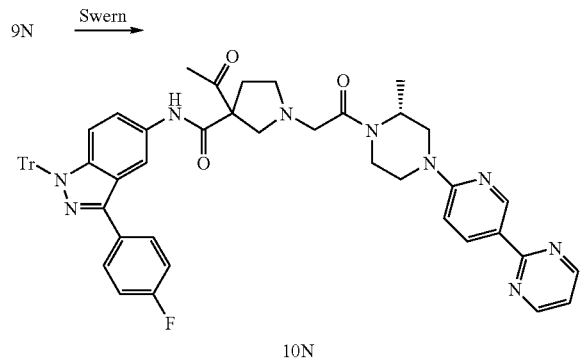

Added DMSO (200 mg, 2.56 mmol) to a solution of oxalyl chloride (180 mg, 1.40 mmol) in MeCl$_2$ (10 ml) at −78° C., then stirred at −78° C. for 1 hour. Added 3-(1-Hydroxy-ethyl)-1-{2-[2-methyl-4-(5-pyrimidin-2-yl-pyridin-2-yl)-piperazin-1-yl]-2-oxo-ethyl}-pyrrolidine-3-carboxylic acid [3-(4-fluoro-phenyl)-1Trityl-indazol-5-yl]-amide (9N) in MeCl$_2$ (5 ml) at −78° C. then stirred at −78° C. for 2 hours. Triethylamine (200 mg, 1.96 mmol) was added, the solution allowed warm to room temperature then stirred overnight. Added water (50 ml) and MeCl$_2$ (150 ml). The organic layer was separated, dried over MgSO$_4$, filtered and solvent evaporated yielding 10N as a solid (600 mg, 66%) ESMS (MH, 904)

Step 3: Preparation of 3-Acetyl-1-{2-[2-methyl-4-(5-pyrimidin-2-yl-pyridin-2-yl)-piperazin-1-yl]-2-oxo-ethyl}-pyrrolidine-3-carboxylic acid [3-(4-fluoro-phenyl)-1H-indazol-5-yl]-amide (11N)

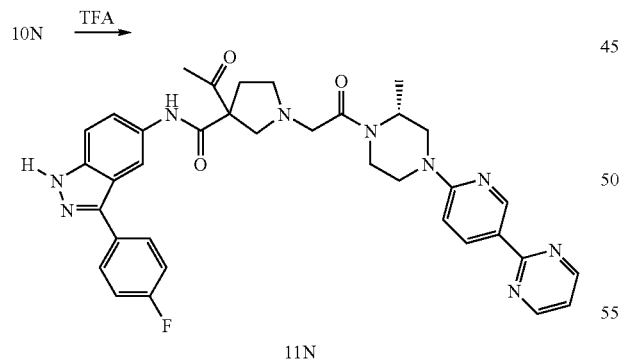

Stirred a solution of 3-Acetyl-1-{2-[2-methyl-4-(5-pyrimidin-2-yl-pyridin-2-yl)-piperazin-1-yl]-2-oxo-ethyl}-pyrrolidine-3-carboxylic acid [3-(4-fluoro-phenyl)-1Trityl-indazol-5-yl]-amide (10N) (600 mg, 0.664 mmol) in trifluoroacetic acid (20 ml) at room temperature overnight. The solvent was evaporated, water (100 ml) and 1N NaOH (10 ml) were added. The mixture was extracted with MeCl$_2$ (2×150 ml), dried over MgSO$_4$, filtered and solvent evaporated yielding a residue which chromatographed on silica gel eluting with 10% v/v MeOH/MeCl$_2$ containing 2% NH$_4$OH yielding product as a white solid. (350 mg, 79%) LCMS (MH 662.4). Retention time (minutes) 2.21

Example 356

Preparation of 3-(1-Methoxyimino-ethyl)-1-{2-[2-methyl-4-(5-pyrimidin-2-yl-pyridin-2-yl)-piperazin-1-yl]-2-oxo-ethyl}-pyrrolidine-3-carboxylic acid [3-(4-fluoro-phenyl)-1H-indazol-5-yl]-amide (12N)

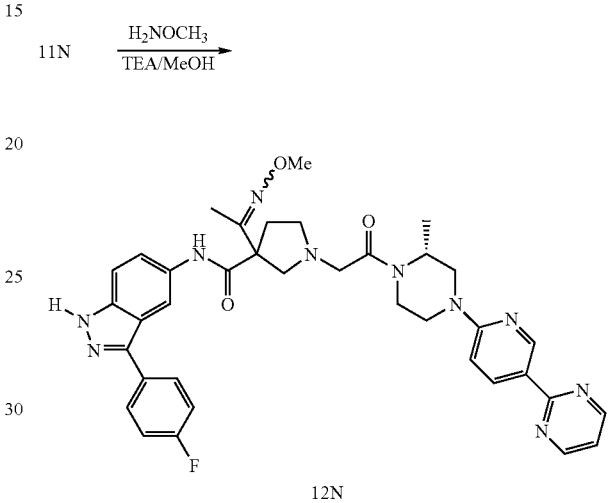

Added methoxylamine hydrochloride (100 mg, 1.197 mmol) and triethylamine (0.2 ml, 1.43 mmol) to a solution of 3-Acetyl-1-{2-[2-methyl-4-(5-pyrimidin-2-yl-pyridin-2-yl)-piperazin-1-yl]-2-oxo-ethyl}-pyrrolidine-3-carboxylic acid [3-(4-fluoro-phenyl)-1H-indazol-5-yl]-amide (11N) (100 mg, 0.15 mmol) in MeOH (5 ml), then stirred for 3 hours at room temperature. The solvent was evaporated and the residue was extracted with MeCl$_2$, washed with water, dried over Na$_2$SO$_4$, filtered and solvent was evaporated yielding a solid which chromatographed on silica gel eluting with 7% v/v MeOH/MeCl$_2$ containing 2% NH$_4$OH yielding 2 isomers:

(6 mg, 6%) (Z)-Isomer LCMS (MH, 691.4) Retention time=2.45 minutes.

(60 mg, 63%) (E)-Isomer LCMS (MH, 691.4) Retention time=2.62 minutes.

Example 357

Preparation of 3-(1-Hydroxyimino-ethyl)-1-{2-[2-methyl-4-(5-pyrimidin-2-yl-pyridin-2-yl)-piperazin-1-yl]-2-oxo-ethyl}-pyrrolidine-3-carboxylic acid [3-(4-fluoro-phenyl)-1H-indazol-5-yl]-amide (13N)

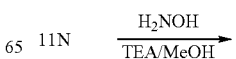

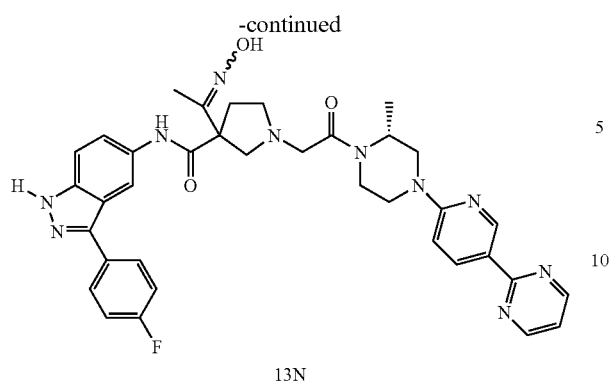

13N

Following essentially the same procedure as described in Example 356, except substituting an equivalent amount of hydroxylamine hydrochloride for methoxylamine hydrochloride, the title compound 13N was obtained as a single isomer (E) in 70% yield. (E-Isomer) LCMS (MH 677) Retention time=2.44 minutes.

Example 358

Preparation of 3-[1-(Acetyl-hydrazono)-ethyl]-1-{2-[2-methyl-4-(5-pyrimidin-2-yl-pyridin-2-yl)-piperazin-1-yl]-2-oxo-ethyl}-pyrrolidine-3-carboxylic acid [3-(4-fluoro-phenyl)-1H-indazol-5-yl]-amide (14N)

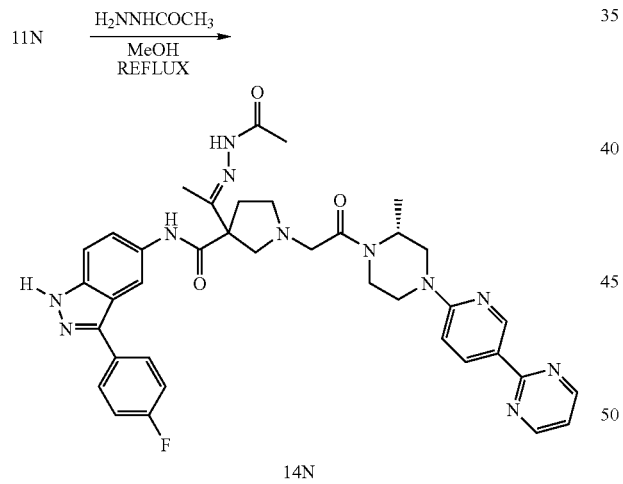

14N

Added acetyl hydrazide (50 mg, 0.674 mmol) to a solution of 3-Acetyl-1-{2-[2-methyl-4-(5-pyrimidin-2-yl-pyridin-2-yl)-piperazin-1-yl]-2-oxo-ethyl}-pyrrolidine-3-carboxylic acid [3-(4-fluoro-phenyl)-1H-indazol-5-yl]-amide (11N) (50 mg, 0.075 mmol) in MeOH (5 ml) at room temperature, then refluxed overnight. The reaction was cooled and solvent evaporated. The residue was extracted with MeCl$_2$ (100 ml) and H$_2$O (40 ml). The organic layer separated, dried over MgSO$_4$, filtered and solvent evaporated. The residue was chromatographed on silica gel eluting with 5% v/v MeOH/MeCl$_2$ containing 2% NH$_4$OH yielding title compound 14N as a white solid (50 mg, 92%) LCMS (MH 718.4) Retention time=2.13 minutes.

Example 359

Preparation of 3-Amino-1-{2-oxo-2-[4-(4-pyrimidin-2-yl-phenyl)-piperazin-1-yl]-ethyl}-pyrrolidine-3-carboxylic acid [3-(4-fluoro-phenyl)-1H-indazol-5-yl]-amide

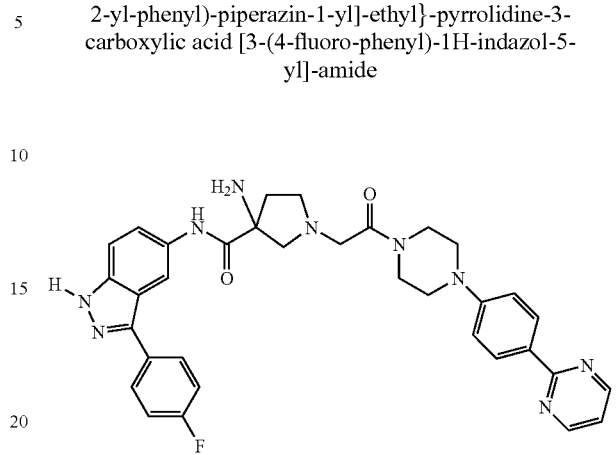

Step 1: Preparation of 3-Amino-3-[3-(4-fluoro-phenyl)-1trityl-indazol-5-ylcarbamoyl]-pyrrolidine-1-carboxylic acid tert-butyl ester (1)

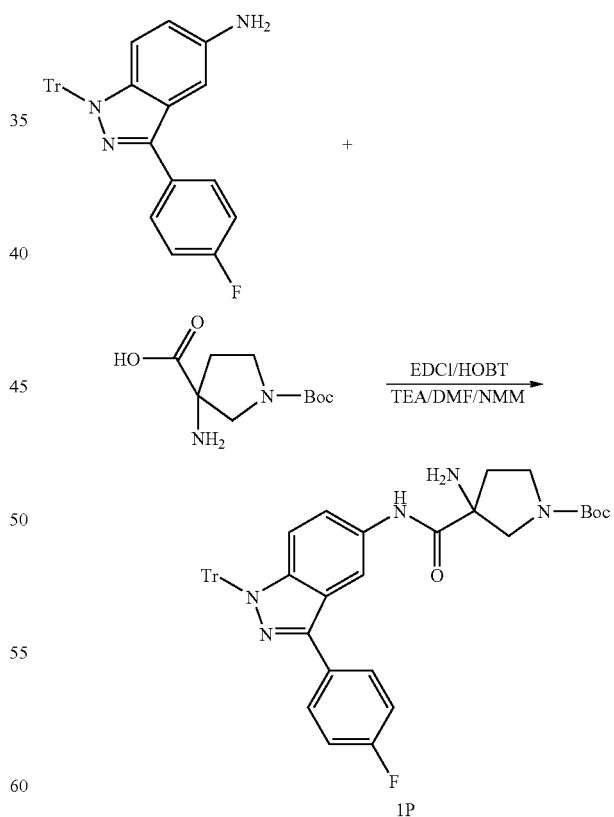

1P

Added 3-Amino-pyrrolidine-1,3-dicarboxylic acid-1-tert-butyl ester (86 mg, 0.373 mmol) to a solution of 3-(4-Fluoro-phenyl)-1H-indazol-5-ylamine (178 mg, 0.379 mmol); EDCl.HCl (150 mg, 0.785 mmol) and HOBT (100 mg, 0.740 mmol) in DMF (2 ml) at room temperature. NMM (0.1 ml) was added and solution stirred overnight. The solvent was evaporated and the residue extracted with MeCl₂ (50 ml) washed with H₂O (25 ml). The organic layer was dried over MgSO₄, filtered and solvent evaporated yielding a residue which chromatographed on silica gel eluting with 3% v/v MeOH/MeCl₂ yielding title compound 1P (185 mg, 71%) ESMS (MH 682).

Step 2: Preparation of 3-Amino-pyrrolidine-3-carboxylic acid [3-(4-fluoro-phenyl)-1H-indazol-5-yl]-amide, Hydrochloride (2P)

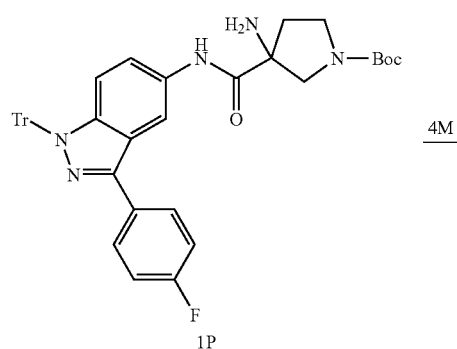

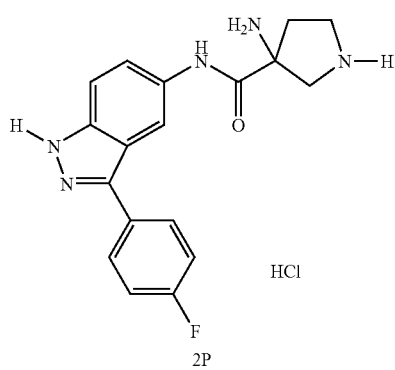

4M HCl/dioxane (2 ml) was added to a solution of 3-Amino-3-[3-(4-fluoro-phenyl)-1H-indazol-5-ylcarbamoyl]-pyrrolidine-1-carboxylic acid tert-butyl ester (1P) (60 mg, 0.088 mmol) in MeCl₂ (1 ml) at room temperature then stirred for 1 hour at room temperature. The solvent was evaporated. Hexanes (20 ml) was added and supernatant decanted. The residue was dried yielding title compound 2P as a white solid (20 mg, 69%). ESMS (MH 340).

Step 3: Preparation of 3-Amino-1-{(2-oxo-2-[4-(4-pyrimidin-2-yl-phenyl)-piperazin-1-yl]-ethyl}-pyrrolidine-3-carboxylic acid [3-(4-fluoro-phenyl)-1H-indazol-5-yl]-amide (3P)

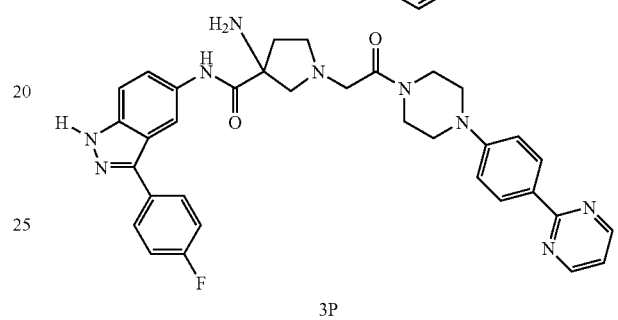

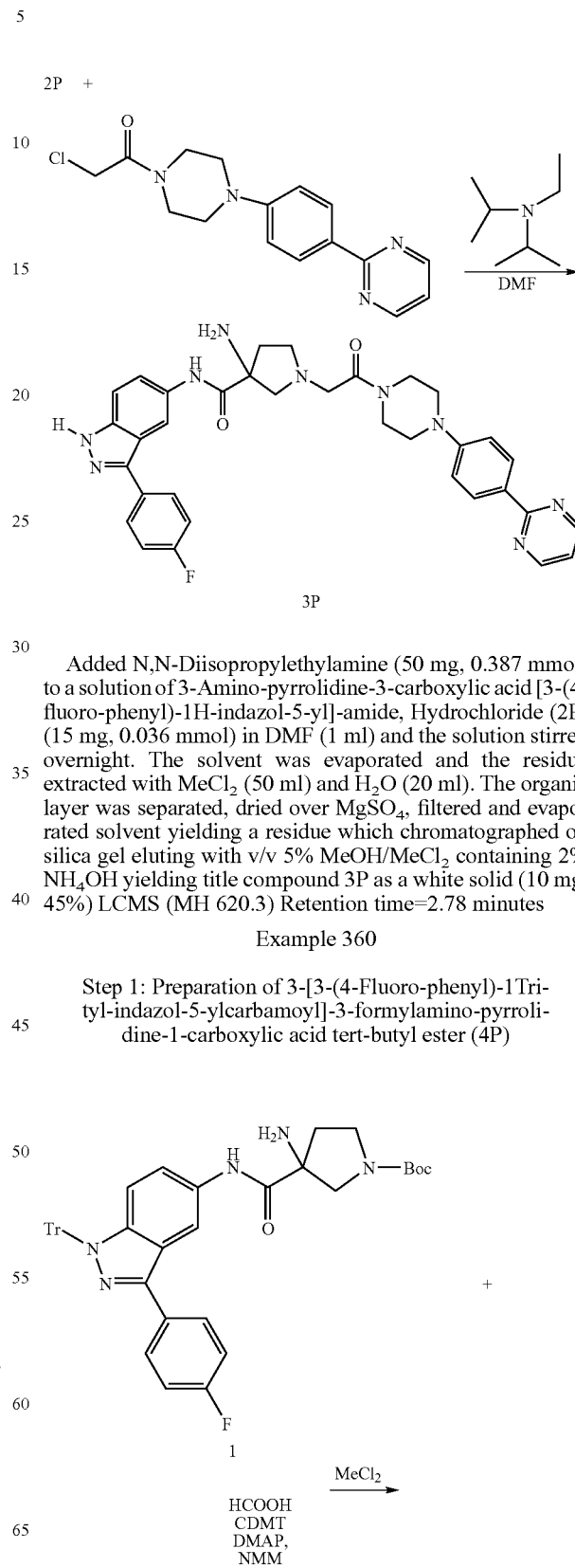

Added N,N-Diisopropylethylamine (50 mg, 0.387 mmol) to a solution of 3-Amino-pyrrolidine-3-carboxylic acid [3-(4-fluoro-phenyl)-1H-indazol-5-yl]-amide, Hydrochloride (2P) (15 mg, 0.036 mmol) in DMF (1 ml) and the solution stirred overnight. The solvent was evaporated and the residue extracted with MeCl₂ (50 ml) and H₂O (20 ml). The organic layer was separated, dried over MgSO₄, filtered and evaporated solvent yielding a residue which chromatographed on silica gel eluting with v/v 5% MeOH/MeCl₂ containing 2% NH₄OH yielding title compound 3P as a white solid (10 mg, 45%) LCMS (MH 620.3) Retention time=2.78 minutes Example 360

Step 1: Preparation of 3-[3-(4-Fluoro-phenyl)-1Trityl-indazol-5-ylcarbamoyl]-3-formylamino-pyrrolidine-1-carboxylic acid tert-butyl ester (4P)

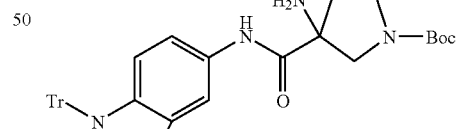

-continued

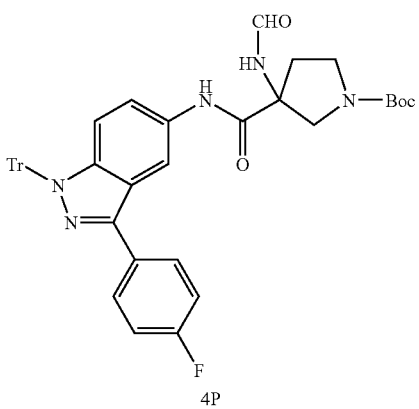

4P

Formic acid (17 mg, 0.36 mmol) was added to a solution of 3-Amino-3-[3-(4-fluoro-phenyl)-1 trityl-indazol-5-ylcarbamoyl]-pyrrolidine-1-carboxylic acid tert-butyl ester (1P) 250 mg, 0.367 mmol); 2-Chloro-4,6-dimethoxy-1,3,5-triazine (77 mg, 0.44 mmol); DMAP (10 mg) and NMM (50 mg, 0.49 mmol) in MeCl$_2$ (3 ml) at room temperature. The solvent was evaporated and residue chromatographed on silica gel eluting with 3% v/v MeOH/MeCl$_2$ yielding 4P as a white solid (210 mg, 80%) ESMS (MH 710).

Step 2: Preparation of 3-Formylamino-pyrrolidine-3-carboxylic acid [3-(4-fluoro-phenyl)-1H-indazol-5-yl]-amide (5P)

4M HCl (2 ml) was added to a solution of 3-[3-(4-Fluoro-phenyl)-1Trityl-indazol-5-ylcarbamoyl]-3-formylamino-pyrrolidine-1-carboxylic acid tert-butyl ester (4P) 0.141 (mmol) in MeCl$_2$ (2 ml) at room temperature, then stirred for 1 hour. The solvent was evaporated, hexanes added to residue and supernatant decanted. The residual solid was dried yielding 5P as a white solid (60 mg, 100%) LCMS (MH, 368.2) Retention time=1.91 minutes.

Step 3: Preparation of 3-Formylamino-1-{2-oxo-2-[4-(4-pyrimidin-2-yl-phenyl)-piperazin-1-yl]-ethyl}-pyrrolidine-3-carboxylic acid [3-(4-fluoro-phenyl)-1H-indazol-5-yl]-amide (6P)

5P +

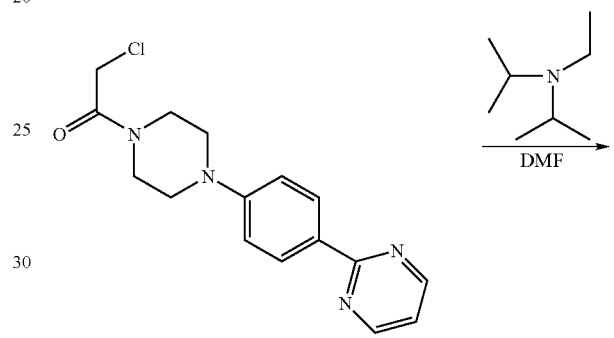

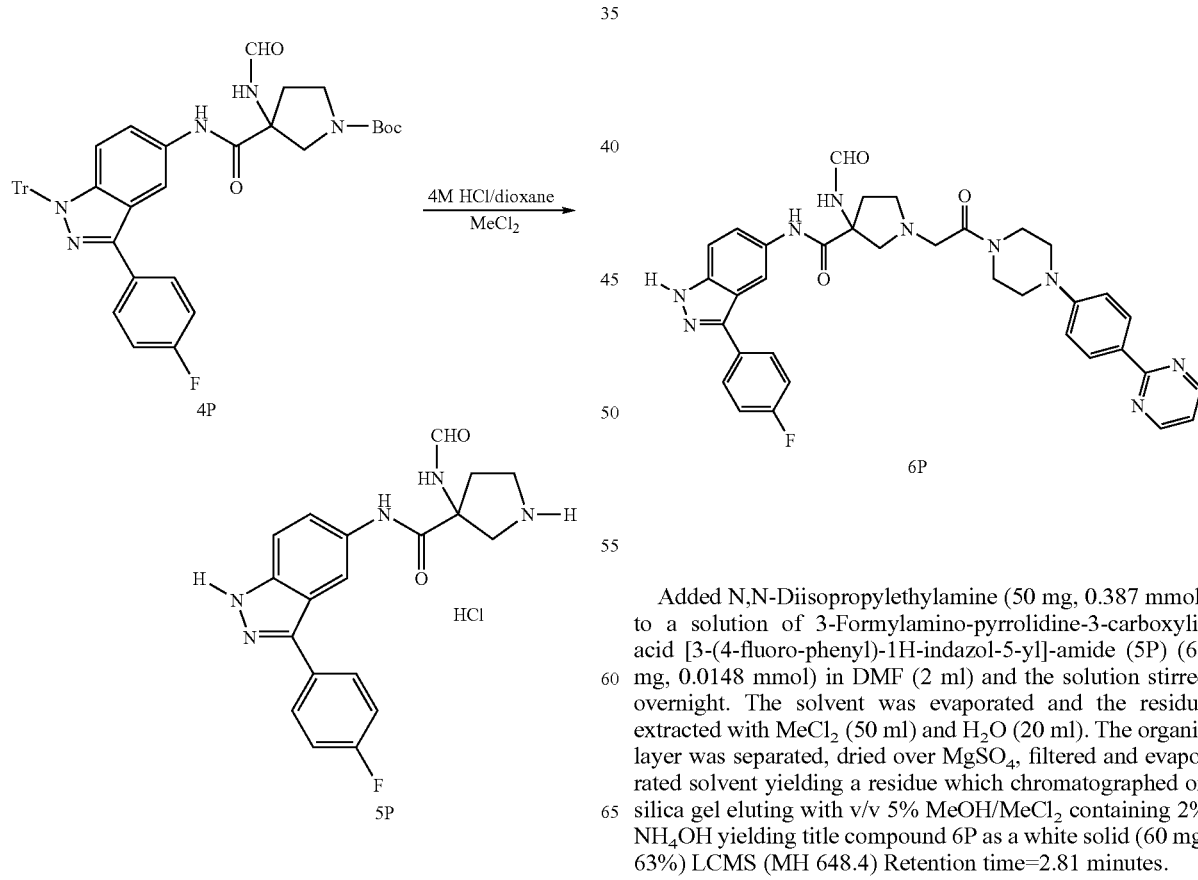

Added N,N-Diisopropylethylamine (50 mg, 0.387 mmol) to a solution of 3-Formylamino-pyrrolidine-3-carboxylic acid [3-(4-fluoro-phenyl)-1H-indazol-5-yl]-amide (5P) (60 mg, 0.0148 mmol) in DMF (2 ml) and the solution stirred overnight. The solvent was evaporated and the residue extracted with MeCl$_2$ (50 ml) and H$_2$O (20 ml). The organic layer was separated, dried over MgSO$_4$, filtered and evaporated solvent yielding a residue which chromatographed on silica gel eluting with v/v 5% MeOH/MeCl$_2$ containing 2% NH$_4$OH yielding title compound 6P as a white solid (60 mg, 63%) LCMS (MH 648.4) Retention time=2.81 minutes.

Example 361

Preparation of 3-Amino-1-{2-oxo-2-[4-(4-pyrimidin-2-yl-phenyl)-piperazin-1-yl]-ethyl}-pyrrolidine-3-carboxylic acid [3-(4-fluoro-phenyl)-1H-indazol-5-yl]-amide (7P)

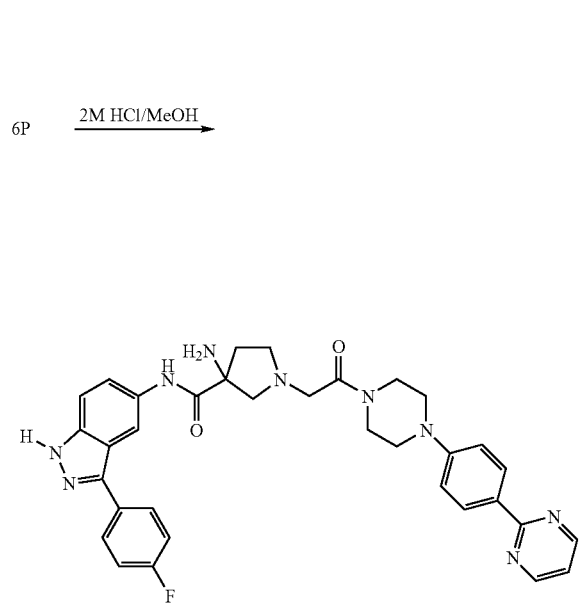

7P

Added 2M HCl (2 ml) to a solution of 3-Formylamino-1-{2-oxo-2-[4-(4-pyrimidin-2-yl-phenyl)-piperazin-1-yl]-ethyl}-pyrrolidine-3-carboxylic acid [3-(4-fluoro-phenyl)-1H-indazol-5-yl]-amide (6P) (10 mg, 0.015 mmol) in MeOH (2 ml) at room temperature, then stirred for 4 days at room temperature. The reaction mixture was diluted with Water (20 ml), basified with 1N NaOH (3 ml) and extracted with MeCl$_2$ (3×50 ml). The organic layers were combined, dried over MgSO$_4$, filtered and solvent evaporated yielding 7P as a white solid (7 mg, 73%) LCMS (MH 620.3) Retention time=2.78 minutes.

Example 362

Preparation of 3-Formylamino-1-(2-{2-methyl-4-[4-(5-methyl-pyrimidin-2-yl)-phenyl]-piperazin-1-yl}-2-oxo-ethyl)-pyrrolidine-3-carboxylic acid [3-(4-fluoro-phenyl)-1H-indazol-5-yl]-amide (8P)

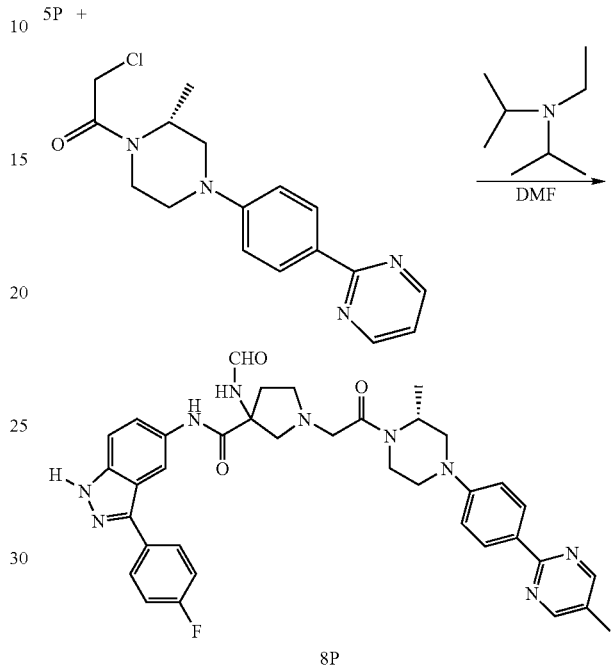

8P

Following essentially the same procedure as described in Step 3 of Example 360 except substituting 2-Chloro-1-[4-(4-pyrimidin-2-yl-phenyl)-piperazin-1-yl]-ethanone with an equivalent quantity of 2-Chloro-1-[2-methyl-4-(4-pyrimidin-2-yl-phenyl)-piperazin-1-yl]-ethanone, the title compound 8P was obtained. Chromatography on silica gel eluting with 5% v/v MeOH/MeCl$_2$ containing 2% NH$_4$OH yields 8P as a white solid (55 mg, 55%). LCMS (MH 676.4) Retention time=2.96 minutes. The product is a mixture of 2 Isomers.

Compound 8P was separated into single isomers on Chiral HPLC (AD Column) Analytical column (Chiralpak AD 4.6× 250). 40% IPA/Hexanes containing 0.2% DEA:

Peak A (isomer A) eluted at 24.501 minutes. LCMS (MH 676.4). Retention time (minutes) 2.96

Isomer A (9P)

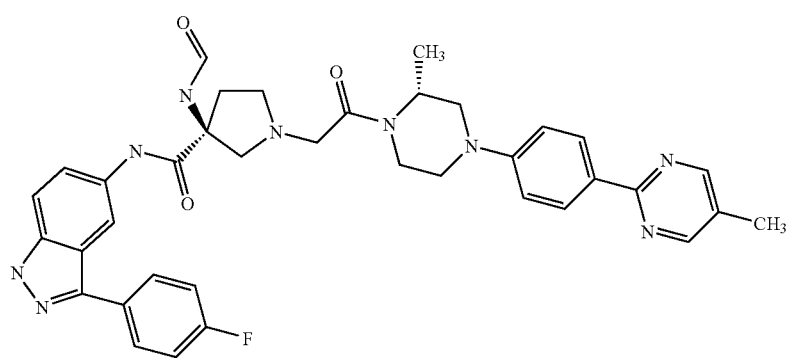

Peak B (isomer B) eluted at 33.036 minutes LCMS (MH 676.4) (10P)

Example 363

Preparation of 3-Amino-1-(2-{2-methyl-4-[4-(5-methyl-pyrimidin-2-yl)-phenyl]-piperazin-1-yl}-2-oxo-ethyl)-pyrrolidine-3-carboxylic acid [3-(4-fluoro-phenyl)-1H-indazol-5-yl]-amide (11P)

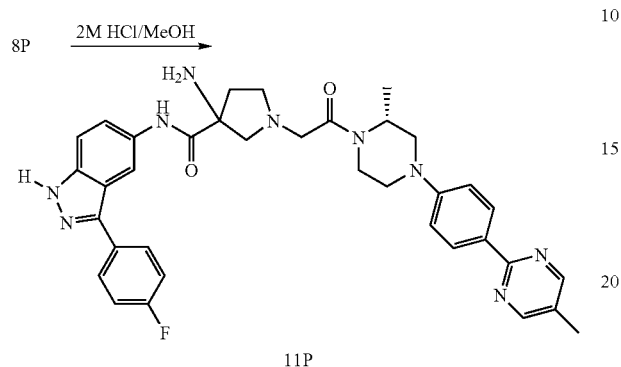

Following essentially the same procedure as Example 361 except substituting compound 6P with an equivalent quantity of 8P, the title compound 11P was obtained as a mixture of 2 isomers. LCMS (MH 648) Retention time=2.90 minutes.

Example 364

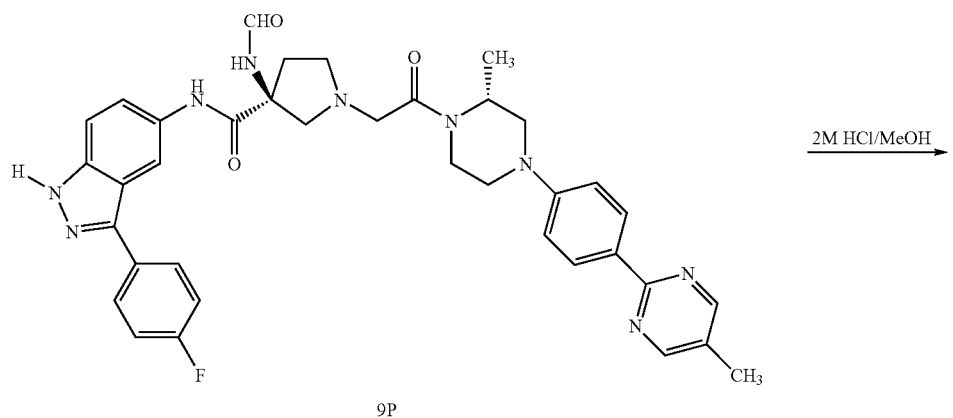

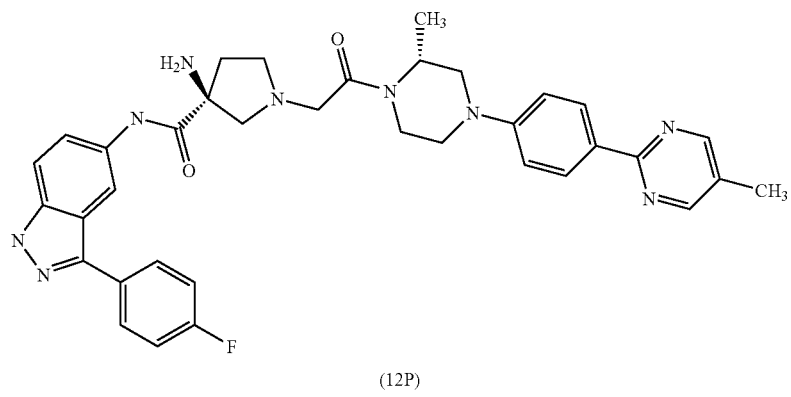

Following essentially the same procedure as Example 361 except substituting compound 6P with an equivalent quantity of compound 9P (isomer A, Example 372), the title compound 12P was obtained as a single isomer. LCMS (MH 648.4) Retention time=2.90 minutes.

Preparation 35

Step 1: Preparation of 5-Pyrimidin-2-yl-3',6'-dihydro-2'H-[2,4']bipyridinyl-1'-carboxylic acid tert-butyl ester (2Q)

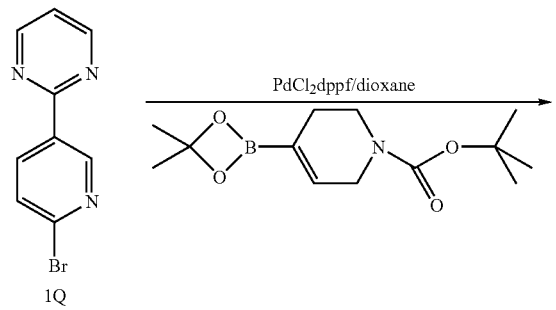

Refluxed mixture of 2-(6-Bromo-pyridin-3-yl)-pyrimidine (1Q) (200 mg, 0.85 mmol), N-tert-butoxycarbonyl-1,2,3,6-tetrahydropyridine-4-boronic acid, pinacol ester (290 mg, 0.93 mmol); Cesium Carbonate (500 mg, 1.538 mmol); PdCl$_2$dppf (30 mg) in dioxane/H$_2$O (10 ml v/v 4/1) for 4 hours. Cooled reaction, then evaporated solvent. Extracted with EtOAc (200 ml) washed with H$_2$O (50 ml), dried over MgSO$_4$, filtered and solvent evaporated yielding a solid which chromatographed on silica gel eluting with 30% v/v acetone/hexanes yielding 2Q as a white solid (110 mg, 38%) ESMS (MH, 339).

Step 2: Preparation of 5-Pyrimidin-2-yl-1',2',3',6'-tetrahydro-[2,4']bipyridinyl (3Q)

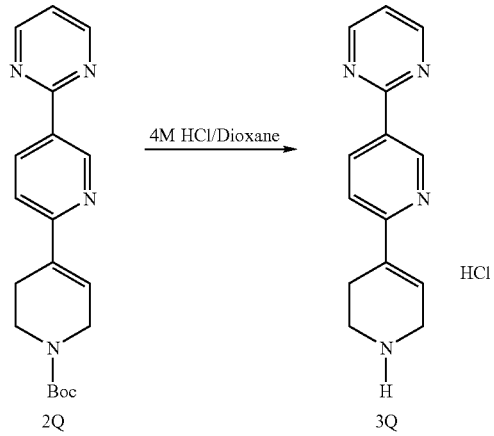 [SMILES: CC(C)(C)OC(=O)N1CC=C(c2ccc(-c3ncccn3)cn2)CC1 ; C1=C(c2ccc(-c3ncccn3)cn2)CCNC1 ; Cl]

Added 4M HCl/dioxane (5 ml) to solution of 5-Pyrimidin-2-yl-3',6'-dihydro-2'H-[2,4']bipyridinyl-1'-carboxylic acid tert-butyl ester (2Q) (110 mg, 0.325 mmol) in MeCl$_2$ (5 ml) at room temperature, then stirred 4 hours. Evaporated solvent. Added MeCl$_2$ (100 ml), H$_2$O (50 ml) and 10% NaOH (3 ml). The organic layer was separated, dried over MgSO$_4$, filtered and solvent evaporated yielding 3Q as a white solid (90 mg, 100%) ESMS (MH, 239) LCMS (MH, 239) Retention time=1.53 minutes.

Step 3: Preparation of 2-Chloro-1-(5-pyrimidin-2-yl-3',6'-dihydro-2'H-[2,4']bipyridinyl-1'-yl)-ethanone (4Q)

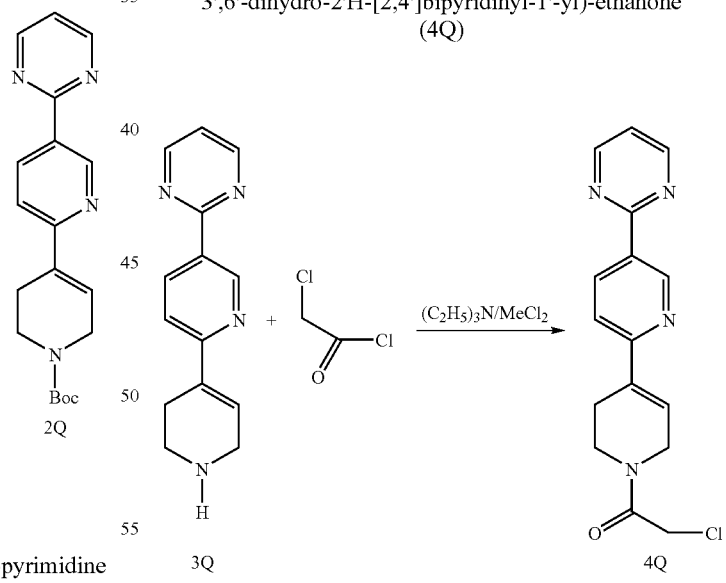

Added chloroacetyl chloride (0.35 g, 4.39 mmol) in MeCl$_2$ (15 ml) to a solution of 5-Pyrimidin-2-yl-1',2',3',6'-tetrahydro-[2,4']bipyridinyl (3Q) (0.4 g, 1.68 mmol) and triethylamine (0.4 g, 2.87 mmol) in MeCl$_2$ (10 ml) at 0° C., then stirred 2 hours at 0° C. Added saturated NaHCO$_3$ solution and stirred an additional hour at 0° C. MeCl$_2$ (100 ml) was added, organic layer separated, dried over Na$_2$SO$_4$, filtered and solvent evaporated yielding 4Q as a pale yellow solid (0.53 g, 100%) ESMS (MH 315).

Example 365

Step 1: Preparation of 3-Amino-pyrrolidine-1,3-dicarboxylic acid 1-tert-butyl ester 3-methyl ester (1T)

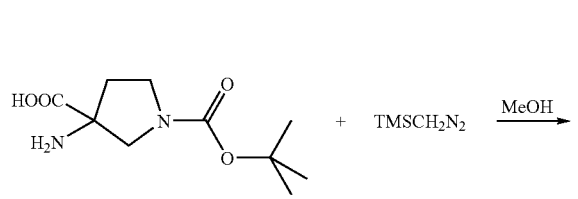

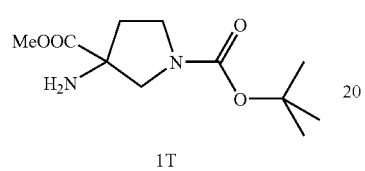

Added (Trimethylsilyl)-diazomethane (2M in hexanes: 15 ml, 30 mmol) to a solution of 3-Amino pyrrolidine 1,3 dicarboxylic acid, 1-tert-butyl ester (900 mg, 3.9 mmol) in MeOH (5 ml) at room temperature. Stirred 10 minutes then evaporated solvent yielding 1T as an oil (0.9 g, 98%).

Step 2: Preparation of 3-Formylamino-pyrrolidine-1,3-dicarboxylic acid 1-tert-butyl ester 3-methyl ester (2T)

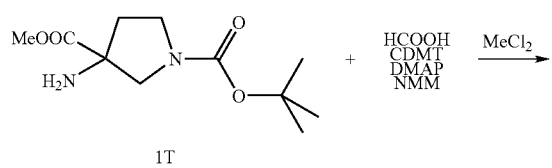

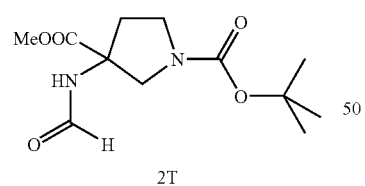

Added formic acid (200 mg, 4.34 mmol) to solution of 3-Amino-pyrrolidine-1,3-dicarboxylic acid 1-tert-butyl ester 3-methyl ester (1T) (900 mg, 3.688 mmol); 2-Chloro-4,6 dimethoxy-1,3,5-Triazine (CDMT) (800 mg, 4.556 mmol); DMAP (20 mg), and NMM (400 mg, 4 mmol) at room temperature, then stirred overnight. The solvent was evaporated and the residue extracted with MeCl$_2$ (200 ml), washed with H$_2$O (50 ml), dried over MgSO$_4$, filtered and solvent evaporated yielding a solid which chromatographed on silica gel eluting with 5% MeOH/MeCl$_2$ containing 2% NH$_4$OH yielding 2T as a white solid (725 mg, 72%) LCMS (MH 273) Retention time=2.53 minutes.

Step 3: Preparation of 3-(Formyl-methyl-amino)-pyrrolidine-1,3-dicarboxylic acid 1-tert-butyl ester 3-methyl ester (3T)

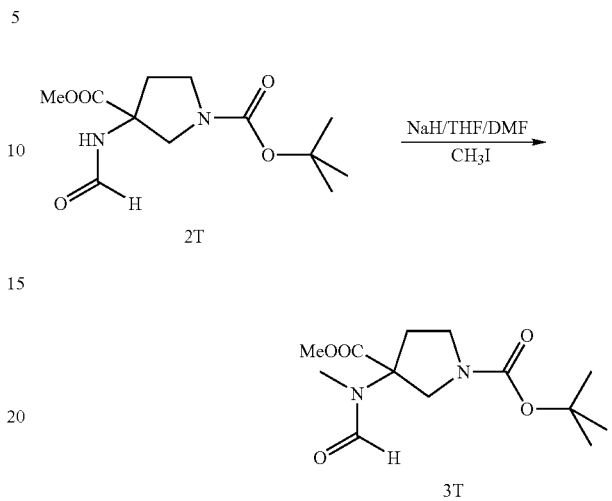

Sodium hydride (60% in oil) (10 mg, 0.25 mmol) was added to a solution of 3-Formylamino-pyrrolidine-1,3-dicarboxylic acid 1-tert-butyl ester 3-methyl ester (2T) (50 mg, 0.183 mmol) in THF (3 ml). DMF (1 ml) was added and stirred for 1 hour. Methyl iodide (0.1 ml, 1.60 mmol) was added and the reaction was stirred overnight. The solvent was evaporated and the residue extracted with EtOAc (50 ml), washed with H$_2$O (20 ml), dried over MgSO$_4$, filtered and solvent evaporated yielding a residue which chromatographed on silica gel eluting with 3% MeOH/MeCl$_2$ yielding 3T (50 mg, 94%). LCMS (MH 287) Retention time=2.77 minutes.

Step 4: Preparation of 3-(Formyl-methyl-amino)-pyrrolidine-3-carboxylic acid methyl ester, Hydrochloride.(4T)

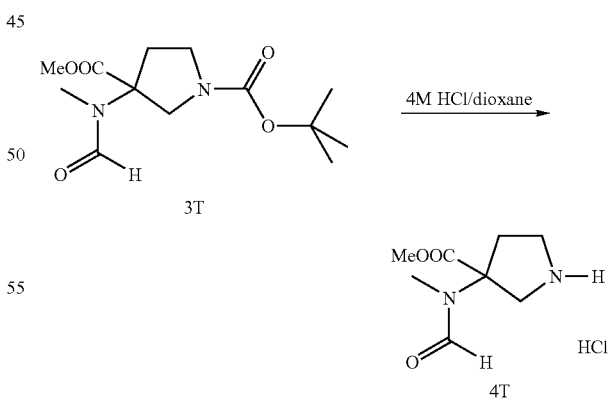

Added 4M HCl/dioxane (2 ml) to a solution of 3-(Formyl-methyl-amino)-pyrrolidine-1,3-dicarboxylic acid 1-tert-butyl ester 3-methyl ester (3T) (50 mg, 0.175 mmol) in MeCl$_2$ (2 ml) at room temperature then stirred for 1 hour. The solvent was evaporated yielding 4T as a white solid (45 mg, 100%) ESMS (MH 187).

Step 5: Preparation of 3-(Formyl-methyl-amino)-1-{2-oxo-2-[4-(4-pyrimidin-2-yl-phenyl)-3,6-dihydro-2H-pyridin-1-yl]-ethyl}-pyrrolidine-3-carboxylic acid methyl ester (5T)

4T +

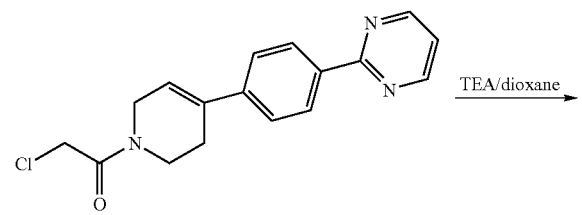

TEA/dioxane →

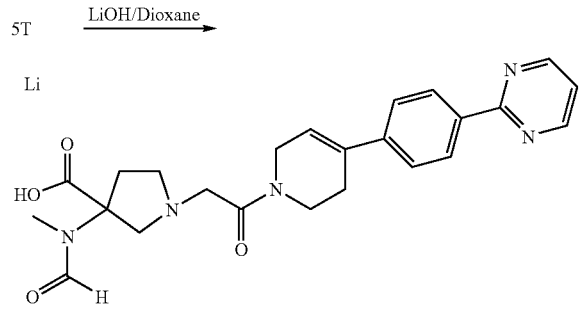

5T

Added triethylamine (0.3 ml, 2.15 mmol) to a solution of (3-(Formyl-methyl-amino)-pyrrolidine-3-carboxylic acid methyl ester, Hydrochloride.(4T) (90 mg, 0.405 mmol) and 2-Chloro-1-[4-(4-pyrimidin-2-yl-phenyl)-3,6-dihydro-2H-pyridin-1-yl]-ethanone (140 mg, 0.447 mmol) in dioxane (5 ml) at room temperature, then stirred at 90° C. for 5 hours. The reaction was cooled and solvent evaporated yielding a residue which chromatographed on silica gel eluting with 7% MeOH/MeCl$_2$ containing 2% NH$_4$OH yielding 5T as a white solid (100 mg, 53%) ESMS (MH 464).

Step 6: Preparation of 3-(Formyl-methyl-amino)-1-{2-oxo-2-[4-(4-pyrimidin-2-yl-phenyl)-3,6-dihydro-2H-pyridin-1-yl]-ethyl}-pyrrolidine-3-carboxylic acid, Lithium salt (6T)

5T $\xrightarrow{\text{LiOH/Dioxane}}$

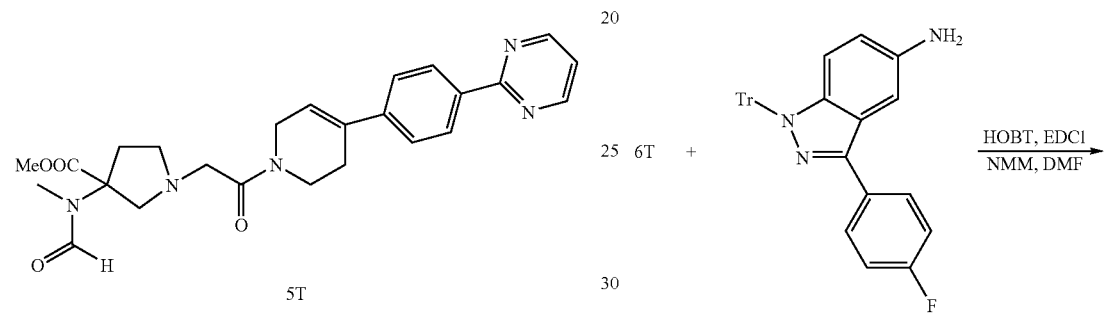

6T

Added Lithium Hydroxide monohydrate (13 mg, 0.22 mmol) to a solution of 3-(Formyl-methyl-amino)-1-{2-oxo-2-[4-(4-pyrimidin-2-yl-phenyl)-3,6-dihydro-2H-pyridin-1-yl]-ethyl}-pyrrolidine-3-carboxylic acid methyl ester (5) (100 mg, 0.2159 mmol) in dioxane (3 ml), then stirred 4 hours at room temperature. The solvent was evaporated yielding 6T as a white solid (95 mg, 98%) LCMS (MH 450.2) Retention time=2.15 minutes.

Step 7: Preparation of 3-(Formyl-methyl-amino)-1-{2-oxo-2-[4-(4-pyrimidin-2-yl-phenyl)-3,6-dihydro-2H-pyridin-1-yl]-ethyl}-pyrrolidine-3-carboxylic acid [3-(4-fluoro-phenyl)-1trityl-indazol-5-yl]-amide (7T)

6T +

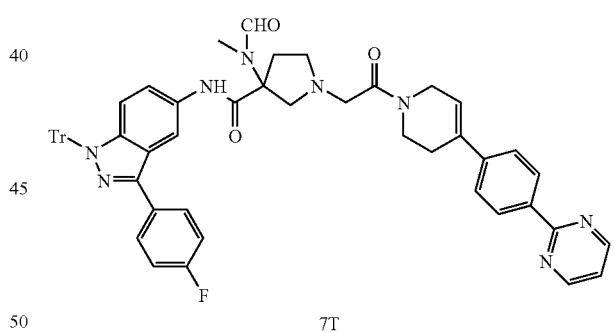

$\xrightarrow[\text{NMM, DMF}]{\text{HOBT, EDCl}}$

7T

Added EDCl.HCl (75 mg, 0.39 mmol) and HOBT.H$_2$O (50 mg, 0.37 mmol) to a solution of 3-(4-Fluoro-phenyl)-1trityl-indazol-5-ylamine (110 mg, 0.234 mmol) and 3-(Formyl-methyl-amino)-1-{2-oxo-2-[4-(4-pyrimidin-2-yl-phenyl)-3,6-dihydro-2H-pyridin-1-yl]-ethyl}-pyrrolidine-3-carboxylic acid, Lithium salt (6T) (95 mg, 0.211 mmol) in DMF (2 ml) and NMM (0.1 ml) at room temperature, then stirred overnight. The solvent was evaporated and residue extracted with MeCl$_2$ (50 ml), washed with H$_2$O (20 ml), dried over MgSO$_4$, filtered and solvent evaporated yielding a residue which chromatographed on silica gel eluting with v/v 9:1 EtOAc:Hexanes yielding 7T as a white solid (89 mg, 44%) ESMS (MH 901).

Step 8: Preparation of 3-(Formyl-methyl-amino)-1-{2-oxo-2-[4-(4-pyrimidin-2-yl-phenyl)-3,6-dihydro-2H-pyridin-1-yl]-ethyl}-pyrrolidine-3-carboxylic acid [3-(4-fluoro-phenyl)-1H-indazol-5-yl]-amide (8T)

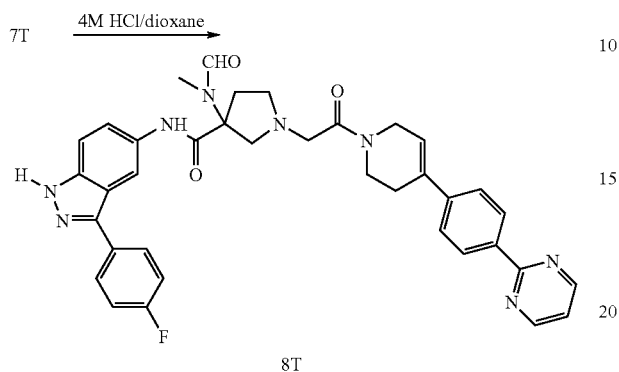

Added 4M HCl/dioxane (2 ml) to a solution of 3-(Formyl-methyl-amino)-1-{2-oxo-2-[4-(4-pyrimidin-2-yl-phenyl)-3,6-dihydro-2H-pyridin-1-yl]-ethyl}-pyrrolidine-3-carboxylic acid [3-(4-fluoro-phenyl)-1trityl-indazol-5-yl]-amide (7T) (89 mg, 0.098 mmol) in MeCl₂ (2 ml) at room temperature, then stirred for 2 hours. The solvent was evaporated and the residue extracted with MeCl₂ (50 ml), H₂O (25 ml) and 3M NaOH (2 ml). The organic layer was separated, dried over MgSO₄, filtered and solvent evaporated yielding a solid. Hexanes (2×50 ml) was added and the supernatant decanted. The residual solid was dried yielding 8T as a white solid (55 mg, 84%) LCMS (MH 659) Retention time=2.98 minutes.

8T is a mixture of 2 Enantiomers which separate on a chiralpak AD (4.6×250) column eluting with 60:40 Hex:IPA containing 0.2% DEA. Flow rate=0.9 ml/minute
Peak A elutes at 29.52 minutes.
Peak B elutes at 35.5 minutes.

Example 366

Preparation of 3-Methylamino-1-{2-oxo-2-[4-(4-pyrimidin-2-yl-phenyl)-3,6-dihydro-2H-pyridin-1-yl]-ethyl}-pyrrolidine-3-carboxylic acid [3-(4-fluoro-phenyl)-1H-indazol-5-yl]-amide (9T)

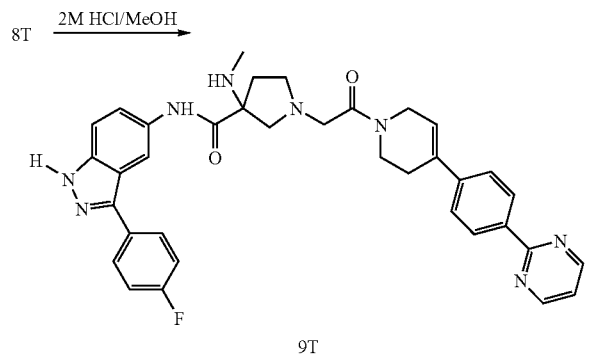

Added 2M HCl (2 ml) to a solution of 3-(Formyl-methyl-amino)-1-{2-oxo-2-[4-(4-pyrimidin-2-yl-phenyl)-3,6-dihydro-2H-pyridin-1-yl]-ethyl}-pyrrolidine-3-carboxylic acid [3-(4-fluoro-phenyl)-1H-indazol-5-yl]-amide (8T) (11 mg, 0.017 mmol) in MeOH (5 ml) at room temperature for 4 days. Evaporated solvent Added H₂O (20 ml), basified with 1N NaOH (2 ml), and extracted with MeCl₂ (50 ml). Separated organic layer, dried over MgSO₄, filtered and evaporated solvent, yielding residue which chromatographed on silica gel eluting with 10% MeCl₂/MeOH yielding 9T (5 mg) ESMS (MH 631)

Example 367

Preparation of 3-Methoxymethyl-1-{2-oxo-2-[4-(4-pyrimidin-2-yl-phenyl)-3,6-dihydro-2H-pyridin-1-yl]-ethyl}-pyrrolidine-3-carboxylic acid [3-(4-fluoro-phenyl)-1H-pyrazolo[4,3-b]pyridin-5-yl]-amide

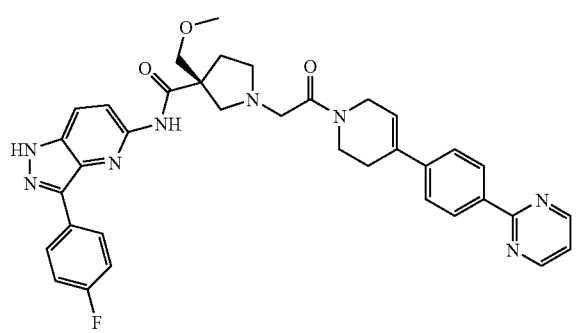 [SMILES: COC[C@@]1(C(=O)Nc2ccc3[nH]nc(-c4ccc(F)cc4)c3n2)CCN(CC(=O)N2CC=C(c3ccc(-c4ncccn4)cc3)CC2)C1]

Step 1: Preparation of 3-bromo-1H-pyrazolo[4,3-b]pyridine

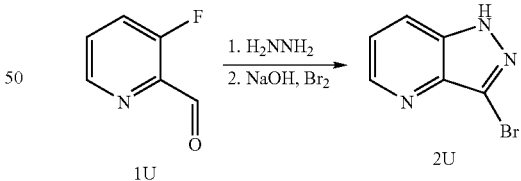

A mixture of 3-fluoro-2-formylpyridine (1.0 g, 8.0 mmol) in 2 mL of anhydrous hydrazine was heated to 110 C and stirred overnight. The reaction was poured to ice water and extracted with ethyl acetate. The combined organic layer was dried and concentrated to give a crude oil (0.5 g), which was subsequently dissolved in 10 mL of NaOH solution (2 N). To this was added bromine (0.6 g, 3.7 mmol) in 5 mL of NaOH solution (2 N) drop-wise. The reaction was stirred at room temperature for 3 hr and quenched by adding NaHSO₃ (0.06 g), then HCl solution (6 mL, 4 N). A solid was precipitated, filtered and air-dried to give 2U (0.66 g).

Step 2: Preparation of 3-(4-Fluoro-phenyl)-1H-pyrazolo[4,3-b]pyridine

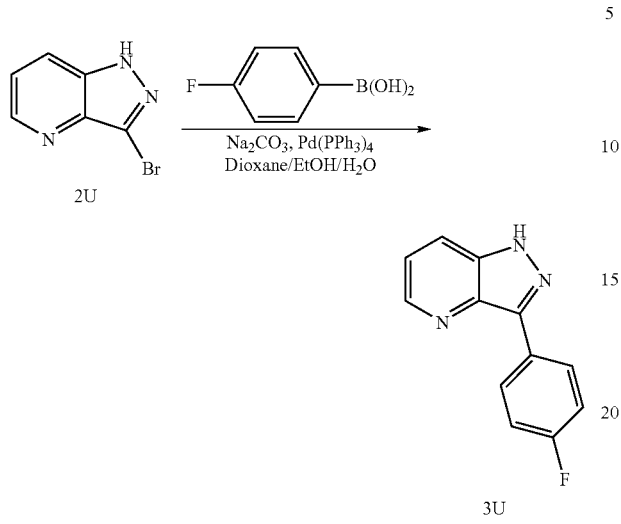

A mixture of 2U (480 mg, 2.45 mmol), Pd(PPh3)4 (141 mg, 0.122 mmol), 4-fluorophenylboronic acid (412 mg, 2.94 mmol) and sodium carbonate solution (2.4 mL, 2 M, 4.90 mmol) in 5 mL of dioxane/EtOH/H2O (7:3:2) was microwaved at 150° C. for 10 minutes. The mixture was diluted with water and extracted with ethyl acetate. The combined organic layer was dried, concentrated and purified by column chromatography to give 3U (362 mg).

Step 3: Preparation of 3-(4-Fluoro-phenyl)-1-trityl-1H-pyrazolo[4,3-b]pyridine 4-oxide

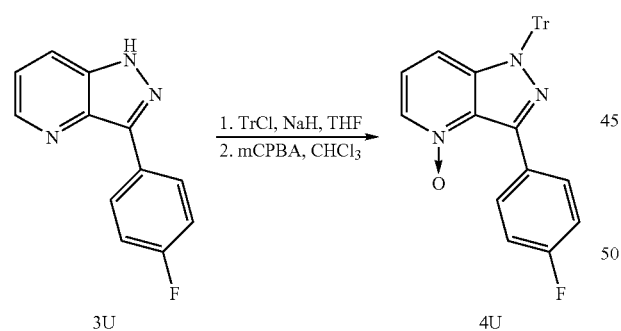

To a solution of 3U (362 mg, 1.46 mmol) in 8 mL of THF was added NaH (96 mg, 60%, 2.40 mmol) at 0° C. followed by addition of chlorotriphenylmethane (570 mg, 2.04 mmol). The reaction was stirred at room temperature for 1.5 hr and quenched with ammonium chloride solution. The aqueous layer was extracted with ethyl acetate, dried and concentrated to afford crude adduct. To a solution of the trityl adduct (260 mg, 0.57 mmol) in chloroform was added mCPBA (216 mg, 0.86 mmol). The reaction was heated to reflux for 6 hr, diluted with dichloromethane and washed with water. The organic layer was dried, concentrated and purified by column chromatography to give 4U (169 mg).

Step 3: Preparation of 3-(4-Fluorophenyl)-1-trityl-1H-pyrazolo[4,3-b]pyridin-5-ylamine

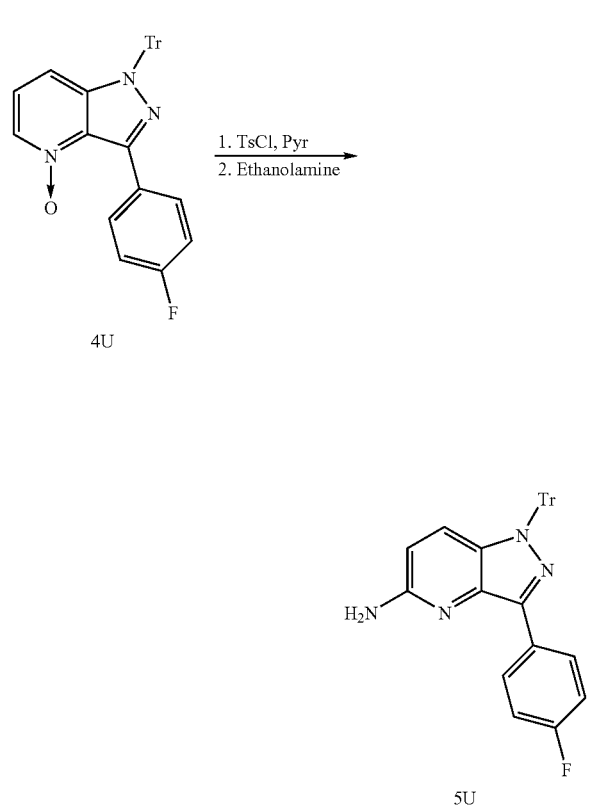

To a solution of 4U (138 mg, 0.293 mmol) in 2 mL of pyridine was added p-toluenesulfonyl chloride (67 mg, 0.352 mmol). The reaction was stirred at room temperature for 2 hr and the solvent was evaporated. To the crude residue was added 3 mL of ethanol amine. The reaction was stirred at room temperature for 2 hr and poured to ice. The yellow solid was collected by filtration and dried under vacuum to afford 5U (117 mg).

Step 4: Preparation of 3-(4-Fluorophenyl)-1H-pyrazolo[4,3-b]pyridin-5-ylamine

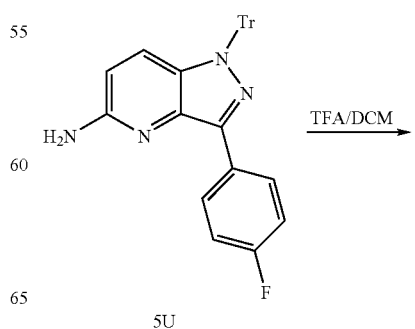

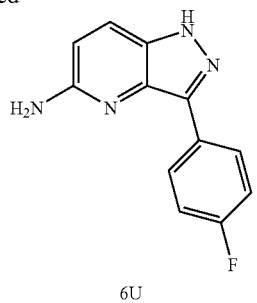
6U
A solution of 5U (112 mg, 0.238 mmol) in 2 mL of TFA/DCM (1:1) was stirred at room temperature for 1 hr and was concentrated. The residue was purified by column chromatography to give 6U (48.1 mg).
Step 5: Preparation of 3-Methoxymethyl-1-{2-oxo-2-[4-(4-pyrimidin-2-yl-phenyl)-3,6-dihydro-2H-pyridin-1-yl]-ethyl}-pyrrolidine-3-carboxylic acid [3-(4-fluoro-phenyl)-1H-pyrazolo[4,3-b]pyridin-5-yl]-amide
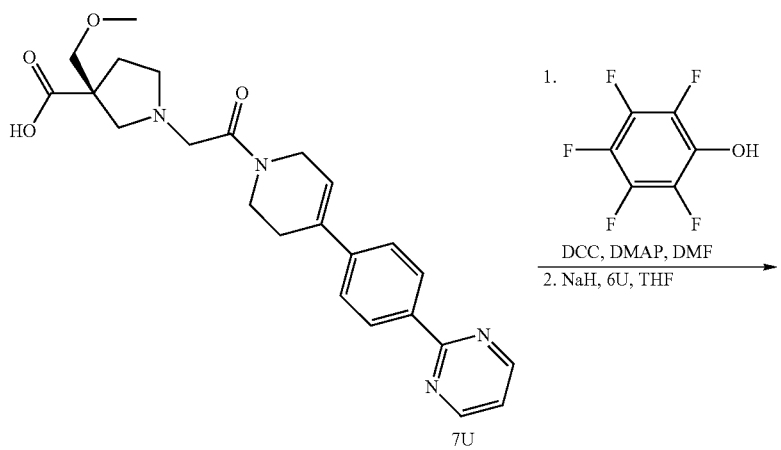
7U
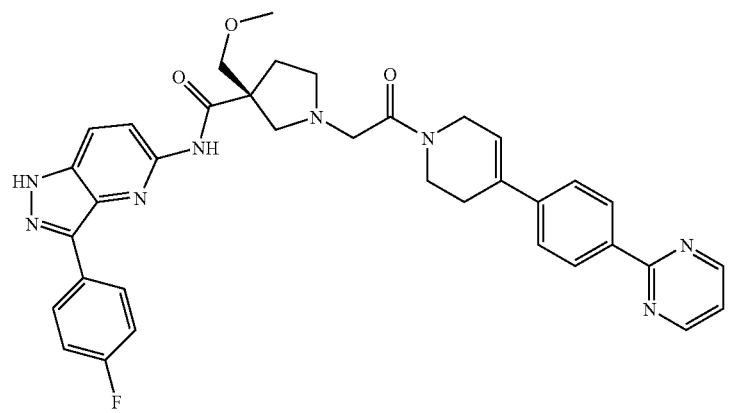
8U To a solution of 7U (see, Example 336, 150 mg, 0.283 mmol), pentafluorophenol (61.8 mg, 0.336 mmol) and DMAP (51.3 mg, 0.42 mmol) in DMF was added dicyclohexylcarbodiimide (0.34 mL, 1 M in DCM, 0.336 mmol). The reaction was stirred at room temperature for 4 hr and concentrated. The residue was purified by column chromatography to give the corresponding ester. To a solution of 6U (62 mg, 0.364 mmol) in THF at 0° C. was added NaH (16.0 mg, 0.437 mmol) and stirred at 0° C. for 0.5 h. To this mixture was added the pentafluorophenyl ester and stirred at room temperature for 1.5 hr. The reaction was quenched by adding ammonium chloride solution. The resulting mixture was concentrated and purified by reverse phase HPLC to afford 8U (16.9 mg).

Preparation 36

Chiral salt resolution of 3-methoxy-pyrrolidine-3-carboxylic acid methyl ester

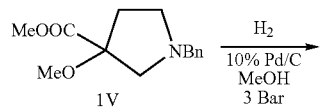

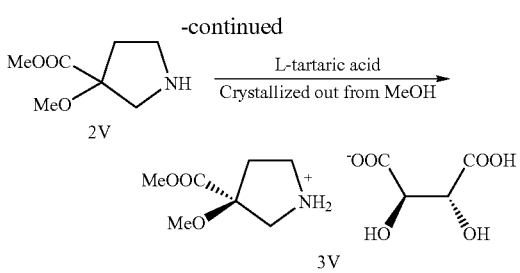

To a solution of compound 1V (660 mg, 2.65 mmols) in MeOH (30 ml) was charged 10% Pd/C (80 mg). The mixture was hydrogenated at 3 bar overnight using standard Parr apparatus, filtered and washed with MeOH several times.

To the methanol solution (20 ml) containing 2V (1.32 mmols) was added L-tartaric acid (180 mg, 1.2 mmols), and solid was taken into solution by sonication. Solvent was removed under reduced pressure to a residue to which MeOH (3 ml) was added and the solution was allowed to stand at −20 C overnight without disturbing. Crystals formed and MeOH was removed by pipette and crystals were rinsed with MeOH twice. Re-crystallization from MeOH gave 200 mg of complex 3V.

Examples 368-383

Following procedures essentially similar to the examples described above, the compounds in Table 20 are prepared.

TABLE 20

| Ex | Compound | M + 1 | Retention time (min) |
|---|---|---|---|
| 368 | (structure) | 678.4 | 3.18 |
| 369 | (structure) | 566.3 | 1.8 |

TABLE 20-continued
| Ex | Compound | M + 1 | Retention time (min) |
|---|---|---|---|
| 370 | 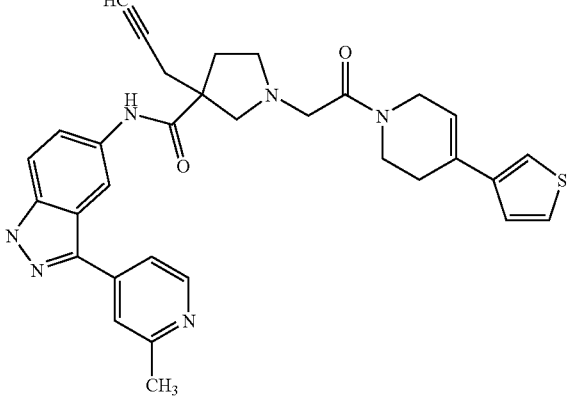 | 565.3 | 2.14 |
| 371 | 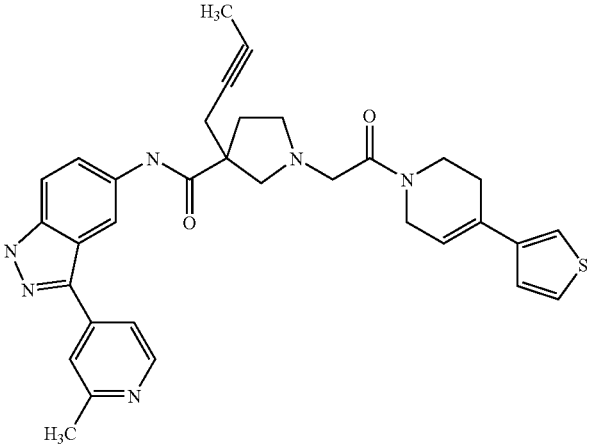 [SMILES: CC#CCC1(C(=O)Nc2ccc3[nH]nc(-c4ccnc(C)c4)c3c2)CCN(CC(=O)N2CC=C(c3ccsc3)CC2)C1] | 579.3 | 2.24 |
| 372 | 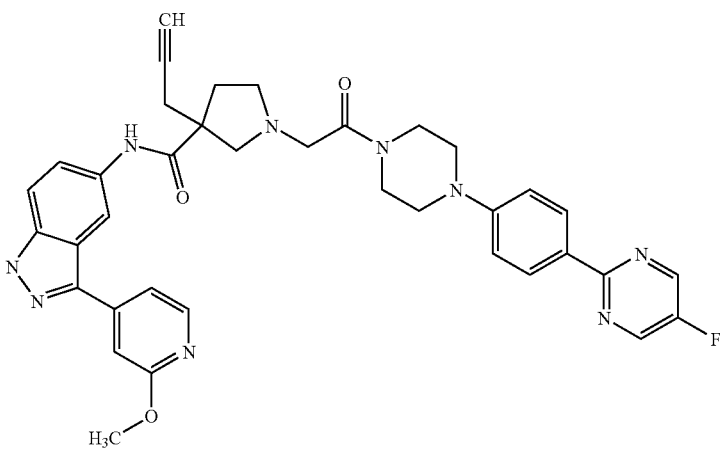 [SMILES: C#CCC1(C(=O)Nc2ccc3[nH]nc(-c4ccnc(OC)c4)c3c2)CCN(CC(=O)N2CCN(c3ccc(-c4ncc(F)cn4)cc3)CC2)C1] | 674.4 | 2.74 |

TABLE 20-continued

| Ex | Compound | M + 1 | Retention time (min) |
|---|---|---|---|
| 373 | | 662.4 | 2.68 |
| 374 | | 585.3 | 2.9 |
| 375 | | 595.3 | 2.78 |

TABLE 20-continued

| Ex | Compound | M + 1 | Retention time (min) |
|---|---|---|---|
| 376 | | 661.4 | 3.16 |
| 377 | | 582.4 | 2.23 |
| 378 | | 581.3 | 2.65 |

TABLE 20-continued

| Ex | Compound | M + 1 | Retention time (min) |
|---|---|---|---|
| 379 | | 658.4 | 2.61 |
| 380 | | 599.3 | 3.45 |
| 381 | | 569.3 | 2.62 |

TABLE 20-continued

| Ex | Compound | M + 1 | Retention time (min) |
|---|---|---|---|
| 382 | (structure: 3-(prop-2-ynyl)pyrrolidine-3-carboxamide linked to indazole-3-(4-fluorophenyl) and to piperazinyl-phenyl-(5-fluoropyrimidin-2-yl) via acetyl) | 661.4 | 3.21 |
| 383 | (structure: enantiomer of 382) | 661.4 | 3.16 |

Examples 384-436

Following procedures essentially similar to the examples described above, the compounds in Table 21 are prepared.

TABLE 21

| Ex. | Compound | M + 1 | Retention time (min) |
|---|---|---|---|
| 384 | (structure: 3-(methoxymethyl)pyrrolidine-3-carboxamide linked to indazole-3-(pyridin-4-yl) and to tetrahydropyridinyl-phenyl-(pyrimidin-2-yl) via acetyl) | 629.2 | 2.94 |

TABLE 21-continued
| Ex. | Compound | M + 1 | Retention time (min) |
|---|---|---|---|
| 385 | 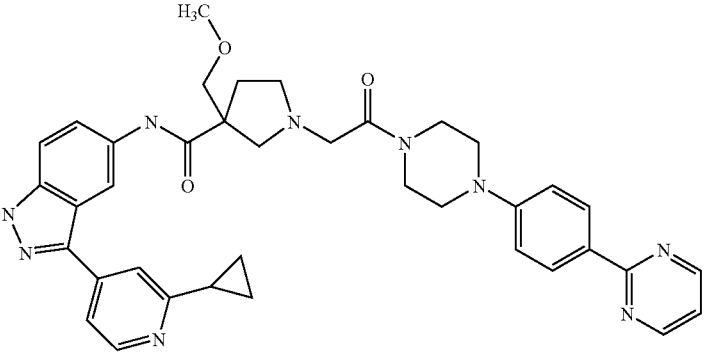 [SMILES: COCC1(C(=O)Nc2ccc3[nH]nc(-c4ccnc(C5CC5)c4)c3c2)CCN(CC(=O)N2CCN(c3ccc(-c4ncccn4)cc3)CC2)C1] | | |
| 386 | 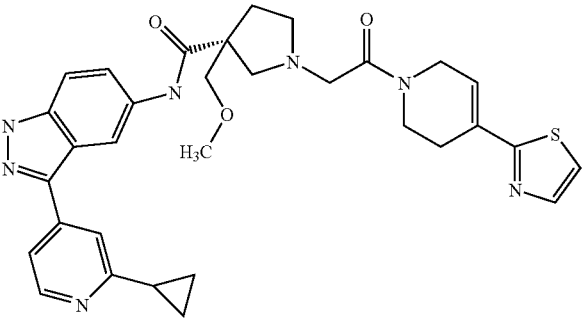 [SMILES: COC[C@@]1(C(=O)Nc2ccc3[nH]nc(-c4ccnc(C5CC5)c4)c3c2)CCN(CC(=O)N2CC=C(c3nccs3)CC2)C1] | 598.25 | 2.67 |
| 387 | 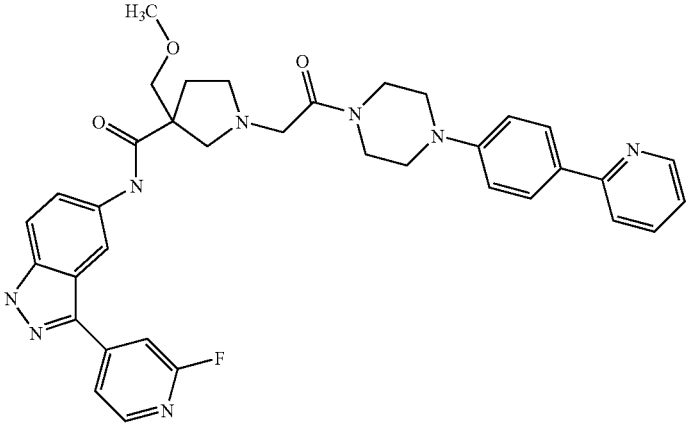 [SMILES: COCC1(C(=O)Nc2ccc3[nH]nc(-c4ccnc(F)c4)c3c2)CCN(CC(=O)N2CCN(c3ccc(-c4ccccn4)cc3)CC2)C1] | 650.3 | 3.55 |
| 388 | 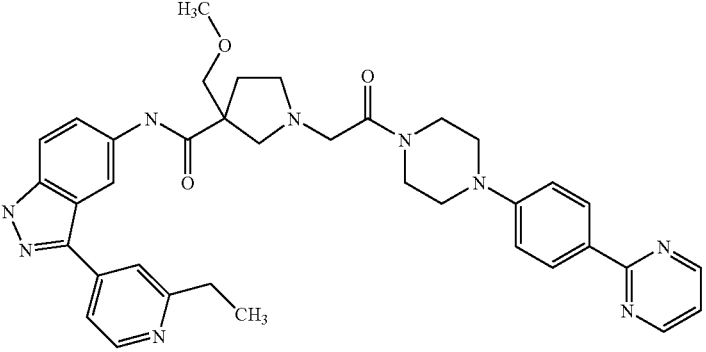 [SMILES: CCc1cc(-c2n[nH]c3ccc(NC(=O)C4(COC)CCN(CC(=O)N5CCN(c6ccc(-c7ncccn7)cc6)CC5)C4)cc23)ccn1] | | |

TABLE 21-continued
| Ex. | Compound | M + 1 | Retention time (min) |
|---|---|---|---|
| 389 | 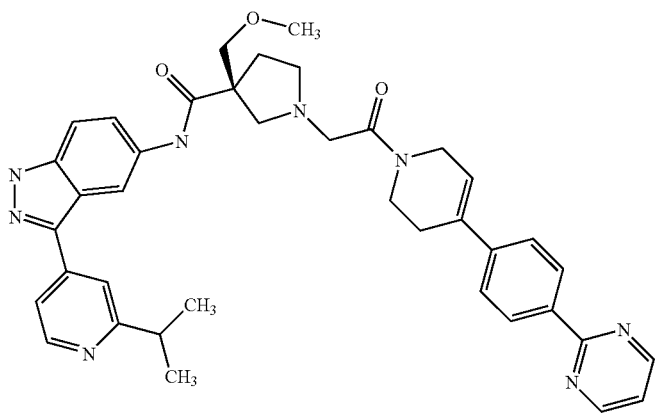 [SMILES: COC[C@@]1(C(=O)Nc2ccc3[nH]nc(-c4ccnc(C(C)C)c4)c3c2)CCN(CC(=O)N2CC=C(c3ccc(-c4ncccn4)cc3)CC2)C1] | 669 | 2.34 |
| 390 | 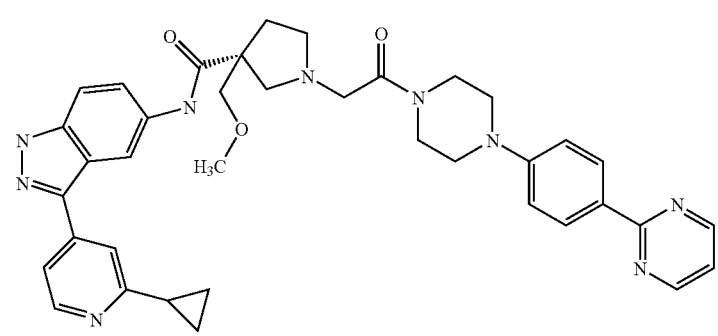 [SMILES: COC[C@@]1(C(=O)Nc2ccc3[nH]nc(-c4ccnc(C5CC5)c4)c3c2)CCN(CC(=O)N2CCN(c3ccc(-c4ncccn4)cc3)CC2)C1] | 672.34 | 2.88 |
| 391 | 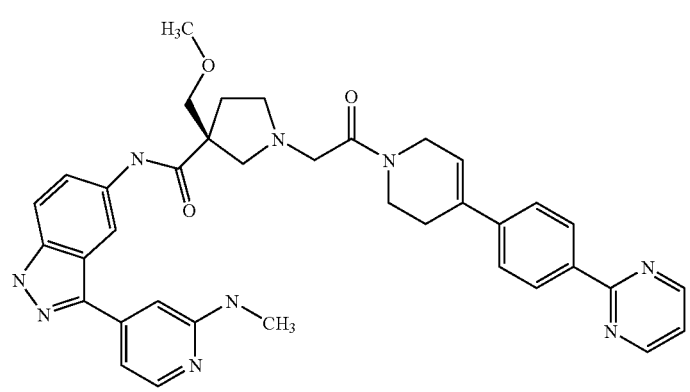 [SMILES: CNc1cc(-c2n[nH]c3ccc(NC(=O)[C@]4(COC)CCN(CC(=O)N5CC=C(c6ccc(-c7ncccn7)cc6)CC5)C4)cc23)ccn1] | | |
| 392 | 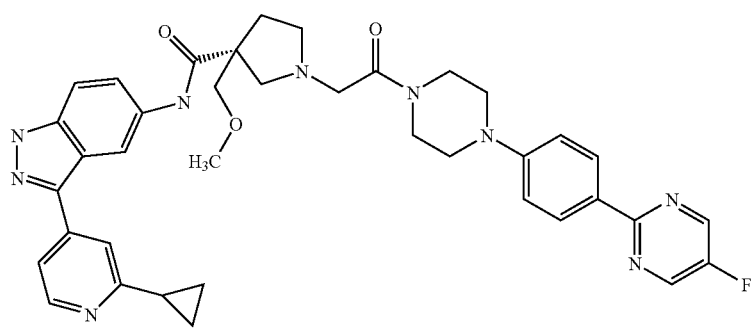 [SMILES: COC[C@@]1(C(=O)Nc2ccc3[nH]nc(-c4ccnc(C5CC5)c4)c3c2)CCN(CC(=O)N2CCN(c3ccc(-c4ncc(F)cn4)cc3)CC2)C1] | 690.32 | 3.26 |

TABLE 21-continued

| Ex. | Compound | M + 1 | Retention time (min) |
|---|---|---|---|
| 393 | | 598.4 | 2.61 |
| 394 | | 643.4 | 2.38 |
| 395 | | 686.35 | 3.1 |
| 396 | | 650.3 | 3.09 |

TABLE 21-continued
| Ex. | Compound | M + 1 | Retention time (min) |
|---|---|---|---|
| 397 | 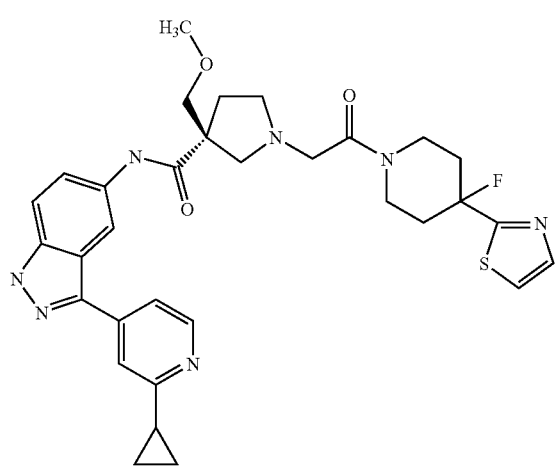 [SMILES: COC[C@@]1(C(=O)Nc2ccc3[nH]nc(-c4ccnc(C5CC5)c4)c3c2)CCN(CC(=O)N2CCC(F)(c3nccs3)CC2)C1] | 618.3 | 2.31 |
| 398 | 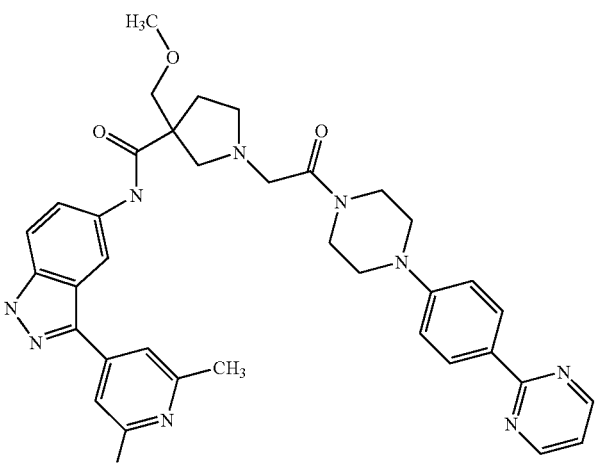 | 660.4 | 2.21 |
| 399 | 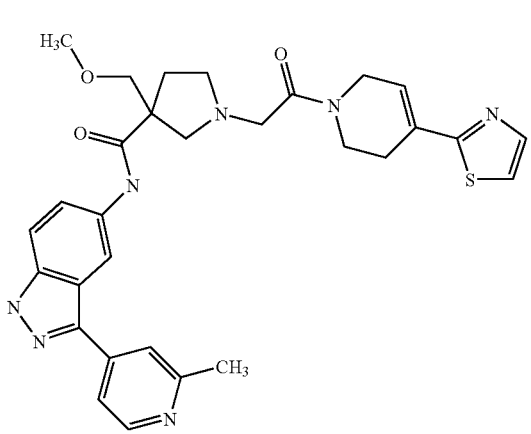 [SMILES: COCC1(C(=O)Nc2ccc3[nH]nc(-c4ccnc(C)c4)c3c2)CCN(CC(=O)N2CC=C(c3nccs3)CC2)C1] | 572.13 | 2.45 |

TABLE 21-continued
| Ex. | Compound | M + 1 | Retention time (min) |
|---|---|---|---|
| 400 | 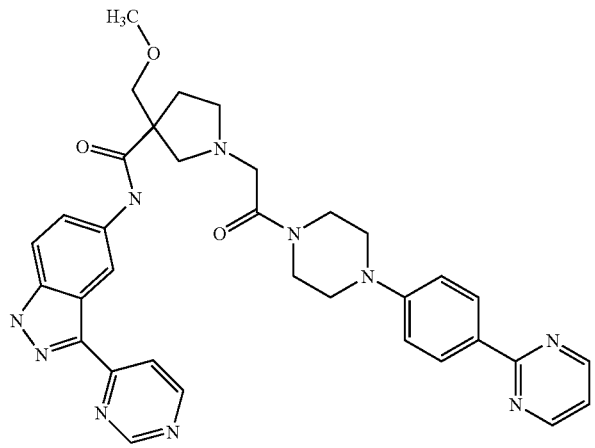 [SMILES: COCC1(C(=O)Nc2ccc3[nH]nc(-c4ccncn4)c3c2)CCN(CC(=O)N2CCN(c3ccc(-c4ncccn4)cc3)CC2)C1] | 633.3 | 3.11 |
| 401 | 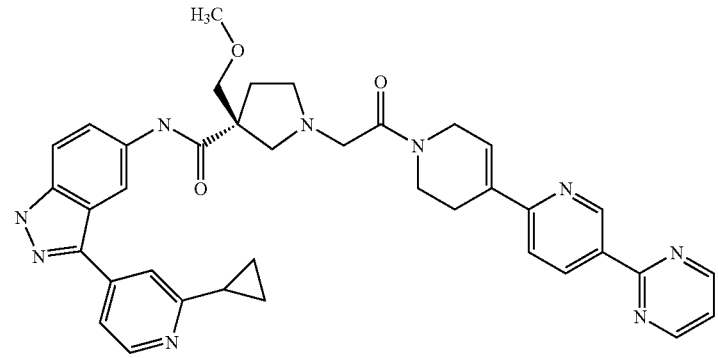 [SMILES: COC[C@@]1(C(=O)Nc2ccc3[nH]nc(-c4ccnc(C5CC5)c4)c3c2)CCN(CC(=O)N2CC=C(c3ccc(-c4ncccn4)cn3)CC2)C1] | 670 | 2.11 |
| 402 | 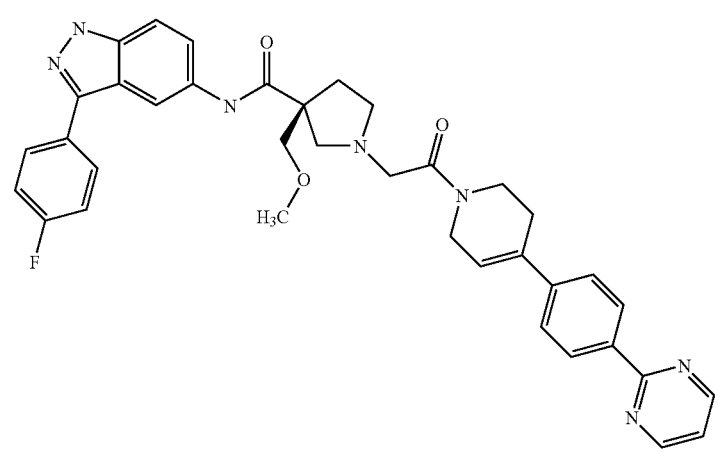 [SMILES: COC[C@@]1(C(=O)Nc2ccc3[nH]nc(-c4ccc(F)cc4)c3c2)CCN(CC(=O)N2CC=C(c3ccc(-c4ncccn4)cc3)CC2)C1] | 640 | 3.1 |

TABLE 21-continued
| Ex. | Compound | M + 1 | Retention time (min) |
|---|---|---|---|
| 403 | 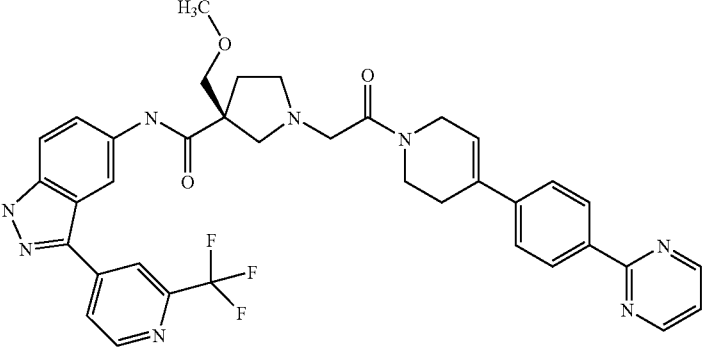 [SMILES: COC[C@@]1(C(=O)Nc2ccc3[nH]nc(-c4ccnc(C(F)(F)F)c4)c3c2)CCN(CC(=O)N2CC=C(c3ccc(-c4ncccn4)cc3)CC2)C1] | 697 | 3.15 |
| 404 | 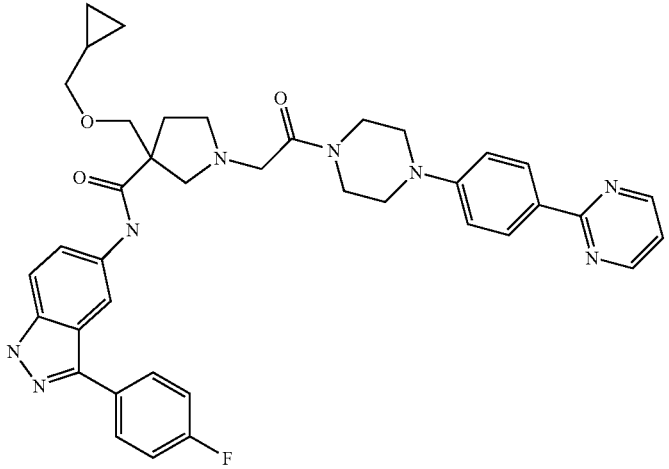 [SMILES: O=C(CN1CCC(COCC2CC2)(C(=O)Nc2ccc3[nH]nc(-c4ccc(F)cc4)c3c2)C1)N1CCN(c2ccc(-c3ncccn3)cc2)CC1] | 689 | 3.05 |
| 405 | 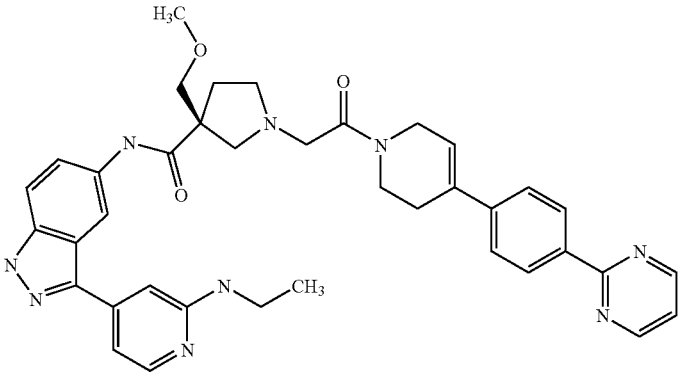 [SMILES: CCNc1cc(-c2n[nH]c3ccc(NC(=O)[C@]4(COC)CCN(CC(=O)N5CC=C(c6ccc(-c7ncccn7)cc6)CC5)C4)cc23)ccn1] | 672 | 2.38 |

TABLE 21-continued

| Ex. | Compound | M + 1 | Retention time (min) |
|---|---|---|---|
| 406 | | 667.28 | 3.98 |
| 407 | | | |
| 408 | | | |
| 409 | | 625.3 | 3.15 |

TABLE 21-continued

| Ex. | Compound | M + 1 | Retention time (min) |
|---|---|---|---|
| 410 | | 686.2 | 3.55 |
| 411 | | 685.2 | 4 |
| 412 | | 697.4 | 3.85 |

TABLE 21-continued

| Ex. | Compound | M + 1 | Retention time (min) |
|---|---|---|---|
| 413 | | 663.31 | 3.8 |
| 414 | | 634.3 | 3.53 |
| 415 | | 611.4 | 3.75 |
| 416 | | 636.32 | 3.46 |

TABLE 21-continued

| Ex. | Compound | M + 1 | Retention time (min) |
|---|---|---|---|
| 417 | | 549.2 | 3.42 |
| 418 | | 705.5 | 3.2 |
| 419 | | 686.31 | 2.64 |

TABLE 21-continued
| Ex. | Compound | M + 1 | Retention time (min) |
|---|---|---|---|
| 420 | 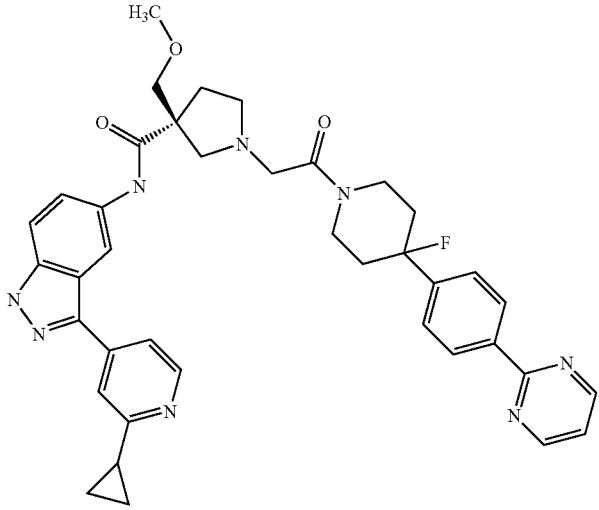 [SMILES: COC[C@@]1(C(=O)Nc2ccc3[nH]nc(-c4ccnc(C5CC5)c4)c3c2)CCN(CC(=O)N2CCC(F)(c3ccc(-c4ncccn4)cc3)CC2)C1] | 689.4 | 2.47 |
| 421 | 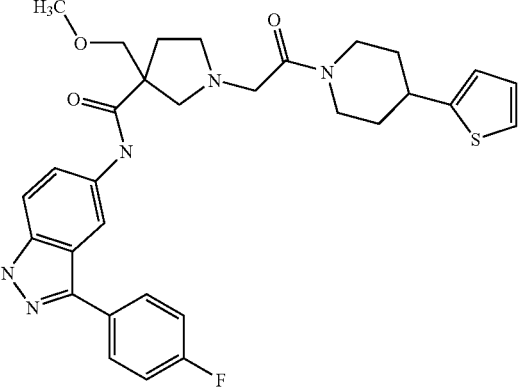 [SMILES: COCC1(C(=O)Nc2ccc3[nH]nc(-c4ccc(F)cc4)c3c2)CCN(CC(=O)N2CCC(c3cccs3)CC2)C1] | 576.2 | 4.3 |
| 422 | 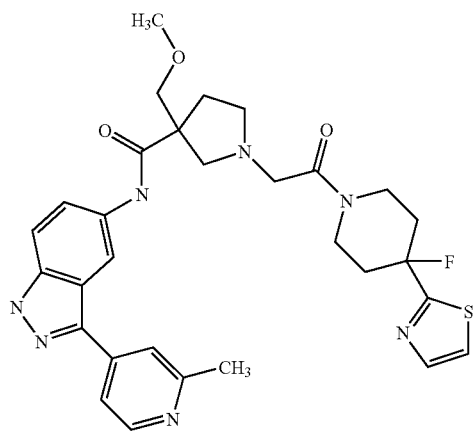 [SMILES: COCC1(C(=O)Nc2ccc3[nH]nc(-c4ccnc(C)c4)c3c2)CCN(CC(=O)N2CCC(F)(c3nccs3)CC2)C1] | 592.3 | 1.8 |

TABLE 21-continued

| Ex. | Compound | M + 1 | Retention time (min) |
|---|---|---|---|
| 423 | | 685.2 | 4 |
| 424 | | 700.4 | 2.72 |
| 425 | | 618.3 | 2.25 |

TABLE 21-continued
| Ex. | Compound | M + 1 | Retention time (min) |
|---|---|---|---|
| 426 | 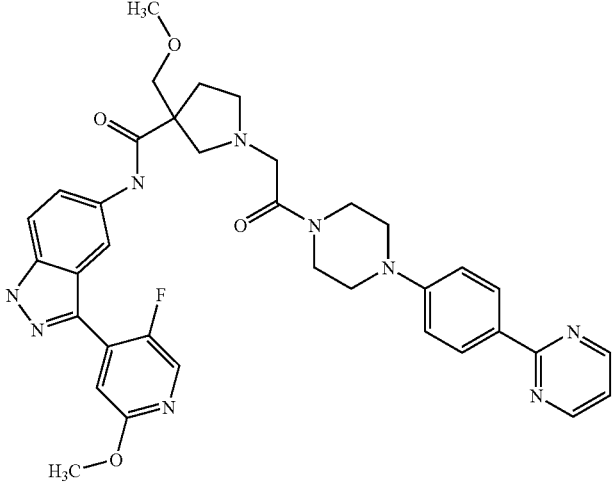 [SMILES: COCC1(C(=O)Nc2ccc3[nH]nc(-c4cc(OC)ncc4F)c3c2)CCN(CC(=O)N2CCN(c3ccc(-c4ncccn4)cc3)CC2)C1] | 680.4 | 3.74 |
| 427 | 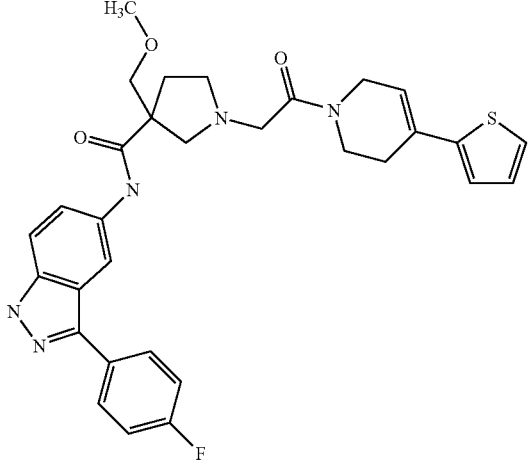 [SMILES: COCC1(C(=O)Nc2ccc3[nH]nc(-c4ccc(F)cc4)c3c2)CCN(CC(=O)N2CC=C(c3cccs3)CC2)C1] | 574.22 | 4.06 |
| 428 | 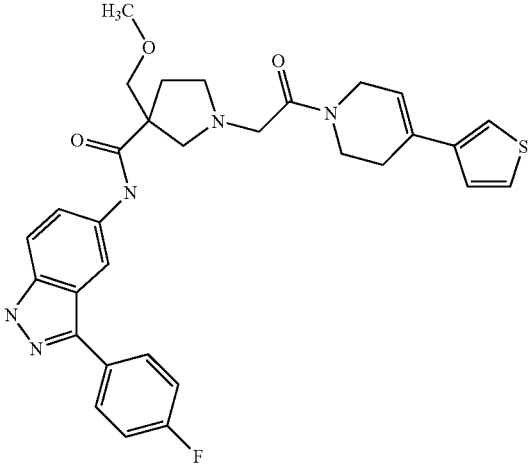 [SMILES: COCC1(C(=O)Nc2ccc3[nH]nc(-c4ccc(F)cc4)c3c2)CCN(CC(=O)N2CC=C(c3ccsc3)CC2)C1] | 574.22 | 4.04 |

TABLE 21-continued
| Ex. | Compound | M + 1 | Retention time (min) |
|---|---|---|---|
| 429 | 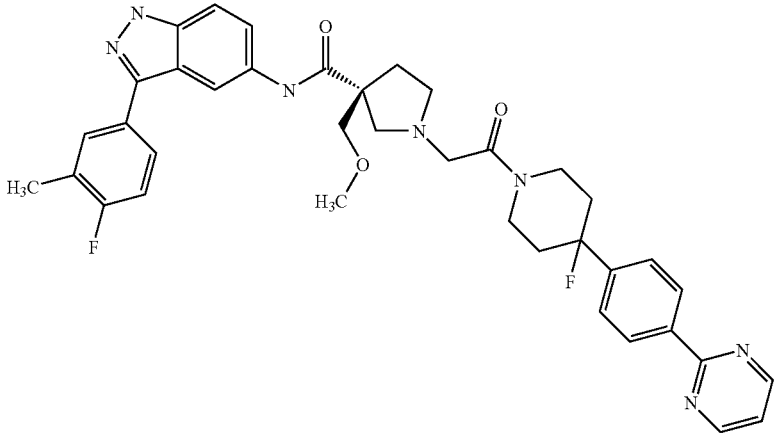 [SMILES: COC[C@@]1(C(=O)Nc2ccc3[nH]nc(-c4ccc(F)c(C)c4)c3c2)CCN(CC(=O)N2CCC(F)(c3ccc(-c4ncccn4)cc3)CC2)C1] | 680.4 | 3.35 |
| 430 | 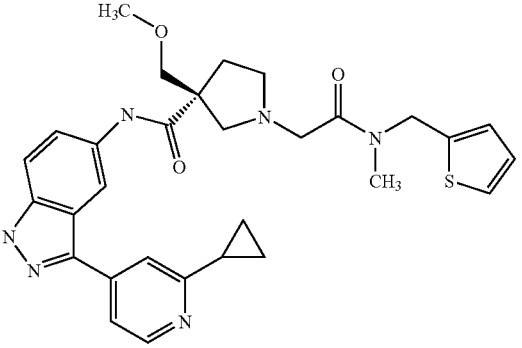 [SMILES: COC[C@@]1(C(=O)Nc2ccc3[nH]nc(-c4ccnc(C5CC5)c4)c3c2)CCN(CC(=O)N(C)Cc2cccs2)C1] | 559.4 | 2.61 |
| 431 | 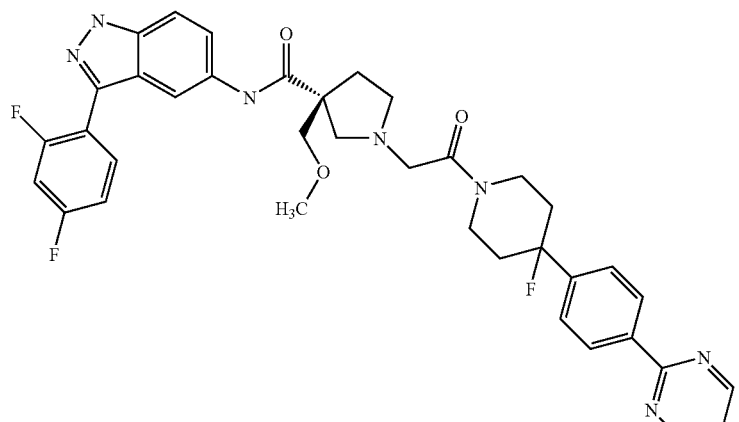 | 684.4 | 2.94 |

TABLE 21-continued
| Ex. | Compound | M + 1 | Retention time (min) |
|---|---|---|---|
| 432 | 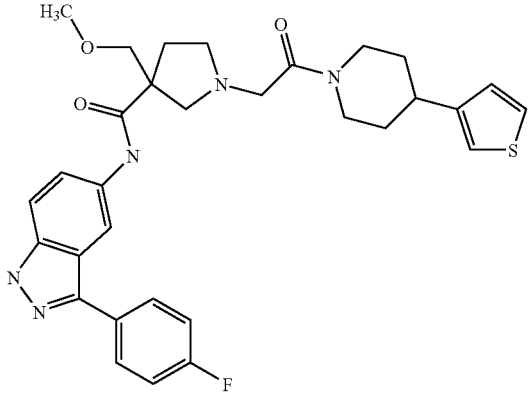 [SMILES: COCC1(C(=O)Nc2ccc3[nH]nc(-c4ccc(F)cc4)c3c2)CCN(CC(=O)N2CCC(c3ccsc3)CC2)C1] | 575.2 | 4.3 |
| 433 | 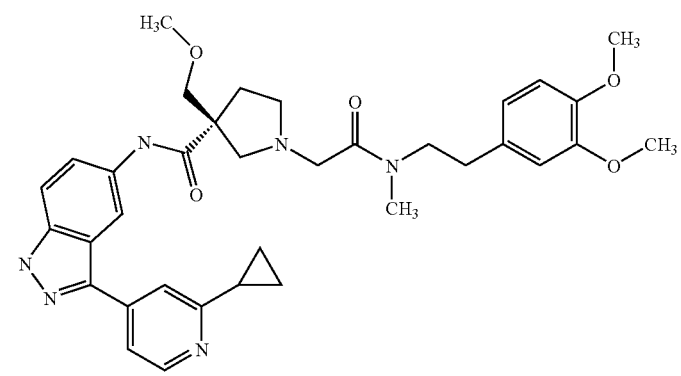 [SMILES: COC[C@@]1(C(=O)Nc2ccc3[nH]nc(-c4ccnc(C5CC5)c4)c3c2)CCN(CC(=O)N(C)CCc2ccc(OC)c(OC)c2)C1] | 627.4 | 2.7 |
| 434 | 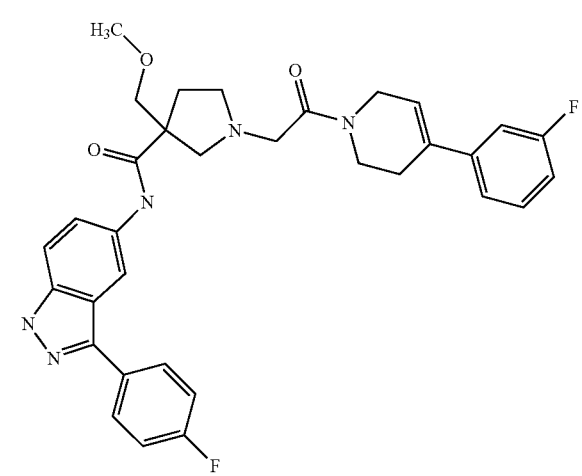 [SMILES: COCC1(C(=O)Nc2ccc3[nH]nc(-c4ccc(F)cc4)c3c2)CCN(CC(=O)N2CC=C(c3cccc(F)c3)CC2)C1] | 586.1 | 4.2 |

TABLE 21-continued

| Ex. | Compound | M + 1 | Retention time (min) |
|---|---|---|---|
| 435 | | 666.4 | 3.23 |
| 436 | | 595.3 | 2.88 |

Examples 437-509

Following procedures essentially similar to the examples described above, the compounds in Table 22 are prepared.

TABLE 22

| Ex. | Compound | M + 1 | Retention time (min) |
|---|---|---|---|
| 437 | | 646.4 | 1.85 |

TABLE 22-continued
| Ex. | Compound | M + 1 | Retention time (min) |
|---|---|---|---|
| 438 | 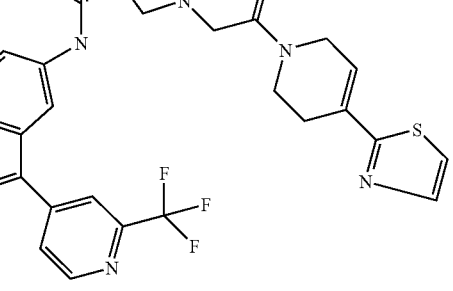 | 612.3 | 2.7 |
| 439 | 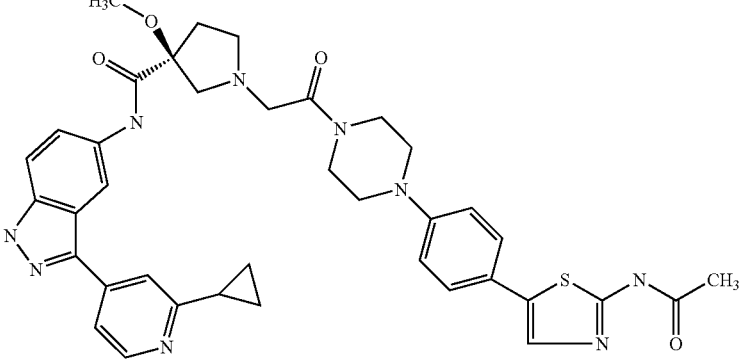 | 720.4 | 2.12 |
| 440 | 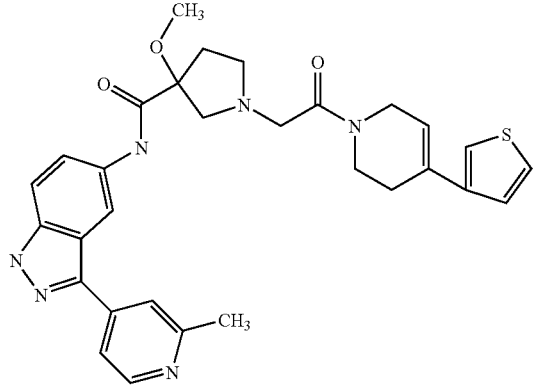 [SMILES: COC1(C(=O)Nc2ccc3[nH]nc(-c4ccnc(C)c4)c3c2)CCN(CC(=O)N2CC=C(c3ccsc3)CC2)C1] | 557.3 | 2.34 |
| 441 | 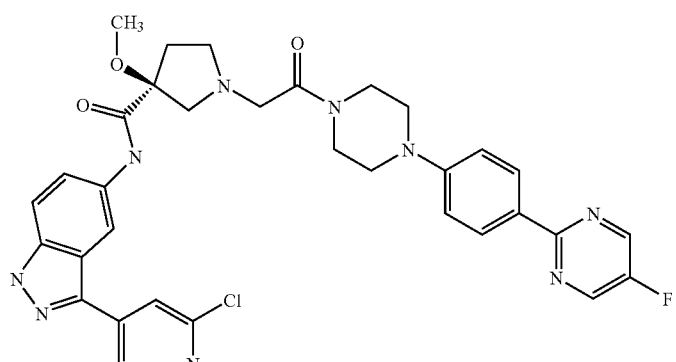 | 670.4 | 4.03 |

TABLE 22-continued

| Ex. | Compound | M + 1 | Retention time (min) |
|---|---|---|---|
| 442 | | 666.4 | 3.81 |
| 443 | | 652.3 | 3.63 |
| 444 | | 584.3 | 2.64 |
| 445 | | 578.3 | 3.4 |

TABLE 22-continued

| Ex. | Compound | M + 1 | Retention time (min) |
|---|---|---|---|
| 446 | | 658.4 | 2.96 |
| 447 | | 664.3 | 3.55 |
| 448 | | 676.4 | 3.27 |

TABLE 22-continued
| Ex. | Compound | M + 1 | Retention time (min) |
|---|---|---|---|
| 449 | 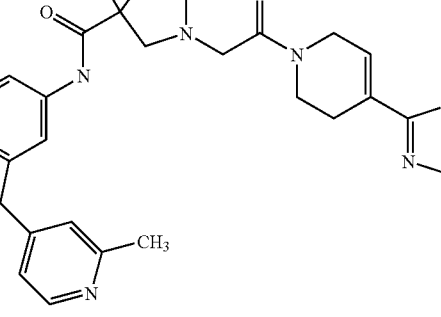 | 558.2 | 2.35 |
| 450 | 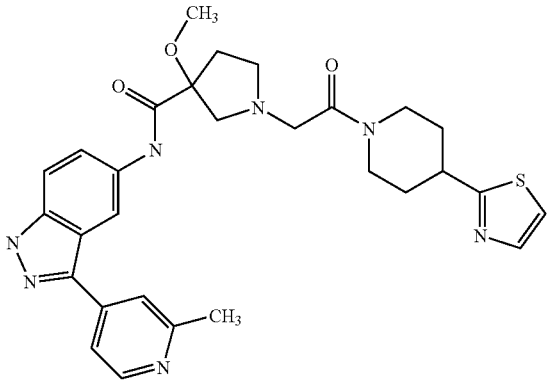 [SMILES: COC1(C(=O)Nc2ccc3[nH]nc(-c4ccnc(C)c4)c3c2)CCN(CC(=O)N2CCC(c3nccs3)CC2)C1] | 560.3 | 2.27 |
| 451 |  | 647.1 | 3.81 |
| 452 | 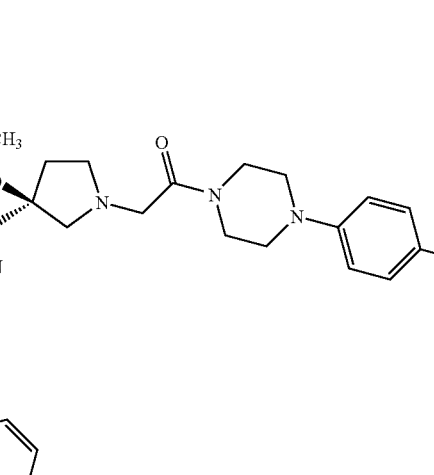 | 672.4 | 3.07 |

TABLE 22-continued

| Ex. | Compound | M + 1 | Retention time (min) |
|---|---|---|---|
| 453 | | 658.4 | 2.88 |
| 454 | | 561.1 | 3.67 |
| 455 | | | |
| 456 | | 649.3 | 4.09 |

TABLE 22-continued

| Ex. | Compound | M + 1 | Retention time (min) |
|---|---|---|---|
| 457 | | | |
| 458 | | | |
| 459 | | 655 | 2.11 |
| 460 | | 640 | 2.75 |

TABLE 22-continued
| Ex. | Compound | M + 1 | Retention time (min) |
|---|---|---|---|
| 461 | 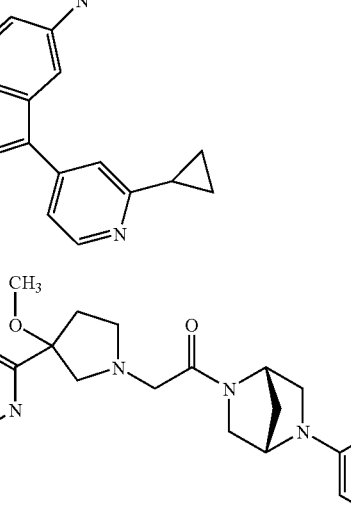 | 604.3 | 2.19 |
| 462 | 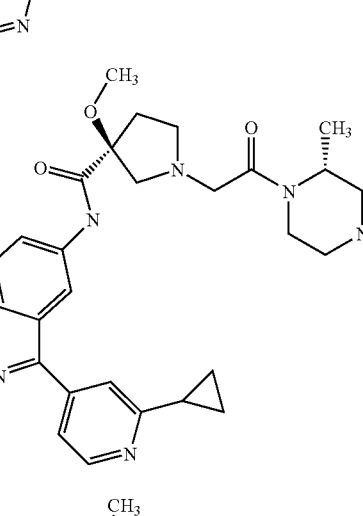 | 662.2 | 3.04 |
| 463 | 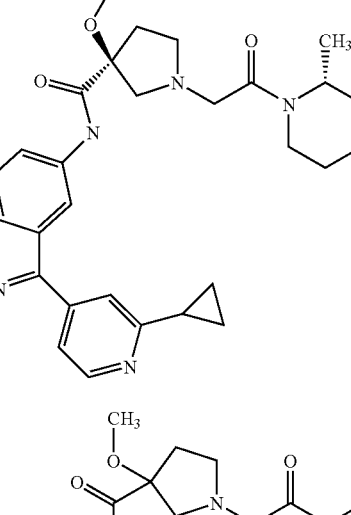 | 647.4 | 3.73 |
| 464 | 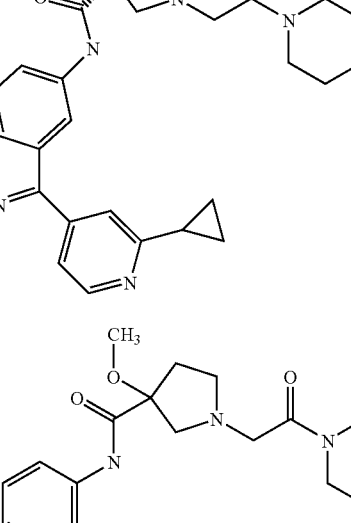 | | |

TABLE 22-continued

| Ex. | Compound | M + 1 | Retention time (min) |
|---|---|---|---|
| 465 | | 665 | 2.6 |
| 466 | | 615.3 | 2.24 |
| 467 | | 658 | 2.28 |

TABLE 22-continued
| Ex. | Compound | M + 1 | Retention time (min) |
|---|---|---|---|
| 468 | 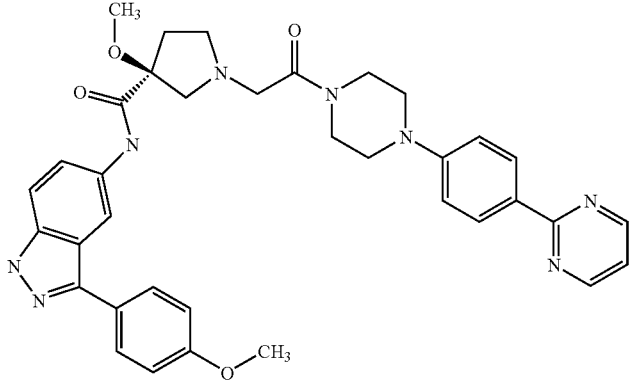 [SMILES: COc1ccc(-c2n[nH]c3ccc(NC(=O)[C@]4(OC)CCN(CC(=O)N5CCN(c6ccc(-c7ncccn7)cc6)CC5)C4)cc23)cc1] | | |
| 469 | 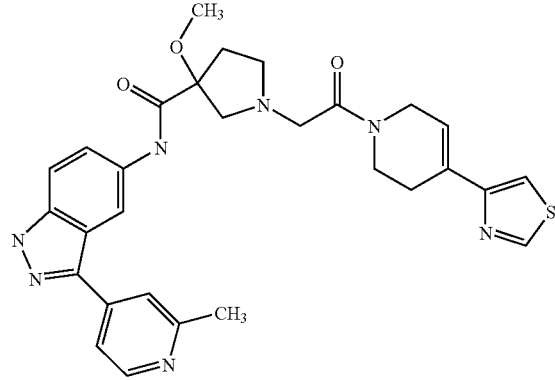 [SMILES: COC1(C(=O)Nc2ccc3[nH]nc(-c4ccnc(C)c4)c3c2)CCN(CC(=O)N2CC=C(c3cscn3)CC2)C1] | 558.1 | 2.35 |
| 470 | 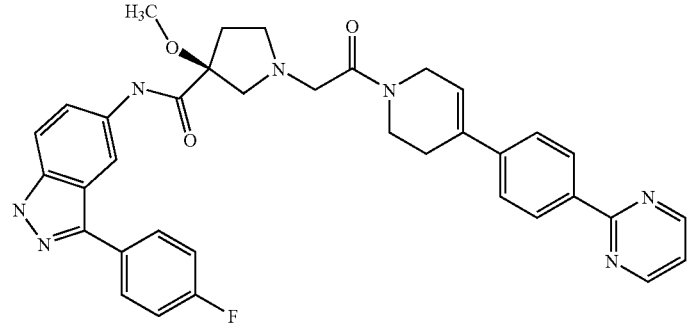 [SMILES: CO[C@@]1(C(=O)Nc2ccc3[nH]nc(-c4ccc(F)cc4)c3c2)CCN(CC(=O)N2CC=C(c3ccc(-c4ncccn4)cc3)CC2)C1] | 632 | 3.09 |
| 471 | 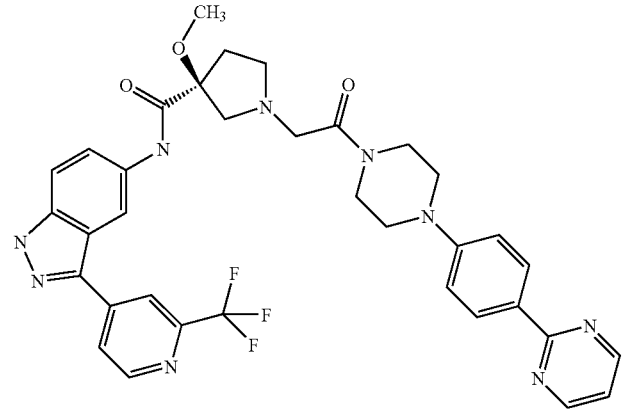 [SMILES: CO[C@@]1(C(=O)Nc2ccc3[nH]nc(-c4ccnc(C(F)(F)F)c4)c3c2)CCN(CC(=O)N2CCN(c3ccc(-c4ncccn4)cc3)CC2)C1] | 686.4 | 2.7 |

TABLE 22-continued

| Ex. | Compound | M + 1 | Retention time (min) |
|---|---|---|---|
| 472 | | | |
| 473 | | 657 | 2.35 |
| 474 | | 592.3 | 1.82 |

TABLE 22-continued
| Ex. | Compound | M + 1 | Retention time (min) |
|---|---|---|---|
| 475 | 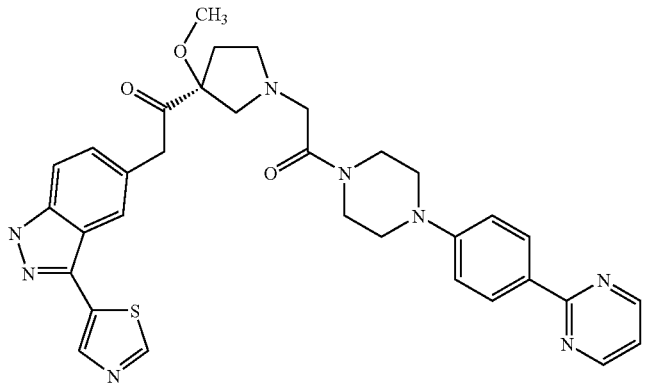 [SMILES: CO[C@@]1(C(=O)Cc2ccc3[nH]nc(-c4cncs4)c3c2)CCN(CC(=O)N2CCN(c3ccc(-c4ncccn4)cc3)CC2)C1] | | |
| 476 | 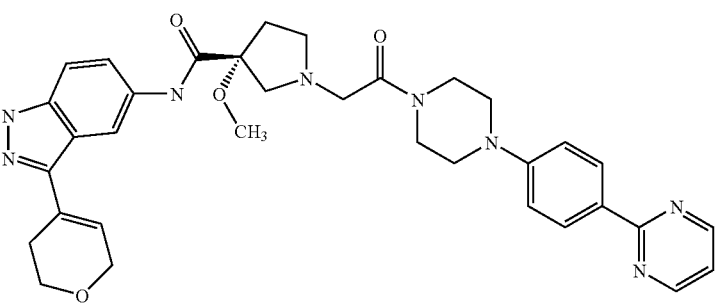 [SMILES: CO[C@]1(C(=O)Nc2ccc3[nH]nc(C4=CCOCC4)c3c2)CCN(CC(=O)N2CCN(c3ccc(-c4ncccn4)cc3)CC2)C1] | 623.3 | 3.17 |
| 477 | 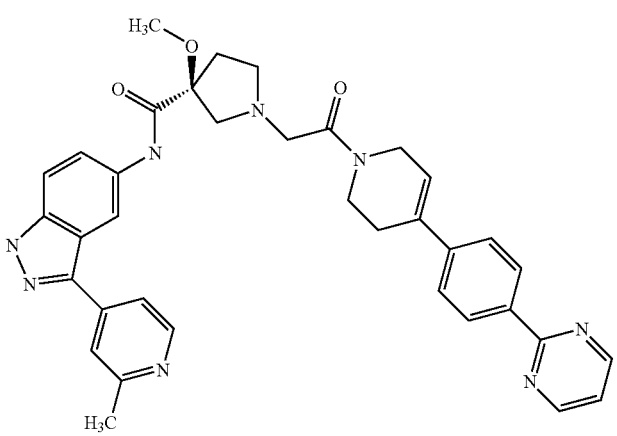 [SMILES: CO[C@@]1(C(=O)Nc2ccc3[nH]nc(-c4ccnc(C)c4)c3c2)CCN(CC(=O)N2CC=C(c3ccc(-c4ncccn4)cc3)CC2)C1] | −2.18 | 2.18 |
| 478 | 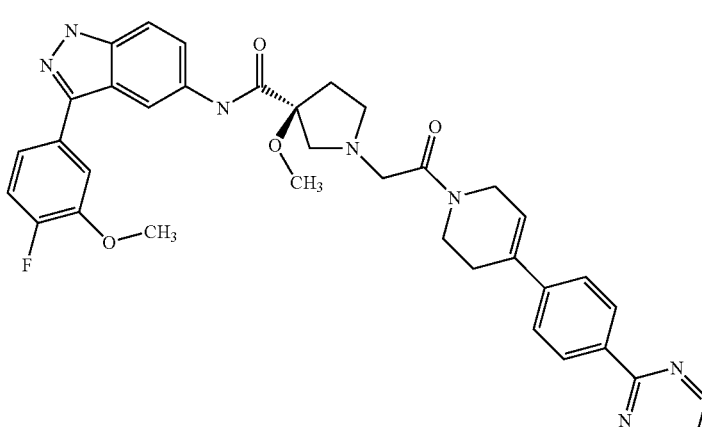 | 662.4 | 3.33 |

TABLE 22-continued

| Ex. | Compound | M + 1 | Retention time (min) |
|---|---|---|---|
| 479 | | 634 | 3.09 |
| 480 | | 663 | 3.21 |
| 481 | | 685.4 | 4.18 |
| 482 | | | |

TABLE 22-continued
| Ex. | Compound | M + 1 | Retention time (min) |
|---|---|---|---|
| 483 | 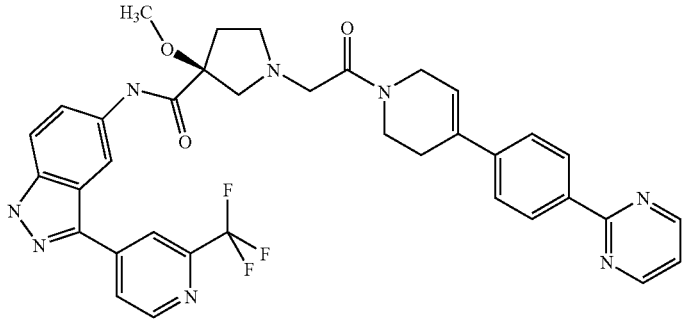 [SMILES: CO[C@@]1(C(=O)Nc2ccc3[nH]nc(-c4ccnc(C(F)(F)F)c4)c3c2)CCN(CC(=O)N2CC=C(c3ccc(-c4ncccn4)cc3)CC2)C1] | 683 | 2.89 |
| 484 | 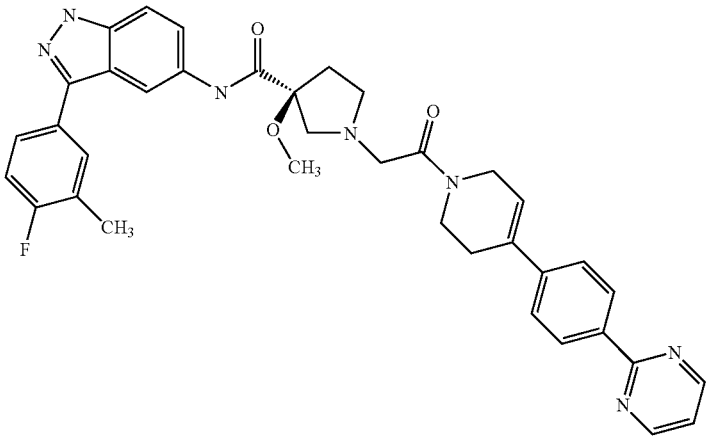 [SMILES: CO[C@@]1(C(=O)Nc2ccc3[nH]nc(-c4ccc(F)c(C)c4)c3c2)CCN(CC(=O)N2CC=C(c3ccc(-c4ncccn4)cc3)CC2)C1] | 646.4 | 3.12 |
| 485 | 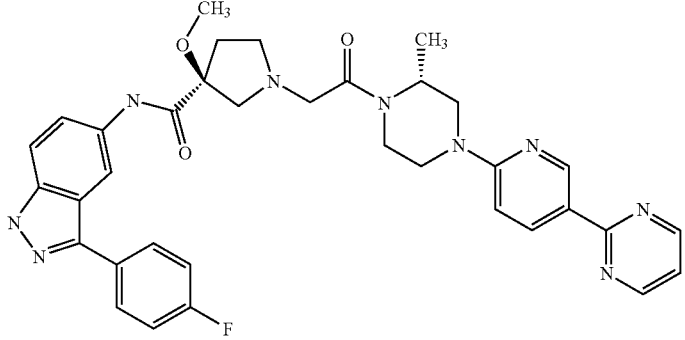 [SMILES: CO[C@@]1(C(=O)Nc2ccc3[nH]nc(-c4ccc(F)cc4)c3c2)CCN(CC(=O)N2CCN(c3ccc(-c4ncccn4)cn3)C[C@H]2C)C1] | 650 | 2.58 |
| 486 | 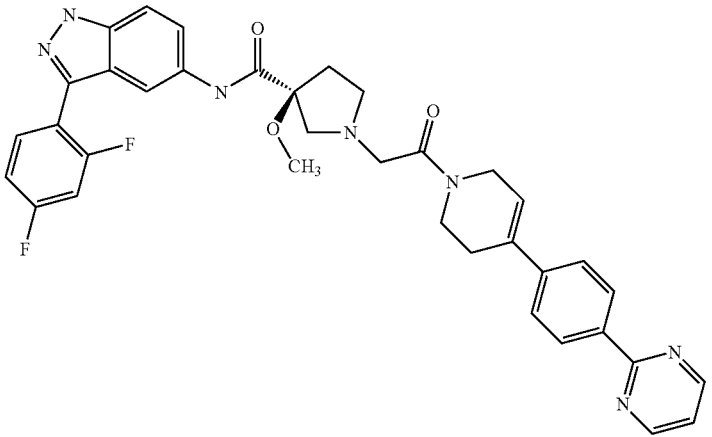 [SMILES: CO[C@@]1(C(=O)Nc2ccc3[nH]nc(-c4ccc(F)cc4F)c3c2)CCN(CC(=O)N2CC=C(c3ccc(-c4ncccn4)cc3)CC2)C1] | 650.4 | 2.96 |

TABLE 22-continued

| Ex. | Compound | M + 1 | Retention time (min) |
|---|---|---|---|
| 487 | | | |
| 488 | | 673 | 2.63 |
| 489 | | 650.4 | 3.11 |
| 490 | | 611.3 | 3.37 |

TABLE 22-continued

| Ex. | Compound | M + 1 | Retention time (min) |
|---|---|---|---|
| 491 | | | |
| 492 | | 644 | 2.75 |
| 493 | | | |
| 494 | | 672.4 | 2.11 |

TABLE 22-continued

| Ex. | Compound | M + 1 | Retention time (min) |
|---|---|---|---|
| 495 | | 650 | 3.47 |
| 496 | | 649.3 | 4.08 |
| 497 | | 675.4 | 2.46 |
| 498 | | | |

TABLE 22-continued
| Ex. | Compound | M + 1 | Retention time (min) |
|---|---|---|---|
| 499 | 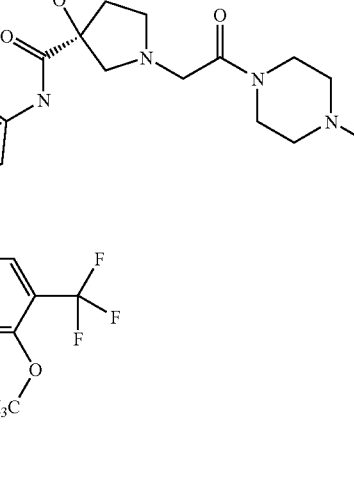 | | |
| 500 | 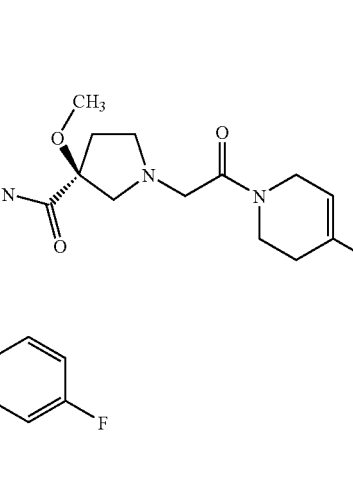 | 633 | 2.73 |
| 501 | 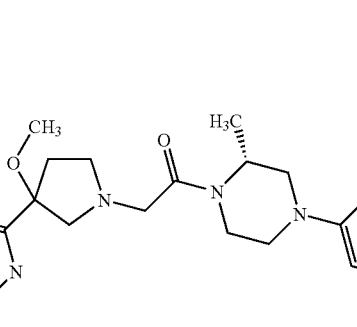 | | |

TABLE 22-continued

| Ex. | Compound | M + 1 | Retention time (min) |
|---|---|---|---|
| 502 | | 689 | 2.22 |
| 503 | | 622.2 | 2.68 |
| 504 | | 673.4 | 1.79 |

TABLE 22-continued
| Ex. | Compound | M + 1 | Retention time (min) |
|---|---|---|---|
| 505 | 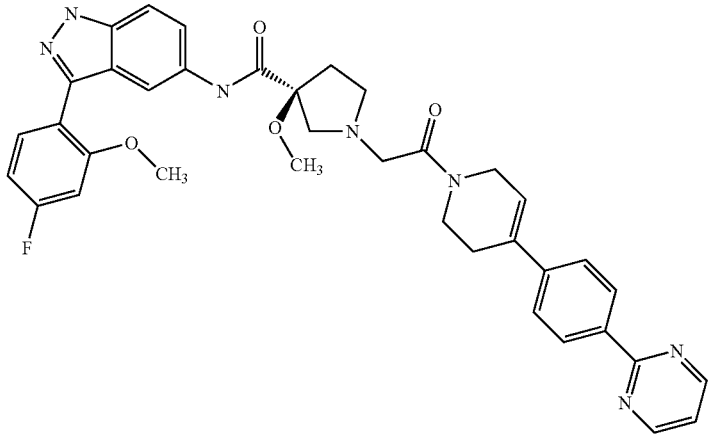 [SMILES: COc1cc(F)ccc1-c1n[nH]c2ccc(NC(=O)[C@]3(OC)CCN(CC(=O)N4CC=C(c5ccc(-c6ncccn6)cc5)CC4)C3)cc12] | | |
| 506 | 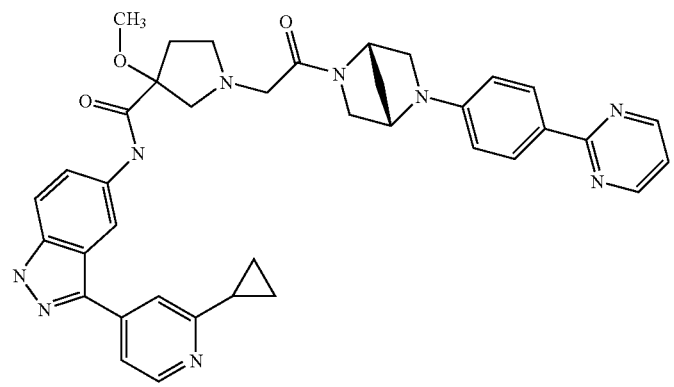 [SMILES: COC1(C(=O)Nc2ccc3[nH]nc(-c4ccnc(C5CC5)c4)c3c2)CCN(CC(=O)N2C[C@@H]3C[C@H]2CN3c2ccc(-c3ncccn3)cc2)C1] | | |
| 507 | 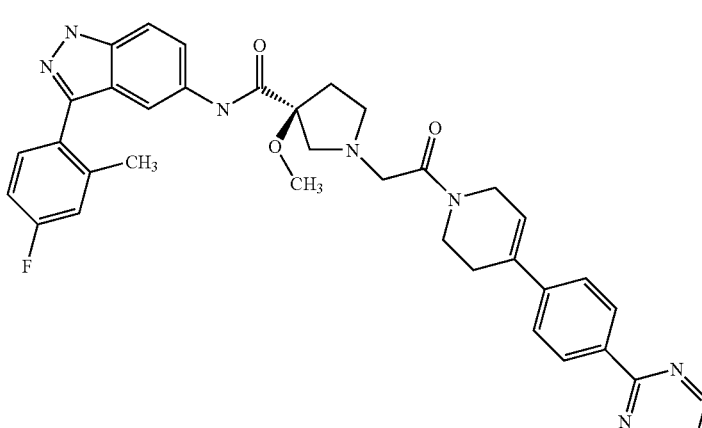 | 646.4 | 3.03 |

TABLE 22-continued

| Ex. | Compound | M + 1 | Retention time (min) |
|---|---|---|---|
| 508 | | 664.4 | 3.02 |
| 509 | | 687.4 | 2.34 |

Examples 510-602

Following procedures essentially similar to the examples described above, the compounds in Table 23 are prepared.

TABLE 23

| Ex. | Compound | M + 1 | Retention time (min) |
|---|---|---|---|
| 510 | | 647.3 | 3.7 |

TABLE 23-continued

| Ex. | Compound | M + 1 | Retention time (min) |
|---|---|---|---|
| 511 | | 553 | 2.42 |
| 512 | | 554 | 1.88 |
| 513 | | 626 | 1.9 |
| 514 | | 551 | 2.94 |

TABLE 23-continued
| Ex. | Compound | M + 1 | Retention time (min) |
|---|---|---|---|
| 515 | 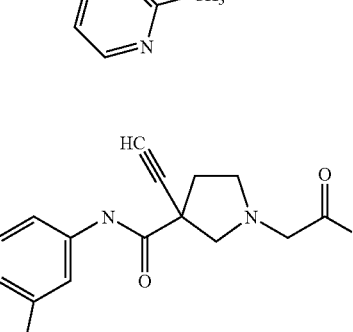 | 626 | 1.9 |
| 516 | 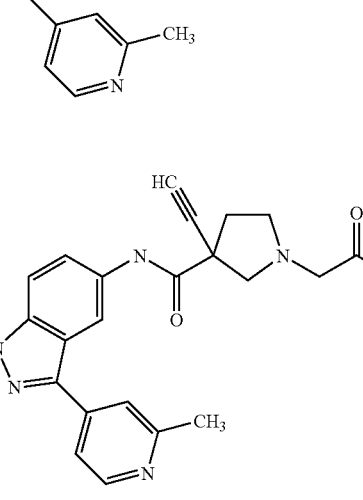 | 652 | 2.19 |
| 517 | 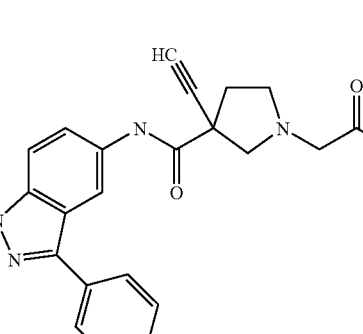 | 638 | 1.84 |
| 518 | 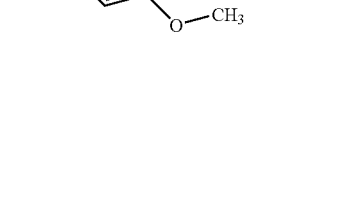 | 641 | 2.93 |

TABLE 23-continued

| Ex. | Compound | M + 1 | Retention time (min) |
|---|---|---|---|
| 519 | | 623 | 1.97 |
| 520 | | 644 | 2.53 |
| 521 | | 564 | 1.74 |
| 522 | | 665 | 3.17 |

TABLE 23-continued
| Ex. | Compound | M + 1 | Retention time (min) |
|---|---|---|---|
| 523 | 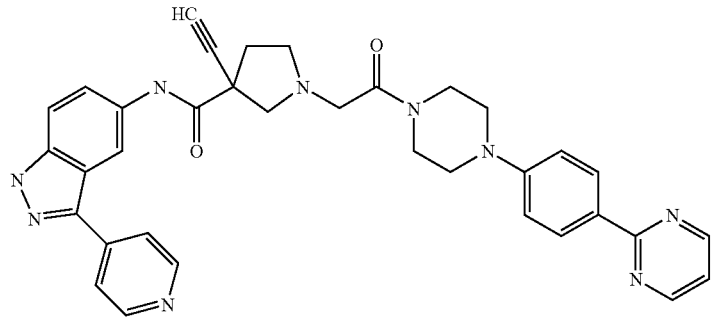 [SMILES: C#CC1(C(=O)Nc2ccc3[nH]nc(-c4ccncc4)c3c2)CCN(CC(=O)N2CCN(c3ccc(-c4ncccn4)cc3)CC2)C1] | 612 | 1.97 |
| 524 | 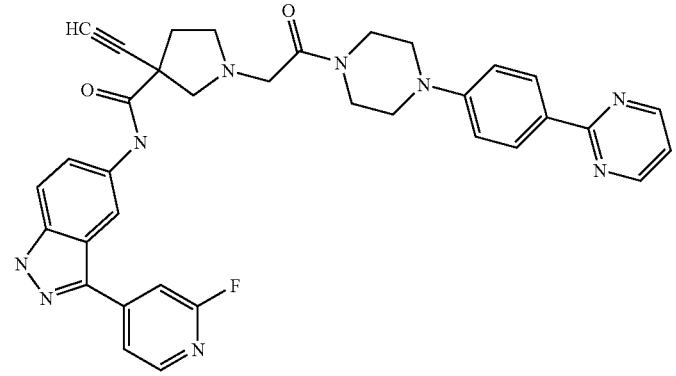 [SMILES: C#CC1(C(=O)Nc2ccc3[nH]nc(-c4ccnc(F)c4)c3c2)CCN(CC(=O)N2CCN(c3ccc(-c4ncccn4)cc3)CC2)C1] | 630 | 2.59 |
| 525 | 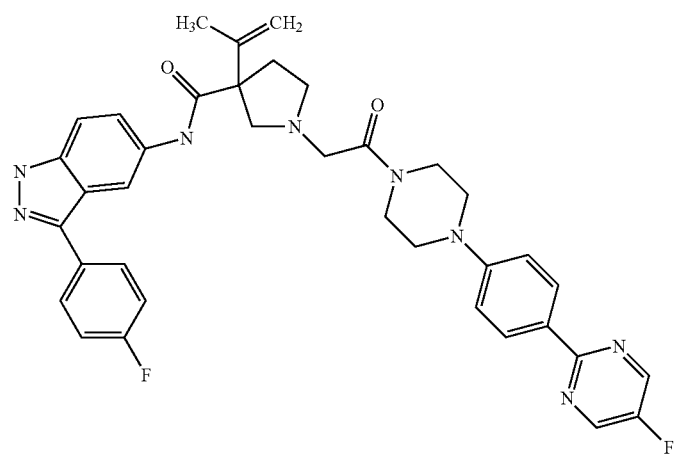 [SMILES: C=C(C)C1(C(=O)Nc2ccc3[nH]nc(-c4ccc(F)cc4)c3c2)CCN(CC(=O)N2CCN(c3ccc(-c4ncc(F)cn4)cc3)CC2)C1] | 663 | 3.17 |
| 526 | 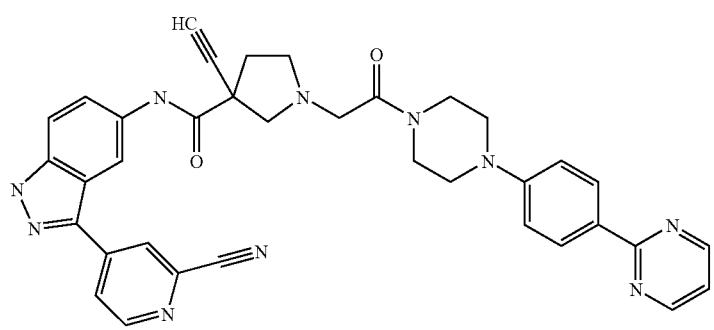 [SMILES: C#CC1(C(=O)Nc2ccc3[nH]nc(-c4ccnc(C#N)c4)c3c2)CCN(CC(=O)N2CCN(c3ccc(-c4ncccn4)cc3)CC2)C1] | 637 | 2.5 |

TABLE 23-continued

| Ex. | Compound | M + 1 | Retention time (min) |
|---|---|---|---|
| 527 | | 701.4 | 2.64 |
| 528 | | | |
| 529 | | 625 | 2.57 |

TABLE 23-continued

| Ex. | Compound | M + 1 | Retention time (min) |
|---|---|---|---|
| 530 | | 644 | 2.53 |
| 531 | | 658.4 | 2.68 |
| 532 | | 652 | 2.26 |
| 533 | | 646 | 2.86 |

TABLE 23-continued

| Ex. | Compound | M + 1 | Retention time (min) |
|---|---|---|---|
| 534 | | 629 | 2.85 |
| 535 | | 626.3 | 2.87 |
| 536 | | 642.4 | 2.25 |
| 537 | | 572.3 | 2.06 |

TABLE 23-continued

| Ex. | Compound | M + 1 | Retention time (min) |
|---|---|---|---|
| 538 | | | |
| 539 | | 649 | 2.68 |
| 540 | | 652 | 1.98 |
| 541 | | 555 | 2.7 |

TABLE 23-continued

| Ex. | Compound | M + 1 | Retention time (min) |
|---|---|---|---|
| 542 | | | |
| 543 | | 555 | 1.43 |
| 544 | | 652.4 (2.21) | 2.21 |
| 545 | | 567.3 | |

TABLE 23-continued

| Ex. | Compound | M + 1 | Retention time (min) |
|---|---|---|---|
| 546 | | 562 | 2.76 |
| 547 | | 526 | 0.82 |
| 548 | | 644.4 | 2.26 |
| 549 | | 557 | 2.61 |

TABLE 23-continued
| Ex. | Compound | M + 1 | Retention time (min) |
|---|---|---|---|
| 550 | 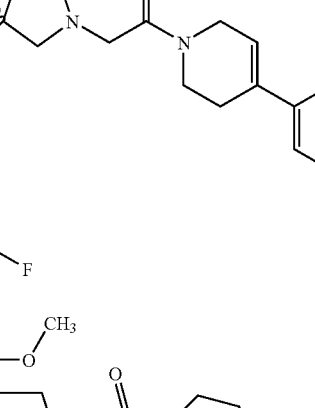 | 646 | 2.8 |
| 551 |  | 676 | 3.12 |
| 552 |  | 643 | 2.02 |
| 553 |  | 571.3 | 2.55 |

TABLE 23-continued

| Ex. | Compound | M + 1 | Retention time (min) |
|---|---|---|---|
| 554 | | 655.4 | 2.87 |
| 555 | | 649 | 3.1 |
| 556 | | 650 | 2.57 |
| 557 | | 571.3 | 2.16 |

TABLE 23-continued

| Ex. | Compound | M + 1 | Retention time (min) |
|---|---|---|---|
| 558 | | 648 | 3.85 |
| 559 | | 660.4 | 2.72 |
| 560 | | 644 | 2.53 |
| 561 | | 592 | 1.88 |

TABLE 23-continued

| Ex. | Compound | M + 1 | Retention time (min) |
|---|---|---|---|
| 562 | | 580 | 1.94 |
| 563 | | 674 | 2.42 |
| 564 | | 645 | 3.35 |
| 565 | | 646 | 2.8 |

TABLE 23-continued

| Ex. | Compound | M + 1 | Retention time (min) |
|---|---|---|---|
| 566 | | | |
| 567 | | 646 | 3.15 |
| 568 | | 676 | 3.12 |
| 569 | | 645 | 3.34 |

TABLE 23-continued

| Ex. | Compound | M + 1 | Retention time (min) |
|---|---|---|---|
| 570 | | 676 | 3.4 |
| 571 | | 686.4 | 2.57 |
| 572 | | 646 | 3.17 |
| 573 | | 681 | 3.05 |

TABLE 23-continued

| Ex. | Compound | M + 1 | Retention time (min) |
|---|---|---|---|
| 574 | | 646 | 2.8 |
| 575 | | 676 | 3.35 |
| 576 | | 629 | 2.72 |
| 577 | | 567 | 2.61 |

TABLE 23-continued

| Ex. | Compound | M + 1 | Retention time (min) |
|---|---|---|---|
| 578 | | 628 | 2.27 |
| 579 | | 651 | 3.48 |
| 580 | | 636 | 2.69 |
| 581 | | 605.4 | 3.72 |

TABLE 23-continued

| Ex. | Compound | M + 1 | Retention time (min) |
|---|---|---|---|
| 582 | | 575.3 | 2.98 |
| 583 | | 583.3 | 2.91 |
| 584 | | 587.3 | 2.76 |
| 585 | | | |

TABLE 23-continued

| Ex. | Compound | M + 1 | Retention time (min) |
|---|---|---|---|
| 586 | | 647.4 | 3.08 |
| 587 | | | |
| 588 | | 568 | 1.96 |
| 589 | | | |

TABLE 23-continued
| Ex. | Compound | M + 1 | Retention time (min) |
|---|---|---|---|
| 590 | 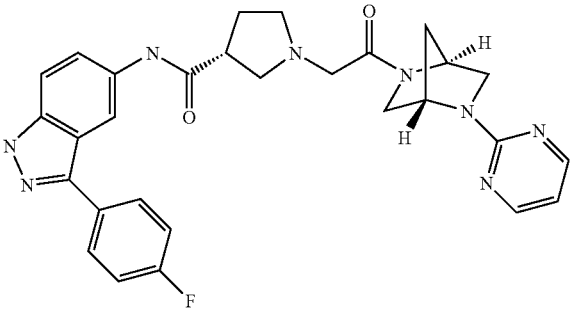 [SMILES: O=C(Nc1ccc2[nH]nc(-c3ccc(F)cc3)c2c1)[C@@H]1CCN(CC(=O)N2C[C@@H]3C[C@H]2CN3c2ncccn2)C1] | 541 | 2.18 |
| 591 | 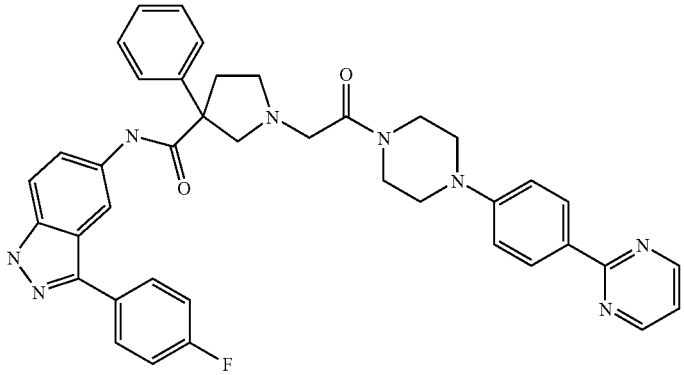 [SMILES: O=C(CN1CCC(C(=O)Nc2ccc3[nH]nc(-c4ccc(F)cc4)c3c2)(c2ccccc2)C1)N1CCN(c2ccc(-c3ncccn3)cc2)CC1] | 681.2 | 4.21 |
| 592 | 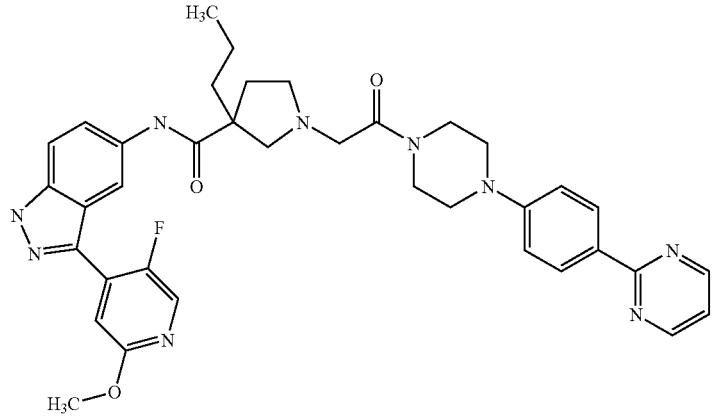 [SMILES: CCCC1(C(=O)Nc2ccc3[nH]nc(-c4cc(OC)ncc4F)c3c2)CCN(CC(=O)N2CCN(c3ccc(-c4ncccn4)cc3)CC2)C1] | 678.4 | 2.95 |
| 593 | 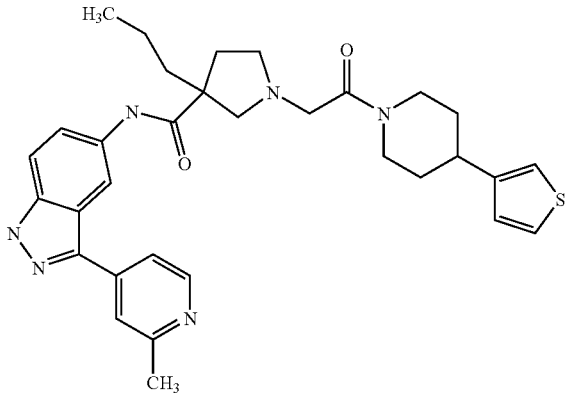 [SMILES: CCCC1(C(=O)Nc2ccc3[nH]nc(-c4ccnc(C)c4)c3c2)CCN(CC(=O)N2CCC(c3ccsc3)CC2)C1] | 571.3 | 2.61 |

TABLE 23-continued
| Ex. | Compound | M + 1 | Retention time (min) |
|---|---|---|---|
| 594 | 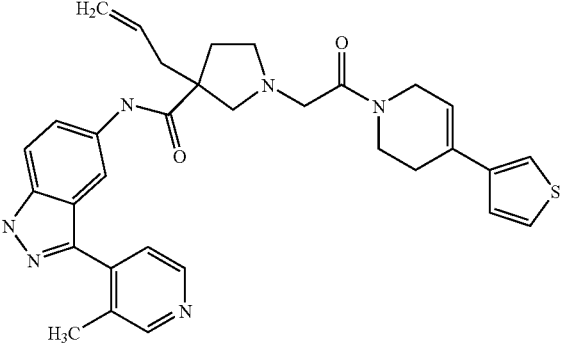 [SMILES: C=CCC1(C(=O)Nc2ccc3[nH]nc(-c4ccncc4C)c3c2)CCN(CC(=O)N2CC=C(c3ccsc3)CC2)C1] | 567.3 | 2.1 |
| 595 | 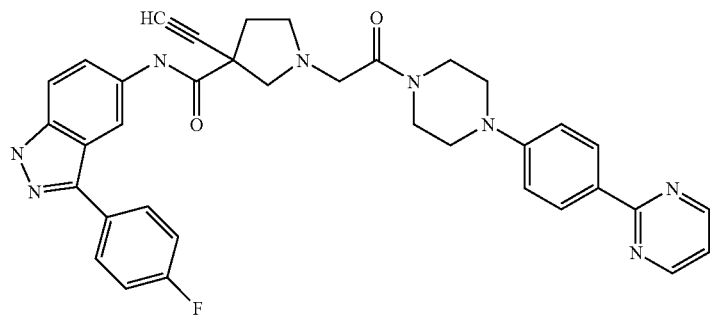 [SMILES: C#CC1(C(=O)Nc2ccc3[nH]nc(-c4ccc(F)cc4)c3c2)CCN(CC(=O)N2CCN(c3ccc(-c4ncccn4)cc3)CC2)C1] | 629 | 2.78 |
| 596 | 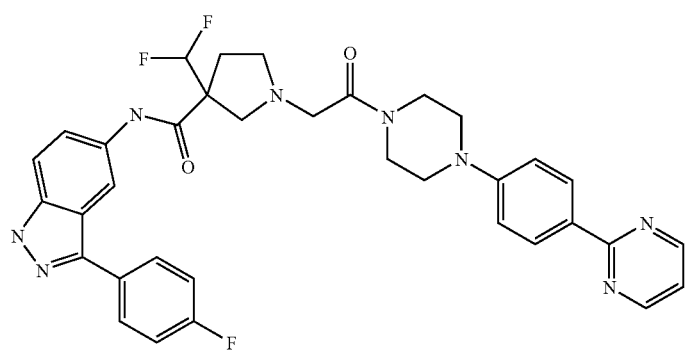 [SMILES: O=C(CN1CCC(C(=O)Nc2ccc3[nH]nc(-c4ccc(F)cc4)c3c2)(C(F)F)C1)N1CCN(c2ccc(-c3ncccn3)cc2)CC1] | 655.4 | |
| 597 | 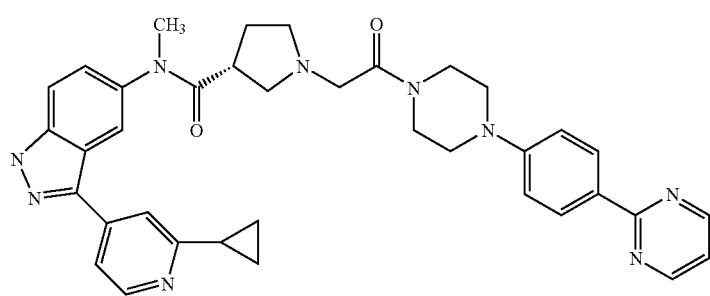 [SMILES: CN(C(=O)[C@@H]1CCN(CC(=O)N2CCN(c3ccc(-c4ncccn4)cc3)CC2)C1)c1ccc2[nH]nc(-c3ccnc(C4CC4)c3)c2c1] | 642.4 | 1.85 |

TABLE 23-continued

| Ex. | Compound | M + 1 | Retention time (min) |
|---|---|---|---|
| 598 | | 619.4 | 3.71 |
| 599 | | 659 | 2.94 |
| 600 | | 647 | 2.91 |
| 601 | | | |

| Ex. | Compound | M + 1 | Retention time (min) |
|---|---|---|---|
| 602 | 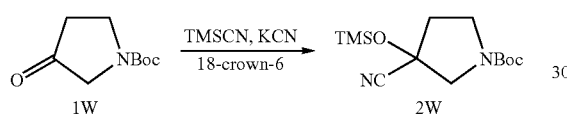 | | |

Preparation of 37

Step 1: Preparation of 3-cyano-3-trimethylsilanyloxy-pyrrolidine-1-carboxylic acid tert-methyl ester

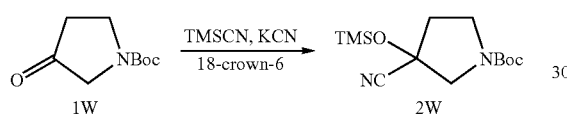

To a solution of 3-oxo-pyrrolidine-1-carboxylic acid tert-butyl ester 1W (10 g, 52.3 mmol) in CH$_2$Cl$_2$ (150 ml) at 0° C. was added trimethylsilyl cyanide (8.5 ml, 63.6 mmol), potassium cyanide (0.34 g, 5.23 mmol) and 18-crown-6 (1.38 g, 5.23 mmol). The reaction mixture was brought to room temperature and stirred overnight. The reaction mixture was cooled to 0° C. and quenched with saturated NaHCO$_3$ (200 ml). The organic layer was separated, dried over Na$_2$SO$_4$, filtered and concentrated. The residue was purified on silica gel eluting with 1/8 EtOAc/hexane to give the desired product 2W (2 g, 81%).

Step 2: Preparation of 3-hydroxy-pyrrolidine-1,3-dicarboxylic acid 1-tert-butyl ester 3-methyl ester

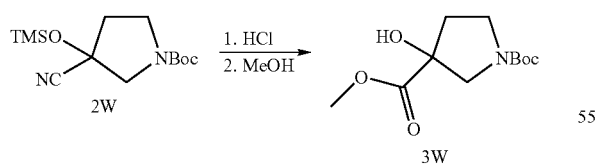

A mixture of compound 2W (5.3 g, 25 mmol), MeOH (50 ml), 4N solution of HCl in dioxane (10 ml) was heated in a sealed tube at 70° C. for overnight. The reaction mixture was concentrated and THF (20 ml) was added followed by CH$_2$Cl$_2$ (50 ml), triethylamine (16 ml) and di-tert-butyl dicarbonate (11 g). The reaction mixture was stirred at room temperature for overnight and then concentrated. Diluted the residue with ether (200 ml) and washed with water (100 ml). The organic layer was separated, dried over Na$_2$SO$_4$, filtered and concentrated. The residue was purified on silica gel eluting with 1/1 EtOAc/hexane then 2/1 EtOAC/hexane to give the desired product 3W (4.35 g, 71%).

Step 3: Preparation of 3-(benzo[1,3]dithiol-2-yloxy)-pyrrolidine-1,3-dicarboxylic acid 1-tert-butyl ester 3-methyl ester

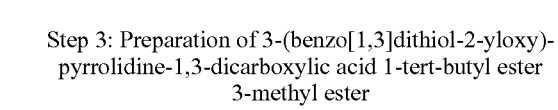

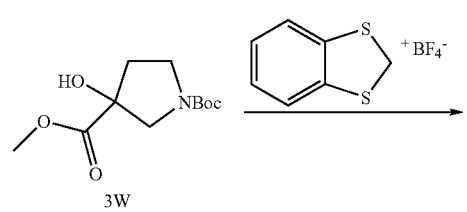

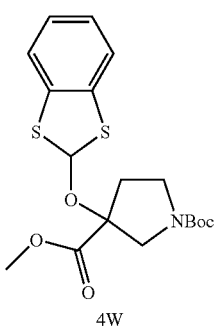

To a solution of compound 3W (2.8 g, 11.4 mmol) in CH$_2$Cl$_2$ (100 ml) was added 1,3-benzodithiol-2-ylium tetrafluoroborate (5.4 g, 22.8 mmol) followed by pyridine (0.2 ml). The reaction mixture was stirred at room temperature for five days. Quenched the reaction mixture with triethylamine (9.6 ml) and stirred for 15 minutes. The reaction mixture was washed with water (100 ml), dried over Na$_2$SO$_4$, filtered and concentrated. The residue was purified on silica gel eluting with 1/4 EtOAc/hexane then 1/2 EtOAC/hexane to give the desired product 4W (2.75 g, 61%).

Step 4: Preparation of 3-difluoromethoxy-pyrrolidine-1,3-dicarboxylic acid 1-tert-butyl ester 3-methyl ester

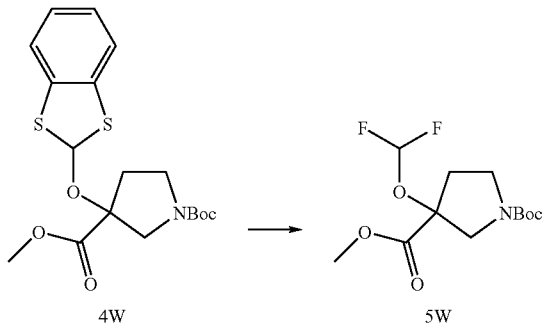

To a solution of compound 4W (2.45 g, 6.16 mmol) in $CH_2Cl_2$ (100 ml) at 0° C. was added DAST (3.97 g, 24.64 mmol). After 5 minutes NIS (4.29 g, 18.5 mmol) was added. The reaction mixture was brought to room temperature and stirred for 2 hours. The reaction mixture was then cooled to 0° C. and treated carefully with saturated $NaHCO_3$ (60 ml) and stirred for 15 minutes. Diluted with $CH_2Cl_2$ (100 ml) and washed with saturated $NaHCO_3$ (2×100 ml). The organic was dried over $Na_2SO_4$, filtered and concentrated. The residue was purified on silica gel eluting with 1/4 EtOAc/hexane desired product 5W (0.45 g, 25%).

Examples 603-605

Following procedures similar to those described herein, for example, Examples 1, 3 to 60, 85, 98, 128, 183, 184, the compounds in Table 24 were prepared from compound 5W. In Table 23 "Ex" represents "Example".

TABLE 23

| Ex | Compound | Mass spec LCMS MH | Retention time (minutes) |
|---|---|---|---|
| 603 | | 668 | 3.16 |
| 604 | | 670 | 3.14 |

TABLE 23-continued

| Ex | Compound | Mass spec LCMS MH | Retention time (minutes) |
|---|---|---|---|
| 605 | 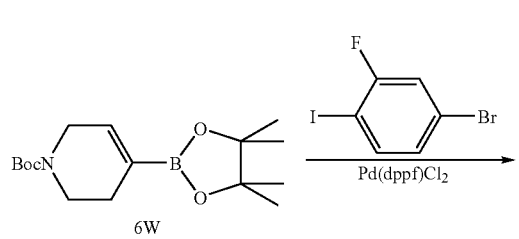 | 671 | 3.13 |

Preparation 38

Step 1: Preparation of 4-(4-bromo-2-fluorphenyl)-3,6-dihydro-2H-pyridine-1-carboxylic acid tert-butyl ester Step 2: Preparation of 4-(2-fluoro-4-pyrimid-2-yl-phenyl)-3,6-dihydro-2H pyridine-1-carboxylic acid 1-tert-butyl ester

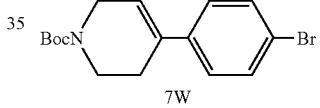

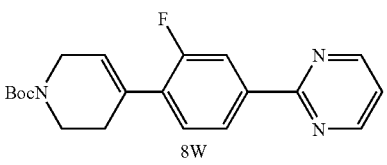

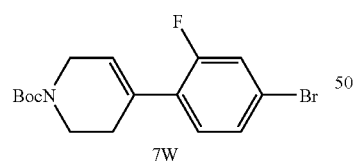

A mixture of compound 6W (1 g, 3.23 mmol), 4-bromo-2-fluoro-1-iodo-benzene (1.46 g, 4.85 mmol), potassium carbonate (1.4 g, 9.69 mmol), Pd(dppf)Cl2 (0.264 g, 0.323 mmol) and 4/1/dioxane/water (10 ml) was degassed for 15 minutes. Then it was heated at 80° C. for overnight. Cooled to room temperature and diluted with EtOAc (200 ml). The organic layer was washed with water (100 ml), dried over Na$_2$SO$_4$, filtered and concentrated. The residue was purified on silica gel eluting with 1/10 EtOAc/hexane to give the desired product 7W (0.9 g, 78%).

A mixture of compound 7W (0.9 g, 2.53 mmol), bis(pinacolato)diboron (0.96 g, 3.79 mmol), potassium acetate (0.74 g, 7.6 mmol), Pd(dppf)Cl$_2$ (0.21 g, 0.25 mmol) and dimethyl sulfoxide (10 ml) was degassed for 10 minutes. Then it was heated at 100° C. for overnight. The reaction mixture was cooled to room temperature and potassium carbonate (1.75 g, 12.63 mmol), 2-bromopyrimidine (0.48 g, 3.03 mmol) and water (10 ml) were added. The mixture was again purged with nitrogen for 20 min. Palladium tetrakistriphenylphosphine (0.29 g, 0.25 mmol) was added and the reaction mixture was stirred at 100° C. for a further 2 hr. Cooled to room temperature, filtered through a pad of celite and washed with ethyl acetate. Diluted with water (50 ml) and the organic layer was separated. The organic layer was dried over Na$_2$SO$_4$, filtered and concentrated. The residue was purified on silica gel eluting with 1/5 EtOAc/hexane to give the desired product 8W.

Preparation of 39

Step 1: Preparation of 4-(4-bromo-3-fluoro-phenyl)-3,6-dihydro-2H-pyridine-1-carboxylic acid tert-butyl ester

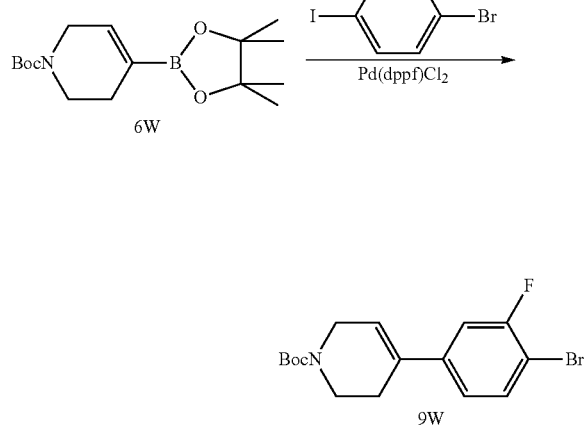

The compound 9W was prepared from compound 6W using essentially the same procedure as described for the preparation of compound 7W from compound 6W.

Step 2: Preparation of 4-(3-fluoro-4-pyrimid-2-yl-phenyl)-3,6-dihydro-2H pyridine-1-carboxylic acid 1-tert-butyl ester

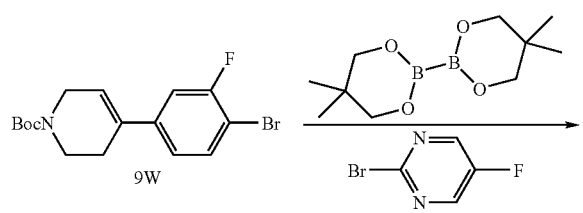

The compound 10W was prepared from compound 9W using essentially the same procedure as described for the preparation of compound 8W from compound 7W but using bis(neopentylglycolato)diboron and 2-bromo-6-fluoro-pyrimidine in place of bis(pinacolato)diboron and 2-bromo-pyrimidine.

Preparation 40

Preparation of Methyl α,α-Dimethoxypropionate

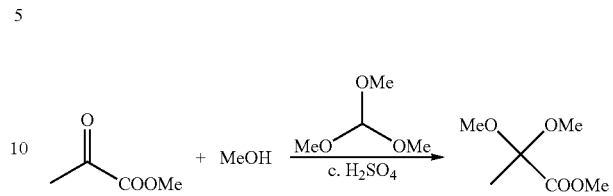

A procedure similar to Ernest Wenkert, et al. (JACS, 1983, 105, 2021-2029) was followed. A solution of methyl pyruvate (44 g), trimethyl orthoformate (62 ml), concentrated $H_2SO_4$ (0.2 ml) in MeOH (120 ml) was refluxed for 4 hours. In the next one hour period, solvent (about 80 ml) was distilled out. The reaction mixture was cooled to 10 C, poured into a KOH solution (1.2 g KOH in 600 ml water), and extracted with ether (3×). Combined ether extracts were washed with brine and dried ($MgSO_4$). After concentration, the residue was distilled under vacuum to provide the acetal (40 g, 62%, 40-43 C/1 torr).

Preparation 41

Preparation of 2-methoxyacrylate

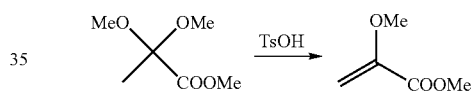

The procedure by Ernest Wenkert, et al. (JACS, 1983, 105, 2021-2029) was followed. To a one neck flask was charged α,α-dimethoxypropionate (150 g) and Toluenesulfonic acid monohydrate (3 g) and a short path distillation head was attached. The mixture was heated at 140 C (oil bath temperature) and methanol began to come out first. The product (76 g) was then distilled out later after oil bath temperature was raised over 190 C.

Preparation 42

Preparation of 1-benzyl-3-methoxy-pyrrolidine-3-carboxylic acid methyl ester

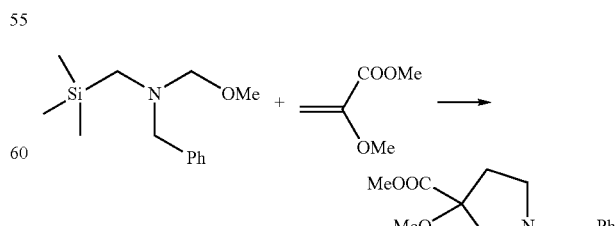

To a stirred solution of methyl 2-methoxyacrylate (20.8 g, 179 mmols) and N-(methoxymethyl)-N-(trimethylsilylmethyl)benzylamine (55 ml, 215 mmols) in dichloromethane (160 ml) was added at 0 C a solution of trifluoroacetic acid (2 ml) in dichloromethane (10 ml). The resulting solution was warmed to room temperature and stirred overnight. After concentration, the crude product was purified by column chromatography on silica gel eluting with a solution of ethyl acetate/hexanes/Et₃N (1000:3000:4 to 1000:1000:3) to give the title compound (17.7 mg, 40%).

Preparation 43

Preparation of 3-methoxy-pyrrolidine-3-carboxylic acid methyl ester tartaric acid salt

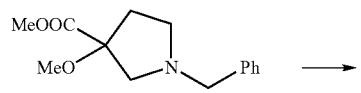

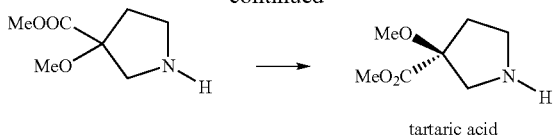

2.49 gm of 1-benzyl-3-methoxy-pyrrolidine-3-carboxylic acid methyl ester was hydrogenated in ethanol using 10% Pd/C at 55 psi hydrogen for 24 hrs. Filtration of the Pd/C followed by evaporation of the ethanol 1.6 gm of crude de-benzylated product. The crude product was dissolved in 95 ml of methanol and 1.35 gm of L-tartaric acid added. After 24 hrs, the crystals were filtered and re-crystallized from methanol to give 13.4 grams of title product.

Examples 606-608

Following procedures similar to those described herein, for example, Preparations 38 to 43, and Examples 1, 3 to 60, 85, 98, 128, 183, 184, the compounds in Table 25 were prepared. In Table 25 "Ex" represents "Example".

TABLE 25

| Ex | Compound | Mass spec LCMS MH | Retention time (minutes) |
|---|---|---|---|
| 606 | | 650 | 3.28 |
| 607 | | 687 | 2.55 |
| 608 | | 638 | 3.33 |

Preparation 44

Preparation of 3-(2-ethylamino-pyridin-4-yl)-1-trityl-1H-indazol-5-ylamine

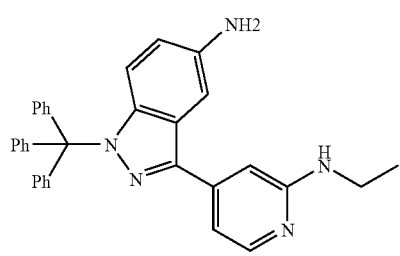 [SMILES: CCNc1cc(-c2nn(C(c3ccccc3)(c3ccccc3)c3ccccc3)c3ccc(N)cc23)ccn1]

Step 1: Preparation of 3-(2-fluoro-pyridin-4-yl)-5-nitro-1-trityl-1H-indazole

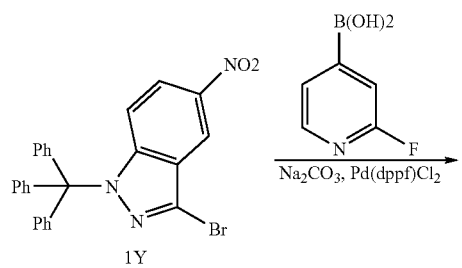

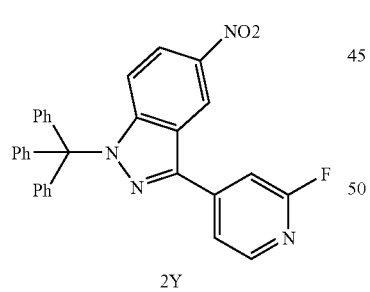

A mixture of 3-bromo-5-nitro-1-trytyl-1H-indazole (200 mg, 0.41 mmol), 2-fluoro-4-pyridine boronic acid (76 mg, 0.54 mmol), K₃PO₄ (174 mg, 0.82 mmol), Pd(dppf)Cl₂ (34 mg, 0.041 mmol) and 4/1/dioxane/H₂O (10 mL) was stirred at 100° C. for 18 hours. Cooled to room temperature, poured into EtOAc (200 mL) and washed with water (100 mL). The organic layer was dried over Na₂SO₄, filtered and concentrated. The crude product was purified by column chromatography on silica get eluting with a solution of 15% ethyl acetate in hexane to give the title compound (90 mg, 44%).

Step 2: Preparation of ethyl-[4-(5-nitro-1-trityl-1H-indazol-3-yl)-pyridin-2-yl]-amine

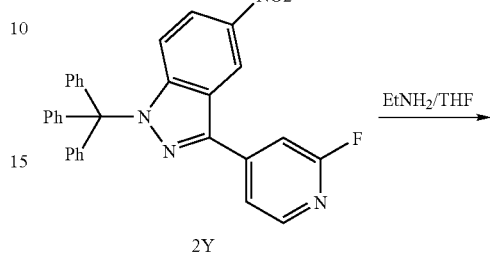

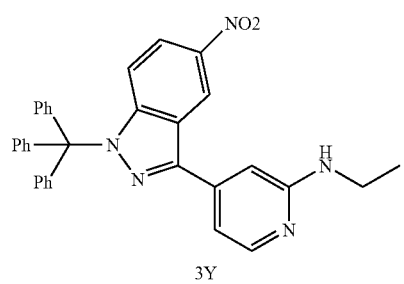

A mixture of 3-(2-fluoro-pyridin-4-yl)-5-nitro-1-trityl-1H-indazole (800 mg, 1.6 mmol) and 2M ethyl amine in THF (20 mL) was heated in a sealed tube at 80° C. for four days. Cooled to room temperature and concentrated. The crude product was purified by column chromatography on silica get eluting with a solution of ethyl acetate in hexane (1:1) to give the title compound (300 mg, 36%).

Step 3: Preparation of 3-(2-ethylamino-pyridin-4-yl)-1-trityl-1H-indazol-5-ylamine

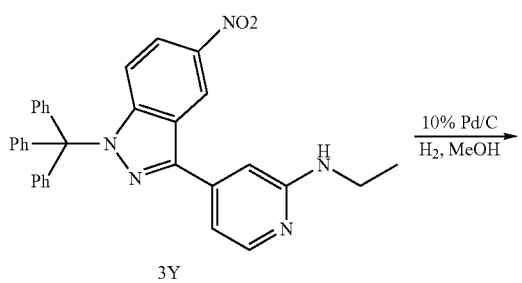

583
-continued

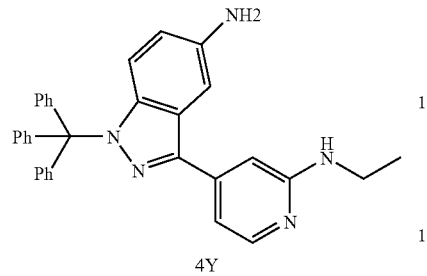

A mixture of ethyl-[4-(5-nitro-1-trityl-1H-indazol-3-yl)-pyridin-2-yl]-amine (30 mg), 10% Pd/C (25 mg) and MeOH (15 mL) was stirred at room temperature under hydrogen atmosphere for 4 hours. Filtered the catalyst, washed with MeOH and concentrated to give the title compound 4 (26 mg) which was used in the next reaction without further purification.

584

Preparation 45

Preparation of 3-(2-methylamino-pyridin-4-yl)-1-trityl-1H-indazol-5-ylamine

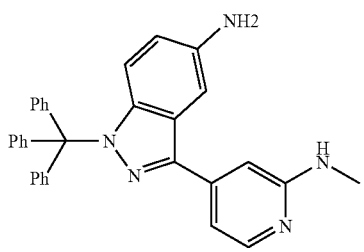 [SMILES: CNc1cc(-c2nn(C(c3ccccc3)(c3ccccc3)c3ccccc3)c3ccc(N)cc23)ccn1]

3-(2-methylamino-pyridin-4-yl)-1-trityl-1H-indazol-5-ylamine was prepared following essentially the same procedure as in Preparation 44, except that methylamine is used in Step 2 instead of ethylamine.

Examples 609-610

Following procedures similar to those described herein, for example, Preparations 44 and 45, and Examples 1, 3 to 60, 85, 98, 128, 183, 184, the compounds in Table 26 were prepared.

In the preparation of the compound of Example 612, cyclopropylamine is used instead of ethylamine in Step 2 of Preparation 44.

In Table 26 "Ex" represents "Example".

TABLE 26

| Ex | Compound |
|---|---|
| 609 | ![structure] |
| 610 | ![structure] |

Example 611

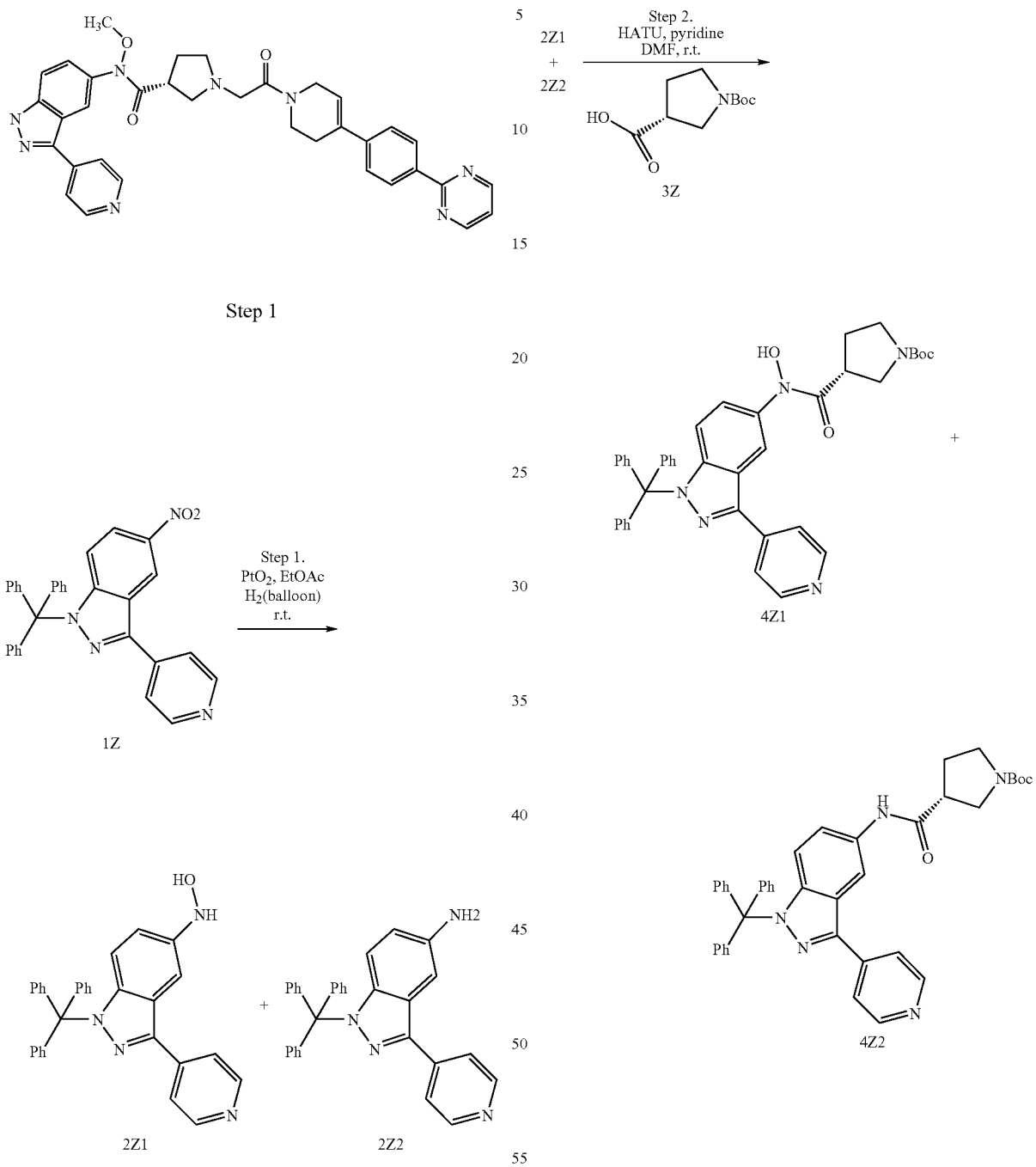

Step 1

To a solution of compound 1Z (510 mg, 1.06 mmol) in ethyl acetate (15 ml), platinum oxide on charcoal (825 mg, 0.011 mmol, 5% Pt, 50% wet) was added. The mixture was stirred under hydrogen (balloon) at r.t. until starting material disappeared. The mixture was filtered through Celite and solvents were removed in vacuum to give a mixture of compound 2Z$^1$ and compound 2Z$^2$. The mixture was used in the next step without further purification.

Step 2

The mixture from step 1 was dissolved in N,N-dimethylformamide (10 ml), HATU (484 mg, 1.27 mmol), compound 3Z (274 mg, 1.27 mmol) followed by pyridine (0.11 ml, 1.27 mmol) were added. The mixture was stirred at r.t. overnight. Water and ethyl acetate were added and layers were separated. The organic layer was washed with water (×2), dried (MgSO$_4$), filtered and solvents were removed in vacuum. Chromatographic purification [hexanes-acetone, 4:1 (v/v)] gave less polar compound 4Z$^2$ (241 mg, 35%) as yellow oil. Continuous elution with the same solvent system gave more polar compound 4Z$^1$ (161 mg, 23%) also as yellow oil.

Step 3

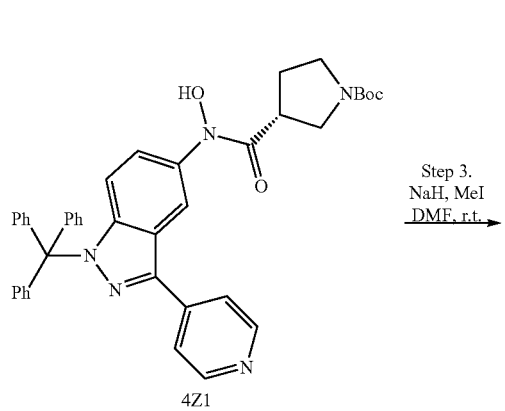

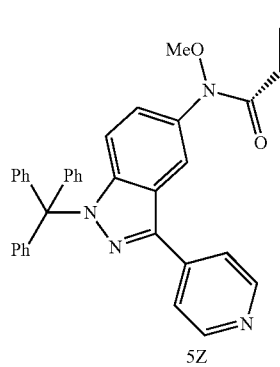

To a suspension of sodium hydride (14 mg, 0.34 mmol, 60% in oil) in N,N-dimethylforamide (5 ml) at 0° C., a solution of compound 4A (152 mg, 0.23 mmol) in N, N-dimethylforamide (2 ml) was added. The mixture was stirred at 0° C. for 20 min and methyl iodide (21 µL, 0.34 mmol) was added. The mixture was warmed to r.t. and was quenched with saturated ammonium chloride solution. Water and ethyl acetate were added and layers were separated. The organic layer was dried (MgSO$_4$), filtered and solvents were removed in vacuum. Chromatographic purification [hexanes-ethyl acetate, 1:1 (v/v)] gave compound 5Z (23 mg, 15%) as yellow oil.

Step 4

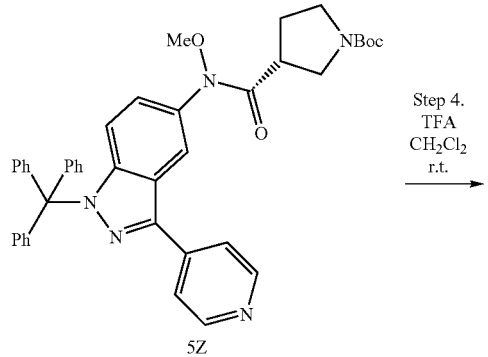

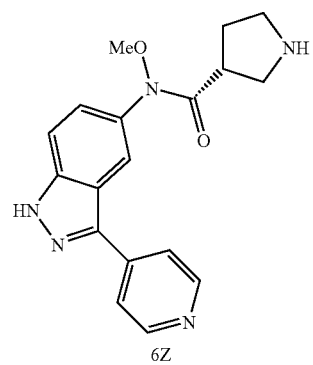

Compound 5Z (15 mg, 0.022 mmol) was stirred in a mixture of dichloromethane (3 ml) and trifluoroacetic acid (1 ml) at r.t. for 5 hr. Solvents were removed in vacuum. Chromatographic purification [methanol (7N ammonia)-dichloromethane, 1:4 (v/v)] gave compound 6Z as yellow oil (3.5 mg, 30%).

Step 5

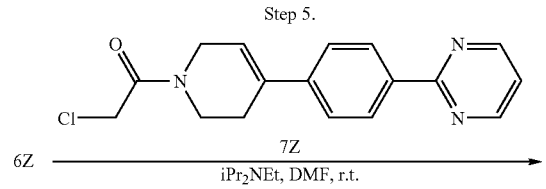

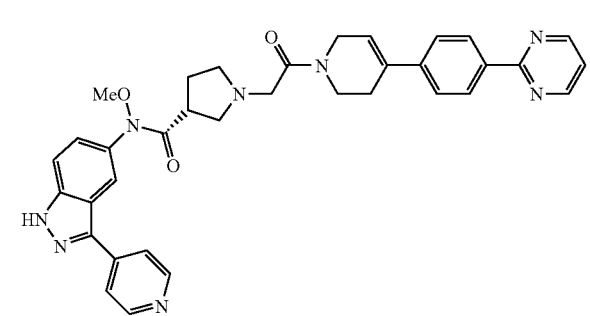

A mixture of compound 6Z (3.5 mg, 0.010 mmol), compound 7Z (3.9 mg, 0.012 mmol) and diisopropylethylamine (4 µL, 0.021 mmol) in N,N-dimethylforamide (0.5 ml) was stirred at r.t. overnight. Water and ethyl acetate were added and layers were separated. The organic layer was washed with water (×2), dried (MgSO$_4$), filtered and solvents were removed in vacuum. Chromatographic purification [methanol (7N ammonia)-dichloromethane, 1:9 (v/v)] gave title compound as yellow oil (2 mg, 31%). LCMS MH$^+$=615 (RT=2.27 min).

Example 612

Step 1

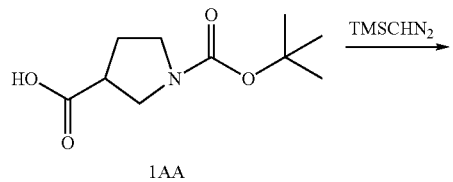

1AA

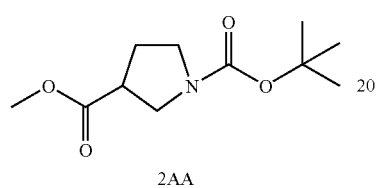

2AA

Pyrrolidine-1,3-dicarboxylic acid 1-tert-butyl ester 1AA (4.3 gm, 20 mmol) was dissolved in 28 mL of toluene and 3.5 ml of methanol. Trimethylsilyldiazomethane 2N solution in hexanes (13 ml, 26 mmol) was added dropwise at 0 C and the reaction mixture stirred for 10 min at ambient temperature. The mixture was evaporated to obtain 4.3 gm of oil.

Step 2

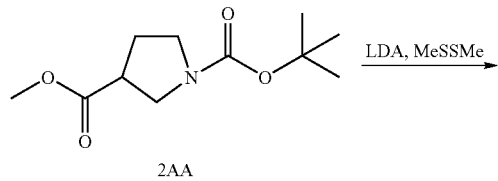

2AA

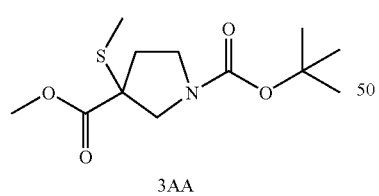

3AA

To the oil 2 (0.5 gm, 2.1 mmol) dissolved in tetrahydrofuran (15 ml) 1.2 ml of lithium diisopropylamide 2N solution in hexanes was added dropwise and the reaction mixture stirred for 1 hr at −78 C. Dimethyldisulfide (0.48 mL, 5.4 mmol) was added slowly and let warm to ambient temperature gradually. The reaction mixture was stirred for 18 hrs. A saturated solution of Ammonium chloride (25 ml) was added and the reaction mixture stirred for 5 min. The reaction mixture was extracted with ethyl acetate three times (3×25 ml), dried over magnesium sulfate, filtered and evaporated to give 0.386 g of title product 3AA after column chromatography.

Step 3

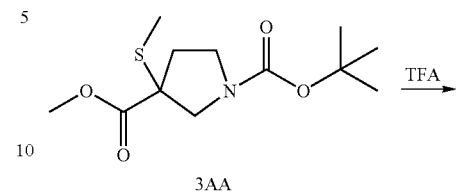

3AA

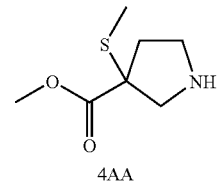

4AA

3-Methylsulfanyl-pyrrolidine-1,3-dicarboxylic acid 1-tert-butyl ester 3-methyl ester 3AA (2.15 gm, 8.8 mmol) was dissolved in 20 ml of 50% trifluoroacetic acid/dichloromethane and stirred for 2 hrs. The reaction mixture was evaporated to an oil and exchanged with hydrochloric acid by dissolving in 20 ml of dichloromethane and adding 10 ml of 1N HCl in ether to obtain 3.35 gm 4AA gummy solid.

Step 4

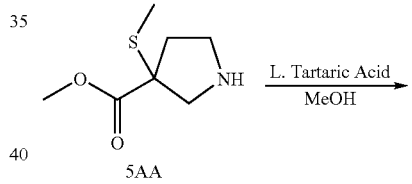

5AA

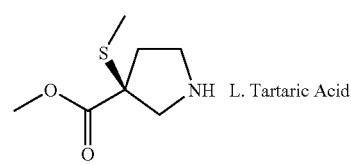

6AA

Compound A (42.9 g, 244.8 mmol) and 1 eq. of L-tartaric acid were placed in a 1 L rbf (round bottom flask) and dissolved with 250 mL of MeOH. The flask was then attached to a rotavapor at 75° C. The mixture was allowed to gently spin at this temperature for about 20 mins. to ensure complete dissolution. After the formation of a clear solution, about 10 mg of pure crystals were added (to aid the crystal formation) was allowed to settle gently settle down for crystal formation. After 3 days, 19.4 g of crystals were recovered which was then washed with cold MeOH to give 18.2 g of crystals.

The chiral purity of the crystals was determined by derivatizing with 4-nitrobenzyl chloroformate and subjecting it to HPLC under the conditions of chiral AD column, 20% isopropanol/hexane solvent system and a flow rate of 1 mL/min. The purity was found to be ~99.9% with a retention time of 16.58 min.

Step 5

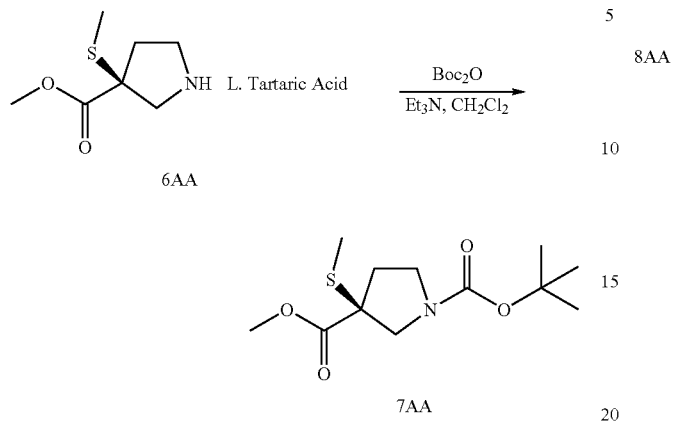

Step 7

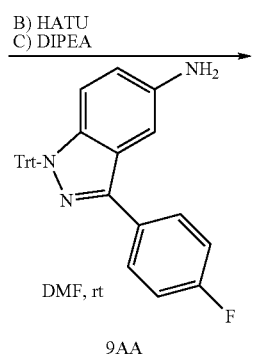

Compound 6AA (3.0 g, 9.2 mmol) was dissolved in 100 mL of $CH_2Cl_2$ at rt. 2.5 eq. of $Et_3N$ was added followed by 1.2 eq. of $Boc_2O$. The reaction mixture was allowed to stir for 1 day after it was diluted with $CH_2Cl_2$ and washed with sat. $NaHCO_3$ followed by sat. NaCl. The organic layer was dried over anhydrous MgSO4 and evaporated to dryness. The crude product was column purified (20% EtAOc/Hex) and evaporated to give 2.43 g of pure product in the yield of ~96%.

Step 5

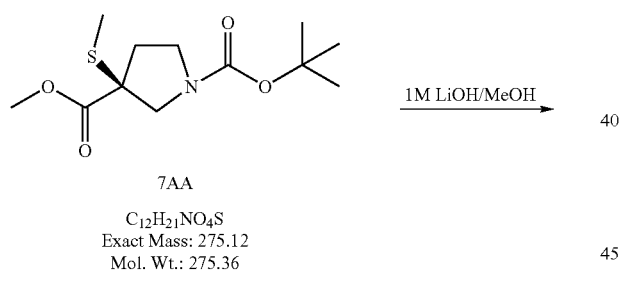

7AA
$C_{12}H_{21}NO_4S$
Exact Mass: 275.12
Mol. Wt.: 275.36

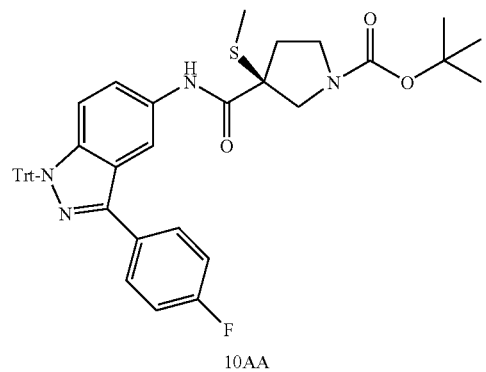

10AA
$C_{43}H_{41}FN_4O_3S$
Exact Mass: 712.29
Mol. Wt.: 712.87

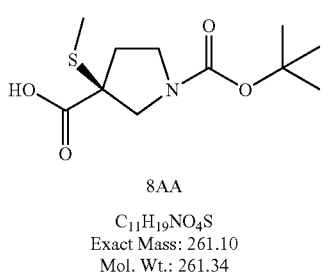

8AA
$C_{11}H_{19}NO_4S$
Exact Mass: 261.10
Mol. Wt.: 261.34

In a rbf equipped with septum inlet was placed 0.26 g of 8AA (0.994 mMol) and 0.467 g of 9AA (0.994 mMol). These 2 components were dissolved in DMF. DIPEA was added to the reaction mixture followed by HATU. The mixture was stirred rt under a stream of nitrogen for 2 days. The crude was then quenched with 50 mL of sat. $NaHCO_3$ and extracted (3×50 mL) with EtOAc. The combined organic extracts was washed with brine and dried over $Na_2SO_4$. It was then filtered and evaporated to dryness to give a crude product which was column purified (30% E/H) to give 0.605 of product.

Step 8

Compound 7AA (0.75 g, 2.73 mmol) was dissolved in 20 mL of MeOH. 6 mL of 1M LiOH was added to the reaction flask and the resulting solution was allowed to stir at rt for 1 overnight. Upon completion of the reaction (determined by TLC), 6 mL of 1N HCl was added to neutralize the LiOH present in the reaction mixture. The mixture was then evaporated to dryness and azeotroped with dioxane to give 1.6 g of 8AA as a white solid.

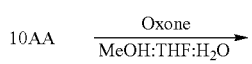

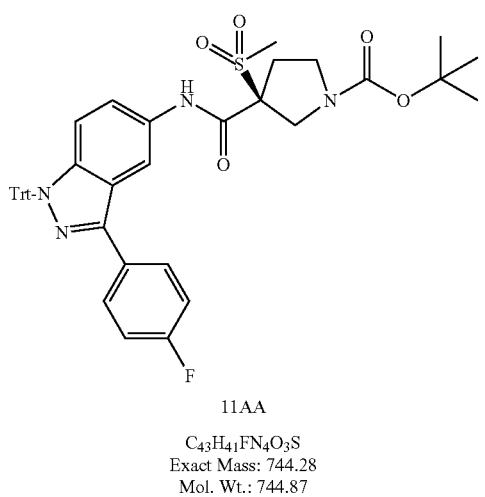

11AA

C₄₃H₄₁FN₄O₃S
Exact Mass: 744.28
Mol. Wt.: 744.87

Compound 10AA (0.9 g, 1.26 mMol) was dissolved in 6 mL each of MeOH:THF:H₂O. Oxone was added and the resulting mixture was allowed to stir for an overnight. Upon completion, the mixture was filtered through a glass fritz and washed with MeOH. The filtrate was then concentrated to give a crude product which was then subjected to the next step.

Step 9

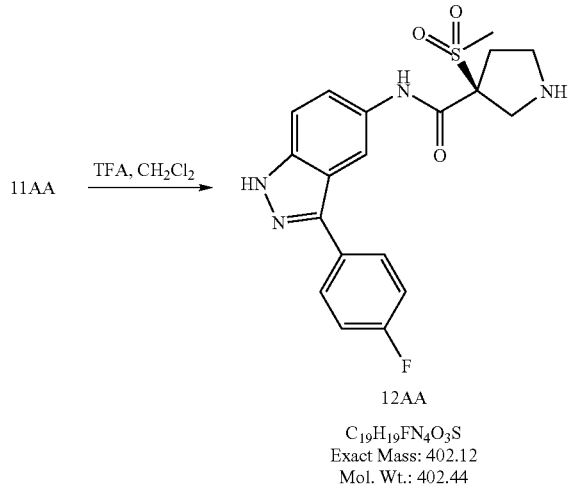 [SMILES: CS(=O)(=O)[C@@]1(C(=O)Nc2ccc3[nH]nc(-c4ccc(F)cc4)c3c2)CCNC1]

12AA

C₁₉H₁₉FN₄O₃S
Exact Mass: 402.12
Mol. Wt.: 402.44

The starting material 11AA (0.64 g, 0.858 mmol) was dissolved in 20 mL of anhydrous CH₂Cl₂. 2.5 mL of TFA was added slowly and was allowed to stir at rt under a stream of nitrogen for 1 overnight. The mixture was evaporated to dryness and column purified (7% 2N NH₃, MeOH/CH₂Cl₂) to give 0.31 g of product in the yield of 91%.

Step 10

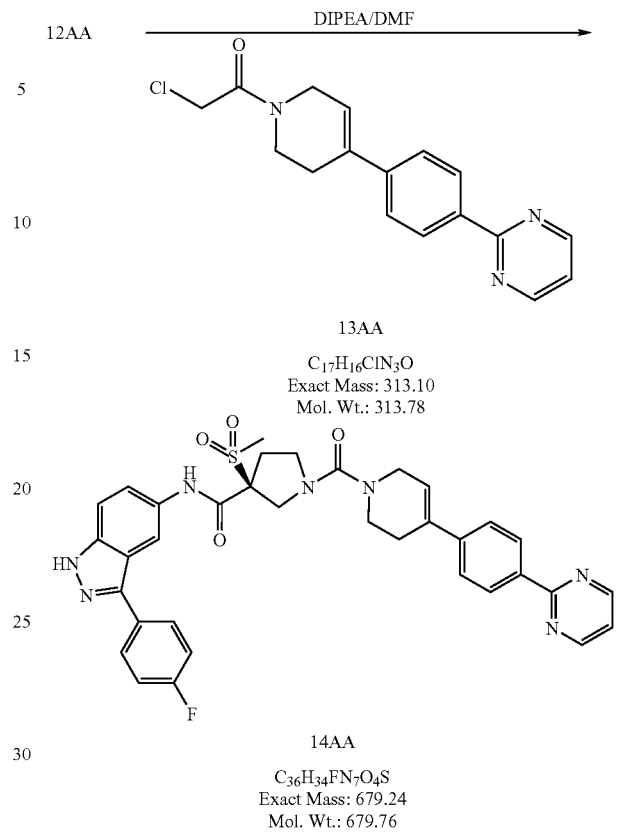

13AA

C₁₇H₁₆ClN₃O
Exact Mass: 313.10
Mol. Wt.: 313.78

14AA

C₃₆H₃₄FN₇O₄S
Exact Mass: 679.24
Mol. Wt.: 679.76

Compound 12AA (0.105 g, 0.261 mmol) was dissolved in 5 mL of DMF. 3 eq. of DIPEA was added followed by 1.1 eq. of 13AA. The reaction mixture was stirred for 3 days at rt under a stream of nitrogen. Upon completion, 25 mL of brine was added to the reaction mixture which was then extracted 3 times with EtOAc. The combined organic extracts was dried over anhydrous MgSO₄, filtered and evaporated to obtain crude title product. The crude product was purified by PTLC (6% 2N NH₃, MeOH/CH₂Cl₂) to give 132 mg of pure product.

Example 613

Step 1

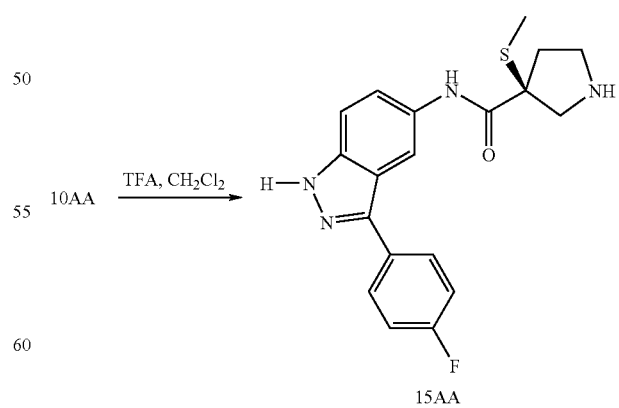

15AA

C₁₉H₁₉FN₄OS
Exact Mass: 370.12636
Mol. Wt.: 370.44376

The starting material 10AA (see Example 612, Step 8) (0.712 g, 1.0 mmol) was dissolved in 20 mL of anhydrous CH$_2$Cl$_2$. 2 mL of TFA was added slowly and was allowed to stir at rt under a stream of nitrogen for 1 overnight. The mixture was evaporated to dryness and treated with 30 mL of 2% 2N NH$_3$, MeOH to give 0.612 g of product.

Step 2

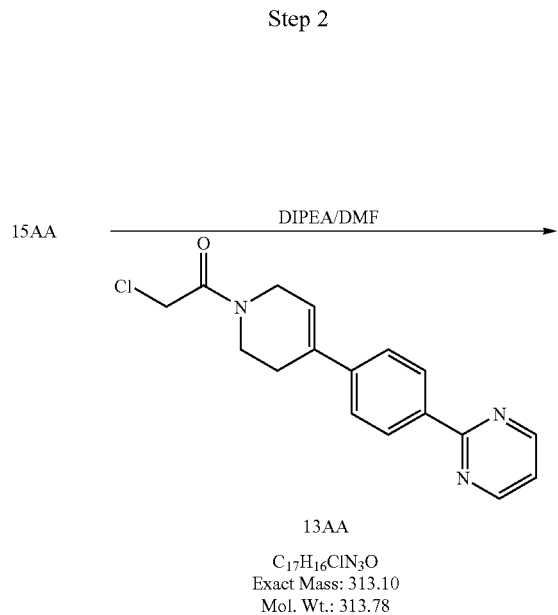

15AA

DIPEA/DMF

13AA
C$_{17}$H$_{16}$ClN$_3$O
Exact Mass: 313.10
Mol. Wt.: 313.78

16AA
C$_{36}$H$_{34}$FN$_7$O$_2$S
Exact Mass: 647.24787
Mol. Wt.: 647.76426

Compound 15AA (0.300 g, 0.81 mmol) was dissolved in 5 mL of DMF. 3 eq. of DIPEA was added followed by 1.1 eq. of 13AA. The reaction mixture was stirred for 2 days at rt under a stream of nitrogen. Upon completion, 25 mL of brine was added to the reaction mixture which was then extracted 3 times with EtOAc. The combined organic extracts was dried over anhydrous MgSO$_4$, filtered and evaporated to obtain crude title product. The crude product was purified by PTLC (6% 2N NH$_3$, MeOH/CH$_2$Cl$_2$) to give 431 mg of pure product.

Preparation 46

Step 1

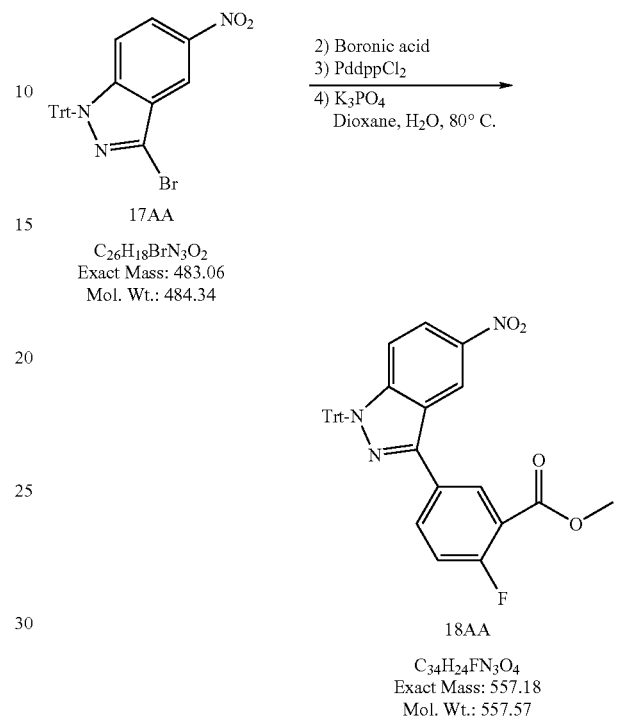

17AA
C$_{26}$H$_{18}$BrN$_3$O$_2$
Exact Mass: 483.06
Mol. Wt.: 484.34

2) Boronic acid
3) PddppCl$_2$
4) K$_3$PO$_4$
Dioxane, H$_2$O, 80° C.

18AA
C$_{34}$H$_{24}$FN$_3$O$_4$
Exact Mass: 557.18
Mol. Wt.: 557.57

In a flame dried sealed tube was placed 3.0 g of compound 17AA (6.19 mMol). 1.5 eq. of 2, 0.1 eq. of 3 and 2.5 eq. of 4 were also added. 65 mL of dioxane and 30 mL of H$_2$O were added to the mixture. The mixture was degassed under nitrogen and then heated to 80° C. for 1 day. After completion, mixture was diluted with EtOAc and filtered through celite. The ethyl acetate layer was washed with water, dried over anhydrous Mg SO$_4$ and evaporated to dryness. The crude product was column purified (5% E/H) to give 1.1 g of product.

Step 2

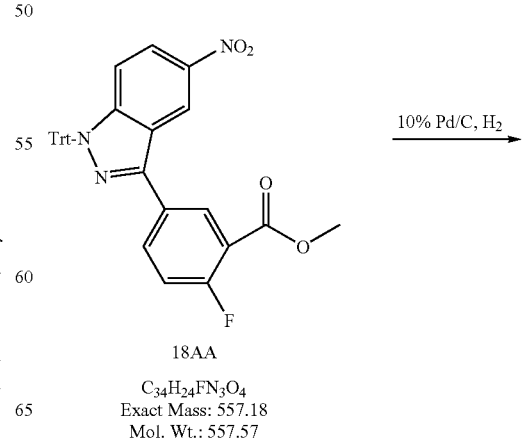

18AA
C$_{34}$H$_{24}$FN$_3$O$_4$
Exact Mass: 557.18
Mol. Wt.: 557.57

10% Pd/C, H$_2$

-continued

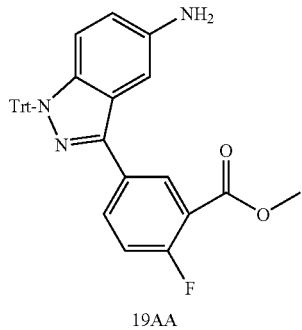

19AA

C₃₄H₂₆FN₃O₂
Exact Mass: 527.20
Mol. Wt.: 527.59

Compound 18AA (1.2 g, 2.15 mmol) was dissolved in 20 mL each of MeOH:Toluene. 20% of 10% Pd/C catalyst was added and the mixture was subjected to H₂ in the form of balloon. After degassing for a number of times, mixture was allowed to stir for 1 day. After completion, the mixture was diluted with CH₂Cl₂ and filtered through celite. It was then washed with 50% E/H. The filtrate was evaporated to dryness to give 1.18 g of title product.

Example 614

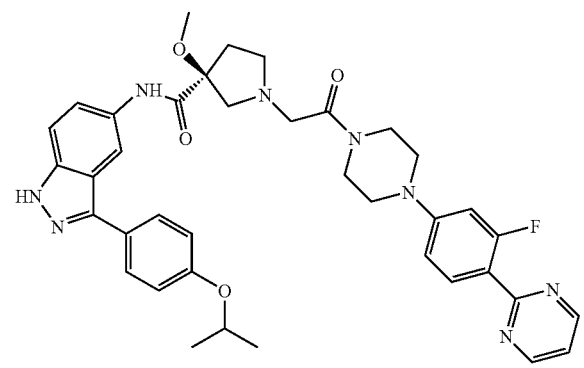

9AB

Step 1: Synthesis of
2-(4-Bromo-2-fluoro-phenyl)-pyrimidine (3AB)

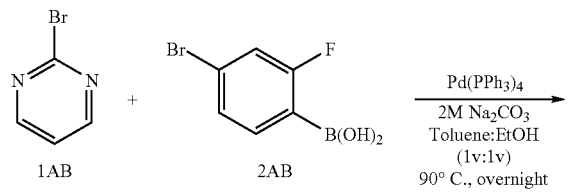

-continued

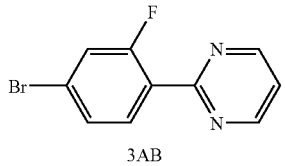

3AB

4-Bromo-2-fluorophenyl boronic acid (2AB) (3.0 g, 13.71 mmol, 1 equiv), 2-bromopyrimidine (1AB) (6.54 g, 41.13 mmol, 3 equiv), and 2M sodium carbonate (34 mL) were added in a pressure vessel (350 mL) and a (1v:1v) mixture of toluene and ethanol (45 mL: 45 mL) was added. The mixture was then bubbled with nitrogen gas for about 10 minutes. Tetrakistriphenylphosphine palladium (0) (793 mg, 0.686 mmol, 0.05 equiv) was added to the mixture. The reaction vessel was tightly capped, placed in an oil bath at 90° C. and stirred overnight.

The reaction mixture was cooled down to room temperature and the content was filtered into a flask and the solvent mixture was evaporated off on the rotovap. The residue was then taken up in one to one mixture of toluene and ethyl acetate and washed with (3v:1v) mixture of brine and DI water twice. The organic layer was separated and combined and dried over magnesium sulfate. The crude product was then filtered into a flask and the solvent was removed on rotovap. The residue was taken up in as little dichloromethane as possible and purified by column chromatography using Analogix purification system with the following conditions: Solvent A: Hexanes; Solvent B: Ethylacetate. Flow Rate: 65 mL/min. Gradient: 0% Solvent B to 50% Solvent B in 60 minutes.

Yield=2.79 g (80.4%)

Step 2: Synthesis of 2-(2-Fluoro-4-piperazin-1-yl-phenyl)-pyrimidine (5AB)

4AB

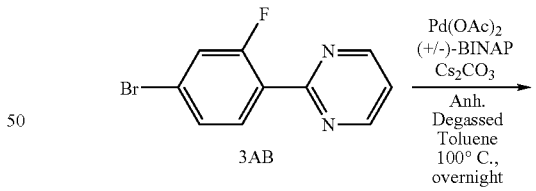

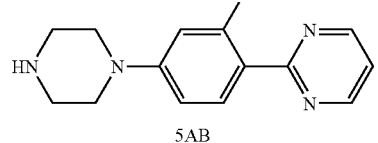

5AB 2-(4-Bromo-2-fluoro-phenyl)-pyrimidine (3AB) (2.0 g, 7.9 mmol, 1 equiv), piperazine (4AB) (2.72 g, 31.6 mmol, 4 equiv), cesium carbonate (20.6 g, 63.2 mmol, 8 equiv), racemic (+/−) BINAP (492 mg, 0.79 mmol, 0.1 equiv), and palladium (II) acetate (89 mg, 0.395 mmol, 0.05 equiv) were all weighed out in a flamed dried pressure vessel and the vessel was sealed with a rubber septa and the content of the reaction vessel was kept under vacuum for 2 hours. Anhydrous degassed toluene (100 mL) was added to the reaction vessel using a cannula. The rubber septa was replaced with a Teflon cap and the vessel was tightly sealed and placed in an oil bath at 100° C. to stir the content overnight.

The reaction vessel was cooled down to room temperature and the content was transferred into a flask. Some water was added to solubilize the excess inorganic base along with some ethyl acetate. The organic layer was then washed with water and brine twice, and separated and dried over magnesium sulfate. The crude product was then filtered into a flask and the solvent was removed on rotovap. The residue was taken up in as little dichloromethane as possible and purified by column chromatography using Analogix purification system with the following conditions: Solvent A: Dichloromethane; Solvent B: 40% 7N NH$_3$ in Methanol. Flow Rate: 65 mL/min. Gradient: 0% Solvent B to 30% Solvent B in 52 minutes and stayed at 30% Solvent B for 10 minutes.

Yield=889 mg (44%).

Step 3: Synthesis of 2-Chloro-1-[4-(3-fluoro-4-pyrimidin-2-yl-phenyl)-piperazin-1-yl]-ethanone (7AB)

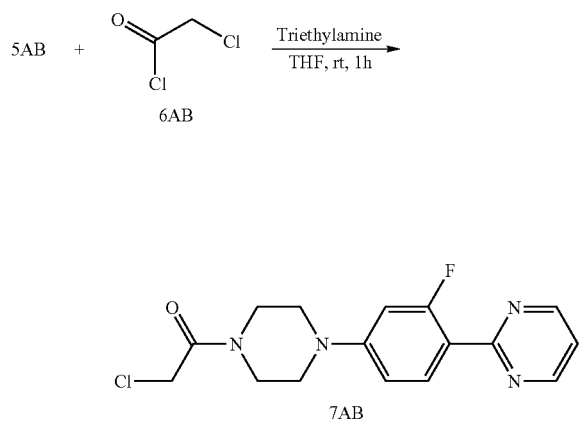

2-(2-Fluoro-4-piperazin-1-yl-phenyl)-pyrimidine (5AB) (889 mg, 3.442 mmol, 1 equiv) was dissolved in anhydrous tetrahydrofuran (5 mL) and triethylamine (697 mg, 959 uL, 6.884 mmol, 2 equiv) was added, followed by slow addition of a solution of chloroacetyl chloride (6AB) (466.5 mg, 330 uL, 4.13 mmol, 1.2 equiv) in tetrahydrofuran at room temperature. The mixture was then stirred for about 1 hour at room temperature.

Upon the completion of the reaction, the solvent was removed on rotovap and the residue was taken up in dichloromethane and washed with a (1v:1v) mixture of brine and water in a separatory funnel. The organic layer was separated, concentrated down, and dried on pump. The crude residue was then taken up in dichloromethane and purified by column chromatography using Analogix purification system with the following conditions: Solvent A: Dichloromethane; Solvent B: 40% 7N NH$_3$ in Methanol. Flow Rate: 65 mL/min. Gradient: 0% Solvent B to 30% Solvent B in 52 minutes and stayed at 30% Solvent B for 10 minutes.

Yield=1.05 g (91.1%)

Step 4: Synthesis of 1-{2-[4-(3-Fluoro-4-pyrimidin-2-yl-phenyl)-piperazin-1-yl]-2-oxo-ethyl}-3-methoxy-pyrrolidine-3-carboxylic acid [3-(4-isopropoxy-phenyl)-1H-indazol-5-yl]-amide (9AB)

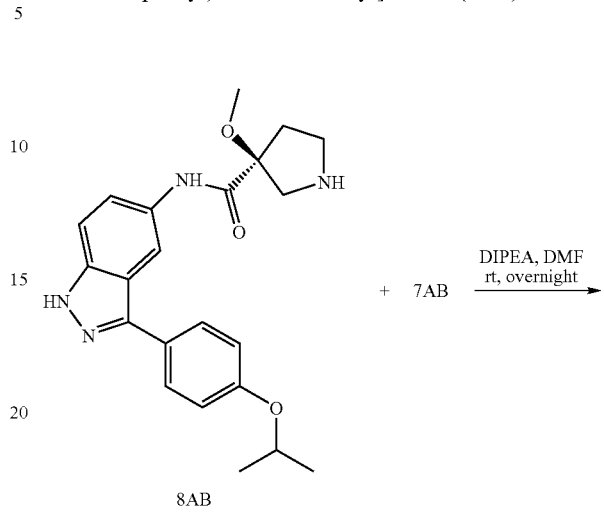

3-Methoxy-pyrrolidine-3-carboxylic acid [3-(4-isopropoxy-phenyl)-1H-indazol-5-yl]-amide (8AB) (40 mg, 0.086 mmol, 1 equiv) and 2-Chloro-1-[4-(3-fluoro-4-pyrimidin-2-yl-phenyl)-piperazin-1-yl]-ethanone (7AB) (35 mg, 0.103 mmol, 1.2 equiv) were weighed out in a flask, and to it was added N,N-dimethylformamide (3 mL) and diisopropylethylamine (22 mg, 30 uL, 0.172 mmol, 2 equiv). The reaction content was stirred at room temperature, overnight.

The crude reaction mixture was diluted out with enough amount of ethylacetate and the organic phase was washed with a (1v:1v) mixture of brine and water twice. The organic layer was separated and concentrated down on rotovap to dryness, and further dried on a high vacuum pump. The residue was taken up in as little dichloromethane as possible and purified by column chromatography using Analogix purification system with the following conditions: Solvent A: Dichloromethane; Solvent B: 40% 7N NH$_3$ in Methanol. Flow Rate: 30 mL/min. Gradient: 0% Solvent B to 20% Solvent B in 30 minutes. The clean fractions were combined in a flask and concentrated down on rotovap. The residue was then dissolved in methanol and acidified with 4N HCl in 1,4-dioxane (80 uL) to make it into HCl salt form before submitting it to biological assay.

Yield=46.4 mg, LCMS [M+H$^+$]=693.4.

Example 615

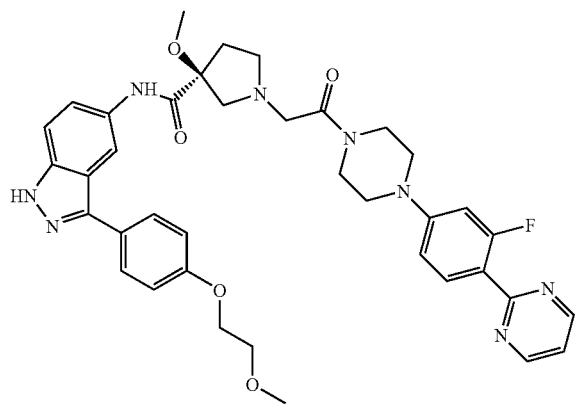

Steps 1 to 3

Steps 1 to 3 are similar to Steps 1 to 3 of Example 614

Step 4: Synthesis of 1-{2-[4-(3-Fluoro-4-pyrimidin-2-yl-phenyl)-piperazin-1-yl]-2-oxo-ethyl}-3-methoxy-pyrrolidine-3-carboxylic acid {3-[4-(2-methoxy-ethoxy)-phenyl]-1H-indazol-5-yl}-amide (11AB)

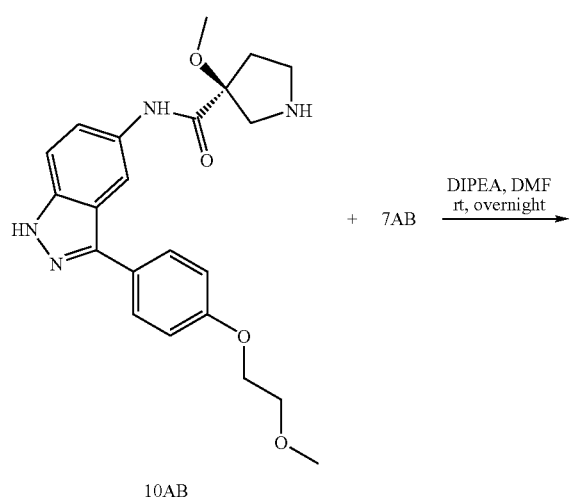

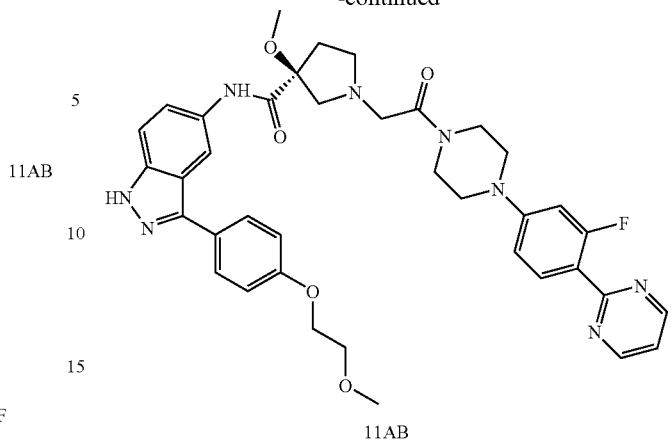

3-Methoxy-pyrrolidine-3-carboxylic acid {3-[4-(2-methoxy-ethoxy)-phenyl]-1H-indazol-5-yl}-amide (10AB) (50 mg, 0.103 mmol, 1 equiv) and 2-Chloro-1-[4-(3-fluoro-4-pyrimidin-2-yl-phenyl)-piperazin-1-yl]-ethanone (7AB) (42 mg, 0.124 mmol, 1.2 equiv) were weighed out in a flask and to it was added N,N-dimethylformamide (3 mL) and diisopropylethylamine (26.6 mg, 36 uL, 0.206 mmol, 2 equiv). The reaction content was stirred at room temperature, overnight.

The crude reaction mixture was diluted out with enough amount of ethylacetate and the organic phase was washed with a (1v:1v) mixture of brine and water twice. The organic layer was separated and concentrated down on rotovap to dryness, and further dried on a high vacuum pump. The residue was taken up in as little dichloromethane as possible and purified by column chromatography using Analogix purification system with the following conditions: Solvent A: Dichloromethane; Solvent B: 40% 7N NH$_3$ in Methanol. Flow Rate: 30 mL/min. Gradient: 0% Solvent B to 20% Solvent B in 30 minutes. The clean fractions were combined in a flask and concentrated down on rotovap. The residue was then dissolved in methanol and acidified with 4N HCl in 1,4-dioxane (100 uL) to make it into HCl salt form before submitting it to biological assay.

Yield=46.4 mg, LCMS [M+H$^+$]=709.4.

Example 616

Steps 1 to 3

Steps 1 to 3 are similar to Steps 1 to 3 of Example 614.

Step 4: Synthesis of 1-{2-[4-(3-Fluoro-4-pyrimidin-2-yl-phenyl)-piperazin-1-yl]-2-oxo-ethyl}-3-methylsulfanyl-pyrrolidine-3-carboxylic acid [3-(4-fluoro-phenyl)-1H-indzol-5-yl]-amide (13AB)

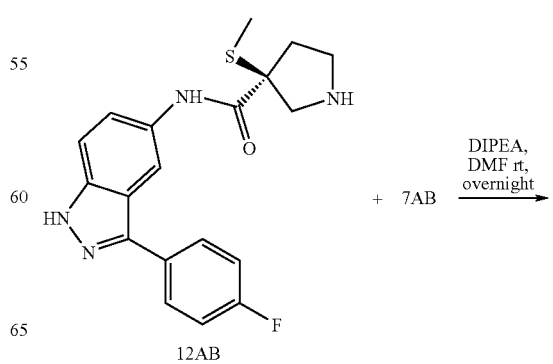

-continued

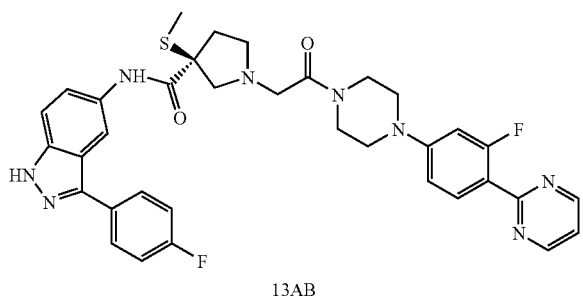

13AB

3-Methylsulfanyl-pyrrolidine-3-carboxylic acid [3-(4-fluoro-phenyl)-1H-indazol-5-yl]-amide (12AB) (40 mg, 0.09 mmol, 1 equiv) and 2-Chloro-1-[4-(3-fluoro-4-pyrimidin-2-yl-phenyl)-piperazin-1-yl]-ethanone (7AB) (37 mg, 0.11 mmol, 1.2 equiv) were weighed out in a flask, and to it was added N,N-dimethylformamide (3 mL) and diisopropylethylamine (23 mg, 32 uL, 0.18 mmol, 2 equiv). The reaction content was stirred at room temperature overnight.

The crude reaction mixture was diluted out with enough amount of ethylacetate and the organic phase was washed with a (1v:1v) mixture of brine and water twice. The organic layer was separated and concentrated down on rotovap to dryness, and further dried on a high vacuum pump. The residue was taken up in as little dichloromethane as possible and purified by column chromatography using Analogix purification system with the following conditions: Solvent A: Dichloromethane; Solvent B: 40% 7N $NH_3$ in Methanol. Flow Rate: 30 mL/min. Gradient: 0% Solvent B to 20% Solvent B in 30 minutes. The clean fractions were combined in a flask and concentrated down on rotovap. The residue was then dissolved in methanol and acidified with 4N HCl in 1,4-dioxane (100 uL) to make it into HCl salt form before submitting it to biological assay.

Yield=58 mg, LCMS [M+H$^+$]=669.4.

Example 617

Step 1: Synthesis of 4-(4-Bromo-3-fluoro-phenyl)-3,6-dihydro-2H-pyridine-1-carboxylic acid tert-butyl ester (16AB)

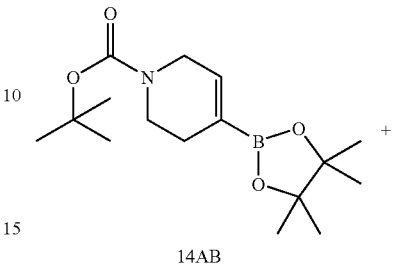

14AB

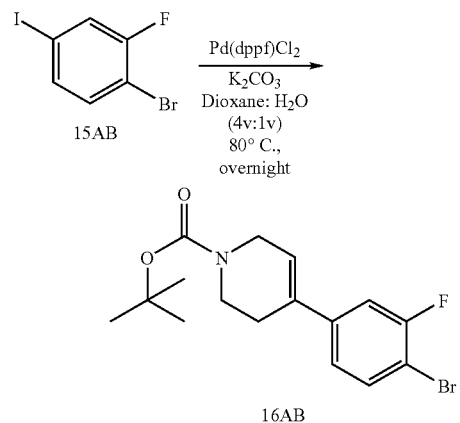

16AB 4-(4,4,5,5-Tetramethyl-[1,3,2]dioxaborolan-2-yl)-3,6-dihydro-2H-pyridine-1-carboxylic acid tert-butyl ester (14AB) (4.0 g, 12.9 mmol, 1 equiv), 1-Bromo-2-fluoro-4-iodo-benzene (15AB) (5.84 g, 19.4 mmol, 1.5 equiv), potassium carbonate (5.4 g, 38.8 mmol, 3 equiv), and a (4v:1v) mixture of 1,4-dioxane and water (120 mL: 30 mL) were all added in a pressure vessel (350 mL) and the mixture was bubbled with nitrogen gas for about 10 minutes. To this mixture was added dichloro[1,1'-bis(diphenylphosphino)ferrocene] palladium (II)/dichloromethane adduct (1.05 g, 1.29 mmol, 0.1 equiv), and the reaction vessel was tightly capped, placed in an oil bath at 80° C., and stirred overnight.

25AB

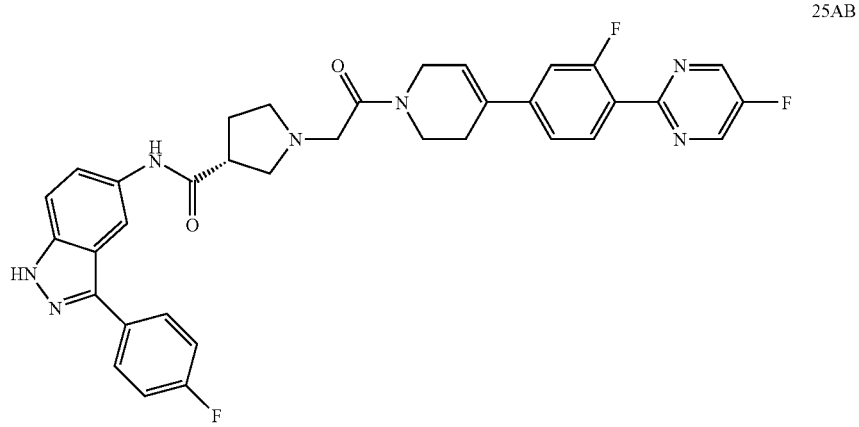 [SMILES: O=C(Nc1ccc2[nH]nc(-c3ccc(F)cc3)c2c1)[C@@H]1CCN(CC(=O)N2CC=C(c3ccc(-c4ncc(F)cn4)c(F)c3)CC2)C1]

The reaction mixture was cooled down to room temperature and the content was transferred into a flask and concentrated down on rotovap. The residue was then taken up in ethyl acetate and, in a separatory funnel; the crude mixture was washed with water, 10% sodium carbonate and brine. The organic layer was dried on magnesium sulfate and passed through a Celite plug. The filtrate was then treated with activated carbon at 65° C. in an Erlenmeyer in a water bath for about 10 minutes to decolorize the solution. The charcoal was separated by a Celite plug. The solvent was removed on rotovap and the residue was dried on pump overnight. The residue was taken up in as little dichloromethane as possible and purified by column chromatography using Analogix purification system with the following conditions: Solvent A: Hexanes; Solvent B: Ethylacetate. Flow Rate: 65 mL/min. Gradient: 0% Solvent B to 50% Solvent B in 60 minutes.

Yield=3.12 g (68%)

Step 2: Synthesis of 4-[4-(5,5-Dimethyl-[1,3,2]dioxaborinan-2-yl)-3-fluoro-phenyl]-3,6-dihydro-2H-pyridine-1-carboxylic acid tert-butyl ester (18AB)

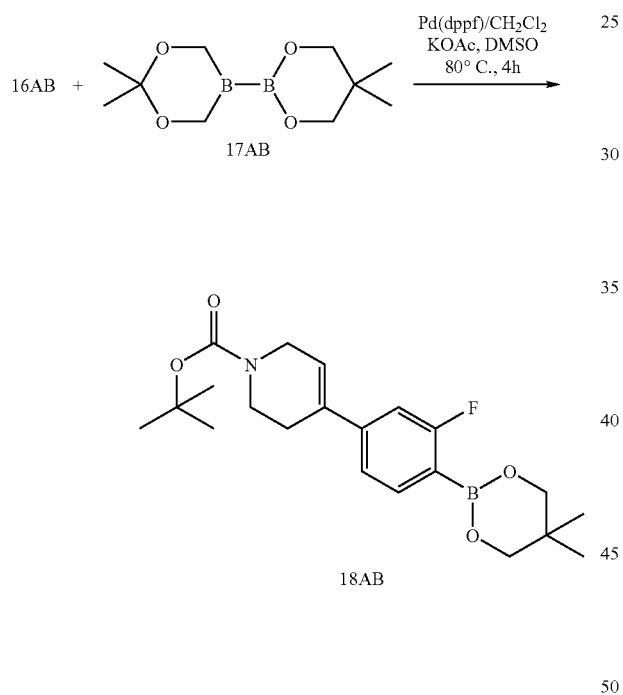

4-(4-Bromo-3-fluoro-phenyl)-3,6-dihydro-2H-pyridine-1-carboxylic acid tert-butyl ester (16AB)(2.3 g, 6.59 mmol, 1 equiv), bis(neopentylglycolato)diboron (17AB)(1.79 g, 7.91 mmol, 1.2 equiv), and potassium acetate (1.94 g, 19.77 mmol, 3 equiv) were all weighed out in a dry pressure vessel and dissolved in dimethylsulfoxide (50 mL). The mixture was bubbled with nitrogen gas for 10 minutes. Dichloro[1,1'-bis (diphenylphosphino) ferrocene] palladium (II)/dichloromethane adduct (540 mg, 0.66 mmol, 0.1 equiv) was added and the reaction vessel was sealed tightly with a cap and placed in on oil bath at 80° C. for 4 hours.

Upon the completion of 4 hours, the reaction vessel was cooled down to room temperature and the content was transferred into a flask. Some water was added to solubilize the excess inorganic base along with some ethyl acetate. The organic layer was then washed with water and brine twice, and separated and dried over magnesium sulfate. The organic layer was concentrated down on rotovap and taken up with dichloromethane. In an Erlenmeyer the crude compound was treated with activated carbon at 65° C. in a water bath for about 10 minutes to decolorize the solution. The charcoal was separated by a Celite plug. The solvent was removed on rotovap and the residue was dried on pump overnight. The residue was taken up in as little dichloromethane as possible and purified by column chromatography using Analogix purification system with the following conditions: Solvent A: Hexanes; Solvent B: Ethylacetate. Flow Rate: 65 mL/min. Gradient: 0% Solvent B to 50% Solvent B in 60 minutes. Relatively clean fractions were combined and the solvent was concentrated down. The product spot on TLC was streaking; that is probably because during the purification of this compound on a silica gel column some of the boronic acid ester was getting hydrolyzed to boronic acid. Therefore, even though the separation was not as desirable, the compound was used as-is in the next reaction after the purification step.

Step 3: Synthesis 4-[3-Fluoro-4-(5-fluoro-pyrimidin-2-yl)-phenyl]-3,6-dihydro-2H-pyridine-1-carboxylic acid tert-butyl ester (21AB)

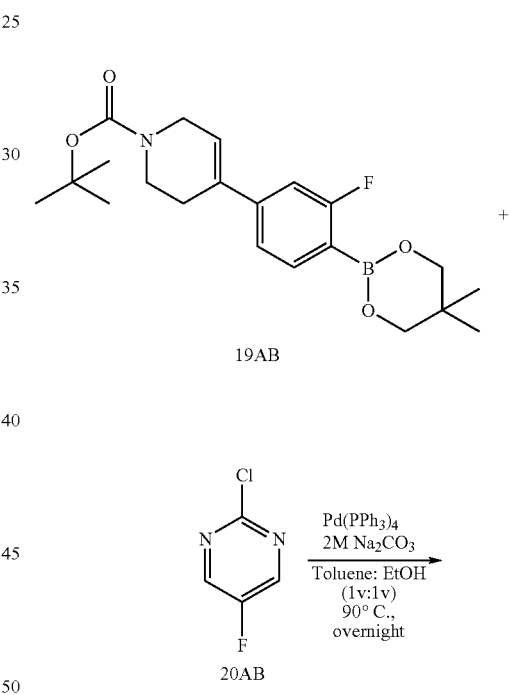

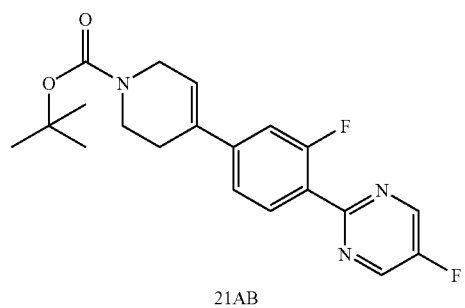

4-[4-(5,5-Dimethyl-[1,3,2]dioxaborinan-2-yl)-3-fluoro-phenyl]-3,6-dihydro-2H-pyridine-1-carboxylic acid tert-butyl ester (19AB)(1.55 g, 3.98 mmol, 1 equiv), 2-Chloro-5-fluoro-pyrimidine (20AB)(634 mg, 591 uL, 4.78 mmol, 1.2 equiv), and 2M sodium carbonate (9.95 mL) were added in a pressure vessel (350 mL) and a (1v:1v) mixture of toluene and ethanol (25 mL: 25 mL) was added. The mixture was then bubbled with nitrogen gas for about 10 minutes. Tetrakis (triphenylphosphine) palladium (0) (462 mg, 0.4 mmol, 0.1 equiv) was added to the mixture. The reaction vessel was tightly capped, placed in an oil bath at 90° C., and stirred overnight.

The reaction mixture was cooled down to room temperature and diluted with ethyl acetate. The crude mixture was transferred into a separatory funnel and washed with a (1v:1v) brine and water mixture. The organic layer was separated and combined and dried over magnesium sulfate. The crude product was then filtered into a flask and the solvent was removed on rotovap. The residue was taken up in as little dichloromethane as possible and purified by column chromatography using Analogix purification system with the following conditions: Solvent A: Dichloromethane; Solvent B: Methanol. Flow Rate: 45 mL/min. Gradient: 0% Solvent B to 10% Solvent B in 60 minutes.

Yield=677 mg (46%)

Step 4: Synthesis of 5-Fluoro-2-[2-fluoro-4-(1,2,3,6-tetrahydro-pyridin-4-yl)-phenyl]-pyrimidine (22AB)

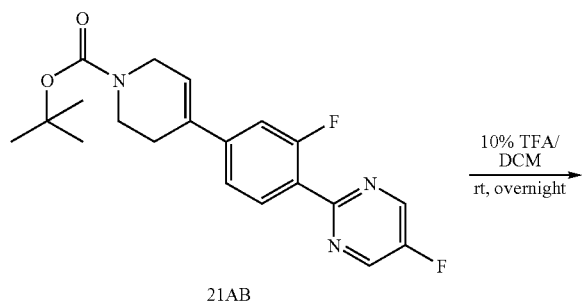

21AB

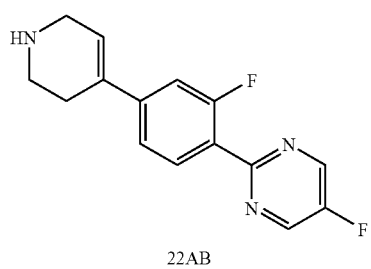

22AB

4-[3-Fluoro-4-(5-fluoro-pyrimidin-2-yl)-phenyl]-3,6-dihydro-2H-pyridine-1-carboxylic acid tert-butyl ester (21AB) (717 mg, 1.92 mmol, 1 equiv) was treated with 10% solution of trifluoroacetic acid in dichloromethane at room temperature overnight.

The solvent was concentrated down and the residue was taken up in ethyl acetate and washed with 10% aqueous sodium carbonate twice. Water layers were combined and saturated with sodium chloride and the remaining product in water layer thus extracted with ethyl acetate. The organic layers were combined and evaporated to dryness on a rotovap. The residue was taken up in as little dichloromethane as possible and purified by column chromatography using Analogix purification system with the following conditions: Solvent A: Dichloromethane; Solvent B: 40% 7N $NH_3$ in Methanol. Flow Rate: 65 mL/min. Gradient: 0% Solvent B to 30% Solvent B in 60 minutes and stayed at 30% Solvent B for 10 minutes. LCMS [M+H$^+$]=274.2.

Step 5: Synthesis of 2-Chloro-1-{4-[3-fluoro-4-(5-fluoro-pyrimidin-2-yl)-phenyl]-3,6-dihydro-2H-pyridin-1-yl}-ethanone (23)

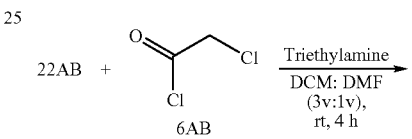

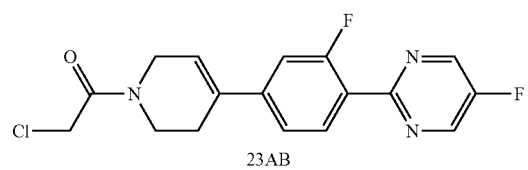

23AB

5-Fluoro-2-[2-fluoro-4-(1,2,3,6-tetrahydro-pyridin-4-yl)-phenyl]-pyrimidine (22AB) (1.94 g, 7.1 mmol, 1 equiv) was dissolved in a (3v:1v) mixture of dichloromethane (30 mL) and N,N-dimethyl formamide (10 mL) and triethylamine (862 mg, 1.19 mL, 8.52 mmol, 1.2 equiv) was added, followed by slow addition of chloroacetyl chloride (962 mg, 678 uL, 8.52 mmol, 1.2 equiv) at room temperature. The mixture was then stirred for about 4 hours at room temperature.

Upon the completion of the reaction, the solvent mixture was removed on rotovap and the residue was taken up in dichloromethane and washed with saturated solution of sodium bicarbonate and a (1v:1v) mixture of brine and water in a separatory funnel. The organic layer was separated, concentrated down, and dried on pump. The crude residue was then taken up in dichloromethane and purified by column chromatography using Analogix purification system with the following conditions: Solvent A: Dichloromethane; Solvent B: 40% 7N $NH_3$ in Methanol. Flow Rate: 65 mL/min. Gradient: 0% Solvent B to 30% Solvent B in 52 minutes and stayed at 30% Solvent B for 10 minutes.

Yield=851 mg (34%)

Step 6: Synthesis of 1-(2-{4-[3-Fluoro-4-(5-fluoro-pyrimidin-2-yl)-phenyl]-3,6-dihydro-2H-pyridin-1-yl}-2-oxo-ethyl)-pyrrolidine-3-carboxylic acid [3-(4-fluoro-phenyl)-1H-indazol-5-yl]-amide (25AB)

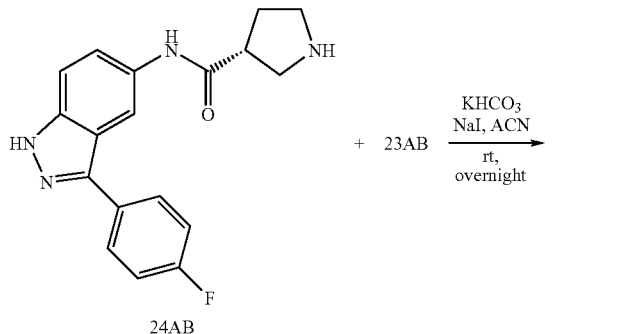

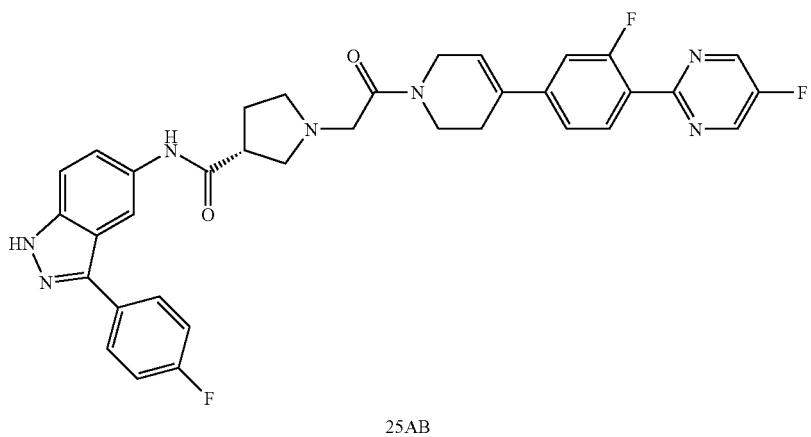

Pyrrolidine-3-carboxylic acid [3-(4-fluoro-phenyl)-1H-indazol-5-yl]-amide (24AB) (30 mg, 0.093 mmol, 1 equiv), 2-Chloro-1-{4-[3-fluoro-4-(5-fluoro-pyrimidin-2-yl)-phenyl]-3,6-dihydro-2H-pyridin-1-yl}-ethanone (23AB) (36 mg, 0.102 mmol, 1.1 equiv), potassium bicarbonate (47 mg, 0.465 mmol, 5 equiv), and sodium iodide (3 mg, 0.019 mmol, 0.2 equiv) were all weighed out in a flask and to it was added acetonitrile (3 mL). The reaction content was stirred at room temperature overnight.

The crude reaction mixture was concentrated down on rotovap and the residue was taken up in ethyl acetate. In a separatory funnel, the organic phase was washed with a (1v:1v) mixture of brine and water twice. The organic layer was separated and concentrated down on rotovap to dryness, and further dried on a high vacuum pump. The residue was taken up in as little dichloromethane as possible and purified by column chromatography using Analogix purification system with the following conditions: Solvent A: Dichloromethane; Solvent B: 40% 7N NH$_3$ in Methanol. Flow Rate: 30 mL/min. Gradient: 0% Solvent B to 20% Solvent B in 30 minutes. The clean fractions were combined in a flask and concentrated down on rotovap. The residue was then dissolved in methanol and acidified with 4N HCl in 1,4-dioxane (100 uL) to make it into HCl salt form before submitting it to biological assay.

Yield=16.9 mg, LCMS [M+H$^+$]=638.4.

Example 618

Synthesis of 1-(2-(4-[3-Fluoro-4-(5-fluoro-pyrimidin-2-yl)-phenyl]-3,6-dihydro-2H-pyridin-1-yl)-2-oxo-ethyl)-3-methoxymethyl-pyrrolidine-3-carboxylic acid [3-(2-cyclopropyl-pyridin-4-yl)-1H-indazol-5-yl]-amide (27AB)

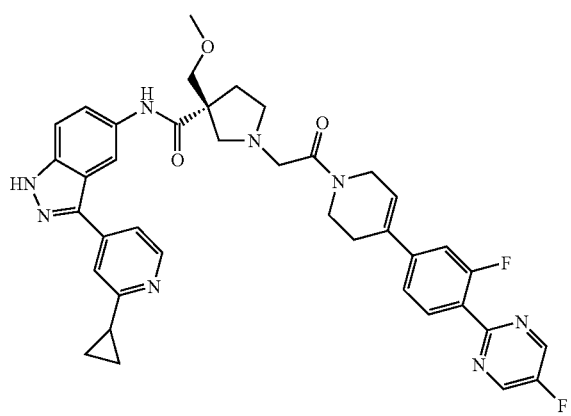

611

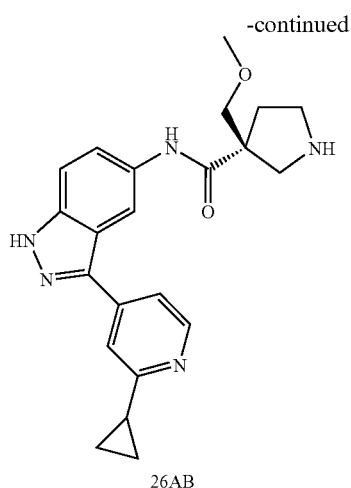

26AB

+ 23AB  →  TEA, DMF, rt, overnight

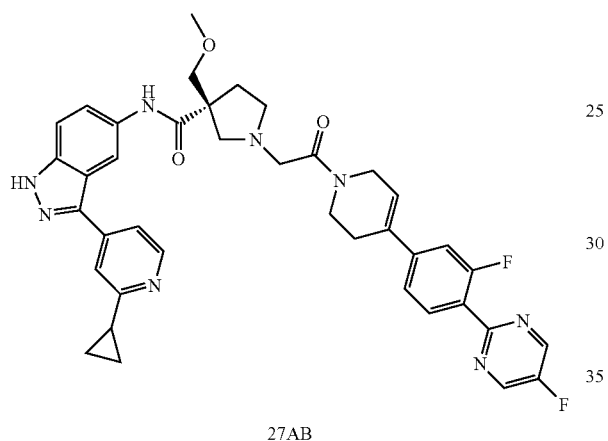

27AB

3-Methoxymethyl-pyrrolidine-3-carboxylic acid [3-(2-cyclopropyl-pyridin-4-yl)-1H-indazol-5-yl]-amide (26AB) (85 mg, 0.217 mmol, 1 equiv) and 2-Chloro-1-{4-[3-fluoro-4-(5-fluoro-pyrimidin-2-yl)-phenyl]-3,6-dihydro-2H-pyridin-1-yl}-ethanone (23AB) (84 mg, 0.239 mmol, 1.1 equiv) were weighed out in a flask and dissolved in anhydrous N,N-dimethylformamide (5 mL). Triethyl amine (33 mg, 46 uL, 0.326 mmol, 1.5 equiv) was added to the reaction mixture and the reaction content was stirred at room temperature overnight.

The crude reaction mixture was diluted out with enough amount of ethylacetate and the organic phase was washed with a saturated solution of sodium bicarbonate and a (1v:1v) mixture of (brine:water) twice. The organic layer was separated and concentrated down on rotovap to dryness, and further dried on a high vacuum pump. The residue was taken up in as little dichloromethane as possible and purified by column chromatography using Analogix purification system with the following conditions: Solvent A: Dichloromethane; Solvent B: 40% 7N $NH_3$ in Methanol. Flow Rate: 30 mL/min. Gradient: 0% Solvent B to 20% Solvent B in 30 minutes. The clean fractions were combined in a flask and concentrated down on rotovap. The residue was then dissolved in methanol and acidified with 4N HCl in 1,4-dioxane (100 uL) to make it into HCl salt form before submitting it to biological assay.

Yield=75 mg (49%), LCMS [M+H$^+$]=705.4.

612

Example 619

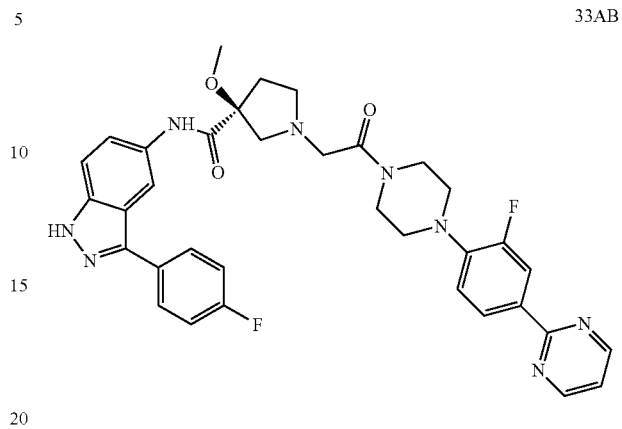

33AB

Step 1: Synthesis of 2-(4-Bromo-3-fluoro-phenyl)-pyrimidine (29AB)

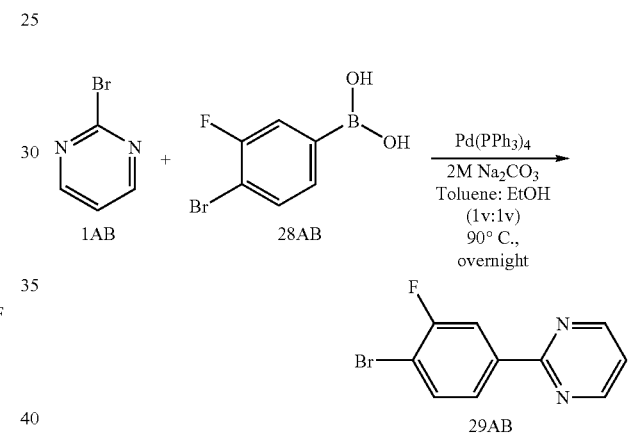

4-Bromo-3-fluorophenyl boronic acid (28AB) (1.0 g, 4.57 mmol, 1 equiv), 2-bromopyrimidine (1AB) (2.18 g, 13.7 mmol, 3 equiv), and 2M sodium carbonate (12 mL) were added in a pressure vessel (150 mL) and a (1v:1v) mixture of toluene and ethanol (25 mL: 25 mL) was added. The mixture was then bubbled with nitrogen gas for about 10 minutes. Tetrakistriphenylphosphine palladium (0) (266 mg, 0.23 mmol, 0.05 equiv) was added to the mixture. The reaction vessel was tightly capped, placed in an oil bath at 90° C., and stirred overnight.

The reaction mixture was cooled down to room temperature and the content was filtered into a flask and the solvent mixture was evaporated off on the rotovap. The residue was then taken up in one to one mixture of toluene and ethyl acetate and washed with (3v:1v) mixture of brine: DI water twice. The organic layer was separated and combined and dried over magnesium sulfate. The crude product was then filtered into a flask and the solvent was removed on rotovap. The residue was taken up in as little dichloromethane as possible and purified by column chromatography using Analogix purification system with the following conditions: Solvent A: Hexanes; Solvent B: Ethylacetate. Flow Rate: 65 mL/min. Gradient: 0% Solvent B to 50% Solvent B in 60 minutes.

Yield=1.08 g (94%)

613

Step 2: Synthesis of 2-(3-Fluoro-4-piperazin-1-yl-phenyl)-pyrimidine (30AB)

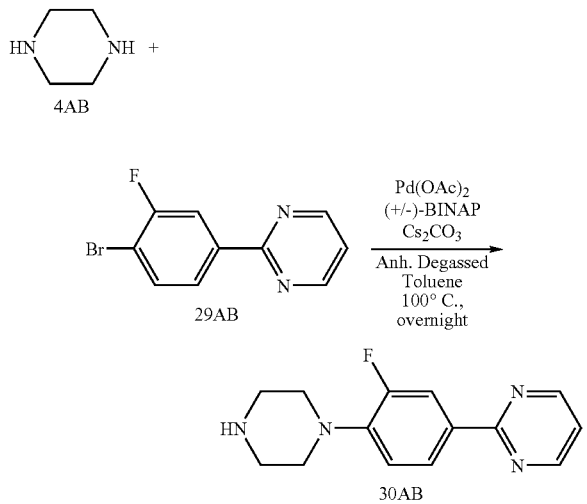

2-(4-Bromo-3-fluoro-phenyl)-pyrimidine (29AB) (874 mg, 3.45 mmol, 1 equiv), piperazine (1.19 g, 13.8 mmol, 4 equiv), cesium carbonate (9.0 g, 27.6 mmol, 8 equiv), racemic (+/−) BINAP (215 mg, 0.345 mmol, 0.1 equiv), and palladium (II) acetate (38.8 mg, 0.173 mmol, 0.05 equiv) were all weighed out in a flamed dried pressure vessel and the vessel was sealed with a rubber septa and the all-solid mixture was kept under vacuum for 2 hours. Anhydrous degassed toluene (30 mL) was added to the reaction vessel using a cannula. The rubber septa was replaced with a Teflon cap and the vessel was tightly sealed and placed in an oil bath at 100° C. to stir the content overnight.

The reaction vessel was cooled down to room temperature and the content was transferred into a flask. Some water was added to solubilize the excess inorganic base along with some ethyl acetate. The organic layer was then washed with water and brine twice, and separated and dried over magnesium sulfate. The crude product was then filtered into a flask and the solvent was removed on rotovap. The residue was taken up in as little dichloromethane as possible and purified by column chromatography using Analogix purification system with the following conditions: Solvent A: Dichloromethane; Solvent B: 40% 7N NH₃ in Methanol. Flow Rate: 40 mL/min. Gradient: 0% Solvent B to 30% Solvent B in 52 minutes and stayed at 30% Solvent B for 10 minutes.

Yield=675 mg (76%)

Step 3: Synthesis of 2-Chloro-1-[4-(2-fluoro-4-pyrimidin-2-yl-phenyl)-piperazin-1-yl]-ethanone (31AB)

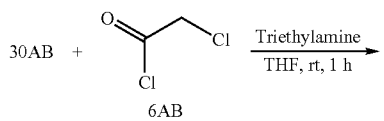

614

-continued

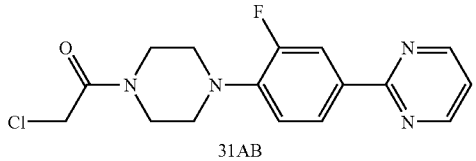

2-(3-Fluoro-4-piperazin-1-yl-phenyl)-pyrimidine (29AB) (675 mg, 2.61 mmol, 1 equiv) was dissolved in anhydrous tetrahydrofuran (5 mL), and triethylamine (1.32 mg, 1.82 mL, 13.05 mmol, 5 equiv) was added, followed by slow addition of a solution of chloroacetyl chloride (591 mg, 417 uL, 5.23 mmol, 2 equiv) in tetrahydrofuran at room temperature. The mixture was then stirred for about 1 hour at room temperature.

Upon the completion of the reaction, the solvent was removed on rotovap and the residue was taken up in dichloromethane and washed with a (1v:1v) mixture of brine and water in a separatory funnel. The organic layer was separated, concentrated down, and dried on pump. The crude residue was then taken up in dichloromethane and purified by column chromatography using Analogix purification system with the following conditions: Solvent A: Dichloromethane; Solvent B: 40% 7N NH₃ in Methanol. Flow Rate: 40 mL/min. Gradient: 0% Solvent B to 30% Solvent B in 52 minutes and stayed at 30% Solvent B for 10 minutes.

Yield=821 mg (94%)

Step 4: Synthesis of 1-{2-[4-(2-Fluoro-4-pyrimidin-2-yl-phenyl)-piperazin-1-yl]-2-oxo-ethyl}-3-methoxy-pyrrolidine-3-carboxylic acid [3-(4-fluoro-phenyl)-1H-indazol-5-yl]-amide (33AB)

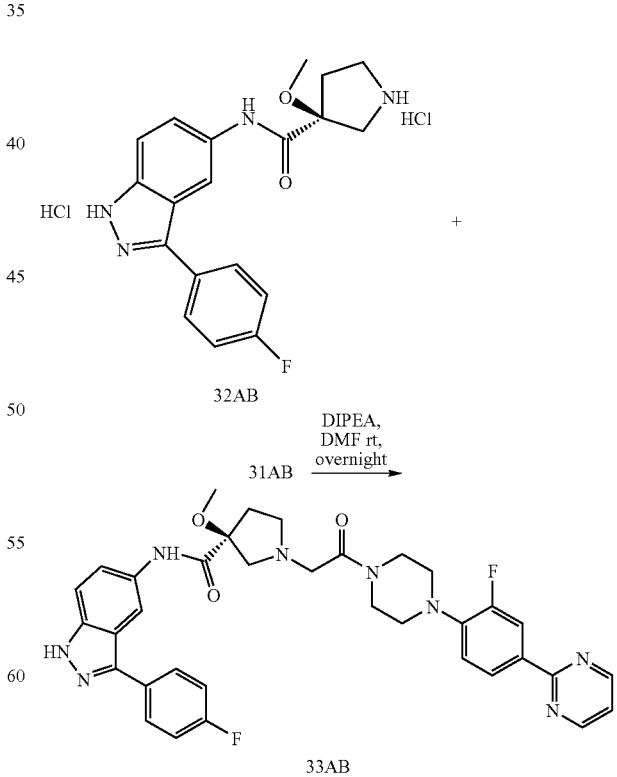

3-Methoxy-pyrrolidine-3-carboxylic acid [3-(4-fluoro-phenyl)-1H-indazol-5-yl]-amide 2.HCl Salt (32AB) (30 mg, 0.07 mmol, 1 equiv) and 2-Chloro-1-[4-(2-fluoro-4-pyrimidin-2-yl-phenyl)-piperazin-1-yl]-ethanone (31AB) (28 mg, 0.08 mmol, 1.2 equiv) were weighed out in a flask and to it was added N,N-dimethylformamide (3 mL) and diisopropylethylamine (54.3 mg, 73 uL, 0.42 mmol, 6 equiv). The reaction content was stirred at room temperature overnight.

The crude reaction mixture was diluted out with enough amount of ethylacetate and the organic phase was washed with a (1v:1v) mixture of brine and water twice. The organic layer was separated and concentrated down on rotovap to dryness, and further dried on a high vacuum pump. The residue was taken up in as little dichloromethane as possible and purified by column chromatography using Analogix purification system with the following conditions: Solvent A: Dichloromethane; Solvent B: 40% 7N $NH_3$ in Methanol. Flow Rate: 30 mL/min. Gradient: 0% Solvent B to 15% Solvent B in 30 minutes. The clean fractions were combined in a flask and concentrated down on rotovap. The residue was then dissolved in methanol and acidified with 4N HCl in 1,4-dioxane (100 uL) to make it into HCl salt form before submitting it to biological assay.

Yield=41 mg (90%), LCMS [M+H$^+$]=653.4.

Preparation 47

Preparation of 2-Chloro-1-(5,8-dichloro-3,4-dihydro-1H-isoquinolin-2-yl)-ethanone

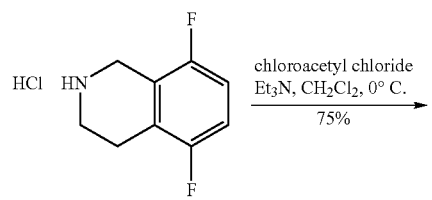

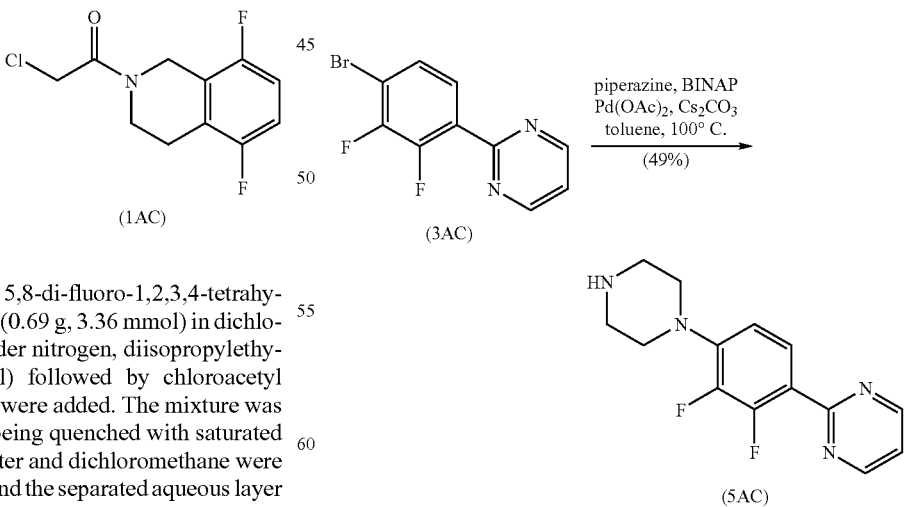

To a stirred suspension of 5,8-di-fluoro-1,2,3,4-tetrahydroisoquinoline hydrochloride (0.69 g, 3.36 mmol) in dichloromethane (20 ml) at 0° C. under nitrogen, diisopropylethylamine (1.40 ml, 8.05 mmol) followed by chloroacetyl chloride (0.32 ml, 4.03 mmol) were added. The mixture was stirred at 0° C. for 2 hr. After being quenched with saturated sodium carbonate solution, water and dichloromethane were added. Layers were separated and the separated aqueous layer was extracted with dichloromethane. The combined organic layers were dried ($MgSO_4$), filtered and solvents were removed in vacuum. Column purification [Hexanes-Ethyl acetate, 4:1 (v/v)] gave chloride 1AC (619 mg, 75%) as colourless oil.

Preparation 48

Step 1: Preparation of 2-(4-Bromo-2,3-difluoro-phenyl)-pyrimidine

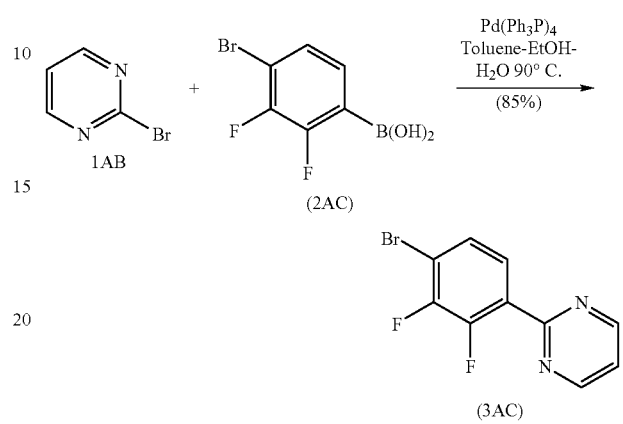

A mixture of 2-bromopyrimidine (2.0 g, 12.7 mmol), 4-bromo-2,3-difluorobenzeneboronic acid (1.0 g, 4.22 mmol), potassium carbonate (2.93 g, 21.1 mmol) in a mixture of toluene (30 ml)/ethanol (30 ml)/water (15 ml) were purged with nitrogen for 15 min. Tetrakis(triphenylphosphine)palladium(0) (488 mg, 0.42 mmol) was added and the mixture was stirred at 90° C. in a sealed-tube for overnight. The mixture was cooled to r.t. and was diluted with water and ethyl acetate. Layers were separated. The separated organic layer was dried ($MgSO_4$), filtered and solvents were removed in vacuum. Column purification [Hexanes-Ethyl acetate, 2:1 (v/v)] gave bromide 3AC (0.97 g, 85%) as white solid.

Step 2: Preparation of 2-(2,3-Difluoro-4-piperazin-1-yl-phenyl)-pyrimidine

A mixture of bromide 3AC (300 mg, 1.11 mmol), piperazine (286 mg, 3.32 mmol), BINAP (69 mg, 0.11 mmol), cesium carbonate (721 mg, 2.21 mmol) in toluene (10 ml)

were purged with nitrogen for 15 min. Palladium (II) acetate (13 mg, 0.055 mmol) was added and the mixture was stirred at 100° C. in a sealed-tube for overnight. The mixture was cooled to r.t. and was diluted with water and ethyl acetate. Layers were separated. The separated organic layer was dried (MgSO$_4$), filtered and solvents were removed in vacuum. Column purification [Methanol-Ethyl acetate, 1:1 (v/v)] gave piperazine 5AC (150 mg, 49%) as white solid.

Step 3: Preparation of 2-Chloro-1-[4-(2,3-Difluoro-4-pyrimidin-2-yl-phenyl)-piperazin-1-yl]-ethanone

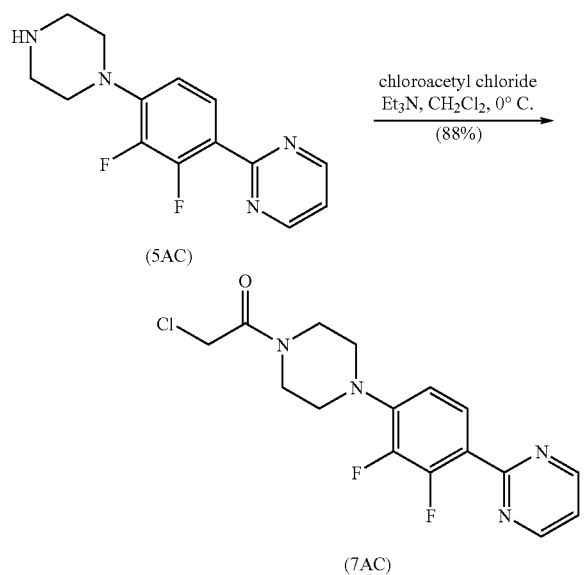

To a stirred solution of piperazine 5AC (150 mg, 0.54 mmol) in dichloromethane (5 ml) at 0° C. under nitrogen, triethylamine (0.076 ml, 0.54 mmol) followed by chloroacetyl chloride (0.043 ml, 0.54 mmol) were added. The mixture was stirred at 0° C. for 2 hr. After being quenched with saturated sodium carbonate solution, water and dichloromethane were added. Layers were separated and the separated aqueous layer was extracted with dichloromethane. The combined organic layers were dried (MgSO$_4$), filtered and solvents were removed in vacuum. Column purification [Hexanes-Ethyl acetate, 1:1 (v/v)] gave chloride 7AC (169 mg, 88%) white solid.

Preparation 49

Step 1: Preparation of 2-(4-Bromo-2,5-difluoro-phenyl)-pyrimidine

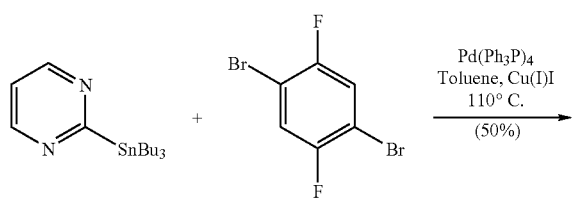

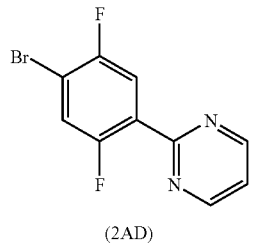

A mixture of 1,4-dibromobenzene (4.4 g, 16.3 mmol), 2-(tributylstannyl)pyrimidine (3.0 g, 8.13 mmol), copper (I) iodide (154 mg, 0.81 mmol) in toluene (50 ml) were purged with nitrogen for 15 min. Tetrakis(triphenylphosphine)palladium(0) (939 mg, 0.81 mmol) was added and the mixture was stirred at 110° C. in a sealed-tube for 1 day. The mixture was cooled to r.t. and was diluted with water and ethyl acetate. Layers were separated. The separated organic layer was dried (MgSO$_4$), filtered and solvents were removed in vacuum. Column purification [Hexanes-Ethyl acetate, 2:1 (v/v)] gave bromide 2AD (1.09 g, 50%) as white solid.

Step 2: Preparation of 2-(2,5-Difluoro-4-piperazin-1-yl-phenyl)-pyrimidine

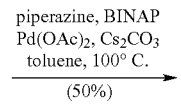

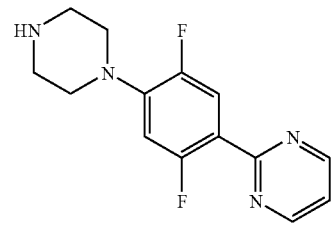

A mixture of bromide 2AD (850 mg, 3.14 mmol), piperazine (810 mg, 9.41 mmol), BINAP (196 mg, 0.31 mmol), cesium carbonate (2.0 g, 6.27 mmol) in toluene (30 ml) were purged with nitrogen for 15 min. Palladium (II) acetate (35 mg, 0.16 mmol) was added and the mixture was stirred at 100° C. in a sealed-tube for overnight. The mixture was cooled to r.t. and was diluted with water and ethyl acetate. Layers were separated. The separated organic layer was dried (MgSO$_4$), filtered and solvents were removed in vacuum.

Column purification [Methanol-Ethyl acetate, 1:1 (v/v)] gave piperazine 4AD (393 mg, 43%) as white solid.

Step 3: Preparation of 2-Chloro-1-[4-(2,5-Difluoro-4-pyrimidin-2-yl-phenyl)-piperazin-1-yl]-ethanone

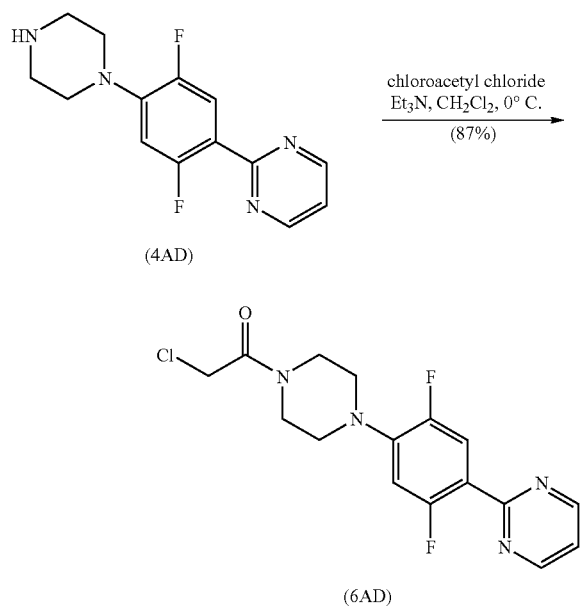 [SMILES: Fc1cc(N2CCNCC2)c(F)cc1-c1ncccn1 ; O=C(CCl)N1CCN(c2cc(F)c(-c3ncccn3)cc2F)CC1]

To a stirred solution of piperazine 4AD (255 mg, 0.92 mmol) in dichloromethane (5 ml) at 0° C. under nitrogen, triethylamine (0.13 ml, 0.92 mmol) followed by chloroacetyl chloride (0.074 ml, 0.92 mmol) were added. The mixture was stirred at 0° C. for 2 hr. After being quenched with saturated sodium carbonate solution, water and dichloromethane were added. Layers were separated and the separated aqueous layer was extracted with dichloromethane. The combined organic layers were dried (MgSO₄), filtered and solvents were removed in vacuum. Column purification [Hexanes-Ethyl acetate, 1:1 (v/v)] gave chloride 6AD (283 mg, 87%) white solid.

Example 620

Step 1: Preparation of 3-Methoxy-3-[3-(2-methyl-1-oxy-pyridin-4-yl)-1-trityl-1H-indazol-5-ylcarbamoyl]-pyrrolidine-1-carboxylic acid tert-butyl ester

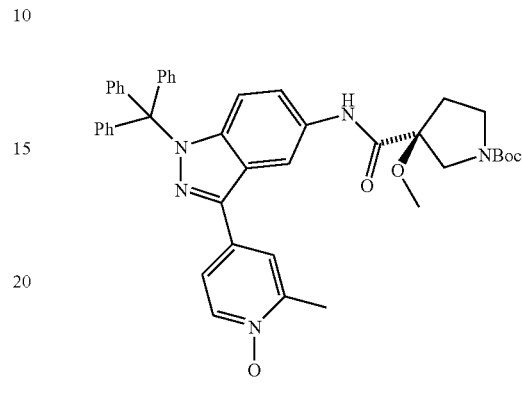

3-Methoxy-3-[3-(2-methyl-pyridin-4-yl)-1-trityl-1H-indazol-5-ylcarbamoyl]-pyrrolidine-1-carboxylic acid tert-butyl ester (2.9 g, 4.2 mmol) was dissolved in CH₂Cl₂ (80 mL) at rt followed by addition of mCPBA (2.0 g, max. 77%). After stirring for 24 hrs, the reaction solution was conc. to a small volume in vacuo and purified using silica gel column eluting with 2%, 5% and 10% methanol in CH₂Cl₂ to yield a brown solid (1.94 g).

Step 2: Preparation of 3-Methoxy-1-{2-oxo-2-[4-(4-pyrimidin-2-yl-phenyl)-piperazin-1-yl]-ethyl}-pyrrolidine-3-carboxylic acid [3-(2-methyl-1-oxy-pyridin-4-yl)-1H-indazol-5-yl]-amide

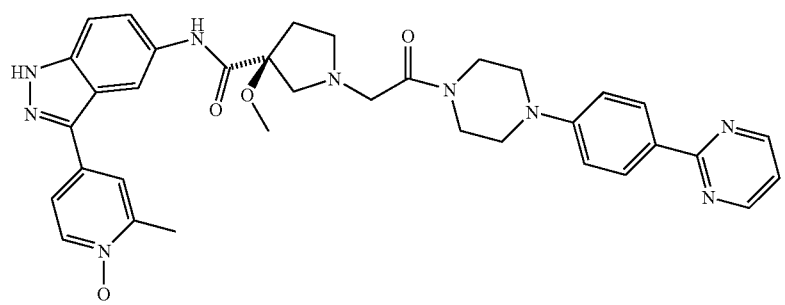

3-Methoxy-3-[3-(2-methyl-1-oxy-pyridin-4-yl)-1-trityl-1H-indazol-5-ylcarbamoyl]-pyrrolidine-1-carboxylic acid tert-butyl ester (170 mg) and triethylsilane (0.1 mL) were dissolved in CH₂Cl₂ (5 mL) at rt followed by addition of TFA (1 mL). After 2 hrs, the reaction mixture was conc. to dryness in vacuo. To this, DMF (5 mL), triethyl amine (0.1 mL) and 2-chloro-1-[4-(4-pyrimidin-2-yl-phenyl)-piperazin-1-yl]-ethanone (170 mg) were added. The resulting mixture was heated at 70° C. for 16 hrs. After cooling to rt, the reaction mixture was conc. to dryness. The resulting crude was purified via reverse phase HPLC (ACN/H2O/0.1% HCOOH) to yield a yellow solid (70.0 mg). LCMS (M+1) 648.4 (rt 2.12)

Preparation 50

Preparation of 4-(3-Methoxy-4-pyrimidin-2-yl-phenyl)-3,6-dihydro-2H-pyridine-1-carboxylic acid tert-butyl ester

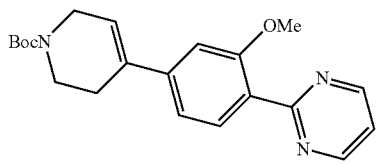 [SMILES: COc1cc(C2=CCN(C(=O)OC(C)(C)C)CC2)ccc1-c1ncccn1]

4-(3-Methoxy-4-pyrimidin-2-yl-phenyl)-3,6-dihydro-2H-pyridine-1-carboxylic acid tert-butyl ester was prepared using essentially the same scheme for Preparation 38 starting from 1-bromo-4-iodo-2-methoxy-benzene.

Preparation 51

Preparation of [5-(5-Amino-1H-indazol-3-yl)-2-fluoro-phenyl]-methanol

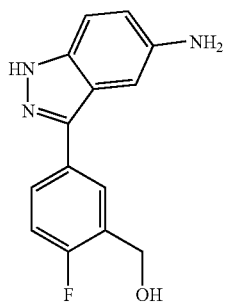 [SMILES: Nc1ccc2[nH]nc(-c3ccc(F)c(CO)c3)c2c1]

[5-(5-Amino-1H-indazol-3-yl)-2-fluoro-phenyl]-methanol was prepared using essentially the same scheme for preparing 10H (see Preparation 17 Step 3). The boronic acid for the first step was 4-fluoro-3-hydroxylmethylphenylboronic acid.

Preparation 52

Preparation of 4-Fluoro-4-(4-pyrimidin-2-yl-phenyl)-piperidine-1-carboxylic acid tert-butyl ester

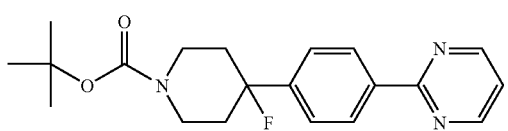 [SMILES: CC(C)(C)OC(=O)N1CCC(F)(c2ccc(-c3ncccn3)cc2)CC1]

The above compound was prepared using a procedure similar to that of Preparation 54 Step 4 by using 4-(4-Bromophenyl)-4-fluoro-piperidine-1-carboxylic acid tert-butyl ester in place of 3AE.

Preparation 53

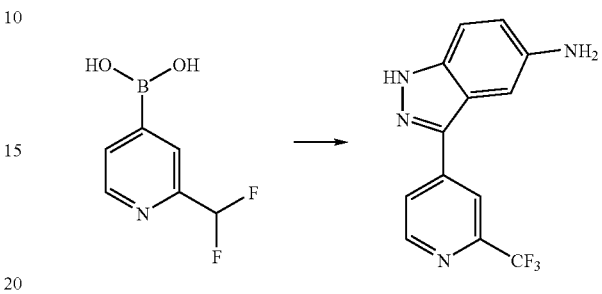

3-(2-Trifluoromethyl-pyridin-4-yl)-1H-indazol-5-ylamine was prepared by a procedure similar to that of Preparation 25 by substituting $CF_3CO_2Et$ with $CF_2CO_2Et$ in Preparation 25 (Chem. Het. Cpds, 1997, p 995) and utilizing the procedure similar to that of Example 98 Steps 2 & 3, Preparation 54

Step 1

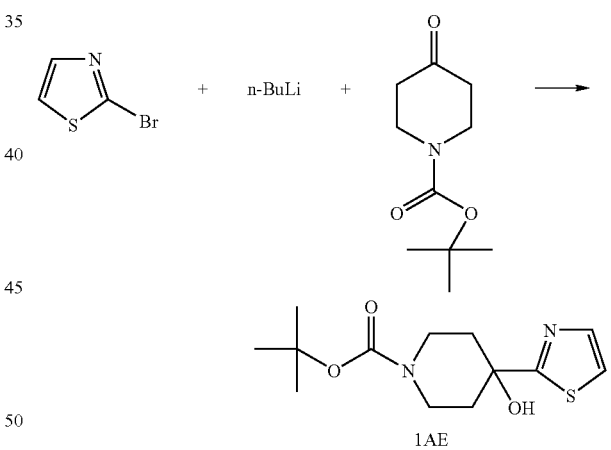

Compound 1AE was prepared following a procedure similar to that of Example 132.

Step 2

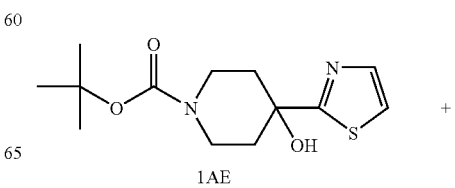

-continued

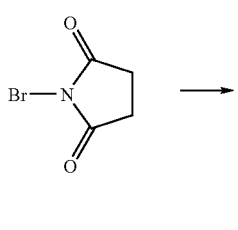

4.03 g (14.18 m.mole) 1AE was dissolved in 50 ml anhy. CH₃CN at r.t. under dry N2 ga this 2.524 g (14.18 m.mole) of N-Bromosuccinimde was added at r.t. and mixture was heated 50° C. under dry N2 gas for 3 hrs. The mixture was evaporated to dryness. The residue was partitioned between 100 ml EtOAc and 100 ml saturated NaHCO₃ solution. The organic phase dried over MgSO₄ and evaporated to dryness. The resulting brown gum was purified on silica (Hexane-30% EtOAc/Hexane) gave 1.3 g (25%) yellow solid.

Step 3

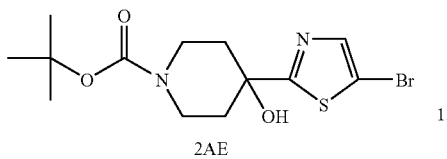

2.38 g (6.55 m.mole) of 3 was dissolved in 30 ml anhy. Dichloromethane at r.t. under dry N₂ gas. The mixture was cooled to 0° C. in ice-bath and 2.112 g (13.1 m. mole) of DAST was added dropwise at 0° C. under dry N₂. The mixture was stirred at 0° C. for 1 hr. The reaction mixture was cautiously (CO₂ gas evolution) basified with saturated NaHCO₃ solution at 0° C. The mixture was transferred to separatory funnel and shaken well. The organic phase was removed and aqueous phase was extracted with 2×50 ml Dichloromethane. The combine organic phases were dried over MgSO₄ and evaporated to dryness, gave 2.368 (99%) off-white low melting solid.

Step 4

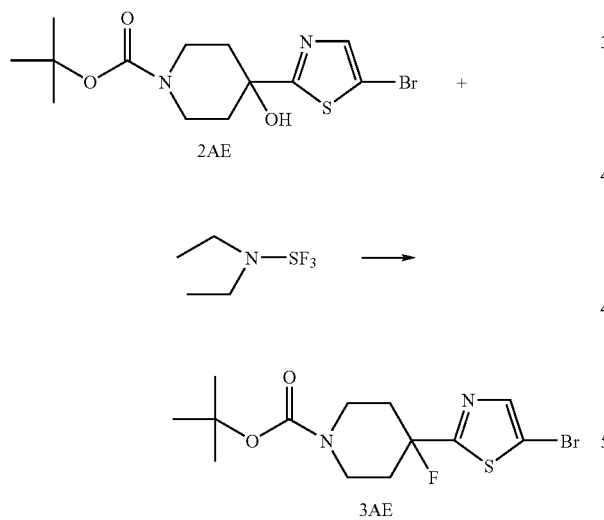

1.7 g (4.65 m. mole) of 4AE was dissolved in 15 ml anhy DMF at r.t. under dry N₂ gas. To this mixture CuI 0.93 g (4.88 m.mole), Tetrakis(triphenylphosphine) palladium 0.537 g (0.465 m.mole) and 2-Tributylstannylpyrimidine 1.762 g (5.2 m.mole) were added and the mixture was stirred at 60° C. under dry N₂ gas for 24 hrs. The mixture was concentrated to small volume, diluted with 50 ml EtOAc and filtered through pad of celite. The filtrate was washed with brine and dried over MgSO₄. The evaporation of the solvent gave dark brown gum which was purified on silica gel (Hexane-25% EtOAc/Hexane) gave 0.300 g (17%) of brown solid.

Preparation 55

Step 1

1-Benzyl-4-hydroxy-4-methyl piperidine (4.927 g, 24 m.mole) was dissolved in Bromobenzene (12 ml, 114 m.mole) at r.t. under dry N₂ gas. AlCl₃ (4.81 g, 36 m.mole) as solid was added to the above mixture at r.t. under dry N₂ gas. There was slightly exothermic reaction. The resulting dark brown solution was heated at 100° C. over the week-end. The reaction was allowed to cool to r.t and was poured into ice-water. Saturated aqueous NaHCO₃ was added till pH 7. The mixture was extracted with 3×100 ml EtOAc. The combined organic extract dried over MgSO₄ and evaporated to dryness. The resulting dark brown gum was purified on silica and was eluted with (Hexane-25% EtOAc/Hexane), gave 4.43 g (53%) as violet clear thick oil.

Step 2

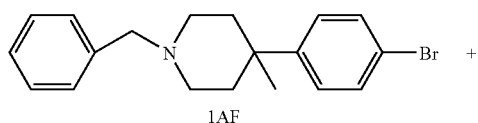

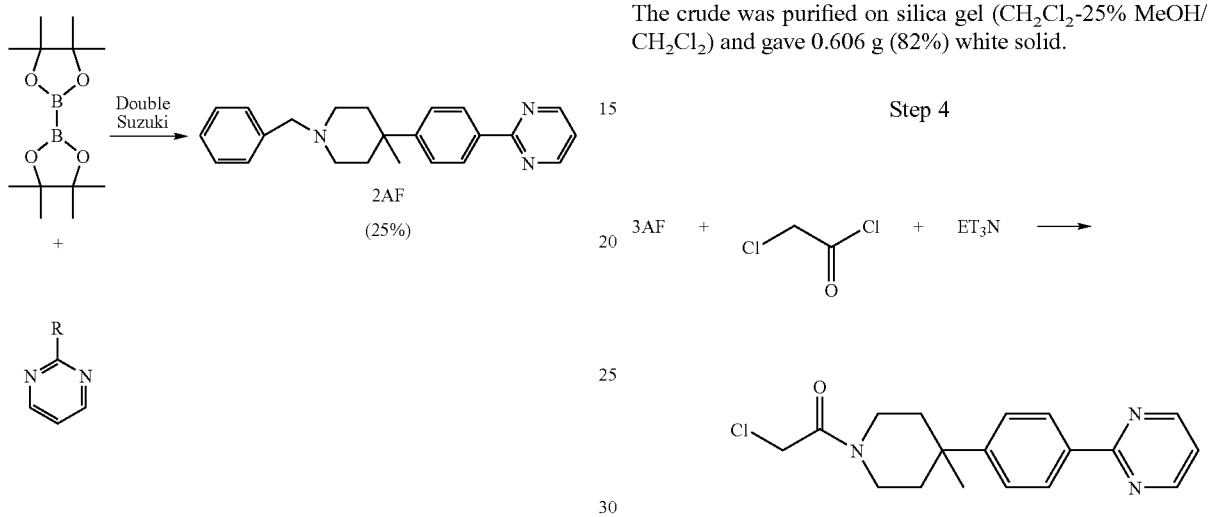

To a solution of 4.43 g (12.87 m.mole) of 1AF in 100 ml anhy. DMSO were added 4.903 g (19.31 m.mole) of Bis(pinacolato)diboron, 3.784 g (38.61 m.mole) of Potassium acetate and 1.051 g (1.287 m.mole) of Pd(dppf)Cl$_2$ at r.t. under dry N$_2$ gas. The contents were degassed couple of times with N$_2$ gas and stirred at 100° C. for 2 hrs. The mixture was allowed to cool to r.t. and 50 ml of water was added followed by 2.455 g (15.44 m.mole) of 2-Bromopyrimidine, 8.894 g (64.35 m.mole) of Potassium carbonate and 1.49 g (1.29 m.mole) of Tetrakis(triphenylphosphine)palladium. The contents were degassed couple of times with N2 gas and stirred at 100 C for 2 hrs. The mixture was allowed to cool to r.t. 100 ml of water and 100 ml of EtOAc were added to the reaction mixture and filtered through pad of celite and washed with EtOAc. The contents were transferred to separatory funnel and the organic phase was separated and the aqueous phase was extracted with EtOAC. The organic phases were combined and washed with water and dried over MgSO4. The solvent was evaporated to dryness and dark brown gum was purified on silica gel (Hexane-25% EtOAC/Hexane), gave 1.00 off white solid.

Step 3

1.00 g (2.9 m.mole) of 2AF was in 20 ml anhy. dichloromethane at r.t. under dry N$_2$ gas. To this solution 0.178 g (0.83 m.mole) Proton Sponge was added at r.t. followed by dropwise addition of 0.713 g (4.99 m.mole) of 2-Chloroethyl chloroformate. The reaction mixture was stirred at r.t. under dry N$_2$ gas for 4 hrs. The mixture was evaporated to dryness and dried under high vacuum for 15 minutes. The resulting residue was dissolved in 20 ml anhy. MeOH under dry N$_2$ gas and was stirred under reflux under dry N$_2$ gas for 4 hrs. The mixture was allowed to cool to r.t. and evaporated to dryness. The crude was purified on silica gel (CH$_2$Cl$_2$-25% MeOH/CH$_2$Cl$_2$) and gave 0.606 g (82%) white solid.

Step 4

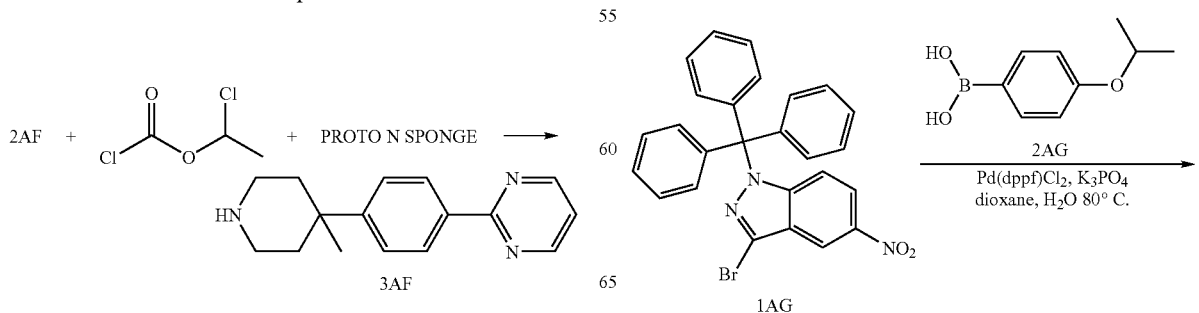

To a stirred solution of 0.60 g (2.37 m.mole) of 3AF in 15 ml anhy. Dichloromethane 1.2 (11.85 m.mole) of Triethylamine was added at r.t. under dry N$_2$ gas. The mixture was cooled to ice-water bath and 0.321 g (2.84 m.mole) of Chloroacetylchloride was added dropwise at 0° C. dry N$_2$ gas. the mixture was stirred at 0° C. for half an hr. 25 ml of CH$_2$Cl$_2$ and aqueous saturate (NaHCO$_3$ solution were added at 0° C. The contents were transferred to separatory funnel and s well. The organic phase was separated, dried over MgSO$_4$ and evaporated to dryness, gave bro solid. This solid was used without purification for subsequent reaction.

Preparation 56

Preparation of 3-(4-isopropoxyphenyl)-1-trityl-1H-indazol-5-amine

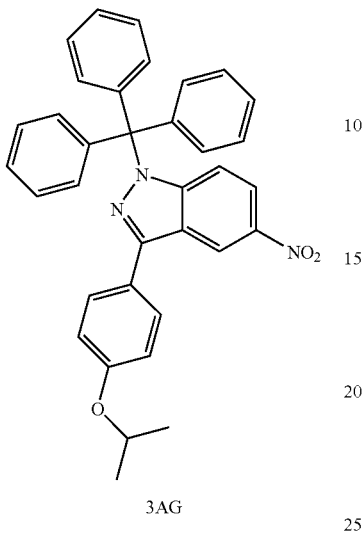

3AG

In a Sealed tube containing 1AG (1.21 g, 2.50 mmol), 2AG (0.67 g, 3.75 mmol), Pd(dppf)Cl₂ (0.21 g, 0.25 mmol) and K₃PO₄ (1.31 g, 6.25 mmol) was added dioxane (25 mL) and water (12 mL) and degassed under nitrogen atmosphere three times. This reaction mixture was stirred at 80° C. for 18 hours. The reaction mixture was diluted with water and EtOAc, then filtered through Celite. The organic layer was washed with water, dried over MgSO₄, filtered and rotovap to dryness. The crude was chromat. (Biotage, 40 L, 5% EtOAc/hexane) to give 3AG (0.68 g, 50.4%), PMR (CDCl₃)

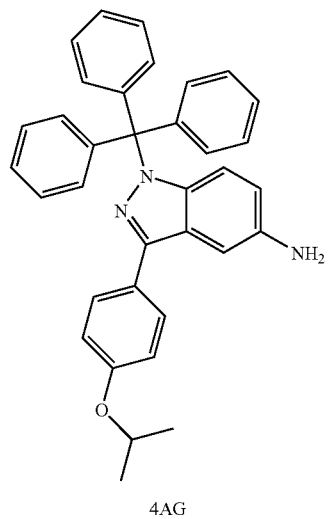

4AG

In a RB compound 3AG (0.6 g, 1.11 mmol) stirred in a mixture of MeOH and EtOAc (10 mL each) was added 0.2 g of Pd/C (10%, 50% water). The reaction mixture was degassed under hydrogen atmosphere (balloon) and stirred overnight. MS of the reaction mixture showed (M+H) at 510. The reaction mixture was filtered (Celite) and rotovap. to dryness to give a crude 4AG, used as is for next reaction.

Example 621

1-[2-(3-Methyl-5'-pyrimidin-2-yl-2,3,5,6-tetrahydro-[1,2']bipyrazinyl-4-yl)-2-oxo-ethyl]-pyrrolidine-3-carboxylic acid [3-(4-fluoro-phenyl)-1H-indazol-5-yl]-amide

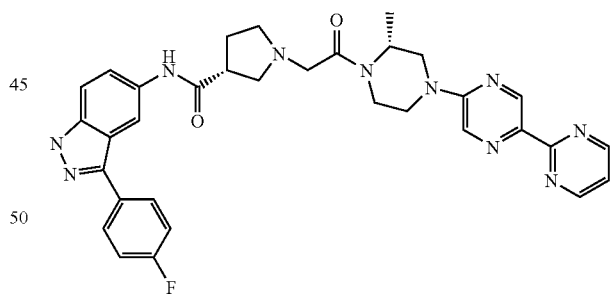

Step 1: 5'-Iodo-3-methyl-3,4,5,6-tetrahydro-2H-[1,2']bipyrazinyl (1)

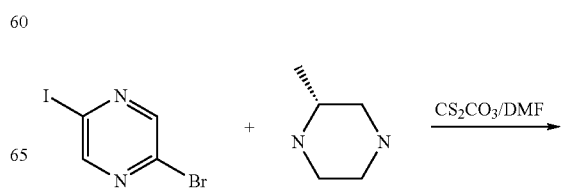

-continued

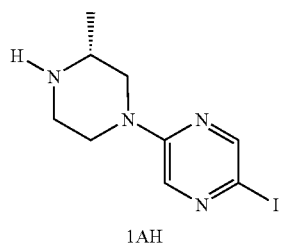

1AH

A mixture of 2-bromo-5-iodopyrazine (200 mg, 0.704 mmol), cesium carbonate (400 mg, 1.23 mmol) and 2R methyl piperazine (85 mg, 0.85 mmol) in DMF (10 ml) was stirred at 100° C. overnight. The reaction was cooled and solvent evaporated. Water (100 ml) was added and insoluble solid was filtered, then dissolved in MeCl$_2$ (100 ml), dried over Na$_2$SO$_4$, filtered and solvent evaporated yielding product (205 mg, 95%) Mass Spec (MH, 305)

Step 2: 3-Methyl-5'-pyrimidin-2-yl-3,4,5,6-tetrahydro-2H-[1,2']bipyrazinyl (2)

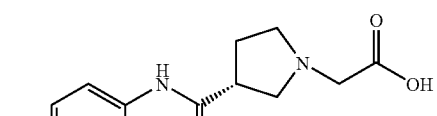

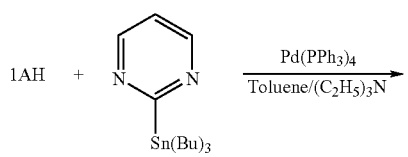

2AH

Added Pd(PPh$_3$)$_4$ (30 mg, 0.025 mmol) to a mixture of 5'-Iodo-3-methyl-3,4,5,6-tetrahydro-2H-[1,2']bipyrazinyl (1AH) (50 mg, 0.164 mmol), 2-tributyl stannyl pyrimidine (0.2 ml), triethylamine (0.2 ml, 1.43 mmol) in toluene (3 ml) at room temperature then stirred at 100° C. for 5 hours. The reaction was cooled, diluted with EtOAc (50 ml) and water (20 ml). The organic layer was separated, dried (Na$_2$SO$_4$) filtered and solvent evaporated. The residue was purified on Prep TLC eluting with 10% MeOH:MeCl$_2$:NH$_4$OH yielding product (10 mg, 24%) Mass Spec MH 256

Step 3: 1-[2-(3-Methyl-5'-pyrimidin-2-yl-2,3,5,6-tetrahydro-[1,2']bipyrazinyl-4-yl)-2-oxo-ethyl]-pyrrolidine-3-carboxylic acid [3-(4-fluoro-phenyl)-1H-indazol-5-yl]-amide

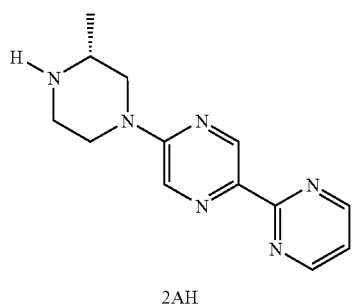

2AH

A mixture of the acid (20 mg, 0.044 mmol); 3-Methyl-5'-pyrimidin-2-yl-3,4,5,6-tetrahydro-2H-[1,2']bipyrazinyl (2AH) (10 mg, 0.039 mmol) EDCl (10 mg, 0.052 mmol); HOBT (7 mg, 0.052 mmol) and NMM (0.1 ml) was stirred in DMF (3 ml) at room temperature overnight. The reaction was diluted with EtOAc (20 ml) and water (10 ml) and organic layer separated. The organics were washed with brine (10 ml) dried over Na$_2$SO$_4$ filtered and solvent evaporated yielding a residue which purified on silica gel eluting with 10% MeOH; MeCl$_2$; NH$_4$OH yielding title product as a solid (10 mg, 31%) Mass Spec (MH, 621)

Preparation 57

2-[6-(3-R-Methyl-piperazin-1-yl)-pyridin-3-yl]-pyrimidine

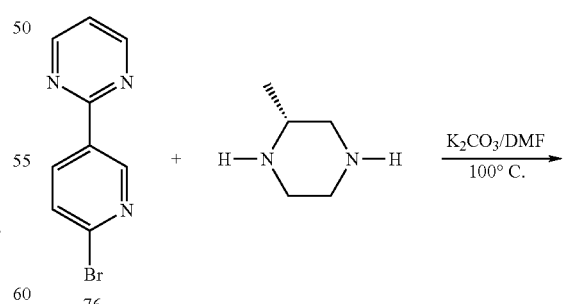

76

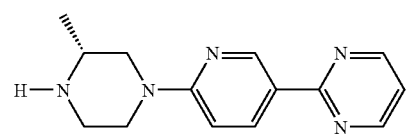

Following the procedure described in Example 98 Step 7, but substituting an equivalent quantity of 2-R-Methyl piperazine for piperazine, the title compound is obtained as a white solid (ESMS MH, 256) 95% Yield.

Preparation 58

Step 1: Preparation of 1-N-Trityl-3-(6-Fluoro-pyridin-3-yl)-1-methyl-5-nitro-1H-indazole

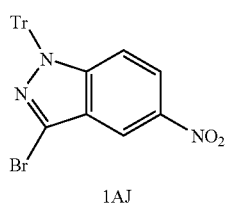
1AJ

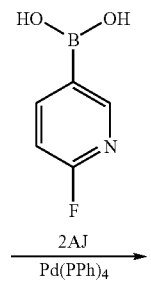
2AJ

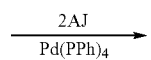
Pd(PPh₃)₄

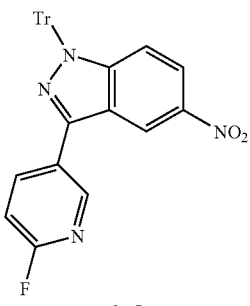
3AJ

A mixture of compound 1AJ (8 g, 16.53 mmol), compound 2AJ (2.33 g, 16.53 mmol), Pd(PPh₃)₄ (1.9 g, 1.653 mmol) and 1:1 dioxane/Na₂CO₃ (2M) (60 ml) was degassed for 15 min. Then it was heated at 120° C. for overnight. Cooled down to room temperature and diluted with DCM (300 ml). The organic layer was washed with water (200 ml), dried over Na₂SO₄, filtered and concentrated. The residue was purified by Biotage to give the desired product 3AJ (6 g, 58%).

Step 2: Preparation of 1-N-Trityl-3-(6-Fluoro-pyridin-3-yl)-1-methyl-5-amino-1H-indazole

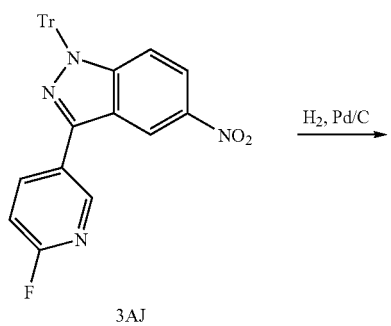
3AJ

H₂, Pd/C

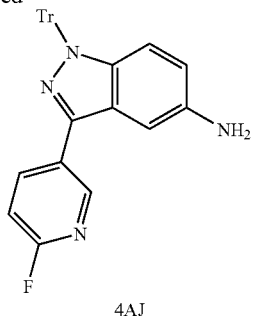
4AJ

A mixture of compound 3AJ (6 g) and Pd/C (10%, 200 mg) in EtOAc (200 ml) was stirred for overnight. Filtered and concentrated. The residue was purified by Biotage to give the desired product 4AJ (5 g, 83%).

Preparation 59

Step 1: 2-Pyrazol-1-yl-pyrimidine

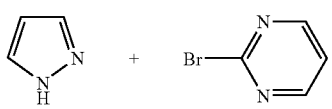

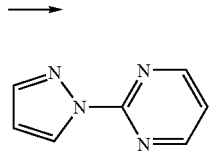

A reaction mixture containing pyrazole (2 g, 29 mmol), 2-bromopyrimidine (3.8 g, 24 mmol), copper (I) iodide (0.91 g, 4.8 mmol) and 1,10-phenanthroline (1.7 g, 9.6 mmol) in DMA was heated at 140° C. in a sealed tube for 6 hours. After the reaction, ethyl acetate (30 mL) was added, followed by water. The aqueous layer was extract three times (20 mL) and the organic layer was collected, dry over sodium sulfate. After concentration under vacuum, the crude product was purified using column chromatography (10% ethyl acetate in dichloromethane) to give 0.55 g of pure product. 15% yield. MS (ESMS, M+H 146).

Step 2: 2-(4-Bromo-pyrazol-1-yl)-pyrimidine

To a solution of 2-pyrazol-1-yl-pyrimidine (0.55 g, 3.7 mmol) in acetic acid (5 mL) was added bromine (1.2 g, 7.5 mmol) in acetic acid (3 mL) dropwisely. After addition, the reaction mixture was stirred at room temperature overnight. After removed the acetic acid, the crude product was purified using column chromatography (2% methanol in dichloromethane) to give 0.7 g of pure product in 85% yield. MS (ESMS, M+H 225).

Step 3: 2-[4-(1,2,3,6-Tetrahydro-pyridin-4-yl)-pyrazol-1-yl]-pyrimidine

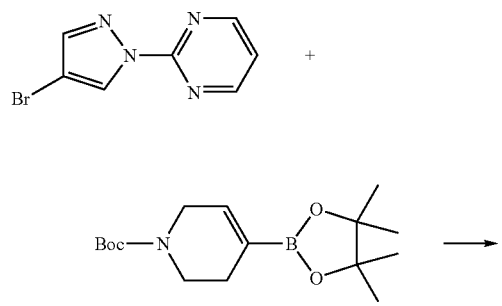

A solution containing 2-(4-bromo-pyrazol-1-yl)-pyrimidine (300 mg, 1.34 mmol), 4-(4,4,5,5-tetramethyl-[1,3,2]dioxaborolan-2-yl)-3,6-dihydro-2H-pyridine-1-carboxylic acid tert-butyl ester (280 mg, 1.34 mmol), PdCl₂(dppf) (95 mg, 0.13 mmol) and potassium phosphate (800 mg, 4 mmol) in dioxane was heated at 80° C. under argon for overnight. After removed the solvent, ethylacetate was added and the mixture was filtered, washed with water. After concentration under vacuum, it was found the product was hard to separated from impurity and the crude product was treated with 90% of TFA for 20 min and TFA was removed under vacuum. The crude product was then purified using prep HPLC to give desired product as TFA salt (120 mg, 0.37 mmol) in 27% overall yield. MS (ESMS, M+H 228)

Preparation 60

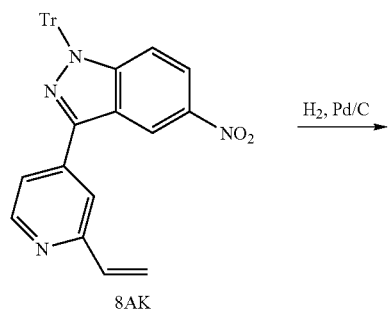

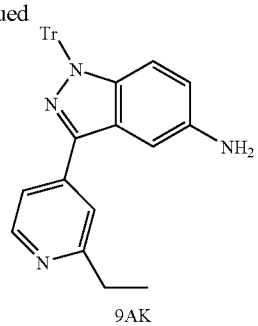

A mixture of compound 8AK (5 g) and Pd/C (10%, 200 mg) in EtOAc (200 ml) was stirred for overnight. Filtered and concentrated. The residue was purified by Biotage to give the desired product 9AK (4.6 g, 92%).

Preparation 61

Step 1

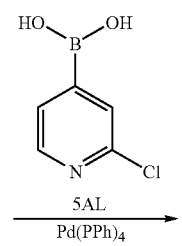

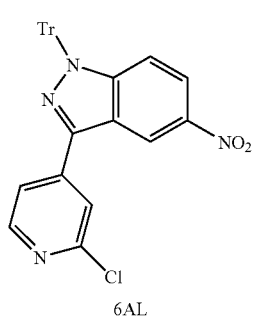

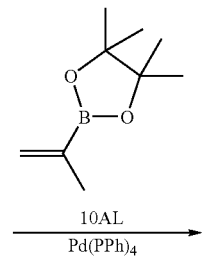

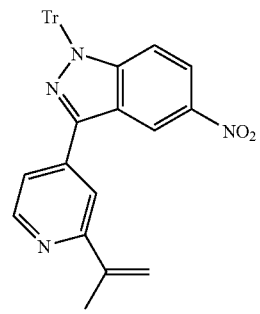

635

A mixture of compound 1AL (10 g, 20.66 mmol), compound 5AL (3.23 g, 20.66 mmol), Pd(PPh₃)₄ (2.3 g, 2 mmol) and 1:1 dioxane/Na₂CO₃ (2M) (70 ml) was degassed for 15 min. Then it was heated at 120° C. for overnight. Cooled down to room temperature and added compound 10AL (3.47 g, 20.66 mmol), then heated at 120° C. for overnight. Cooled down to room temperature and diluted with DCM (400 ml). The organic layer was washed with water (250 ml), dried over Na₂SO₄, filtered and concentrated. The residue was purified by Biotage to give the desired product 11AL (6 g, 50%).

Step 2

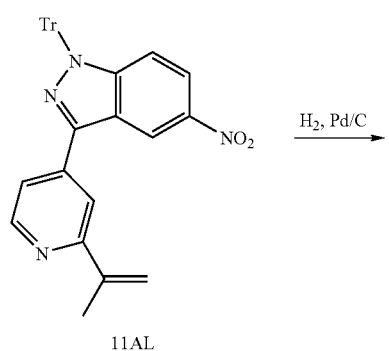

11AL

H₂, Pd/C →

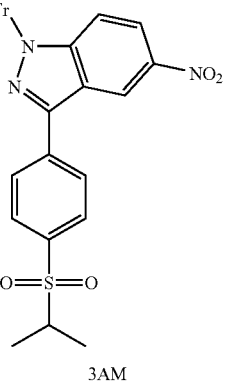

12AL

A mixture of compound 11AL (6 g) and Pd/C (10%, 200 mg) in EtOAc (200 ml) was stirred for overnight. Filtered and concentrated. The residue was purified by Biotage to give the desired product 12AL (5 g, 83%).

Preparation 62

Step 1

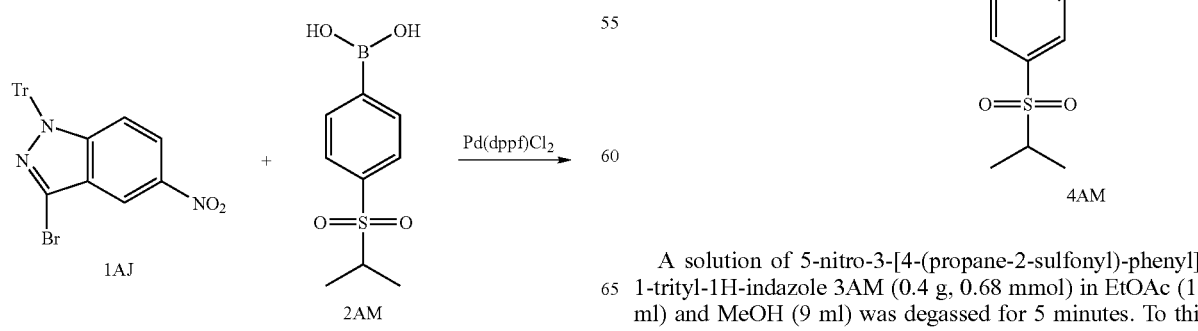

1AJ + 2AM  Pd(dppf)Cl₂ →

636

-continued

3AM

A mixture of 3-bromo-5-nitro-1-trityl-1H-indazole 1AJ (0.43 g, 0.9 mmol), 4-(propane-2-sulfonyl)-phenyl boronic acid 2AM (0.3 g, 1.35 mmol), potassium carbonate (0.38 g, 2.7 mmol), Pd(dppf)Cl₂ (0.07 g, 0.09 mmol) and 4/1/dioxane/water (5 ml) was degassed for 5 minutes. Then it was heated at 80° C. for overnight. Cooled to room temperature and diluted with EtOAc (60 ml). The organic layer was washed with water (20 ml), dried over MgSO₄, filtered and concentrated. The residue was purified on silica gel eluting with 1/2 EtOAc/Hexane to give the desired product 3AM (0.4 g, 76%).

Step 2

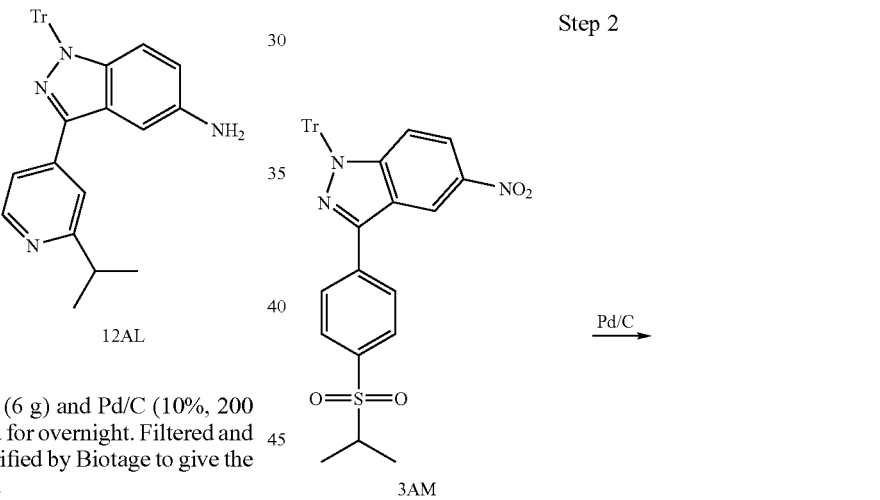

3AM   Pd/C →

4AM

A solution of 5-nitro-3-[4-(propane-2-sulfonyl)-phenyl]-1-trityl-1H-indazole 3AM (0.4 g, 0.68 mmol) in EtOAc (18 ml) and MeOH (9 ml) was degassed for 5 minutes. To this solution 10% Pd/C (38 mg) was added. After stirring for overnight at 40° C., it was cooled and filtered on a celite pad. The filtrate was concentrated to give the desired product 4AM (0.36 g, 99%).

Preparation 63

Step 1

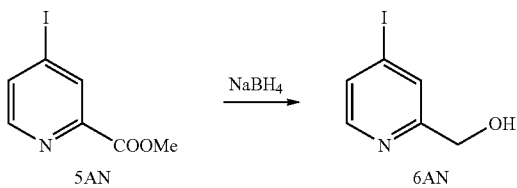 [SMILES: COC(=O)c1cc(I)ccn1 ; "NaBH4" ; OCc1cc(I)ccn1]

To a solution of methyl 4-iodopicolinate 5AN (2.83 g, 10.78 mmol) in MeOH (30 ml) was added NaBH$_4$ (1.59 g, 43.12 mmol) portion wise at 0° C. Reaction mixture was allowed to warm up to r.t. After stirring for 3 days at r.t, it was quenched with, 14 ml of 1N NaOH. Reaction mixture was diluted with DCM (200 ml). The organic layer was washed with water (2×30 ml), dried over MgSO$_4$, filtered and concentrated. The residue was purified on silica gel eluting with 3/1 EtOAc/Hexane to give the desired product (4-iodo-pyridin-2-yl)-methanol 6AN (2.27 g, 90%).

Step 2

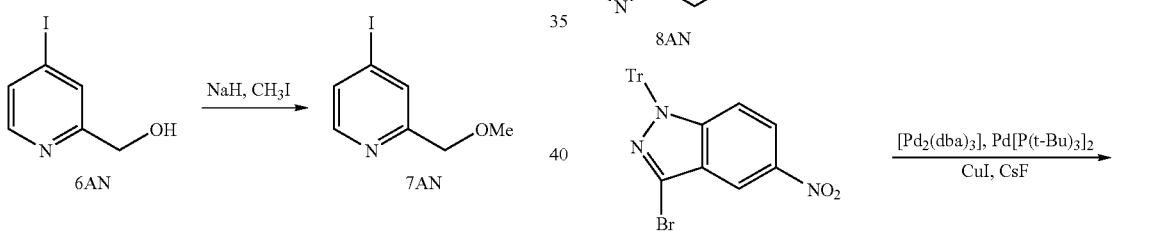

A solution of (4-iodo-pyridin-2-yl)-methanol 6AN (0.51 g, 2.16 mmol) in THF (7.5 ml) was added in a dry NaH (0.17 g, 4.32 mmol). Reaction mixture was stirred for 20 min at r.t. It was cooled to 0° C. and CH$_3$I 0.16 ml, 2.59 mmol) was added drop wise. After 30 mins at 0° C., it was warmed up to r.t. and stirred further for 2 hr. Then it was diluted with EtOAc (50 ml) and washed with water (2×10 ml) and brine (1×15 ml). Organic extracts were dried over MgSO$_4$, filtered and concentrated. The residue was purified on silica gel eluting with 1/2 EtOAc/Hexane to give the desired product 4-Iodo-2-methoxymethyl-pyridine 7AN (0.39, 72%).

Step 3

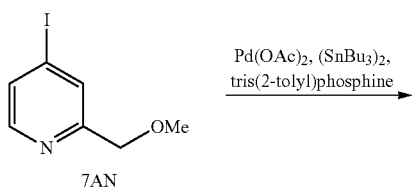

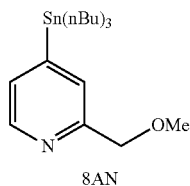

To a mixture of 4-iodo-2-methoxymethyl-pyridine 7AN (0.22 g, 0.89 mmol), Pd(OAc)$_2$ (9 mg, 0.04 mmol) and tris(2-tolyl)phosphine (72 mg, 0.23 mmol) in ACN (7 ml) was added TEA (0.27 ml, 1.78 mmol) and bis(tributyltin) (0.53 ml, 1.07 mmol). It was degassed for 5 minutes. Then it was heated at 85° C. for 2 hr. Cooled to room temperature and diluted with EtOAc (50 ml). The organic layer was washed with water (15 ml), dried over MgSO$_4$, filtered on a celite pad and concentrated. The residue was purified on silica gel eluting with 1/2 EtOAc/Hexane to give the desired product 2-methoxymethyl-4-tributylstannanyl-pyridine 8AN (0.36 g, 80%).

Step 4

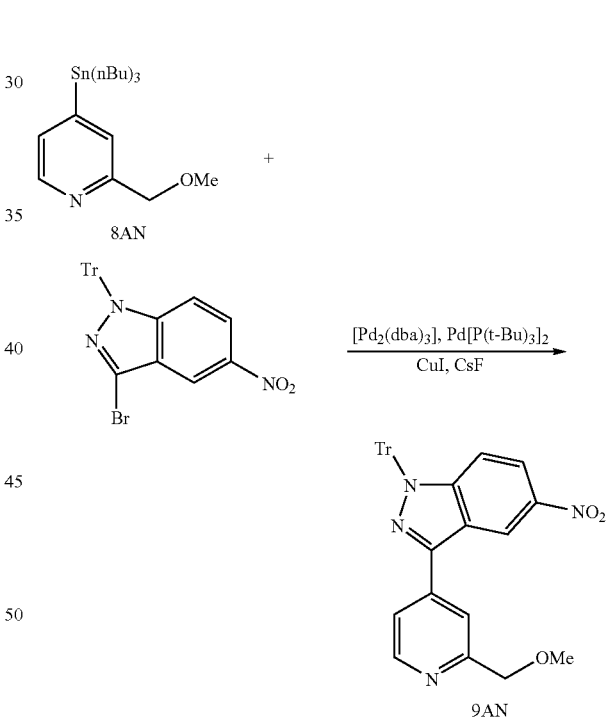

A mixture of 2-methoxymethyl-4-tributylstannanyl-pyridine 8AN (0.1 g, 0.24 mmol), 3-bromo-5-nitro-1-trityl-1H-indazole 1AJ (0.12 g, 0.24 mmol), CsF (0.08 g, 0.53 mmol), [Pd$_2$(dba)$_3$] (5 mg, 0.005 mmol), Pd[P(t-Bu)$_3$]$_2$, and CuI (4 mg, 0.024 mmol) in DMF (2 ml) was degassed for 5 minutes. Then it was heated at 120° C. for two hours. Cooled to room temperature and diluted with EtOAc (10 ml). It was then filtered on a celite pad. Filtrate was washed with water (3 ml) and the organic extracts were dried over MgSO$_4$. It was filtered again on a celite pad and concentrated. The residue was purified on silica gel eluting with 2/1 EtOAc/Hexane to give the desired product 3-(2-methoxymethyl-pyridin-4-yl)-5-nitro-1-trityl-1H-indazole 9AN (0.095 g, 76%).

Step 5

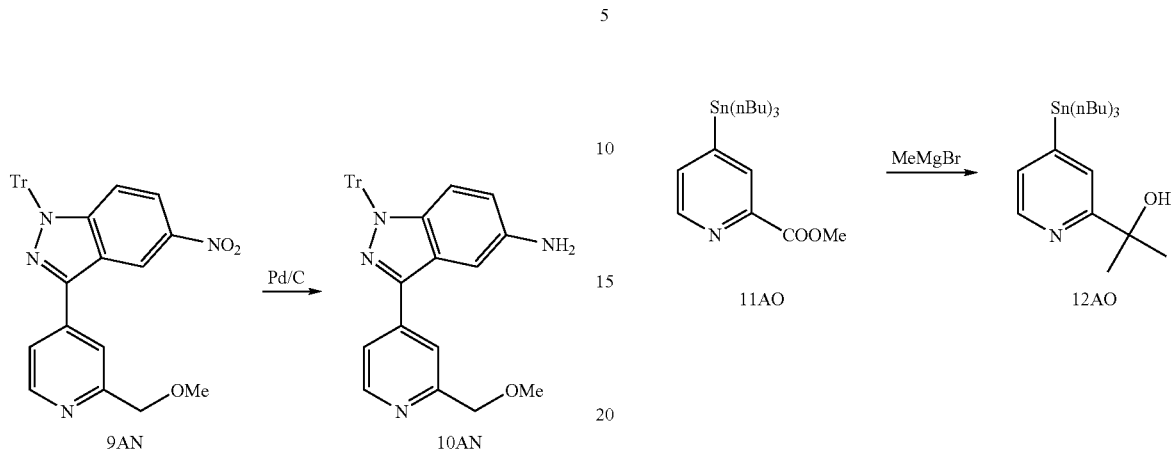

A solution of 3-(2-methoxymethyl-pyridin-4-yl)-5-nitro-1-trityl-1H-indazole 9AN (0.095 g 0.18 mmol) in EtOAc (5 ml) was degassed for 5 minutes. To this solution 10% Pd/C (20 mg) was added. After stirring for overnight at r.t, it was cooled and filtered on a celite pad. The filtrate was concentrated to give the desired product 3-(2-methoxymethyl-pyridin-4-yl)-1-trityl-1H-indazol-5-ylamine 10AN (0.086 g, 96%).

Preparation 64

Step 1

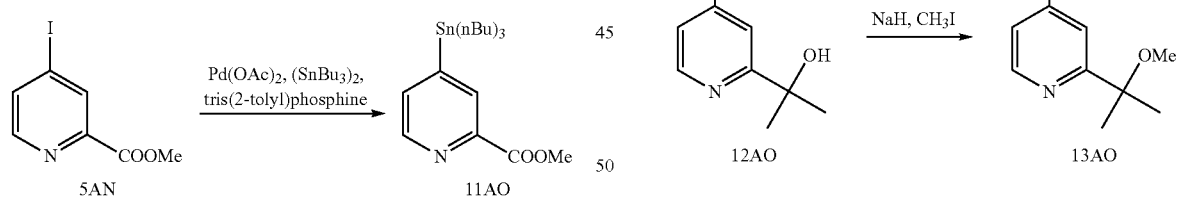

To a mixture of methyl 4-iodopicolinate 5AN (2.6 g, 9.89 mmol), Pd(OAc)$_2$ (0.1 g, 0.45 mmol) and tris(2-tolyl)phosphine (0.79 g, 2.58 mmol) in ACN (20 ml) was added TEA (2.8 ml, 19.89 mmol) and bis(tributyltin) (6 ml, 11.93 mmol). It was degassed for 5 minutes. Then it was heated at 85° C. for 2 hr. Cooled to room temperature and diluted with EtOAc (200 ml). The organic layer was washed with water (50 ml), dried over MgSO$_4$, filtered on a celite pad and concentrated. The residue was purified on silica gel eluting with 1/2 EtOAc/Hexane to give the desired product 4-tributylstannanyl-pyridine-2-carboxylic acid methyl ester 11AO (3.48 g, 82%).

Step 2

In a solution of 4-tributylstannanyl-pyridine-2-carboxylic acid methyl ester 11AO (0.34 g, 0.8 mmol) in THF (7 ml) at −78° C. was added MeMgBr (1.15 ml, 1.6 mmol, 1.4M in toluene/THF) drop wise. It was stirred at −78° C. for 30 mins. Reaction mixture was warmed up to r.t. After 1.5 hr, it was cooled again to 0° C. and quenched with 5 ml of saturated. NH$_4$Cl. Organic extracts were washed with water (3 ml) and brine (3 ml) and dried over MgSO$_4$. The residue was purified on silica gel eluting with 1/2 EtOAc/Hexane to give the desired product 2-(4-tributylstannanyl-pyridin-2-yl)-propan-2-ol 12AO (012 g, 77%).

Step 3

A solution of 2-(4-tributylstannanyl-pyridin-2-yl)-propan-2-ol 12AO (0.12 g, 0.27 mmol) in THF (2 ml) was added in a dry NaH (0.02 g, 0.54 mmol). Reaction mixture was stirred for 20 min at r.t. It was cooled to 0° C. and CH$_3$I (0.02 ml, 0.32 mmol) was added drop wise. After 30 mins at 0° C., reaction mixture was warmed up to r.t. It was diluted with EtOAc (15 ml) after 2 hr and washed with water (2×3 ml) and brine (5 ml). Organic extracts were dried over MgSO$_4$, filtered and concentrated. The residue was purified on silica gel eluting with 1/4 EtOAc/Hexane to give the desired product 2-(1-methoxy-1-methyl-ethyl)-4-tributylstannanyl-pyridine 13AO (0.1 g, 88%).

Step 4

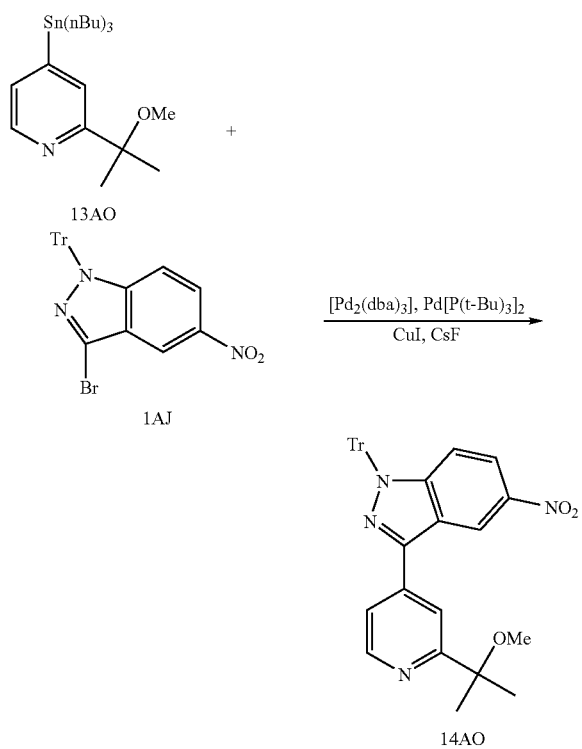

2-(1-methoxy-1-methyl-ethyl)-4-tributylstannanyl-pyridine 13AO (0.1 g, 0.24 mmol), 3-bromo-5-nitro-1-trityl-1H-indazole 1AJ (0.12 g, 0.24 mmol), CsF (0.08 g, 0.53 mmol), [Pd$_2$(dba)$_3$] (5 mg, 0.005 mmol), Pd[P(t-Bu)$_3$]$_2$, and CuI (4 mg, 0.024 mmol) in DMF (2 ml) was degassed for 5 minutes. Then it was heated at 120° C. for two hours. Cooled to room temperature and diluted with EtOAc (10 ml). It was then filtered on a celite pad. Filtrate was washed with water (3 ml) and the organic extracts were dried over MgSO$_4$. It was filtered again on a celite pad and concentrated. The residue was purified on silica gel eluting with 1/3 EtOAc/Hexane to give the desired product 3-[2-(1-methoxy-1-methyl-ethyl)-pyridin-4-yl]-5-nitro-1-trityl-1H-indazole 14AO (0.05 g, 39%).

Step 5

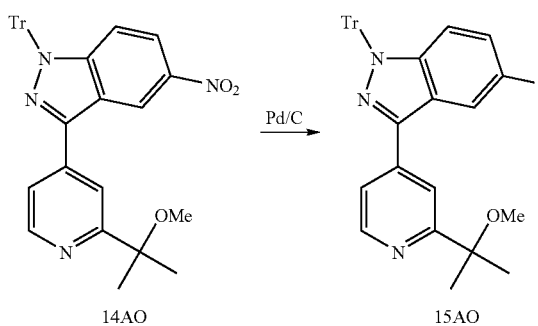

A solution of 33-[2-(1-methoxy-1-methyl-ethyl)-pyridin-4-yl]-5-nitro-1-trityl-1H-indazole 14AO (0.05 g, 0.09 mmol) in EtOAc (5 ml) was degassed for 5 minutes. To this solution 10% Pd/C (10 mg) was added. After stirring for overnight at r.t, it was cooled and filtered on a celite pad. The filtrate was concentrated to give the desired product 3-[2-(1-methoxy-1-methyl-ethyl)-pyridin-4-yl]-1-trityl-1H-indazole-5-ylamine 15AO (0.046 g, 97%).

Procedure 65

Step 1

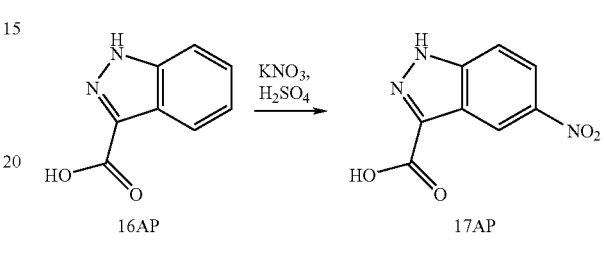

To a suspension of indazole-3-carboxylic acid 16AP (10.5 g, 64.8 mmol) in concentrated sulfuric acid (125 ml) at 0° C. was added KNO$_3$ (64.8 mmol, 6.55 g). The reaction mixture was warmed up to r.t. After stirring for 4 hr at r.t, it was poured into a 525 ml of ice/water. Solid was collected by filtration and washed with water to give desired 5-nitro-1H-indazole-3-carboxylic acid 17AP (10.74 g, 80%).

Step 2

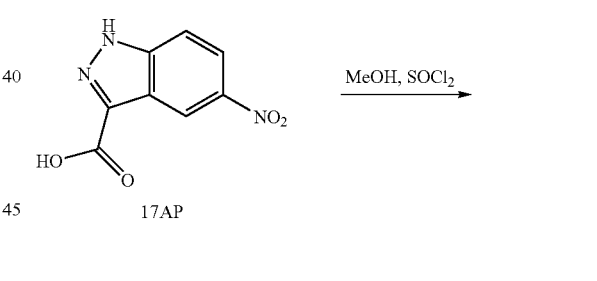

To a suspension of 5-nitro-1H-indazole-3-carboxylic acid 17AP (10.74 g, 51.88 mmol) in MeOH (145 ml) at 0° C. was added SOCl$_2$ (35 ml) dropwise. After stirring for 10 min at 0° C., the reaction mixture was refluxed overnight. HCl gas was evolved (Condenser was equipped with empty balloon to trap HCl). It was then cooled to room temperature, solid was collected by filtration and washed with MeOH to give desired 5-nitro-1H-indazole-3-carboxylic acid methyl ester 18AP (7 g, 61%).

Step 3

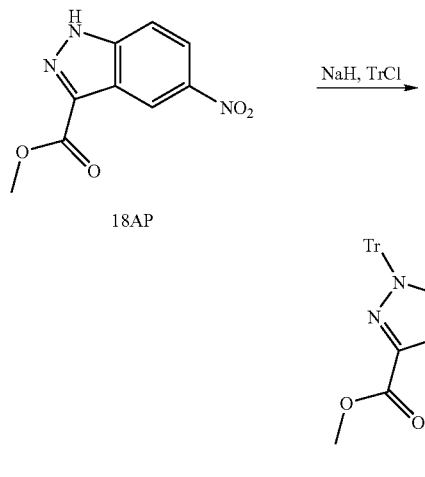

Suspension of 5-nitro-1H-indazole-3-carboxylic acid methyl ester 18AP (7 g, 31.67 mmol) in THF (130 ml) and DCM (15 ml) was added to a NaH (60% in Mineral Oil, 1.61 g, 41.17 mmol) at 0° C. H₂ gas was evolved. Chlorotriphenyl methane (8.83 g, 31.67 mmol) was added after stirring for 20 min at 0° C. Reaction mixture was subjected to heat at 60° C. for overnight. It was then cooled to room temperature and concentrated under reduced pressure. Solid was redissolved in DCM and filtered. Filtrate was concentrated under reduced pressure to give desired 5-nitro-1-trityl-1H-indazole-3-carboxylic acid methyl ester 19AP (12.95 g, 88%).

Step 4

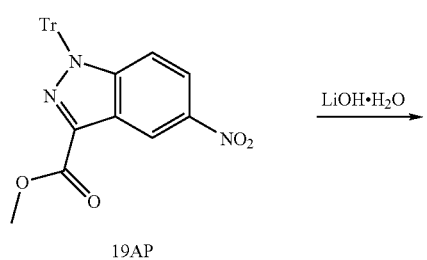

To a solution of 5-nitro-1-trityl-1H-indazole-3-carboxylic acid methyl ester 19AP (12.95 g, 27.96 mmol) in THF (270 ml) and H₂O (135 ml) was added LiOH.H₂O (2.34 g, 55.92 mmol) at room temperature. After stirring for overnight at room temperature, it was cooled to 0° C. and acidified with slow addition of 1N HCl (55.9 ml, 55.92 mmol). Reaction mixture was concentrated under reduced pressure. Solid was collected by filtration and washed with water to give desired 5-nitro-1-trityl-1H-indazole-3-carboxylic acid 2AP (12.06 g, 96%).

Step 5

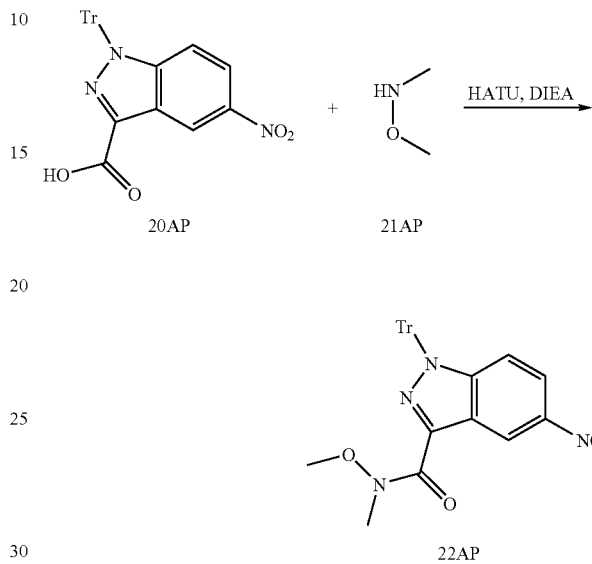

5-nitro-1-trityl-1H-indazole-3-carboxylic acid 20AP (12.06 g, 26.85 mmol) and HATU (10.2 g, 26.85 mmol) was dissolved in DMF (100 ml). After stirring for 10 min at room temperature, N,O-dimethylhydroxylamine hydrochloride 21AP (2.62 g, 26.85 mmol) and DIEA (14.1 ml, 80.55 mmol) was added. It was stirred further for 1 hr at room temperature. Reaction mixture was poured into 300 ml of water. Solid was collected by filtration. This solid was redissolved in EtOAc (300 ml) and 75 ml of sat. NaHCO₃ was added. Organic fraction was washed with water (2×75 ml), brine (75 ml) and dried over MgSO₄. Solvent was removed under reduced pressure to give desired 5-nitro-1-trityl-1H-indazole-3-carboxylic acid methoxy-methyl-amide 22AP (12.56 g, 95%).

Step 6

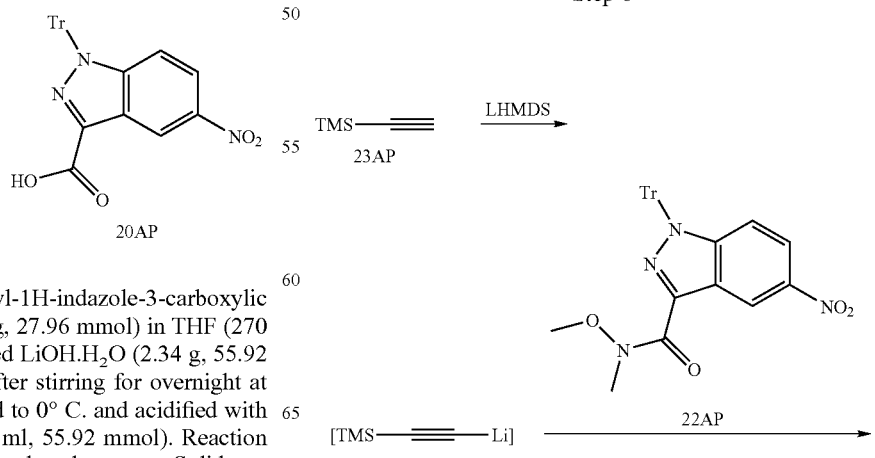

-continued

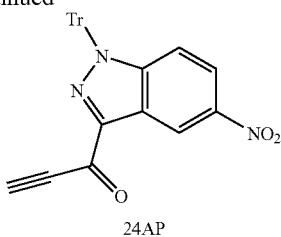

24AP

To a cold (−20° C.) solution of TMS-acetylene 23AP (5.5 ml, 38.28 mmol) in toluene (23 ml) was added LHMDS (33.2 ml, 1M in THF, 33.2 mmol) dropwise over 5 min keeping T<−5° C. The mixture was stirred at 0° C. for 30 min, then transferred to the cold, (−10° C.) reaction mixture that contains 5-nitro-1-trityl-1H-indazole-3-carboxylic acid methoxy-methyl-amide 22AP (12.56 g, 25.52 mmol) in THF (120 ml) at a rate that kept T<−5° C. The resulting mixture was stirred for 20 min at −5° C. then 1.5 hr at room temperature. Reaction mixture was cooled to 0° C. and quenched by a slow addition of 1N HCl (40 ml) under N$_2$. It was stirred further for 5 min. Reaction mixture was diluted with EtOAc (500 ml). The organic fraction was separated and washed with water (2×100 ml) and brine (1×125 ml). It was dried over MgSO$_4$, filtered and concentrated. The residue was purified on silica gel eluting with 2/1 EtOAc/Hexane to give the desired 1-(5-nitro-1-trityl-1H-indazol-3-yl-)-propynone 24AP (6.99 g, 60%).

Step 7

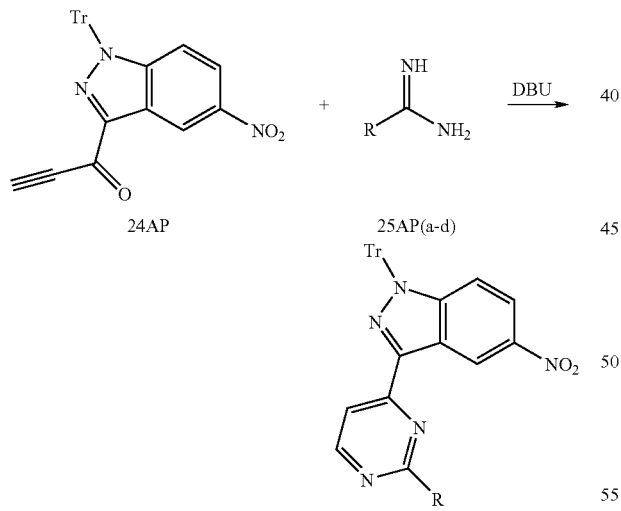

a. R = methyl (60%)
b. R = ethyl (58%)
c. R = Isopropyl (54%)
d. R = t-butyl (43%)

A mixture of 1-(5-nitro-1-trityl-1H-indazol-3-yl-)-propynone 24AP (0.5 g, 1.09 mmol), amidine hydrochloride 25AP (1.75 mmol) and DBU (1.6 ml, 10.9 mmol) in acetonitrile (10 ml) was heated at 120° C. for 50 minutes under microwave. It was then cooled to room temperature and diluted with DCM (60 ml). The organic layer was washed with water (10 ml), dried over MgSO$_4$, filtered and concentrated. The residue was purified on silica gel eluting with 1/1 EtOAc/Hexane to give the desired product 26AP.

Step 8

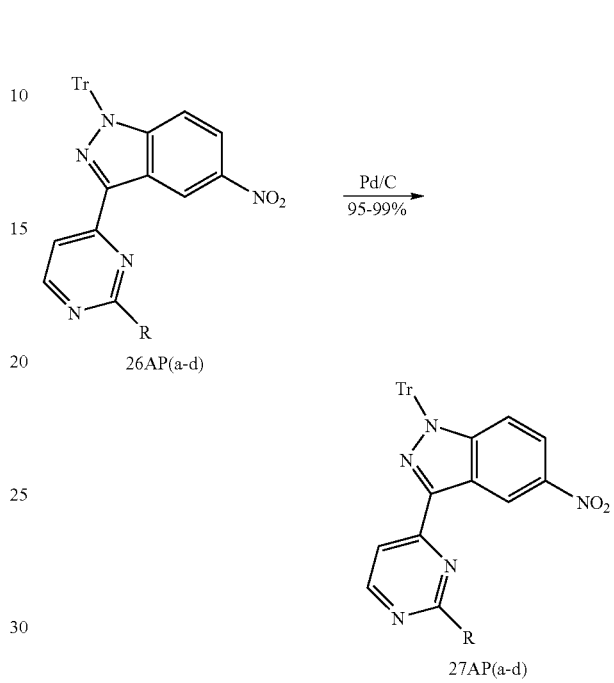

a. R = methyl
b. R = ethyl
c. R = Isopropyl
d. R = t-butyl

A solution of 26AP (0.96 mmol) in EtOAc (20 ml) and MeOH (5 ml) was degassed for 5 minutes. To this solution 10% Pd/C (0.08 g) was added. After stirring for overnight at 40° C., it was cooled and filtered on a celite pad. The filtrate was concentrated to give the desired 27AP.

Preparation 66

Preparation of 4-(2,5-Difluoro-4-pyrimidin-2-yl-phenyl)-3,6-dihydro-2H-pyridine-1-carboxylic acid tert-butyl ester (Compound 12AQ)

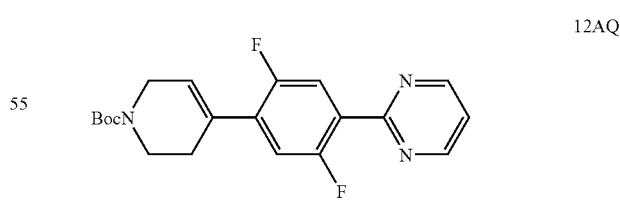

12AQ

The Compound 12AQ was prepared from 4-(4,4,5,5-tetramethyl-[1,3,2]dioxaborolan-2-yl)-3,6-dihydro-2H-pyridine-1-carboxylic acid tert-butyl ester using the procedure as described for the preparation of Compound 4-(2-fluoro-4-pyrimidin-2-yl-phenyl)-3,6-dihydro-2H-pyridine-1-carboxylic acid tert-butyl ester but using 1,4-dibromo-2,5-difluoro-benzene in place of 4-bromo-2-fluoro-1-iodobenzene.

Example 622

Preparation of 1-(2-{4-[4-(5-Ethylamino-[1,3,4]oxadiazol-2-yl)-2-fluoro-phenyl]-3,6-dihydro-2H-pyridin-1-yl}-2-oxo-ethyl)-3-methoxy-pyrrolidine-3-carboxylic acid [3-(4-fluoro-phenyl)-1 indazol-5-yl]-amide Example 622

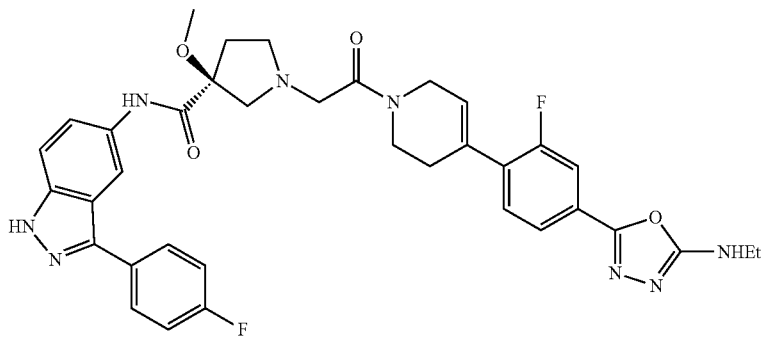

Step 1: Preparation of 4-Bromo-3-fluoro-benzoic acid hydrazide

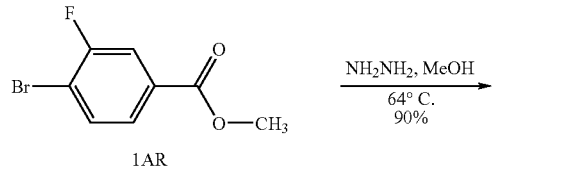

A mixture of compound 4-bromo-3-fluoro-benzoic acid methyl ester (1 g, 4.29 mmol), hydrazine hydrate (2.2 mL, 42.9 mmol) and MeOH (20 mL) was heated at 70° C. for overnight. Concentrated, diluted with EtOAc (300 mL) and washed with water (100 mL). The organic layer was dried over Na₂SO₄, filtered and concentrated give the desired product 2AR (0.9 g, 90%).

Step 2: Preparation of [5-(4-Bromo-3-fluoro-phenyl)-[1,3,4]oxadiazol-2-yl]-ethyl-amine

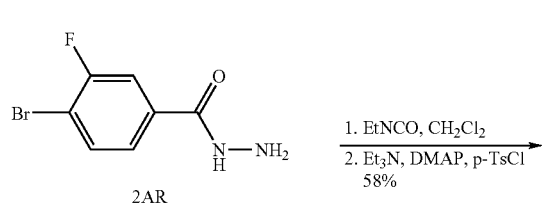

-continued

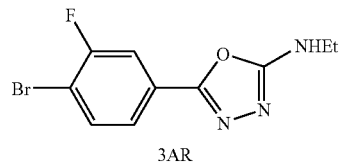

A mixture of Compound 2AR (0.9 g, 2.53 mmol), CH₂Cl₂ (5 mL) and ethyl isocyanate (0.34 mL, 4.35 mmol) was stirred at room temperature for 3 hours. To the reaction mixture was added triethylamine (0.94 mL, 6.7 mmol), DMAP (0.205 g, 1.675 mmol) and a solution of p-toluenesulfonyl chloride (0.83 g, 4.36 mmol) in CH₂Cl₂ (10 mL). Reaction mixture was stirred at room temperature for 18 hours. Diluted with CH₂Cl₂ (200 mL) and washed with water (100 mL). The organic layer was dried over Na₂SO₄, filtered and concentrated. The residue was purified on silica gel eluting with 3% MeOH/CH₂Cl₂ to give the desired product 3AR (0.56 g, 58%).

Step 3: Preparation of 4-[4-(5-Ethylamino-[1,3,4]oxadiazol-2-yl)-2-fluoro-phenyl]-3,6-dihydro-2H-pyridine-1-carboxylic acid tert-butyl ester

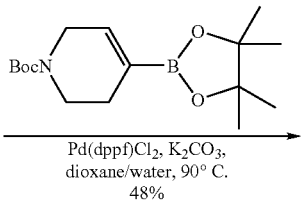

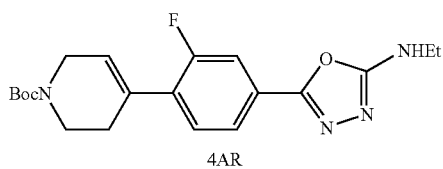

4AR

A mixture of Compound 3AR (0.56 g, 1.96 mmol), 4-(4,4,5,5-tetramethyl-[1,3,2]dioxaborolan-2-yl)-3,6-dihydro-2H-pyridine-1-carboxylic acid tert-butyl ester (0.73 g, 2.35 mmol), potassium carbonate (0.81 g, 5.88 mmol), Pd(dppf)Cl$_2$ (0.192 g, 0.235 mmol) and 4/1/dioxane/water (10 ml) was degassed for 15 minutes. Then it was heated at 80° C. for overnight. Cooled to room temperature and diluted with EtOAc (200 ml). The organic layer was washed with water (100 ml), dried over Na$_2$SO$_4$, filtered and concentrated. The residue was purified on silica gel eluting with 5% MeOH/CH$_2$Cl$_2$ to give the desired product 4AR (0.44 g, 48%).

Step 4: Preparation of Ethyl-{5-[3-fluoro-4-(1,2,3,6-tetrahydro-pyridin-4-yl]-[1,3,4]oxadiazol-2yl}-amine

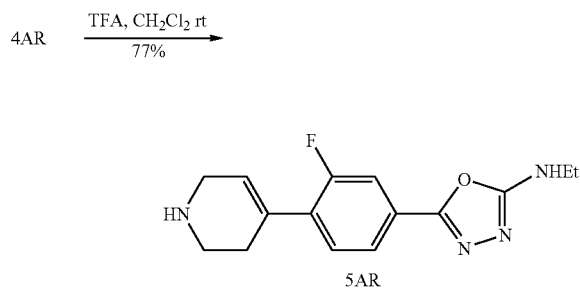

A mixture of Compound 4AR (0.44 g, 1.13 mmol), CH$_2$Cl$_2$ (20 mL) and TFA (2 mL) was stirred at room temperature for 18 hours. Concentrated and purified on silica gel eluting with 5% MeOH(NH$_3$)/CH$_2$Cl$_2$ to give the desired product 5AR (0.25 g, 77%).

Step 5: Preparation of 2-Chloro-1-{4-[4-(5-ethylamino-[1,3,4]oxadiazol-2-yl)-2-fluoro-phenyl]-3,6-dihydro-2H-pyridin-1-yl}-ethanone

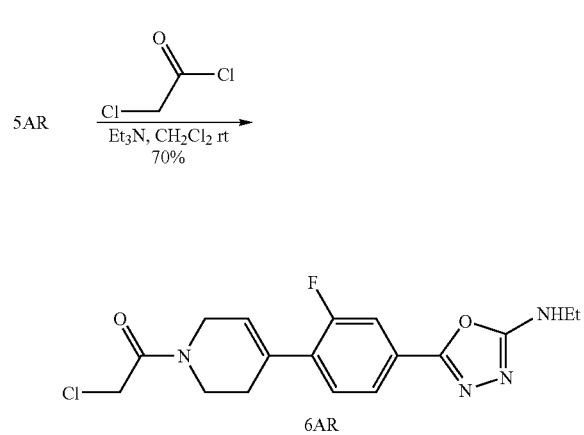

To a mixture of Compound 5AR (0.1 g, 0.35 mmol), CH$_2$Cl$_2$ (5 mL), MeOH (1 mL) and triethyl amine (0.041 mL, 0.29 mmol) at −78° C. was added chloroacetyl chloride (0.021 mL, 0.264 mmol). Reaction mixture was stirred at −78° C. for 10 minutes then warm to 0° C. and stirred for 1 hour. Diluted with CH$_2$Cl$_2$ (100 mL) and washed with saturated aq. NaHCO$_3$ (100 mL). The organic layer was dried over Na$_2$SO$_4$, filtered and concentrated. The residue was purified on silica gel eluting with 2% MeOH/CH$_2$Cl$_2$ to give the desired product 6AR (0.09 g, 70%).

Step 6

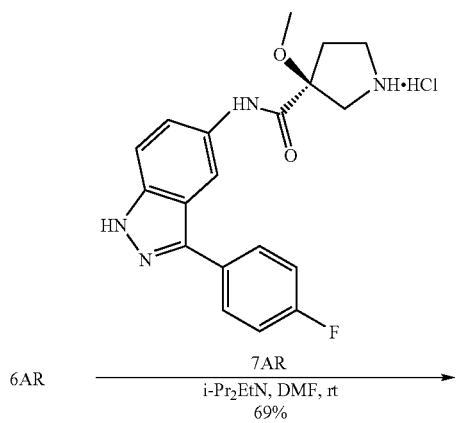

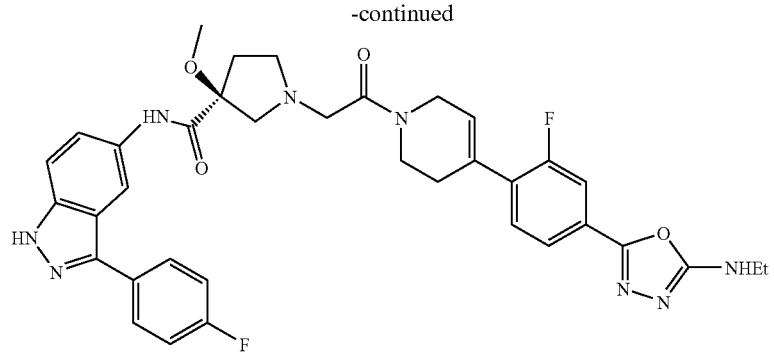

Compound of Example 622

A mixture of Compound 6AR (0.09 g, 0.247 mmol), compound 7AR (0.073 g, 0.2 mmol), DMF (2 mL) and N,N-diisopropylethylamine (0.131 mL, 0.74 mmol) was stirred at room temperature for 18 hours. Diluted with EtOAc (100 mL) and washed with water (2×100 mL). The organic layer was dried over $Na_2SO_4$, filtered and concentrated. The residue was purified on silica gel eluting with 5% $MeOH(NH_3)$/ $CH_2Cl_2$ to give the desired compound of Example 622 (0.11 g, 69%).

Preparation 67

Step 1

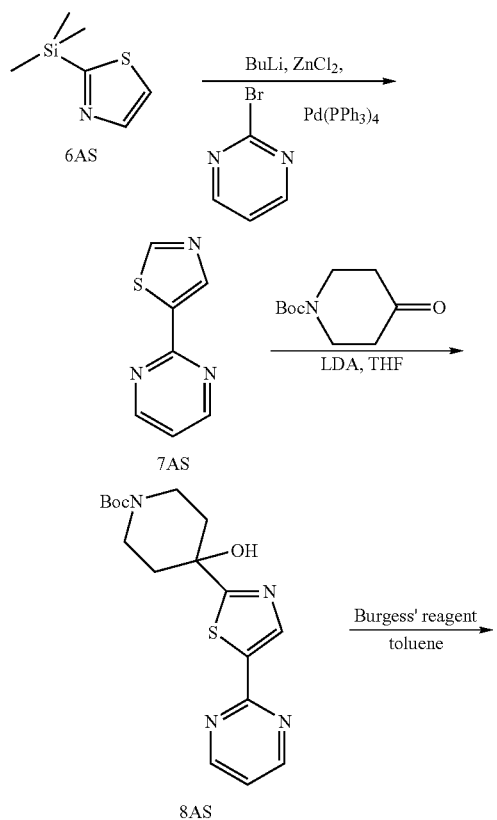

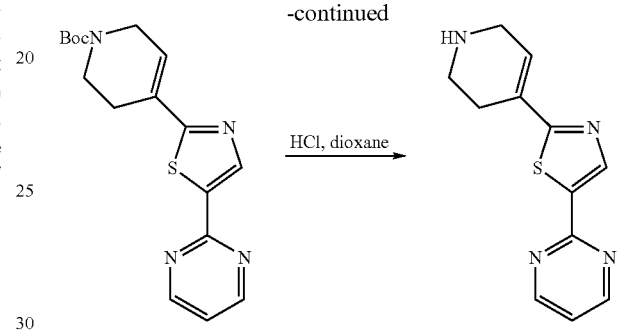

In a 250 round bottom flask was placed butyl lithium (6.1 mL, 2.5 M in hexanes, 15.2 mmol) in THF at −78° C. under Ar. To this was added 6 (2.0 g, 12.7 mmol), stirred for 15 min and added Zinc chloride (38.1 mL, 0.5 M in THF, 19.1 mmol). The mixture was warmed up to room temperature and stirred for 1 hr. To this was added 2-bromopyrimidine (2.4 g, 15.2 mmol) and $Pd(PPh_3)_4$ (293 mg, 0.252 mmol). The reaction was heated to reflux overnight, cooled to room temperature and filtered. The filtrate was partitioned between brine and ethyl acetate. The organic layer was dried over sodium sulfate and concentrated. The resulting mixture was purified by biotage column chromatography to afford 7AS (936 mg, 54.2%)

To a solution of 7AS (710 mg, 4.35 mmol) in THF at −78° C. was added LDA (2.61 mL, 2.0 M, 5.22 mmol), and then Boc-4-piperidone (1.04 g, 5.22 mmol). The reaction was stirred at −78° C. for 1 hr, warmed up to room temperature and quenched with ammonium chloride solution. The mixture was extracted with ethyl acetate. The combined organic layer was dried over sodium sulfate and concentrated. The resulting oil was purified by biotage column chromatography to afford 8AS (1.08 g, 68%)

To a solution of 8AS (800 mg, 2.21 mmol) in toluene was added Burgess reagent (1.09 g, 4.58 mmol). The mixture was heated to 100° C., stirred for 2 hrs, cooled to room temperature and concentrated. The residue was purified biotage column chromatography to afford 9AS (562 mg, 74%)

Step 2

To 9AS (560 mg, 1.63 mmol) in a 20 mL vial was added 4 mL of HCl in dioxane (4 M). The reaction was stirred at room temperature for 4 hrs and the precipitate was filtered. The resulting solid was pump dried to afford 10 (350 mg, 88%)

Step 3

9AS $\xrightarrow{\text{Pd/C}}_{\text{Ammonium formate}}$

11AS $\xrightarrow{\text{TFA/dioxane}}$ 12AS

To a solution of 9AS (100 mg, 0.291 mmol) and ammonium formate (183 mg, 2.91 mmol) in methanol was added catalytic amount of 10% Palladium on carbon. The mixture was heated to reflux overnight, cooled to room temperature and filtrated. The filtrate was concentrated and the residue was purified biotage column chromatography to afford 11AS (52 mg, 52%) and recovered 9 (18 mg, 18%)

To 11AS (52 mg, 0.15 mmol) in 1 mL of DCM was added 1 mL of TFA. The reaction was stirred at room temperature for 2 hrs and concentrated to afford crude 12AS.

Preparation 68

1AT + 2-bromopyrimidine $\xrightarrow{\text{Pd(PPh}_3)_4}_{\text{THF}}$ 2AT

2AT + 3AT $\xrightarrow{\text{Pd(PPh}_3)_4, \text{Na}_2\text{CO}_3 \text{ (2M)}}_{\text{Dioxane/EtOH/H}_2\text{O}}$ 4AT $\xrightarrow{\text{HCl, dioxane}}$ 5AT In a 250 mL of round bottom flask was placed 1AT (0.5 M in THF, 20.0 mL, 10.0 mol). To this was added 2-bromopyrimidine (2.00 g, 12.6 mol) and Pd(PPh$_3$)$_4$ (346 mg, 0.3 mmol). The mixture was heated to reflux under Ar overnight and cooled down to room temperature. The reaction was quenched with ammonium chloride solution and extracted with ethyl acetate. The combined organic layer was dried over sodium sulfate and concentrated. The resulting oil was purified by biotage column chromatography to afford 2AT (1.62 g, 69%)

In a 5 mL of biotage microwave vessel was placed 2AT (136 mg, 0.568 mmol), pinacol ester 3AT (193 mg, 0.625 mmol), Pd(PPh$_3$)$_4$ (32.8 mg, 0.0284 mmol) and sodium carbonate solution (0.85 mL, 2 M) in dioxane/EtOH/H2O (7:3:2, 2.5 mL) under Ar. The vessel was sealed and heated in microwave reactor at 150° C. for 10 minutes. The reaction was partitioned between ethyl acetate and water. The organic layer was dried over sodium sulfate and concentrated. The resulting oil was purified by biotage column chromatography to afford 4AT (149 mg, 76%).

To 4AT (144 mg, 0.420 mmol) in a 20 mL vial was added 2 mL of HCl in dioxane (4 M). The reaction was stirred at room temperature for 4 hrs and the precipitate was filtered. The resulting solid was pump dried to afford 5AT (83 mg, 82%)

Preparation 69

Step 1: Preparation of 3-(4-Fluoro-3-hydroxyphenyl)-5-nitro-1-trityl-1H-indazole 1AJ + 6AU $\xrightarrow{\text{Pd(dppf)Cl}_2}_{\text{K}_3\text{PO}_4}$

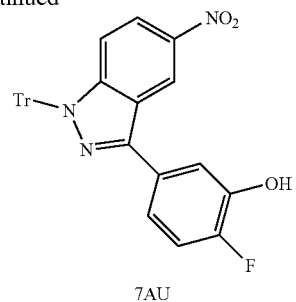

7AU

A suspension of 3-bromo-5-nitro-1-trityl-1H-indazole 1AJ (10.0 g, 20.68 mmol), 4-fluoro-3-hydroxyphenylboronic acid 6AU (3.55 g, 22.78 mmol), Pd(dppf)Cl₂ (1.6 mg, 1.96 mmol) and K₃PO₄ (10.6 g, 4.99 mmol) in 200 mL of dioxane/H₂O (4/1) was heated to 75° C. for overnight. After removal of most of the solvent, the black residue was diluted with EtOAc (250 mL) and H2O (60 mL). The resulting mixture was filtered through a pad of Celite. Additional 150 mL of EtOAc was used to wash the Celite cake. The filtrates were combined. The aqueous layer was separated and the organic layer was washed with brine, dried (MgSO₄) and concentrated to give a green solid, which was recrystallized from CH₂Cl₂/hexane to give 3-(4-fluoro-3-hydroxyphenyl)-5-nitro-1-trityl-1H-indazole 7AU (8.1 g).

Step 2: Preparation of 3-[4-Fluoro-3-(2-methoxy-ethoxy)-phenyl]-1-trityl-5-nitro-1H-indazole

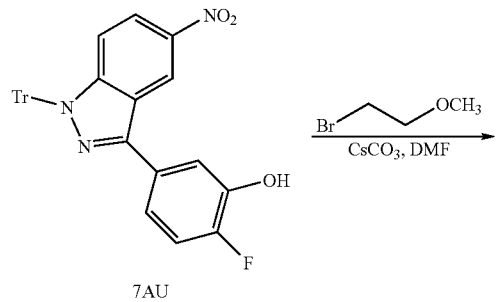

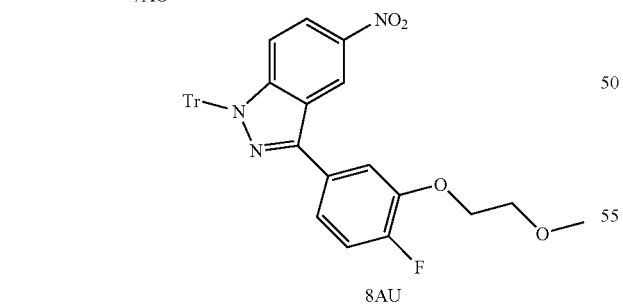

8AU

To a stirred mixture of 3-(4-fluoro-3-hydroxyphenyl)-5-nitro-1-trityl-1H-indazole 7AU (2 g, 3.88 mmol) in DMF (25 mL) was added CsCO₃ 1.9 g, 5.82 mmol) and bromoethylmethyl ether (474 μL, 5.04 mmol). The resulting mixture was stirred at rt for overnight then diluted with EtOAc (300 mL), which was washed with brine, dried (MgSO₄) and concentrated. Chromatograph on silica gel (2:1, hexanes/EtOAc) gave 3-[4-fluoro-3-(2-methoxy-ethoxy)-phenyl]-1-trityl-5-nitro-1H-indazole 8AU (1.8 g) as a yellow solid.

Step 3: Preparation of 3-[4-Fluoro-3-(2-methoxy-ethoxy)-phenyl]-1-trityl-1H-indazol-5-ylamine

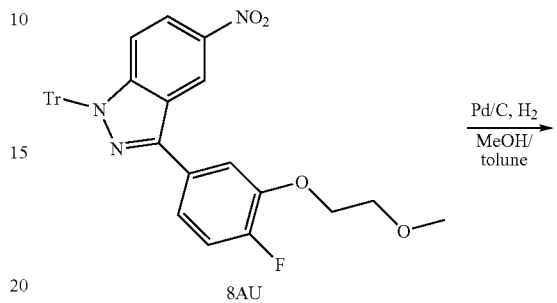

8AU

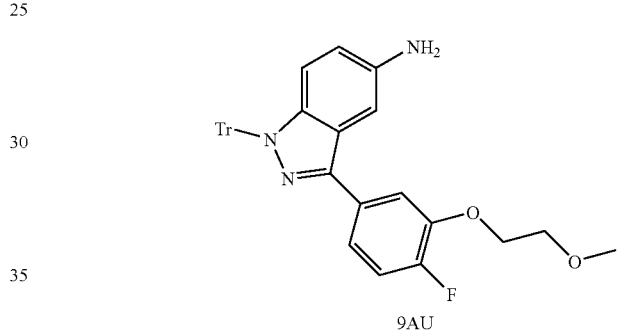

9AU

A suspension of 8AU (890 mg, 1.55 mmol) and catalytic amount of Pd on carbon (5 wt %, 180 mg) in 45 mL of methanol/toluene/CH₂Cl₂ (4:4:1) was stirred under a hydrogen atmosphere for 2 d and filtered through Celite. The filtrate was concentrated and purified on silica gel column (1:1, hexanes/EtOAc) provide 3-[4-fluoro-3-(2-methoxy-ethoxy)-phenyl]-1-trityl-1H-indazol-5-ylamine 9AU (680 mg) as a white solid.

Preparation 70

Step 1: Preparation of 3-(4-Fluoro-3-hydroxymethylphenyl)-5-nitro-1-trityl-1H-indazole

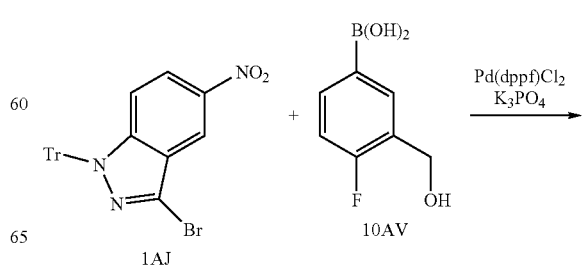

1AJ          10AV

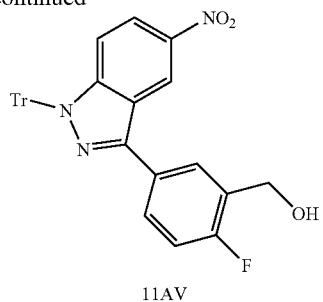

11AV

A suspension of 3-bromo-5-nitro-1-trityl-1H-indazole 1 (6 g, 12.41 mmol), 4-fluoro-3-hydroxymethylphenylboronic acid 10AV (2 g, 12.87 mmol), Pd(dppf)Cl$_2$ (800 mg, 0.98 mmol) and K$_3$PO$_4$ (6 g, 28.30 mmol) in 124 mL of dioxane/H$_2$O (25:6) was heated to 80° C. for overnight. After removal of most of the solvent, the black residue was diluted with EtOAc (250 mL) and H$_2$O (60 mL). The resulting mixture was filtered through a pad of Celite. Additional 150 mL of EtOAc was used to wash the Celite cake. The filtrates were combined. The aqueous layer was separated and the organic layer was washed with brine, dried (MgSO$_4$) and concentrated to give crude 3-(4-fluoro-3-hydroxymethylphenyl)-5-nitro-1-trityl-1H-indazole 11AV (8.2 g) as a greenish yellow solid.

Step 2: Preparation of 3-[4-Fluoro-3-(2-methoxymethyl)-phenyl]-1-trityl-5-nitro-1H-indazole

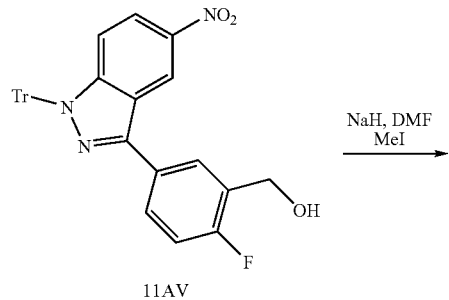

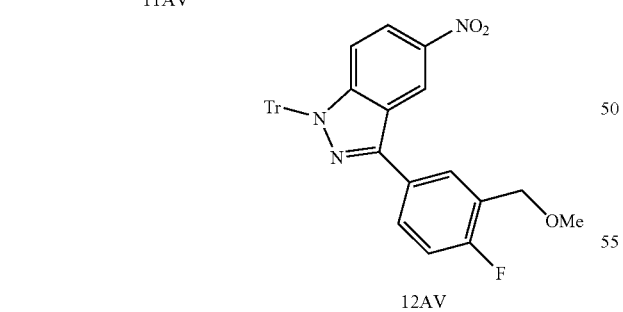

To a stirred solution of 3-(4-fluoro-3-hydroxymethylphenyl)-5-nitro-1-trityl-1H-indazole 11AV (5.5 g, 10.4 mmol) in DMF (120 mL) at 0° C. under N$_2$ was added NaH (60% in mineral oil, 500 mg, 12.5 mmol) in portions over 10 min. After 15 min, MeI (1 mL, 16.06 mmol) was added dropwise. The reaction mixture was stirred at 0° C. to rt for overnight and quenched with H$_2$O. The resulting mixture was extracted with EtOAc, washed with brine, dried (MgSO$_4$) and concentrated to give the crude 3-[4-fluoro-3-(2-methoxymethyl)-phenyl]-1-trityl-5-nitro-1H-indazole 12AV (7.2 g) as a yellow solid.

Step 3: Preparation of 3-[4-Fluoro-3-(2-methoxymethyl)-phenyl]-1-trityl-1H-indazol-5-ylamine

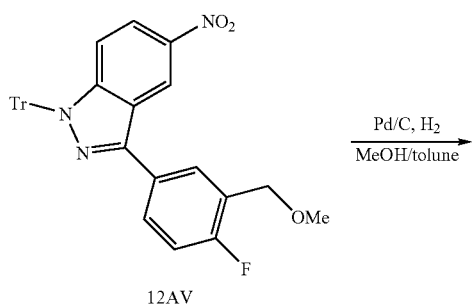

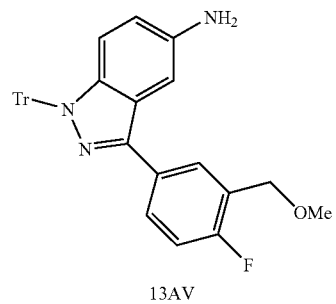

13AV

A suspension of the crude 3-[4-fluoro-3-(2-methoxymethyl)-phenyl]-1-trityl-5-nitro-1H-indazole 12AV (7.2 g) from step 2 and catalytic amount of Pd on carbon (5 wt %, 1.3 g) in 150 mL of methanol/toluene (1:1) was stirred under a hydrogen atmosphere for overnight and filtered through Celite. The filtrate was concentrated and purified on silica gel column (4:1, hexanes/EtOAc) provide 3-[4-fluoro-3-(2-methoxymethyl)-phenyl]-1-trityl-1H-indazol-5-ylamine 13AV (5 g) as a white solid.

Preparation 71

Step 1: Preparation of 3-(3-Fluoro-4-hydroxyphenyl)-5-nitro-1-trityl-1H-indazole

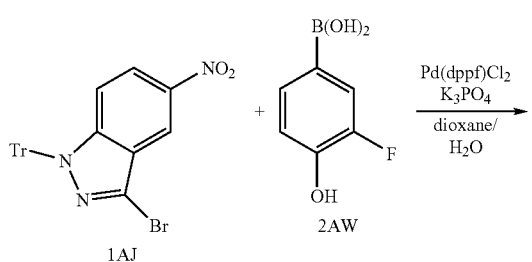

-continued

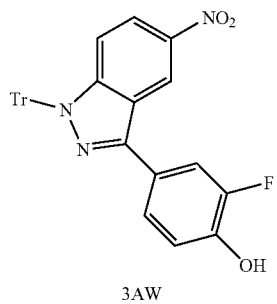

A suspension of 3-bromo-5-nitro-1-trityl-1H-indazole 1AJ (10.0 g, 20.68 mmol), 3-fluoro-4-hydroxyphenylboronic acid 2AW (3.55 g, 22.78 mmol), Pd(dppf)Cl₂ (1.6 g, 1.96 mmol) and K₃PO₄ (10.6 g, 4.99 mmol) in 200 mL of dioxane/H₂O (4/1) was heated to 75° C. for overnight. After removal of most of the solvent, the black residue was diluted with EtOAc (250 mL) and H₂O (60 mL). The resulting mixture was filtered through a pad of Celite. Additional 150 mL of EtOAc was used to wash the Celite cake. The filtrates were combined. The aqueous layer was separated and the organic layer was washed with brine, dried (MgSO₄) and concentrated to give a green solid, which was recrystallized from CH₂Cl₂/hexane to give 3-(3-fluoro-4-hydroxyphenyl)-5-nitro-1-trityl-1H-indazole 3AW (8.1 g).

Step 2: Preparation of 3-[3-Fluoro-4-(2-methoxy-ethoxy)-phenyl]-1-trityl-5-nitro-1H-indazole

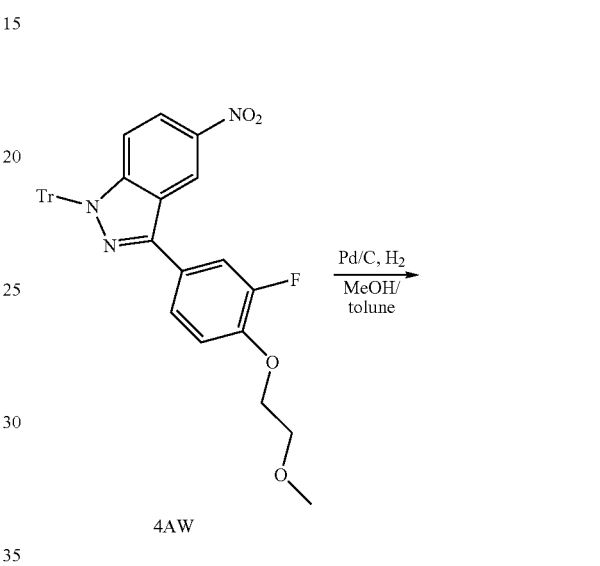

To a stirred mixture of 3-(3-fluoro-4-hydroxyphenyl)-5-nitro-1-trityl-1H-indazole 3AW (3 g, 5.82 mmol) in DMF (40 mL) was added CsCO₃ (2.85 g, 8.75 mmol) and bromoethyl-methyl ether (711 µL, 7.57 mmol). The resulting mixture was stirred at rt for overnight then diluted with EtOAc (300 mL), which was washed with brine, dried (MgSO₄) and concentrated. Chromatograph on silica gel (2:1, hexanes/EtOAc) gave 3-[3-fluoro-4-(2-methoxy-ethoxy)-phenyl]-1-trityl-5-nitro-1H-indazole 4AW (2.8 g).

Step 3: Preparation of 3-[3-Fluoro-4-(2-methoxy-ethoxy)-phenyl]-1-trityl-1H-indazol-5-ylamine

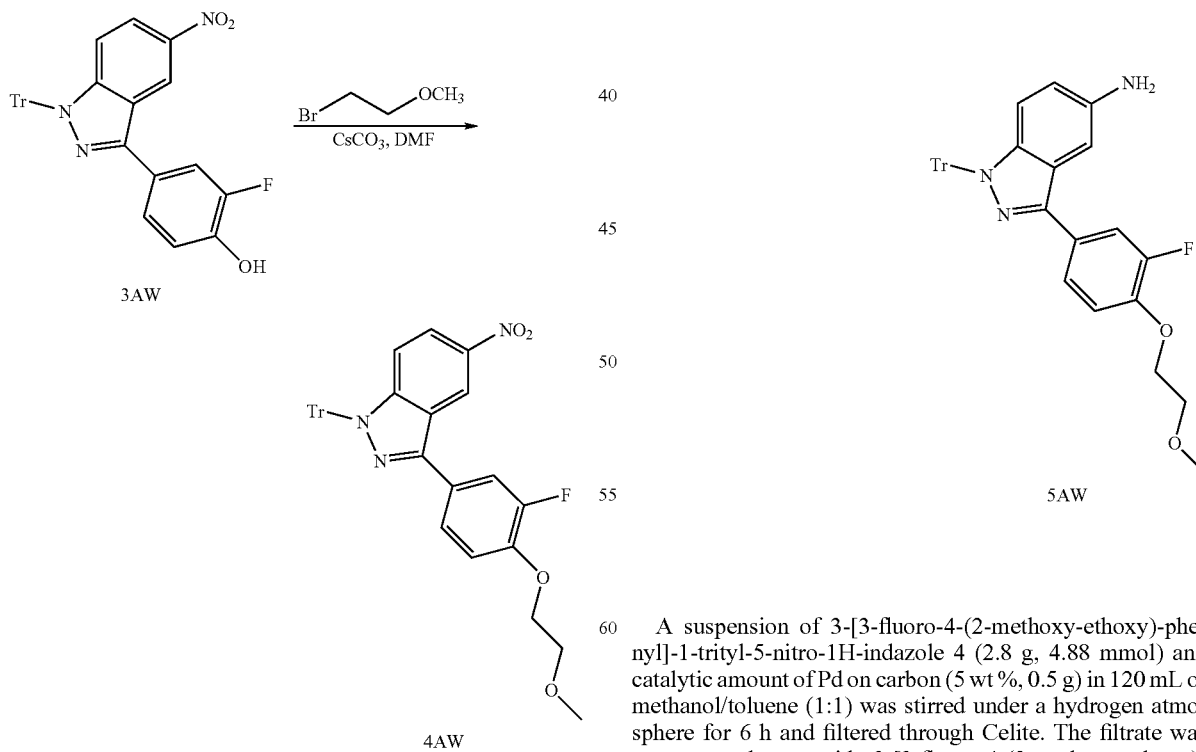

A suspension of 3-[3-fluoro-4-(2-methoxy-ethoxy)-phenyl]-1-trityl-5-nitro-1H-indazole 4 (2.8 g, 4.88 mmol) and catalytic amount of Pd on carbon (5 wt %, 0.5 g) in 120 mL of methanol/toluene (1:1) was stirred under a hydrogen atmosphere for 6 h and filtered through Celite. The filtrate was concentrated to provide 3-[3-fluoro-4-(2-methoxy-ethoxy)-phenyl]-1-trityl-1H-indazol-5-ylamine 5 (2.6 g) as an off-white solid.

Preparation 72

Step 1: Preparation of 3-[4-Fluoro-3-(2-hydroxy-ethoxy)-phenyl]-1-trityl-5-nitro-1H-indazole

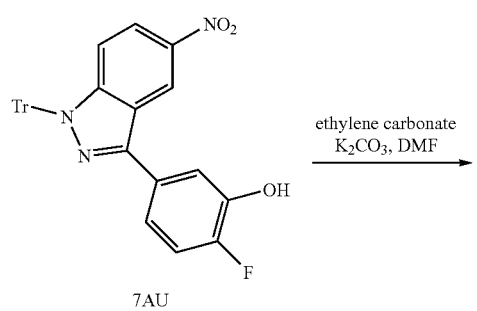

7AU

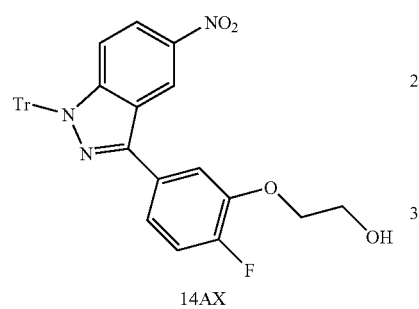

14AX

A mixture of 3-(4-fluoro-3-hydroxyphenyl)-5-nitro-1-trityl-1H-indazole 7AU (1.25 g, 2.42 mmol), $K_2CO_3$ (402 mg, 2.91 mmol) and ethylene carbonate (2.6 mL, 24.00 mmol) in DMF (10 mL) was stirred in a sealed tube at 160° C. for 4 h and cooled to rt. $H_2O$ was added to quench the reaction. The resulting mixture was extracted with EtOAc, which was washed with $H_2O$, brine, dried ($MgSO_4$) and concentrated to give a yellow oil. Chromatograph on silica gel (4:1, hexanes/EtOAc) gave 3-[4-fluoro-3-(2-hydroxy-ethoxy)-phenyl]-1-trityl-5-nitro-1H-indazole 14AX (1.4 g) as a yellow oil.

Step 2: Preparation of 3-[4-Fluoro-3-(2-hydroxy-ethoxy)-phenyl]-1-trityl-1H-indazol-5-ylamine

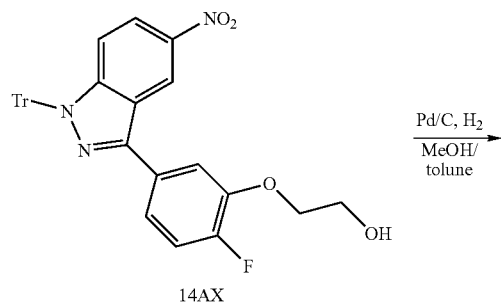

14AX

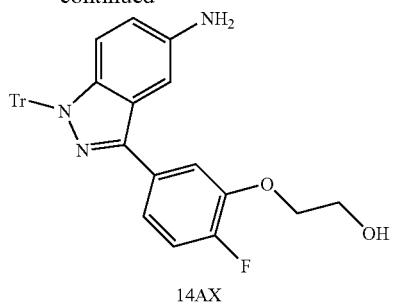

14AX

A suspension of 3-[4-fluoro-3-(2-hydroxy-ethoxy)-phenyl]-1-trityl-5-nitro-1H-indazole 14AX (1.5 g) and catalytic amount of Pd on carbon (5 wt %, 300 mg) in 40 mL of methanol/toluene (1:1) was stirred under a hydrogen atmosphere for 1 d and filtered through Celite. The filtrate was concentrated to provide 3-[4-fluoro-3-(2-hydroxy-ethoxy)-phenyl]-1-trityl-1H-indazol-5-ylamine 15AX (1.4 g) as an off-white solid.

Preparation 73

Synthesis of 6-Pyrimidin-2-yl-1,2,3,4-tetrahydro-isoquinoline

To a Schlenk tube were charged $Pd_2(dba)_3$ (10 mg, 0.01 mmol), bis(tri-tert-butylphosphine)palladium (20 mg, 0.04 mmol), CuI (16 mg, 0.08 mmol) and CsF (334 mg, 2.2 mmol). The tube was evacuated under high vacuum and back-filled with nitrogen for three cycles. DMF (2 ml) was introduced, followed by 2-tributylstannylpyrimidine (537 mg, 1.4 mmol). The tube was sealed with a Teflon cap and the reaction mixture was heated with stirring at 120° C. for 2 hours. After cooling, the mixture was filtered through Celite, washed with ethyl acetate. Filtrate was washed with water three times, brine and dried ($MgSO_4$). After concentration the residue was purified on silica gel eluting with ethyl acetate in hexanes (0-100%) to give 6-pyrimidin-2-yl-3,4-dihydro-1H-isoquinoline-2-carboxylic acid tert-butyl ester (28 mg). The compound was treated with 4N HCl in dioxane for 30 minutes. After concentration title compound was obtained as hydrochloride salt.

Preparation 74

Preparation of 2-[5-(5-amino-1-trityl-1H-indazol-3-yl)-2-fluoro-phenylamino]-ethanol

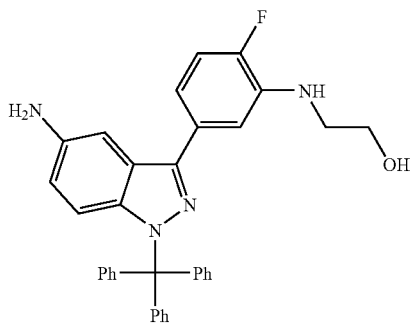 [SMILES: Nc1ccc2c(c1)c(-c1ccc(F)c(NCCO)c1)nn2C(c1ccccc1)(c1ccccc1)c1ccccc1]

Step 1: Preparation of 2-fluoro-5-(5-nitro-1-trityl-1 indazol-3-yl)-phenylamine

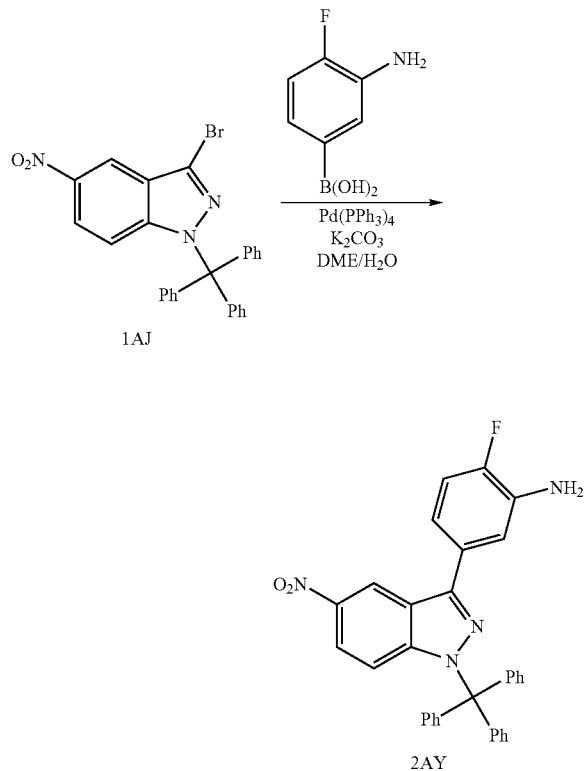

To a pressure tube were charged compound 1AJ (1 g, 2.1 mmol), 3-amino-4-fluoro-phenylboronic acid (448 mg, 2.89 mmol), Pd(PPh$_3$)$_4$ (120 mg, 0.1 mmol), K$_2$CO$_3$ (1.4 g, 10.1 mmol), DME (8 ml) and water (2 ml). The resulting mixture was degassed with nitrogen for 20 seconds and the tube was sealed with a Teflon cap, and heated at 100 C with stirring overnight. After cooling the reaction mixture was diluted with ethyl acetate, organic layer was isolated, washed with brine. After concentration, the residue was purified on silica gel. Elution with ethyl acetate in hexanes (0-70%) gave compound 2AJ (1 g).

Step 2: Synthesis of 3-[2-fluoro-5-(5-nitro-1-trityl-1H-indazol-3-yl)-henyl]-oxazolidin-2-one

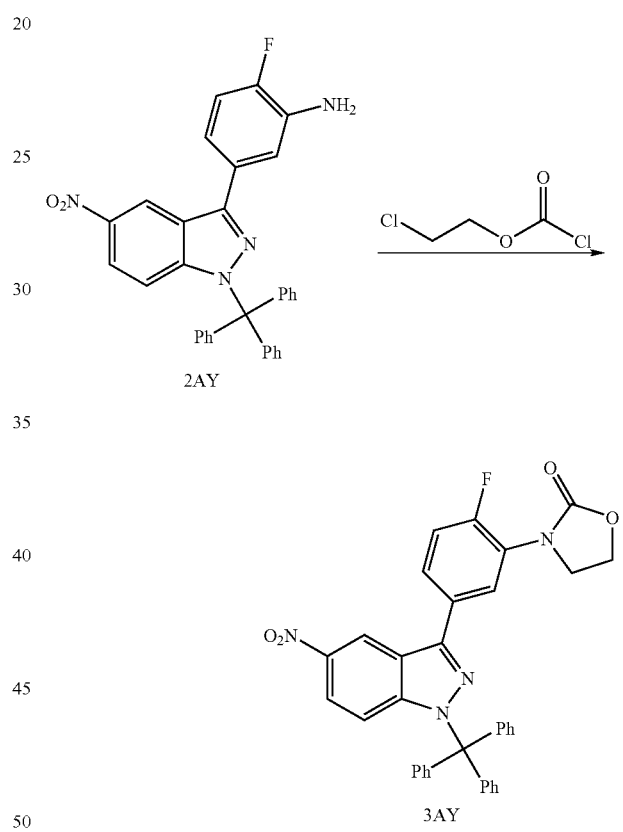

To a mixture of compound 2AY (1 g, 1.95 mmol), Cs$_2$CO$_3$ (1.2 g, 3.68 mmol) in acetonitrile (20 ml) was added 2-chloroethyl chloroformate (200 µl, 1.94 mmol) and the resulting mixture was refluxed for 20 minutes. After addition of 2-chloroethyl chloroformate (150 µl) the reaction mixture was allowed to reflux overnight. A solution of 40% KOH was added and the mixture was further refluxed for 2 hours. After cooling the reaction mixture was diluted with ethyl acetate and water, and aqueous layer was separated and extracted with ethyl acetate twice. Combined organic layers were washed with brine and dried (MgSO$_4$). After concentration the residue was purified on silica gel eluting with ethyl acetate in hexanes (0-40%) to give compound 3AY (1 g).

Step 3: Preparation of 2-[2-fluoro-5-(5-nitro-1-trityl-1H-indazol-3-yl)-phenylamino]-ethanol

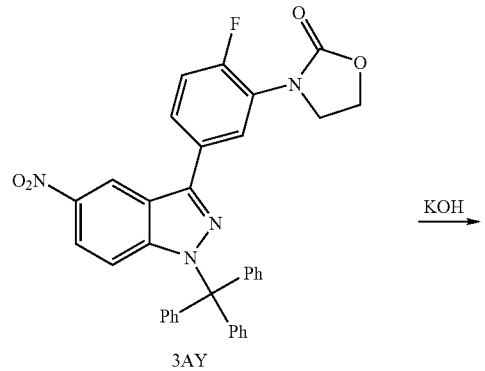
3AY

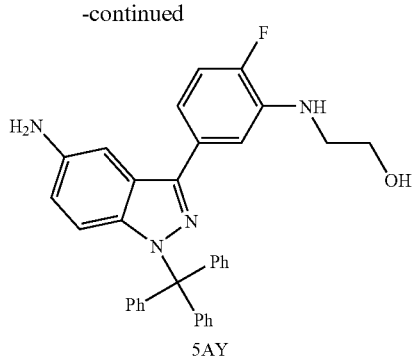
5AY

A mixture of compound 4AY (173 mg), 10% Pd/C (50 mg) in ethyl acetate (10 ml) was stirred under hydrogen (balloon pressure) overnight. After filtration and concentration, the residue was purified on silica eluting with ethyl acetate to provide compound 5AY (81 mg).

Preparation 75

Synthesis of 2-[4-(5-amino-1-trityl-1H-indazol-3-yl)-phenylamino]-ethanol

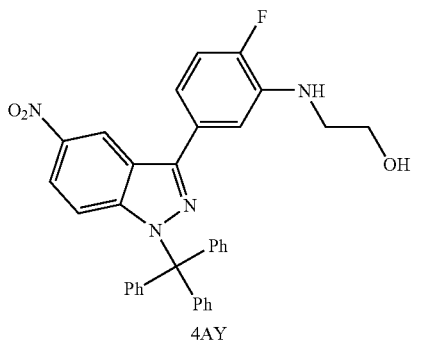
4AY

A mixture of compound 3AY (658 mg) in DME (15 ml), MeOH (6 ml) and 40% KOH (4 ml) was refluxed overnight. After cooling, the mixture was diluted with ethyl acetate, organic layer was separated, washed with brine and dried (MgSO$_4$). After concentration the residue was purified on silica gel eluting with ethyl acetate in hexanes (0-100%) to give compound 4AY (559 mg).

Step 4: Preparation of 2-[5-(5-amino-1-trityl-1H-indazol-3-yl)-2-fluoro-phenylamino]-ethanol

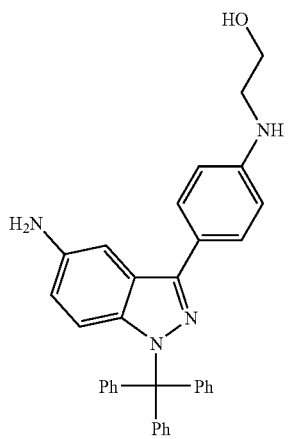 [SMILES: Nc1ccc2c(c1)c(-c1ccc(NCCO)cc1)nn2C(c1ccccc1)(c1ccccc1)c1ccccc1]

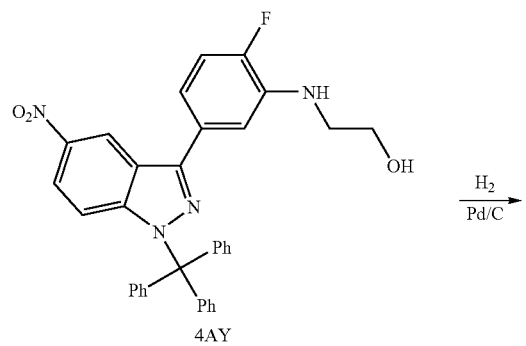
4AY

Step 1: Preparation of 4-(5-nitro-1-trityl-1H-indazol-3-yl)-phenylamine

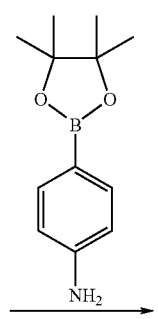
1AJ

-continued

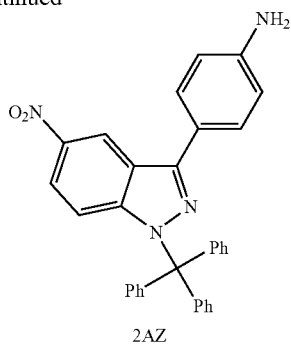

2AZ

To a pressure tube were charged with compound 1AJ (1 g, 2.1 mmol), 4-(4,4,5,5-tetramethyl-[1,3,2]dioxaborolan-2-yl)-phenylamine (0.635 g, 2.9 mmol), Pd(PPh₃)₄ (0.12 g, 0.1 mmol), K₂CO₃ (1.4 g, 10.1 mmol), DME (8 ml) and water (2 ml). The resulting mixture was degassed with nitrogen briefly and the tube was sealed with a Teflon cap, and heated at 100 C with stirring overnight. After cooling, the reaction mixture was diluted with ethyl acetate, organic layer was isolated, washed with brine. After concentration, the residue was purified on silica gel. Elution with ethyl acetate in hexanes (0-70%) gave compound 2AZ (0.956 g).

Step 2 Preparation of 3-[4-(5-nitro-1-trityl-1H-indazol-3-yl)-phenyl]-oxazolidin-2-one

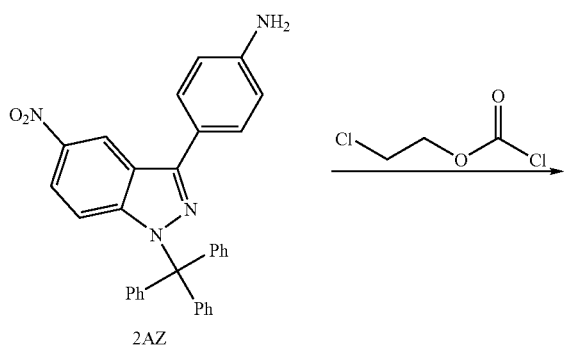

To a mixture of compound 2AZ (409 mg, 0.82 mmol), 10% NaOH (2 ml) in DME (8 ml) was added 2-chloroethyl chloroformate (102 μl, 1 mmol) and the resulting mixture was stirred at rt for overnight. The mixture was diluted with ethyl acetate and water, and aqueous layer was separated and extracted with ethyl acetate twice. Combined organic layers were washed with brine and dried (MgSO₄). After concentration the residue was purified on silica gel eluting with ethyl acetate in hexanes (0-80%) to give compound 3AZ (340 mg).

Step 3: Preparation of 2-[4-(5-nitro-1-trityl-1H-indazol-3-yl)-phenylamino]-ethanol

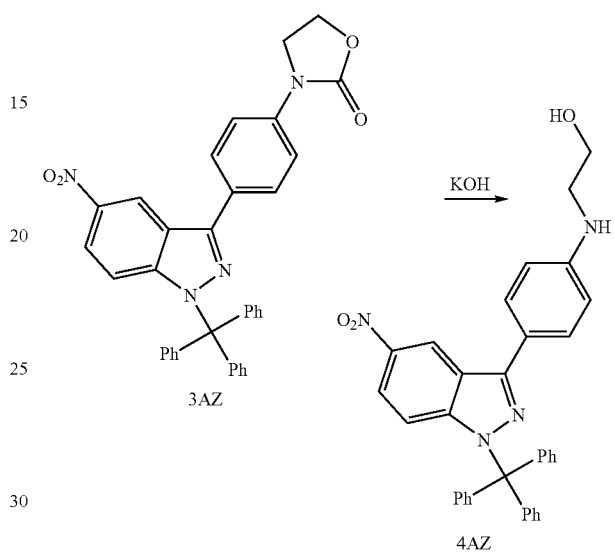

A mixture of compound 3AZ (340 mg) in DME (6 ml), MeOH (4 ml) and 40% KOH (2 ml) was refluxed for two hours. After cooling, solvents were removed, diluted with water, extracted with dichloromethane three times, combined organic layers were washed with brine and dried (MgSO₄). After concentration the residue was purified on silica gel eluting with ethyl acetate in hexanes (0-100%) to give compound 4AZ (280 mg).

Step 4: Preparation of 2-[4-(5-amino-1-trityl-1H-indazol-3-yl)-phenylamino]-ethanol

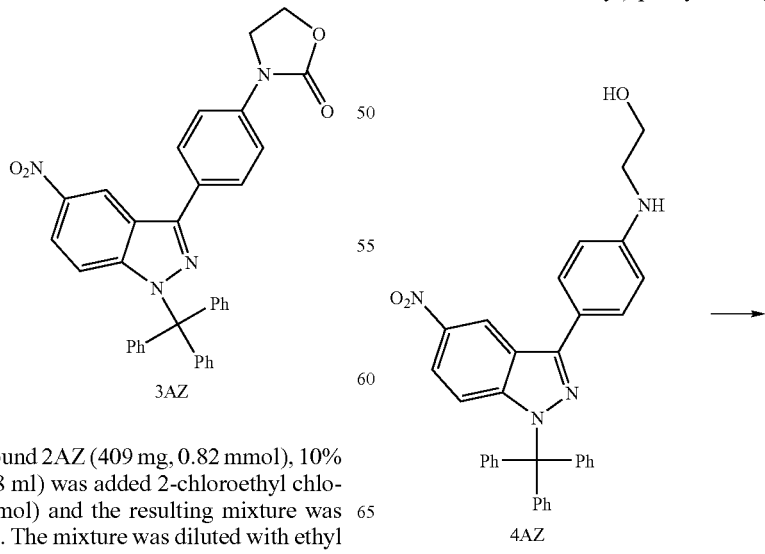

-continued

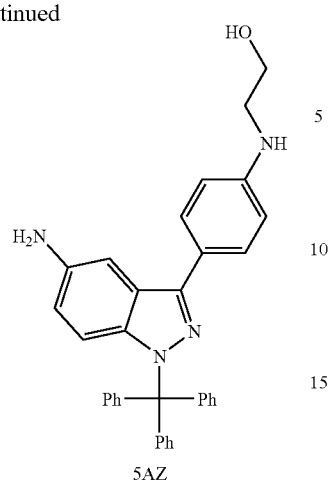

5AZ

A mixture of compound 4AZ (280 mg), 10% Pd/C (70 mg) in ethanol (10 ml) was stirred at 45° C. under hydrogen (balloon pressure) overnight. After filtration and concentration, the residue was purified on silica eluting with ethyl acetate to provide compound 5AZ (224 mg).

Preparation 76

Synthesis of 3-(2-Isobutyl-thiazol-5-yl)-1-trityl-1H-indazol-5-ylamine

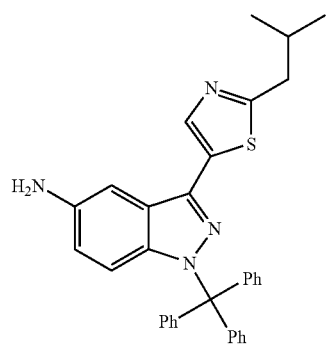 [SMILES: CC(C)Cc1ncc(-c2nn(C(c3ccccc3)(c3ccccc3)c3ccccc3)c3ccc(N)cc23)s1]

Step 1: Preparation of 3-(2-Isobutyl-thiazol-5-yl)-5-nitro-1-trityl-1H-indazole

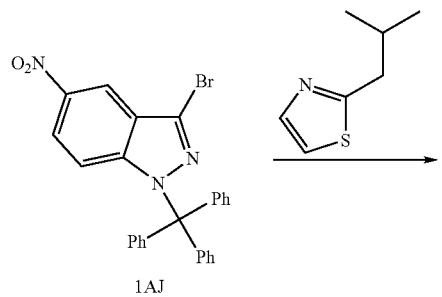

1AJ

-continued

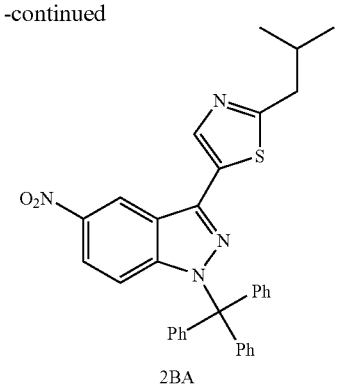

2BA

To a pressure tube were charged compound 1AJ (194 mg, 0.4 mmol), Pd(OAc)$_2$ (90 mg, 0.4 mmol), (2-biphenyl)-di-tert-butylphospine (12 mg, 0.1 mmol), C$_2$CO$_3$ (313 mg, 0.96 mmol) and the tube was evacuated under vacuum and back-filled with nitrogen. Dioxane (4 ml) was introduced, followed by 2-isobutylthiazole (114 μl, 0.8 mmol). The tube was sealed and heated at 100° C. with stirring overnight. After cooling the reaction mixture was filtered through Celite, washed with ethyl acetate several times. Filtrate was concentrated and the residue was purified on silica gel. Elution with ethyl acetate in hexanes (0-30%) gave compound 2BA (124 mg).

Step 2: Preparation of 3-(2-Isobutyl-thiazol-5-yl)-1-trityl-1H-indazol-5-ylamine

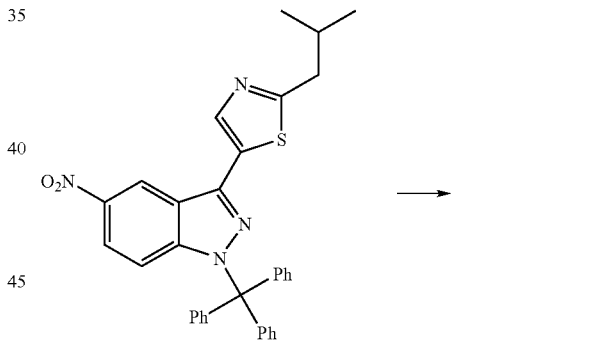

2BA

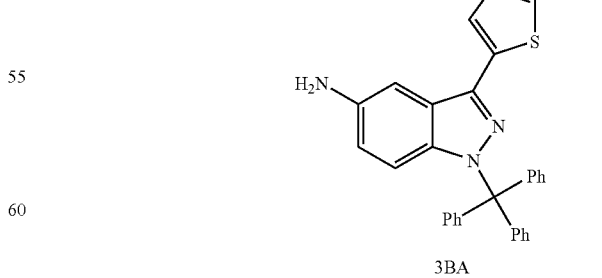

3BA

A mixture of compound 2BA (180 mg), 10% Pd/C (50 mg) in ethyl acetate (8 ml) was stirred at 45° C. under hydrogen (balloon pressure) overnight. After filtration and concentration, the residue was purified on silica eluting with ethyl acetate to provide compound 3BA (75 mg).

Preparation 77

Synthesis of 3-(2-methyl-thiazol-5-yl)-1-trityl-1H-indazol-5-ylamine

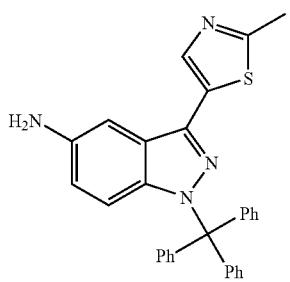 [SMILES: Cc1ncc(-c2nn(C(c3ccccc3)(c3ccccc3)c3ccccc3)c3ccc(N)cc23)s1]

Preparation of 3-(2-methyl-thiazol-5-yl)-1-trityl-1H-indazol-5-ylamine was similar to that of 3-(2-isobutyl-thiazol-5-yl)-1-trityl-1H-indazol-5-ylamine as illustrated above except using 2-methylthiazole in the cross-coupling reaction.

Preparation 78

Synthesis of 3-[5-(5-amino-1-trityl-1H-indazol-3-yl)-2-fluoro-phenyl]-oxazolidin-2-one

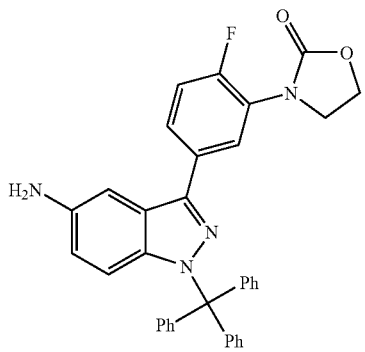

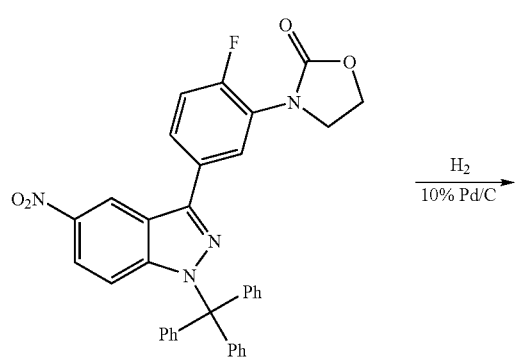

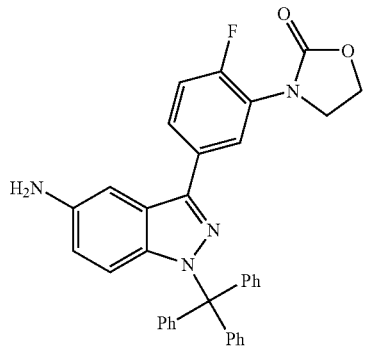

The hydrogenation of 3-[2-fluoro-5-(5-nitro-1-trityl-1H-indazol-3-yl)-phenyl]-oxazolidin-2-one was conducted in similar way to the other examples as illustrated above.

Preparation 79

Synthesis of 3-[4-(5-amino-1-trityl-1H-indazol-3-yl)-phenyl]-oxazolidin-2-one

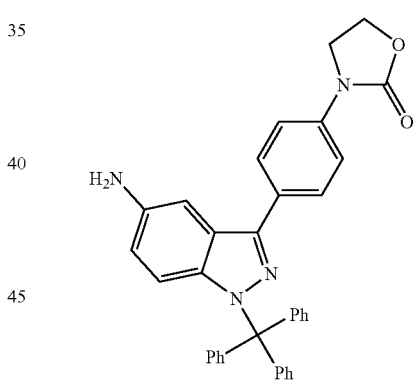

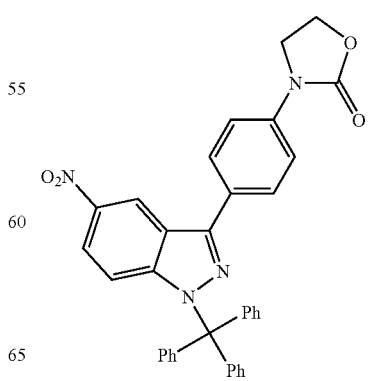

-continued

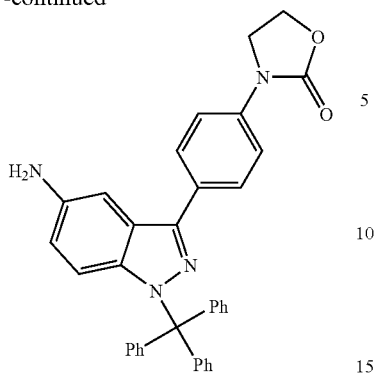

The hydrogenation of 3-[4-(5-nitro-1-trityl-1H-indazol-3-yl)-phenyl]-oxazolidin-2-one was conducted in similar way to the other examples as illustrated above.

Preparation 80

Synthesis of 6-Pyrimidin-2-yl-1,2,3,4-tetrahydro-isoquinoline

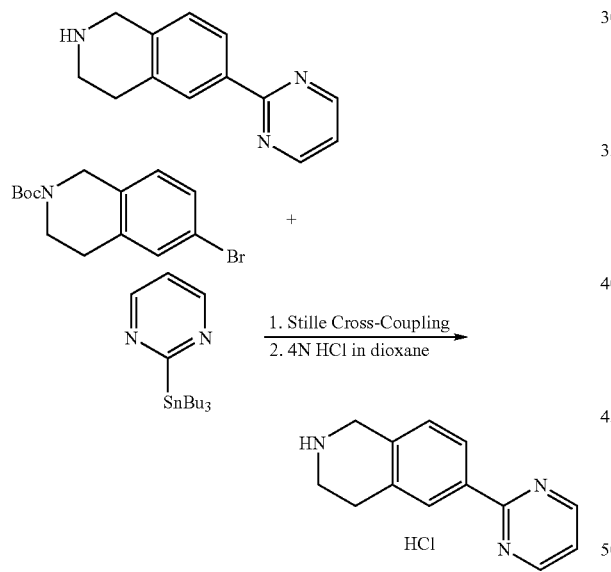

To a Schlenk tube were charged Pd₂(dba)₃ (10 mg, 0.01 mmol), bis(tri-tert-butylphosphine)palladium (20 mg, 0.04 mmol), CuI (16 mg, 0.08 mmol) and CsF (334 mg, 2.2 mmol). The tube was evacuated under high vacuum and back-filled with nitrogen for three cycles. DMF (2 ml) was introduced, followed by 2-tributylstannylpyrimidine (537 mg, 1.4 mmol). The tube was sealed with a Teflon cap and the reaction mixture was heated with stirring at 120° C. for 2 hours. After cooling, the mixture was filtered through Celite, washed with ethyl acetate. Filtrate was washed with water three times, brine and dried (MgSO₄). After concentration the residue was purified on silica gel eluting with ethyl acetate in hexanes (0-100%) to give 6-pyrimidin-2-yl-3,4-dihydro-1H-isoquinoline-2-carboxylic acid tert-butyl ester (28 mg). The compound was treated with 4N HCl in dioxane for 30 minutes. After concentration title compound was obtained as hydrochloride salt.

Preparation 81

Preparation of 4-Benzothiazol-2-yl-3,6-dihydro-2H-pyridine-1-carboxylic acid tert-butyl ester (Compound 21BB)

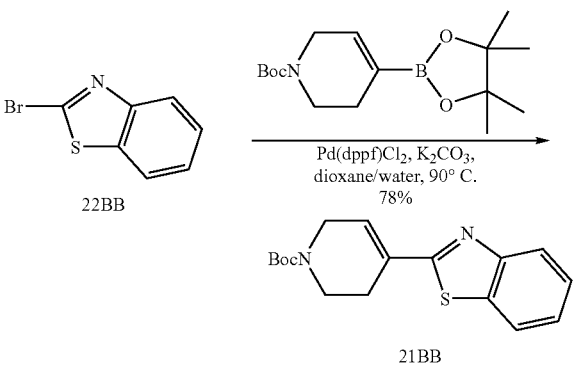

A mixture of 2-bromo-benzothiazole (0.38 g, 1.1 mmol), 4-(4,4,5,5-tetramethyl-[1,3,2]dioxaborolan-2-yl)-3,6-dihydro-2H-pyridine-1-carboxylic acid tert-butyl ester (0.5 g, 1.62 mmol), potassium carbonate (0.67 g, 4.85 mmol), Pd(dppf)Cl₂ (0.132 g, 0.16 mmol) and 4/1/dioxane/water (10 ml) was degassed for 15 minutes. Then it was heated at 90° C. for overnight. Cooled to room temperature and diluted with EtOAc (200 mL). The organic layer was washed with water (100 ml), dried over Na₂SO₄, filtered and concentrated. The residue was purified on silica gel to give the desired product 21BB (0.4 g, 78%).

Preparation 82

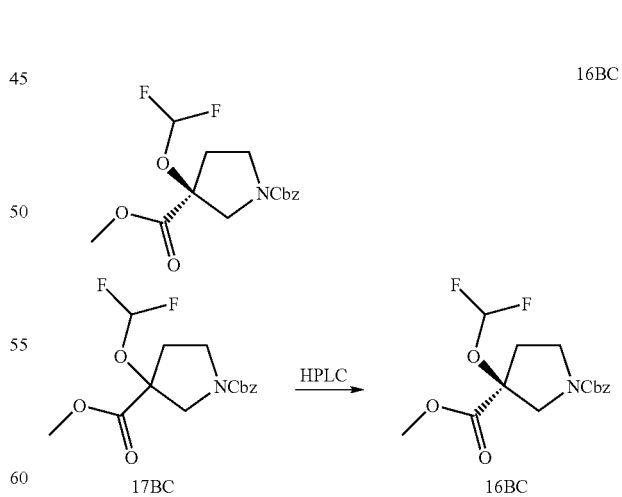

The Compound 17BC is prepared following a procedure similar to that of Preparation 37 Steps 1 to 4 by substituting 3-oxo-pyrrolidine-1-carboxylic acid benzyl ester for 3-oxo-pyrrolidine-1-carboxylic acid tert-butyl ester in Step 1 of Preparation 37. Compound 17BC was separated on HPLC using ChiralCel AS column eluting with 25% isopropanol/ 75% hexane. The first peak (retention time 46 minutes) was the desired product 16BC.

Preparation 83

Preparation of 3-(4,4-Difluoro-piperidin-1-yl)-1-trityl-1H-indazol-5-ylamine (Compound 13BD)

Step 1: Preparation of 3-(4,4-Difluoro-piperidin-1-yl)-5-nitro-1-trityl-1H-indazole The Compound 14BD was converted to Compound 15BD using the procedure as described for the preparation of Compound 4AD (Preparation 49 Step 2) from Compound 2AD (Preparation 49 Step 2).

Step 2

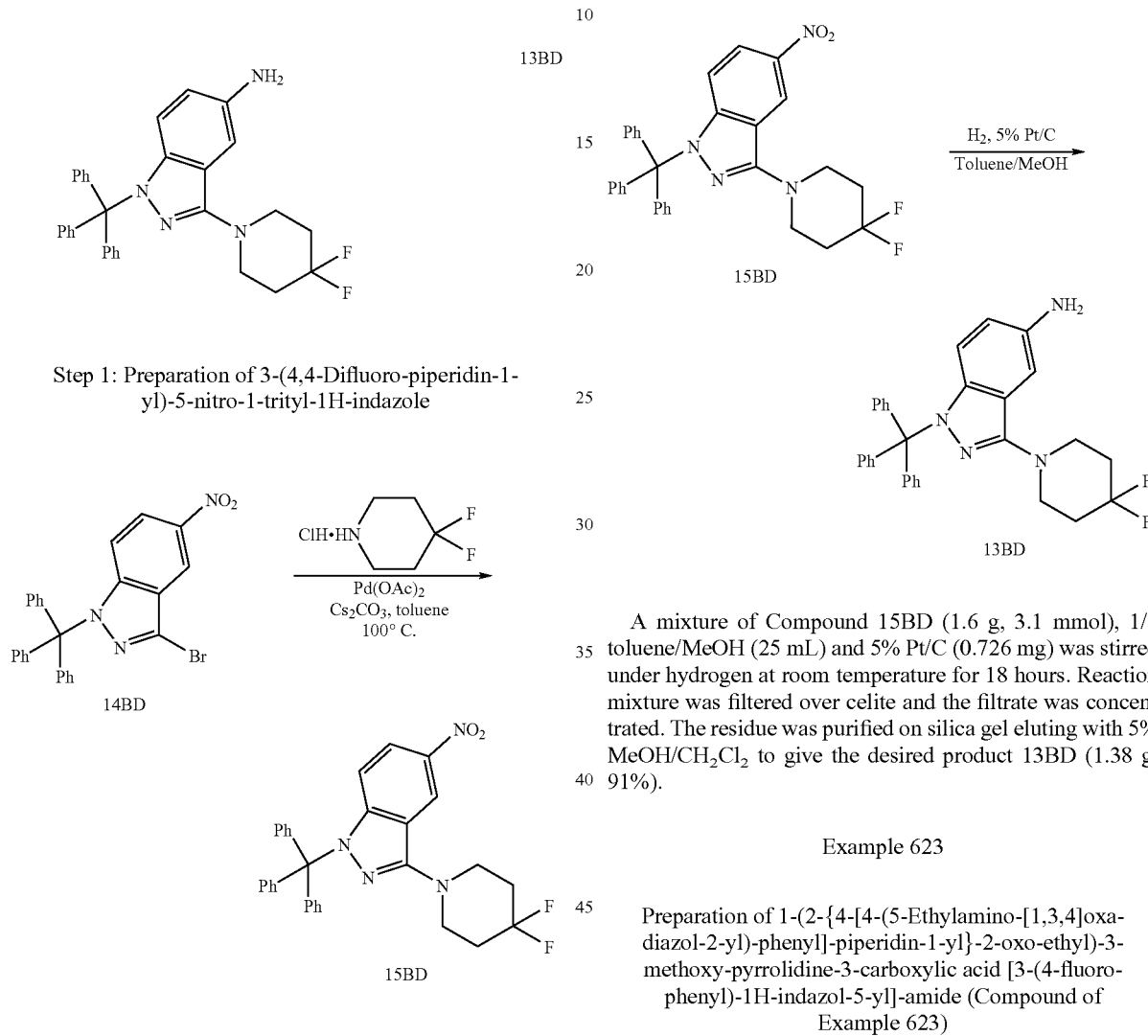

A mixture of Compound 15BD (1.6 g, 3.1 mmol), 1/1 toluene/MeOH (25 mL) and 5% Pt/C (0.726 mg) was stirred under hydrogen at room temperature for 18 hours. Reaction mixture was filtered over celite and the filtrate was concentrated. The residue was purified on silica gel eluting with 5% MeOH/$CH_2Cl_2$ to give the desired product 13BD (1.38 g, 91%).

Example 623

Preparation of 1-(2-{4-[4-(5-Ethylamino-[1,3,4]oxadiazol-2-yl)-phenyl]-piperidin-1-yl}-2-oxo-ethyl)-3-methoxy-pyrrolidine-3-carboxylic acid [3-(4-fluoro-phenyl)-1H-indazol-5-yl]-amide (Compound of Example 623)

Compound of Example 623

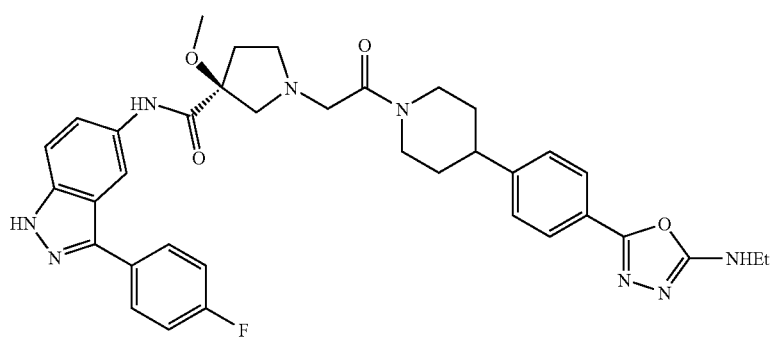

Step 1: Preparation of 4-(4-Methoxycarbonyl-phenyl)-piperidine-1-carboxylic acid tert-butyl ester

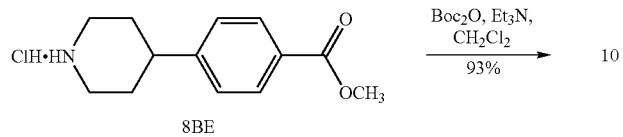

8BE

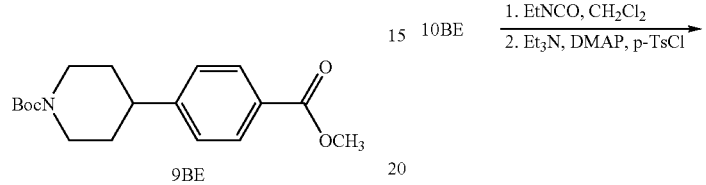

9BE

A mixture of Compound 8BE (3 g, 11.73 mmol), CH₂Cl₂ (30 mL), triethyl amine (4.9 mL, 35.19 mmol) and di-tert-butyl dicarbonate (3.83 g, 17.55 mmol) was stirred at room temperature for 3 hours. Diluted with CH₂Cl₂ (100 mL) and washed with water (100 mL). The organic layer was dried over Na₂SO₄, filtered and concentrated. The residue was purified on silica gel eluting with 100% EtOAc to give the desired product 9BE (3.5 g, 93%).

Step 2: Preparation of 4-(4-Hydrazinocarbonyl-phenyl)-piperidine-1-carboxylic acid tert-butyl ester

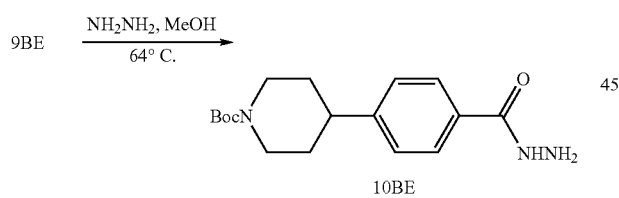

10BE

The Compound 9BE was converted to Compound 10BE using the procedure as described for the preparation of Compound 2AR from Compound 1AR (Example 622 Step 1).

Step 3: Preparation of 4-[4-(5-Ethylamino-[1,3,4]oxadiazol-2-yl)-phenyl]-piperidine-1-carboxylic acid tert-butyl ester (Compound 11BE)

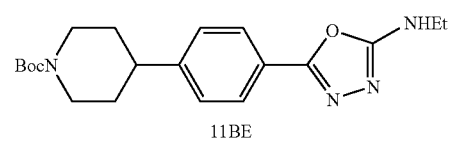

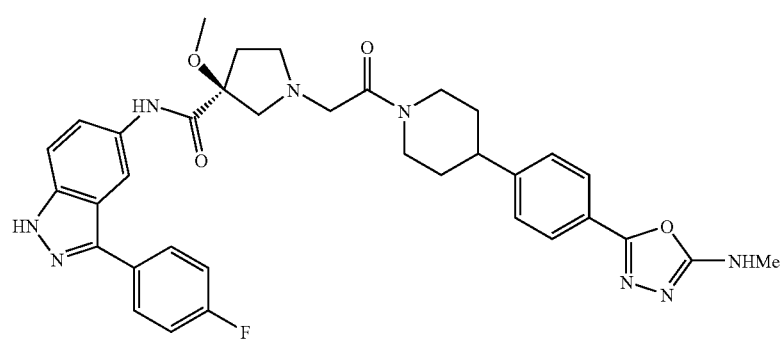

11BE

The Compound 10BE was converted to Compound 11BE using the procedure as described for the preparation of Compound 3AR from Compound 2AR (Example 622 Step 2).

Step 4

The Compound 11BE was converted to the compound of Example 623 using the procedure as described for the preparation of the compound of Example 622 from Compound 4AR.

Example 624

Preparation of 1-(2-{4-[4-(5-methylamino-[1,3,4]oxadiazol-2-yl)-phenyl]-piperidin-1-yl}-2-oxo-ethyl)-3-methoxy-pyrrolidine-3-carboxylic acid [3-(4-fluoro-phenyl)-1H-indazol-5-yl]-amide (Compound of Example 624)

Compound of Example 624

The compound of Example 624 was prepared from Compound 10BE (Example 623 Step 3) using the procedure as described for the preparation of the compound of Example 623 from Compound 10BE but using methyl isocyanate in place of ethyl isocyanate.

Preparation 84

Preparation of 2-Chloro-1-{4-[2-Fluoro-4-(5-methyl-[1,3,4]oxadiazol-2-yl)-phenyl]-3,6-dihydro-2H-pyridin-1-yl}-ethanone (Compound 20BF)

Compound 20BF

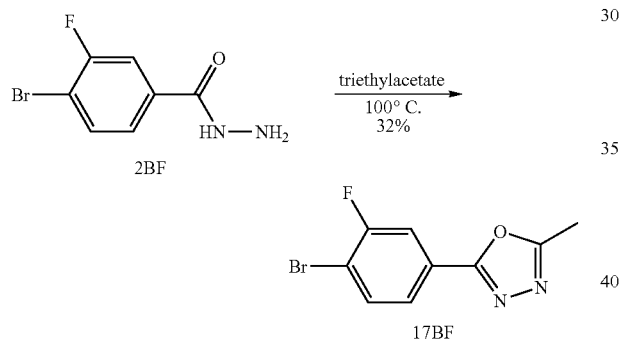

Step 1: Preparation of 2-(4-Bromo-3-fluoro-phenyl)-5-methyl-[1,3,4]oxadiazole

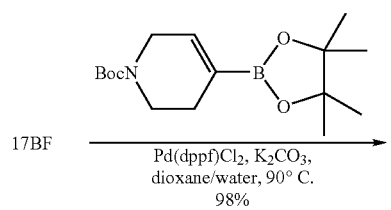

A mixture of Compound 2BF (0.9 g, 2.53 mmol) and triethylacetate (5 mL) was heated at 100° C. for 18 hours. Cooled to room temperature and poured into water (100 mL). Extracted with EtOAc (100 mL). The organic layer was dried (Na₂SO₄), filtered and concentrated. The residue was purified on silica gel eluting with 20% EtOAc/hexane to give the desired product 17BF (0.36 g, 32%).

Step 2: Preparation of 4-[2-Fluoro-4-(5-methyl-[1,3,4]oxadiazol-2-yl)-phenyl]-3,6-dihydro-2H-pyridine-1-carboxylic acid tert-butyl

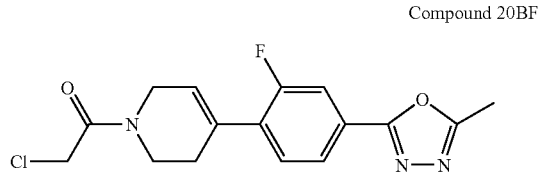 [SMILES: Cc1nnc(-c2ccc(C3=CCN(C(=O)CCl)CC3)c(F)c2)o1]

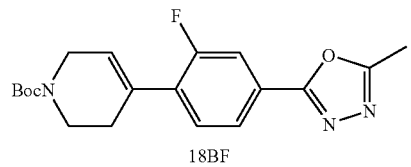

A mixture of Compound 17BF (0.34 g, 0.99 mmol), 4-(4,4,5,5-tetramethyl-[1,3,2]dioxaborolan-2-yl)-3,6-dihydro-2H-pyridine-1-carboxylic acid tert-butyl ester (0.37 g, 1.19 mmol), potassium carbonate (0.41 g, 2.97 mmol), Pd(dppf)Cl₂ (0.081 g, 0.099 mmol) and 4/1/dioxane/water (10 ml) was degassed for 15 minutes. Then it was heated at 90° C. for overnight. Cooled to room temperature and diluted with EtOAc (200 ml). The organic layer was washed with water (100 ml), dried over Na₂SO₄, filtered and concentrated. The residue was purified on silica gel to give the desired product 18BF (0.35 g, 98%).

Step 3: Preparation of 4-[2-Fluoro-4-(5-methyl-[1,3,4]oxadiazol-2-yl)-phenyl]-1,2,3,6-tetrahydro-pyridine

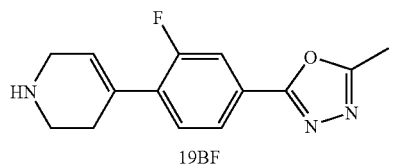

The Compound 18BF (0.44 g, 1.13 mmol) was converted to Compound 19BF using the procedure as described for the preparation of Compound 5AR from Compound 4AR (Example 622 Step 4).

Step 4

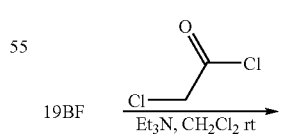

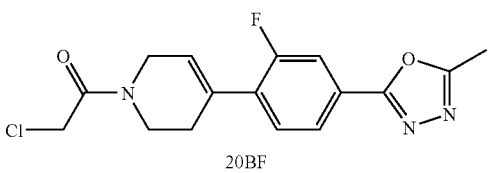

The Compound 19BF (0.44 g, 1.13 mmol) was converted to Compound 20BF using the procedure as described for the preparation of Compound 6AR from Compound 5AR (Example 622 Step 5).

Preparation 85

3-(1-Methyl-1H-pyrazol-3-yl)-5-nitro-1-trityl-1H-indazole

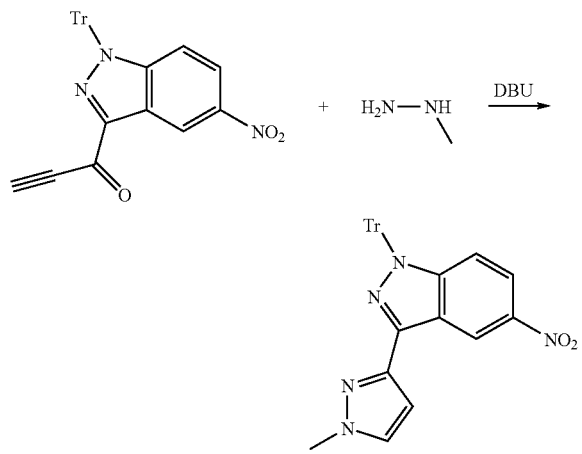

A mixture of 1-(5-nitro-1-trityl-1H-indazol-3-yl-)-propynone (0.5 g, 1.09 mmol), methyl hydrazine hydrochloride (1.75 mmol) and DBU (1.6 ml, 10.9 mmol) in acetonitrile (10 ml) was heated at 120° C. for 50 minutes under microwave. It was then cooled to room temperature and diluted with DCM (60 ml). The organic layer was washed with water (10 ml), dried over MgSO$_4$, filtered and concentrated. The residue was purified on silica gel eluting with 1/1 EtOAc/Hexane to give the desired product (0.42 g, 79%). MS (ESMS, M+H 486)

Reduction of the 5-nitro compound was achieved by hydrogenation as stated previously Preparation 63

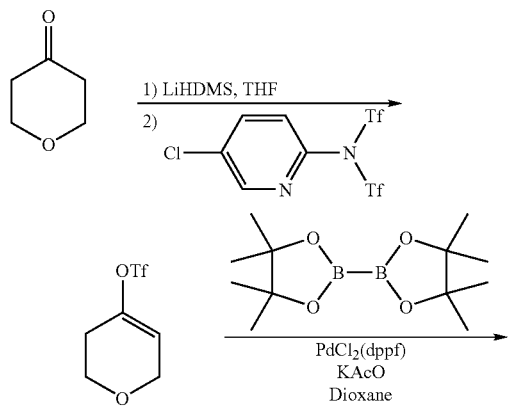

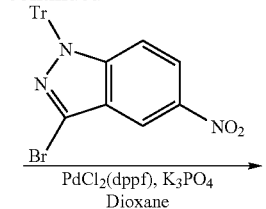

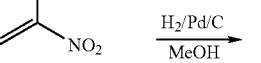

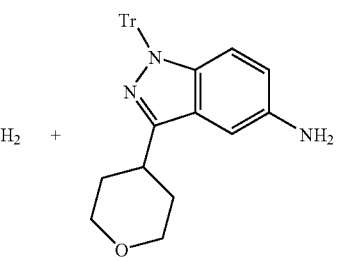

Step 1: Preparation of Trifluoro-methanesulfonic acid 3,6-dihydro-2H-pyran-4-yl ester To a solution of 4-tetrahydropyranone (2 g, 0.02 mol) in THF (10 mL) at −78° C., LiHMDS (1 M, 11 ml) was added dropwise through a syringe. The formed solution was then stirred at −78° C. for about 1 hour. The reaction was warmed up to room temperature briefly and was cooled back to −78° C. Then 2-[N,N-bis(trifluoromethylsulfonyl)amino]-5-chloropyrine (7.85 g, 0.02 mol) was added in four portions. The resulted reaction mixture was gradually warmed up to room temperature and was stirred for overnight. After removal of solvent, the residue was purified using chromatography (eluted with DCM/Hexane=80/20) to give product as a colorless oil (3 g).

Step 2: Preparation of 4-(4,4,5,5-Tetramethyl-[1,3,2] dioxaborolan-2-yl)-3,6-dihydro-2H-pyran A 250 mL round bottom flask containing trifluoro-methanesulfonic acid 3,6-dihydro-2H-pyran-4-yl ester (2.7 g, 11.6 mmol), PdCl$_2$(dppf) (440 mg, 0.6 mmol) and potassium acetate (3 g, 36 mmol) in dioxane (20 mL) was flushed with Ar three times. The reaction mixture was heated at 80° C. for overnight. After the reaction was cooled to room temperature, the reaction mixture was filter through a column packed with celite and the filtrate was concentrated. The residue was purified using column chromatography (10% hexane in dichloromethane) and product was obtained as white solid (2 g, 81% yield).

Step 3: Preparation of 3-(3,6-Dihydro-2H-pyran-4-yl)-5-nitro-1-trityl-1H-indazole A mixture containing 4-(4,4,5,5-Tetramethyl-[1,3,2]dioxaborolan-2-yl)-3,6-dihydro-2H-pyran (0.8 g, 3.8 mmol), 3-Bromo-5-nitro-1-trityl-1H-indazole (2 g, 4.0 mmol), PdCl$_2$ (dppf) (150 mg, 0.2 mmol) and potassium phosphate (2.6 g, 12 mmol) in dioxane (10 mL) was flushed with Ar and was heated at 80° C. for overnight under Ar. LC-MS indicated the completion of reaction and the mixture was filter through celite. The filtrate was concentrated and was purified on a column (10 hexane in dichloromethane) to give 1.2 g of product (64% yield).

Step 4: Preparation of 3-(3,6-Dihydro-2H-pyran-4-yl)-1-trityl-1H-indazol-5-ylamine and 3-(Tetrahydro-pyran-4-yl)-1-trityl-1H-indazol-5-ylamine To a solution of 3-(3,6-Dihydro-2H-pyran-4-yl)-5-nitro-1-trityl-1H-indazole (100 mg, 0.2 mmol) in methanol was added and Pd/C (10%, 20 mg). The reaction mixture was evacuated under vacuum and hydrogen gas was filled. After repeated three times the reaction was kept under hydrogen atmosphere overnight at room temperature. LCMS showed the starting material was consumed completely and both 3-(3,6-dihydro-2H-pyran-4-yl)-1-trityl-1H-indazol-5-ylamine and 3-(tetrahydro-pyran-4-yl)-1-trityl-1H-indazol-5-ylamine were obtained. The two products were separated using prep-HPLC to give both product in 60% and 40% yield respectively.

Preparation 87

4-Quinoxalin-6-yl-3,6-dihydro-2H-pyridine-1-carboxylic acid tert-butyl ester

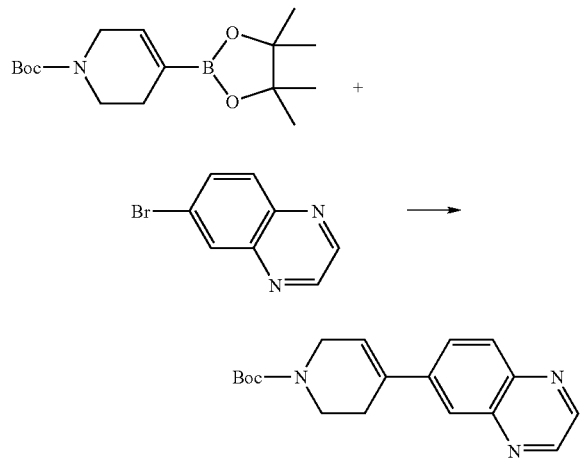

A solution containing 6-bromo-quinoxaline (417 mg, 2.0 mmol), 4-(4,4,5,5-tetramethyl-[1,3,2]dioxaborolan-2-yl)-3,6-dihydro-2H-pyridine-1-carboxylic acid tert-butyl ester (600 mg, 1.94 mmol), tetrakis [triphenylphosphine] palladium (108 mg, 0.1 mmol) and sodium carbonate (2 M solution, 3 mL) in 5 mL of dioxane/ethanol/water (7:3:1) was heated at 160° C. using microwave reactor for 15 minutes. After the reaction, ethylacetate was added and the mixture was filtered, washed with water. After concentration under vacuum, the product was purified using column chromatography (5% methanol in dichloromethane)

Preparation 88

1-N Trityl-4-(5-Amino-1-methyl-1H-indazol-3-yl)-pyrazole-1-carboxylic acid tert-butyl ester Step 1

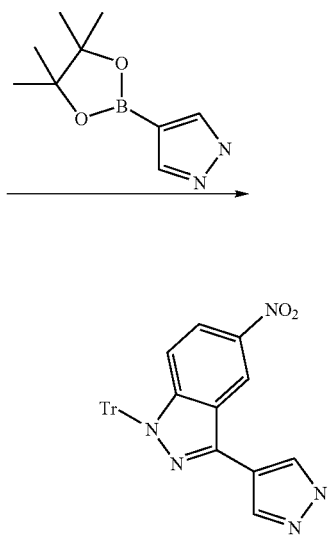

To a vial containing 3-bromo-5-nitro-1-trityl-1H-indazole (1.45 g, 3.00 mmol), 4-(4,4,5,5-TETRAMETHYL-1,3,2-DI-OXABOROLAN-2-YL)-1H-PYRAZOLE (0.873 g, 4.50 mmol) [1,1'-Bis(diphenylphosphino)ferrocene]dichloropalladium(II), complex with dichloromethane (1:1) (0.245 g, 0.300 mmol) and Potassium phosphate (1.59 g, 7.50 mmol) in a mixture of 1,4-Dioxane (25 mL, 320 mmol) Water (12 mL, 670 mmol) was degassed under an atmosphere of Nitrogen. This rxn mixture was heated at 80° C. overnight under an atmosphere of Nitrogen. TLC (20% EtOAc/hexane) showed starting material. MS showed (M+H) at 472. The rxn was diluted with EtOAc and Water (50/50 mL) and filtered through Celite. The org. layer was washed with water, dried over Magnesium sulfate (2 g, 20 mmol) and rotavap to give a crude, 2.2 g. The crude was chrom. (30% EtOAc/Hexane) on Biotage (40 L) to obtain the product (fraction 2), M+H at 472, 5-nitro-3-(1H-pyrazol-4-yl)-1-trityl-1H-indazole (0.54 g; Yield=38%)

Step 2

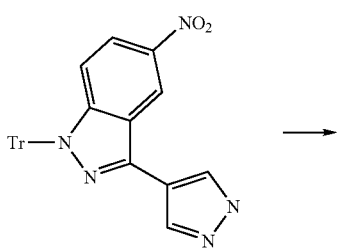

-continued

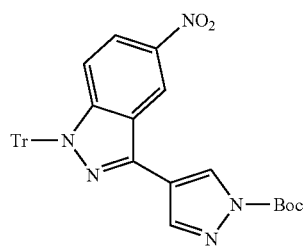

Into a Round bottom flask was added 5-nitro-3-(1H-pyrazol-4-yl)-1-trityl-1H-indazole (0.390 g, 0.827 mmol, recovered unreacted starting material, Methylene chloride (5.00 mL, 78.0 mmol), Di-tert-Butyldicarbonate (0.228 g, 1.04 mmol) 4-Dimethylaminopyridine (0.127 g, 1.04 mmol) The rxn was stirred for 2 days under an atmosphere of Nitrogen. TLC (20% EtOAc/Hexane) showed rxn complete. The rxn was loaded onto Biotage, 40S and eluted with 20% EtOAc/hexane to give tert-butyl 4-(5-nitro-1-trityl-1H-indazol-3-yl)-1H-pyrazole-1-carboxylate (0.44 g; Yield=93%)

Step 3

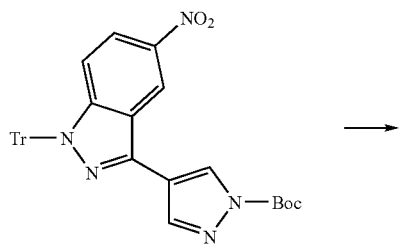

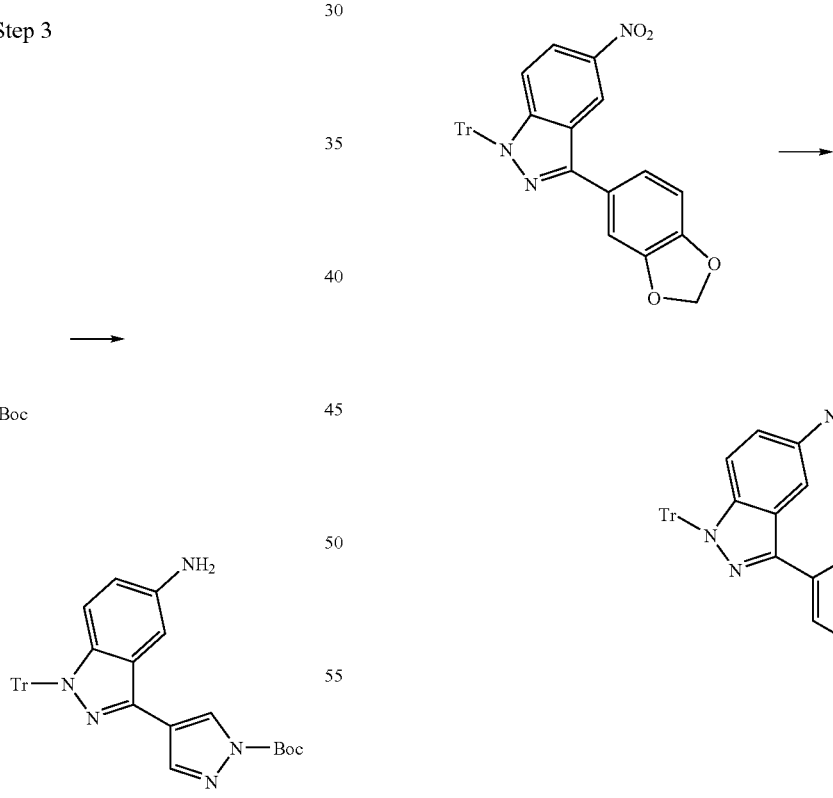

Into a Round bottom flask was added tert-butyl 4-(5-nitro-1-trityl-1H-indazol-3-yl)-1H-pyrazole-1-carboxylate (0.440 g, 0.770 mmol) and 10 mL of MeOH and 5 mL of EtOAc followed by Palladium (0.100 g, 0.000470 mmol). The rxn was degassed under Hydrogen (2000 mL, 90 mmol) in balloon, was stirred overnight. TLC (20% EtOAc/Hexane) and MS showed rxn complete. The rxn was filtered through Celite and was rotovaped to dryness to give tert-butyl 4-(5-amino-1-trityl-1H-indazol-3-yl)-1H-pyrazole-1-carboxylate (0.400 g; Yield=95.9%)

Preparation 89

Preparation of 1-N-Trityl-3-Benzo[1,3]dioxol-5-yl-1-methyl-1H-indazol-5-ylamine

1-N-Trityl-3-Benzo[1,3]dioxol-5-yl-1-methyl-1H-indazol-5-ylamine was prepared by substituting 5-(4,4,5,5-Tetramethyl-[1,3,2]dioxaborolan-2-yl)-benzo[1,3]dioxole for 4-(4,4,5,5-Tetramethyl-[1,3,2]dioxaborolan-2-yl)-1H-pyrazole in Preparation 88 in Steps 1 & 3.

Table 27 provides data for the compounds of Examples 613 to 623.

TABLE 27
| Ex No. | COMPOUND | M + 1 | Retention Time (min) |
|---|---|---|---|
| 613 (16AA) | 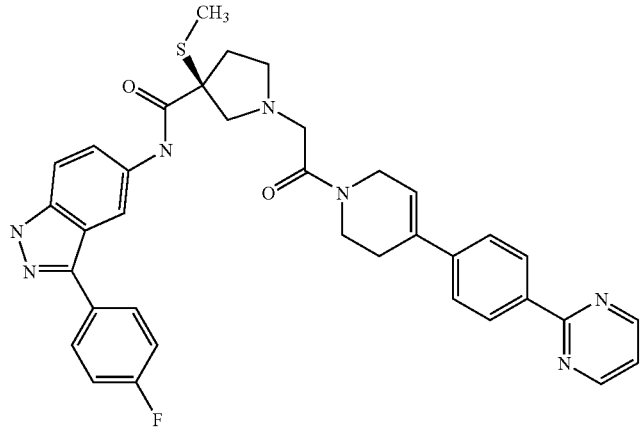 [SMILES: CS[C@@]1(C(=O)Nc2ccc3[nH]nc(-c4ccc(F)cc4)c3c2)CCN(CC(=O)N2CC=C(c3ccc(-c4ncccn4)cc3)CC2)C1] | 648.4 | 2.8 |
| 614 (9AB) | 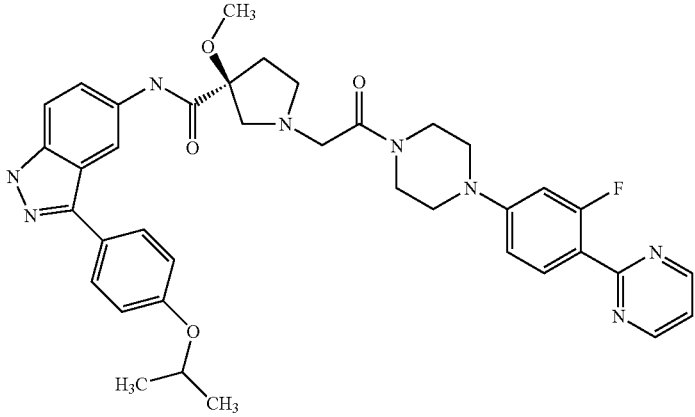 [SMILES: CO[C@@]1(C(=O)Nc2ccc3[nH]nc(-c4ccc(OC(C)C)cc4)c3c2)CCN(CC(=O)N2CCN(c3ccc(-c4ncccn4)c(F)c3)CC2)C1] | 693.4 | 2.84 |
| 615 11AB | 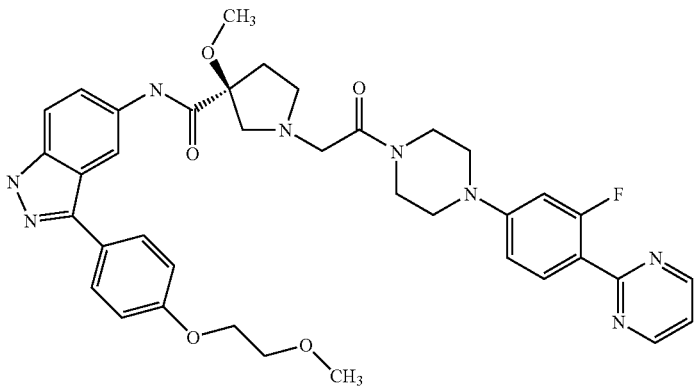 [SMILES: COCCOc1ccc(-c2n[nH]c3ccc(NC(=O)[C@]4(OC)CCN(CC(=O)N5CCN(c6ccc(-c7ncccn7)c(F)c6)CC5)C4)cc23)cc1] | 709.4 | 2.54 |

TABLE 27-continued

| Ex No. | COMPOUND | M + 1 | Retention Time (min) |
|---|---|---|---|
| 616 (13AB) | | 669.4 | 2.75 |
| 617 (25AB) | | 638.4 | 3.33 |
| 619 (33AB) | | 653.4 | 2.89 |
| 620 | | 648.4 | 2.12 |

TABLE 27-continued
| Ex No. | COMPOUND | M + 1 | Retention Time (min) |
|---|---|---|---|
| 621 | 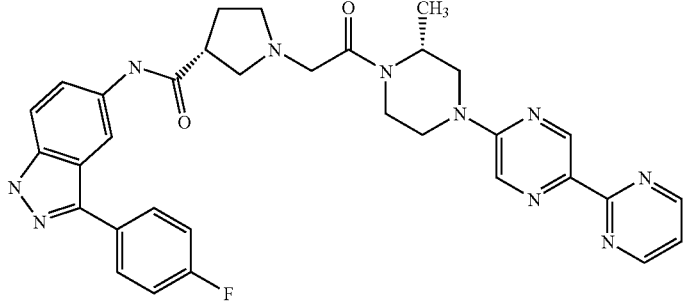 [SMILES: C[C@@H]1CN(c2cnc(-c3ncccn3)cn2)CCN1C(=O)CN1CC[C@@H](C(=O)Nc2ccc3[nH]nc(-c4ccc(F)cc4)c3c2)C1] | 623 | 2.42 |
| 622 | 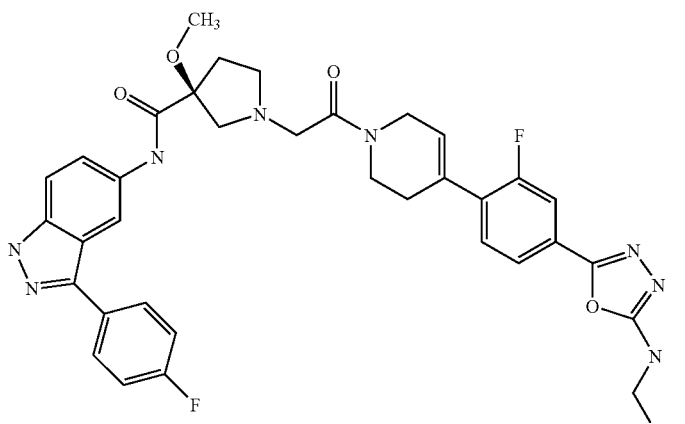 | 683.4 | 2.98 |
| 623 | 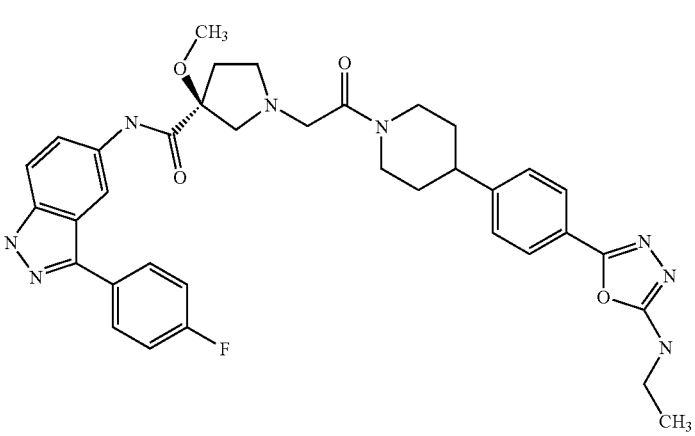 [SMILES: CCNc1nnc(-c2ccc(C3CCN(C(=O)CN4CC[C@@](OC)(C(=O)Nc5ccc6[nH]nc(-c7ccc(F)cc7)c6c5)C4)CC3)cc2)o1] | 667.4 | 2.69 |
Examples 625 to 825
Following the procedures described above, as well as those indicated in Table 28, the compounds in Table 28 were prepared.

TABLE 28

| Ex No. | COMPOUND | M + 1 | Retention Time (min) |
|---|---|---|---|
| 625 | | 701.4 | 3.05 |
| 626 | | 680.4 | 2.99 |
| 627 | (see also Example 619) | 680.4 | 2.8 |

TABLE 28-continued
| Ex No. | COMPOUND | M + 1 | Retention Time (min) |
|---|---|---|---|
| 628 | 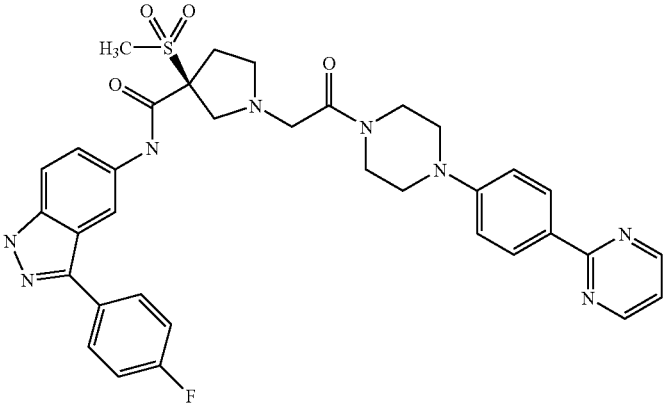 [SMILES: CS(=O)(=O)[C@@]1(C(=O)Nc2ccc3[nH]nc(-c4ccc(F)cc4)c3c2)CCN(CC(=O)N2CCN(c3ccc(-c4ncccn4)cc3)CC2)C1] | 683.4 | 2.93 |
| 629 | 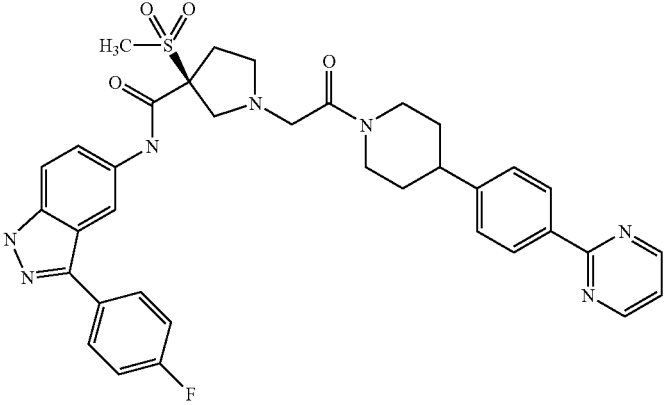 [SMILES: CS(=O)(=O)[C@@]1(C(=O)Nc2ccc3[nH]nc(-c4ccc(F)cc4)c3c2)CCN(CC(=O)N2CCC(c3ccc(-c4ncccn4)cc3)CC2)C1] | 682.4 | 2.83 |
| 630 | 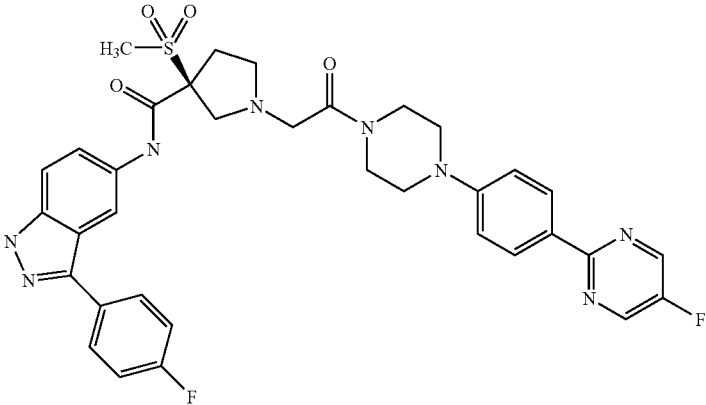 [SMILES: CS(=O)(=O)[C@@]1(C(=O)Nc2ccc3[nH]nc(-c4ccc(F)cc4)c3c2)CCN(CC(=O)N2CCN(c3ccc(-c4ncc(F)cn4)cc3)CC2)C1] | 701.4 | 3.04 |

TABLE 28-continued

| Ex No. | COMPOUND | M + 1 | Retention Time (min) |
|---|---|---|---|
| 631 | | 698.4 | 3.1 |
| 632 | | 681.4 | 2.5 |
| 633 | | 687.4 | 2.54 |

TABLE 28-continued

| Ex No. | COMPOUND | M + 1 | Retention Time (min) |
|---|---|---|---|
| 634 | | 703.4 | 2.33 |
| 635 | | 705.4 | 2.25 |
| 636 | | 721.4 | 2.38 |
| 637 | | 706.4 | 2.14 |

TABLE 28-continued
| Ex No. | COMPOUND | M + 1 | Retention Time (min) |
|---|---|---|---|
| 638 | 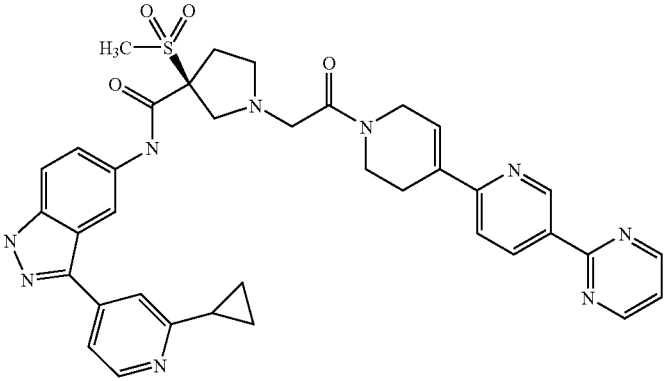 [SMILES: CS(=O)(=O)[C@@]1(C(=O)Nc2ccc3[nH]nc(-c4ccnc(C5CC5)c4)c3c2)CCN(CC(=O)N2CC=C(c3ccc(-c4ncccn4)cn3)CC2)C1] | 704.4 | 1.93 |
| 639 | 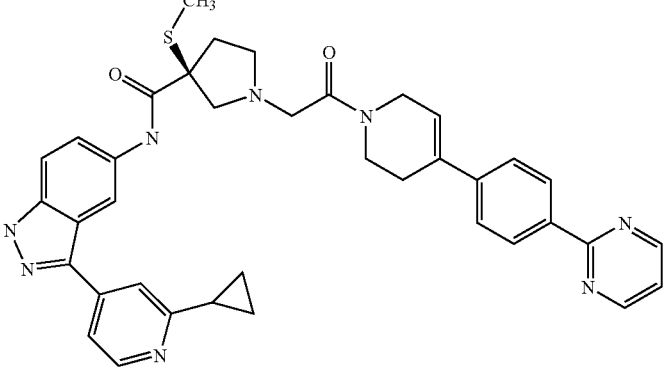 | 671.4 | 2.31 |
| 640 | 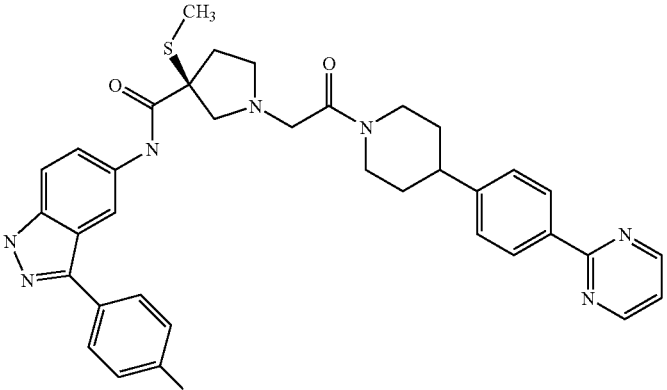 | 650.4 | 2.8 |

TABLE 28-continued
| Ex No. | COMPOUND | M + 1 | Retention Time (min) |
|---|---|---|---|
| 641 | 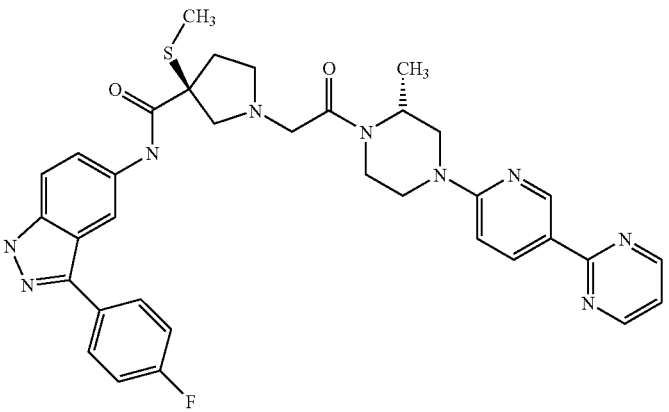 | 666.4 | 2.37 |
| 642 | 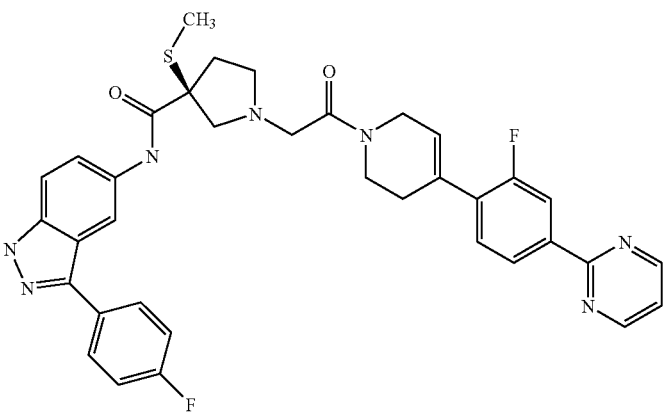 [SMILES: CS[C@@]1(C(=O)Nc2ccc3[nH]nc(-c4ccc(F)cc4)c3c2)CCN(CC(=O)N2CC=C(c3ccc(-c4ncccn4)cc3F)CC2)C1] | 666.4 | 3.14 |
| 643 | 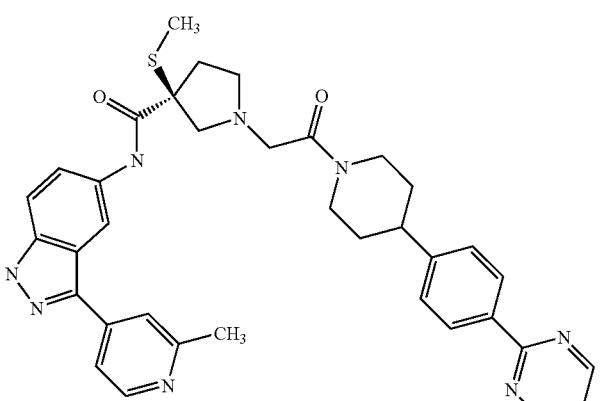 | 647.4 | 2.16 |

TABLE 28-continued

| Ex No. | COMPOUND | M + 1 | Retention Time (min) |
|---|---|---|---|
| 644 | | 645.4 | 2.03 |
| 645 | | 663.4 | 2.14 |
| 646 | | 704.4 | 2.7 |

TABLE 28-continued
| Ex No. | COMPOUND | M + 1 | Retention Time (min) |
|---|---|---|---|
| 647 | 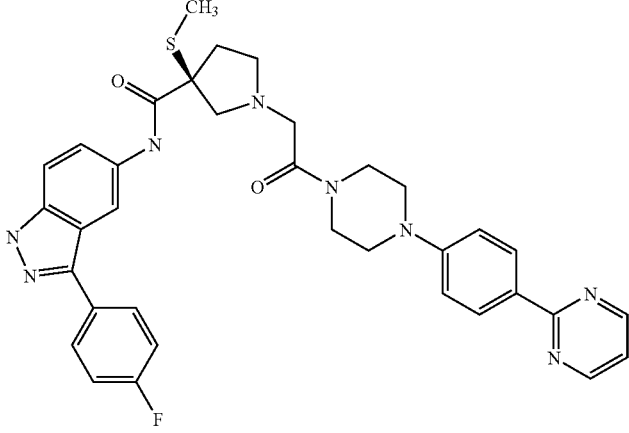 [SMILES: CS[C@@]1(C(=O)Nc2ccc3[nH]nc(-c4ccc(F)cc4)c3c2)CCN(CC(=O)N2CCN(c3ccc(-c4ncccn4)cc3)CC2)C1] | 651.4 | 2.74 |
| 648 | 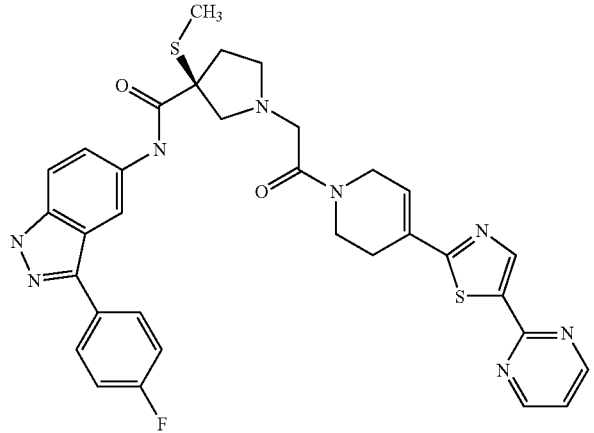 [SMILES: CS[C@@]1(C(=O)Nc2ccc3[nH]nc(-c4ccc(F)cc4)c3c2)CCN(CC(=O)N2CC=C(c3ncc(-c4ncccn4)s3)CC2)C1] | 655.4 | 2.72 |
| 649 | 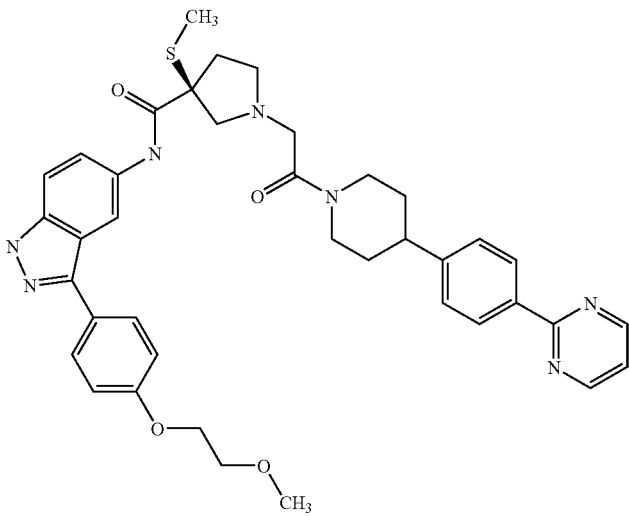 [SMILES: COCCOc1ccc(-c2n[nH]c3ccc(NC(=O)[C@]4(SC)CCN(CC(=O)N5CCC(c6ccc(-c7ncccn7)cc6)CC5)C4)cc23)cc1] | 706.4 | 2.8 |

TABLE 28-continued

| Ex No. | COMPOUND | M + 1 | Retention Time (min) |
|---|---|---|---|
| 650 | | 673.4 | 2.29 |
| 651 | | 689.4 | 2.4 |
| 652 | | 674.4 | 2.17 |
| 653 | | 672.4 | 2.01 |

TABLE 28-continued
| Ex No. | COMPOUND | M + 1 | Retention Time (min) |
|---|---|---|---|
| 654 | 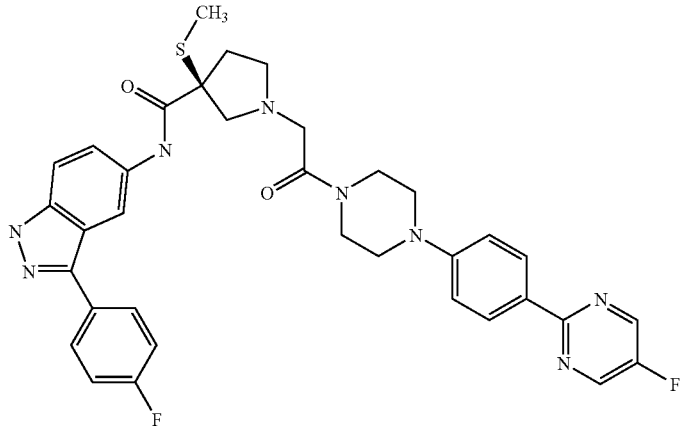 [SMILES: CS[C@@]1(C(=O)Nc2ccc3[nH]nc(-c4ccc(F)cc4)c3c2)CCN(CC(=O)N2CCN(c3ccc(-c4ncc(F)cn4)cc3)CC2)C1] | 669.4 | 3.16 |
| 655 | 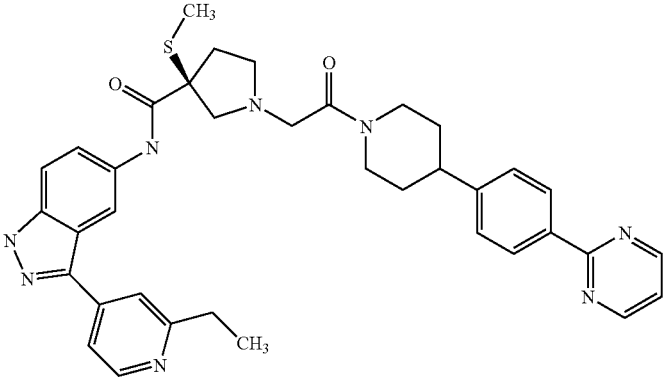 [SMILES: CCc1cc(-c2n[nH]c3ccc(NC(=O)[C@]4(SC)CCN(CC(=O)N5CCC(c6ccc(-c7ncccn7)cc6)CC5)C4)cc23)ccn1] | 661.4 | 2.82 |
| 656 | 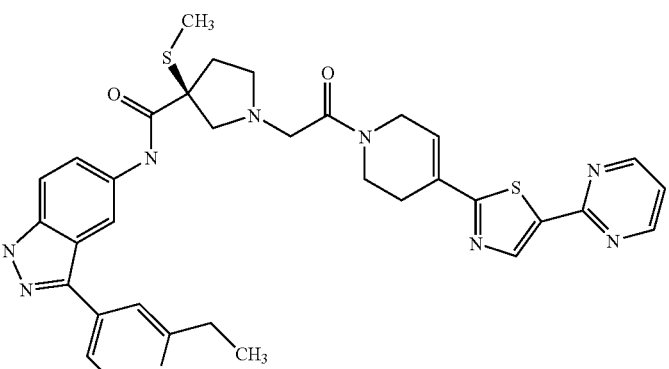 | 666.3 | 2.66 |

TABLE 28-continued

| Ex No. | COMPOUND | M + 1 | Retention Time (min) |
|---|---|---|---|
| 657 | | 695.3 | 2.83 |
| 658 | (see also Preparation 46) | 692.4 | 2.92 |
| 659 | | 736.4 | 2.8 |

TABLE 28-continued

| Ex No. | COMPOUND | M + 1 | Retention Time (min) |
|---|---|---|---|
| 660 | (see also Example 618) | 705.4 | 2.51 |
| 661 | | 668.4 | 3.06 |
| 662 | (see also Preparation 47) | 587.3 | 2.46 |

TABLE 28-continued

| Ex No. | COMPOUND | M + 1 | Retention Time (min) |
|---|---|---|---|
| 663 | (see also Preparation 49) | 671.4 | 2.8 |
| 664 | (see also Preparation 48) | 671.4 | 2.78 |
| 665 1389076 | | 645.4 | 2.48 |
| 666 1394448 | (see also Example 620) | 645.4 | 2.31 |

TABLE 28-continued
| Ex No. | COMPOUND | M + 1 | Retention Time (min) |
|---|---|---|---|
| 667 | 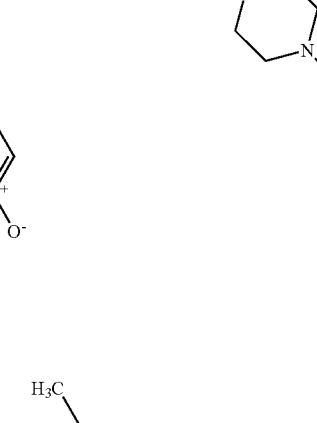 | 648.4 | 2.15 |
| 668 | 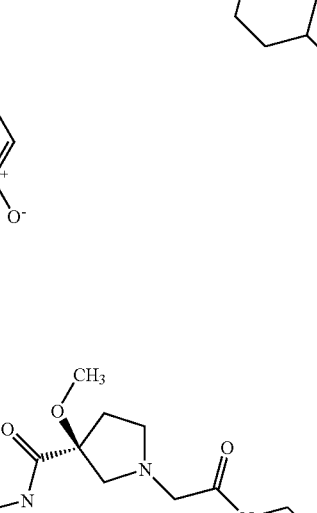 | 647.4 | 2.28 |
| 669 | 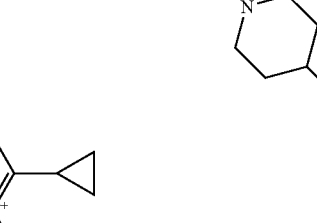 | 673.4 | 2.56 |

TABLE 28-continued
| Ex No. | COMPOUND | M + 1 | Retention Time (min) |
|---|---|---|---|
| 670 | 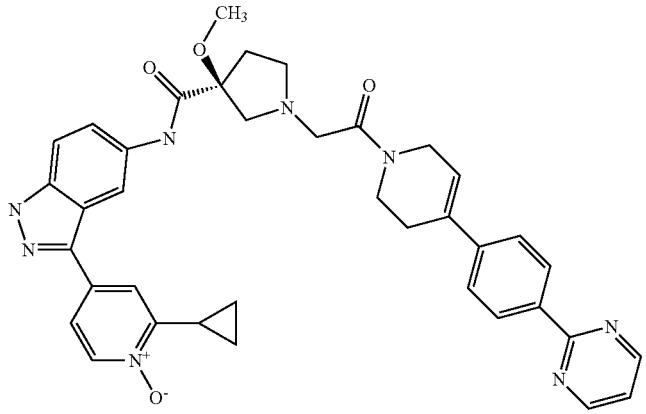 [SMILES: CO[C@@]1(C(=O)Nc2ccc3[nH]nc(-c4cc[n+]([O-])c(C5CC5)c4)c3c2)CCN(CC(=O)N2CC=C(c3ccc(-c4ncccn4)cc3)CC2)C1] | 671.4 | 2.58 |
| 671 | 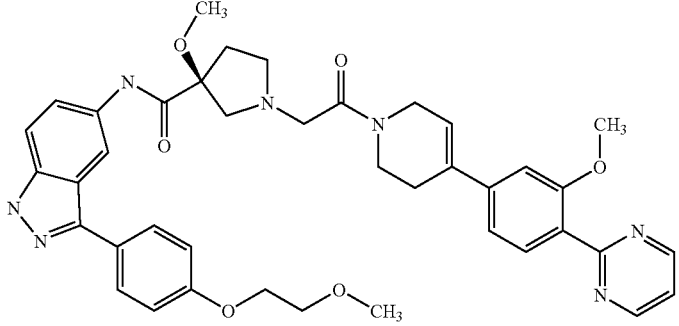 [SMILES: COCCOc1ccc(-c2n[nH]c3ccc(NC(=O)[C@]4(OC)CCN(CC(=O)N5CC=C(c6ccc(-c7ncccn7)c(OC)c6)CC5)C4)cc23)cc1] (see also Preparation 50) | 718.4 | 2.67 |
| 672 | 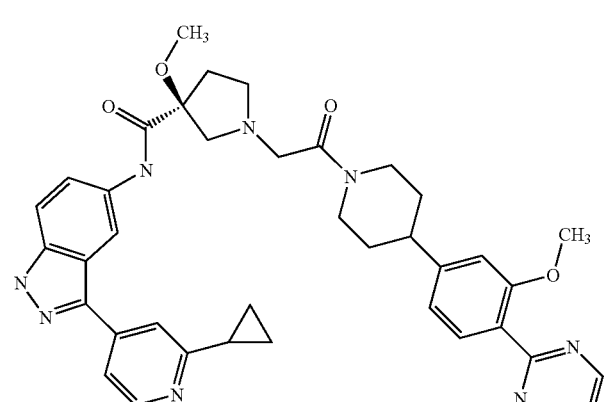 | 687.4 | 2.18 |

TABLE 28-continued

| Ex No. | COMPOUND | M + 1 | Retention Time (min) |
| --- | --- | --- | --- |
| 673 | | 685.4 | 2.13 |
| 674 | (see also Preparation 51) | 669.4 | 2.45 |
| 675 | (see also Preparation 52) | 685.4 | 2.98 |

TABLE 28-continued
| Ex No. | COMPOUND | M + 1 | Retention Time (min) |
|---|---|---|---|
| 676 | 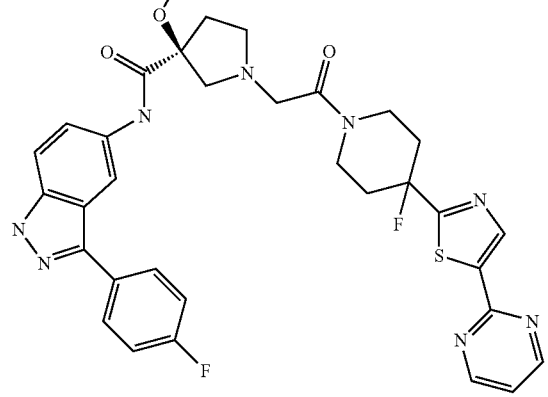 (see also Preparation 54) | 659.4 | 2.86 |
| 677 | 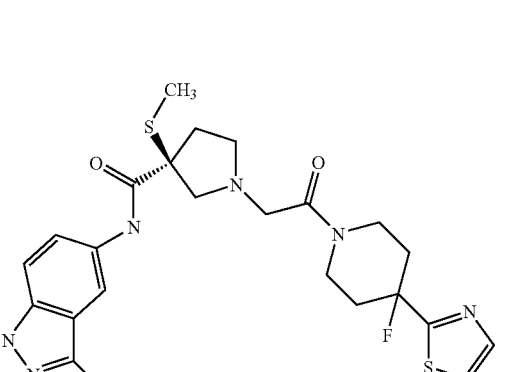 | 672.4 | 2.01 |
| 678 | 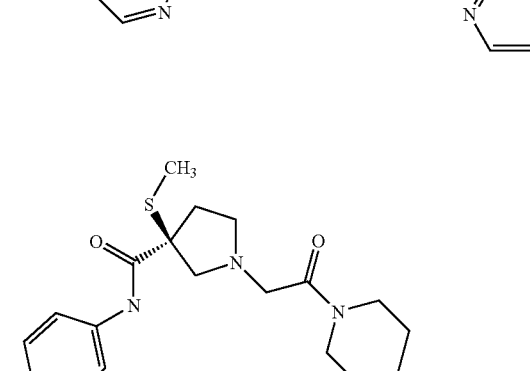 | 749.4 | 2.9 |

TABLE 28-continued
| Ex No. | COMPOUND | M + 1 | Retention Time (min) |
|---|---|---|---|
| 679 | 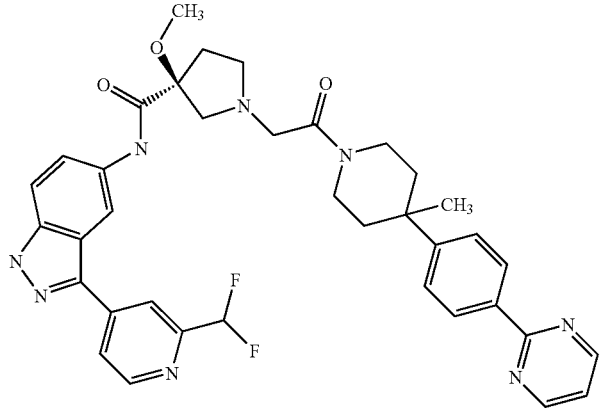 [SMILES: CO[C@@]1(C(=O)Nc2ccc3[nH]nc(-c4ccnc(C(F)F)c4)c3c2)CCN(CC(=O)N2CCC(C)(c3ccc(-c4ncccn4)cc3)CC2)C1] | 681.4 | 2.85 |
| 680 | 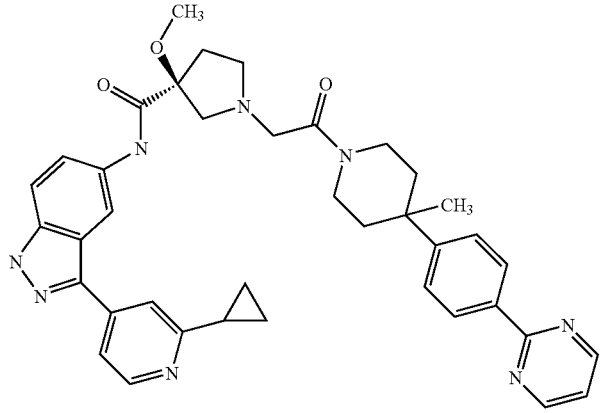 [SMILES: CO[C@@]1(C(=O)Nc2ccc3[nH]nc(-c4ccnc(C5CC5)c4)c3c2)CCN(CC(=O)N2CCC(C)(c3ccc(-c4ncccn4)cc3)CC2)C1] (see also Preparation 55) | 671.4 | 2.47 |
| 681 | 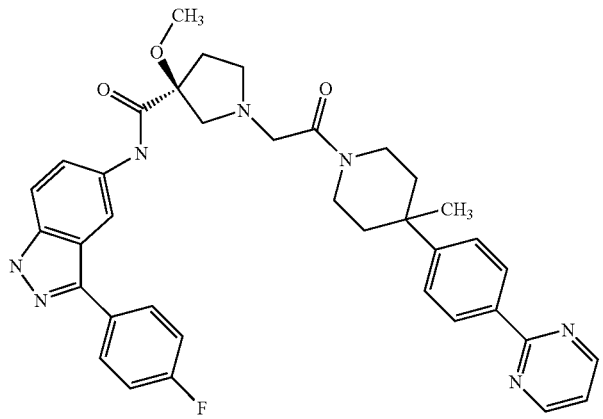 [SMILES: CO[C@@]1(C(=O)Nc2ccc3[nH]nc(-c4ccc(F)cc4)c3c2)CCN(CC(=O)N2CCC(C)(c3ccc(-c4ncccn4)cc3)CC2)C1] | 648.4 | 2 |

TABLE 28-continued
| Ex No. | COMPOUND | M + 1 | Retention Time (min) |
|---|---|---|---|
| 682 | 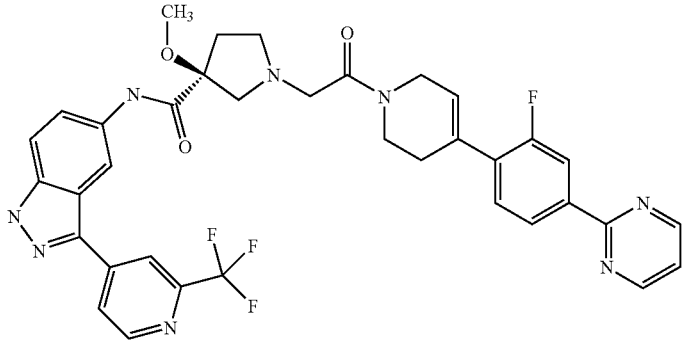 [SMILES: CO[C@@]1(C(=O)Nc2ccc3[nH]nc(-c4ccnc(C(F)(F)F)c4)c3c2)CCN(CC(=O)N2CC=C(c3ccc(-c4ncccn4)cc3F)CC2)C1] | 701.4 | 3.36 |
| 683 | 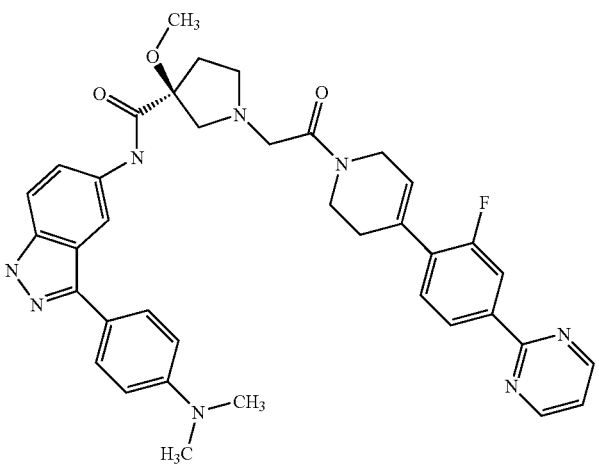 [SMILES: CO[C@@]1(C(=O)Nc2ccc3[nH]nc(-c4ccc(N(C)C)cc4)c3c2)CCN(CC(=O)N2CC=C(c3ccc(-c4ncccn4)cc3F)CC2)C1] | 675.4 | 2.33 |
| 684 | 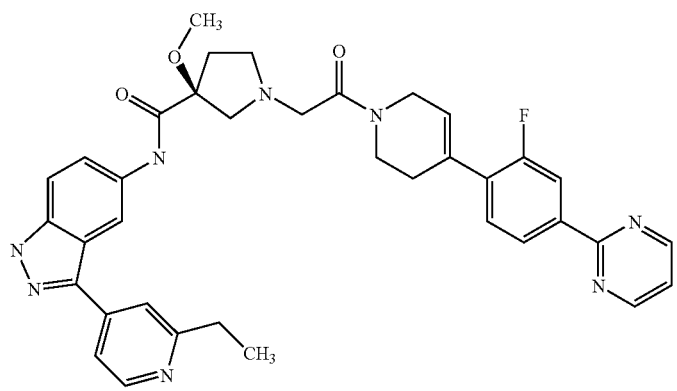 [SMILES: CCc1cc(-c2n[nH]c3ccc(NC(=O)[C@]4(OC)CCN(CC(=O)N5CC=C(c6ccc(-c7ncccn7)cc6F)CC5)C4)cc23)ccn1] | 661.7 | 3.21 |

TABLE 28-continued
| Ex No. | COMPOUND | M + 1 | Retention Time (min) |
|---|---|---|---|
| 685 | 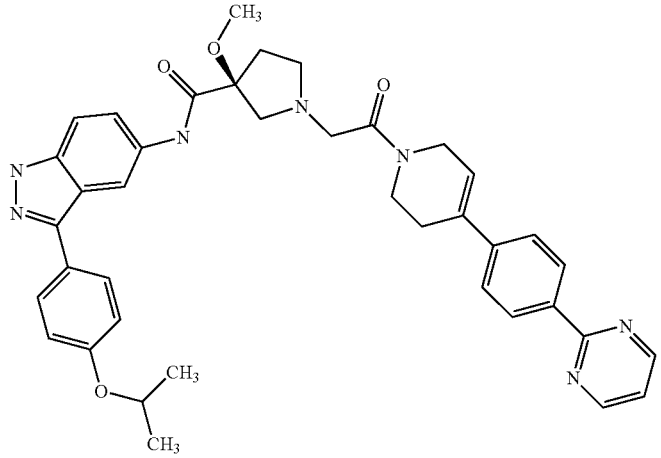 [SMILES: CO[C@@]1(C(=O)Nc2ccc3[nH]nc(-c4ccc(OC(C)C)cc4)c3c2)CCN(CC(=O)N2CC=C(c3ccc(-c4ncccn4)cc3)CC2)C1] (see also Preparation 56) | 623 | 2.41 |
| 686 | 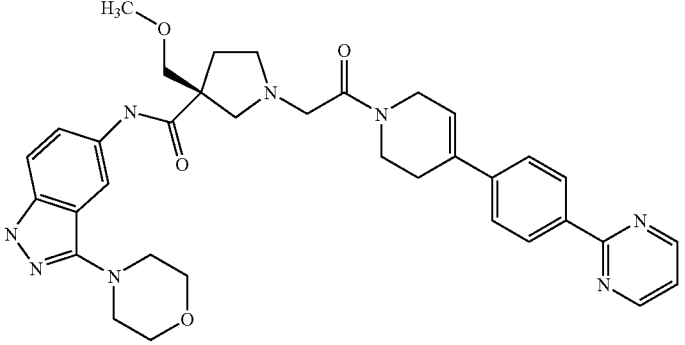 [SMILES: COC[C@@]1(C(=O)Nc2ccc3[nH]nc(N4CCOCC4)c3c2)CCN(CC(=O)N2CC=C(c3ccc(-c4ncccn4)cc3)CC2)C1] | 637 | 2.65 |
| 687 | 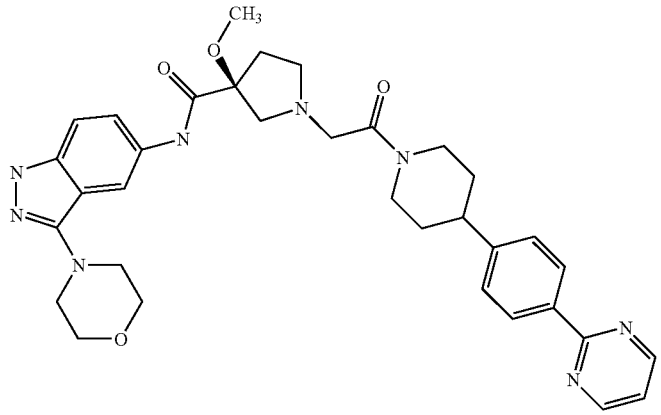 [SMILES: CO[C@@]1(C(=O)Nc2ccc3[nH]nc(N4CCOCC4)c3c2)CCN(CC(=O)N2CCC(c3ccc(-c4ncccn4)cc3)CC2)C1] | 625 | 2.47 |

TABLE 28-continued
| Ex No. | COMPOUND | M + 1 | Retention Time (min) |
|---|---|---|---|
| 688 | 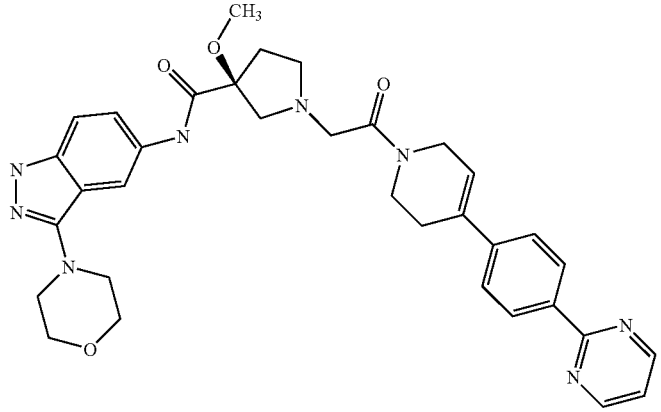 [SMILES: CO[C@@]1(C(=O)Nc2ccc3[nH]nc(N4CCOCC4)c3c2)CCN(CC(=O)N2CC=C(c3ccc(-c4ncccn4)cc3)CC2)C1] | 672 | 3.08 |
| 689 | 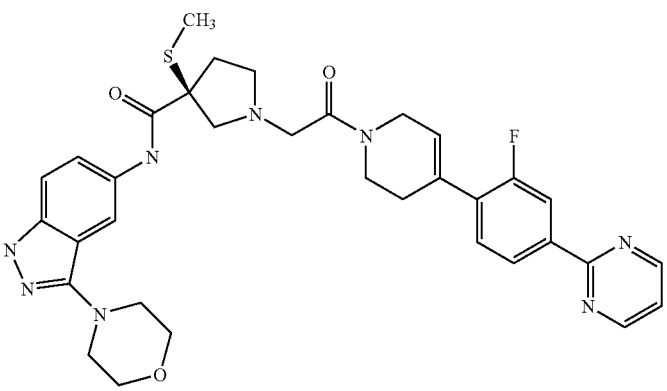 | 657 | 2.63 |
| 690 | 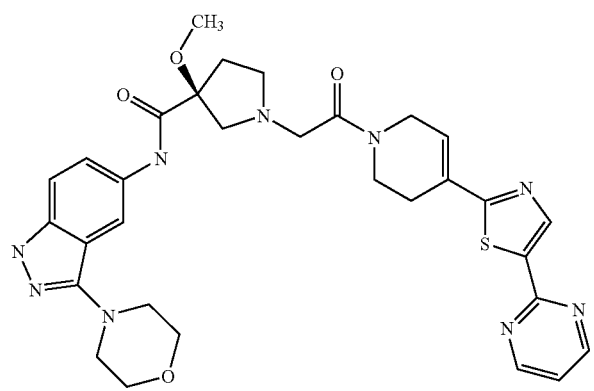 [SMILES: CO[C@@]1(C(=O)Nc2ccc3[nH]nc(N4CCOCC4)c3c2)CCN(CC(=O)N2CC=C(c3ncc(-c4ncccn4)s3)CC2)C1] | 630 | 2.18 |
| 691 | 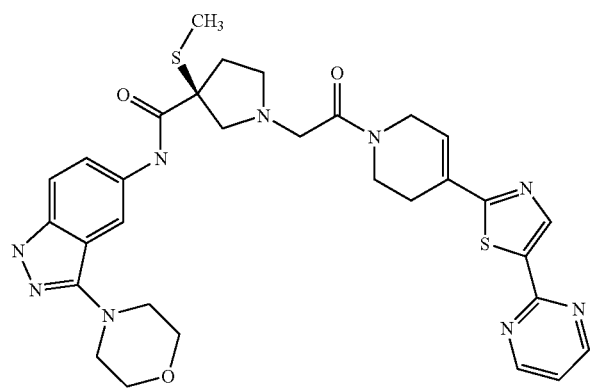 [SMILES: CS[C@@]1(C(=O)Nc2ccc3[nH]nc(N4CCOCC4)c3c2)CCN(CC(=O)N2CC=C(c3ncc(-c4ncccn4)s3)CC2)C1] | 646 | 2.29 |

TABLE 28-continued
| Ex No. | COMPOUND | M + 1 | Retention Time (min) |
|---|---|---|---|
| 692 | 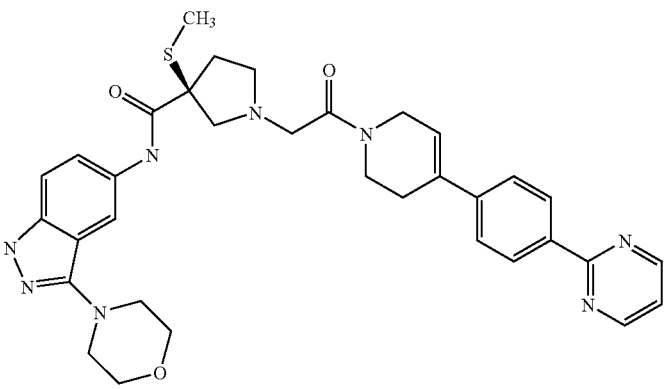 [SMILES: CS[C@@]1(C(=O)Nc2ccc3[nH]nc(N4CCOCC4)c3c2)CCN(CC(=O)N2CC=C(c3ccc(-c4ncccn4)cc3)CC2)C1] | 639 | 2.46 |
| 693 | 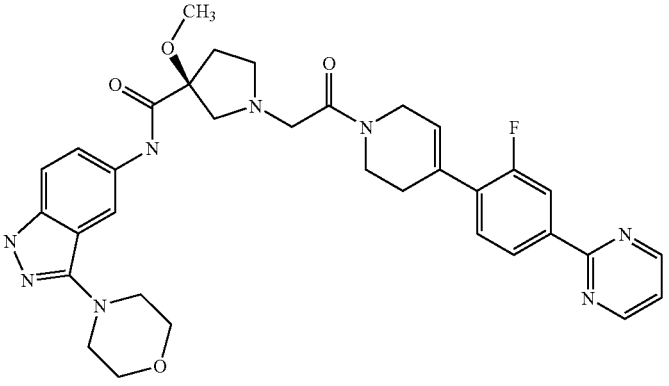 [SMILES: CO[C@@]1(C(=O)Nc2ccc3[nH]nc(N4CCOCC4)c3c2)CCN(CC(=O)N2CC=C(c3ccc(-c4ncccn4)cc3F)CC2)C1] | 641 | 2.51 |
| 694 | 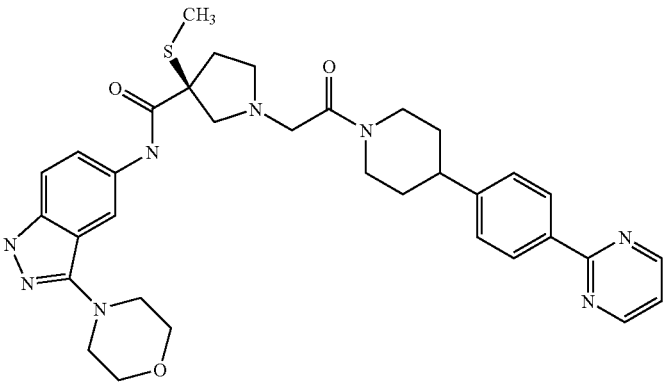 [SMILES: CS[C@@]1(C(=O)Nc2ccc3[nH]nc(N4CCOCC4)c3c2)CCN(CC(=O)N2CCC(c3ccc(-c4ncccn4)cc3)CC2)C1] | 641 | 2.49 |

TABLE 28-continued
| Ex No. | COMPOUND | M + 1 | Retention Time (min) |
|---|---|---|---|
| 695 | 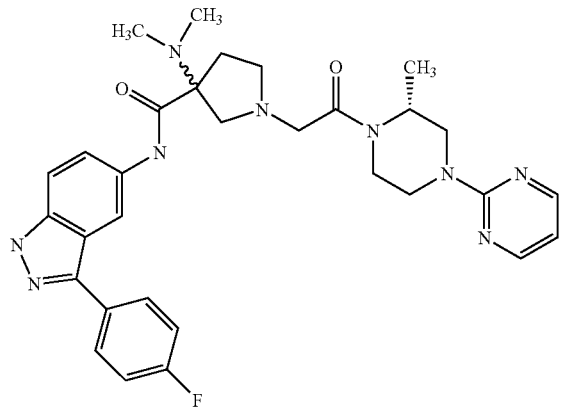 [SMILES: C[C@@H]1CN(c2ncccn2)CCN1C(=O)CN1CCC(C(=O)Nc2ccc3[nH]nc(-c4ccc(F)cc4)c3c2)(N(C)C)C1] | 586 | 2.62 |
| 696 | 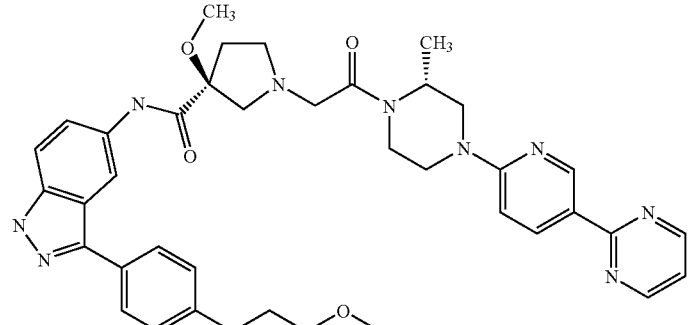 (see also Preparation 57) | 706 | 2.46 |
| 697 | 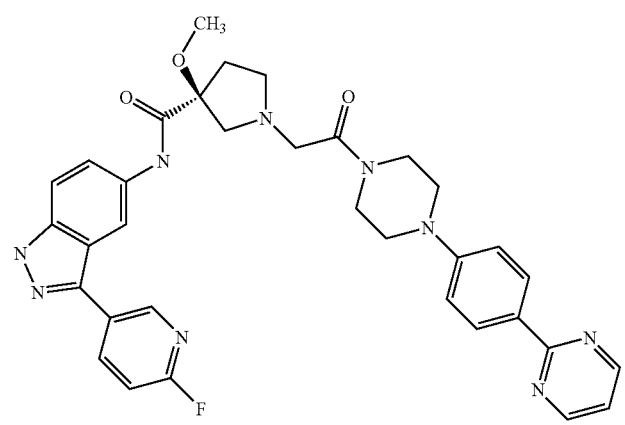 [SMILES: CO[C@@]1(C(=O)Nc2ccc3[nH]nc(-c4ccc(F)nc4)c3c2)CCN(CC(=O)N2CCN(c3ccc(-c4ncccn4)cc3)CC2)C1] | 636.7 | 3.12 |

TABLE 28-continued

| Ex No. | COMPOUND | M + 1 | Retention Time (min) |
| --- | --- | --- | --- |
| 698 | | 633.7 | 3.46 |
| 699 | | 635.7 | 3.33 |
| 700 | | 650.7 | 3.24 |

(see also Preparation 58)

TABLE 28-continued
| Ex No. | COMPOUND | M + 1 | Retention Time (min) |
|---|---|---|---|
| 701 | 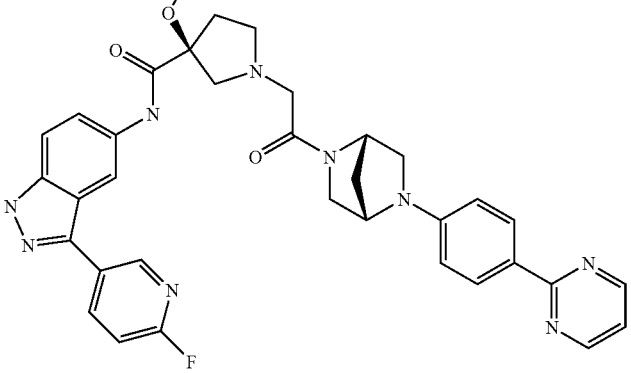 | 648.7 | 3.05 |
| 702 | 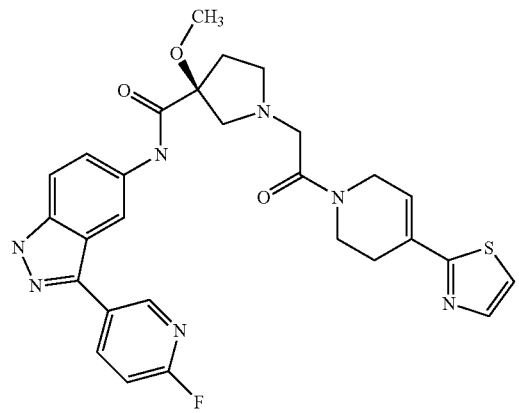 [SMILES: CO[C@@]1(C(=O)Nc2ccc3[nH]nc(-c4ccc(F)nc4)c3c2)CCN(CC(=O)N2CC=C(c3nccs3)CC2)C1] | 562.6 | 2.83 |
| 703 | 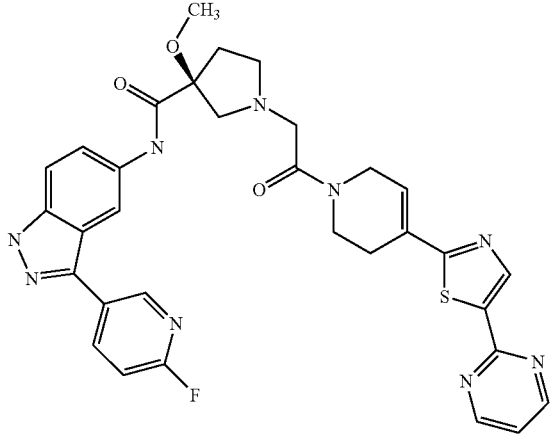 [SMILES: CO[C@@]1(C(=O)Nc2ccc3[nH]nc(-c4ccc(F)nc4)c3c2)CCN(CC(=O)N2CC=C(c3ncc(-c4ncccn4)s3)CC2)C1] | 640.7 | 3.12 |

TABLE 28-continued
| Ex No. | COMPOUND | M + 1 | Retention Time (min) |
|---|---|---|---|
| 704 | 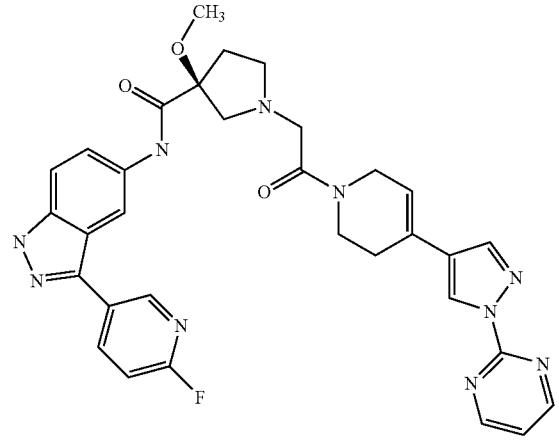 [SMILES: CO[C@@]1(C(=O)Nc2ccc3[nH]nc(-c4ccc(F)nc4)c3c2)CCN(CC(=O)N2CC=C(c3cnn(-c4ncccn4)c3)CC2)C1]<br>(see also Preparation 59) | 623.7 | 2.88 |
| 705 | 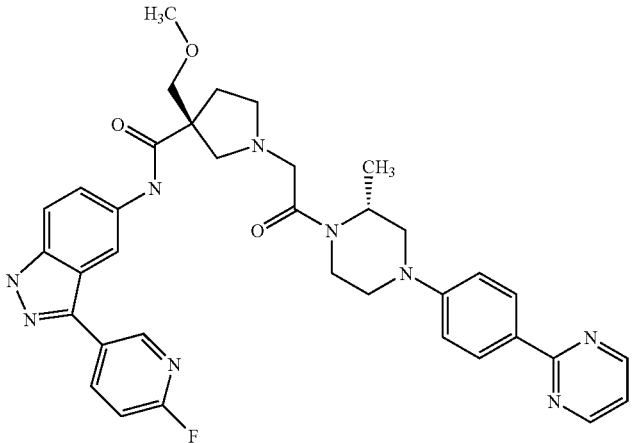 [SMILES: COC[C@@]1(C(=O)Nc2ccc3[nH]nc(-c4ccc(F)nc4)c3c2)CCN(CC(=O)N2CCN(c3ccc(-c4ncccn4)cc3)C[C@H]2C)C1] | 664.7 | 3.4 |
| 706 | 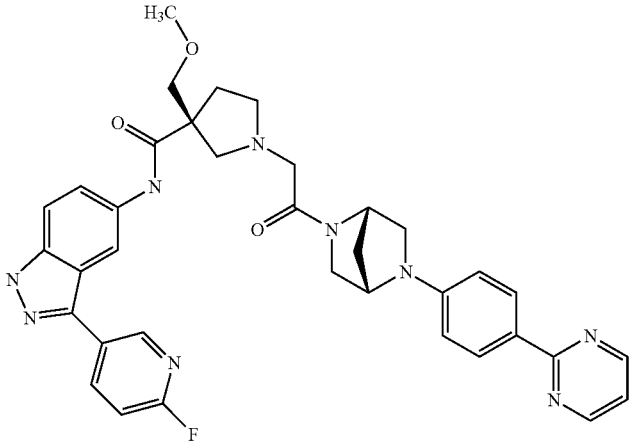 [SMILES: COC[C@@]1(C(=O)Nc2ccc3[nH]nc(-c4ccc(F)nc4)c3c2)CCN(CC(=O)N2C[C@@H]3C[C@H]2CN3c2ccc(-c3ncccn3)cc2)C1] | 662.7 | 3.16 |

TABLE 28-continued
| Ex No. | COMPOUND | M + 1 | Retention Time (min) |
|---|---|---|---|
| 707 | 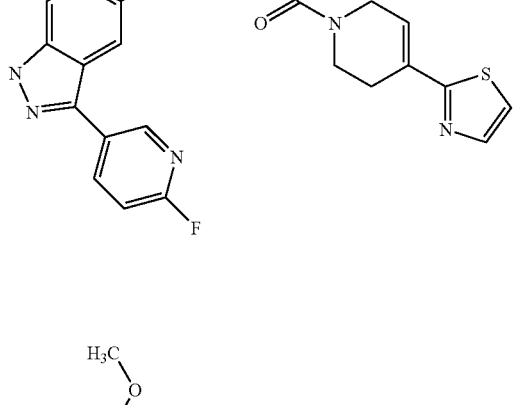 | 576.7 | 2.97 |
| 708 | 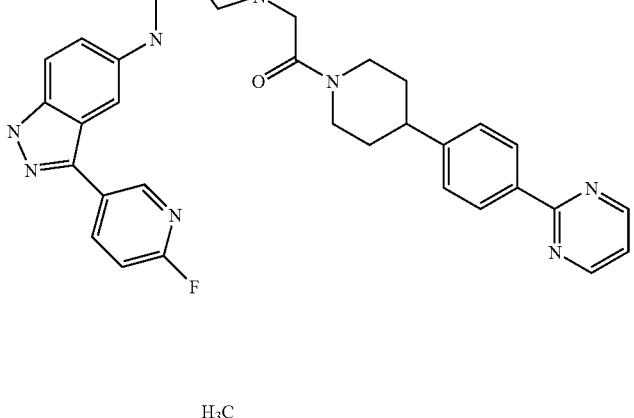 | 649.7 | 3.45 |
| 709 | 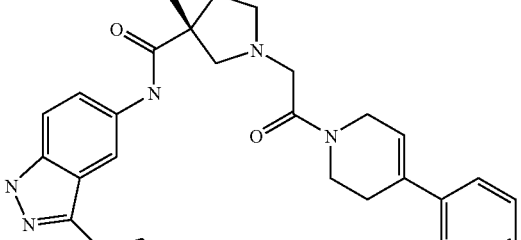 | 587.6 | 3.58 |

TABLE 28-continued
| Ex No. | COMPOUND | M + 1 | Retention Time (min) |
|---|---|---|---|
| 710 | 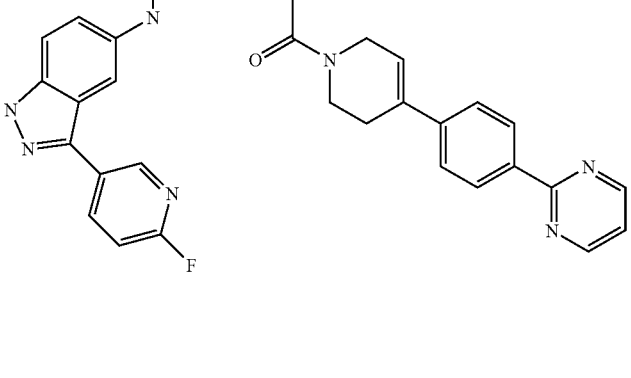 | 647.7 | 3.49 |
| 711 | 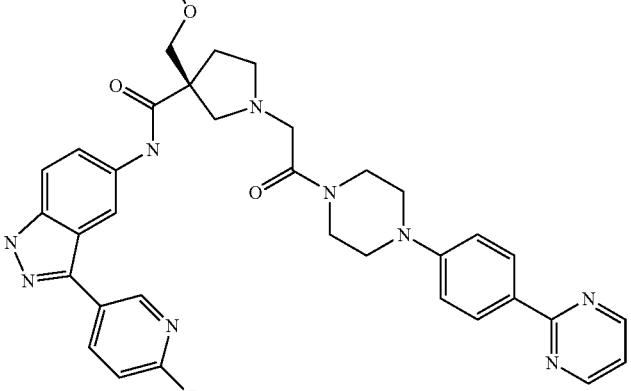 | 650.7 | 3.23 |
| 712 | 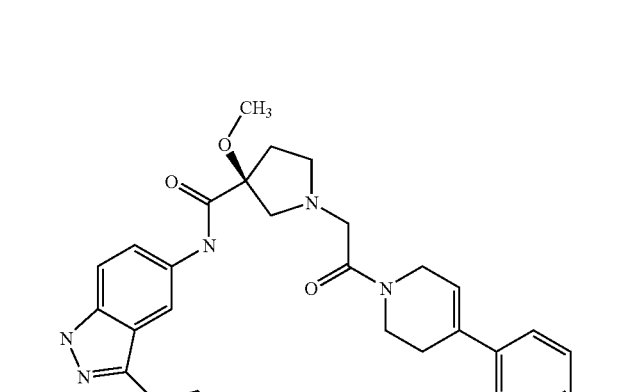 | 573.6 | 3.45 |

TABLE 28-continued
| Ex No. | COMPOUND | M + 1 | Retention Time (min) |
|---|---|---|---|
| 713 | 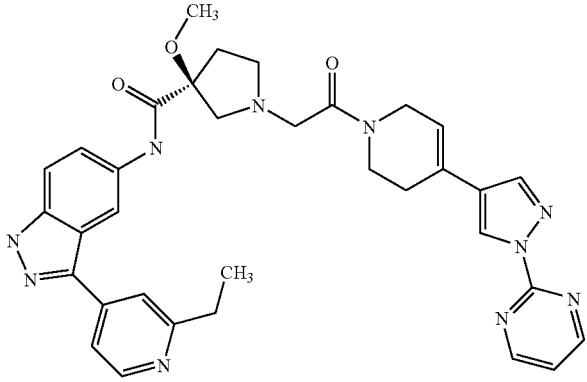 [SMILES: CCc1cc(-c2n[nH]c3ccc(NC(=O)[C@]4(OC)CCN(CC(=O)N5CC=C(c6cnn(-c7ncccn7)c6)CC5)C4)cc23)ccn1] | 633.7 | 2.34 |
| 714 | 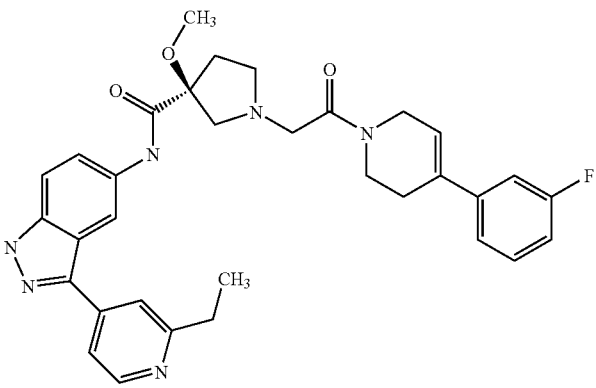 [SMILES: CCc1cc(-c2n[nH]c3ccc(NC(=O)[C@]4(OC)CCN(CC(=O)N5CC=C(c6cccc(F)c6)CC5)C4)cc23)ccn1] (see also Preparation 60) | 583.7 | 2.81 |
| 715 | 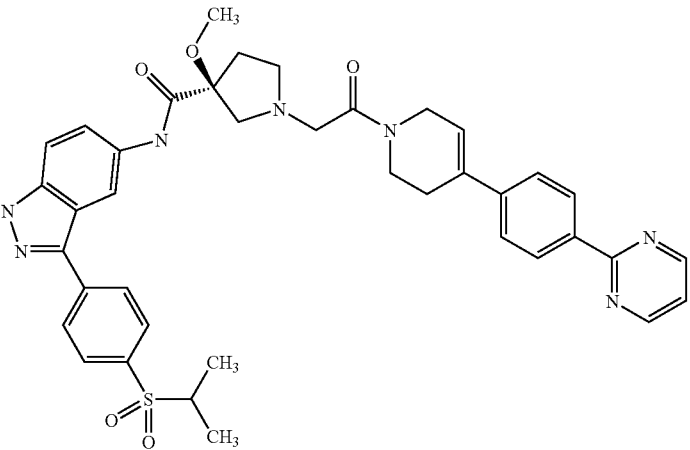 [SMILES: CO[C@@]1(C(=O)Nc2ccc3[nH]nc(-c4ccc(S(=O)(=O)C(C)C)cc4)c3c2)CCN(CC(=O)N2CC=C(c3ccc(-c4ncccn4)cc3)CC2)C1] (see also Preparation 62) | 602.8 | 3.65 |

TABLE 28-continued
| Ex No. | COMPOUND | M + 1 | Retention Time (min) |
|---|---|---|---|
| 716 | 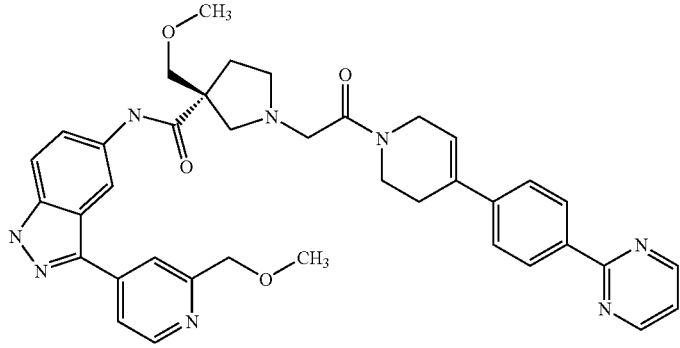 [SMILES: COCc1cc(-c2n[nH]c3ccc(NC(=O)[C@]4(COC)CCN(CC(=O)N5CC=C(c6ccc(-c7ncccn7)cc6)CC5)C4)cc23)ccn1] (see also Preparation 63) | 709.8 | 2.62 |
| 717 | 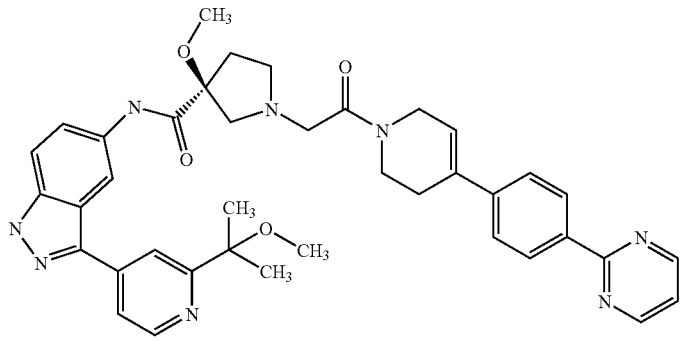 [SMILES: COC(C)(C)c1cc(-c2n[nH]c3ccc(NC(=O)[C@]4(OC)CCN(CC(=O)N5CC=C(c6ccc(-c7ncccn7)cc6)CC5)C4)cc23)ccn1] (see also Preparation 64) | 683.9 | 3 |
| 718 1396854 | 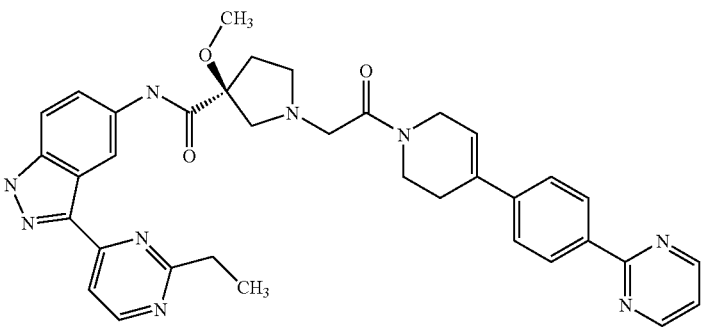 [SMILES: CCc1nccc(-c2n[nH]c3ccc(NC(=O)[C@]4(OC)CCN(CC(=O)N5CC=C(c6ccc(-c7ncccn7)cc6)CC5)C4)cc23)n1] (see also Preparation 65) | 676.8 | 3.09 |
| 719 | 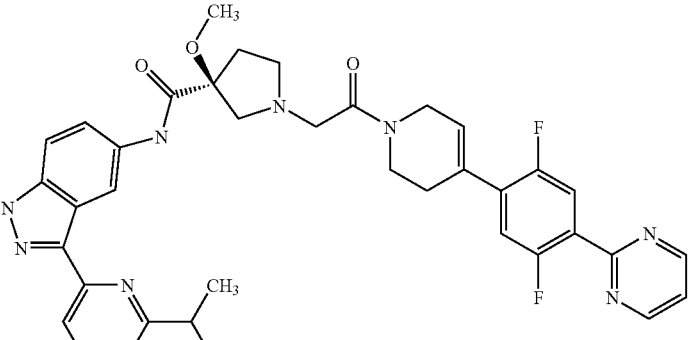 (see also Preparation 65) | 694.3 | 3.71 |

TABLE 28-continued
| Ex No. | COMPOUND | M + 1 | Retention Time (min) |
|---|---|---|---|
| 720 | 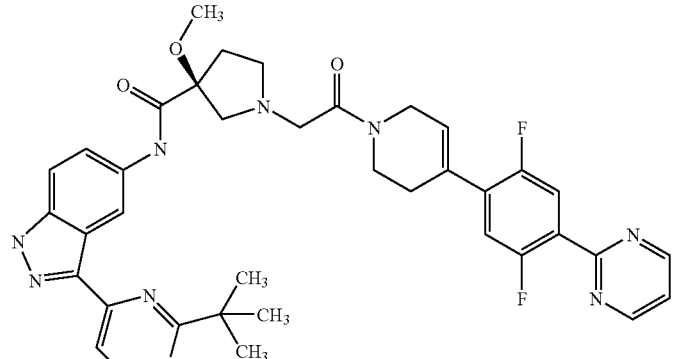 (see also Preparation 65) | 708.4 | 4.08 |
| 721 | 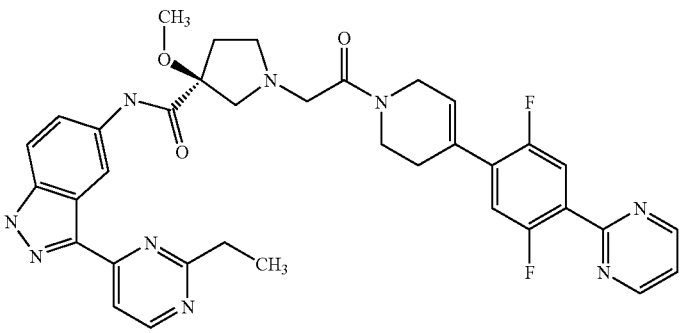 [SMILES: CCc1nccc(-c2n[nH]c3ccc(NC(=O)[C@]4(OC)CCN(CC(=O)N5CC=C(c6cc(F)c(-c7ncccn7)cc6F)CC5)C4)cc23)n1] (see also Preparation 65) | 680.3 | 3.09 |
| 722 | 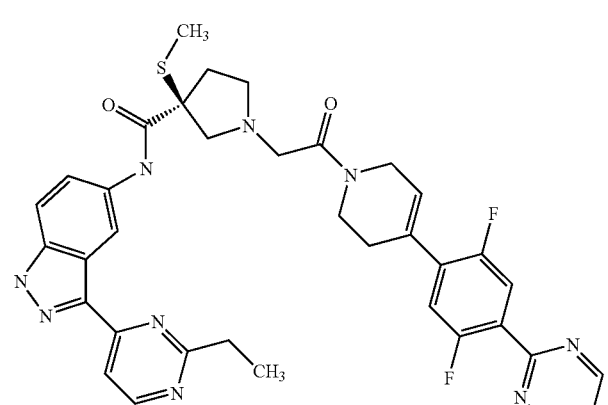 | 696.2 | 3.52 |
| 723 | 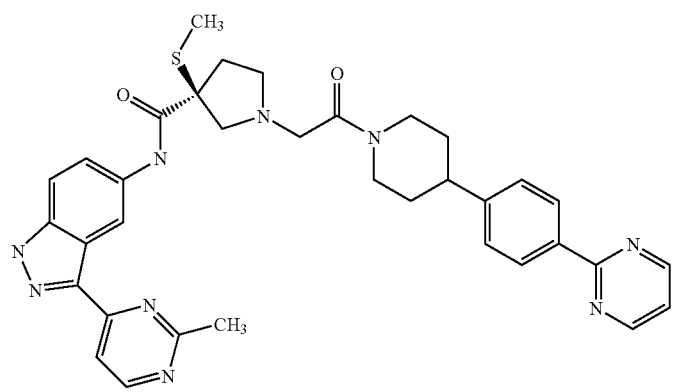 [SMILES: CS[C@@]1(C(=O)Nc2ccc3[nH]nc(-c4ccnc(C)n4)c3c2)CCN(CC(=O)N2CCC(c3ccc(-c4ncccn4)cc3)CC2)C1] | 648.3 | 2.98 |

TABLE 28-continued

| Ex No. | COMPOUND | M + 1 | Retention Time (min) |
|---|---|---|---|
| 724 | | 682.2 | 3.01 |
| 725 | | 667.3 | 3.12 |
| 726 | (see also Preparation 66) | 668.4 | 3.21 |
| 727 | | 630.3 | 3.29 |

TABLE 28-continued

| Ex No. | COMPOUND | M + 1 | Retention Time (min) |
|---|---|---|---|
| 728 | | 656 | 322 |
| 729 | | 658.3 | 3.38 |
| 730 | | 674 | 3.84 |
| 731 | | 692 | 3.41 |

TABLE 28-continued
| Ex No. | COMPOUND | M + 1 | Retention Time (min) |
|---|---|---|---|
| 732 | 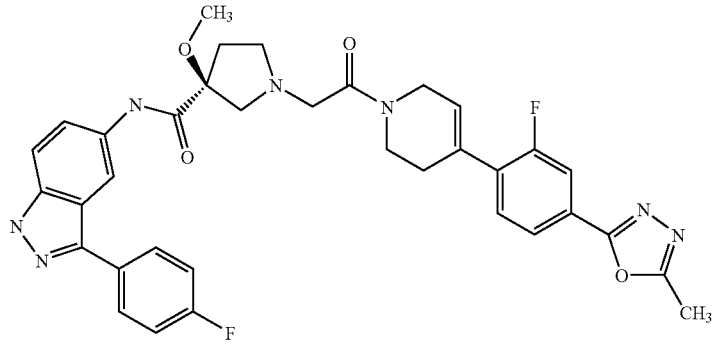 [SMILES: CO[C@@]1(C(=O)Nc2ccc3[nH]nc(-c4ccc(F)cc4)c3c2)CCN(CC(=O)N2CC=C(c3ccc(-c4nnc(C)o4)cc3F)CC2)C1] (see also Preparation 84) | 654.4 | 3.2 |
| 733 | 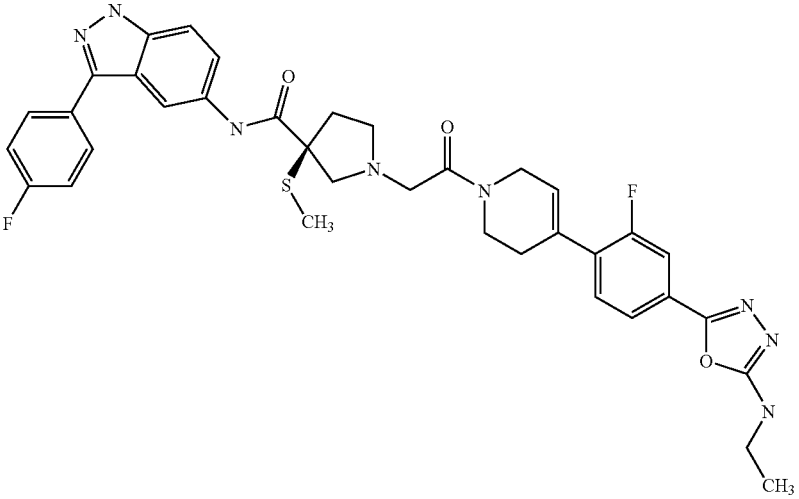 [SMILES: CCNc1nnc(-c2ccc(C3=CCN(C(=O)CN4CC[C@@](SC)(C(=O)Nc5ccc6[nH]nc(-c7ccc(F)cc7)c6c5)C4)CC3)c(F)c2)o1] | 699.4 | 2.9 |
| 734 | 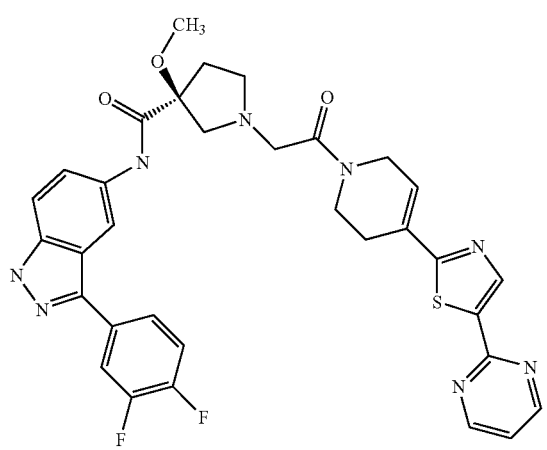 [SMILES: CO[C@@]1(C(=O)Nc2ccc3[nH]nc(-c4ccc(F)c(F)c4)c3c2)CCN(CC(=O)N2CC=C(c3ncc(-c4ncccn4)s3)CC2)C1] (see also Preparation 67) | 657.4 | 2.73 |

TABLE 28-continued
| Ex No. | COMPOUND | M + 1 | Retention Time (min) |
|---|---|---|---|
| 735 | 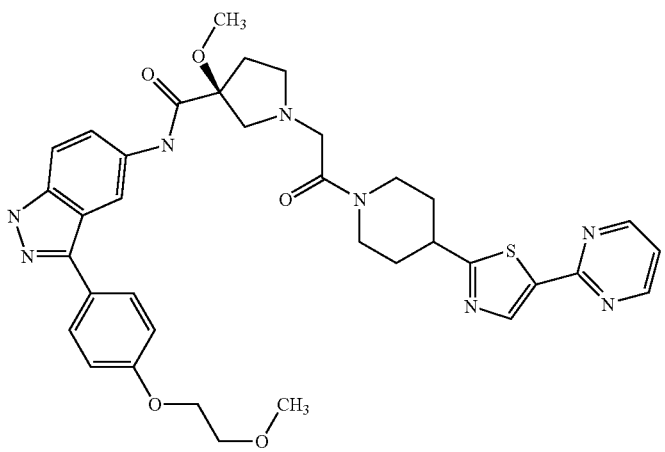 [SMILES: COCCOc1ccc(-c2n[nH]c3ccc(NC(=O)[C@]4(OC)CCN(CC(=O)N5CC=C(c6ccc(-c7ncccn7)s6)CC5)C4)cc23)cc1] (see also Preparation 67) | 697.3 | 3.31 |
| 736 | 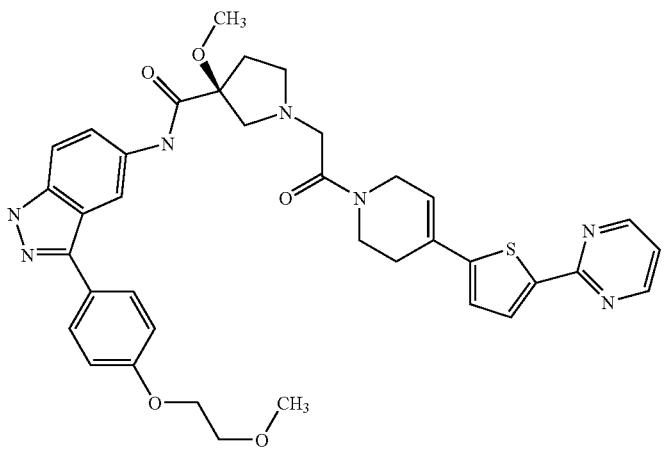 (see also Preparation 68) | 694.2 | 4.07 |
| 737 | 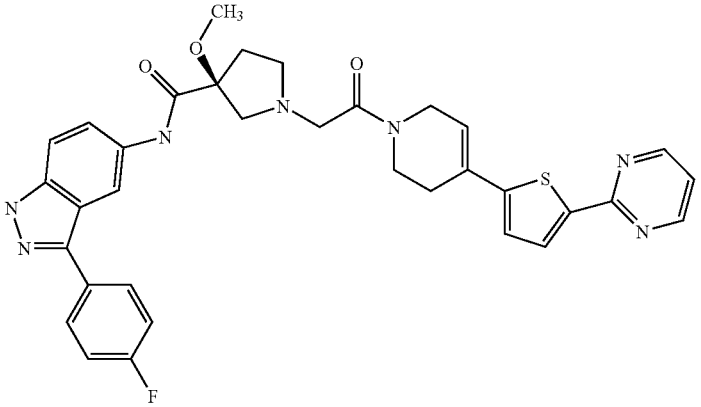 [SMILES: CO[C@@]1(C(=O)Nc2ccc3[nH]nc(-c4ccc(F)cc4)c3c2)CCN(CC(=O)N2CC=C(c3ccc(-c4ncccn4)s3)CC2)C1] | 638.3 | 3.56 |

TABLE 28-continued
| Ex No. | COMPOUND | M + 1 | Retention Time (min) |
|---|---|---|---|
| 738 | 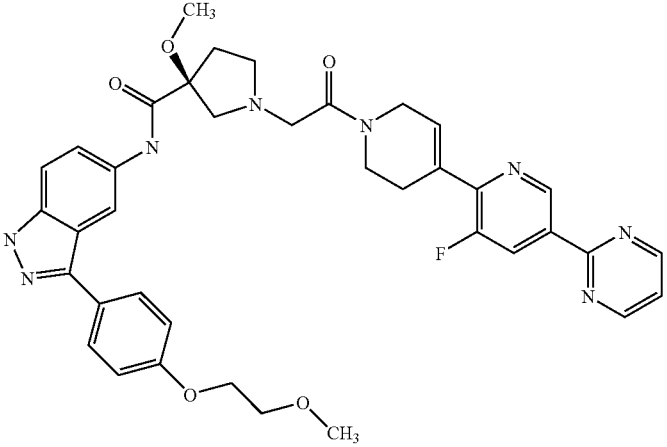 [SMILES: COCCOc1ccc(-c2n[nH]c3ccc(NC(=O)[C@]4(OC)CCN(CC(=O)N5CC=C(c6ncc(-c7ncccn7)cc6F)CC5)C4)cc23)cc1] | 707.3 | 3.57 |
| 739 | 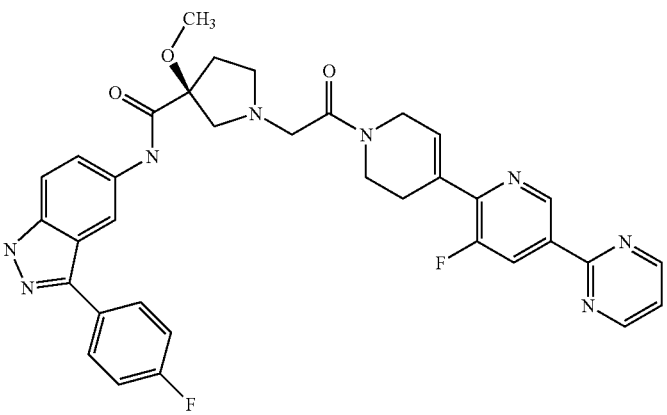 [SMILES: CO[C@@]1(C(=O)Nc2ccc3[nH]nc(-c4ccc(F)cc4)c3c2)CCN(CC(=O)N2CC=C(c3ncc(-c4ncccn4)cc3F)CC2)C1] | 651.3 | 3.69 |
| 740 | 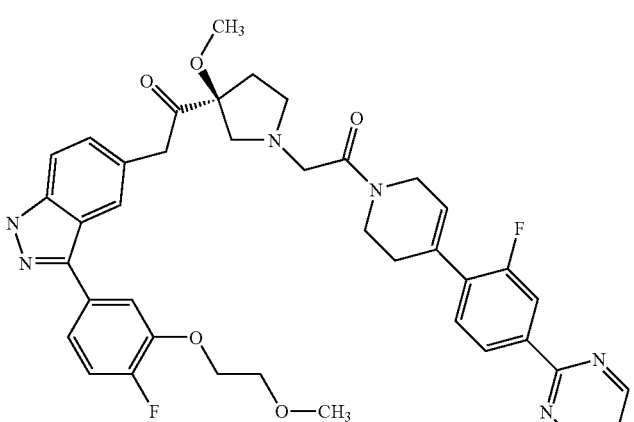 (see also Preparation 69) | 724.4 | 3.16 |

TABLE 28-continued
| Ex No. | COMPOUND | M + 1 | Retention Time (min) |
|---|---|---|---|
| 741 | 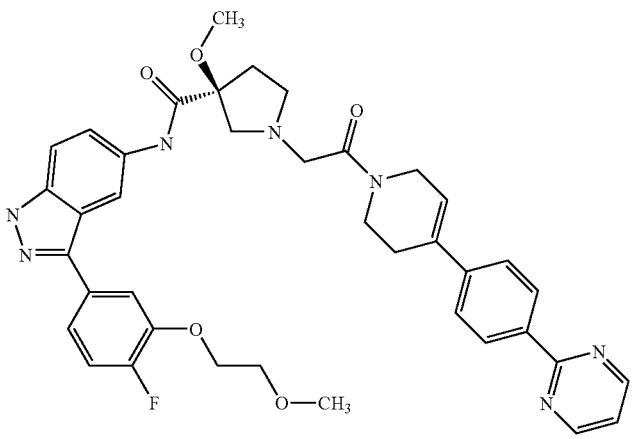 [SMILES: COCCOc1cc(-c2n[nH]c3ccc(NC(=O)[C@]4(OC)CCN(CC(=O)N5CC=C(c6ccc(-c7ncccn7)cc6)CC5)C4)cc23)ccc1F] | 706.4 | 3.24 |
| 742 | 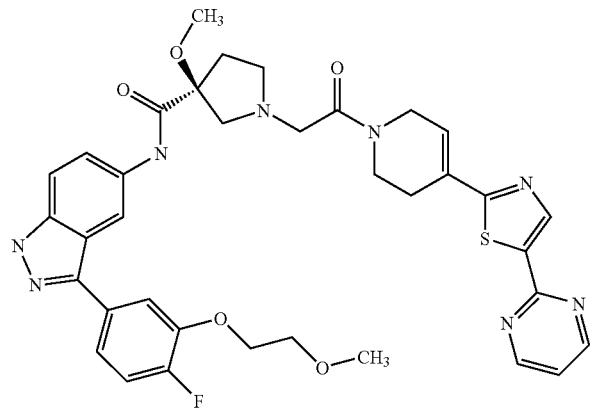 [SMILES: COCCOc1cc(-c2n[nH]c3ccc(NC(=O)[C@]4(OC)CCN(CC(=O)N5CC=C(c6ncc(-c7ncccn7)s6)CC5)C4)cc23)ccc1F] | 713.4 | 2.7 |
| 743 | 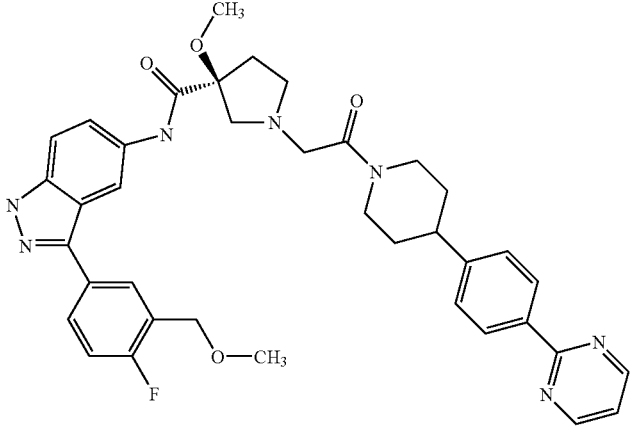 [SMILES: COCc1cc(-c2n[nH]c3ccc(NC(=O)[C@]4(OC)CCN(CC(=O)N5CCC(c6ccc(-c7ncccn7)cc6)CC5)C4)cc23)ccc1F] (see also Preparation 70) | 678.4 | 3.2 |

TABLE 28-continued
| Ex No. | COMPOUND | M + 1 | Retention Time (min) |
|---|---|---|---|
| 744 | 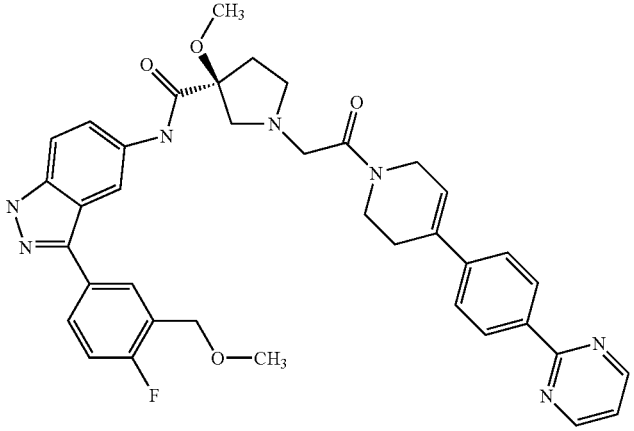 [SMILES: COCc1cc(-c2n[nH]c3ccc(NC(=O)[C@]4(OC)CCN(CC(=O)N5CC=C(c6ccc(-c7ncccn7)cc6)CC5)C4)cc23)ccc1F] | 676.4 | 3.18 |
| 745 | 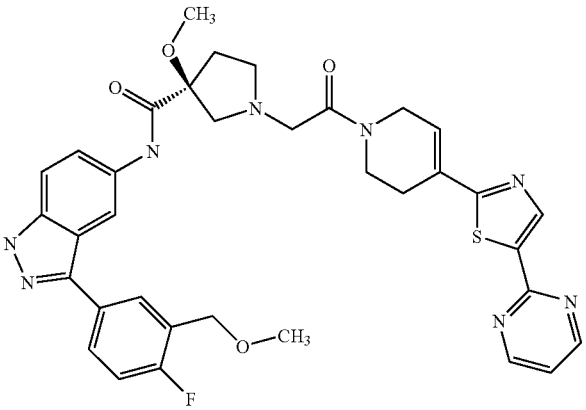 [SMILES: COCc1cc(-c2n[nH]c3ccc(NC(=O)[C@]4(OC)CCN(CC(=O)N5CC=C(c6ncc(-c7ncccn7)s6)CC5)C4)cc23)ccc1F] | 683.4 | 2.71 |
| 746 | 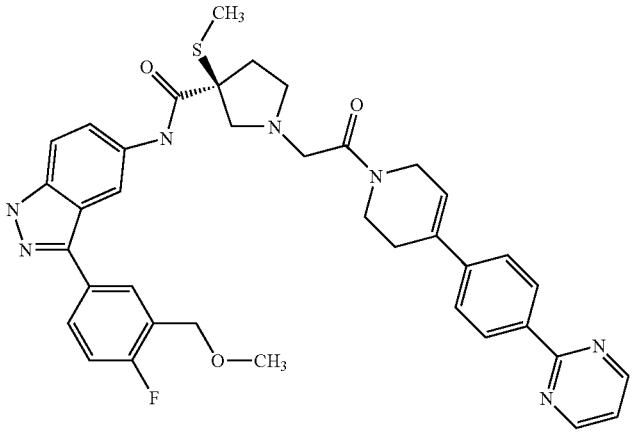 [SMILES: COCc1cc(-c2n[nH]c3ccc(NC(=O)[C@]4(SC)CCN(CC(=O)N5CC=C(c6ccc(-c7ncccn7)cc6)CC5)C4)cc23)ccc1F] | 692.4 | 2.91 |

TABLE 28-continued
| Ex No. | COMPOUND | M + 1 | Retention Time (min) |
|---|---|---|---|
| 747 | 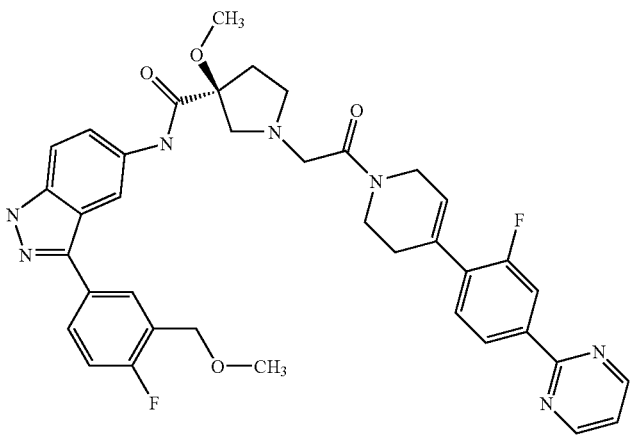 [SMILES: COCc1cc(-c2n[nH]c3ccc(NC(=O)[C@]4(OC)CCN(CC(=O)N5CC=C(c6ccc(-c7ncccn7)cc6F)CC5)C4)cc23)ccc1F] | 694.4 | 2.91 |
| 748 | 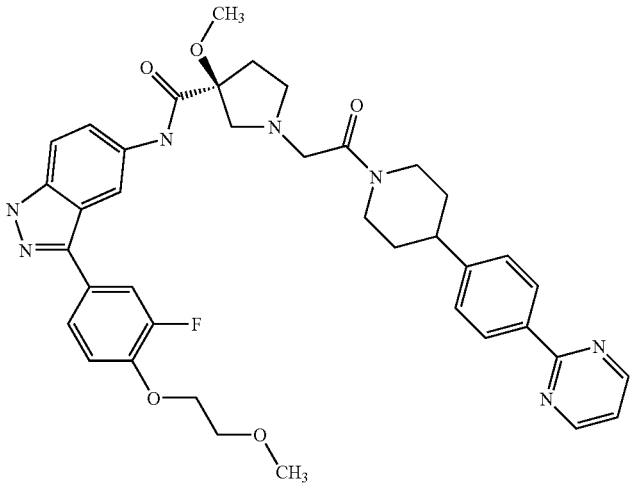 [SMILES: COCCOc1ccc(-c2n[nH]c3ccc(NC(=O)[C@]4(OC)CCN(CC(=O)N5CCC(c6ccc(-c7ncccn7)cc6)CC5)C4)cc23)cc1F] | 708.4 | 2.81 |
| 749 | 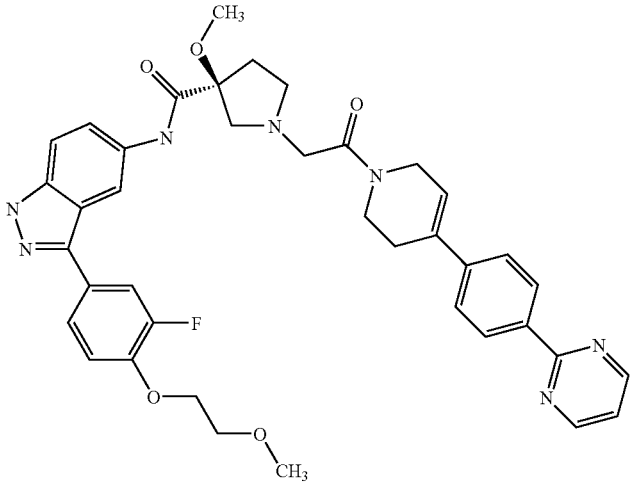
(see also Preparation 71) | 706.4 | 2.85 |

TABLE 28-continued
| Ex No. | COMPOUND | M + 1 | Retention Time (min) |
|---|---|---|---|
| 750 | 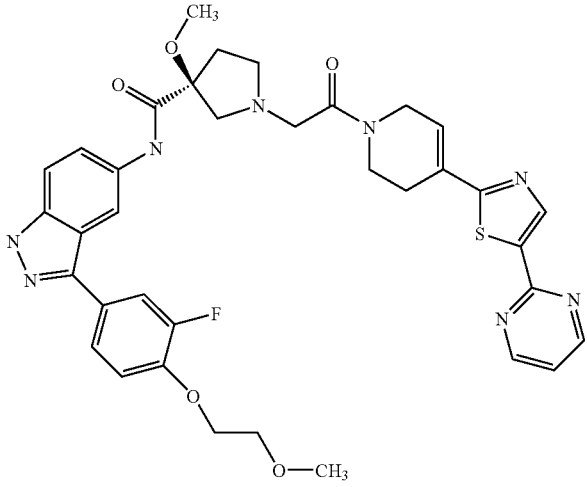 [SMILES: COCCOc1ccc(-c2n[nH]c3ccc(NC(=O)[C@]4(OC)CCN(CC(=O)N5CC=C(c6ncc(-c7ncccn7)s6)CC5)C4)cc23)cc1F] | 713.4 | 2.68 |
| 751 | 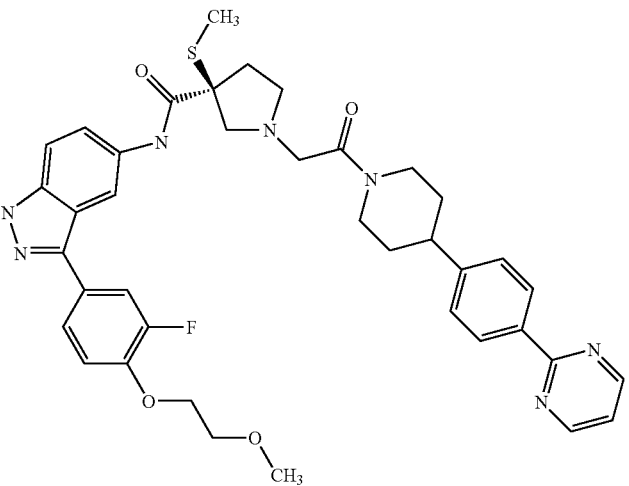 [SMILES: COCCOc1ccc(-c2n[nH]c3ccc(NC(=O)[C@]4(SC)CCN(CC(=O)N5CCC(c6ccc(-c7ncccn7)cc6)CC5)C4)cc23)cc1F] | 724.4 | 2.94 |
| 752 | 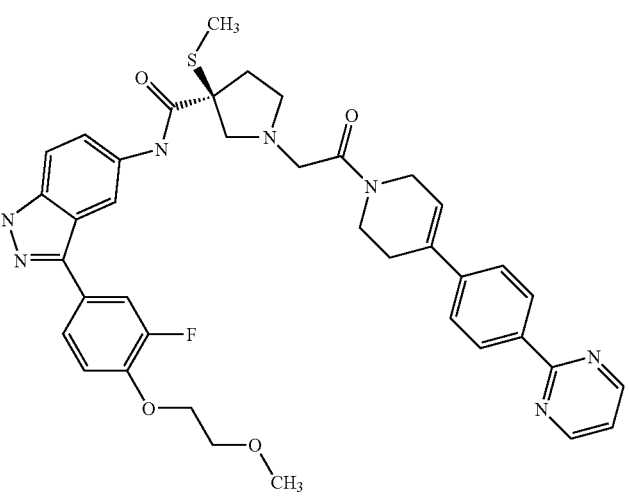 [SMILES: COCCOc1ccc(-c2n[nH]c3ccc(NC(=O)[C@]4(SC)CCN(CC(=O)N5CC=C(c6ccc(-c7ncccn7)cc6)CC5)C4)cc23)cc1F] | 722.4 | 2.97 |

TABLE 28-continued
| Ex No. | COMPOUND | M + 1 | Retention Time (min) |
|---|---|---|---|
| 753 | 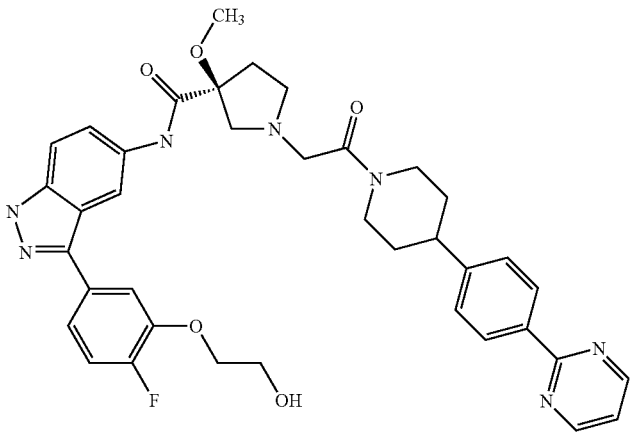 [SMILES: CO[C@@]1(C(=O)Nc2ccc3[nH]nc(-c4ccc(F)c(OCCO)c4)c3c2)CCN(CC(=O)N2CCC(c3ccc(-c4ncccn4)cc3)CC2)C1] (see also Preparation 72) | 694.4 | 2.62 |
| 754 | 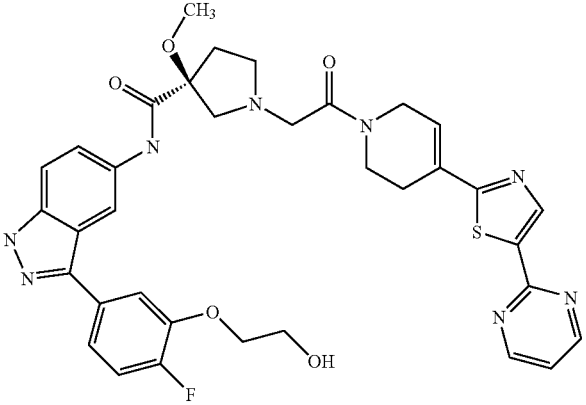 [SMILES: CO[C@@]1(C(=O)Nc2ccc3[nH]nc(-c4ccc(F)c(OCCO)c4)c3c2)CCN(CC(=O)N2CC=C(c3ncc(-c4ncccn4)s3)CC2)C1] | 699.4 | 2.44 |
| 755 | 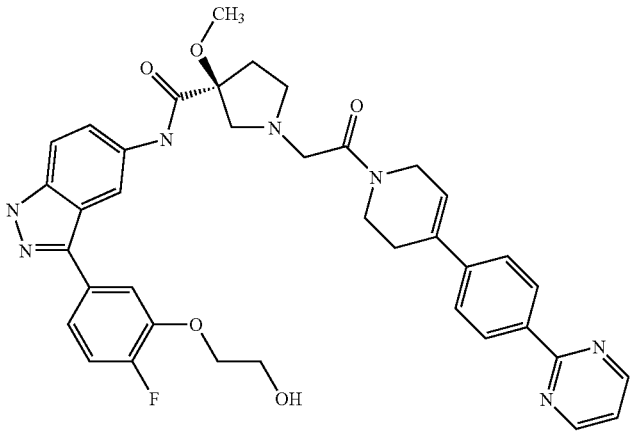 [SMILES: CO[C@@]1(C(=O)Nc2ccc3[nH]nc(-c4ccc(F)c(OCCO)c4)c3c2)CCN(CC(=O)N2CC=C(c3ccc(-c4ncccn4)cc3)CC2)C1] | 692.4 | 2.65 |

TABLE 28-continued
| Ex No. | COMPOUND | M + 1 | Retention Time (min) |
|---|---|---|---|
| 756 | 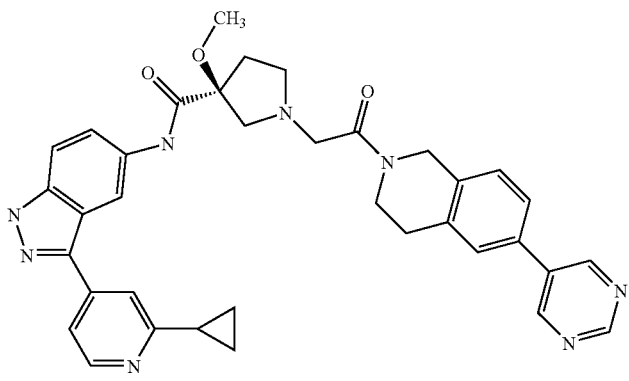 [SMILES: CO[C@@]1(C(=O)Nc2ccc3[nH]nc(-c4ccnc(C5CC5)c4)c3c2)CCN(CC(=O)N2CCc3cc(-c4cncnc4)ccc3C2)C1] (see also Preparation 73) | 629.7 | 2.57 |
| 757 | 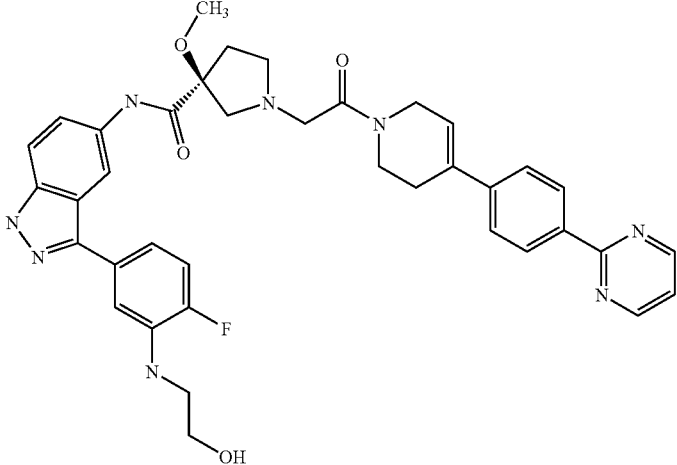 [SMILES: CO[C@@]1(C(=O)Nc2ccc3[nH]nc(-c4ccc(F)c(NCCO)c4)c3c2)CCN(CC(=O)N2CC=C(c3ccc(-c4ncccn4)cc3)CC2)C1] (see also Preparation 74) | 691.2 | 3.54 |
| 758 | 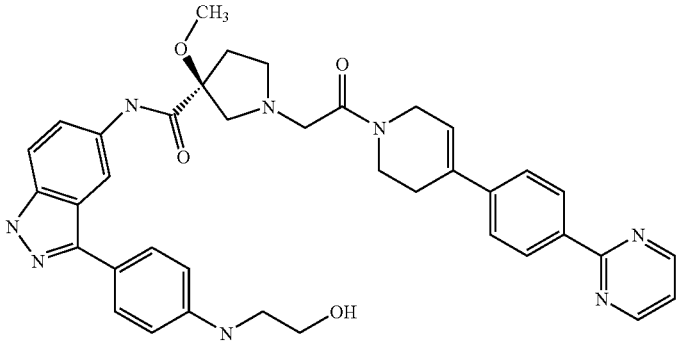 [SMILES: CO[C@@]1(C(=O)Nc2ccc3[nH]nc(-c4ccc(NCCO)cc4)c3c2)CCN(CC(=O)N2CC=C(c3ccc(-c4ncccn4)cc3)CC2)C1] | 673.2 | 2.92 |

TABLE 28-continued
| Ex No. | COMPOUND | M + 1 | Retention Time (min) |
|---|---|---|---|
| 759 | 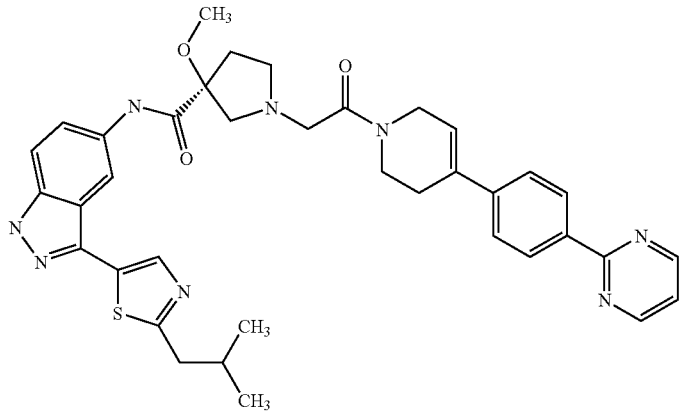 [SMILES: CO[C@@]1(C(=O)Nc2ccc3[nH]nc(-c4cnc(CC(C)C)s4)c3c2)CCN(CC(=O)N2CC=C(c3ccc(-c4ncccn4)cc3)CC2)C1] (see also Preparation 76) | 677.2 | 3.93 |
| 760 | 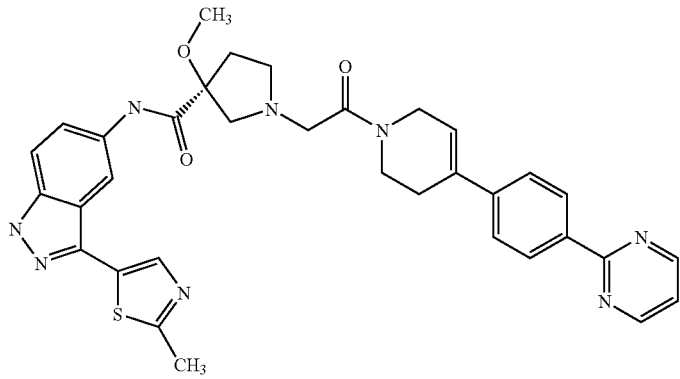 [SMILES: CO[C@@]1(C(=O)Nc2ccc3[nH]nc(-c4cnc(C)s4)c3c2)CCN(CC(=O)N2CC=C(c3ccc(-c4ncccn4)cc3)CC2)C1] (see also Preparation 77) | 635.2 | 3.33 |
| 761 | 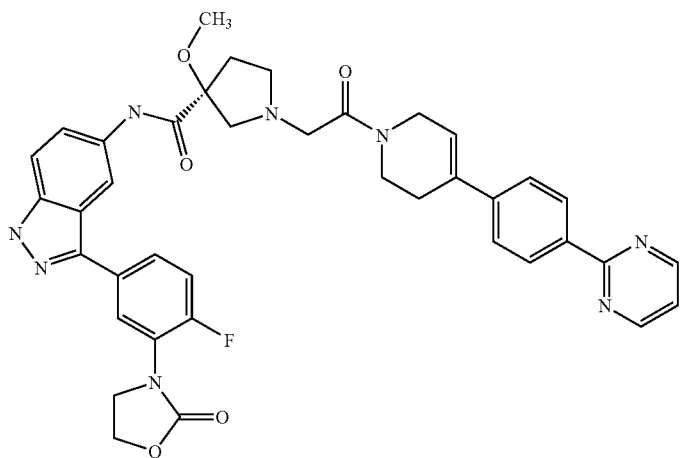 [SMILES: CO[C@@]1(C(=O)Nc2ccc3[nH]nc(-c4ccc(F)c(N5CCOC5=O)c4)c3c2)CCN(CC(=O)N2CC=C(c3ccc(-c4ncccn4)cc3)CC2)C1] (see also Preparation 78) | 717.2 | 3.8 |

TABLE 28-continued
| Ex No. | COMPOUND | M + 1 | Retention Time (min) |
|---|---|---|---|
| 762 | 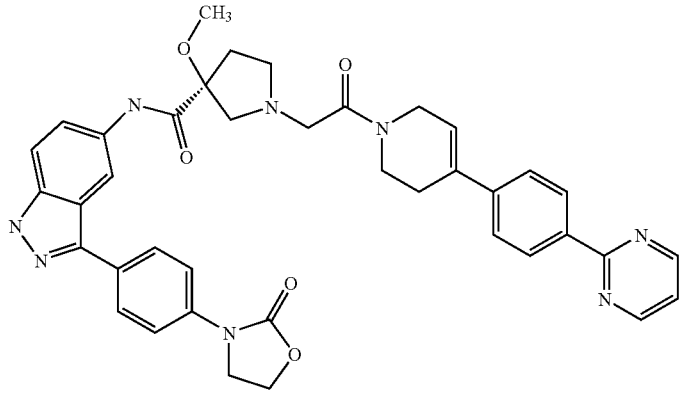 [SMILES: CO[C@@]1(C(=O)Nc2ccc3[nH]nc(-c4ccc(N5CCOC5=O)cc4)c3c2)CCN(CC(=O)N2CC=C(c3ccc(-c4ncccn4)cc3)CC2)C1] (see also Preparation 79) | 699.7 | 3.31 |
| 763 | 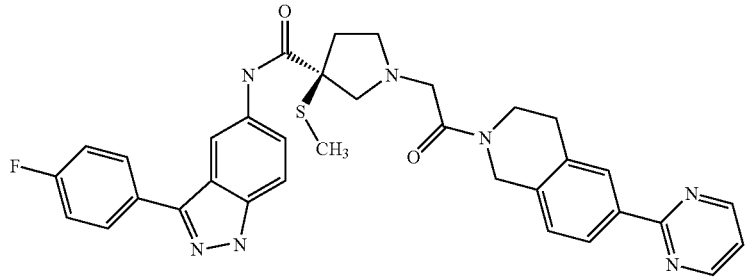 [SMILES: CS[C@@]1(C(=O)Nc2ccc3[nH]nc(-c4ccc(F)cc4)c3c2)CCN(CC(=O)N2CCc3cc(-c4ncccn4)ccc3C2)C1] (see also Preparation 80) | 622.3 | 3.52 |
| 764 | 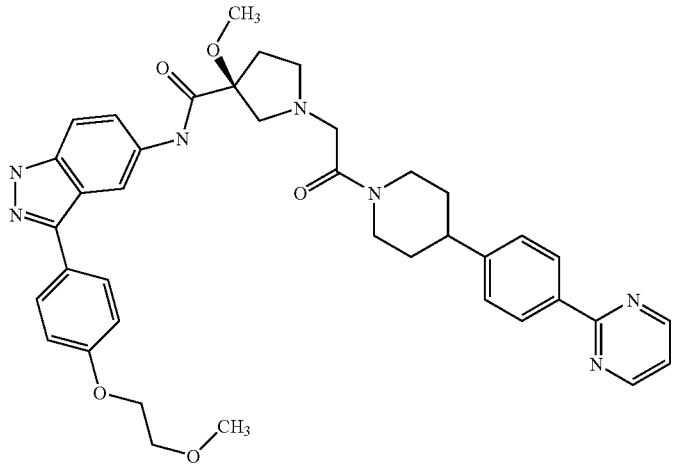 [SMILES: COCCOc1ccc(-c2n[nH]c3ccc(NC(=O)[C@]4(OC)CCN(CC(=O)N5CCC(c6ccc(-c7ncccn7)cc6)CC5)C4)cc23)cc1] | 690.3 | 3.8 |

TABLE 28-continued

| Ex No. | COMPOUND | M + 1 | Retention Time (min) |
|---|---|---|---|
| 765 | | 695.3 | 3.56 |
| 766 | | 688.4 | 3.43 |
| 767 | | 706.4 | 3.05 |
| 768 (see also Preparation 81) | | 611.3 | 3.17 |

TABLE 28-continued

| Ex No. | COMPOUND | M + 1 | Retention Time (min) |
|---|---|---|---|
| 769 | | 691.4 | 2.44 |
| 770 | (see also Preparation 82) | 691.4 | 2.31 |
| 771 | (see also Preparation 83) | 657.4 | 2.78 |
| 772 | | 723.4 | 2.64 |

TABLE 28-continued

| Ex No. | COMPOUND | M + 1 | Retention Time (min) |
|---|---|---|---|
| 773 | | 683.4 | 2.67 |
| 774 | (see also Example 624) | 653.4 | 2.54 |
| 775 | | 669.4 | 2.58 |

TABLE 28-continued

| Ex No. | COMPOUND | M + 1 | Retention Time (min) |
|---|---|---|---|
| 776 | | 639.7 | 3.41 |
| 777 | (see also Preparation 67) | 662 | 2.72 |
| 778 | (see also Preparation 85) | 618 | 3.19 |
| 779 | (see also Preparation 86) | 622 | 3.16 |

TABLE 28-continued
| Ex No. | COMPOUND | M + 1 | Retention Time (min) |
|---|---|---|---|
| 780 | 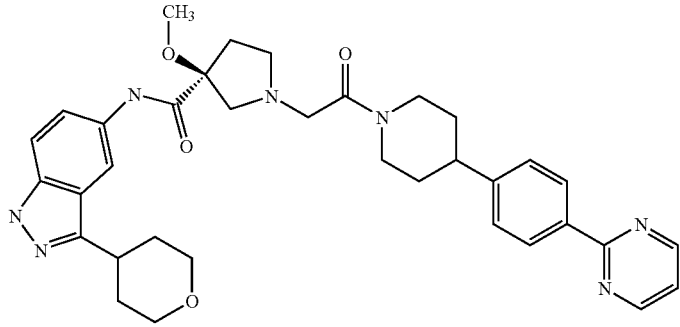 [SMILES: CO[C@@]1(C(=O)Nc2ccc3[nH]nc(C4CCOCC4)c3c2)CCN(CC(=O)N2CCC(c3ccc(-c4ncccn4)cc3)CC2)C1] | 624 | 3.13 |
| 781 | 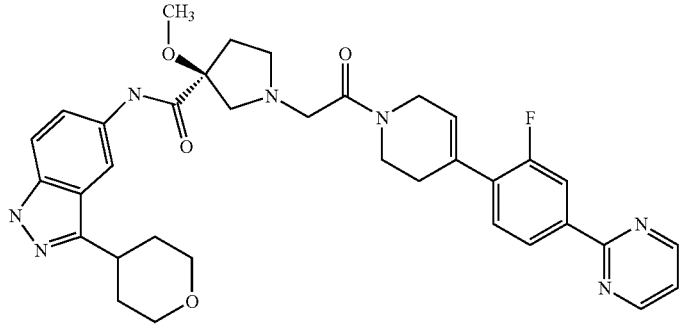 [SMILES: CO[C@@]1(C(=O)Nc2ccc3[nH]nc(C4CCOCC4)c3c2)CCN(CC(=O)N2CC=C(c3ccc(-c4ncccn4)cc3F)CC2)C1] | 640 | 3.37 |
| 782 | 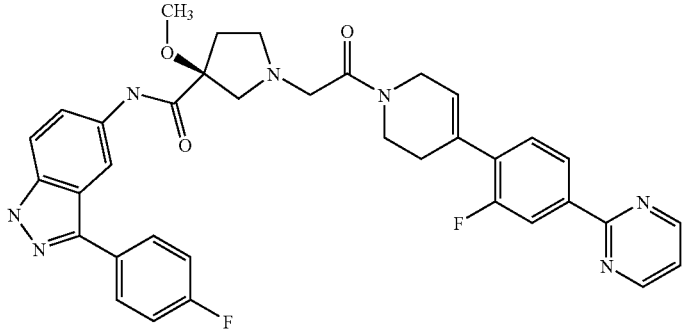 [SMILES: CO[C@@]1(C(=O)Nc2ccc3[nH]nc(-c4ccc(F)cc4)c3c2)CCN(CC(=O)N2CC=C(c3ccc(-c4ncccn4)cc3F)CC2)C1] | 652.4 | 3.35 |
| 783 | 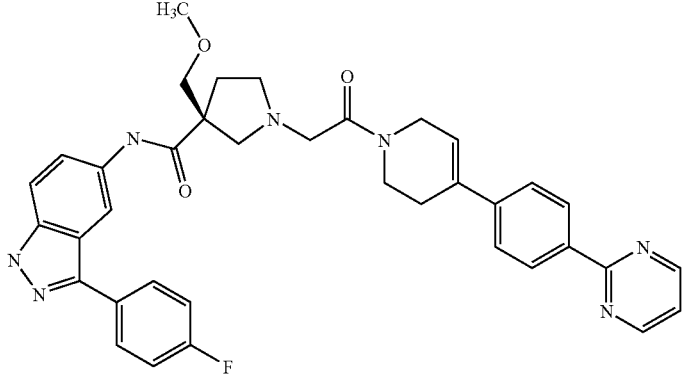 [SMILES: COC[C@@]1(C(=O)Nc2ccc3[nH]nc(-c4ccc(F)cc4)c3c2)CCN(CC(=O)N2CC=C(c3ccc(-c4ncccn4)cc3)CC2)C1] | 648.4 | 3.11 |

TABLE 28-continued

| Ex No. | COMPOUND | M + 1 | Retention Time (min) |
|---|---|---|---|
| 784 | | 699.4 | 3 |
| 785 | | 665.4 | 2.97 |
| 786 | | 667.4 | 2.89 |
| 787 | | 662.4 | 2.84 |

TABLE 28-continued

| Ex No. | COMPOUND | M + 1 | Retention Time (min) |
|---|---|---|---|
| 788 | | 685.4 | 2.92 |
| 789 | | 631.3 | 2.07 |
| 790 | | 690.4 | 2.75 |
| 791 | | 652.4 | 1.83 |

TABLE 28-continued
| Ex No. | COMPOUND | M + 1 | Retention Time (min) |
| --- | --- | --- | --- |
| 792 | 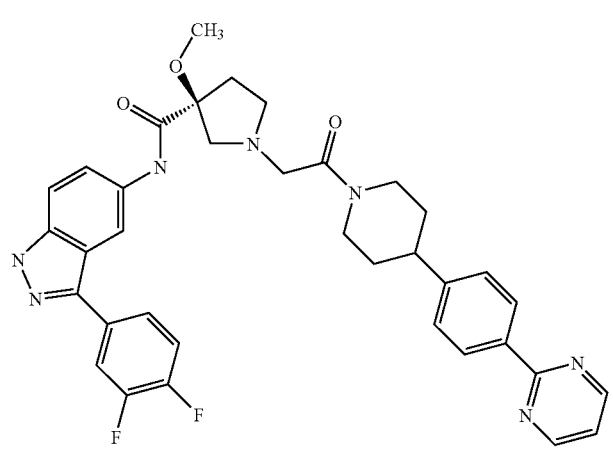 [SMILES: CO[C@@]1(C(=O)Nc2ccc3[nH]nc(-c4ccc(F)c(F)c4)c3c2)CCN(CC(=O)N2CCC(c3ccc(-c4ncccn4)cc3)CC2)C1] | 652.4 | 2.94 |
| 793 | 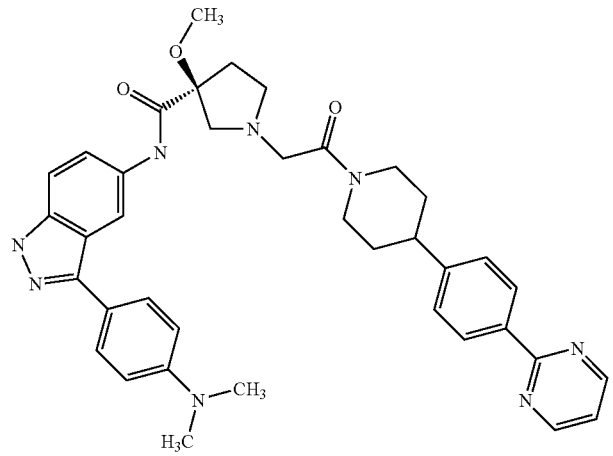 [SMILES: CO[C@@]1(C(=O)Nc2ccc3[nH]nc(-c4ccc(N(C)C)cc4)c3c2)CCN(CC(=O)N2CCC(c3ccc(-c4ncccn4)cc3)CC2)C1] | 659.4 | 2.41 |
| 794 | 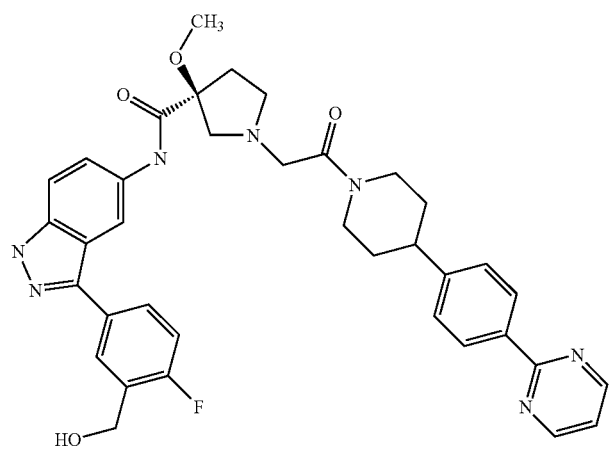 [SMILES: CO[C@@]1(C(=O)Nc2ccc3[nH]nc(-c4ccc(F)c(CO)c4)c3c2)CCN(CC(=O)N2CCC(c3ccc(-c4ncccn4)cc3)CC2)C1] | 664.4 | 2.76 |

TABLE 28-continued

| Ex No. | COMPOUND | M + 1 | Retention Time (min) |
| --- | --- | --- | --- |
| 795 | | 671 | 2.59 |
| 796 | | 604 | 2.33 |
| 797 | | 663 | 3.26 |
| 798 | | 663 | 3.26 |

TABLE 28-continued

| Ex No. | COMPOUND | M + 1 | Retention Time (min) |
|---|---|---|---|
| 799 | | 676 | 2.49 |
| 800 | | 660.8 | 2.71 |
| 801 | | 658.8 | 2.5 |
| 802 | | 572.7 | 2.27 |

TABLE 28-continued

| Ex No. | COMPOUND | M + 1 | Retention Time (min) |
|---|---|---|---|
| 803 | | 645.8 | 2.73 |
| 804 | | 546.7 | 2.02 |
| 805 | | 643.7 | 2.76 |
| 806 | | 646.8 | 2.55 |

TABLE 28-continued

| Ex No. | COMPOUND | M + 1 | Retention Time (min) |
|---|---|---|---|
| 807 | | 651.7 | 3.99 |
| 808 | | 586.7 | 2.28 |
| 809 | | 576.7 | 2.75 |
| 810 | | 634.3 | 3.52 |

TABLE 28-continued

| Ex No. | COMPOUND | M + 1 | Retention Time (min) |
|---|---|---|---|
| 811 | | 631.3 | 2.25 |
| 812 | | 680.4 | 2.91 |
| 813 | | 668.4 | 3.31 |

TABLE 28-continued

| Ex No. | COMPOUND | M + 1 | Retention Time (min) |
|---|---|---|---|
| 814 | | 708.4 | 3.07 |
| 815 | | 696.4 | 2.84 |
| 816 | | 647.2 | 3.34 |
| 817 | | 637.4 | 3.34 |

TABLE 28-continued
| Ex No. | COMPOUND | M + 1 | Retention Time (min) |
|---|---|---|---|
| 818 | 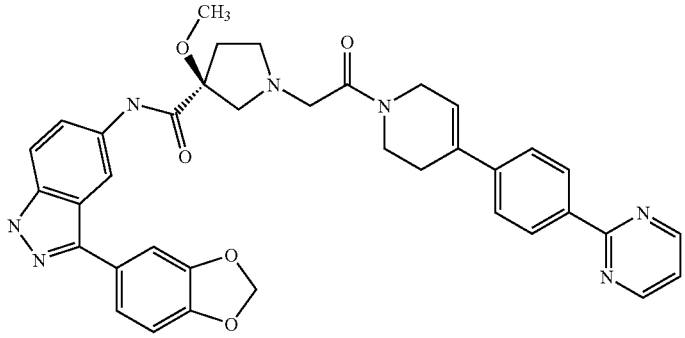 [SMILES: CO[C@@]1(C(=O)Nc2ccc3[nH]nc(-c4ccc5c(c4)OCO5)c3c2)CCN(CC(=O)N2CC=C(c3ccc(-c4ncccn4)cc3)CC2)C1] (see also Preparation 89) | 658.4 | 3.13 |
| 819 | 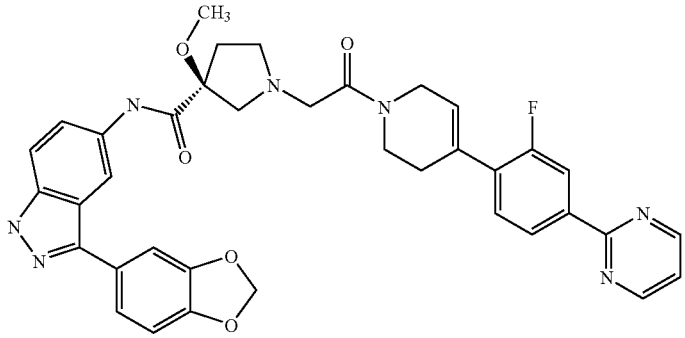 [SMILES: CO[C@@]1(C(=O)Nc2ccc3[nH]nc(-c4ccc5c(c4)OCO5)c3c2)CCN(CC(=O)N2CC=C(c3ccc(-c4ncccn4)cc3F)CC2)C1] | 676.4 | 3.11 |
| 820 | 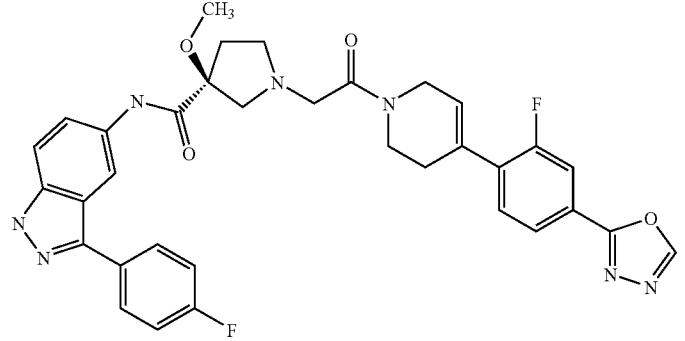 [SMILES: CO[C@@]1(C(=O)Nc2ccc3[nH]nc(-c4ccc(F)cc4)c3c2)CCN(CC(=O)N2CC=C(c3ccc(-c4nnco4)cc3F)CC2)C1] | 640.4 | 2.78 |
| 821 | 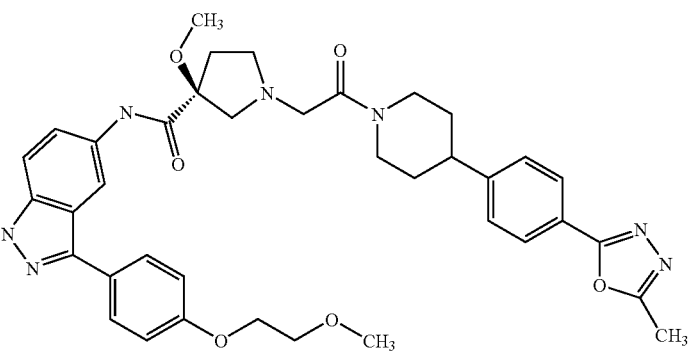 [SMILES: COCCOc1ccc(-c2n[nH]c3ccc(NC(=O)[C@]4(OC)CCN(CC(=O)N5CCC(c6ccc(-c7nnc(C)o7)cc6)CC5)C4)cc23)cc1] | 694.4 | 2.64 |

TABLE 28-continued

| Ex No. | COMPOUND | M + 1 | Retention Time (min) |
|---|---|---|---|
| 822 | | 674.4 | 2.53 |
| 823 | | 647.4 | 2.38 |
| 824 | (see also Preparation 87) | 606 | 3.32 |
| 825 | | 650.4 | 3.28 |

Examples 826 and 827

Synthesis of 5-Nitro-3-trimethylsilanylethynyl-1-trityl-1H-indazole

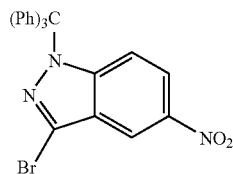 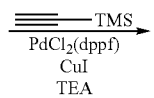

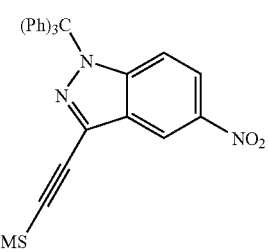

A mixture of 3-bromo-5-nitro-1-trityl-1H-indazole (4.83 g, 10 mmol), ethynyl-trimethyl-silane (1 g, 10 mmol), copper (I) iodide (91 mg, 0.5 mmol), PdCl$_2$(dppf) (337 mg, 0.5 mmol) and triethylamine (1.2 g, 12 mmol) in DMF (50 mL) was stirred overnight at 80° C. under argon. Then ethyl acetate (100 mL) was added, followed by water. The organic layer was collected and aqueous layer was extracted three times with ethyl acetate. The combined organic fraction was washed with water and then brine. The solvent was removed under vacuum and the product was purified using chromatography (20% hexane in dichloromethane) to give desired product (3.4 g) in 67% yield.

Synthesis of 3-ethynyl-5-nitro-1-trityl-1H-indazole

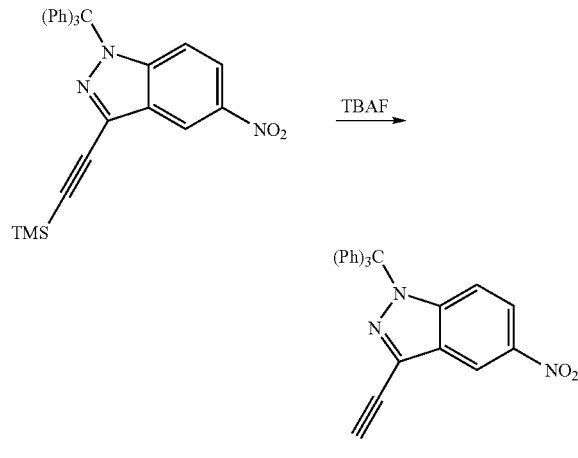

To a solution of 5-nitro-3-trimethylsilanylethynyl-1-trityl-1H-indazole (700 mg, 1.4 mmol) in THF (5 mL) was added tributylammonium fluoride (1M, 2.8 mL, 2.8 mmol). The resulted solution was stirred at room temperature for 2 hours. TLC showed the completion of reaction. After removal the solvent under vacuum, the product was purified using silica (20 hexane in dichloromethane) to give 560 mg of titled product (93% yield).

Synthesis of 2-(5-Nitro-1-trityl-1H-indazol-3-yl)-furo[3,2-c]pyridine

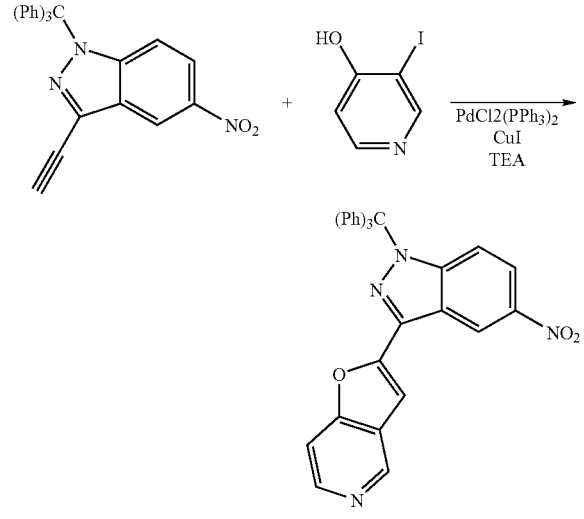

A reaction mixture containing 3-ethynyl-5-nitro-1-trityl-1H-indazole (215 mg, 0.5 mmol), 3-iodo-pyridin-4-ol (132 mg, 0.6 mmol), copper (I) iodide (4.5 mg, 0.025 mmol), PdCl$_2$(PPh$_3$)$_2$ and triethylamine (120 mg, 1.2 mmol) in DMF (3 mL) was heated at 100° C. overnight under argon. After the completion of reaction (shown by TLC), ethyl acetate (50 mL) was added and the reaction mixture was added to water. The organic layer was collected, washed with water, brine and concentrated under vacuum. After purification using silica (7% methanol in dichloromethane), the desired product was obtained (210 mg, 0.4 mmol) in 80% yield.

Synthesis of 2-(5-amino-1-trityl-1H-indazol-3-yl)-furo[3,2-c]pyridine

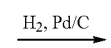

-continued

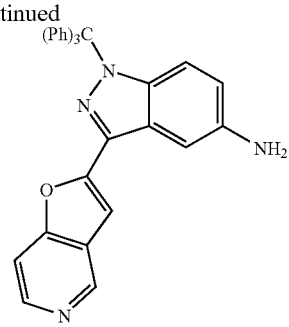

In a round-bottom flask equipped with a balloon, a mixture 2-(5-Nitro-1-trityl-1H-indazol-3-yl)-furo[3,2-c]pyridine (210 mg, 0.4 mmol) and 5% Pd on carbon (21 mg) in ethyl acetate and methanol (10 mL, 1:1) was hydrogenated overnight at room temperature to give 157 mg desired product (80% yield).

Following procedures described above the compounds in Table 29 were prepared.

TABLE 29

| Compound | Retention Time (min) | M + 1 |
|---|---|---|
| (Example 826) | 2.67 | 655 |
| (Example 827) | 2.18 | 584 |

ASSAYS

Coupled ERK2 Assay:

Activity of compounds against inactive ERK2 was tested in a coupled MEK1/ERK2 IMAP assay as follows: Compounds were diluted to 25× final test concentration in 100% DMSO. 14 µl of kinase buffer (10 mM Tris.HCl pH 7.2, 10 mM $MgCl_2$, 0.01% Tween-20, 1 mM DTT) containing 0.4 ng unphosphorylated Mouse ERK2 protein was added to each well of a black 384-well assay plate. 1 µl of 25× compound was added to each well and incubated at room temperature for 30 minutes to allow an opportunity for the compound to bind to the inactive enzyme. DMSO concentration during initial incubation is 6.7%. ERK2 activity was determined to be insensitive to DMSO concentrations up to 20%. ERK2 was then activated and it's kinase activity measured by the addition of 10 µl kinase buffer with the following components (final concentration per reaction): 2 ng active (phosphorylated) human MEK1 protein and 4 µM (total) ERK2 IMAP substrate peptides (3.9 µM unlabeled IPTTPITTTYFFFK-$CONH_2$ and 100 nM IPTTPITTTYFFFK(5-carboxyfluorescein)-$CONH_2$) and 30 µM ATP. DMSO concentration during ERK activation was 4%. After one hour, reactions were terminated by addition of 60 µl IMAP detections beads in binding buffer (Molecular Devices). Binding was allowed to equilibrate for 30 minutes before reading the plate on an LJL Analyst Fluorescence Polarization plate reader. Compound inhibition was calculated relative to DMSO and fully inhibited standards. Active compounds were reconfirmed in an independent assay.

Active ERK2 Assay:

Activated ERK2 activity was also determined in the IMAP assay format using the procedure outlined above. 1 µl of 25× compound was added to 14 µl of kinase buffer containing 0.25 ng fully phosphorylated, active Mouse ERK2 protein. Following a 30 minute incubation, the reactions were initiated by addition of 10 µl of kinase buffer containing 1 µM ERK2

IMAP substrate peptide (0.9 µM unlabeled IPTTPITTTY-FFFK-CONH$_2$ and 100 nM IPTTPITTTYFFFK(5-carboxyfluorescein)-CONH$_2$) and 30 µM ATP. Reactions proceeded for 30 minutes before termination by addition of 60 µl IMAP detection beads in binding buffer. Plates were read as above after 30 minute binding equilibration. Active compounds were reconfirmed in an independent assay.

Soft Agar Assay:

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of ERK1 and ERK2 inhibitor as the top layer. After the top layer is solidified, plates can be incubated for 10-16 days at 37° C. under 5% CO$_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the IC$_{50}$'s can be determined.

The AUC (Area Under the Concentration-Time Curve During the First 6 Hours (AUC$_{6hr}$) in Table 30 Below was Determined Using the Protocol of Cassette Accelerating Rapid Rat Screen (CARRS)

Animal Dosing and Sample Collection

Male Sprague-Dawley rats (Charles River, Co.) were pre-cannulated (femoral artery) in order to facilitate precise blood sampling times, and to reduce the stress on the animals caused by serial bleedings. Following an overnight fast, two rats were dosed orally with one compound at a dose of 10 mg/kg in a 5-mL/kg dose volume. Blood was collected into heparin-containing tubes serially from each animal at 0.5, 1, 2, 3, 4 and 6 h post-dosing and centrifuged to generate plasma. Approximately 100 µL of plasma were collected at the individual time points. The plasma samples were stored at −20° C. until analysis.

Plasma Sample and Standard Curve Preparation

A set of 12 rat plasma samples was generated for each NCE (i.e. 6 timepoints and n=2 rats). These 12 samples were pooled across the two rats at each timepoint to provide 6 pooled samples (one sample per time point) for each NCE. The pooled samples were assayed as cassettes of six (36 samples total) to provide data on the six compounds. The 50-µL aliquots of the 36 plasma samples were placed into individual wells of a 96-well plate. An additional compound (often a structural analog of the test compounds) was selected as the internal standard. A mini-calibration curve was prepared (three points plus a zero) for each compound assayed. Drug-free rat plasma was measured into 1-mL aliquots and each aliquot was spiked with known concentrations of the compounds to generate standards of the desired concentrations. The concentrations of the standards were chosen to bracket the expected concentration of the pooled samples based on historical data from previous studies on other compounds. For this work, the standards were set to contain concentrations of 25, 250 and 2500 ng NCE/mL plasma. The plasma standards were precipitated in duplicate along with the samples. Protein precipitation occurred after addition of 150 µL of acetonitrile containing the internal standard at a concentration of 1 ng/mL into each sample well using the Tomtec Quadra 96 system. The precipitated samples and standards were vortexed and centrifuged in the 96-well plate. Approximately 50-100 µL of the supernatant were removed and placed into a fresh 96-well plate using the Tomtec Quadra 96 system. A volume of 5-10 µL of the supernatant was used for analysis by HPLC-MS/MS. The mini-standard curve was run in duplicate, once before and once after the samples. Thus, a total of 14 study samples plus standards were analyzed per compound. In addition, solvent blanks were injected before and after each set of 14 and after the highest calibration standard for each compound; therefore, a total of 103 injections were made into each HPLC system for each set of six compounds. Multiple solvent blank injections could be made from a single well. Twelve solvent blank wells were designated in each 96-well plate. Thus, one batch (cassette) of six NCEs was prepared and assayed using one 96-well plate format.

HPLC-MS/MS Analysis

All the compounds were analyzed using selected reaction monitoring (SRM) methods with LC/MS/MS instruments. Once the method development had been completed, the assay was quickly set up using a standard injection sequence template for the CARRS assay.

The final compounds of Examples 1, 2, 4-61, 65-73, 77-84, 86, 88-98, 100, 102-114, 116-118, 120, 121, 124, 125, 151-155, 159-179, 183, 184, 186, 188-193, 196-199, 202-205, 250, 253-259, 260-299, 301-318, 320-323, 332-347, 356 (Isomer Z), 356 (Isomer E), 357-360, 362, 362 (compound 9P), 364, 368-436, 440-509, 511-602, 606, 607, 609-623, and 625 to 824 had an AERK2 IC50 in the range of 0.16 to 20,000 nM.

The final compounds of Examples 1, 2, 4-28, 61, 86, 88, 89, 92, 95, 98, 100, 120, 125, 132, 142, 152, 154, 168, 176, 183, 184, 186, 188-193, 196-199, 202-205, 250, 251, 253-259, 261, 264, 269, 271, 274-276, 282, 286, 289, 290, 292, 294, 302, 303, 304, 306, 314-316, 332, 333, 335, 338, 343, 358, 362, 368-370, 384-390, 440-493, 510-558, 606, 611, 613-617, 620, 622, 623, 627-630, 634, 635, 639, 641, 643-645, 647, 651, 654-658, 661, 663, 666, 669, 670, 672, 673, 675-677, 679, 680, 682, 685, 688-694, 696-703, 705-707, 710-735, 737, 738, 740, 741, 743-745, 747, 749, 751-753, 755, 757, 758, 760-762, 764, 765, 767, 770-772, 776, 777, 779, 785, 786, 788, 789, 792, 793, 794, 796, 799, 802, 803-805, 807-809, 811-812, 814-816, 818-820, 822, and 823 had an AERK2 IC$_{50}$ in the range of 0.16 to 18 nM.

The final compounds of Examples 6, 100, 183, 184, 186, 188-192, 261, 440-450, 510-517 and 787 had an AERK2 IC$_{50}$ in the range of 0.16 to 1.5 nM.

The final compound of Example 183 had an AERK2 IC$_{50}$ of 0.16 nM. The final compound of Example 186 had an AERK2 IC$_{50}$ of 0.78 nM. The final compound of Example 335 had an AERK2 IC$_{50}$ of 4.9 nM.

Table 30 provides AERK2 IC$_{50}$ data and Rat Auc data for compounds of this invention.

TABLE 30

| Ex. | Compound | AERK2 IC50 (nM) | Rat AUC PO (nM·h) |
|---|---|---|---|
| 336 | | 18.1 | 7219 |
| 469 | | 2.5 | 1200 |
| 480 | | 4.8 | 1880 |
| 489 | | 9.1 | 723 |

TABLE 30-continued

| Ex. | Compound | AERK2 IC50 (nM) | Rat AUC PO (nM·h) |
|---|---|---|---|
| 571 | | 19.5 | 6466 |
| 413 | | 37.6 | 8946 |
| 412 | | 38.45 | 7836 |

TABLE 30-continued
| Ex. | Compound | AERK2 IC50 (nM) | Rat AUC PO (nM·h) |
|---|---|---|---|
| 462 | 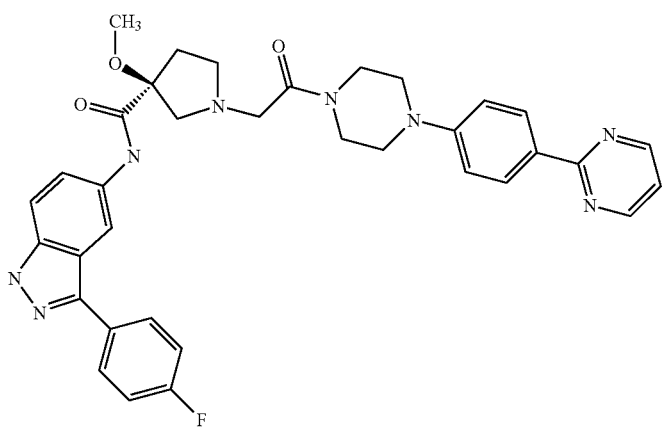 [SMILES: CO[C@@]1(C(=O)Nc2ccc3[nH]nc(-c4ccc(F)cc4)c3c2)CCN(CC(=O)N2CCN(c3ccc(-c4ncccn4)cc3)CC2)C1] | 2.1 | 352 |
| 487 | 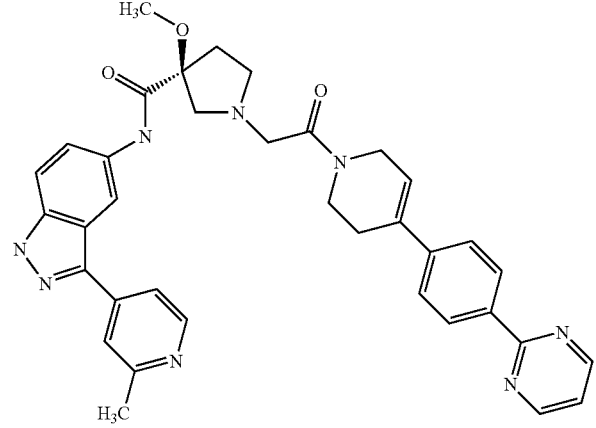 [SMILES: CO[C@@]1(C(=O)Nc2ccc3[nH]nc(-c4ccnc(C)c4)c3c2)CCN(CC(=O)N2CC=C(c3ccc(-c4ncccn4)cc3)CC2)C1] | 8.2 | 38 |
| 6 | 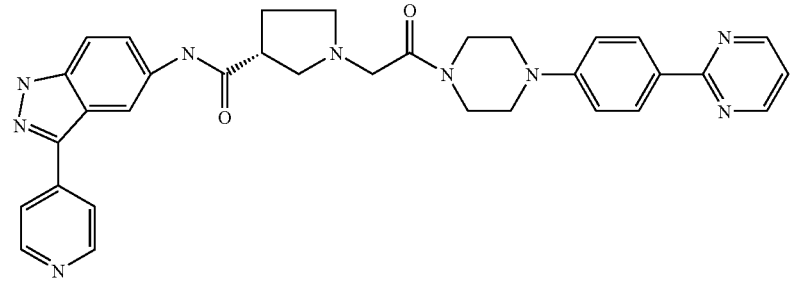 [SMILES: O=C(Nc1ccc2[nH]nc(-c3ccncc3)c2c1)[C@@H]1CCN(CC(=O)N2CCN(c3ccc(-c4ncccn4)cc3)CC2)C1] | 0.8 | 0 |

TABLE 30-continued
| Ex. | Compound | AERK2 IC50 (nM) | Rat AUC PO (nM · h) |
|---|---|---|---|
| 622 | 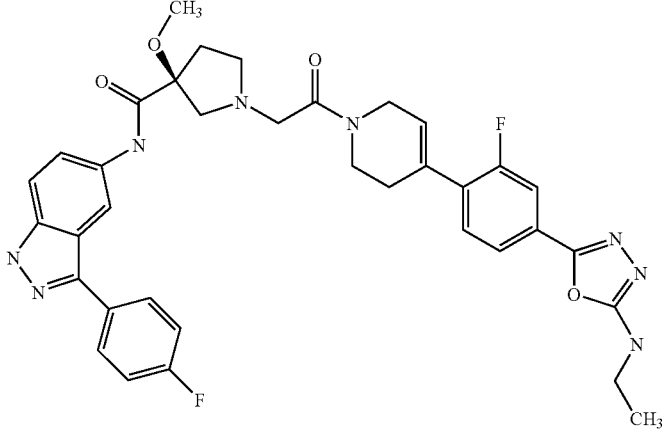 [SMILES: CCNc1nnc(-c2ccc(C3=CCN(C(=O)CN4CC[C@@](OC)(C(=O)Nc5ccc6[nH]nc(-c7ccc(F)cc7)c6c5)C4)CC3)c(F)c2)o1] | 5 | 1128 |
| 613 | 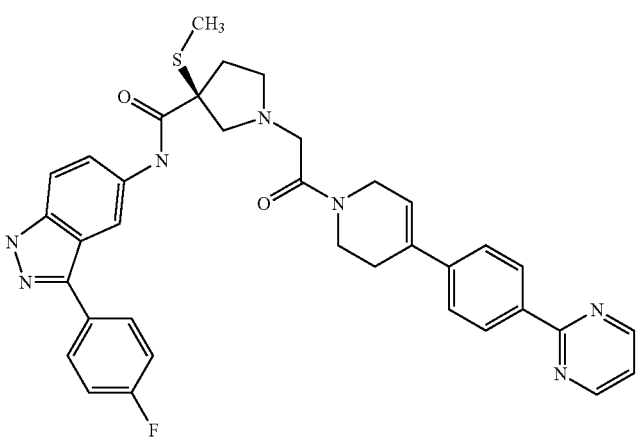 [SMILES: CS[C@@]1(C(=O)Nc2ccc3[nH]nc(-c4ccc(F)cc4)c3c2)CCN(CC(=O)N2CC=C(c3ccc(-c4ncccn4)cc3)CC2)C1] | 10 | 25914 |
| 825 | 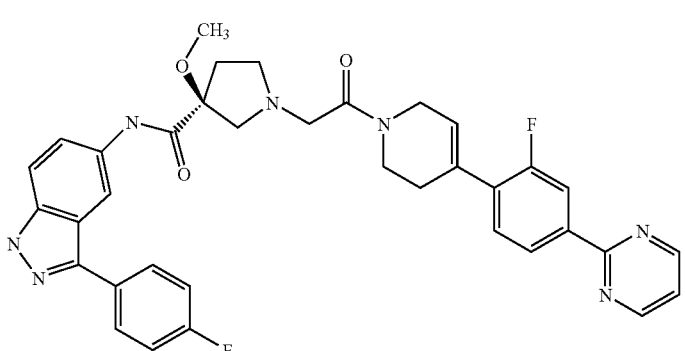 | 20 | 1101 |
| 479 | 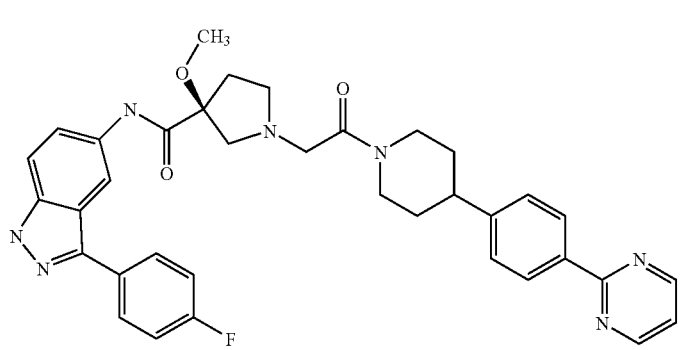 [SMILES: CO[C@@]1(C(=O)Nc2ccc3[nH]nc(-c4ccc(F)cc4)c3c2)CCN(CC(=O)N2CCC(c3ccc(-c4ncccn4)cc3)CC2)C1] | 9.1 | 2200 |

TABLE 30-continued

| Ex. | Compound | AERK2 IC50 (nM) | Rat AUC PO (nM · h) |
|---|---|---|---|
| 459 | 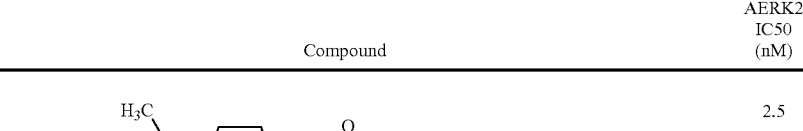 | 2.5 | 1200 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of formula 1.0:

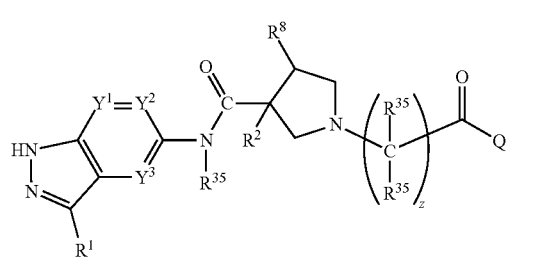

(1.0)

or the pharmaceutically acceptable salts, esters and solvates thereof, wherein:

$Y^1$, $Y^2$, and $Y^3$ are each independently selected from the group consisting of:

—CH═, and —CR$^9$═;

z is 1 to 3;

Q is a substituent selected from the group consisting of:

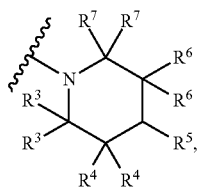 (2.1)

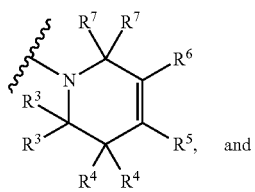 (2.2) and

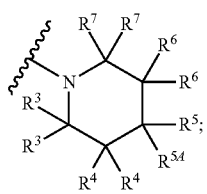 (2.17)

$Z^2$ is selected from the group consisting of: —N($R^{44}$)—, —O— and —C($R^{46}$)$_2$—;

m is 1 to 6;
n is 1 to 6;
p is 0 to 6;
t is 0, 1, or 2;
$R^1$ is selected from the group consisting of:
(1) —CN,
(2) —NO$_2$,
(3) —OR$^{10}$,
(4) —SR$^{10}$
(5) —N(R$^{10}$)$_2$,
(6) R$^{10}$,
(7) —C(O)R$^{10}$,
(8) —(C(R$^{30}$)$_2$)$_n$—NR$^{32}$—C(O)—R$^{10}$,
(9) —(C(R$^{30}$$_2$)$_n$—NR$^{32}$—S(O)$_t$—R$^{10}$,
(10) —(C(R$^{30}$)$_2$)$_n$—NR$^{32}$—C(O)—N(R$^{32}$)—R$^{10}$,
(11)

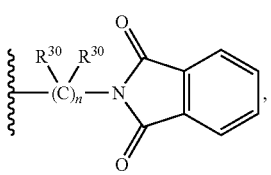

(12) —CF$_3$,
(13) —C(O)OR$^{10}$,
(14) —(C(R$^{30}$)$_2$)$_n$R$^{13}$ wherein n is 1, each R$^{30}$ is H, and R$^{13}$ is selected from the group consisting of: —OH and —N(R$^{10}$)$_2$, wherein each R$^{10}$ is independently selected,
(15) alkenyl,
(16) —NR$^{32}$—C(O)—R$^{14}$, (17)

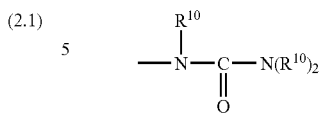

wherein each R$^{10}$ is independently selected,
(18)

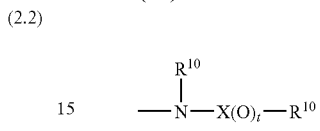

wherein each R$^{10}$ is independently selected,
(19)

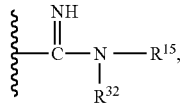

(20) —C(O)—NR$^{32}$—(C(R$^{30}$$_2$)$_p$—OR$^{10}$,
(21) —C(O)N(R$^{10}$)$_2$ wherein each R$^{10}$ is independently selected,
(22) —C(O)—NR$^{32}$—C(R$^{18}$)$_3$ wherein each R$^{18}$ is independently selected from the group consisting of: R$^{10}$ and —C(O)OR$^{19}$, and R$^{19}$ is selected from the group consisting of: alkyl and substituted arylalkyl,
(23) —C(O)—NR$^{32}$—(C(R$^{30}$$_2$)$_n$—C(O)—N(R$^{10}$)$_2$,
(24) heterocycloalkenyl,
(25)

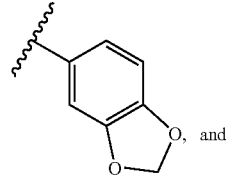 and

(26) arylalkenyl-;
$R^2$ is selected from the group consisting of:
(1) H,
(2) —CN,
(3) halo,
(4) alkyl,
(5) substituted alkyl wherein said substituted alkyl is substituted with 1 to 3 substitutents selected from the group consisting of: (a) —OH, (b) —O-alkyl, (c) —O-alkyl substituted with 1 to 3 F atoms, and (d) —N(R$^{40}$)$_2$ wherein each R$^{40}$ is independently selected from the group consisting of: (i) H, (ii) C$_1$-C$_3$ alkyl, (iii) —CF$_3$, and (e) halo,
(6) alkynyl,
(7) alkenyl,
(8) —(CH$_2$)$_m$R$^{11}$,
(9) —N(R$^{26}$)$_2$,
(10) —OR$^{23}$,
(11) —N(R$^{26}$)C(O)R$^{42}$,

(12) cycloalkyl,
(13) cycloalkylalkyl,
(14)

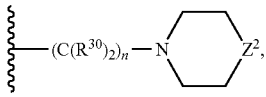

(15) —O-(substituted alkyl) wherein said substituted alkyl is substituted with 1 to 3 F atoms,
(16) —S(O)$_t$-alkyl,
(17) —C(O)-alkyl,
(18)

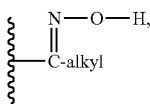

(19)

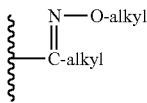

wherein each alkyl is independently selected,
(20)

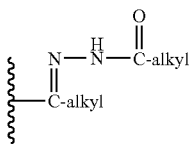

which each alkyl is independently selected,
(21)

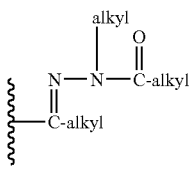

wherein each alkyl is independently selected,
(22) —N(R$^{48}$)—C(O)—R$^{48}$ wherein each R$^{48}$ is independently selected from the group consisting of: H and alkyl, and
(23) —C(O)-alkyl;
each R$^3$, R$^4$, R$^5$, R$^6$ and R$^7$ is independently selected from the group consisting of:
(1) H,
(2) alkenyl,
(3) substituted alkenyl,
(4) alkyl,
(5) substituted alkyl,
(6) cycloalkyl,
(7) substituted cycloalkyl,
(8) cycloalkylalkyl-,
(9) substituted cycloalkylalkyl-,
(10) heterocycloalkyl,
(11) substituted heterocycloalkyl,
(12) heterocycloalkylalkyl-,
(13) substituted heterocycloalkylalkyl-,
(14) —C(O)R$^{10}$,
(15) arylheteroaryl-,
(16) substituted arylheteroaryl-,
(17) heteroarylaryl-,
(18) substituted heteroarylaryl-,
(19) aryl,
(20) substituted aryl,
(21) heteroaryl,
(22) substituted heteroaryl,
(23) heteroarylheteroaryl-,
(24) substituted heteroarylheteroaryl-,
(25) arylaminoheteroaryl-,
(26) substituted arylaminoheteroaryl-,
(27) arylalkynyl-,
(28) substituted arylalkynyl-,
(29) heteroarylalkynyl-,
(30) substituted heteroarylalkynyl-, and
(31) benzoheteroaryl,
wherein said R$^3$, R$^4$, R$^5$, R$^6$ and R$^7$ substituted groups (7), (9), (11), (13), (16), (18), (20), (22), (24), (26), (28) and (30) are substituted with 1 to 3 substituents independently selected from the group consisting of: —NH$_2$, —NHR$^{20}$, —N(R$^{20}$)$_2$ wherein each R$^{20}$ is independently selected, alkyl, alkenyl, halo, —C(O)—NH—R$^{28}$, —C(O)OR$^{28}$, —C(O)R$^{28}$, and —OR$^{20}$, and
wherein said R$^3$, R$^4$, R$^5$, R$^6$ and R$^7$ substituted groups (3) and (5) are substituted with 1 to 3 substituents independently selected from the group consisting of: —NH$_2$, halo, —C(O)—NH—R$^{28}$, —C(O)OR$^{28}$, and —C(O)R$^{28}$;
R$^5$A is selected from the group consisting of: halo, —OH, alkyl, and —O-alkyl;
R$^8$ is selected from the group consisting of: H, —OH, —N(R$^{10}$)$_2$, —NR$^{10}$C(O)R$^{12}$, and alkyl;
each R$^9$ is independently selected from the group consisting of: halogen, —CN, —NO$_2$, —OR$^{10}$, —SR$^{10}$, —N(R$^{10}$)$_2$, and R$^{10}$;
each R$^{10}$ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl-, substituted alkylaryl-, heterocycloalkenyl, and substituted heterocycloalkenyl, and wherein:
said R$^{10}$ substituted alkyl is substituted with 1 to 3 substituents independently selected from the group consisting of: —NH$_2$, —NHR$^{20}$, —NO$_2$, —CN, —OR$^{26}$, halo, —C(O)—NH—R$^{26}$, —C(O)OR$^{26}$, and —C(O)R$^{26}$, and
said R$^{10}$ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —NH$_2$, (2) —NO$_2$, (3) —CN, (4) —OH, (5) —OR$^{20}$, (6) —OCF$_3$, (7) alkyl substituted with 1 to 3 independently selected halo atoms, (8) —C(O)R³⁸, (9) alkyl, (10) alkenyl, (11) halo, (12) —C(O)—NH—R²⁶, (13) —C(O)OR³⁸, (14) —C(O)—NR³²—(C(R³⁰)₂)ₙ—N(R³⁸)₂, (15) —S(O)ₜR³⁸, (16) —C(O)—NR³²—R³⁸, (17) —NR³²—C(O)—R³⁸, (18)

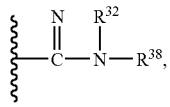

(19) —NHR²⁰, (20) cycloalkyl, (21) —O-alkyl-O—R²⁰, (22) hydroxyalkyl, (23) —N(R²⁰)₂ wherein each R²⁰ is independently selected, (24) -alkyl-OR²⁰, (25) —O-alkyl-OH, (26) —NH(hydroxyalkyl), and (27) oxazolidinone;

R¹¹ is selected from the group consisting of: F, —OH, —CN, —OR¹⁰, —NHNR¹R¹⁰, —SR¹⁰ and heteroaryl;

R¹² is selected from the group consisting of: alkyl, aryl, heteroaryl, cycloalkyl, cycloalkylalkyl, heterocycloalkyl and heterocycloalkylalkyl;

R¹⁴ is selected from the group consisting of: alkyl, aryl, heteroaryl, cycloalkyl, cycloalkylalkyl-, heterocycloalkyl, alkylheterocycloalkyl, heterocycloalkylalkyl-, alkylheteroaryl- and alkylaryl-;

R¹⁵ is selected from the group consisting of: H, —OH, alkyl, aryl, heteroaryl, cycloalkyl, cycloalkylalkyl-, heterocycloalkyl and heterocycloalkylalkyl-, alkylheteroaryl- and alkylaryl-;

R²⁰ represents alkyl;

R²³ is selected from the group consisting of: H, alkyl, aryl, cycloalkyl, and cycloalkylalkyl-;

each R²⁶ is independently selected from the group consisting of: H and alkyl;

R²⁸ is alkyl;

each R³⁰ is independently selected from the group consisting of: H, alkyl, and F;

each R³² is independently selected from the group consisting of: H and alkyl, and wherein each R³² is generally H;

each R³⁵ is independently selected from the group consisting of: H and C₁ to C₆ alkyl;

R³⁶ is selected from the group consisting of: H, alkyl, and —O-alkyl;

each R³⁸ is independently selected from the group consisting of: H, alkyl, aryl, arylalkyl, heteroaryl, heteroarylalkyl, cycloalkyl, cycloalkylalkyl, heterocycloalkyl, heterocycloalkylalkyl, alkylheteroaryl-, alkylaryl-, substituted alkyl, substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl-, and wherein:

said R³⁸ substituted alkyl is substituted with 1 to 3 substituents independently selected from the group consisting of: —NH₂, —NO₂, —CN, —OR²⁶, halo, —C(O)—NH—R²⁸, —C(O)OR²⁸, and —C(O)R²⁸, and said R³⁸ substituted aryl, substituted arylalkyl, substituted heteroaryl, substituted heteroarylalkyl, substituted cycloalkyl, substituted cycloalkylalkyl, substituted heterocycloalkyl, substituted heterocycloalkylalkyl, substituted alkylheteroaryl- and substituted alkylaryl- are substituted with 1 to 3 substituents independently selected from the group consisting of: (1) —NH₂, (2) —NO₂, (3) —CN, (4) —OH, (5) —OR²⁰, (6) —OCF₃, (7) —CF₃, (8) —C(O)R²⁶, (9) alkyl, (10) alkenyl, (11) halo, (12) —C(O)—NH—R²⁶, (13) —C(O)OR²⁶, (14) —C(O)—NR³²—(C(R³⁰)₂)ₙ—N(R²⁶)₂, (15) —S(O)ₜR²⁶, (16) —C(O)N(R³²)(R²⁶), (17) —NR³²C(O)R²⁶, (18)

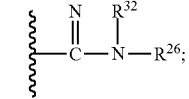

and

(19) —NHR²⁰;

R⁴² is selected from the group consisting of: alkyl, aryl, heteroaryl, and cycloalkyl;

R⁴⁴ is selected from the group consisting of: H, alkyl, cycloalkyl, and cycloalkylalkyl; and Each R⁴⁶ is independently selected from the group consisting of: H, alkyl, cycloalkyl, and cycloalkylalkyl.

2. The compound of claim 1 having the formula:

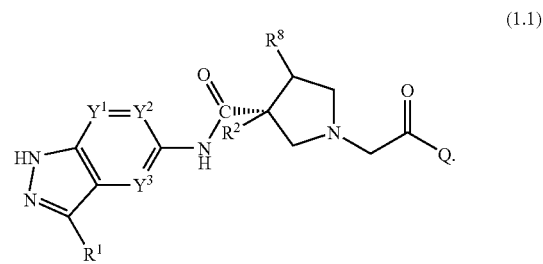

(1.1)

3. The compound of claim 1 having the formula:

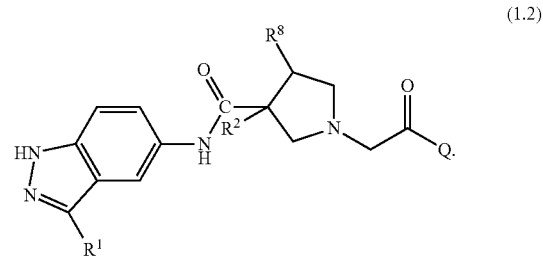

(1.2)

4. The compound of claim 1 having the formula:

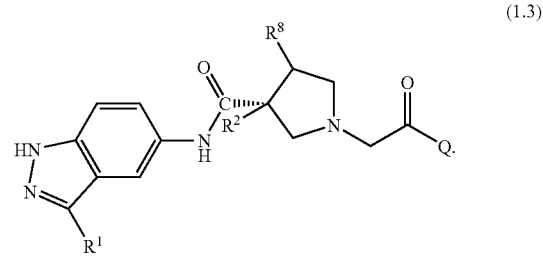

(1.3)

5. The compound of claim 1 wherein Q is selected from the group consisting of: 2.1, and 2.2.

6. The compound of claim 3 wherein Q is selected from the group consisting of: 2.1, and 2.2.

7. The compound of claim 4 wherein Q is selected from the group consisting of: 2.1, and 2.2.

8. The compound of claim 1 wherein Q is 2.17.

9. The compound of claim 3 wherein Q is 2.17.

10. The compound of claim 4 wherein Q is 2.17.

11. The compound of claim 1 wherein each $R^3$, $R^4$, $R^6$, and $R^7$ is independently selected from the group consisting of: H and alkyl.

12. The compound of claim 11 wherein each $R^3$, $R^4$, $R^6$, and $R^7$ is independently selected from the group consisting of: H and methyl.

13. The compound of claim 5 wherein each $R^3$, $R^4$, $R^6$, and $R^7$ is independently selected from the group consisting of: H and alkyl.

14. The compound of claim 13 wherein each $R^3$, $R^4$, $R^6$, and $R^7$ is independently selected from the group consisting of: H and methyl.

15. The compound of claim 14 wherein each $R^3$, $R^4$, $R^6$, and $R^7$ is H.

16. The compound of claim 15 wherein Q is 2.1.

17. The compound of claim 1 wherein Q is 2.17.

18. The compound of claim 1 wherein Q is 2.17 wherein each $R^3$, $R^4$, $R^6$, and $R^7$ is independently selected from the group consisting of: H and methyl.

19. The compound of claim 1 wherein Q is 2.17 wherein each $R^3$, $R^4$, $R^6$, and $R^7$ is H.

20. The compound of claim 16 wherein the compound of formula 1.0 is:

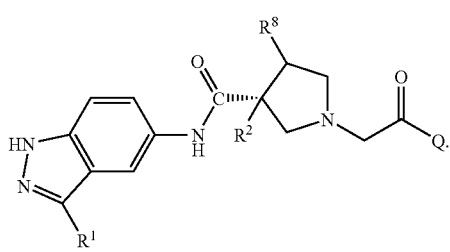

(1.3)

21. The compound of claim 4 wherein Q is selected from the group consisting of: 2.1, and 2.2 and $R^3$, $R^4$, $R^6$, and $R^7$ are each independently selected from the group consisting of: H and alkyl.

22. The compound of claim 21 wherein $R^3$, $R^4$, $R^6$, and $R^7$ are selected from the group consisting of: H and methyl.

23. The compound of claim 22 wherein Q is 2.1.

24. The compound of claim 23 wherein $R^3$, $R^4$, $R^6$, and $R^7$ are each H.

25. The compound of claim 1 wherein Q is

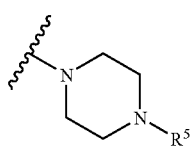

substituted with one or two substituents independently selected from the group consisting of $R^3$ groups, provided that said one or two substitutents are not H.

26. The compound of claim 1 wherein Q is

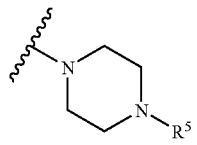

substituted with one or two alkyl groups.

27. The compound of claim 1 wherein Q is

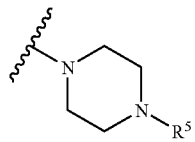

substituted with one or two methyl groups.

28. The compound of claim 1 wherein Q is

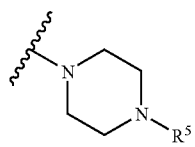

substituted with one methyl group.

29. The compound of claim 1 wherein $R^1$ is selected from the group consisting of:

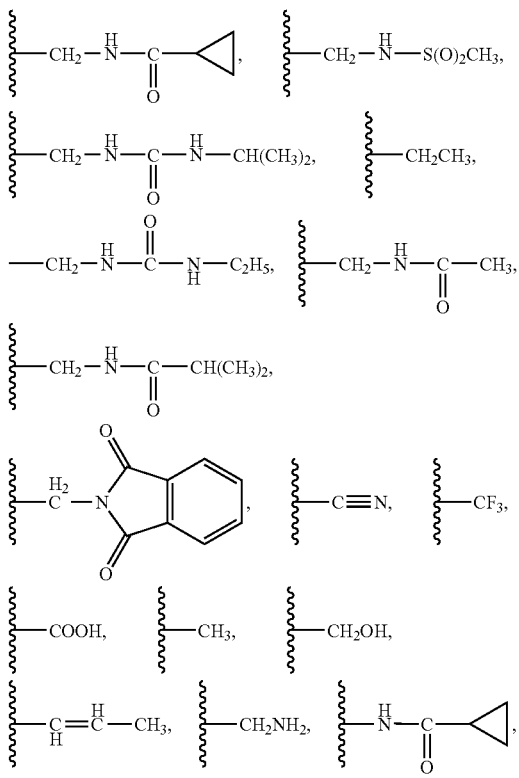

837
-continued
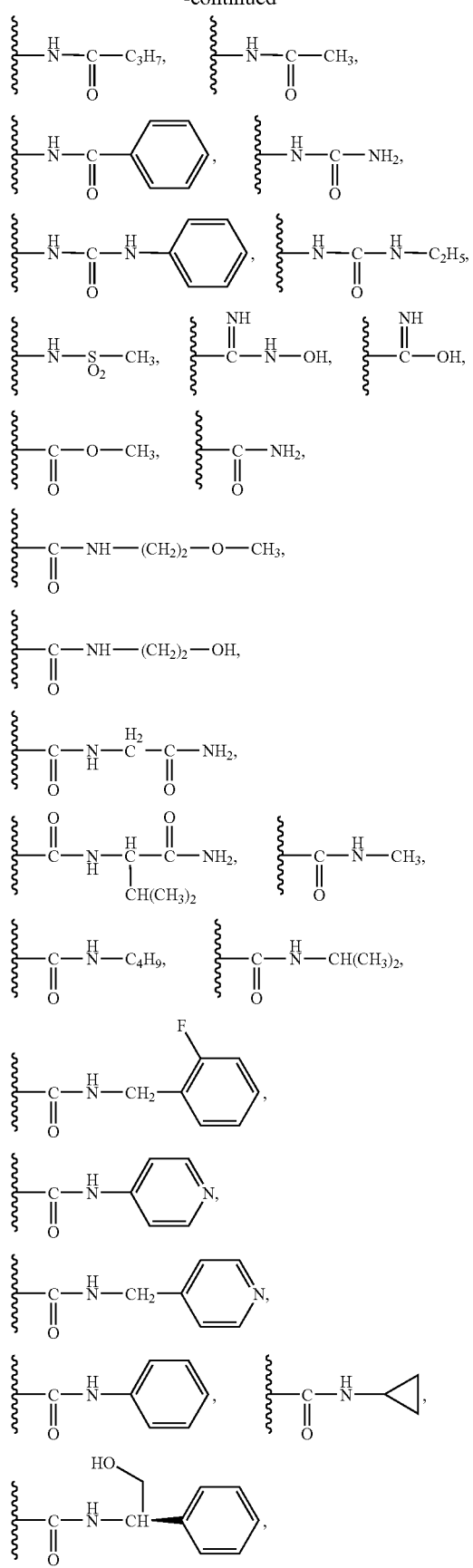
838
-continued
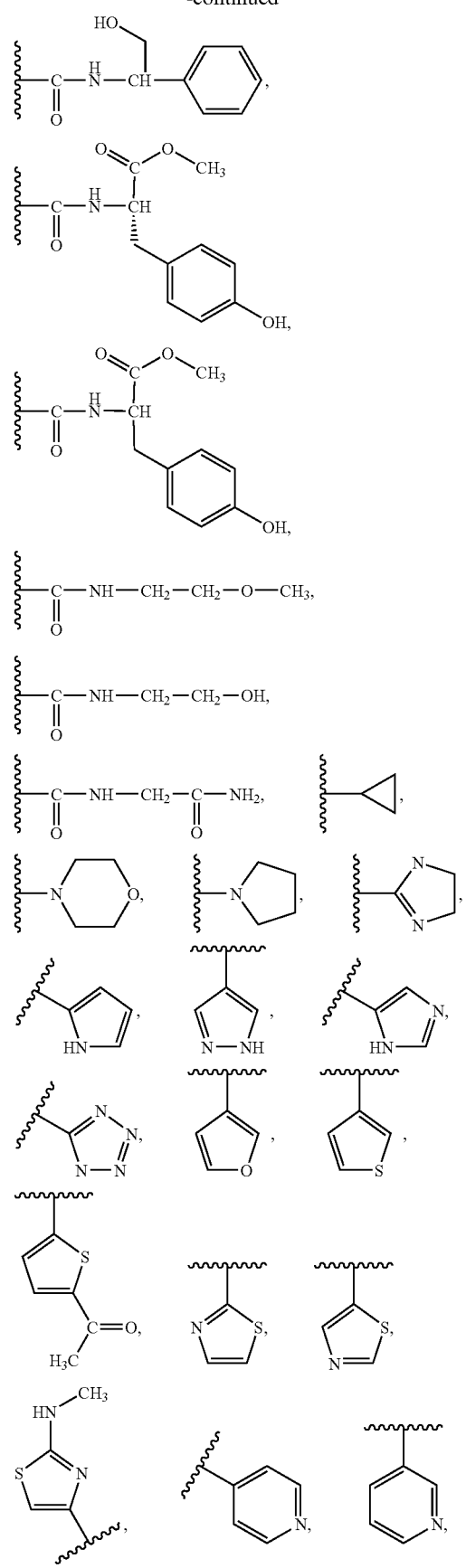

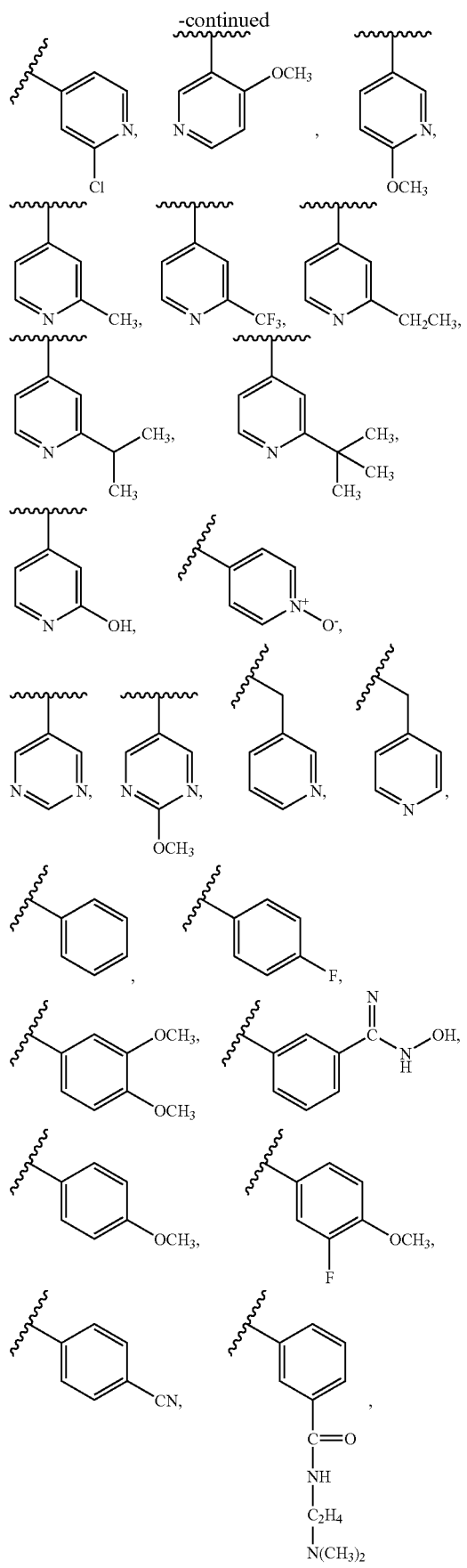
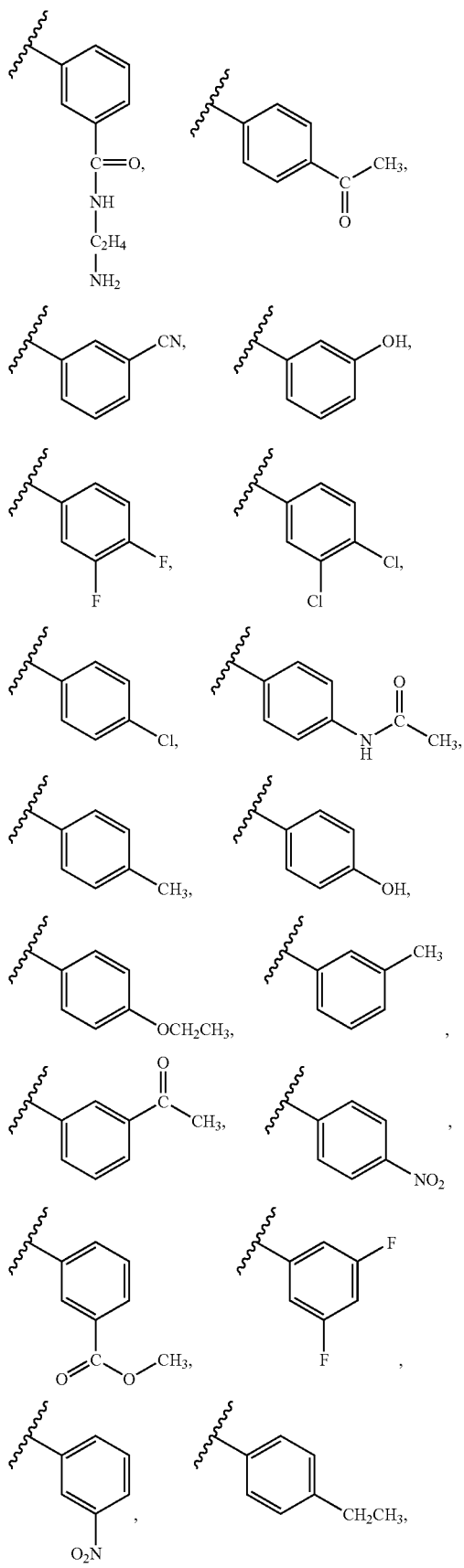

841
-continued
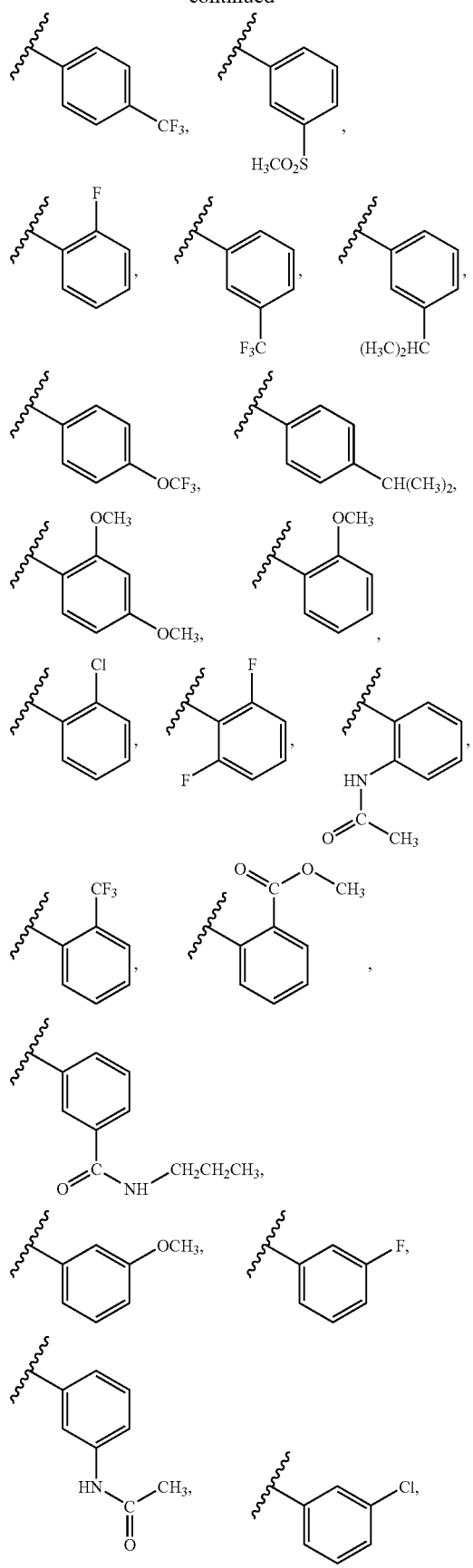
842
-continued
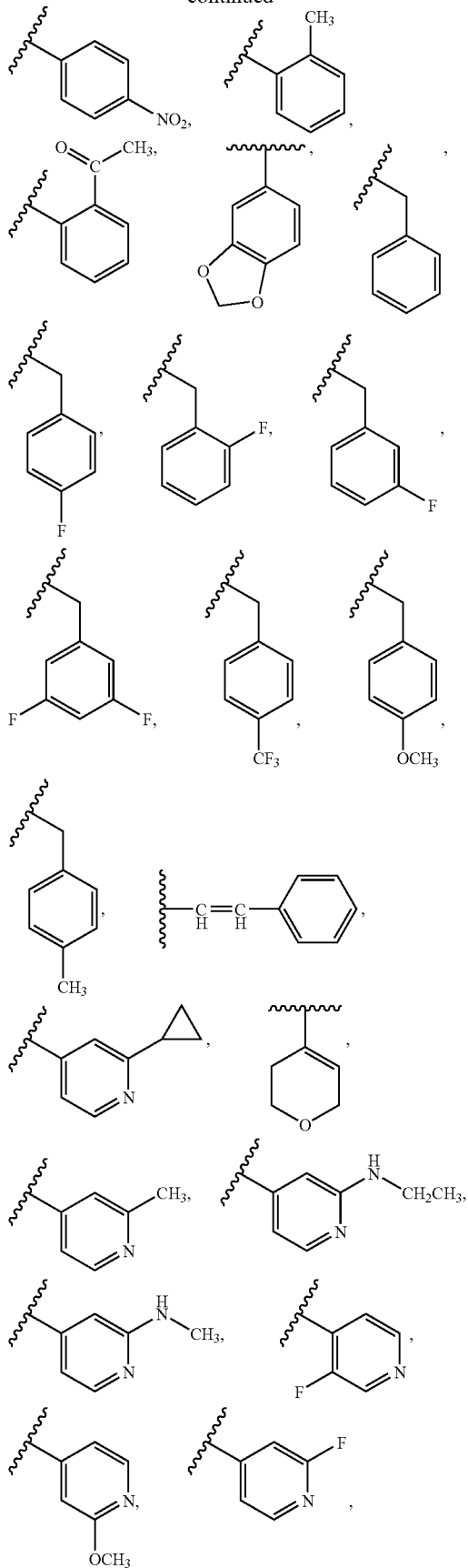

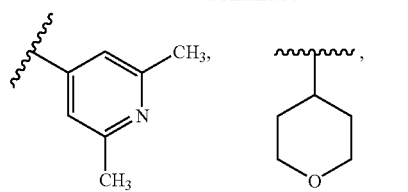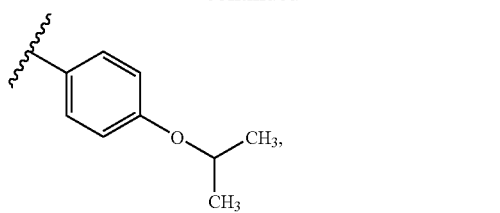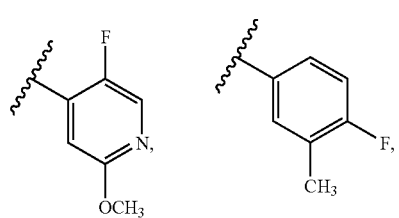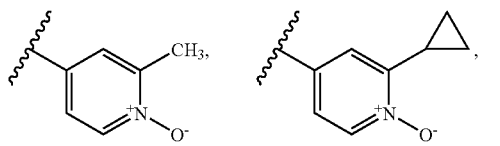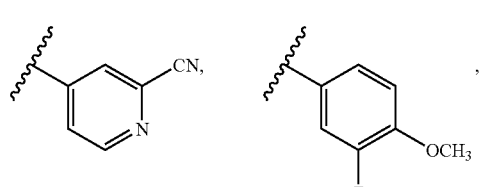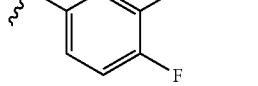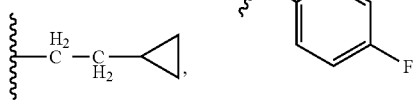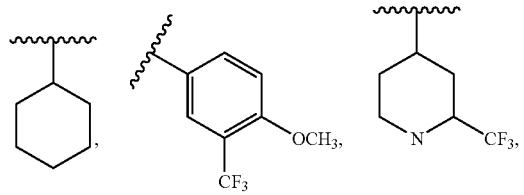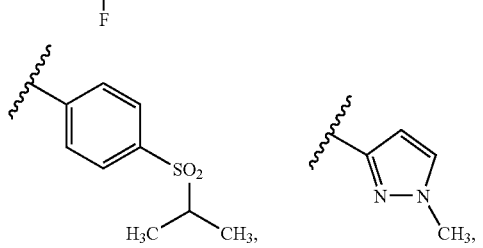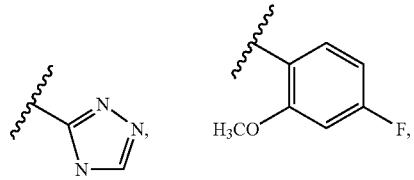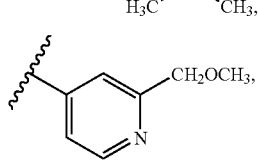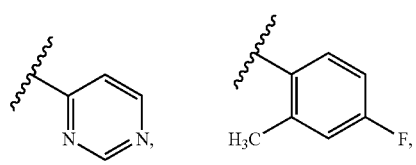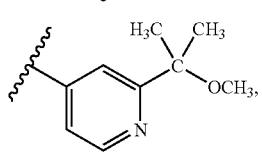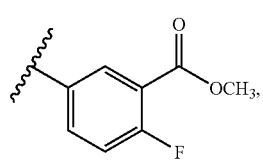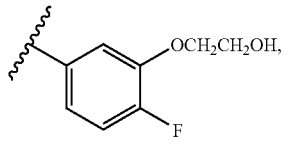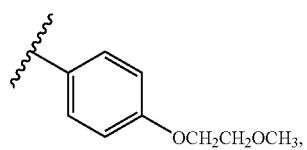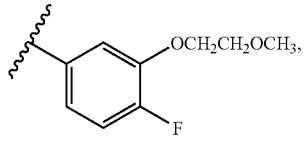

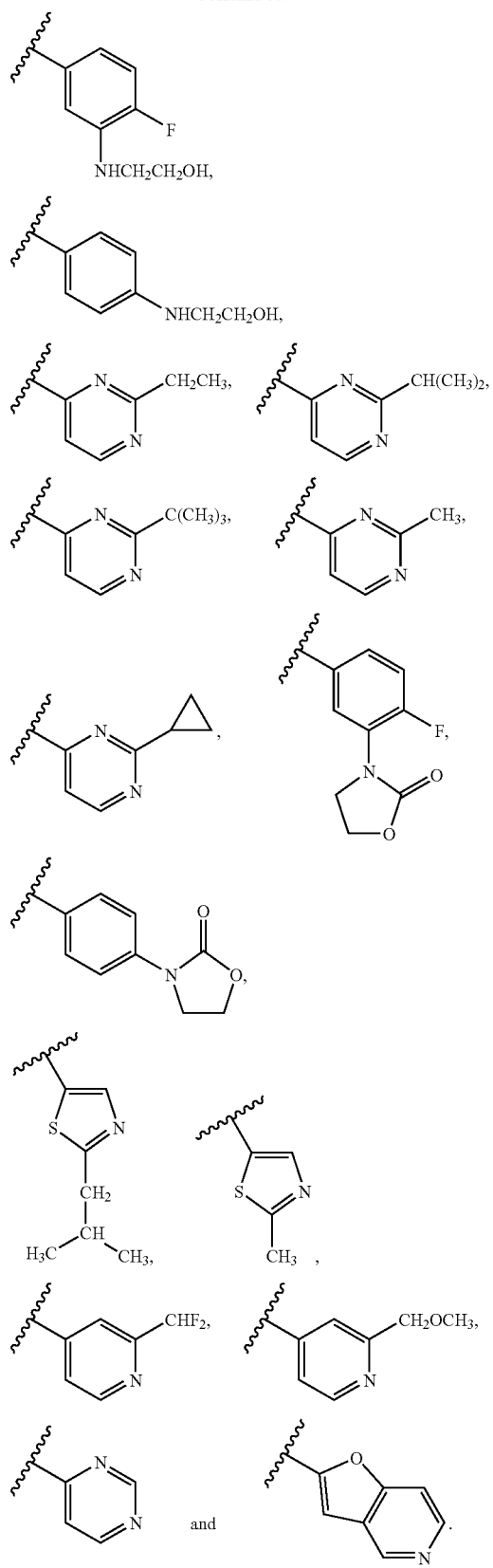
30. The compound of claim 7 wherein $R^1$ is selected from the group consisting of:

847
-continued
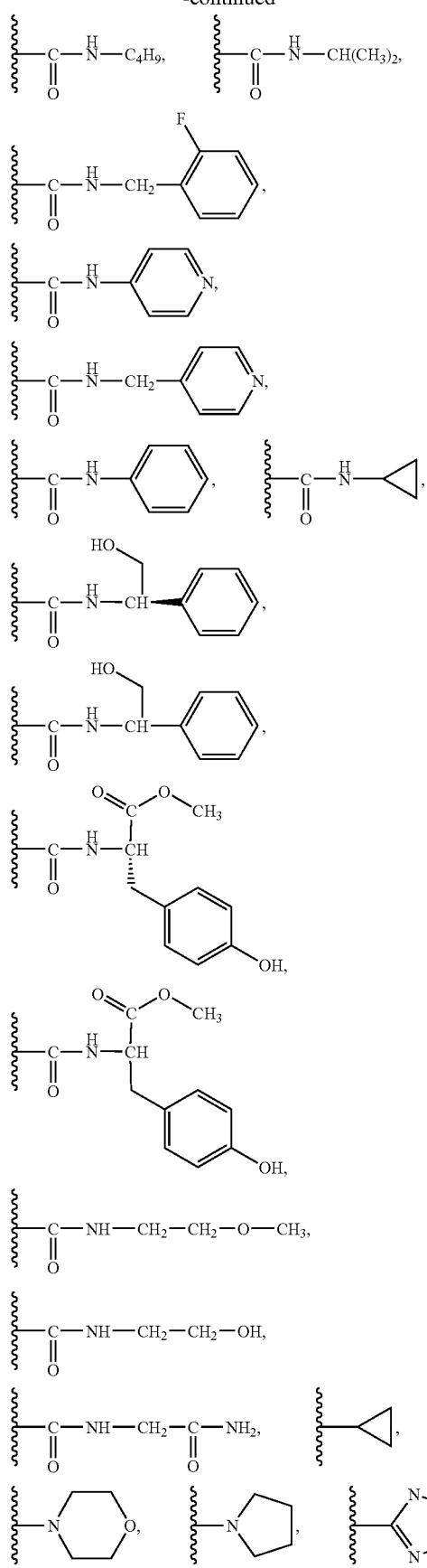
848
-continued
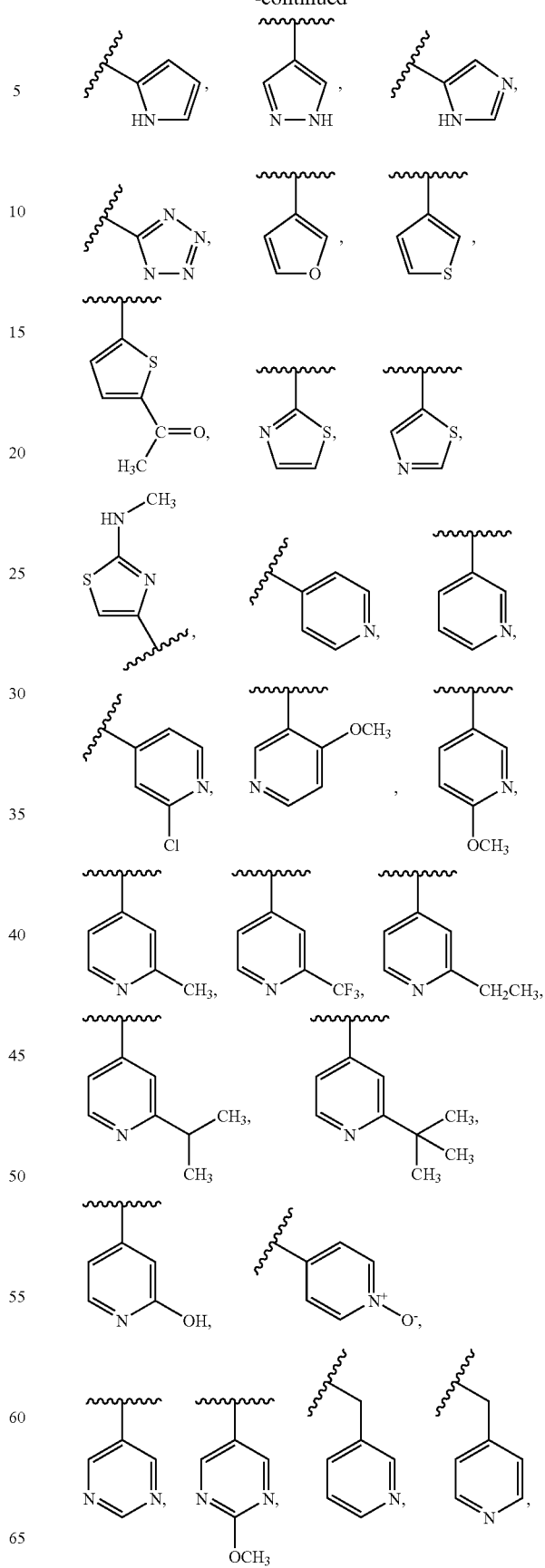

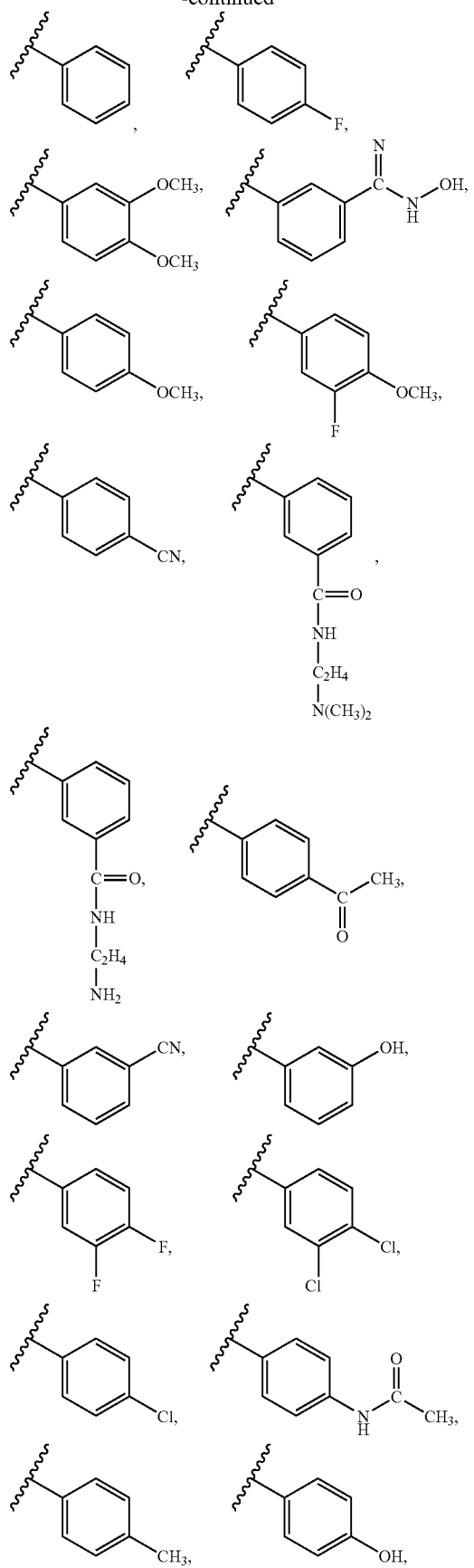
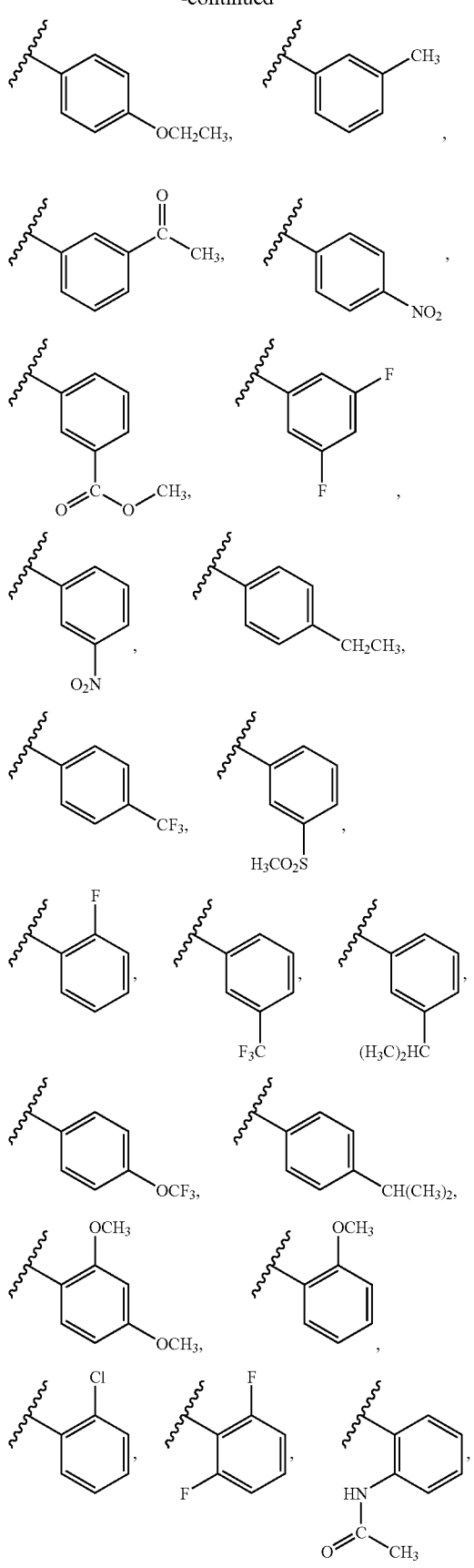

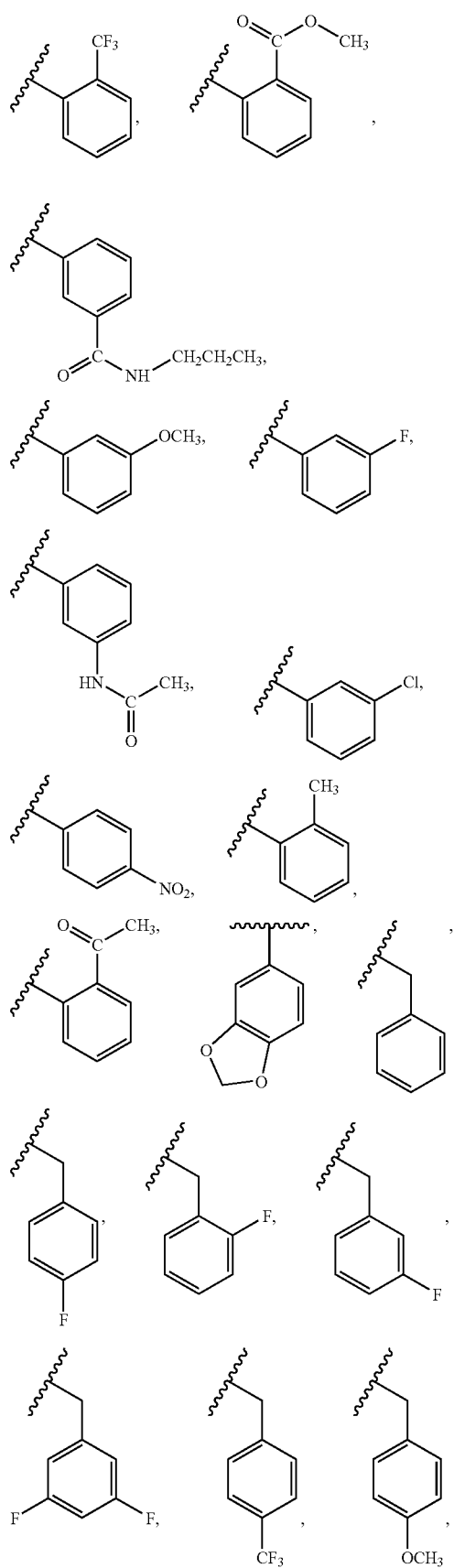
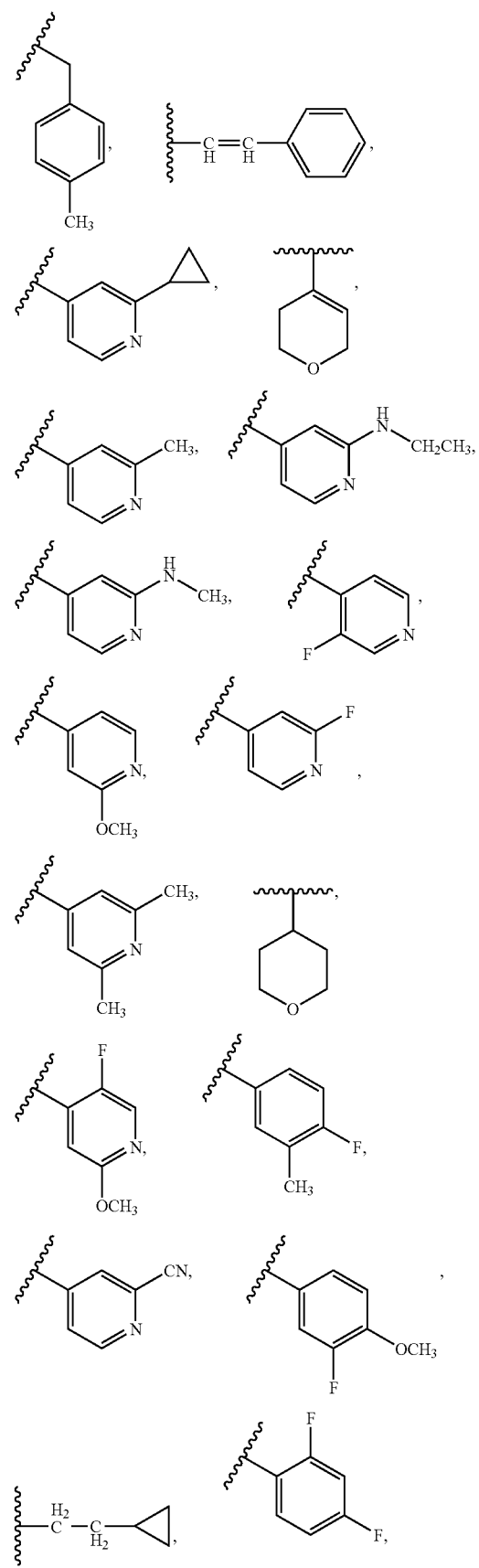

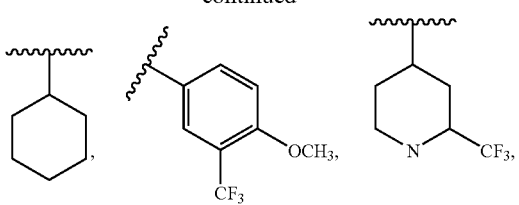
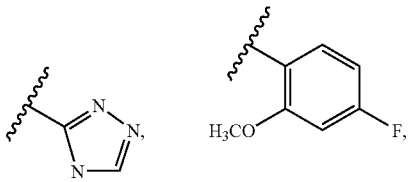
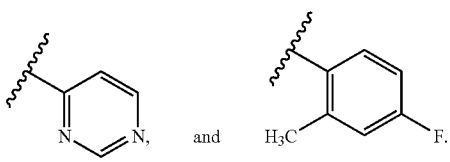
31. The compound of claim 1 wherein $R^1$ is aryl.
32. The compound of claim 1 wherein $R^1$ is heteroaryl or substituted heteroaryl.
33. The compound of claim 1 wherein $R^5$ is selected from the group consisting of:
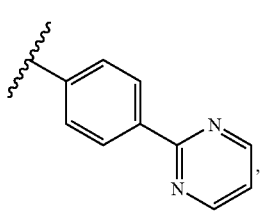
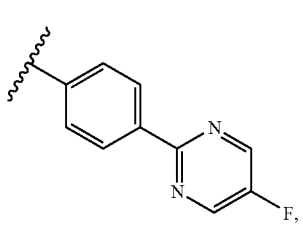
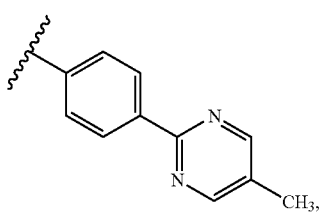
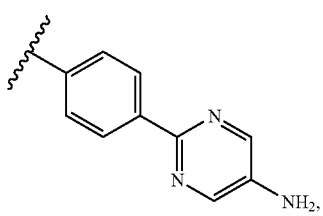
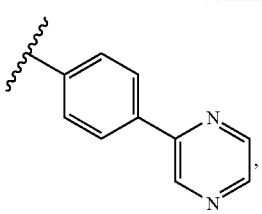
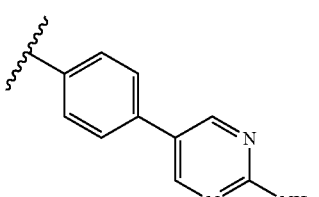
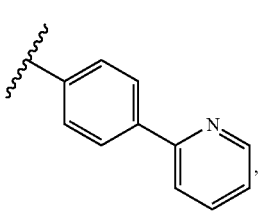
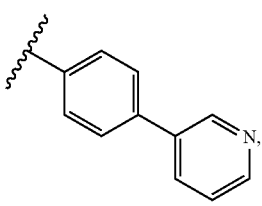
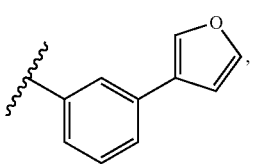
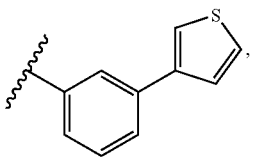
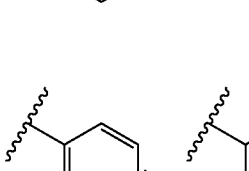
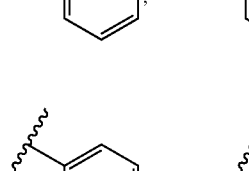
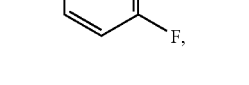

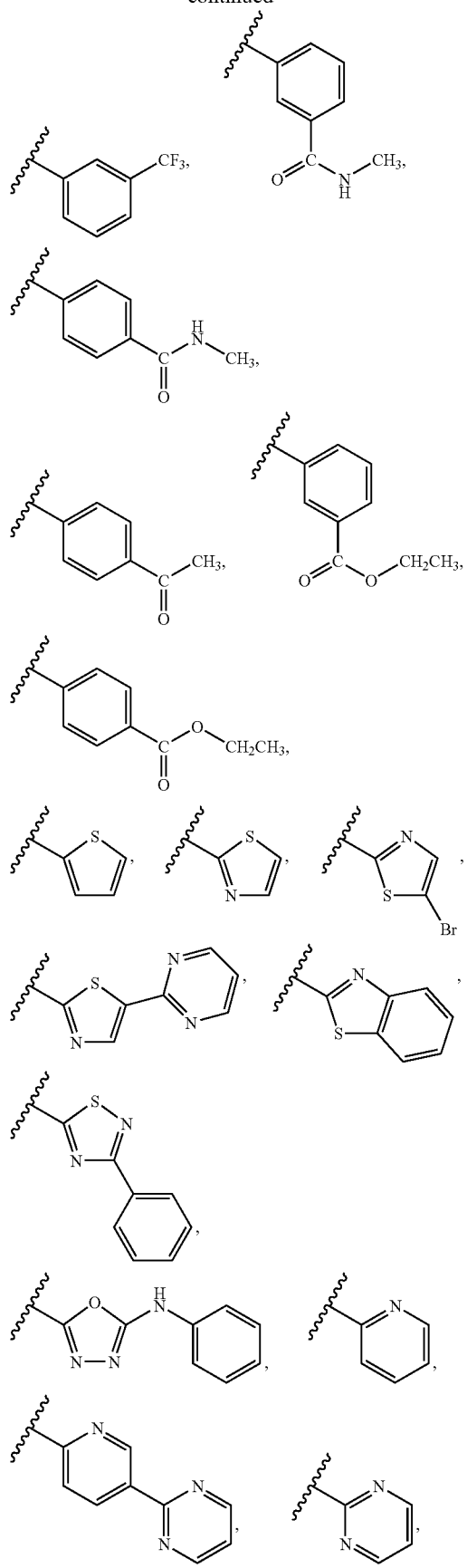
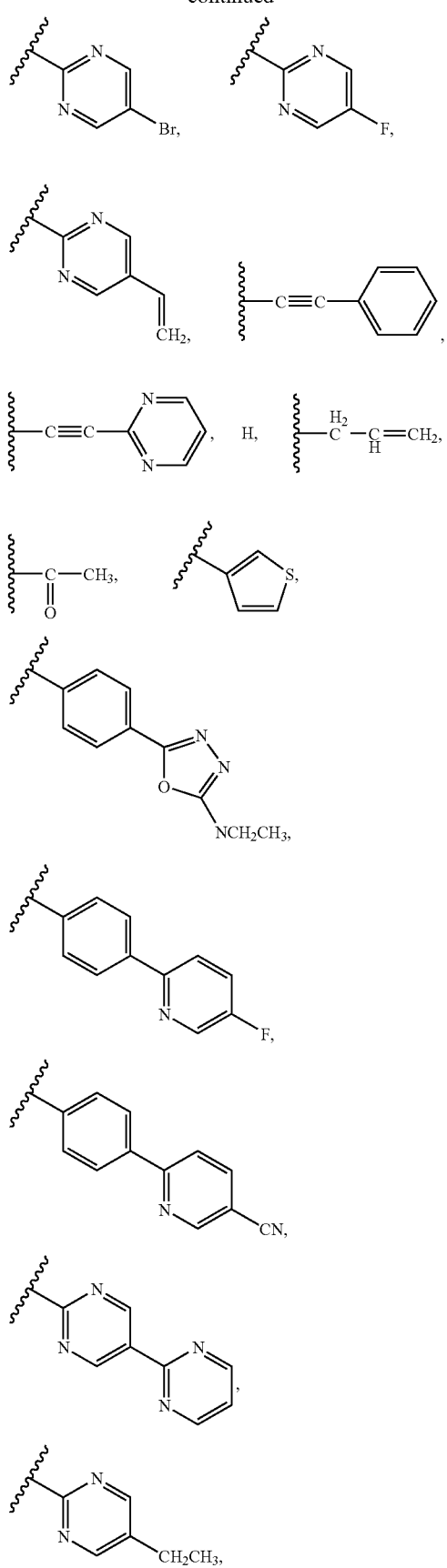

857
-continued
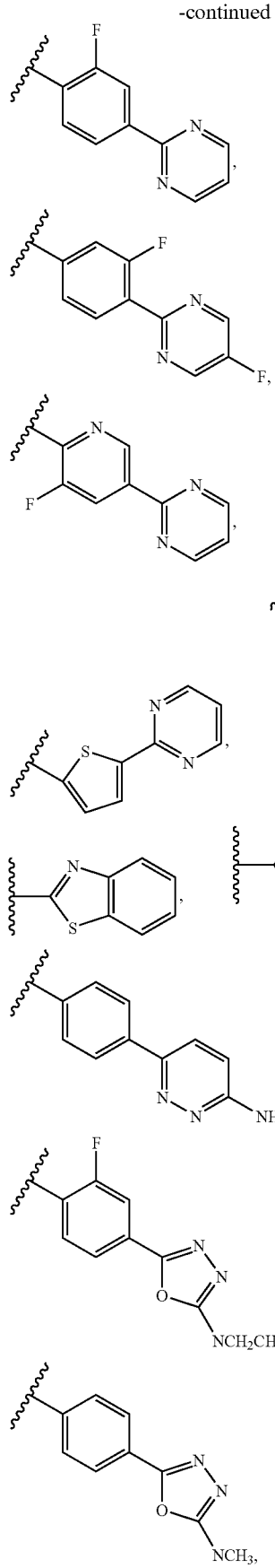
858
-continued
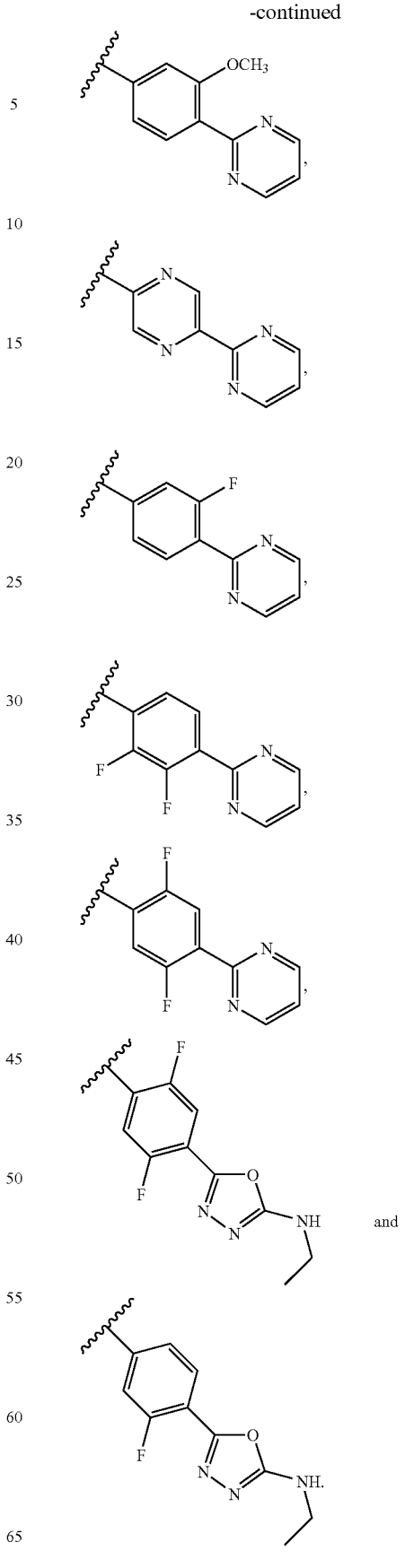

34. The compound of claim 7 wherein $R^5$ is selected from the group consisting of:
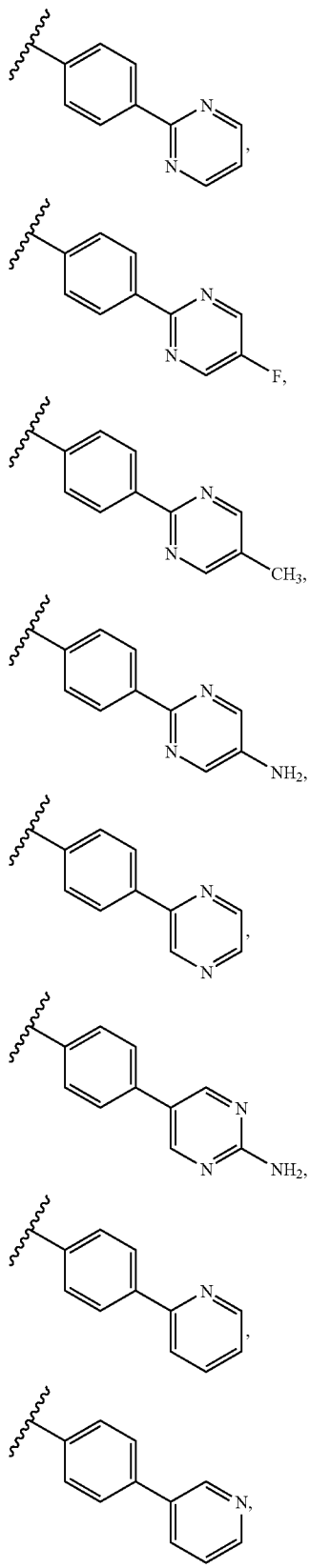
-continued
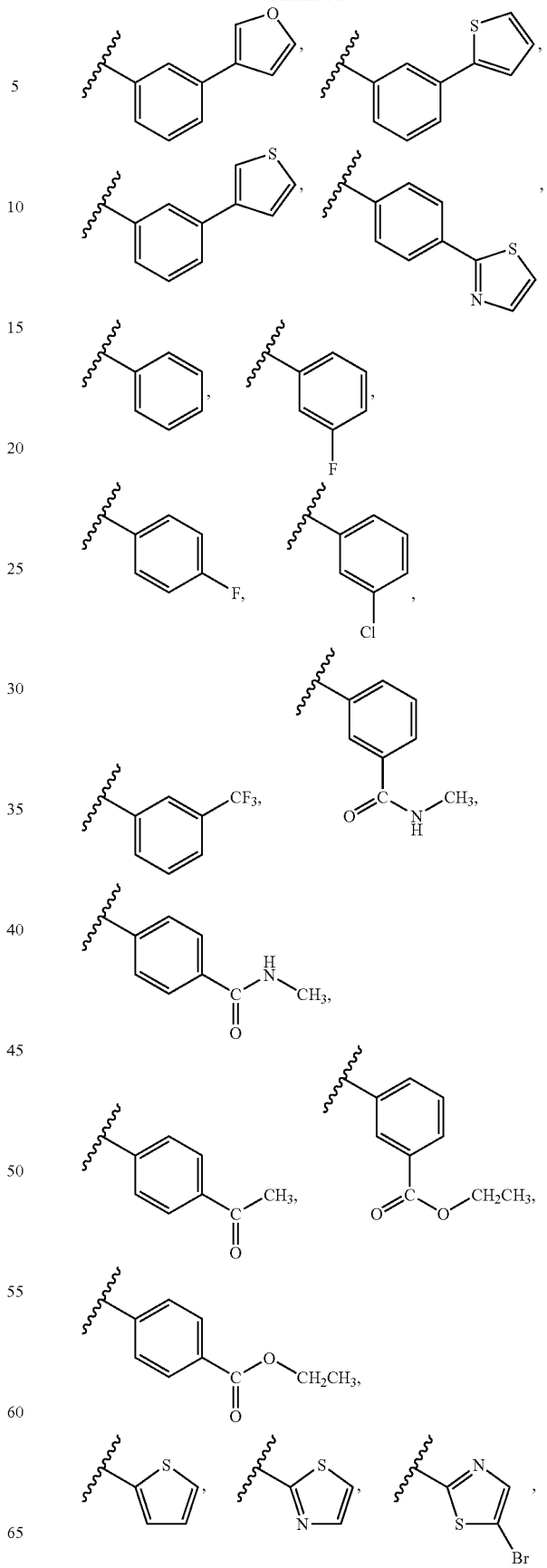

-continued
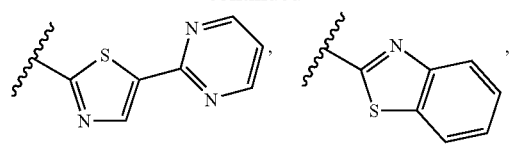
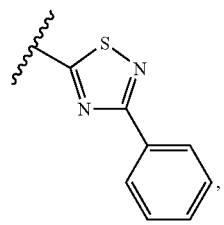
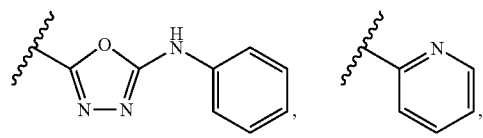
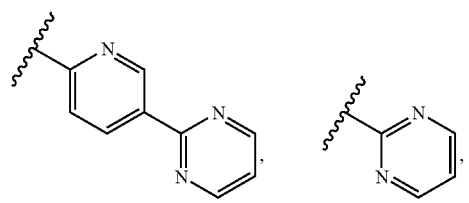
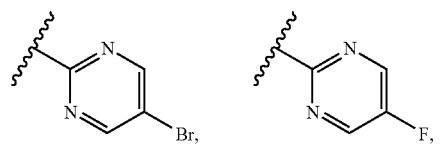
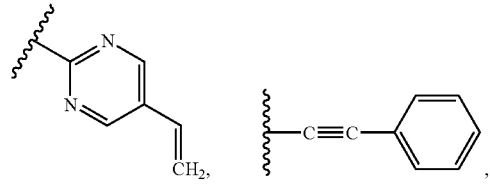
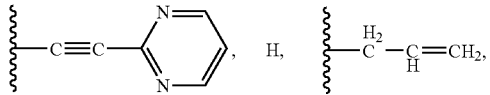
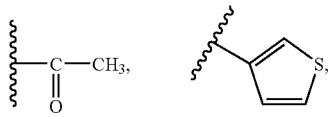
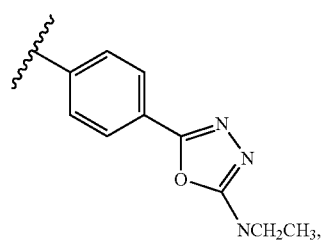
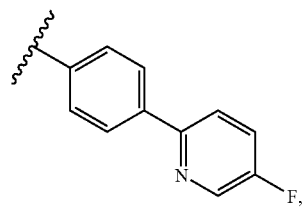
-continued
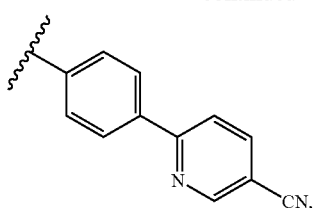
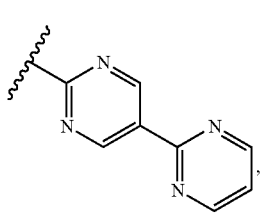
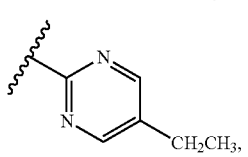
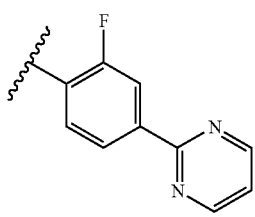
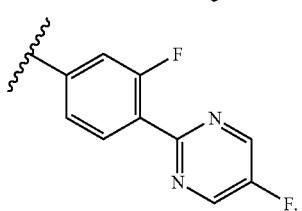
and
35. The compound of claim 1 wherein $R^1$ is selected from the group consisting of:
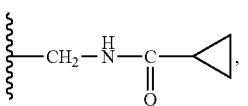
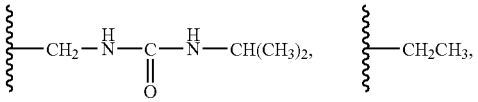
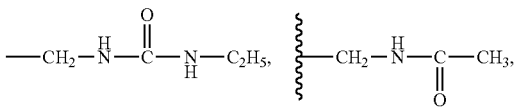
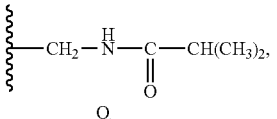
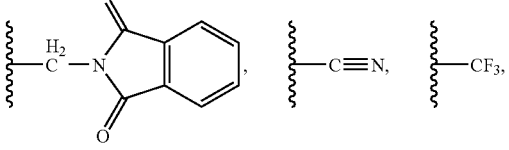

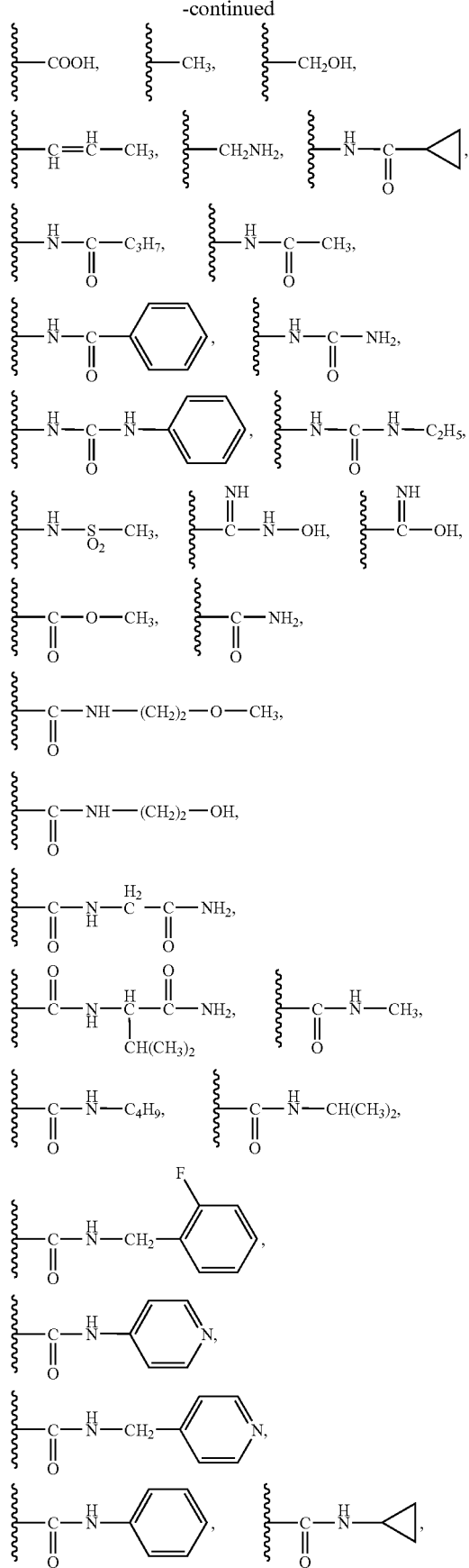
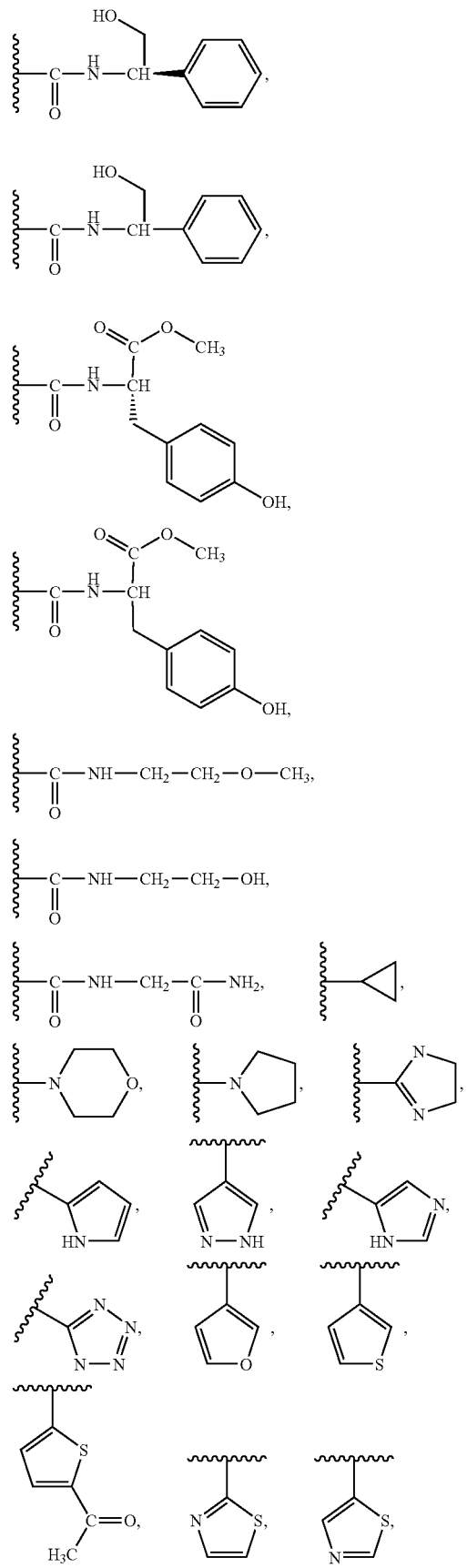

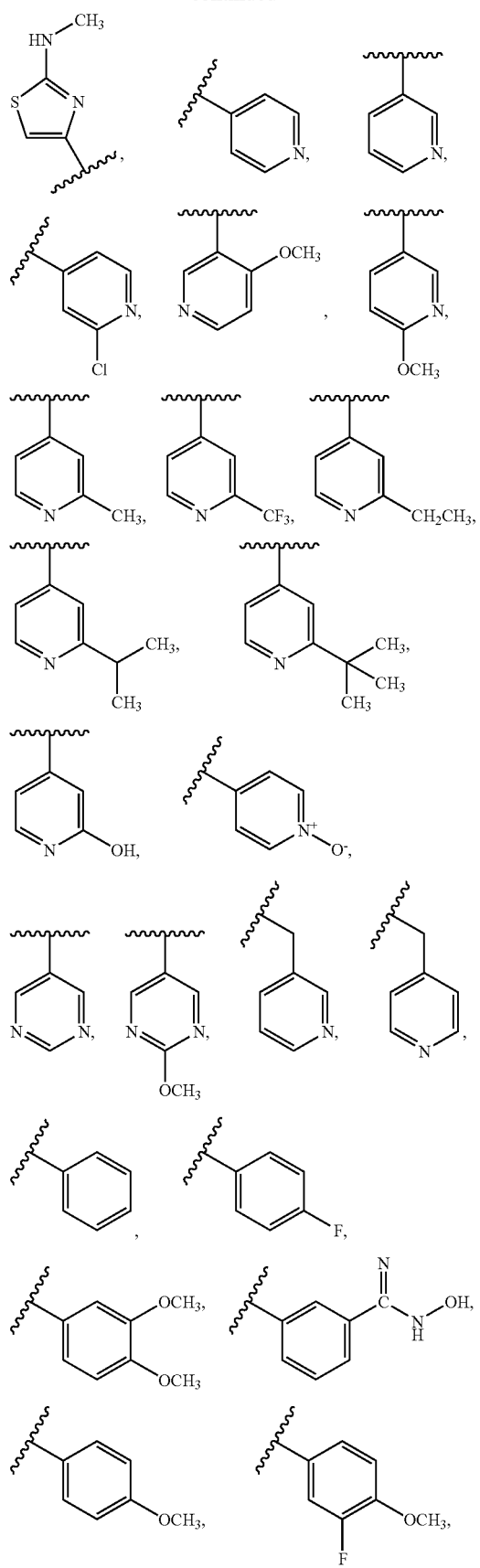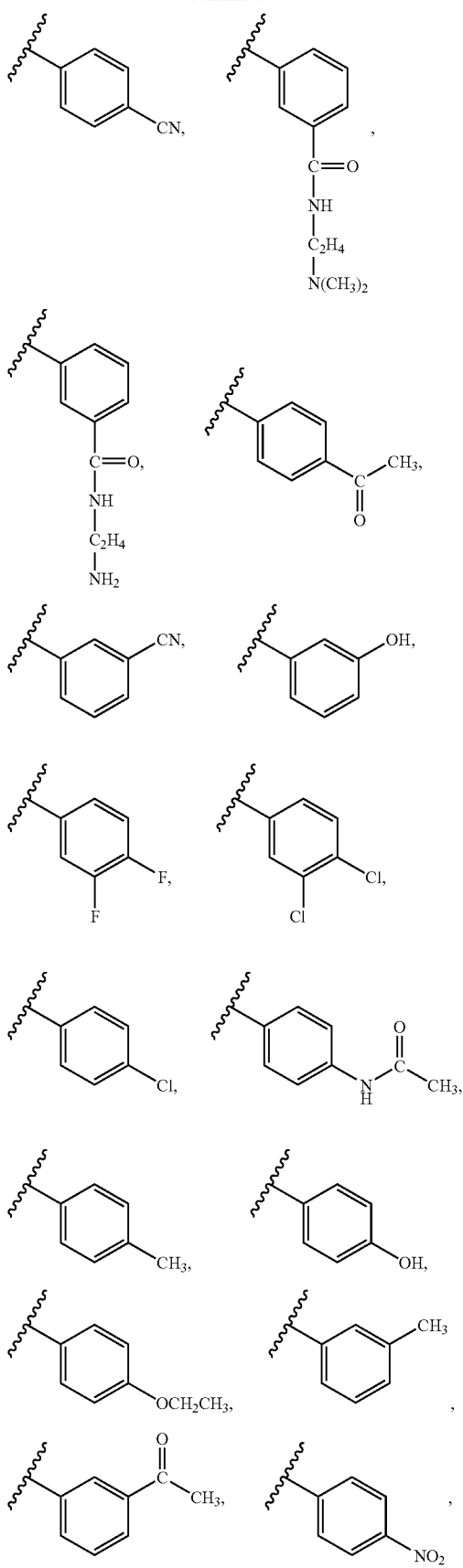

867
-continued
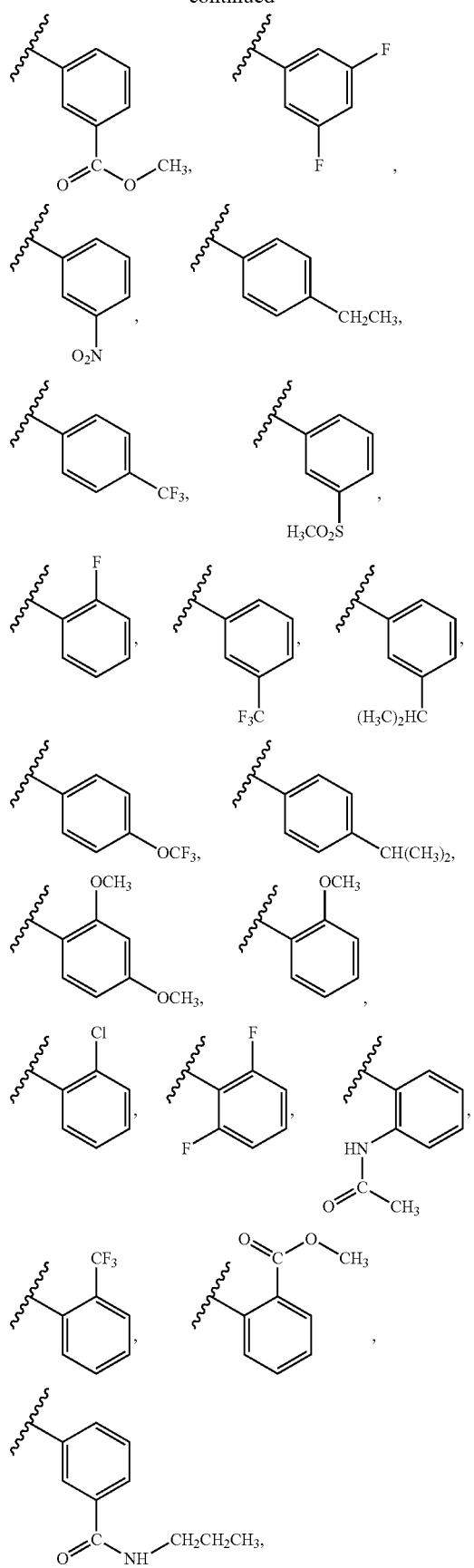
868
-continued
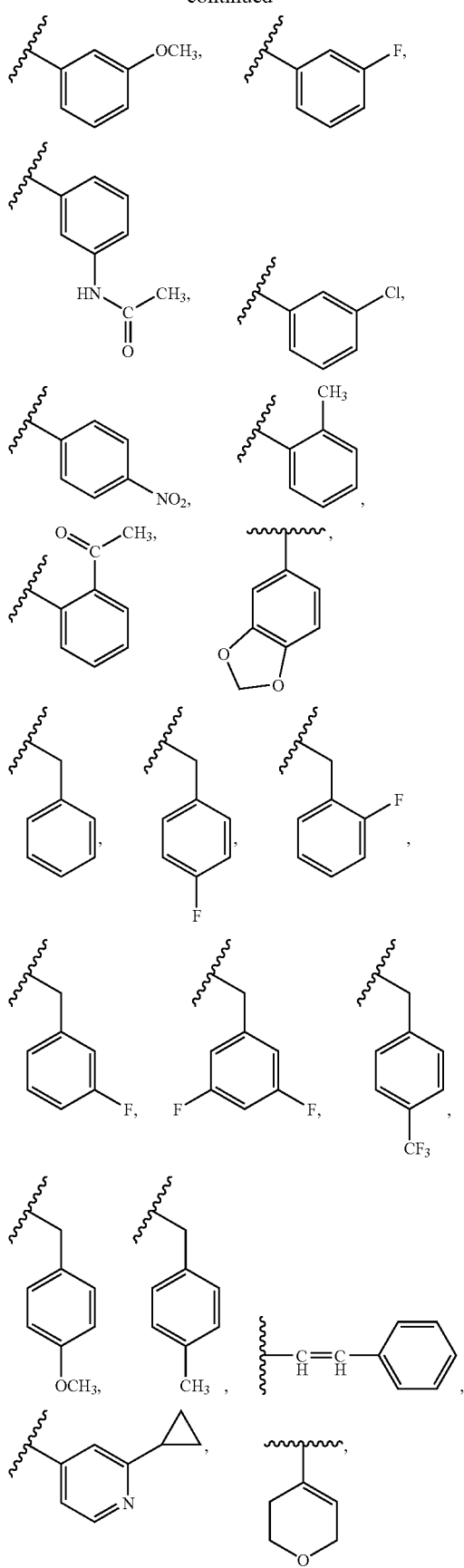

869
-continued
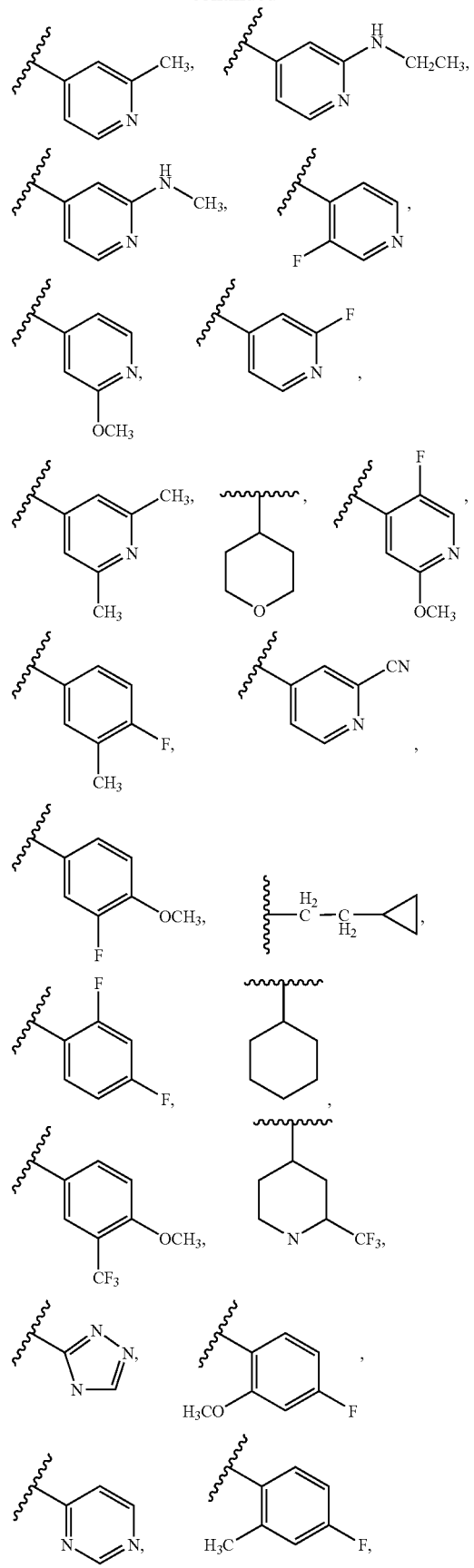
870
-continued
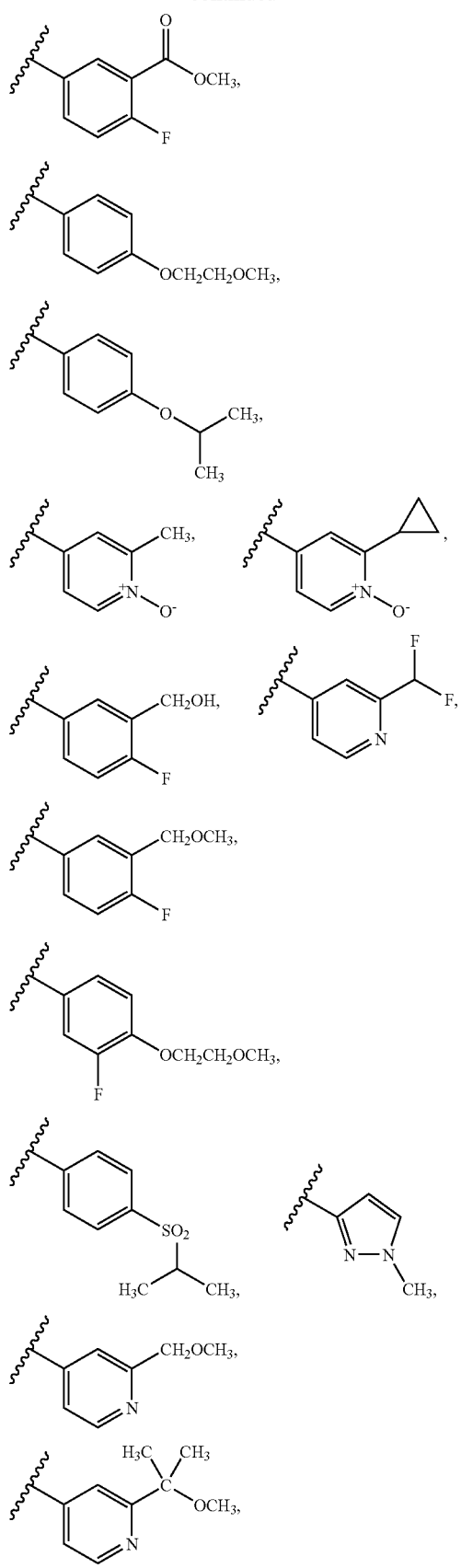

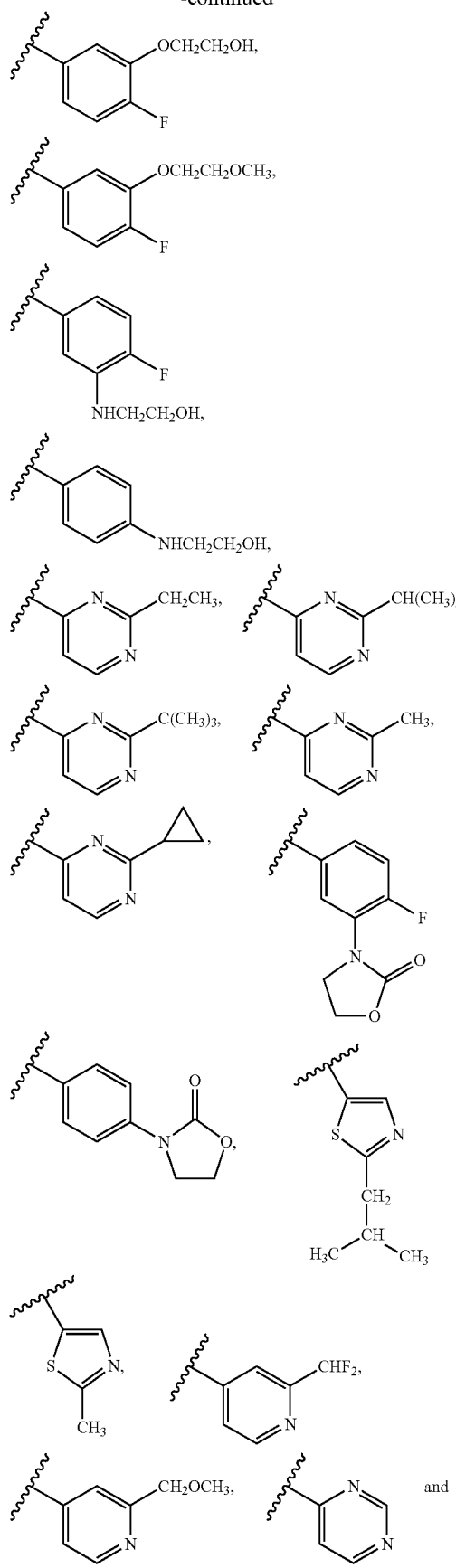
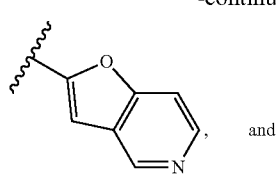
$R^5$ is selected from the group consisting of:
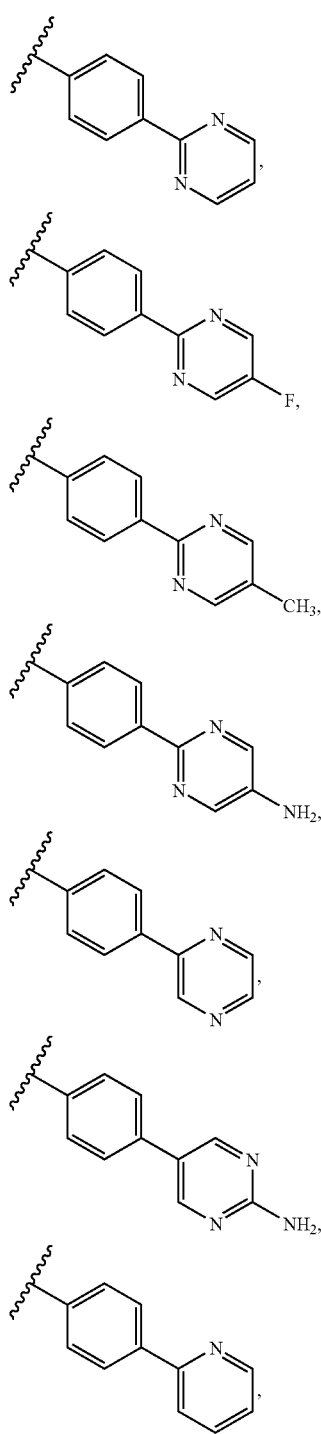

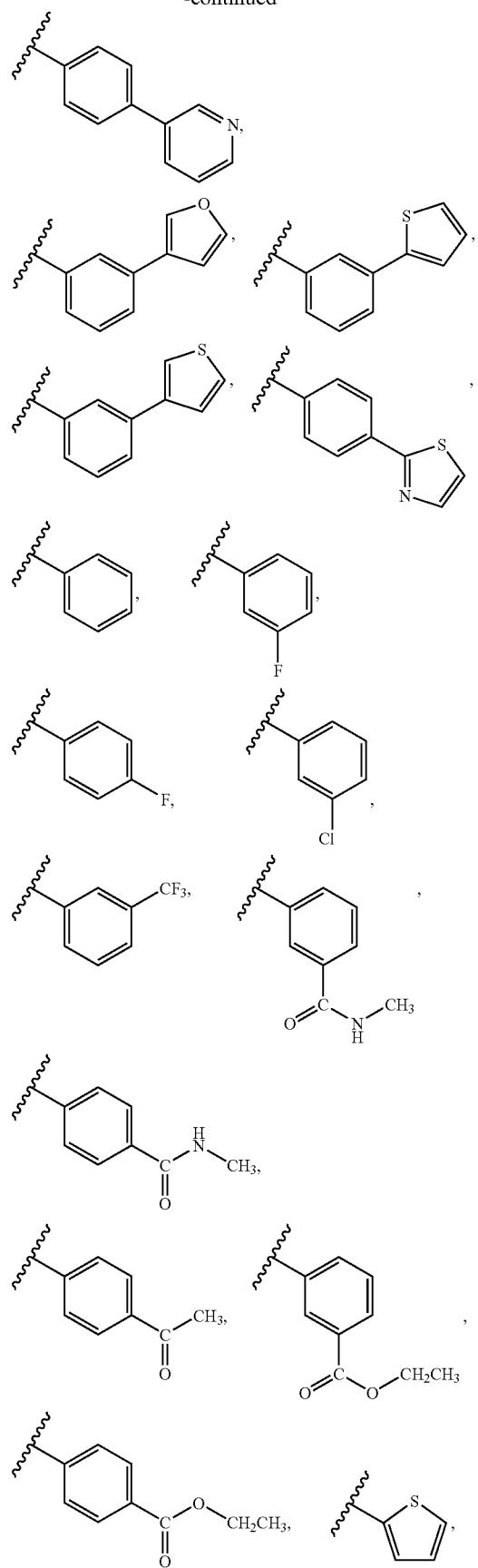
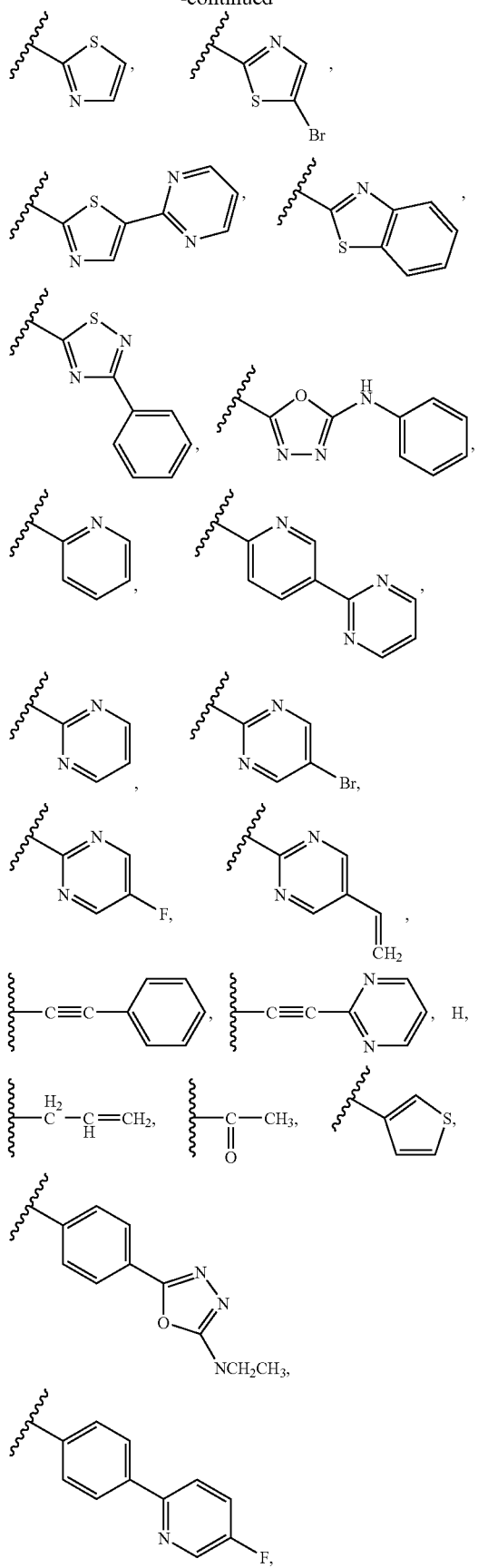

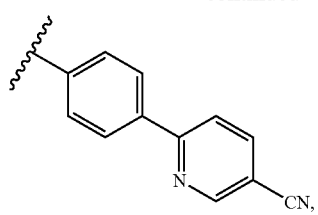
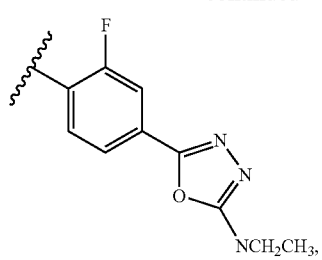
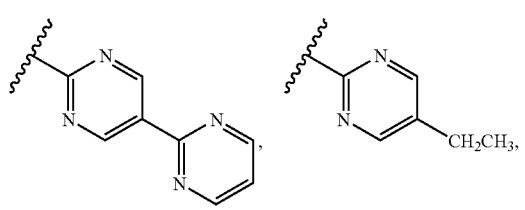
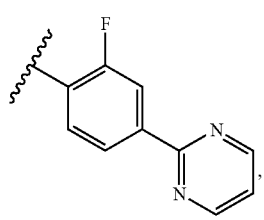
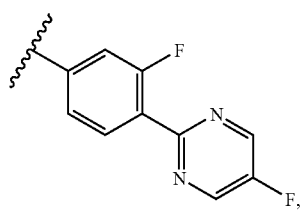
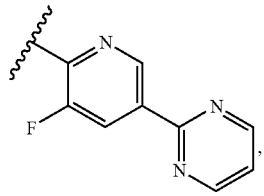
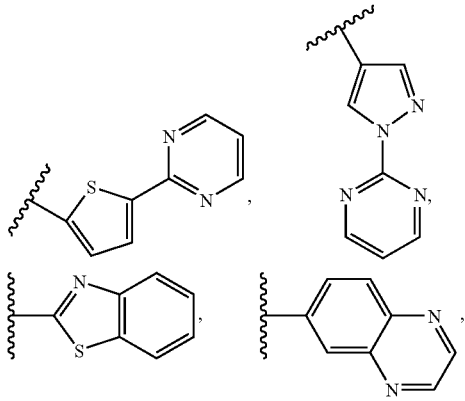
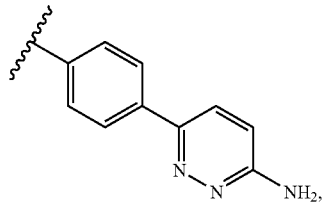

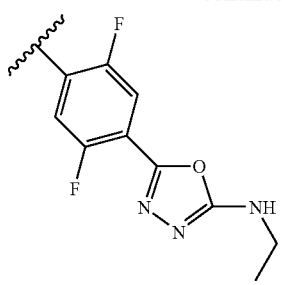
and
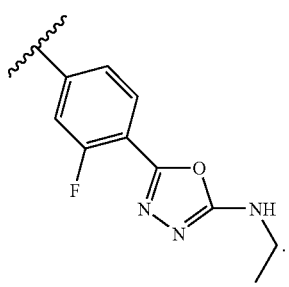 [SMILES: *c1ccc(-c2nnc(NCC)o2)c(F)c1]
36. The compound of claim 7 wherein $R^1$ is selected from the group consisting of:
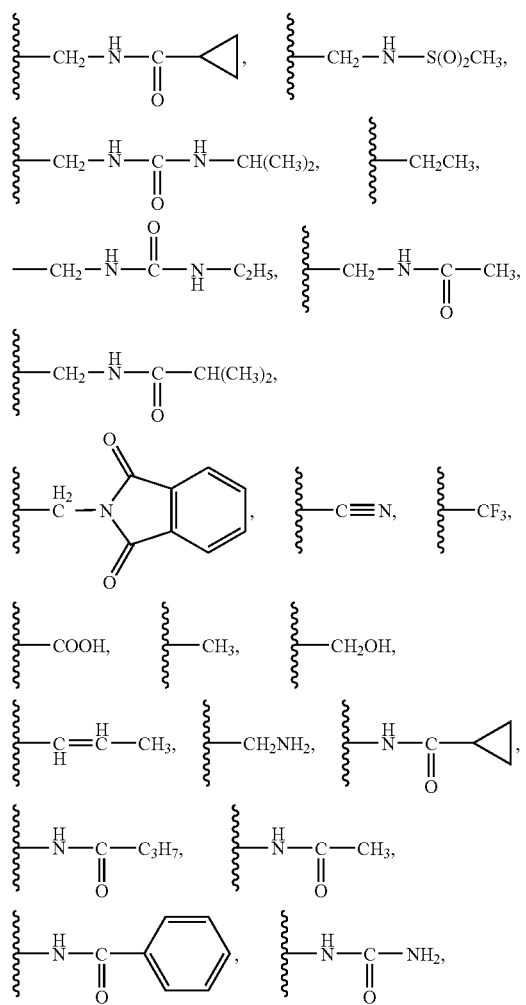
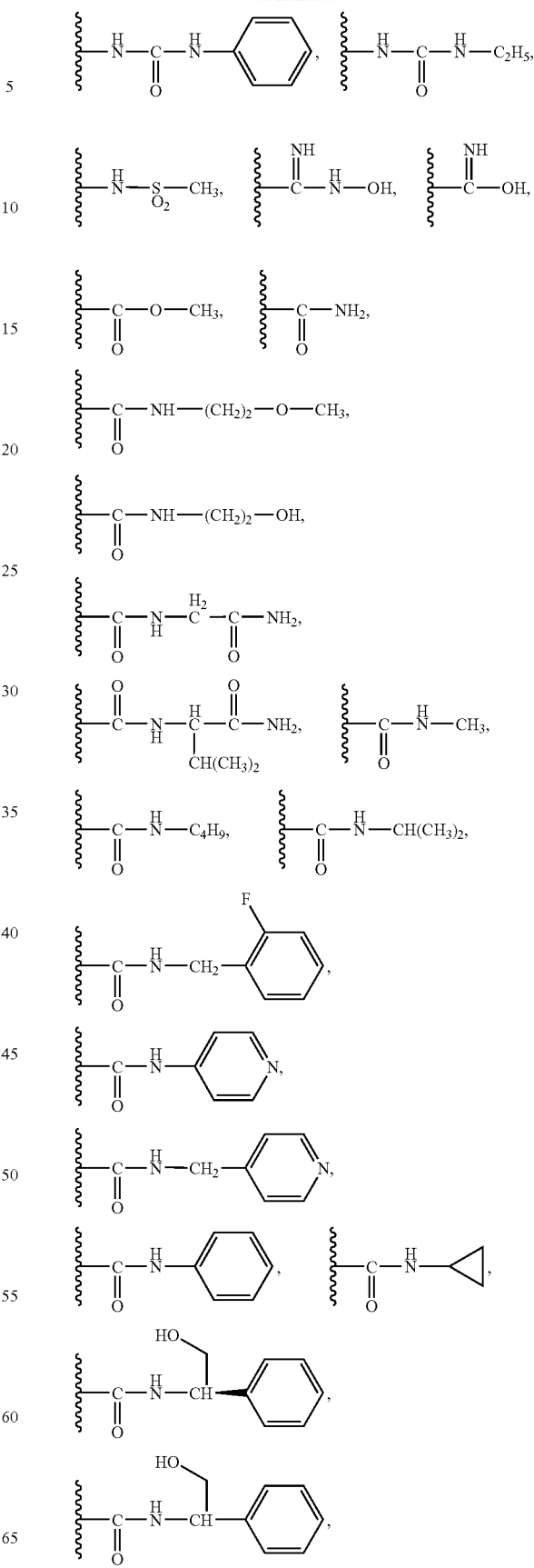

879
-continued
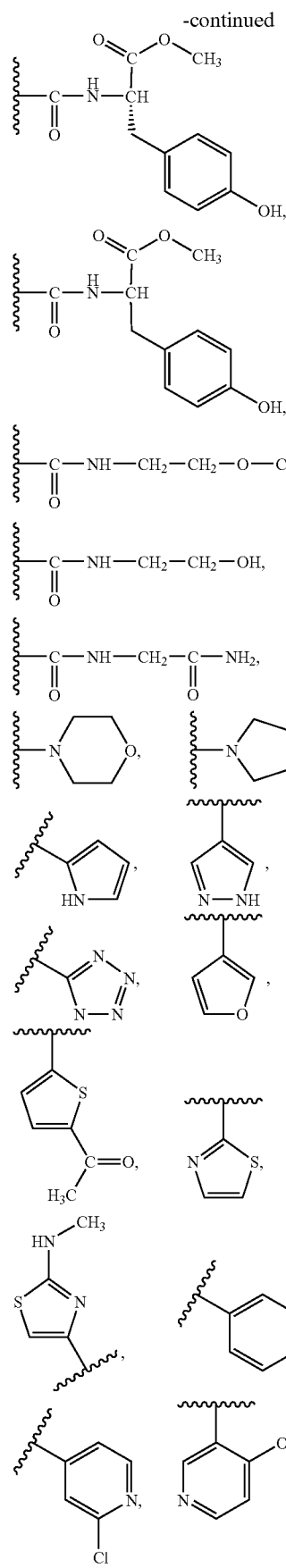
880
-continued
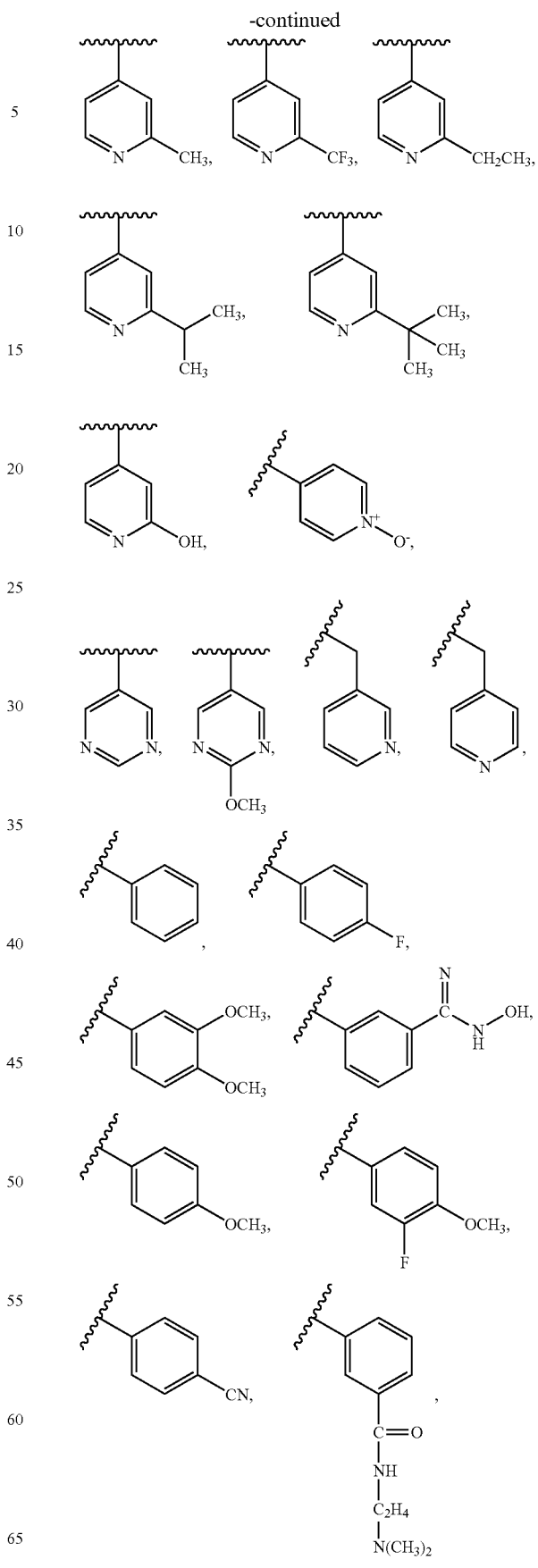

881
-continued
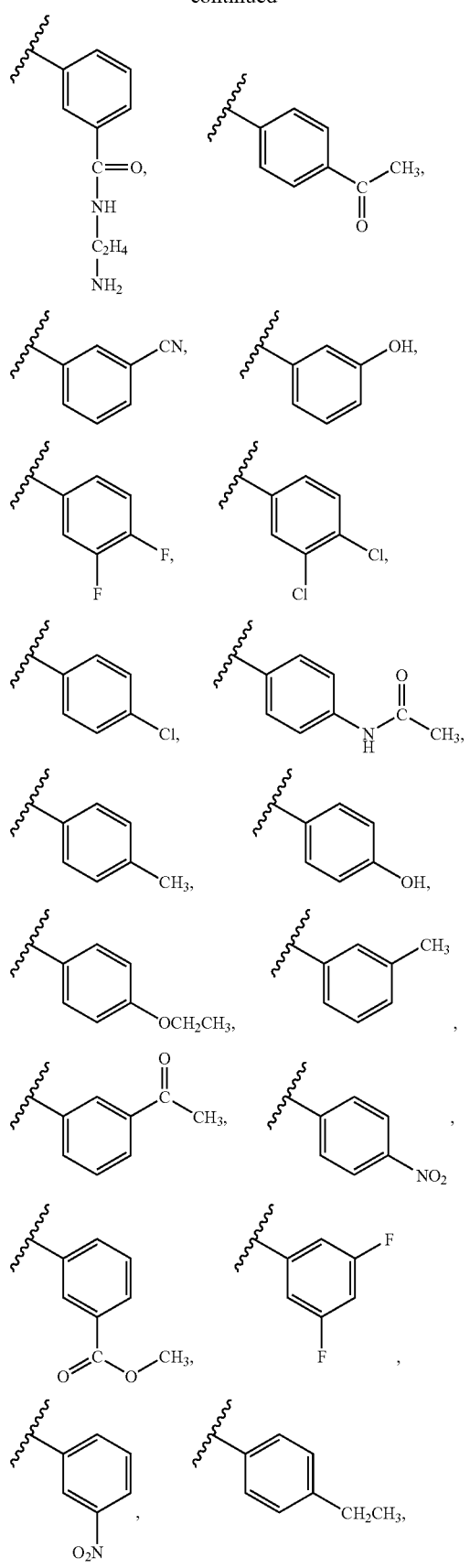
882
-continued
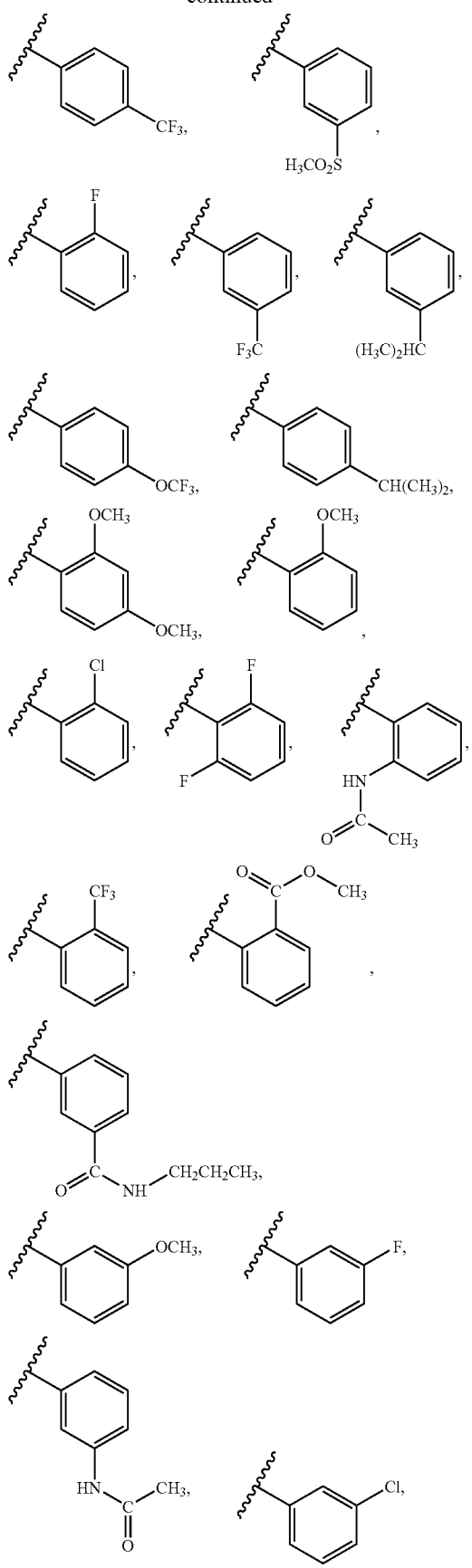

883
-continued
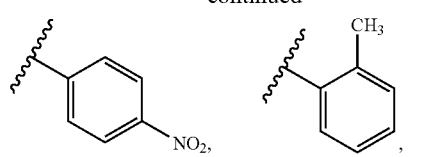
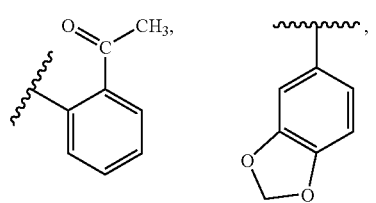
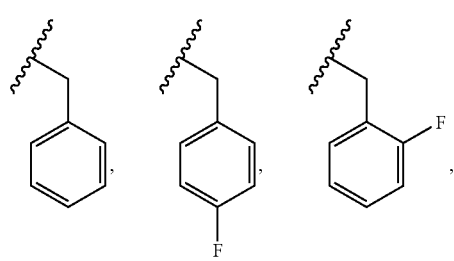
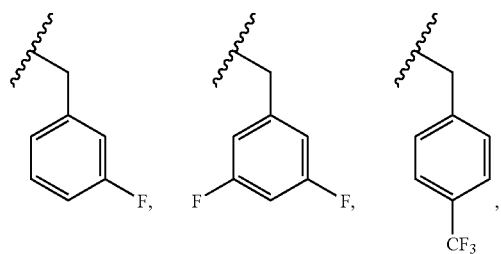
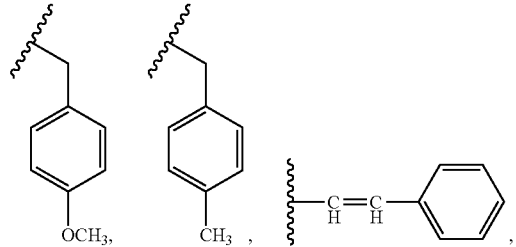
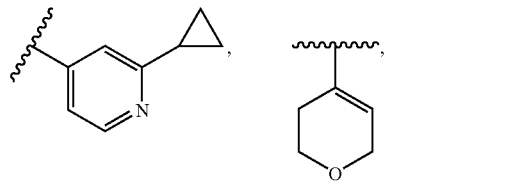
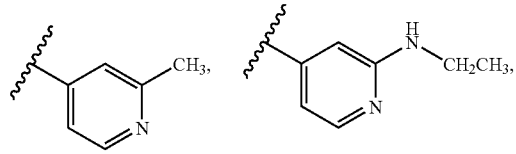
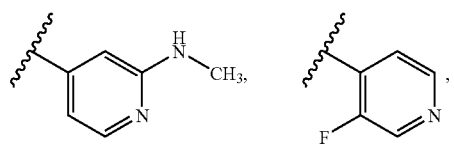

884
-continued
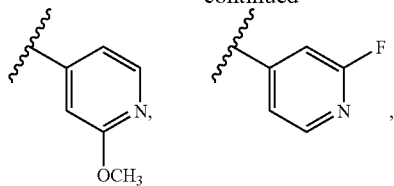
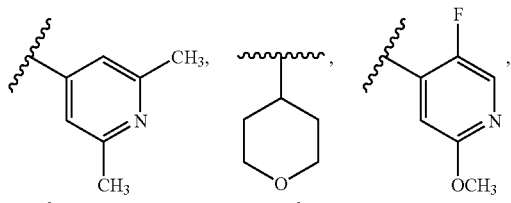
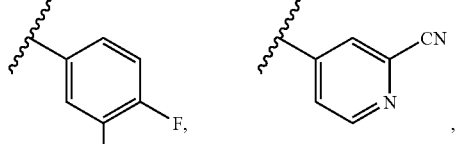
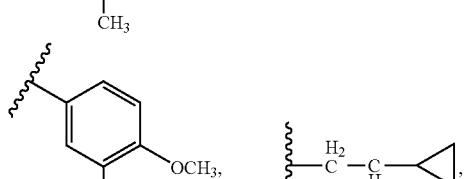
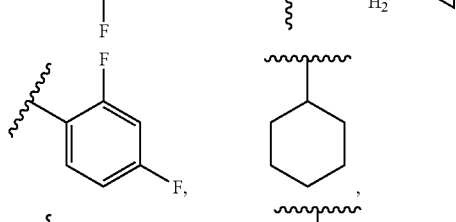
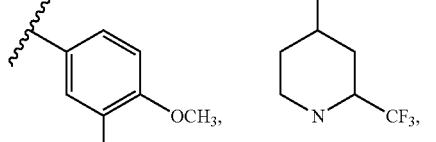
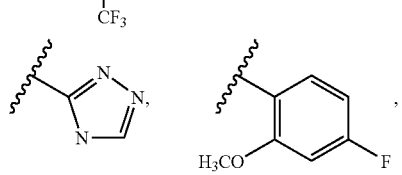
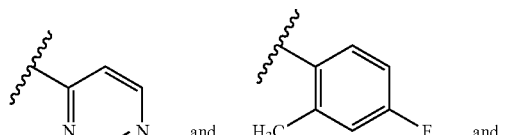
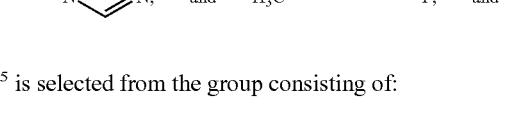 and
$R^5$ is selected from the group consisting of:
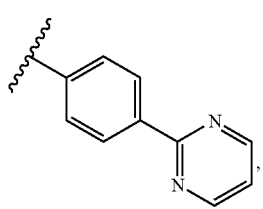

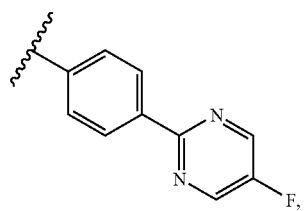
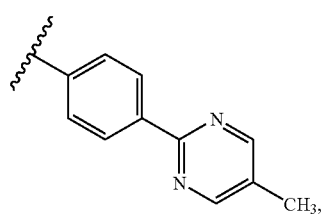
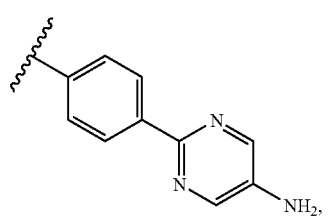
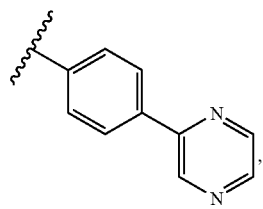
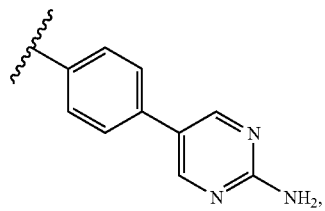
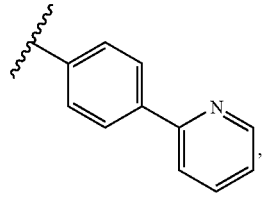
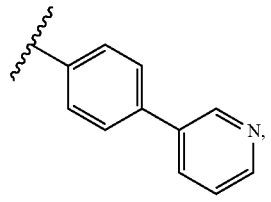
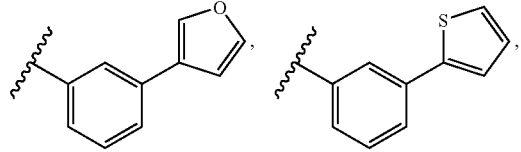
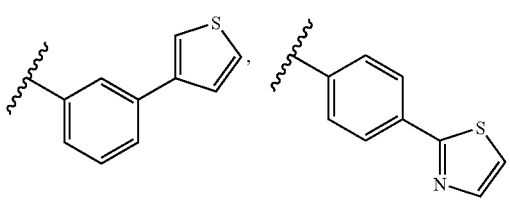
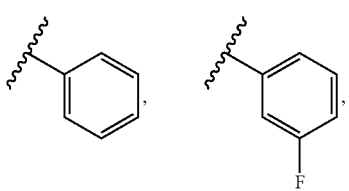
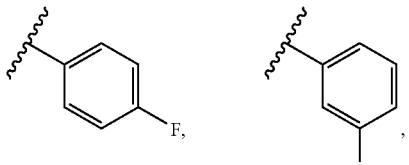
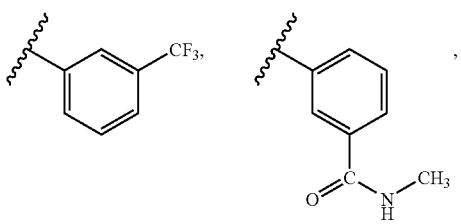
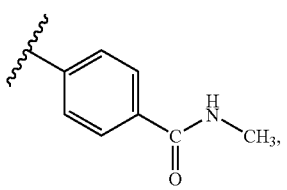
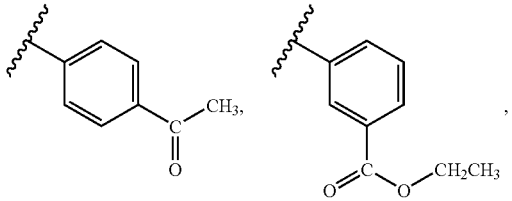
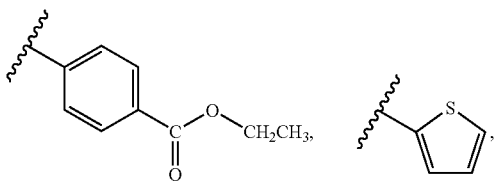
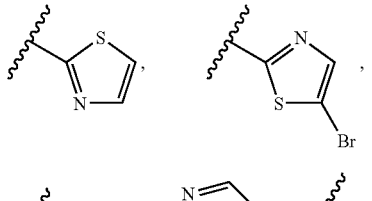
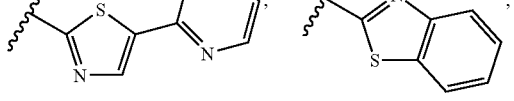

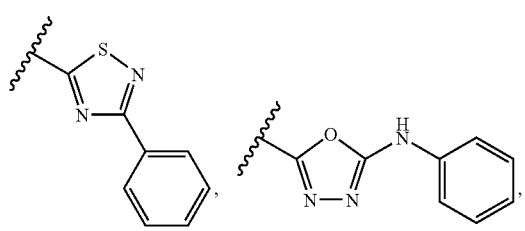
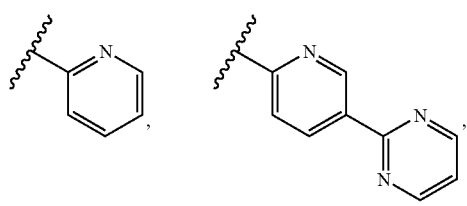
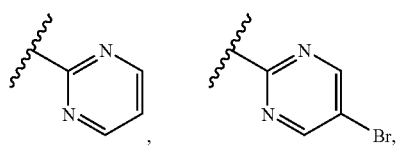
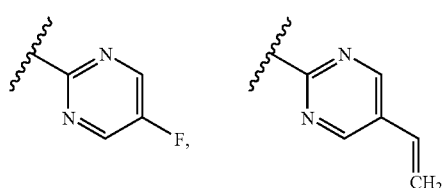
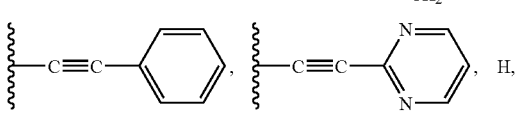
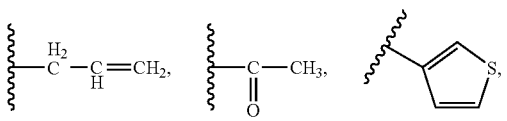
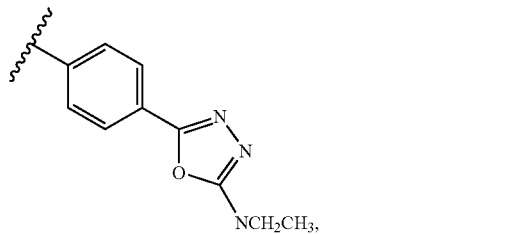
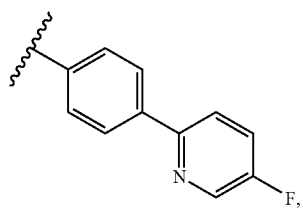
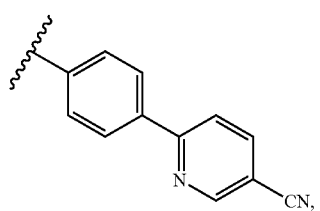
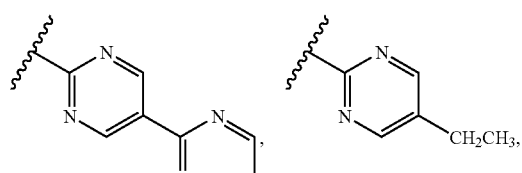
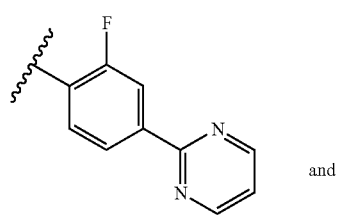
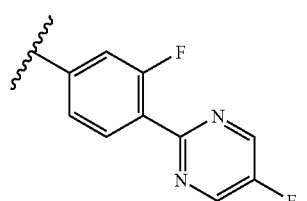
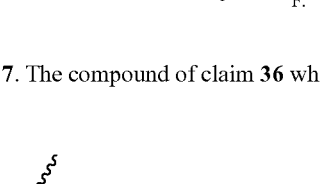
37. The compound of claim 36 wherein $R^1$ is
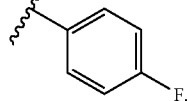
38. The compound of claim 36 wherein $R^1$ is
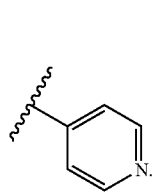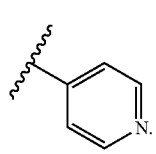
39. The compound of claim 36 wherein $R^1$ is
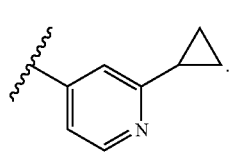
40. The compound of claim 1 wherein $R^2$ is selected from the group consisting of:
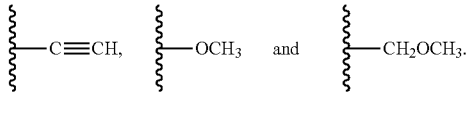

41. The compound of claim 36 wherein $R^2$ is selected from the group consisting of:

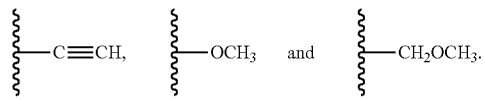

42. The compound of claim 36 wherein the $R^3$, $R^4$, $R^6$, and $R^7$ are each independently selected from the group consisting of: H and alkyl.

43. The compound of claim 42 wherein $R^3$, $R^4$, $R^6$, and $R^7$ are each H.

44. The compound of claim 43 wherein Q is 2.1.

45. The compound of claim 4 wherein Q is 2.17, $R^3$, $R^4$, $R^6$, and $R^7$ are each independently selected from the group consisting of: H and alkyl, $R^1$ is selected from the group consisting of:

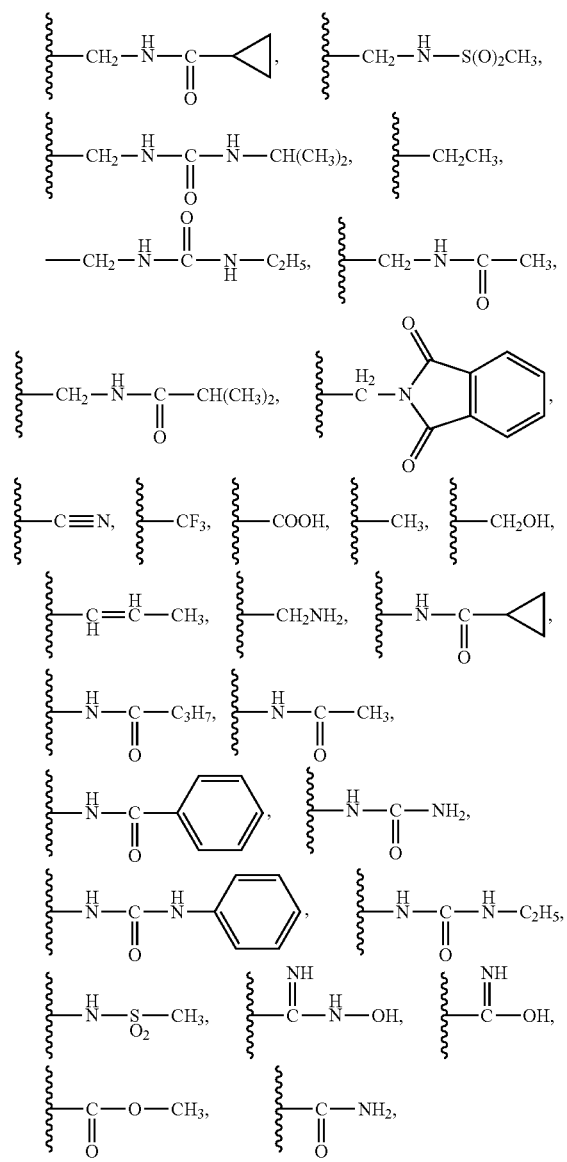

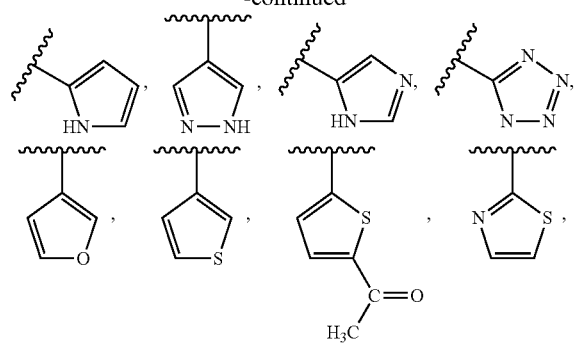
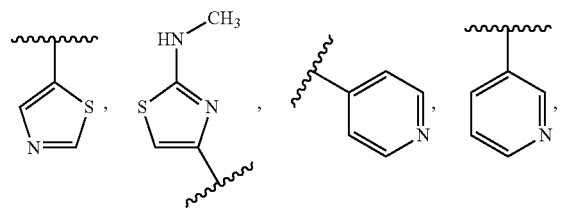
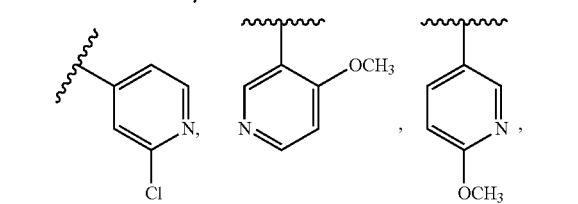
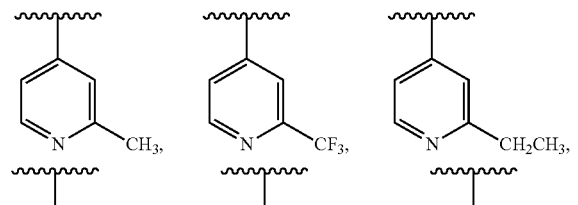
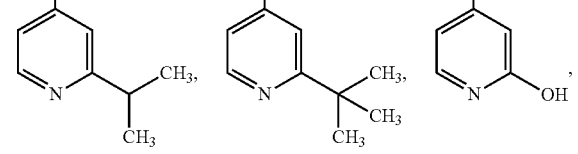
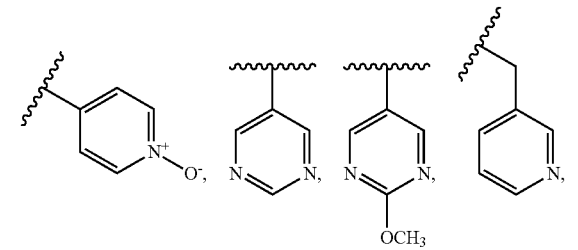
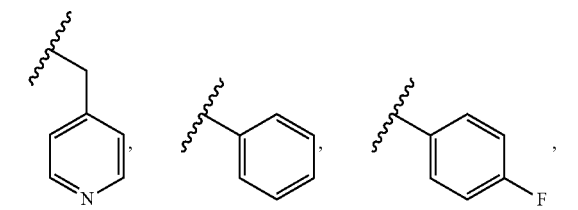
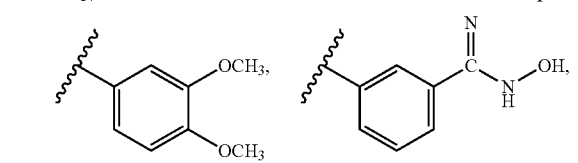
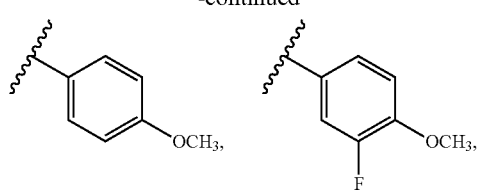
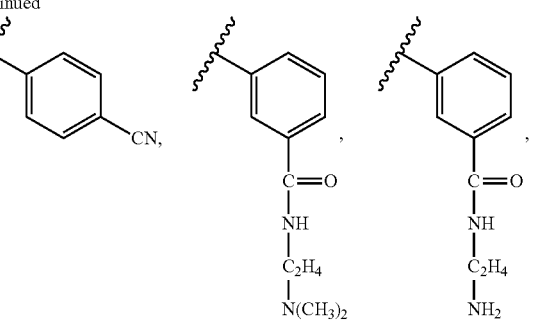
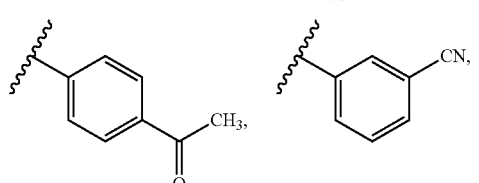
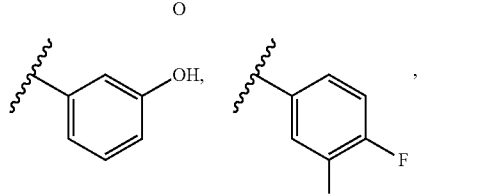
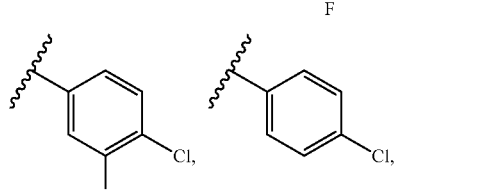
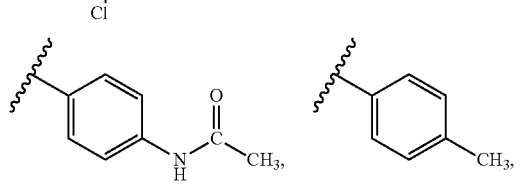
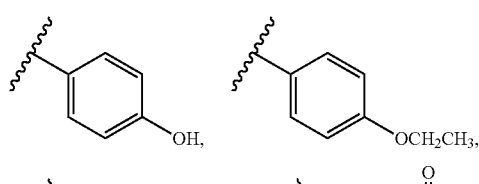
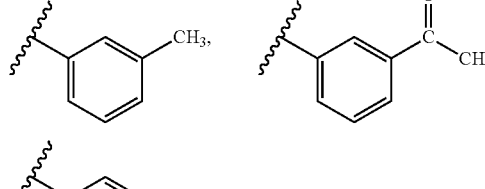
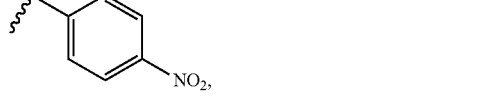

893
-continued
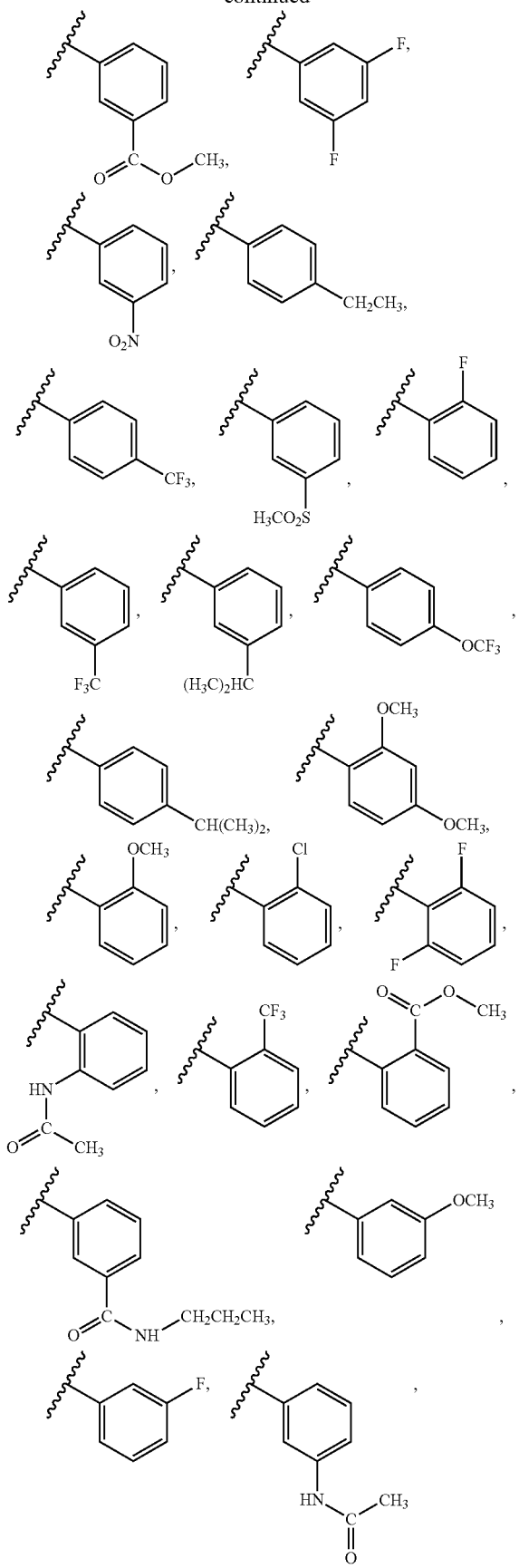
894
-continued
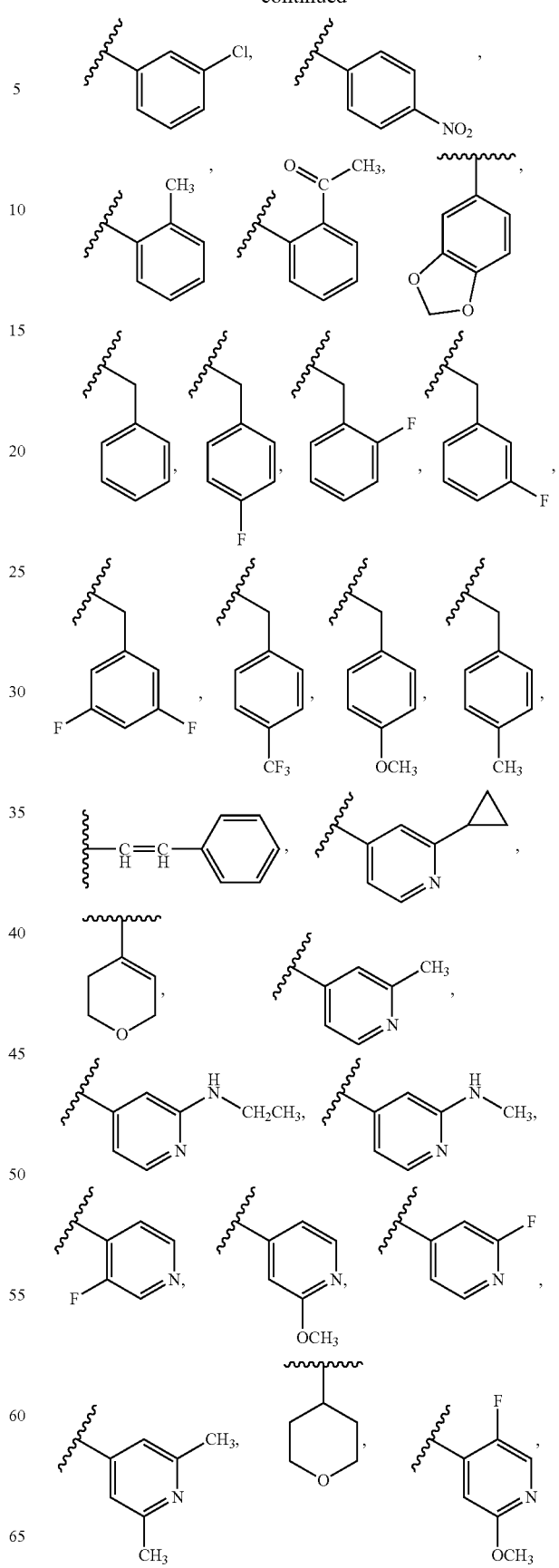

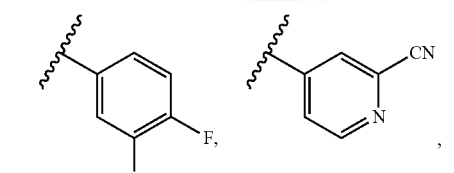
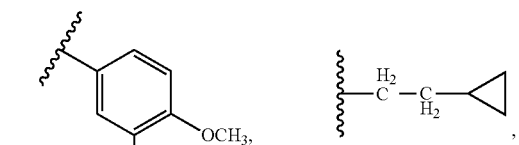
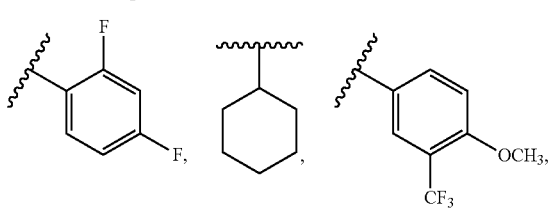
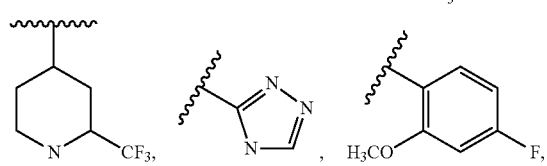
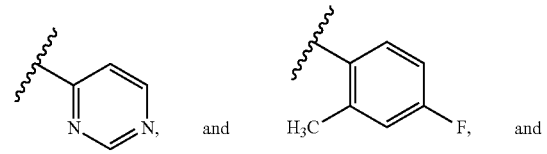
R⁵ is selected from the group consisting of:
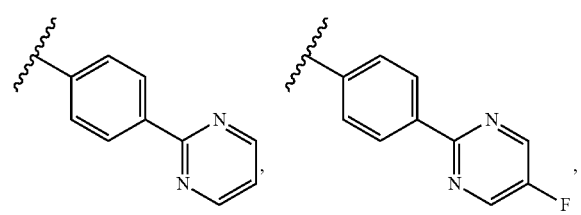
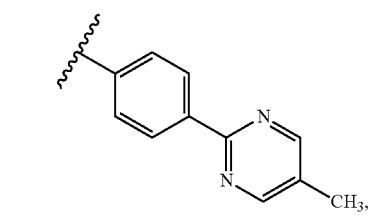
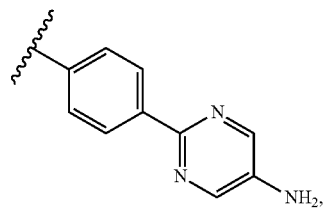
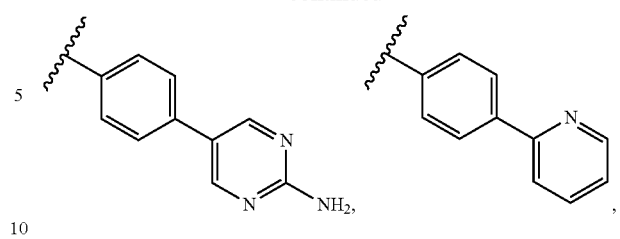
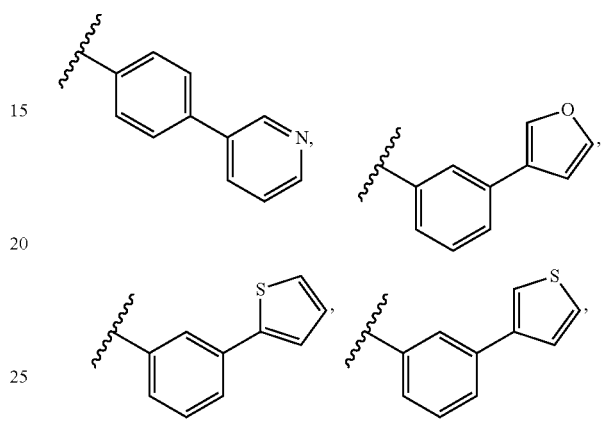
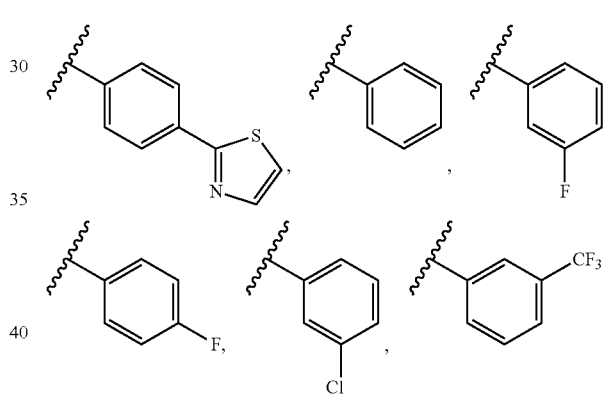
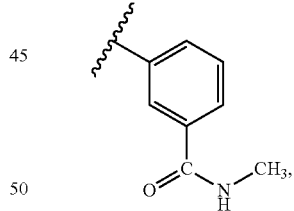
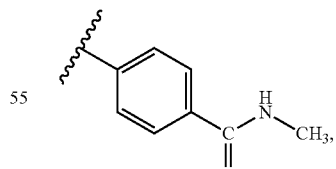
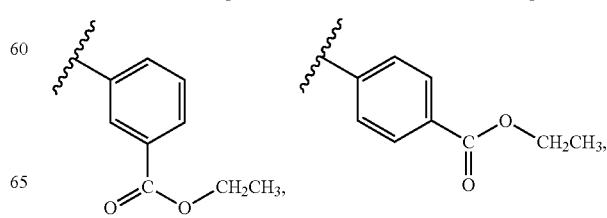

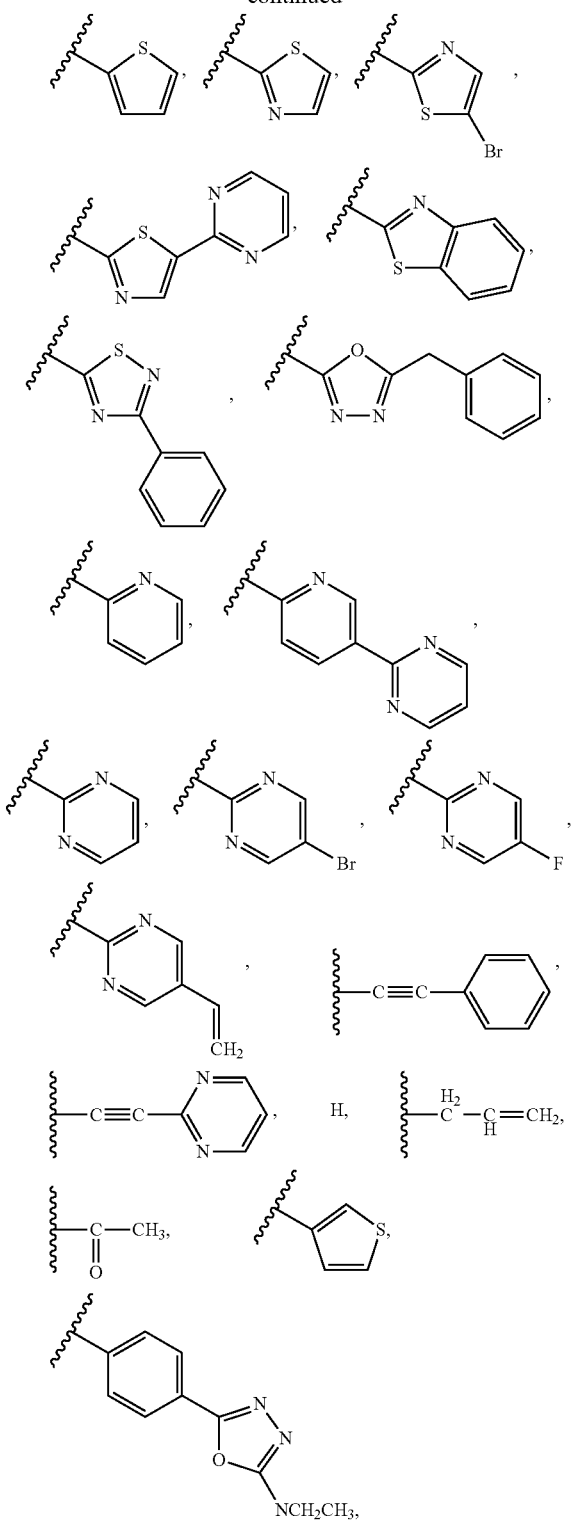
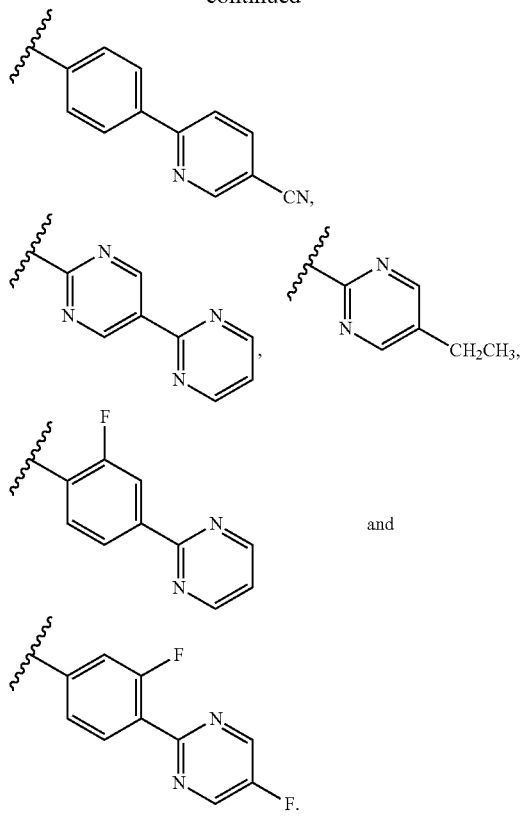
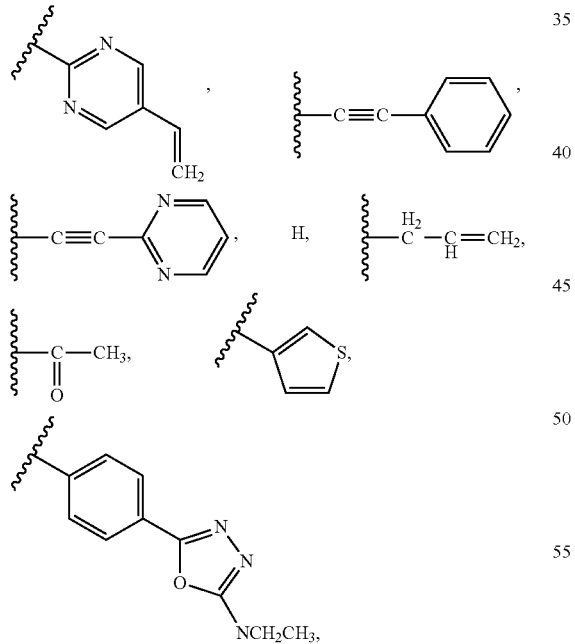
46. The compound of claim 1 wherein Q is
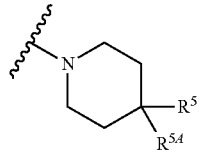
47. The compound of claim 1 wherein Q is:
(2.17A)
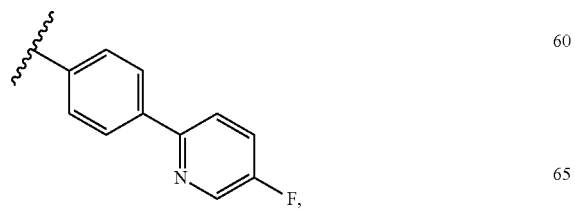
and $R^{5A}$ is selected from the group consisting of: halo, —OH, alkoxy, and alkyl.
48. The compound of claim 1 wherein Q is selected from the group consisting of:
(2.17B)
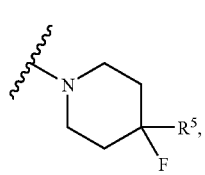

-continued
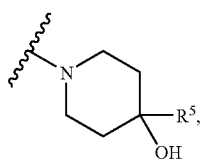
(2.17C)
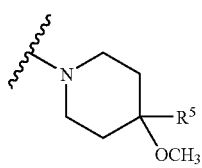
(2.17E) and
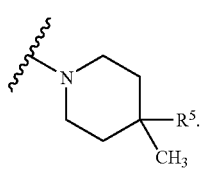
(2.17G)
49. The compound of claim 1 wherein Q is selected from the group consisting of:
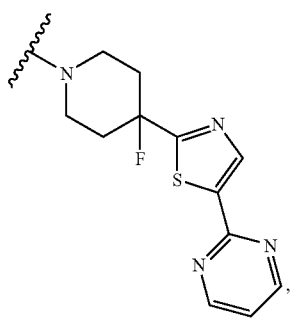
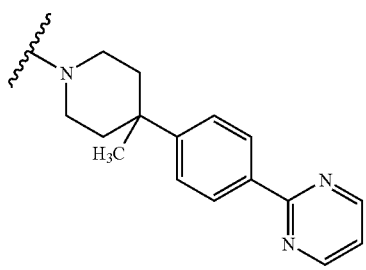
and
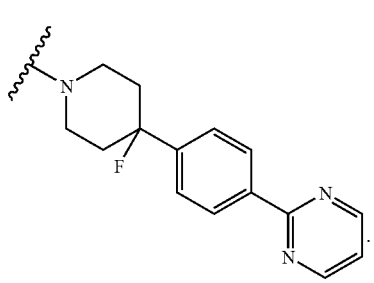
50. The compound of claim 1 wherein Q is selected from the group consisting of:
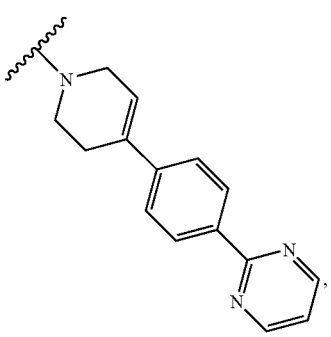
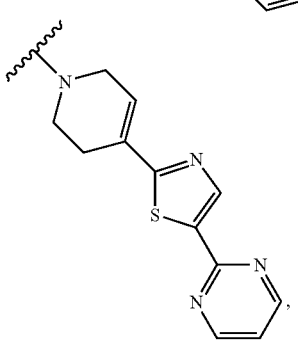
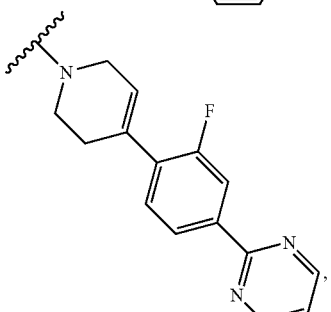
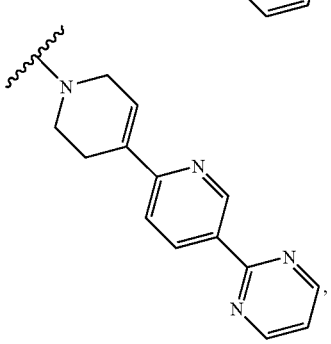
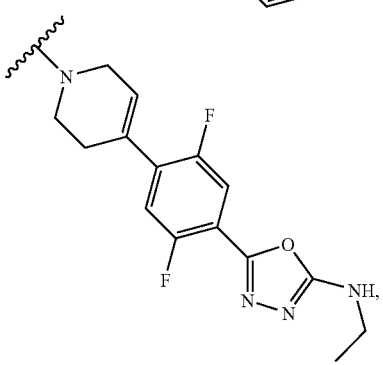

901
-continued
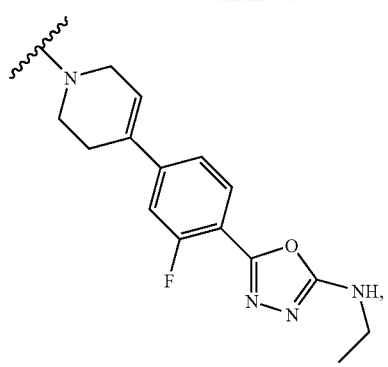
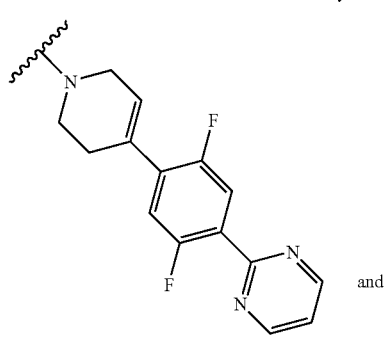 and
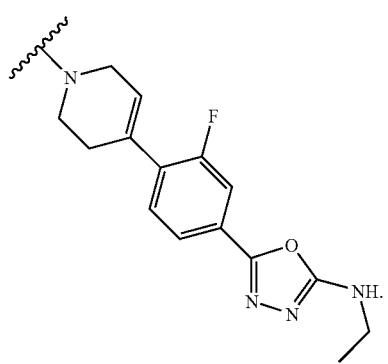
51. The compound of claim 1 wherein R¹ is selected from the group consisting of:
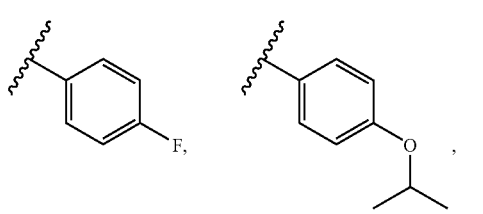
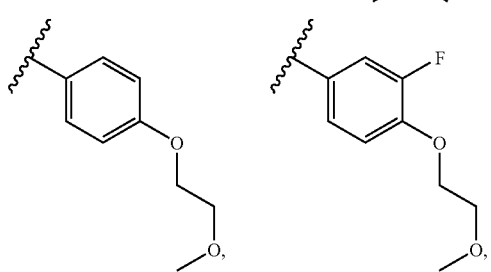
902
-continued
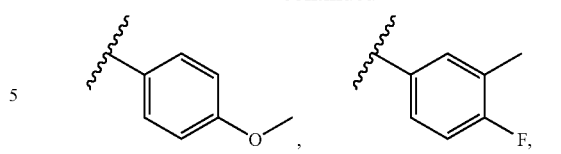
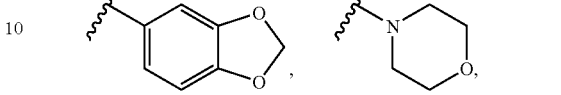
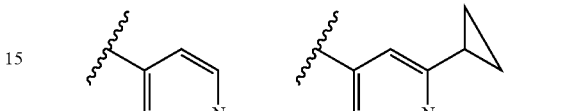
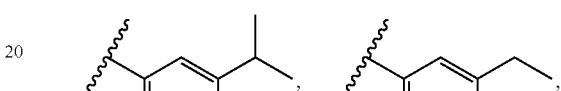
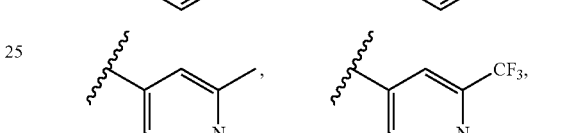
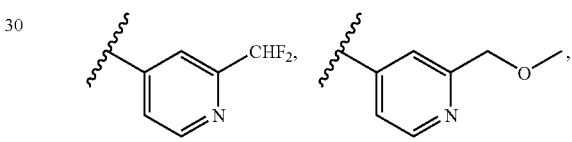
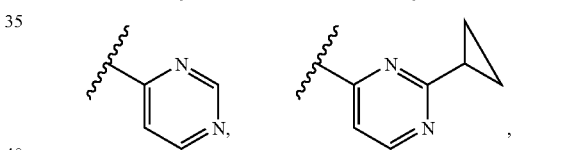
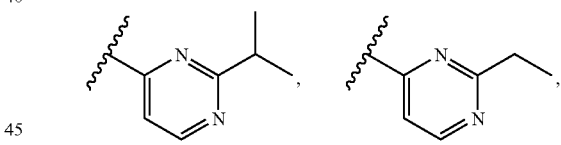
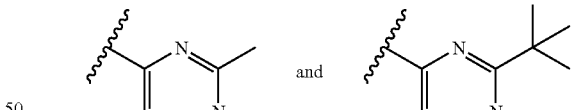 and
52. The compound of claim 1 wherein R⁵ is selected from the group consisting of:
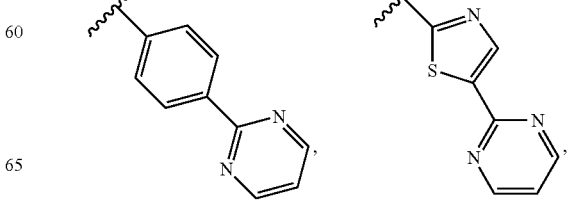

903
-continued
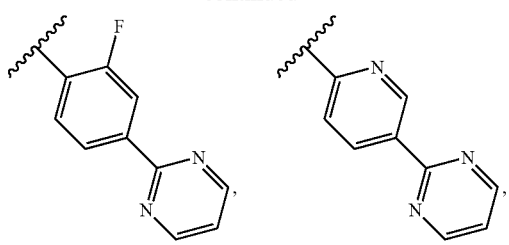
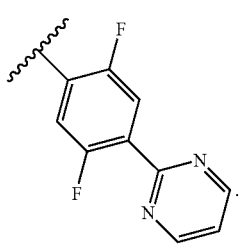
904
53. The compound of claim 1 wherein:
R¹ is selected from the group consisting of:
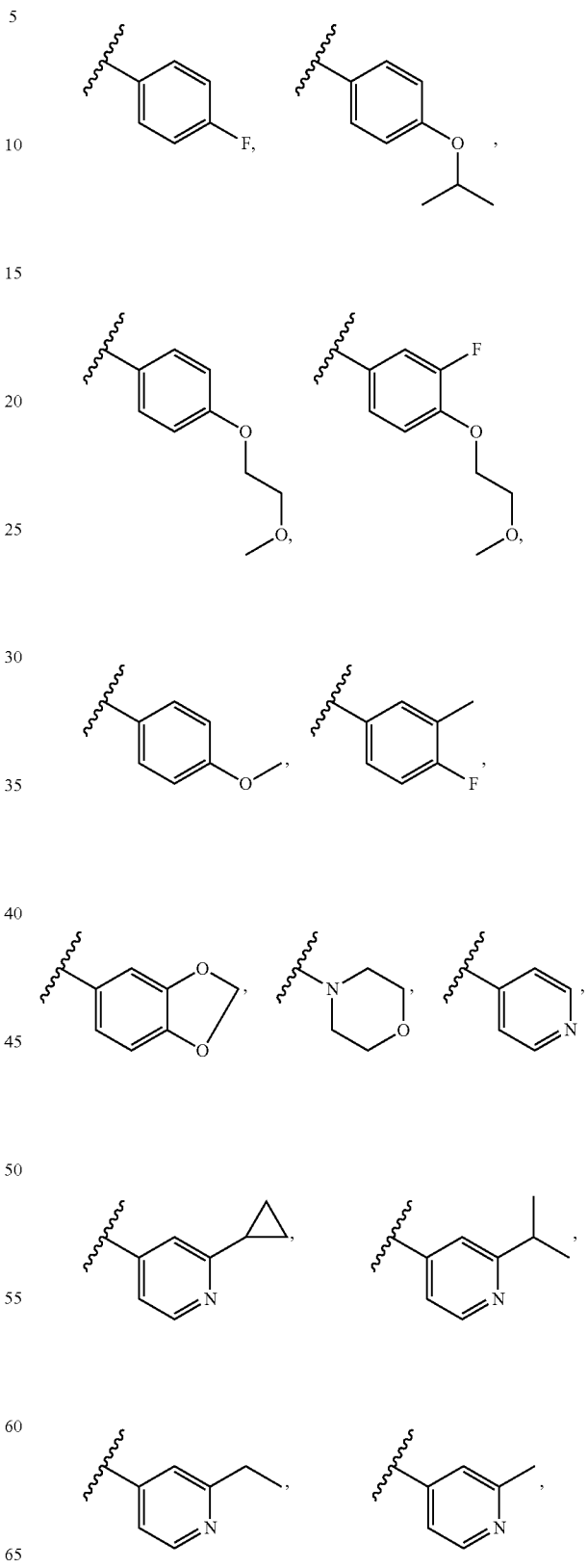

-continued

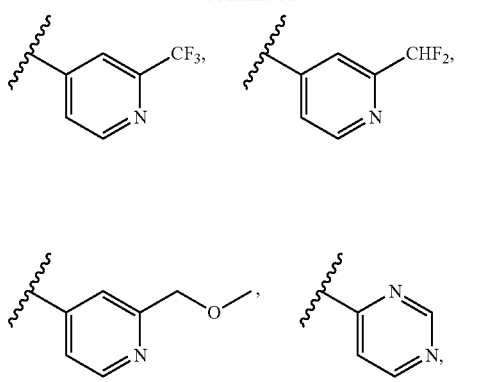

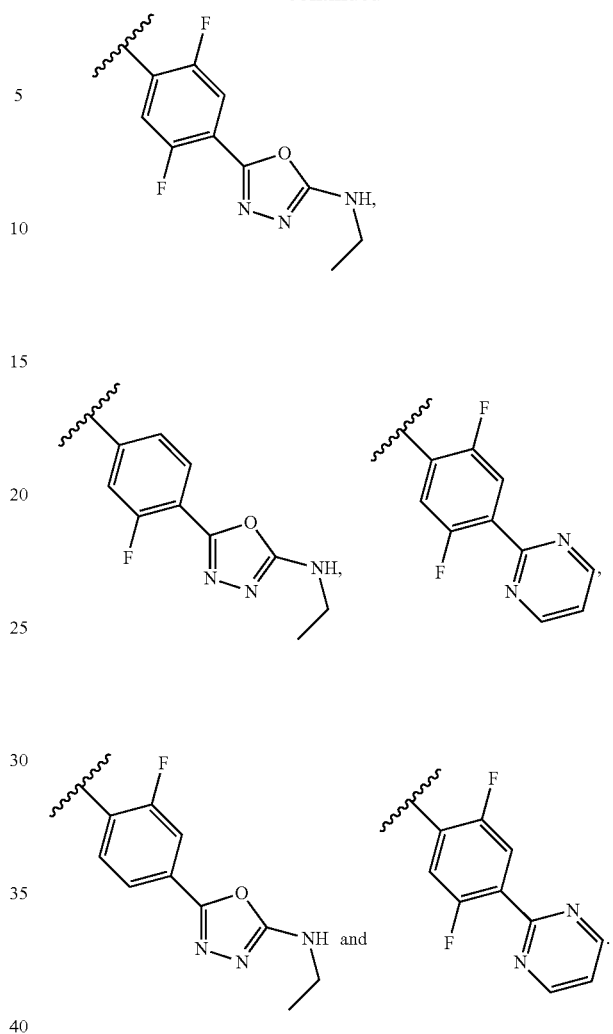

R⁵ is selected from the group consisting of:

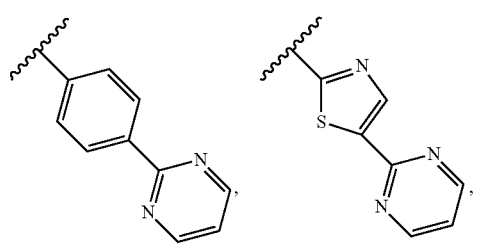

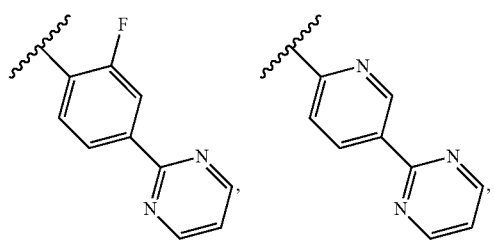

54. The compound of claim 1 wherein R² is selected from the group consisting of: —S(O)₂-alkyl and —S-alkyl.

55. The compound of claim 1 wherein R² is selected from the group consisting of: —SCH₃ and —S(O)₂CH₃.

56. The compound of claim 53 wherein R² is selected from the group consisting of: —S(O)₂-alkyl and —S-alkyl.

57. The compound of claim 53 wherein R² is selected from the group consisting of: —SCH₃ and —S(O)₂CH₃.

58. The compound of claim 53 wherein R² is selected from the group consisting of:

59. The compound of claim 1 wherein said compound is a compound of formula 1.0.

60. The compound of claim 1 wherein said compound is a salt of the compound of formula 1.0.

61. The compound of claim 1 selected from the group consisting of:
(Ex 141)
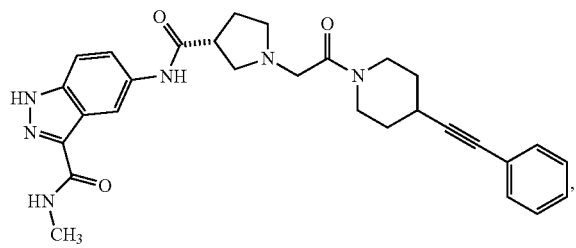
(Ex. 142)
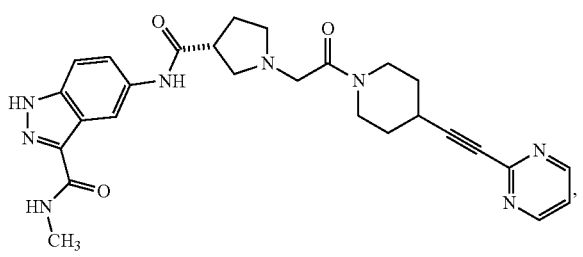
(Ex. 166)
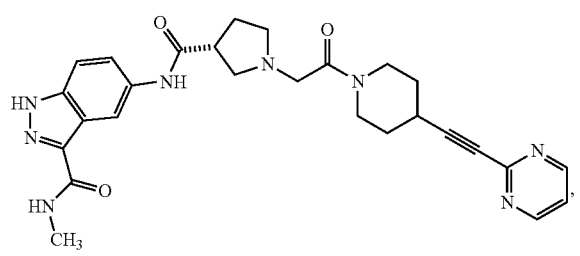
(Ex. 167)
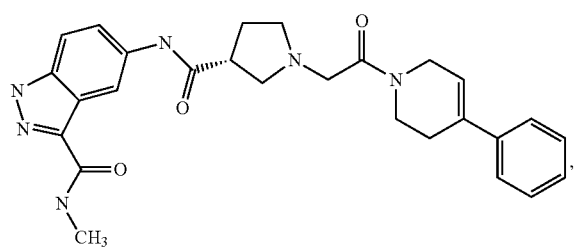
(Ex. 168)
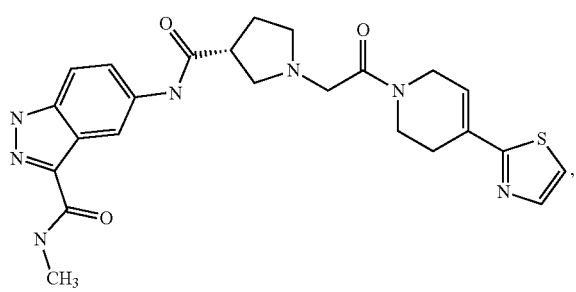

-continued
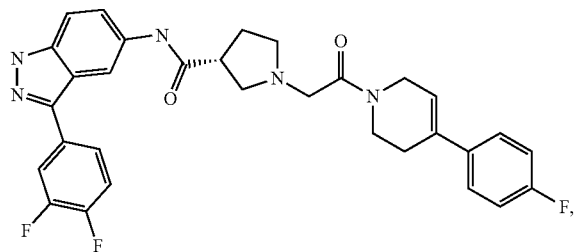
(Ex. 169)
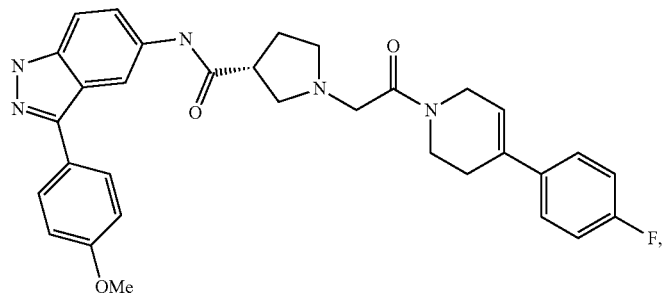
(Ex. 170)
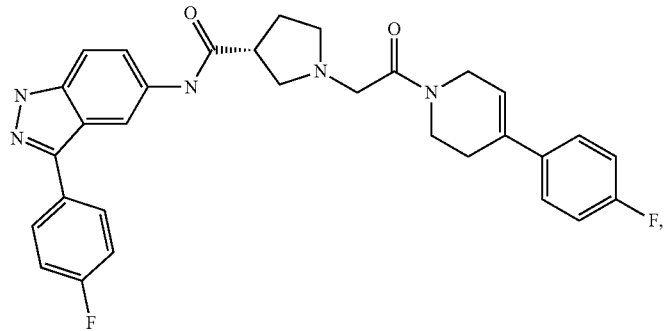
(Ex. 171)
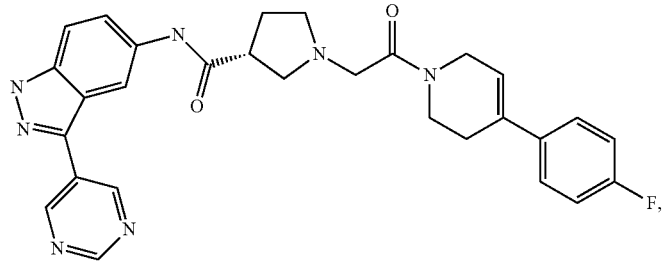
(Ex. 172)
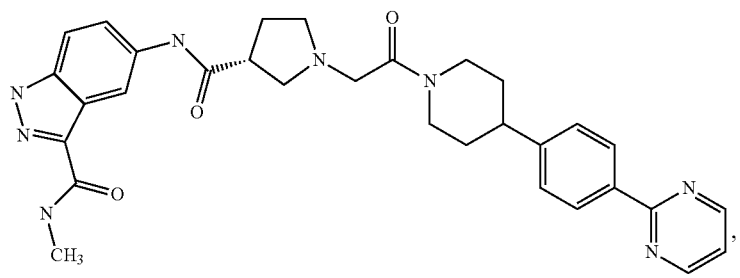
(Ex. 254)

-continued
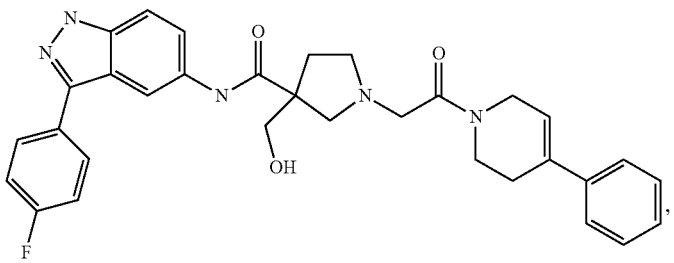
(Ex. 260)
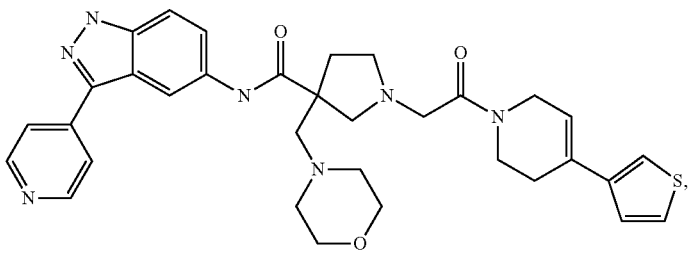
(Ex. 285)
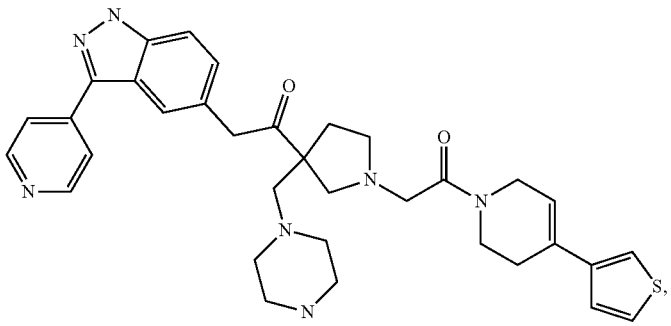
(Ex. 288)
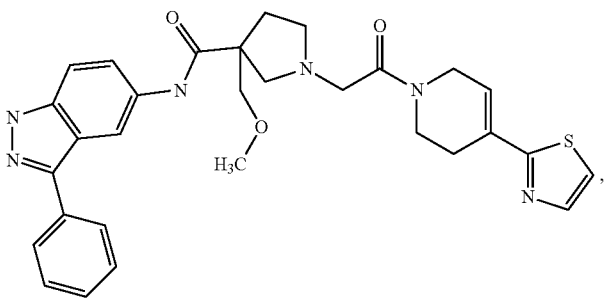
(Ex. 306)
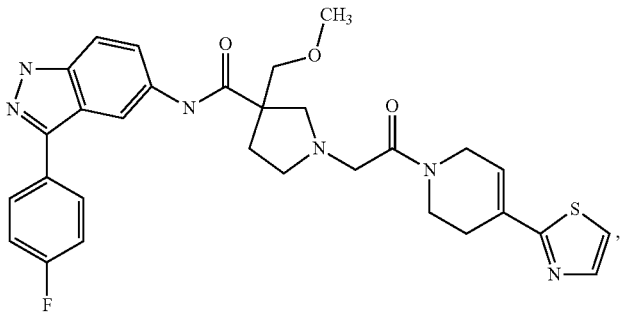
(Ex. 311)

(Ex. 326)
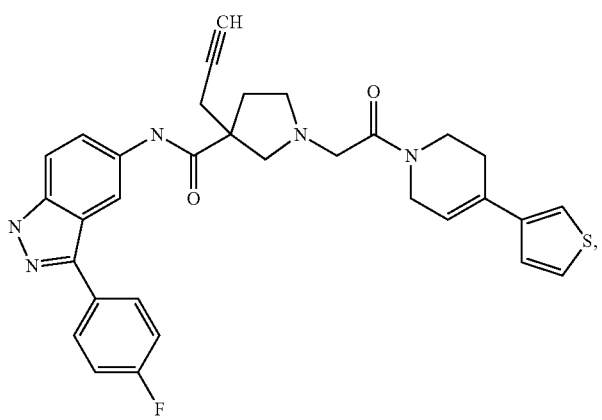
(Ex. 336)
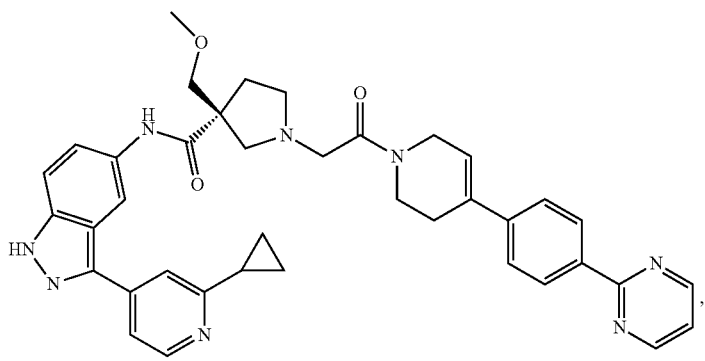
(Ex. 339)
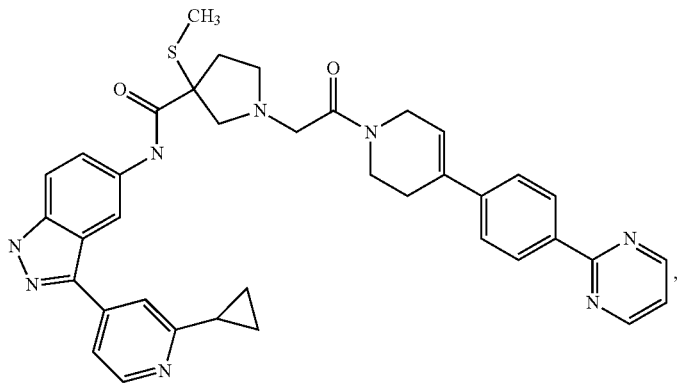
(Ex. 340)
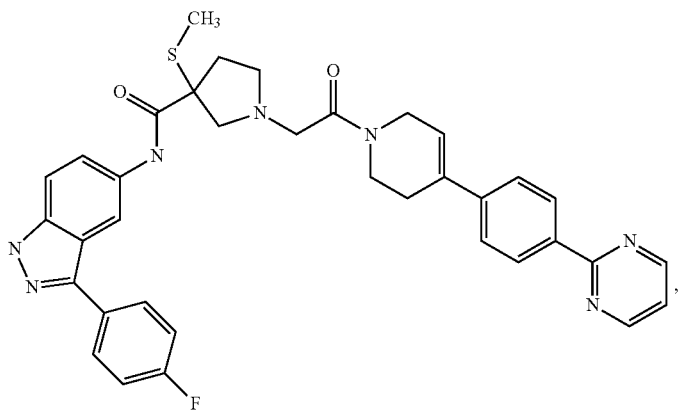

(Ex. 348)
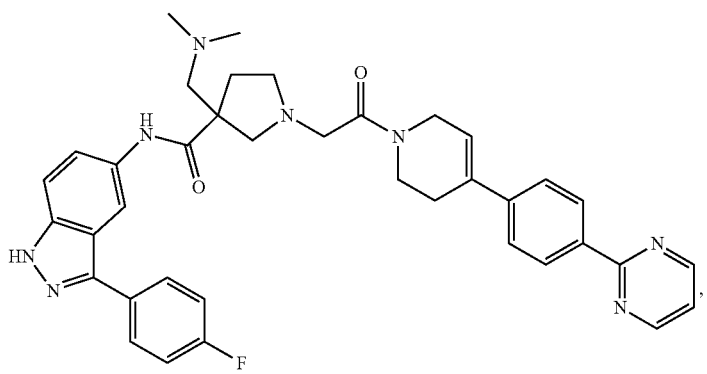
(Ex. 349)
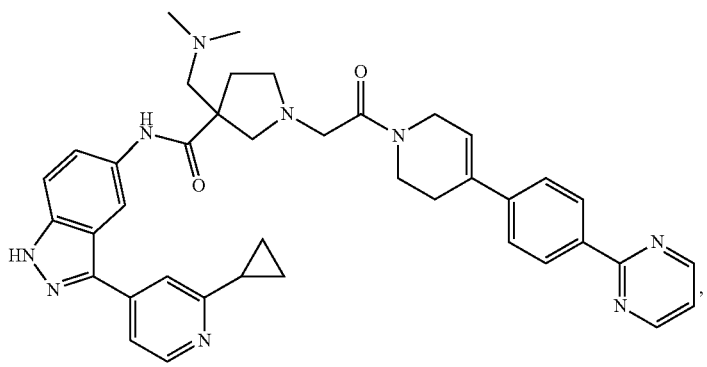
(Ex. 350)
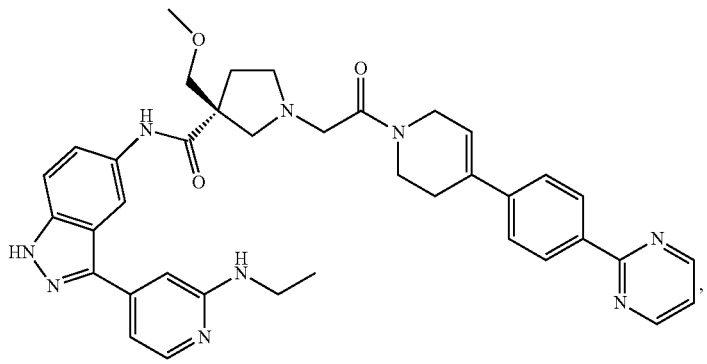
(Ex. 351)
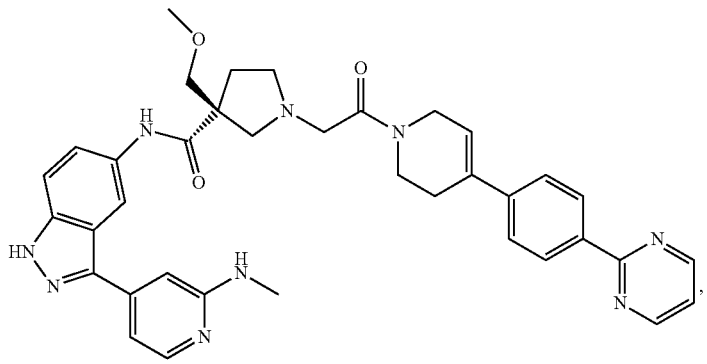

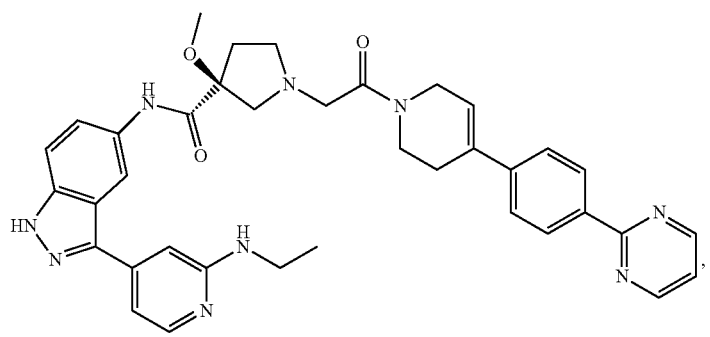
(Ex. 352)
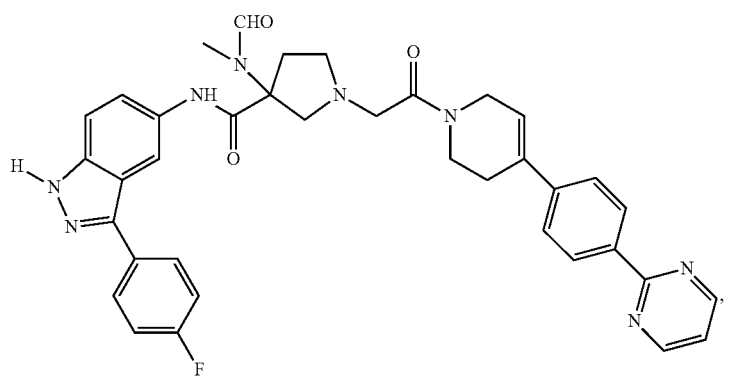
(Ex. 365)
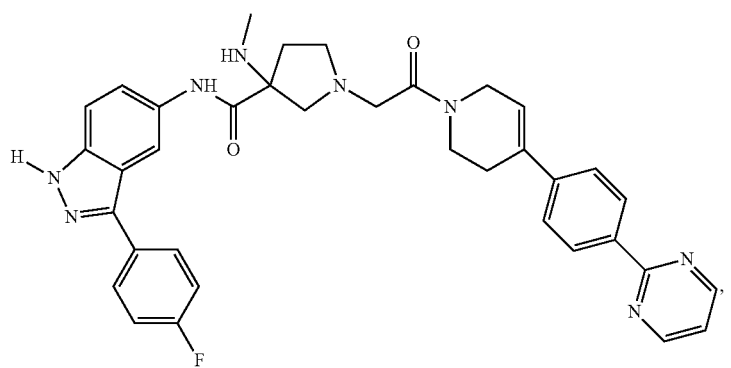
(Ex. 366)
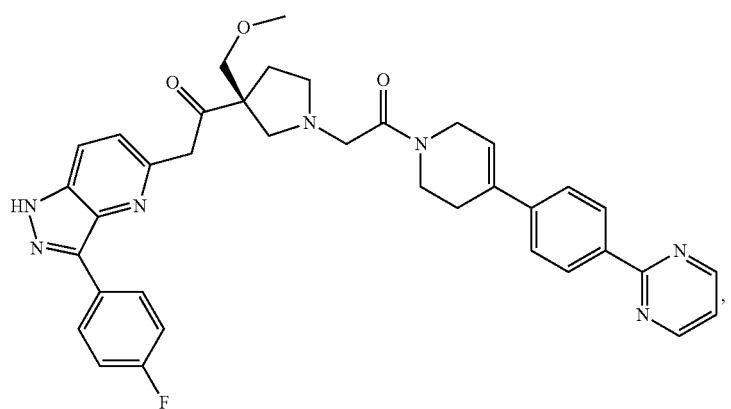
(Ex. 367)

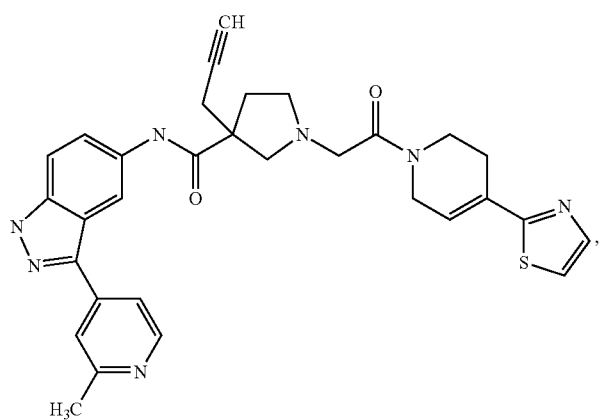
(Ex. 369)
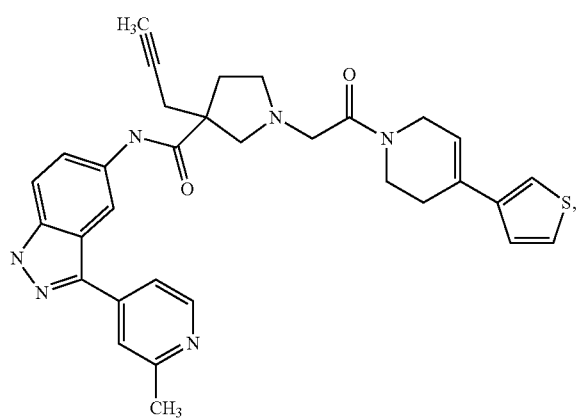
(Ex. 370)
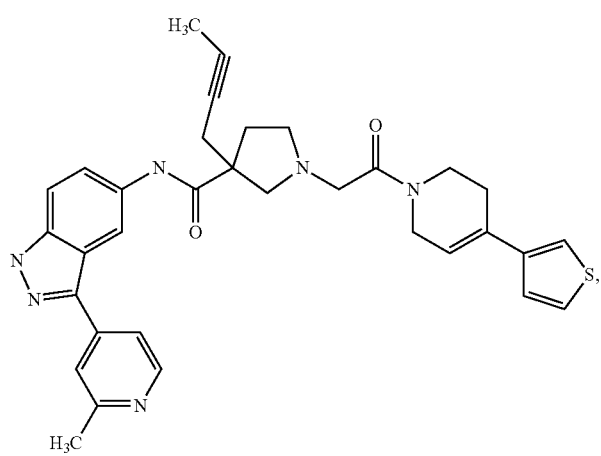
(Ex. 371)

-continued
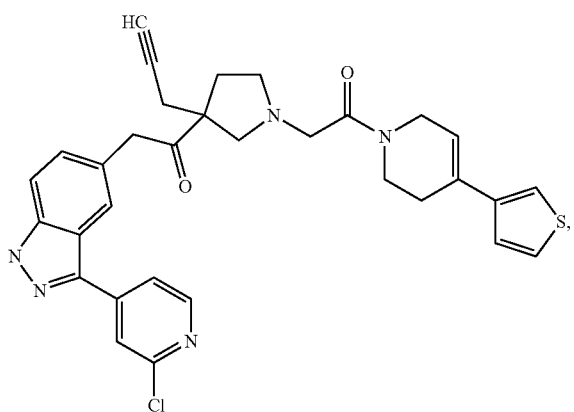
(Ex. 374)
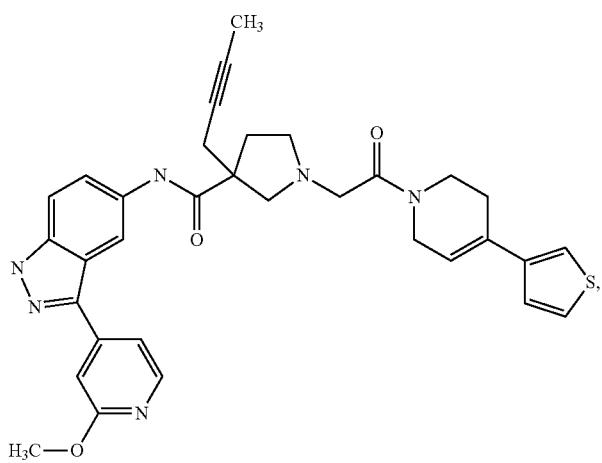
(Ex. 375)
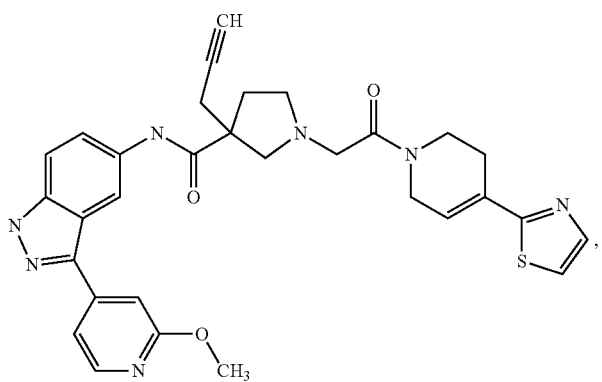
(Ex. 377)

(Ex. 378)
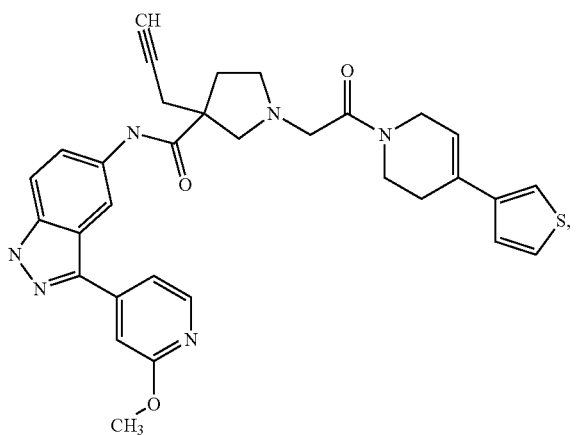
(Ex. 380)
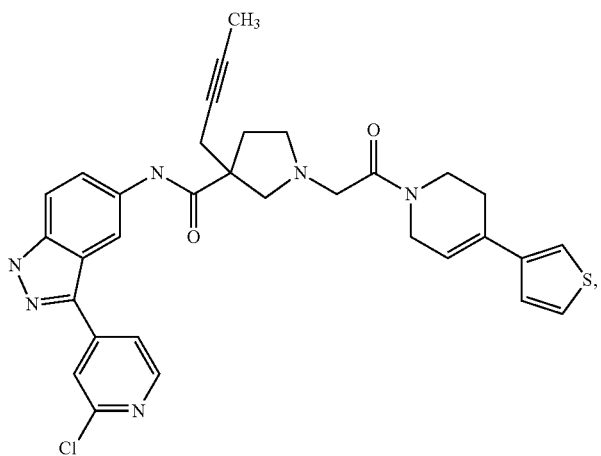
(Ex. 381)
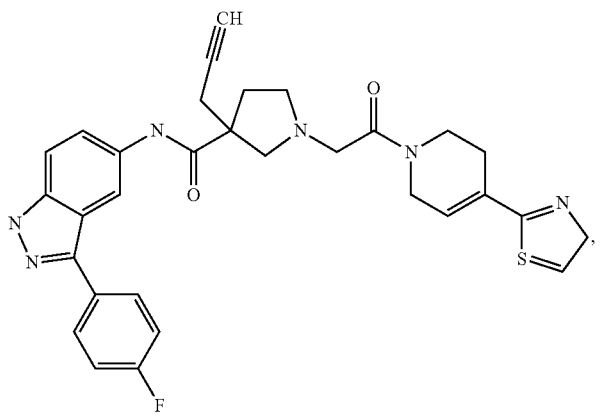
(Ex. 384)
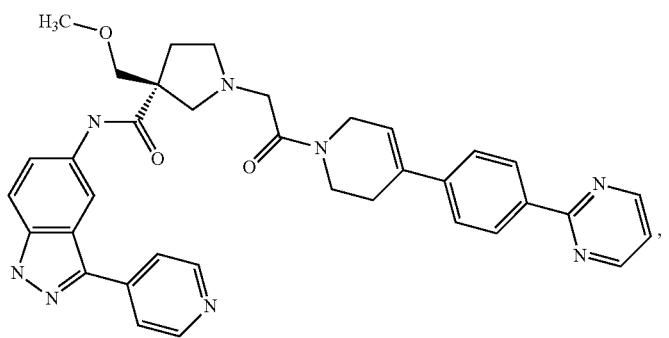

-continued
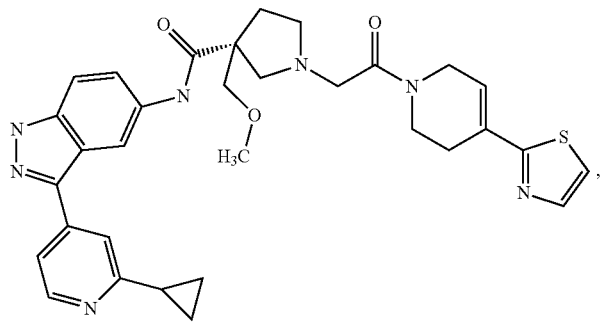
(Ex. 386)
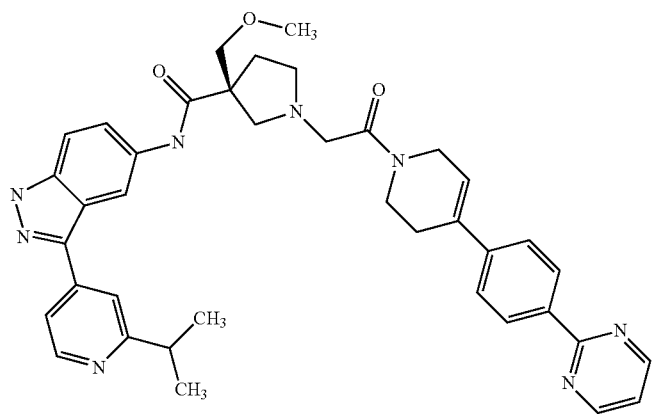
(Ex. 389)
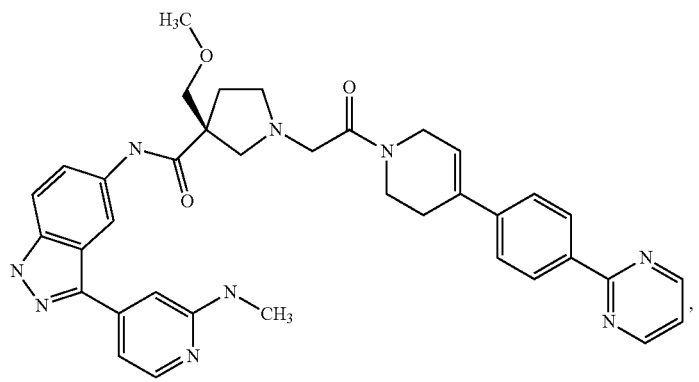
(Ex. 391)
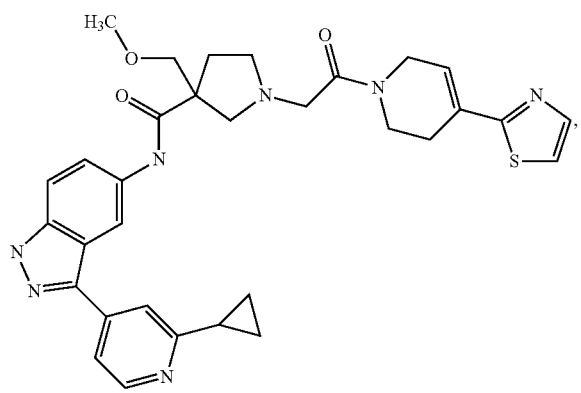
(Ex. 393)

-continued
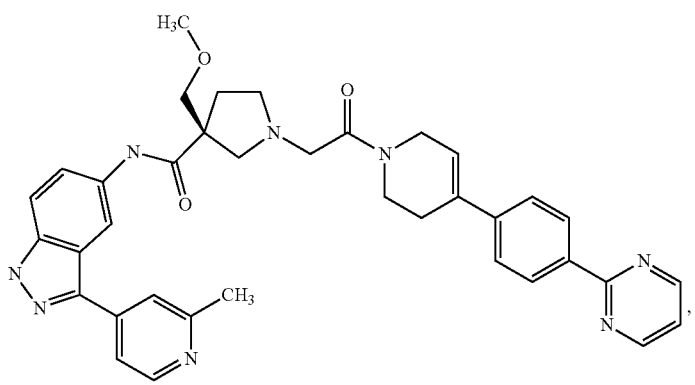
(Ex. 394)
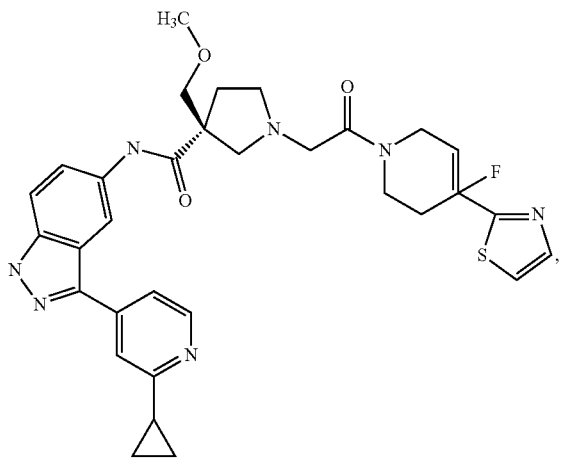
(Ex. 397)
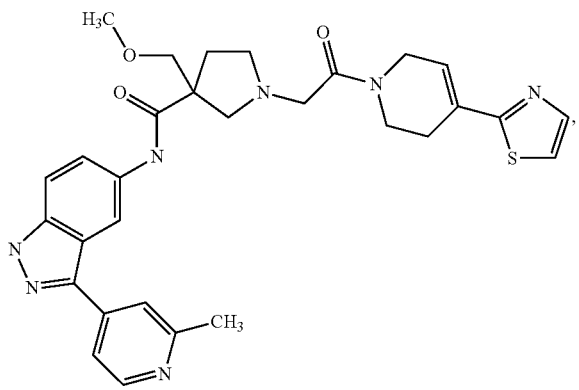
(Ex. 399)
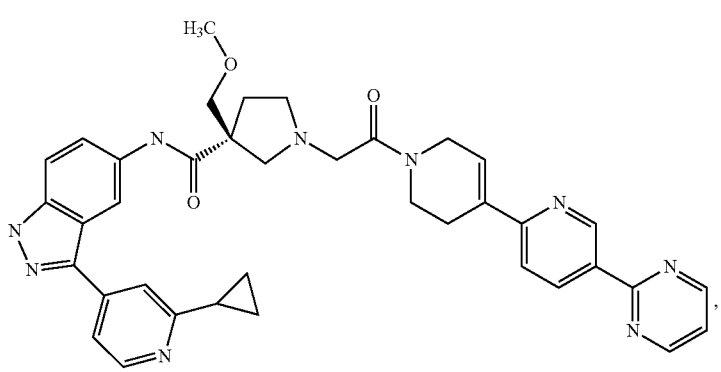
(Ex. 401)

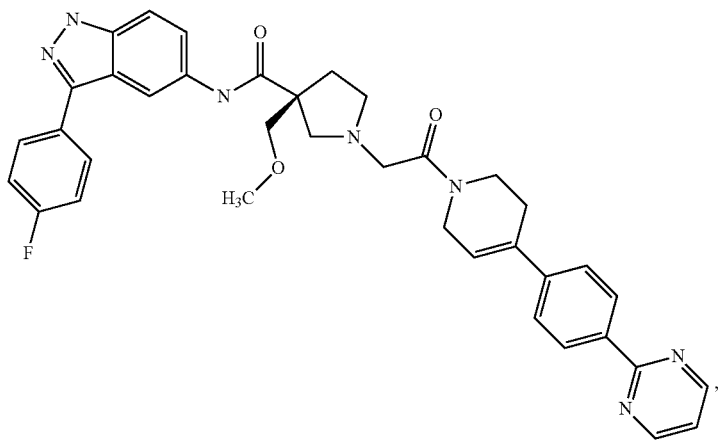 [SMILES: COC[C@@]1(C(=O)Nc2ccc3[nH]nc(-c4ccc(F)cc4)c3c2)CCN(CC(=O)N2CC=C(c3ccc(-c4ncccn4)cc3)CC2)C1]
(Ex. 402)
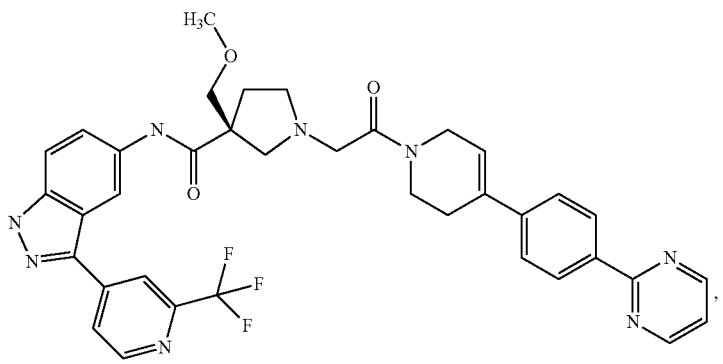
(Ex. 403)
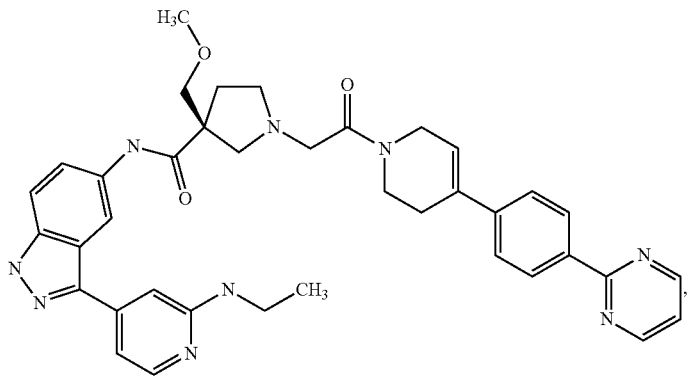
(Ex. 405)
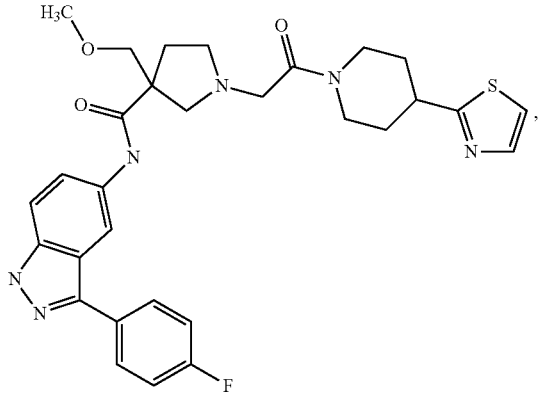
(Ex. 407)

-continued
(Ex. 409)
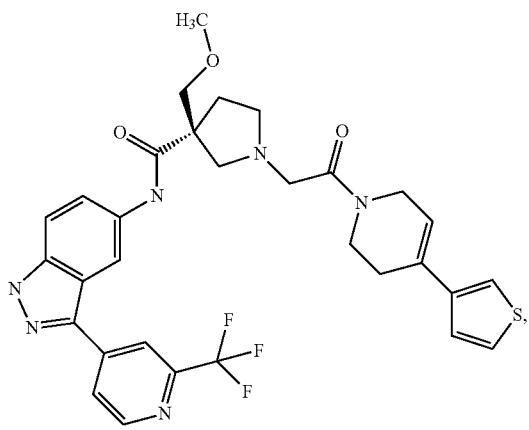
(Ex. 414)
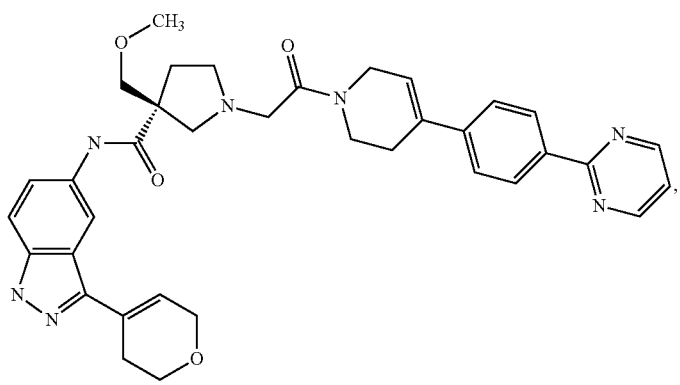
(Ex. 415)
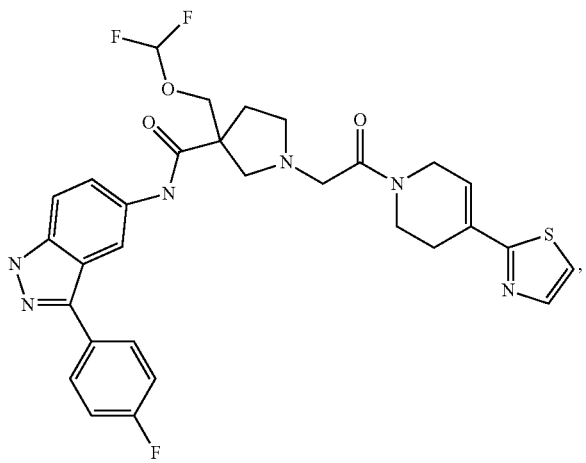
(Ex. 416)
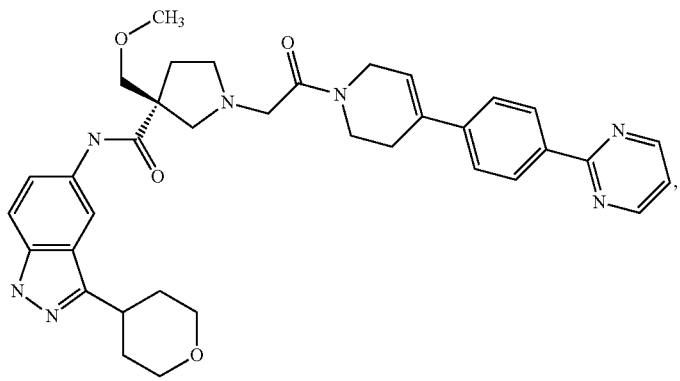

(Ex. 418)
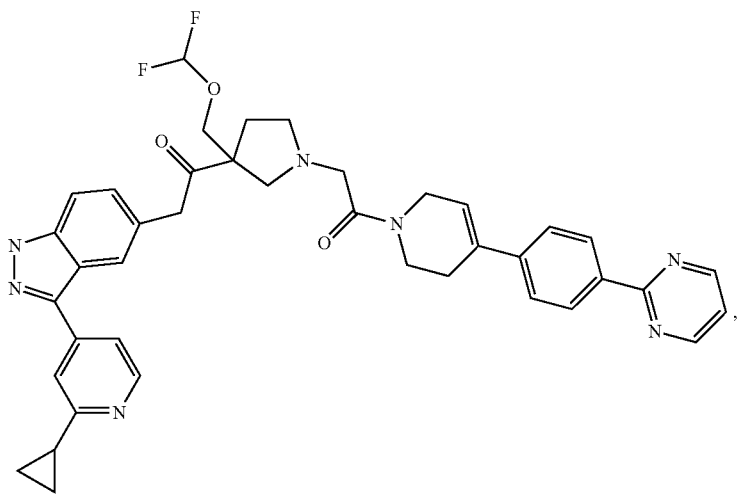
(Ex. 420)
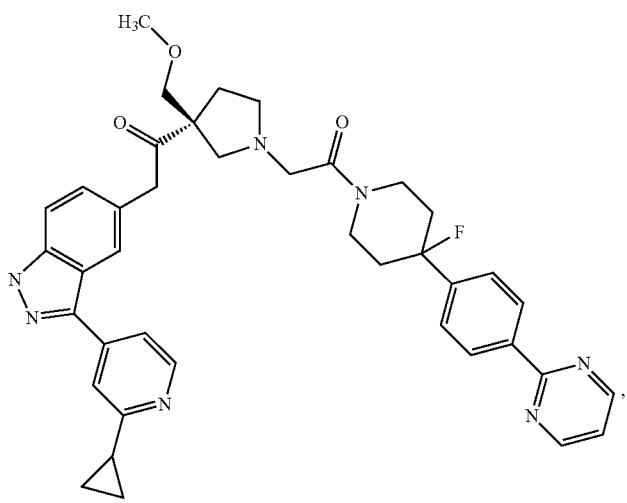
(Ex. 421)
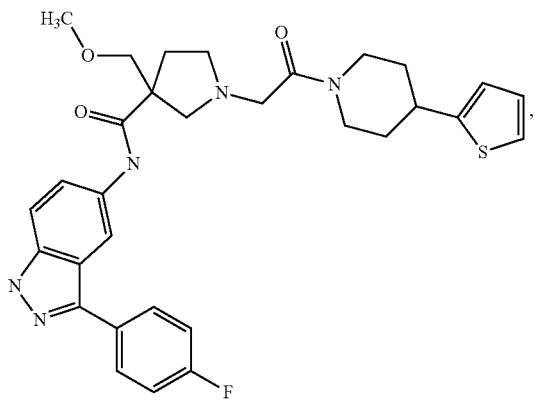

(Ex. 422)
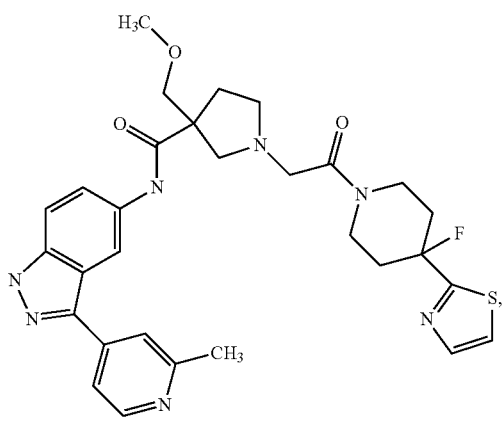
(Ex. 425)
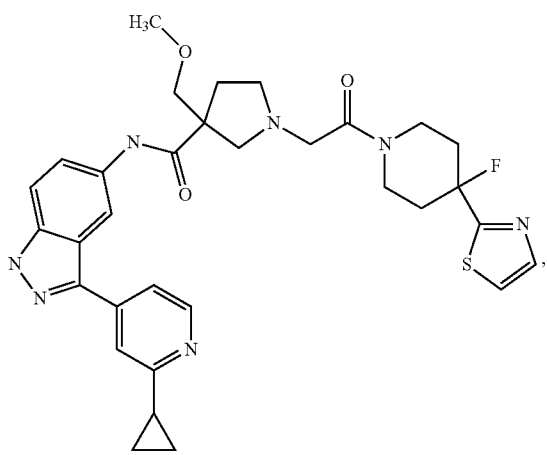
(Ex. 427)
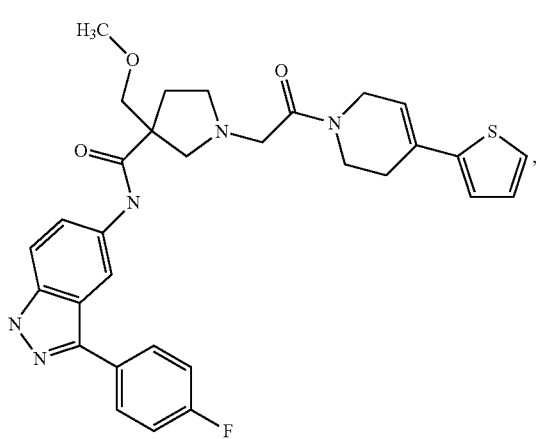

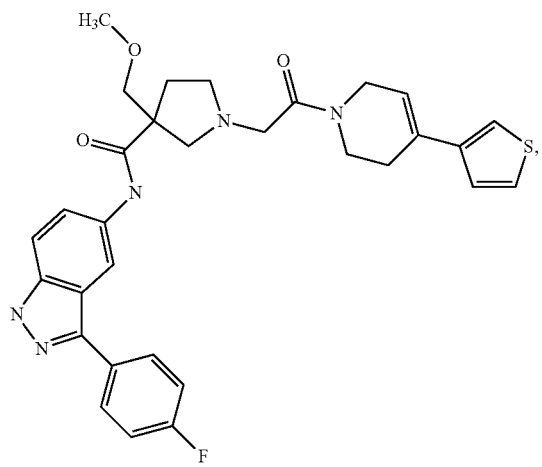
(Ex. 428)
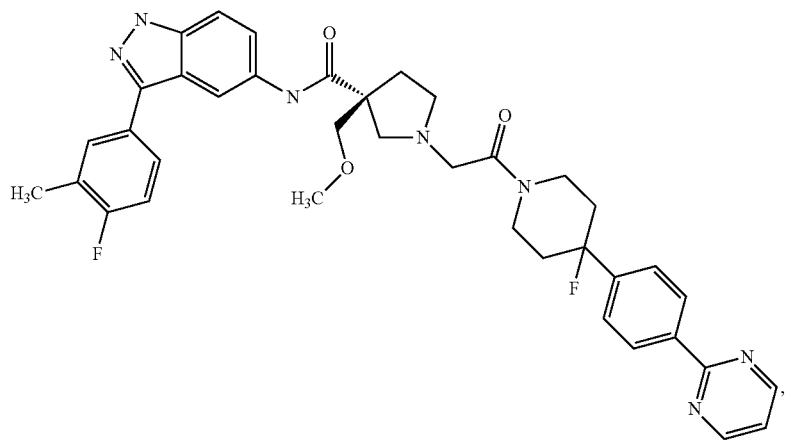
(Ex. 429)
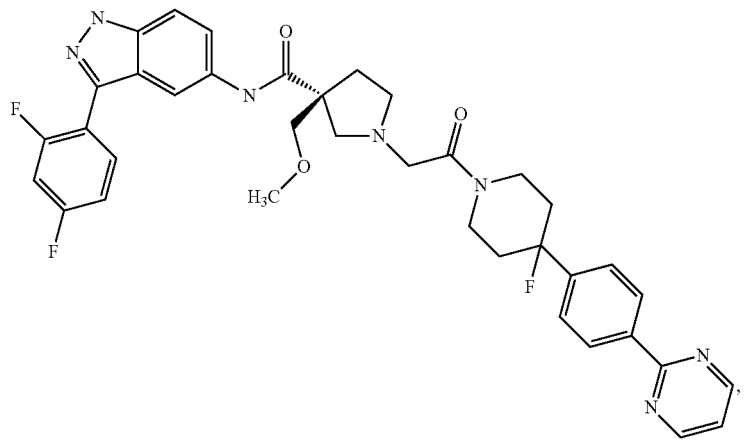
(Ex. 431)

(Ex. 432)
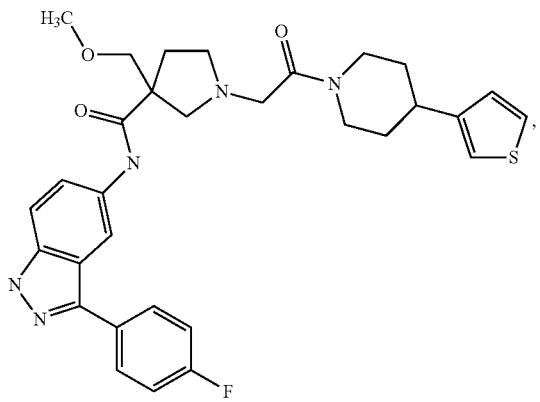
(Ex. 434)
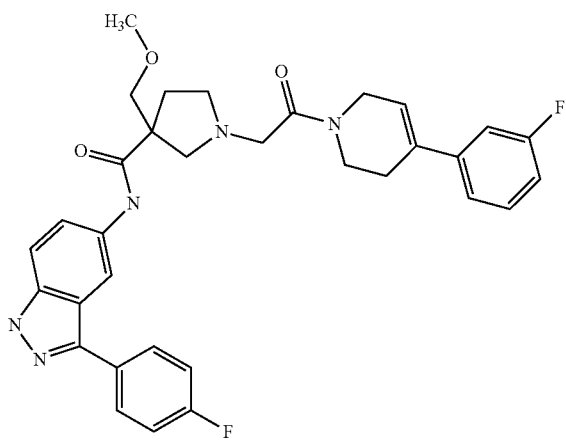
(Ex. 435)
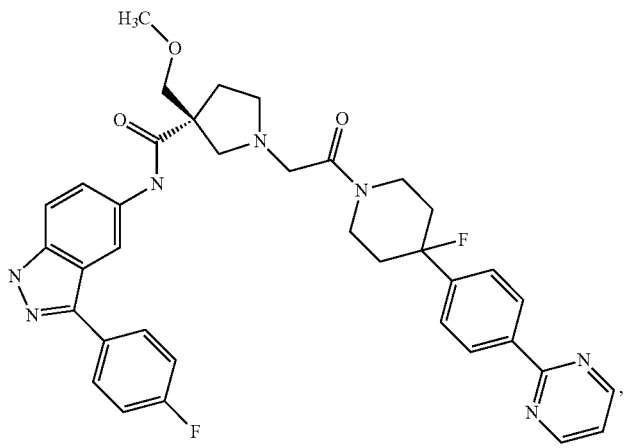
(Ex. 436)
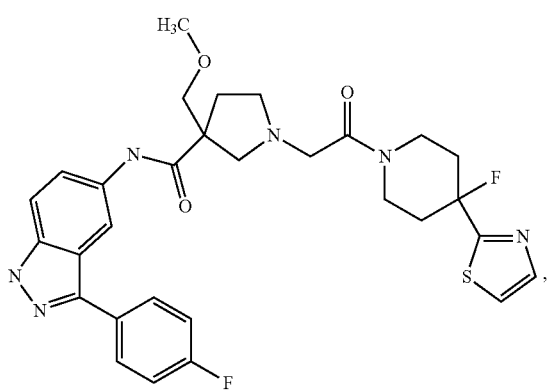

(Ex. 438)
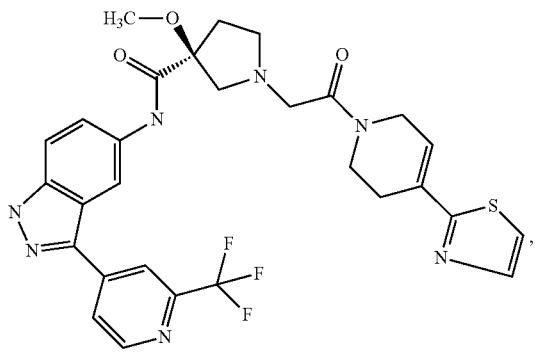
(Ex. 440)
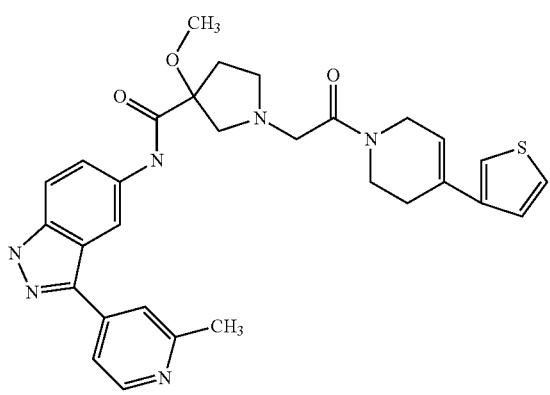
(Ex. 444)
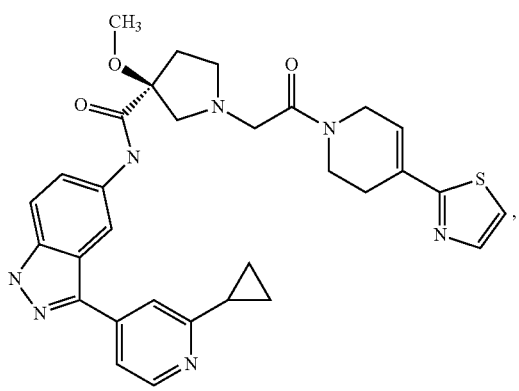
(Ex. 445)
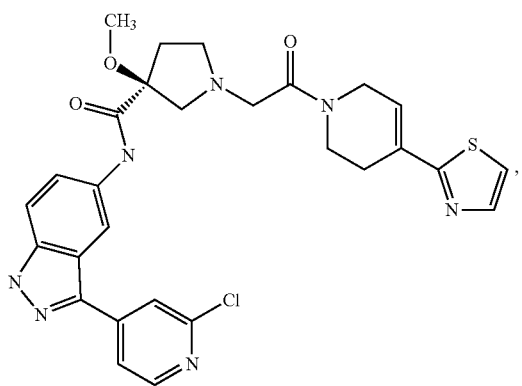

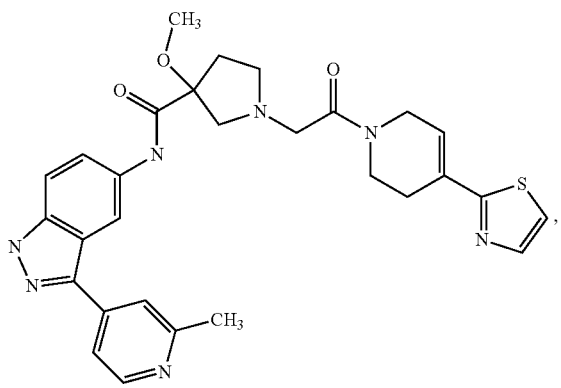
(Ex. 449)
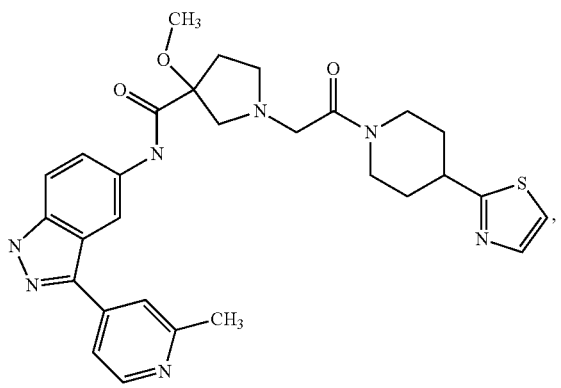
(Ex. 450)
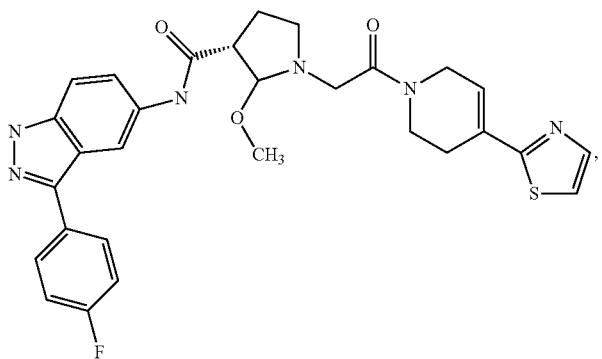
(Ex. 454)
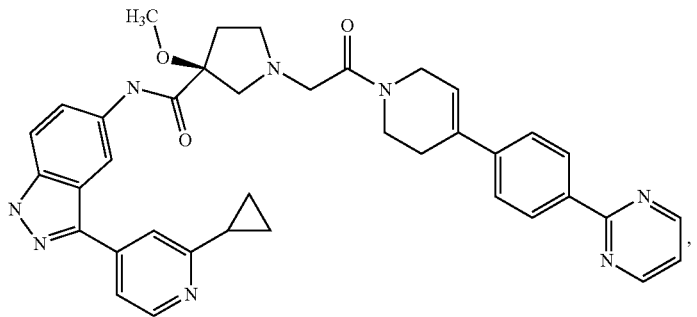
(Ex. 459)

(Ex. 460)
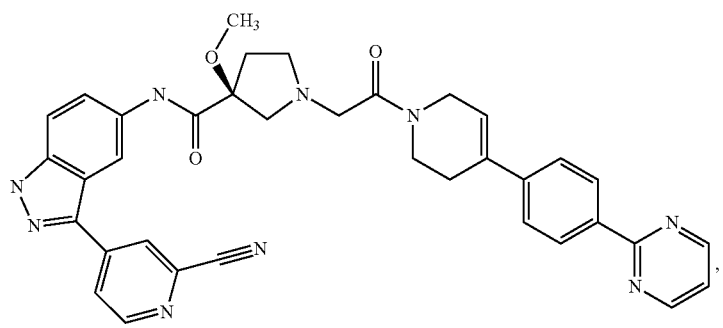
(Ex. 461)
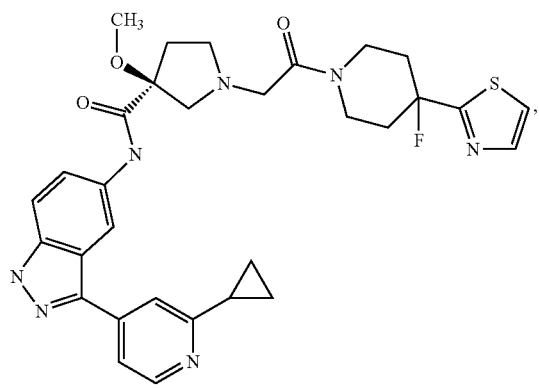
(Ex. 465)
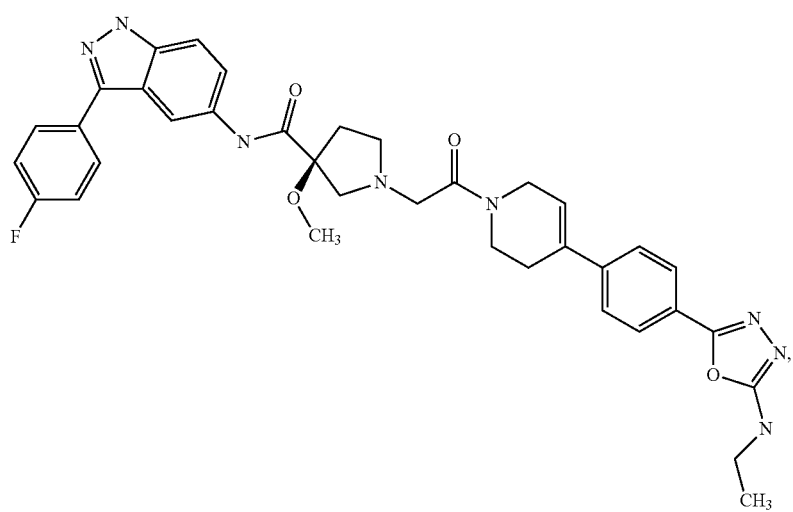
(Ex. 467)
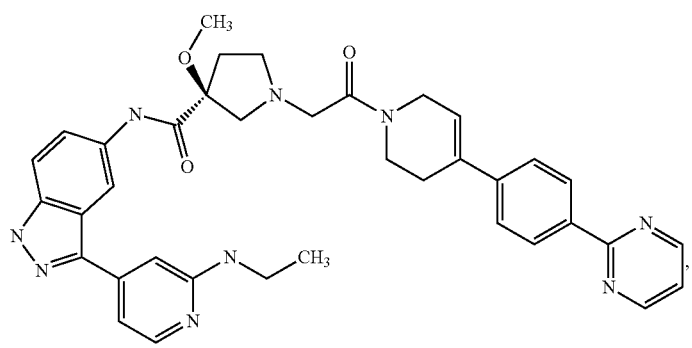

-continued
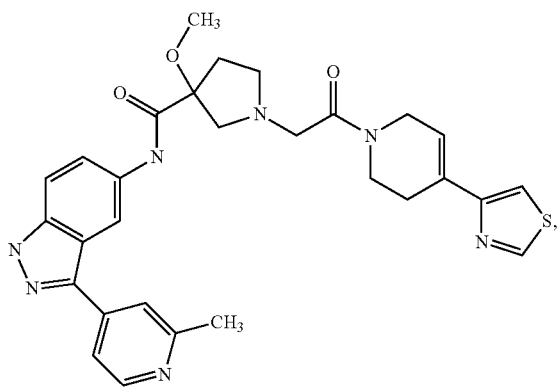
(Ex. 469)
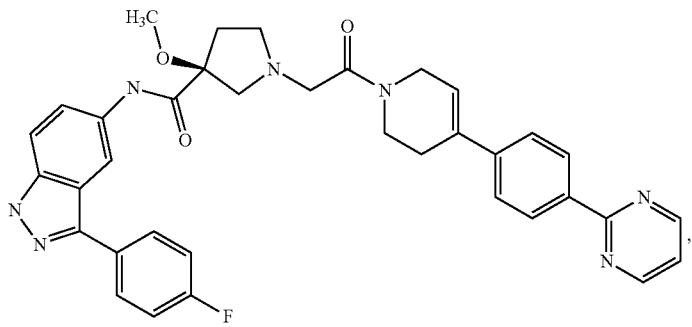
(Ex. 470)
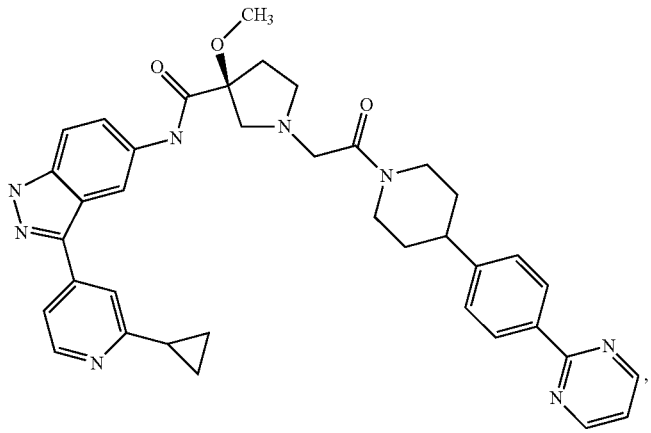
(Ex. 473)
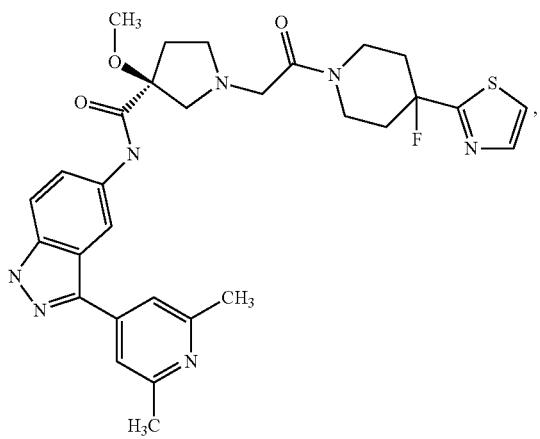
(Ex. 474)

(Ex. 477)
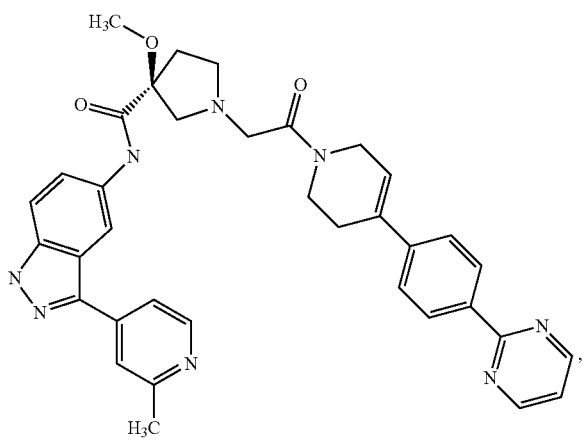
(Ex. 478)
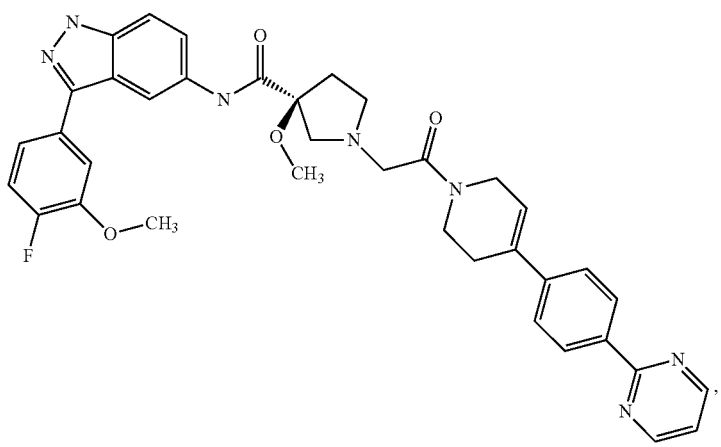
(Ex. 479)
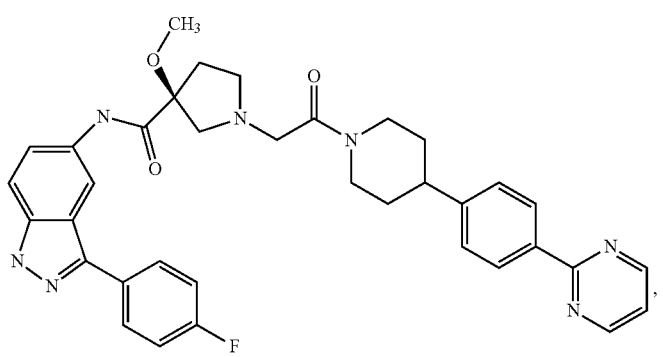
(Ex. 481)
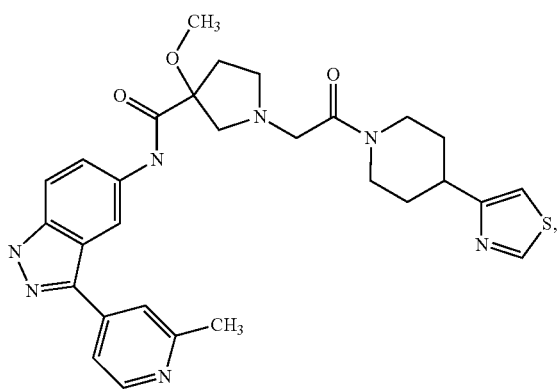

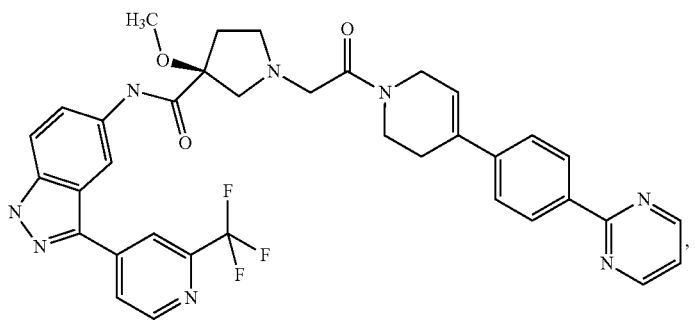
(Ex. 483)
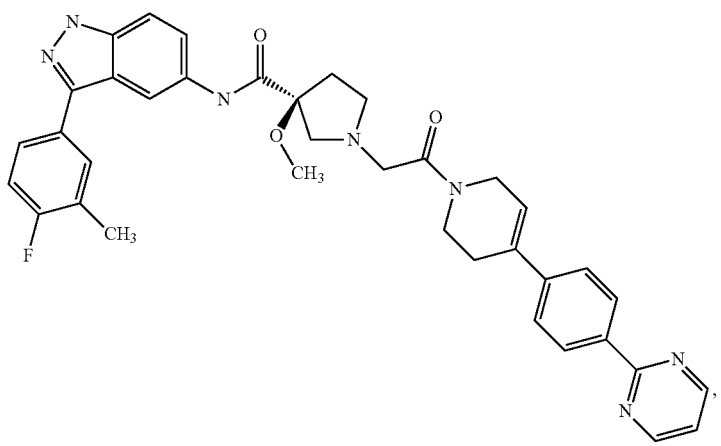
(Ex. 484)
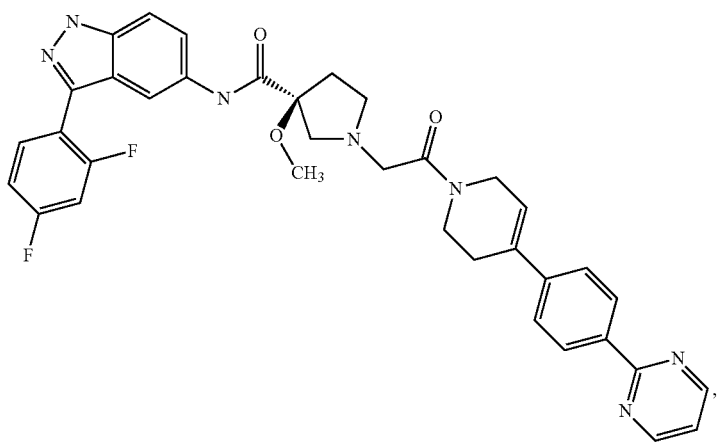
(Ex. 486)

(Ex. 488)
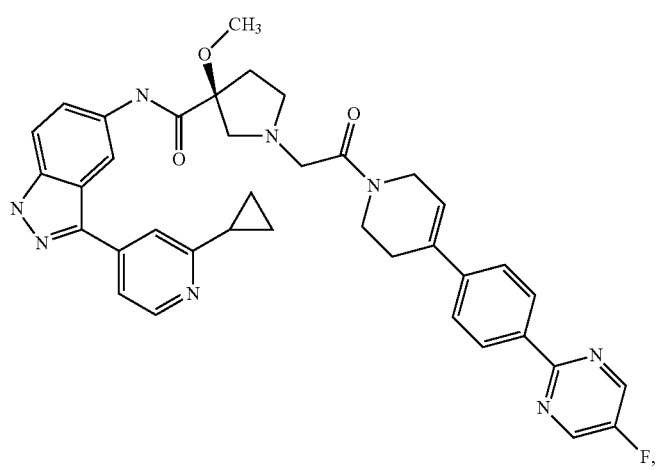
(Ex. 489)
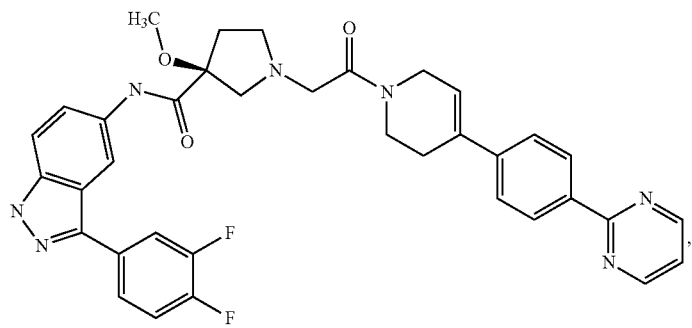
(Ex. 490)
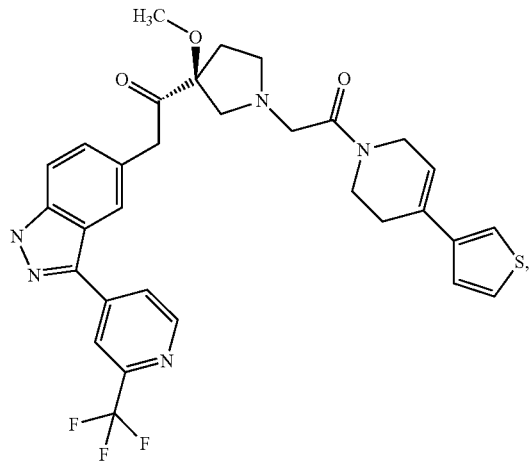
(Ex. 492)
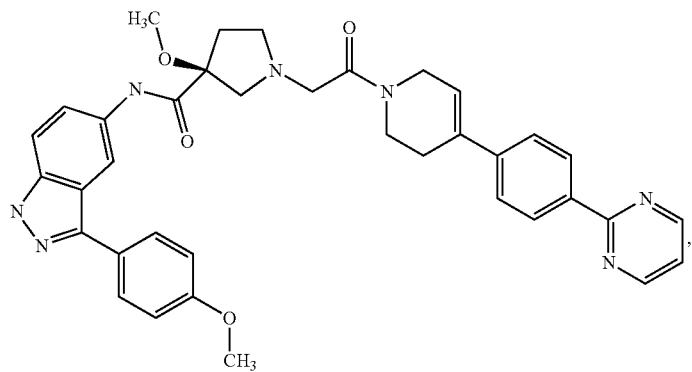

(Ex. 495)
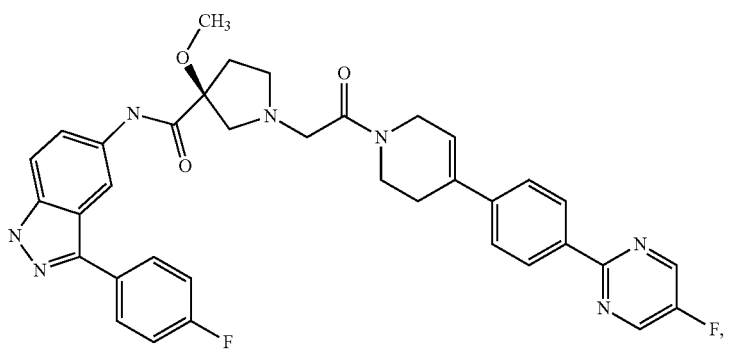
(Ex. 497)
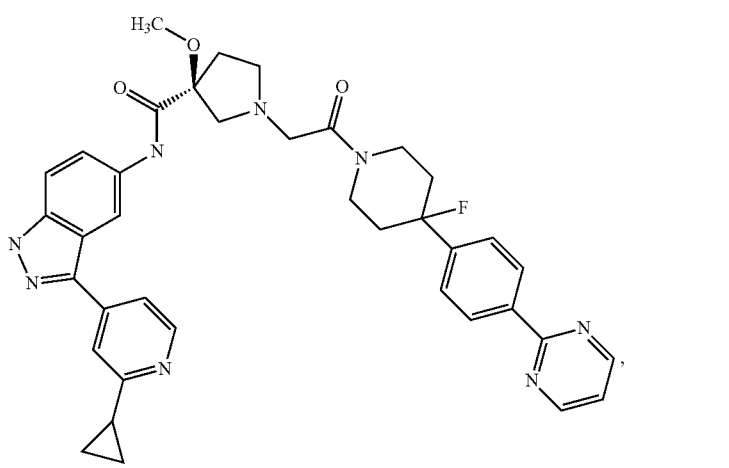
(Ex. 500)
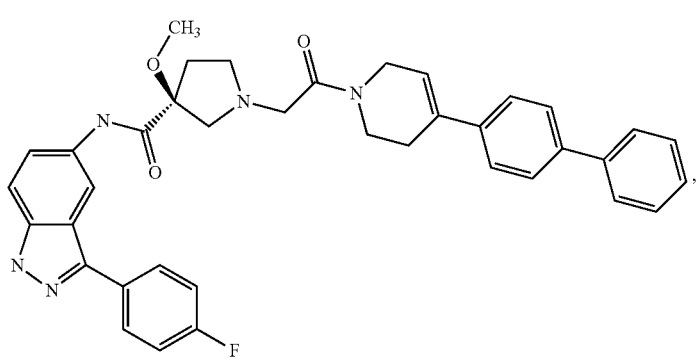
(Ex. 502)
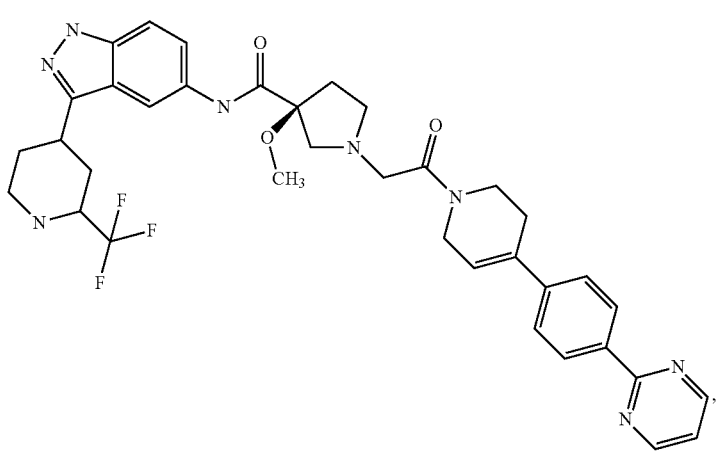

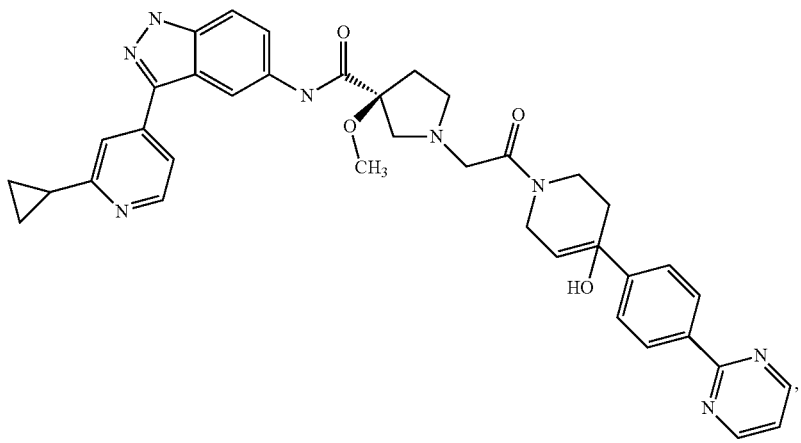
(Ex. 504)
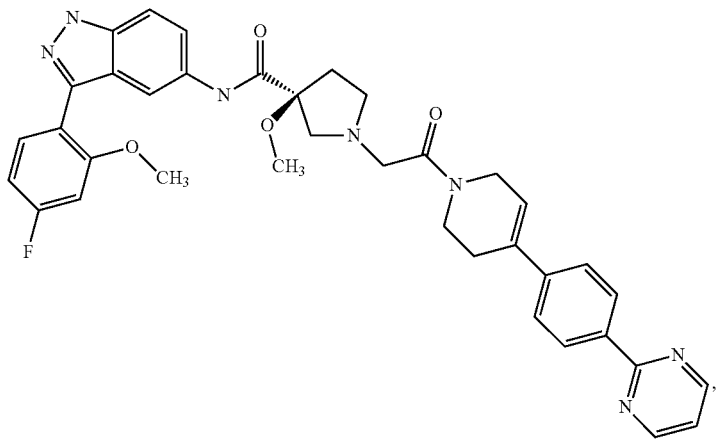
(Ex. 505)
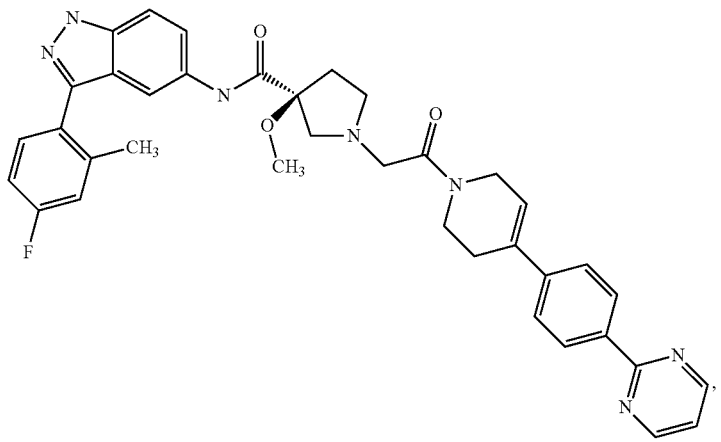
(Ex. 507)

-continued
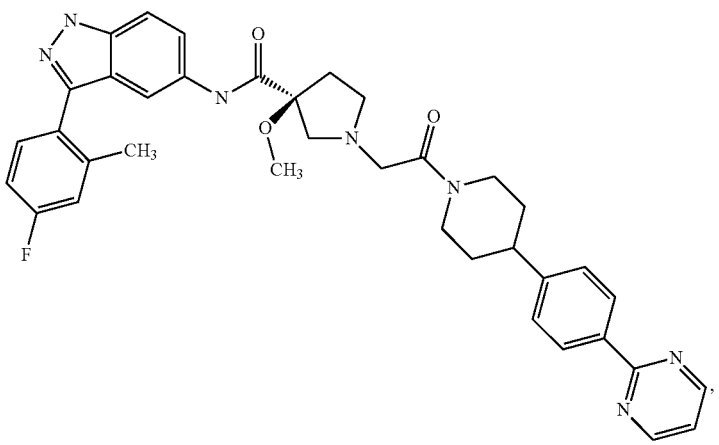
(Ex. 508)
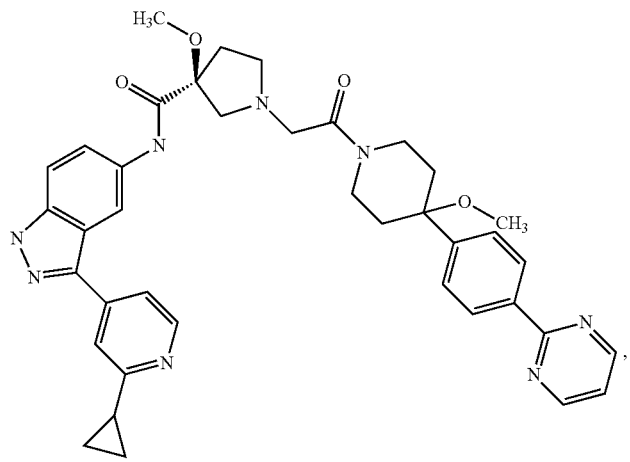
(Ex. 509)
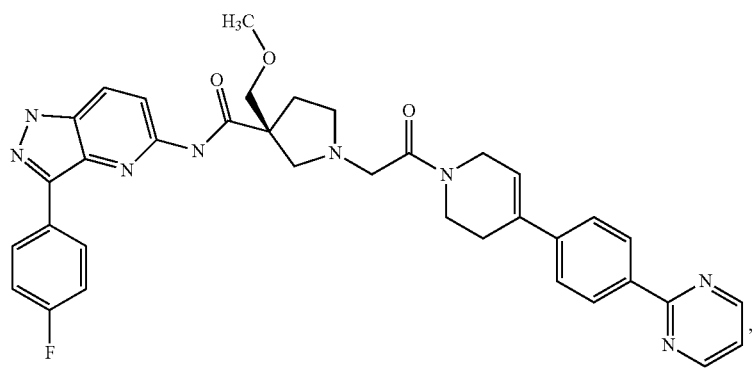
(Ex. 510)
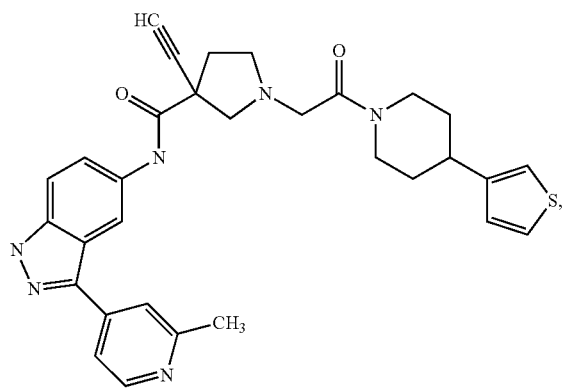
(Ex. 511)

(Ex. 512)
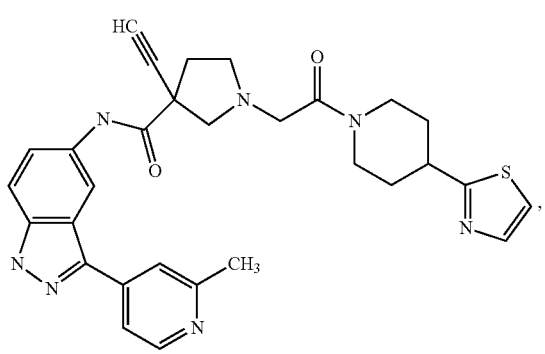
(Ex. 513)
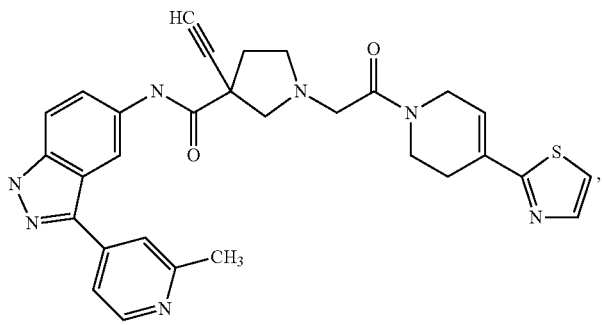
(Ex. 514)
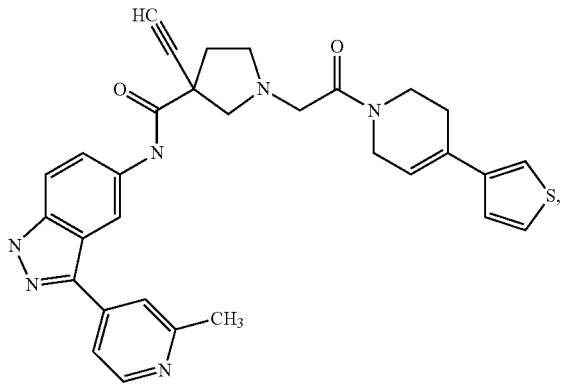
(Ex. 519)
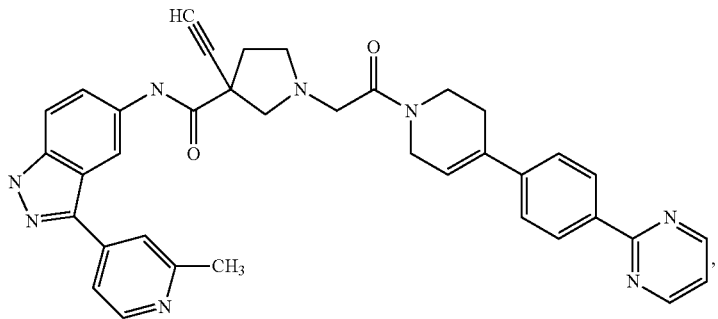

(Ex. 529)
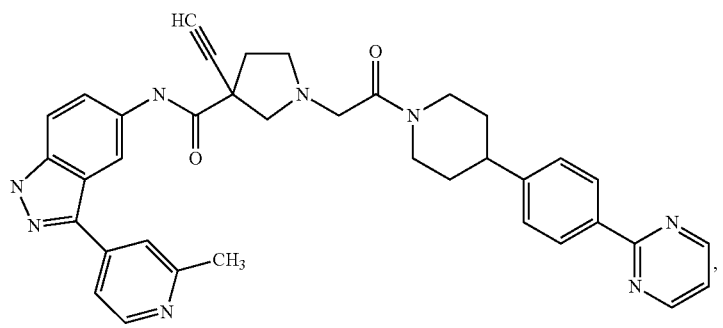
(Ex. 353)
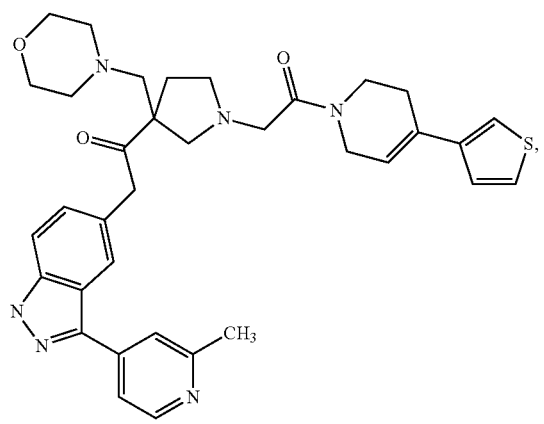
(Ex. 537)
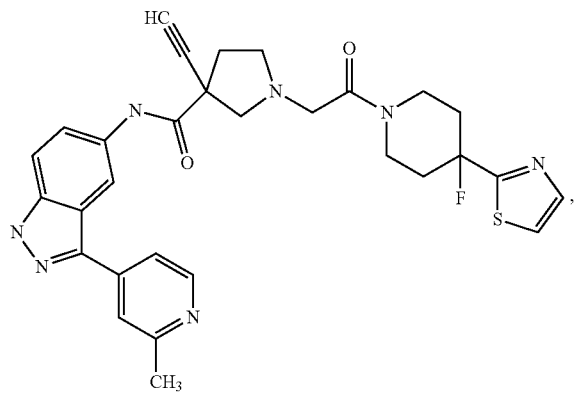
(Ex. 541)
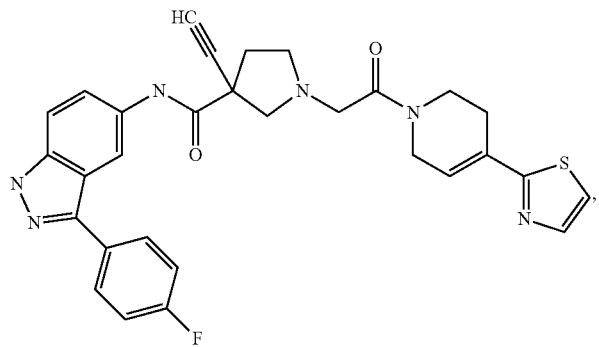

(Ex. 545)
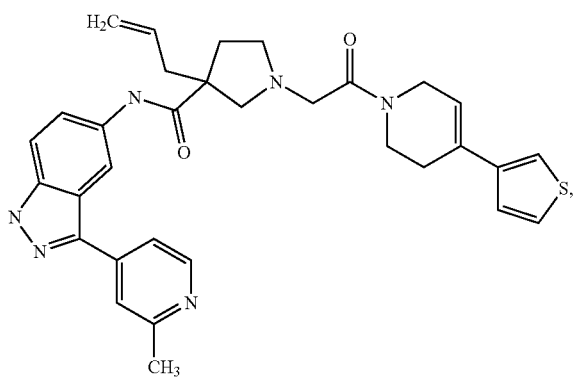
(Ex. 546)
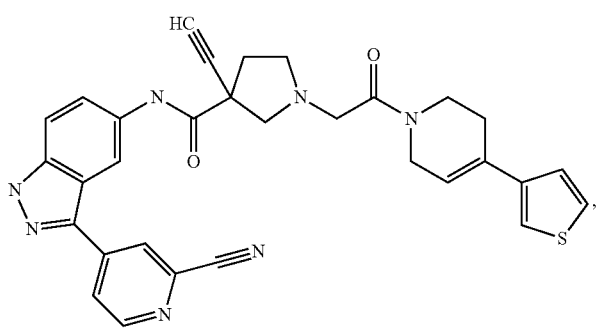
(Ex. 549)
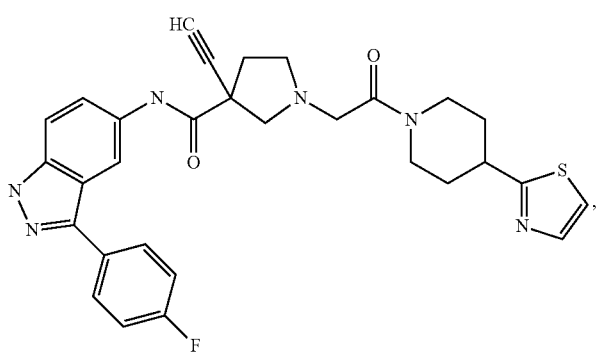
(Ex. 550)
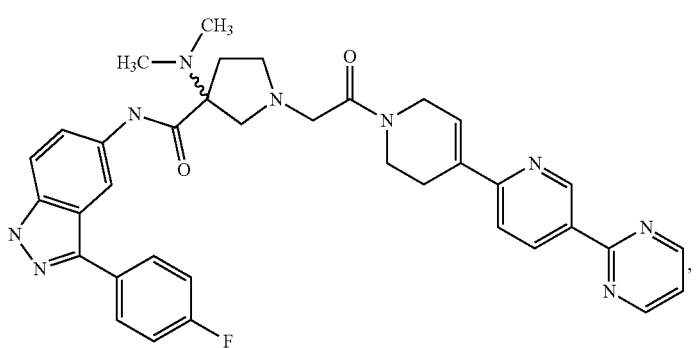

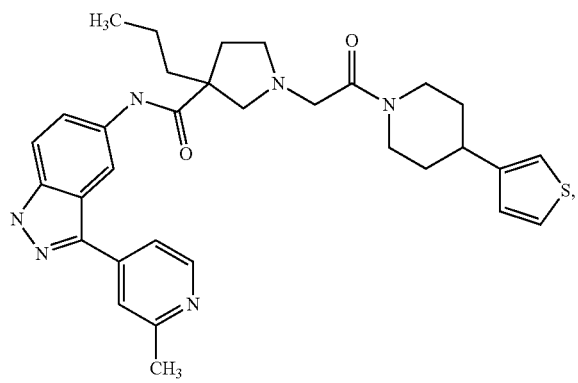
(Ex. 553)
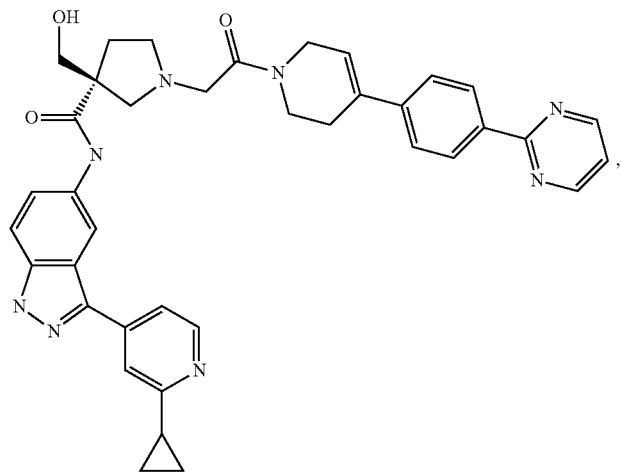
(Ex. 554)
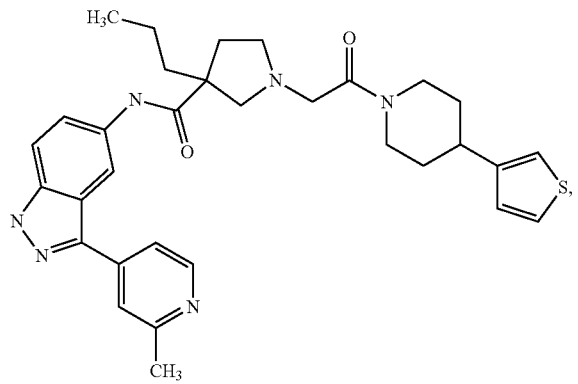
(Ex. 557)
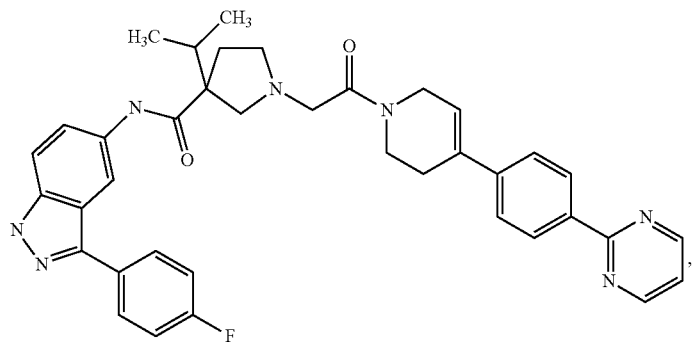
(Ex. 564)

(Ex. 565)
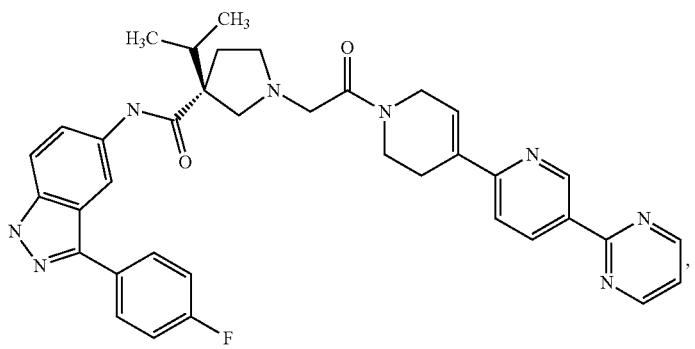
(Ex. 567)
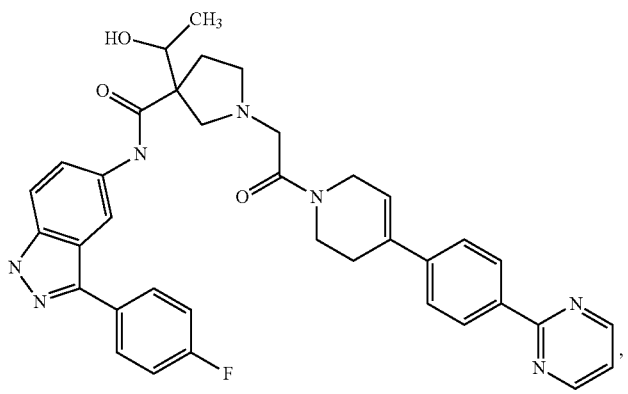
(Ex. 569)
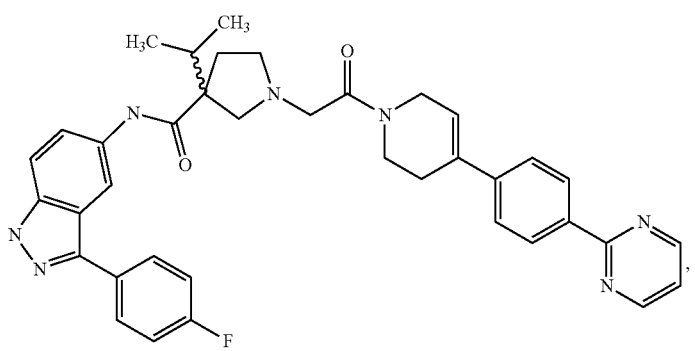
(Ex. 572)
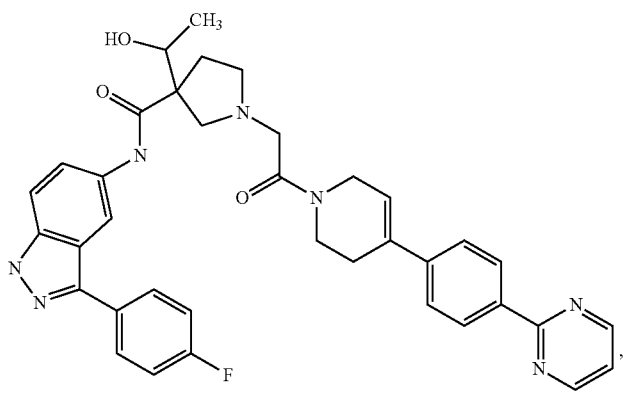

(Ex. 574)
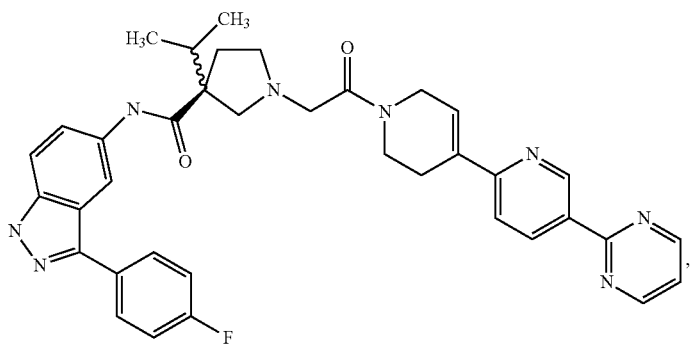
(Ex. 582)
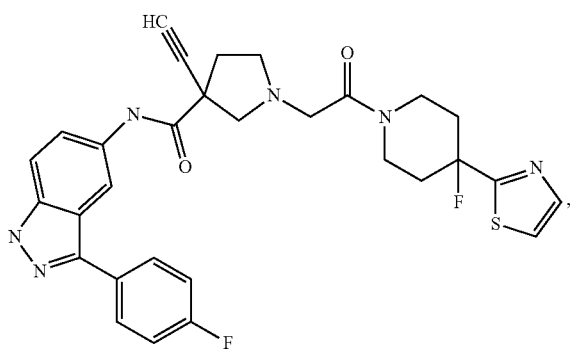
(Ex. 583)
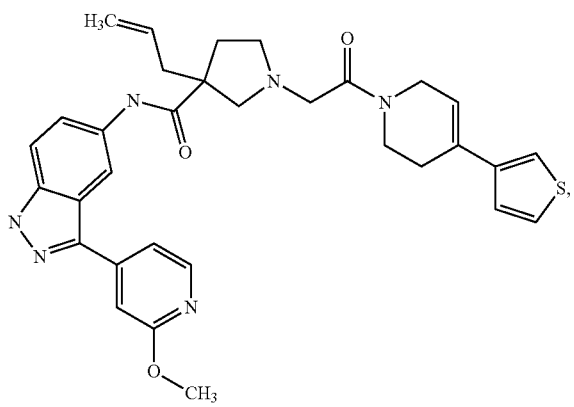
(Ex. 584)
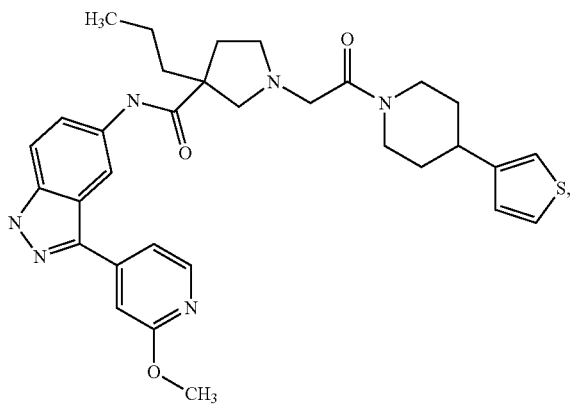

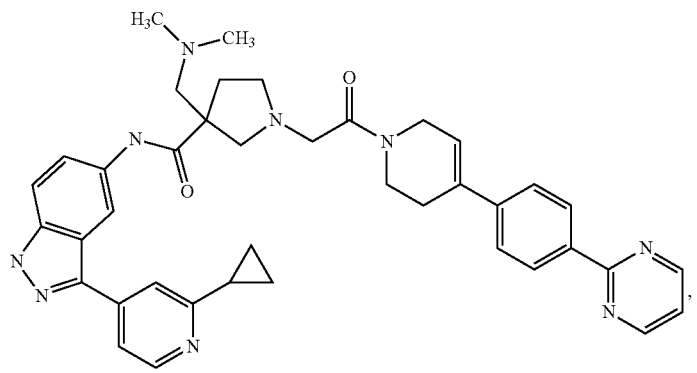
(Ex. 585)
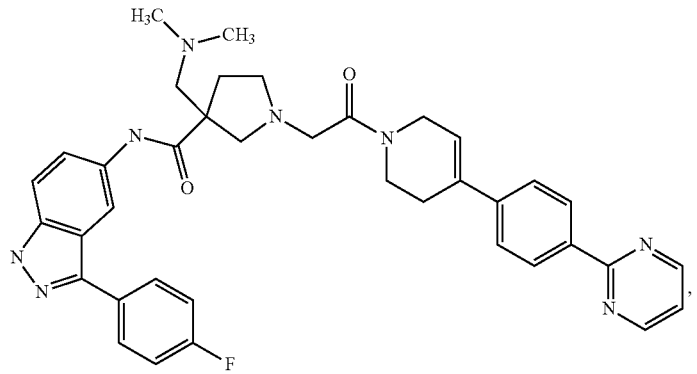
(Ex. 589)
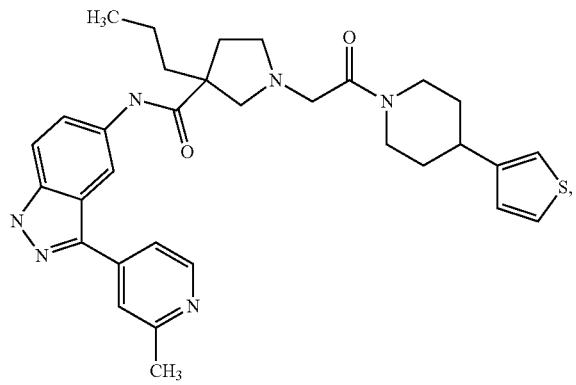
(Ex. 593)
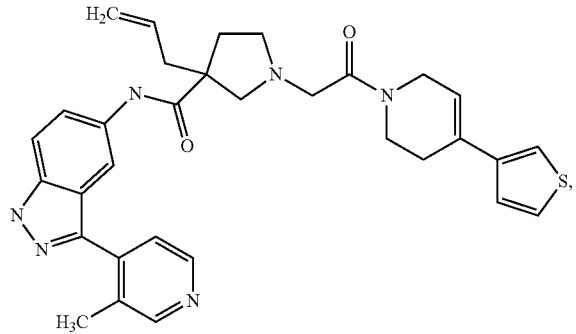
(Ex. 594)

-continued
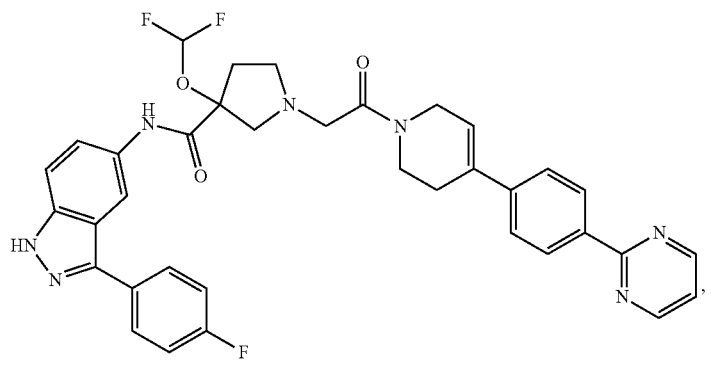
(Ex. 603)
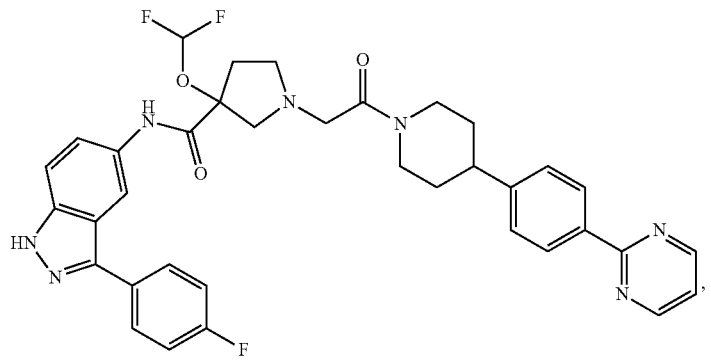
(Ex. 604)
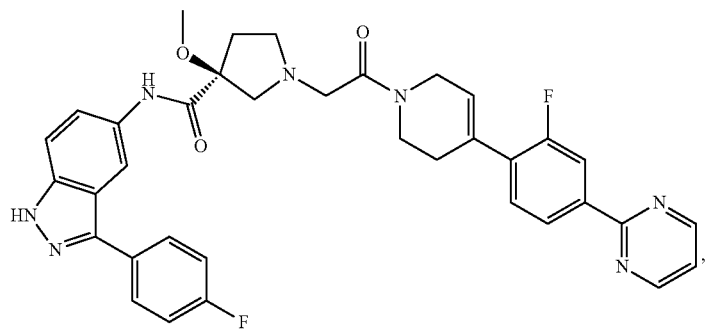
(Ex. 606)
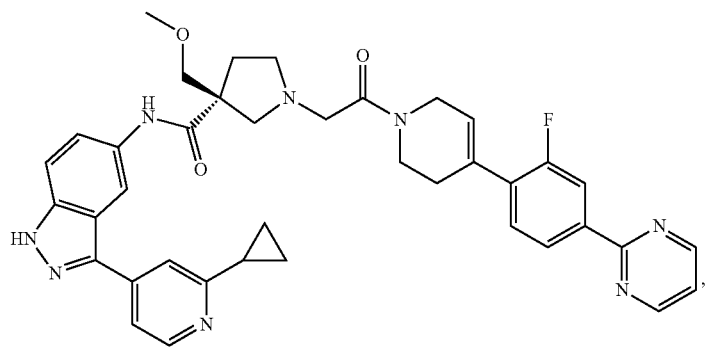
(Ex. 607)

(Ex. 608)
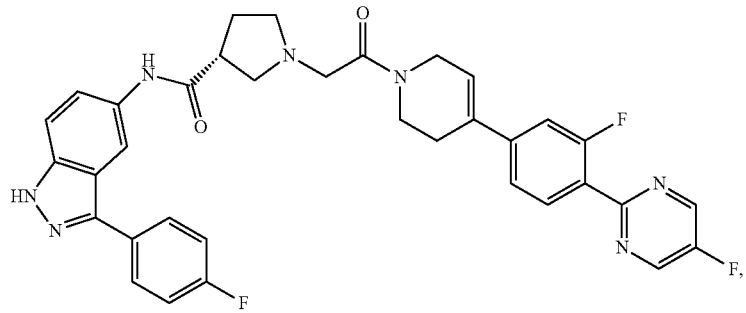
(Ex. 609)
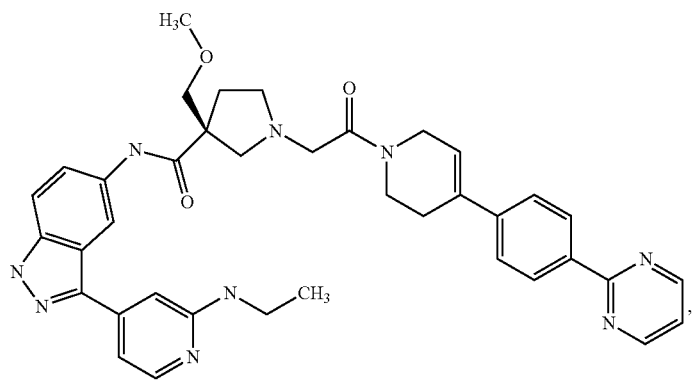
(Ex. 610)
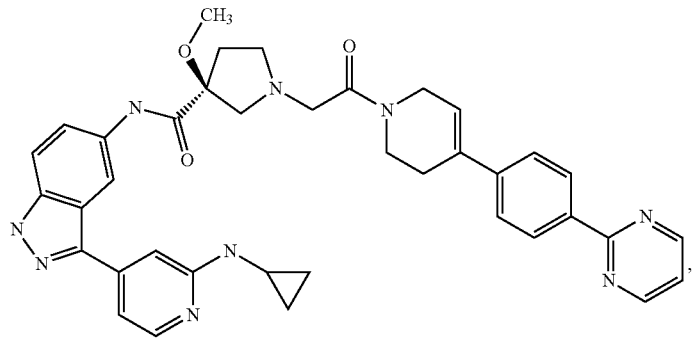
(Ex. 611)
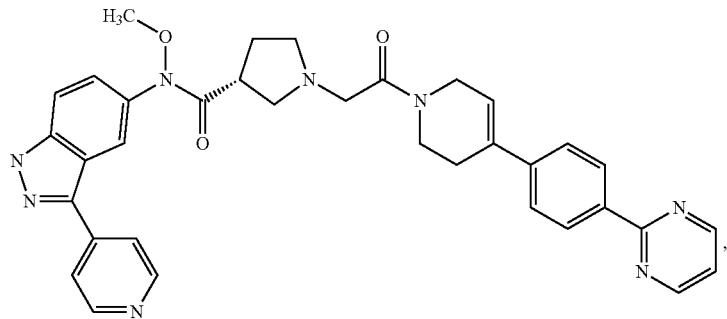

-continued
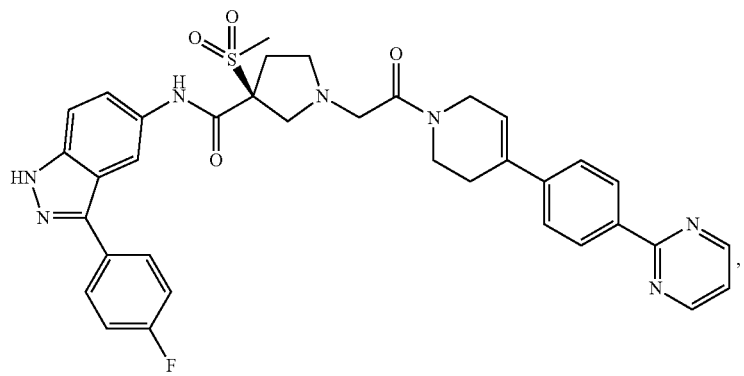
(Ex. 612)
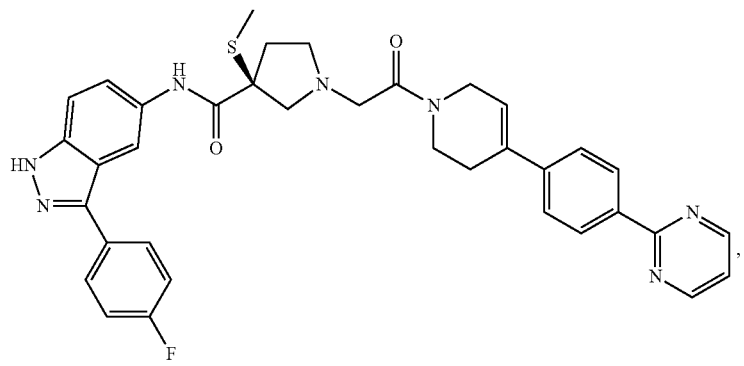
(Ex. 613)
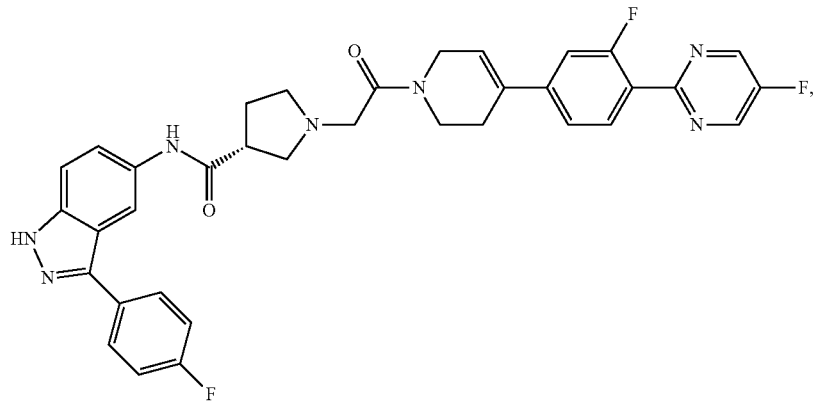
(Ex. 617)
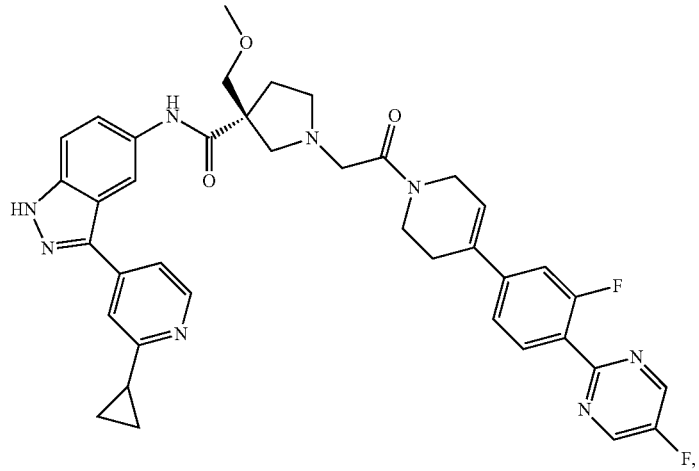
(Ex. 618)

(Ex. 622)
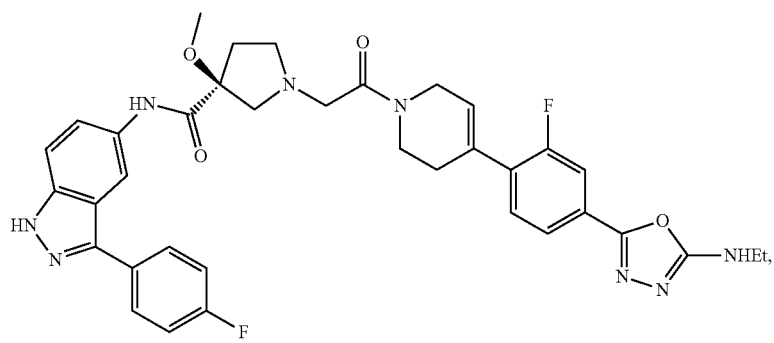
(Ex. 623)
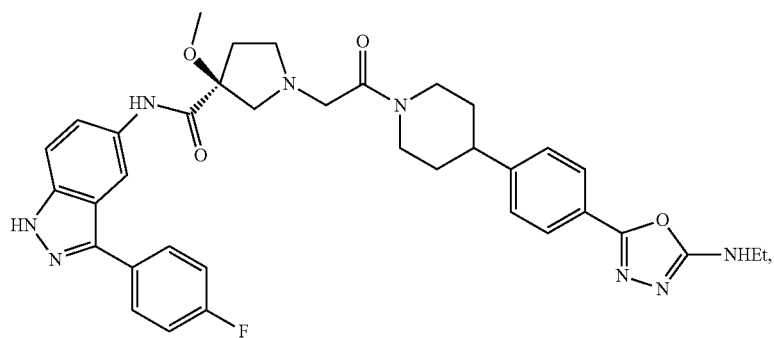
(Ex. 624)
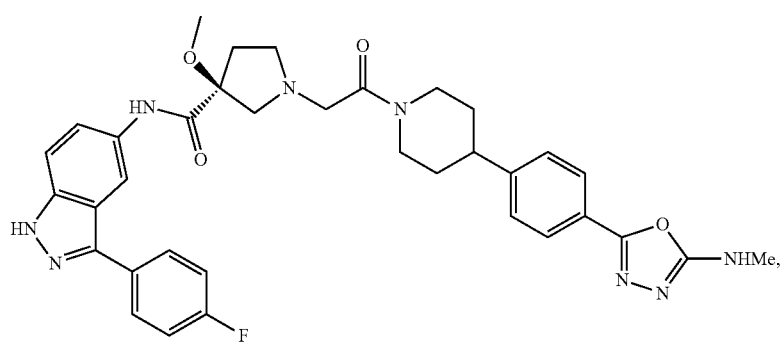
(Ex. 626)
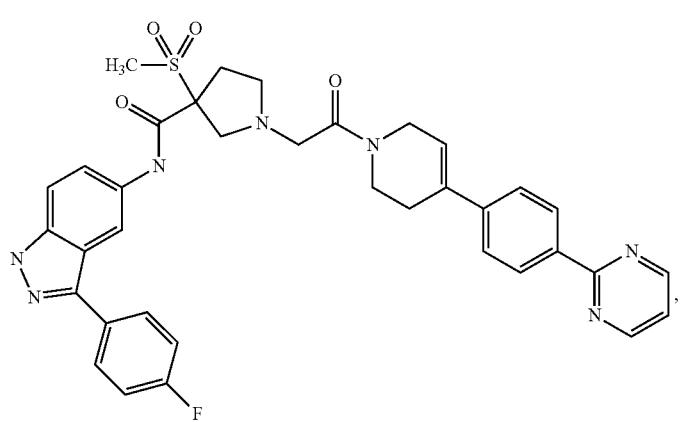

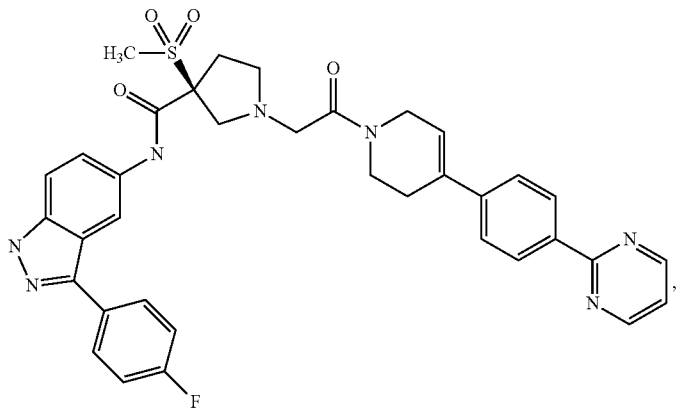
(Ex. 627)

(Ex. 629)

(Ex. 631)
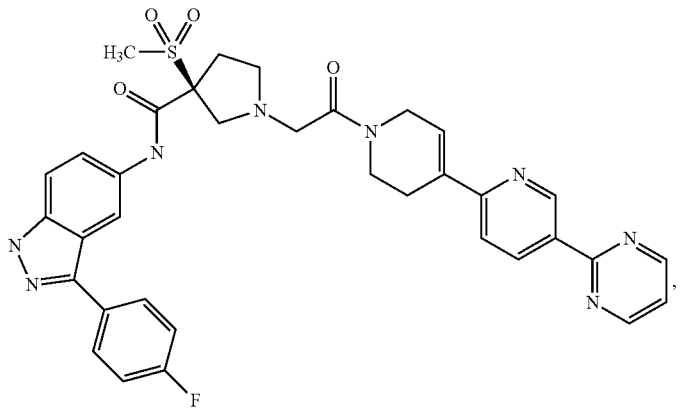
(Ex. 632)

-continued
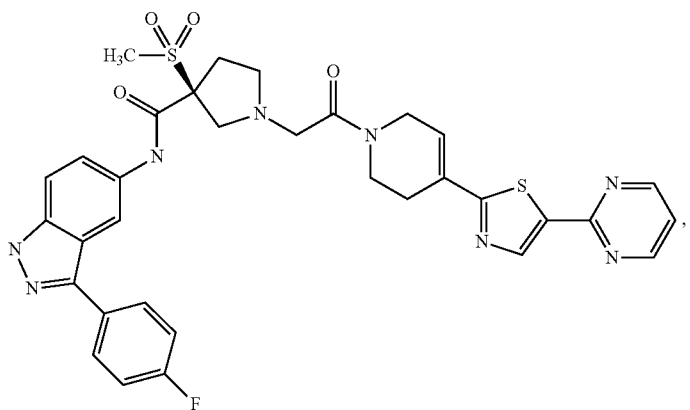
(Ex. 633)
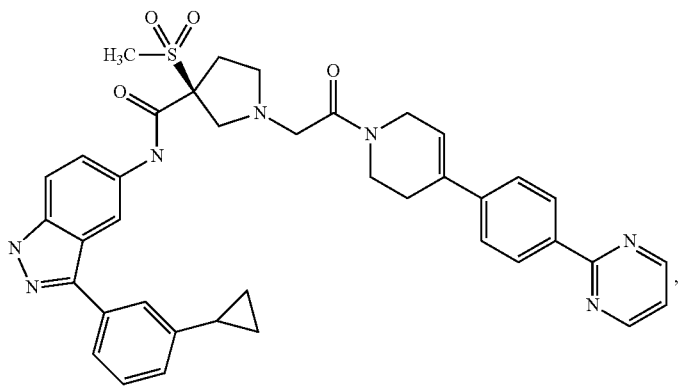
(Ex. 634)
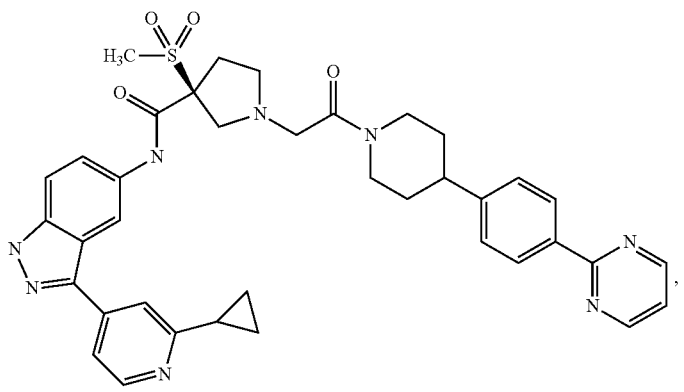
(Ex. 635)
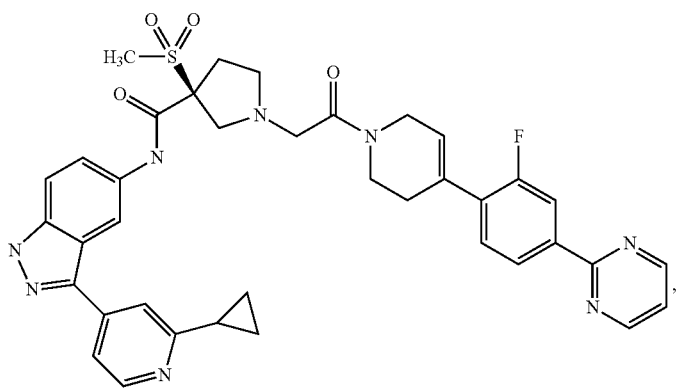
(Ex. 636)

(Ex. 638)
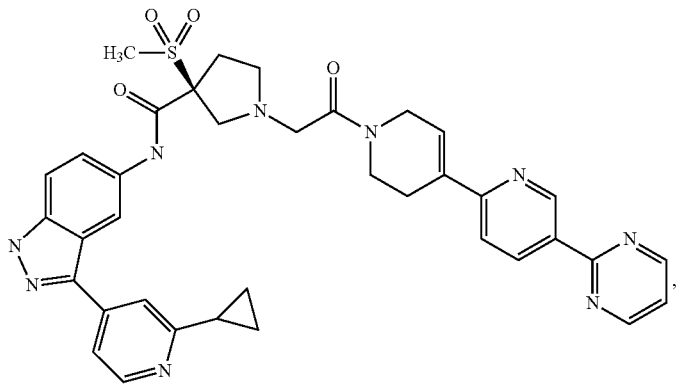
(Ex. 639)
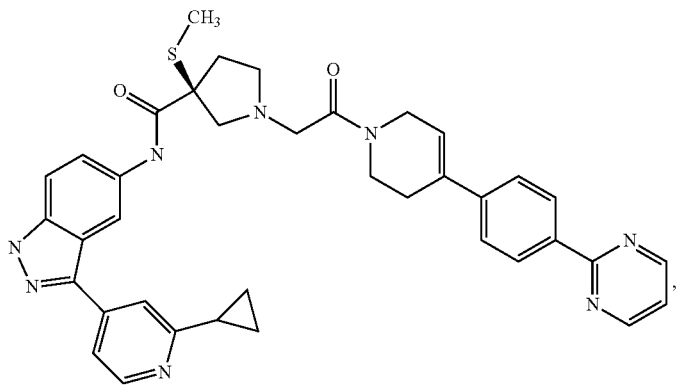
(Ex. 640)
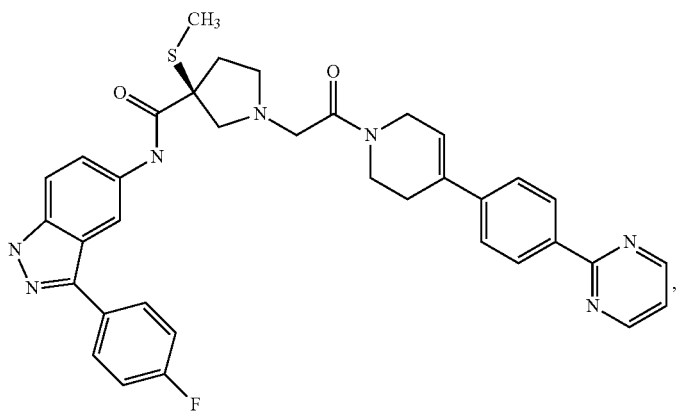
(Ex. 642)
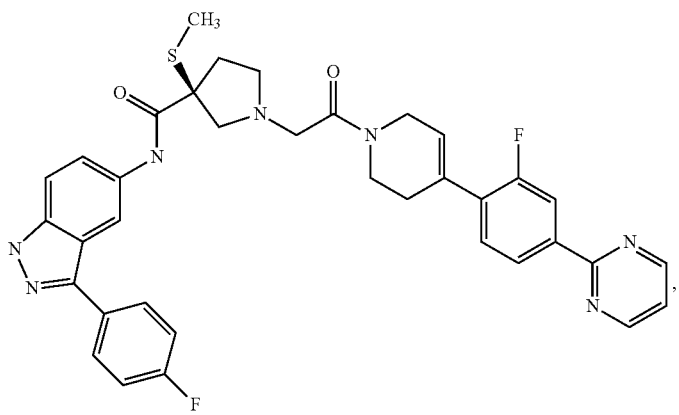

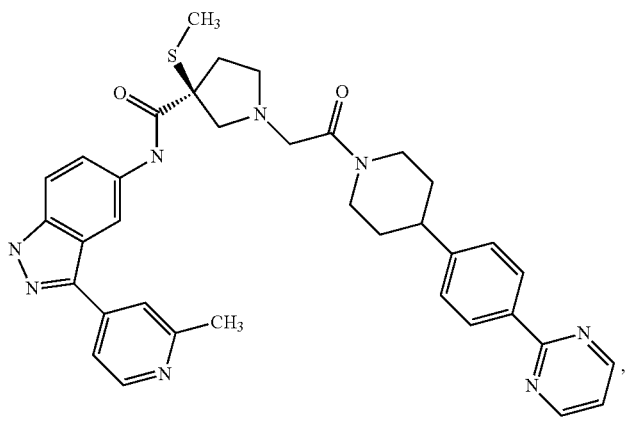
(Ex. 643)

(Ex. 644)
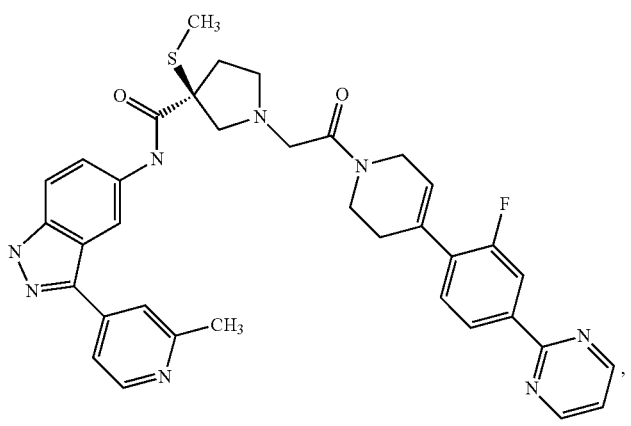
(Ex. 645)

-continued
(Ex. 646)
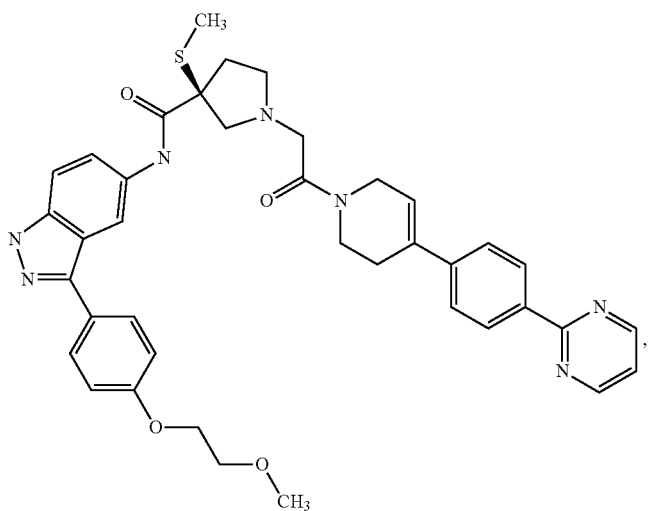
(Ex. 648)
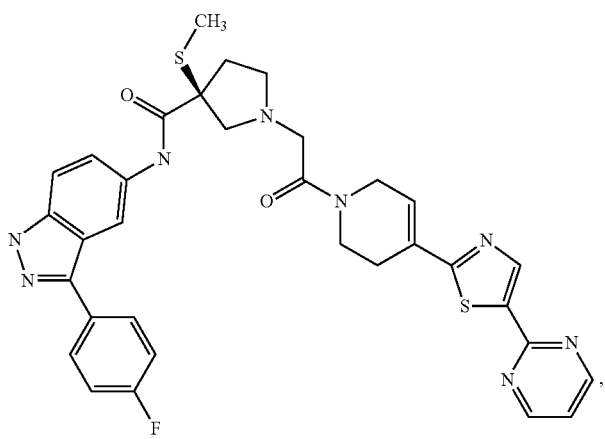
(Ex. 649)
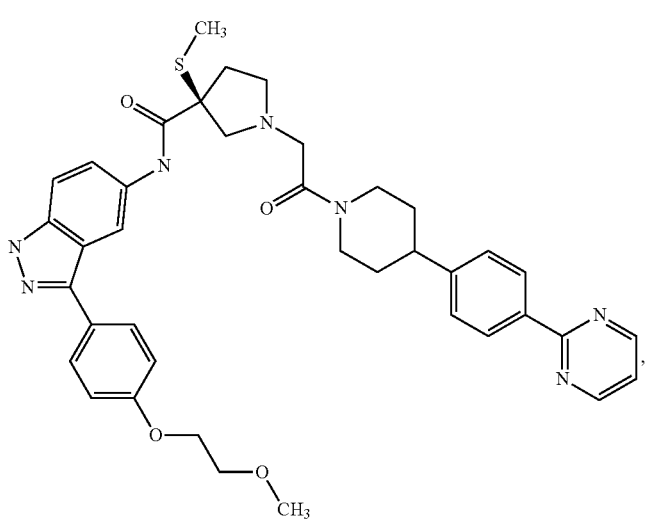

-continued
(Ex. 650)
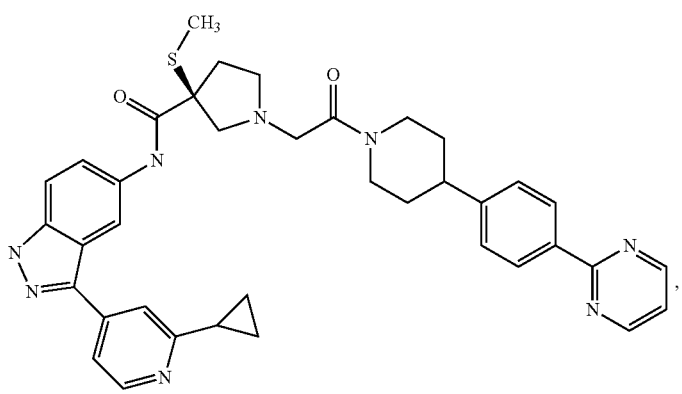
(Ex. 651)
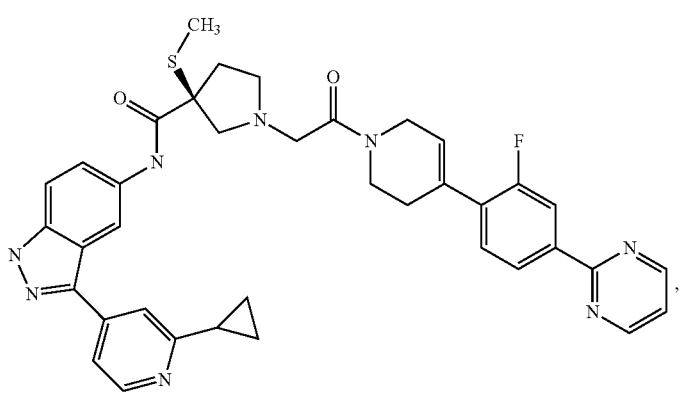
(Ex. 653)
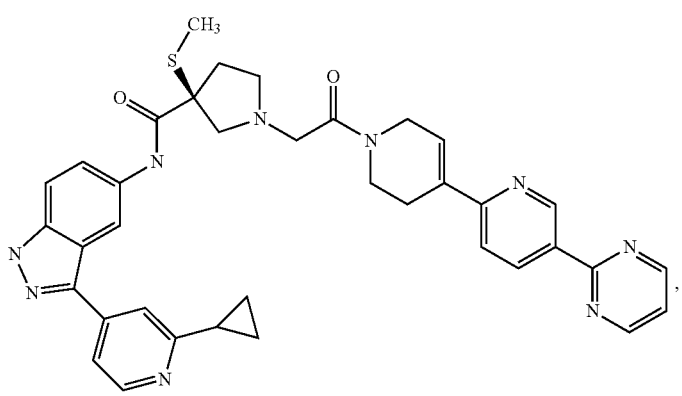
(Ex. 655)
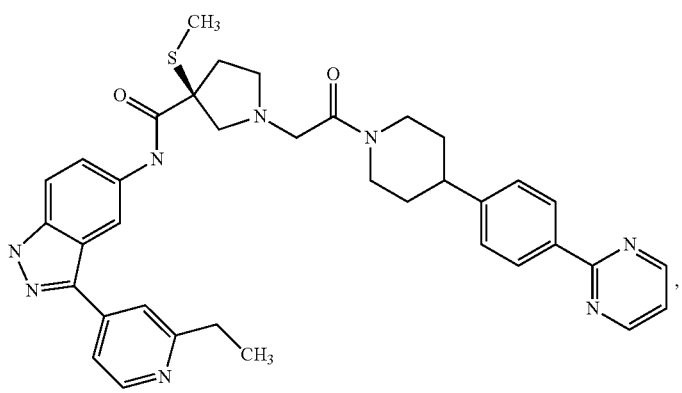

-continued
(Ex. 656)
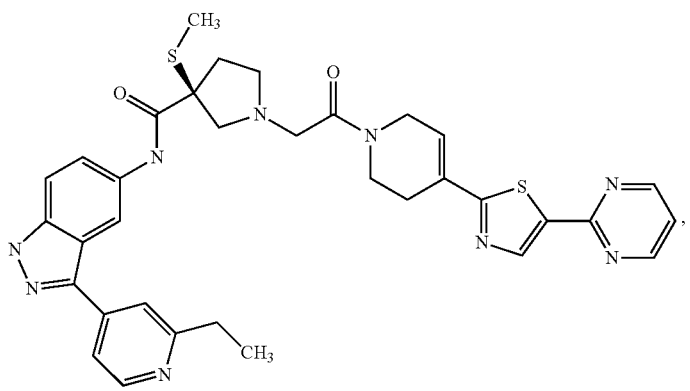
(Ex. 657)
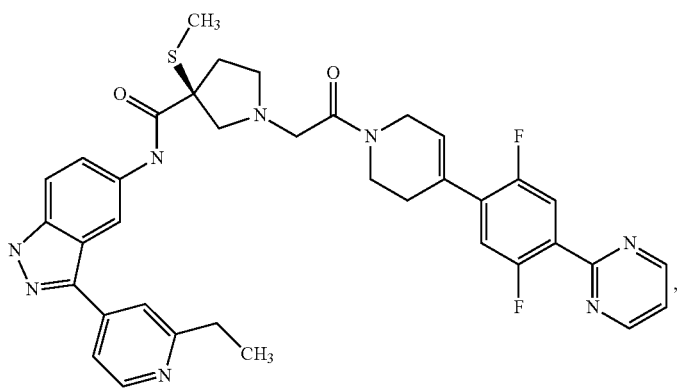
(Ex. 658)
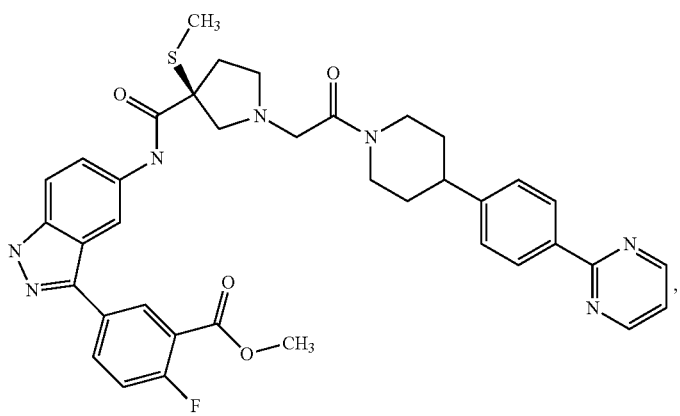
(Ex. 659)
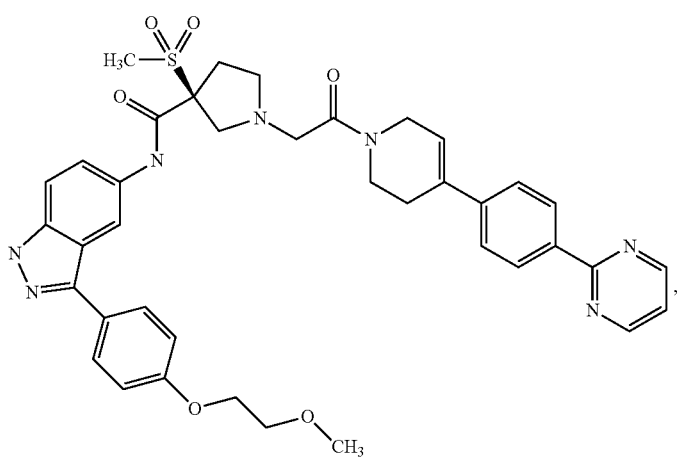

(Ex. 660)
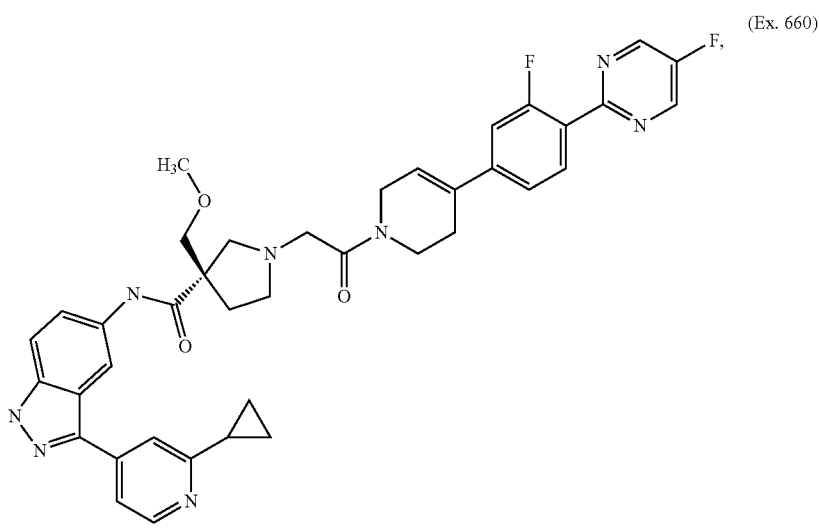
(Ex. 661)
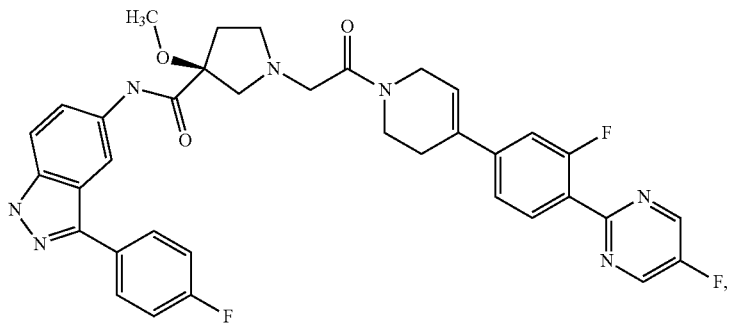
(Ex. 665)
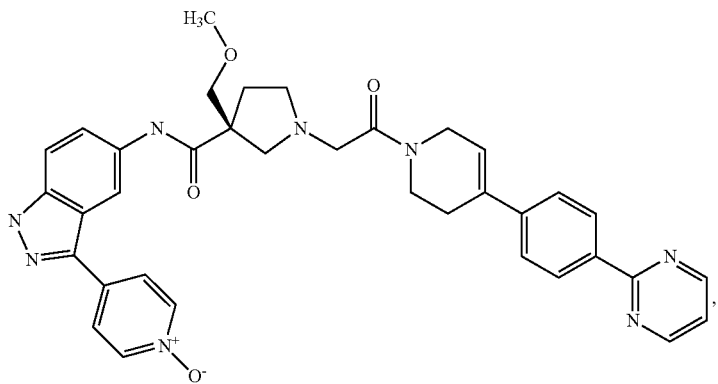
(Ex. 666)
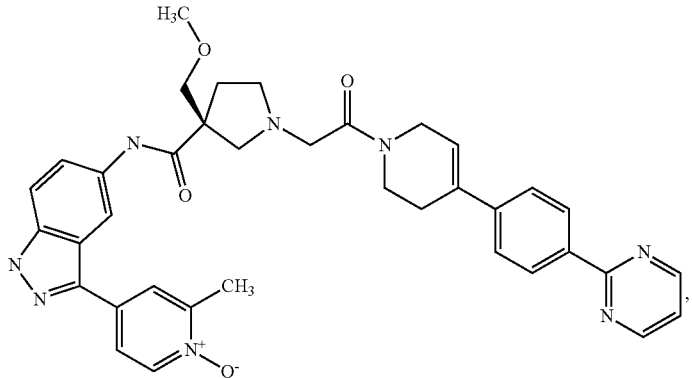

(Ex. 668)
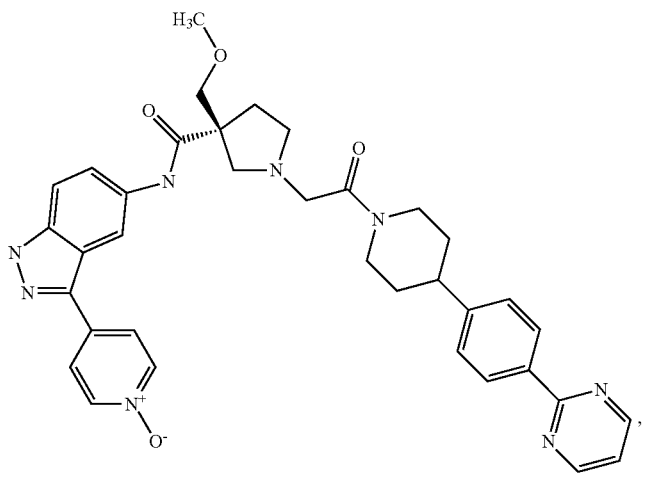
(Ex. 669)
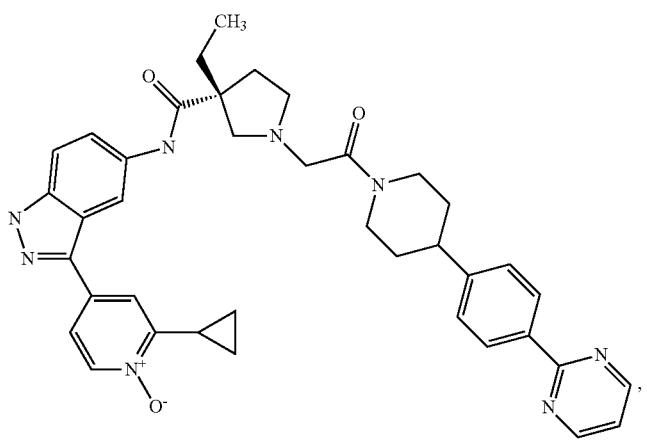
(Ex. 670)
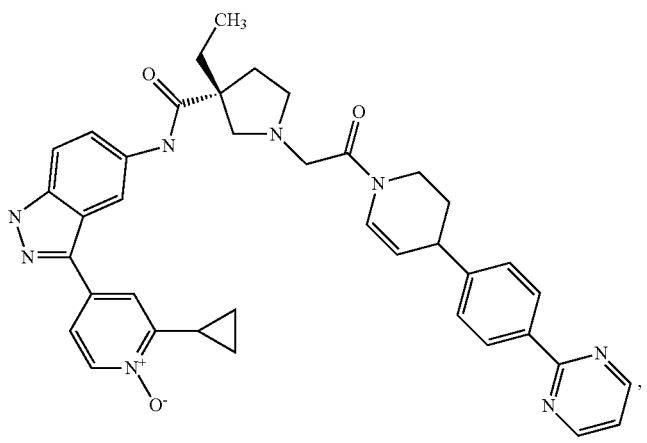

-continued
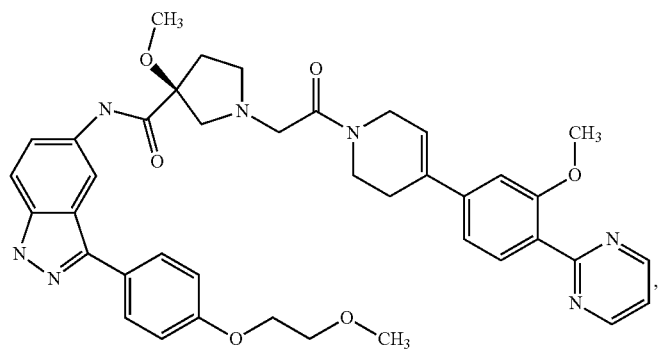
(Ex. 671)
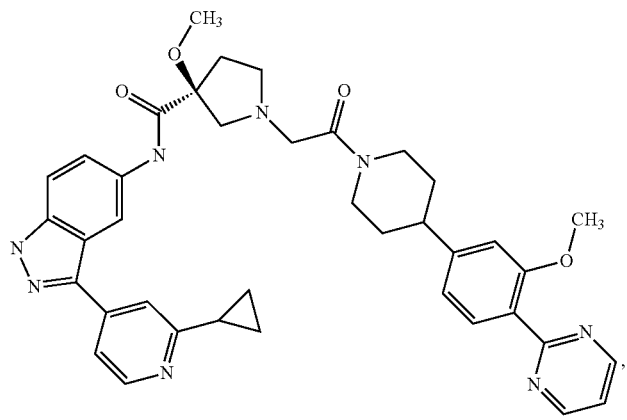
(Ex. 672)
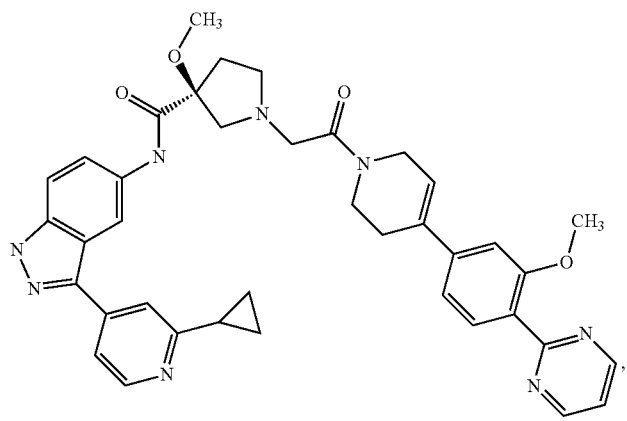
(Ex. 673)
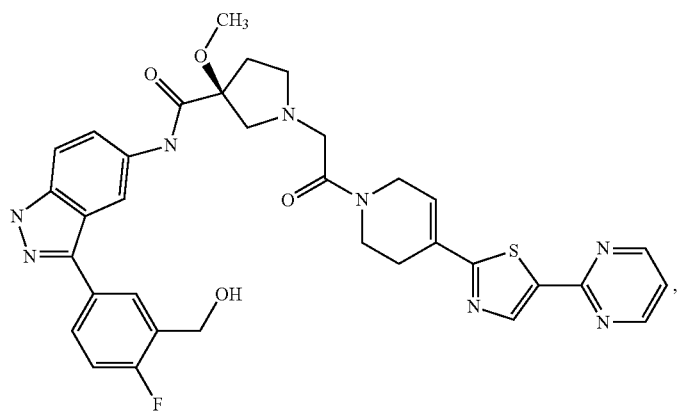
(Ex. 674)

(Ex. 675)
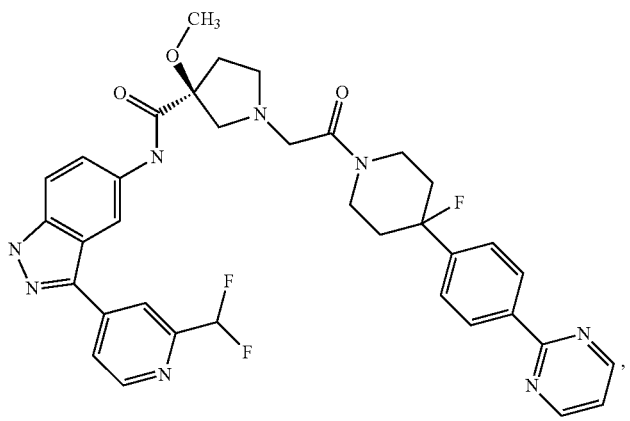
(Ex. 676)
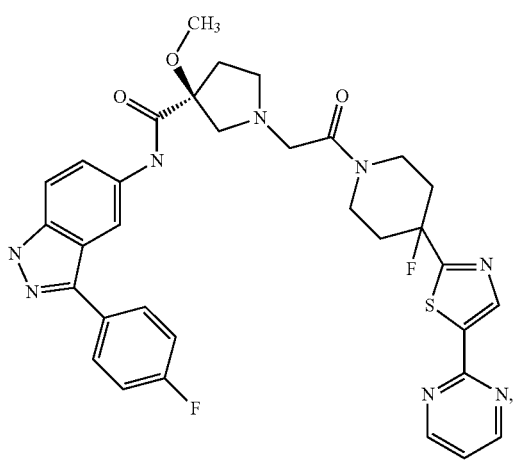
(Ex. 677)
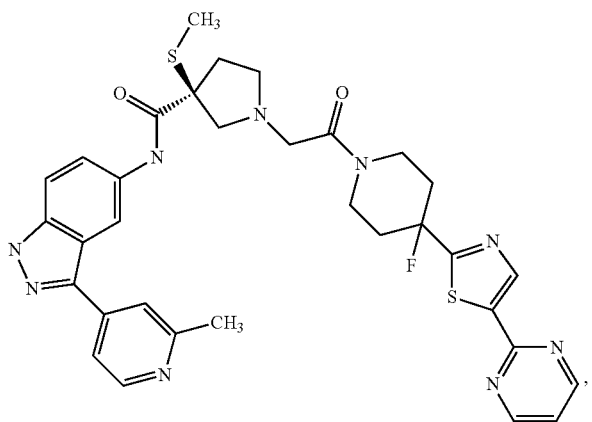

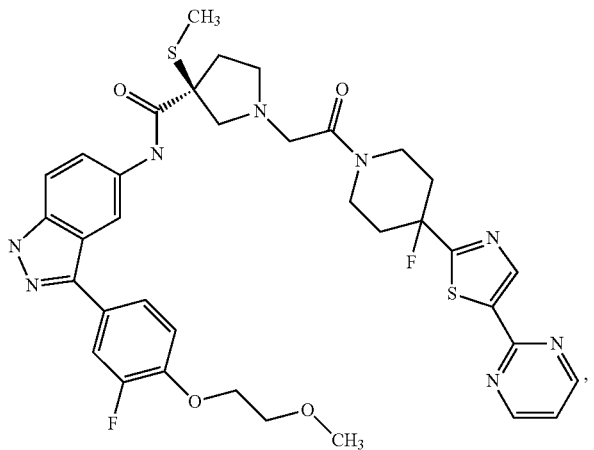
(Ex. 678)
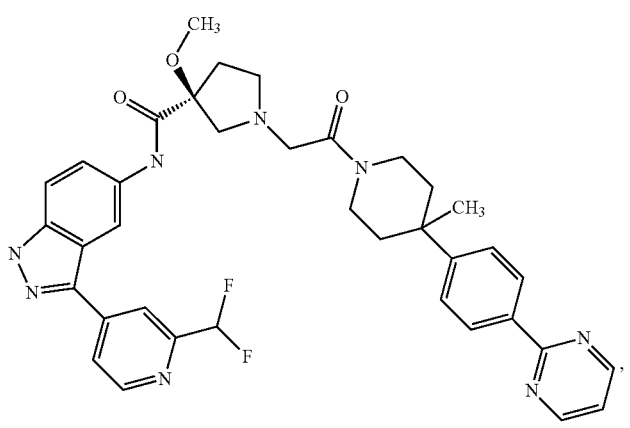
(Ex. 679)
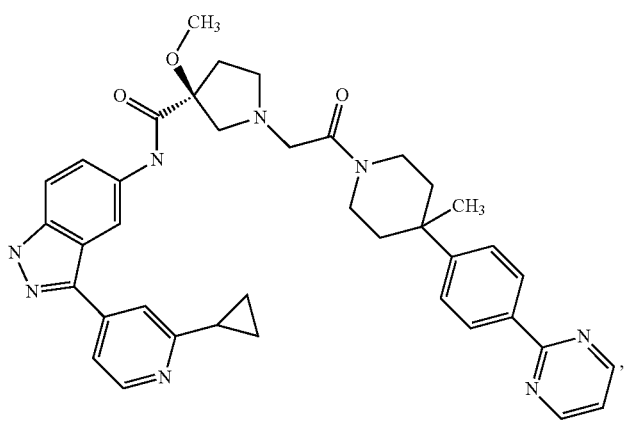
(Ex. 680)

(Ex. 681)
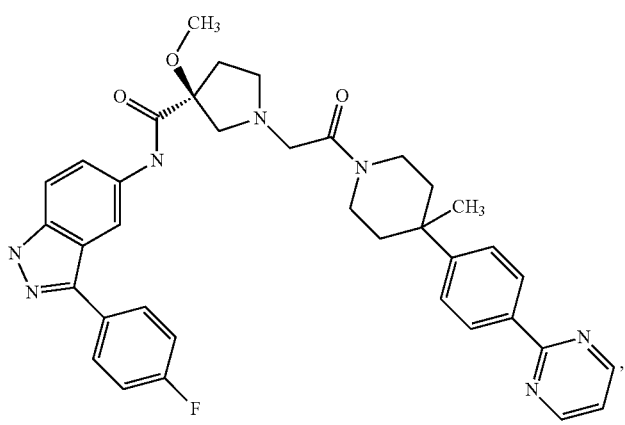
(Ex. 682)
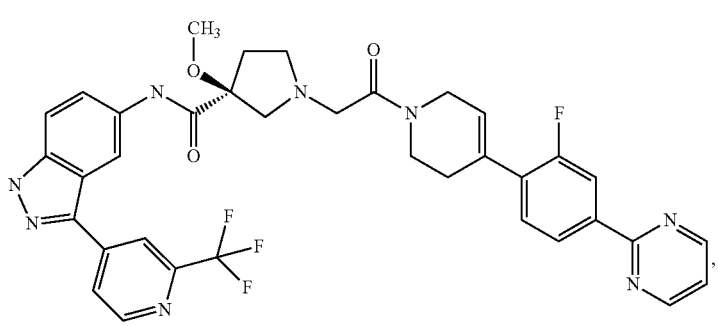
(Ex. 683)
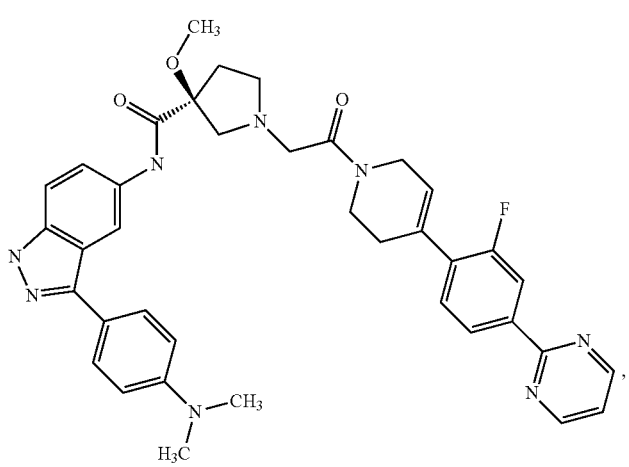
(Ex. 684)
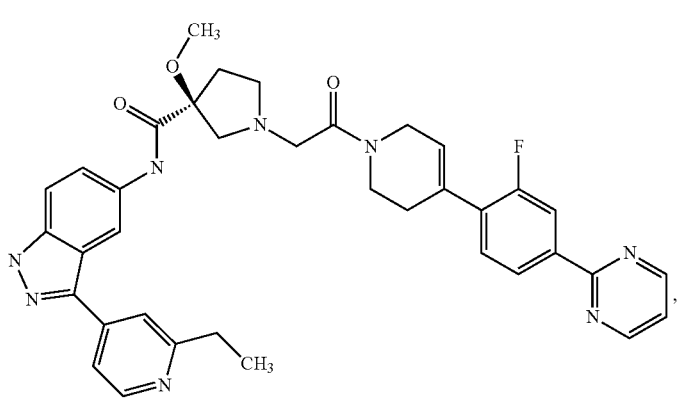

(Ex. 685)
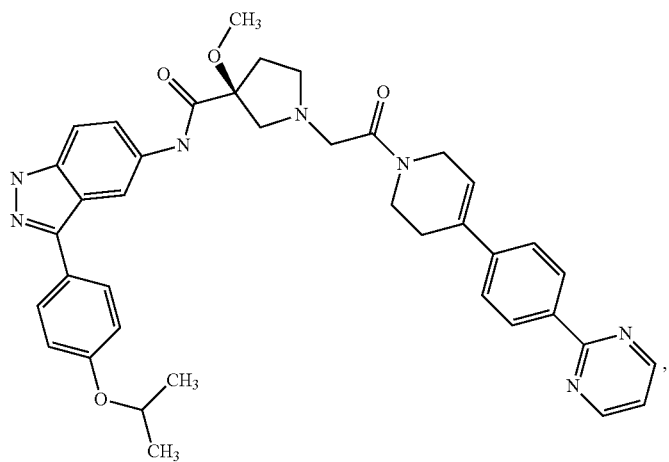
(Ex. 686)
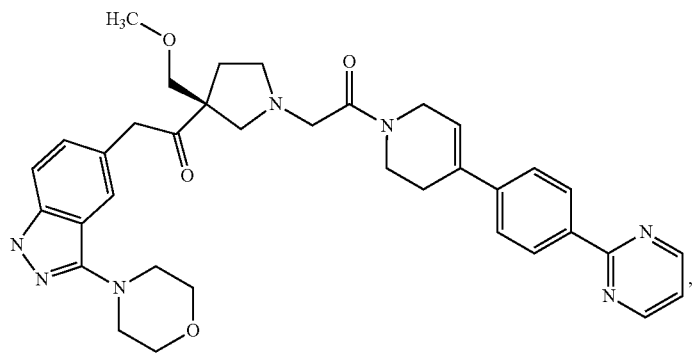
(Ex. 687)
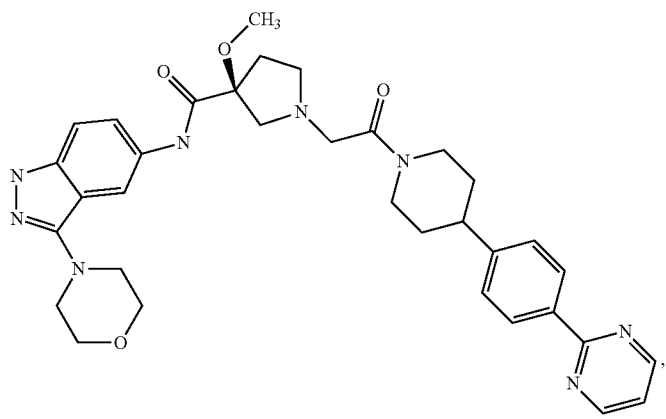
(Ex. 688)
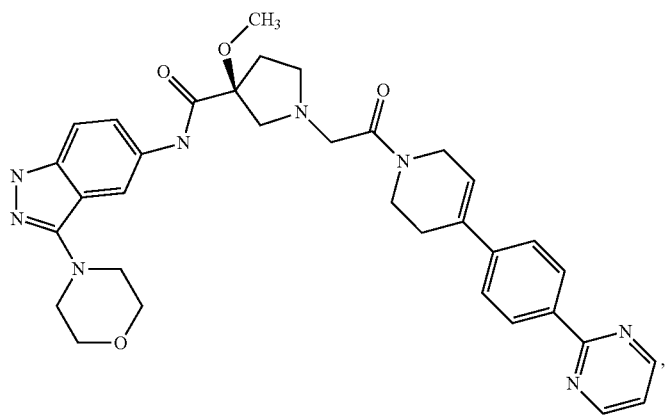

(Ex. 689)
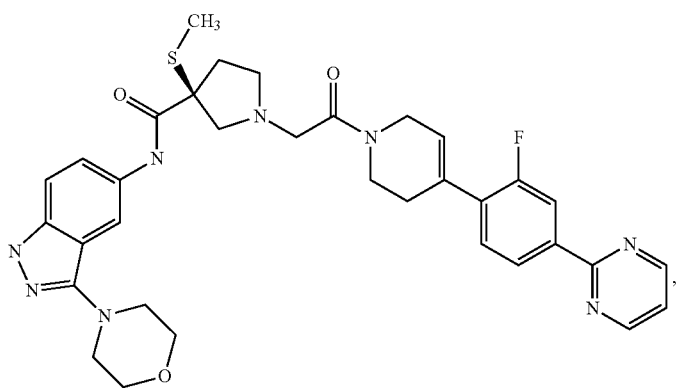
(Ex. 690)
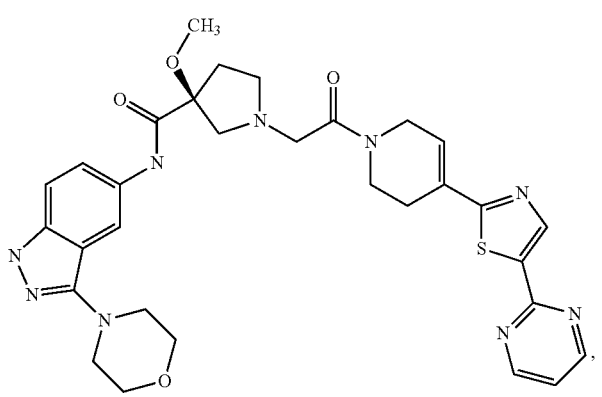
(Ex. 691)
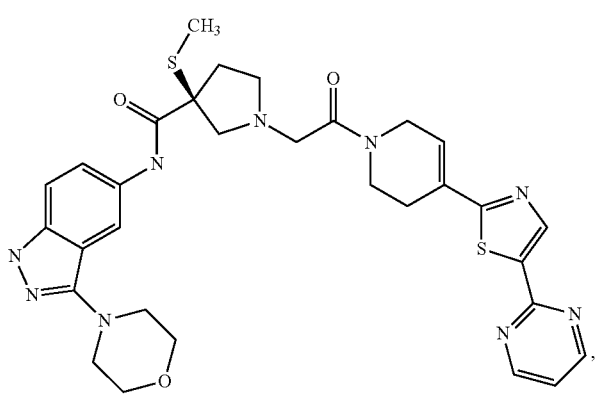
(Ex. 692)
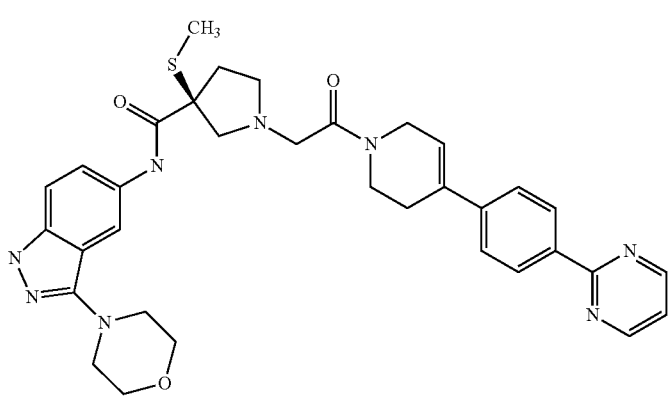

(Ex. 693)
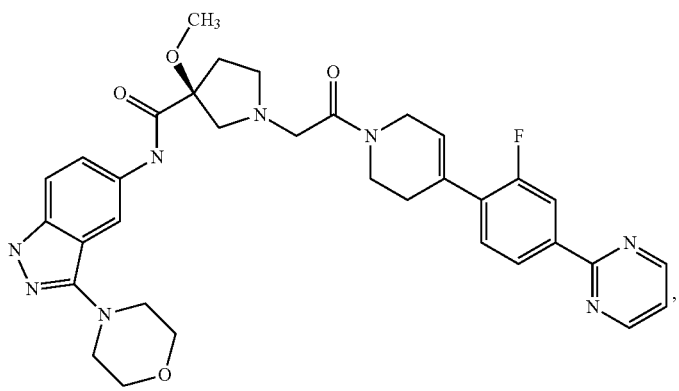
(Ex. 694)
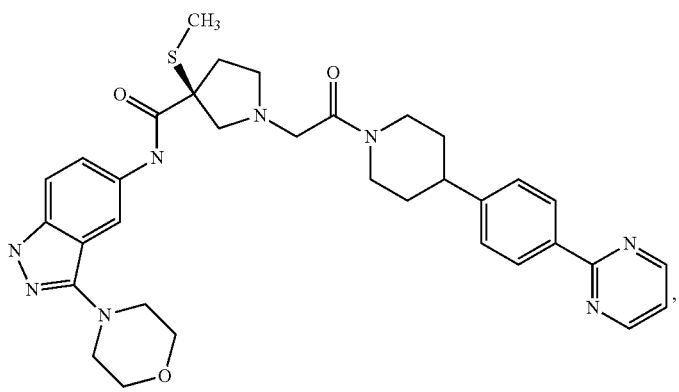
(Ex. 698)
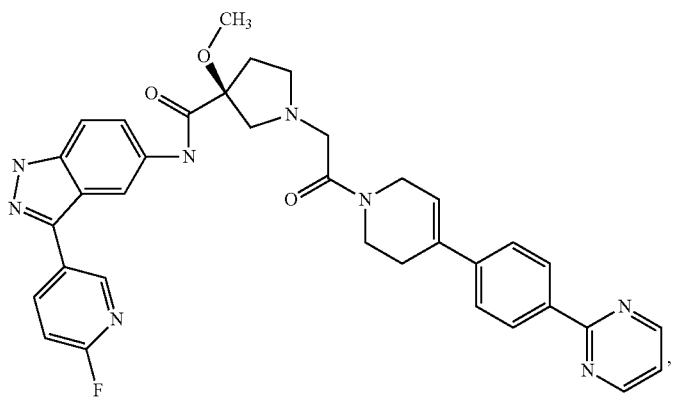
(Ex. 699)
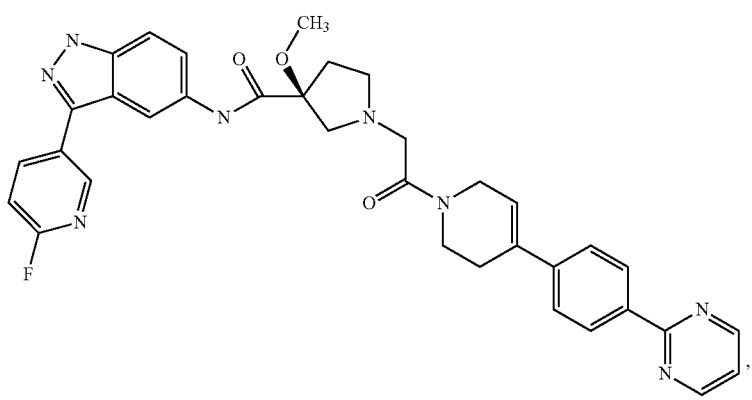

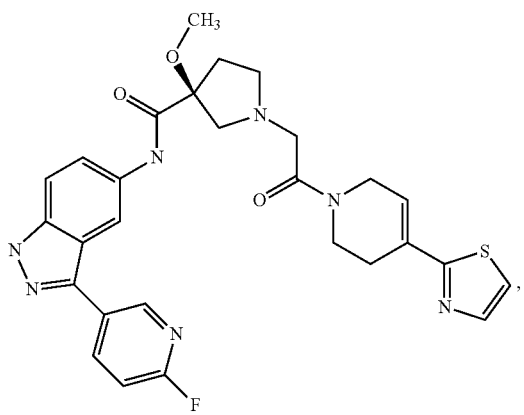
(Ex. 702)
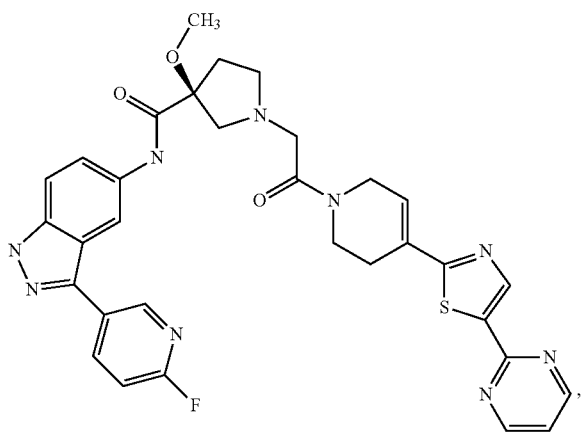
(Ex. 703)
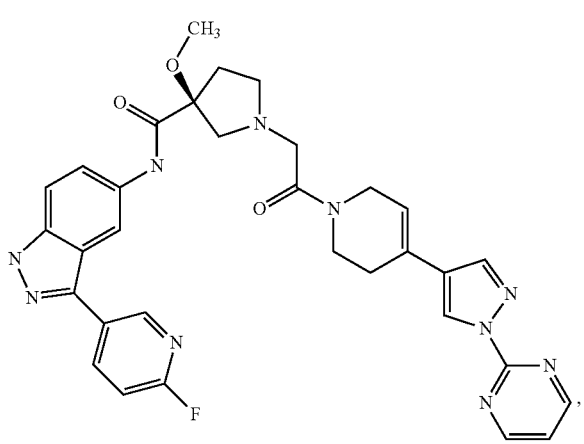
(Ex. 704)

(Ex. 707)
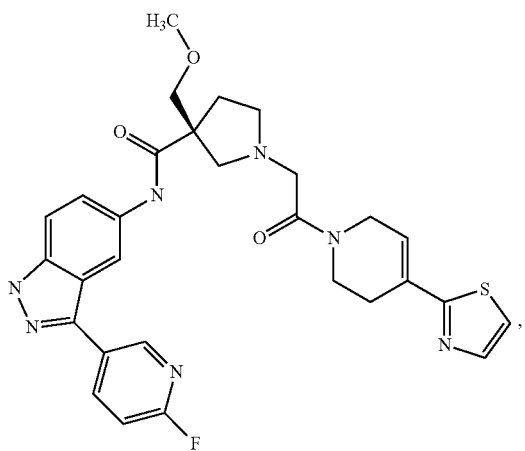
(Ex. 708)
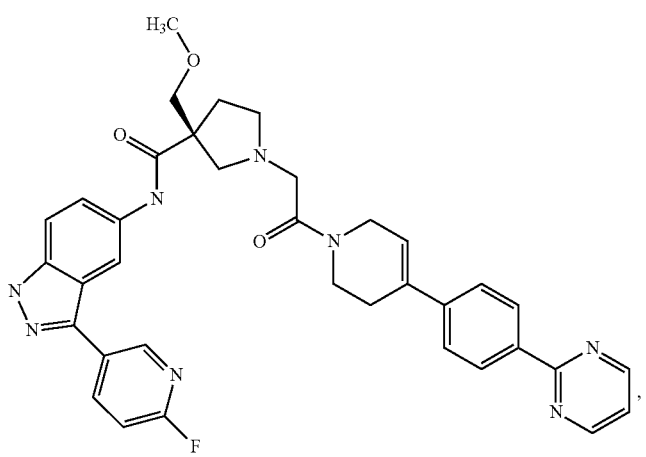
(Ex. 709)
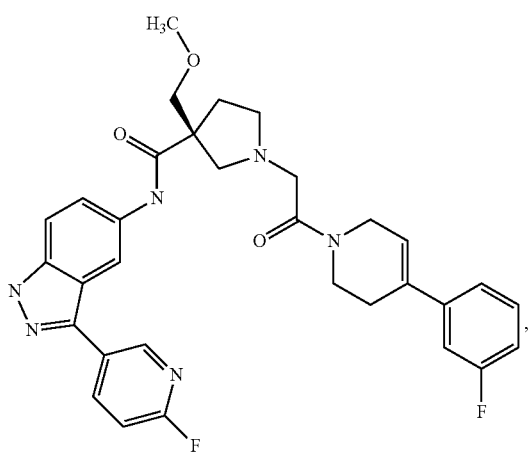

-continued
(Ex. 710)
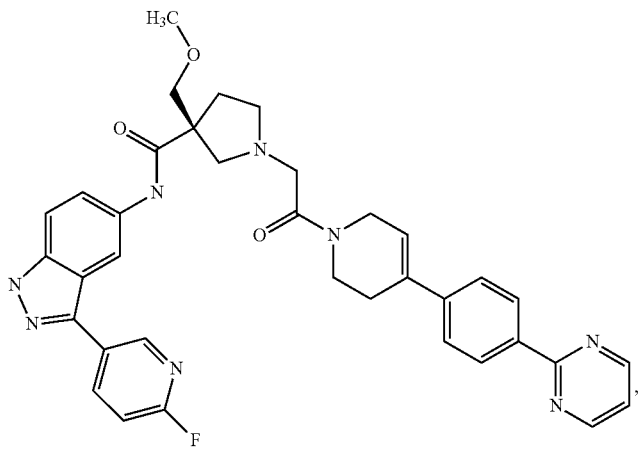
(Ex. 712)
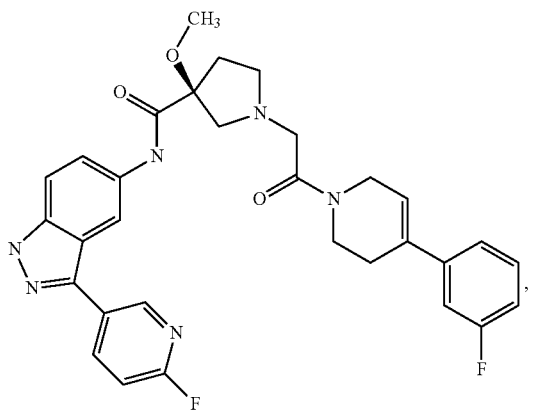
(Ex. 713)
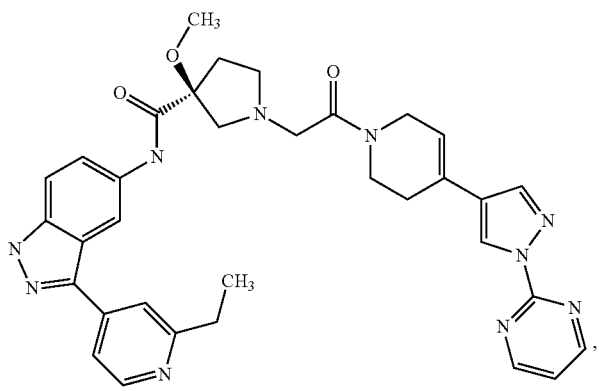
(Ex. 714)
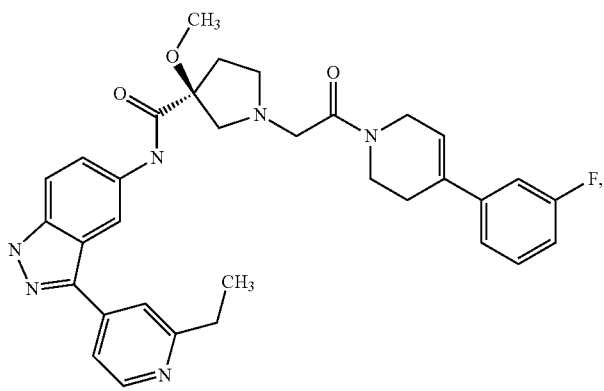

(Ex. 715)
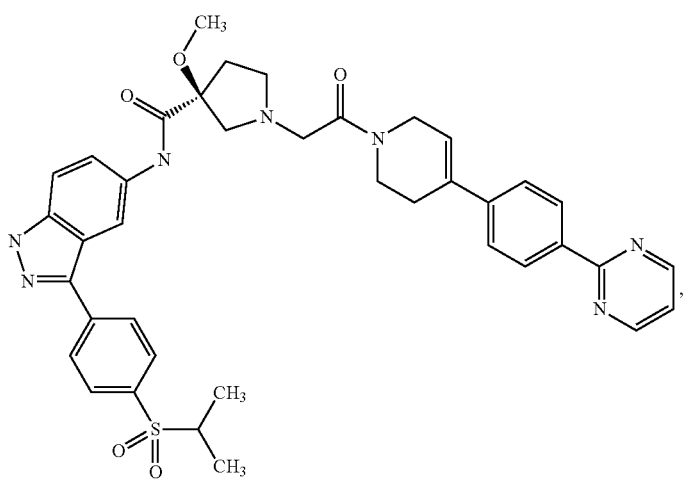
(Ex. 716)
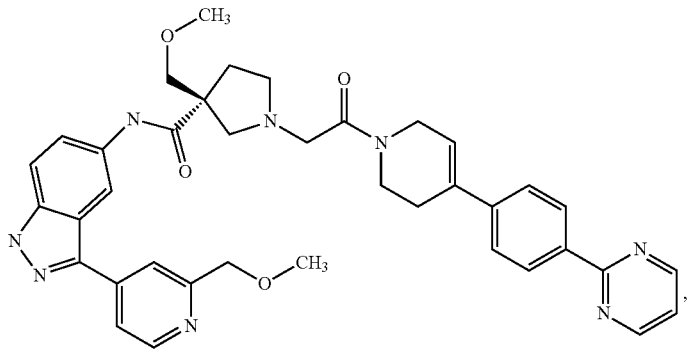
(Ex. 717)
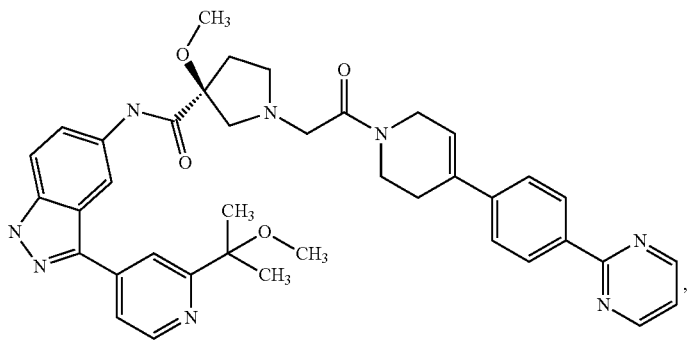
(Ex. 718)
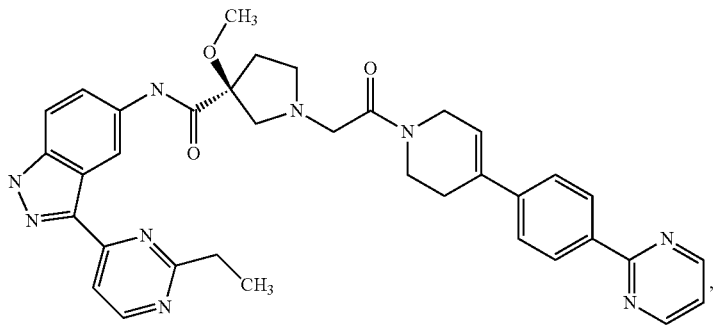

(Ex. 719)
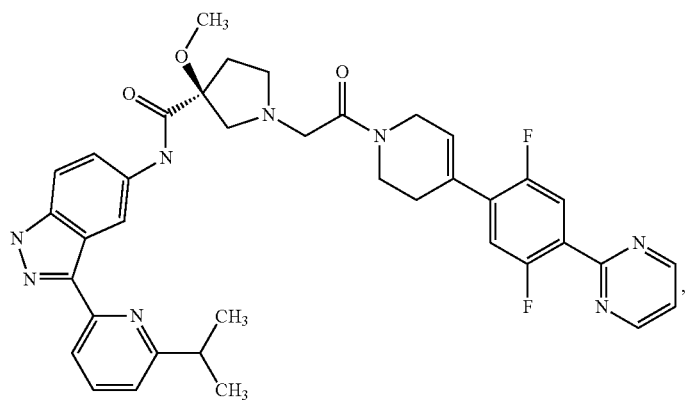
(Ex. 720)
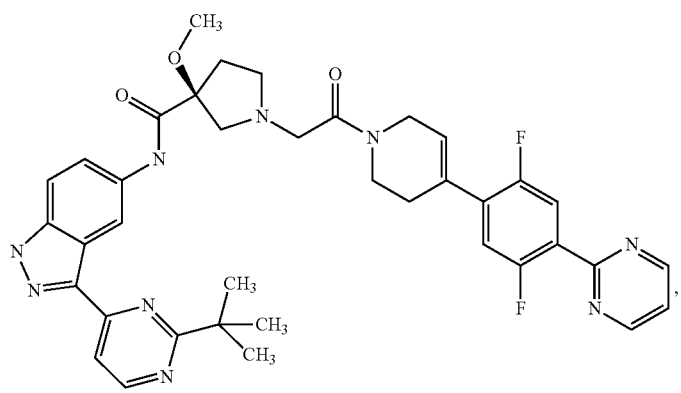
(Ex. 721)
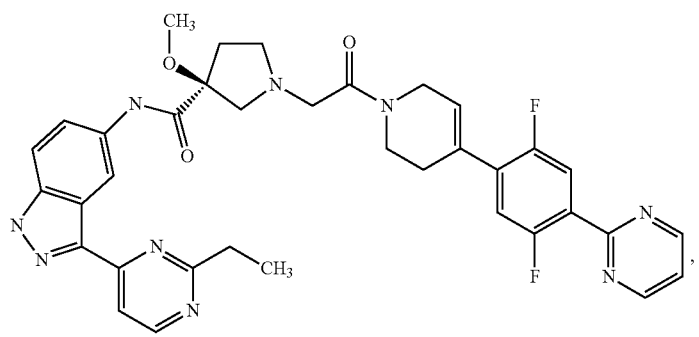
(Ex. 722)
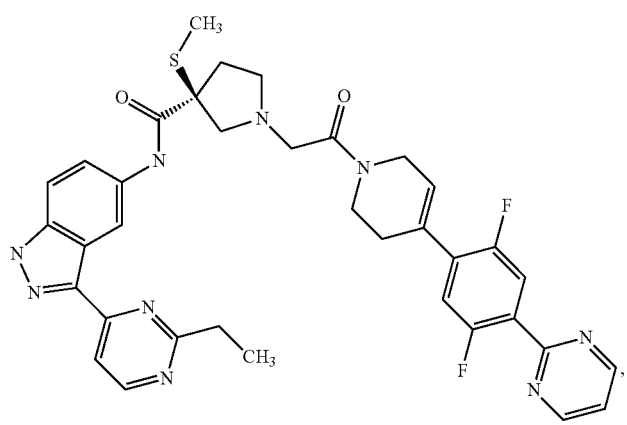

(Ex. 723)
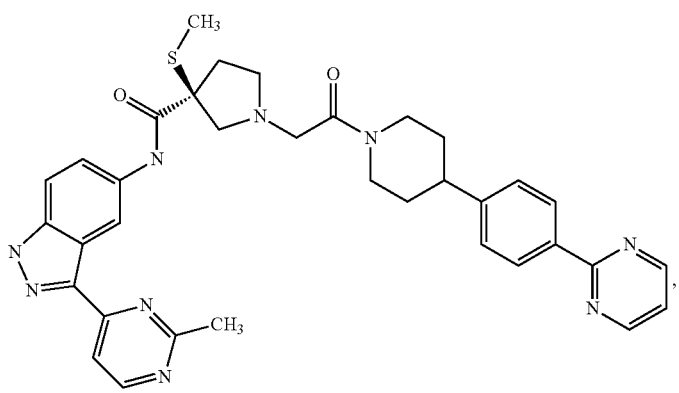
(Ex. 724)
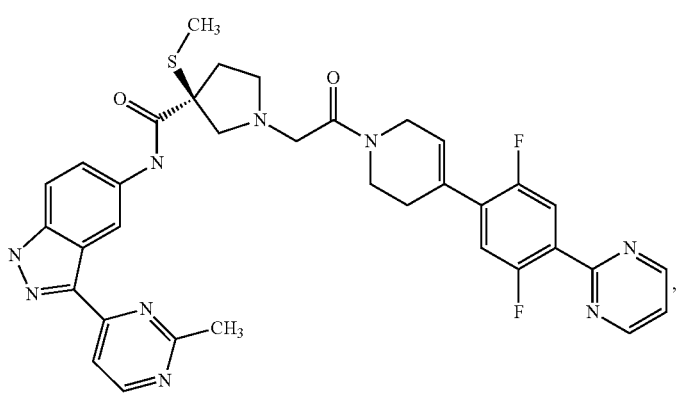
(Ex. 725)
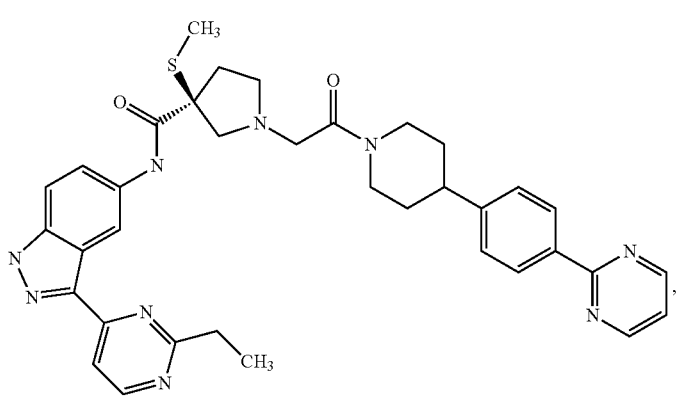
(Ex. 726)
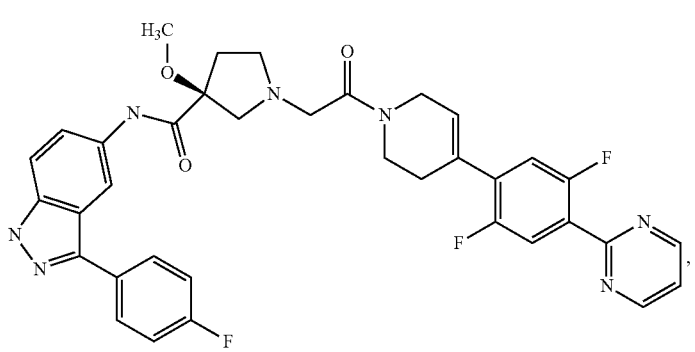

(Ex. 727)
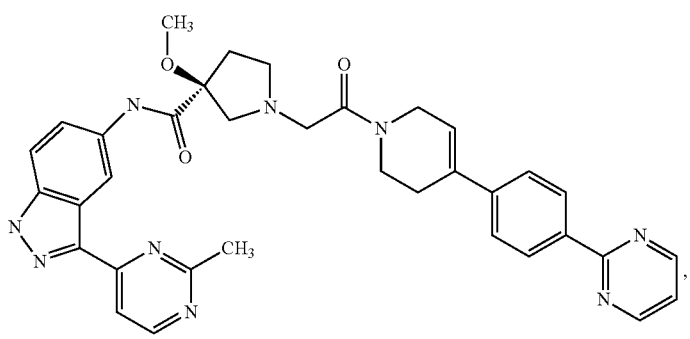
(Ex. 728)
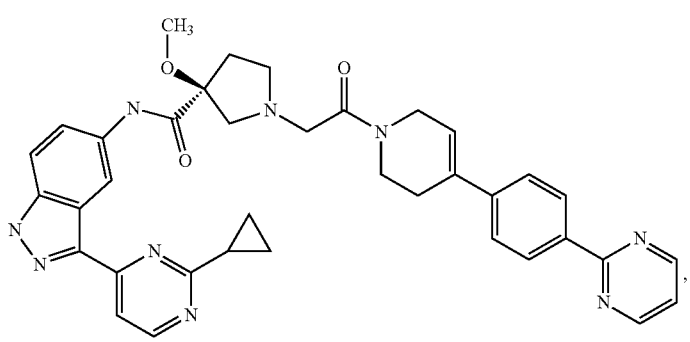
(Ex. 729)
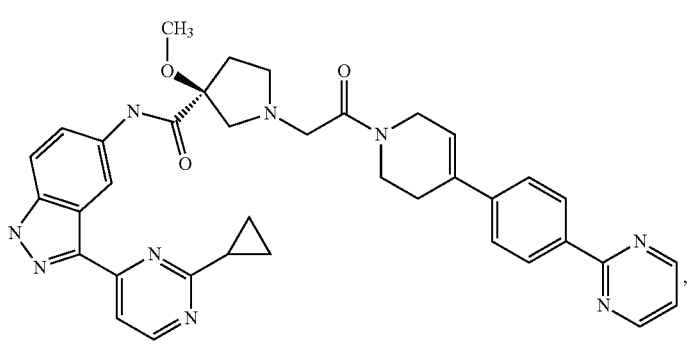
(Ex. 730)
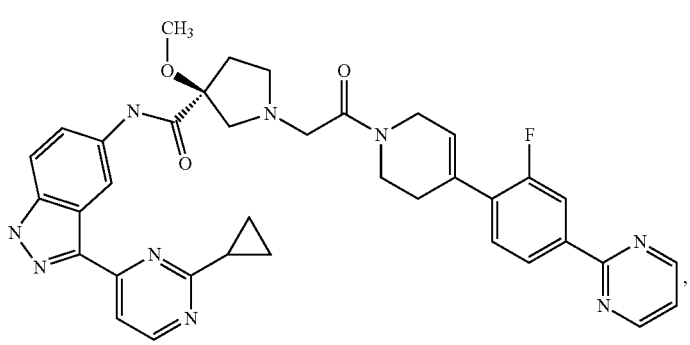

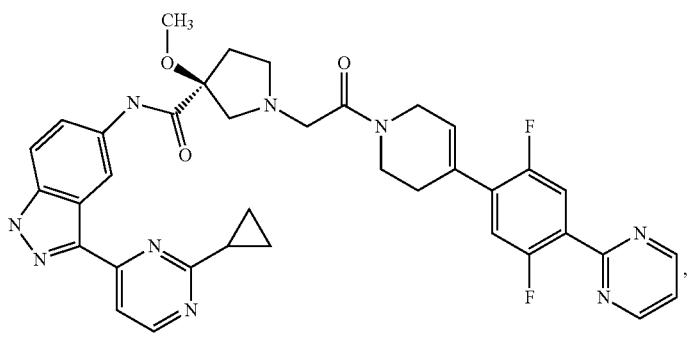
(Ex. 731)
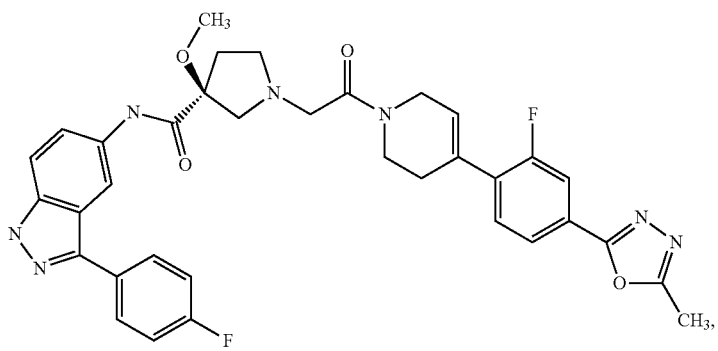
(Ex. 732)
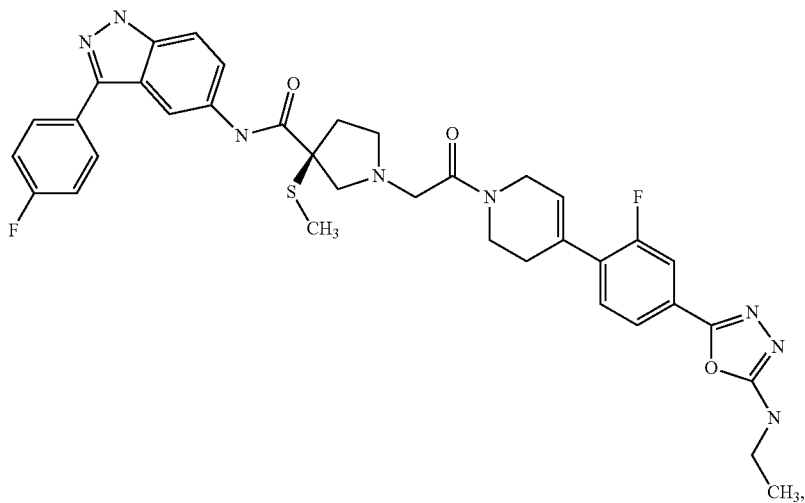
(Ex. 733)
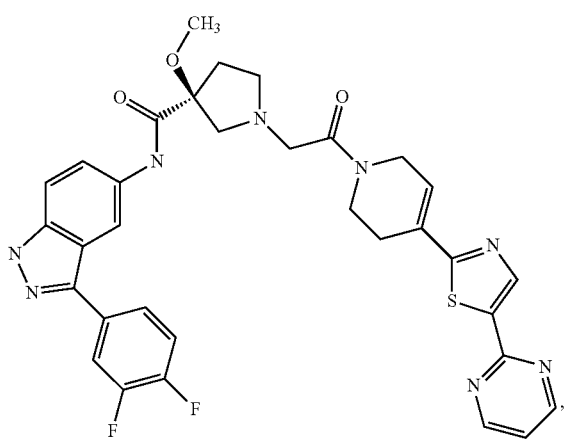
(Ex. 734)

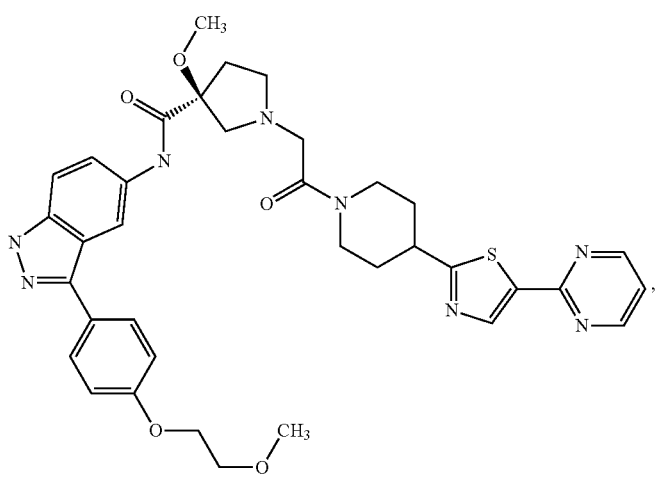
(Ex. 735)
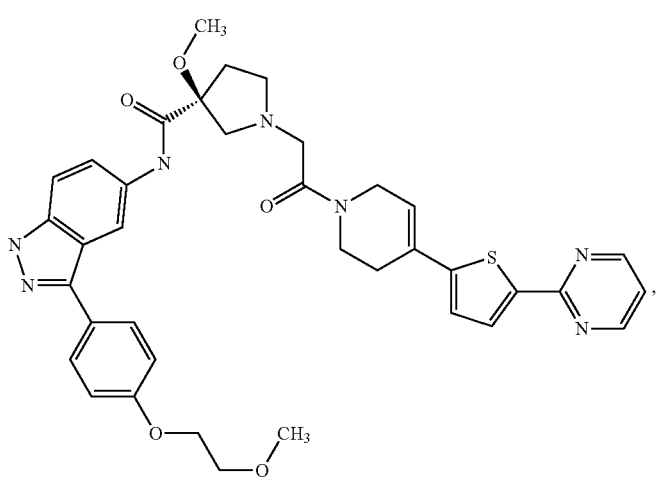
(Ex. 736)
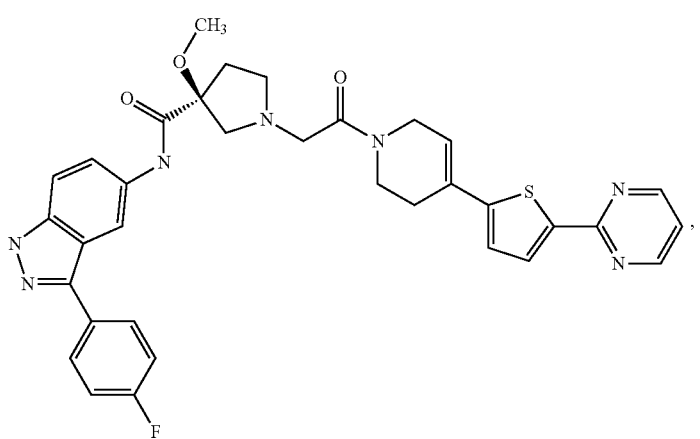
(Ex. 737)

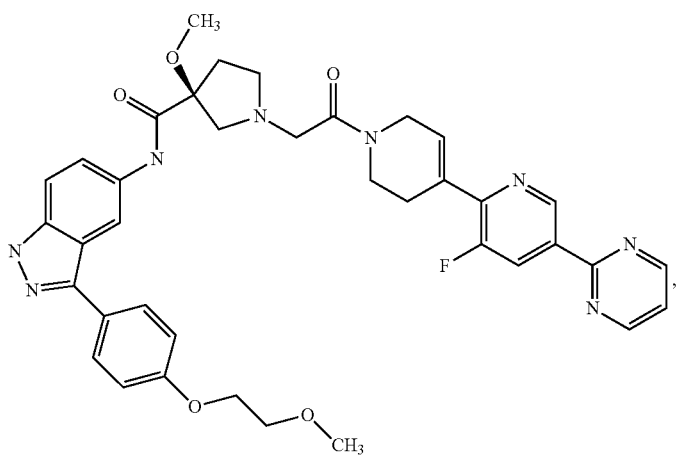
(Ex. 738)
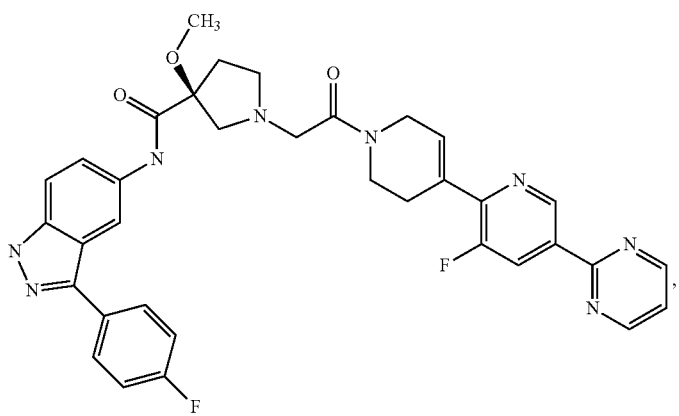
(Ex. 739)
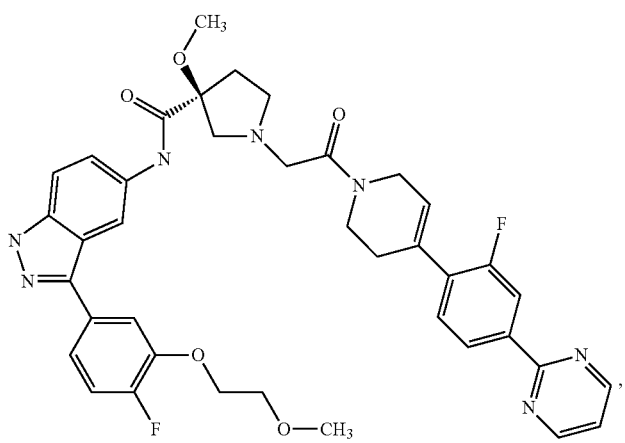
(Ex. 740)

(Ex. 741)
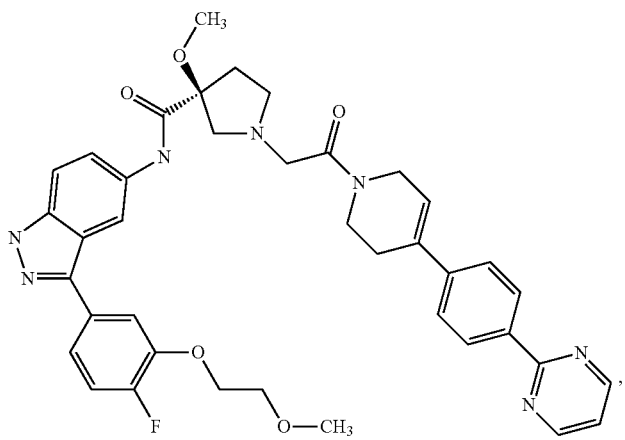
(Ex. 742)
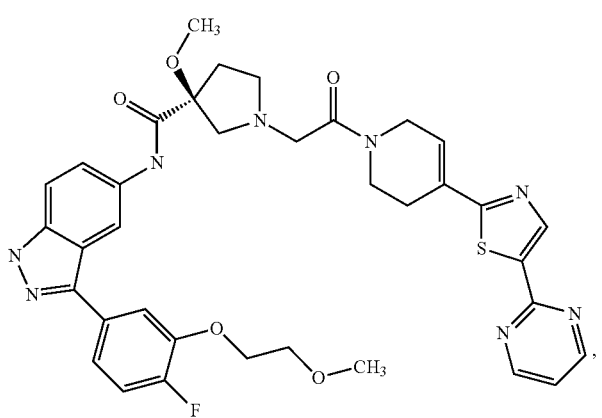
(Ex. 743)
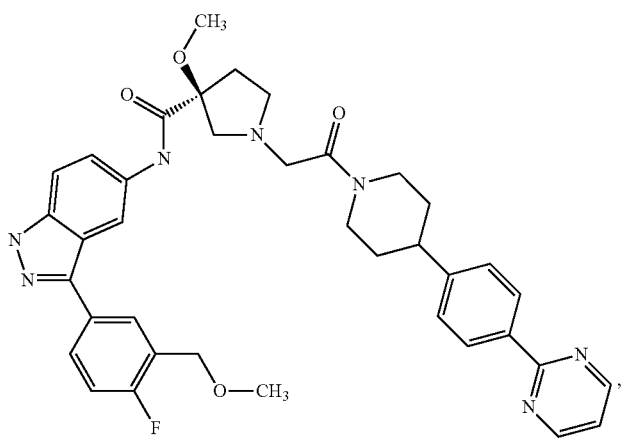

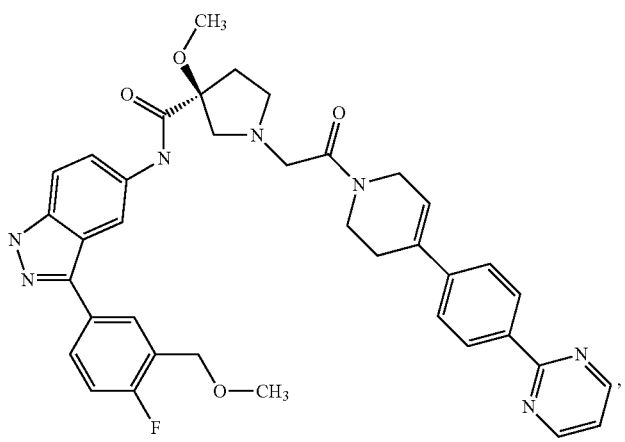
(Ex. 744)
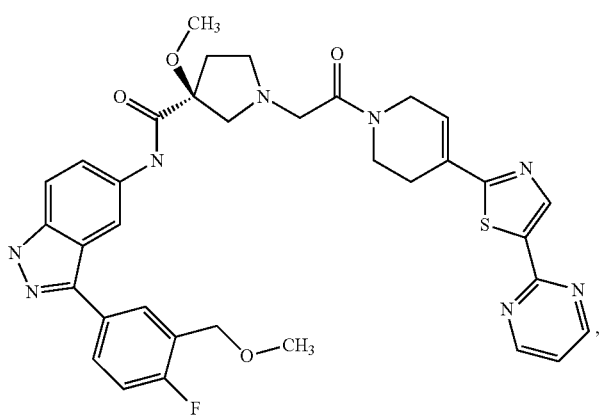
(Ex. 745)
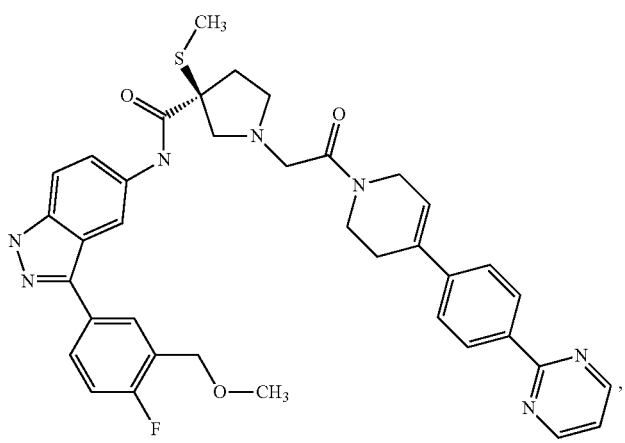
(Ex. 746)

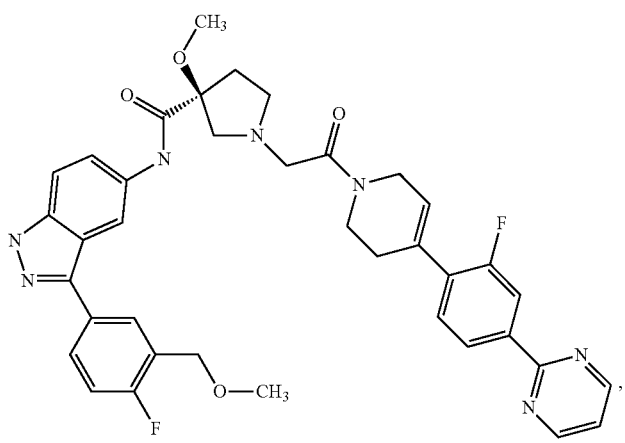
(Ex. 747)
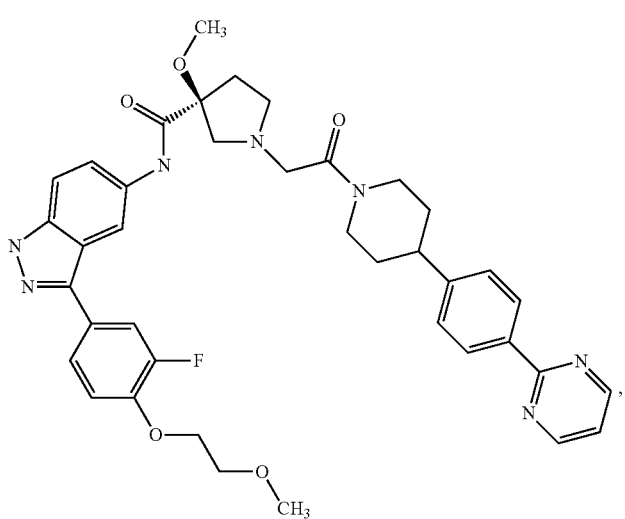
(Ex. 748)
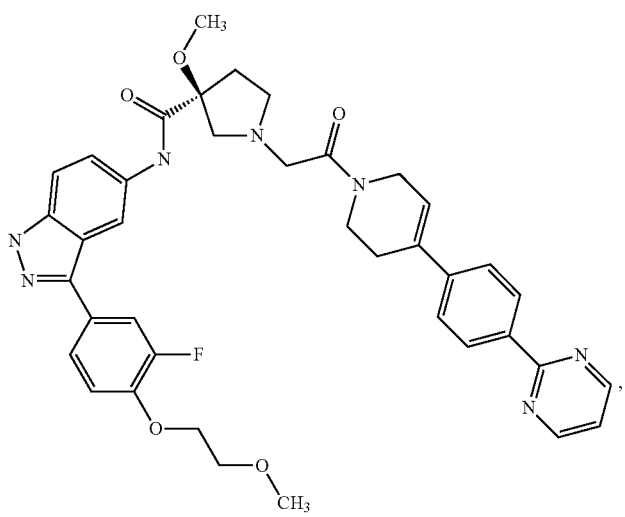
(Ex. 749)

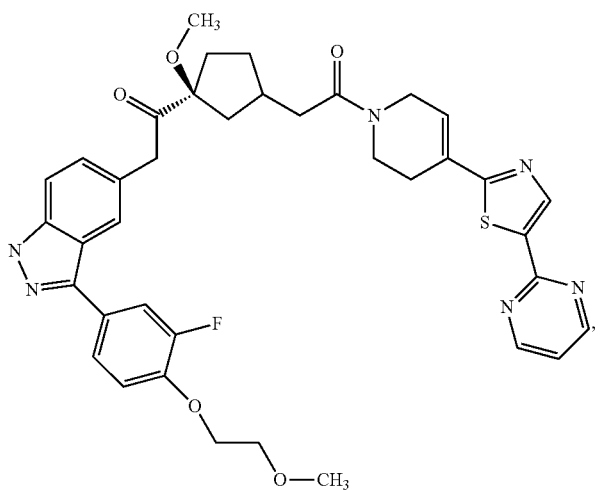
(Ex. 750)
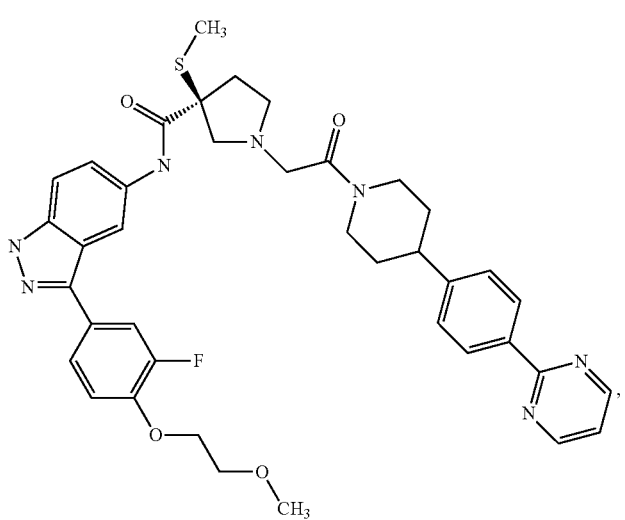
(Ex. 751)
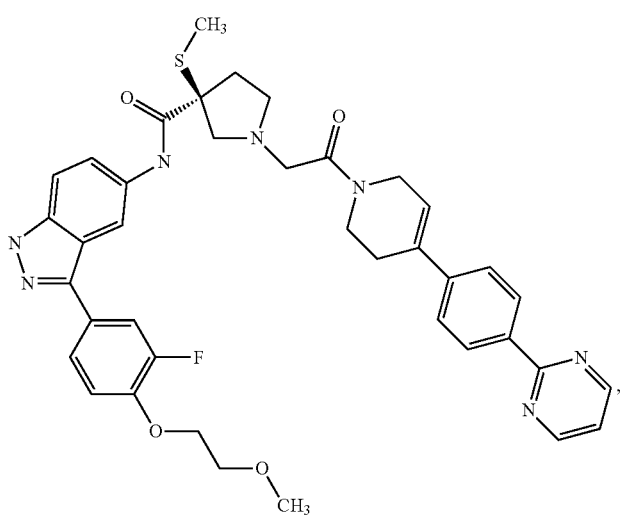
(Ex. 752)

(Ex. 753)
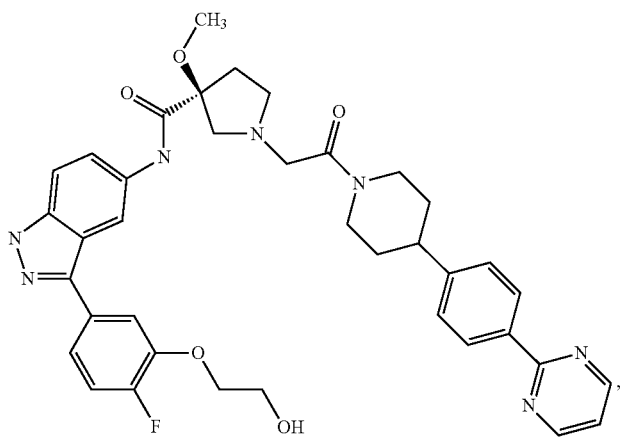
(Ex. 754)
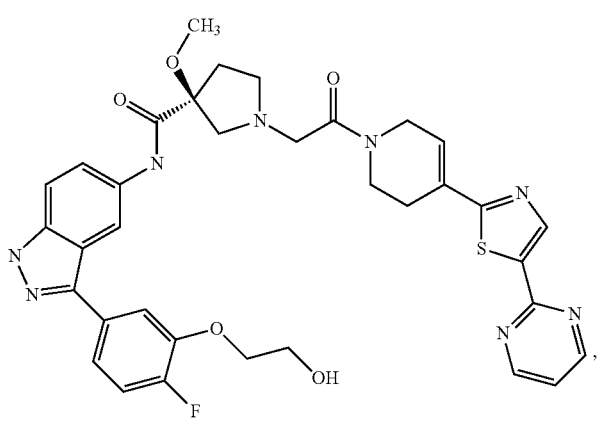
(Ex. 755)
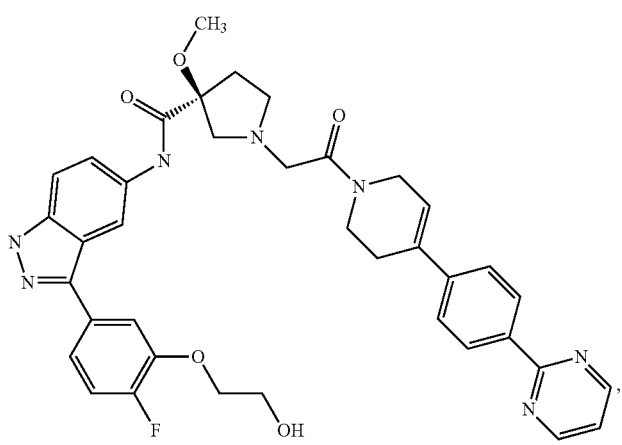

(Ex. 757)
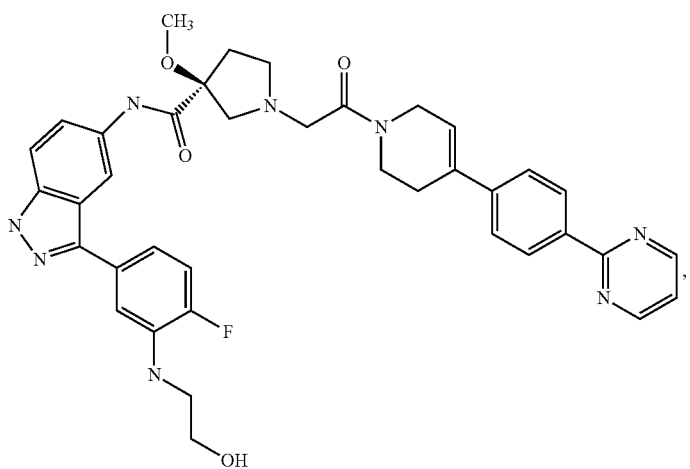
(Ex. 758)
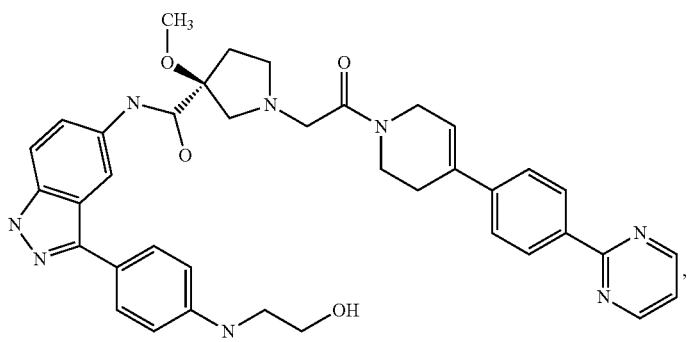
(Ex. 759)
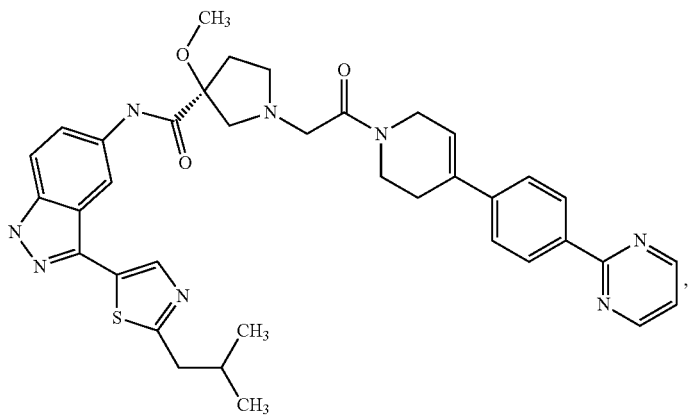
(Ex. 760)
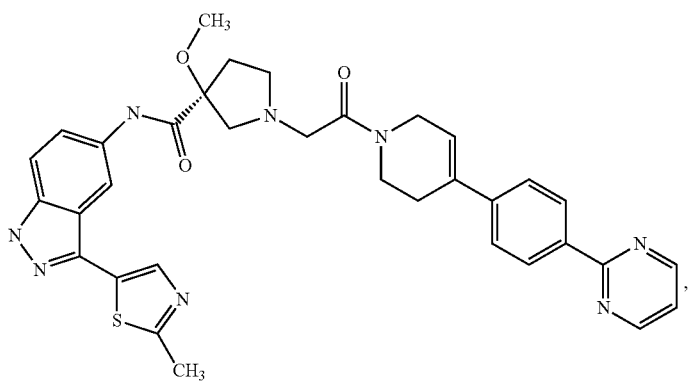

(Ex. 761)
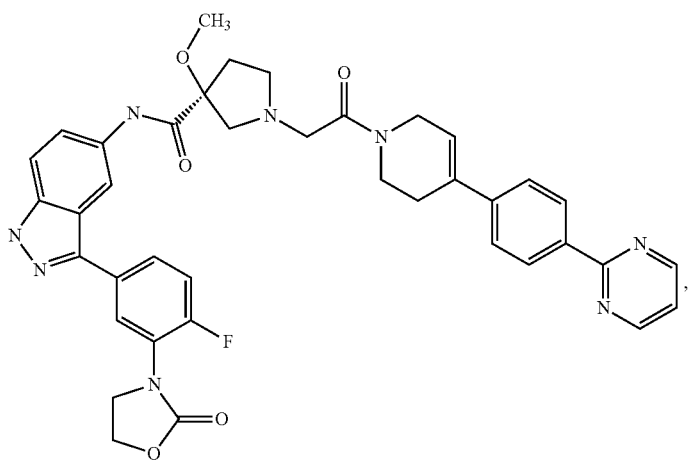
(Ex. 762)
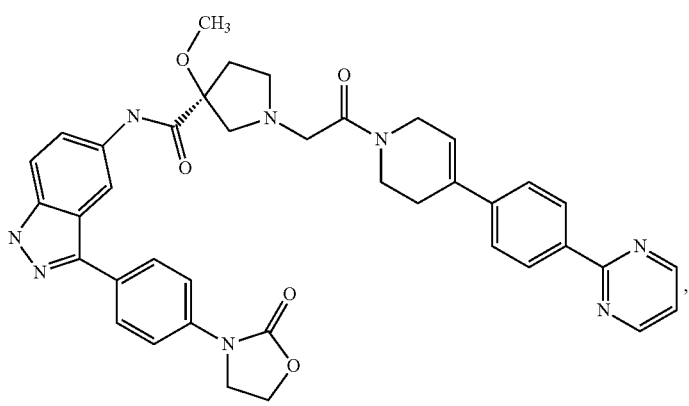
(Ex. 764)
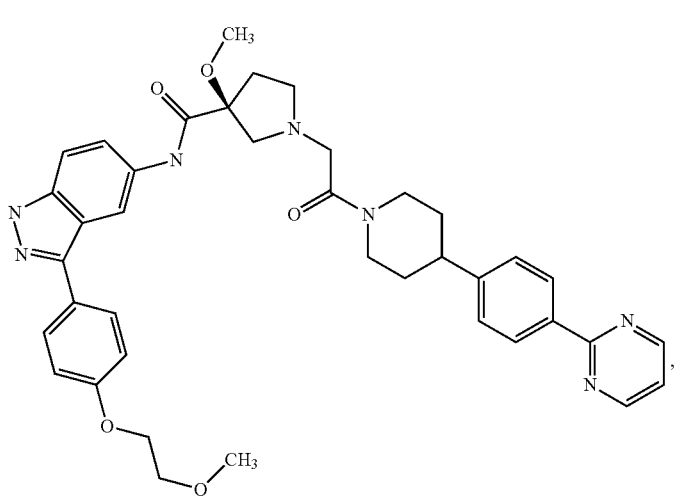

(Ex. 765)
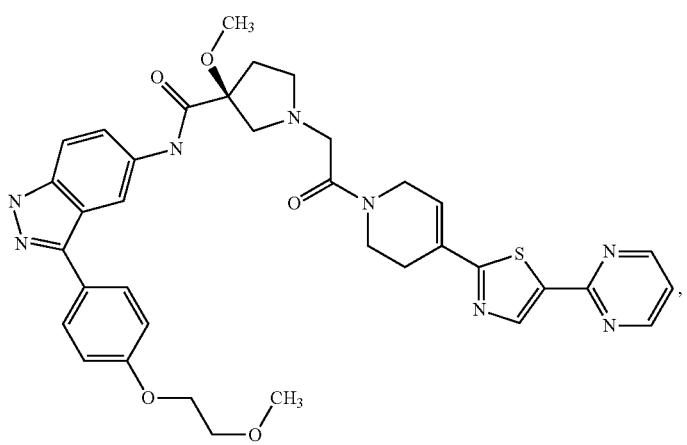
(Ex. 766)
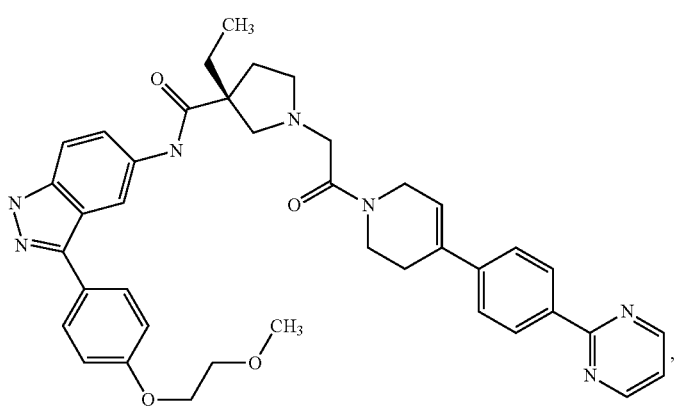
(Ex. 767)
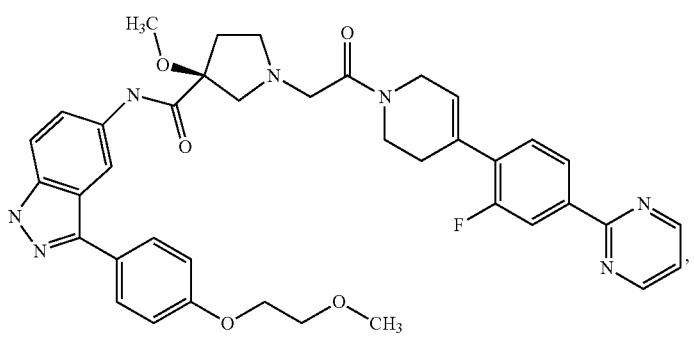
(Ex. 768)
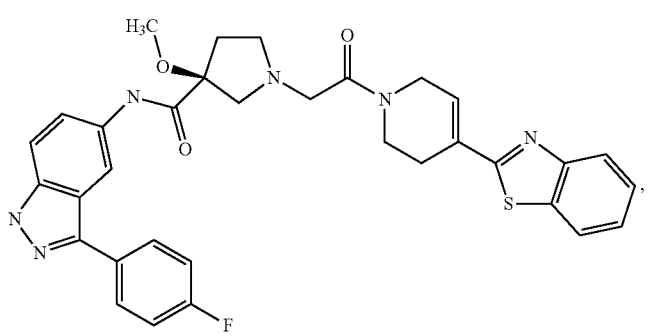

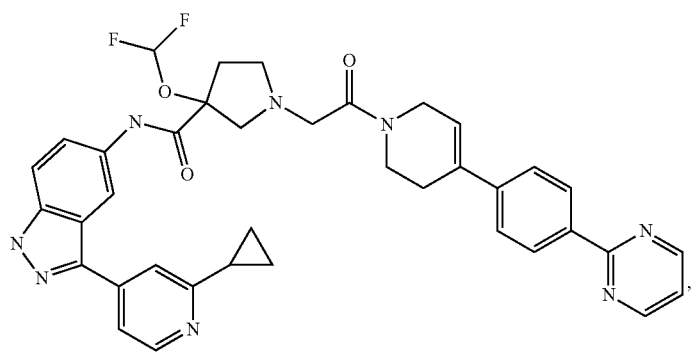
(Ex. 769)
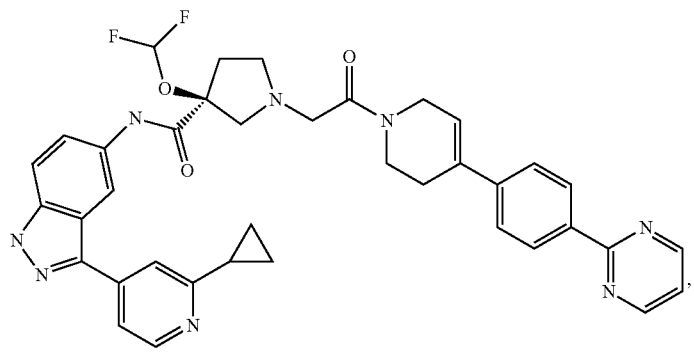
(Ex. 770)
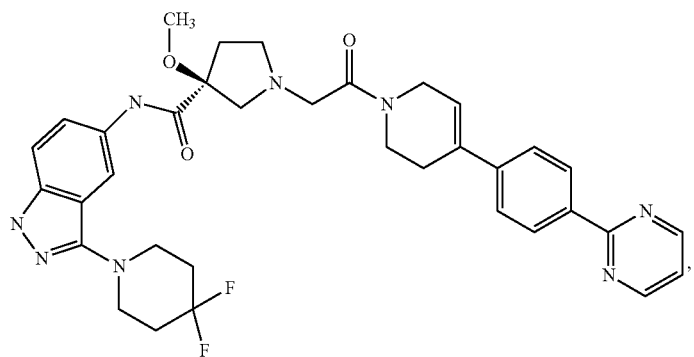
(Ex. 771)
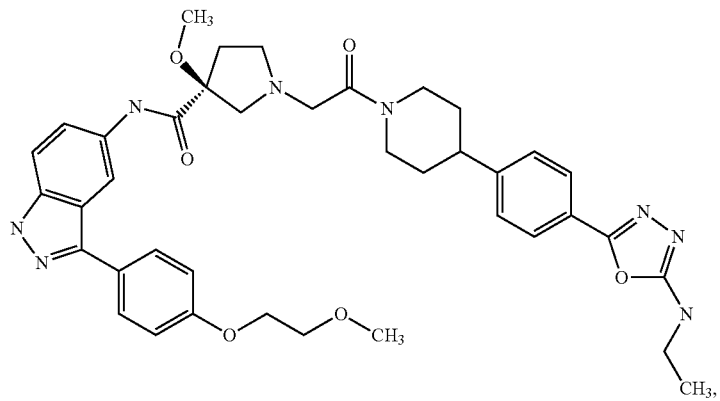
(Ex. 772)

-continued
(Ex. 773)
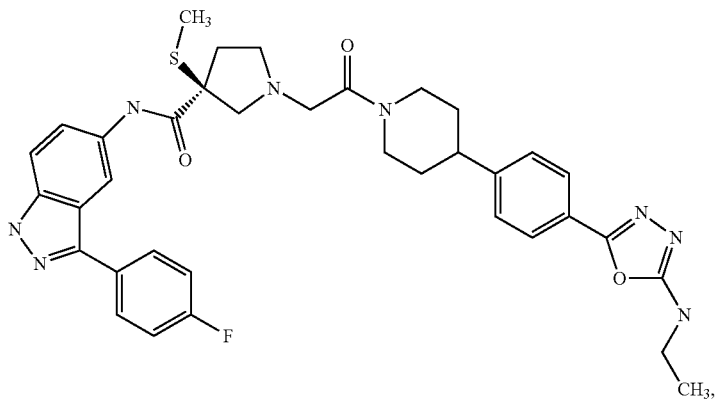
(Ex. 774)
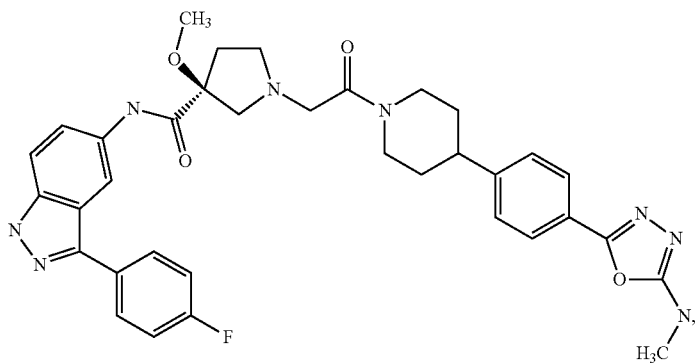
(Ex. 775)
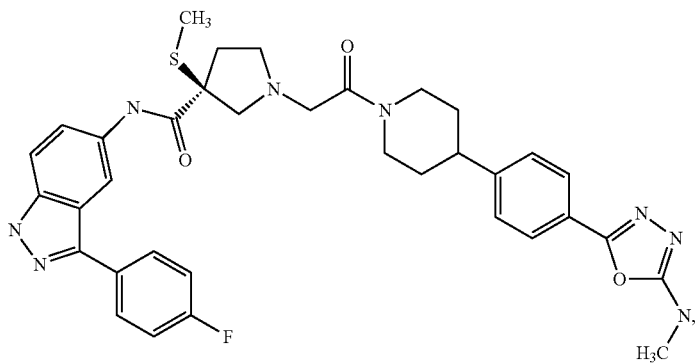
(Ex. 776)
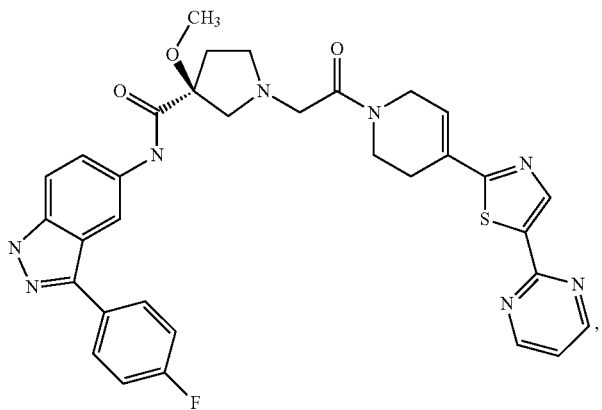

(Ex. 777)
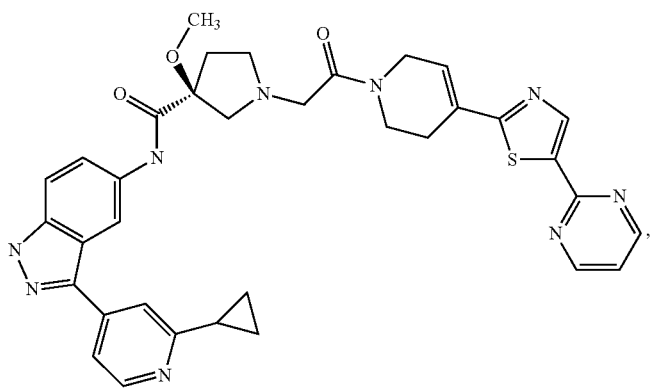
(Ex. 778)
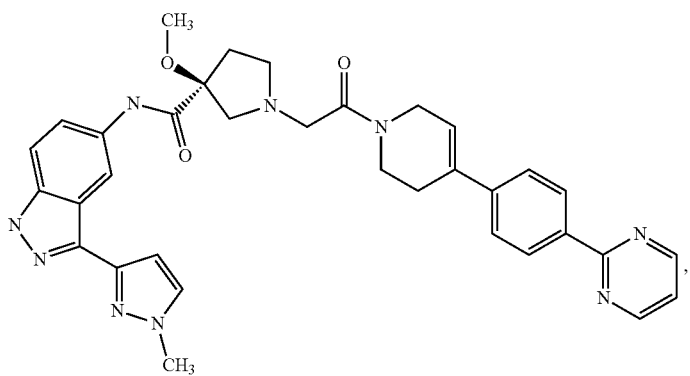
(Ex. 779)
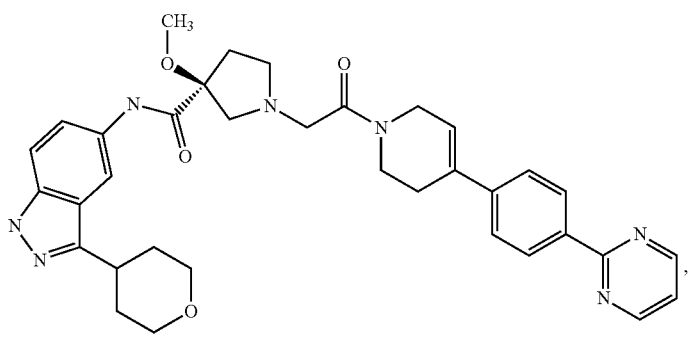
(Ex. 780)
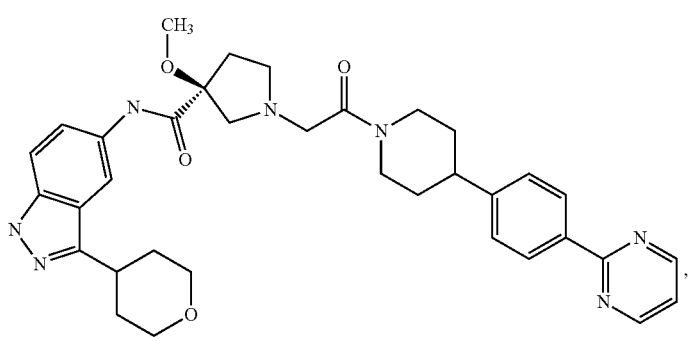

-continued
(Ex. 781)
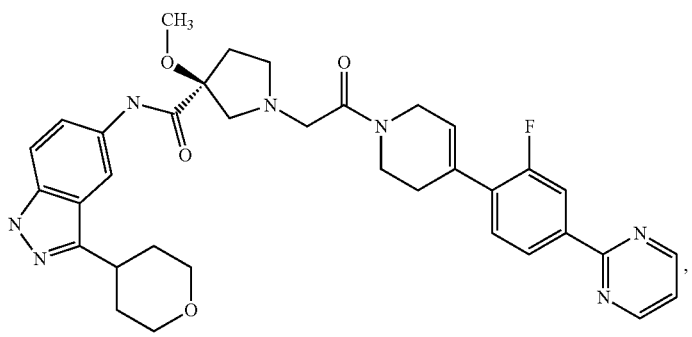
(Ex. 782)
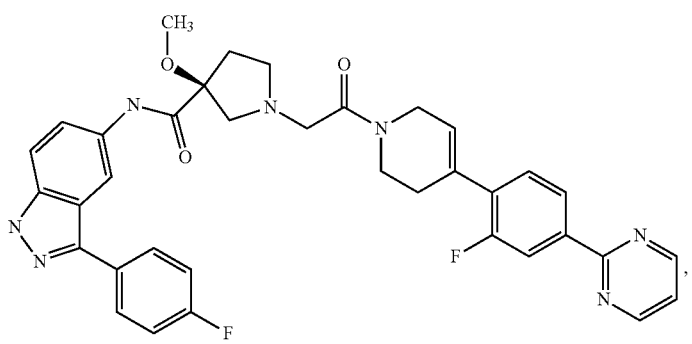
(Ex. 783)
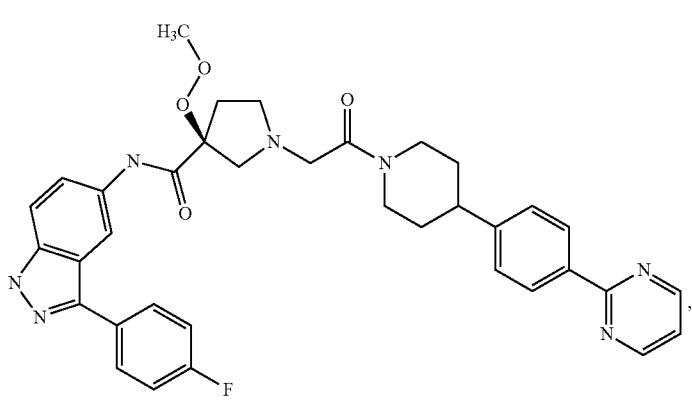
(Ex. 784)
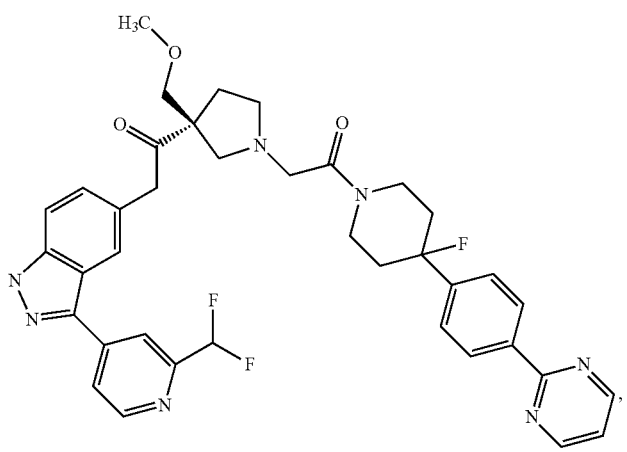

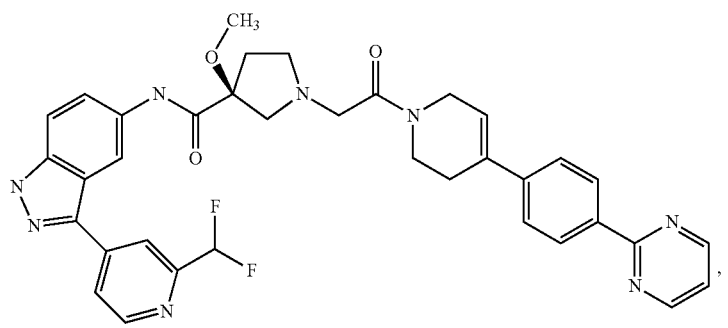
(Ex. 785)
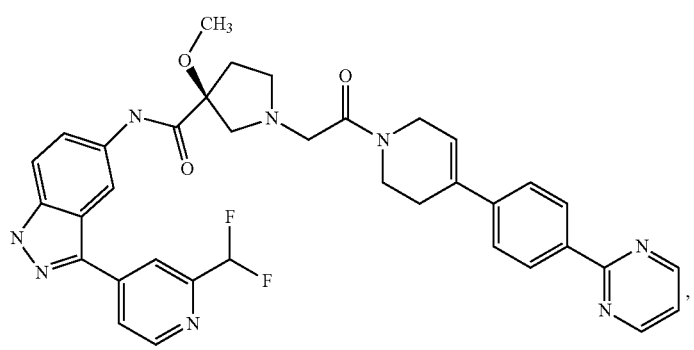
(Ex. 786)
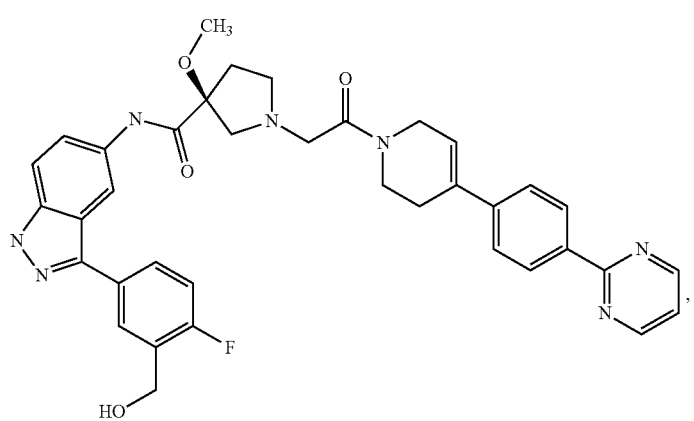
(Ex. 787)
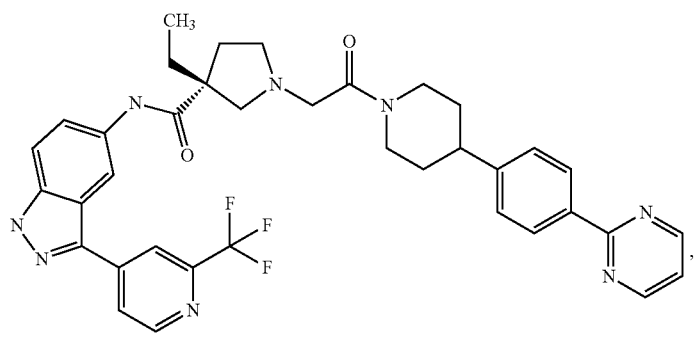
(Ex. 788)

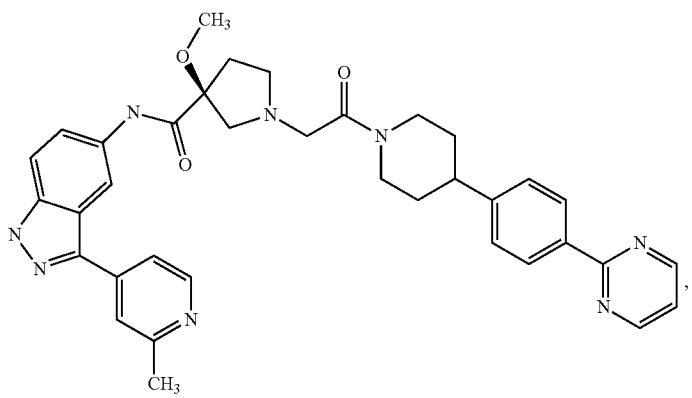
(Ex. 789)
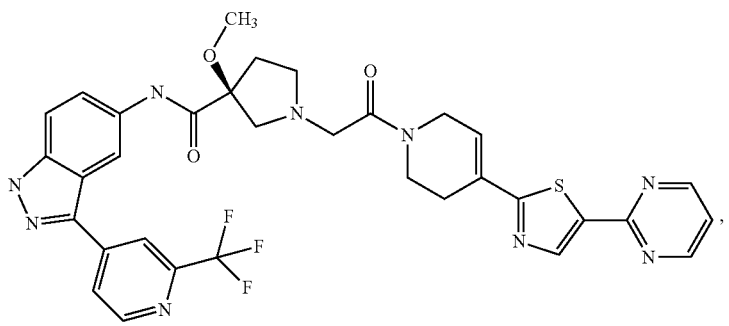
(Ex. 790)
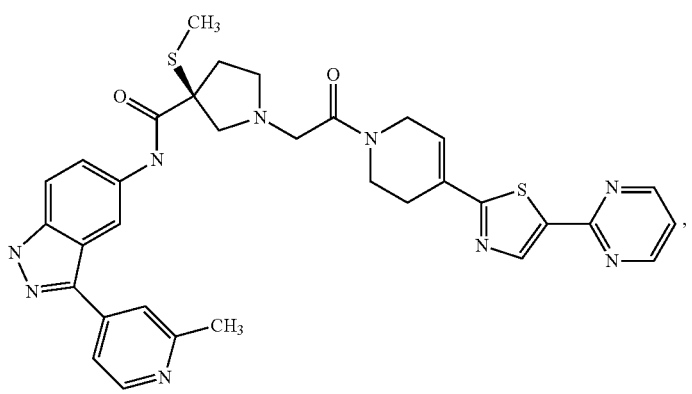
(Ex. 791)
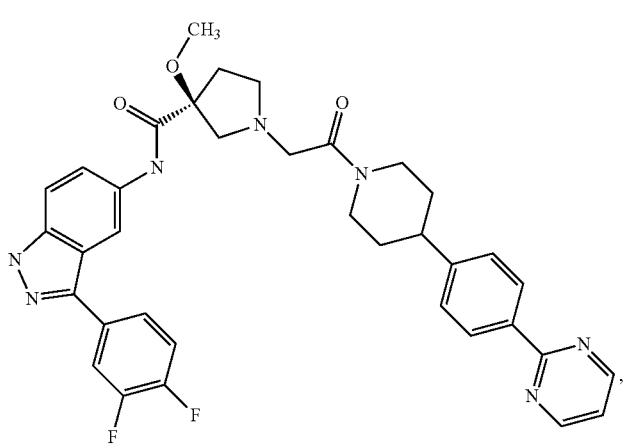
(Ex. 792)

-continued
(Ex. 793)
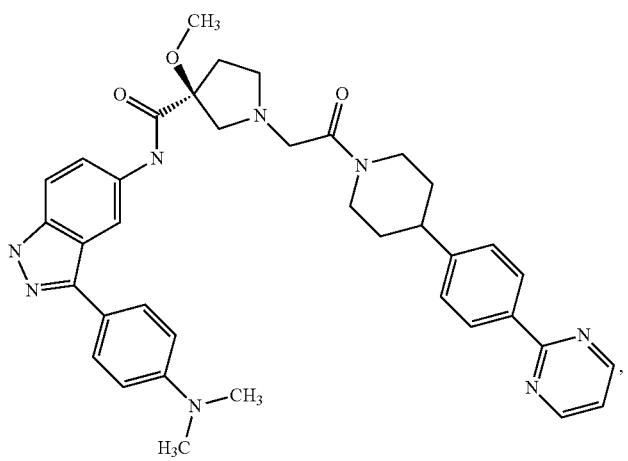
(Ex. 794)
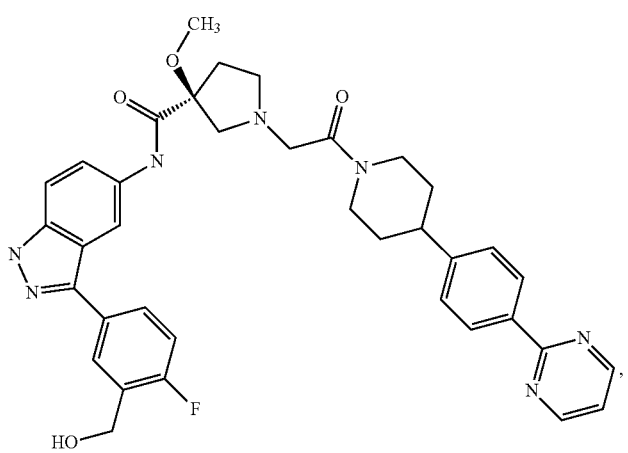
(Ex. 795)
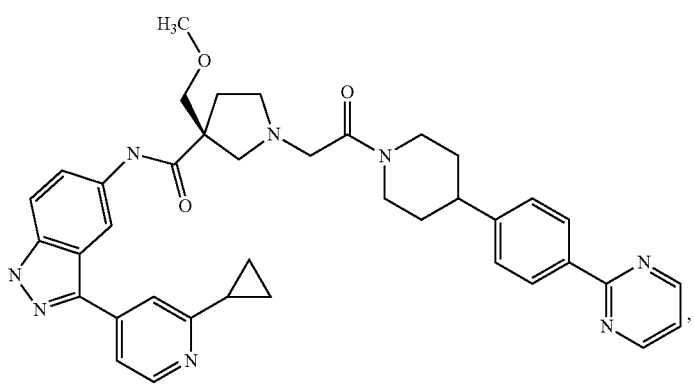
(Ex. 796)
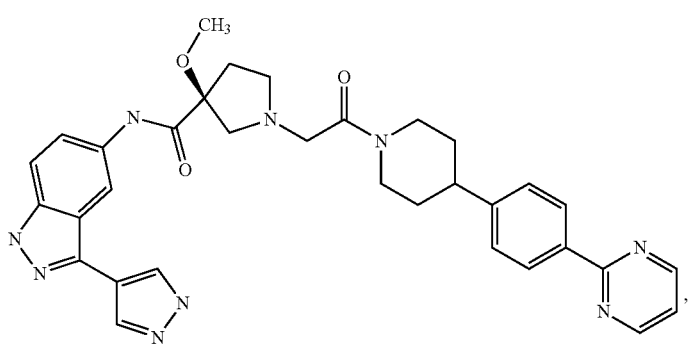

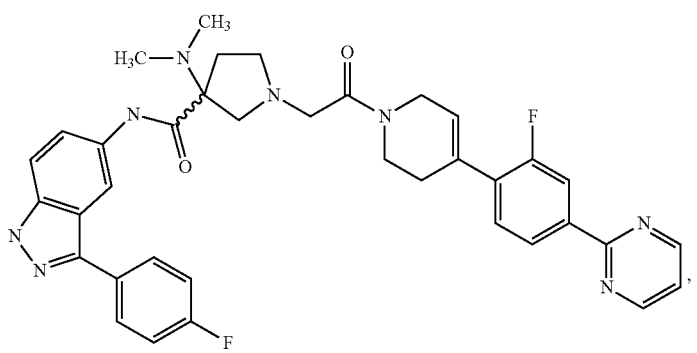
(Ex. 797)
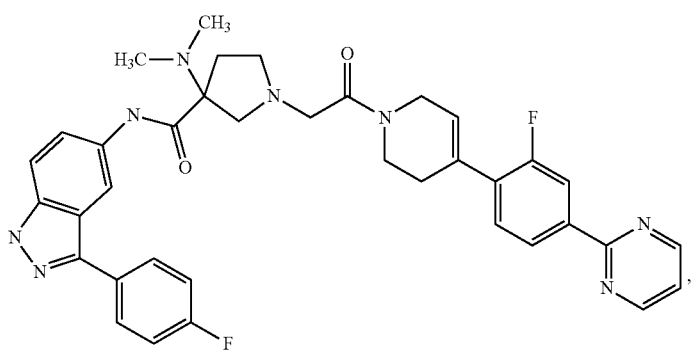
(Ex. 798)
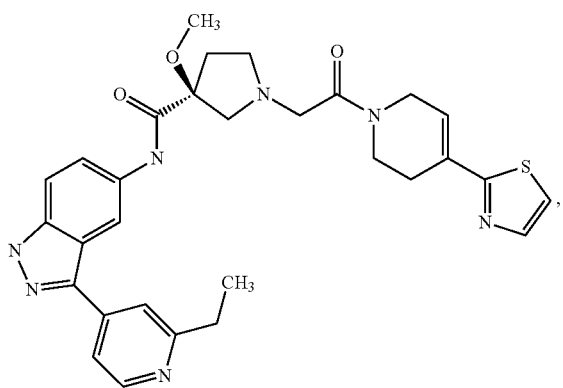
(Ex. 802)
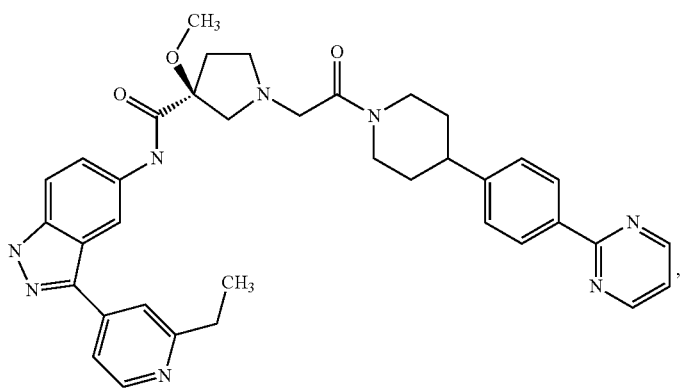
(Ex. 803)

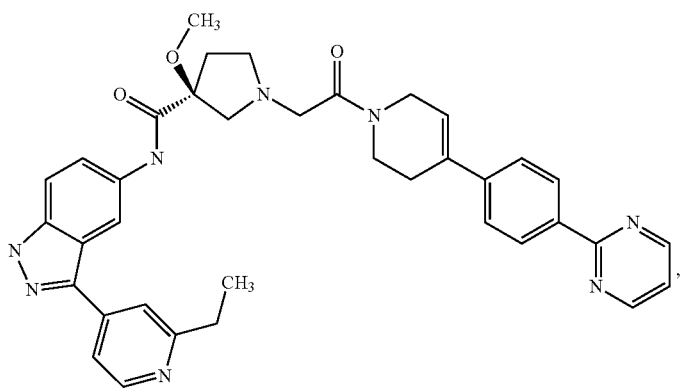
(Ex. 805)
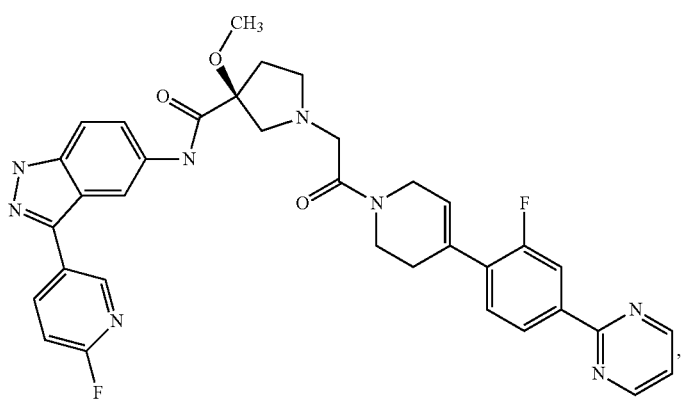
(Ex. 807)
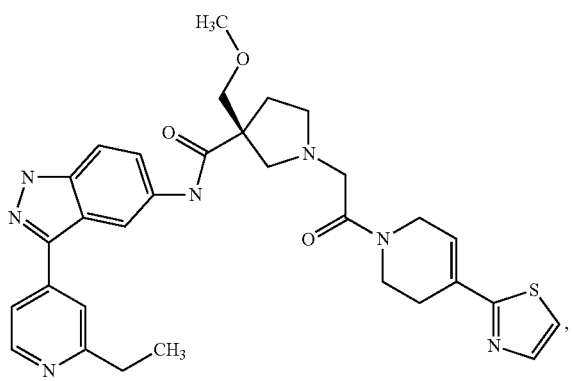
(Ex. 808)
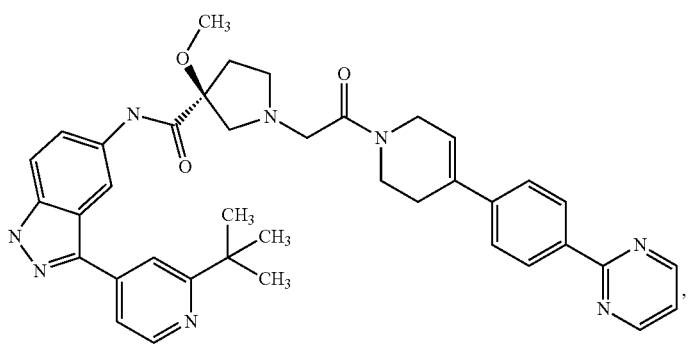
(Ex. 809)

(Ex. 810)
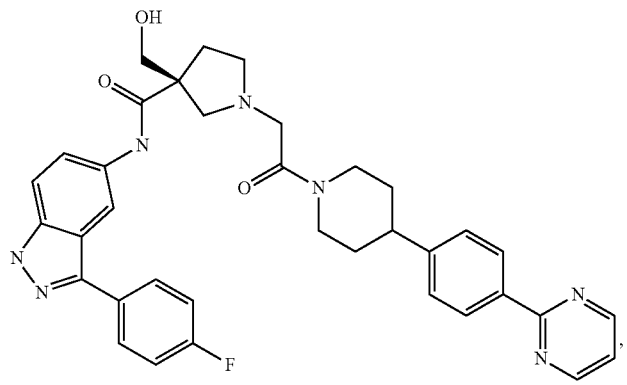
(Ex. 811)
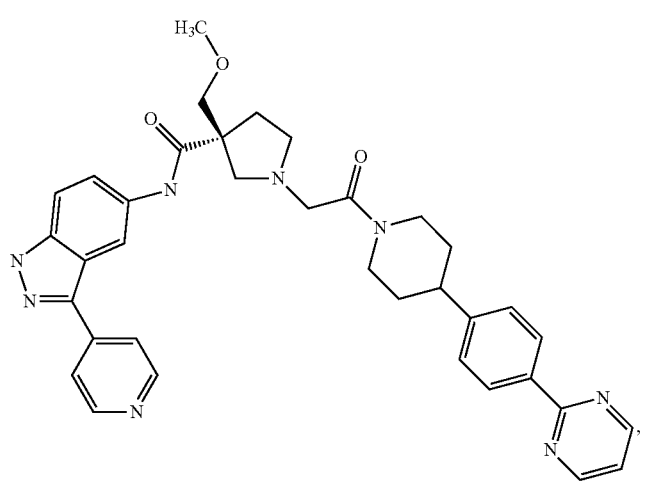
(Ex. 812)
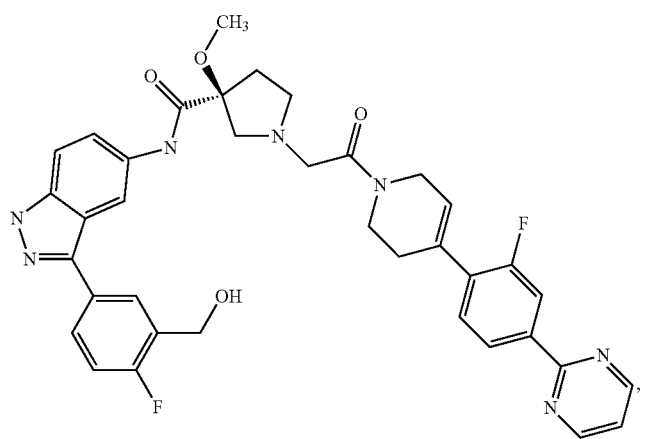

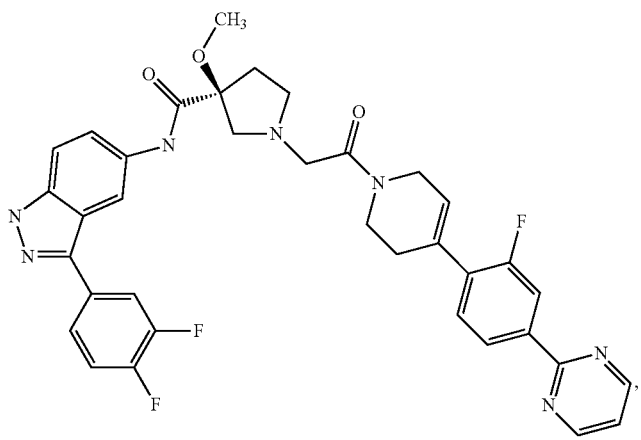
(Ex. 813)
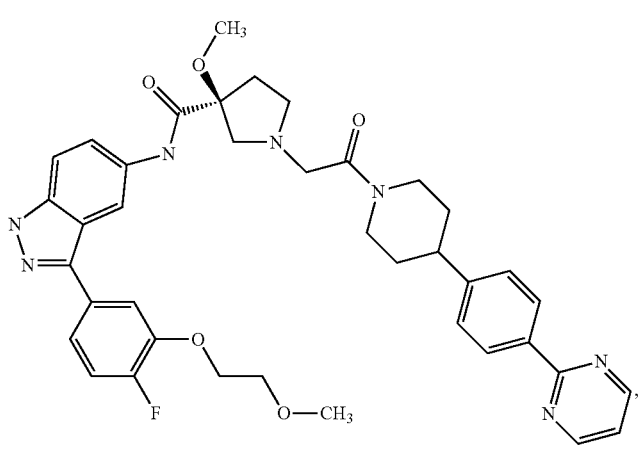
(Ex. 814)
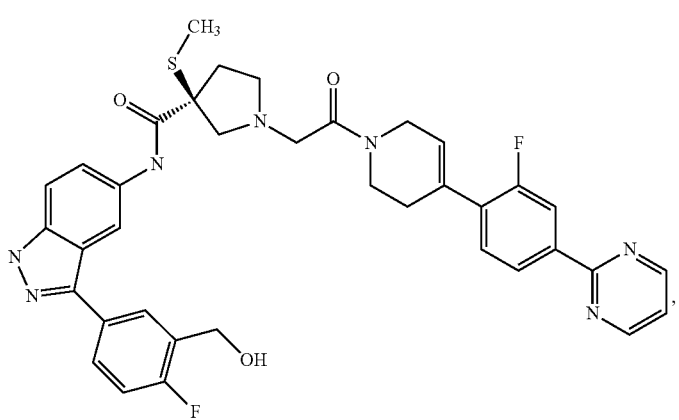
(Ex. 815)

(Ex. 816)
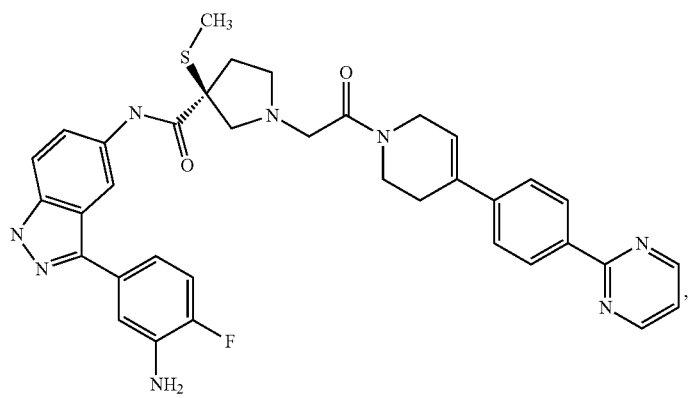
(Ex. 817)
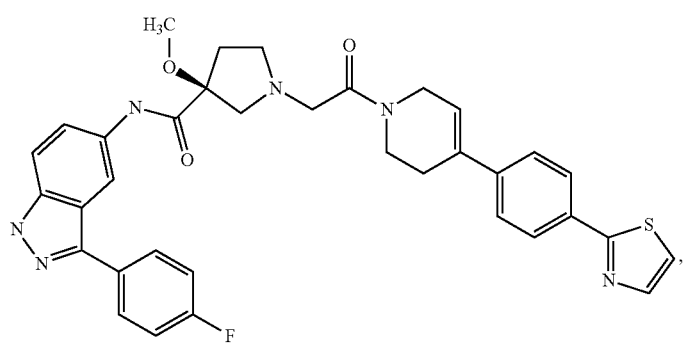
(Ex. 818)
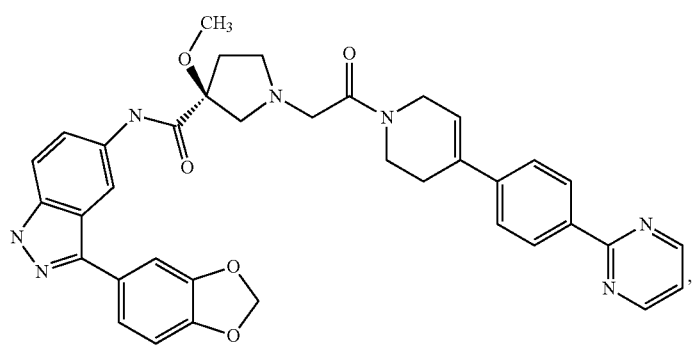
(Ex. 819)
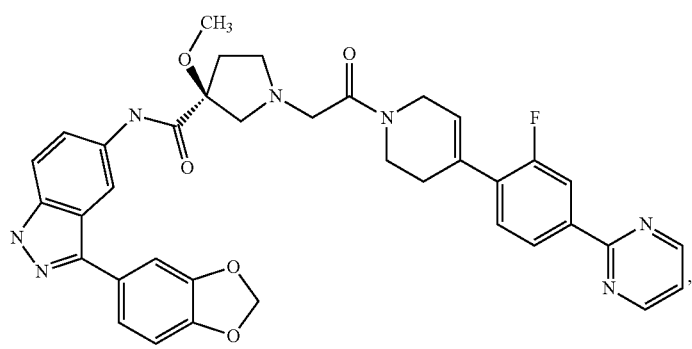

-continued
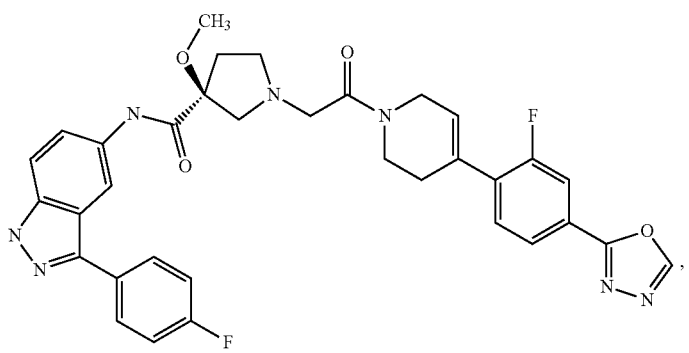
(Ex. 820)
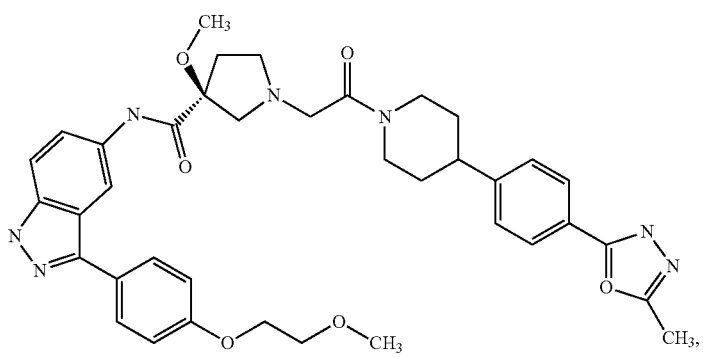
(Ex. 821)
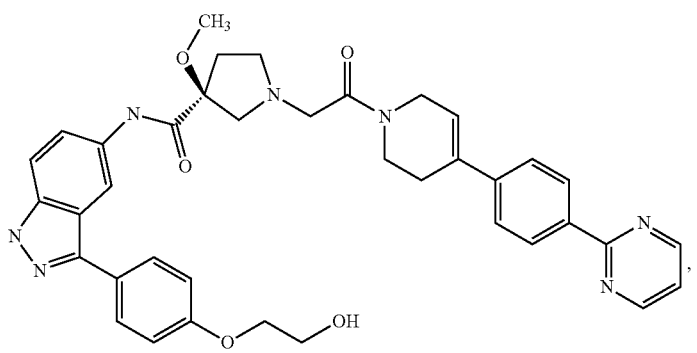
(Ex. 822)
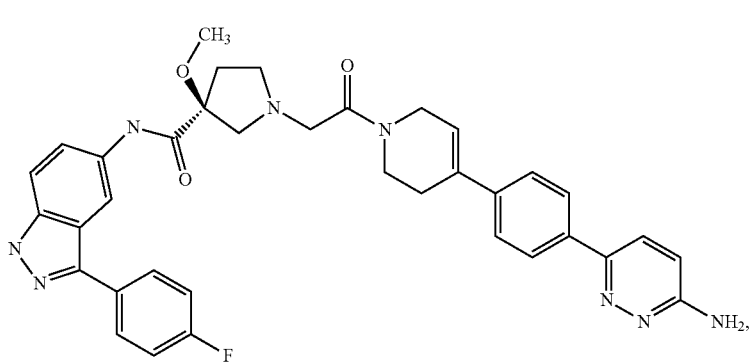
(Ex. 823)

-continued
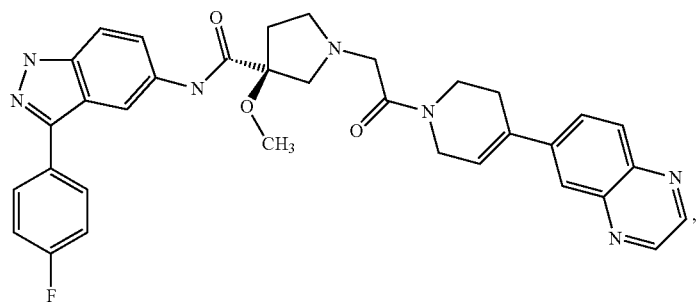
(Ex. 824)
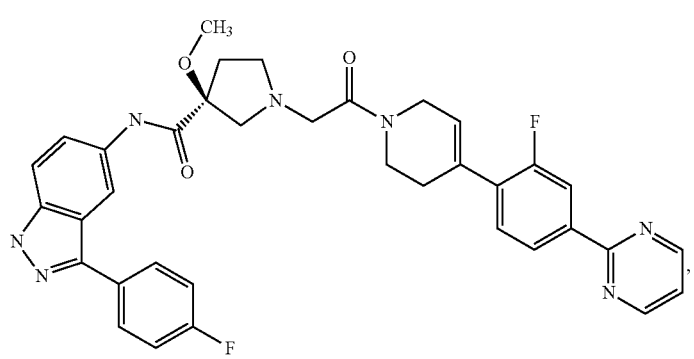
(Ex. 825)
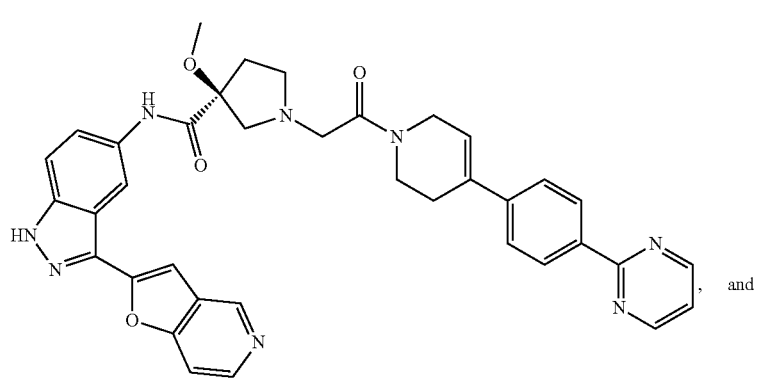
(Ex. 826)
, and
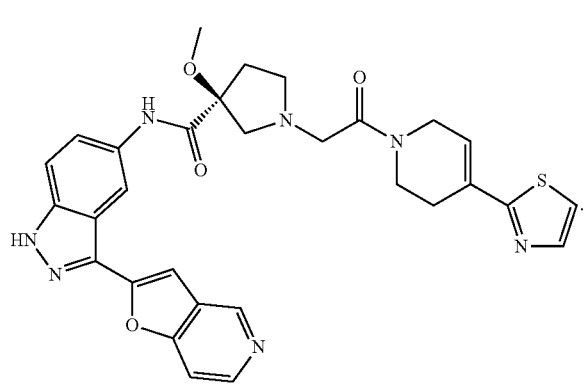
(Ex. 827)

62. The compound of claim 1 selected from the group consisting of:
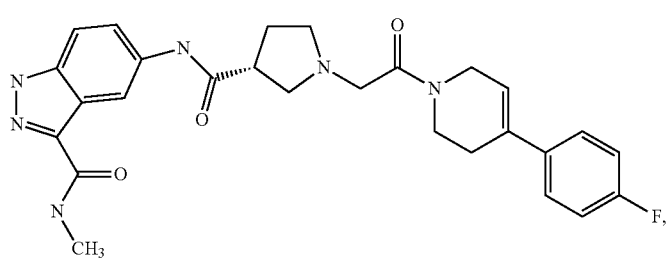
(Ex. 166)
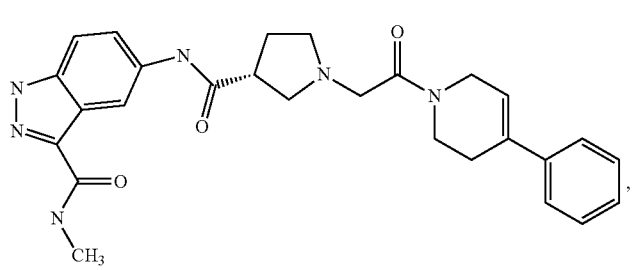
(Ex. 167)
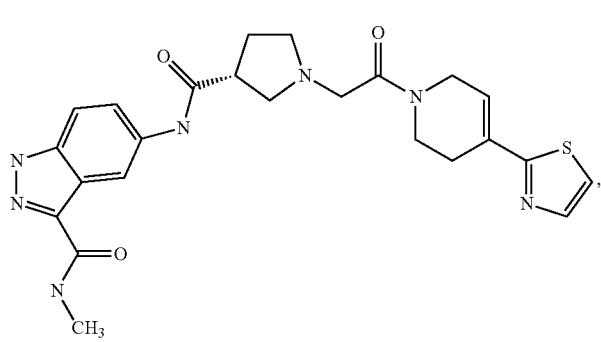
(Ex. 168)
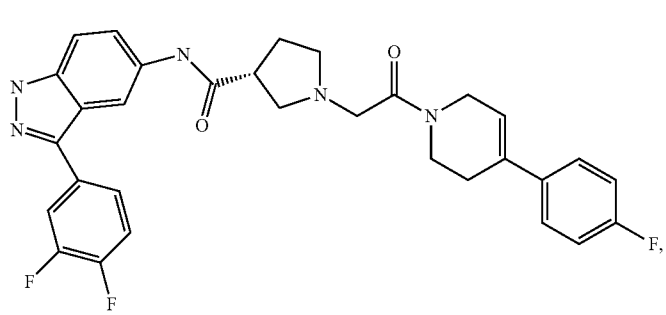
(Ex. 169)
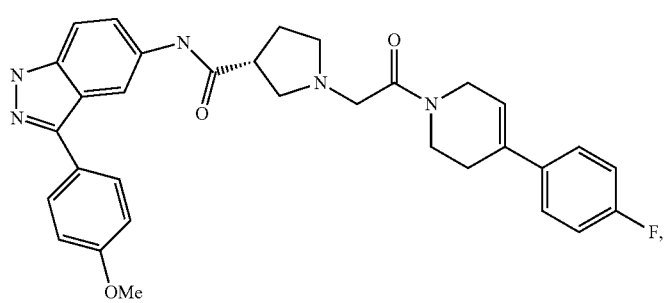
(Ex. 170)

-continued
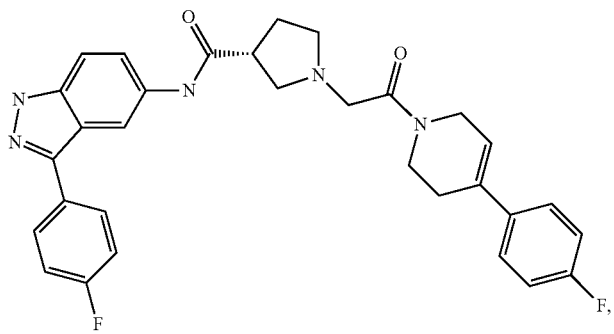
(Ex. 171)
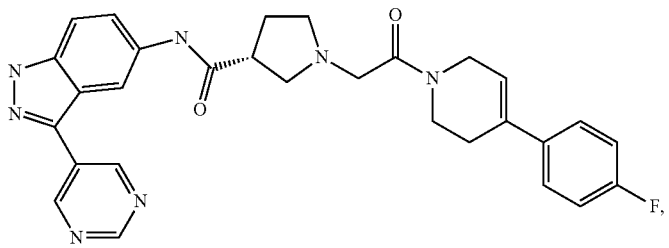
(Ex. 172)
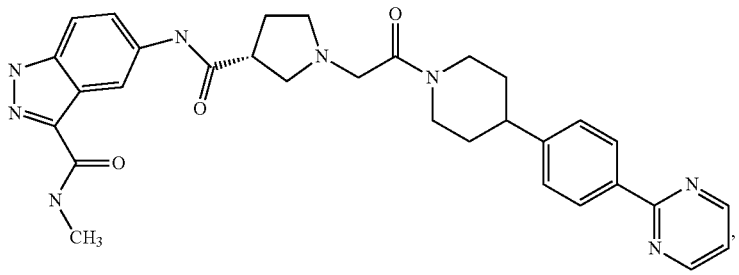
(Ex. 254)
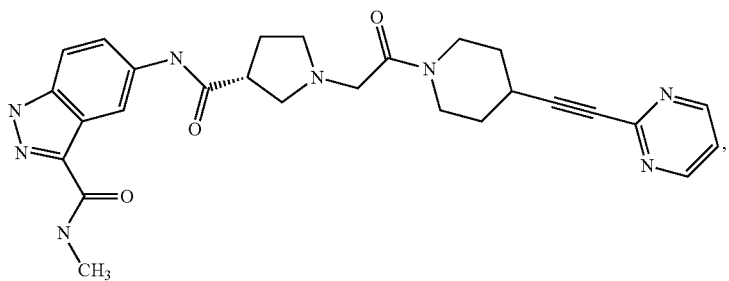
(Ex. 259)
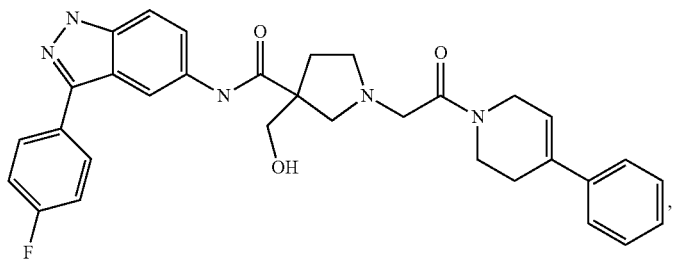
(Ex. 260)

1083 1084
-continued
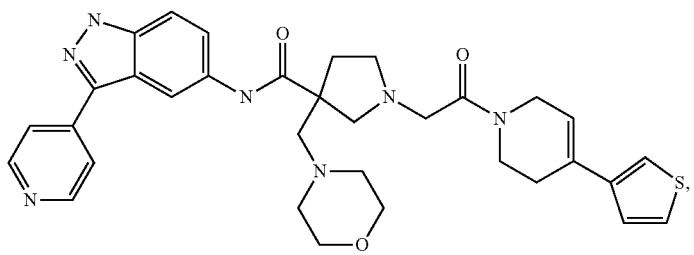
(Ex. 285)
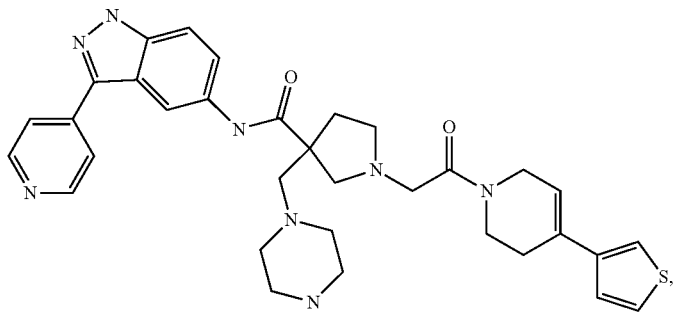
(Ex. 288)
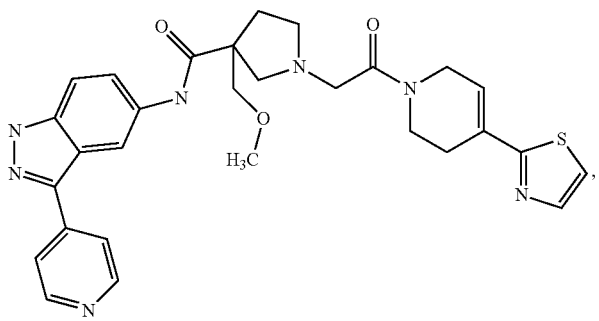
(Ex. 306)
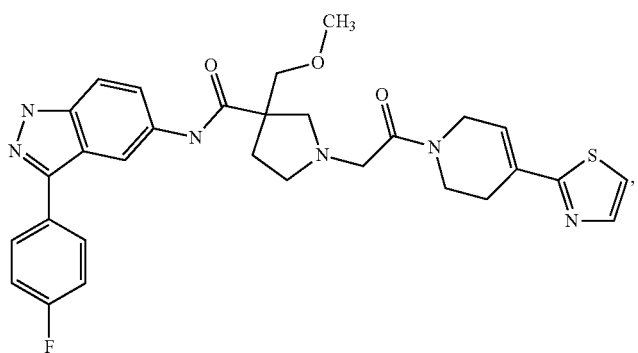
(Ex. 311)
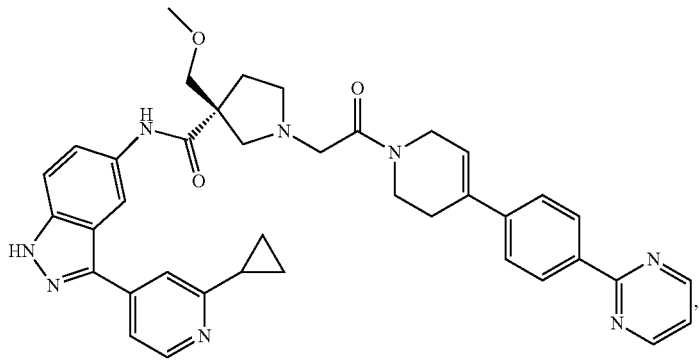
(Ex. 336)

-continued
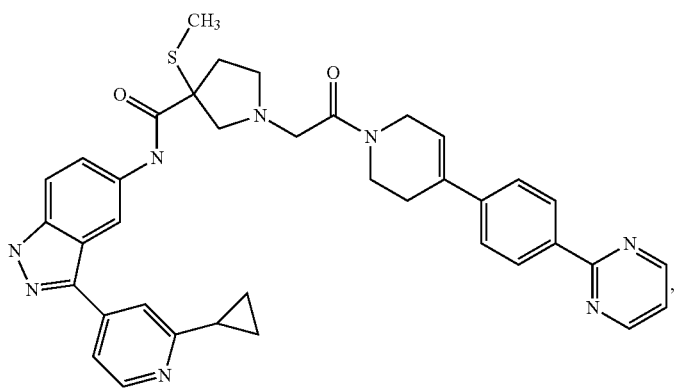
(Ex. 339)
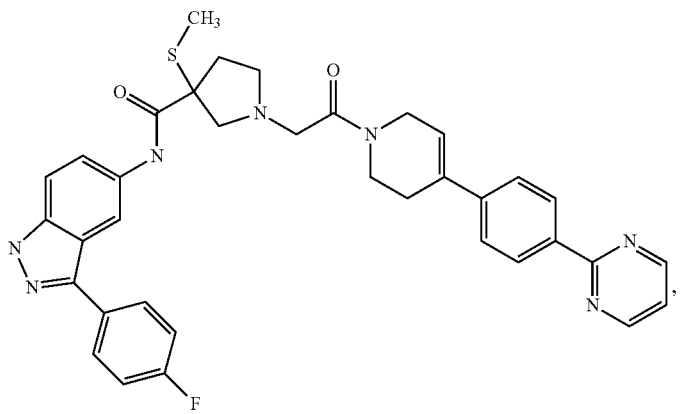
(Ex. 340)
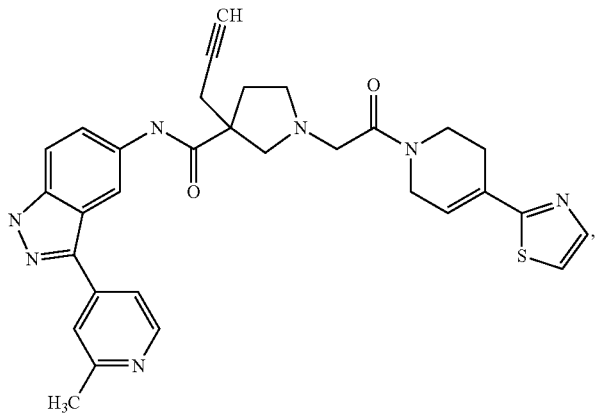
(Ex. 369)
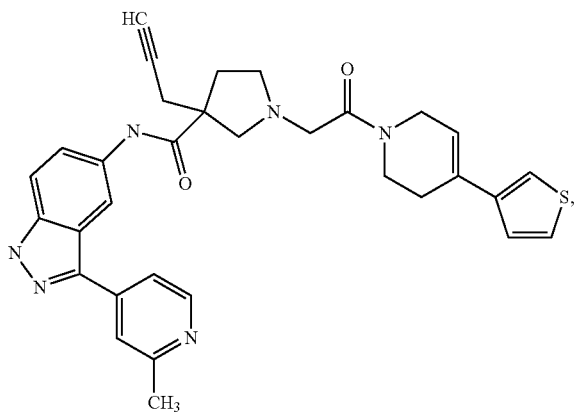
(Ex. 370)

(Ex. 371)
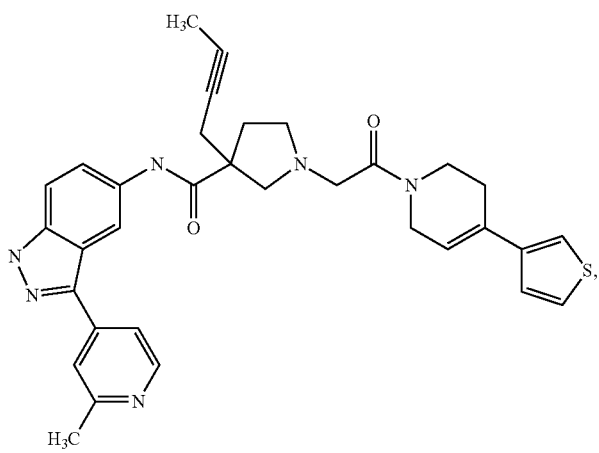
(Ex. 374)
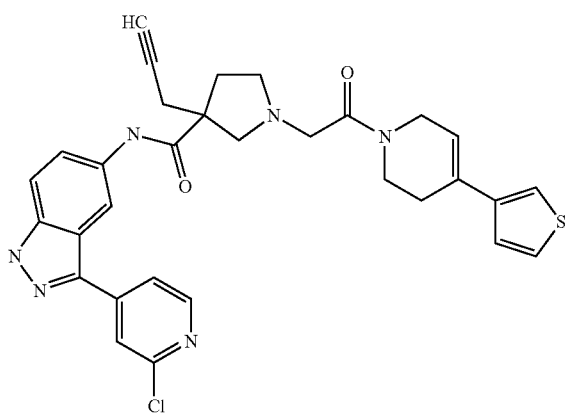
(Ex. 375)
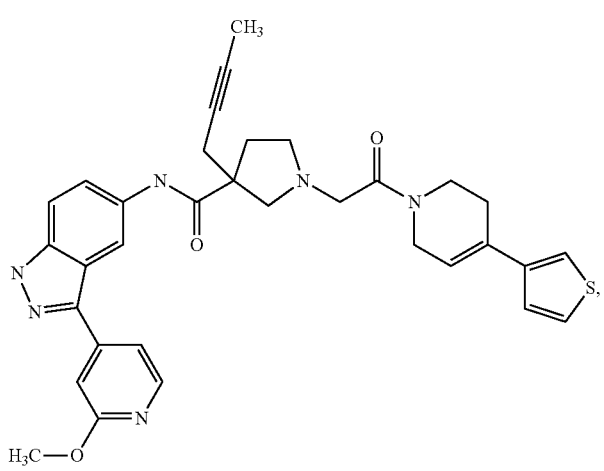

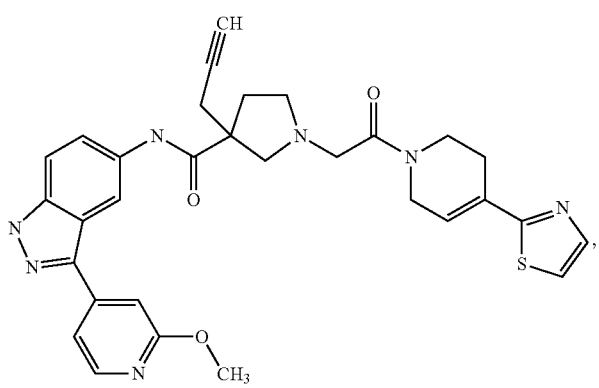
(Ex. 377)
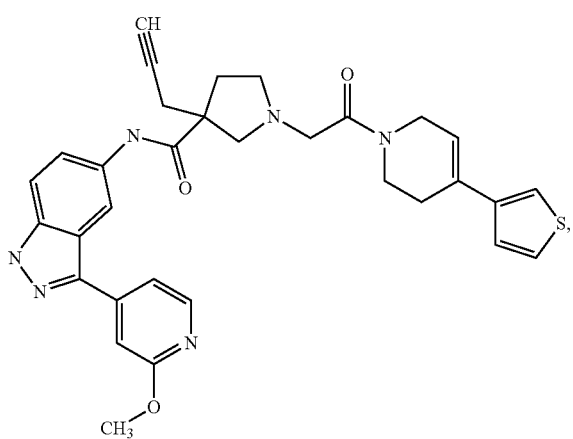
(Ex. 378)
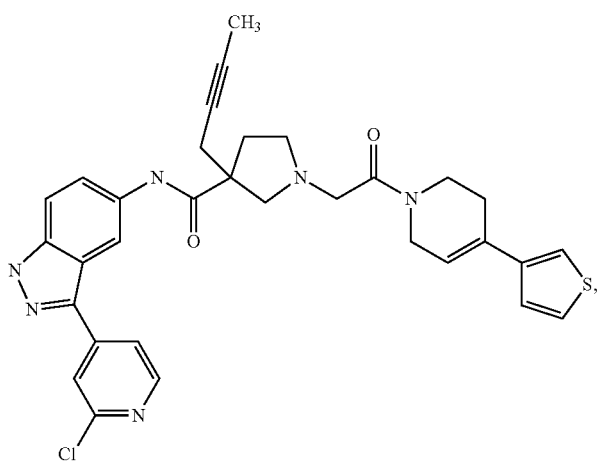
(Ex. 380)

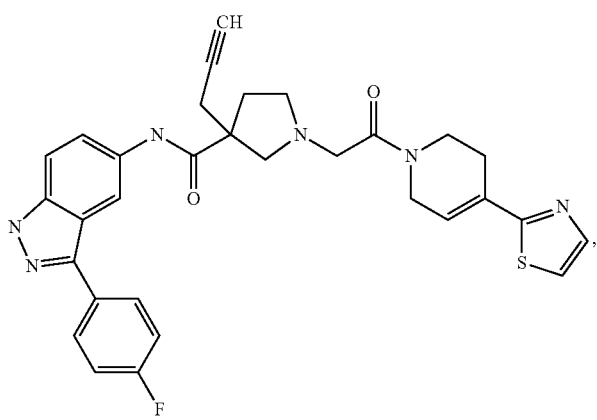
(Ex. 381)
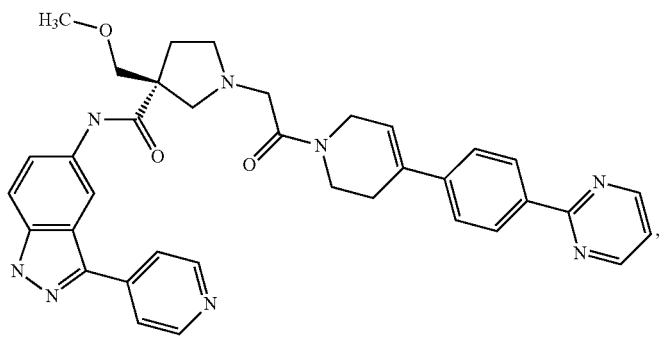
(Ex. 384)
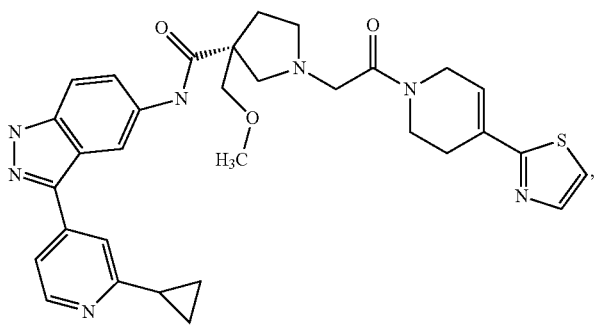
(Ex. 386)
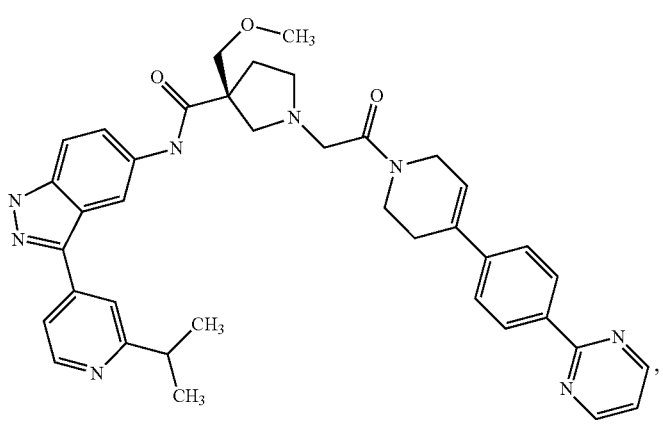
(Ex. 389)

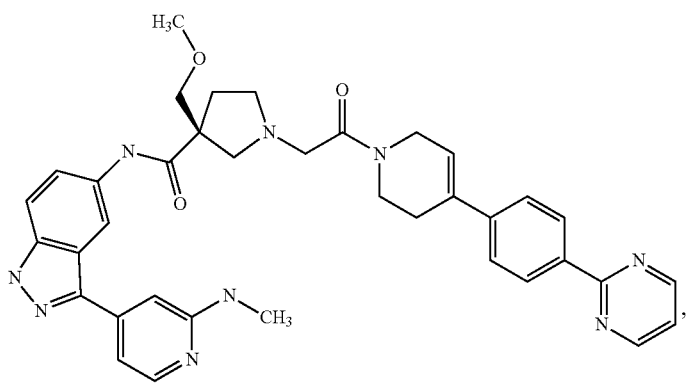
(Ex. 391)
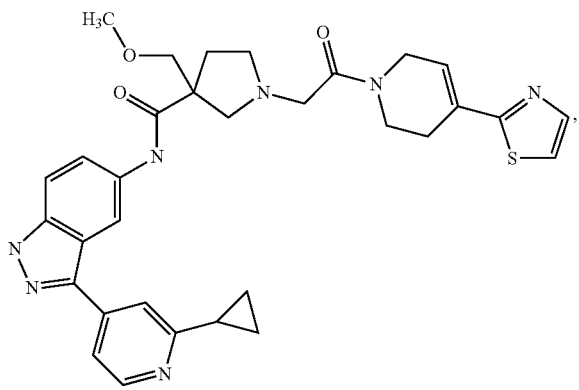
(Ex. 393)
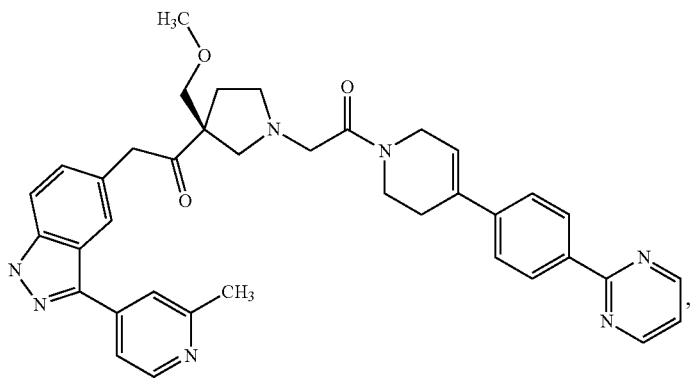
(Ex. 394)
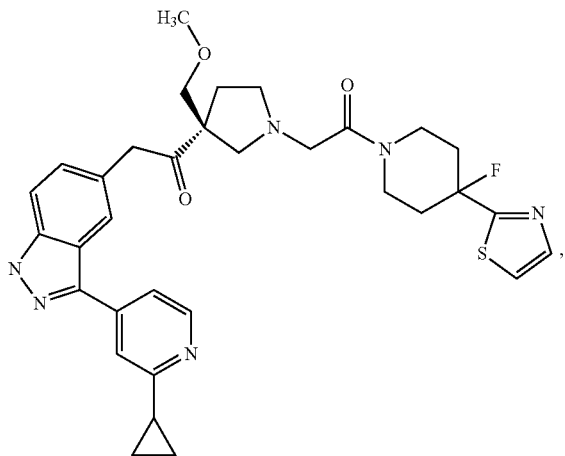
(Ex. 397)

(Ex. 399)
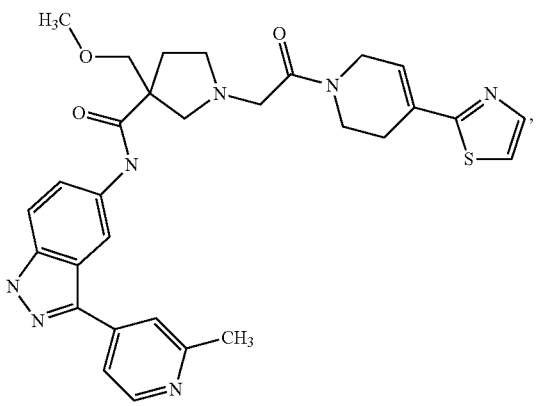
(Ex. 401)
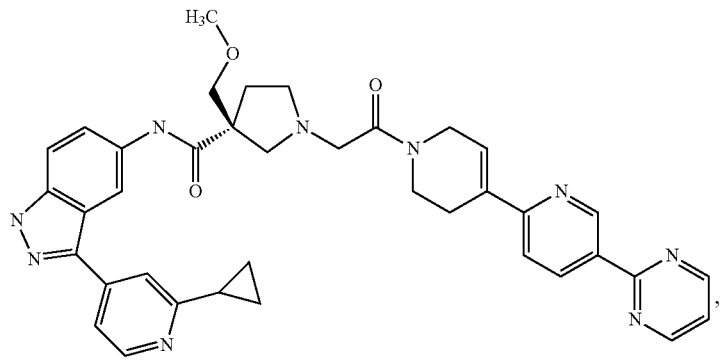
(Ex. 402)
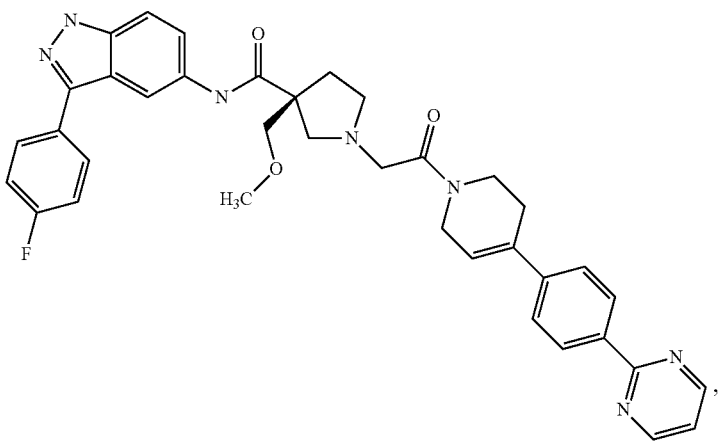
(Ex. 403)
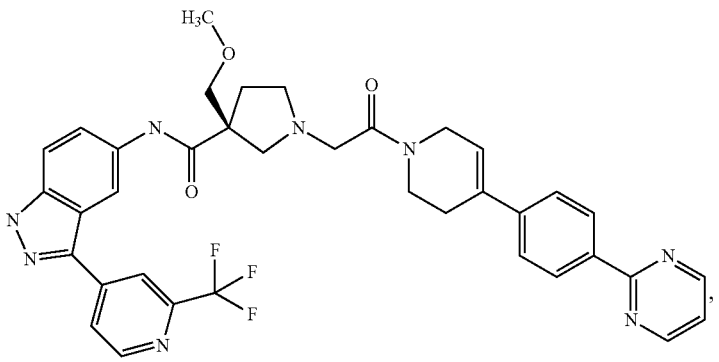 [SMILES: COC[C@@]1(C(=O)Nc2ccc3[nH]nc(-c4ccnc(C(F)(F)F)c4)c3c2)CCN(CC(=O)N2CC=C(c3ccc(-c4ncccn4)cc3)CC2)C1 ; "."]

(Ex. 405)
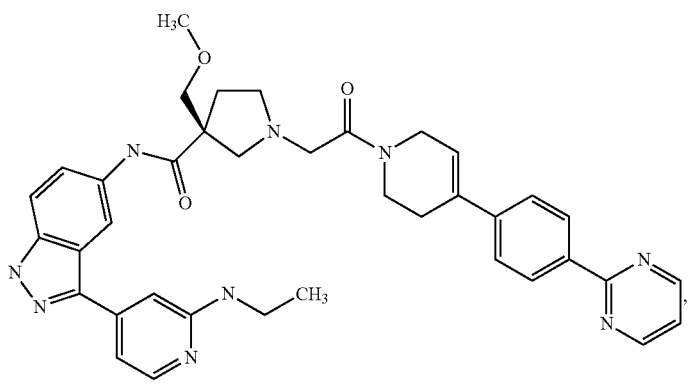
(Ex. 407)
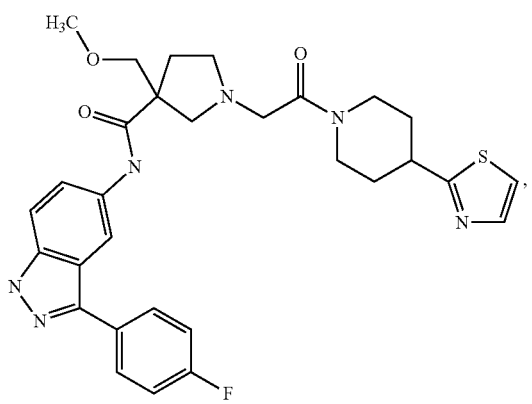
(Ex. 409)
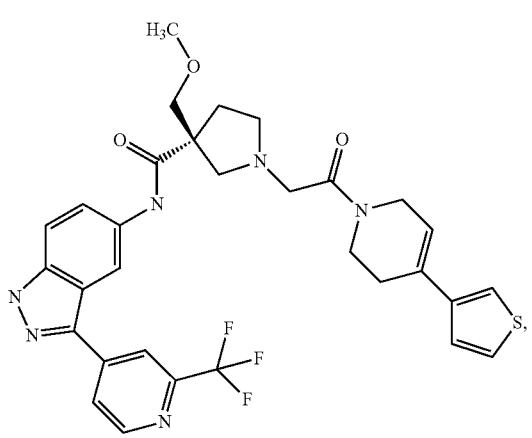
(Ex. 414)
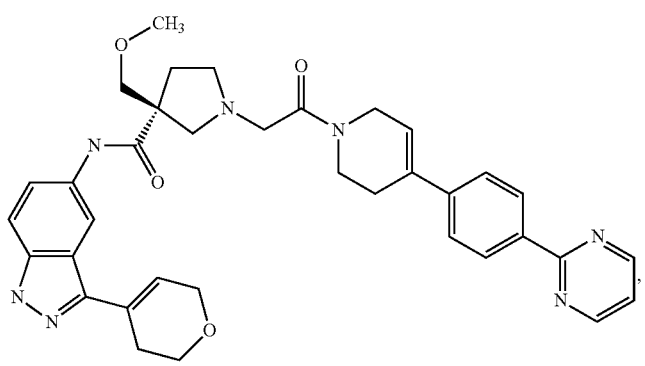

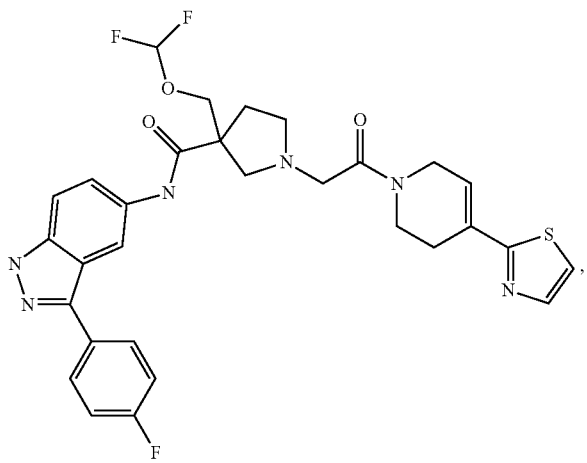
(Ex. 415)
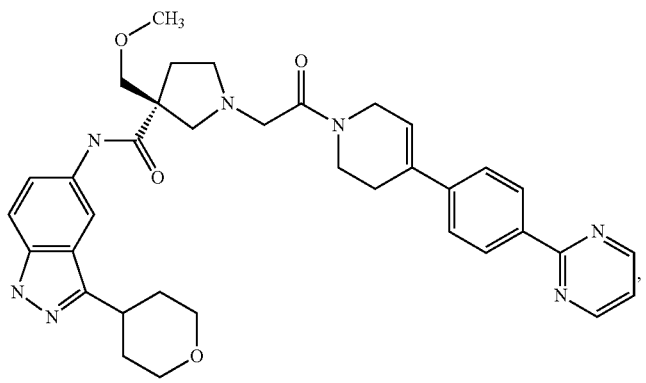
(Ex. 416)
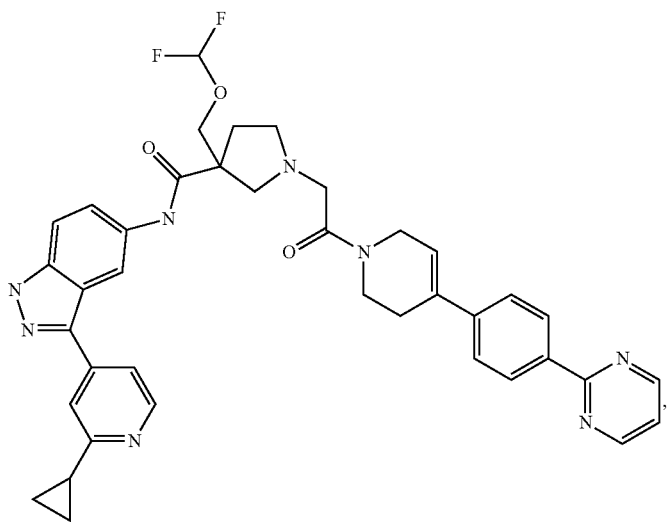
(Ex. 418)

(Ex. 420)
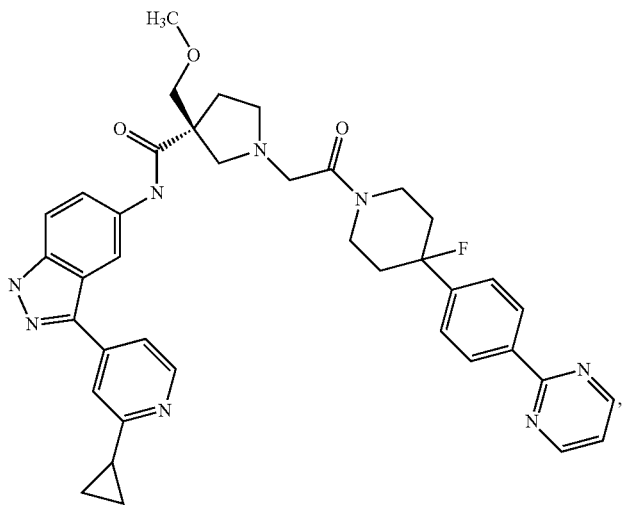
(Ex. 421)
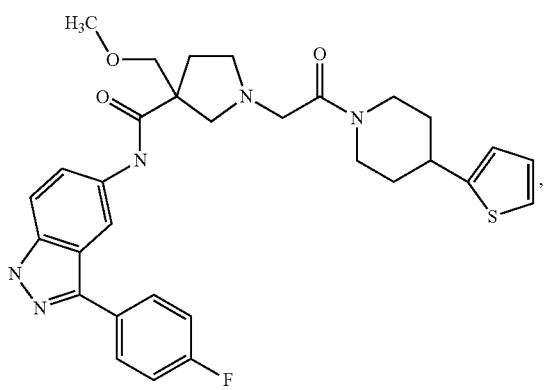
(Ex. 422)
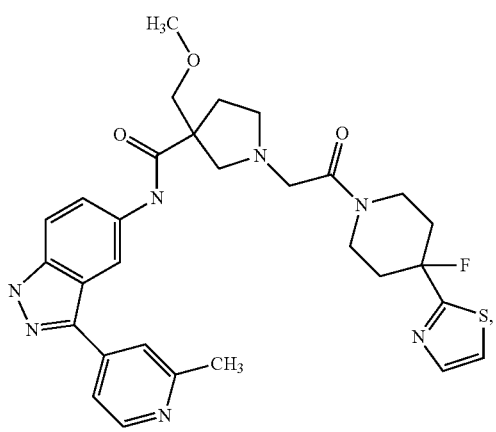

1103
-continued
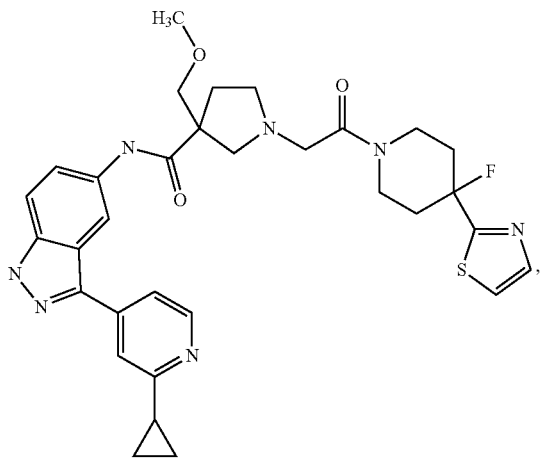
(Ex. 425)
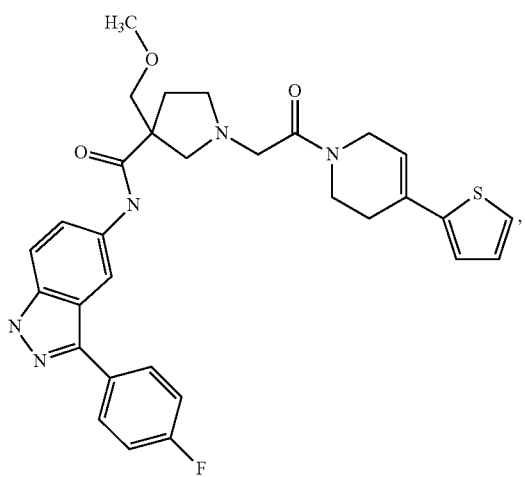
(Ex. 427)
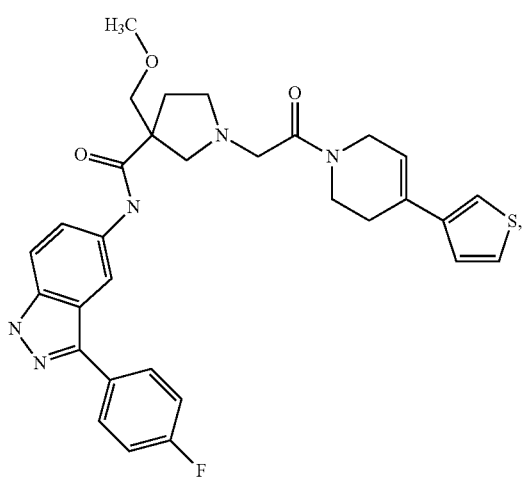
(Ex. 428)

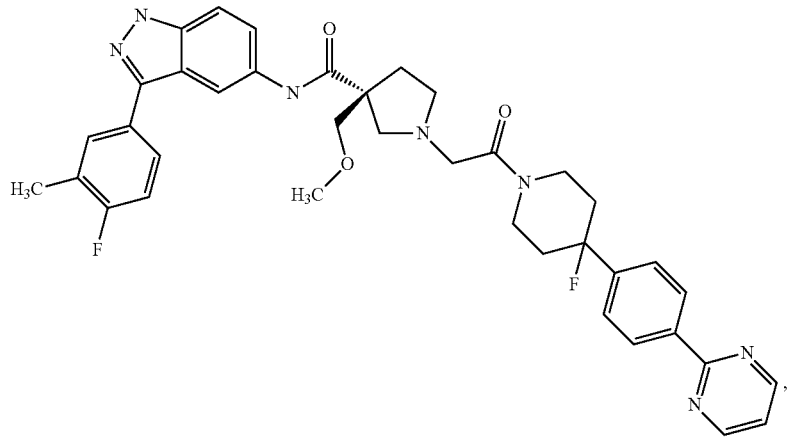
(Ex. 429)
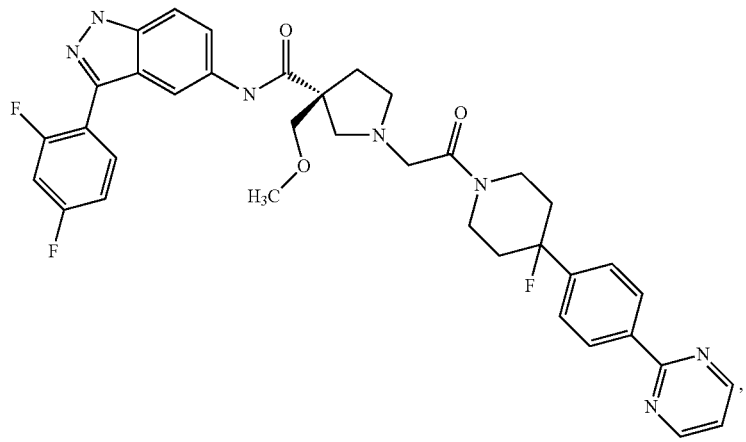
(Ex. 431)
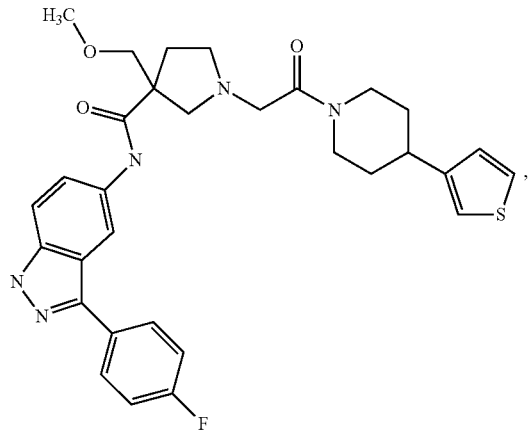
(Ex. 432)

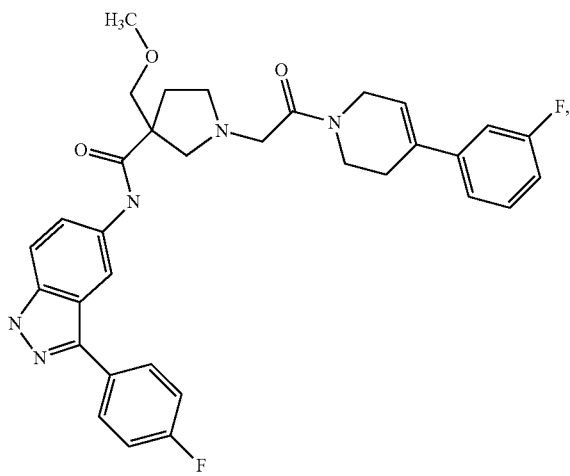
(Ex. 434)
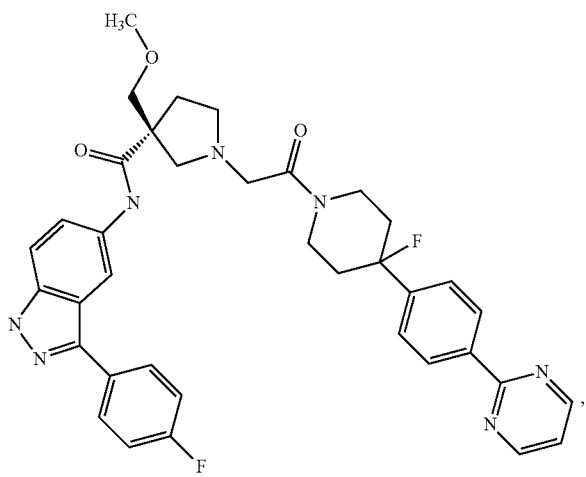
(Ex. 435)
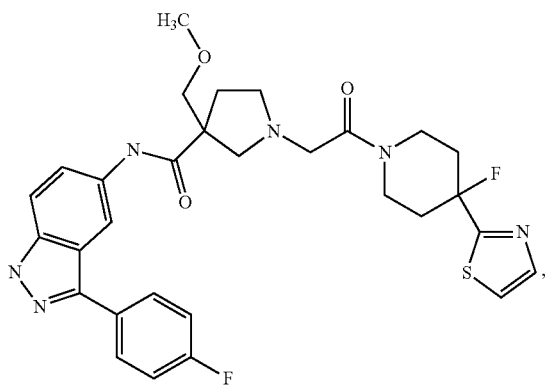
(Ex. 436)

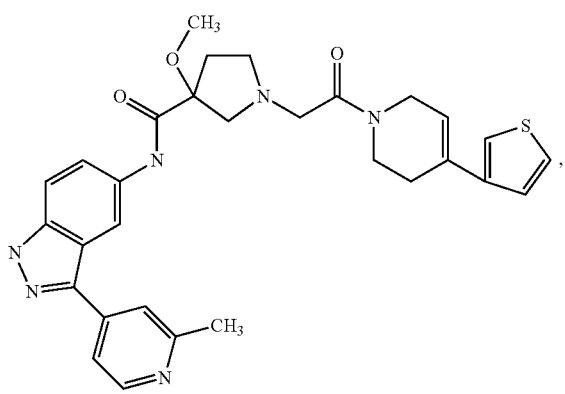
(Ex. 440)
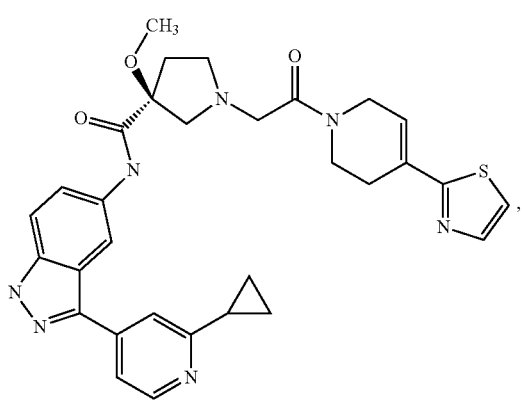
(Ex. 444)
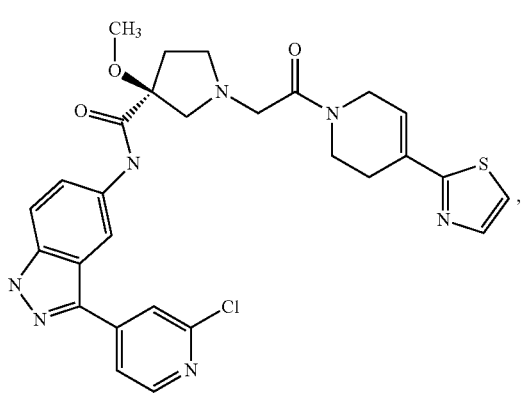
(Ex. 445)
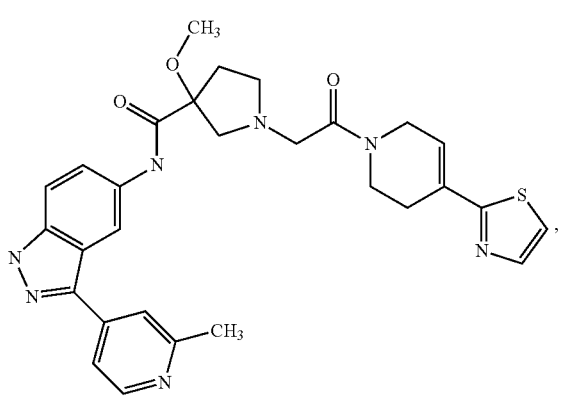
(Ex. 449)

-continued
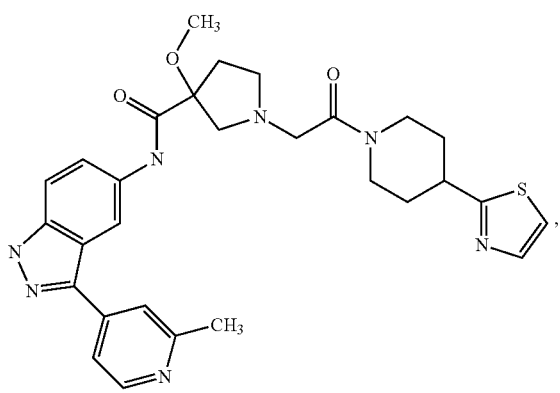
(Ex. 450)
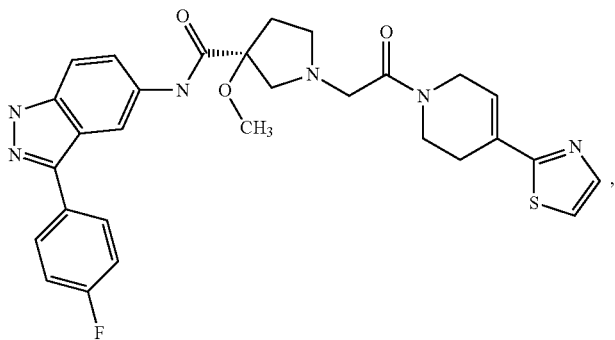
(Ex. 454)
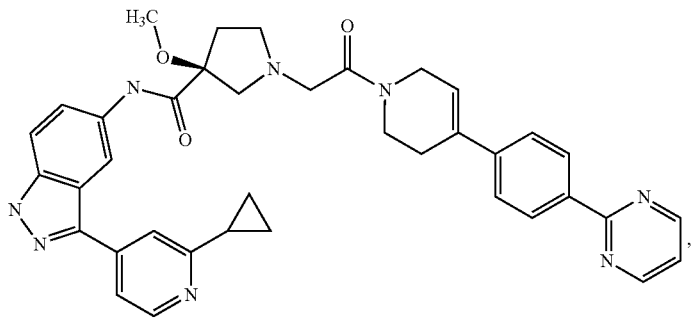
(Ex. 459)
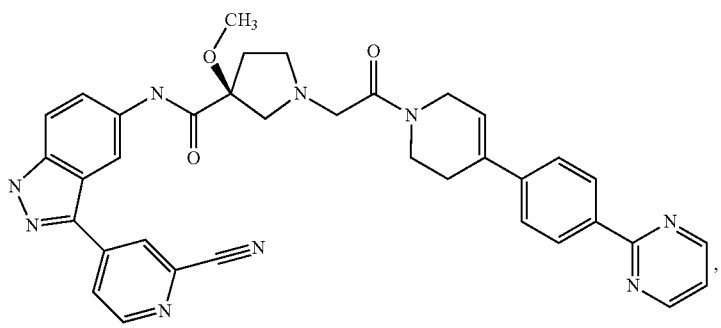
(Ex. 460)

1113                                                1114
-continued
(Ex. 461)
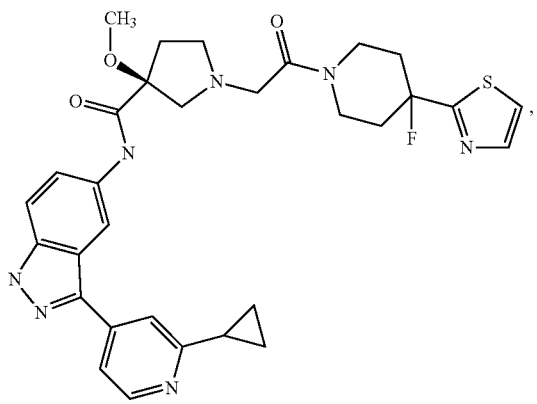
(Ex. 465)
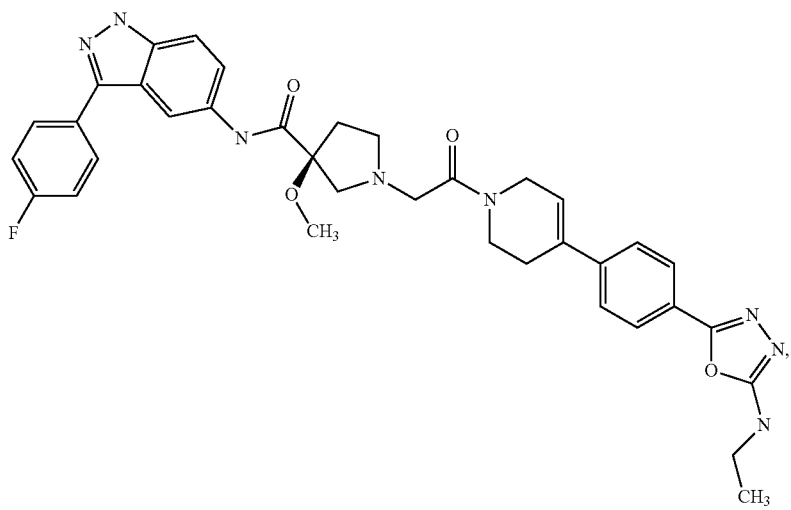
(Ex. 467)
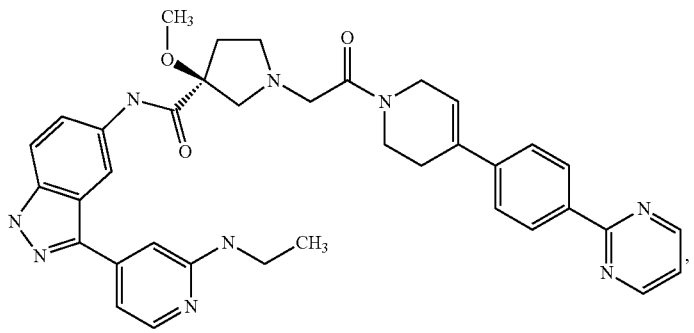
(Ex. 469)
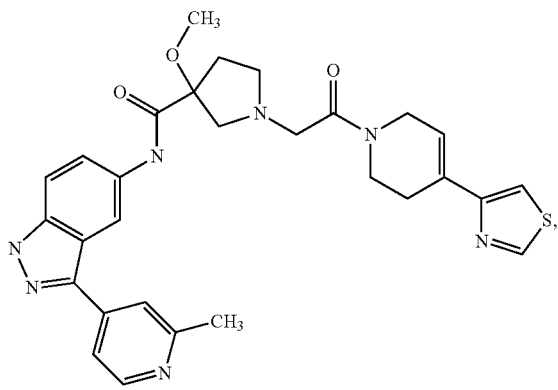

1115
-continued
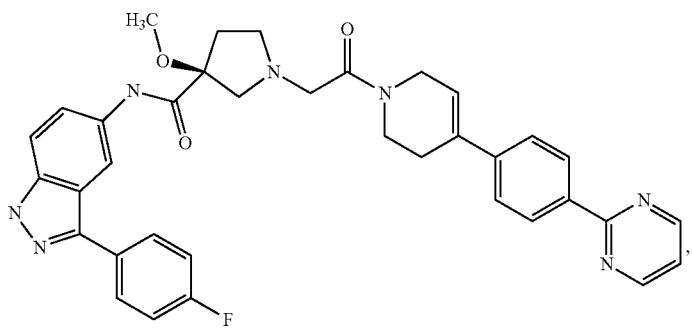
(Ex. 470)
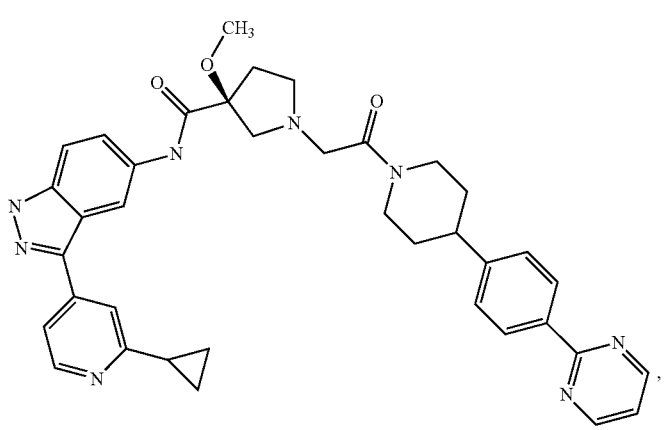
(Ex. 473)
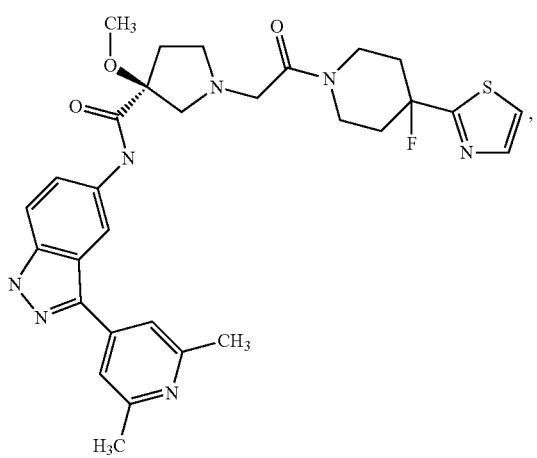
(Ex. 474)
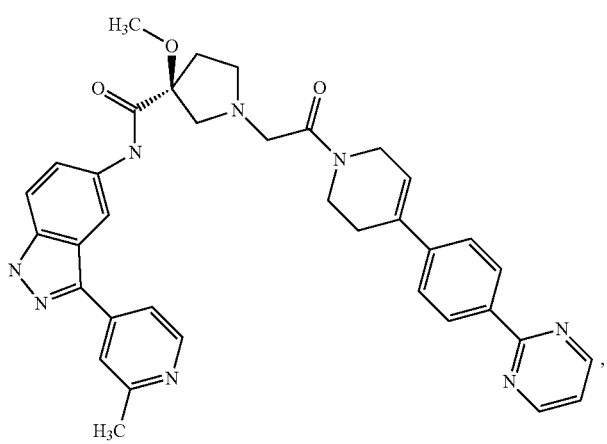
(Ex. 477)

-continued
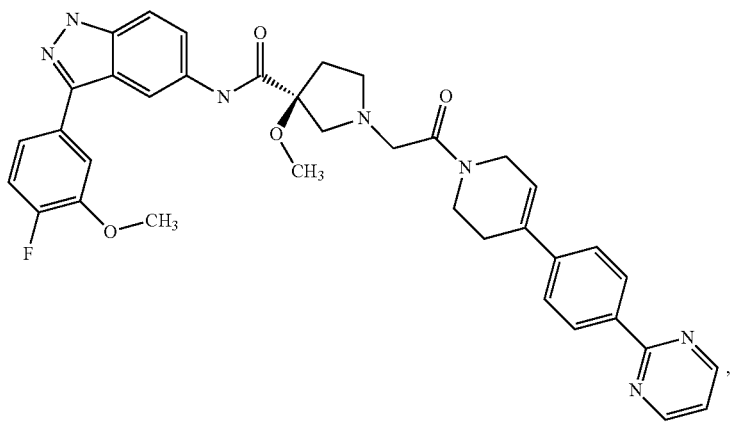
(Ex. 478)
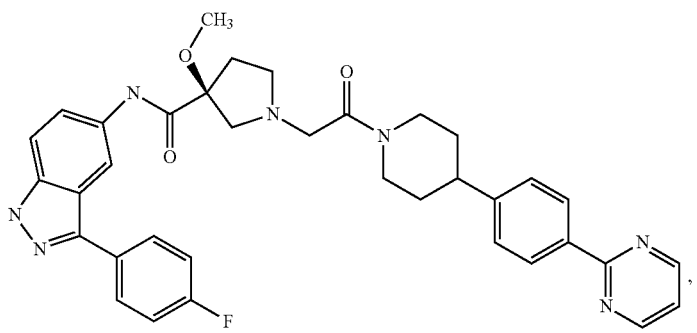
(Ex. 479)
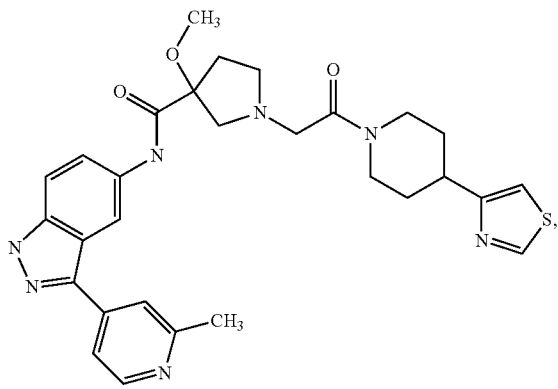
(Ex. 481)
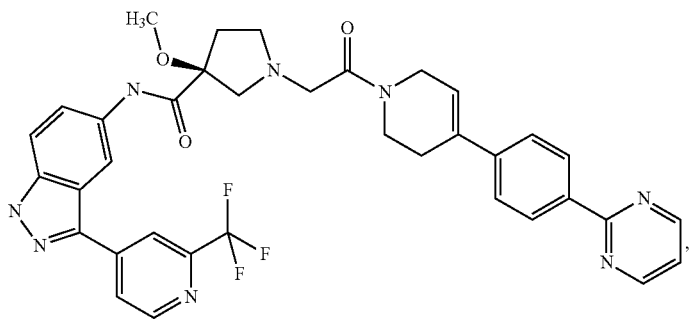
(Ex. 483)

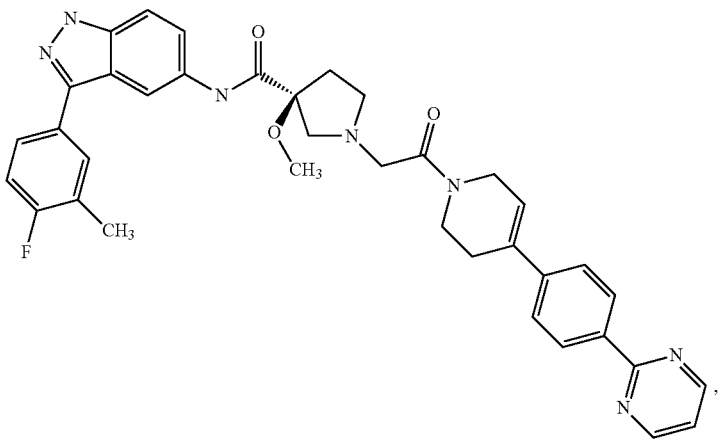
(Ex. 484)
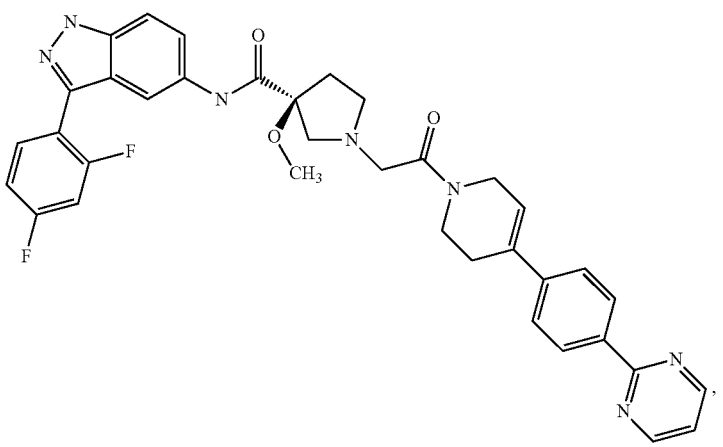
(Ex. 486)
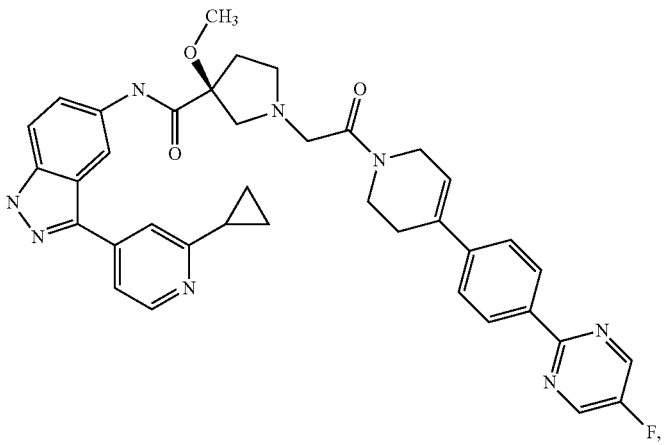
(Ex. 488)
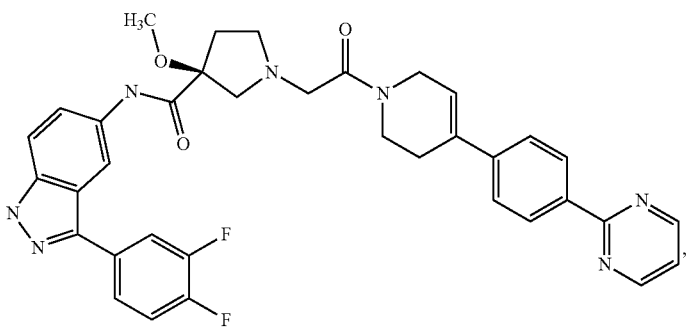
(Ex. 489)

1121
-continued
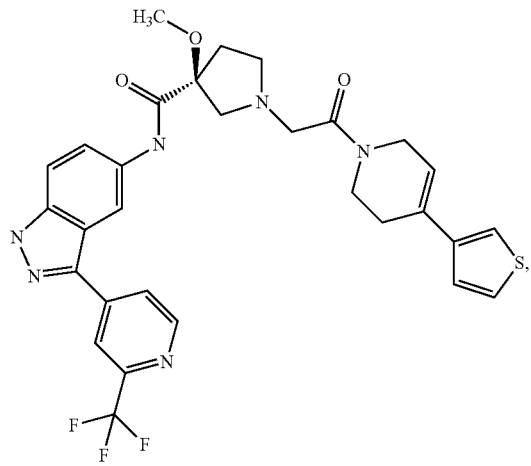
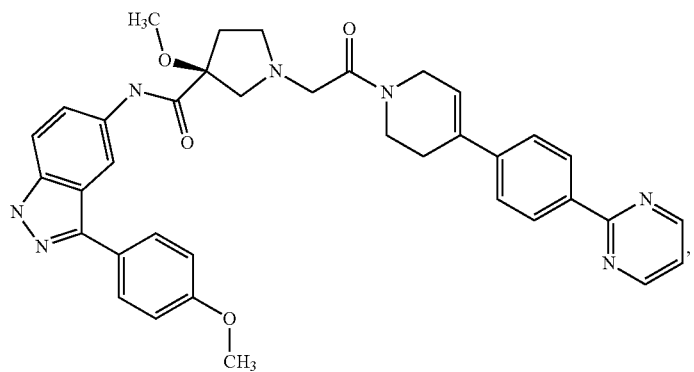
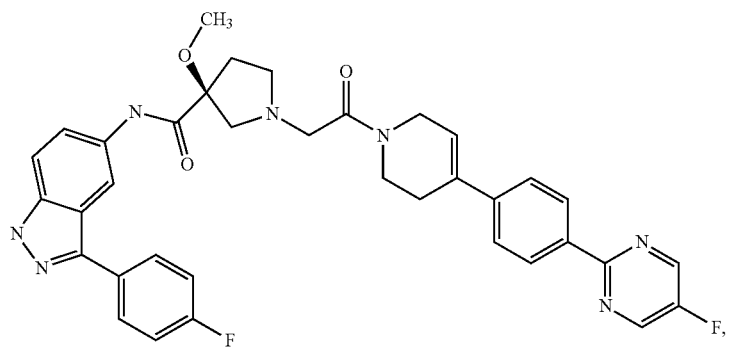
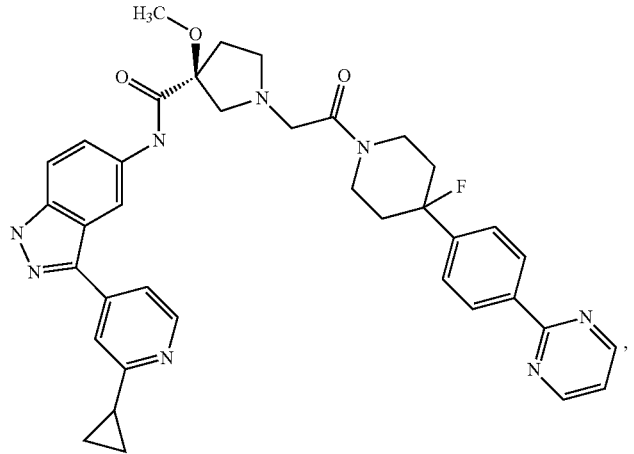
1122
(Ex. 490)
(Ex. 492)
(Ex. 495)
(Ex. 497)

(Ex. 500)
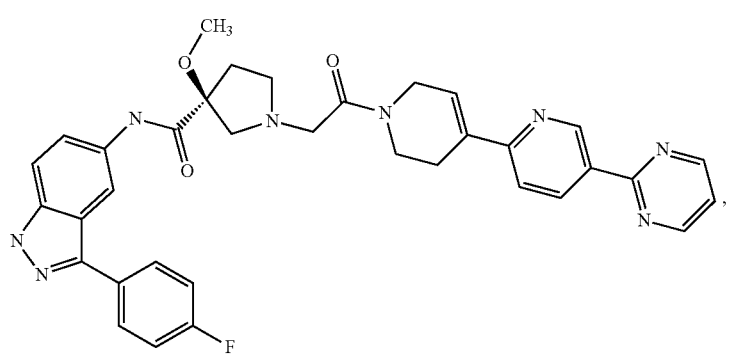
(Ex. 502)
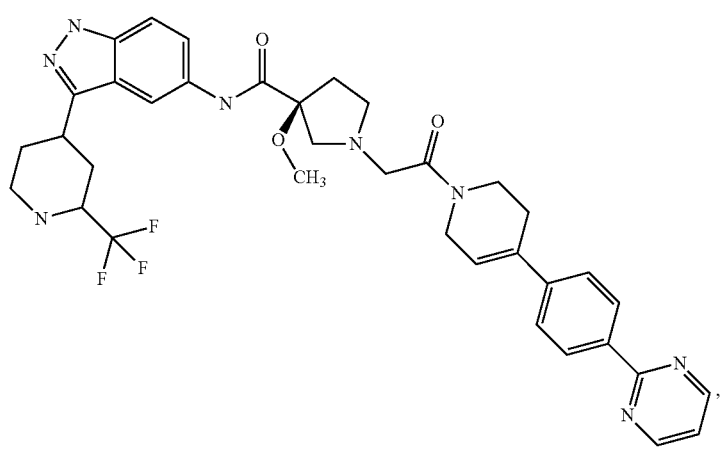
(Ex. 504)
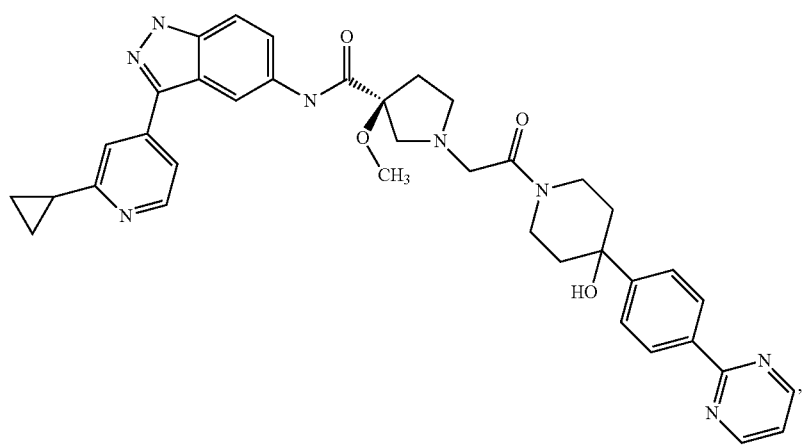

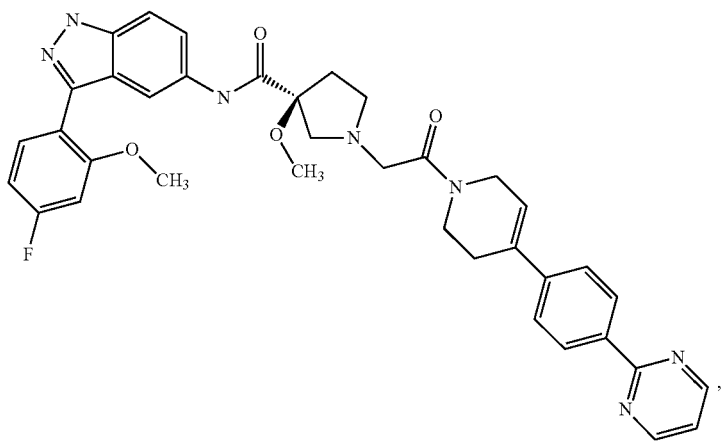
(Ex. 505)
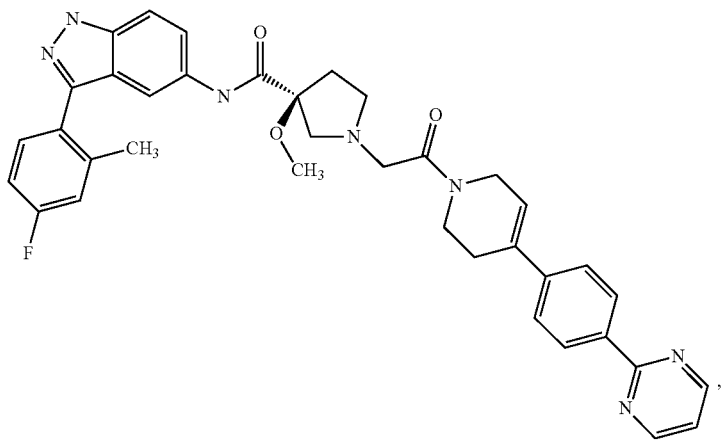
(Ex. 507)
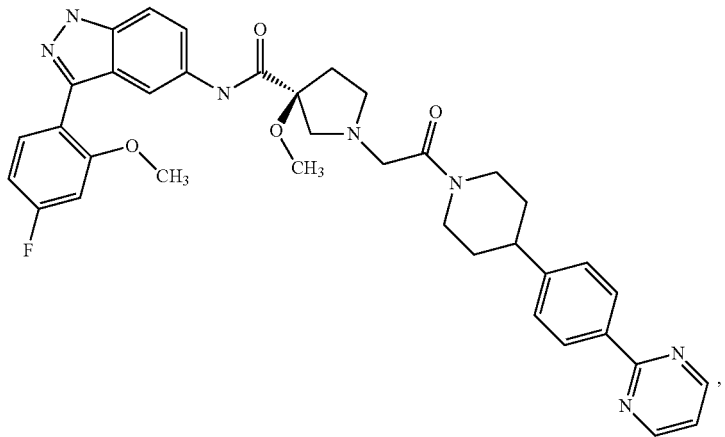
(Ex. 508)

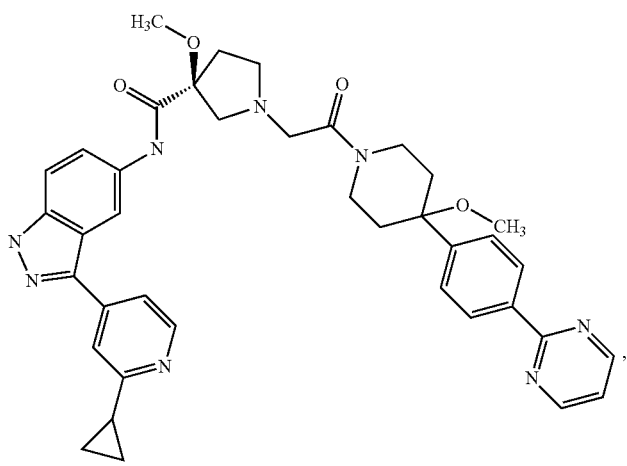
(Ex. 509)
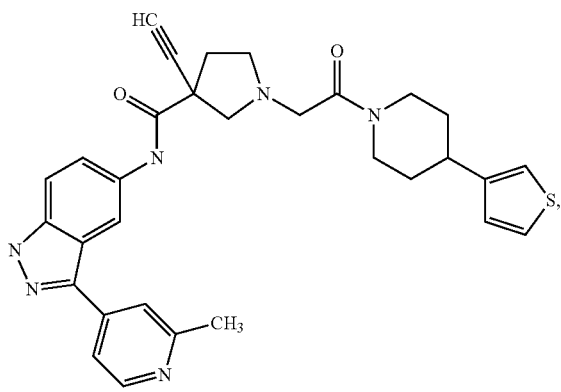
(Ex. 511)
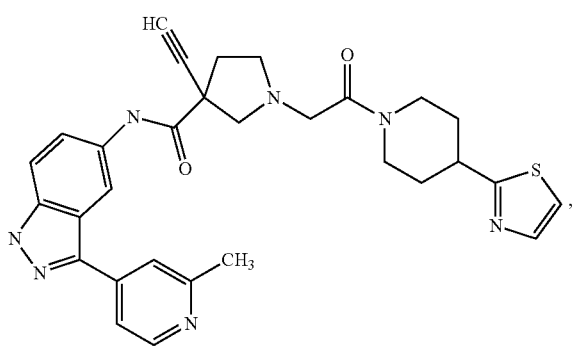
(Ex. 512)
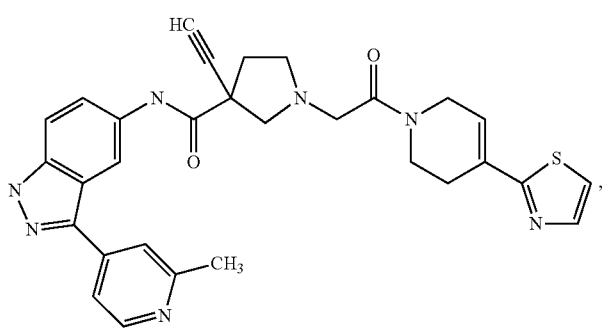
(Ex. 513)

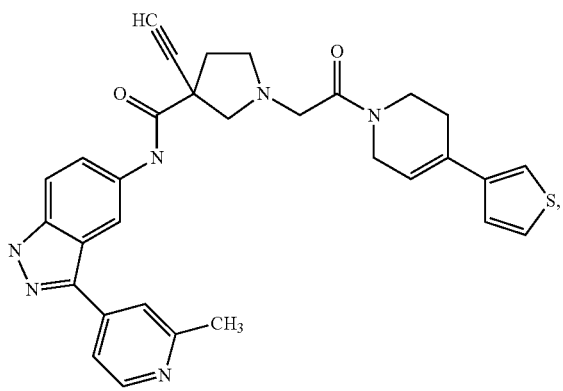
(Ex. 514)
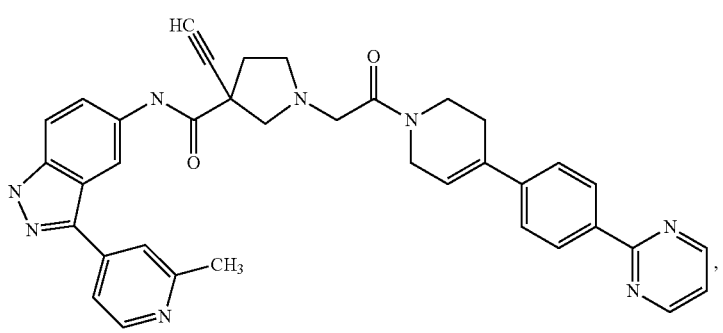
(Ex. 519)
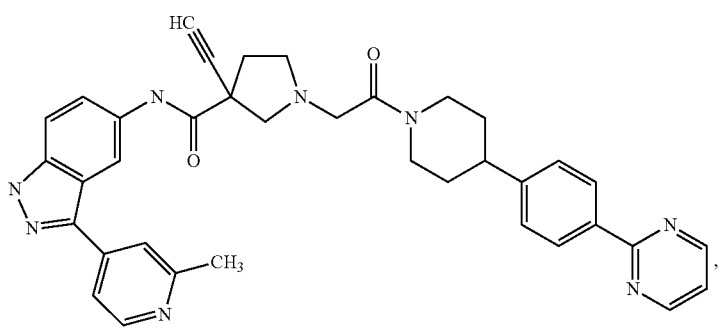
(Ex. 529)
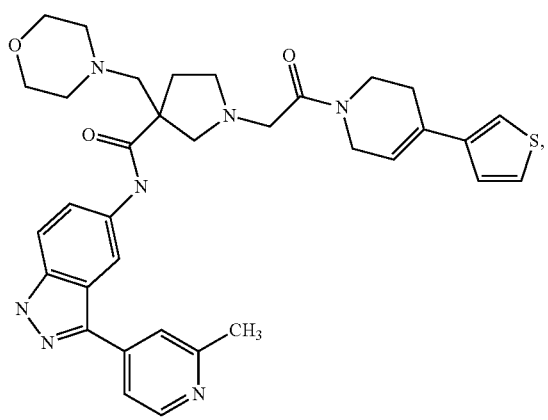
(Ex. 535)

| 1131 | 1132 |
|---|---|
| -continued | |
| 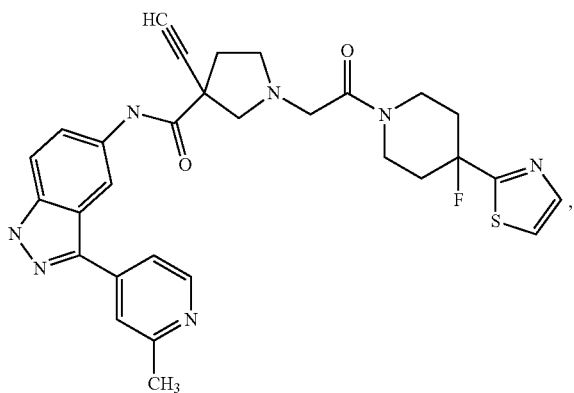 | (Ex. 537) |
| 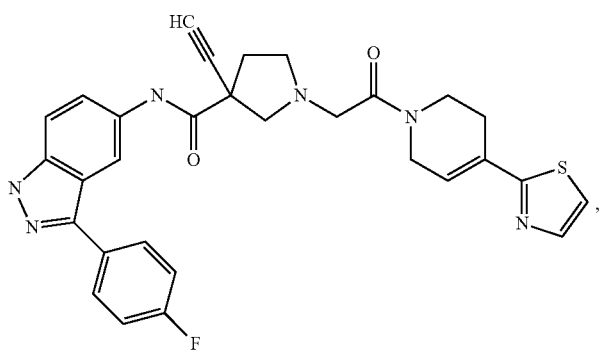 | (Ex. 541) |
| 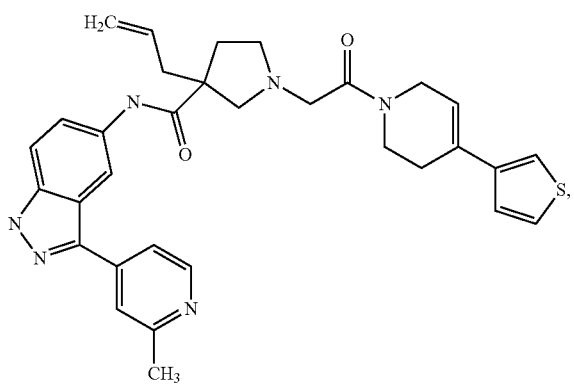 | (Ex. 545) |
| 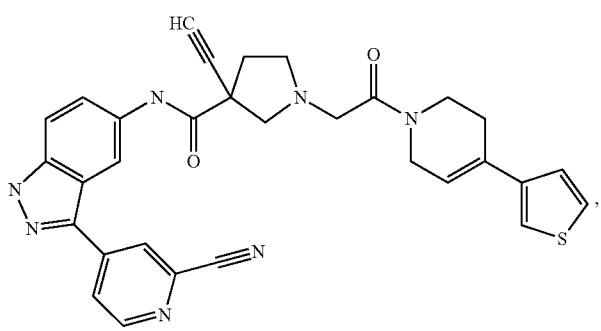 | (Ex. 546) |

1133 1134
-continued
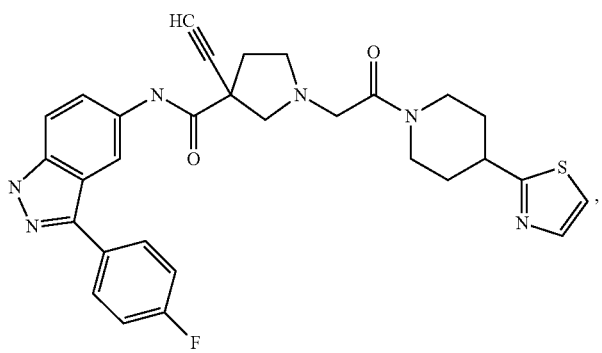
(Ex. 549)
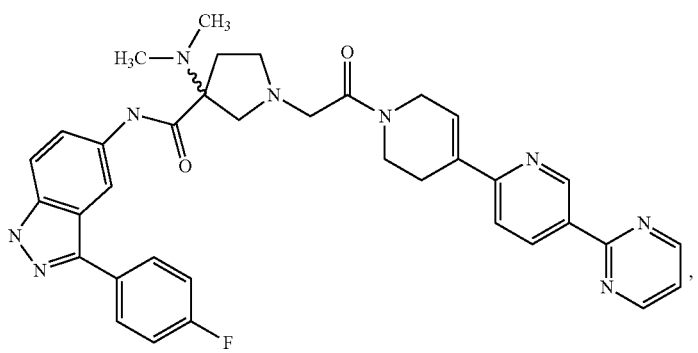
(Ex. 550)
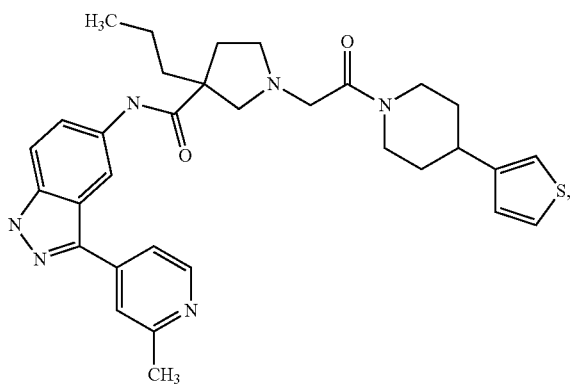
(Ex. 553)
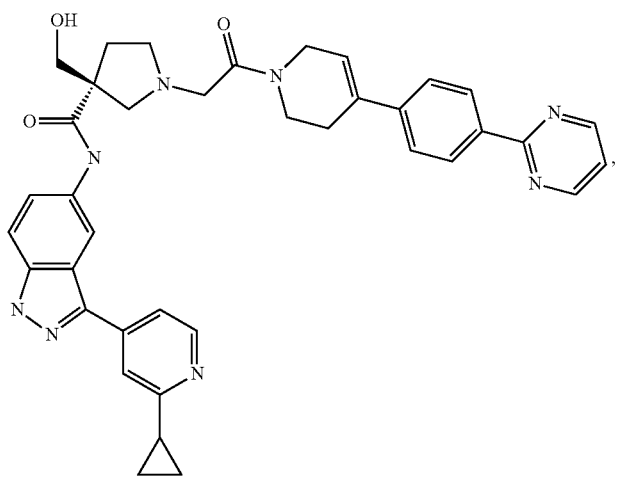
(Ex. 554)

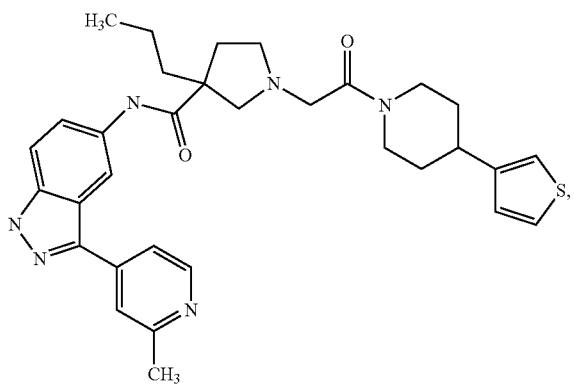
(Ex. 557)
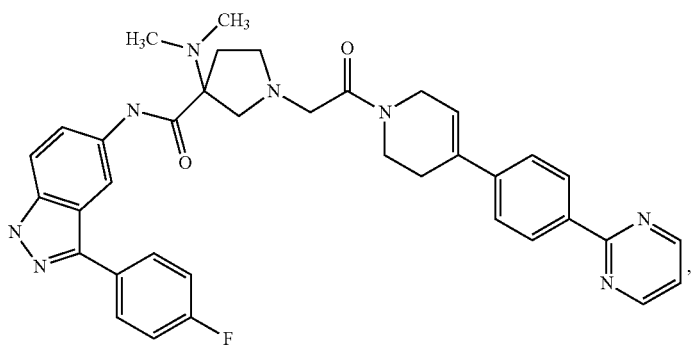
(Ex. 564)
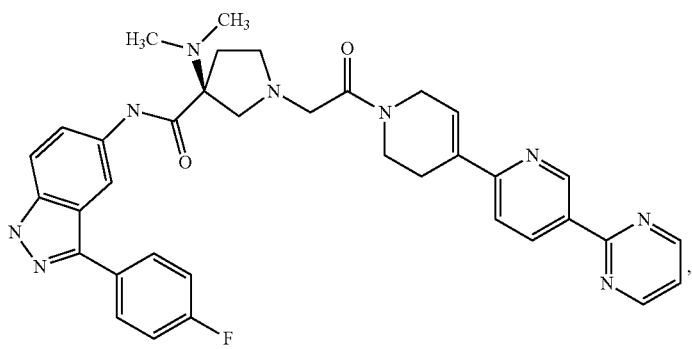
(Ex. 565)
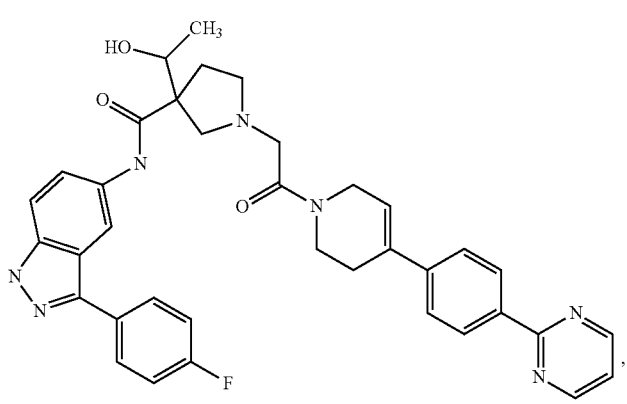
(Ex. 567)

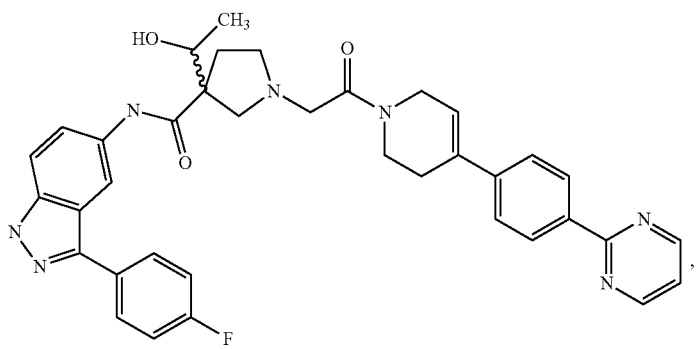
(Ex. 569)
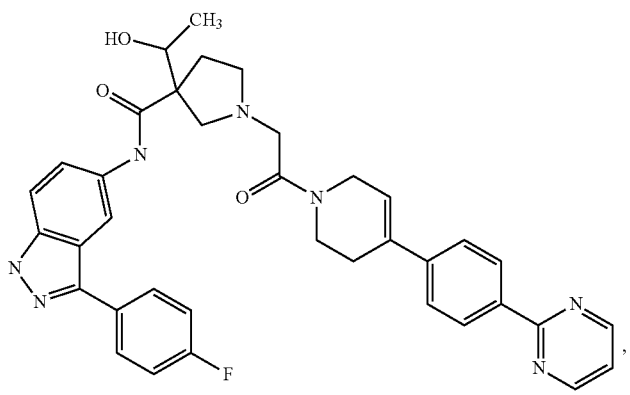
(Ex. 572)
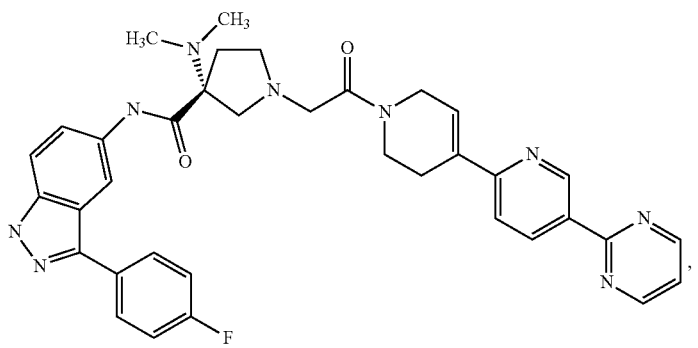
(Ex. 574)
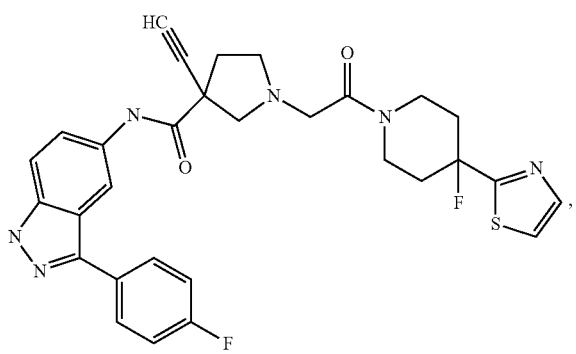
(Ex. 582)

-continued
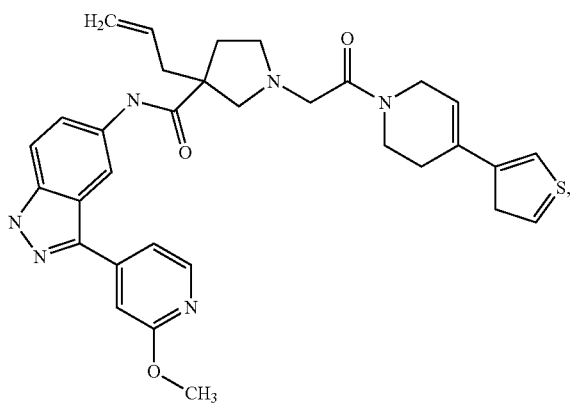 (Ex. 583)
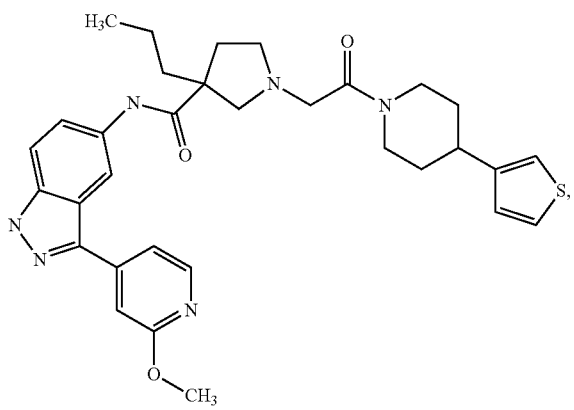 (Ex. 584)
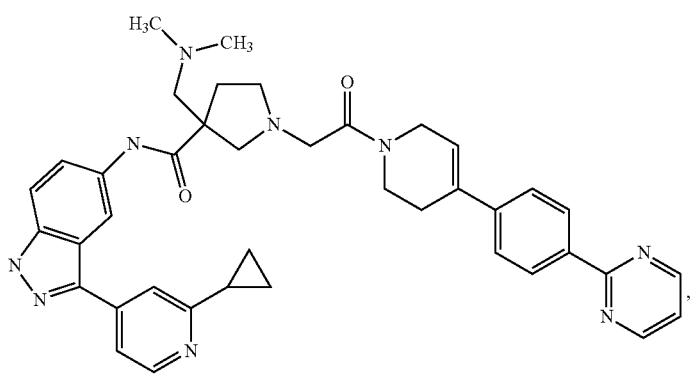 (Ex. 585)
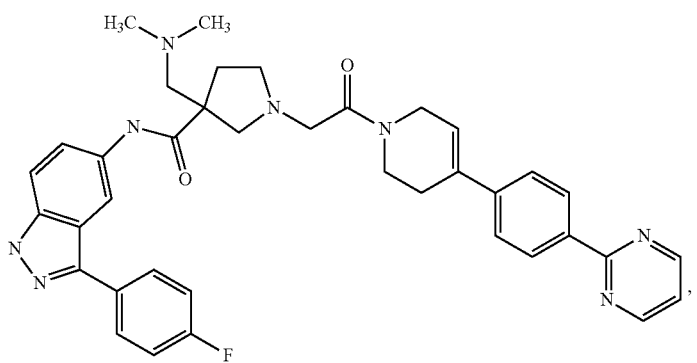 (Ex. 589)

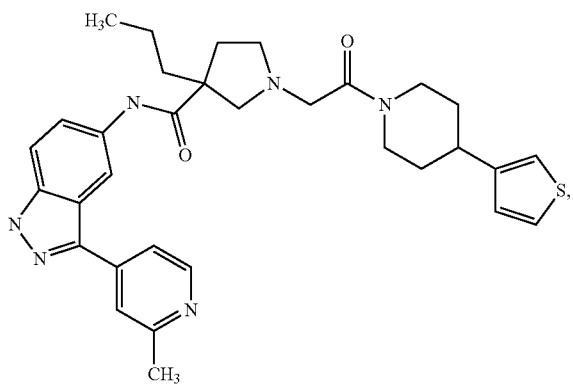
(Ex. 593)
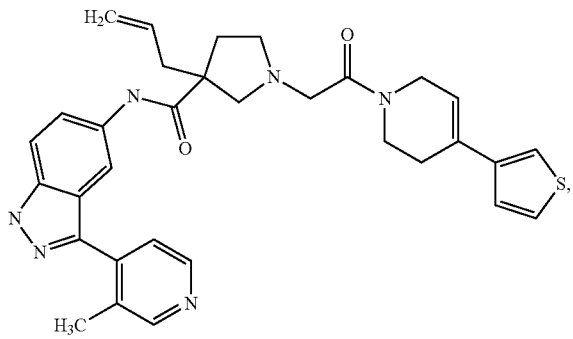
(Ex. 594)
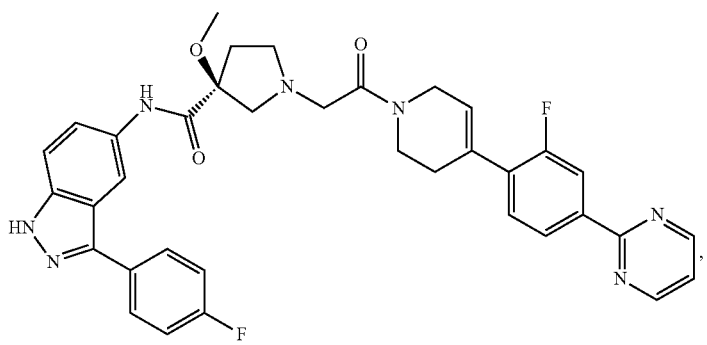
(Ex. 606)
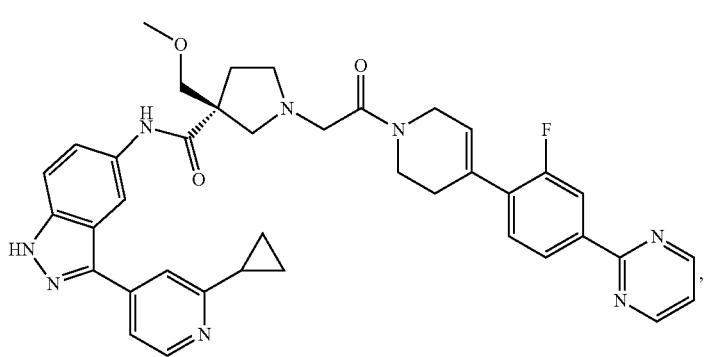
(Ex. 607)

(Ex. 609)
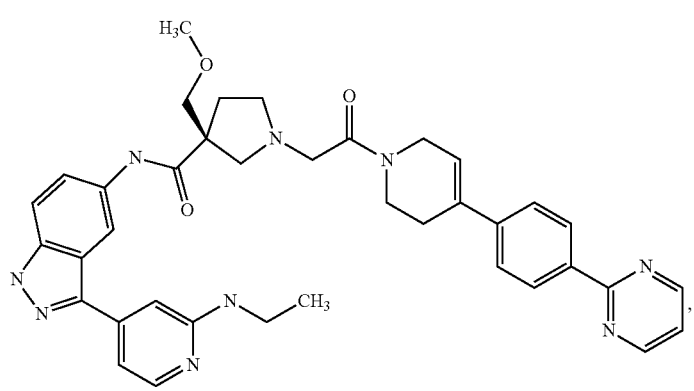
(Ex. 610)
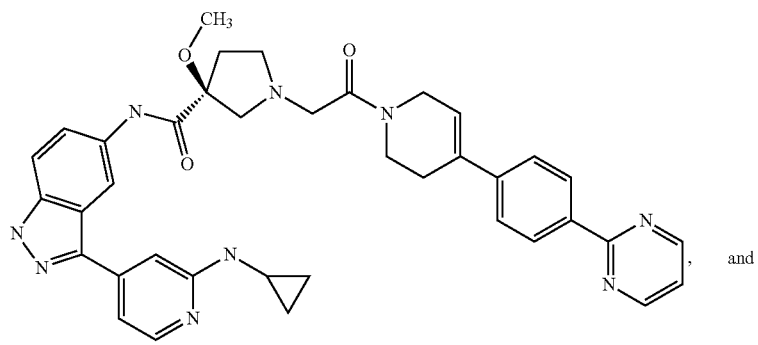
and
(Ex. 611)
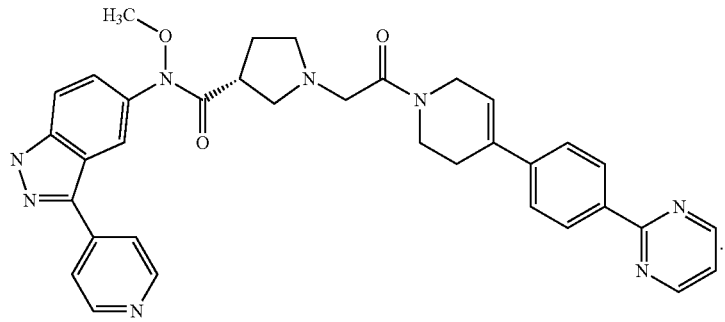
63. The compound of claim 1 selected from the group consisting of:
(EX. 440)
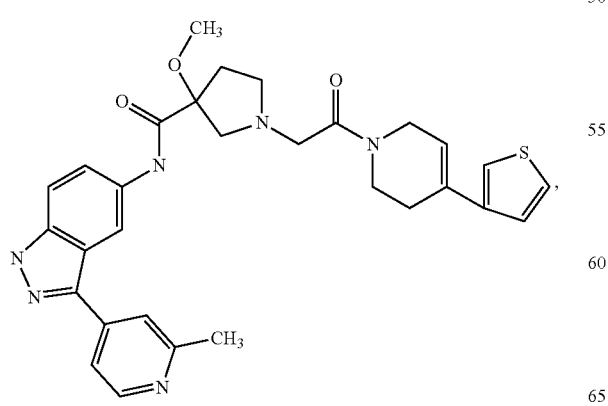
(Ex. 444)
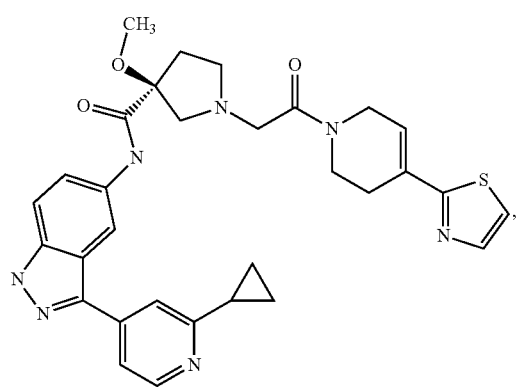

1145
-continued
(Ex. 445)
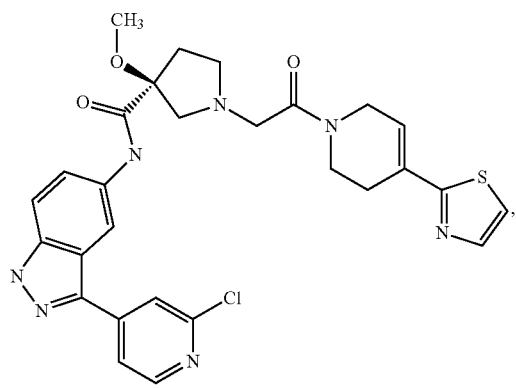
(Ex. 449)
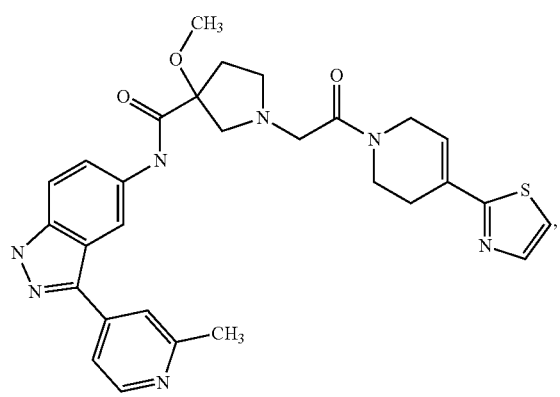
(Ex. 450)
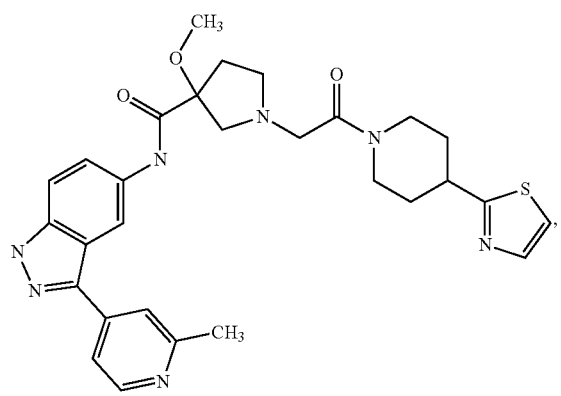
(Ex. 510)
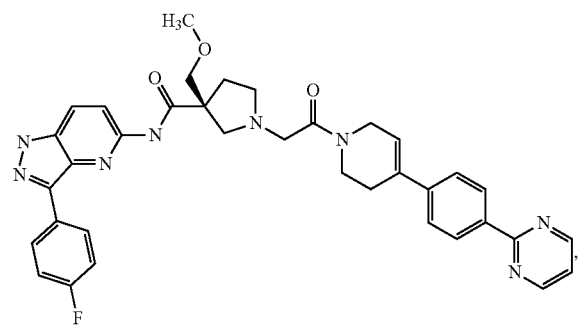
1146
-continued
(Ex. 511)
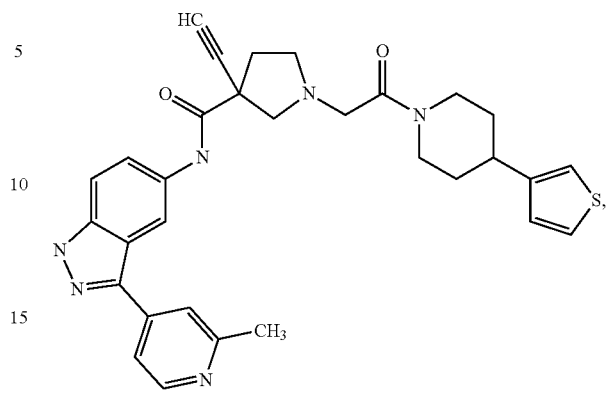
(Ex. 512)
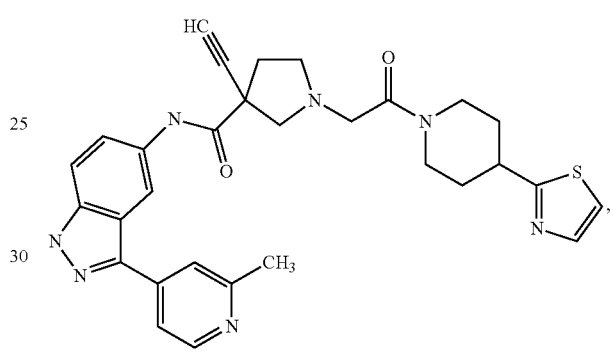
(Ex. 513)
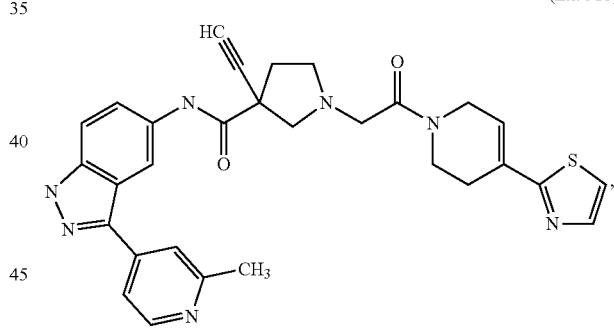
and
(Ex. 514)
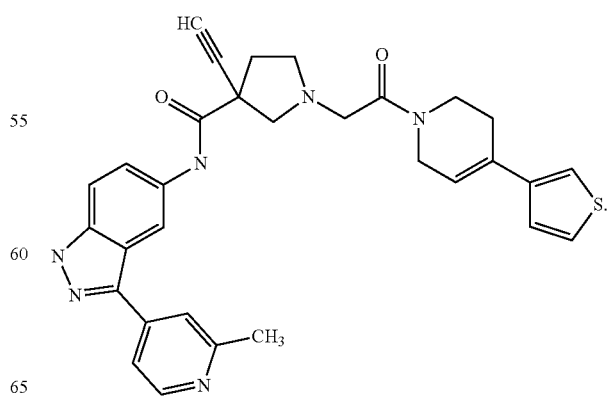

64. The compound of claim 1 selected from the group consisting of:
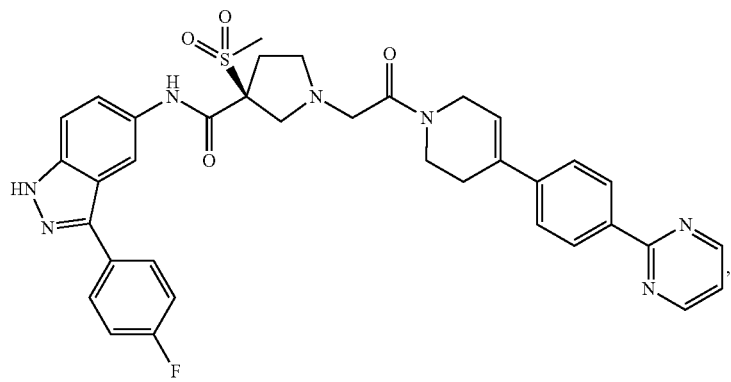
(Ex. 612)
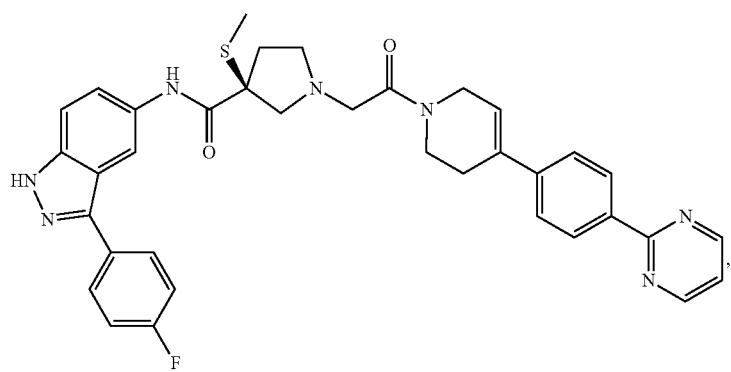
(Ex. 613)
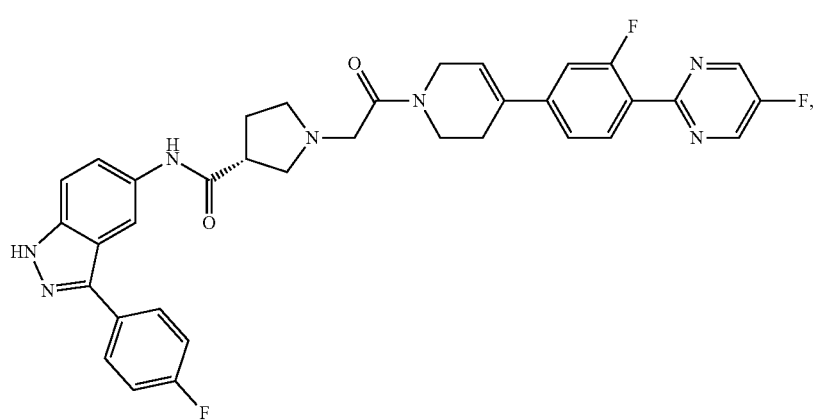
(Ex. 617)

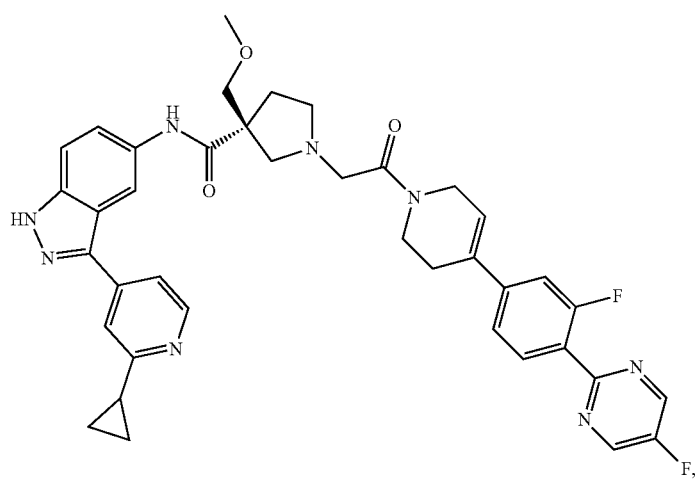
(Ex. 618)
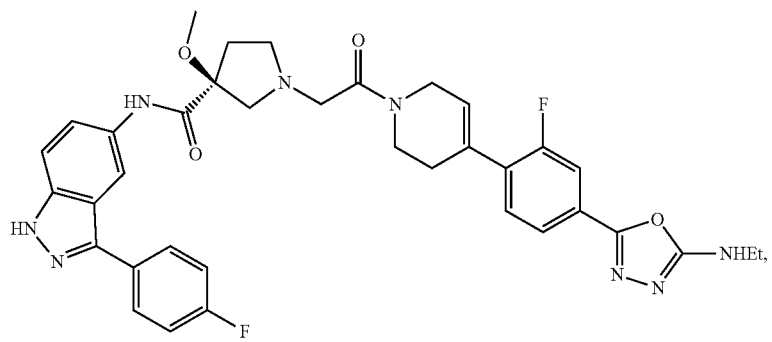
(Ex. 622)
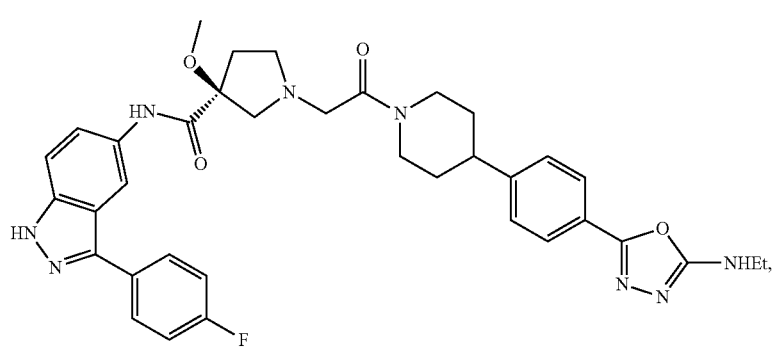
(Ex. 623)
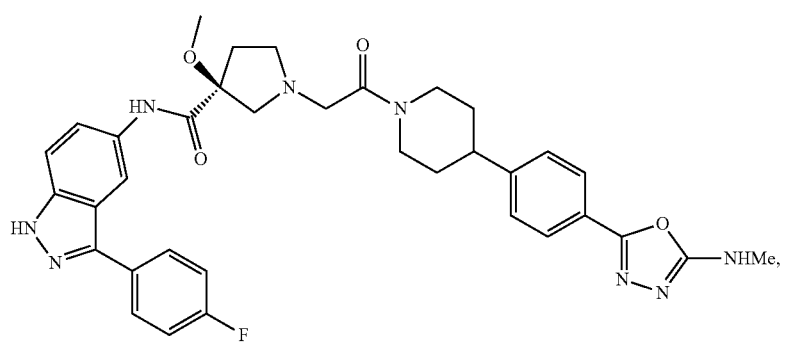
(Ex. 624)

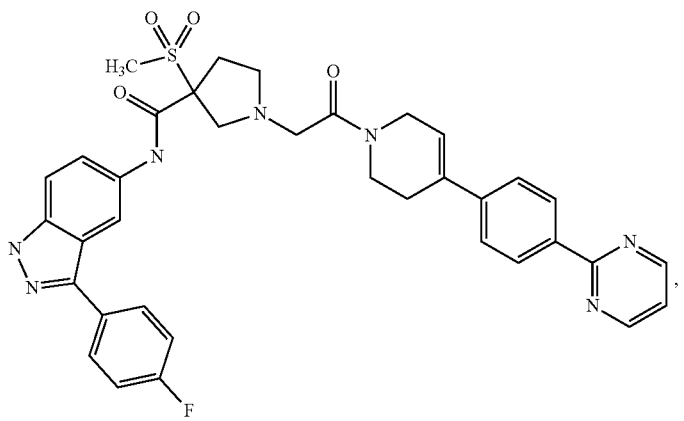
(Ex. 626)
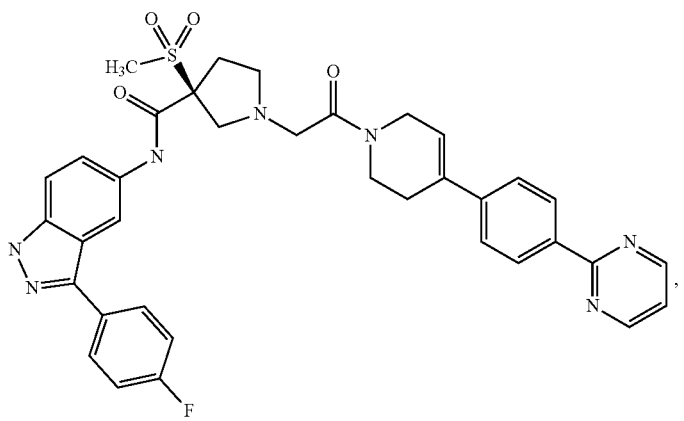
(Ex. 627)
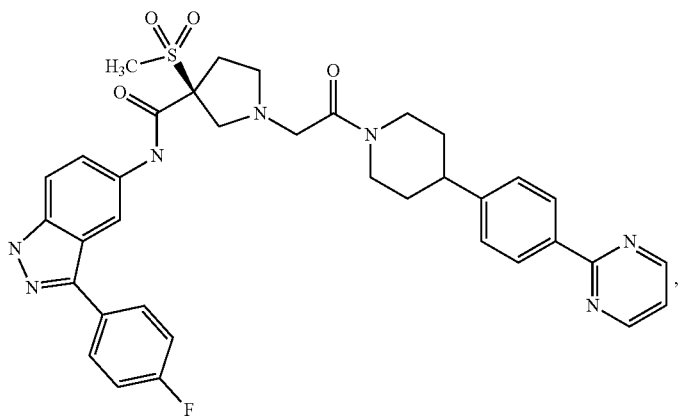
(Ex. 629)

(Ex. 631)
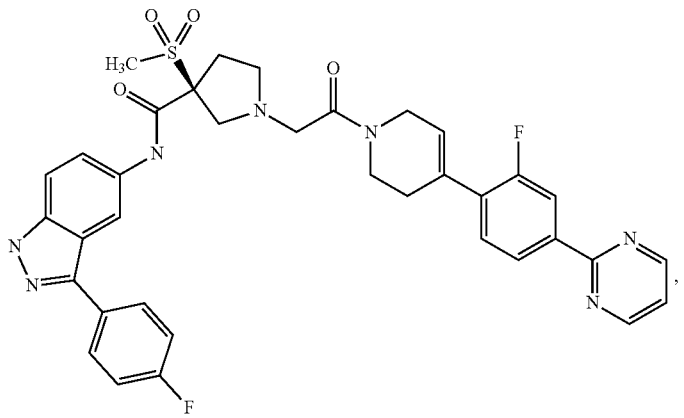
(Ex. 632)
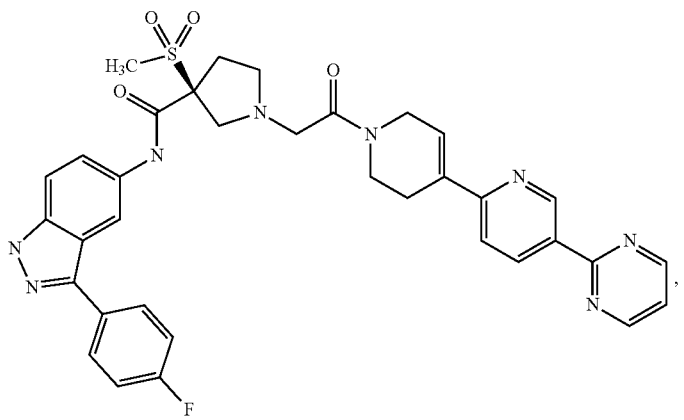
(Ex. 633)
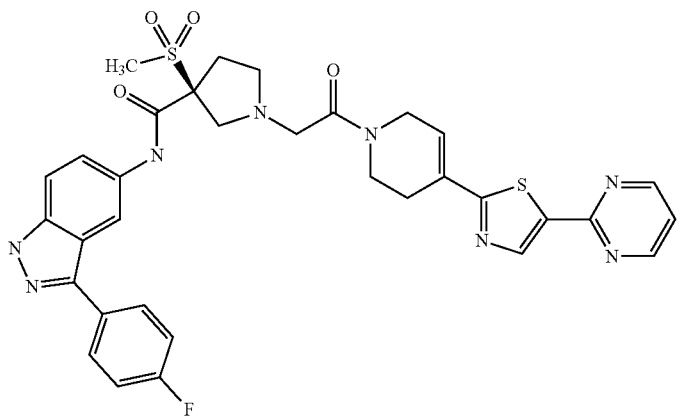
(Ex. 634)
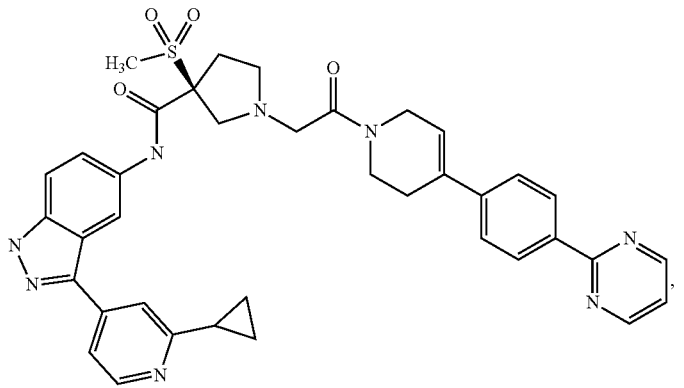

-continued
(Ex. 635)
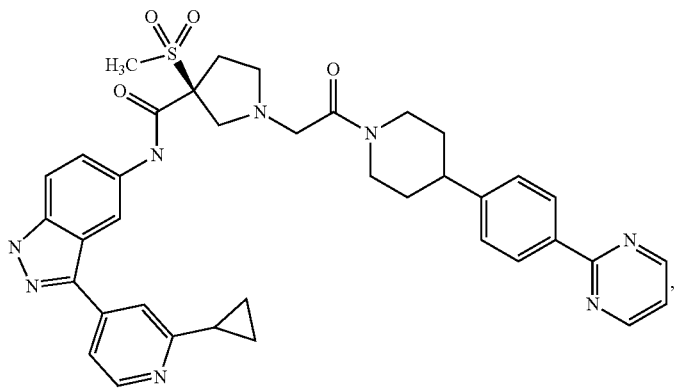
(Ex. 636)
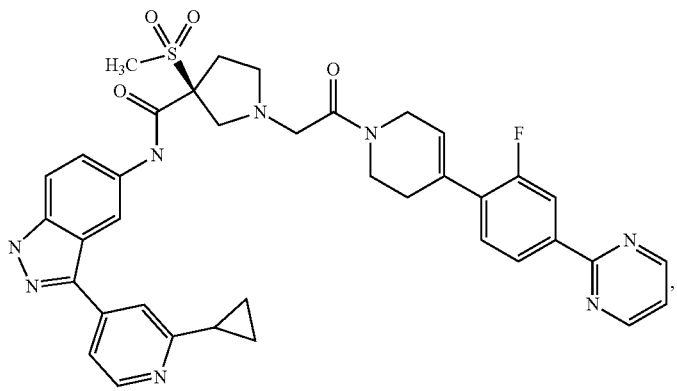
(Ex. 638)
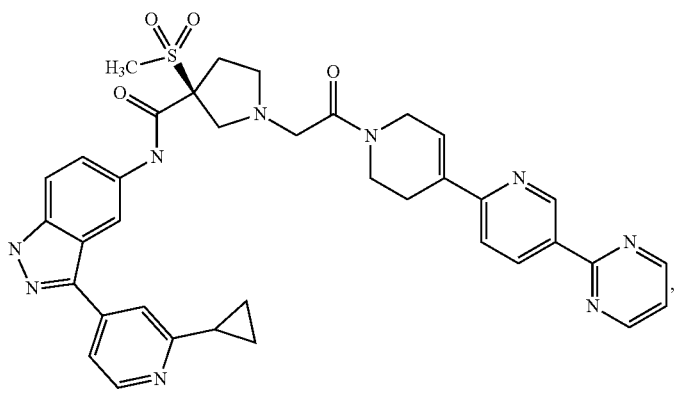
(Ex. 639)
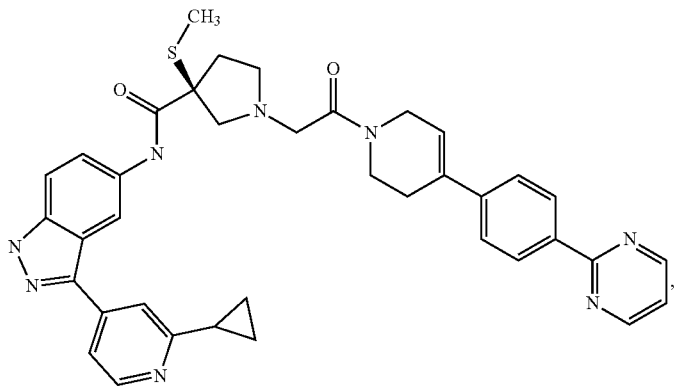

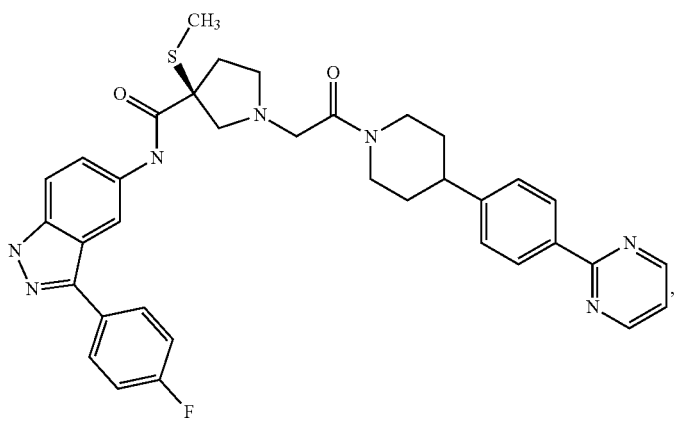
(Ex. 640)
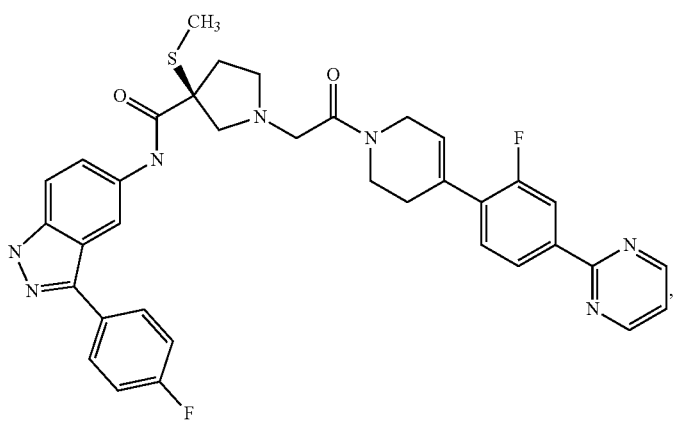
(Ex. 642)
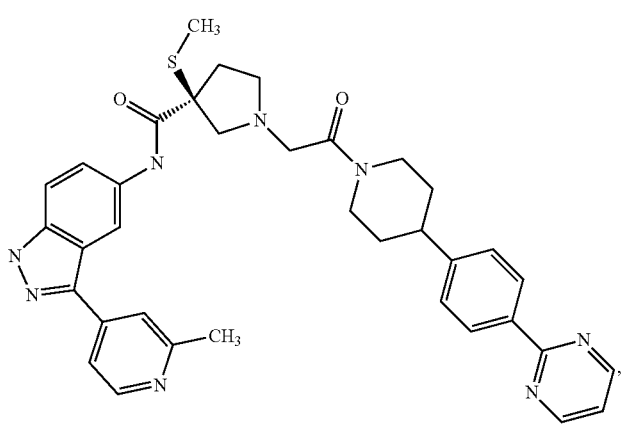
(Ex. 643)

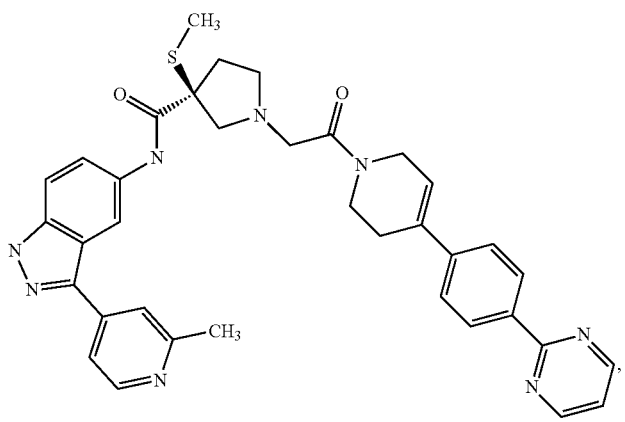
(Ex. 644)
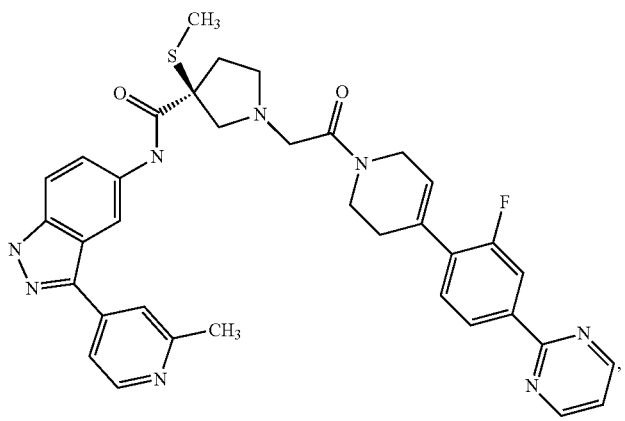
(Ex. 645)
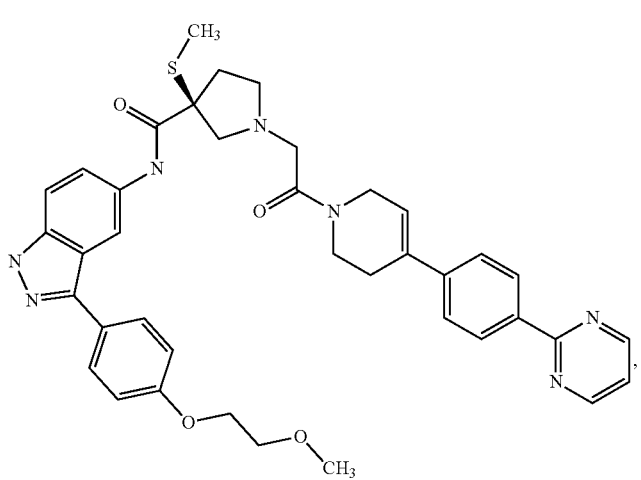
(Ex. 646)

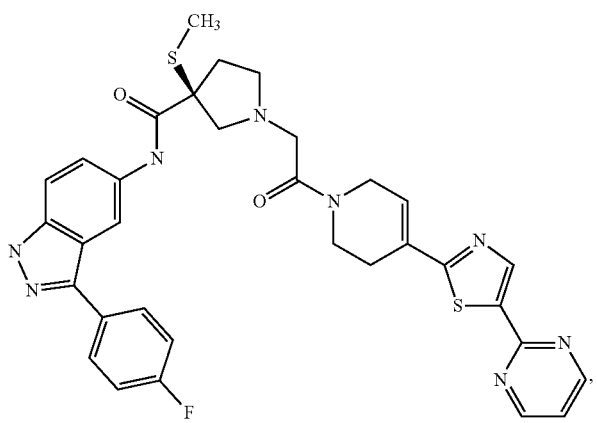
(Ex. 648)
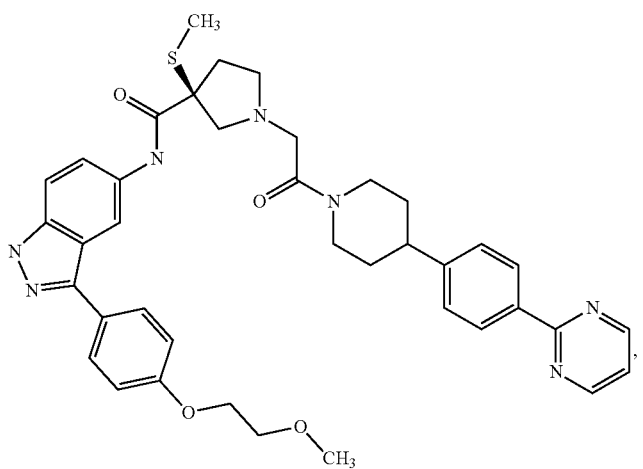
(Ex. 649)
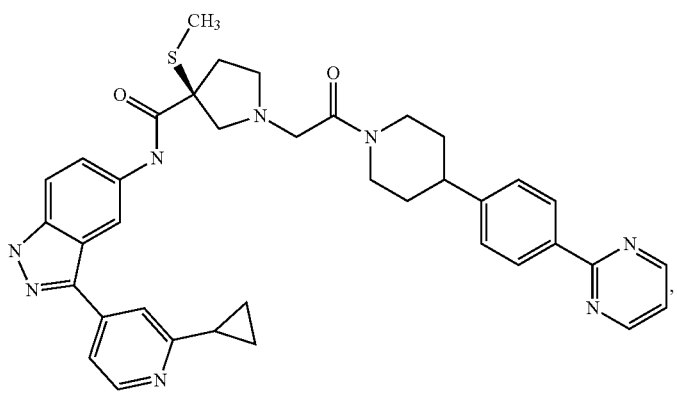
(Ex. 650)

-continued
(Ex. 651)
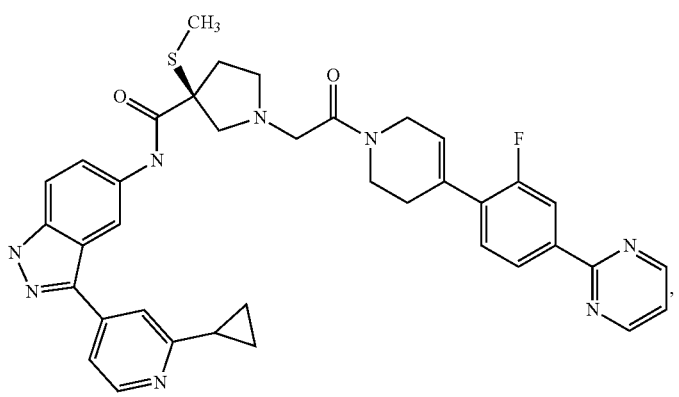
(Ex. 653)
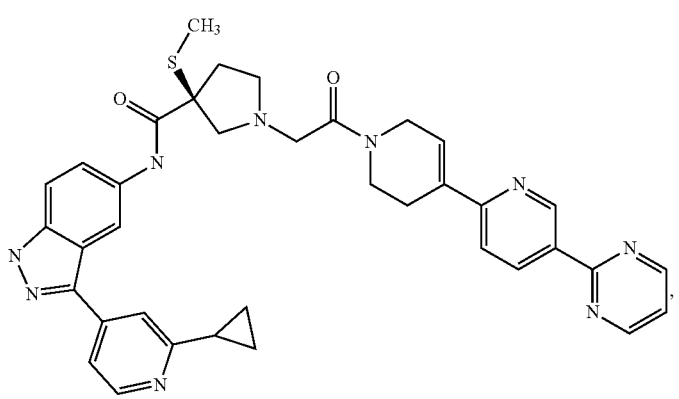
(Ex. 655)
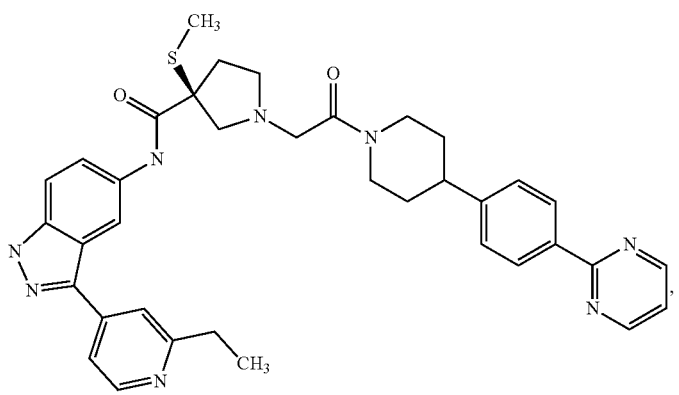
(Ex. 656)
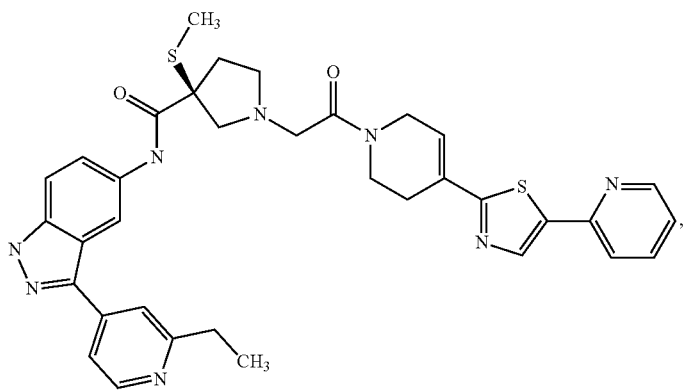

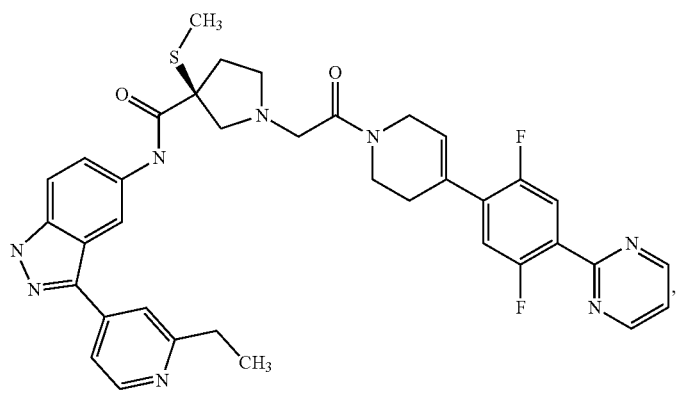
(Ex. 657)
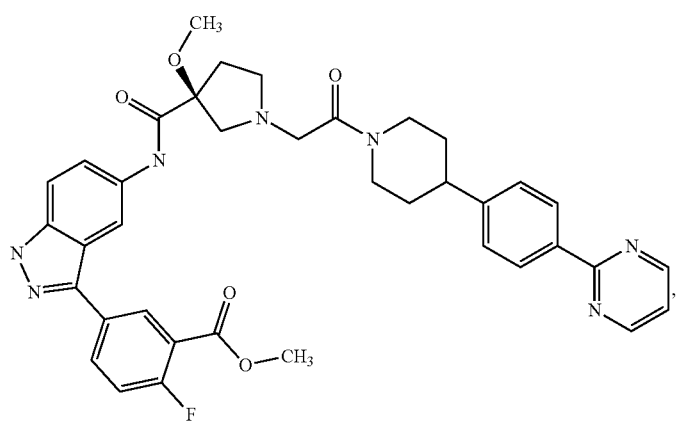
(Ex. 658)
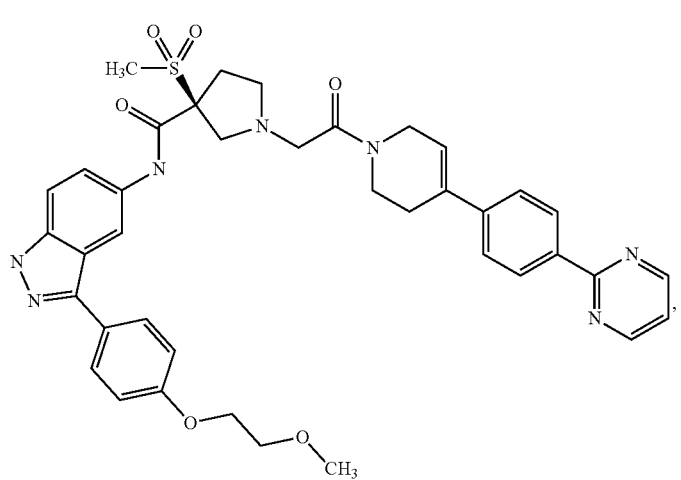
(Ex. 659)

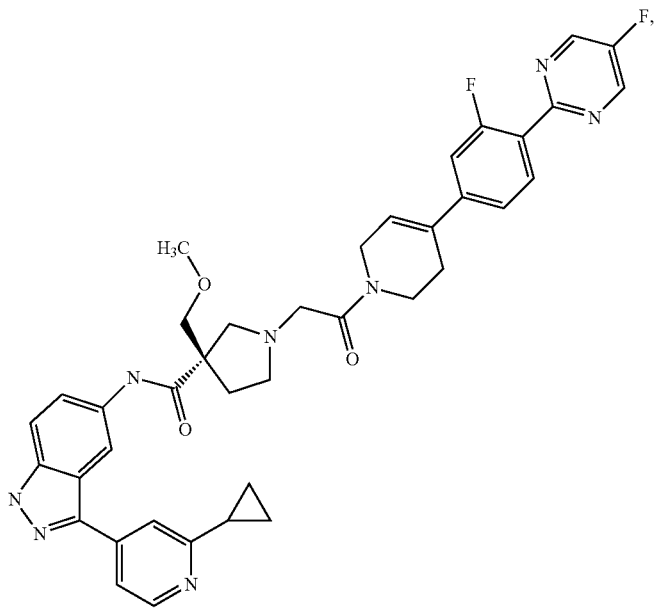
(Ex. 660)
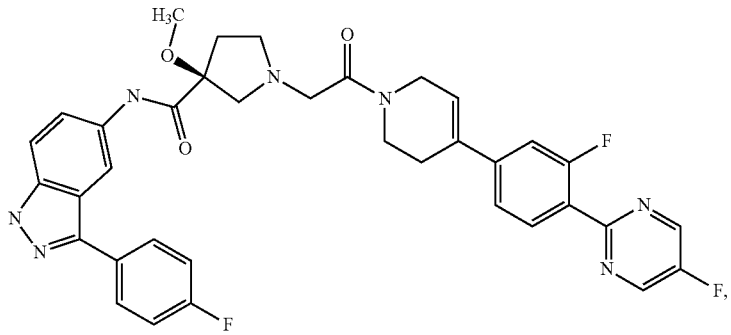
(Ex. 661)
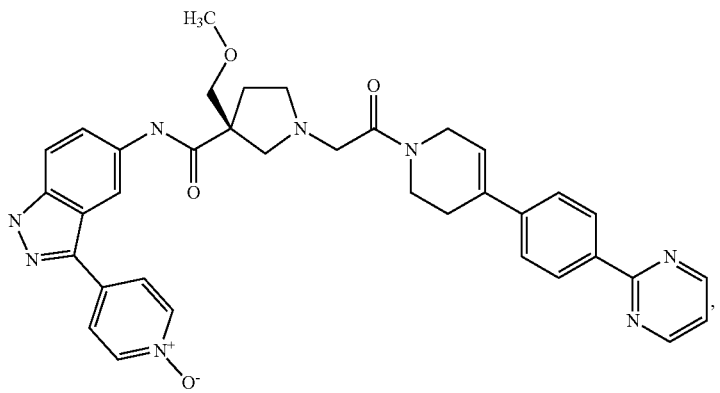
(Ex. 665)

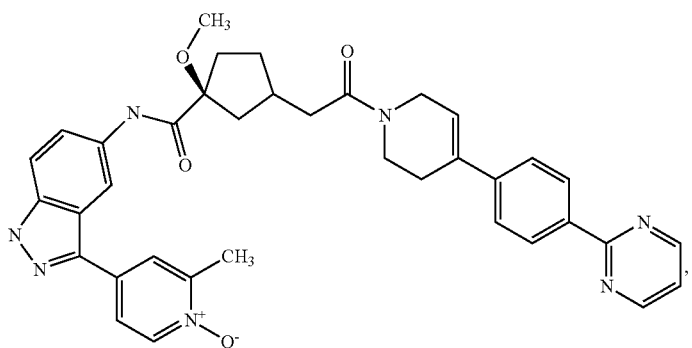
(Ex. 666)
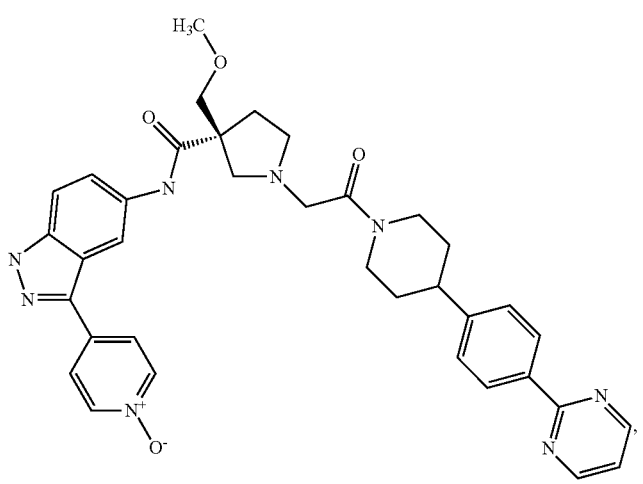
(Ex. 668)
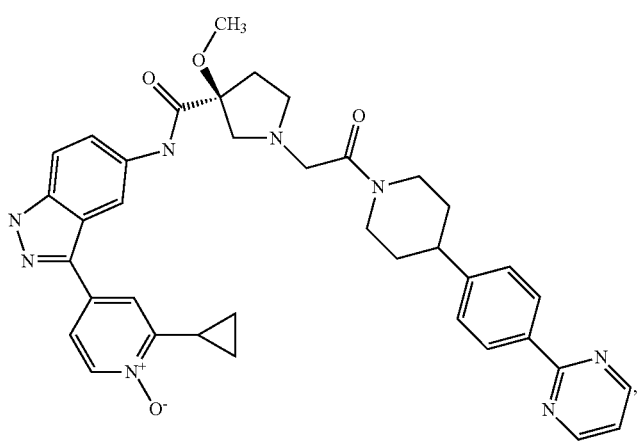
(Ex. 669)

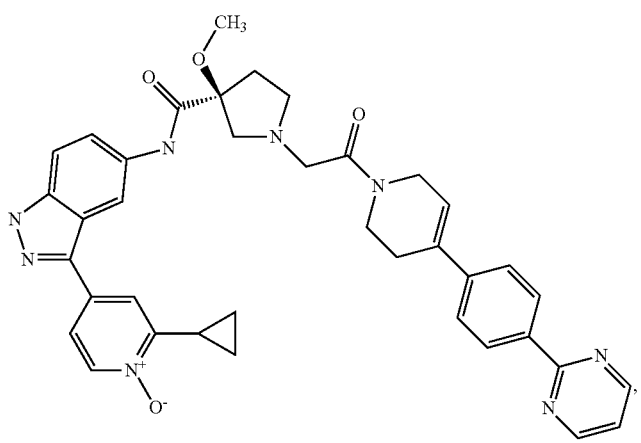
(Ex. 670)
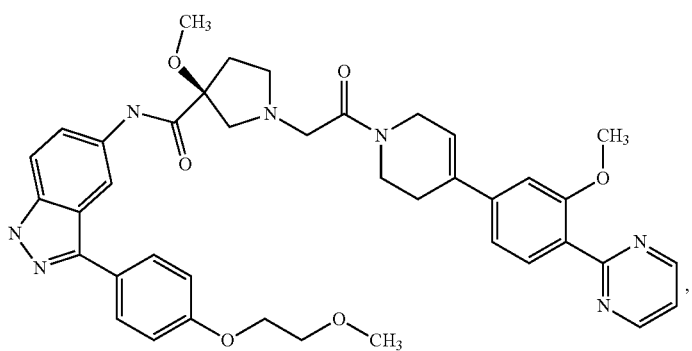
(Ex. 671)
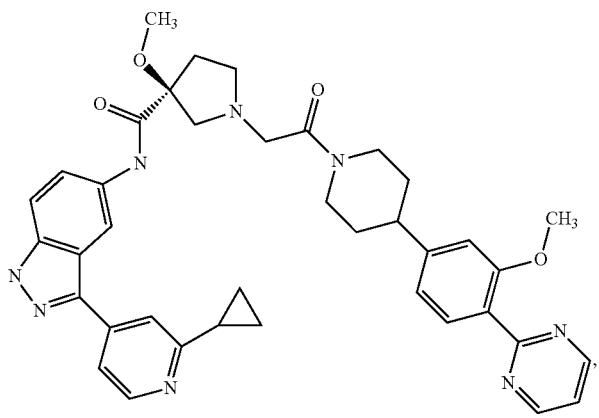
(Ex. 672)
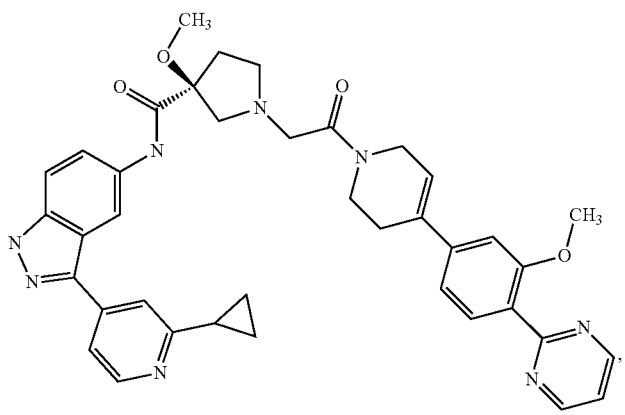
(Ex. 673)

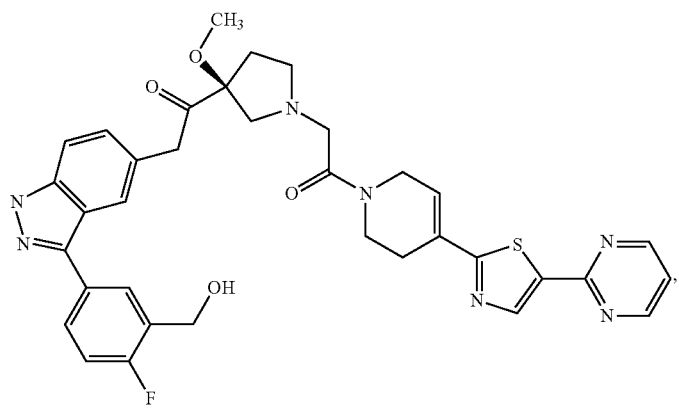
(Ex. 674)
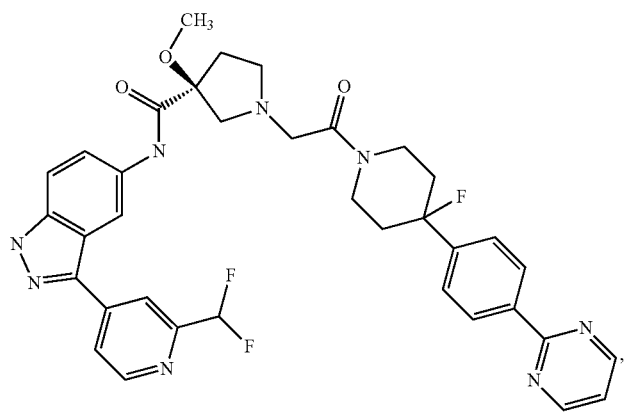
(Ex. 675)
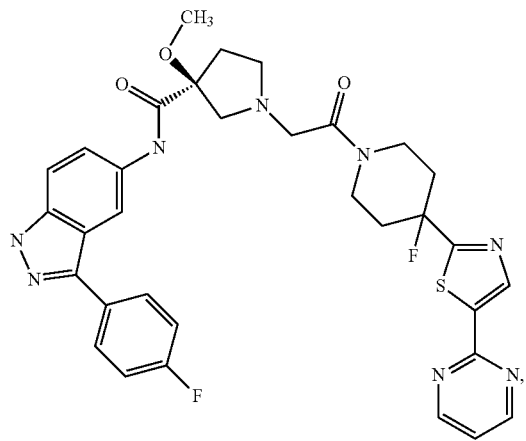
(Ex. 676)

-continued
(Ex. 677)
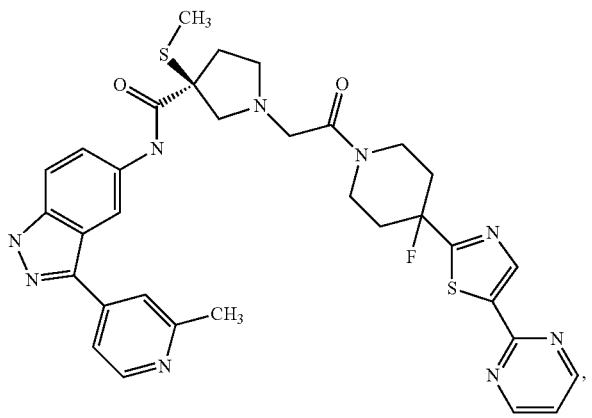
(Ex. 678)
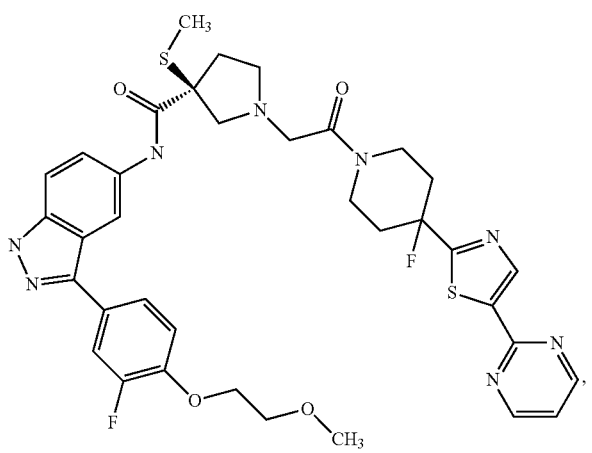
(Ex. 679)
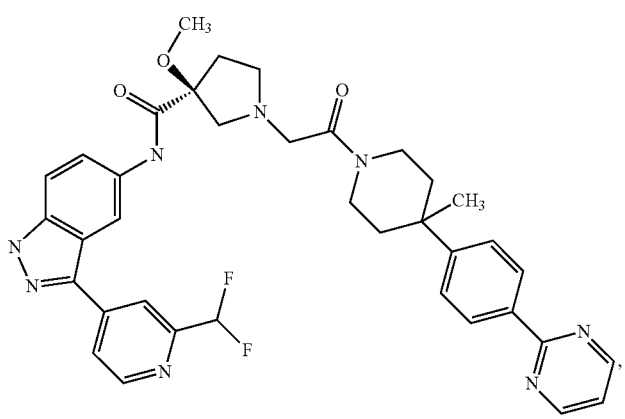

(Ex. 680)
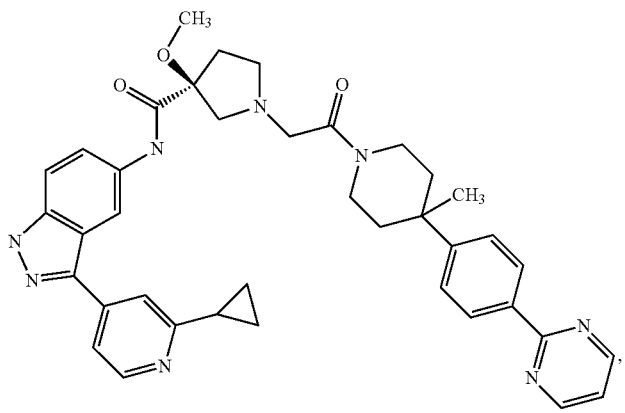
(Ex. 681)
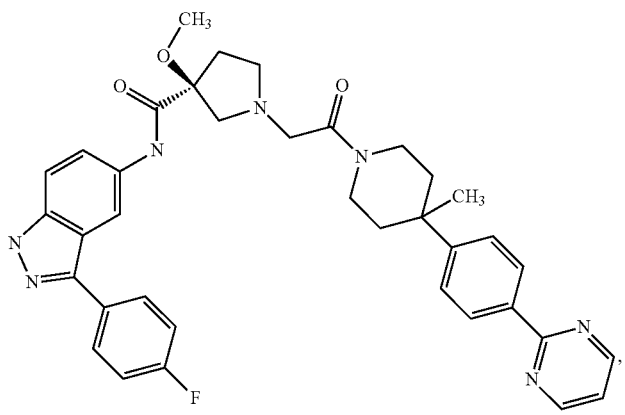
(Ex. 682)
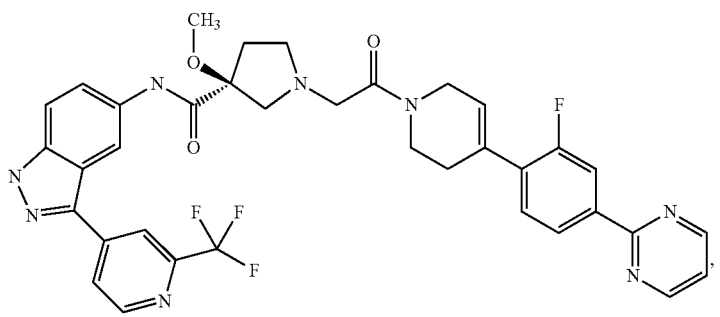
(Ex. 683)
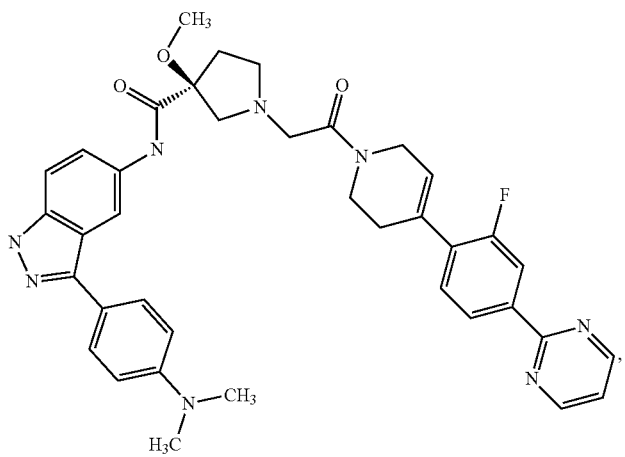

(Ex. 684)
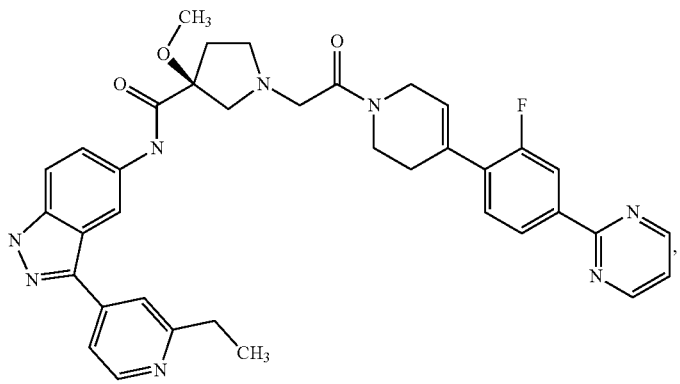
(Ex. 685)
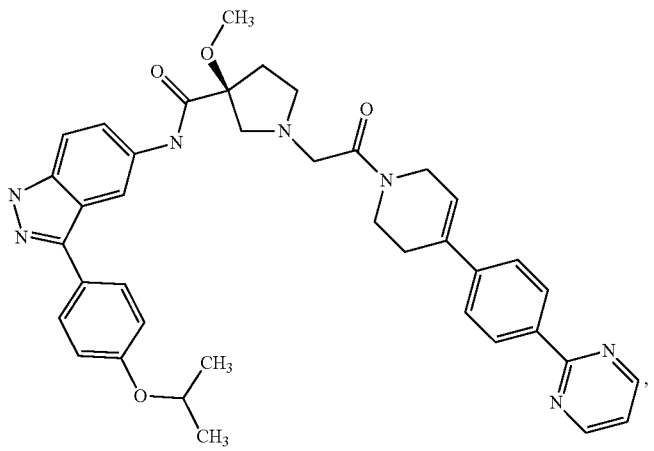
(Ex. 686)
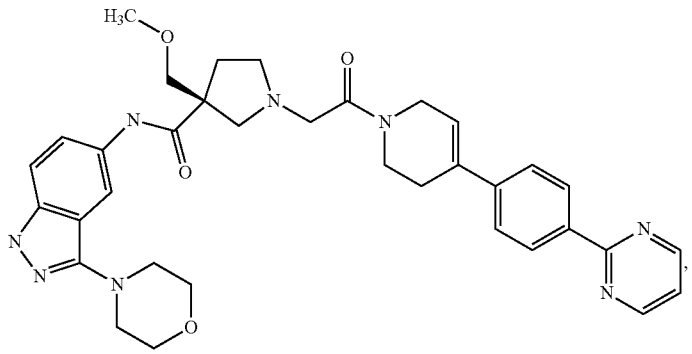
(Ex. 687)
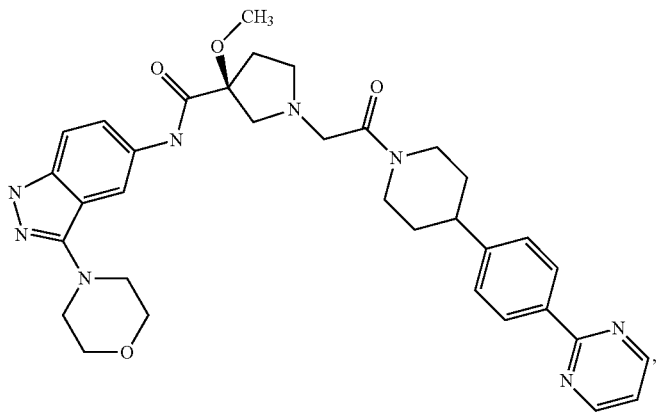

-continued
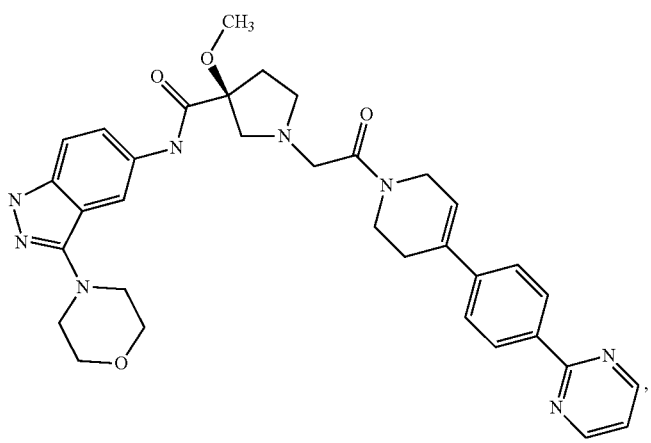
(Ex. 688)
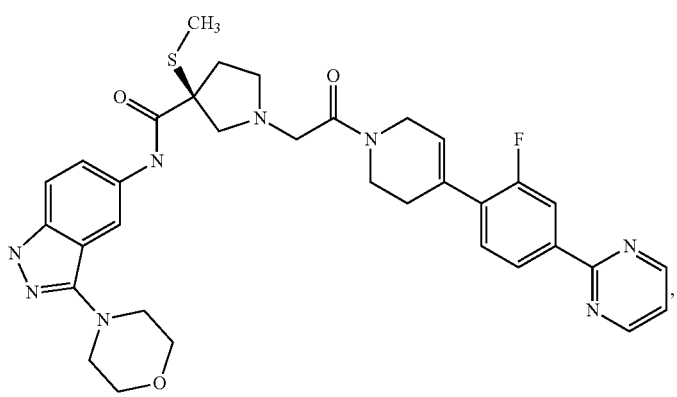
(Ex. 689)
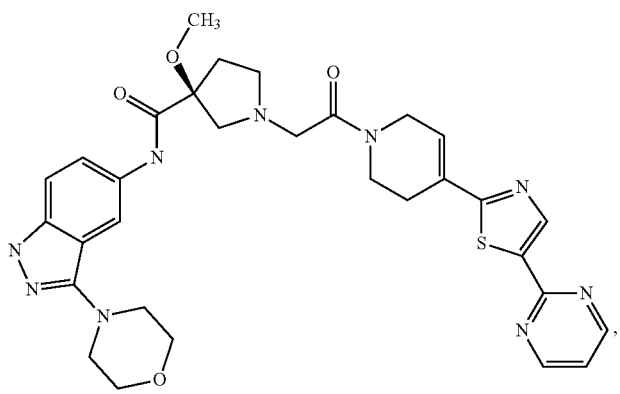
(Ex. 690)
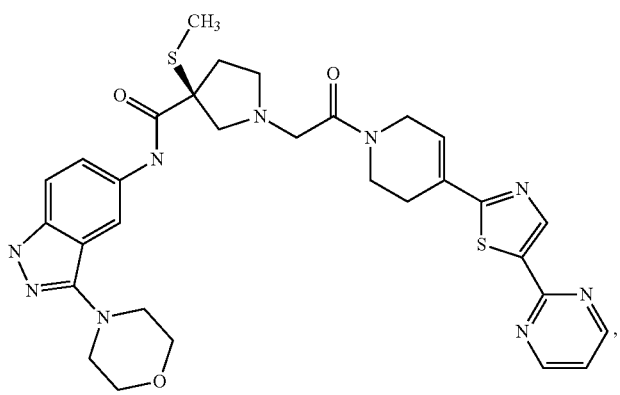
(Ex. 691)

-continued
(Ex. 692)
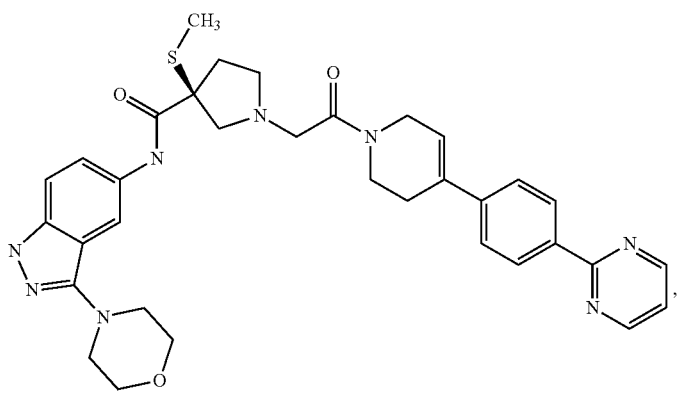
(Ex. 963)
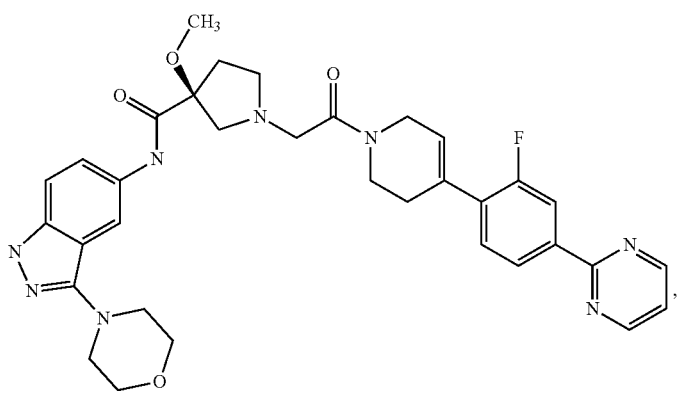
(Ex. 694)
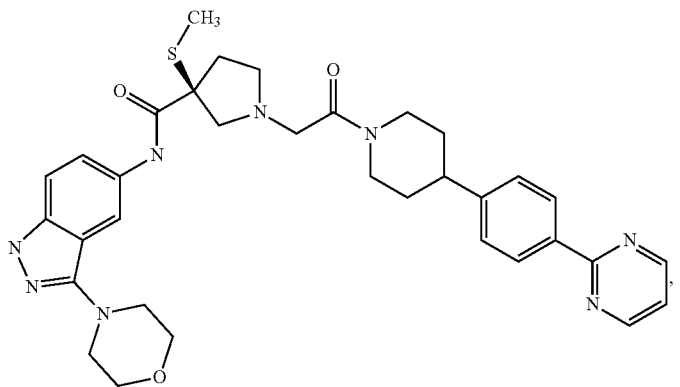
(Ex. 698)
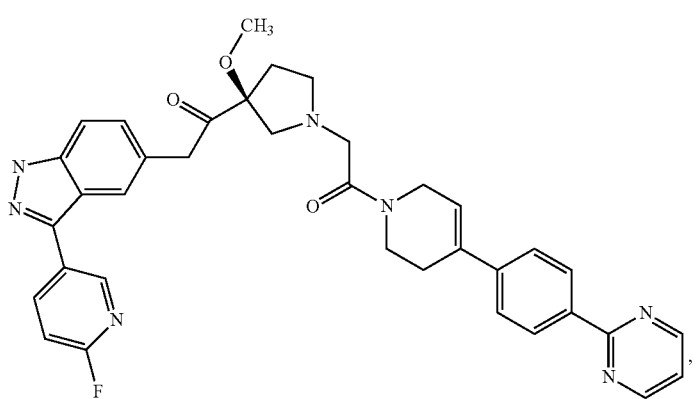

-continued
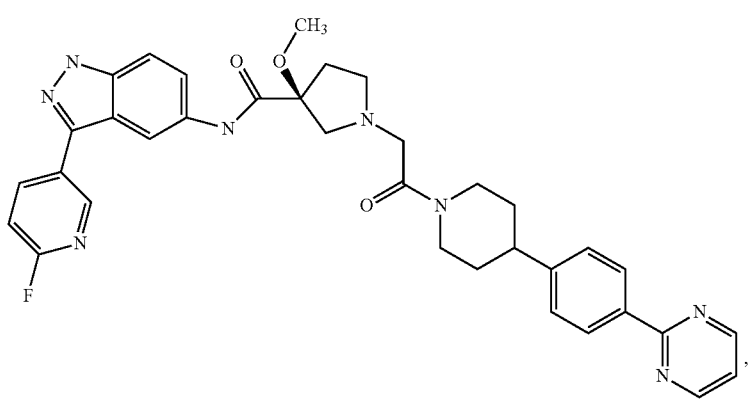
(Ex. 699)
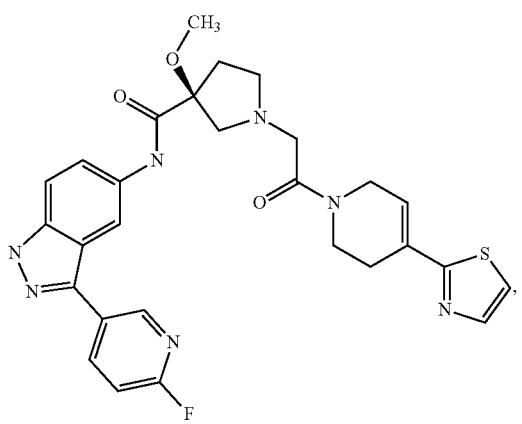
(Ex. 702)
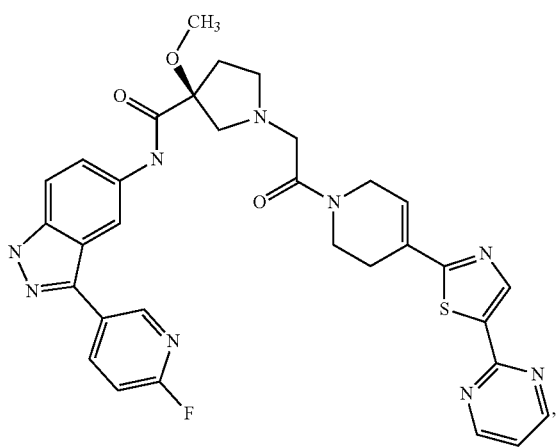
(Ex. 703)

(Ex. 704)
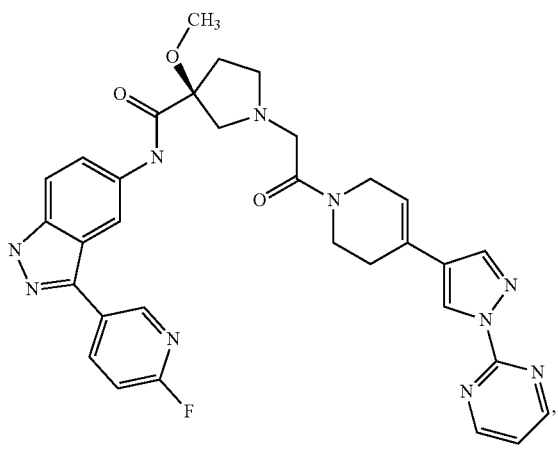
(Ex. 707)
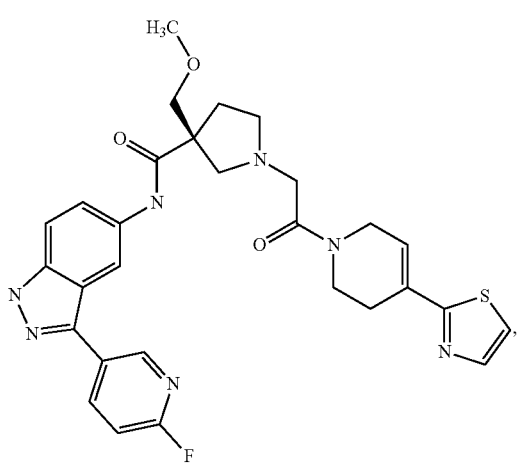
(Ex. 708)
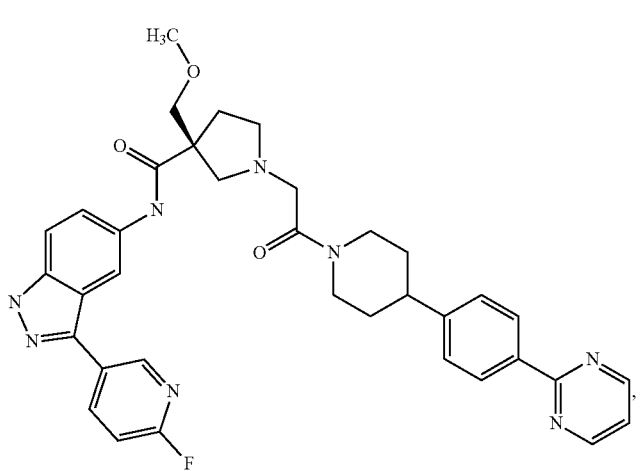

-continued
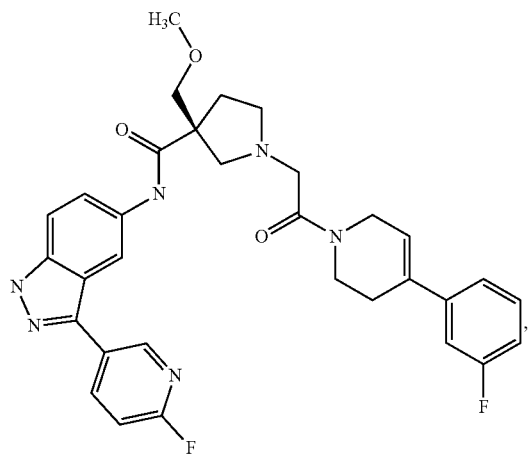
(Ex. 709)
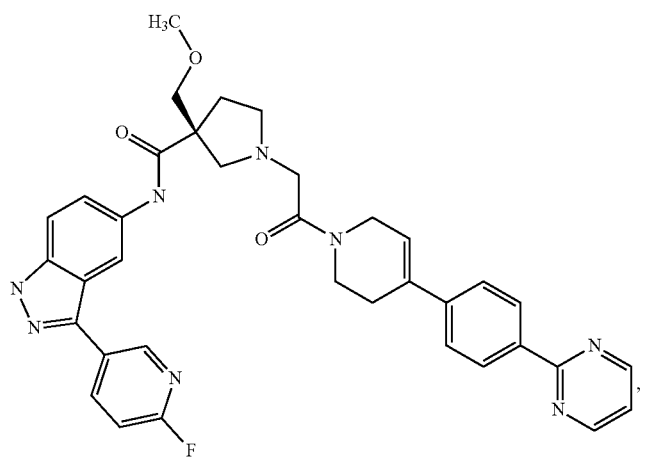
(Ex. 710)
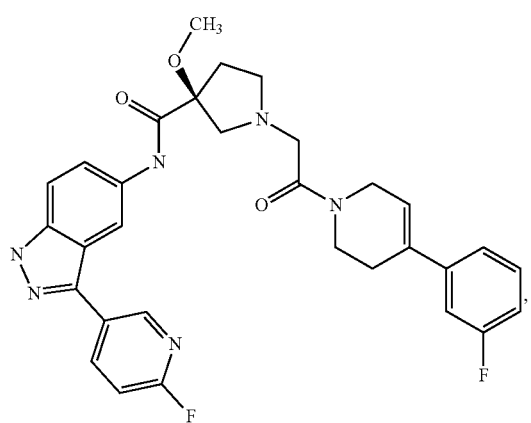
(Ex. 712)

-continued
(Ex. 713)
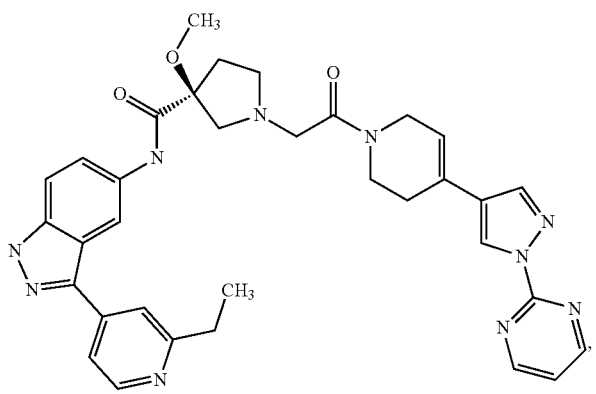
(Ex. 714)
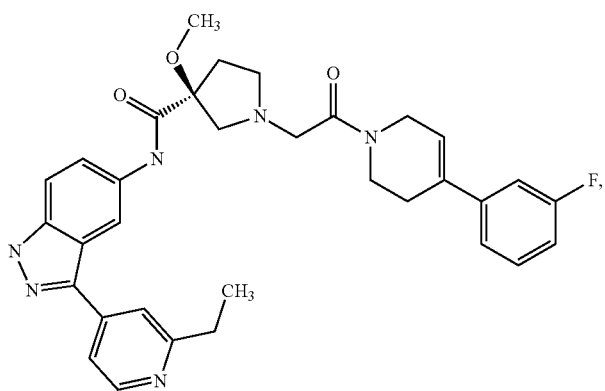
(Ex. 715)
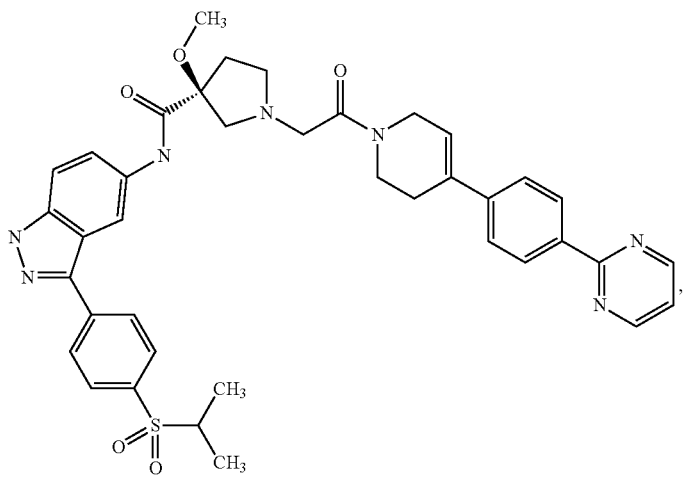
(Ex. 716)
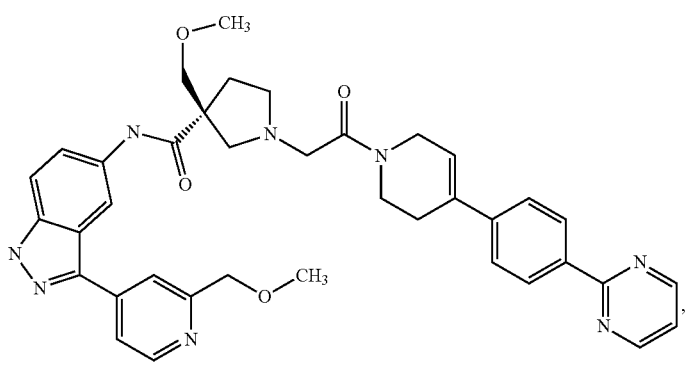

(Ex. 717)
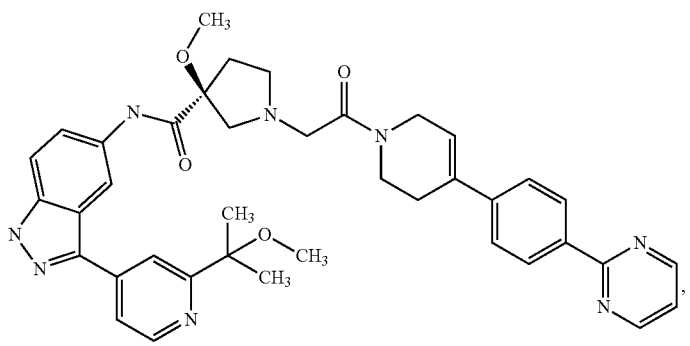
(Ex. 718)
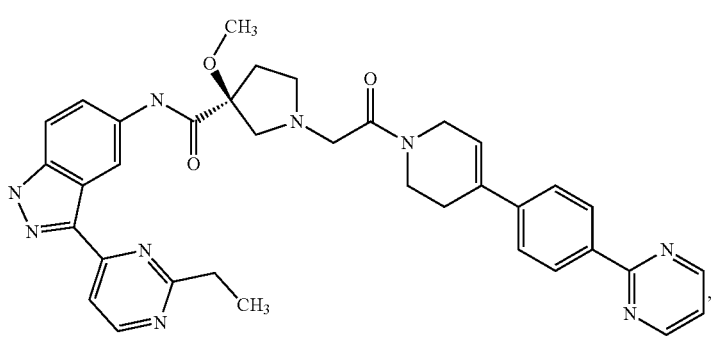
(Ex. 719)
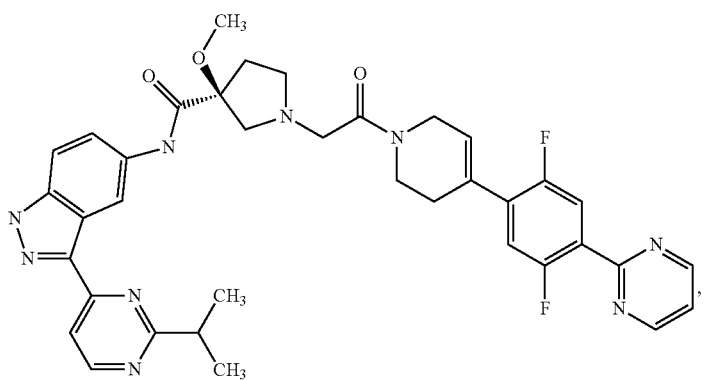
(Ex. 720)
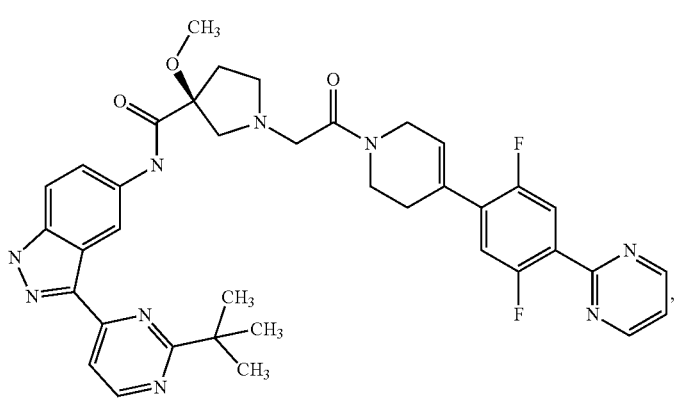

(Ex. 721)
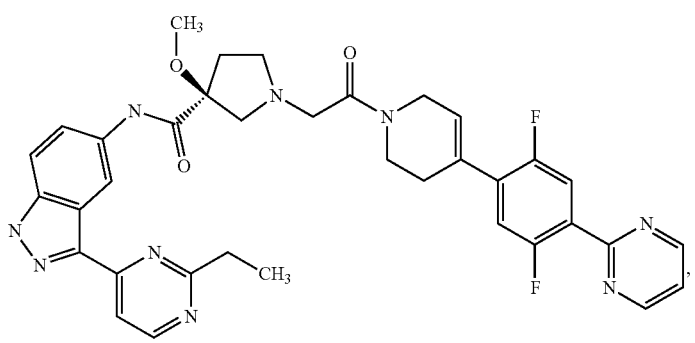
(Ex. 722)
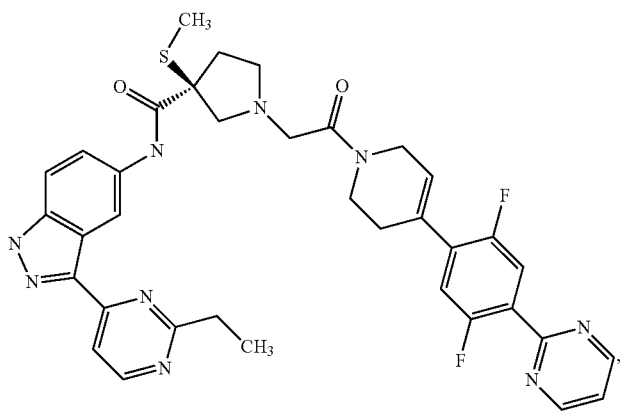
(Ex. 723)
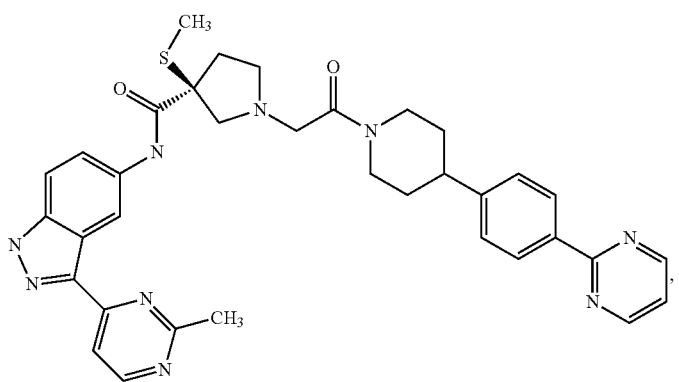
(Ex. 724)
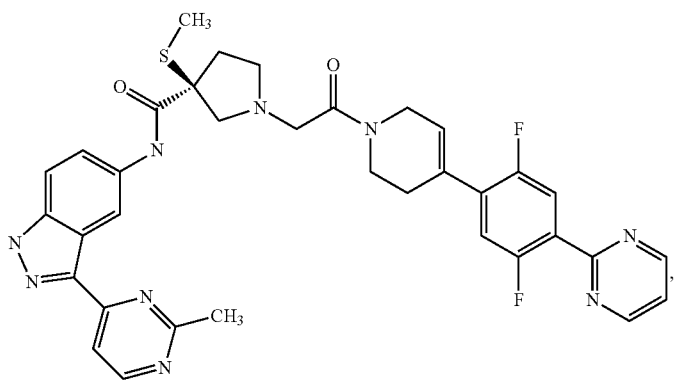

(Ex. 725)
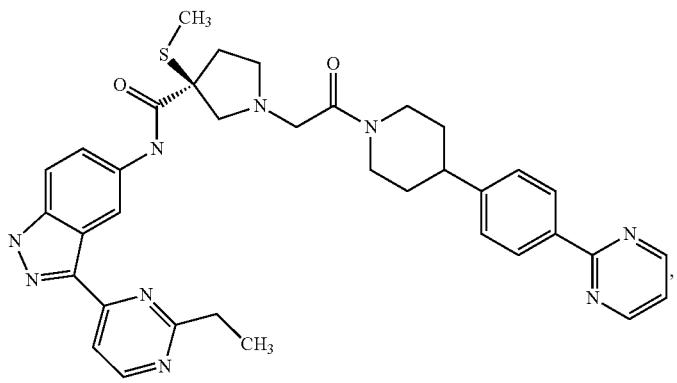
(Ex. 726)
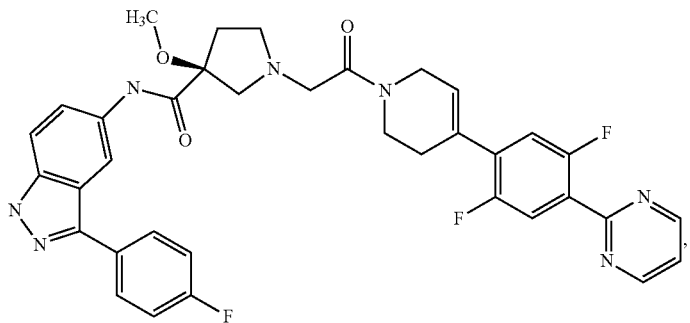
(Ex. 727)
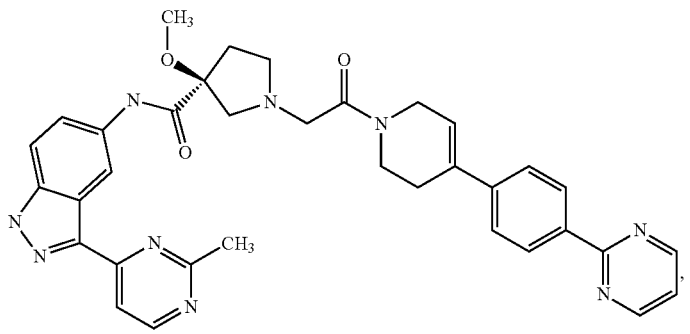
(Ex. 728)
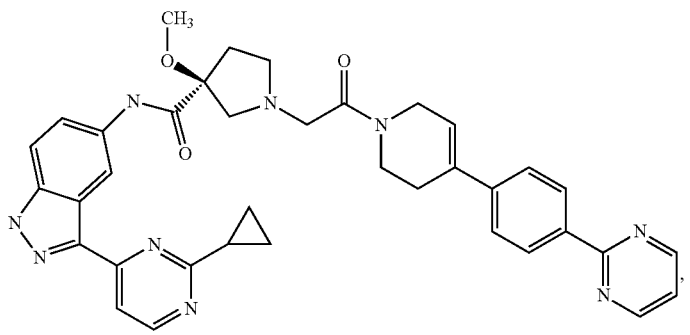

(Ex. 729)
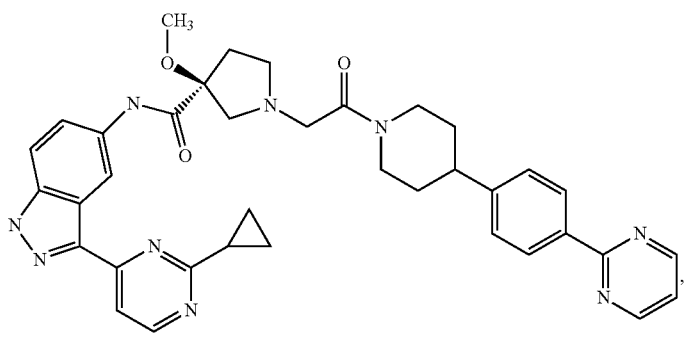
(Ex. 730)
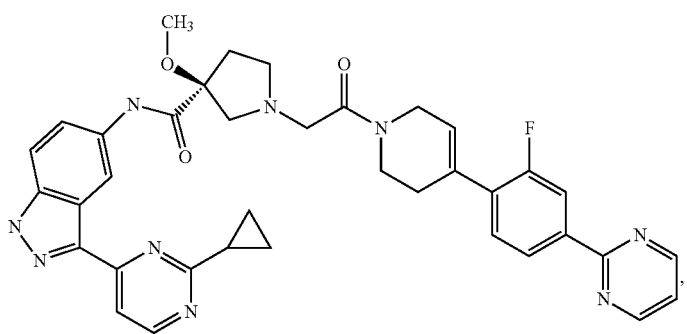
(Ex. 731)
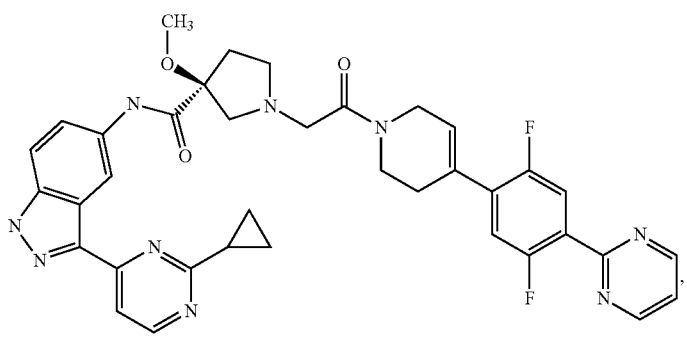
(Ex. 732)
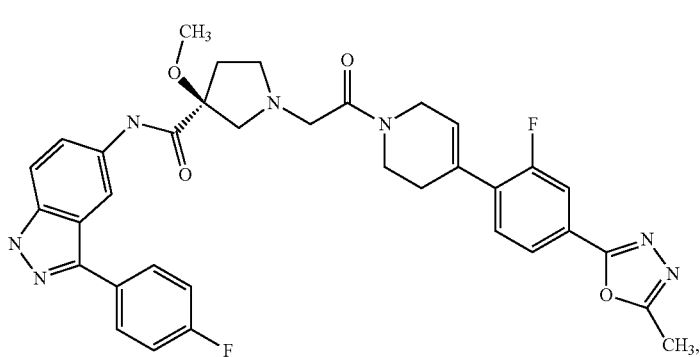

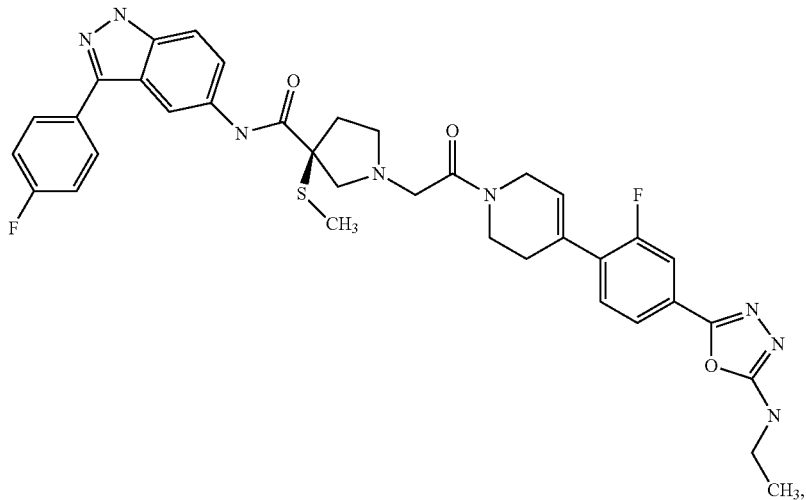
(Ex. 733)
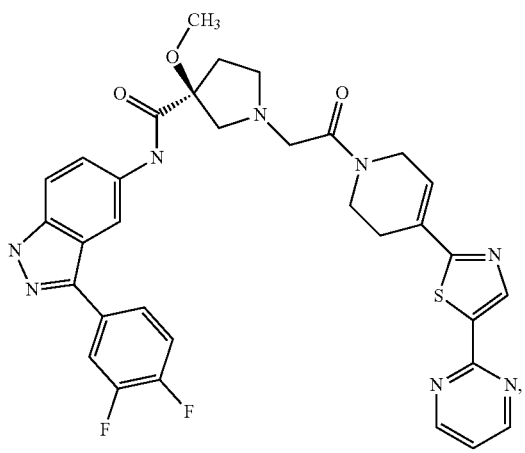
(Ex. 734)
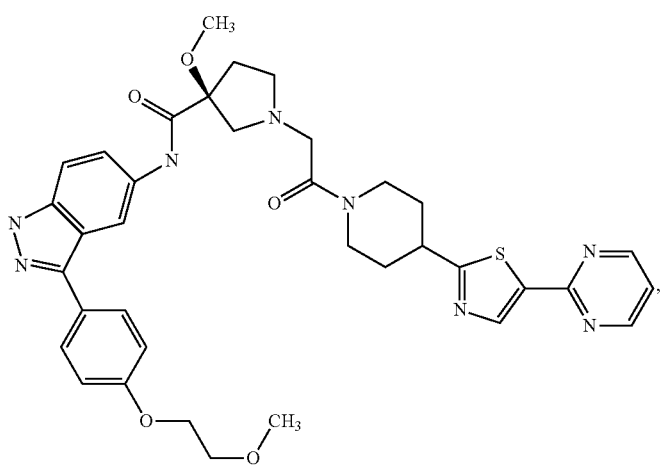
(Ex. 735)

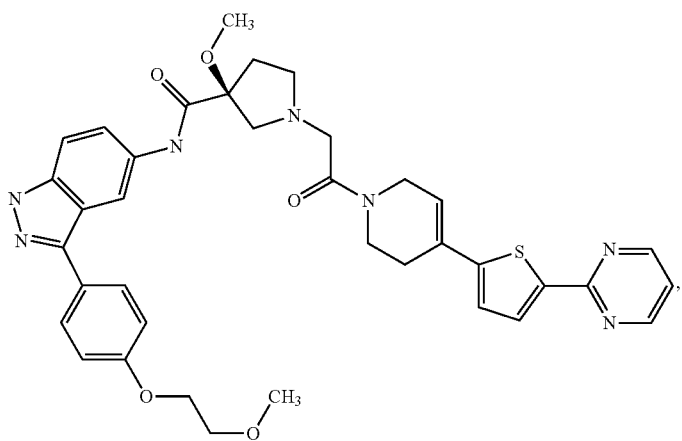
(Ex. 736)
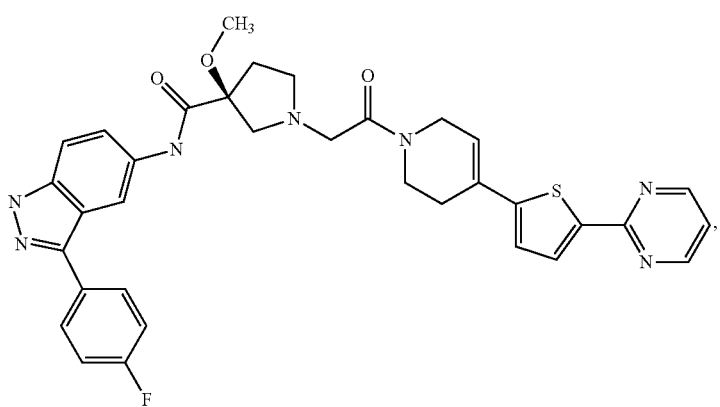
(Ex. 737)
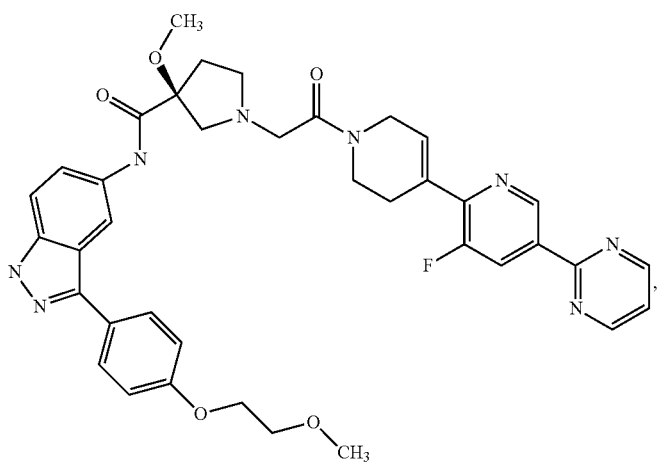
(Ex. 738)

(Ex. 739)
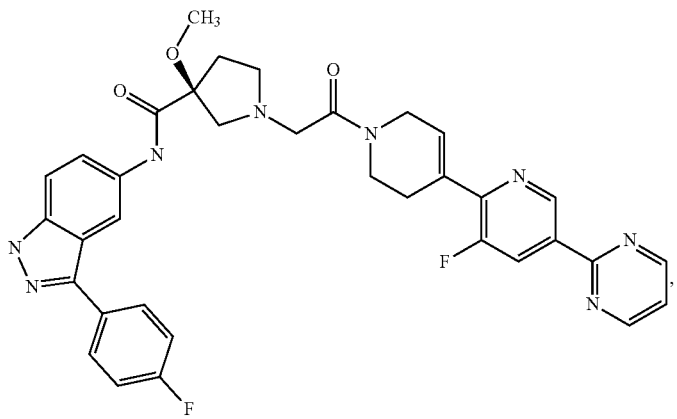
(Ex. 740)
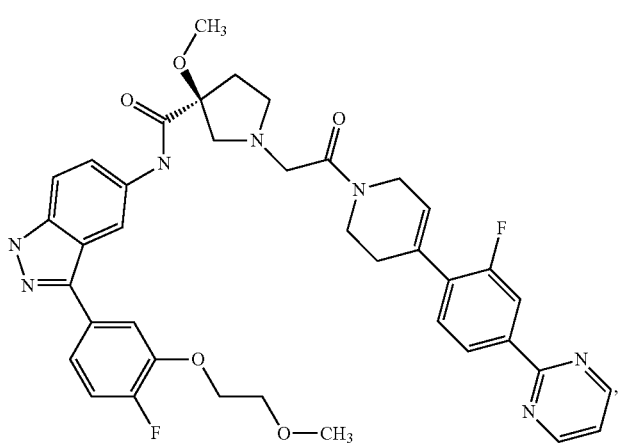
(Ex. 741)
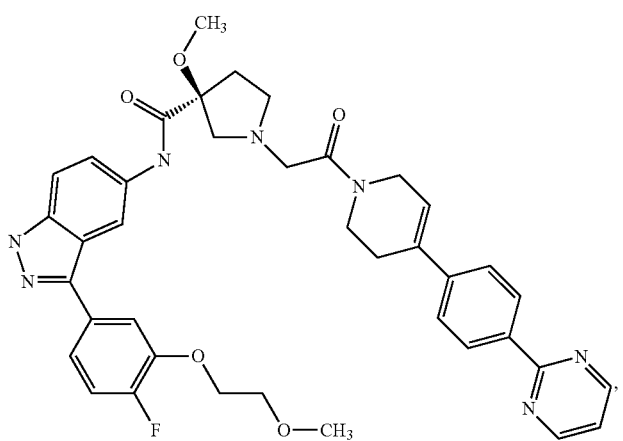

(Ex. 742)
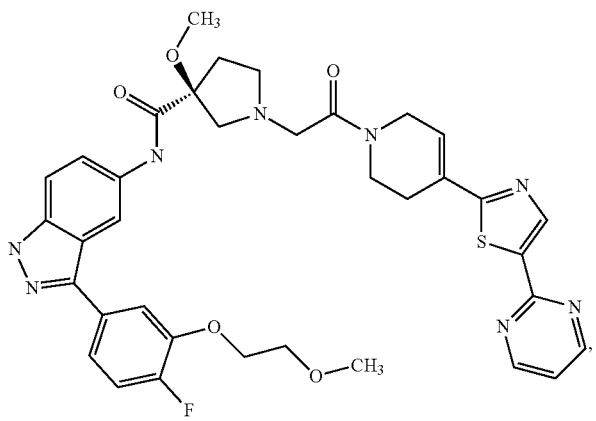
(Ex. 743)
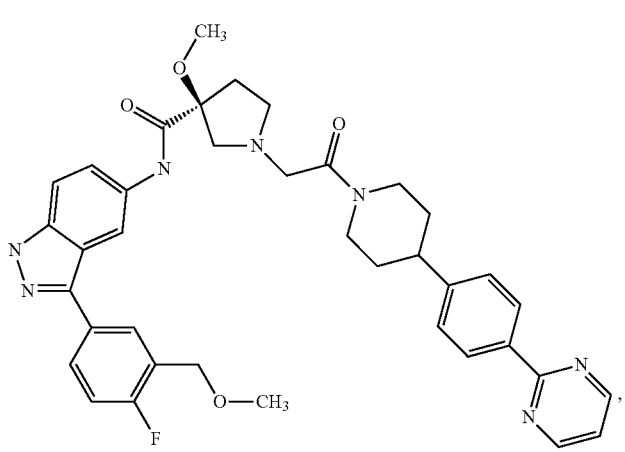
(Ex. 744)
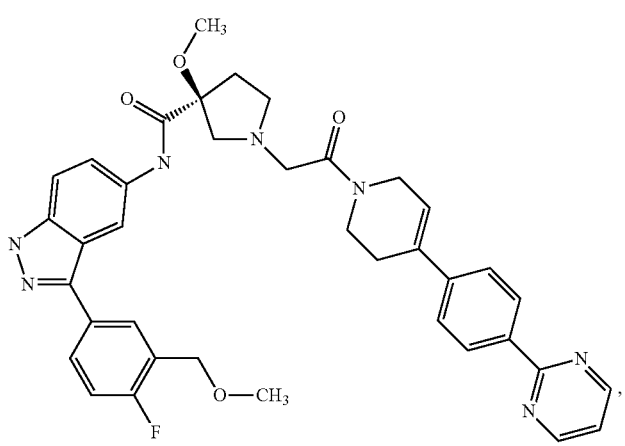

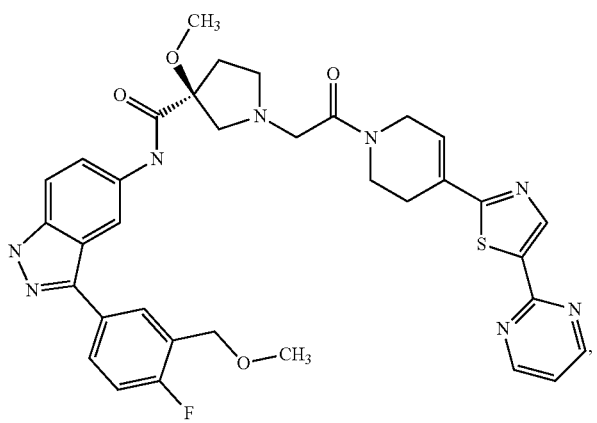
(Ex. 745)
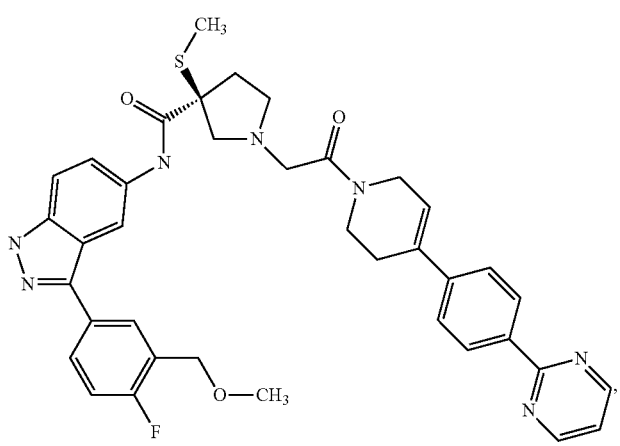
(Ex. 746)
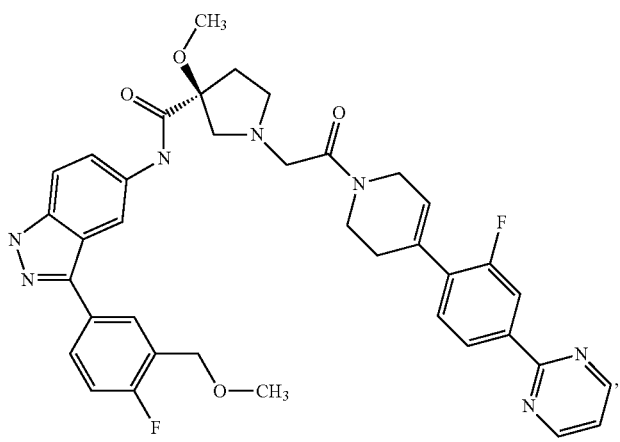
(Ex. 747)

(Ex. 748)
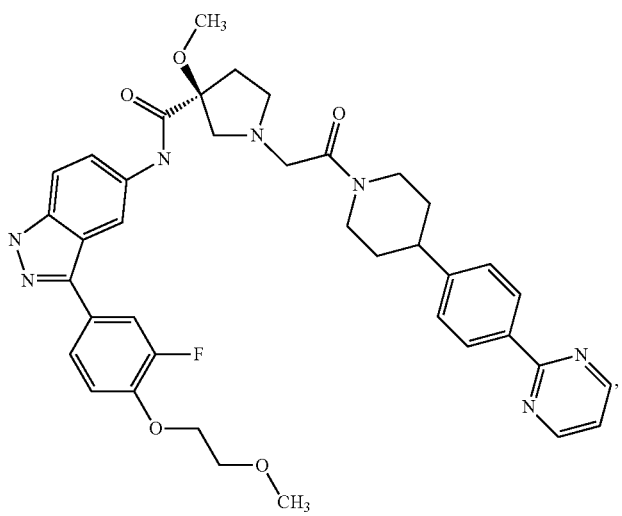
(Ex. 749)
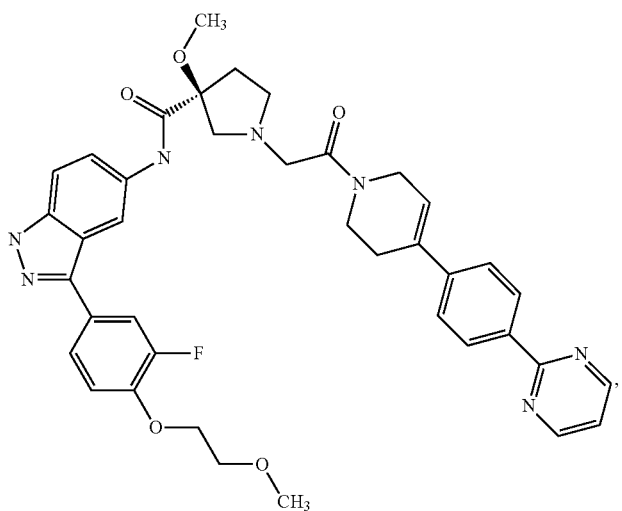
(Ex. 750)
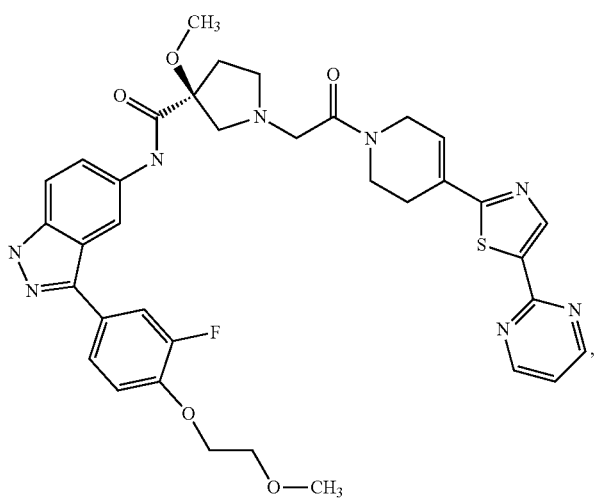

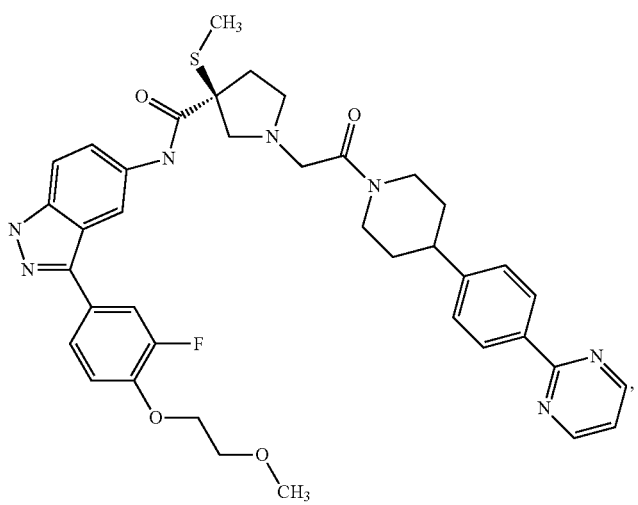
(Ex. 751)
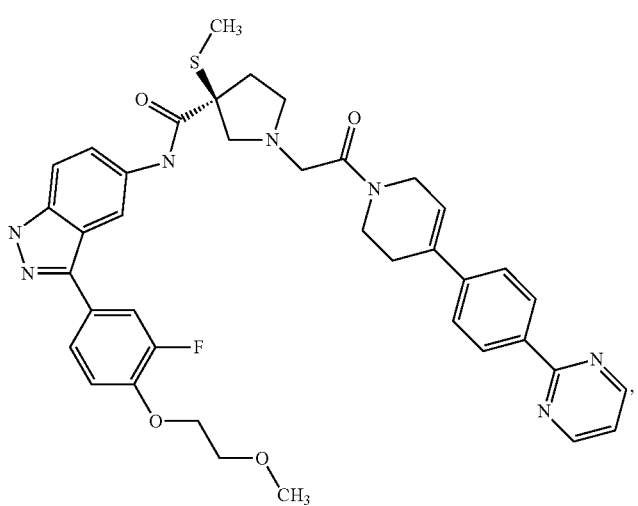
(Ex. 752)
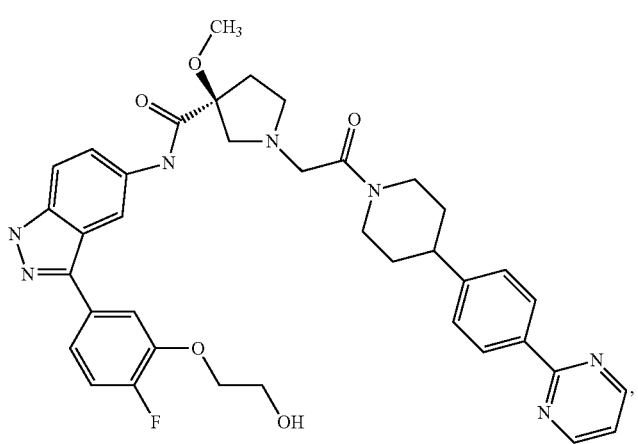
(Ex. 753)

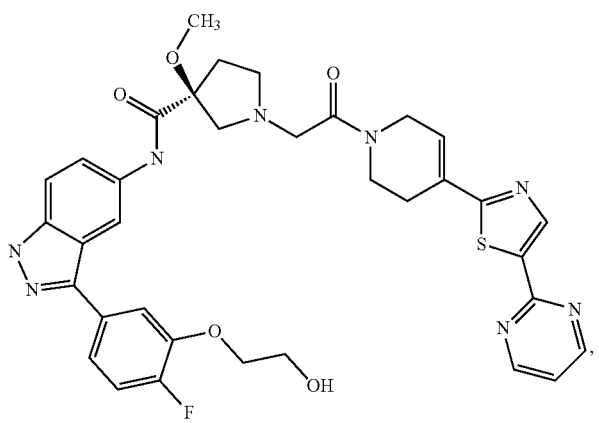
(Ex. 754)
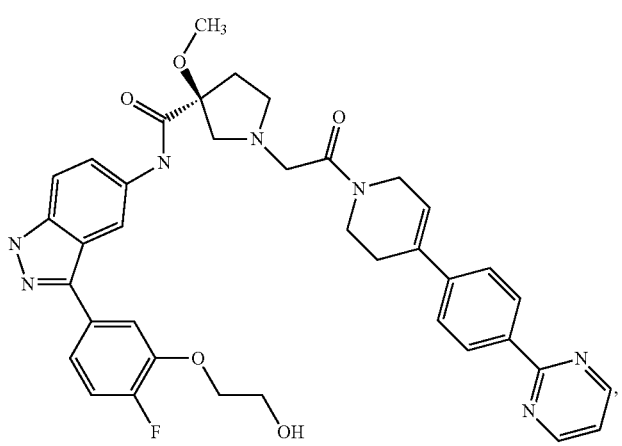
(Ex. 755)
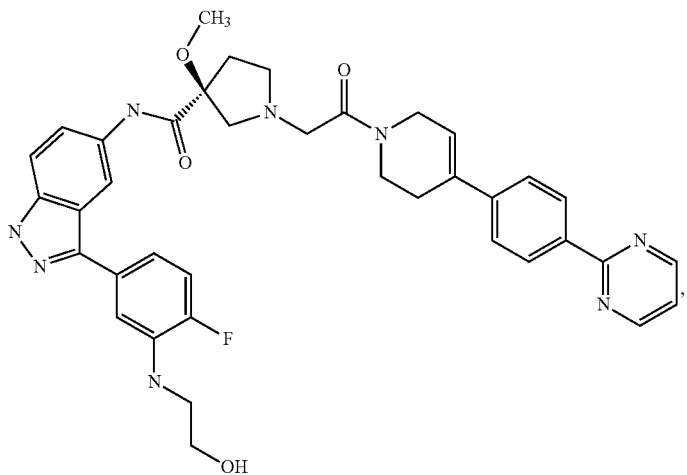
(Ex. 757)

(Ex. 758)
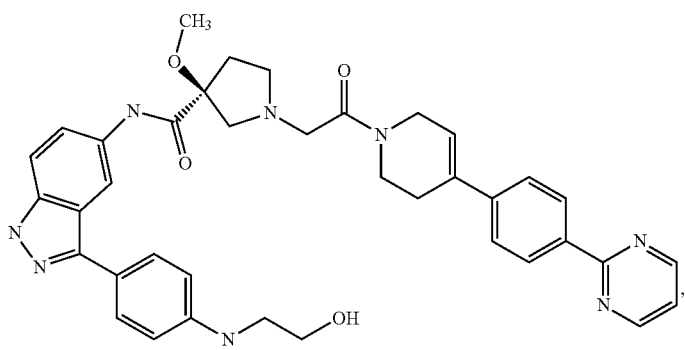
(Ex. 759)
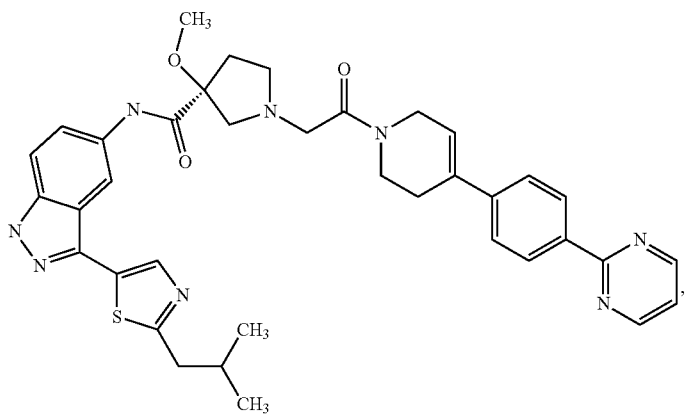
(Ex. 760)
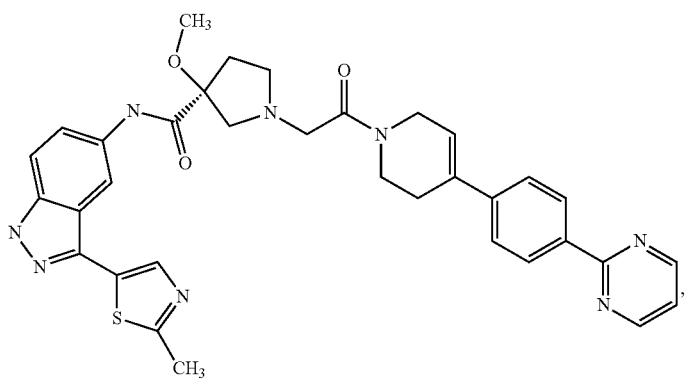
(Ex. 761)
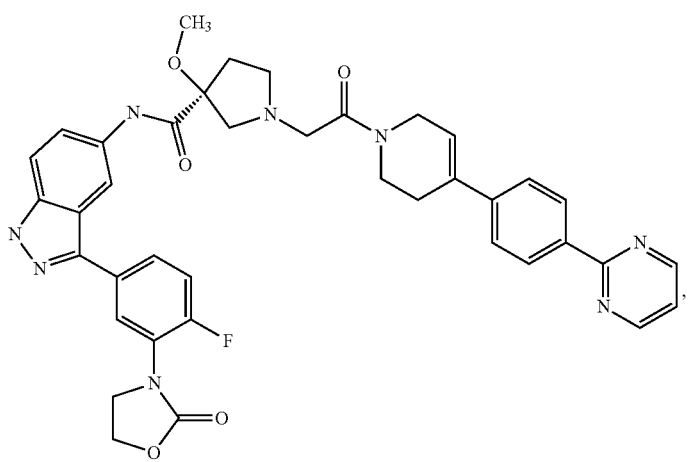

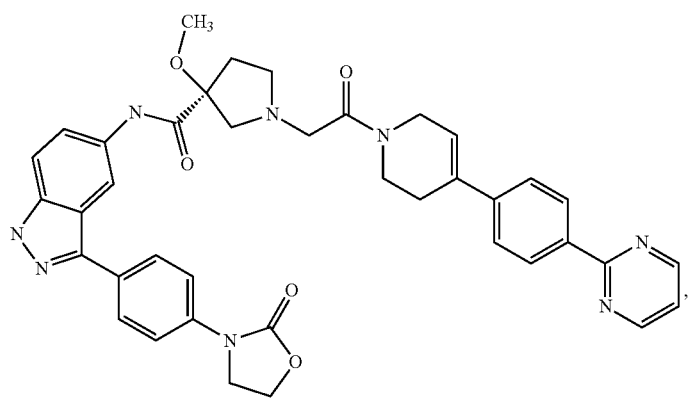
(Ex. 762)
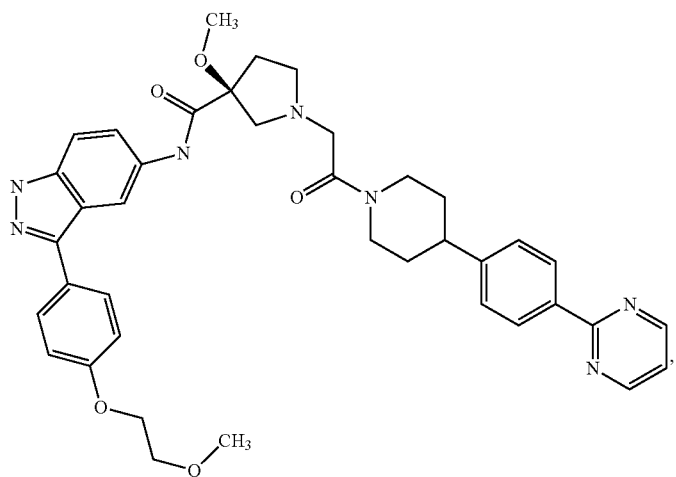
(Ex. 764)
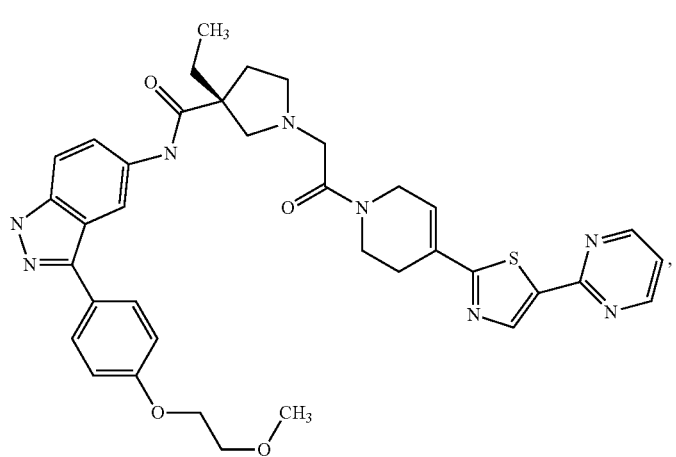
(Ex. 765)

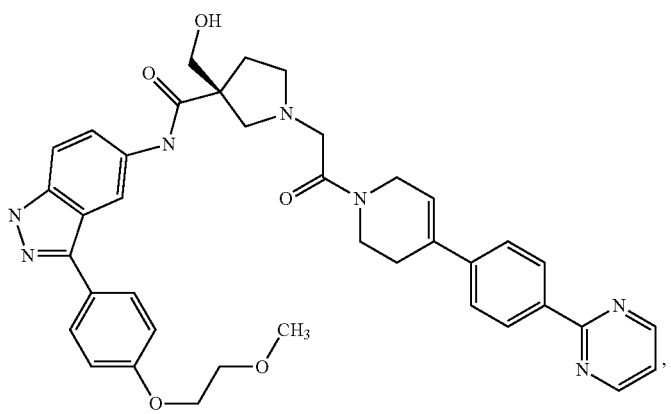
(Ex. 766)
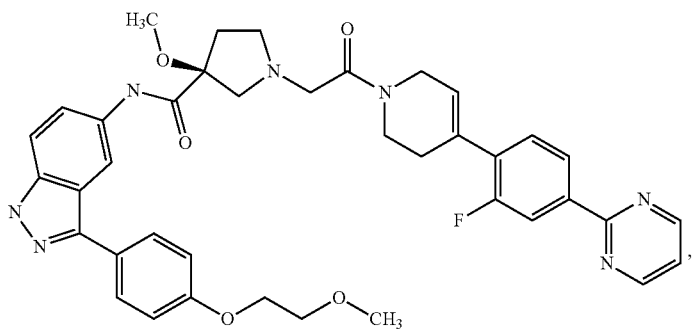
(Ex. 767)
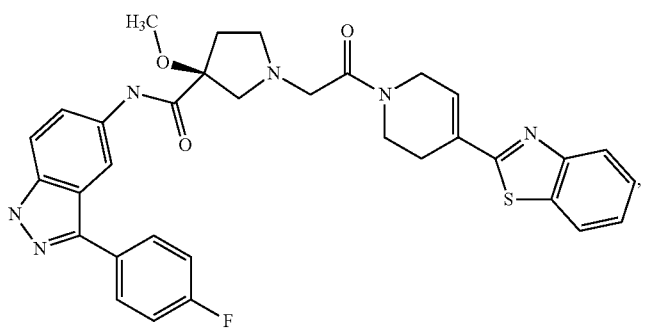
(Ex. 768)
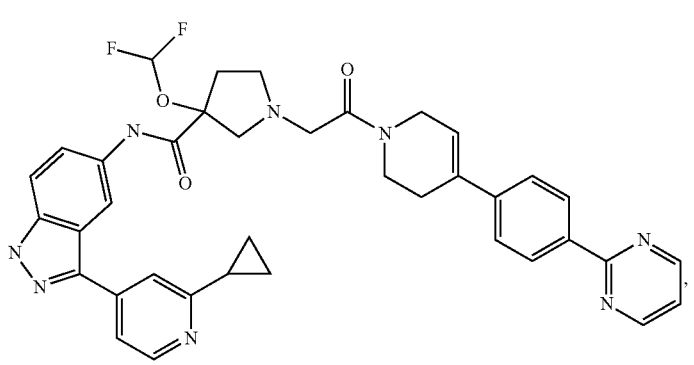
(Ex. 769)

(Ex. 770)
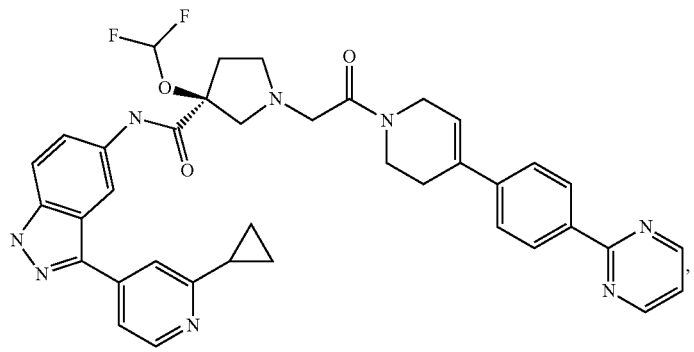
(Ex. 771)
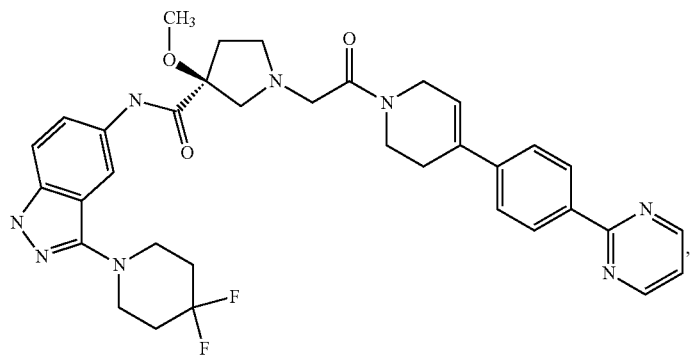
(Ex. 772)
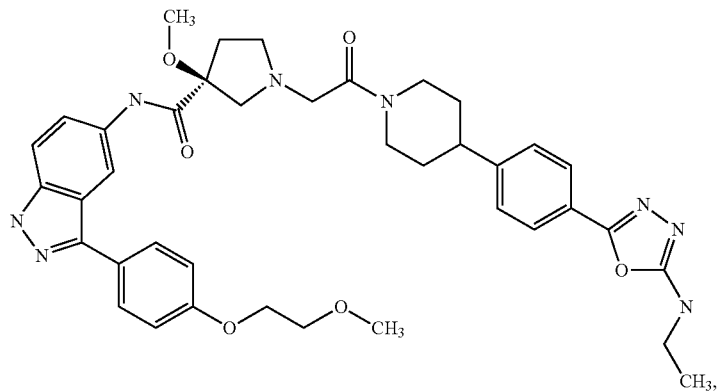
(Ex. 773)
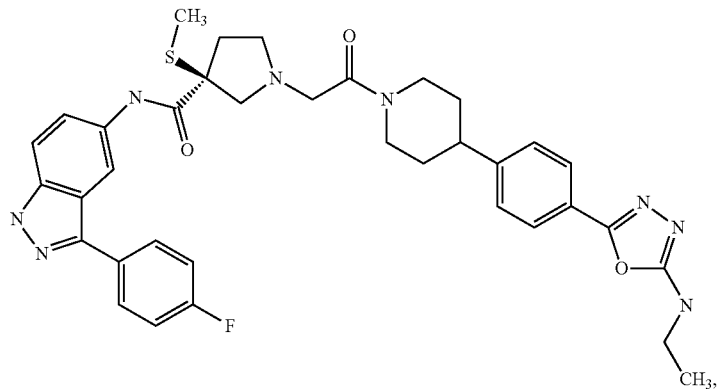

(Ex. 774)
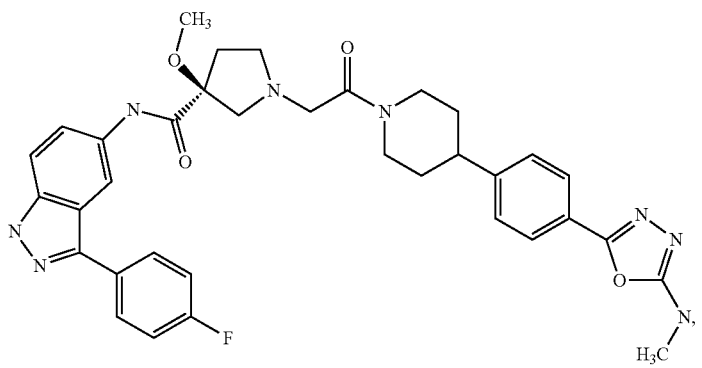
(Ex. 775)
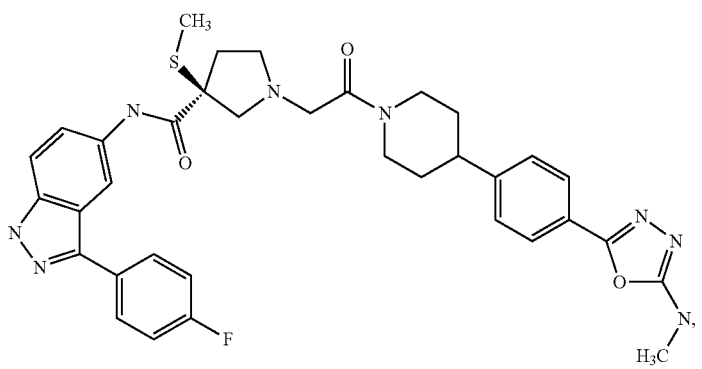
(Ex. 776)
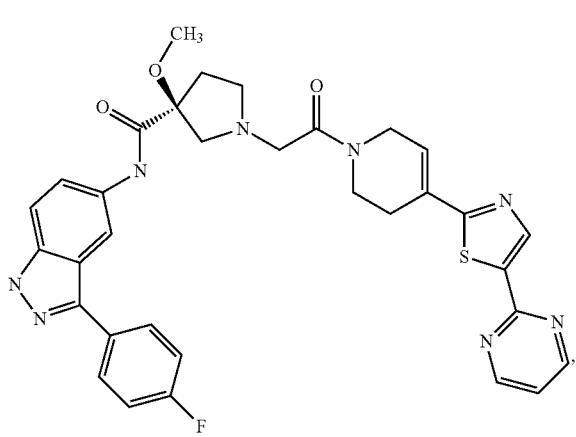
(Ex. 777)
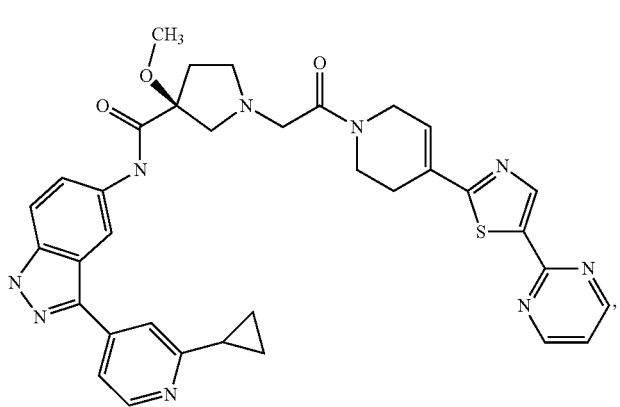

-continued
(Ex. 778)
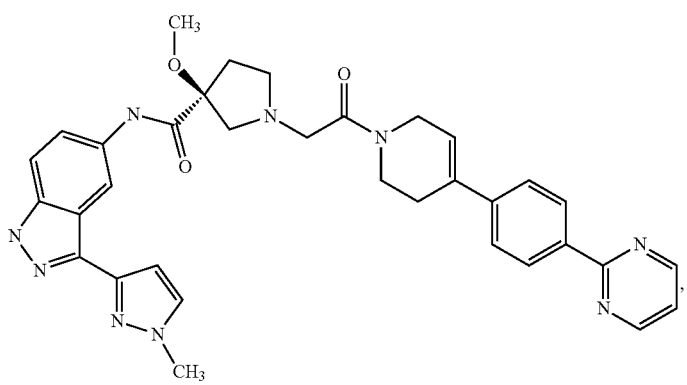
(Ex. 779)
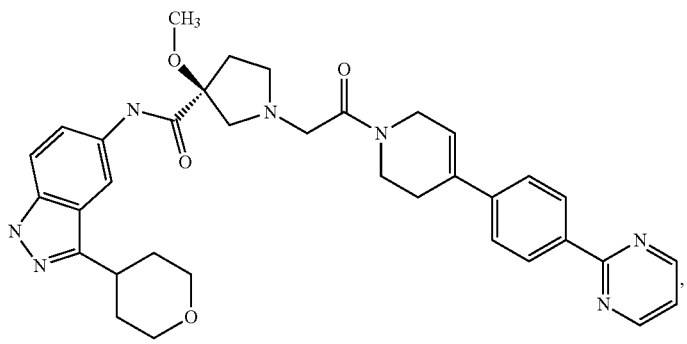
(Ex. 780)
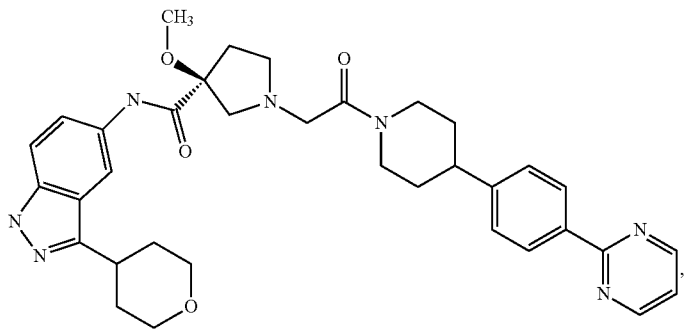
(Ex. 781)
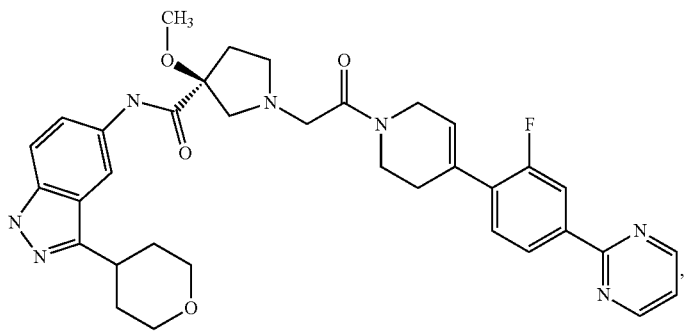

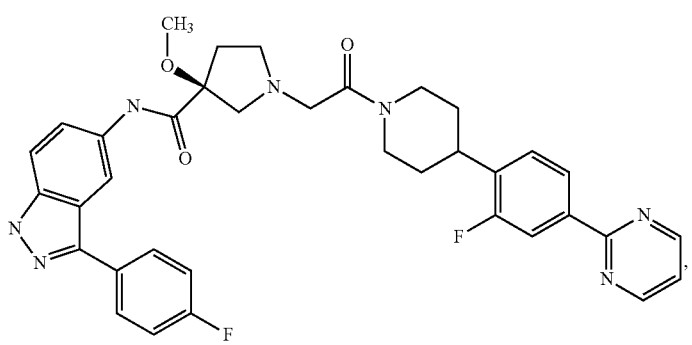
(Ex. 782)
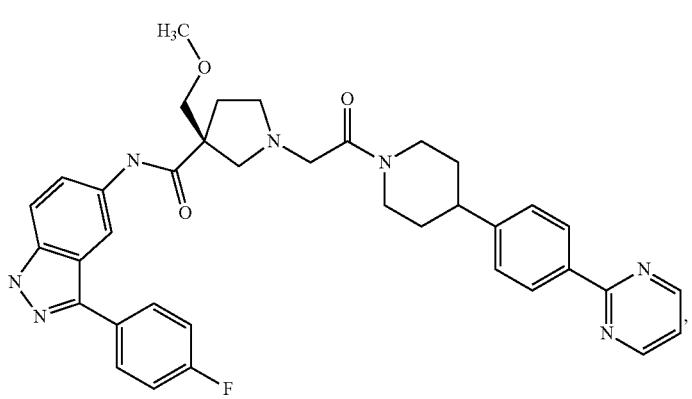
(Ex. 783)
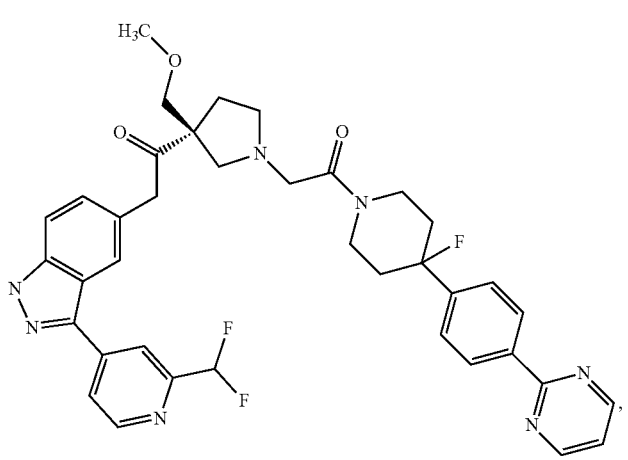
(Ex. 784)
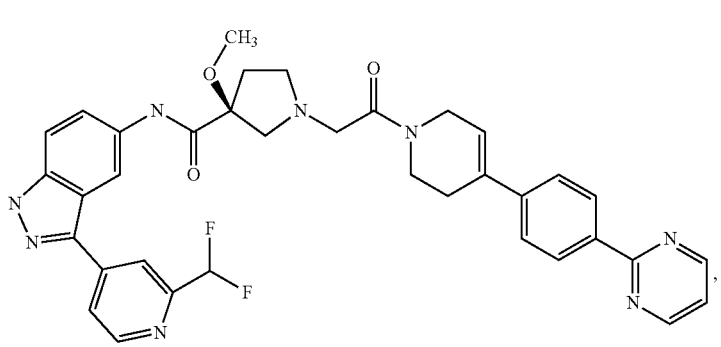
(Ex. 785)

(Ex. 786)
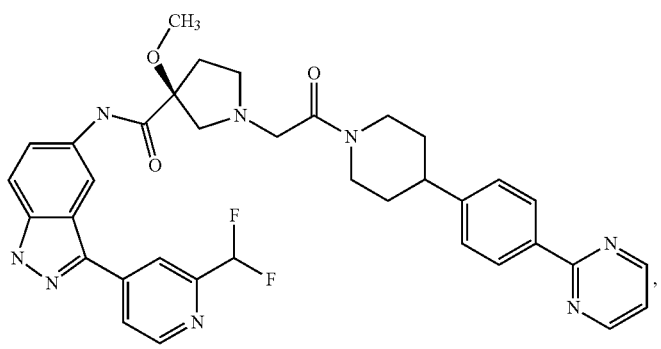
(Ex. 787)
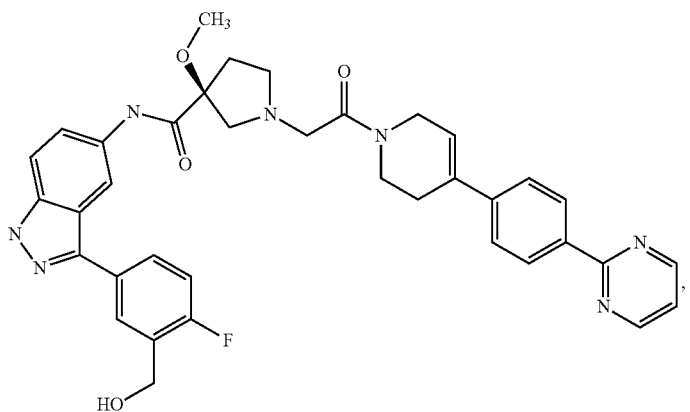
(Ex. 788)
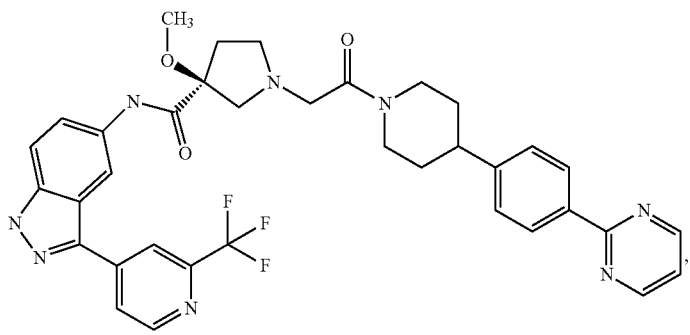
(Ex. 789)
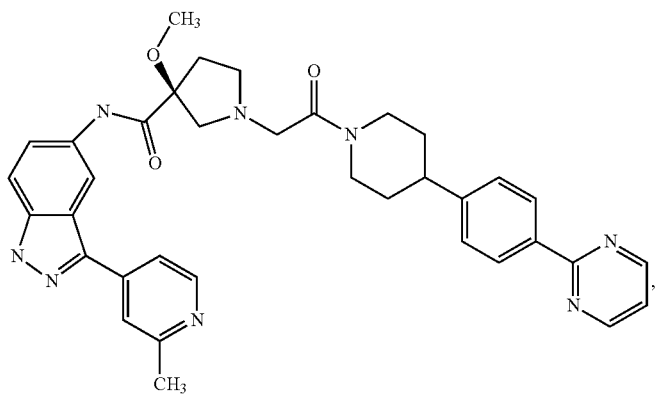

(Ex. 790)
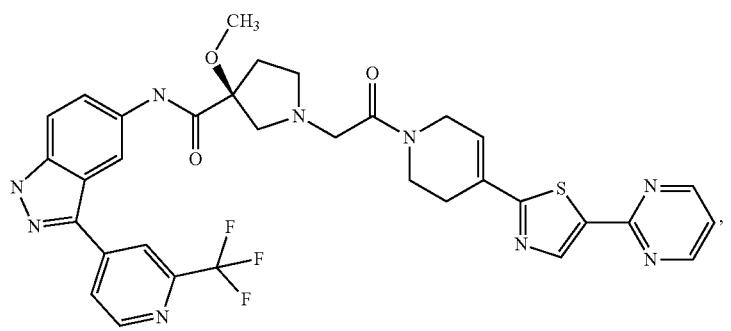
(Ex. 791)
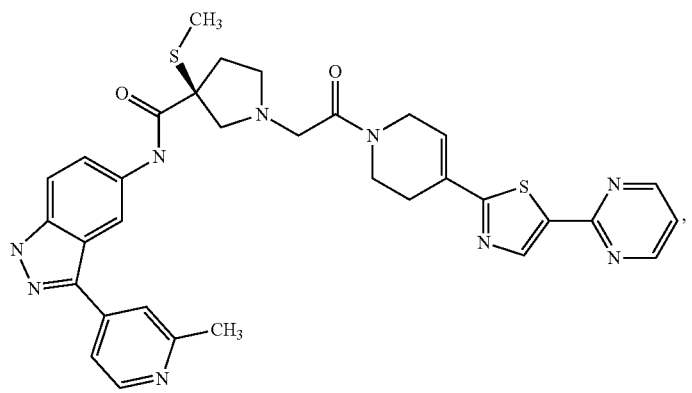
(Ex. 792)
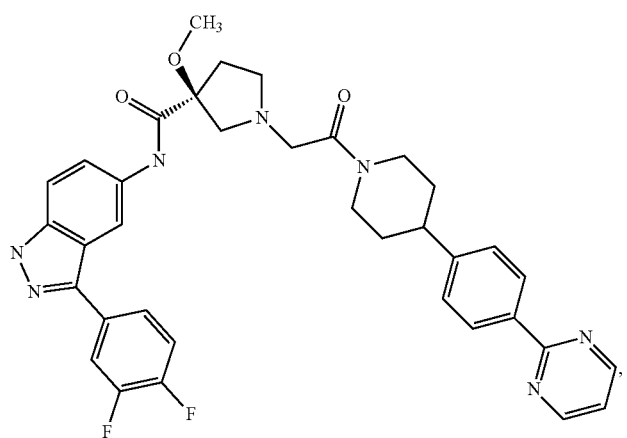
(Ex. 793)
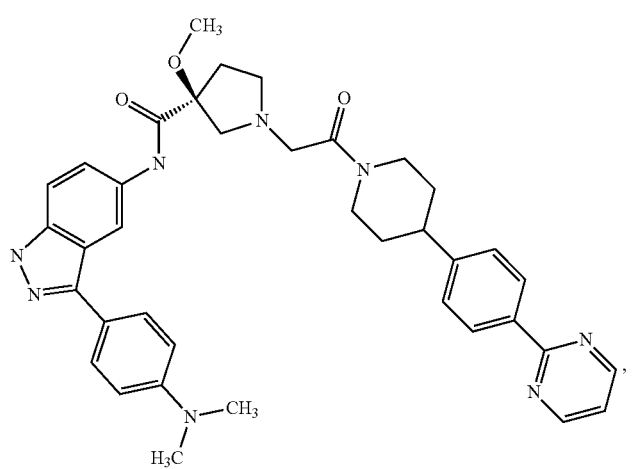

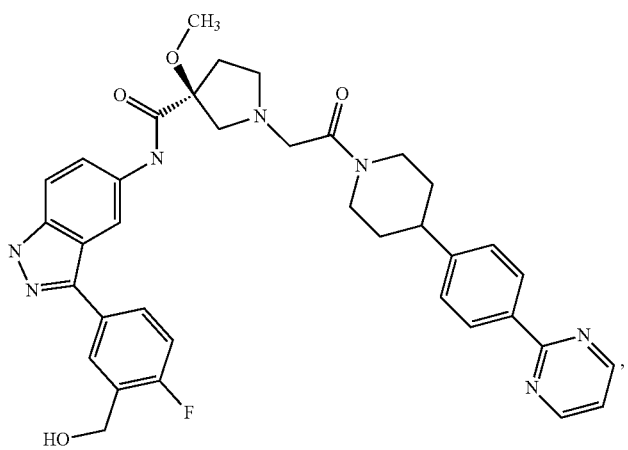
(Ex. 794)
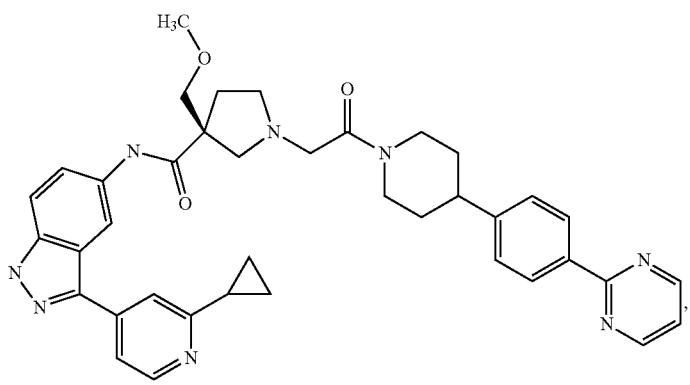
(Ex. 795)
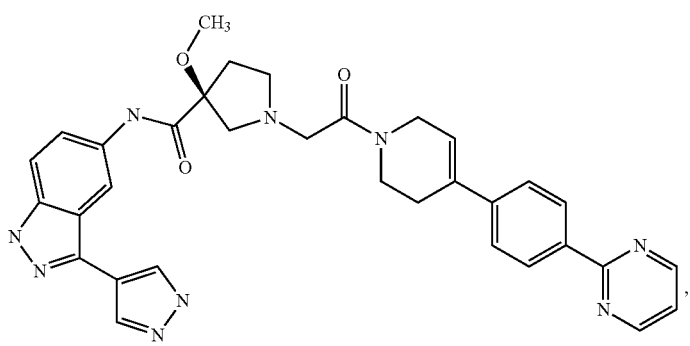
(Ex. 796)
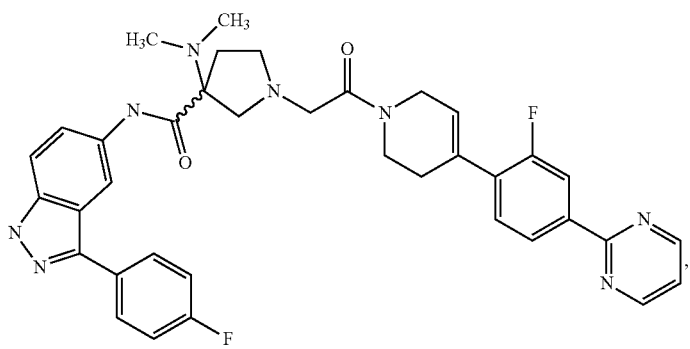
(Ex. 797)

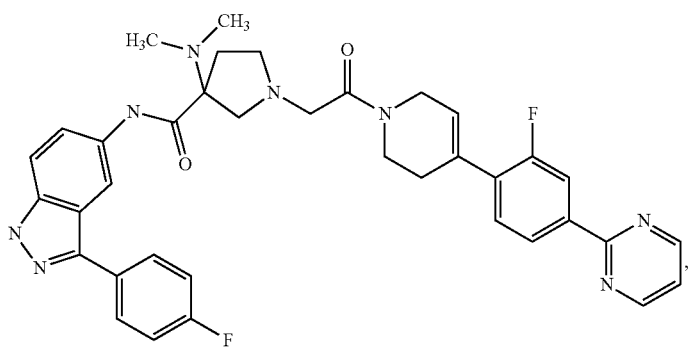
(Ex. 798)
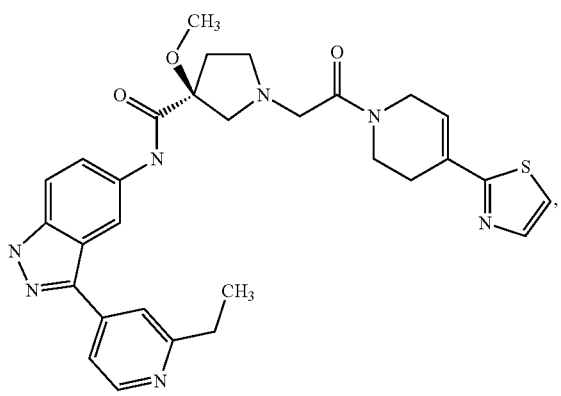
(Ex. 802)
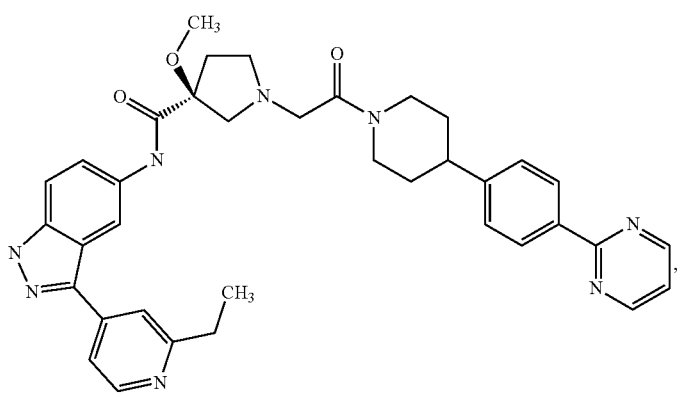
(Ex. 803)
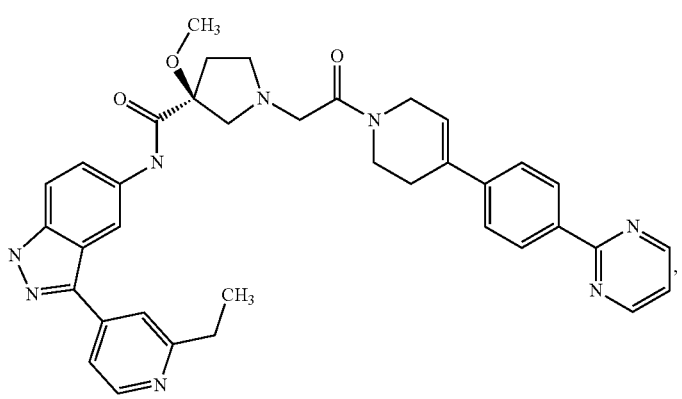
(Ex. 805)

(Ex. 807)
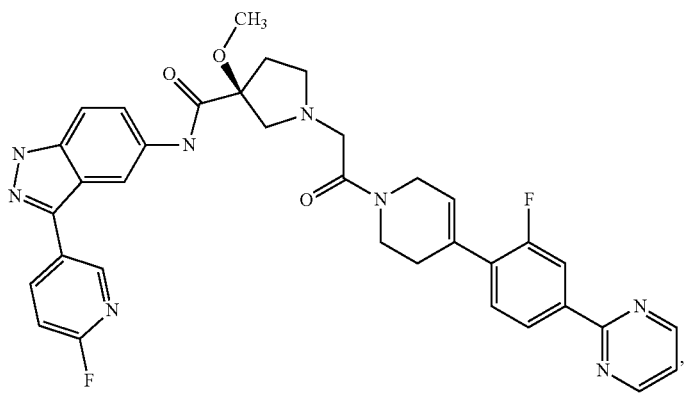
(Ex. 808)
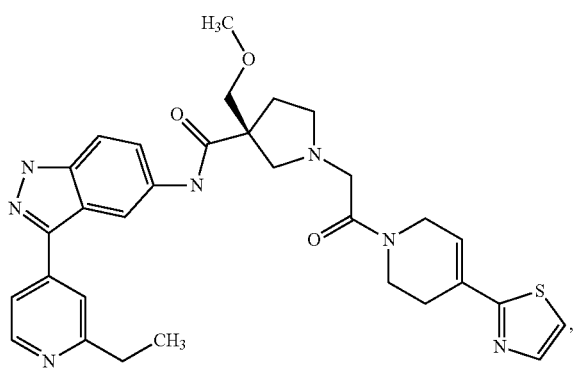
(Ex. 809)
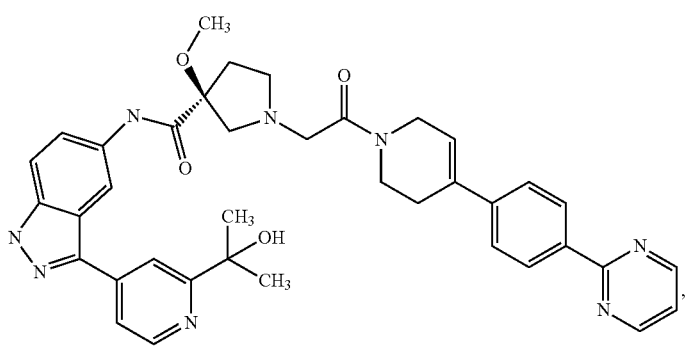
(Ex. 810)
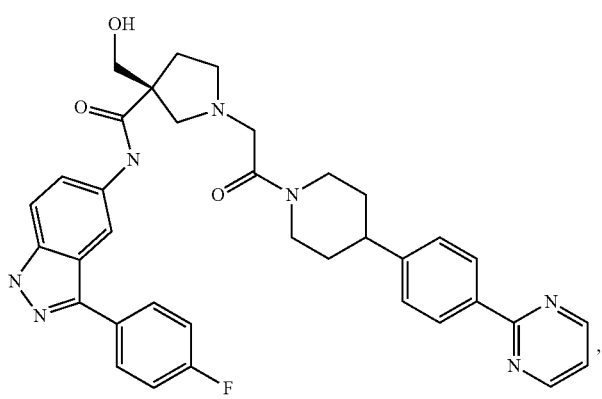

(Ex. 811)
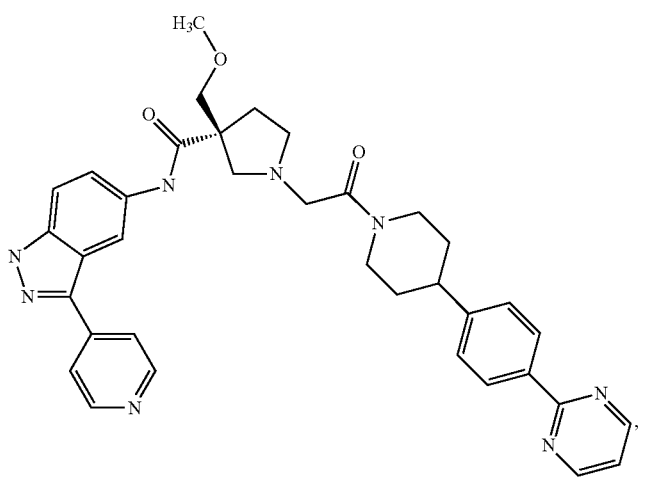
(Ex. 812)
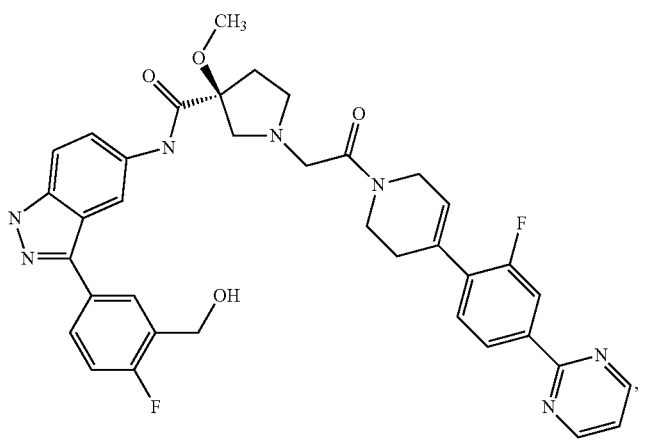
(Ex. 813)
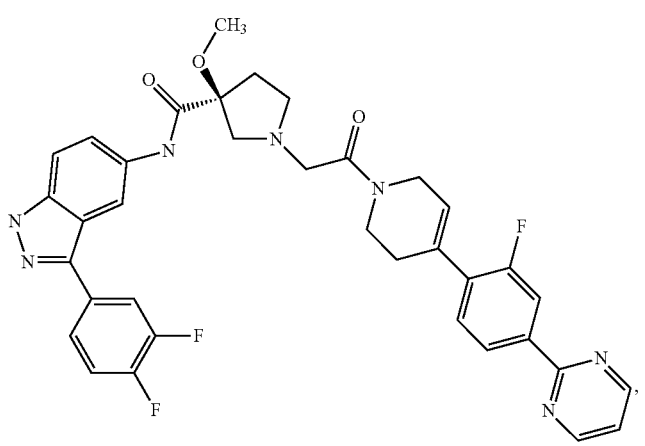

(Ex. 814)
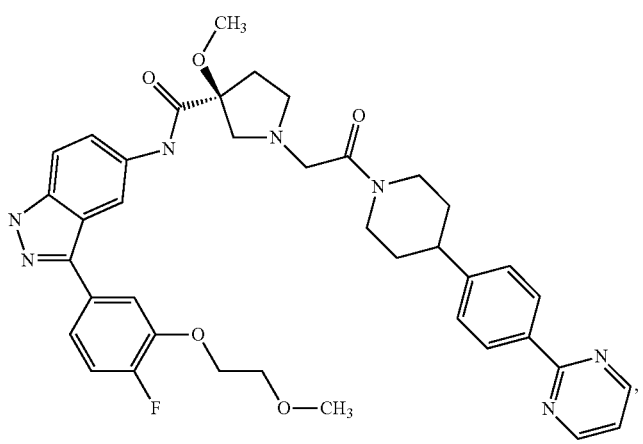
(Ex. 815)
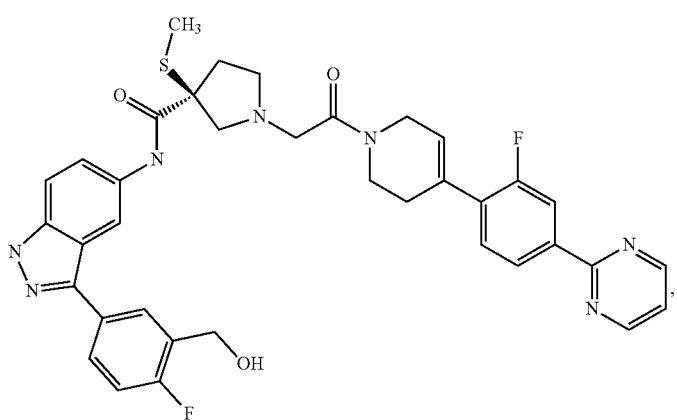
(Ex. 816)
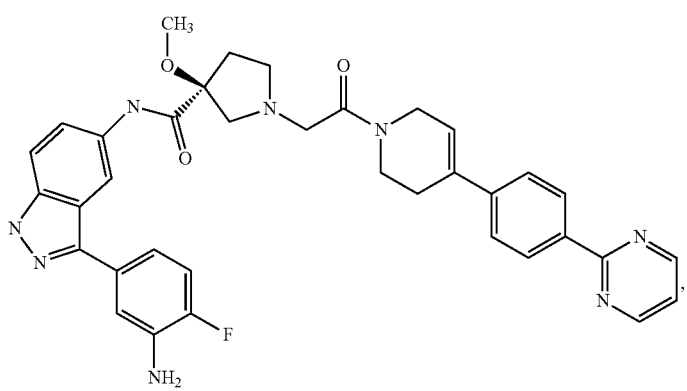
(Ex. 817)
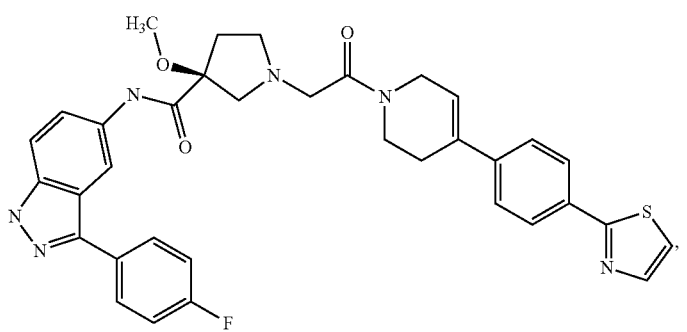

(Ex. 818)
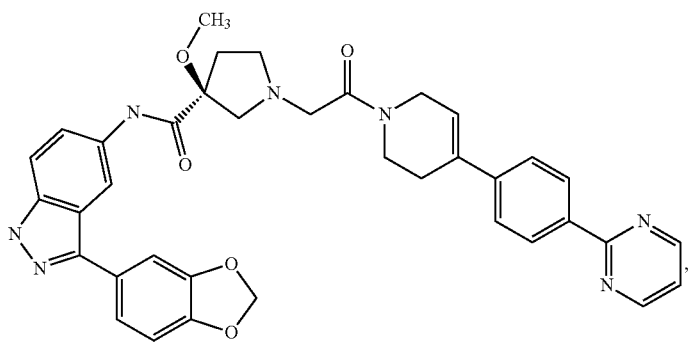
(Ex. 819)
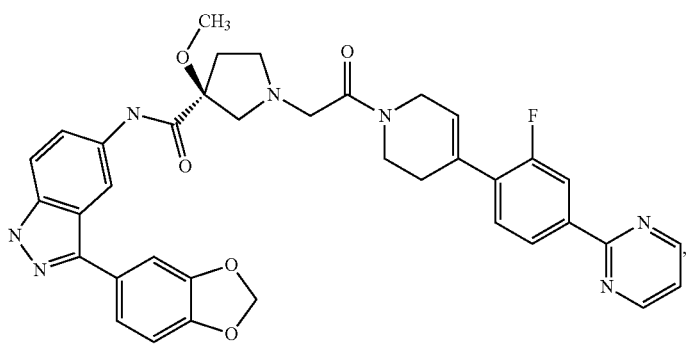
(Ex. 820)
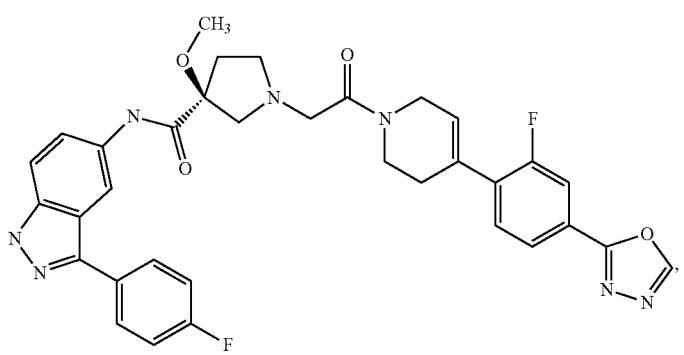
(Ex. 821)
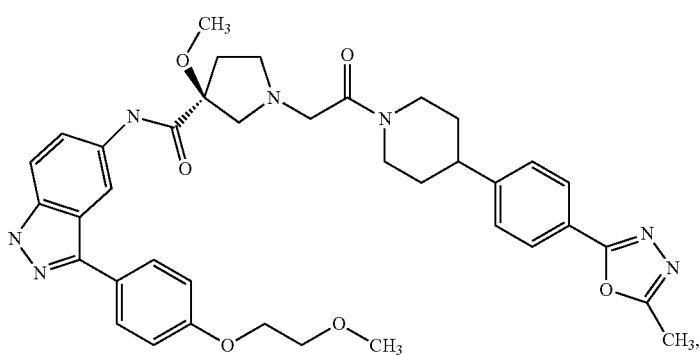

(Ex. 822)
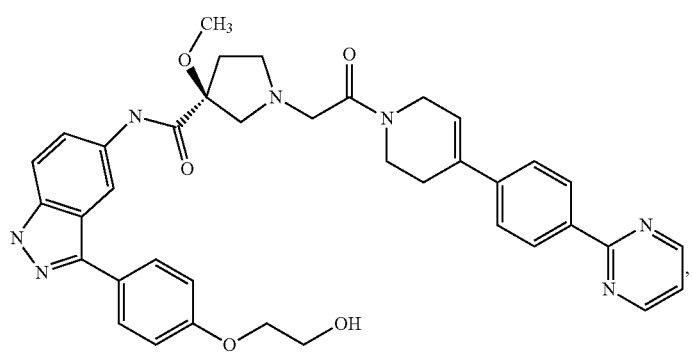
(Ex. 823)
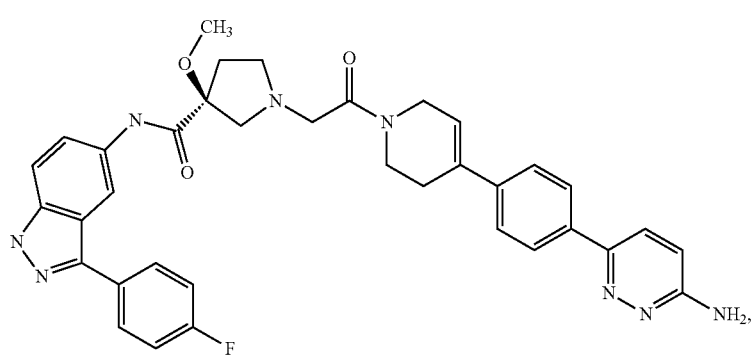
(Ex. 824)
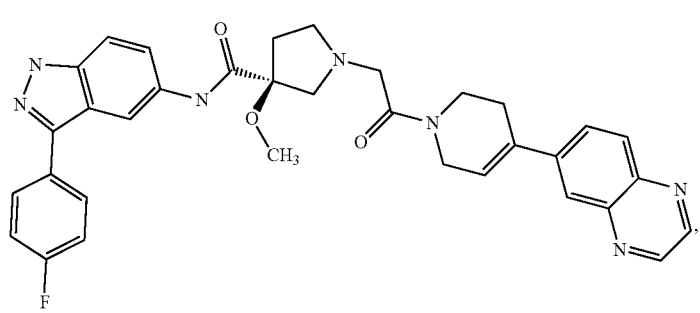
(Ex. 825)
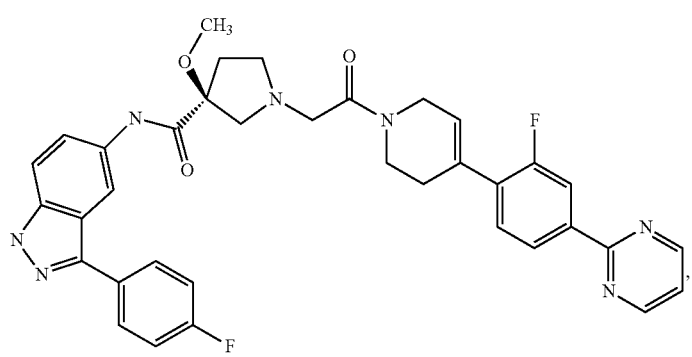

(Ex. 826)
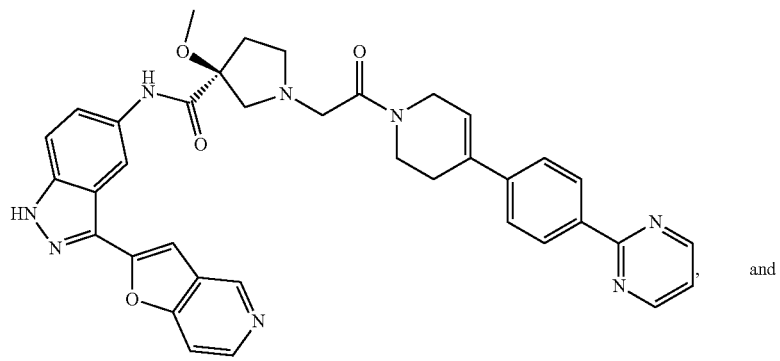
and
(Ex. 827)
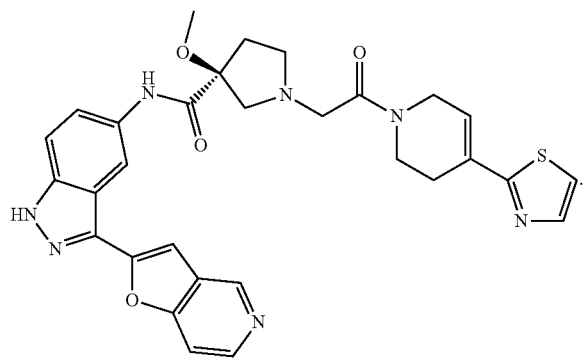
65. The compound of claim 1 having the formula:
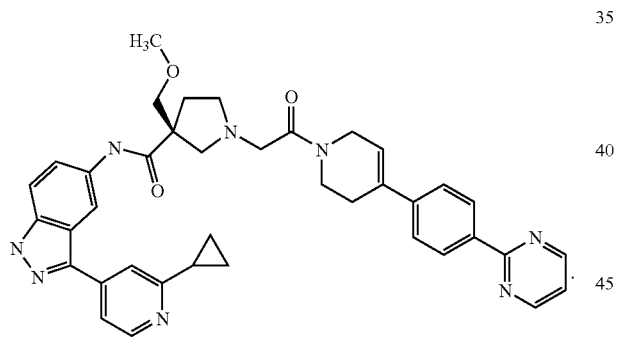
66. The compound of claim 1 having the formula:
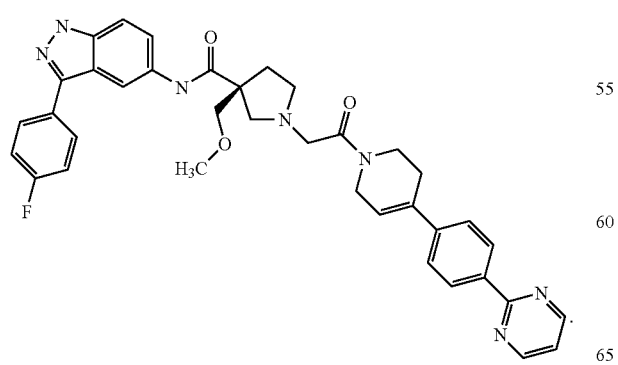
67. The compound of claim 1 having the formula:
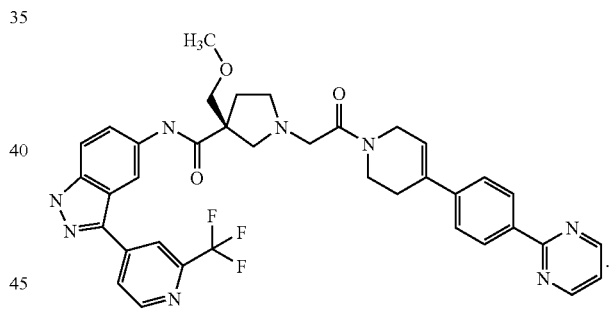
68. The compound of claim 1 having the formula:
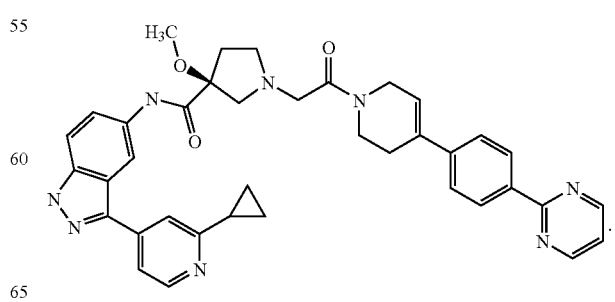

69. The compound of claim 1 having the formula:

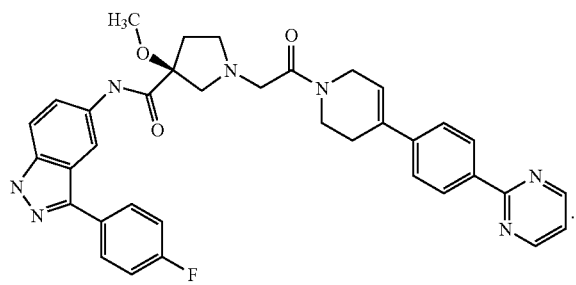 [SMILES: CO[C@@]1(C(=O)Nc2ccc3[nH]nc(-c4ccc(F)cc4)c3c2)CCN(CC(=O)N2CC=C(c3ccc(-c4ncccn4)cc3)CC2)C1 ; "."]

70. The compound of claim 1 having the formula:

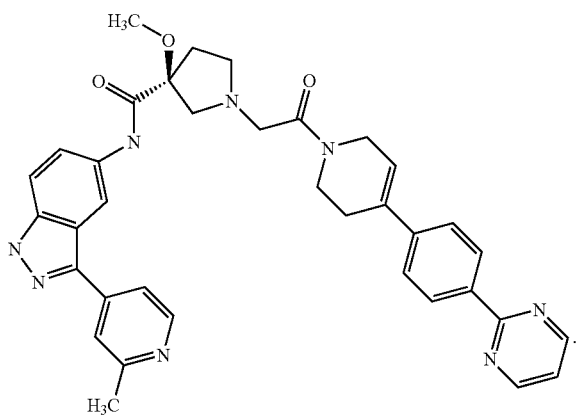 [SMILES: CO[C@@]1(C(=O)Nc2ccc3[nH]nc(-c4ccnc(C)c4)c3c2)CCN(CC(=O)N2CC=C(c3ccc(-c4ncccn4)cc3)CC2)C1]

71. The compound of claim 1 having the formula:

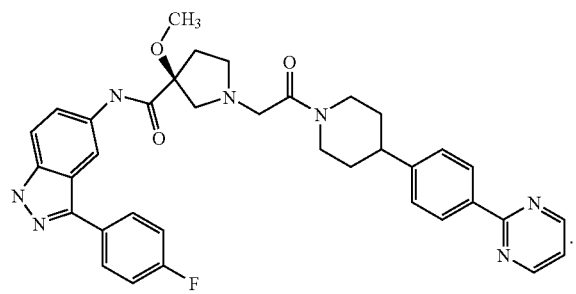 [SMILES: CO[C@@]1(C(=O)Nc2ccc3[nH]nc(-c4ccc(F)cc4)c3c2)CCN(CC(=O)N2CCC(c3ccc(-c4ncccn4)cc3)CC2)C1 ; "."]

72. The compound of claim 1 having the formula;

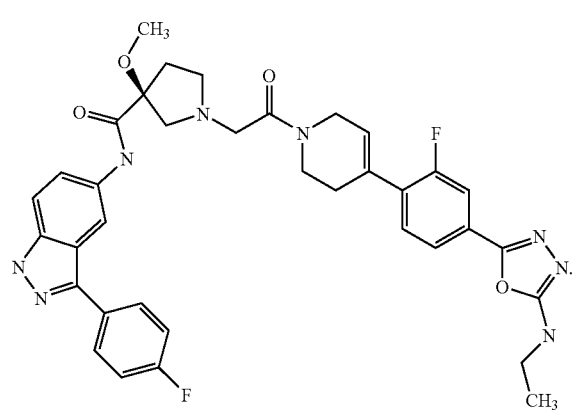 [SMILES: CCNc1nnc(-c2ccc(C3=CCN(C(=O)CN4CC[C@@](OC)(C(=O)Nc5ccc6[nH]nc(-c7ccc(F)cc7)c6c5)C4)CC3)c(F)c2)o1]

73. The compound of claim 1 having the formula

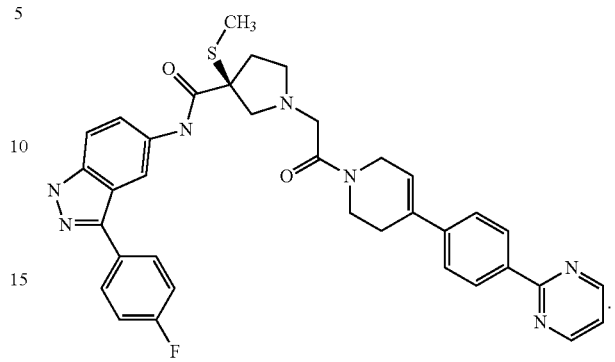

74. The compound of claim 1 having the formula

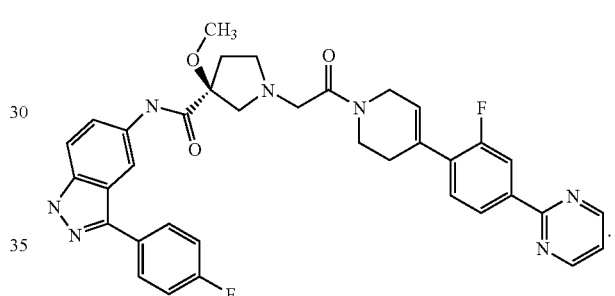

75. The compound of claim 1 having the formula

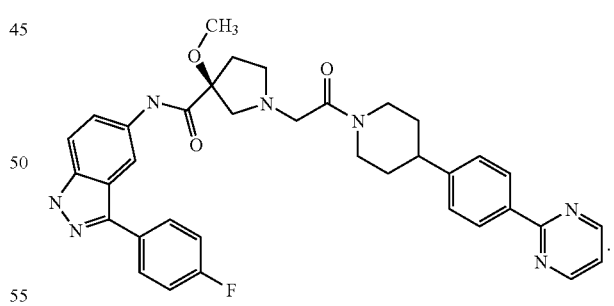

76. A pharmaceutical composition comprising at least one compound of claim 1 and a pharmaceutically acceptable carrier.

* * * * *

UNITED STATES PATENT AND TRADEMARK OFFICE
CERTIFICATE OF CORRECTION

| | | |
|---|---|---|
| PATENT NO. | : 8,546,404 B2 | Page 1 of 1 |
| APPLICATION NO. | : 11/810282 | |
| DATED | : October 1, 2013 | |
| INVENTOR(S) | : Cooper et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1693 days.

Signed and Sealed this
Third Day of March, 2015

Michelle K. Lee
*Deputy Director of the United States Patent and Trademark Office*